(12) United States Patent
Aicher et al.

(10) Patent No.: US 10,442,798 B2
(45) Date of Patent: Oct. 15, 2019

(54) TETRAHYDROQUINOLINE SULFONAMIDE AND RELATED COMPOUNDS FOR USE AS AGONISTS OF RORγ AND THE TREATMENT OF DISEASE

(71) Applicant: Lycera Corporation, Ann Arbor, MI (US)

(72) Inventors: Thomas D. Aicher, Ann Arbor, MI (US); Clarke B. Taylor, Ann Arbor, MI (US); Chad A. VanHuis, Hartland, MI (US)

(73) Assignee: Lycera Corporation, Ann Arbor, MI (US)

( * ) Notice: Subject to any disclaimer, the term of this patent is extended or adjusted under 35 U.S.C. 154(b) by 0 days.

(21) Appl. No.: 15/890,648

(22) Filed: Feb. 7, 2018

(65) Prior Publication Data

US 2018/0265502 A1    Sep. 20, 2018

Related U.S. Application Data

(62) Division of application No. 15/308,736, filed as application No. PCT/US2015/029240 on May 5, 2015, now Pat. No. 9,896,441.

(60) Provisional application No. 62/121,800, filed on Feb. 27, 2015, provisional application No. 61/988,710, filed on May 5, 2014.

(51) Int. Cl.

| C07D 413/12 | (2006.01) |
|---|---|
| C07D 413/14 | (2006.01) |
| C07D 311/22 | (2006.01) |
| C07D 215/58 | (2006.01) |
| C07D 401/06 | (2006.01) |
| C07D 401/12 | (2006.01) |
| C07D 413/06 | (2006.01) |
| C07D 417/06 | (2006.01) |
| C07D 417/12 | (2006.01) |
| C07D 417/14 | (2006.01) |
| C07D 471/04 | (2006.01) |
| C07D 487/04 | (2006.01) |
| C07D 491/10 | (2006.01) |
| C07D 265/36 | (2006.01) |
| C07D 498/08 | (2006.01) |
| C07D 279/16 | (2006.01) |
| C07D 513/04 | (2006.01) |

(52) U.S. Cl.
CPC ......... *C07D 413/12* (2013.01); *C07D 215/58* (2013.01); *C07D 265/36* (2013.01); *C07D 279/16* (2013.01); *C07D 311/22* (2013.01); *C07D 401/06* (2013.01); *C07D 401/12* (2013.01); *C07D 413/06* (2013.01); *C07D 413/14* (2013.01); *C07D 417/06* (2013.01); *C07D 417/12* (2013.01); *C07D 417/14* (2013.01); *C07D 471/04* (2013.01); *C07D 487/04* (2013.01); *C07D 491/10* (2013.01); *C07D 498/08* (2013.01); *C07D 513/04* (2013.01)

(58) Field of Classification Search
CPC .................................................... C07D 413/12
USPC ........................................................ 514/230.5
See application file for complete search history.

(56) References Cited

U.S. PATENT DOCUMENTS

| 3,803,184 A | 4/1974 | Njimi et al. |
|---|---|---|
| 3,936,478 A | 2/1976 | Takeshita et al. |
| 4,952,235 A | 8/1990 | Andree et al. |
| 5,229,109 A | 7/1993 | Grimm et al. |
| 5,229,115 A | 7/1993 | Lynch |
| 5,583,152 A | 12/1996 | Bernstein et al. |
| 5,776,451 A | 7/1998 | Hsu et al. |
| 5,985,903 A | 11/1999 | Assmann et al. |
| 6,020,354 A | 2/2000 | Assmann et al. |
| 6,037,367 A | 3/2000 | Christensen, IV et al. |
| 6,160,001 A | 12/2000 | Assmann et al. |
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,392,010 B1 | 5/2002 | Salvino et al. |
| 6,403,607 B1 | 6/2002 | Hidaka et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |
| 7,084,176 B2 | 8/2006 | Morie et al. |
| 7,115,750 B1 | 10/2006 | Kato et al. |

(Continued)

FOREIGN PATENT DOCUMENTS

| EP | 0882718 A1 | 12/1998 |
|---|---|---|
| EP | 1531848 A2 | 5/2005 |

(Continued)

OTHER PUBLICATIONS

U.S. Appl. No. 15/729,910, Tetrahydro[1,8]Naphthyridine Sulfonamide and Related Compounds for Use as Agonists of Rorγ and the Treatment of Disease, filed Oct. 11, 2017.

(Continued)

*Primary Examiner* — Kahsay Habte
(74) *Attorney, Agent, or Firm* — Dechert LLP

(57) ABSTRACT

The invention provides tetrahydroquinoline sulfonamide compounds, tetrahydronaphthalene sulfonyl compounds, and related compounds, pharmaceutical compositions, methods of promoting RORγ activity, methods of increasing the amount of IL-17 in a subject, and methods of treating cancer and other medical disorders using such compounds.

30 Claims, No Drawings

(56) References Cited

U.S. PATENT DOCUMENTS

| | | |
|---|---|---|
| 7,138,401 B2 | 11/2006 | Kasibhatla et al. |
| 7,329,675 B2 | 2/2008 | Cox et al. |
| 7,420,059 B2 | 9/2008 | O'Connor et al. |
| 7,482,342 B2 | 1/2009 | D'Orchymont et al. |
| 7,569,571 B2 | 8/2009 | Dong et al. |
| 7,652,043 B2 | 1/2010 | Beachy et al. |
| 7,696,200 B2 | 4/2010 | Ackermann et al. |
| 7,713,996 B2 | 5/2010 | Ackermann et al. |
| 7,741,495 B2 | 6/2010 | Liou et al. |
| 7,799,933 B2 | 9/2010 | Ceccarelli et al. |
| 7,973,135 B2 | 7/2011 | Liik et al. |
| 7,993,638 B2 | 8/2011 | Cai et al. |
| 7,998,736 B2 | 8/2011 | Morgan et al. |
| 8,067,608 B2 | 11/2011 | Beachy et al. |
| 8,383,099 B2 | 2/2013 | Dudley et al. |
| 8,389,738 B2 | 3/2013 | Kousaka et al. |
| 8,389,739 B1 | 3/2013 | Thacher et al. |
| 8,541,185 B2 | 9/2013 | Oved et al. |
| 8,741,812 B2 | 6/2014 | Javitt |
| 9,095,583 B2 | 8/2015 | Karstens et al. |
| 9,266,827 B2 | 2/2016 | Aicher et al. |
| 9,394,315 B2 | 7/2016 | Aicher et al. |
| 9,487,490 B2 | 11/2016 | Barr et al. |
| 9,512,111 B2 | 12/2016 | Glick et al. |
| 9,556,168 B2 | 1/2017 | Barr et al. |
| 9,603,838 B2 | 3/2017 | Karstens et al. |
| 9,657,033 B2 | 5/2017 | Aicher et al. |
| 9,663,502 B2 | 5/2017 | Aicher et al. |
| 9,663,522 B2 | 5/2017 | Barr et al. |
| 9,783,511 B2 | 10/2017 | Aicher et al. |
| 9,802,958 B2 | 10/2017 | Aicher et al. |
| 9,809,561 B2 | 10/2017 | Aicher et al. |
| 9,896,441 B2 | 2/2018 | Aicher et al. |
| 10,208,061 B2 | 2/2019 | Aicher et al. |
| 10,221,146 B2 | 3/2019 | Aicher et al. |
| 2005/0037925 A1 | 2/2005 | Tsukamoto et al. |
| 2006/0004000 A1 | 1/2006 | D'Orchymont et al. |
| 2006/0100230 A1 | 5/2006 | Bischoff et al. |
| 2006/0111421 A1 | 5/2006 | Chadwick et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0185136 A1 | 8/2007 | Courtemanche et al. |
| 2007/0191603 A1 | 8/2007 | Ackermann et al. |
| 2007/0197782 A1 | 8/2007 | Clough et al. |
| 2007/0219257 A1 | 9/2007 | Beachy et al. |
| 2007/0232661 A1 | 10/2007 | Beachy et al. |
| 2007/0281922 A1 | 12/2007 | Liu et al. |
| 2008/0027002 A1 | 1/2008 | Liik et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0199486 A1 | 8/2008 | Argon et al. |
| 2008/0305169 A1 | 12/2008 | Miki et al. |
| 2009/0005410 A1 | 1/2009 | Charvat et al. |
| 2009/0042851 A1 | 2/2009 | Despeyroux et al. |
| 2009/0075973 A1 | 3/2009 | Newcom et al. |
| 2009/0131523 A1 | 5/2009 | Yosef et al. |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0087376 A1 | 4/2010 | Kazantseva et al. |
| 2010/0130484 A1 | 5/2010 | Ackermann et al. |
| 2010/0234340 A1 | 9/2010 | Schunk et al. |
| 2010/0310533 A1 | 12/2010 | Yee |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0142814 A1 | 6/2011 | Zanin-Zhorov et al. |
| 2011/0151478 A1 | 6/2011 | Liik et al. |
| 2011/0178063 A1 | 7/2011 | Baldwin et al. |
| 2011/0229504 A1 | 9/2011 | Fritsche et al. |
| 2011/0236363 A1 | 9/2011 | Chang et al. |
| 2012/0135011 A1 | 5/2012 | Podack et al. |
| 2013/0039911 A1 | 2/2013 | Bedi et al. |
| 2013/0045191 A1 | 2/2013 | Weinschenk et al. |
| 2013/0102075 A1 | 4/2013 | Vera et al. |
| 2013/0102542 A1 | 4/2013 | Kazantseva et al. |
| 2014/0038942 A1 | 2/2014 | Karstens et al. |
| 2014/0088094 A1 | 3/2014 | Glick et al. |
| 2014/0186295 A1 | 7/2014 | Kupper et al. |
| 2014/0187504 A1 | 7/2014 | Chaturvedi |
| 2014/0187554 A1 | 7/2014 | Kamenecka et al. |
| 2014/0314795 A1 | 10/2014 | Riddell et al. |
| 2014/0343023 A1 | 11/2014 | Wolfrum et al. |
| 2015/0017120 A1 | 1/2015 | Wittrup et al. |
| 2015/0111877 A1 | 4/2015 | Aicher et al. |
| 2015/0126493 A1 | 5/2015 | Aicher et al. |
| 2015/0133437 A1 | 5/2015 | Aicher et al. |
| 2015/0191434 A1 | 7/2015 | Barr et al. |
| 2015/0210687 A1 | 7/2015 | Barr et al. |
| 2015/0218096 A1 | 8/2015 | Barr et al. |
| 2015/0218169 A1 | 8/2015 | Barr et al. |
| 2015/0297566 A1 | 10/2015 | Karstens et al. |
| 2016/0304476 A1 | 10/2016 | Aicher et al. |
| 2016/0304505 A1 | 10/2016 | Aicher et al. |
| 2016/0311787 A1 | 10/2016 | Aicher et al. |
| 2016/0318951 A1 | 11/2016 | Aicher et al. |
| 2017/0007686 A1 | 1/2017 | Glick et al. |
| 2017/0183331 A1 | 6/2017 | Aicher et al. |
| 2017/0190659 A1 | 7/2017 | Aicher et al. |
| 2017/0313722 A1 | 11/2017 | Aicher et al. |
| 2018/0030005 A1 | 2/2018 | Aicher et al. |
| 2018/0111922 A1 | 4/2018 | Aicher et al. |
| 2018/0179224 A1 | 6/2018 | Aicher et al. |
| 2018/0208587 A1 | 7/2018 | Aicher et al. |

FOREIGN PATENT DOCUMENTS

| | | |
|---|---|---|
| EP | 1768662 A2 | 4/2007 |
| EP | 1820515 A1 | 8/2007 |
| EP | 2038301 A2 | 3/2009 |
| EP | 2158327 A2 | 3/2010 |
| EP | 2181710 A1 | 5/2010 |
| EP | 2321407 A1 | 5/2011 |
| EP | 2462165 A1 | 6/2012 |
| EP | 2542590 A2 | 1/2013 |
| EP | 2547354 A2 | 1/2013 |
| EP | 2158327 B1 | 5/2013 |
| EP | 2649086 A1 | 10/2013 |
| EP | 2688594 A2 | 1/2014 |
| EP | 2689010 A1 | 1/2014 |
| EP | 2825197 A1 | 1/2015 |
| JP | 6-250441 A | 9/1994 |
| JP | 2000-511558 A | 9/2000 |
| JP | 2004307487 A | 11/2004 |
| JP | 2006-512357 A | 4/2006 |
| JP | 2013-541597 A | 11/2013 |
| JP | 2017-507950 A | 3/2017 |
| JP | 2018-515491 A | 6/2018 |
| WO | WO-92/13856 A1 | 8/1992 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/012600 A1 | 2/2001 |
| WO | WO-2001/012186 A1 | 2/2001 |
| WO | WO-02/14361 A2 | 2/2002 |
| WO | WO-2002/058622 A2 | 8/2002 |
| WO | WO-02/100819 A1 | 12/2002 |
| WO | WO-03/014075 A2 | 2/2003 |
| WO | WO-03/104428 A2 | 12/2003 |
| WO | WO-2004/050631 A1 | 6/2004 |
| WO | WO-2004/056820 A1 | 7/2004 |
| WO | WO-2004/056830 A1 | 7/2004 |
| WO | WO-05/028434 A2 | 3/2005 |
| WO | WO-2005/030225 A2 | 4/2005 |
| WO | WO-2005/033048 A2 | 4/2005 |
| WO | WO-2005/033288 A2 | 4/2005 |
| WO | WO-2005/037834 A1 | 4/2005 |
| WO | WO-2005/058847 A1 | 6/2005 |

(56) References Cited

FOREIGN PATENT DOCUMENTS

| | | |
|---|---|---|
| WO | WO-2005/084208 A2 | 9/2005 |
| WO | WO-2005/120558 A2 | 12/2005 |
| WO | WO-2006/007486 A2 | 1/2006 |
| WO | WO-2006/057460 A1 | 6/2006 |
| WO | WO-2006/065495 A2 | 6/2006 |
| WO | WO-2006/115509 A2 | 11/2006 |
| WO | WO-2007/010259 A1 | 1/2007 |
| WO | WO-2007/024944 A1 | 3/2007 |
| WO | WO-2007/031429 A1 | 3/2007 |
| WO | WO-2007/093507 A1 | 8/2007 |
| WO | WO-2007/113337 A1 | 10/2007 |
| WO | WO-2007/125405 A2 | 11/2007 |
| WO | WO-2007/138998 A1 | 12/2007 |
| WO | WO-2008/003703 A1 | 1/2008 |
| WO | WO-2008/008923 A2 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/150827 A1 | 12/2008 |
| WO | WO-2008/151200 A2 | 12/2008 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/030947 A1 | 3/2010 |
| WO | WO-2010/038901 A1 | 4/2010 |
| WO | WO-2010/057101 A2 | 5/2010 |
| WO | WO-2010/058023 A1 | 5/2010 |
| WO | WO-2010/059602 A2 | 5/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2011/017303 A1 | 2/2011 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/109059 A1 | 9/2011 |
| WO | WO-2011/109789 A2 | 9/2011 |
| WO | WO-2011/113819 A2 | 9/2011 |
| WO | WO-2011/115892 A1 | 9/2011 |
| WO | WO-2012/020100 A2 | 2/2012 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/079000 A1 | 6/2012 |
| WO | WO-2012/127464 A2 | 9/2012 |
| WO | WO-2012/129394 A2 | 9/2012 |
| WO | WO-2012/129514 A1 | 9/2012 |
| WO | WO-2012/139775 A1 | 10/2012 |
| WO | WO-2012/129394 A9 | 11/2012 |
| WO | WO-2012/178108 A1 | 12/2012 |
| WO | WO-2013/045431 A1 | 4/2013 |
| WO | WO-2013/074916 A1 | 5/2013 |
| WO | WO-2013/135588 A1 | 9/2013 |
| WO | WO-2013/167136 A1 | 11/2013 |
| WO | WO-2013/169588 A1 | 11/2013 |
| WO | WO-2013/169704 A1 | 11/2013 |
| WO | WO-2013/169864 A2 | 11/2013 |
| WO | WO-2013/176740 A1 | 11/2013 |
| WO | WO-2014/028669 A1 | 2/2014 |
| WO | WO-2014/031174 A1 | 2/2014 |
| WO | WO-2014/095757 A1 | 6/2014 |
| WO | WO-2014/201378 A1 | 12/2014 |
| WO | WO-2014/201378 A9 | 1/2015 |
| WO | WO-2015/131035 A1 | 9/2015 |
| WO | WO-2015/171610 A2 | 11/2015 |
| WO | WO-2016/179343 A1 | 11/2016 |

OTHER PUBLICATIONS

U.S. Appl. No. 14/559,082, Retinoid-Related Orphan Receptor Gamma Modulators for Treatment of Cancer, Autoimmune Disorders, and Inflammatory Disorders and Use in Diagnostic Methods, filed Dec. 3, 2014.

U.S. Appl. No. 15/120,798, Adoptive Cellular Therapy Using an Agonist of Retinoic Acid Receptor-Related Orphan Receptor Gamma & Related Therapeutic Methods, filed Aug. 23, 2016.

U.S. Appl. No. 15/308,734, Benzenesulfonamido and Related Compounds for Use as Agonists of RORy and the Treatment of Disease, filed Nov. 3, 2016.

U.S. Appl. No. 15/848,241, Tetrahydroquinoline Sulfonamide and Related Compounds for Use as Agonists of RORy and the Treatment of Disease, filed Dec. 20, 2017.

U.S. Appl. No. 15/568,573, Dihydro-2H-Benzo[b][1,4]Oxazine Sulfonamide and Related Compounds for Use as Agonists of RORy and the Treatement of Disease, filed Oct. 23, 2017.

U.S. Appl. No. 15/580,414, Aryl Dihydro-2H-Benzo[B][1,4]Oxazine Sulfonamide and Related Compounds for Use as Agonists of RORY and the Treatment of Disease, filed Dec. 7, 2017.

Garcia-Hernandez, M. et al. "Adoptive Transfer of Tumor-Specific Tc17 Effector T Cells Controls the Growth of B16 Melanoma in Mice," J. Immunology. (2010), vol. 184, No. 8, pp. 4215-4227.

International Search Report and Written Opinion for International Application No. PCT/US2015/017977 dated Jun. 23, 2015 (10 pages).

Zhang et al., "Increasing Human Th17 Differentiation Through Activation of Orphan Nuclear Receptor Retinoid Acid-Related Orphan Receptor γ (RORγ) by a Class of Aryl Amide Compounds," Molecular Pharmacology, vol. 82, pp. 583-590 (2012).

English Abstract JP6-250441 published 1994 (1 page).

English Abstract of JP2004307487A published 2004 (2 pages).

International Search Report and Written Opinion for PCT/US2011/059788 dated May 23, 2012 (23 pages).

International Search Report and Written Opinion for PCT/US2013/040085 dated Oct. 23, 2013 (9 pages).

Annunziato et al., "Type 17 T helper cells-origins, features and possible roles in rheumatic disease," 5 Nat. Rev. Rheumatol. 325-31 (2009).

Boaventura et al., "Human mucosal leishmaniasis: Neutrophils infiltrate areas of tissue damage that express high levels of Th17-related cytokines," 40 Eur. J. Immunol. 2830-36 (2010).

Buonocore et al., "Innate lymphoid cells drive interleukin-23-dependent innate intestinal pathology," 464 Nature 1371-75 (2010).

Eberl et al., "An essential function for the nuclear receptor RORγt in the generation of fetal lymphoid tissue inducer cells," 5(1) Nat. Immunol. 64-73 (2004).

Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).

Gennaro (ed.), Remington: The Science and Practice of Pharmacy, 20th edition (2000).

He et al., "RORγt, a Novel Isoform of an Orphan Receptor, Negatively Regulates Fas Ligand Expression and IL-2 Production in T Cells," 9 Immunity 797-806 (1998).

Hirose et al., "RORγ: the third member of ROR/RZR orphan receptor subfamily that is highly expressed in skeletal muscle," 205 Biochem. Biophys. Res. Comm. 1976-83 (1994).

Hueber et al., "Cutting Edge: Mast Cells Express IL-17A in Rheumatoid Arthritis Synovium," 184 J. Immunol. 3336-40 (2010).

Ivanov et al., "The Orphan Nuclear Receptor RORγt Directs the Differentiation Program of Proinflammatory IL-17+ T Helper Cells," 126 Cell 1121-33 (2006).

Jia et al., "The T helper type 17/regulatory T cell imbalance in patients with acute Kawasaki disease," 162 Clin. Exp. Immunol. 131-37 (2010).

(56) References Cited

OTHER PUBLICATIONS

Jin et al., "Structural Basis for Hydroxycholesterols as Natural Ligands of Orphan Nuclear Receptor RORγ," Mol. Endocrinol. (2010) vol. 24, No. 5, pp. 923-929.
Kastelein et al., "Discovery and Biology of IL-23 and IL-27: Related but Functionally Distinct Regulators of Inflammation," 25 Annu. Rev. Immunol. 221-42 (2007).
Kurebayashi et al., "Selective LXXLL peptides antagonize transcriptional activation by the retinoid-related orphan receptor RORγ," 315 Biochem. Biophys. Res. Comm. 919-27 (2004).
Louten et al., "Development and function of TH17 cells in health and disease," 123(5) J. Allergy Clin. Immunol. 1004-11 (2009).
Miossec et al., "Interleukin-17 and Type 17 Helper T Cells," 361(9) New Eng. J. Med. 888-98 (2009).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Wang et al., "Identification of SR1078, A Synthetic Agonist for the Orphan Nuclear Receptors RORα and RORγ," 5(11) ACS Chem. Biol. 1029-34 (2010).
Xie et al., "RORγt Recruits Steroid Receptor Coactivators to Ensure Thymocyte Survival," 175(6) J. Immunol. 3800-09 (2005).
Yang et al., "T Helper 17 Lineage Differentiation is programmed by Orphan Nuclear Receptors RORα and RORγ," 28 Immunity 29-39 (2008).
André et al., "Disruption of retinoid-related orphan receptor β changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Burris et al., "Targeting Orphan Nuclear Receptors for Treatment of Metabolic Diseases and Autoimmunity," 19(1) Chem. Biol. 51-59 (2012).
Cai et al "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
Giguère et al., "Isoform-specific amino-terminal domains dictate DNA-binding properties of RORα, a novel family of orphan hormone nuclear receptors," 8 Genes & Develop. 538-53 (1994).
Huh et al., "Small molecule inhibitors of RORγt: Targeting Th17 cells and other applications," 42 Eur. J. Immunol. 2232-2237 (2012).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, J. et al. "Pharmacologic Inhibition of RORγt Regulates Th17 Signature Gene Expression and Suppresses Cutaneous Inflammation In Vivo," downloaded from the Internet at http://www.jimmunol.org/cgi/doi/10.4049/jimmunol.1302190 on Feb. 17, 2014, published in final edited form in J. Immunol. (2014) vol. 192, No. 6, pp. 2564-2575.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation—Isomerization—Acylation Cascade," 13 Org. Lett. 5456-59 (2011).
De et al., Methods in Molecular Biology 1184, second edition, Human Press (2014).
Gould, "Salt selection for basic drugs," 33 Int'l J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).
Guimond et al., "Rhodium(III)-Catalyzed Isoquinolone Synthesis: The N—O Bond as a Handle for C—N Bond Formation and Catalyst Turnover," 132(20) J. Am. Chem. Soc. 6908-09 (2010).

(56) References Cited

OTHER PUBLICATIONS

Hanessian et al., "A versatile protocol for the stereocontrolled elaboration of vicinal secondary and tertiary centers of relevance to natural product synthesis," 52(6) J. Org. Chem. 1170-72 (1987).
Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C—H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).
Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).
Santilli et al., "Synthesis of 5,6,7,8-Tetrahydro-5-oxopyrido[2,3-d] pyrimidine-6-carbonitriles and -6-carboxylic Acid Esters," 12 J. Het. Chem. 311-16 (1975).
Skraup, "Eine Synthese des Chinolins," 13 Berichte 2086-87 (1880).
Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (−)-desmosterol," 14 J. Chem. Soc., Chem. Commun. 760-61 (1983).
Van Heerden et al., "Dibutylboron triflate promoted conjugate addition of benzylic and allylic organocopper reagents to chiral $\alpha,\beta$-unsaturated N-acyl imidazolidinones" 38(10) Tet. Lett. 182-124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).
Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, $\alpha,\beta$-Unsaturated Ketones, and Allylic, Aryl, and Vinyl Halides," 56 J. Org. Chem. 1445-53 (1991).
International Search Report and Written Opinion for PCT/US2014/071663 dated Apr. 17, 2015 (6 pages).
International Search Report and Written Opinion for PCT/US2014/071671 dated Apr. 28, 2015 (10 pages).
International Search Report and Written Opinion for PCT/US2014/071656 dated Mar. 12, 2015 (8 pages).
Yang, T. et al. "Discovery of Tertiary Amine and Indole Derivatives as Potent RORγt Inverse Agonists," ACS Med. Chem. Lett. (2014) vol. 5, pp. 65-68.
June, C. H. "Adoptive T cell therapy for cancer in the clinic," J. Clin. Invest. (2007) vol. 117, No. 6, pp. 1466-1476.
Zhu, J. et al. "Differentiation of Effector CD4 T Cell Populations," Author manuscript available in PMC on Nov. 20, 2012, published in final edited form in Annu. Rev. Immunol. (2010) vol. 28, pp. 445-489.
Martin-Orozco, N. et al. "Th17 cells promote cytotoxic T cell activation in tumor immunity," Author manuscript available in PMC on Nov. 20, 2010, published in final edited form in Immunity (2009) vol. 31, pp. 787-798.
Pardoll, D. M. "The blockade of immune checkpoints in cancer immunotherapy," Nature Rev. Cancer (2012) vol. 12, pp. 252-264.
Restifo, N. P. et al. "Adoptive immunotherapy for cancer: harnessing the T cell response," Nature Rev. Immunol. (2012) vol. 12, pp. 269-281.
Drug Discovery & Development "Lycera's Oral Immunotherapy May Have Anti-Cancer Activity," Dated Nov. 7, 2014. (2 pages).
Lycera "Lycera Announces Research Showing Promising Anti-Cancer Activity of Novel, Oral Immunotherapy Candidates," Press release dated Feb. 9, 2015. (2 pages).
X. Hu et al. In Poster Presentation Entitled "Novel, Synthetic RORgamma Agonist Compounds as a Potential Anti-Cancer Approach" at Society for Immunotherapy of Cancer (SITC) Meeting 2014, Nov. 6-9, 2014.
Huang, Z. et al. "Retinoid-related orphan receptor γt is a potential therapeutic target for controlling inflammatory autoimmunity," Expert Opin. Ther. Targets (2007) vol. 11, No. 6, pp. 737-743.
Wang et al., "Modulation of Retinoic Acid Receptor-related Orphan Receptor α and γ Activity by 7-Oxygenated Sterol Ligands," J. Biol. Chem. (2010) vol. 285, No. 7, pp. 5013-5025.
Bai et al., "Sulfation of 25-hydroxycholesterol by SULT2B1b decreases cellular lipids via the LXR/SREBP-1c signaling pathway in human aortic endothelial cells," Atherosclerosis, vol. 214, pp. 350-356 (author's manuscript pp. 1-14) (2011).
Bensinger et al., "LXR signaling couples sterol metabolism to proliferation in the acquired immune response," Cell, vol. 134, pp. 97-111 (2008).
Brown et al., "Oxysterols and atherosclerosis," Atherosclerosis, vol. 142, pp. 1-28 (1999).
Chen et al., "Enzymatic reduction of oxysterols impairs LXR signaling in cultured cells and the livers of mice," Cell Metab., vol. 5, pp. 73-79 (2007).
Cheng et al., "Increased cholesterol content in Gammadelta (γδ) T lymphocytes differentially regulates their activation," PLoS ONE 8, pp. 1-9 (2013).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metab. Dispos., vol. 37, pp. 2069-2078 (2009).
Hanyu et al., "Cholesterol sulfate induces expression of the skin barrier protein filaggrin in normal human epidermal keratinocytes through induction of RORα," Biochem. Biophys. Res. Commun., vol. 428, pp. 99-104 (2012).
Hu et al., "Sterol metabolism controls $T_H17$ differentiation by generating endogenous RORγ agonists," Nature Chemical Biology, vol. 11, pp. 141-147 (2015).
Iida et al., "Tumor-Infiltrating CD4+Th17 Cells Produce IL-17 in Tumor Microenvironment and Promote Tumor Progression in Human Gastric Cancer," Oncology Reports, vol. 25, pp. 1271-1277 (2011).
Ikonen, "Cellular cholesterol trafficking and compartmentalization," Nat. Rev. Mol. Cell Biol., vol. 9, pp. 125-138 (2008).
Kallen et al., "Crystal structure of the human RORα ligand binding domain in complex with cholesterol sulfate at 2.2 Å," J. Biol. Chem., vol. 279, pp. 14033-14038 (2004).
Kidani et al., "The sterol regulatory element binding proteins are essential for the metabolic programming of effector T cells and adaptive immunity," Nat. Immunol., vol. 14, pp. 489-499 (2013).

(56) References Cited

OTHER PUBLICATIONS

Liao et al., "Association Between Th17-Related Cytokines and Risk of Non-Small Cell Lung Cancer Among Patients With or Without Chronic Obstructive Pulmonary Disease," Cancer, pp. 3122-3129 (2015).
Ma et al., "25-Hydroxycholesterol-3-sulfate regulates macrophage lipid metabolism via the LXR/SREBP-1 signaling pathway," *Am. J. Physiol. Endocrinol. Metab.*, vol. 295, pp. E1369-E1379 (2008).
Solt et al., "Identification of a selective RORγ ligand that suppresses $T_H17$ cells and stimulates T regulatory cells," *ACS Chem. Biol.*, vol. 7, pp. 1515-1519 (2012).
Song et al., "Auto-oxidized cholesterol sulfates are antagonistic ligands of liver X receptors: implications for the development and treatment of atherosclerosis," *Steroids*, vol. 66, pp. 473-479 (2001).
Spann et al., "Regulated accumulation of desmosterol integrates macrophage lipid metabolism and inflammatory responses," *Cell*, vol. 151, pp. 138-152 (2012).
Spann et al., "Sterols and oxysterols in immune cell function," *Nat. Immunol.*, vol. 14, pp. 893-900 (2013).
Wang et al., "A second class of nuclear receptors for oxysterols: Regulation of RORα and RORγ activity by 24S-hydroxycholesterol (cerebrosterol)," *Biochim. Biophys. Acta*, vol. 1801, pp. 917-923 (2010).
Yang et al., "Sterol intermediates from cholesterol biosynthetic pathway as liver X receptor ligands," *J. Biol. Chem.*, vol. 281, pp. 27816-27826 (2006).
Arellano et al., "Clinical uses of GM-CSF, a critical appraisal and update," *Biologics: Targets & Therapy*, vol. 2, pp. 13-27 (2008).
Chang et al., "Synthetic RORγt Agonists Enhance Protective Immunity," ACS Chem. Biol., Just Accepted Manuscript—DOI: 10.1021/acschembio.5b00899—Publication Date (Web): Jan. 19, 2016, (30 pages).
Chen et al., "Th1-, Th2-, and Th17-associated cytokine expression in hypopharyngeal carcinoma and clinical significance," *Eur Arch Otorhinolaryngol*, DOI: 10.1007/s00405-015-3779-2, 8 pages, (2015).
Codarri et al., "RORγt drives production of the cytokine GM-CSF in helper T cells, which is essential for the effector phase of autoimmune neuroinflammation," *Nature Immunology*, vol. 12, pp. 560-568, (2011).
Gnerlich et al., "Induction of Th17 Cells in the Tumor Microenvironment Improves Survival in a Murine Model of Pancreatic Cancer," *The Journal of Immunology*, vol. 185, pp. 4063-4071, (2010).
Hinrichs et al., "Type 17 CD8+ T cells display enhanced antitumor immunity," *Blood*, vol. 114, pp. 596-599, (2009).
Hu et al. in "RORγ Agonists as a Novel Immunotherapy Approach for Cancer" in American Association for Cancer Research Annual Meeting in Philadelphia, Pennsylvania, Apr. 21, 2015, Poster Session: Novel Immunomodulators, Abstract No. 4273.
Kryczek et al., "Phenotype, distribution, generation, and functional and clinical relevance of Th17 cells in the human tumor environments," *The American Society of Hematology*, vol. 114, pp. 1141-1149, (2009).
Ma et al., "Contribution of IL-17-producing γδ T cells to the efficacy of anticancer chemotherapy," *J. Exp. Med.*, vol. 208, pp. 491-503, (2011).
Munegowda et al., "Th17 and Th17-stimulated CD8 + T cells play a distinct role in Th17-induced preventive and therapeutic antitumor Immunity," *Cancer Immunol Immunother*, vol. 60, (2011), one page, Abstract only.
Muranski et al., "Tumor-specific Th17-polarized cells eradicate large established melanoma," *Blood*, vol. 112, pp. 362-373, (2008).
Nelson et al., "The Inducible Costimulator Augments Tc17 Cell Responses to Self and Tumor Tissue," *The Journal of Immunology*, vol. 194, pp. 1737-1747, (2015).
Nunez et al., "T helper type 17 cells contribute to anti-tumour immunity and promote the recruitment of T helper type 1 cells to the tumour," *Immunology*, vol. 139, pp. 61-71, (2012).
Soroosh et al., "Oxysterols are agonist ligands of RORγt and drive Th17 cell differentiation," PNAS, vol. 111, pp. 12163-12168, (2014).
International Search Report and Written Opinion for International Application No. PCT/US2015/029167 dated Jun. 13, 2017 (25 pages).
International Search Report and Written Opinion for International Application No. PCT/US2015/029240 dated Jan. 29, 2016 (14 pages).
International Search Report and Written Opinion for International Application No. PCT/US2016/030882 dated Jun. 6, 2016 (17 pages).
International Search Report and Written Opinion for International Application No. PCT/US2016/036889 dated Sep. 9, 2016 (17 pages).
Yang, S. M. and Murray, W. V. "Microwave assisted ring-opening of epoxides with N-biaryl sulfonamides in the synthesis of matrix metalloproteinase-9 inhibitors," *Tetrahedron Lett.* (2008) vol. 49, No. 5, pp. 835-839.
CAS Registry No. 1012413-39-6; STN Entry Date: Apr. 6, 2008.
CAS Registry No. 632292-33-2; STN Entry Date: Dec. 30, 2003.
Zhu, W. et al. "Potent 11β-Hydroxylase Inhibitors with Inverse Metabolic Stability in Human Plasma and Hepatic S9 Fractions to Promote Wound Healing," *J. Med. Chem.* (2014) vol. 57, No. 18, pp. 7811-7817.
Zhao, S.-H. et al. "3,4-Dihydro-2H-benzo[1,4]oxazine Derivatives as 5-$HT_6$ Receptor Antagonists," *Bioorg. Med. Chem. Lett.* (2007) vol. 17, pp. 3504-3507.
Tavares, F. X. et al. "Potent, Selective, and Orally Efficacious Antagonists of Melanin-Concentrating Hormone Receptor 1," *J. Med. Chem.* (2006) vol. 49, No. 24, pp. 7095-7107.
STN Chemical Structure Search Results (dated Jun. 5, 2015; 13 pages).
STN Chemical Structure Search Results (dated May 2, 2014; 10 pages).
STN Chemical Structure Search Results (dated May 2, 2014; 28 pages).
International Preliminary Report on Patentability for International Application No. PCT/US2015/029167 dated Jul. 4, 2017 (13 pages).
U.S. Appl. No. 16/234,681, Retinoid-Related Orphan Receptor Gamma Modulators for Treatment of Cancer, Autoimmune Disorders, and Inflammatory Disorders and use in Diagnostis Methods, filed Dec. 28, 2018.

TETRAHYDROQUINOLINE SULFONAMIDE AND RELATED COMPOUNDS FOR USE AS AGONISTS OF RORγ AND THE TREATMENT OF DISEASE

CROSS-REFERENCE TO RELATED APPLICATIONS

This application is a divisional of U.S. patent application Ser. No. 15/308,736, filed Nov. 3, 2016, which is the national stage of International (PCT) Patent Application Serial No. PCT/US2015/029240, filed May 5, 2015, which claims the benefit of and priority to U.S. Provisional Patent Application Ser. No. 61/988,710, filed May 5, 2014, and U.S. Provisional Patent Application Ser. No. 62/121,800, filed Feb. 27, 2015; the contents of each of which are hereby incorporated by reference.

FIELD OF THE INVENTION

The invention provides tetrahydroquinoline sulfonamide compounds, tetrahydronaphthalene sulfonyl compounds, and related compounds (collectively "tetrahydroquinolinyl and related compounds"), methods of promoting RORγ activity and/or increasing the amount of IL-17 in a subject, and therapeutic uses of the tetrahydroquinolinyl and related compounds, such as treating medical conditions in which activation of immune response is beneficial.

BACKGROUND

Retinoid-related orphan receptors (ROR) are reported to have an important role in numerous biological processes. See, for example, Dussault et al. in *Mech. Dev.* (1998) vol. 70, 147-153; and Andre et al. in *EMBO J.* (1998) vol. 17, 3867-3877. Scientific investigations relating to each of retinoid-related orphan receptors RORα, RORβ, and RORγ have been described in the literature. See, for example, Hirose et al. in *Biochem. Biophys. Res. Commun.* (1994) vol. 205, 1976-1983; Giguere et al. in *Genes. Dev.* (1994) vol. 8, 538-553; Medvedev et al. in *Gene* (1996) vol. 181, 199-206; Ortiz et al. in *Mol. Endocrinol.* (1995) vol. 9, 1679-1691; and A. M. Jetten in *Curr Drug Targets Inflamm Allergy* (2004) vol. 3, 395-412). Continuing research in this field is spurred by the promise of developing new therapeutic agents to treat medical disorders associated with retinoid-related orphan receptor activity.

RORγ has been reported to be expressed in high concentration in various tissues, such as thymus, kidney, liver, muscle, and certain fat tissue. See, for example, Hirose et al. in *Biochem. Biophys. Res. Commun.* (1994) vol. 205, 1976-1983; Medvedev et al. in *Gene* (1996) vol. 181, 199-206; Ortiz et al. in *Mol. Endocrinol.* (1995) vol. 9, 1679-1691; and He et al. in *Immunity* (1998) vol. 9, 797-806. Two isoforms of RORγ have been identified and are referred to as γ1 and γ2 (also referred to as RORγt). See, for example, He et al. in *Immunity* (1998) vol. 9, 797-806. Expression of the γ2 isoform has been reported to appear in, for example, double-positive thymocytes. See, for example, He et al. in *Immunity* (1998) vol. 9, 797-806; and Villey et al. in *Eur. J. Immunol.* (1999) vol. 29, 4072-4080. RORγt plays a critical role in regulating differentiation of Th17 cells, a subset of T helper lymphocytes. See, for example, Ivanov et al. in *Cell* (2006) vol. 126, 1121-1133. Th17 cells are important for recruiting tumor-killing cytotoxic CD8+ T cells and natural killer cells into the tumor microenvironment. The level of Th17 cells correlated positively with patient survival or slower disease progression in certain cancers. See, for example, Kryczek et al. in *Blood* (2009) vol 114, 1141-1149; and Sfanos et al. in *Clinical Cancer Research* (2008) vol 14, 3254-3261. Compounds capable of enhancing RORγt activity are thus contemplated to provide a therapeutic benefit in the treatment of cancer.

Cancer continues to be a significant health problem despite the substantial research efforts and scientific advances reported in the literature for treating this disease. Some of the most frequently diagnosed cancers include prostate cancer, breast cancer, and lung cancer. Prostate cancer is the most common form of cancer in men. Breast cancer remains a leading cause of death in women. Current treatment options for these cancers are not effective for all patients and/or can have substantial adverse side effects.

Accordingly, a need exists for improved treatments for cancer. The present invention addresses this need and provides other related advantages.

SUMMARY

The invention provides tetrahydroquinoline sulfonamide compounds, tetrahydronaphthalene sulfonyl compounds, and related compounds (collectively "tetrahydroquinolinyl and related compounds"), pharmaceutical compositions, methods of promoting RORγ activity and/or increasing the amount of IL-17 in a subject, and methods of treating various medical disorders using such compounds. In particular, one aspect of the invention provides a collection of tetrahydroquinoline sulfonamide and related compounds, such as a compound represented by Formula I:

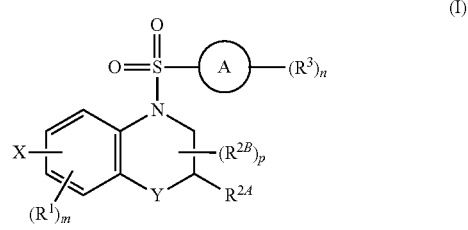

or a pharmaceutically acceptable salt thereof; wherein the variables are as defined in the detailed description. Another aspect of the invention provides a collection of tetrahydronaphthalene sulfonyl compounds, such as a compound represented by Formula II:

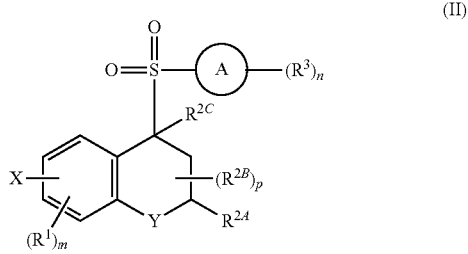

or a pharmaceutically acceptable salt thereof; wherein the variables are as defined in the detailed description. Further description of additional collections of tetrahydroquinoline sulfonamide, tetrahydronaphthalene sulfonyl, and related compounds are described in the detailed description.

Another aspect of the invention provides a method of treating a subject suffering from a medical disorder. The method comprises administering to the subject a therapeutically effective amount of one or more tetrahydroquinolinyl or related compounds described herein, e.g., a compound of Formula I, I-1, I-A, I-B, II, II-1, II-A, or II-B. A large number of disorders can be treated using the tetrahydroquinolinyl and related compounds described herein. For example, the compounds described herein can be used to treat cancer, a bacterial infection, a fungal infection, or an immune deficiency disorder.

Another aspect of the invention provides a method of promoting the activity of RORγ. The method comprises exposing a RORγ to an effective amount of one or more tetrahydroquinolinyl or related compounds described herein, e.g., a compound of Formula I, I-1, I-A, I-B, II, II-1, II-A, or II-B, or a pharmaceutical composition described herein.

Another aspect of the invention provides a method of increasing the amount of IL-17 in a subject. The method comprises administering to a subject an effective amount of one or more tetrahydroquinolinyl or related compounds described herein, e.g., a compound of Formula I, I-1, I-A, I-B, II, II-1, II-A, or II-B, or a pharmaceutical composition described herein, to increase the amount of IL-17 in the subject.

DETAILED DESCRIPTION

The invention provides tetrahydroquinolinyl and related compounds, pharmaceutical compositions, methods of promoting RORγ activity and/or increasing the amount of IL-17 in a subject, and therapeutic uses of the tetrahydroquinolinyl and related compounds. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "—O-alkyl" etc.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. Exemplary alkylene groups include —CH$_2$—, —CH$_2$CH$_2$—, and —CH$_2$C(H)(CH$_3$)CH$_2$—.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl.

The term "cycloalkylene" refers to a diradical of a cycloalkyl group. Exemplary cycloalkylene groups include

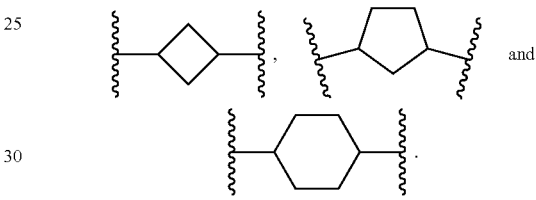

The term "haloalkyl" refers to an alkyl group that is substituted with at least one halogen. Exemplary haloalkyl groups include —CH$_2$F, —CHF$_2$, —CF$_3$, —CH$_2$CF$_3$, —CF$_2$CF$_3$, and the like.

The term "hydroxyalkyl" refers to an alkyl group that is substituted with at least one hydroxyl. Exemplary hydroxyalkyl groups include —CH$_2$CH$_2$OH, —C(H)(OH)CH$_3$, —CH$_2$C(H)(OH)CH$_2$CH$_2$OH, and the like.

The term "aralkyl" refers to an alkyl group substituted with an aryl group. Exemplary aralkyl groups include

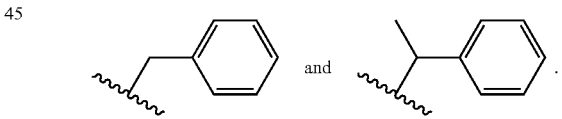

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group.

The term "phenylene" refers to a multivalent radical (e.g., a divalent or trivalent radical) of benzene. To illustrate, a divalent valent radical of benzene is illustrated by the formula

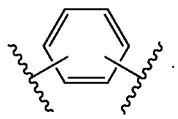

The term "partially unsaturated bicyclic carbocyclyl" refers to a bicyclic carbocyclic group that comprises at least one carbon-carbon double bond between ring carbon atoms and at least one ring in the bicyclic carbocyclic group is not aromatic. Representative examples of a partially unsaturated bicyclic carbocyclyl include, for example:

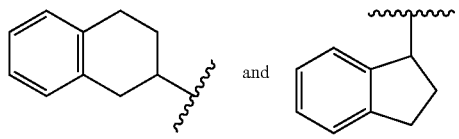

The term "heteroaryl" is art-recognized and refers to aromatic groups that include at least one ring heteroatom. In certain instances, a heteroaryl group contains 1, 2, 3, or 4 ring heteroatoms (e.g., O, N, and S). Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more ring atoms are common to two adjoining rings (the rings are "fused rings") wherein all of the fused rings are heteroaromatic, e.g., in a naphthyridinyl group. In certain embodiments, the heteroaryl is a 5-6 membered monocylic ring or a 9-10 membered bicyclic ring.

The term "heteroarylene" refers to a multi-valent (e.g., di-valent or trivalent) aromatic group that comprises at least one ring heteroatom. An exemplary "heteroarylene" is pyridinylene, which is a multi-valent radical of pyridine. For example, a divalent radical of pyridine is illustrated by the formula

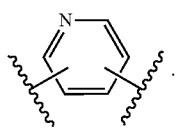

In certain embodiments, the "heteroarylene" is a divalant, 5-6 membered heteroaromatic group containing 1, 2, or 3 ring heteroatoms (e.g., O, N, or S).

The terms ortho, meta, and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-7 membered ring that, unless specified otherwise, is substituted or unsubstituted.

The term "heterocycloalkyl" refers to a saturated heterocyclyl group having, for example, 3-7 ring atoms (e.g., O, N, or S).

The term "heterocycloalkylene" refers to a multi-valent (e.g., di-valent or trivalent) saturated heterocyclyl group having, for example, 3-7 ring atoms. An exemplary "heterocycloalkylene" is piperidinylene, which is a multi-valent radical of piperidine. In certain embodiments, the "heterocycloalkylene" is a divalant, 5-6 membered saturated heterocyclyl containing 1 or 2 ring heteroatoms (e.g., O, N, or S).

The term "partially unsaturated bicyclic heterocyclyl" refers to a bicyclic heterocyclic group that comprises at least one double bond between ring atoms and at least one ring in the bicyclic heterocyclic group is not aromatic. Representative examples of a partially unsaturated bicyclic heterocyclyl include, for example:

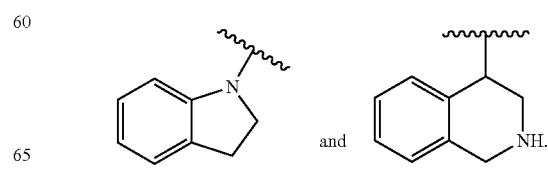

The term "partially unsaturated bicyclic oxo-heterocyclyl" refers to a bicyclic heterocyclic group that comprises at least one double bond between ring atoms, one oxo substituent, and at least one ring in the bicyclic heterocyclic group is not aromatic. Representative examples of a partially unsaturated bicyclic oxo-heterocyclyl include, for example:

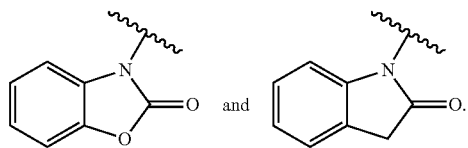 [SMILES: *n1c(=O)oc2ccccc21 ; "and" ; *N1C(=O)Cc2ccccc21]

The terms "amine" and "amino" are art-recognized and refer to both unsubstituted and substituted amines, e.g., a moiety that may be represented by the general formulas:

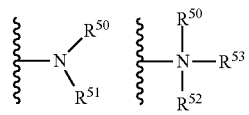

wherein $R^{50}$, $R^{51}$, $R^{52}$ and $R^{53}$ each independently represent a hydrogen, an alkyl, an alkenyl, —$(CH_2)_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —$(CH_2)_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O— alkenyl, —O-alkynyl, and —O—$(CH_2)_m$—$R^{61}$, where m and $R^{61}$ are described above.

The term "oxo" is art-recognized and refers to a "=O" substituent. For example, a cyclopentane substituted with an oxo group is cyclopentanone.

The symbol " ⌇ " indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound' or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Nonlimiting examples of suitable solvates include ethanolates, methanolates, and the like. "Hydrate" is a solvate wherein the solvent molecule is $H_2O$.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$EC_{50}$" is art-recognized and refers to the concentration of a compound that is required to achieve 50% of the maximum possible activation of the target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quartemized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

The abbreviation "THF" is art-recognized and refers to tetrahydrofuran. The abbreviation "DCM" is art-recognized and refers to dichloromethane. The abbreviation "DMF" is art-recognized and refers to dimethylformamide. The abbreviation "DMA" is art-recognized and refers to dimethylacetamide. The abbreviation "EDTA" is art-recognized and refers to ethylenediaminetetraacetic acid. The abbreviation "TFA" is art-recognized and refers to trifluoroacetic acid.

As a general matter, compositions specifying a percentage are by weight unless otherwise specified.

I. Tetrahydroquinolinyl and Related Compounds

The invention provides tetrahydroquinoline sulfonamide compounds, tetrahydronaphthalene sulfonyl compounds, and related compounds (collectively "tetrahydroquinolinyl and related compounds"). Exemplary compounds are described in the following sections, along with exemplary procedures for making the compounds. Additional exemplary compounds and synthetic procedures are described in the Examples.

Part I: Tetrahydroquinoline Sulfonamide and Related Compounds

One aspect of the invention provides a compound represented by Formula I:

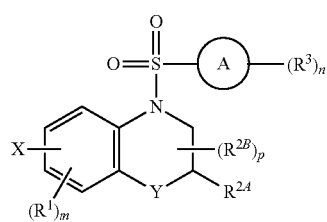

(I)

or a pharmaceutically acceptable salt thereof, wherein:

A is phenylene, 5-6 membered heteroarylene, or $C_{3-6}$ heterocycloalkylene;

$R^1$ represents independently for each occurrence halogen, $C_{1-6}$ alkyl, $C_{1-6}$ haloalkyl, or $C_{3-6}$ cycloalkyl;

$R^{2A}$ is one of the following:
(i) hydrogen, $C_{1-6}$ alkyl, $C_{1-3}$ haloalkyl, $C_{3-6}$ cycloalkyl, —($C_{1-6}$ alkylene)-($C_{3-6}$ cycloalkyl), —O—($C_{1-6}$ alkylene)-$CO_2R^4$, —O—($C_{1-6}$ alkylene)-C(O)—($C_{1-6}$ alkyl), —N($R^4$)—($C_{1-6}$ alkylene)-$CO_2R^4$, or —N($R^4$)—($C_{1-6}$ alkylene)-C(O)—($C_{1-6}$ alkyl), wherein the $C_{1-6}$ alkyl, $C_{3-6}$ cycloalkyl, and $C_{1-6}$ alkylene are optionally substituted with 1 or 2 substituents independently selected from the group consisting of —$CO_2R^4$, —C(O)N($R^4$)($R^5$), —C(O)—N($R^4$)—($C_{1-4}$ alkylene)-$CO_2R^4$, —N($R^4$)C(O)$R^8$, —CN, halogen, hydroxyl, $C_{1-6}$ alkoxy, $C_{1-6}$ haloalkoxy, $C_{1-6}$ haloalkyl, —N($R^4$)($R^5$), —N($R^4$)C(O)N($R^4$)($R^5$), —N($R^4$)$CO_2R^9$, —N($R^4$)S(O)$_2R^9$, and —N($R^4$)S(O)$_2$N($R^4$)($R^5$); or
(ii) —$CO_2R^4$, —N($R^4$)C(O)$R^9$, —N($R^4$)$CO_2R^9$, —N($R^4$)C(O)N($R^4$)($R^5$), —N($R^4$)C(O)N($R^4$)(heteroaryl), —N($R^4$)S(O)$_2R^9$, —N($R^4$)($R^5$), or —OH;

$R^{2B}$ is $C_{1-6}$ alkyl, $C_{1-3}$ haloalkyl, or fluoro;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —N($R^4$)($R^8$), —O—($C_{1-6}$ hydroxyalkyl), or —O—($C_{1-6}$ alkylene)-$CO_2R^4$; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring;

$R^6$ and $R^7$ each represent independently for each occurrence hydrogen, fluoro, or $C_{1-6}$ alkyl, or $R^6$ and $R^7$ are taken together with the carbon atom to which they are attached to form a 3-6 membered carbocyclic ring; or $R^6$ and a vicinal occurrence of $R^{2B}$ are taken together to form a bond;

$R^8$ represents independently for each occurrence $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —$CO_2R^4$; or $R^8$ is —$CO_2R^4$;

$R^9$ represents independently for each occurrence $C_{1-6}$ alkyl, $C_{3-6}$ cycloalkyl, —($C_{1-6}$ alkylene)-($C_{3-6}$ cycloalkyl), $C_{1-6}$ haloalkyl, or $C_{1-6}$ hydroxyalkyl;

X is one of the following:
(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$;
(ii) —S-aralkyl, —S-heteroaralkyl, —S-phenyl, —S-heteroaryl, —S-(partially unsaturated bicyclic carbocyclyl), —S—($C_{1-6}$ alkylene)-($C_{3-6}$ cycloalkyl), or —S—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$;
(iii) —($C_{2-6}$ alkenylene)-phenyl, —($C_{2-6}$ alkenylene)-heteroaryl, —($C_{2-6}$ alkenylene)-(partially unsaturated 8-10 membered bicyclic ring containing 0-3 heteroatoms), —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), —($C_{1-6}$ alkylene)-($C_3$-$C_6$ cycloalkyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$;

(iv) —($C_{2-6}$ alkenylene)-($C_{1-6}$ alkyl), —($C_{2-6}$ alkenylene)-($C_{3-6}$ cycloalkyl), or

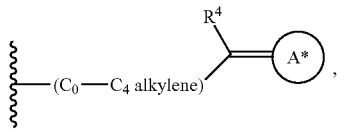

each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —CO$_2R^4$, and —SO$_2R^9$, wherein A* is a 5-8 membered, partially saturated carbocyclic or heterocyclic ring; or (v) —($C_{1-6}$ alkylene)-$Z^1$ or —($C_{2-6}$ alkenylene)-$Z^1$, wherein $Z^1$ is —O-aralkyl, —O-heteroaralkyl, —O— phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$ alkylene)-($C_{3-6}$ cycloalkyl), or —N($R^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$;

Y is —C($R^6$)($R'$)—, —O—, —C(O)—, or —S(O)$_p$—;

m and p each represent independently for each occurrence 0, 1, or 2; and n is 1, 2, or 3.

In certain embodiments, A is phenylene or 5-6 membered heteroarylene.

In certain embodiments, $R^1$ represents independently for each occurrence halogen or $C_{1-6}$ alkyl. In certain other embodiments, $R^1$ is fluoro, chloro, methyl, or trifluoromethyl.

In certain embodiments, $R^{2A}$ is $C_{1-6}$ alkyl substituted with 1 or 2 substituents independently selected from the group consisting of —CO$_2R^4$, —C(O)N($R^4$)($R^5$), —C(O)—N($R^4$)—($C_{1-4}$ alkylene)-CO$_2R^4$, —N($R^4$)C(O)$R^8$, —CN, halogen, hydroxyl, $C_{1-6}$ alkoxy, $C_{1-6}$ haloalkoxy, $C_{1-6}$ haloalkyl, —N($R^4$)($R^5$), —N($R^4$)C(O)N($R^4$)($R^5$), —N($R^4$)CO$_2R^9$, —N($R^4$)S(O)$_2R^9$, and —N($R^4$)S(O)$_2$N($R^4$)($R^5$). In certain other embodiments, $R^{2A}$ is $C_{1-6}$ alkyl substituted by —C(O)N($R^4$)($R^5$), where $R^4$ and $R^5$ are taken together with the nitrogen atom to which they are attached to form a 3-8 membered heterocyclic ring substituted with 1, 2, or 3 substituents independently selected from the group consisting of $C_{1-6}$ haloalkyl, $C_{1-6}$ alkyl, and —CO$_2R^{10}$, where $R^{10}$ is hydrogen or $C_{1-6}$ alkyl.

In certain embodiments, $R^3$ represents independently for each occurrence hydrogen, $C_{1-6}$ haloalkyl, halogen, hydroxyl, $C_{1-6}$ alkyl, $C_{3-4}$ cycloalkyl, $C_{1-6}$ alkoxy, or $C_{1-6}$ haloalkoxy.

In certain embodiments, $R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring, wherein the heterocyclic ring is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, cyano, oxo, —CO$_2R^{10}$, —C(O)$R^9$, —SO$_2R^9$, —N($R^{10}$)C(O)$R^{12}$, and —C(O)N($R^{10}$)($R^{11}$); wherein $R^{10}$ and $R^{11}$ each represent independently for each occurrence hydrogen or $C_{1-6}$ alkyl, or $R^{10}$ and $R^{11}$ are taken together with the carbon atom to which they are attached to form a 3-6 membered carbocyclic ring; and $R^{12}$ is $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —CO$_2R^{10}$. In certain other embodiments, $R^4$ and $R^5$ are taken together with the nitrogen atom to which they are attached to form a 3-8 membered heterocyclic ring substituted with 1, 2, or 3 substituents independently selected from the group consisting of $C_{1-6}$ haloalkyl, $C_{1-6}$ alkyl, and —CO$_2R^{10}$, where $R^{10}$ is hydrogen or $C_{1-6}$ alkyl.

In certain embodiments, X is —O-aralkyl, —O-heteroaralkyl, —O-phenyl, —O— heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$.

In certain embodiments, X is —S-aralkyl, —S-heteroaralkyl, —S-phenyl, —S— heteroaryl, —S-(partially unsaturated bicyclic carbocyclyl), —S—($C_{1-6}$ alkylene)-($C_{3-6}$ cycloalkyl), or —S—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$.

In certain embodiments, X is —($C_{2-6}$ alkenylene)-phenyl, —($C_{2-6}$ alkenylene)-heteroaryl, —($C_{2-6}$ alkenylene)-(partially unsaturated 8-10 membered bicyclic ring containing 0-3 heteroatoms), —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), —($C_{1-6}$ alkylene)-($C_3$-$C_6$ cycloalkyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$.

In certain embodiments, X is —($C_{2-6}$ alkenylene)-($C_{1-6}$ alkyl), —($C_{2-6}$ alkenylene)-($C_{3-6}$ cycloalkyl), or

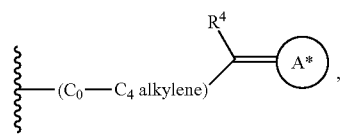

each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2$$R^9$, wherein A* is a 5-8 membered, partially saturated carbocyclic or heterocyclic ring.

In certain embodiments, X is —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$ alkylene)-($C_{3-6}$ cycloalkyl), or —N($R^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2$$R^9$.

In certain embodiments, X is attached at the meta or para position on the phenyl group relative to variable Y. In certain embodiments, X is attached on the phenyl at the position located para to group Y.

In certain embodiments, Y is —C($R^6$)($R^7$)—. In certain other embodiments, Y is —O—. In yet other embodiments, Y is —S(O)$_p$—.

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

Another aspect of the invention provides a compound represented by Formula I-1:

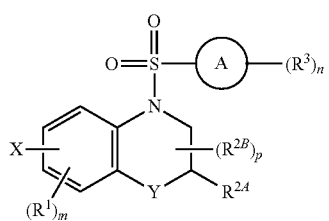

(I-1)

or a pharmaceutically acceptable salt thereof, wherein:

A is phenylene, 5-6 membered heteroarylene, or $C_{3-6}$ heterocycloalkylene;

$R^1$ represents independently for each occurrence halogen, $C_{1-6}$ alkyl, $C_{1-6}$ haloalkyl, or $C_{3-6}$ cycloalkyl;

$R^{2A}$ is hydrogen, $C_{1-6}$ alkyl, $C_{3-6}$ cycloalkyl, —O—($C_{1-6}$ alkylene)-CO$_2$$R^4$, —O—($C_{1-6}$ alkylene)-C(O)—($C_{1-6}$ alkyl), —N($R^4$)—($C_{1-6}$ alkylene)-CO$_2$$R^4$, or —N($R^4$)—($C_{1-6}$ alkylene)-C(O)—($C_{1-6}$ alkyl), wherein the $C_{1-6}$ alkyl, $C_{3-6}$ cycloalkyl, and $C_{1-6}$ alkylene are optionally substituted with 1 or 2 substituents independently selected from the group consisting of —CO$_2$$R^4$, —N($R^4$)C(O)($C_{1-6}$ alkyl), —CN, halogen, hydroxyl, $C_{1-6}$ alkoxy, $C_{1-6}$ haloalkoxy, $C_{1-6}$ haloalkyl, —N($R^4$)($R^5$), —N($R^4$)C(O)N($R^4$)($R^5$), —N($R^4$)CO$_2$—($C_{1-6}$ alkyl), —N($R^4$)S(O)$_2$—($C_{1-6}$ alkyl), and —N($R^4$)S(O)$_2$N($R^4$)($R^5$); or $R^{2A}$ is —CO$_2$$R^4$ or —N($R^4$)C(O)($C_{1-6}$ alkyl);

$R^{2B}$ is $C_{1-6}$ alkyl or $C_{1-3}$ haloalkyl;

$R^3$ represents independently for each occurrence hydrogen, $C_{1-6}$ haloalkyl, halogen, hydroxyl, $C_{1-6}$ alkyl, $C_{1-6}$ alkoxy, $C_{1-6}$ haloalkoxy, or —O—($C_{1-6}$ alkylene)-OH; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and $R^{2A}$ are taken together to form a bond;

X is one of the following:

(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

(ii) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano; or (iii) —($C_{1-6}$ alkylene)-$Z^1$ or —($C_{2-6}$ alkenylene)-$Z^1$, wherein $Z^1$ is —O-aralkyl, —O-heteroaralkyl, —O— phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$ alkylene)-($C_{3-6}$ cycloalkyl), or —N($R^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

Y is —C($R^6$)($R^7$)—, —O—, —C(O)—, or —S(O)$_p$—;

m and p each represent independently for each occurrence 0, 1, or 2; and n is 1, 2, or 3.

In certain embodiments, A is phenylene or 5-6 membered heteroarylene.

In certain embodiments, $R^1$ represents independently for each occurrence halogen or $C_{1-6}$ alkyl.

In certain embodiments, X is attached at the meta or para position on the phenyl group relative to variable Y. In certain embodiments, X is attached on the phenyl at the position located para to group Y.

In certain embodiments, Y is —C($R^6$)($R^7$)—. In certain other embodiments, Y is —O—. In yet other embodiments, Y is —S(O)$_p$—.

The definitions of variables in Formula I-1 above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

Another aspect of the invention provides a compound represented by Formula I-2:

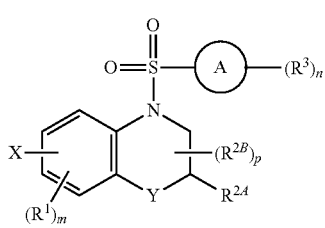

(I-2)

or a pharmaceutically acceptable salt thereof, wherein:

A is phenylene, 5-6 membered heteroarylene, or $C_{3-6}$ heterocycloalkylene;

$R^1$ represents independently for each occurrence halogen, $C_{1-6}$ alkyl, $C_{1-6}$ haloalkyl, or $C_{3-6}$ cycloalkyl;

$R^{2A}$ is hydrogen, $C_{1-6}$ alkyl, $C_{3-6}$ cycloalkyl, —O—($C_{1-6}$ alkylene)-$CO_2R^4$, —O—($C_{1-6}$ alkylene)-C(O)—($C_{1-6}$ alkyl), —N($R^4$)—($C_{1-6}$ alkylene)-$CO_2R^4$, or —N($R^4$)— ($C_{1-6}$ alkylene)-C(O)—($C_{1-6}$ alkyl), wherein the $C_{1-6}$ alkyl, $C_{3-6}$ cycloalkyl, and $C_{1-6}$ alkylene are optionally substituted with 1 or 2 substituents independently selected from the group consisting of —$CO_2R^4$, —N($R^4$)C(O)($C_{1-6}$ alkyl), —CN, halogen, hydroxyl, $C_{1-6}$ alkoxy, $C_{1-6}$ haloalkoxy, $C_{1-6}$ haloalkyl, —N($R^4$)($R^5$), —N($R^4$)C(O)N($R^4$)($R^5$), —N($R^4$)$CO_2$—($C_{1-6}$ alkyl), —N($R^4$)S(O)$_2$—($C_{1-6}$ alkyl), and —N($R^4$)S(O)$_2$N($R^4$)($R^5$); or $R^{2A}$ is —$CO_2R^4$ or —N($R^4$)C(O)($C_{1-6}$ alkyl);

$R^{2B}$ is $C_{1-6}$ alkyl or $C_{1-3}$ haloalkyl;

$R^3$ represents independently for each occurrence hydrogen, $C_{1-6}$ haloalkyl, halogen, hydroxyl, $C_{1-6}$ alkyl, $C_{1-6}$ alkoxy, $C_{1-6}$ haloalkoxy, or —O—($C_{1-6}$ alkylene)-OH; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and a vicinal occurrence of $R^{2B}$ are taken together to form a bond;

X is one of the following:

(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)— ($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

(ii) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano; or (iii) —($C_{1-6}$ alkylene)-$Z^1$ or —($C_{2-6}$ alkenylene)-$Z^1$, wherein $Z^1$ is —O-aralkyl, —O-heteroaralkyl, —O— phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$ alkylene)-($C_{3-6}$ cycloalkyl), or —N($R^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

Y is —C($R^6$)($R^7$)—, —O—, —C(O)—, or —S(O)$_p$—;

m and p each represent independently for each occurrence 0, 1, or 2; and n is 1, 2, or 3.

In certain embodiments, A is phenylene or 5-6 membered heteroarylene.

In certain embodiments, $R^1$ represents independently for each occurrence halogen or $C_{1-6}$ alkyl.

In certain embodiments, Y is —C($R^6$)($R^7$)—. In certain other embodiments, Y is —O—. In yet other embodiments, Y is —S(O)$_p$—.

The definitions of variables in Formula I-2 above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

Another aspect of the invention provides a compound represented by Formula I-A:

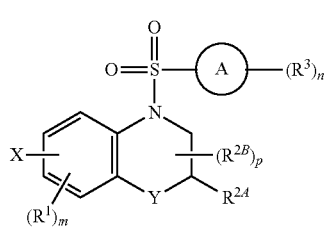

(I-A)

or a pharmaceutically acceptable salt thereof, wherein:

A is phenylene or a 5-6 membered heteroarylene;

$R^1$ represents independently for each occurrence halogen, $C_{1-6}$ alkyl, or $C_{3-6}$ cycloalkyl;

$R^{2A}$ is hydrogen, $C_{1-6}$ alkyl or $C_{3-6}$ cycloalkyl, wherein the $C_{1-6}$ alkyl or $C_{3-6}$ cycloalkyl are optionally substituted with 1 or 2 substituents independently selected from the group consisting of —$CO_2R^4$, —$N(R^4)C(O)(C_{1-6}$ alkyl), —CN, halogen, hydroxyl, $C_{1-6}$ alkoxy, $C_{1-6}$ haloalkoxy, $C_{1-6}$ haloalkyl, and —$N(R^4)(R^5)$; or $R^{2A}$ is —$CO_2R^4$ or —$N(R^4)C(O)(C_{1-6}$ alkyl);

$R^{2B}$ is $C_{1-6}$ alkyl or $C_{1-3}$ haloalkyl;

$R^3$ represents independently for each occurrence hydrogen, $C_{1-6}$ haloalkyl, halogen, hydroxyl, $C_{1-6}$ alkyl, $C_{1-6}$ alkoxy, $C_{1-6}$ haloalkoxy, or —O—$(C_{1-6}$ alkylene)-OH; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and $R^{2A}$ are taken together to form a bond;

X is one of the following:
(i) —O-aralkyl, —O-heteroaralkyl, —O-phenyl, —O-heteroaryl, —O-(partially unsaturated bicyclic carbocyclyl), —O—$(C_{1-6}$ alkylene)-$(C_{3-6}$ cycloalkyl), —$N(R^4)$-aralkyl, —$N(R^4)$-phenyl, —$N(R^4)$-(partially unsaturated bicyclic carbocyclyl), or —$N(R^4)$—$(C_{1-6}$ alkylene)-$(C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;
(ii) —$(C_{2-6}$ alkenylene)-phenyl, —$(C_{2-6}$ alkenylene)-heteroaryl, —$(C_{1-6}$ alkylene)-phenyl, —$(C_{1-6}$ alkylene)-heteroaryl, —$(C_{1-6}$ alkylene)-(partially unsaturated bicyclic heterocyclyl), —$(C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy; or
(iii) —$(C_{1-6}$ alkylene)-$Z^1$ or —$(C_{2-6}$ alkenylene)-$Z^1$, wherein $Z^1$ is —O-aralkyl, —O-heteroaralkyl, —O— phenyl, —O-heteroaryl, —O-(partially unsaturated carbocyclyl), —O—$(C_{1-6}$ alkylene)-$(C_{3-6}$ cycloalkyl), —O—$(C_{3-6}$ cycloalkyl), —$N(R^4)$-aralkyl, —$N(R^4)$-phenyl, —$N(R^4)$-(partially unsaturated bicyclic carbocyclyl), or —$N(R^4)$—$(C_{1-6}$ alkylene)-$(C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

Y is —$C(R^6)(R^7)$—, —O—, or —C(O)—;

m and p are independently 0, 1, or 2; and n is 1, 2, or 3.

In certain embodiments, A is phenylene. In certain other embodiments, A is a 5-6 membered heteroarylene. In yet other embodiments, -A-$(R^3)_n$ is one of the following:

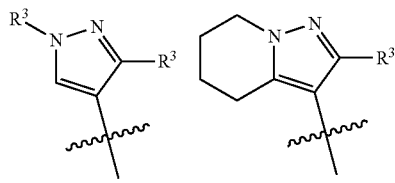

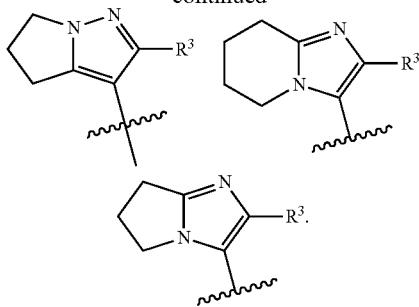

In yet other embodiments, -A-$(R^3)_n$ is

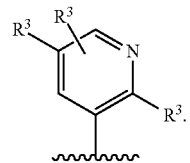

In certain embodiments, $R^1$ represents independently for each occurrence halogen, methyl, or cyclopropyl.

In certain embodiments, $R^{2A}$ is $C_{1-6}$ alkyl optionally substituted with 1 or 2 substituents independently selected from the group consisting of —$CO_2R^4$, —$N(R^4)C(O)(C_{1-6}$ alkyl), —CN, halogen, hydroxyl, $C_{1-6}$ alkoxy, $C_{1-6}$ haloalkoxy, and —$N(R^4)(R^5)$. In certain other embodiments, $R^{2A}$ is $C_{1-6}$ alkyl substituted with 1 or 2 substituents independently selected from the group consisting of —$CO_2R^4$, —$N(R^4)C(O)(C_{1-6}$ alkyl), —CN, hydroxyl, and $C_{1-6}$ alkoxy. In certain other embodiments, $R^{2A}$ is —$CO_2R^4$.

In certain embodiments, $R^{2B}$ is $C_{1-6}$ alkyl. In certain embodiments, $R^{2B}$ is methyl.

In certain embodiments, n is 1. In certain other embodiments, n is 1 or 2.

In certain embodiments, $R^3$ represents independently for each occurrence $C_{1-6}$ haloalkyl, halogen, $C_{1-6}$ alkyl, $C_{1-6}$ alkoxy, or —O—$(C_{1-6}$ alkylene)-OH. In certain other embodiments, $R^3$ is trifluoromethyl, fluoro, chloro, or methoxy. In certain other embodiments, $R^3$ is trifluoromethyl.

In certain embodiments, $R^4$ and $R^5$ each represent independently for each occurrence hydrogen or $C_{1-6}$ alkyl.

In certain embodiments, X is —O-aralkyl, —O-heteroaralkyl, —O-phenyl, —O— heteroaryl, —O-(partially unsaturated bicyclic carbocyclyl), —O—$(C_{1-6}$ alkylene)-$(C_{3-6}$ cycloalkyl), —$N(R^4)$-aralkyl, —$N(R^4)$-phenyl, —$N(R^4)$-(partially unsaturated bicyclic carbocyclyl), or —$N(R^4)$—$(C_{1-6}$ alkylene)-$(C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain other embodiments, X is —O—aralkyl, —O-phenyl, —O-(partially unsaturated bicyclic carbocyclyl), —O—$(C_{1-6}$ alkylene)-$(C_{3-6}$ cycloalkyl), —$N(R^4)$-aralkyl, —$N(R^4)$-phenyl, —$N(R^4)$-(partially unsaturated bicyclic carbocyclyl), or —$N(R^4)$—$(C_{1-6}$ alkylene)-$(C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain other embodiments, X is —O— aralkyl or —$N(R^4)$-aralkyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain other embodiments, X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy, where at least one substituent is present at the ortho position on the phenyl group in variable X. In certain other embodiments, X is —O— benzyl or —N($R^4$)-benzyl, each of which is substituted with 1 or 2 substituents independently selected from the group consisting of chloro, bromo, and fluoro.

In certain embodiments, X is —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain other embodiments, X is —($C_{2-6}$ alkenylene)-phenyl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain other embodiments, X is —($C_{2-6}$ alkenylene)-phenyl, —($C_{1-6}$ alkylene)-phenyl, or —($C_{1-6}$ alkylene)-heteroaryl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

In certain embodiments, X is —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain other embodiments, X is —($C_{1-6}$ alkylene)-$Z^1$, wherein $Z^1$ is —O-aralkyl, —O-phenyl, —O-(partially unsaturated bicyclic carbocyclyl), —O—($C_{1-6}$alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

In certain embodiments, Y is —C($R^6$)($R^7$)—.

In certain embodiments, $R^6$ and $R^7$ are independently hydrogen or methyl.

In certain embodiments, Y is —C($R^6$)($R^7$)—, $R^6$ and $R^7$ are independently hydrogen or methyl, and X is attached at the 7-position of the 1,2,3,4-tetrahydroquinolinyl ring.

In certain embodiments, Y is —O—.

In certain embodiments, X is attached at the meta or para position on the phenyl group relative to variable Y. In certain embodiments, X is attached on the phenyl at the position located para to group Y. In certain embodiments, X is attached at the 6-position of the 3,4-dihydro-2H-benzo[b][1,4]oxazinyl ring.

In certain embodiments, m is 0 or 1. In certain other embodiments, m is 1.

In certain embodiments, p is 0. In certain other embodiments, p is 1.

The definitions of variables in Formula I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

Another aspect of the invention provides a compound represented by Formula I-B:

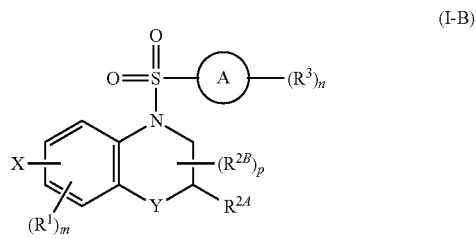

(I-B)

or a pharmaceutically acceptable salt thereof, wherein:

A is phenylene;

$R^1$ represents independently for each occurrence halogen, methyl, ethyl, or cyclopropyl;

$R^{2A}$ is $C_{1-6}$ alkyl substituted with 1 or 2 substituents independently selected from the group consisting of —$CO_2R^4$, —N($R^4$)C(O)($C_{1-6}$ alkyl), —CN, halogen, hydroxyl, $C_{1-6}$ alkoxy, $C_{1-6}$ haloalkoxy, $C_{1-6}$ haloalkyl, and —N($R^4$)($R^5$);

$R^{2B}$ is methyl or ethyl;

$R^3$ represents independently for each occurrence $C_{1-3}$ haloalkyl, halogen, and $C_{1-3}$ alkyl;

$R^4$ and $R^5$ each represent independently for each occurrence hydrogen or methyl;

$R^6$ and $R^7$ each represent independently for each occurrence hydrogen, methyl, or ethyl;

X is attached at the meta or para position on the phenyl group relative to variable Y, and X is one of the following:
(i) —O—($C_1$-6 alkylene)-phenyl, —O-(partially unsaturated bicyclic carbocyclyl), or —O—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, and $C_{1-6}$ alkoxy;
(ii) —($C_{2-6}$ alkenylene)-phenyl or —($C_{1-6}$ alkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy; or
(iii) —($C_{1-6}$ alkylene)-$Z^1$, wherein $Z^1$ is —O-aralkyl, —O-phenyl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, and $C_{1-6}$ alkoxy;

Y is —C($R^6$)(R')— or —O—;

m and p are independently 0 or 1; and n is 1 or 2.

In certain embodiments, X is —O—($C_{1-6}$ alkylene)-phenyl optionally substituted with 1 or 2 substituents independently selected from the group consisting of halogen, $C_{1-6}$ haloalkyl, and $C_{1-6}$ alkyl.

In certain embodiments, Y is —C($R^6$)($R^7$)—. In certain embodiments, Y is O.

In certain embodiments, X is —O—($C_{1-6}$ alkylene)-phenyl optionally substituted with 1 or 2 substituents independently selected from the group consisting of halogen, $C_{1-6}$ haloalkyl, and $C_{1-6}$ alkyl; Y is O; and X is attached at the para position on the phenyl group relative to variable Y.

The definitions of variables in Formula I-B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

Another aspect of the invention provides a compound represented by Formula I-C:

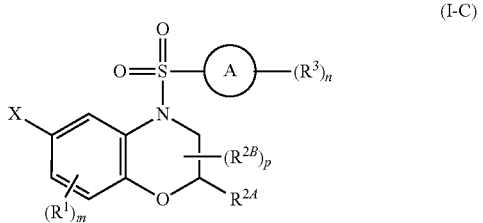

(I-C)

or a pharmaceutically acceptable salt thereof, wherein:

A is phenylene or pyridinylene;

$R^1$ represents independently for each occurrence halogen, methyl, ethyl, or cyclopropyl;

$R^{2A}$ is $C_{1-6}$ alkyl substituted with 1 or 2 substituents independently selected from the group consisting of —$CO_2R^4$, —C(O)N($R^4$)($R^5$), —N($R^4$)C(O)$R^8$, halogen, hydroxyl, $C_{1-6}$ alkoxy, $C_{1-6}$ haloalkoxy, and —N($R^4$)($R^5$);

$R^{2B}$ is methyl or ethyl;

$R^3$ represents independently for each occurrence $C_{1-3}$ haloalkyl, halogen, $C_{1-3}$ alkyl, or —O—($C_{1-6}$ hydroxyalkyl);

$R^4$ and $R^5$ each represent independently for each occurrence hydrogen or methyl; or an occurrence of $R^4$ and $R^5$ attached to the same nitrogen atom are taken together with the nitrogen atom to which they are attached to form a 3-7 membered heterocyclic ring;

$R^8$ represents independently for each occurrence $C_{1-6}$ alkyl, $C_{3-6}$ cycloalkyl, or —($C_{1-6}$ alkylene)-($C_{3-6}$ cycloalkyl), each of which is optionally substituted with 1, 2, or 3 substituents independently selected from the group consisting of halogen, hydroxyl, and —$CO_2R^4$;

X is —($C_{2-6}$ alkenylene)-phenyl substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

m and p are independently 0 or 1; and n is 1 or 2.

In certain embodiments, A is phenylene. In certain other embodiments, A is pyridinylene.

In certain embodiments, $R^1$ is fluoro or methyl.

In certain embodiments, $R^{2A}$ is $C_{1-6}$ alkyl substituted with —$CO_2R^4$. In certain other embodiments, $R^{2A}$ is $C_{1-6}$ alkyl substituted with —C(O)N($R^4$)($R^5$). In certain other embodiments, $R^{2A}$ is $C_{1-6}$ alkyl substituted by —C(O)N($R^4$)($R^5$), where $R^4$ and $R^5$ are taken together with the nitrogen atom to which they are attached to form a 3-8 membered heterocyclic ring substituted with 1, 2, or 3 substituents independently selected from the group consisting of $C_{1-6}$ haloalkyl, $C_{1-6}$ alkyl, and —$CO_2R^{10}$, where $R^{10}$ is hydrogen or $C_{1-6}$ alkyl.

In certain embodiments, $R^3$ represents independently for each occurrence trifluoromethyl, halogen, or —O—($C_{1-6}$ hydroxyalkyl).

In certain embodiments, $R^4$ and $R^5$ are taken together with the nitrogen atom to which they are attached to form a 3-7 membered heterocyclic ring. In certain other embodiments, $R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring, wherein the heterocyclic ring is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, cyano, oxo, —$CO_2R^{10}$, —C(O)$R^9$, —$SO_2R^9$, —N($R^{10}$)C(O)$R^{12}$, and —C(O)N($R^{10}$)($R^{11}$); wherein $R^{10}$ and $R^{11}$ each represent independently for each occurrence hydrogen or $C_{1-6}$ alkyl, or $R^{10}$ and $R^{11}$ are taken together with the carbon atom to which they are attached to form a 3-6 membered carbocyclic ring; and $R^{12}$ is $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —$CO_2R^{10}$. In certain other embodiments, $R^4$ and $R^5$ are taken together with the nitrogen atom to which they are attached to form a 3-8 membered heterocyclic ring substituted with 1, 2, or 3 substituents independently selected from the group consisting of $C_{1-6}$ haloalkyl, $C_{1-6}$ alkyl, and —$CO_2R^{10}$, where $R^{10}$ is hydrogen or $C_{1-6}$ alkyl.

In certain embodiments, $R^8$ is $C_{1-6}$ alkyl.

In certain embodiments, X is —($C_{2-4}$ alkenylene)-phenyl substituted with 1, 2, or 3 substituents independently selected from the group consisting of halogen and $C_{1-6}$ haloalkyl. In certain embodiments, X is —($C_{2-4}$ alkenylene)-phenyl substituted with 1, 2, or 3 substituents independently selected from the group consisting of chloro, fluoro, and trifluoromethyl. In certain embodiments, X is —($C_{2-4}$ alkenylene)-phenyl substituted with 1 or 2 substituents independently selected from the group consisting of chloro, fluoro, and trifluoromethyl, and said substituents are located at the ortho positions of the phenyl group.

In certain embodiments, m and p are independently 0. In certain embodiments, n is 1.

In certain embodiments, the compound is further selected from a solvate of Formula I-C or a pharmaceutically acceptable salt thereof.

The definitions of variables in Formula I-C above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

Another aspect of the invention provides a compound represented by Formula I-D:

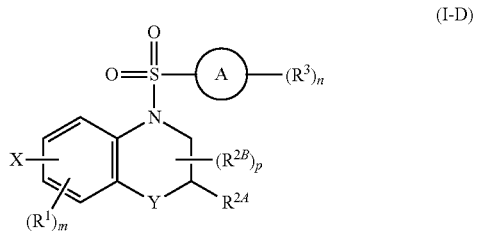

(I-D)

or a pharmaceutically acceptable salt thereof; wherein:

A is phenylene or 5-6 membered heteroarylene;

$R^1$ represents independently for each occurrence halogen, $C_{1-6}$ alkyl, $C_{1-6}$ haloalkyl, or $C_{3-6}$ cycloalkyl;

$R^{2A}$ is $C_{1-6}$ alkyl, $C_{3-6}$ cycloalkyl, or —($C_{1-6}$ alkylene)-($C_{3-6}$ cycloalkyl), wherein the $C_{1-6}$ alkyl, $C_{3-6}$ cycloalkyl, and $C_{1-6}$ alkylene are optionally substituted with 1 or 2 substituents independently selected from the group consisting of —$CO_2R^4$, —$C(O)N(R^4)(R^5)$, —$C(O)$—$N(R^4)$—($C_{1-4}$ alkylene)-$CO_2R^4$, —$N(R^4)C(O)R^8$, —CN, halogen, hydroxyl, $C_{1-6}$ alkoxy, $C_{1-6}$ haloalkoxy, $C_{1-6}$ haloalkyl, —$N(R^4)(R^5)$, —$N(R^4)CO_2R^9$, and —$N(R^4)S(O)_2R^9$; or $R^{2B}$ is $C_{1-6}$ alkyl, $C_{1-3}$ haloalkyl, or fluoro;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —$N(R^4)(R^8)$, —O—($C_{1-6}$ hydroxyalkyl), or —O—($C_{1-6}$ alkylene)-$CO_2R^4$;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring; $R^6$ and $R^7$ each represent independently for each occurrence hydrogen, fluoro, or $C_{1-6}$ alkyl, or $R^6$ and $R^7$ are taken together with the carbon atom to which they are attached to form a 3-6 membered carbocyclic ring; or $R^6$ and a vicinal occurrence of $R^{2B}$ are taken together to form a bond;

$R^8$ represents independently for each occurrence $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —$CO_2R^4$; or $R^8$ is —$CO_2R^4$;

$R^9$ represents independently for each occurrence $C_{1-6}$ alkyl, $C_{3-6}$ cycloalkyl, —($C_{1-6}$ alkylene)-($C_{3-6}$ cycloalkyl), $C_{1-6}$ haloalkyl, or $C_{1-6}$ hydroxyalkyl;

X is attached at the meta or para position on the phenyl group relative to variable Y, and X is —($C_{2-6}$ alkenylene)-phenyl, —($C_{2-6}$ alkenylene)-heteroaryl, —($C_{2-6}$ alkenylene)-(partially unsaturated 8-10 membered bicyclic ring containing 0-3 heteroatoms), —($C_1$-6 alkylene)-phenyl, —($C_1$-6 alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), —($C_{1-6}$ alkylene)-($C_3$-$C_6$ cycloalkyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$;

Y is —$C(R^6)(R^7)$— or —O—, m and p each represent independently for each occurrence 0, 1, or 2; and n is 1, 2, or 3.

In certain embodiments, A is phenylene. In certain other embodiments, A is pyridinylene.

In certain embodiments, $R^1$ is fluoro or methyl.

In certain embodiments, $R^{2A}$ is $C_{1-6}$ alkyl substituted with —$CO_2R^4$. In certain other embodiments, $R^{2A}$ is $C_{1-6}$ alkyl substituted with —$C(O)N(R^4)(R^5)$. In certain other embodiments, $R^{2A}$ is $C_{1-6}$ alkyl substituted by —$C(O)N(R^4)(R^5)$, where $R^4$ and $R^5$ are taken together with the nitrogen atom to which they are attached to form a 3-8 membered heterocyclic ring substituted with 1, 2, or 3 substituents independently selected from the group consisting of $C_{1-6}$ haloalkyl, $C_{1-6}$ alkyl, and —$CO_2R^{10}$, where $R^{10}$ is hydrogen or $C_{1-6}$ alkyl.

In certain embodiments, $R^3$ represents independently for each occurrence trifluoromethyl, halogen, or —O—($C_{1-6}$ hydroxyalkyl).

In certain embodiments, $R^4$ and $R^5$ are taken together with the nitrogen atom to which they are attached to form a 3-7 membered heterocyclic ring. In certain other embodiments, $R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring, wherein the heterocyclic ring is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, cyano, oxo, —$CO_2R^{10}$, —$C(O)R^9$, —$SO_2R^9$, —$N(R^{10})C(O)R^{12}$, and —$C(O)N(R^{10})(R^{11})$; wherein $R^{10}$ and $R^{11}$ each represent independently for each occurrence hydrogen or $C_{1-6}$ alkyl, or $R^{10}$ and $R^{11}$ are taken together with the carbon atom to which they are attached to form a 3-6 membered carbocyclic ring; and $R^{12}$ is $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —$CO_2R^{10}$. In certain other embodiments, $R^4$ and $R^5$ are taken together with the nitrogen atom to which they are attached to form a 3-8 membered heterocyclic ring substituted with 1, 2, or 3 substituents independently selected from the group consisting of $C_{1-6}$ haloalkyl, $C_{1-6}$ alkyl, and —$CO_2R^{10}$, where $R^{10}$ is hydrogen or $C_{1-6}$ alkyl.

In certain embodiments, $R^8$ is $C_{1-6}$ alkyl.

In certain embodiments, X is attached at the para position on the phenyl group relative to variable Y.

In certain embodiments, X is —($C_{2-4}$ alkenylene)-phenyl substituted with 1, 2, or 3 substituents independently selected from the group consisting of halogen and $C_{1-6}$ haloalkyl. In certain embodiments, X is —($C_{2-4}$ alkenylene)-phenyl substituted with 1, 2, or 3 substituents independently selected from the group consisting of chloro, fluoro, and trifluoromethyl. In certain embodiments, X is —($C_{2-4}$ alkenylene)-phenyl substituted with 1 or 2 substituents independently selected from the group consisting of chloro, fluoro, and trifluoromethyl, and said substituents are located at the ortho positions of the phenyl group.

In certain embodiments, m and p are independently 0. In certain embodiments, n is 1.

In certain embodiments, the compound is further selected from a solvate of Formula I-D or a pharmaceutically acceptable salt thereof.

The definitions of variables in Formula I-D above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

Another aspect of the invention provides a compound represented by Formulae III or IV:

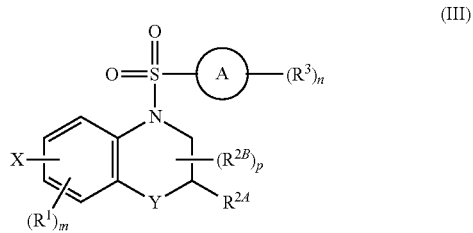

(III)

or a pharmaceutically acceptable salt thereof, wherein:

A is phenylene, 5-6 membered heteroarylene, or $C_{3-6}$ heterocycloalkylene;

$R^1$ represents independently for each occurrence halogen, $C_{1-6}$ alkyl, $C_{1-6}$ haloalkyl, or $C_{3-6}$ cycloalkyl;

$R^{2A}$ is —($C_{1-2}$ alkylene)-(2-8 membered heteroalkylene)-$CO_2R^4$, —($C_{1-6}$ alkylene)-$C(O)N(R^4)(C_{1-6}$ hydroxyalkylene)-$CO_2R^4$, or —($C_{1-6}$ alkylene)-$N(R^4)C(O)N(R^4)$—($C_{1-6}$ alkylene)-$CO_2R^4$; wherein the $C_{1-6}$ alkylene is optionally substituted with 1 or 2 substituents independently selected from the group consisting of —$CO_2R^4$, —$C(O)N(R^4)(R^5)$, —CN, halogen, hydroxyl, $C_{1-6}$ alkoxy, $C_{1-6}$ haloalkoxy, $C_{1-6}$ haloalkyl, and —$N(R^4)(R^5)$;

$R^{2B}$ is $C_{1-6}$ alkyl, $C_{1-3}$ haloalkyl, or fluoro;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —$N(R^4)(R^8)$, —O—($C_{1-6}$ hydroxyalkyl), or —O—($C_{1-6}$ alkylene)-$CO_2R^4$; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring;

$R^6$ and $R^7$ each represent independently for each occurrence hydrogen, fluoro, or $C_{1-6}$ alkyl, or $R^6$ and $R^7$ are taken together with the carbon atom to which they are attached to form a 3-6 membered carbocyclic ring; or $R^6$ and a vicinal occurrence of $R^{2B}$ are taken together to form a bond;

$R^8$ represents independently for each occurrence $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —$CO_2R^4$; or $R^8$ is —$CO_2R^4$;

$R^9$ represents independently for each occurrence $C_{1-6}$ alkyl, $C_{3-6}$ cycloalkyl, —($C_{1-6}$ alkylene)-($C_{3-6}$ cycloalkyl), $C_{1-6}$ haloalkyl, or $C_{1-6}$ hydroxyalkyl;

X is one of the following:

(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —$N(R^4)$-aralkyl, —$N(R^4)$-phenyl, —$N(R^4)$-(partially unsaturated bicyclic carbocyclyl), or —$N(R^4)$—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$;

(ii) —S-aralkyl, —S-heteroaralkyl, —S-phenyl, —S-heteroaryl, —S-(partially unsaturated bicyclic carbocyclyl), —S—($C_{1-6}$ alkylene)-($C_{3-6}$ cycloalkyl), or —S—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$;

(iii) —($C_{2-6}$ alkenylene)-phenyl, —($C_{2-6}$ alkenylene)-heteroaryl, —($C_{2-6}$ alkenylene)-(partially unsaturated 8-10 membered bicyclic ring containing 0-3 heteroatoms), —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), —($C_{1-6}$ alkylene)-($C_3$-$C_6$ cycloalkyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$;

(iv) —($C_{2-6}$ alkenylene)-($C_{1-6}$ alkyl), —($C_{2-6}$ alkenylene)-($C_{3-6}$ cycloalkyl), or

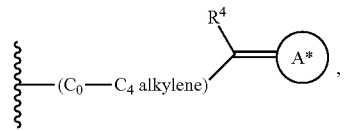

each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$, wherein A* is a 5-8 membered, partially saturated carbocyclic or heterocyclic ring; or (v) —($C_{1-6}$ alkylene)-$Z^1$ or —($C_{2-6}$ alkenylene)-$Z^1$, wherein $Z^1$ is —O-aralkyl, —O-heteroaralkyl, —O— phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —$N(R^4)$-aralkyl, —$N(R^4)$-phenyl, —$N(R^4)$-(partially unsaturated bicyclic carbocyclyl), —$N(R^4)$—($C_{1-6}$ alkylene)-($C_{3-6}$ cycloalkyl), or —$N(R^4)$—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$;

Y is —C($R^6$)($R^7$)—, —O—, —C(O)—, or —S(O)$_p$—;
m and p each represent independently for each occurrence 0, 1, or 2; and
n is 1, 2, or 3; and
Formula IV is represented by:

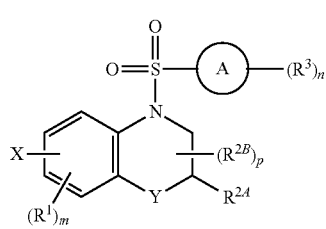

(IV)

or a pharmaceutically acceptable salt thereof, wherein:

A is phenylene, 5-6 membered heteroarylene, or $C_{3-6}$ heterocycloalkylene;

$R^1$ represents independently for each occurrence halogen, $C_{1-6}$ alkyl, $C_{1-6}$ haloalkyl, or $C_{3-6}$ cycloalkyl;

$R^{2A}$ is one of the following:
(i) hydrogen, $C_{1-6}$ alkyl, $C_{1-3}$ haloalkyl, $C_{3-6}$ cycloalkyl, —($C_{1-6}$ alkylene)-($C_{3-6}$ cycloalkyl), —O—($C_{1-6}$ alkylene)-CO$_2$R$^4$, —O—($C_{1-6}$ alkylene)-C(O)—($C_{1-6}$ alkyl), —N(R$^4$)—($C_{1-6}$ alkylene)-CO$_2$R$^4$, or —N(R$^4$)—($C_{1-6}$ alkylene)-C(O)—($C_{1-6}$ alkyl), wherein the $C_{1-6}$ alkyl, $C_{3-6}$ cycloalkyl, and $C_{1-6}$ alkylene are optionally substituted with 1 or 2 substituents independently selected from the group consisting of —CO$_2$R$^4$, —C(O)N(R$^4$)(R$^5$), —C(O)—N(R$^4$)—($C_{1-4}$ alkylene)-CO$_2$R$^4$, N(R$^4$)C(O)R$^8$, —CN, halogen, hydroxyl, $C_{1-6}$ alkoxy, $C_{1-6}$ haloalkoxy, $C_{1-6}$ haloalkyl, —N(R$^4$)(R$^5$), —N(R$^4$)C(O)N(R$^4$)(R$^5$), —N(R$^4$)CO$_2$R$^9$, —N(R$^4$)S(O)$_2$R$^9$, and —N(R$^4$)S(O)$_2$N(R$^4$)(R$^5$); or
(ii) —CO$_2$R$^4$, —N(R$^4$)C(O)R$^9$, —N(R$^4$)CO$_2$R$^9$, —N(R$^4$)C(O)N(R$^4$)(R$^5$), —N(R$^4$)C(O)N(R$^4$)(heteroaryl), —N(R$^4$)S(O)$_2$R$^9$, —N(R$^4$)(R$^5$), —OH, or —($C_{1-2}$ alkylene)-(2-8 membered heteroalkylene)-CO$_2$R$^4$;

$R^{2B}$ is $C_{1-6}$ alkyl, $C_{1-3}$ haloalkyl, or fluoro;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —N(R$^4$)(R$^8$), —O—($C_{1-6}$ hydroxyalkyl), or —O—($C_{1-6}$ alkylene)-CO$_2$R$^4$; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring;

$R^6$ and $R^7$ each represent independently for each occurrence hydrogen, fluoro, or $C_{1-6}$ alkyl, or $R^6$ and $R^7$ are taken together with the carbon atom to which they are attached to form a 3-6 membered carbocyclic ring; or $R^6$ and a vicinal occurrence of $R^{2B}$ are taken together to form a bond;

$R^8$ represents independently for each occurrence $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —CO$_2$R$^4$; or $R^8$ is —CO$_2$R$^4$;

$R^9$ represents independently for each occurrence $C_{1-6}$ alkyl, $C_{3-6}$ cycloalkyl, —($C_{1-6}$ alkylene)-($C_{3-6}$ cycloalkyl), $C_{1-6}$ haloalkyl, or $C_{1-6}$ hydroxyalkyl;

X is $C_{4-7}$ cycloalkenyl, $C_{3-7}$ cycloalkyl, or an 8-10 membered, bicyclic partially saturated carbocyclyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)R$^9$, and —SO$_2$R$^9$;

Y is —C($R^6$)($R^7$)—, —O—, —C(O)—, or —S(O)$_p$—;
m and p each represent independently for each occurrence 0, 1, or 2; and
n is 1, 2, or 3.

In certain embodiments, the compound is a compound of Formula III or a pharmaceutically acceptable salt thereof. In certain embodiments, the compound is a compound of Formula IV or a pharmaceutically acceptable salt thereof.

In certain embodiments, A is phenylene or 5-6 membered heteroarylene.

In certain embodiments, $R^1$ represents independently for each occurrence halogen or $C_{1-6}$ alkyl.

In certain embodiments, $R^3$ represents independently for each occurrence hydrogen, $C_{1-6}$ haloalkyl, halogen, hydroxyl, $C_{1-6}$ alkyl, $C_{3-4}$ cycloalkyl, $C_{1-6}$ alkoxy, or $C_{1-6}$ haloalkoxy.

In certain embodiments, $R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring, wherein the heterocyclic ring is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, cyano, oxo, —CO$_2$R$^{10}$, —C(O)R$^9$, —SO$_2$R$^9$, —N(R$^{10}$)C(O)R$^{12}$, and —C(O)N(R$^{10}$)(R$^{11}$); wherein $R^{10}$ and $R^{11}$ each represent independently for each occurrence hydrogen or $C_{1-6}$ alkyl, or $R^{10}$ and $R^{11}$ are taken together with the carbon atom to which they are attached to form a 3-6 membered carbocyclic ring; and $R^{12}$ is $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —CO$_2$R$^{10}$. In certain other embodiments, $R^4$ and $R^5$ are taken together with the nitrogen atom to which they are attached to form a 3-8 membered heterocyclic ring substituted with 1, 2, or 3 substituents independently selected from the group consisting of $C_{1-6}$ haloalkyl, $C_{1-6}$ alkyl, and —CO$_2$R$^{10}$, where $R^{10}$ is hydrogen or $C_{1-6}$ alkyl.

In certain embodiments, Y is —C($R^6$)($R^7$)—. In certain other embodiments, Y is —O—. In yet other embodiments, Y is —S(O)$_p$—.

In connection with Formula III, in certain embodiments, X is —O-aralkyl, —O— heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N(R$^4$)-aralkyl, —N(R$^4$)-phenyl, —N(R$^4$)-(partially unsaturated bicyclic carbocyclyl), or —N(R$^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)R$^9$, and —SO$_2$R$^9$. In certain embodiments, X is —S-aralkyl, —S-heteroaralkyl, —S-phenyl, —S-heteroaryl, —S-(partially unsaturated bicyclic carbocyclyl), —S—($C_{1-6}$ alkylene)-($C_{3-6}$ cycloalkyl), or —S—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)R$^9$, and —SO$_2$R$^9$. In certain embodiments, X is —($C_{2-6}$ alkenylene)-phenyl, —($C_{2-6}$ alkenylene)-heteroaryl, —($C_{2-6}$ alkenylene)-(partially unsaturated 8-10 membered bicyclic ring containing 0-3 heteroatoms), —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), —($C_{1-6}$ alkylene)-($C_3$-$C_6$ cycloalkyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)R$^9$, and —SO$_2$R$^9$. In certain embodiments, X is —($C_{2-6}$ alkenylene)-($C_{1-6}$ alkyl), —($C_{2-6}$ alkenylene)-($C_{3-6}$ cycloalkyl), or

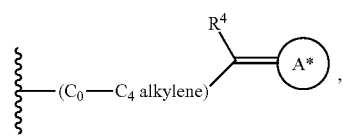

each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)R$^9$, and —SO$_2$R$^9$, wherein A* is a 5-8 membered, partially saturated carbocyclic or heterocyclic ring. In certain embodiments, X is —($C_{1-6}$ alkylene)-Z$^1$ or —($C_{2-6}$ alkenylene)-Z$^1$, wherein Z$^1$ is —O-aralkyl, —O—heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N(R$^4$)-aralkyl, —N(R$^4$)-phenyl, —N(R$^4$)-(partially unsaturated bicyclic carbocyclyl), —N(R$^4$)—($C_{1-6}$ alkylene)-($C_{3-6}$ cycloalkyl), or —N(R$^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)R$^9$, and —SO$_2$R$^9$. In certain embodiments, X is attached at the meta or para position on the phenyl group relative to variable Y. In certain embodiments, X is attached on the phenyl at the position located para to group Y.

In connection with Formula IV, in certain embodiments, R$^{2A}$ is $C_{1-6}$ alkyl substituted with 1 or 2 substituents independently selected from the group consisting of —CO$_2$R$^4$, —C(O)N(R$^4$)(R$^5$), —C(O)—N(R$^4$)—($C_{1-4}$ alkylene)-CO$_2$R$^4$, —N(R$^4$)C(O)R$^8$, —CN, halogen, hydroxyl, $C_{1-6}$ alkoxy, $C_{1-6}$ haloalkoxy, $C_{1-6}$ haloalkyl, —N(R$^4$)(R$^5$), —N(R$^4$)C(O)N(R$^4$)(R$^5$), —N(R$^4$)CO$_2$R$^9$, —N(R$^4$)S(O)$_2$R$^9$, and —N(R$^4$)S(O)$_2$N(R$^4$)(R$^5$). In certain other embodiments, R$^{2A}$ is $C_{1-6}$ alkyl substituted by —C(O)N(R$^4$)(R$^5$), where R$^4$ and R$^5$ are taken together with the nitrogen atom to which they are attached to form a 3-8 membered heterocyclic ring substituted with 1, 2, or 3 substituents independently selected from the group consisting of $C_{1-6}$ haloalkyl, $C_{1-6}$ alkyl, and —CO$_2$R$^{10}$, where R$^{10}$ is hydrogen or $C_{1-6}$ alkyl.

The definitions of variables in Formula III and IV above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain other embodiments, the compound is a compound defined by one of the following formulae where variables X and Z are as defined in Table 1, or a pharmaceutically acceptable salt thereof.

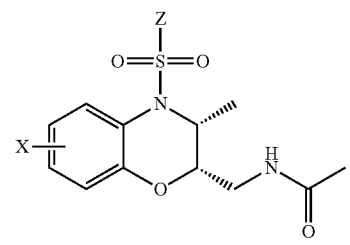

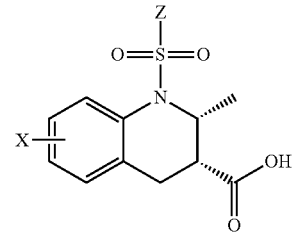

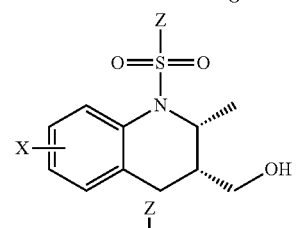

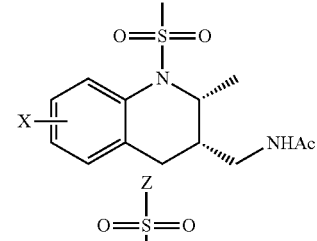

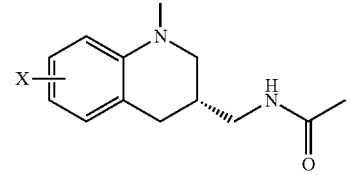

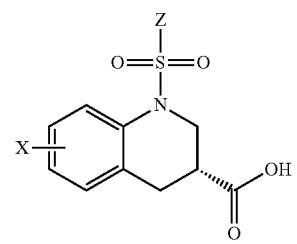

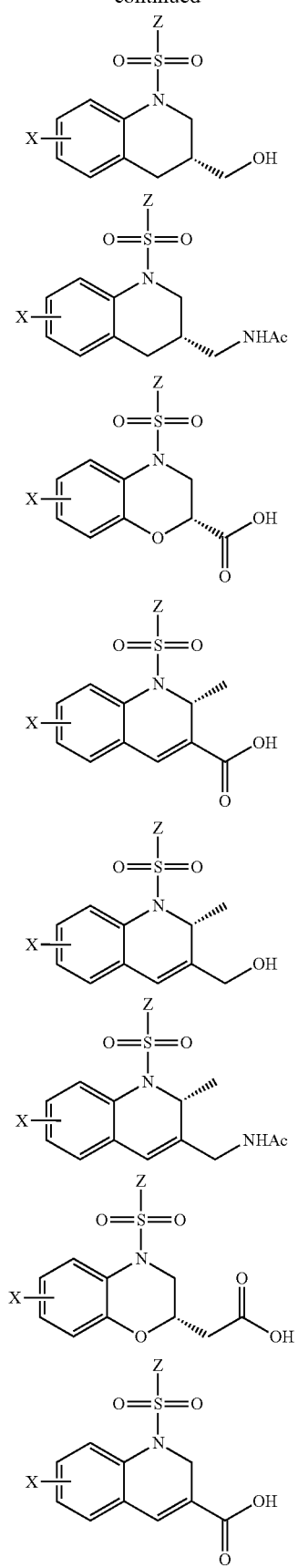
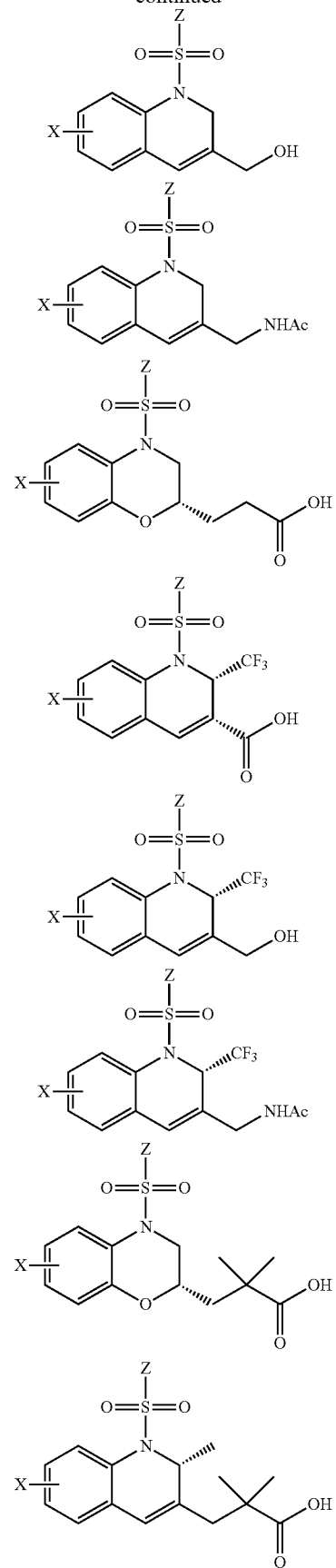

35
-continued
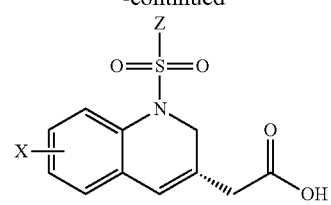
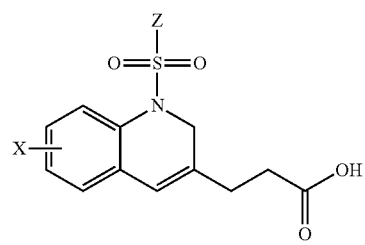
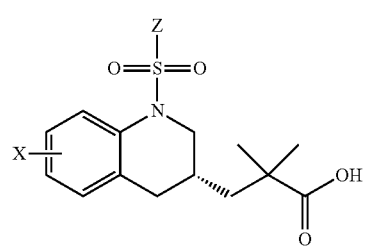
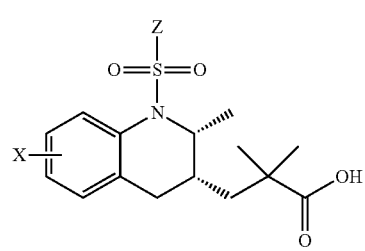
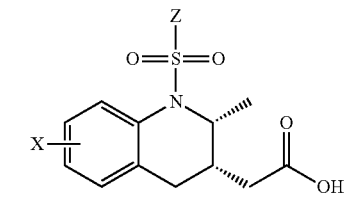
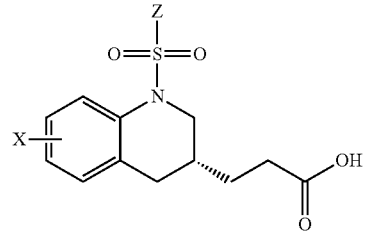
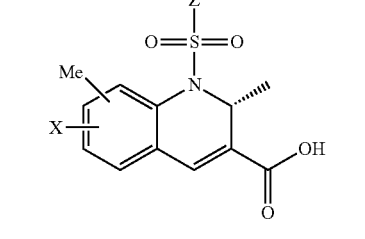
36
-continued
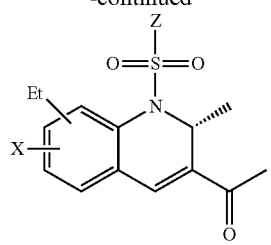
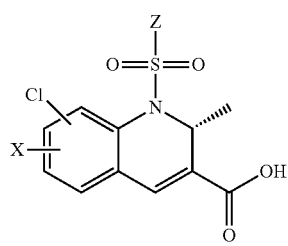
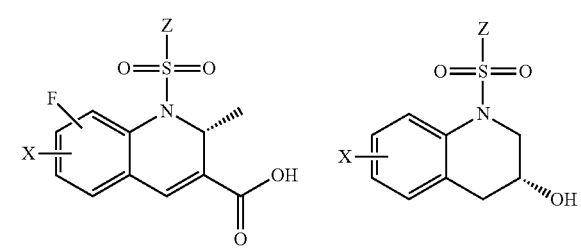
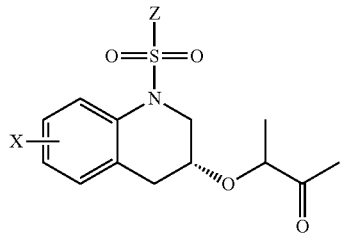
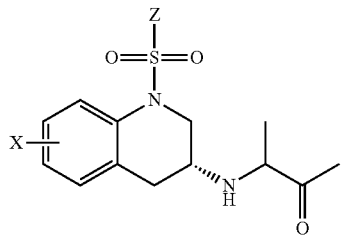
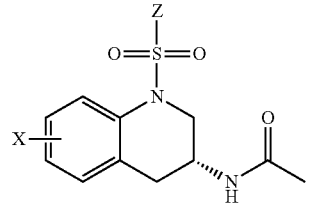
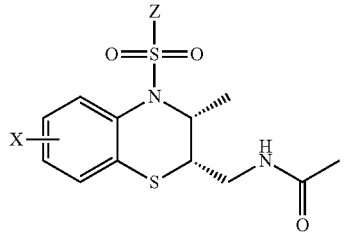

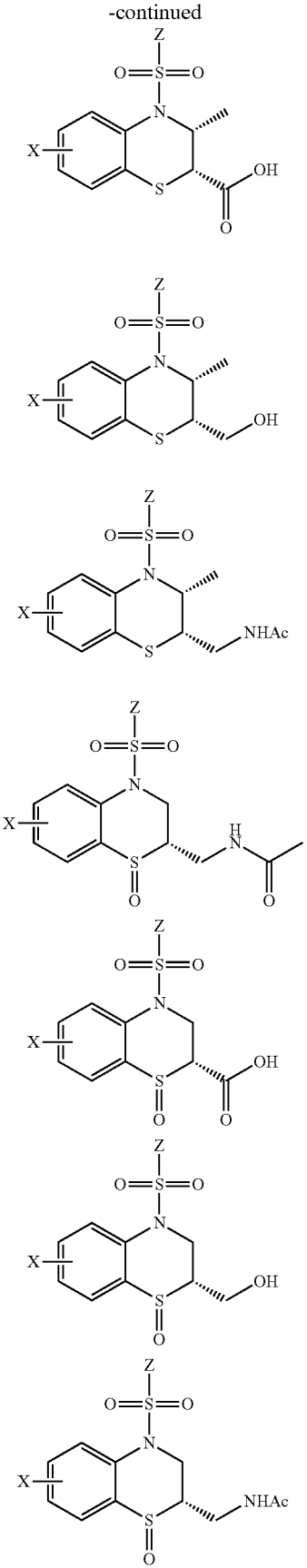

TABLE 1

| No. | X | Z |
|---|---|---|
| I-1 | 2-chloro-6-fluorobenzyloxy | 4-fluoro-3-methoxyphenyl |
| I-2 | 2,6-dichlorobenzyloxy | 3-chlorophenyl |
| I-3 | 2,6-difluorobenzyloxy | 3-cyclopropylphenyl |
| I-4 | 2,6-dichlorobenzyloxy | 4-fluoro-3-trifluoromethylphenyl |
| I-5 | 2-chloro-6-fluorobenzyloxy | 1-ethyl-4-chloro-1H-pyrazol-3-yl |
| I-6 | 2-chloro-6-fluorobenzyloxy | 1-ethyl-3-ethoxy-1H-pyrazol-4-yl |
| I-7 | 2-chloro-6-fluorobenzyloxy | 1-ethyl-4-(2-hydroxyethoxy)-1H-pyrazol-3-yl |
| I-8 | 2-chloro-6-fluorobenzyloxy | 3,5-dimethylpiperidin-1-yl |
| I-9 | 2-chloro-6-fluorobenzyloxy | 4-methylpiperidin-1-yl |

TABLE 1-continued

| No. | X | Z |
|---|---|---|
| I-10 | 2-chloro-6-fluorobenzyl-NH- | 4-fluoro-3-methoxyphenyl |
| I-11 | 1-(2-chloro-6-fluorophenyl)-1-propen-2-yl | 4-fluoro-3-methoxyphenyl |
| I-12 | cyclohexylmethyl-O- | 4-fluoro-3-methoxyphenyl |
| I-13 | indan-1-yl-O- | 4-fluoro-3-methoxyphenyl |
| I-14 | indan-1-yl-CH₂- | 4-fluoro-3-methoxyphenyl |
| I-15 | 1,2,3,4-tetrahydronaphthalen-1-yl-O- | 4-fluoro-3-methoxyphenyl |
| I-16 | 7-chloro-indan-1-yl-O- | 4-fluoro-3-methoxyphenyl |
| I-17 | indan-1-yl-NH- | 4-fluoro-3-methoxyphenyl |
| I-18 | 2-(2-chloro-6-fluorophenyl)-2-methylcyclopropyl | 4-fluoro-3-methoxyphenyl |
| I-19 | 1-(2-chloro-6-fluorophenyl)-1-buten-2-yl | 4-fluoro-3-methoxyphenyl |
| I-20 | 1-(2-chloro-6-fluorophenyl)-2-trifluoromethyl-vinyl | 4-fluoro-3-methoxyphenyl |
| I-21 | indan-1-ylidene-methyl | 4-fluoro-3-methoxyphenyl |
| I-22 | 3-(2-chloro-6-fluorophenyl)-2-methyl-2-propenyl | 4-fluoro-3-methoxyphenyl |
| I-23 | 3-(2-chloro-6-fluorophenyl)-2-methyl-2-buten-2-yl | 4-fluoro-3-methoxyphenyl |
| I-24 | 1,2,3,4-tetrahydronaphthalen-2-yl | 4-fluoro-3-methoxyphenyl |

TABLE 1-continued
| No. | X | Z |
|---|---|---|
| I-25 | 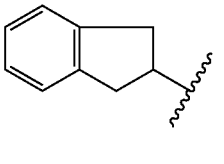 [SMILES: *C1Cc2ccccc2C1] | 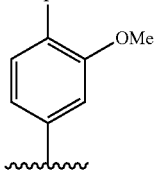 |
| I-26 | 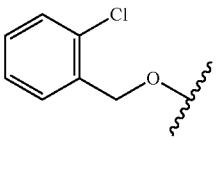 [SMILES: *OCc1ccccc1Cl] | 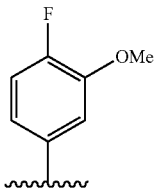 [SMILES: *c1ccc(F)c(OC)c1] |
| I-27 | 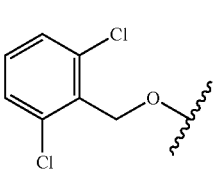 | 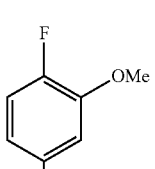 |
| I-28 | 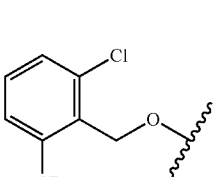 | 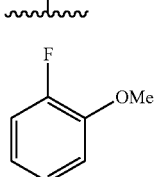 |
| I-29 | 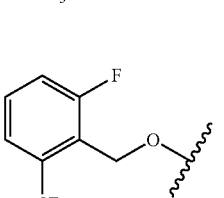 | 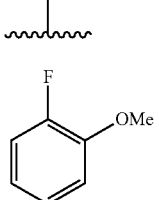 |
| I-30 | 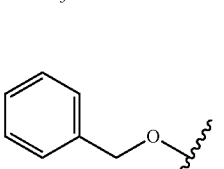 | 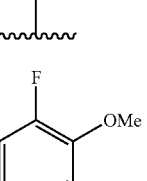 |
| I-31 | 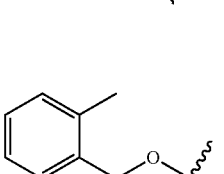 | 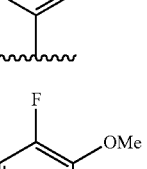 |
| I-32 | 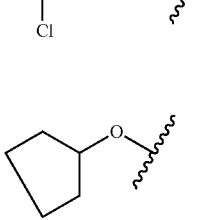 | 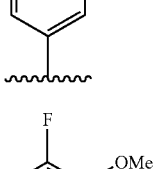 |
| I-33 | 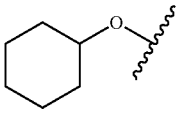 [SMILES: *OC1CCCCC1] | 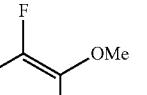 |
| I-34 | 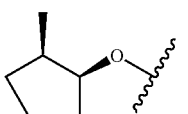 | 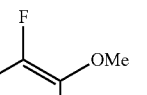 |
| I-35 | 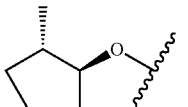 | 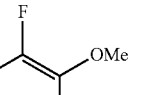 |
| I-36 | 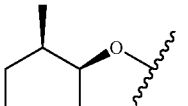 | 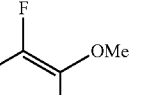 |
| I-37 | 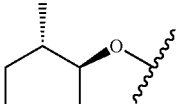 | 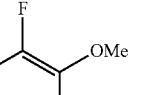 |
| I-38 | 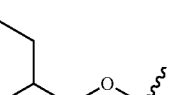 | 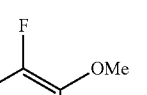 |
| I-39 | 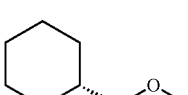 | 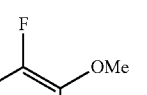 |

TABLE 1-continued

| No. | X | Z |
|---|---|---|
| I-40 | (2-methylcyclohexyl)methyl-O- | 4-fluoro-3-methoxyphenyl |
| I-41 | (2,6-dimethylcyclohexyl)methyl-O- | 4-fluoro-3-methoxyphenyl |
| I-42 | norbornyl-methyl-O- | 4-fluoro-3-methoxyphenyl |
| I-43 | norbornyl-methyl-O- | 4-fluoro-3-methoxyphenyl |
| I-44 | (3-methylcyclopentyl)-O- | 4-fluoro-3-methoxyphenyl |
| I-45 | (3-isopropylcyclopentyl)-O- | 4-fluoro-3-methoxyphenyl |
| I-46 | (3,3-dimethylcyclopentyl)-O- | 4-fluoro-3-methoxyphenyl |
| I-47 | (3-methylcyclopentyl)-O- | 4-fluoro-3-methoxyphenyl |
| I-48 | (3-methylcyclopentyl)-O- | 4-fluoro-3-methylphenyl |
| I-49 | (2,6-dichlorophenyl)methyl-O- | 5-(trifluoromethyl)pyridin-3-yl |
| I-50 | (2-chloro-6-fluorophenyl)methyl-NH- | 5-(trifluoromethyl)pyridin-3-yl |
| I-51 | (2,6-dichlorophenyl)methyl-O- | 1-methyl-1H-imidazol-4-yl |
| I-52 | (2-chloro-6-fluorophenyl)methyl-NH- | 1-methyl-1H-imidazol-4-yl |
| I-53 | (E)-2-(2-chloro-6-fluorophenyl)vinyl- | 5-methylpyridin-3-yl |
| I-54 | indan-1-yl-O- | 5-methylpyridin-3-yl |
| I-55 | (E)-2-(2-chloro-6-fluorophenyl)vinyl- | 1-isopropyl-1H-imidazol-4-yl |

TABLE 1-continued

| No. | X | Z |
|---|---|---|
| I-56 | 2,3-dihydro-1H-inden-1-yloxy | 1-isopropyl-1H-imidazol-4-yl |
| I-57 | (2,6-dichlorobenzyl)oxy | oxazol-4-yl |
| I-58 | (2-chloro-6-fluorobenzyl)amino | oxazol-4-yl |
| I-59 | (E)-2-(2-chloro-6-fluorophenyl)vinyl | oxazol-4-yl |
| I-60 | 2,3-dihydro-1H-inden-1-yloxy | oxazol-4-yl |
| I-61 | (2,6-dichlorobenzyl)oxy | 1-methyl-1H-pyrrol-3-yl |
| I-62 | (2-chloro-6-fluorobenzyl)amino | 1-methyl-1H-pyrrol-3-yl |
| I-63 | (E)-2-(2-chloro-6-fluorophenyl)vinyl | 1-isopropyl-1H-pyrrol-3-yl |
| I-64 | 2,3-dihydro-1H-inden-1-yloxy | 1-isopropyl-1H-pyrrol-3-yl |
| I-65 | (5-(trifluoromethyl)pyridin-3-yl)oxy | 4-fluoro-3-methoxyphenyl |
| I-66 | (5-(trifluoromethyl)pyridin-3-yl)oxy | 3-chlorophenyl |
| I-67 | (pyridin-3-ylmethoxy) | 3-cyclopropylphenyl |
| I-68 | (pyridin-3-ylmethoxy) | 4-fluoro-3-(trifluoromethyl)phenyl |
| I-69 | (oxazol-5-ylmethoxy) | 4-chloro-1-ethyl-1H-pyrazol-3-yl |
| I-70 | (oxazol-5-ylmethoxy) | 4-fluoro-3-methoxyphenyl |
| I-71 | (pyridin-3-yloxy) | 3-chlorophenyl |

TABLE 1-continued

| No. | X | Z |
|---|---|---|
| I-72 | 3-pyridyl-O- | 1-ethyl-4-chloro-pyrazol-3-yl |
| I-73 | 2,6-dichlorobenzyl-O- | 3-(trifluoromethyl)phenyl |
| I-74 | 2-chloro-6-fluorobenzyl-NH- | 3-(trifluoromethyl)phenyl |
| I-75 | 2-chloro-6-fluorostyryl | 3-(trifluoromethyl)phenyl |
| I-76 | 2-(2-chloro-6-fluorophenyl)ethyl | 3-(trifluoromethyl)phenyl |
| I-77 | 2,6-dichlorobenzyl-O- | 3-fluoro-5-(trifluoromethyl)phenyl |
| I-78 | 2-chloro-6-fluorobenzyl-NH- | 3-fluoro-5-(trifluoromethyl)phenyl |
| I-79 | 2,6-dichlorobenzyl-O- | 2-chloro-4,5,6,7-tetrahydropyrazolo[1,5-a]pyridin-3-yl |
| I-80 | 2-chloro-6-fluorostyryl | 2-chloro-4,5,6,7-tetrahydropyrazolo[1,5-a]pyridin-3-yl |
| I-81 | 2,6-dichlorobenzyl-O- | 2-(2-hydroxyethoxy)-4,5,6,7-tetrahydropyrazolo[1,5-a]pyridin-3-yl |
| I-82 | 2-chloro-6-fluorostyryl | 2-(2-hydroxyethoxy)-4,5,6,7-tetrahydropyrazolo[1,5-a]pyridin-3-yl |
| I-83 | 2,6-dichlorobenzyl-O- | 2-ethoxy-5,6-dihydro-4H-pyrrolo[1,2-b]pyrazol-3-yl |
| I-84 | 2-chloro-6-fluorostyryl | 2-ethoxy-5,6-dihydro-4H-pyrrolo[1,2-b]pyrazol-3-yl |
| I-85 | 2,6-dichlorobenzyl-O- | 2-chloro-6,7-dihydro-5H-pyrrolo[1,2-a]imidazol-3-yl |
| I-86 | 2-chloro-6-fluorostyryl | 2-chloro-6,7-dihydro-5H-pyrrolo[1,2-a]imidazol-3-yl |

In certain other embodiments, the compound is a compound defined by one of the following formulae where variables X and Z are as defined in Table 1-A, or a pharmaceutically acceptable salt thereof.

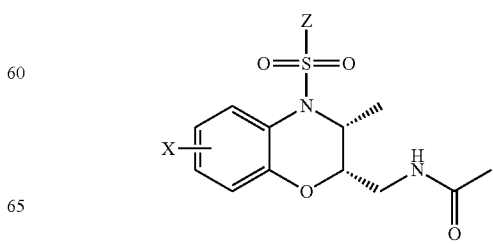

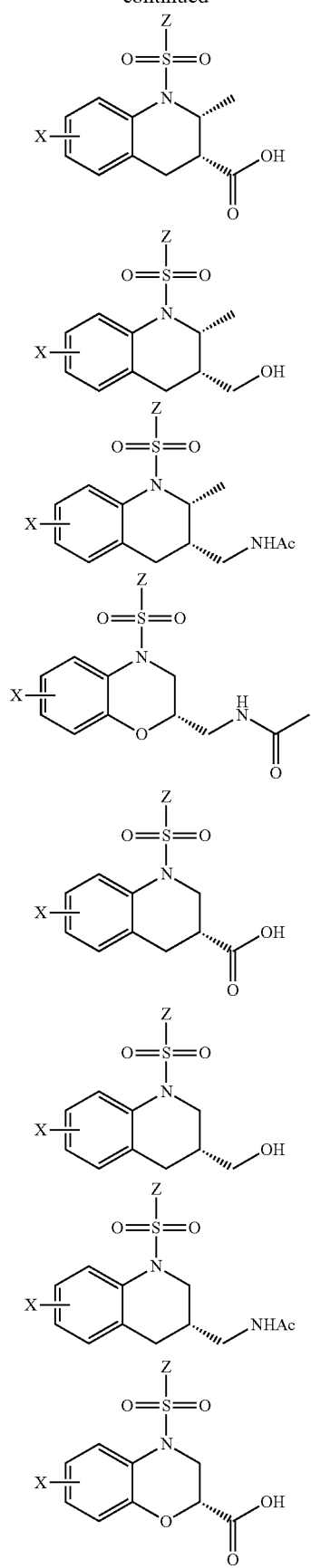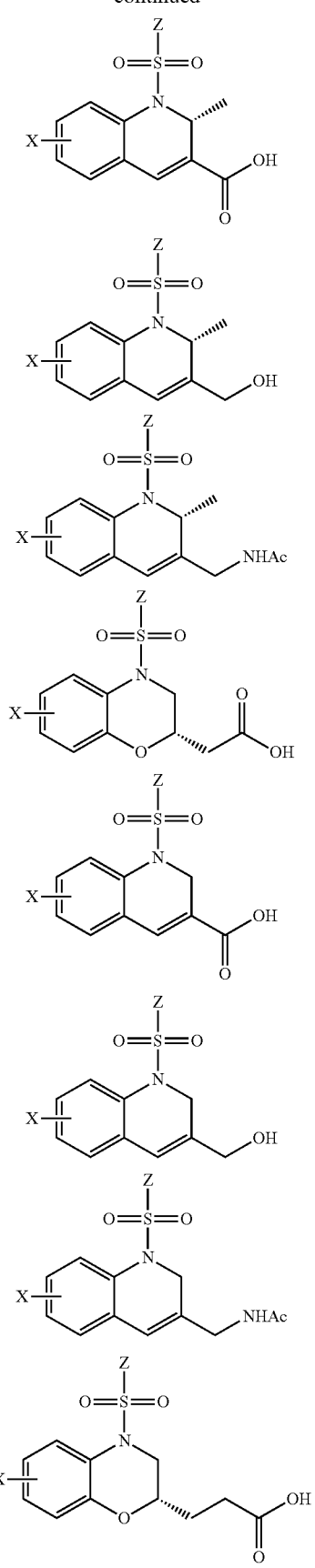

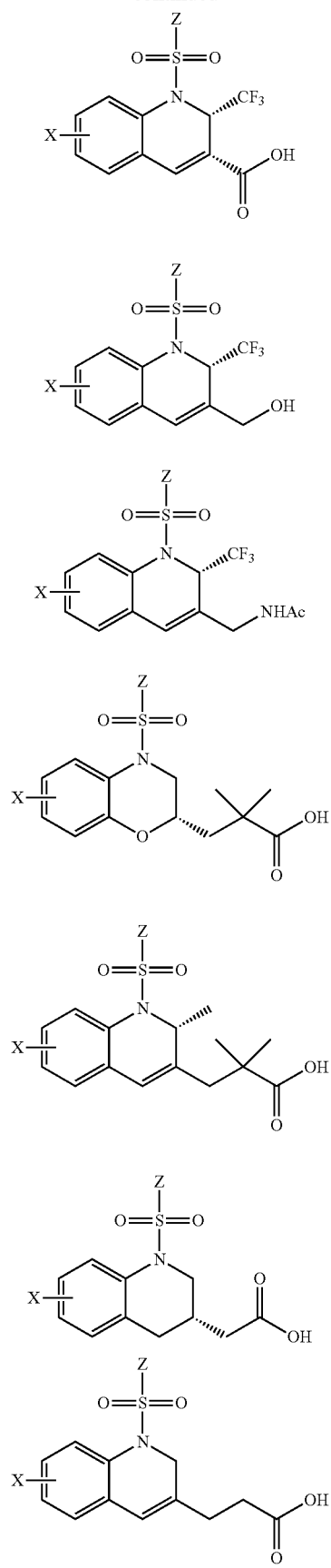
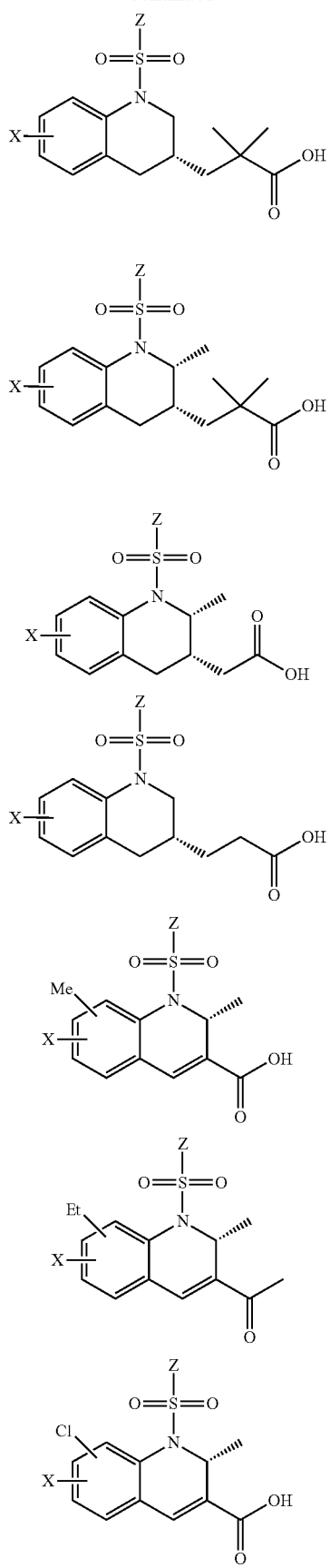

53
-continued
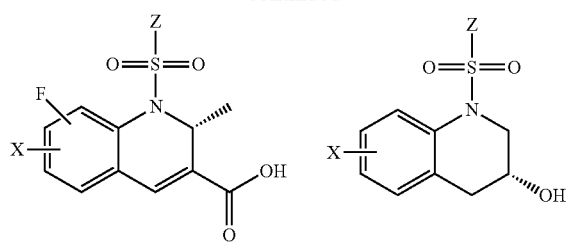
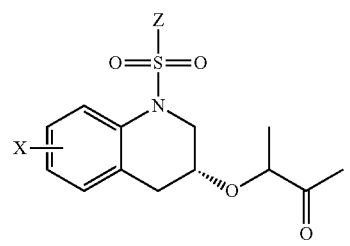
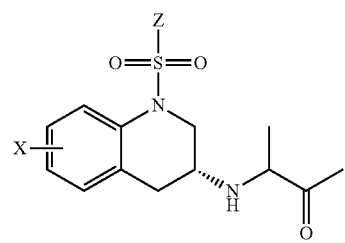
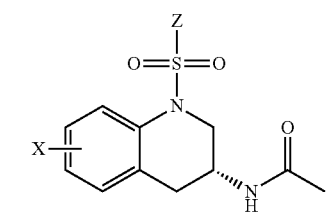
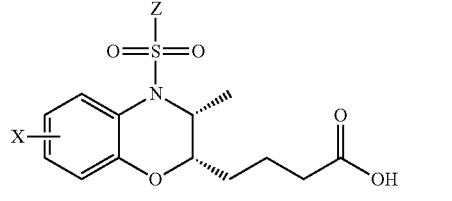
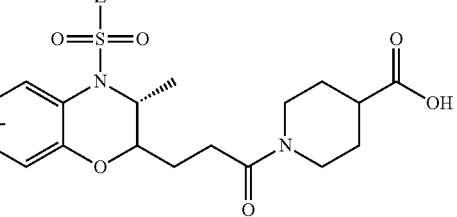
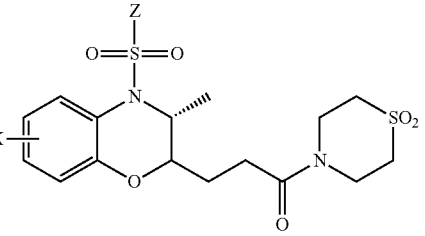
54
-continued
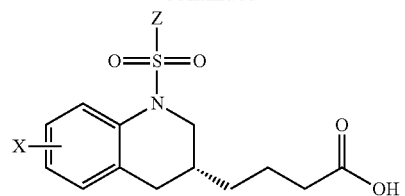
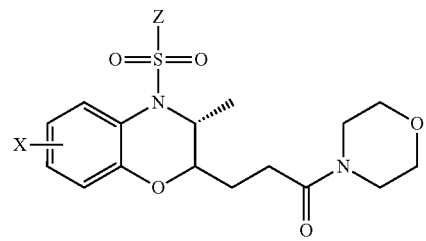
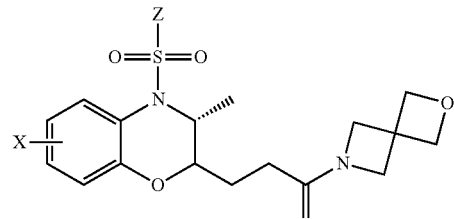
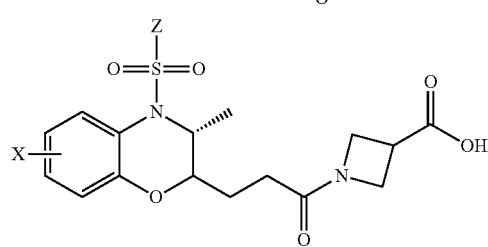
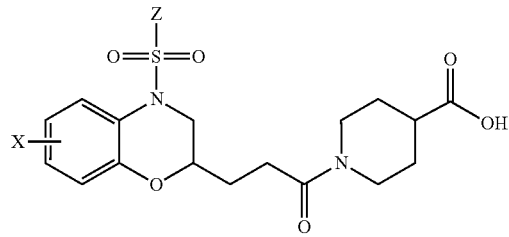
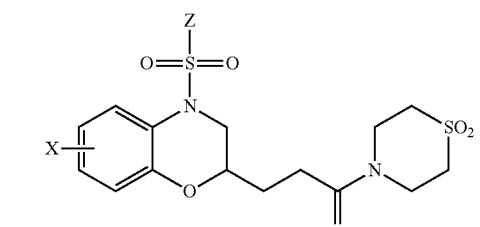
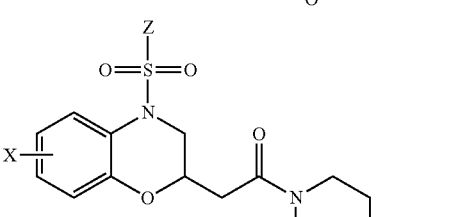

-continued
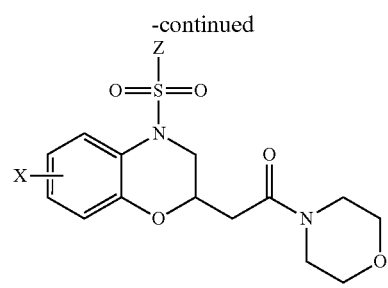
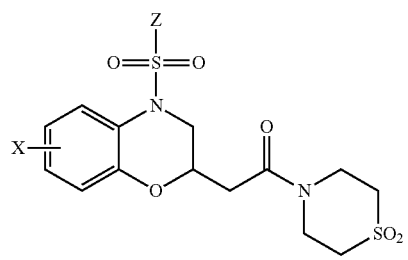
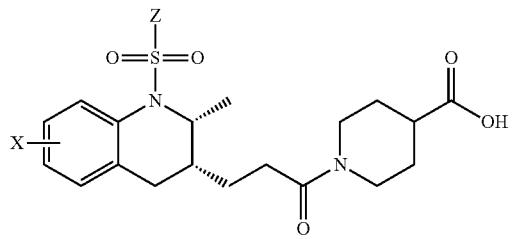
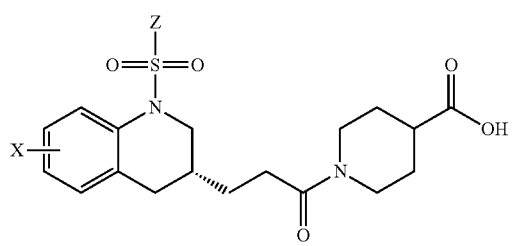
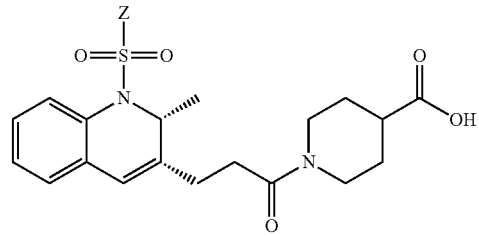
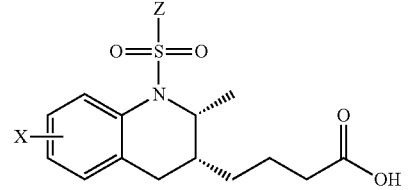
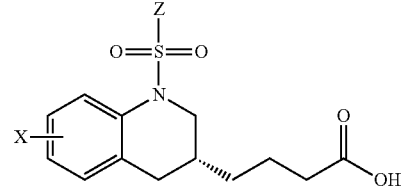
-continued
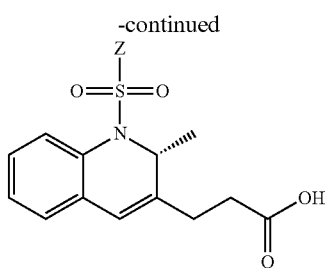
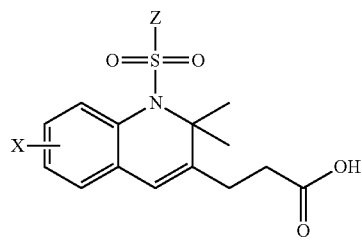
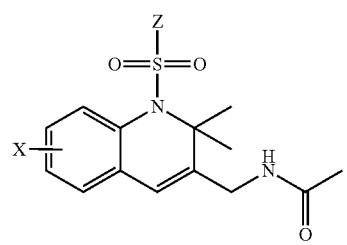
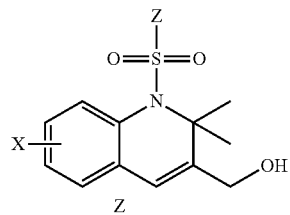
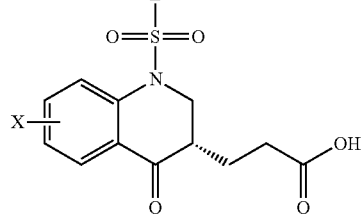
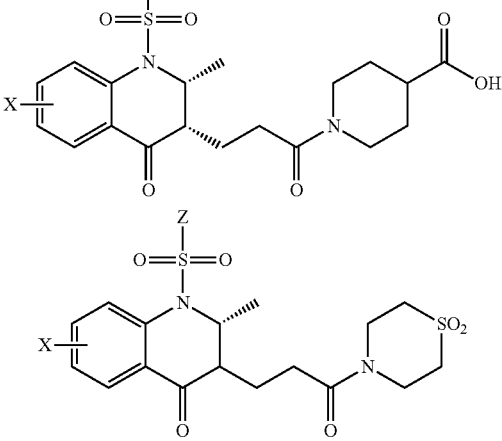

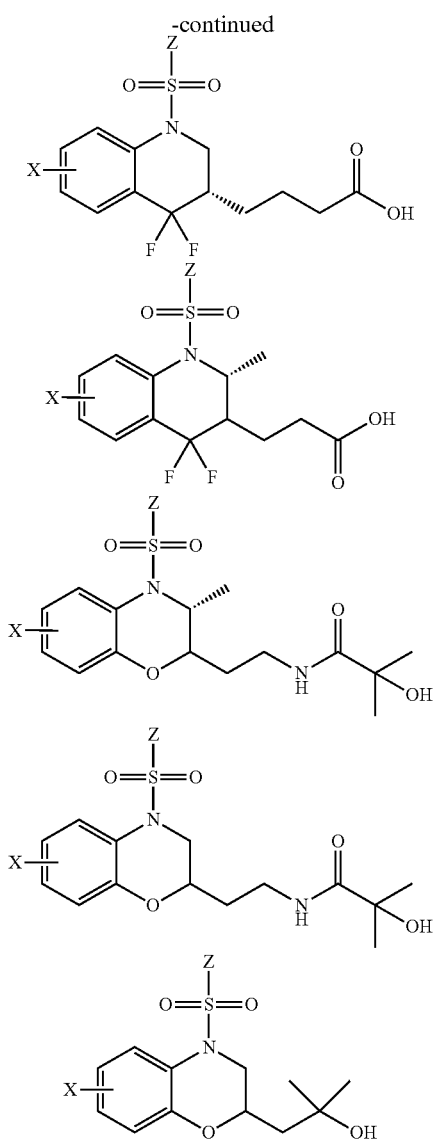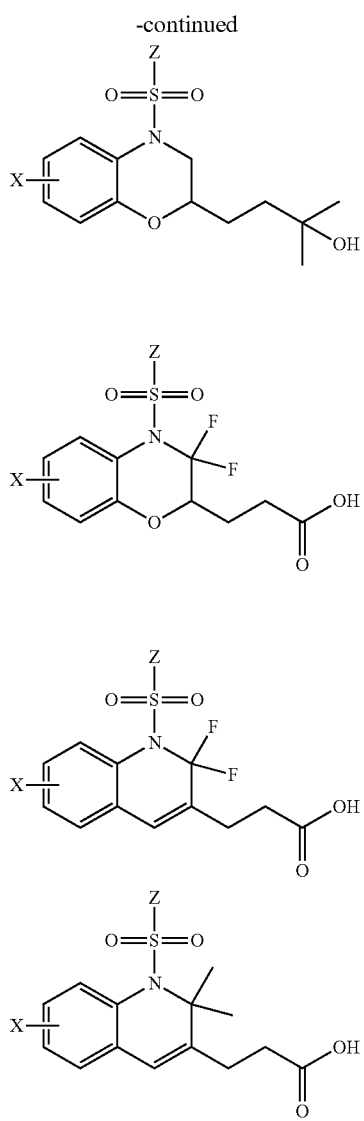
TABLE 1-A
| No. | X | Z |
|---|---|---|
| I-A1 | 2-chloro-6-fluorobenzyloxy | 4-fluoro-3-methoxyphenyl |
| I-A2 | 2-chloro-6-fluorobenzyloxy | 3-chlorophenyl |

TABLE 1-A-continued
| No. | X | Z |
|---|---|---|
| I-A3 | 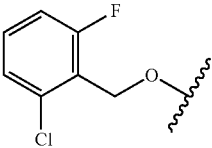 [SMILES: *OCc1c(F)cccc1Cl] | 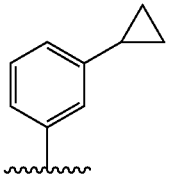 [SMILES: *c1cccc(C2CC2)c1] |
| I-A4 | 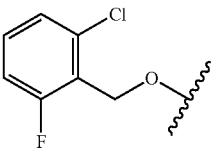 [SMILES: *OCc1c(F)cccc1Cl] | 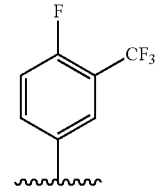 [SMILES: *c1ccc(F)c(C(F)(F)F)c1] |
| I-A5 | 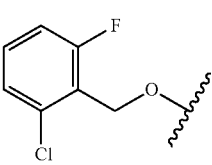 [SMILES: *OCc1c(F)cccc1Cl] | 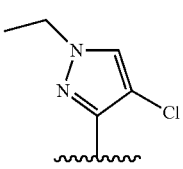 [SMILES: *c1nn(CC)cc1Cl] |
| I-A6 | 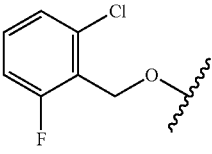 | 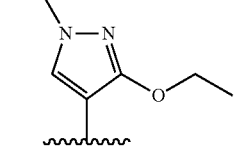 |
| I-A7 | 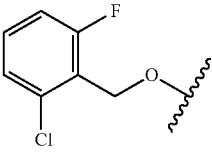 [SMILES: *OCc1c(F)cccc1Cl] | 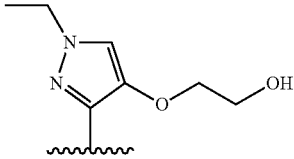 [SMILES: *c1nn(CC)cc1OCCO] |
| I-A8 | 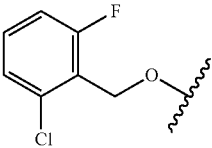 | 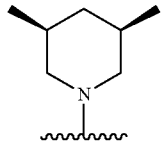 |
| I-A9 | 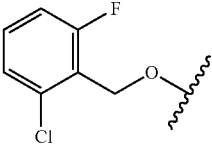 [SMILES: *OCc1c(F)cccc1Cl] | 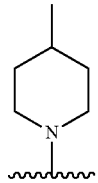 |
| I-A10 | 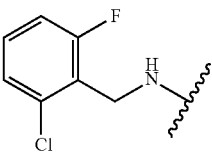 [SMILES: *NCc1c(F)cccc1Cl] | 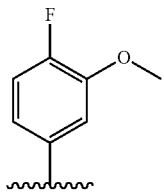 [SMILES: *c1ccc(F)c(OC)c1] |

TABLE 1-A-continued

| No. | X | Z |
|---|---|---|
| I-A11 | 2-F, 6-Cl phenyl with C(Me)=CH— | 4-F, 3-OMe phenyl |
| I-A12 | cyclohexyl-CH2-O— | 4-F, 3-OMe phenyl |
| I-A13 | indan-1-yl-O— | 4-F, 3-OMe phenyl |
| I-A14 | indan-1-yl-CH2— | 4-F, 3-OMe phenyl |
| I-A15 | 1,2,3,4-tetrahydronaphthalen-1-yl-O— | 4-F, 3-OMe phenyl |
| I-A16 | 7-Cl-indan-1-yl-O— | 4-F, 3-OMe phenyl |
| I-A17 | indan-1-yl-NH— | 4-F, 3-OMe phenyl |
| I-A18 | 2-F, 6-Cl phenyl-(trans-2-methylcyclopropyl)— | 4-F, 3-OMe phenyl |

TABLE 1-A-continued

| No. | X | Z |
|---|---|---|
| I-A19 | 2-chloro-6-fluorophenyl with C=C(Et) linker | 4-fluoro-3-methoxyphenyl |
| I-A20 | 2-chloro-6-fluorophenyl with C=C(CF₃) linker | 4-fluoro-3-methoxyphenyl |
| I-A21 | indan-1-ylidene-methyl | 4-fluoro-3-methoxyphenyl |
| I-A22 | 2-chloro-6-fluorophenyl-CH=C(Me)– | 4-fluoro-3-methoxyphenyl |
| I-A23 | 2-chloro-6-fluorophenyl-C(Me)=C(Me)– | 4-fluoro-3-methoxyphenyl |
| I-A24 | tetralin-2-yl | 4-fluoro-3-methoxyphenyl |
| I-A25 | indan-2-yl | 4-fluoro-3-methoxyphenyl |

TABLE 1-A-continued
| No. | X | Z |
|---|---|---|
| I-A26 | 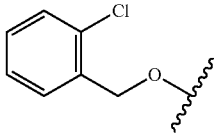 [SMILES: *OCc1ccccc1Cl] | 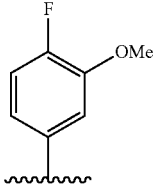 [SMILES: *c1ccc(F)c(OC)c1] |
| I-A27 | 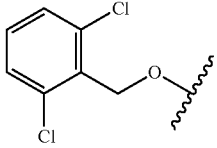 [SMILES: *OCc1c(Cl)cccc1Cl] | 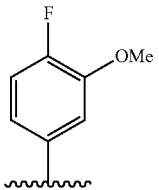 [SMILES: *c1ccc(F)c(OC)c1] |
| I-A28 | 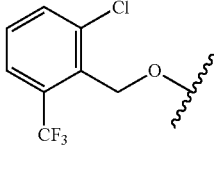 [SMILES: *OCc1c(Cl)cccc1C(F)(F)F] | 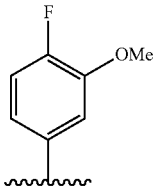 [SMILES: *c1ccc(F)c(OC)c1] |
| I-A29 | 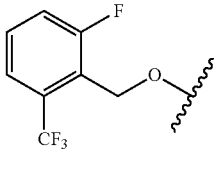 [SMILES: *OCc1c(F)cccc1C(F)(F)F] | 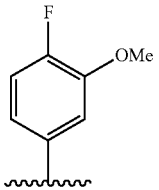 [SMILES: *c1ccc(F)c(OC)c1] |
| I-A30 | 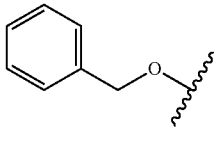 [SMILES: *OCc1ccccc1] | 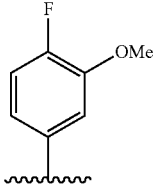 [SMILES: *c1ccc(F)c(OC)c1] |
| I-A31 | 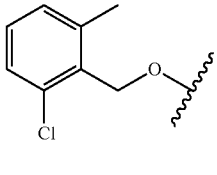 [SMILES: *OCc1c(C)cccc1Cl] | 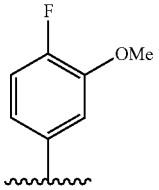 [SMILES: *c1ccc(F)c(OC)c1] |
| I-A32 | 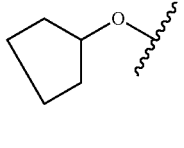 [SMILES: *OC1CCCC1] | 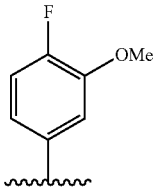 [SMILES: *c1ccc(F)c(OC)c1] |
| I-A33 | 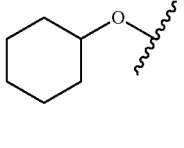 [SMILES: *OC1CCCCC1] | 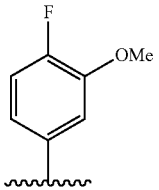 [SMILES: *c1ccc(F)c(OC)c1] |

TABLE 1-A-continued
| No. | X | Z |
|---|---|---|
| I-A34 | 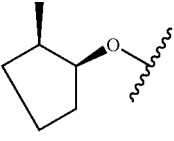 [SMILES: *O[C@H]1CCC[C@H]1C] | 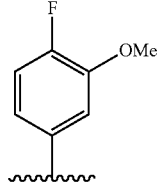 [SMILES: *c1ccc(F)c(OC)c1] |
| I-A35 | 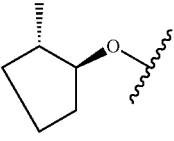 [SMILES: *O[C@H]1CCC[C@@H]1C] | 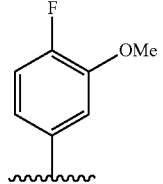 [SMILES: *c1ccc(F)c(OC)c1] |
| I-A36 | 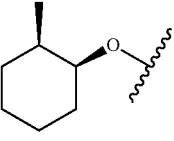 [SMILES: *O[C@H]1CCCC[C@H]1C] | 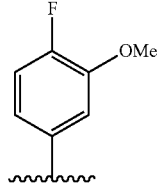 [SMILES: *c1ccc(F)c(OC)c1] |
| I-A37 | 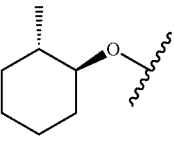 [SMILES: *O[C@H]1CCCC[C@@H]1C] | 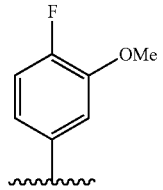 [SMILES: *c1ccc(F)c(OC)c1] |
| I-A38 | 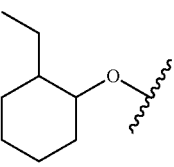 [SMILES: *OC1CCCCC1CC] | 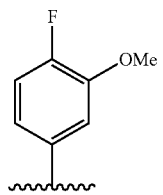 [SMILES: *c1ccc(F)c(OC)c1] |
| I-A39 | 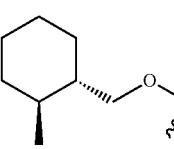 |  |
| I-A40 | 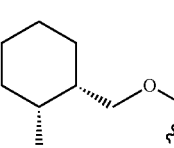 | 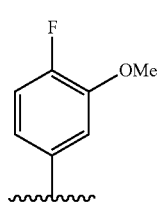 [SMILES: *c1ccc(F)c(OC)c1] |

TABLE 1-A-continued
| No. | X | Z |
|---|---|---|
| I-A41 | 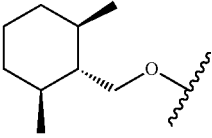 [SMILES: *OC[C@H]1[C@H](C)CCC[C@@H]1C] | 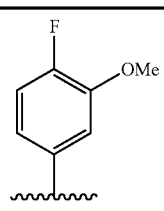 |
| I-A42 | 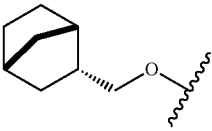 | 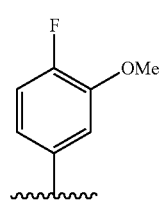 [SMILES: *c1ccc(F)c(OC)c1] |
| I-A43 | 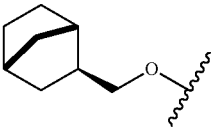 | 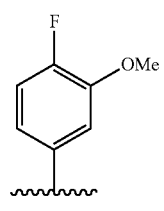 [SMILES: *c1ccc(F)c(OC)c1] |
| I-A44 | 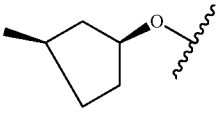 [SMILES: *O[C@H]1CC[C@@H](C)C1] | 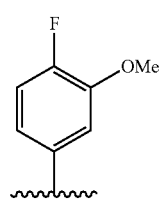 [SMILES: *c1ccc(F)c(OC)c1] |
| I-A45 | 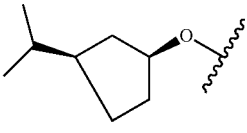 [SMILES: *O[C@H]1CC[C@@H](C(C)C)C1] | 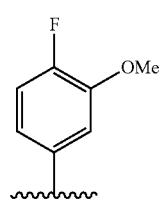 [SMILES: *c1ccc(F)c(OC)c1] |
| I-A46 | 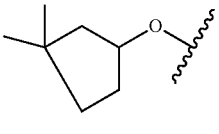 [SMILES: *OC1CCC(C)(C)C1] | 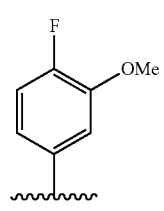 [SMILES: *c1ccc(F)c(OC)c1] |
| I-A47 | 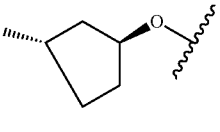 [SMILES: *O[C@H]1CC[C@H](C)C1] | 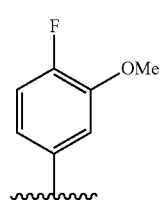 [SMILES: *c1ccc(F)c(OC)c1] |
| I-A48 | 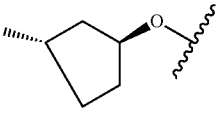 [SMILES: *O[C@H]1CC[C@H](C)C1] | 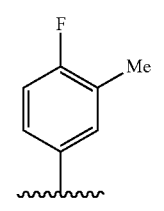 [SMILES: *c1ccc(F)c(C)c1] |

TABLE 1-A-continued
| No. | X | Z |
|---|---|---|
| I-A49 | 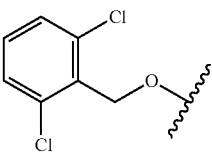 [SMILES: *OCc1c(Cl)cccc1Cl] | 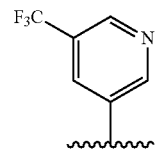 |
| I-A50 | 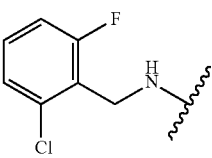 [SMILES: *NCc1c(F)cccc1Cl] | 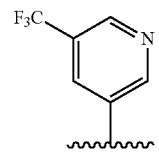 |
| I-A51 | 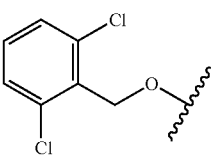 [SMILES: *OCc1c(Cl)cccc1Cl] | 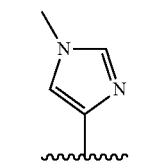 [SMILES: *c1cn(C)cn1] |
| I-A52 | 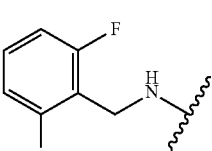 | 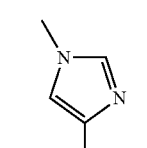 |
| I-A53 | 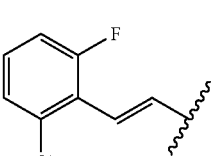 | 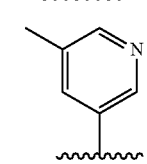 |
| I-A54 | 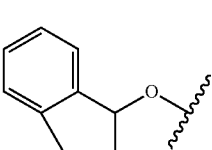 | 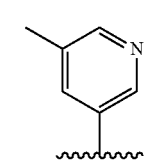 [SMILES: *c1cncc(C)c1] |
| I-A55 | 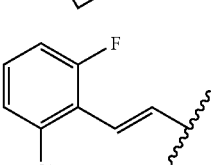 | 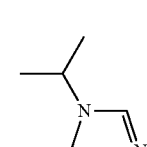 |
| I-A56 | 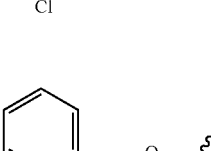 | 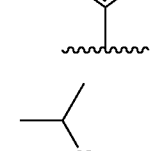 |
| I-A57 | 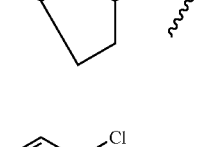 | 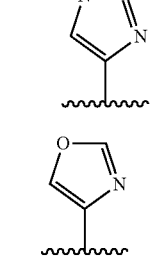 |

TABLE 1-A-continued
| No. | X | Z |
|---|---|---|
| I-A58 | 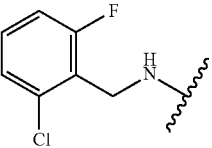 [SMILES: *NCc1c(F)cccc1Cl] | 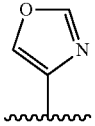 |
| I-A59 | 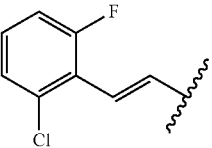 [SMILES: */C=C/c1c(F)cccc1Cl] | 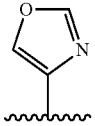 [SMILES: *c1cocn1] |
| I-A60 | 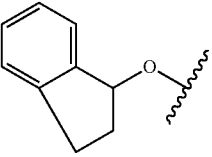 [SMILES: *OC1CCc2ccccc21] | 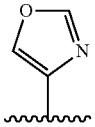 |
| I-A61 | 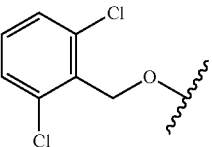 [SMILES: *OCc1c(Cl)cccc1Cl] | 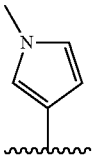 [SMILES: *c1ccn(C)c1] |
| I-A62 | 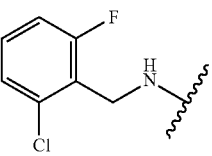 [SMILES: *NCc1c(F)cccc1Cl] | 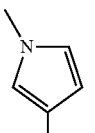 |
| I-A63 | 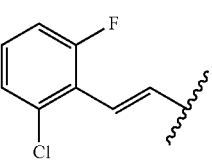 [SMILES: */C=C/c1c(F)cccc1Cl] | 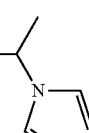 |
| I-A64 | 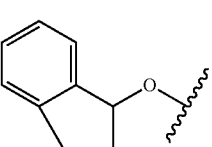 | 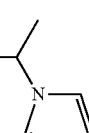 |
| I-A65 | 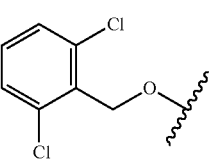 [SMILES: *OCc1c(Cl)cccc1Cl] | 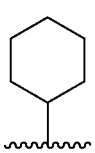 |
| I-A66 | 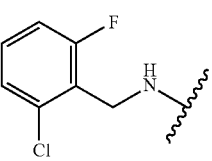 | 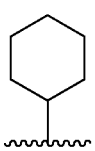 [SMILES: *C1CCCCC1] |

TABLE 1-A-continued

| No. | X | Z |
|---|---|---|
| I-A67 | 2-chloro-6-fluorophenyl vinyl | 3,5-dimethylcyclohexyl |
| I-A68 | 2,3-dihydro-1H-inden-1-yloxy | 3,5-dimethylcyclohexyl |
| I-A69 | (2,6-dichlorobenzyl)oxy | cyclopentyl |
| I-A70 | (2-chloro-6-fluorobenzyl)amino | cyclopentyl |
| I-A71 | 2-chloro-6-fluorophenyl vinyl | 3,4-dimethylcyclopentyl |
| I-A72 | 2,3-dihydro-1H-inden-1-yloxy | 3,4-dimethylcyclopentyl |
| I-A73 | 2-chloro-6-fluorophenyl vinyl | 2-((5-(trifluoromethyl)pyridin-2-yl)oxy)ethanol |
| I-A74 | 1-(2-chloro-6-fluorophenyl)propenyl | 2-((5-(trifluoromethyl)pyridin-2-yl)oxy)ethanol |
| I-A75 | 2-(trifluoromethyl)but-2-enyl | 2-((5-(trifluoromethyl)pyridin-2-yl)oxy)ethanol |

TABLE 1-A-continued
| No. | X | Z |
|---|---|---|
| I-A76 | 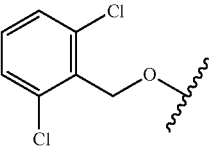 [SMILES: *OCc1c(Cl)cccc1Cl] | 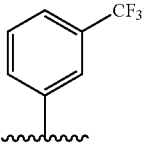 [SMILES: *c1cccc(C(F)(F)F)c1] |
| I-A77 | 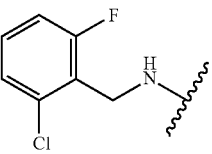 | 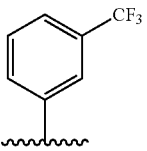 [SMILES: *c1cccc(C(F)(F)F)c1] |
| I-A78 | 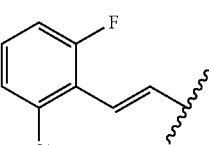 | 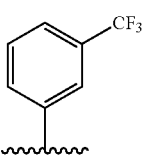 [SMILES: *c1cccc(C(F)(F)F)c1] |
| I-A79 | 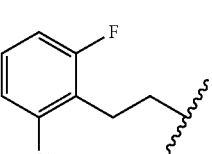 | 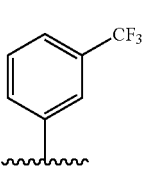 [SMILES: *c1cccc(C(F)(F)F)c1] |
| I-A80 | 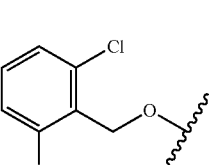 | 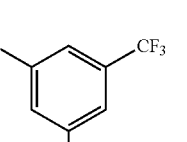 |
| I-A81 | 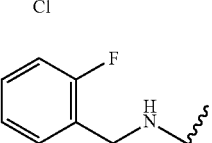 | 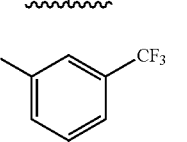 |
| I-A82 | 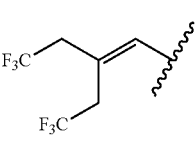 | 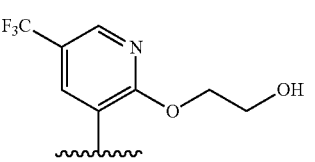 |
| I-A83 | 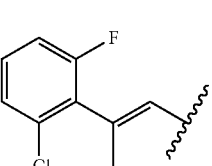 | 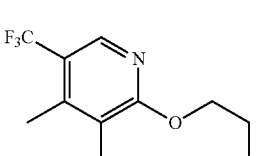 |
| I-A84 | 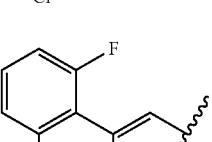 | 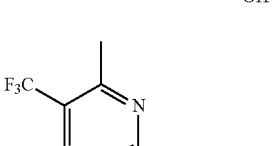 |

TABLE 1-A-continued

| No. | X | Z |
|---|---|---|
| I-A85 | (F3C)C=CH-CH2CH3 | 5-CF3-pyridin-2-yl, 2-OCH2CH2OH |
| I-A86 | 2-F-6-Cl-phenyl-C(CH3)=CH- | 5-cyclopropyl-pyridin-2-yl, 2-OCH2CH2OH |
| I-A87 | 2-F-6-Cl-phenyl-C(CH3)=CH- | 5-CF3-pyridin-2-yl, 2-NHCH2CH2OH |
| I-A88 | 2-F-6-Cl-phenyl-C(CH3)=CH- | 5-CF3-pyridin-2-yl, 2-OCHF2 |
| I-A89 | cyclohexylidene-CH- | 5-CF3-pyridin-2-yl, 2-OCH2CH2OH |
| I-A90 | cyclohexylidene-CH- | 3-CF3-phenyl |
| I-A91 | 2,2-difluorocyclohexylidene-CH- | 3-CF3-phenyl |
| I-A92 | (CF3)(Et)C=CH- | 5-CF3-pyridin-2-yl, 2-NHCH2CH2OH |
| I-A93 | cyclohexyl-CH2- | 5-CF3-pyridin-2-yl, 2-OCH2CH2OH |

TABLE 1-A-continued

| No. | X | Z |
|---|---|---|
| I-A94 | cyclohexyl-S- | 3-(trifluoromethyl)phenyl |
| I-A95 | (2-chlorophenyl)-S- | 5-(trifluoromethyl)-2-(2-hydroxyethoxy)pyridin-3-yl |
| I-A96 | 1-(2-chloro-6-fluorophenyl)prop-1-en-2-yl | 5-(trifluoromethyl)-2-methoxypyridin-3-yl |
| I-A97 | 1-(2-chloro-6-fluorophenyl)prop-1-en-2-yl | 3-(2-hydroxyethoxy)-6,7-dihydro-5H-cyclopenta[c]pyridin-4-yl |
| I-A98 | 1-(2-chloro-6-methoxyphenyl)prop-1-en-2-yl | 5-(trifluoromethyl)-2-(2-hydroxyethoxy)pyridin-3-yl |
| I-A99 | 1-(2-chloro-6-fluorophenyl)prop-1-en-2-yl | 5-(trifluoromethyl)-2-(2,2,2-trifluoroethoxy)pyridin-3-yl |
| I-A100 | (2,2-dimethylcyclopentylidene)methyl | 5-(trifluoromethyl)-2-(2-hydroxyethoxy)pyridin-3-yl |
| I-A101 | (2,2-dimethylcyclopentylidene)methyl | 3-(trifluoromethyl)phenyl |
| I-A102 | (2,2-difluorocyclohexylidene)methyl | 5-(trifluoromethyl)pyridin-3-yl |

TABLE 1-A-continued

| No. | X | Z |
|---|---|---|
| I-A103 | (2-ethylbut-1-en-1-yl group) | 5-(trifluoromethyl)-2-(2-hydroxyethoxy)pyridin-3-yl |
| I-A104 | (1-methylcyclohexyl)methyl | 5-(trifluoromethyl)-2-(2-hydroxyethoxy)pyridin-3-yl |
| I-A105 | (2-chlorobenzyl)thio | 3-(trifluoromethyl)phenyl |
| I-A106 | (3-chlorophenyl)thio | 5-(trifluoromethyl)-2-(2-hydroxyethoxy)pyridin-3-yl |

In certain embodiments, the compound is a compound in Table 1, 1-A, 23, or 24, or a pharmaceutically acceptable salt thereof. In certain embodiments, the compound is a compound in Table 1, 1-A, 24, or 25, or a pharmaceutically acceptable salt thereof. In certain embodiments, the compound is a compound in Table 26, or a pharmaceutically acceptable salt Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

The synthetic route illustrated in Scheme 1 is a general method for preparing substituted 1,2,3,4-tetrahydroquinoline compounds F and G. Reaction of aniline A with diethyl 2-(ethoxymethylene)malonate B followed by thermally induced cyclization with acid affords the substituted ethyl 4-oxo-1,4-dihydroquinoline-3-carboxylate C. Treatment of compound C with phosphoryl trichloride affords the ethyl 4-chloroquinoline-3-carboxylate D. Reduction with borane in pyridine or with transition metal-mediated hydrogenation affords the ethyl 1,2,3,4-tetrahydroquinoline-3-carboxylate E, which can be reacted with a sulphonyl chloride or sulfamoyl chloride to provide the substituted sulfonamide-tetrahydroquinoline F. The ester group of F can be hydrolyzed to afford the substituted 1,2,3,4-tetrahydroquinoline-3-carboxylic acid G. Compound G can be obtained in enanteriomerically enriched form by chiral separation techniques described in the literature for carboxylic acids.

The reaction procedures in Scheme 1 are contemplated to be amenable to preparing a wide variety of 3-substituted 1,2,3,4-tetrahydroquinoline compounds having different substituents at the R, X, and 3-positions. For example, numerous substituted anilines are known in the literature and/or are commercially available or readily prepared from nitroaromatic compounds. Furthermore, if a functional group on a molecule would not be amenable to a reaction condition described in Scheme 1, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, 2$^{nd}$ ed.; Wiley: New York, 1991, for further description of protecting chemistry and strategies. For example, if X is OMe, the methyl moiety can be removed from F with boron tribromide to afford a 6- or 7-hydroxytetrahydroquinoline. The resulting compound can be subjected to either alkylation with halides or with the Mitsunobu reaction to afford a wide variety of OR groups as X. In other embodiments, the —OH may be converted to triflate and be subjected to Pd-mediated catalyzed reactions to afford a wide variety of carbon linked substituents. In certain other embodiments, the ester group in compound F can be converted to another functional group using standard functional group manipulation procedures known in the art. See, for example, "Comprehensive Organic Synthesis" (B. M. Trost & I. Fleming, eds., 1991-1992).

SCHEME 1.

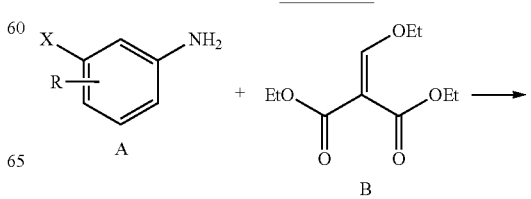

85

-continued

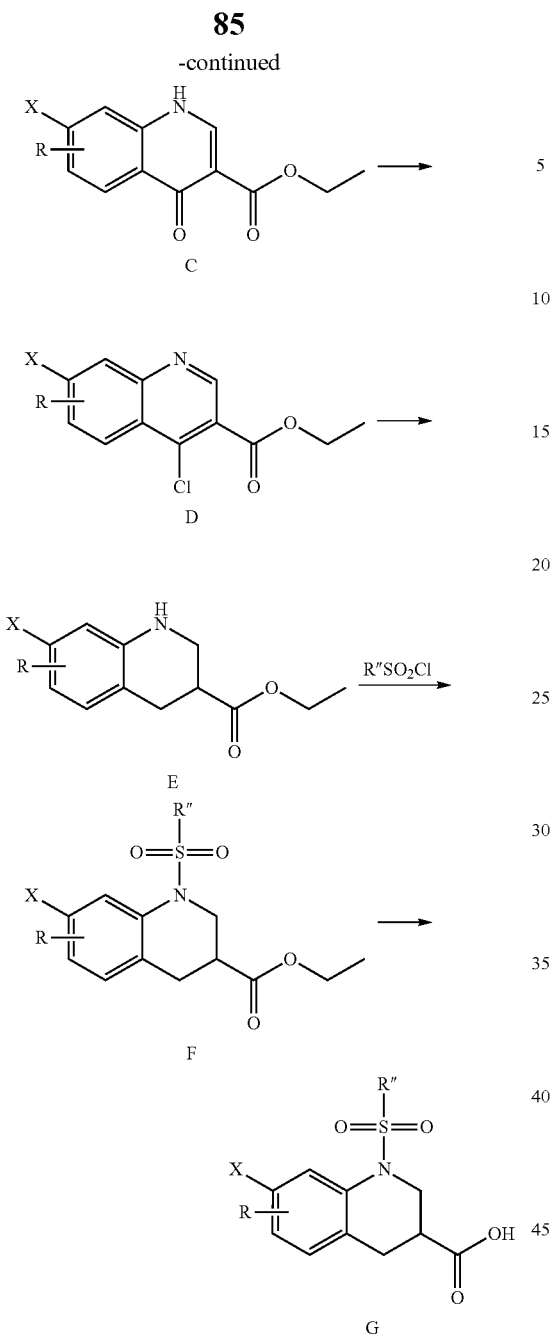

R may be, for example, hydrogen or a substituent, such as methyl or halogen;
X may be for example an O-alkylene-cycloalkyl; and
R″ may be an aromatic or heteroaromatic substituent.

Scheme 2 illustrates a general method for preparing substituted 1,2,3,4-tetrahydroquinoline compound F. Condensation of a substituted 2-nitrobenzaldehyde A with diethyl malonate affords α-β-unsaturated diester B. Reduction of B with sodium borohydride affords diester C. Reduction of the nitro moiety of C with either metal-mediated hydrogenation or dissolving metal reductions (for example Zn/AcOH or Fe in HCl) affords 2-oxo-1,2,3,4-tetrahydroquinoline-3-carboxylate D. Selective reduction of the 2-keto moiety of D affords ethyl 1,2,3,4-tetrahydroquinoline-3-carboxylate E. The ester group in E can be converted to additional functional groups via the methodology described above in connection with Scheme 1.

86

SCHEME 2.

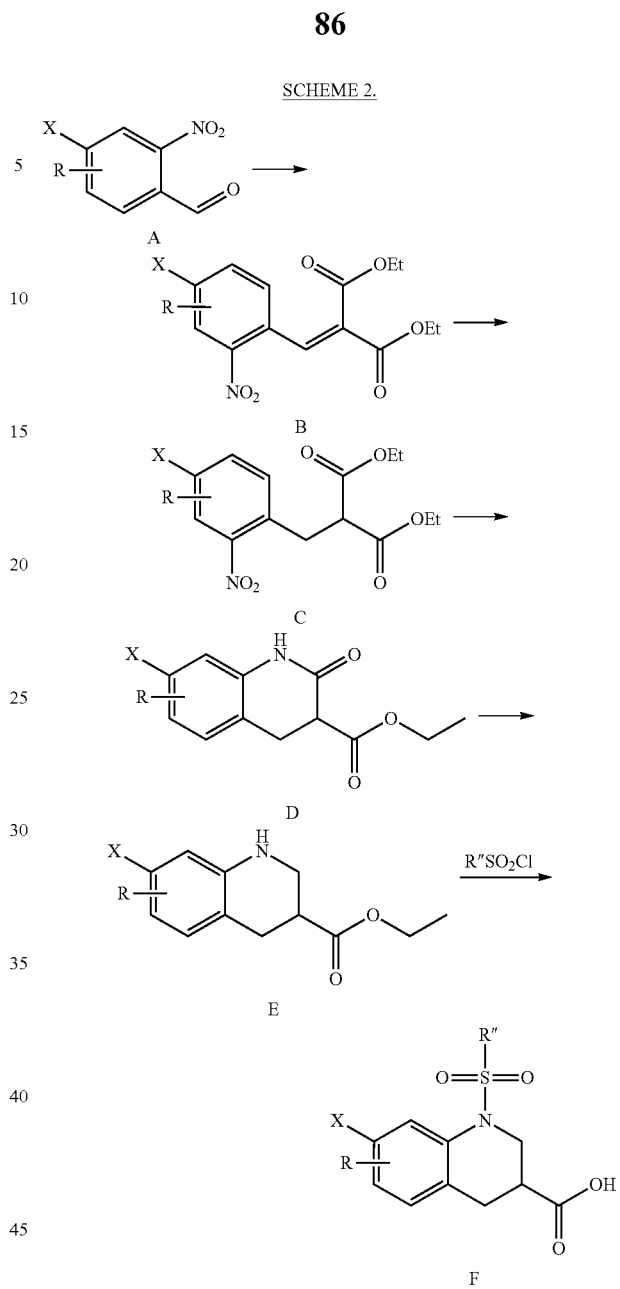

R may be, for example, hydrogen or a substituent, such as methyl or halogen;
X may be for example an O-alkylene-cycloalkyl; and
R″ may be an aromatic or heteroaromatic substituent.

Scheme 3 illustrates a general method for preparing substituted (R)-2-alkyl-1-(aryl or heteroaryl sulfonyl)-1,2-dihydroquinoline-3-carboxylic acids D. A tandem Michael-aldol dehydration of a substituted N-(2-formylphenyl)(aryl or heteroaryl)sulfonamide A with a 3-substituted acrylaldehyde B catalyzed by the (S)-diphenylprolinol triethyl silyl ether (see, for example, W. Wang et al., Org. Lett. 9: 965-968, 2007; and A. Cordova et al., Adv. Synth. Catal. 349: 827-832, 2007) affords substituted (R)-2-alkyl-1-(aryl or heteroaryl sulfonyl)-1,2-dihydroquinoline-3-carbaldehyde C. Oxidation (see, for example, Y. K. Bae et al. Synlett. 24: 1848-1850, 2013; S. J. Williams et al. in WO2011/047432) of the aldehyde in C affords substituted (R)-2-alkyl-1-(aryl or heteroaryl sulfonyl)-1,2-dihydroquinoline-3-carboxylic acid D.

SCHEME 3.

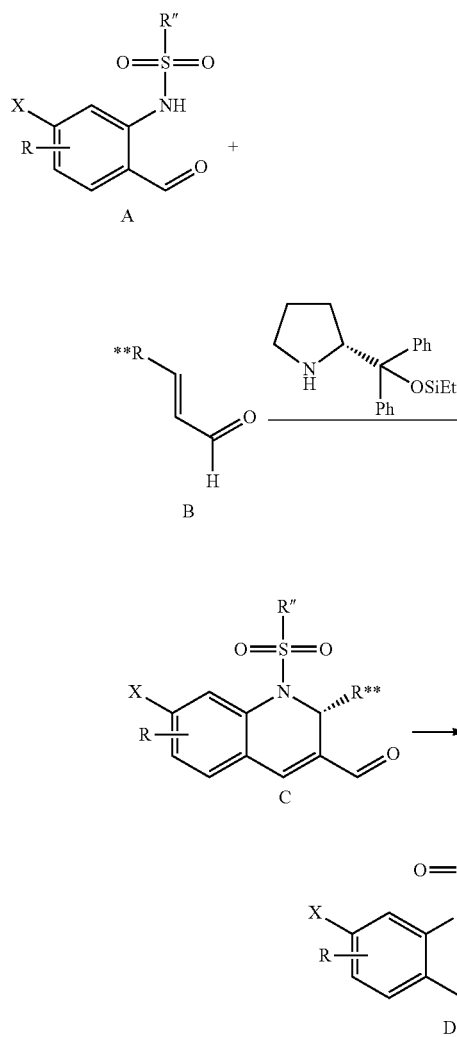

Scheme 4 illustrates a general method for preparing substituted (R)-(2-alkyl-1-(aryl or heteroaryl sulfonyl)-1,2-dihydroquinolin-3-yl)alkyl alcohol B. Reduction of the aldehyde in compound A with sodium borohydride in the presence of cerium (III) chloride (Y. Hamada et al., *Tetrahedron* 64: 11568-11579, 2008) yields compound B where R' is hydrogen. Addition of an alkyl magnesium or alkyl lithium halide in the presence of cerium (III) chloride affords the secondary alcohol B where R' is a lower alkyl (i.e., $C_{1-6}$ alkyl).

Scheme 5 illustrates a general procedure for preparing substituted (R)-3-(2-alkyl-1-(aryl or heteroaryl sulfonyl)-1,2-dihydroquinolin-3-yl)propanoic acid D. Treatment of allylic alcohol A with methane sulfonyl halide (or a tosyl halide or triflic anhydride may be used to activate the hydroxyl group, and alternatively the hydroxyl group may be converted to an allylic halide by methods known in the literature) affords compound B where the allylic hydroxyl is activated with a leaving group. When R' is the same as R", an ester of an appropriate substituted (or unsubstituted) acetic acid is converted to an anion with an appropriate base (e.g., LDA, lithium hexamethyldisilazide, etc.) and is alkylated with B to yield compound C where variable Q is oxygen. When R' is not the same as R", various chiral enolate chemistry methods from the literature may be used to provide a chiral acid (where variable Q may be, for example, oxygen or N(R''')). For example, the anion of an acyloxazolidinone may be be utilized. Removal of the chiral auxiliary with an appropriate base (e.g., potassium carbonate, lithium hydroxide in the presence of peroxide) or an acid (for tert-butyl esters) affords (R)-3-(2-alkyl-1-(aryl or heteroaryl sulfonyl)-1,2-dihydroquinolin-3-yl)propanoic acid D.

-continued

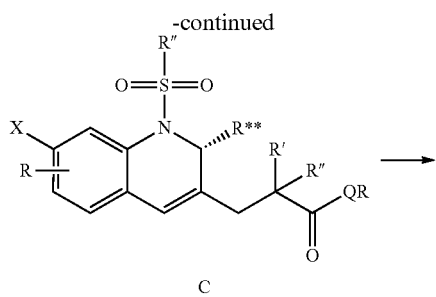

C

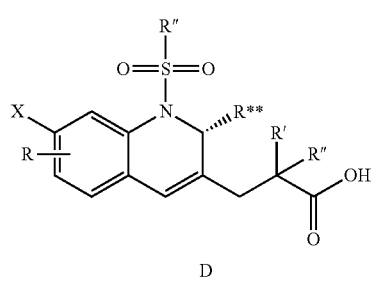

D

Scheme 6 illustrates a general procedure for preparing substituted (R)-(2-alkyl-1-(aryl or heteroarylsulfonyl)-1,2-dihydroquinolin-3-yl)alkylamines C and D. Mitsunobu reaction (D. L. Hughes et al. *Organic Reactions* 42: 1992) of allylic alcohol A with phthalamide affords substituted phthamide B. Treatment of compound B with hydrazine in an appropriate solvent (for example, ethanol or isopropanol; see, for example, H. Itoh et al. in *J. Org Chem.* 43: 2320, 1978) affords (R)-(2-alkyl-1-(aryl or heteroarylsulfonyl)-1,2-dihydroquinolin-3-yl)alkylamine C. Reductive amination of the amine group in compound C (C. A. Maryanoff et al. *J. Org. Chem.* 61: 3849-3860, 1996) affords (R)-(2-alkyl-1-(aryl or heteroarylsulfonyl)-1,2-dihydroquinolin-3-yl)alkylamine D.

-continued

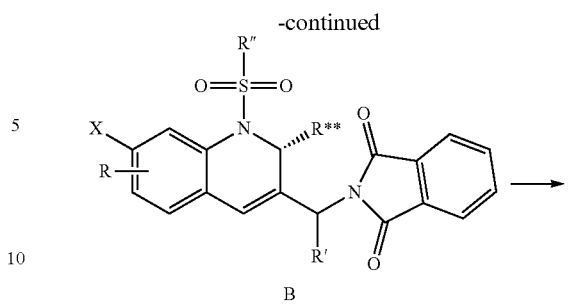

B

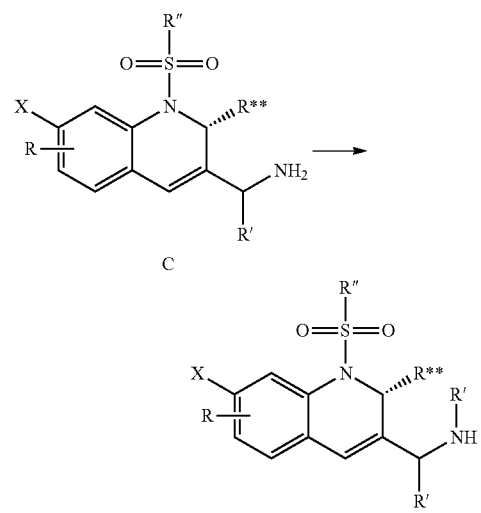

Scheme 7 illustrates a general procedure for preparing substituted (R)—N-((2-alkyl-1-(aryl or heteroarylsulfonyl)-1,2-dihydroquinolin-3-yl)alkyl)amide B, substituted (R)—N-((2-alkyl-1-(aryl or heteroarylsulfonyl)-1,2-dihydroquinolin-3-yl)alkyl)carbamate C, substituted (R)—N-((2-alkyl-1-(aryl or heteroarylsulfonyl)-1,2-dihydroquinolin-3-yl)alkyl)ureas or substituted (R)—N-((2-alkyl-1-(aryl or heteroarylsulfonyl)-1,2-dihydroquinolin-3-yl)alkyl)thiourea D, substituted (R)—N-((2-alkyl-1-(aryl or heteroarylsulfonyl)-1,2-dihydroquinolin-3-yl)alkyl)sulfonamide E, and substituted (R)—N-((2-alkyl-1-(aryl or heteroarylsulfonyl)-1,2-dihydroquinolin-3-yl)alkyl)sulfamide F. Reaction of substituted (R)-(2-alkyl-1-(aryl or heteroarylsulfonyl)-1,2-dihydroquinolin-3-yl)alkylamine A with an appropriate base and an acyl halide affords amide B. Alternatively, a coupling agent (e.g., a carbodiimide, PyBOP, treatment of the acid with a chloroformate to make a mixed anhydride, etc.) may be utilized to couple a wide variety of acids to form amide B. The amine A may also be coupled with a choroformate to afford compound C; with an isocyanate, carbamoyl choride, or isothiocyanate to afford D; with a sulfonyl halide to afford E; or with a sulfamoyl halide to afford F.

SCHEME 6.

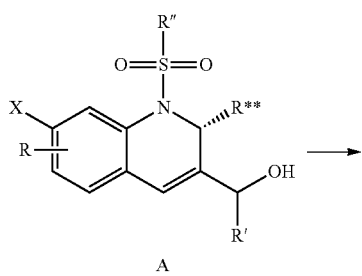

A

SCHEME 7.

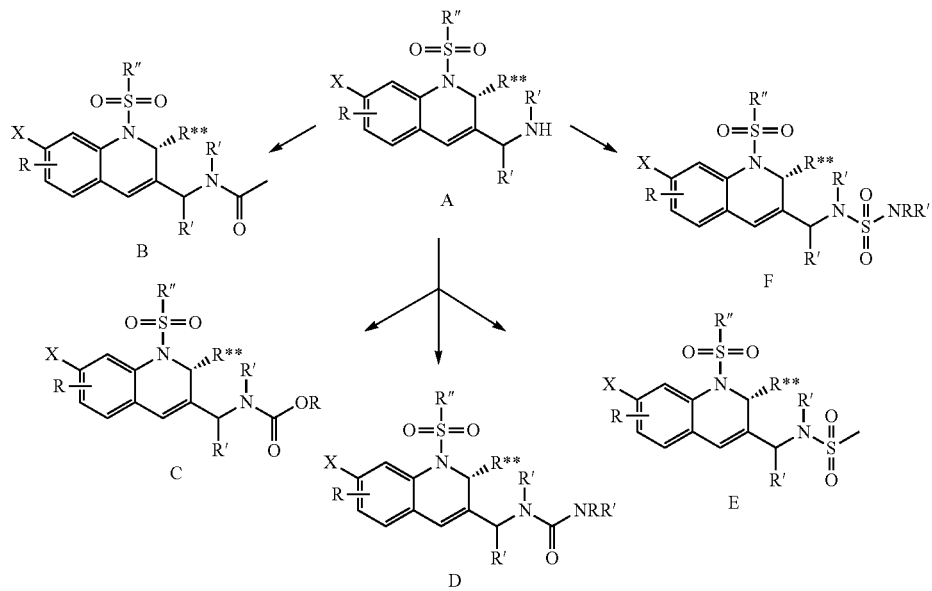

Scheme 8 illustrates a general method of preparing substituted cis-(2R,3)-3-substituted-2-alkyl-1-(aryl or heteroarylsulfonyl)-1,2,3,4-tetrahydroquinoline B. Hydrogenation of the substituted (R)-2-alkyl-1-(aryl or heteroarylsulfonyl)-1,2-dihydroquinoline A prepared via the above methods in the presence of a catalyst affords the substituted cis-(2R,3)-3-substituted-2-alkyl-1-(aryl or heteroarylsulfonyl)-1,2,3,4-tetrahydroquinoline B. The choice of the catalyst depends on the substituents X and R. In cases where dehalogenation or reductive removal of benzylic heteroatom is not an issue, Pd or Pt on C may be utilized. In other cases Rh and/or a heterogeneous catalyst which does not reduce these functionalities is more appropriate as is known to those skilled in the art.

a substituted acrylate B affords substituted 3,4-dihydroquinolin-2-one C (N. Jiao et al. *Tetrahedron* 65: 1982-1987, 2009). Reduction of the amide group in C with a hydride (e.g., a borane or lithium aluminum hydride) affords substituted 1,2,3,4-tetrahydroquinoline D. Sulfonylation of D with a sulfonyl halide yields the substituted 3-substituted-1-(aryl or heteroarylsulfonyl)-1,2,3,4-tetrahydroquinoline E.

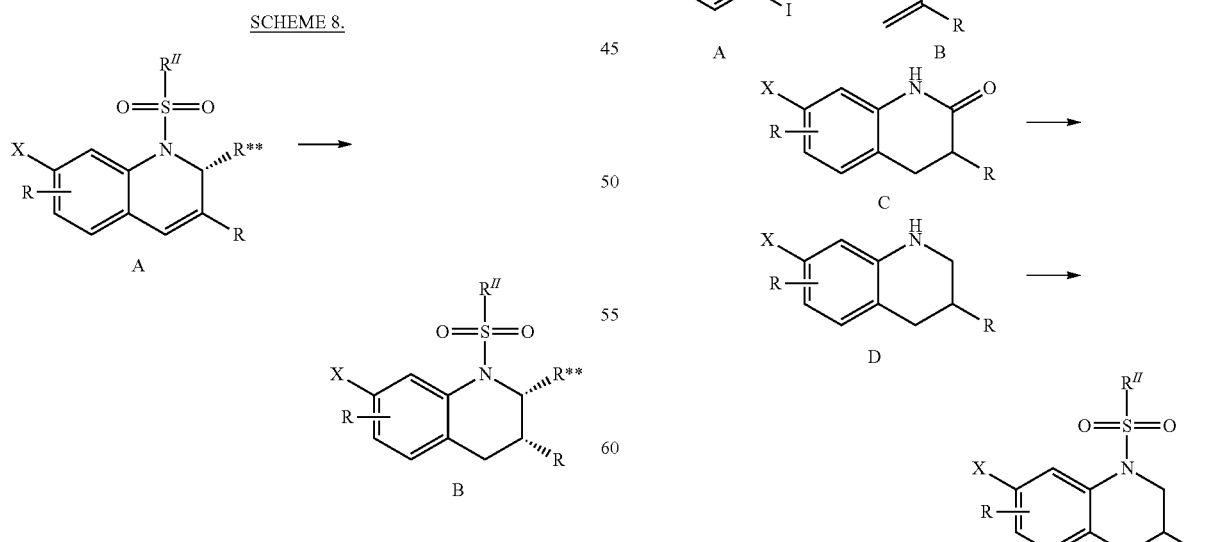

Scheme 9 is an alternative general method to prepare substituted 3-substituted-1-(aryl or heteroarylsulfonyl)-1,2,3,4-tetrahydroquinoline E. A tandem reaction combining radical and ionic cyclization of an halogenated aniline A and Scheme 10 illustrates an alternative general method to prepare chiral substituted 3-substituted-1-(aryl or heteroarylsulfonyl)-1,2,3,4-tetrahydroquinolines. Alkylation of an acylated oxazolidinedione B with a 2-nitrobenzylic halide A affords with high diastereomeric excess the 3-arylpropionamide C. Reduction of C with dissolving metal conditions affords chiral substituted 3,4-dihydroquinolin-2-one D which can be elaborated to the substituted 3-substituted-1-(aryl or heteroarylsulfonyl)-1,2,3,4-tetrahydroquinolines E and F based on procedures described above.

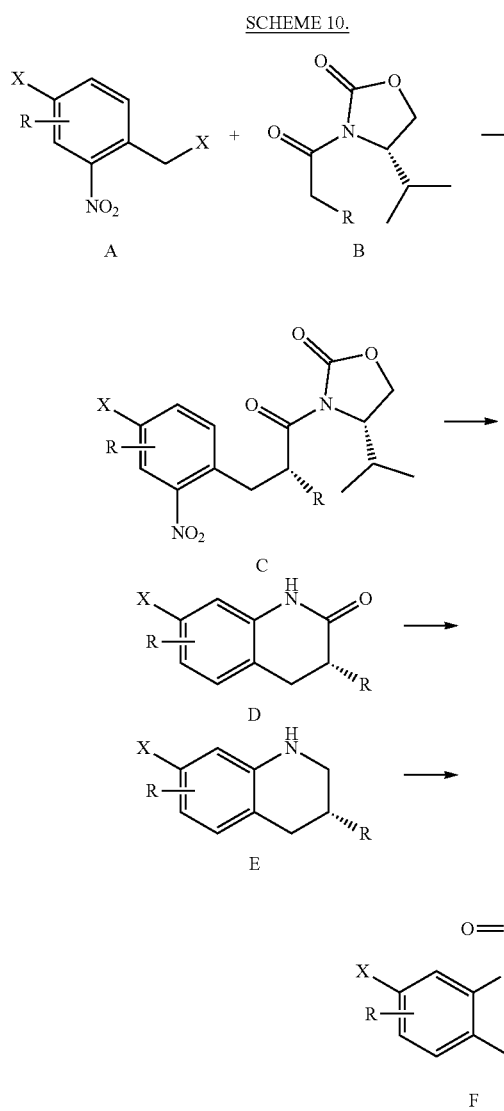

SCHEME 10.

Scheme 11 illustrates an alternative general method of preparing substituted cis-2,3-disubstituted-1-(aryl or heteroarylsulfonyl)-1,2,3,4-tetrahydroquinoline E. Alkylation of β-ketoester B with 2-nitrobenzylic halide A affords substituted 2-(2-nitrobenzyl)-β-ketoester C. Reduction of C affords substituted ethyl cis-2-alkyl-1,2,3,4-tetrahydroquinoline-3-carboxylate D (R. A. Bunce et al. *J. Heterocyclic Chem.* 44: 1059-1064, 2007). This material can be sulfonylated as described above to afford the substituted cis-2,3-disubstituted-1-(aryl or heteroarylsulfonyl)-1,2,3,4-tetrahydroquinoline E.

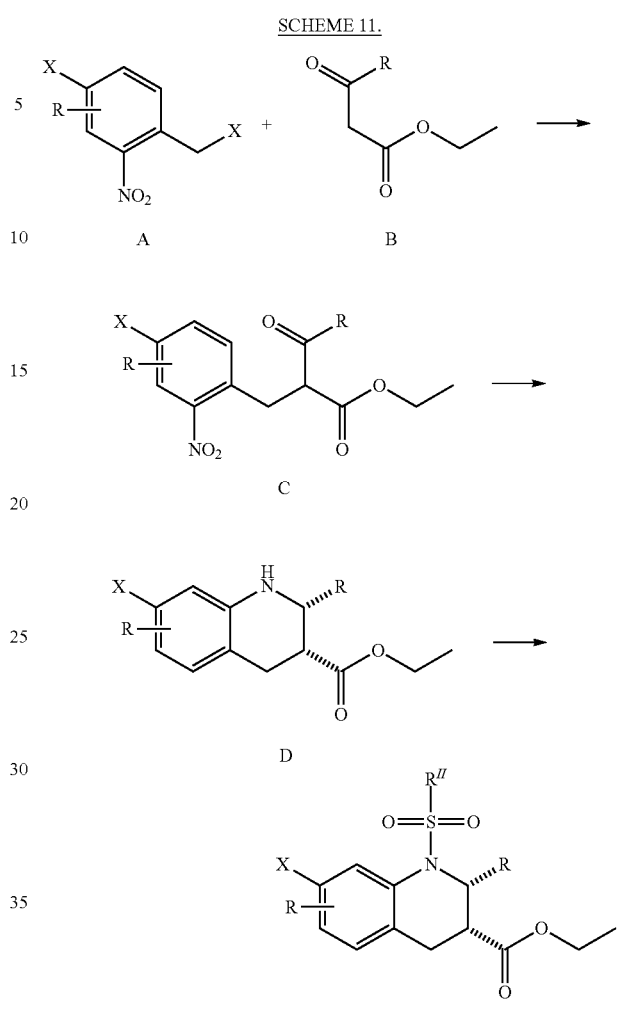

SCHEME 11.

Scheme 12 illustrates a general method of preparing chiral substituted 1-(aryl or hetereoarylsulfonyl)-1,2,3,4-tetrahydroquinoline E substituted at the 3-position with an oxygen bearing group. Wittig reaction of 2-nitroaldehyde A forms α,β-unsaturated ester B, which is subjected to Os-catalyzed asymmetric dihydroxylation with the (DHQ)₂-PHAL ligand (see, for example, K. B. Sharpless et al. *Chem. Rev.* 94: 2483-2547, 1994) followed by treatment of the diol with thionyl chloride to form cyclic sulfite C (see, for example, K. B. Sharpless et al. *J. Am. Chem. Soc.* 110: 7538-7539, 1988). Sulfite C undergoes a one-pot cobalt chloride catalyzed reductive cyclization with sodium borohydride (see, for example, A. Sudalai et al. *Organic Letters* 11: 803-806, 2009) to form the substituted chiral 3-hydroxy-1,2,3,4-tetrahydroquinoline D. This material is sulfonylated as described above to afford chiral substituted 1-(aryl or hetereoarylsulfonyl)-3-hydroxy-1,2,3,4-tetrahydroquinoline E. The pendant hydroxyl may be alkylated (for example with 2-chloroacetic acid). When using a different, suitable ligand in the chiral osmylation, the enantiomers of C and then D and E can be produced. The hydroxyl group in E can be mesylated and displaced with azide, and the resulting azido product reduced to afford access to a wide variety of chiral 3-aminosubsituted-1,2,3,4-tetrahydroquinolines.

SCHEME 12.

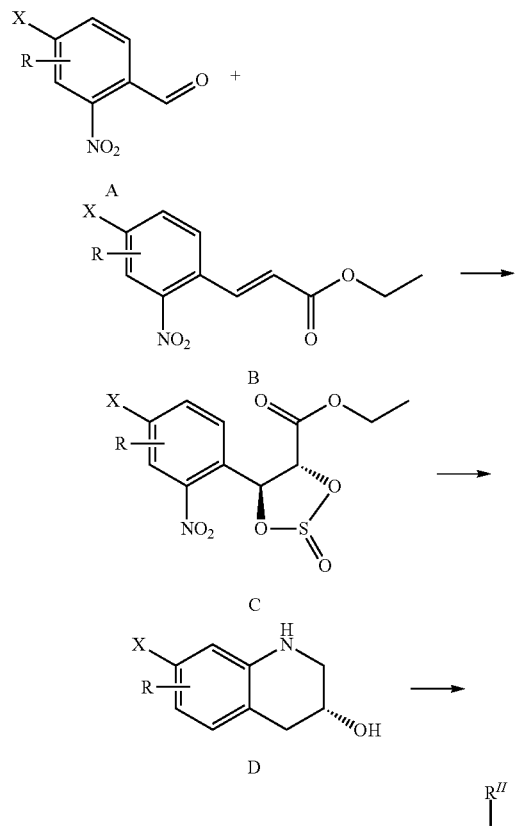

Scheme 13 illustrates a general method of forming substituted (E)-7-(2-aryl-alken-1-en-1-yl)-1-(aryl or heteroarylsulfonyl)-1,2,3,4-tetrahydroquinolines, substituted (E)-6-(2-aryl-alken-1-en-1-yl)-4-(aryl or heteroarylsulfonyl)-3,4-dihydro-2H-benzo[b][1,4]oxazines, and substituted (E)-N-alkyl-N-(3-(2-aryl-alken-1-en-1-yl)phenyl)(arene or heteroarene)sulfonamides. Copper(I)-catalyzed carboboration (R. Alfaro et al. *J. Am. Chem. Soc.* 134: 15165-15168, 2012) of an aryl-alkyne affords tri- and tetrasubstitued vinylboronates that are suitable for Pd-mediated stereoselective addition to the appropriate 7-halo or triflate-1,2,3,4-tetrahydroquinoline (variable A is CRR'), or 6-halo or triflate-3,4-dihydro-2H-benzo[b][1,4]oxazine (variable A is O) to afford the final product.

SCHEME 13.

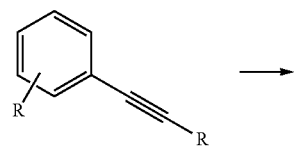

-continued

Scheme 14 illustrates a general method of forming chiral substituted 7-cyclopropyl-1-(aryl or heteroarylsulfonyl)-1,2,3,4-tetrahydroquinolines, 6-cyclopropyl-4-(aryl or heteroarylsulfonyl)-3,4-dihydro-2H-benzo[b][1,4]oxazines, or N-(3-cyclopropylphenyl)-N-alkyl(aryl or heteroaryl)sulfonamides C. Chiral cyclopropylboronic acids (M.-Z. Deng et al. *Angew. Chem. Ed.* 37: 2845-2847, 1998) A are added to the appropriate haloarenes or triflates B to afford compound C.

SCHEME 14.

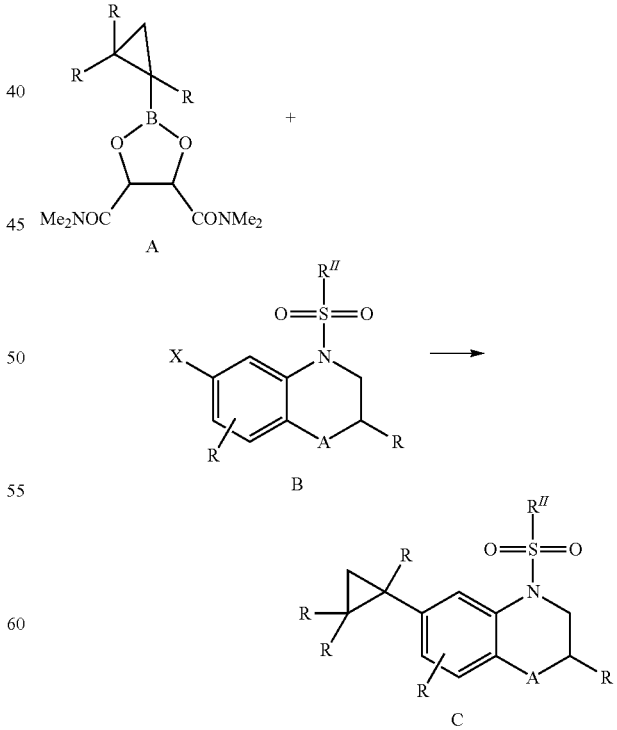

Scheme 15 illustrates a general method of forming chiral 3-substituted-1-(aryl or heteroarylsulfonyl)-1,2,3,4-tetrahydroquinolines (A is CRR') or chiral substituted benzoxazines (A is O). Esterification of the carboxylic acid A with a chiral allylic alcohol forms allylic ester B. Treatment of the enolate of ester B with TMSCl, followed by a Claisen rearrangement (see, for example, J. Kallmerten et al. *J. Org. Chem.* 52: 3889-3901, 1987) affords carboxylic acid C. Esterification of carboxylic acid C with an alcohol followed by a dissolving metal reduction affords lactam D. Reduction of lactam D with borane or lithium aluminum hydride affords tetrahydroquinoline or benzoxazine E, which is sulfonylated to afford the chiral 3-substituted-1-(aryl or heteroarylsulfonyl)-1,2,3,4-tetrahydroquinoline (A is CRR') or chiral substituted benzoxazine (A is O) F. The alkene of F, may be converted to other functional groups (for example to a COOH by oxidation).

Scheme 16 is a general method for preparing various substituted benzoxazine compounds. Reaction of aryl sulfonamide A with an epoxide provides benzoxazine B.

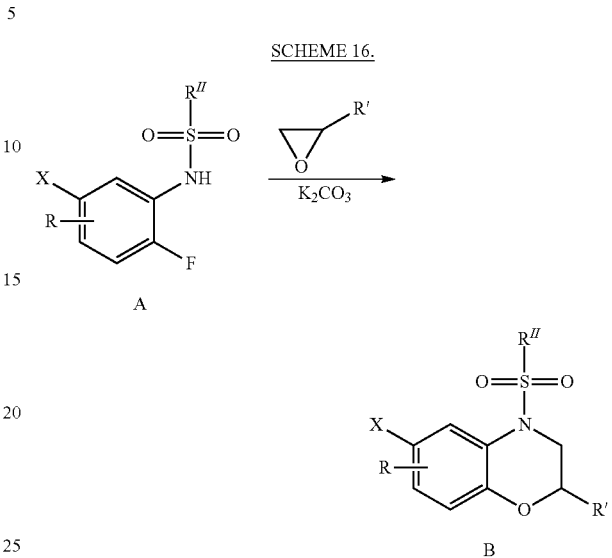

Scheme 17 is another general method for preparing various substituted benzoxazine compounds. Reaction of a 2-fluoro-nitrobenzene A with a 2-hydroxyester B provides 2-O-arylacetic acid ester C. Reduction of the nitro moiety in C with a dissolving metal in an acid forms benzoxazinone D. The amide group in benzoxazinone D can be reduced using, for example, lithium aluminum hydride (LiAlH$_4$) or a borane to provide benzoxazine E, which is treated with a sulfonyl halide and base to afford sulfonylated benzoxazine F.

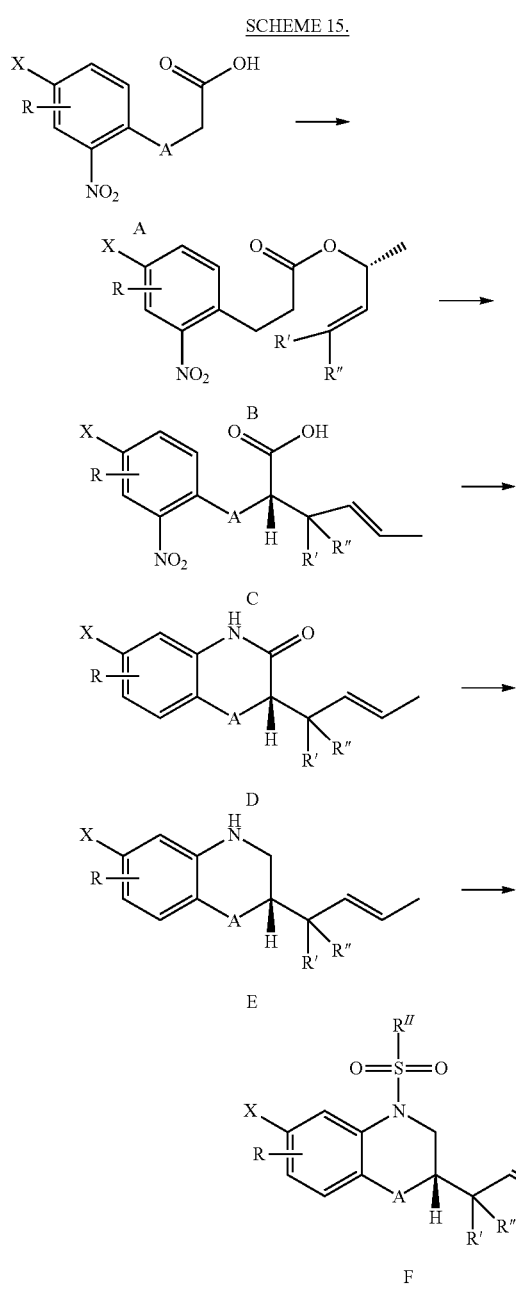

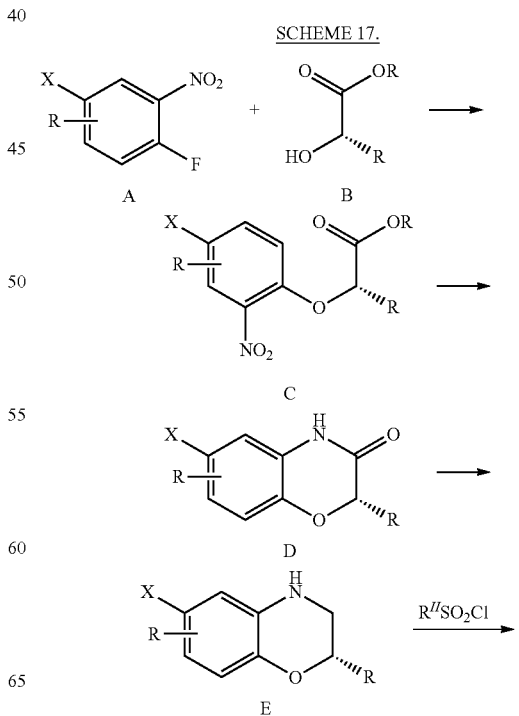

99
-continued

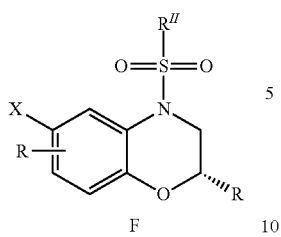

Scheme 18 is a general method for preparing various substituted benzoxazine compounds. Mitsunobu addition of sulfonamide A to chiral α-hydroxyester B affords O-aryl ether C. Treatment of compound C with DIBAL affords aldehyde D, to which vinyl magnesium bromide adds to form the anti-aminoalcohol E (see, for example, D. Gryko et al. *Tetrahedron: Asymmetry* 8: 4059-4067, 1997). Treatment of compound E with base affords benzoxazine F. The vinyl moiety in F is then converted to other alkenes via olefin metathesis chemistry which can be reduced to substituted alkanes, or oxidized to a hydroxyl group, a diol, a carboxylic acid, or other functional group.

SCHEME 18.

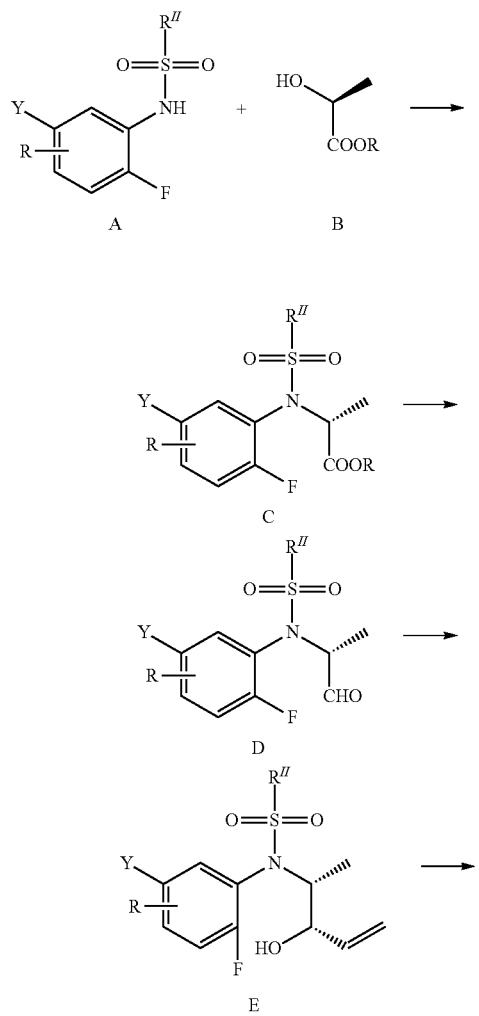

100
-continued

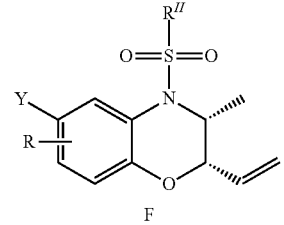

Scheme 19 is a general method for preparing various thioether substituted compounds. Palladium-mediated addition of a thiol A in presence of a base (such as Hunig's base) and a ligand (such as Xantphos) to bromide B (X' is Br) affords thioether C.

SCHEME 19.

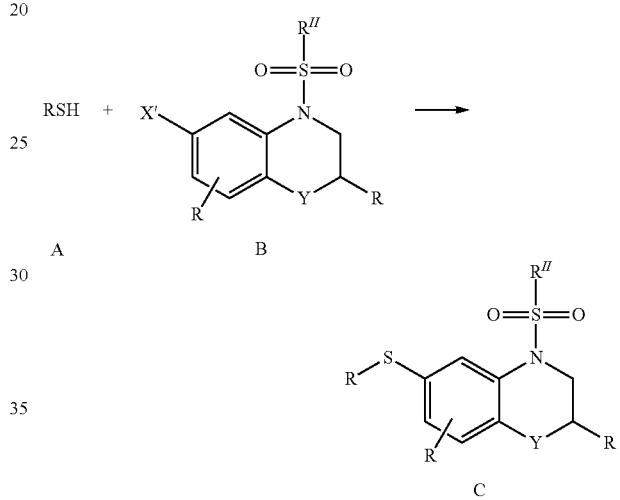

Part II: Tetrahydronaphthalene Sulfonyl and Related Compounds

Another aspect of the invention provides a compound represented by Formula II:

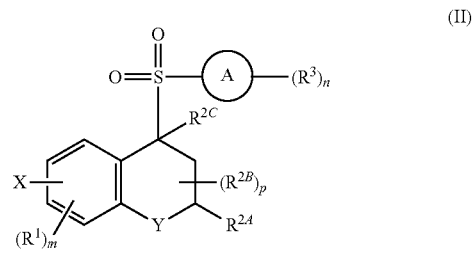

(II)

or a pharmaceutically acceptable salt thereof, wherein:

A is phenylene, 5-6 membered heteroarylene, or $C_{3-6}$ heterocycloalkylene;

$R^1$ represents independently for each occurrence halogen, $C_{1-6}$ alkyl, $C_{1-6}$ haloalkyl, or $C_{3-6}$ cycloalkyl;

$R^{2A}$ is one of the following:

(i) hydrogen, $C_{1-6}$ alkyl, $C_{1-3}$ haloalkyl, $C_{3-6}$ cycloalkyl, —($C_{1-6}$ alkylene)-($C_{3-6}$ cycloalkyl), —O—($C_{1-6}$ alkylene)-$CO_2R^4$, —O—($C_{1-6}$ alkylene)-C(O)—($C_{1-6}$ alkyl), —N($R^4$)—($C_{1-6}$ alkylene)-$CO_2R^4$, or —N(R⁴)—(C₁₋₆ alkylene)-C(O)—(C₁₋₆ alkyl), wherein the C₁₋₆ alkyl, C₃₋₆ cycloalkyl, and C₁₋₆ alkylene are optionally substituted with 1 or 2 substituents independently selected from the group consisting of —CO₂R⁴, —C(O)N(R⁴)(R⁵), —C(O)—N(R⁴)—(C₁₋₄ alkylene)-CO₂R⁴, —N(R⁴)C(O)R⁸, —CN, halogen, hydroxyl, C₁₋₆ alkoxy, C₁₋₆ haloalkoxy, C₁₋₆ haloalkyl, —N(R⁴)(R⁵), —N(R⁴)C(O)N(R⁴)(R⁵), —N(R⁴)CO₂R⁹, —N(R⁴)S(O)₂R⁹, and —N(R⁴)S(O)₂N(R⁴)(R⁵); or (ii) —CO₂R⁴, —N(R⁴)C(O)R⁹, —N(R⁴)CO₂R⁹, —N(R⁴)C(O)N(R⁴)(R⁵), —N(R⁴)C(O)N(R⁴) (heteroaryl), —N(R⁴)S(O)₂R⁹, —N(R⁴)(R⁵), or —OH;

R²ᴮ is C₁₋₆ alkyl, C₁₋₃ haloalkyl, or fluoro;

R²ᶜ is hydrogen or C₁₋₆ alkyl;

R³ represents independently for each occurrence hydrogen, C₁₋₆ haloalkyl, halogen, hydroxyl, C₁₋₆ alkyl, C₃₋₆ cycloalkyl, C₁₋₆ alkoxy, C₁₋₆ haloalkoxy, —N(R⁴)(R⁸), —O—(C₁₋₆ hydroxyalkyl), or —O—(C₁₋₆ alkylene)-CO₂R⁴; or two vicinal occurrences of R³ are taken together with intervening atoms to form a 4-6 membered ring;

R⁴ and R⁵ each represent independently for each occurrence hydrogen, C₁₋₆ alkyl, or C₃₋₆ cycloalkyl; or an occurrence of R⁴ and R⁵ attached to the same nitrogen atom are taken together with the nitrogen atom to which they are attached to form a 3-8 membered heterocyclic ring;

R⁶ and R⁷ each represent independently for each occurrence hydrogen, fluoro, or C₁₋₆ alkyl, or R⁶ and R⁷ are taken together with the carbon atom to which they are attached to form a 3-6 membered carbocyclic ring; or R⁶ and a vicinal occurrence of R²ᴮ are taken together to form a bond;

R⁸ represents independently for each occurrence C₁₋₆ alkyl, C₃₋₆ cycloalkyl, —(C₁₋₆ alkylene)-(C₃₋₆ cycloalkyl), or aryl, each of which is optionally substituted with 1, 2, or 3 substituents independently selected from the group consisting of halogen, hydroxyl, or —CO₂R⁴; or R⁸ is —CO₂R⁴;

R⁹ represents independently for each occurrence C₁₋₆ alkyl, C₃₋₆ cycloalkyl, —(C₁₋₆ alkylene)-(C₃₋₆ cycloalkyl), C₁₋₆ haloalkyl, or C₁₋₆ hydroxyalkyl;

X is one of the following:

(i) —O-aralkyl, —O-heteroaralkyl, —O-phenyl, —O-heteroaryl, —O-(partially unsaturated bicyclic carbocyclyl), —O—(C₁₋₆ alkylene)-(C₃₋₆ cycloalkyl), —O—(C₃₋₆ cycloalkyl), —N(R⁴)-aralkyl, —N(R⁴)-phenyl, —N(R⁴)-(partially unsaturated bicyclic carbocyclyl), or —N(R⁴)—(C₁₋₆ alkylene)-(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

(ii) —S-aralkyl, —S-heteroaralkyl, —S-phenyl, —S-heteroaryl, —S-(partially unsaturated bicyclic carbocyclyl), —S—(C₁₋₆ alkylene)-(C₃₋₆ cycloalkyl), or —S—(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

(iii) —(C₂₋₆ alkenylene)-phenyl, —(C₂₋₆ alkenylene)-heteroaryl, —(C₂₋₆ alkenylene)-(partially unsaturated 8-10 membered bicyclic ring containing 0-3 heteroatoms), —(C₁₋₆ alkylene)-phenyl, —(C₁₋₆ alkylene)-heteroaryl, —(C₁₋₆ alkylene)-(partially unsaturated bicyclic heterocyclyl), —(C₁₋₆ alkylene)-(partially unsaturated bicyclic oxo-heterocyclyl), —(C₁₋₆ alkylene)-(C₃-C₆ cycloalkyl), -(5-6 membered heterocycloalkylene)-phenyl, or —(C₃₋₆ cycloalkylene)-phenyl, each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

(iv) —(C₂₋₆ alkenylene)-(C₁₋₆ alkyl), —(C₂₋₆ alkenylene)-(C₃₋₆ cycloalkyl), or

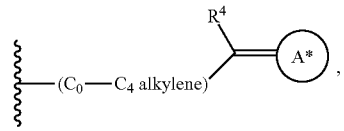

each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹, wherein A* is a 5-8 membered, partially saturated carbocyclic or heterocyclic ring; or (v) —(C₁₋₆ alkylene)-Z¹ or —(C₂₋₆ alkenylene)-Z¹, wherein Z¹ is —O-aralkyl, —O— heteroaralkyl, —O-phenyl, —O-heteroaryl, —O-(partially unsaturated bicyclic carbocyclyl), —O—(C₁₋₆ alkylene)-(C₃₋₆ cycloalkyl), —O—(C₃₋₆ cycloalkyl), —N(R⁴)-aralkyl, —N(R⁴)-phenyl, —N(R⁴)-(partially unsaturated bicyclic carbocyclyl), —N(R⁴)—(C₁₋₆ alkylene)-(C₃₋₆ cycloalkyl), or —N(R⁴)—(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

Y is —C(R⁶)(R')—, —O—, —C(O)—, or —S(O)ₚ—;

m and p each represent independently for each occurrence 0, 1, or 2; and n is 1, 2, or 3.

In certain embodiments, A is phenylene or 5-6 membered heteroarylene.

In certain embodiments, R¹ represents independently for each occurrence halogen or C₁₋₆ alkyl. In certain other embodiments, R¹ is fluoro, chloro, methyl, or trifluoromethyl.

In certain embodiments, R²ᴬ is C₁₋₆ alkyl substituted with 1 or 2 substituents independently selected from the group consisting of —CO₂R⁴, —C(O)N(R⁴)(R⁵), —C(O)—N(R⁴)—(C₁₋₄ alkylene)-CO₂R⁴, —N(R⁴)C(O)R⁸, —CN, halogen, hydroxyl, C₁₋₆ alkoxy, C₁₋₆ haloalkoxy, C₁₋₆ haloalkyl, —N(R⁴)(R⁵), —N(R⁴)C(O)N(R⁴)(R⁵), —N(R⁴)CO₂R⁹, —N(R⁴)S(O)₂R⁹, and —N(R⁴)S(O)₂N(R⁴)(R⁵).

In certain embodiments, R³ represents independently for each occurrence hydrogen, C₁₋₆ haloalkyl, halogen, hydroxyl, C₁₋₆ alkyl, C₃₋₄ cycloalkyl, C₁₋₆ alkoxy, or C₁₋₆ haloalkoxy.

In certain embodiments, R⁴ and R⁵ each represent independently for each occurrence hydrogen, C₁₋₆ alkyl, or C₃₋₆ cycloalkyl; or an occurrence of R⁴ and R⁵ attached to the same nitrogen atom are taken together with the nitrogen atom to which they are attached to form a 3-8 membered heterocyclic ring, wherein the heterocyclic ring is substituted with 1, 2, or 3 substituents independently selected from the group consisting of halogen, C₁₋₆ haloalkyl, C₁₋₆ alkyl, $C_{3-6}$ cycloalkyl, $C_{1-6}$ alkoxy, $C_{1-6}$ haloalkoxy, hydroxyl, cyano, oxo, —$CO_2R^{10}$, —$C(O)R^9$, —$SO_2R^9$, —$N(R^{10})C(O)R^{12}$, and —$C(O)N(R^{10})(R^{11})$; wherein $R^{10}$ and $R^{11}$ each represent independently for each occurrence hydrogen or $C_{1-6}$ alkyl, or $R^{10}$ and $R^{11}$ are taken together with the carbon atom to which they are attached to form a 3-6 membered carbocyclic ring; and $R^{12}$ is $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —$CO_2R^{10}$.

In certain embodiments, X is —O-aralkyl, —O-heteroaralkyl, —O-phenyl, —O— heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$.

In certain embodiments, X is —S-aralkyl, —S-heteroaralkyl, —S-phenyl, —S— heteroaryl, —S-(partially unsaturated bicyclic carbocyclyl), —S—($C_{1-6}$ alkylene)-($C_{3-6}$ cycloalkyl), or —S—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$.

In certain embodiments, X is —($C_{2-6}$ alkenylene)-phenyl, —($C_{2-6}$ alkenylene)-heteroaryl, —($C_{2-6}$ alkenylene)-(partially unsaturated 8-10 membered bicyclic ring containing 0-3 heteroatoms), —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), —($C_{1-6}$ alkylene)-($C_3$-$C_6$ cycloalkyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$.

In certain embodiments, X is —($C_{2-6}$ alkenylene)-($C_{1-6}$ alkyl), —($C_{2-6}$ alkenylene)-($C_{3-6}$ cycloalkyl), or

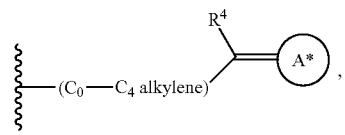

each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$, wherein A* is a 5-8 membered, partially saturated carbocyclic or heterocyclic ring.

In certain embodiments, X is —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$ alkylene)-($C_{3-6}$ cycloalkyl), or —N($R^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —$C(O)R^9$, and —$SO_2R^9$.

In certain embodiments, Y is —$C(R^6)(R^7)$—. In certain other embodiments, Y is —O—. In yet other embodiments, Y is —$S(O)_p$—.

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

Another aspect of the invention provides a compound represented by Formula II-1:

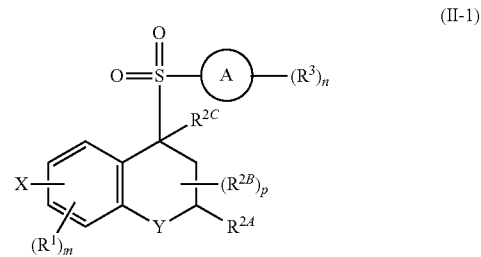

(II-1)

or a pharmaceutically acceptable salt thereof, wherein:

A is phenyl, 5-6 membered heteroaryl, or $C_{3-6}$ heterocycloalkyl;

$R^1$ represents independently for each occurrence halogen, $C_{1-6}$ alkyl, $C_{1-6}$ haloalkyl, or $C_{3-6}$ cycloalkyl;

$R^{2A}$ is hydrogen, $C_{1-6}$ alkyl, $C_{3-6}$ cycloalkyl, —O—($C_{1-6}$ alkylene)-$CO_2R^4$, —O—($C_{1-6}$ alkylene)-$C(O)$—($C_{1-6}$ alkyl), —N($R^4$)—($C_{1-6}$ alkylene)-$CO_2R^4$, or —N($R^4$)—($C_{1-6}$ alkylene)-$C(O)$—($C_{1-6}$ alkyl), wherein the $C_{1-6}$ alkyl, $C_{3-6}$ cycloalkyl, and $C_{1-6}$ alkylene are optionally substituted with 1 or 2 substituents independently selected from the group consisting of —$CO_2R^4$, —$N(R^4)C(O)(C_{1-6}$ alkyl), —CN, halogen, hydroxyl, $C_{1-6}$ alkoxy, $C_{1-6}$ haloalkoxy, $C_{1-6}$ haloalkyl, —$N(R^4)(R^5)$, —$N(R^4)C(O)N(R^4)(R^5)$, —$N(R^4)CO_2$—($C_{1-6}$ alkyl), —$N(R^4)S(O)_2$—($C_{1-6}$ alkyl), and —$N(R^4)S(O)_2N(R^4)(R^5)$; or $R^{2A}$ is —$CO_2R^4$ or —$N(R^4)C(O)(C_{1-6}$ alkyl);

$R^{2B}$ is $C_{1-6}$ alkyl or $C_{1-3}$ haloalkyl;

$R^{2C}$ is hydrogen or $C_{1-6}$ alkyl;

$R^3$ represents independently for each occurrence hydrogen, $C_{1-6}$ haloalkyl, halogen, hydroxyl, $C_{1-6}$ alkyl, $C_{1-6}$ alkoxy, $C_{1-6}$ haloalkoxy, or —O—($C_{1-6}$ alkylene)-OH; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and $R^{2A}$ are taken together to form a bond;

X is one of the following:
(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$haloalkoxy, and cyano;
(ii) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$haloalkoxy, and cyano; or
(iii) —($C_{1-6}$ alkylene)-$Z^1$ or —($C_{2-6}$ alkenylene)-$Z^1$, wherein $Z^1$ is —O-aralkyl, —O— heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$ alkylene)-($C_{3-6}$ cycloalkyl), or —N($R^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

Y is —C($R^6$)($R^7$)—, —O—, —C(O)—, or —S(O)$_p$—;

m and p each represent independently for each occurrence 0, 1, or 2; and n is 0, 1, 2, or 3.

In certain embodiments, A is phenylene or 5-6 membered heteroarylene.

In certain embodiments, $R^1$ represents independently for each occurrence halogen or $C_{1-6}$ alkyl.

In certain embodiments, Y is —C($R^6$)($R^7$)—. In certain other embodiments, Y is —O—. In yet other embodiments, Y is —S(O)$_p$—.

The definitions of variables in Formula II-1 above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

Another aspect of the invention provides a compound represented by Formula II-A:

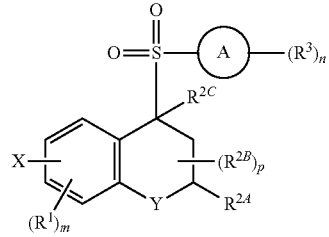

(II-A)

or a pharmaceutically acceptable salt thereof, wherein:

A is phenylene or a 5-6 membered heteroarylene;

$R^1$ represents independently for each occurrence halogen, $C_{1-6}$ alkyl, or $C_{3-6}$ cycloalkyl;

$R^{2A}$ is hydrogen, $C_{1-6}$ alkyl or $C_{3-6}$ cycloalkyl, wherein the $C_{1-6}$ alkyl or $C_{3-6}$ cycloalkyl are optionally substituted with 1 or 2 substituents independently selected from the group consisting of —CO$_2$$R^4$, —N($R^4$)C(O)($C_{1-6}$ alkyl), —CN, halogen, hydroxyl, $C_{1-6}$ alkoxy, $C_{1-6}$ haloalkoxy, $C_{1-6}$ haloalkyl, and —N($R^4$)($R^5$); or $R^{2A}$ is —CO$_2$$R^4$ or —N($R^4$)C(O)($C_{1-6}$ alkyl);

$R^{2B}$ is $C_{1-6}$ alkyl or $C_{1-3}$ haloalkyl;

$R^{2C}$ is hydrogen or $C_{1-6}$ alkyl;

$R^3$ represents independently for each occurrence hydrogen, $C_{1-6}$ haloalkyl, halogen, hydroxyl, $C_{1-6}$ alkyl, $C_{1-6}$ alkoxy, $C_{1-6}$ haloalkoxy, or —O—($C_{1-6}$ alkylene)-OH; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and $R^{2A}$ are taken together to form a bond;

X is one of the following:
(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;
(ii) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy; or
(iii) —($C_{1-6}$ alkylene)-$Z^1$ or —($C_{2-6}$ alkenylene)-$Z^1$, wherein $Z^1$ is —O-aralkyl, —O— heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N(R$^4$)-phenyl, —N(R$^4$)-(partially unsaturated bicyclic carbocyclyl), or —N(R$^4$)—(C$_{1-6}$ alkylene)-(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy;

Y is —C(R$^6$)(R$^7$)—, —O—, or —C(O)—;

m and p are independently 0, 1, or 2; and n is 1, 2, or 3.

In certain embodiments, A is phenylene. In certain other embodiments, A is a 5-6 membered heteroarylene. In yet other embodiments, -A-(R$^3$)$_n$ is one of the following:

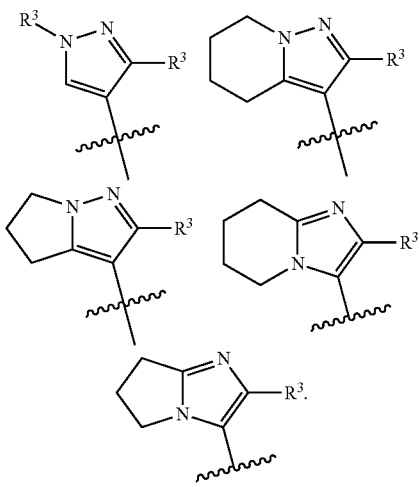

In yet other embodiments, -A-(R$^3$)$_n$ is

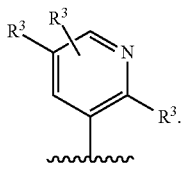

In certain embodiments, R$^1$ represents independently for each occurrence halogen, methyl, or cyclopropyl.

In certain embodiments, R$^{2A}$ is C$_{1-6}$ alkyl optionally substituted with 1 or 2 substituents independently selected from the group consisting of —CO$_2$R$^4$, —N(R$^4$)C(O)(C$_{1-6}$ alkyl), —CN, halogen, hydroxyl, C$_{1-6}$ alkoxy, C$_{1-6}$ haloalkoxy, and —N(R$^4$)(R$^5$). In certain other embodiments, R$^{2A}$ is C$_{1-6}$ alkyl substituted with 1 or 2 substituents independently selected from the group consisting of —CO$_2$R$^4$, —N(R$^4$)C(O)(C$_{1-6}$ alkyl), —CN, hydroxyl, and C$_{1-6}$ alkoxy. In certain other embodiments, R$^{2A}$ is —CO$_2$R$^4$.

In certain embodiments, R$^{2B}$ is C$_{1-6}$ alkyl. In certain other embodiments, R$^{2B}$ is methyl. In certain embodiments, R$^{2C}$ is hydrogen.

In certain embodiments, n is 1. In certain other embodiments, n is 1 or 2.

In certain embodiments, R$^3$ represents independently for each occurrence C$_{1-6}$ haloalkyl, halogen, C$_{1-6}$ alkyl, C$_{1-6}$ alkoxy, or —O—(C$_{1-6}$ alkylene)-OH. In certain other embodiments, R$^3$ is trifluoromethyl, fluoro, chloro, or methoxy. In certain other embodiments, R$^3$ is trifluoromethyl.

In certain embodiments, R$^4$ and R$^5$ each represent independently for each occurrence hydrogen or C$_{1-6}$ alkyl.

In certain embodiments, X is —O-aralkyl, —O-heteroaralkyl, —O-phenyl, —O— heteroaryl, —O-(partially unsaturated bicyclic carbocyclyl), —O—(C$_{1-6}$ alkylene)-(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$ alkylene)-(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain other embodiments, X is —O— aralkyl, —O-phenyl, —O-(partially unsaturated bicyclic carbocyclyl), —O—(C$_{1-6}$ alkylene)-(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$ alkylene)-(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain other embodiments, X is —O— aralkyl or —N(R$^4$)-aralkyl, each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain other embodiments, X is —O—(C$_{1-6}$ alkylene)-phenyl or —N(R$^4$)—(C$_{1-6}$ alkylene)-phenyl, each of which is substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy, where at least one substituent is present at the ortho position on the phenyl group in variable X. In certain other embodiments, X is —O— benzyl or —N(R$^4$)-benzyl, each of which is substituted with 1 or 2 substituents independently selected from the group consisting of chloro, bromo, and fluoro.

In certain embodiments, X is —(C$_{2-6}$ alkenylene)-phenyl, —(C$_{2-6}$ alkenylene)-heteroaryl, —(C$_{1-6}$ alkylene)-phenyl, —(C$_{1-6}$ alkylene)-heteroaryl, —(C$_{1-6}$ alkylene)-(partially unsaturated bicyclic heterocyclyl), —(C$_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain other embodiments, X is —(C$_{2-6}$ alkenylene)-phenyl, —(C$_{1-6}$ alkylene)-phenyl, —(C$_{1-6}$ alkylene)-heteroaryl, —(C$_{1-6}$ alkylene)-(partially unsaturated bicyclic heterocyclyl), —(C$_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain other embodiments, X is —(C$_{2-6}$ alkenylene)-phenyl, —(C$_{1-6}$ alkylene)-phenyl, or —(C$_{1-6}$ alkylene)-heteroaryl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy.

In certain embodiments, X is —(C$_{1-6}$ alkylene)-Z$^1$ or —(C$_{2-6}$ alkenylene)-Z$^1$, wherein Z$^1$ is —O-aralkyl, —O-heteroaralkyl, —O-phenyl, —O-heteroaryl, —O-(partially unsaturated bicyclic carbocyclyl), —O—(C$_{1-6}$ alkylene)-(C$_{3-6}$ cycloalkyl), —O—(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$ alkylene)-(C$_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain other embodiments, X is —($C_{1-6}$ alkylene)-$Z^1$, wherein $Z^1$ is —O-aralkyl, —O-phenyl, —O-(partially unsaturated bicyclic carbocyclyl), —O—($C_{1-6}$alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

In certain embodiments, Y is —C($R^6$)($R^7$)—.

In certain embodiments, $R^6$ and $R^7$ are independently hydrogen or methyl.

In certain embodiments, Y is —C($R^6$)($R^7$)—, $R^6$ and $R^7$ are independently hydrogen or methyl, and X is attached at the 7-position of the 1,2,3,4-tetrahydronaphthalenyl ring.

In certain other embodiments, Y is —O—. In certain embodiments, Y is —O—, and X is attached at the 4-position of the chromanyl ring.

In certain embodiments, m is 0. In certain other embodiments, m is 1.

In certain embodiments, p is 0. In certain other embodiments, p is 1.

The definitions of variables in Formula II-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

Another aspect of the invention provides a compound represented by Formula II-B:

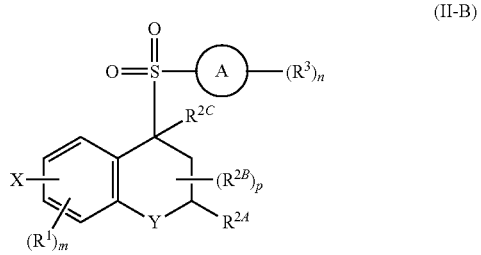

(II-B)

or a pharmaceutically acceptable salt thereof; wherein:
A is phenylene;
$R^1$ represents independently for each occurrence halogen, methyl, ethyl, or cyclopropyl;
$R^{2A}$ is $C_{1-6}$ alkyl substituted with 1 or 2 substituents independently selected from the group consisting of —$CO_2R^4$, —N($R^4$)C(O)($C_{1-6}$ alkyl), —CN, halogen, hydroxyl, $C_{1-6}$ alkoxy, $C_{1-6}$ haloalkoxy, $C_{1-6}$ haloalkyl, and —N($R^4$)($R^5$);
$R^{2B}$ is methyl or ethyl;
$R^{2C}$ is hydrogen.
$R^3$ represents independently for each occurrence $C_{1-3}$ haloalkyl, halogen, and $C_{1-3}$ alkyl;

$R^4$ and $R^5$ each represent independently for each occurrence hydrogen or methyl;
$R^6$ and $R^7$ each represent independently for each occurrence hydrogen, methyl, or ethyl;
X is attached at the meta or para position on the phenyl group relative to variable Y, and X is one of the following:
(i) —O—($C_{1-6}$ alkylene)-phenyl, —O-(partially unsaturated bicyclic carbocyclyl), or —O—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, and $C_{1-6}$ alkoxy;
(ii) —($C_{2-6}$ alkenylene)-phenyl or —($C_{1-6}$ alkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy; or
(iii) —($C_{1-6}$ alkylene)-$Z^1$, wherein $Z^1$ is —O-aralkyl, —O-phenyl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, and $C_{1-6}$ alkoxy;
Y is —C($R^6$)($R^7$)— or —O—;
m and p are independently 0 or 1; and
n is 1 or 2.

In certain embodiments, X is —O—($C_{1-6}$ alkylene)-phenyl optionally substituted with 1 or 2 substituents independently selected from the group consisting of halogen, $C_{1-6}$ haloalkyl, and $C_{1-6}$ alkyl.

In certain embodiments, Y is —C($R^6$)($R^7$)—.

The definitions of variables in Formula II-B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

Another aspect of the invention provides a compound represented by Formulae V or VI:

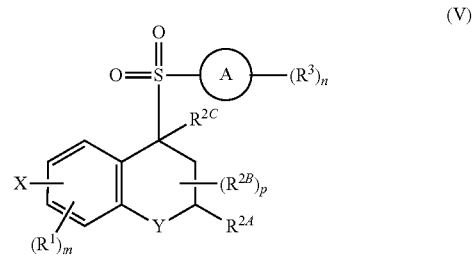

(V)

or a pharmaceutically acceptable salt thereof, wherein:
A is phenylene, 5-6 membered heteroarylene, or $C_{3-6}$ heterocycloalkylene;
$R^1$ represents independently for each occurrence halogen, $C_{1-6}$ alkyl, $C_{1-6}$ haloalkyl, or $C_{3-6}$ cycloalkyl;
$R^{2A}$ is —($C_{1-2}$ alkylene)-(2-8 membered heteroalkylene)-$CO_2R^4$, —($C_{1-6}$ alkylene)-C(O)N($R^4$)($C_{1-6}$ hydroxyalkylene)-CO₂R⁴, or —(C₁₋₆ alkylene)-N(R⁴)C(O)N(R⁴)—(C₁₋₆ alkylene)-CO₂R⁴; wherein the C₁₋₆ alkylene is optionally substituted with 1 or 2 substituents independently selected from the group consisting of —CO₂R⁴, —C(O)N(R⁴)(R⁵), —CN, halogen, hydroxyl, C₁₋₆ alkoxy, C₁₋₆ haloalkoxy, C₁₋₆ haloalkyl, and —N(R⁴)(R⁵);

R$^{2B}$ is C₁₋₆ alkyl, C₁₋₃ haloalkyl, or fluoro;

R$^{2C}$ is hydrogen or C₁₋₆ alkyl;

R³ represents independently for each occurrence hydrogen, C₁₋₆ haloalkyl, halogen, hydroxyl, C₁₋₆ alkyl, C₃₋₆ cycloalkyl, C₁₋₆ alkoxy, C₁₋₆ haloalkoxy, —N(R⁴)(R⁸), —O—(C₁₋₆ hydroxyalkyl), or —O—(C₁₋₆ alkylene)-CO₂R⁴; or two vicinal occurrences of R³ are taken together with intervening atoms to form a 4-6 membered ring;

R⁴ and R⁵ each represent independently for each occurrence hydrogen, C₁₋₆ alkyl, or C₃₋₆ cycloalkyl; or an occurrence of R⁴ and R⁵ attached to the same nitrogen atom are taken together with the nitrogen atom to which they are attached to form a 3-8 membered heterocyclic ring;

R⁶ and R⁷ each represent independently for each occurrence hydrogen, fluoro, or C₁₋₆ alkyl, or R⁶ and R⁷ are taken together with the carbon atom to which they are attached to form a 3-6 membered carbocyclic ring; or R⁶ and a vicinal occurrence of R$^{2B}$ are taken together to form a bond;

R⁸ represents independently for each occurrence C₁₋₆ alkyl, C₃₋₆ cycloalkyl, —(C₁₋₆ alkylene)-(C₃₋₆ cycloalkyl), or aryl, each of which is optionally substituted with 1, 2, or 3 substituents independently selected from the group consisting of halogen, hydroxyl, or —CO₂R⁴; or R⁸ is —CO₂R⁴;

R⁹ represents independently for each occurrence C₁₋₆ alkyl, C₃₋₆ cycloalkyl, —(C₁₋₆ alkylene)-(C₃₋₆ cycloalkyl), C₁₋₆ haloalkyl, or C₁₋₆ hydroxyalkyl;

X is one of the following:
(i) —O-aralkyl, —O-heteroaralkyl, —O-phenyl, —O-heteroaryl, —O-(partially unsaturated bicyclic carbocyclyl), —O—(C₁₋₆ alkylene)-(C₃₋₆ cycloalkyl), —O—(C₃₋₆ cycloalkyl), —N(R⁴)-aralkyl, —N(R⁴)-phenyl, —N(R⁴)-(partially unsaturated bicyclic carbocyclyl), or —N(R⁴)—(C₁₋₆ alkylene)-(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;
(ii) —S-aralkyl, —S-heteroaralkyl, —S-phenyl, —S-heteroaryl, —S-(partially unsaturated bicyclic carbocyclyl), —S—(C₁₋₆ alkylene)-(C₃₋₆ cycloalkyl), or —S—(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;
(iii) —(C₂₋₆ alkenylene)-phenyl, —(C₂₋₆ alkenylene)-heteroaryl, —(C₂₋₆ alkenylene)-(partially unsaturated 8-10 membered bicyclic ring containing 0-3 heteroatoms), —(C₁₋₆ alkylene)-phenyl, —(C₁₋₆ alkylene)-heteroaryl, —(C₁₋₆ alkylene)-(partially unsaturated bicyclic heterocyclyl), —(C₁₋₆ alkylene)-(partially unsaturated bicyclic oxo-heterocyclyl), —(C₁₋₆ alkylene)-(C₃-C₆ cycloalkyl), -(5-6 membered heterocycloalkylene)-phenyl, or —(C₃₋₆ cycloalkylene)-phenyl, each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;
(iv) —(C₂₋₆ alkenylene)-(C₁₋₆ alkyl), —(C₂₋₆ alkenylene)-(C₃₋₆ cycloalkyl), or

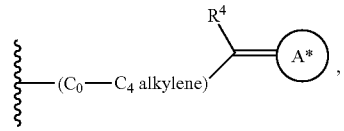

each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹, wherein A* is a 5-8 membered, partially saturated carbocyclic or heterocyclic ring; or
(v) —(C₁₋₆ alkylene)-Z¹ or —(C₂₋₆ alkenylene)-Z¹, wherein Z¹ is —O-aralkyl, —O— heteroaralkyl, —O-phenyl, —O-heteroaryl, —O-(partially unsaturated bicyclic carbocyclyl), —O—(C₁₋₆ alkylene)-(C₃₋₆ cycloalkyl), —O—(C₃₋₆ cycloalkyl), —N(R⁴)-aralkyl, —N(R⁴)-phenyl, —N(R⁴)-(partially unsaturated bicyclic carbocyclyl), —N(R⁴)—(C₁₋₆ alkylene)-(C₃₋₆ cycloalkyl), or —N(R⁴)—(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

Y is —C(R⁶)(R')—, —O—, —C(O)—, or —S(O)$_p$—;

m and p each represent independently for each occurrence 0, 1, or 2; and n is 1, 2, or 3; and Formula VI is represented by:

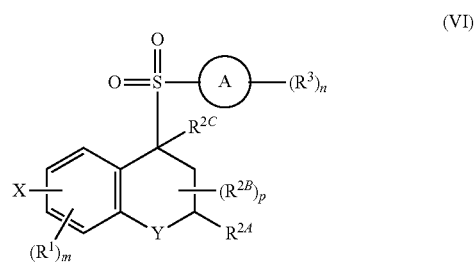

(VI)

or a pharmaceutically acceptable salt thereof, wherein:

A is phenylene, 5-6 membered heteroarylene, or C₃₋₆ heterocycloalkylene;

R¹ represents independently for each occurrence halogen, C₁₋₆ alkyl, C₁₋₆ haloalkyl, or C₃₋₆ cycloalkyl;

R$^{2A}$ is one of the following:
(i) hydrogen, C₁₋₆ alkyl, C₁₋₃ haloalkyl, C₃₋₆ cycloalkyl, —(C₁₋₆ alkylene)-(C₃₋₆ cycloalkyl), —O—(C₁₋₆ alkylene)-CO₂R⁴, —O—(C₁₋₆ alkylene)-C(O)—(C₁₋₆ alkyl), —N(R⁴)—(C₁₋₆ alkylene)-CO₂R⁴, or —N(R⁴)—(C₁₋₆ alkylene)-C(O)—(C₁₋₆ alkyl), wherein the C₁₋₆ alkyl, C₃₋₆ cycloalkyl, and C₁₋₆ alkylene are optionally substituted with 1 or 2 substituents independently selected from the group consisting of —CO₂R⁴, —C(O)N(R⁴)(R⁵), —C(O)—N(R⁴)—(C₁₋₄ alkylene)-CO₂R⁴, —N(R⁴)C(O)R⁸, —CN, halogen, hydroxyl, $C_{1-6}$ alkoxy, $C_{1-6}$ haloalkoxy, $C_{1-6}$ haloalkyl, —N($R^4$)($R^5$), —N($R^4$)C(O)N($R^4$)($R^5$), —N($R^4$)$CO_2R^9$, —N($R^4$)S(O)$_2R^9$, and —N($R^4$)S(O)$_2$N($R^4$)($R^5$); or
(ii) —$CO_2R^4$, —N($R^4$)C(O)$R^9$, —N($R^4$)$CO_2R^9$, —N($R^4$)C(O)N($R^4$)($R^5$), —N($R^4$)C(O)N($R^4$) (heteroaryl), —N($R^4$)S(O)$_2R^9$, —N($R^4$)($R^5$), —OH, or —($C_{1-2}$ alkylene)-(2-8 membered heteroalkylene)-$CO_2R^4$;

$R^{2B}$ is $C_{1-6}$ alkyl, $C_{1-3}$ haloalkyl, or fluoro;

$R^{2C}$ is hydrogen or $C_{1-6}$ alkyl;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —N($R^4$)($R^8$), —O—($C_{1-6}$ hydroxyalkyl), or —O—($C_{1-6}$ alkylene)-$CO_2R^4$; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring;

$R^6$ and $R^7$ each represent independently for each occurrence hydrogen, fluoro, or $C_{1-6}$ alkyl, or $R^6$ and $R^7$ are taken together with the carbon atom to which they are attached to form a 3-6 membered carbocyclic ring; or $R^6$ and a vicinal occurrence of $R^{2B}$ are taken together to form a bond;

$R^8$ represents independently for each occurrence $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —$CO_2R^4$; or $R^8$ is —$CO_2R^4$;

$R^9$ represents independently for each occurrence $C_{1-6}$ alkyl, $C_{3-6}$ cycloalkyl, —($C_{1-6}$ alkylene)-($C_{3-6}$ cycloalkyl), $C_{1-6}$ haloalkyl, or $C_{1-6}$ hydroxyalkyl;

X is $C_{4-7}$ cycloalkenyl, $C_{3-7}$ cycloalkyl, or an 8-10 membered, bicyclic partially saturated carbocyclyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —$SO_2R^9$;

Y is —C($R^6$)($R^7$)—, —O—, —C(O)—, or —S(O)$_p$—;

m and p each represent independently for each occurrence 0, 1, or 2; and n is 1, 2, or 3.

In certain embodiments, the compound is a compound of Formula V or a pharmaceutically acceptable salt thereof. In certain embodiments, the compound is a compound of Formula VI or a pharmaceutically acceptable salt thereof.

In certain embodiments, A is phenylene or 5-6 membered heteroarylene.

In certain embodiments, $R^1$ represents independently for each occurrence halogen or $C_{1-6}$ alkyl.

In certain embodiments, $R^3$ represents independently for each occurrence hydrogen, $C_{1-6}$ haloalkyl, halogen, hydroxyl, $C_{1-6}$ alkyl, $C_{3-4}$ cycloalkyl, $C_{1-6}$ alkoxy, or $C_{1-6}$ haloalkoxy.

In certain embodiments, $R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring, wherein the heterocyclic ring is substituted with 1, 2 or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, cyano, oxo, —$CO_2R^{10}$, —C(O)$R^9$, —$SO_2R^9$, —N($R^{10}$)C(O)$R^{12}$, and —C(O)N($R^{10}$)($R^{11}$); wherein $R^{10}$ and $R^{11}$ each represent independently for each occurrence hydrogen or $C_{1-6}$ alkyl, or $R^{10}$ and $R^{11}$ are taken together with the carbon atom to which they are attached to form a 3-6 membered carbocyclic ring; and $R^{12}$ is $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, or —$CO_2R^{10}$. In certain other embodiments, $R^4$ and $R^5$ are taken together with the nitrogen atom to which they are attached to form a 3-8 membered heterocyclic ring substituted with 1, 2, or 3 substituents independently selected from the group consisting of $C_{1-6}$ haloalkyl, $C_{1-6}$ alkyl, and —$CO_2R^{10}$, where $R^{10}$ is hydrogen or $C_{1-6}$ alkyl.

In certain embodiments, Y is —C($R^6$)($R^7$)—. In certain other embodiments, Y is —O—. In yet other embodiments, Y is —S(O)$_p$—.

In connection with Formula V, in certain embodiments, X is —O-aralkyl, —O— heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —$SO_2R^9$. In certain embodiments, X is —S-aralkyl, —S-heteroaralkyl, —S-phenyl, —S-heteroaryl, —S-(partially unsaturated bicyclic carbocyclyl), —S—($C_{1-6}$ alkylene)-($C_{3-6}$ cycloalkyl), or —S—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —$SO_2R^9$. In certain embodiments, X is —($C_{2-6}$ alkenylene)-phenyl, —($C_{2-6}$ alkenylene)-heteroaryl, —($C_{2-6}$ alkenylene)-(partially unsaturated 8-10 membered bicyclic ring containing 0-3 heteroatoms), —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), —($C_{1-6}$ alkylene)-($C_3$-$C_6$ cycloalkyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —$SO_2R^9$. In certain embodiments, X is —($C_{2-6}$ alkenylene)-($C_{1-6}$ alkyl), —($C_{2-6}$ alkenylene)-($C_{3-6}$ cycloalkyl), or

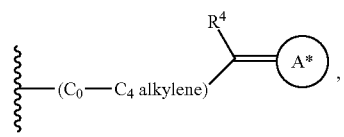

each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —$SO_2R^9$, wherein $A^*$ is a 5-8 membered, partially saturated carbocyclic or heterocyclic ring. In certain embodiments, X is —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$ alkylene)-($C_{3-6}$ cycloalkyl), or —N($R^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2$$R^9$. In certain embodiments, X is attached at the meta or para position on the phenyl group relative to variable Y. In certain embodiments, X is attached on the phenyl at the position located para to group Y.

In connection with Formula VI, in certain embodiments, $R^{2A}$ is $C_{1-6}$ alkyl substituted with 1 or 2 substituents independently selected from the group consisting of —CO$_2$$R^4$, —C(O)N($R^4$)($R^5$), —C(O)—N($R^4$)—($C_{1-4}$ alkylene)-CO$_2$$R^4$, —N($R^4$)C(O)$R^8$, —CN, halogen, hydroxyl, $C_{1-6}$ alkoxy, $C_{1-6}$ haloalkoxy, $C_{1-6}$ haloalkyl, —N($R^4$)($R^5$), —N($R^4$)C(O)N($R^4$)($R^5$), —N($R^4$)CO$_2$$R^9$, —N($R^4$)S(O)$_2$$R^9$, and —N($R^4$)S(O)$_2$N($R^4$)($R^5$). In certain other embodiments, $R^{2A}$ is $C_{1-6}$ alkyl substituted by —C(O)N($R^4$)($R^5$), where $R^4$ and $R^5$ are taken together with the nitrogen atom to which they are attached to form a 3-8 membered heterocyclic ring substituted with 1, 2, or 3 substituents independently selected from the group consisting of $C_{1-6}$ haloalkyl, $C_{1-6}$ alkyl, and —CO$_2$$R^{10}$, where $R^{10}$ is hydrogen or $C_{1-6}$ alkyl.

The definitions of variables in Formula V and VI above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain other embodiments, the compound is a compound defined by one of the following formulae where variables X and Z are as defined in Table 2, or a pharmaceutically acceptable salt thereof.

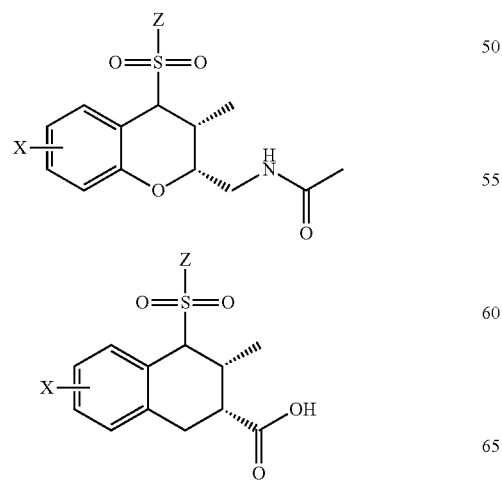

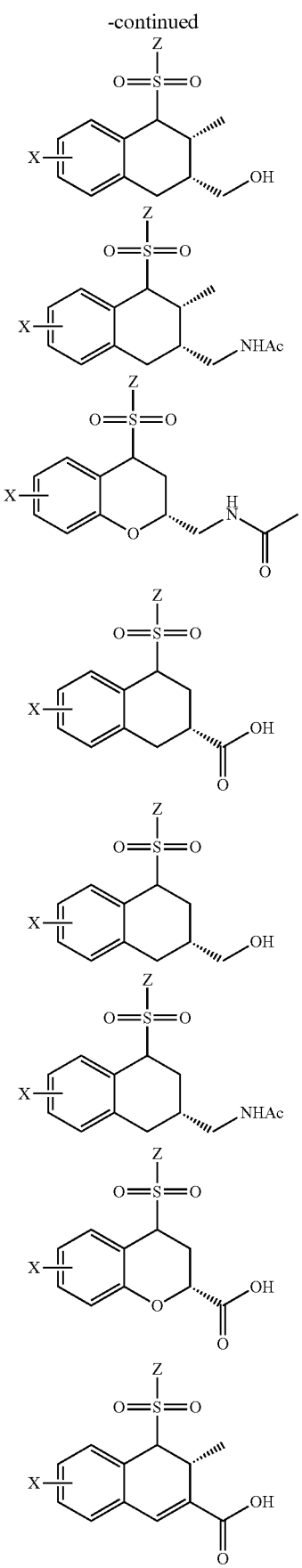

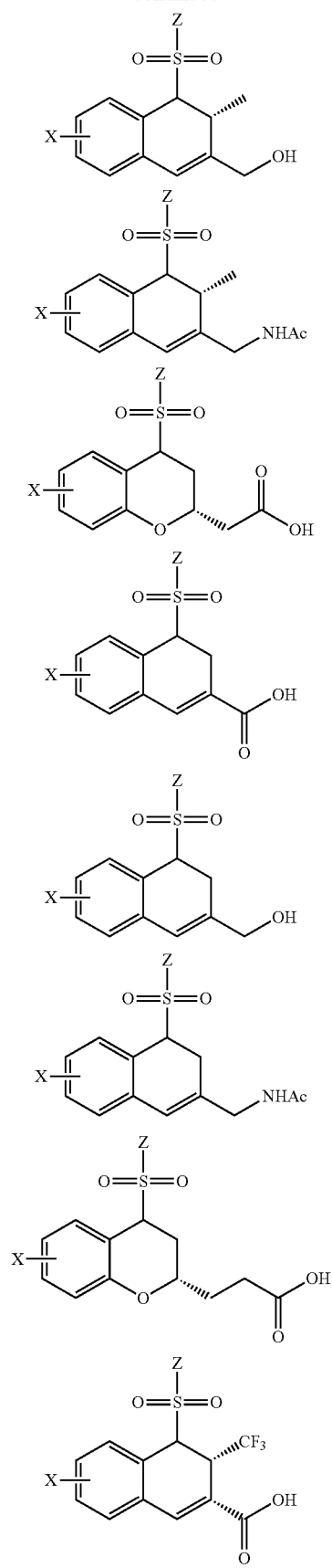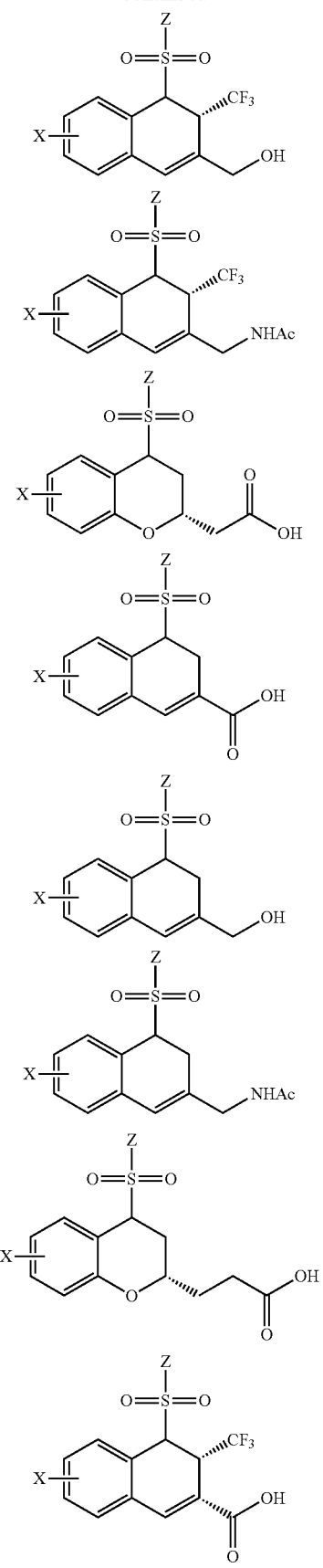

119
-continued
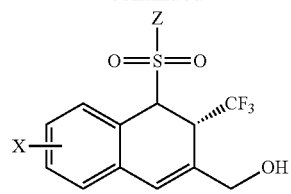
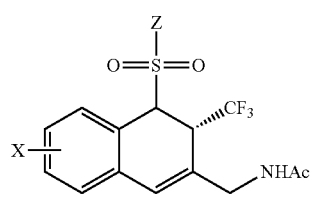
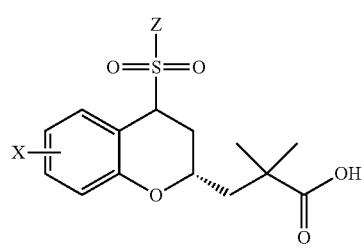
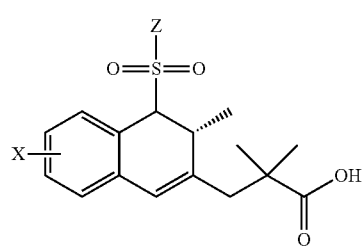
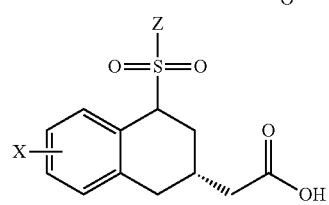
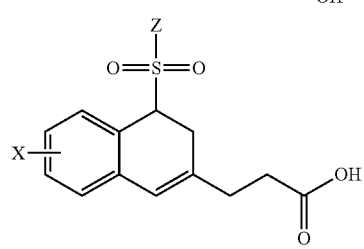
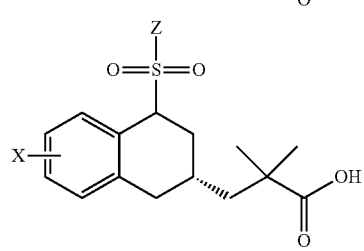
120
-continued
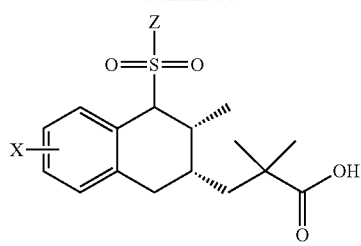
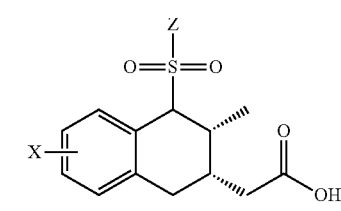
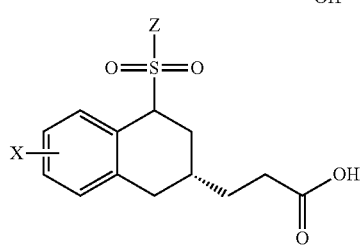
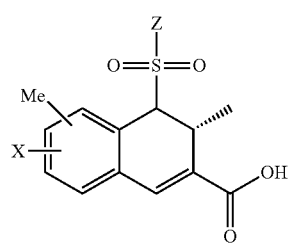
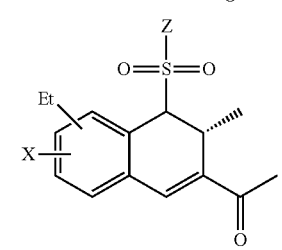
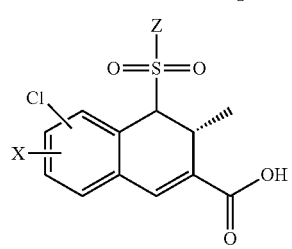
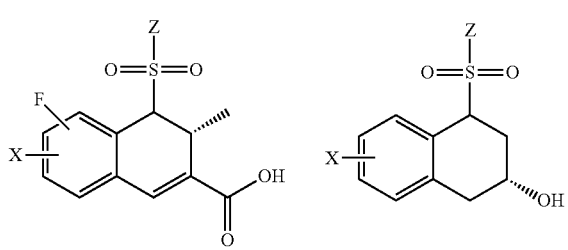

121
-continued
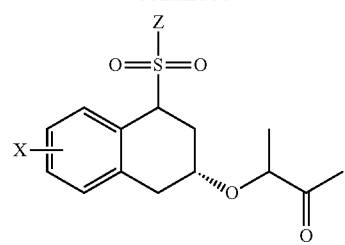
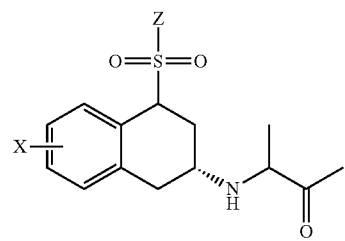
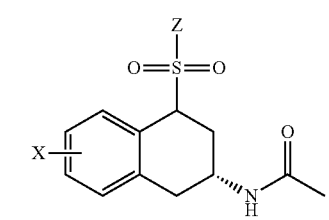
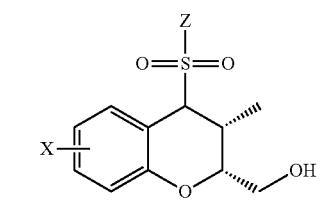
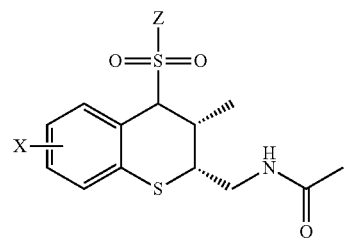
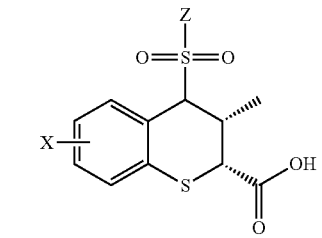
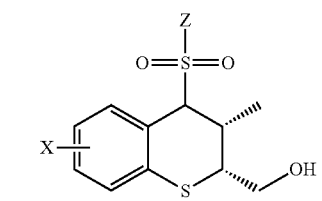
122
-continued
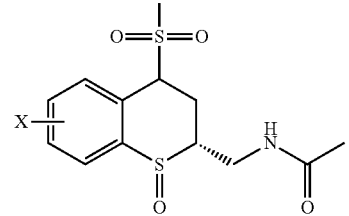
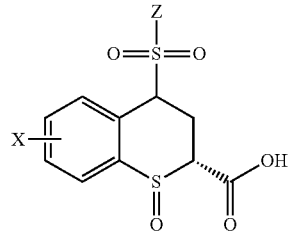
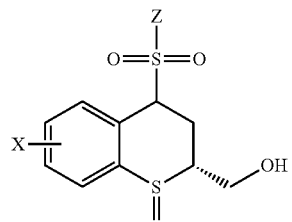
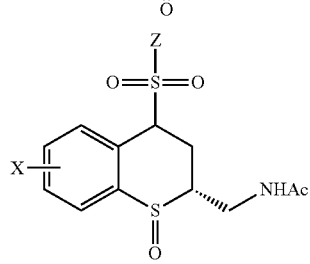
TABLE 2
| No. | X | Z |
|---|---|---|
| II-1 | 2-chloro-6-fluorobenzyloxy | 3-fluoro-4-methoxyphenyl |
| II-2 | 2-chloro-6-fluorobenzyloxy | 3-chlorophenyl |
| II-3 | 2-chloro-6-fluorobenzyloxy | 3-cyclopropylphenyl |

TABLE 2-continued
| No. | X | Z |
|---|---|---|
| II-4 | 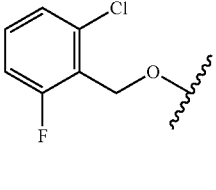 | 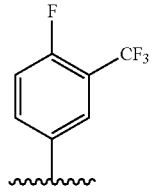 [SMILES: *c1ccc(F)c(C(F)(F)F)c1] |
| II-5 | 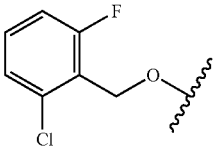 | 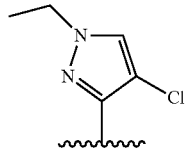 [SMILES: *c1nn(CC)cc1Cl] |
| II-6 | 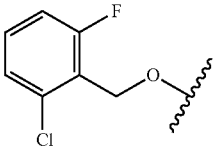 [SMILES: *OCc1c(F)cccc1Cl] | 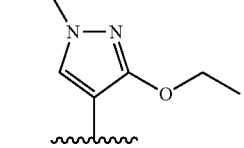 |
| II-7 | 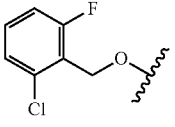 [SMILES: *OCc1c(F)cccc1Cl] | 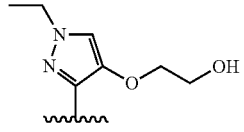 [SMILES: *c1nn(CC)cc1OCCO] |
| II-8 | 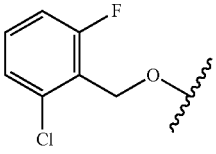 [SMILES: *OCc1c(F)cccc1Cl] | 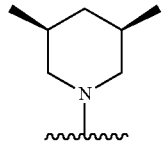 |
| II-9 | 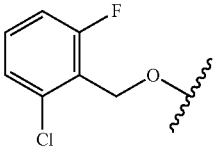 | 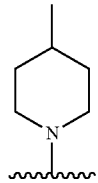 |
| II-10 | 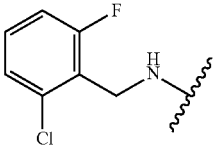 [SMILES: *NCc1c(F)cccc1Cl] | 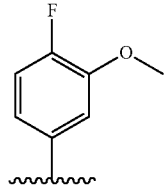 [SMILES: *c1ccc(F)c(OC)c1] |
| II-11 | 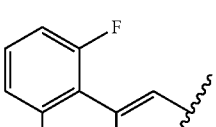 | 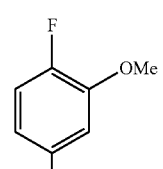 |
| II-12 | 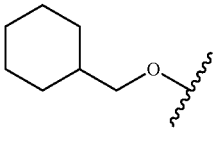 [SMILES: *OCC1CCCCC1] | 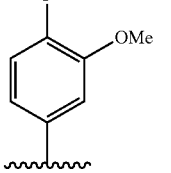 |
| II-13 | 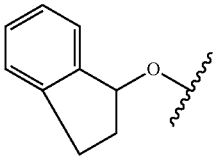 [SMILES: *OC1CCc2ccccc21] | 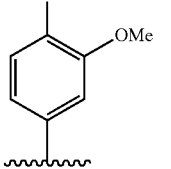 |
| II-14 | 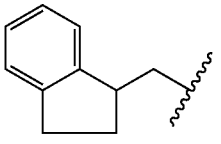 [SMILES: *CC1CCc2ccccc21] | 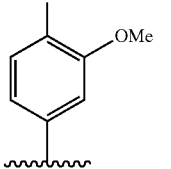 |
| II-15 | 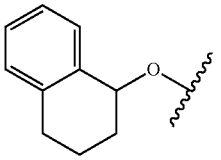 [SMILES: *OC1CCCc2ccccc21] | 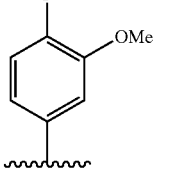 |
| II-16 | 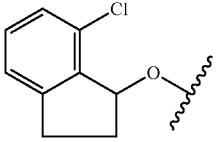 [SMILES: *OC1CCc2cccc(Cl)c21] | 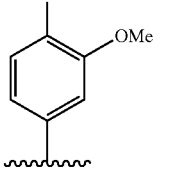 |
| II-17 | 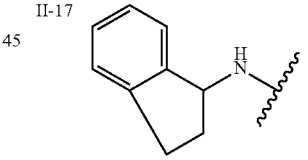 | 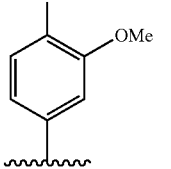 |
| II-18 | 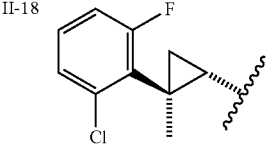 | 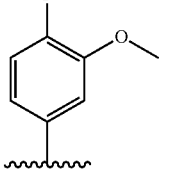 |
| II-19 | 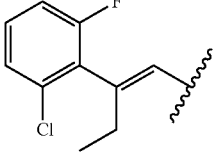 | 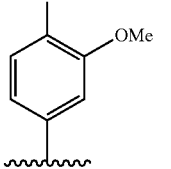 |

TABLE 2-continued
| No. | X | Z |
|---|---|---|
| II-20 | 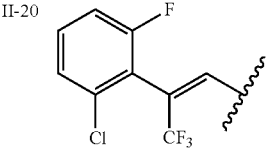 | 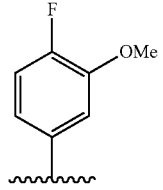 [SMILES: *c1ccc(F)c(OC)c1] |
| II-21 | 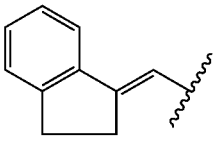 [SMILES: */C=C1\CCc2ccccc21] | 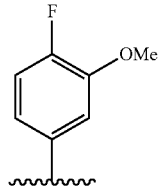 [SMILES: *c1ccc(F)c(OC)c1] |
| II-22 | 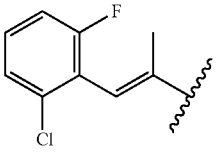 [SMILES: */C(C)=C/c1c(F)cccc1Cl] | 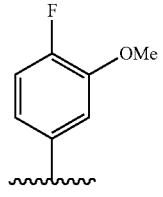 [SMILES: *c1ccc(F)c(OC)c1] |
| II-23 | 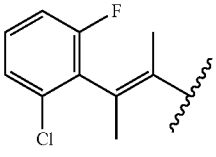 [SMILES: */C(C)=C(\C)c1c(F)cccc1Cl] | 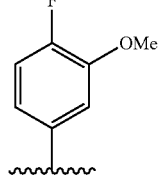 |
| II-24 | 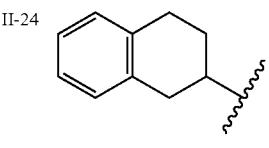 | 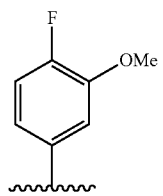 [SMILES: *c1ccc(F)c(OC)c1] |
| II-25 | 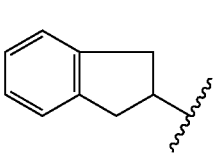 |  |
| II-26 | 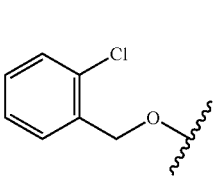 [SMILES: *OCc1ccccc1Cl] |  |
| II-27 | 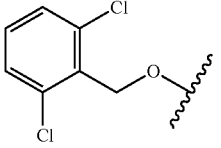 | 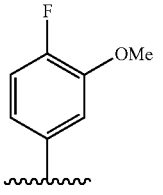 |
| II-28 | 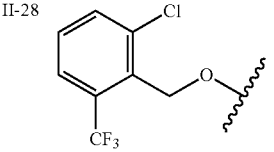 | 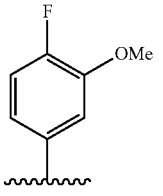 |
| II-29 | 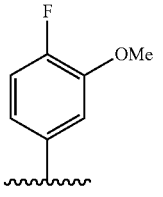 | 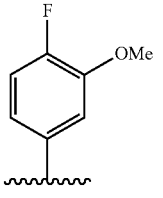 |
| II-30 | 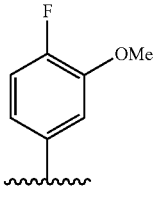 | 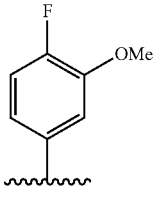 |
| II-31 | 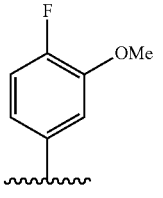 | 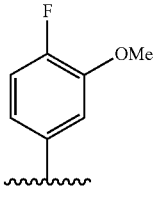 |
| II-32 | | |
| II-33 | | |
| II-34 | | |

TABLE 2-continued

| No. | X | Z |
|---|---|---|
| II-35 | (1-methylcyclopentyl)oxy | 4-fluoro-3-methoxyphenyl |
| II-36 | (2-methylcyclohexyl)oxy | 4-fluoro-3-methoxyphenyl |
| II-37 | (2-methylcyclohexyl)oxy | 4-fluoro-3-methoxyphenyl |
| II-38 | (2-ethylcyclohexyl)oxy | 4-fluoro-3-methoxyphenyl |
| II-39 | ((2-methylcyclohexyl)methoxy) | 4-fluoro-3-methoxyphenyl |
| II-40 | ((2-methylcyclohexyl)methoxy) | 4-fluoro-3-methoxyphenyl |
| II-41 | ((2,6-dimethylcyclohexyl)methoxy) | 4-fluoro-3-methoxyphenyl |
| II-42 | (bicyclo[2.2.1]heptylmethoxy) | 4-fluoro-3-methoxyphenyl |
| II-43 | (bicyclo[2.2.1]heptylmethoxy) | 4-fluoro-3-methoxyphenyl |
| II-44 | ((3-methylcyclopentyl)oxy) | 4-fluoro-3-methoxyphenyl |
| II-45 | ((3-isopropylcyclopentyl)oxy) | 4-fluoro-3-methoxyphenyl |
| II-46 | ((3,3-dimethylcyclopentyl)oxy) | 4-fluoro-3-methoxyphenyl |
| II-47 | ((3-methylcyclopentyl)oxy) | 4-fluoro-3-methoxyphenyl |
| II-48 | ((3-methylcyclopentyl)oxy) | 4-fluoro-3-methylphenyl |
| II-49 | ((2,6-dichlorobenzyl)oxy) | 5-(trifluoromethyl)pyridin-3-yl |

TABLE 2-continued

| No. | X | Z |
|---|---|---|
| II-50 | 2-F, 6-Cl benzyl NH | 5-(F₃C)-pyridin-3-yl |
| II-51 | 2,6-dichlorobenzyl-O- | 1-methyl-imidazol-4-yl |
| II-52 | 2-F, 6-Cl benzyl NH | 1-methyl-imidazol-4-yl |
| II-53 | 2-F, 6-Cl styryl | pyridin-3-yl (5-methyl) |
| II-54 | indan-1-yl-O- | pyridin-3-yl (5-methyl) |
| II-55 | 2-F, 6-Cl styryl | 1-isopropyl-imidazol-4-yl |
| II-56 | indan-1-yl-O- | 1-isopropyl-imidazol-4-yl |
| II-57 | 2,6-dichlorobenzyl-O- | oxazol-4-yl |
| II-58 | 2-F, 6-Cl benzyl NH | oxazol-4-yl |
| II-59 | 2-F, 6-Cl styryl | oxazol-4-yl |
| II-60 | indan-1-yl-O- | oxazol-4-yl |
| II-61 | 2,6-dichlorobenzyl-O- | 1-methyl-pyrrol-3-yl |
| II-62 | 2-F, 6-Cl benzyl NH | 1-methyl-pyrrol-3-yl |
| II-63 | 2-F, 6-Cl styryl | 1-isopropyl-pyrrol-3-yl |
| II-64 | indan-1-yl-O- | 1-isopropyl-pyrrol-3-yl |
| II-65 | 5-(F₃C)-pyridin-3-yl-O- | 2-MeO, 3-F phenyl (5-position) |
| II-66 | 5-(F₃C)-pyridin-3-yl-O- | 3-chlorophenyl |

TABLE 2-continued
| No. | X | Z |
|---|---|---|
| II-67 |  |  |
| II-68 |  |  |
| II-69 |  |  |
| II-70 |  |  |
| II-71 |  |  |
| II-72 |  |  |
| II-73 |  |  |
| II-74 |  |  |
| II-75 |  |  |
| II-76 | | |
| II-77 | | |
| II-78 | | |
| II-79 | | |
| II-80 | | |
| II-81 | | |
| II-82 | | |
| II-83 | | |

TABLE 2-continued

| No. | X | Z |
|---|---|---|
| II-84 | | |
| II-85 | | |
| II-86 | | |

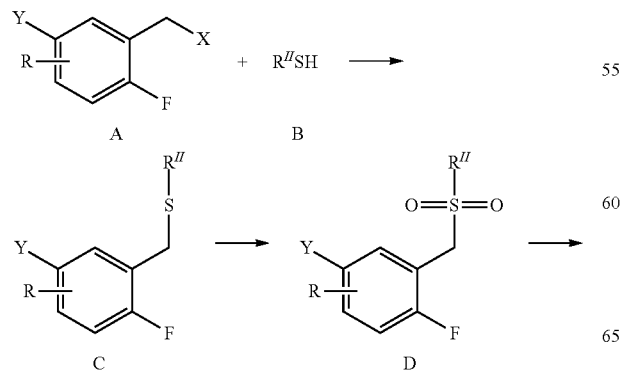

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

Scheme 20 is a general method of preparing substituted (2S,4R)-2-substituted-4-(aryl or heteroaryl sulfonyl)chroman F. Treatment of benzylic halide A with mercaptan B affords thioether C. Oxidation of thioether C with meta-chloroperbenzoic acid or another oxidant affords sulfone D. Treatment of sulfone D with n-butyl lithium, tert-butoxide or another suitable base forms an anion which can be alkylated with an epoxide to afford alcohol E. Treatment of alcohol E with sodium hydride or another suitable base affords the chroman F.

SCHEME 20.

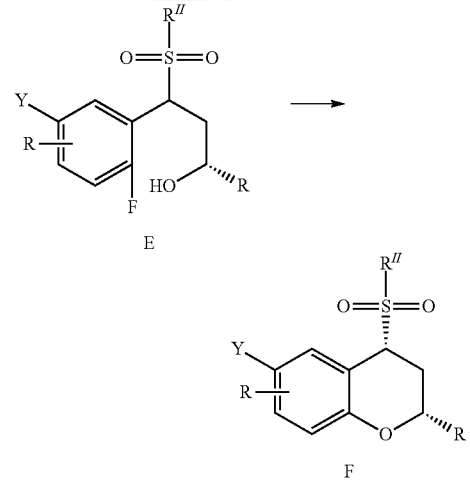

Scheme 21 illustrates another general method of forming substituted (benzyl or heteroarylalkyl sulfonyl)benzene E. Condensation of 2-hydroxyacetophenone A with aldehyde B catalyzed by pryrrolidine affords chromanone C. Addition of a thiol to chromanone C under acidic conditions (e.g., $BF_3$-etherate or trifluoroacetic acid) in the presence of a reductant (e.g., triethylsilane or pyridine borane) affords sulfide D. Oxidation of sulfide D with metachloroperbenzoic acid, oxone, or other suitable oxidant affords substituted (benzyl or heteroarylalkyl sulfonyl)benzene E.

SCHEME 21.

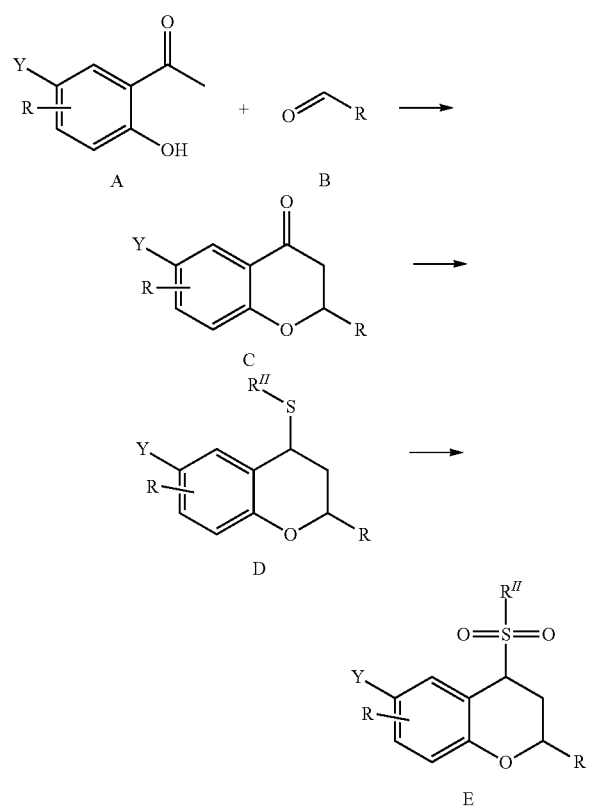

Scheme 22 illustrates a general method of forming substituted 1-(phenyl or heteroarylsulfonyl)-1,2,3,4-tetrahydronaphthalene C. Addition of a thiol under acidic conditions (e.g., BF$_3$-etherate or trifluoroacetic acid) in the presence of a reductant (triethylsilane or pyridine borane) to the tetralone A affords sulfide B. Oxidation of sulfide B with metachloroperbenzoic acid, oxone, or other suitable oxidant affords the 1-(phenyl or heteroarylsulfonyl)-1,2,3,4-tetrahydronaphthalene C.

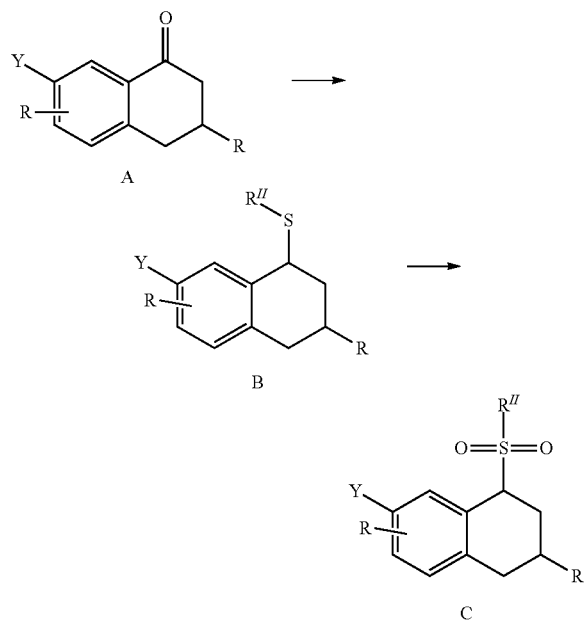

SCHEME 22.

II. Therapeutic Applications of Tetrahydroquinolinyl and Related Compounds

It is contemplated that the tetrahydroquinolinyl and related compounds described herein, such as a compound of Formula I, I-1, I-A, I-B, II, II-1, II-A, II-B, or other compounds in Section I such as a compound of Formula III, IV, V, or VI, provide therapeutic benefits to subjects suffering from a cancer, bacterial infection, fungal infection, or immune deficiency disorder. Accordingly, one aspect of the invention provides a method of treating a disorder selected from the group consisting of cancer, bacterial infection, fungal infection, and immune deficiency disorder. The method comprises administering a therapeutically effective amount of a tetrahydroquinolinyl or related compound described herein, such as a compound of Formula I, I-1, I-A, I-B, II, II-1, II-A, II-B, or other compounds in Section I such as a compound of Formula III, IV, V, or VI, to a subject in need thereof to ameliorate a symptom of the disorder. In certain embodiments, the particular compound of Formula I, I-1, I-A, I-B, II, II-1, II-A, or II-B is a compound defined by one of the embodiments described above.

In certain embodiments, the disorder is cancer. In certain embodiments, the cancer is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, espophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

In certain embodiments, the cancer is non-Hodgkin's lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma.

In certain embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

In certain embodiments, the leukemia is chronic lymphocytic leukemia, acute myelogenous leukemia, chronic myelogenous leukemia, or acute lymphoblastic leukemia.

In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondrosarcoma, choriod plexus papilloma/carcinoma, gastric antrum cancer, gastric fundus cancer, gastrinoma, glioblastoma, glucagonoma, heart cancer, hemangioblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, interepithelial squamous cell neoplasia, intrahepatic bile duct cancer, invasive squamous cell carcinoma, jejunum cancer, joint cancer, Kaposi's sarcoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancerneuroepithelial adenocarcinoma nodular melanoma, nonepithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, larynx cancer, parotid cancer, bilary tract cancer, thyroid cancer, acral lentiginous melanoma, actinic keratoses, acute lymphocytic leukemia, acute myeloid leukemia, adenoid cycstic carcinoma, adenomas, adenosarcoma, adenosquamous carcinoma, anal canal cancer, anal cancer, or anorectum cancer.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, and hemangioblastoma.

In certain embodiments, the cancer is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waidenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

In certain embodiments, the disorder is a bacterial infection. The bacterial infection can be characterized according to classifications known in the art. For example, in certain embodiments, the bacterial infection is a gram-positive bacterial infection, such as a gram-positive cocci bacterial infection or a gram-positive bacilli bacterial infection. In other embodiments, the bacterial infection is a gram-negative bacterial infection, such as a gram-negative cocci bacterial infection or a gram-negative bacilli bacterial infection. The bacterial infection can also be characterized according to whether it is caused by anaerobic or aerobic bacteria. Accordingly, in certain embodiments, the bacterial infection is an anaerobic bacterial infection. In certain other embodiments, the bacterial infection is an aerobic bacterial infection.

A variety of bacteria are contemplated to be susceptible to the tetrahydroquinoline compounds. Representative bacteria include Staphylococci species, e.g., *S. aureus*; Enterococci species, e.g., *E. faecalis* and *E. faecium*; Streptococci species, e.g., *S. pyogenes* and *S. pneumoniae*; *Escherichia* species, e.g., *E. coli*, including enterotoxigenic, enteropathogenic, enteroinvasive, enterohemorrhagic and enteroaggregative *E. coli* strains; *Haemophilus* species, e.g., *H. influenza*; and *Moraxella* species, e.g., *M. catarrhalis*. Other examples include Mycobacteria species, e.g., *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum*; Corynebacteria species, e.g., *C. diphtheriae*; *Vibrio* species, e.g., *V. cholerae*; *Campylobacter* species, e.g., *C. jejuni*; *Helicobacter* species, e.g., *H. pylori*; *Pseudomonas* species, e.g., *P. aeruginosa*; *Legionella* species, e.g., *L. pneumophila*; *Treponema* species, e.g., *T. pallidum*; *Borrelia* species, e.g., *B. burgdorferi*; *Listeria* species, e.g., *L monocytogenes*; *Bacillus* species, e.g., *B. cereus*; *Bordatella* species, e.g., *B. pertussis*; *Clostridium* species, e.g., *C. perfringens, C. tetani, C. difficile* and *C. botulinum*; *Neisseria* species, e.g., *N. meningitidis* and *N. gonorrhoeae*; *Chlamydia* species, e.g., *C. psittaci, C. pneumoniae* and *C. trachomatis*; *Rickettsia* species, e.g., *R. rickettsii* and *R. prowazekii*; *Shigella* species, e.g., *S. sonnei*; *Salmonella* species, e.g., *S. typhimurium*; *Yersinia* species, e.g., *Y. enterocolitica* and *Y. pseudotuberculosis*; *Klebsiella* species, e.g., *K. pneumoniae*; *Mycoplasma* species, e.g., *M. pneumoniae*; and *Trypanosoma brucei*. In certain embodiments, the compounds described herein are used to treat a subject suffering from a bacterial infection selected from the group consisting of *S. aureus, E. faecalis, E. faecium, S. pyogenes, S. pneumonia*, and *P. aeruginosa*.

The antibacterial activity of compounds described herein may be evaluated using assays known in the art, such as the microbroth dilution minimum inhibition concentration (MIC) assay, as further described in National Committee for Clinical Laboratory Standards. Performance Standards for Antimicrobial Susceptibility Testing; Fourteenth Informational Supplement. NCCLS document M100-S14 {ISBN 1-56238-516-X}. This assay may be used to determine the minimum concentration of a compound necessary to prevent visible bacterial growth in a solution. In general, the drug to be tested is serially diluted into wells, and aliquots of liquid bacterial culture are added. This mixture is incubated under appropriate conditions, and then tested for growth of the bacteria. Compounds with low or no antibiotic activity (a high MIC) will allow growth at high concentrations of compound, while compounds with high antibiotic activity will allow bacterial growth only at lower concentrations (a low MIC).

The assay uses stock bacterial culture conditions appropriate for the chosen strain of bacteria. Stock cultures from the permanent stock culture collection can be stored as frozen suspensions at −70° C. Cultures may be suspended in 10% skim milk (BD) prior to snap freezing in dry ice/ethanol and then placed in a −70° C. freezer. Cultures may be maintained on Tryptic Soy Agar containing 5% Sheep Blood at room temperature (20° C.), and each culture may be recovered from frozen form and transferred an additional time before MIC testing. Fresh plates are inoculated the day before testing, incubated overnight, and checked to confirm purity and identity.

The identity and purity of the cultures recovered from the stock culture can be confirmed to rule out the possibility of contamination. The identity of the strains may be confirmed by standard microbiological methods (See, e.g., Murray et al., Manual of Clinical Microbiology, Eighth Edition. ASM Press {ISBN 1-55581-255-4}). In general, cultures are streaked onto appropriate agar plates for visualization of purity, expected colony morphology, and hemolytic patterns. Gram stains can also be utilized. The identities are confirmed using a MicroScan WalkAway 40 SI Instrument (Dade Behring, West Sacramento, Calif.). This device utilizes an automated incubator, reader, and computer to assess for identification purposes the biochemical reactions carried out by each organism. The MicroScan WalkAway can also be used to determine a preliminary MIC, which may be confirmed using the method described below.

Frozen stock cultures may be used as the initial source of organisms for performing microbroth dilution minimum inhibition concentration (MIC) testing. Stock cultures are passed on their standard growth medium for at least 1 growth cycle (18-24 hours) prior to their use. Most bacteria may be prepared directly from agar plates in 10 mL aliquots of the appropriate broth medium. Bacterial cultures are adjusted to the opacity of a 0.5 McFarland Standard (optical density value of 0.28-0.33 on a Perkin-Elmer Lambda EZ150 Spectrophotometer, Wellesley, Mass., set at a wavelength of 600 nm). The adjusted cultures are then diluted 400 fold (0.25 mL inoculum+100 mL broth) in growth media to produce a starting suspension of approximately 5×10$^5$ colony forming units (CFU)/mL. Most bacterial strains may be tested in cation adjusted Mueller Hinton Broth (CAMHB).

Test compounds ("drugs") are solubilized in a solvent suitable for the assay, such as DMSO. Drug stock solutions may be prepared on the day of testing. Microbroth dilution stock plates may be prepared in two dilution series, 64 to 0.06 μg drug/mL and 0.25 to 0.00025 μg drug/mL. For the high concentration series, 200 μL of stock solution (2 mg/mL) is added to duplicate rows of a 96-well microtiter plate. This is used as the first well in the dilution series. Serial two-fold decremental dilutions are made using a BioMek FX robot (Beckman Coulter Inc., Fullerton, Calif.) with 10 of the remaining 11 wells, each of which will contain 100 μL of the appropriate solvent/diluent. Row 12 contains solvent/diluent only and serves as the control. For the first well of the low concentration series, 200 μL of an 8 μg/mL stock are added to duplicate rows of a 96-well plate. Serial two-fold dilutions are made as described above.

Daughter 96-well plates may be spotted (3.2 μL/well) from the stock plates listed above using the BioMek FX robot and used immediately or frozen at −70° C. until use. Aerobic organisms are inoculated (100 μL volumes) into the thawed plates using the BioMek FX robot. The inoculated plates are be placed in stacks and covered with an empty plate. These plates are then incubated for 16 to 24 hours in ambient atmosphere according to CLSI guidelines (National Committee for Clinical Laboratory Standards, Methods for Dilution, Antimicrobial Tests for Bacteria that Grow Aerobically; Approved Standard-Sixth Edition. NCCLS document M7-A6 {ISBN 1-56238-486-4}).

After inoculation and incubation, the degree of bacterial growth can be estimated visually with the aid of a Test Reading Mirror (Dynex Technologies 220 16) in a darkened room with a single light shining directly through the top of the microbroth tray. The MIC is the lowest concentration of drug that prevents macroscopically visible growth under the conditions of the test.

In certain embodiments, the disorder is a fungal infection. Exemplary fungi that may be treated include, for example, *Acremonium*, *Absidia* (e.g., *Absidia corymbifera*), *Alternaria*, *Aspergillus* (e.g., *Aspergillus clavatus*, *Aspergillus flavus*, *Aspergillus fumigatus*, *Aspergillus nidulans*, *Aspergillus niger*, *Aspergillus terreus*, and *Aspergillus versicolor*), *Aureobasidium*, *Basidiobolus*, *Blastomyces* (e.g., *Blastomyces dermatitidis*), *Candida* (e.g., *Candida albicans*, *Candida glabrata*, *Candida guilliermondii*, *Candida kefyr*, *Candida krusei*, *Candida lusitaniae*, *Candida parapsilosis*, *Candida pseudotropicalis*, *Candida stellatoidea*, *Candida tropicalis*, *Candida utilis*, *Candida lipolytica*, Candidafamata and *Candida rugosa*), *Cephalosporium*, *Chaetomium*, *Chrysosporium*, *Cladosporium* (e.g., *Cladosporium carrionii* and *Cladosporium trichloides*), *Coccidioides* (e.g., *Coccidioides immitis*), *Conidiobolus*, *Coprinus*, *Corynespora*, *Cryptococcus* (e.g., *Cryptococcus neoformans*), *Curvularia*, *Cunninghamella* (e.g., *Cunninghamella elegans*), *Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Hendersonula*, *Histoplasma*, *Leptosphaeria*, *Loboa*, *Madurella*, *Malassezia* (e.g., *Malassezia furfur*), *Microsporum* (e.g., *Microsporum canis* and *Microsporum gypseum*), *Mycocentrospora*, *Mucor*, *Neotestudina*, *Paecilomyces*, *Paracoccidioides* (e.g., *Paracoccidioides brasiliensis*), *Penicillium* (e.g., *Penicillium marneffei*), *Phialophora*, *Pneumocystis* (e.g., *Pneumocystis carinii*), *Pseudallescheria* (e.g., *Pseudallescheria boydii*), *Rhinosporidium*, *Rhizomucor*, *Rhizopus* (e.g., *Rhizopus microsporus* var. *rhizopodiformis* and *Rhizopus oryzae*), *Saccharomyces* (e.g., *Saccharomyces cerevisiae*), *Scopulariopsis*, *Sporothrix* (e.g., *Sporothrix schenckii*), *Trichophyton* (e.g., *Trichophyton mentagrophytes* and *Trichophyton rubrum*), *Trichosporon* (e.g., *Trichosporon asahii*, *Trichosporon beigelii* and *Trichosporon cutaneum*), and *Wangiella*.

In certain embodiments, the disorder is an immune deficiency disorder. Exemplary immune deficiency disorders include, for example, a human immunodeficiency viral infection, a patient with a deficient immune system due to chemotherapy, or a patient recovering from surgery who has a deficient immune system.

In certain embodiments, the subject is a human.

Another aspect of the invention provides for the use of a compound described herein (such as a compound of Formula I, I-1, I-A, I-B, II, II-1, II-A, II-B, or other compounds in Section I such as a compound of Formula III, IV, V, or VI) in the manufacture of a medicament. In certain embodiments, the medicament is for treating a disorder described herein, such as cancer.

Another aspect of the invention provides for the use of a compound described herein (such as a compound of Formula I, I-1, I-A, I-B, II, II-1, II-A, II-B, or other compounds in Section I such as a compound of Formula III, IV, V, or VI) for treating a medical disorder, such a medical disorder described herein (e.g., cancer).

Further, it is contemplated that tetrahydroquinolinyl and related compounds described herein, such as a compound of Formula I, I-1, I-A, I-B, II, II-1, II-A, II-B, or other compounds in Section I such as a compound of Formula III, IV, V, or VI, can promote the activity of RORγ. Accordingly, another aspect of the invention provides a method of promoting the activity of RORγ. The method comprises exposing a RORγ to an effective amount of a tetrahydroquinolinyl or related compound described herein, such as a compound of Formula I, I-1, I-A, I-B, II, II-1, II-A, II-B, or other compounds in Section I such as a compound of Formula III, IV, V, or VI, to promote RORγ activity. In certain embodiments, the particular compound of Formula I, I-1, I-A, I-B, II, II-1, II-A, or II-B is the compound defined by one of the embodiments described above. Promoting the activity of RORγ means to increase the activity of RORγ. In certain embodiments, exposing a RORγ to an effective amount of a tetrahydroquinolinyl or related compound described herein (such as a compound of Formula I, I-1, I-A, I-B, II, II-1, II-A, II-B, or other compounds in Section I such as a compound of Formula III, IV, V, or VI) results in an increase in RORγ activity of at least 5%, 10%, 20%, or 50% relative to the activity of RORγ under substantially the same conditions but without the presence of the tetrahydroquinolinyl or related compound.

Further, it is contemplated that tetrahydroquinolinyl and related compounds described herein, such as a compound of Formula I, I-1, I-A, I-B, II, II-1, II-A, II-B, or other compounds in Section I such as a compound of Formula III, IV, V, or VI, can increase the amount of interleukin-17 (IL-17) in a subject. IL-17 is a cytokine that affects numerous biological functions. Accordingly, another aspect of the invention provides a method of increasing the amount of IL-17 in a subject. The method comprises administering to a subject an effective amount of a tetrahydroquinolinyl or related compound described herein, such as a compound of Formula I, I-1, I-A, I-B, II, II-1, II-A, II-B, or other compounds in Section I such as a compound of Formula III, IV, V, or VI, to increase the amount of IL-17 in the subject. In certain embodiments, the particular compound of Formula I, I-1, I-A, I-B, II, II-1, II-A, or II-B is the compound defined by one of the embodiments described above.

In certain embodiments, the subject is a human. In certain embodiments, administering the compound increases the amount of IL-17 produced by Th-17 cells in the subject. A change in the amount of IL-17 produced by, for example, Th-17 cells can be measured using procedures described in the literature, such as an ELISA assay or intracellular staining assay.

Further, it is contemplated that tetrahydroquinolinyl and related compounds described herein, such as a compound of Formula I, I-1, I-A, I-B, II, II-1, II-A, II-B, or other compounds in Section I such as a compound of Formula III, IV, V, or VI, may increase the synthesis of IL-17 in a subject. Accordingly, another aspect of the invention provides a method of increasing the synthesis of IL-17 in a subject. The method comprises administering to a subject an effective amount of a compound described herein, e.g., a compound of Formula I, I-1, I-A, I-B, II, II-1, II-A, II-B, or other compounds in Section I such as a compound of Formula III, IV, V, or VI, to increase the synthesis of IL-17 in the subject. In certain embodiments, the particular compound of Formula I, I-1, I-A, I-B, II, II-1, II-A, or II-B is the compound defined by one of the embodiments described above.

Adoptive Cellular Therapy

RORγ agonist compounds described herein may also be used in adoptive cellular therapy to treat various medical disorders, such as cancer, bacterial infections, fungal infections, and immune disorders. Cells, e.g., lymphocyte cells or dendritic cells, are exposed ex vivo to an RORγ agonist compound herein, and then the treated cells are administered to a patient. In adoptive cellular transfer, cells are obtained from a source (typically the patient in need of treatment), cultured ex vivo with an agent, and then the resulting cells are administered to the patient in need of therapy. The culturing typically subjects the cells to conditions whereby the cells increase in number (i.e., expansion) and/or acquire features providing improved therapeutic benefit. General features of the adoptive cellular therapy methods and compositions are described below, along with more specific embodiments of the lymphocyte cells, dendritic cells, and procedures for isolating and culturing cells.

Accordingly, one aspect of the invention provides a method of delivering to a patient a RORγ agonist treated cell selected from the group consisting of a lymphocyte cell and dendritic cell. The method comprises administering to a patient in need thereof a pharmaceutical composition comprising said cell that has been exposed ex vivo to an agonist of RORγ described herein, such as a compound of Formula I, I-1, I-A, or II. The method may further comprise a culturing step. In such embodiments, the method further comprises culturing a cell (i.e., the lymphocyte cell or dendritic cell) with an agonist of RORγ to provide the cell that has been exposed ex vivo to the agonist of RORγ. The culturing may comprise exposing the cell to a cytokine (e.g., IL-1β, IL-2, IL-6, IL-7, IL-10, IL-12, IL-15, IL-18, IL-21, IL-23, or transforming growth factor beta). During the culturing step, the cell may be exposed to an antigen associated with a medical disorder. Although not to be bound by theory, cells having an receptor specific to an antigen associated with a medical disorder can provide a more effective therapy than cells lacking such a receptor. Accordingly, in certain embodiments, the culturing step comprises exposing the cell to an antigen associated with a medical disorder. The antigen may be an antigen presenting cell. Alternatively, the antigen may comprise cancer tissue. Further, as described below, the cell may be genetically altered to express a receptor specific to an antigen associated with a medical disorder.

The cell may be autologous or allogenic. Autologous cells are cells obtained from the patient whom will receive the cell exposed ex vivo to an agonist of RORγ. As such, in certain embodiments, the method may further comprise obtaining a cell from said patient, for use in the culturing step. Alternatively, the cells may be allogenic, i.e., obtained from a subject that produces cells allogenic to cells of the patient. In such embodiments, the method may further comprise obtaining a cell from a subject that produces cells allogenic to lymphocyte cells of the patient, for use in the culturing step.

In certain embodiments, the cell is a lymphocyte cell. Lymphocyte cells can be obtained from human or animal tissues according to procedures described in the literature. In certain embodiments, the lymphocyte cell is obtained from blood, cancer tissue, bone marrow, the spleen, a lymph node, or the thymus. In certain other embodiments, the lymphocyte cell is obtained from a population of peripheral blood mononuclear cells, such as human peripheral blood mononuclear cells. In certain other embodiments, the lymphocyte cell is obtained from a lymph node in proximity to a tumor or site of infection. In certain other embodiments, the lymphocyte cell is obtained from cancer tissue. In yet other embodiments, the lymphocyte cell is a tumor-infiltrating-lymphocyte cell.

Cells can be characterized according to the presence of a receptor for an antigen specific for a medical disorder. In certain embodiments, the cell expresses a receptor for an antigen specific for a medical disorder. As indicate above, such cells may provide more effective therapies for treating disease since the cells are more likely to target tissue specific to the disease to be treated. In certain embodiments, the medical disorder is a cancer, bacterial infection, fungal infection, or immune disorder. In yet other embodiments, the cell may express a receptor that, while not specific for a medical disorder, has utility in enhancing cell efficacy in treating the disorder.

Various types of lymphocyte cells have been described in the literature for use in adoptive cellular transfer. In certain embodiments, the lymphocyte cell is a T cell. In certain other embodiments, the lymphocyte cell is a CD8$^+$ T cell, CD4$^+$ T cell, or T$_H$17 cell. In certain other embodiments, the lymphocyte cell is a CD8$^+$ T cell, CD4$^+$ T cell, or a combination thereof. In certain other embodiments, the lymphocyte cell is a natural killer cell. In certain other embodiments, the lymphocyte cell is a Tc17 cell, natural killer T cell, or γδ T cell. In yet other embodiments, the lymphocyte cell is a genetically altered lymphocyte cell.

Cells may be administered to the patient according to procedures described in the literature. In certain embodiments, the administering comprises injecting into the patient the pharmaceutical composition. The injecting may be intravenous injection or injection directly into diseased tissue, such as a tumor. In yet other embodiments, the injecting may be subcutaneous injection into the patient.

The therapeutic method embraces combination therapies, such as administering (i) an agent that enhances the efficacy of the cell exposed to the agonist of RORγ and/or (ii) an agent having independent efficacy in treating the target medical disorder.

Another aspect of the invention provides a method of preparing a population of cells that have been exposed ex vivo to an agonist of RORγ described herein, where the cells are lymphocyte cells and/or dendritic cells. The method comprises exposing a population of cells selected from the group consisting of lymphocyte cells and dendritic cells ex vivo to an agonist of RORγ described herein to thereby provide said population of cells that have been exposed ex vivo to an agonist of RORγ. The population of cells may be used in therapeutic methods described herein. The exposing step may comprise culturing a population of cells with the agonist of RORγ for a duration of time sufficient to increase the number of cells in the population. The culturing may comprise exposing the cell to a cytokine (e.g., IL-1β, IL-2, IL-6, IL-7, IL-10, IL-12, IL-15, IL-18, IL-21, IL-23, or transforming growth factor beta). Further during the culturing step, the cell may optionally be exposed to an antigen associated with a medical disorder. Accordingly, in certain embodiments, the culturing step comprises exposing the cell to an antigen associated with a medical disorder. The antigen may be an antigen presenting cell. Alternatively, the antigen may comprise cancer tissue. The cell may be autologous or allogenic. Autologous cells are cells obtained from the patient whom will receive the cell exposed ex vivo to an agonist of RORγ. As such, in certain embodiments, the method may further comprise obtaining a cell (i.e., a lymphocyte or dendritic cell) from said patient for use in the culturing step. Alternatively, the cells may be allogenic, i.e., obtained from subject that produces cells allogenic to cells of the patient. In such embodiments, the method may further comprise obtaining a cell from a subject that produces cells allogenic to cells of the patient, for use in the culturing step.

In certain embodiments, the cell is a lymphocyte cell. Lymphocyte cells can be obtained from human or animal tissues according to procedures described in the literature. In certain embodiments, the lymphocyte cell is obtained from blood, cancer tissue, bone marrow, the spleen, a lymph node, or the thymus. In certain other embodiments, the lymphocyte cell is obtained from a population of peripheral blood mononuclear cells, such as human peripheral blood mononuclear cells. In certain other embodiments, the lymphocyte cell is obtained from a lymph node in proximity to a tumor or site of infection. In certain other embodiments, the lymphocyte cell is obtained from cancer tissue. In yet other embodiments, the lymphocyte cell is a tumor-infiltrating-lymphocyte cell.

Cells can be characterized according to the presence of a receptor for an antigen specific for a medical disorder. In certain embodiments, the cell expresses a receptor for an antigen specific for a medical disorder. As indicated above, such cells may provide more effective therapies for treating disease since the cells is more likely to target tissue specific to the disease to be treated. In certain embodiments, the medical disorder is a cancer, bacterial infection, fungal infection, or immune disorder. In yet other embodiments, the cell may express a receptor that, while not specific for a medical disorder, has utility in enhancing cell efficacy in treating the disorder.

As described above, various types of lymphocyte cells have been described in the literature for use in adoptive cellular transfer. In certain embodiments, the lymphocyte cell is a T cell. In certain other embodiments, the lymphocyte cell is a CD8$^+$ T cell, CD4$^+$ T cell, or T$_H$17 cell. In certain other embodiments, the lymphocyte cell is a CD8$^+$ T cell, CD4$^+$ T cell, or a combination thereof. In certain other embodiments, the lymphocyte cell is a natural killer cell. In certain other embodiments, the lymphocyte cell is a Tc17, natural killer T cell, or γδ T cell. In yet other embodiments, the lymphocyte cell is a genetically altered lymphocyte cell.

Another aspect of the invention provides a method of treating a medical disorder. The method comprises administering to a patient in need thereof a cell that has been exposed ex vivo to an agonist of RORγ described herein to treat the medical disorder, wherein the cell is a lymphocyte cell or dendritic cell. The medical disorder can be, for example, a cancer, bacterial infection, fungal infection, or immune disorder. Additional exemplary medical disorders are described above, and in certain embodiments, the medical disorder is a cancer selected from the group consisting of a solid tumor, lymphoma, and leukemia. In certain other embodiments, the medical disorder is a cancer selected from the group consisting of ovarian cancer, melanoma, colorectal cancer, lung cancer, breast cancer, prostate cancer, pancreatic cancer, renal cell carcinoma, leukemia, a B-cell lymphoma, and non-Hodgkin lymphoma.

Another aspect of the invention provides a population of lymphocyte cells that have been exposed ex vivo to an agonist of RORγ described herein. The population may be characterized by the presence and/or quantity of particular types of cells in the population. For example, in certain embodiments, the population comprises one or more of the following: T cells and natural killer cells. In certain other embodiments, a majority of lymphocyte cells in the population are T cells. In certain other embodiments, a majority of lymphocyte cells in the population are CD8$^+$ T cells, CD4$^+$ T cells, T$_H$17 cells, or a combination thereof. In yet other embodiments, a majority of lymphocyte cells in the population are natural killer cells. In yet other embodiments, a single type of lymphocyte cell (e.g., a T cell, CD8$^+$ T cell, CD4+ T cell, T$_H$17 cell, Tc17 cell, natural killer T cell, or γδ T cell) comprises at least 60%, 70% 80%, 90% or 95% of the cells in the population. In yet other embodiments, the population is characterized by: (i) a majority of lymphocyte cells in the population are T cells, (ii) a majority of lymphocyte cells in the population are CD8+ T cells, CD4+ T cells, T$_H$17 cells, or a combination thereof, (iii) a majority of lymphocyte cells in the population are Tc17 cells, (iv) a majority of lymphocyte cells in the population are natural killer cells, or (v) a majority of lymphocyte cells in the population are natural killer T cells, γδ T cells, or a combination thereof. In yet other embodiments, a majority of lymphocyte cells in the population are CD8+ T cells, CD4+ T cells, or a combination thereof. In yet other embodiments, the population is characterized by a majority of lymphocyte cells in the population are Tc17 cells, CD4+Th0 T lymphocyte cells, Th17-polarized CD4+T lymphocyte cells, CD8+Tc17 T lymphocyte cells, or a combination thereof.

In each of the above aspects and embodiments, lymphocyte cells may be characterized according to whether they are a tumor infiltrating lymphocyte, naïve T lymphocyte, memory T lymphocyte, effector T lymphocyte, CD8+ T cell, CD4+ T cell, CD4+/CD8+ double positive T lymphocyte, CD28+CD8+ T cell, or T$_H$17 cell. CD8+ T cells can be separated into naïve CD8+ T cells, memory CD8+ T cells, and effector CD8+ T cells, according to cell surface antigens characteristic to each type of cell. Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, and positive refers to uniform staining of the cell population above the isotype control. For instance, CD4+ T helper cells can be sorted into naive, central memory, and effector cells by identifying cell populations that have cell surface antigens. In certain embodiments, central memory CD4+ T cells are CD62L positive and CD45RO positive. In certain embodiments, effector CD4+ T cells are CD62L and CD45RO negative. In yet other embodiments, the lymphocyte cell is a Th1 cell, Tc1 cell, Th0 cell, or Tc0 cell. In certain embodiments, the lymphocyte cell is a CD8+ T cell, which is optionally further characterized according to the whether the CD8+ T cell is a naïve CD8+ T cell, a memory CD8+ T cell, or an effector CD8+ T cell. In certain embodiments, the lymphocyte cell is a memory CD8+ T cell, which may be further characterized according to whether the cell is CD62L positive or CD45RO positive. In certain other embodiments, the lymphocyte cell is an effector CD8+ T cell, which may be further characterized according to whether the cell is CD62L negative or CD45RO negative. In yet other embodiments, the lymphocyte cell is a CD4+Th0 T lymphocyte, Th17-polarized CD4+T lymphocyte, or CD8+Tc17 T lymphocyte. In still other embodiments, the lymphocyte cell is a memory T cell present in CD62L+ or CD62L− subsets of CD8+ peripheral blood lymphocytes. In certain embodiments, the central memory T cells may be CD45RO+, CD62L+, CD8+ T cells. In certain embodiments, effector T cells are negative for CD62L, CCR7, CD28, and CD127, and positive for granzyme B and perforin.

T cells can be characterized according to identity of a T cell receptor located on the surface of the T cell. The T cell receptor is a disulfide-linked membrane-anchored heterodimer that normally consists of highly variable alpha (α) and beta (β) chains expressed as part of a complex with the invariant CD3 chain molecules. T cells expressing this receptor are referred to as α:β (or αβ) T cells. A minority of T cells express an alternate receptor, formed by variable gamma (γ) and delta (δ) chains, and such T cells are referred as γδ T cells. One subtype of T cells is natural killer T (NKT) cells. NKT cells are a heterogeneous group of T cells that share properties of both T cells and natural killer NK cells. Many NKT cells recognize the non-polymorphic CD1d molecule, an antigen-presenting molecule that binds self- and foreign lipids and glycolipids. Other subtypes of T cells include, for example, CD8+ T cells, CD4+ T cells, Tc17 cells, natural killer T cells, and γδ T cells. Still other subtypes of T cells include, for example, CD4−CD8− T cells and CD28+ CD8+ T cells.

Preferably the lymphocyte cell comprises a receptor specific for an antigen of a medical condition. The receptor can be the endogenous lymphocyte cell receptor, i.e., the antigen-specific lymphocyte cell receptor that is endogenous (i.e., native to) the lymphocyte. In such instances, the lymphocyte comprising the endogenous lymphocyte cell receptor can be a lymphocyte cell that was isolated from the patient, which is known to express the particular medical condition-specific antigen. Alternatively, the lymphocyte comprising the endogenous lymphocyte cell receptor can be a lymphocyte cell that was isolated from a subject that produces allogenic lymphocyte cells (i.e., lymphocyte cells that are histocompatible with the patient that will receive the lymphocyte cells). In certain embodiments, the subject from which lymphocyte cells are obtained may be immunized prior to obtaining the lymphocyte cells, so that the lymphocyte cells to be administered to the patient will have specificity for the medical disorder to be treated.

The antigen of a disease recognized by the endogenous lymphocyte cell receptor can be any antigen which is characteristic of the disease. For example, the antigen may be, for example, a tumor antigen, such as gp100, MART-1, TRP-1, TRP-2, tyrosinase, NY-ESO-1, MAGE-1, or MAGE-3.

Lymphocyte cells may also be characterized according to the presence of a phenotypic marker of activation for tumor reactivity, such as the presence of 4-1BBL. Populations of lymphocyte cells enriched for such a phenotypic marker may provide therapeutic advantages. Lymphocyte cells may also be characterized according to the level of expression of the RORγ. In certain embodiments, the lymphocyte cell may be induced to express or engineered to express RORγ, thereby increasing the amount of RORγ.

The lymphocyte cell may be a genetically modified lymphocyte cell, such as a genetically modified lymphocyte cell described in, for example, International Patent Application Publication No. WO 2012/129514, which is hereby incorporated by reference. Genetic modification of the lymphocyte may improve the efficacy of therapy by promoting the viability and/or function of transferred lymphocyte cells, provide a genetic marker to permit selection and/or evaluation of in vivo survival or migration, or may incorporate functions that improve the safety of immunotherapy, for example, by making the cell susceptible to negative selection in vivo. The lymphocyte may be genetically modified so that the lymphocyte cell expresses certain proteins, such as a survival cytokine (e.g., granulocyte-macrophage colony-stimulating factor) and/or receptor for an antigen (e.g., a tumor antigen).

Accordingly, in embodiments, lymphocyte cells are modified with chimeric antigen receptors (CAR). The CARs may comprise a single-chain antibody fragment (scFv) that is derived from the variable heavy (VH) and variable light (VL) chains of a monoclonal antibody (mAb) linked to the TCR CD3+ chain that mediates T-cell activation and cytotoxicity. Costimulatory signals can also be provided through the CAR by fusing the costimulatory domain of CD28 or 4-1 BB to the CD3+ chain. CARs are specific for cell surface molecules independent from HLA, thus overcoming the limitations of TCR-recognition including HLA-restriction and low levels of HLA-expression on tumor cells.

The description above describes multiple embodiments providing definitions for variables used herein. The application specifically contemplates all combinations of such variables, e.g., particular combinations of the definitions set forth for variables A and X.

III. Combination Therapy

Another aspect of the invention provides for combination therapy. Tetrahydroquinolinyl and related compounds (e.g., a compound of Formula I, I-1, I-A, I-B, II, II-1, II-A, II-B, or other compounds in Section I such as a compound of Formula III, IV, V, or VI) or their pharmaceutically acceptable salts may be used in combination with additional therapeutic agents to treat medical disorders, such as a cancer, bacterial infection, fungal infection, and immune deficiency disorder.

Exemplary therapeutic agents that may be used as part of a combination therapy in treating cancer, include, for example, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

An additional class of agents that may be used as part of a combination therapy in treating cancer is immune checkpoint inhibitors (also referred to as immune checkpoint blockers). Immune checkpoint inhibitors are a class of therapeutic agents that have the effect of blocking immune checkpoints. See, for example, Pardoll in *Nature Reviews Cancer* (2012) vol. 12, pages 252-264. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAB3, (v) B7-H3, (vi) B7-H4, and (vii) TIM3. The CTLA4 inhibitor Ipilumumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytoxic agents (e.g., tyrosine-kinase inhibitors).

Exemplary therapeutic agents that may be used as part of a combination therapy in treating a bacterial infection, include, for example, amoxicillin, azithromycin, cefazolin, ceftriaxone, cefuroxime, cephalexin, ciprofloxacin, clindamycin, doxycycline, levofloxacin, linezolid, metronidazole, moxifloxacin, and penicillin.

Exemplary therapeutic agents that may be used as part of a combination therapy in treating a fungal infection, include, for example, 2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide, hexaconazole; hymexazole; imazalil; imibenconazole; iminoctadine triacetate; iminoctadine tris (albesil); iodocarb; ipconazole; iprobenfos; iprodione; iprovalicarb; irumamycin; isoprothiolane; isovaledione; kasugamycin; kresoxim-methyl; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; tetraconazole; thiabendazole; thicyofen; thifluzamide; thiophanate-methyl; thiram; tioxymid; tricyclazole; tridemorph; trifloxystrobin; triflumizole; triforine; triticonazole; uniconazole; validamycin A; vinclozolin; zineb; ziram; and zoxamide.

The amount of tetrahydroquinolinyl or related compound (e.g., a compound of Formula I, I-1, I-A, I-B, II, II-1, II-A, II-B, or other compounds in Section I such as a compound of Formula III, IV, V, or VI) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a tetrahydroquinolinyl or related compound (e.g., a compound of any one of Formula I, I-1, I-A, I-B, II, II-1, II-A, II-B, or other compounds in Section I such as a compound of Formula III, IV, V, or VI) may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the tetrahydroquinolinyl or related compound (e.g., a compound of any one of Formula I, I-1, I-A, I-B, II, II-1, II-A, II-B, or other compounds in Section I such as a compound of Formula III, IV, V, or VI) and the additional therapeutic agent(s) are administered in doses commonly employed when such agents are used as monotherapy for treating the disorder. In other embodiments, the tetrahydroquinolinyl or related compound (e.g., a compound of any one of Formula I, I-1, I-A, I-B, II, II-1, II-A, II-B, or other compounds in Section I such as a compound of Formula III, IV, V, or VI) and the additional therapeutic agent(s) are administered in doses lower than the doses commonly employed when such agents are used as monotherapy for treating the disorder. In certain embodiments, the tetrahydroquinolinyl or related compound (e.g., a compound of any one of Formula I, I-1, I-A, I-B, II, II-1, II-A, II-B, or other compounds in Section I such as a compound of Formula III, IV, V, or VI) and the additional therapeutic agent(s) are present in the same composition, which is suitable for oral administration.

In certain embodiments, the tetrahydroquinolinyl or related compound (e.g., a compound of any one of Formula I, I-1, I-A, I-B, II, II-1, II-A, II-B, or other compounds in Section I such as a compound of Formula III, IV, V, or VI) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the tetrahydroquinolinyl or related compound (e.g., a compound of any one of Formula I, I-1, I-A, I-B, II, II-1, II-A, II-B, or other compounds in Section I such as a compound of Formula III, IV, V, or VI), a pharmaceutically acceptable carrier, vehicle or diluent, and optionally at least one additional therapeutic agent listed above.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a tetrahydroquinolinyl or related compound described herein in a therapeutically effective amount for the treatment of a medical disorder described herein.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those of skill in the art.

Example 1—Synthesis of (S)-6-((2-Chloro-6-fluorophenoxy)methyl)-2-methyl-4-((3-(trifluoromethyl)phenyl)sulfonyl)-3,4-dihydro-2H-benzo[b][1,4]oxazine

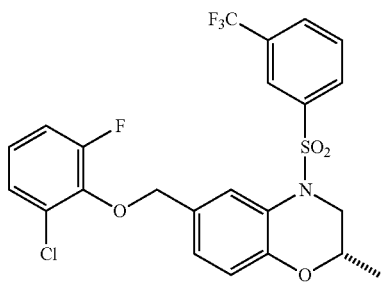 [SMILES: C[C@H]1CN(S(=O)(=O)c2cccc(C(F)(F)F)c2)c2cc(COc3c(F)cccc3Cl)ccc2O1]

Part I—Synthesis of Methyl (S)-4-((1-methoxy-1-oxopropan-2-yl)oxy)-3-nitrobenzoate

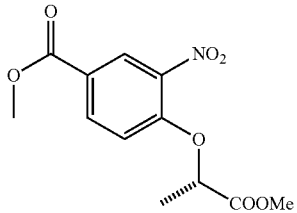 [SMILES: COC(=O)c1ccc(O[C@@H](C)C(=O)OC)c([N+](=O)[O-])c1]

Methyl-4-hydroxy-3-nitrobenzoate (3 g, 13.76 mmol), methyl-(R)-lactate (1.433 g, 13.8 mmol), and triphenylphosphine (4.33 g, 16.5 mmol) were suspended in dichloromethane (36 mL), and diisopropyl azodicarboxylate (3.25 mL, 16.51 mmol) was added dropwise. The reaction mixture was stirred at room temperature for one hour, and then the crude was washed with water, dried (Na$_2$SO$_4$), and concentrated to provide a residue. The residue was purified via MPLC eluting with a gradient of ethyl acetate in hexanes, followed by a second MPLC purification eluting with dichloromethane to afford methyl (S)-4-((1-methoxy-1-oxopropan-2-yl)oxy)-3-nitrobenzoate (2.56 g, 66%) as a light yellow oil. $^1$H-NMR (400 MHz, DMSO-d$_6$) δ 8.37 (s, 1H), 8.12 (d, 1H), 7.36 (d, 1H), 5.40 (q, 1H), 3.83 (s, 3H), 3.65 (s, 3H), 1.54 (d, 3H).

Part II—Synthesis of Methyl (S)-2-methyl-3-oxo-3,4-dihydro-2H-benzo[b][1,4]oxazine-6-carboxylate

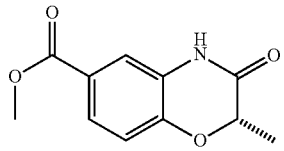 [SMILES: COC(=O)c1ccc2c(c1)NC(=O)[C@H](C)O2]

Methyl (S)-4-((1-methoxy-1-oxopropan-2-yl)oxy)-3-nitrobenzoate (2.38 g, 8.42 mmol) was dissolved in acetic acid (30 mL) and powdered iron (2.35 g, 42.1 mmol) was added. The mixture was heated to 70° C. for two hours. Then, the resulting suspension was filtered through a pad of Celite, and the material was washed through with ethyl acetate. The filtrate was then partitioned between ethyl acetate and water, and the organic phase was washed a second time with water, washed with brine, and concentrated to provide a residue. The residue was purified by MPLC, eluting with a gradient of hexanes and ethyl acetate (85:15 to 3:7) to afford methyl (S)-2-methyl-3-oxo-3,4-dihydro-2H-benzo[b][1,4]oxazine-6-carboxylate (1.16 g, 62%) as a white solid. $^1$H-NMR (400 MHz, DMSO-d$_6$) δ 10.81 (s, 1H), 7.52 (m, 2H), 7.02 (d, 1H), 4.77 (q, 1H), 3.79 (s, 3H), 1.42 (d, 3H).

Part III—Synthesis of (S)-(2-Methyl-3,4-dihydro-2H-benzo[b][1,4]oxazin-6-yl)methanol

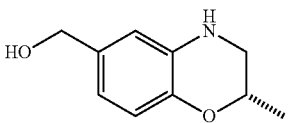

To a solution of methyl (S)-2-methyl-3-oxo-3,4-dihydro-2H-benzo[b][1,4]oxazine-6-carboxylate (1.16 g, 5.24 mmol) in anhydrous THF (26 mL) at ambient temperature was carefully added 1M solution of lithium aluminum hydride in diethyl ether (20.98 mL, 20.98 mmol). The mixture was heated in an oil bath at 50° C. overnight. The resulting crude mixture was carefully treated with 0.75 mL water, then 0.75 mL of 15% NaOH solution, and then 2.25 mL of water. The resulting mixture was stirred vigorously for several minutes, and then filtered. The filtrate was concentrated to afford the title compound (0.96 g, 102%) which was used without purification. $^1$H-NMR (400 MHz, DMSO-d$_6$) δ 6.50 (m, 2H), 6.36 (d, 1H), 5.66 (s, 1H), 4.86 (t, 1H), 4.26 (d, 2H), 4.01 (m, 1H), 3.24 (m, 1H), 2.87 (m, 1H), 1.22 (d, 3H).

Part IV—Synthesis of (S)-(2-Methyl-4-((3-(trifluoromethyl)phenyl)sulfonyl)-3,4-dihydro-2H-benzo[b][1,4]oxazin-6-yl)methanol

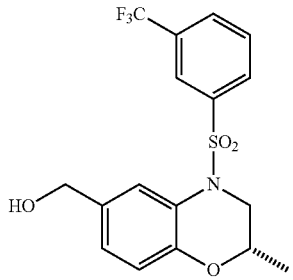 [SMILES: C[C@H]1CN(S(=O)(=O)c2cccc(C(F)(F)F)c2)c2cc(CO)ccc2O1]

(S)-(2-Methyl-3,4-dihydro-2H-benzo[b][1,4]oxazin-6-yl)methanol (0.9 g, 5.02 mmol), 3-(trifluoromethyl)benzenesulfonyl chloride (3.07 g, 12.5 mmol), and potassium carbonate (2.08 g, 15.1 mmol) were suspended in acetone, and the mixture was shaken at room temperature for 18 hours. Next, the crude was filtered, and the filtrate was concentrated onto silica gel and purified by chromatography delivering the title compound. $^1$H-NMR (400 MHz, DMSO-$d_6$) δ 8.08 (d, 1H), 7.97 (m, 2H), 7.81 (t, 1H), 7.65 (s, 1H), 6.99 (d, 1H), 6.74 (d, 1H), 5.18 (bs, 1H), 4.40 (s, 2H), 4.35 (d, 1H), 3.45 (m, 1H), 3.22 (m, 1H), 1.18 (d, 3H).

Part V—Synthesis of (S)-6-((2-Chloro-6-fluorophenoxy)methyl)-2-methyl-4-((3-(trifluoromethyl)phenyl)sulfonyl)-3,4-dihydro-2H-benzo[b][1,4]oxazine

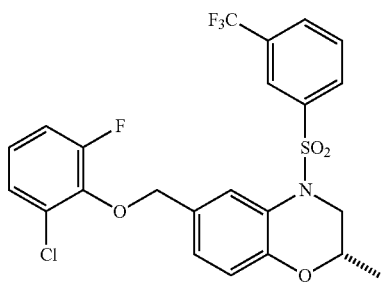 [SMILES: C[C@H]1CN(S(=O)(=O)c2cccc(C(F)(F)F)c2)c2cc(COc3c(F)cccc3Cl)ccc2O1]

(S)-(2-Methyl-4-((3-(trifluoromethyl)phenyl)sulfonyl)-3,4-dihydro-2H-benzo[b][1,4]oxazin-6-yl)methanol (1.28 g, 3.304 mmol), 2-chloro-6-fluorophenol (0.484 g, 3.304 mmol), and triphenylphosphine (1.04 g, 3.965 mmol) were suspended in dichloromethane (7 mL), and diisopropylazodicarboxylate (0.78 mL, 3.965 mmol) was added dropwise. The reaction mixture was stirred at room temperature for one hour, then washed with water, dried (Na$_2$SO$_4$) and concentrated to provide a residue. The residue was purified via MPLC, eluting with a gradient of 0-5% methanol in dichloromethane to afford the title compound (1.3 g, 73%). $^1$H-NMR (400 MHz, DMSO-$d_6$) δ 8.08 (d, 1H), 7.94 (m, 2H), 7.80 (m, 2H), 7.27 (m, 2H), 7.13 (m, 2H), 6.80 (d, 1H), 5.03 (s, 2H), 4.36 (d, 1H), 3.49 (m, 1H), 3.25 (m, 1H), 1.19 (d, 3H).

Example 2—Preparation of (S)-6-((2-Chloro-6-fluorophenoxy)methyl)-4-((4-fluorophenyl)sulfonyl)-2-methyl-3,4-dihydro-2H-benzo[b][1,4]oxazine

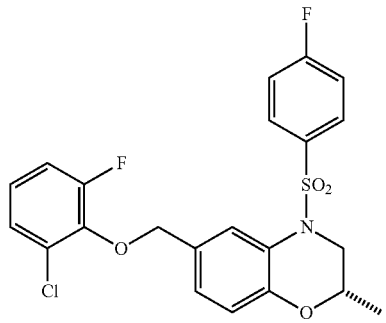 [SMILES: C[C@H]1CN(S(=O)(=O)c2ccc(F)cc2)c2cc(COc3c(F)cccc3Cl)ccc2O1]

The title compound was prepared based on experimental procedures described in Examples 4 and 5 and the detailed description. (ES, m/z): (M+NH$_4$)$^+$466.

Example 3—Synthesis of (S)-2-(6-((2-Chloro-6-fluorophenoxy)methyl)-4-((3-(trifluoromethyl)phenyl)sulfonyl)-3,4-dihydro-2H-benzo[b][1,4]oxazin-2-yl)ethan-1-ol

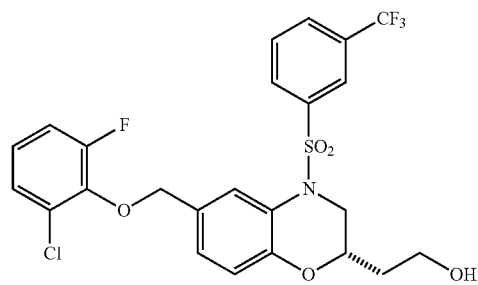 [SMILES: O=S(=O)(c1cccc(C(F)(F)F)c1)N1C[C@H](CCO)Oc2ccc(COc3c(F)cccc3Cl)cc21]

Part I—Synthesis of Methyl (R)-3-Nitro-4-((2-oxotetrahydrofuran-3-yl)oxy)benzoate

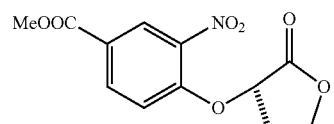

Methyl 4-hydroxy-3-nitrobenzoate (2.0 g, 10.2 mmol), (3R)-3-hydroxytetrahydrofuran-2-one (1.036 g, 10.2 mmol), and triphenylphosphine (3.19 g, 12.2 mmol) were suspended in dichloromethane (25 mL), the reaction vessel was cooled in an ice bath, and diisopropyl azodicarboxylate (2.40 mL, 12.2 mmol) was added dropwise to the reaction mixture. The reaction mixture was stirred at room temperature for one hour, then washed with water, dried (Na$_2$SO$_4$), and concentrated. The concentrate was purified via MPLC (Two columns: the first column eluting first with dichloromethane, the second column to purify further eluting with a gradient of 15-70% ethyl acetate in hexanes) to afford methyl (R)-

3-nitro-4-((2-oxotetrahydrofuran-3-yl)oxy)benzoate (2.15 g, 75%). $^1$H-NMR (400 MHz, DMSO-d$_6$) δ 8.38 (s, 1H), 8.20 (d, 1H), 7.62 (d, 1H), 5.71 (t, 1H), 4.44 (t, 1H), 4.28 (m, 1H), 3.84 (s, 3H), 2.80 (m, 1H), 2.35 (m, 1H).

Part II—Synthesis of Methyl (S)-2-(2-hydroxyethyl)-3-oxo-3,4-dihydro-2H-benzo[b][1,4]oxazine-6-carboxylate

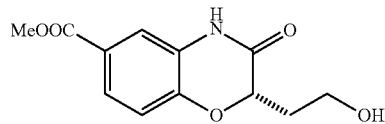 [SMILES: COC(=O)c1ccc2c(c1)NC(=O)[C@H](CCO)O2]

Methyl (R)-3-nitro-4-((2-oxotetrahydrofuran-3-yl)oxy)benzoate (2.15 g, 7.65 mmol) was dissolved in acetic acid (25 mL) and powdered iron (2.14 g, 38.2 mmol) was added. The reaction mixture was heated to 70° C. for two hours. Then, the suspension was filtered through a pad of Celite. The filtrate was partitioned between ethyl acetate and water. The organic phase was washed with saturated sodium bicarbonate, washed with brine, and then concentrated to provide a residue. The residue was purified via MPLC eluting with a gradient of 15-70% ethyl acetate in hexanes to afford methyl (S)-2-(2-hydroxyethyl)-3-oxo-3,4-dihydro-2H-benzo[b][1,4]oxazine-6-carboxylate. $^1$H-NMR (400 MHz, DMSO-d$_6$) δ 10.81 (bs, 1H), 7.52 (d, 1H), 7.47 (s, 1H), 7.02 (d, 1H), 4.75 (m, 1H), 4.63 (t, 1H), 3.78 (s, 3H), 3.55 (m, 2H), 1.95 (m, 1H), 1.80 (m, 1H).

Part III—Synthesis of Methyl (S)-2-(2-((tert-butyldimethylsilyl)oxy)ethyl)-3-oxo-3,4-dihydro-2H-benzo[b][1,4]oxazine-6-carboxylate

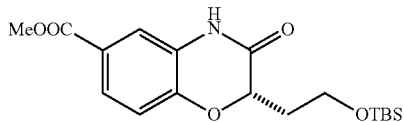 [SMILES: COC(=O)c1ccc2c(c1)NC(=O)[C@H](CCO[Si](C)(C)C(C)(C)C)O2]

Methyl (S)-2-(2-hydroxyethyl)-3-oxo-3,4-dihydro-2H-benzo[b][1,4]oxazine-6-carboxylate (1.24 g, 4.94 mmol), tert-butyldimethylsilyl chloride (0.967 g, 6.42 mmol), and imidazole (0.672 g, 9.87 mmol) were suspended in DMF (16 mL), and stirred at room temperature overnight. The resulting mixture was partitioned between water and ethyl acetate, and the organic layer was washed twice with water, washed with brine, dried (Na$_2$SO$_4$), and concentrated to provide a residue. The residue was purified via MPLC, eluting with a gradient of 5-30% ethyl acetate in hexanes to afford methyl (S)-2-(2-((tert-butyldimethylsilyl)oxy)ethyl)-3-oxo-3,4-dihydro-2H-benzo[b][1,4]oxazine-6-carboxylate (1.20 g, 67%). $^1$H-NMR (400 MHz, DMSO-d$_6$) δ 10.82 (bs, 1H), 7.52 (d, 1H), 7.46 (s, 1H), 7.01 (d, 1H), 4.70 (m, 1H), 3.79 (s, 3H), 3.73 (m, 2H), 2.00 (m, 1H), 1.87 (m, 1H), 0.81 (s, 9H), 0.00 (s, 6H).

Part IV—Synthesis of (S)-2-(6-(Hydroxymethyl)-3,4-dihydro-2H-benzo[b][1,4]oxazin-2-yl)ethan-1-ol

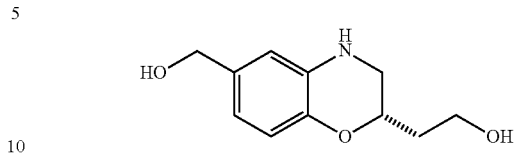

Methyl (S)-2-(2-((tert-butyldimethylsilyl)oxy)ethyl)-3-oxo-3,4-dihydro-2H-benzo[b][1,4]oxazine-6-carboxylate (1.2 g, 3.283 mmol) was dissolved in anhydrous THF (16 mL) and a 1M solution of lithium aluminum hydride in ether (13.1 mL, 13.1 mmol) was added. The mixture was heated in an oil bath at 50° C. overnight. Then, the crude mixture was carefully treated with water (0.5 mL), 15% NaOH (0.5 mL), and then treated again with water (1.5 mL). The resulting mixture was stirred vigorously for several minutes and then filtered. The filtrate was concentrated onto silica gel and purified by MPLC delivering (S)-2-(6-(hydroxymethyl)-3,4-dihydro-2H-benzo[b][1,4]oxazin-2-yl)ethan-1-ol as a clear oil (0.62 g, 90%). $^1$H-NMR (400 MHz, DMSO-d$_6$) δ 6.51 (m, 2H), 6.36 (d, 1H), 5.65 (bs, 1H), 4.85 (t, 1H), 4.51 (t, 1H), 4.23 (d, 2H), 4.02 (m, 1H), 3.53 (m, 2H), 3.27 (m, 1H), 2.92 (m, 1H), 1.67 (m, 2H).

Part V—Synthesis of (S)-2-(6-(Hydroxymethyl)-4-((3-(trifluoromethyl)phenyl)sulfonyl)-3,4-dihydro-2H-benzo[b][1,4]oxazin-2-yl)ethan-1-ol

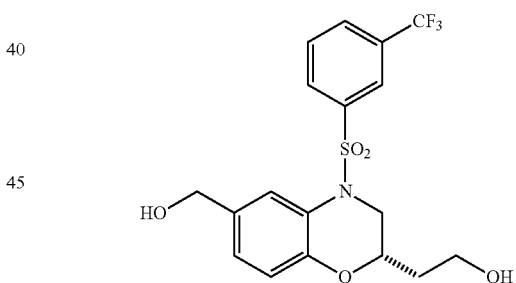

(S)-2-(6-(Hydroxymethyl)-3,4-dihydro-2H-benzo[b][1,4]oxazin-2-yl)ethan-1-ol (0.62 g, 2.96 mmol) and 3-(trifluoromethyl)benzenesulfonyl chloride (1.812 g, 7.408 mmol) were suspended in acetone (30 mL), and potassium carbonate (1.23 g, 8.89 mmol) was added. The mixture was stirred at room temperature overnight. Then, the crude mixture was then filtered, and the filtrate was concentrated onto silica gel and purified by MPLC affording (S)-2-(6-(hydroxymethyl)-4-((3-(trifluoromethyl)phenyl)sulfonyl)-3,4-dihydro-2H-benzo[b][1,4]oxazin-2-yl)ethan-1-ol (0.8 g, 65%). $^1$H-NMR (400 MHz, DMSO-d$_6$) δ 8.06 (d, 1H), 7.92 (m, 2H), 7.80 (t, 1H), 7.64 (s, 1H), 6.98 (d, 1H), 6.73 (d, 1H), 5.15 (t, 1H), 4.55 (t, 1H), 4.39 (m, 3H), 3.43 (m, 3H), 3.26 (m, 1H), 1.61 (m, 2H).

Part VI—Synthesis of (S)-2-(6-((2-Chloro-6-fluorophenoxy)methyl)-4-((3-(trifluoromethyl)phenyl)sulfonyl)-3,4-dihydro-2H-benzo[b][1,4]oxazin-2-yl)ethan-1-ol

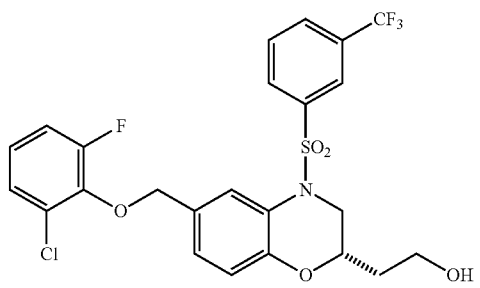 [SMILES: O=S(=O)(c1cccc(C(F)(F)F)c1)N1C[C@H](CCO)Oc2ccc(COc3c(F)cccc3Cl)cc21]

(S)-2-(6-(Hydroxymethyl)-4-((3-(trifluoromethyl)phenyl)sulfonyl)-3,4-dihydro-2H-benzo[b][1,4]oxazin-2-yl)ethan-1-ol (0.1 g, 0.24 mmol), 2-chloro-6-fluorophenol (0.035 g, 0.24 mmol), and triphenylphosphine (0.075 g, 0.287 mmol) were suspended in dichloromethane (3 mL), and diisopropylazodicarboxylate (0.057 mL, 0.287 mmol) was added dropwise. The reaction mixture was stirred at room temperature for one hour, washed with water, dried (Na$_2$SO$_4$) and concentrated to provide a residue. The residue was purified by MPLC twice (2 columns: first, eluting with a gradient of 10-40% ethyl acetate in hexanes; second eluting with dichloromethane) to afford (S)-2-(6-((2-chloro-6-fluorophenoxy)methyl)-4-((3-(trifluoromethyl)phenyl)sulfonyl)-3,4-dihydro-2H-benzo[b][1,4]oxazin-2-yl)ethan-1-ol (0.125 g, 89%). $^1$H-NMR (400 MHz, DMSO-d$_6$) δ 8.07 (d, 1H), 7.93 (s, 1H), 7.84 (d, 1H), 7.78 (m, 2H), 7.27 (m, 2H), 7.13 (m, 2H), 6.81 (d, 1H), 5.05 (s, 2H), 4.56 (t, 1H), 4.40 (d, 1H), 3.43 (m, 3H), 3.25 (m, 1H), 1.64 (m, 2H).

Example 4—Synthesis of (S)-2-(6-((2-Chloro-6-fluorophenoxy)methyl)-4-((3-(trifluoromethyl)phenyl)sulfonyl)-3,4-dihydro-2H-benzo[b][1,4]oxazin-2-yl)acetic acid

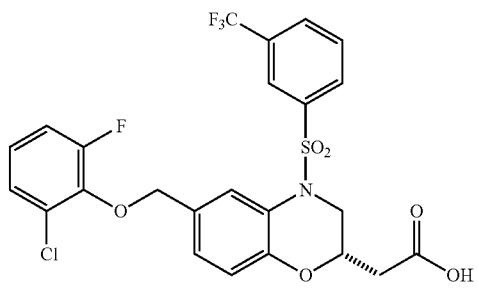 [SMILES: O=C(O)C[C@H]1CN(S(=O)(=O)c2cccc(C(F)(F)F)c2)c2cc(COc3c(F)cccc3Cl)ccc2O1]

(S)-2-(6-((2-Chloro-6-fluorophenoxy)methyl)-4-((3-(trifluoromethyl)phenyl) sulfonyl)-3,4-dihydro-2H-benzo[b][1,4]oxazin-2-yl)ethan-1-ol (30 mg, 0.055 mmol) was dissolved in acetone (2 mL) and Jones' reagent was added dropwise until the orange color remained. Then, isopropyl alcohol was added dropwise until the orange color was gone. Next, the solution was decanted, and concentrated, then re-dissolved in methanol and purified by preparative HPLC eluting with a gradient of water (containing 0.05% trifluoroacetic acid) and acetonitrile to afford (S)-2-(6-((2-chloro-6-fluorophenoxy)methyl)-4-((3-(trifluoromethyl) phenyl)sulfonyl)-3,4-dihydro-2H-benzo[b][1,4]oxazin-2-yl)acetic acid (10 mg, 33%) as a white solid. $^1$H-NMR (400 MHz, DMSO-d$_6$) δ 8.10 (m, 1H), 7.96 (s, 1H), 7.81 (m, 3H), 7.27 (m, 2H), 7.13 (m, 2H), 6.80 (d, 1H), 6.49 (bs, 1H), 5.04 (s, 2H), 4.45 (d, 1H), 3.63 (m, 1H), 3.33 (m, 1H), 2.78 (dd, 1H), 2.58 (dd, 1H).

Example 5—Synthesis of (S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanenitrile

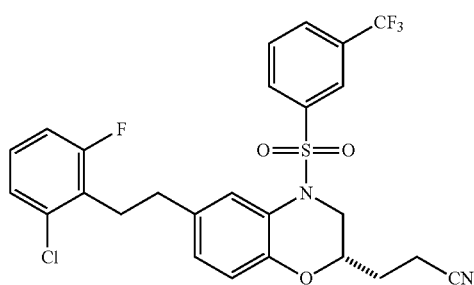 [SMILES: N#CCC[C@H]1CN(S(=O)(=O)c2cccc(C(F)(F)F)c2)c2cc(CCc3c(F)cccc3Cl)ccc2O1]

Part I—Synthesis of (R)-3-(4-Bromo-2-nitrophenoxy)dihydrofuran-2(3H)-one

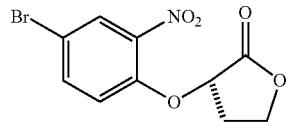 [SMILES: O=C1OCC[C@@H]1Oc1ccc(Br)cc1[N+](=O)[O-]]

4-Bromo-2-nitrophenol (3 g, 13.76 mmol), (3R)-3-hydroxytetrahydrofuran-2-one (1.405 g, 13.76 mmol), and triphenylphosphine (4.33 g, 16.51 mmol) were suspended in dichloromethane (36 mL), and diisopropylazodicarboxylate (3.25 mL, 16.5 mmol) was added dropwise. The reaction mixture was stirred at room temperature for one hour, washed with water, dried (Na$_2$SO$_4$), and concentrated onto silica gel. The residue on the silica gel was purified by MPLC (2 columns: first, dichloromethane; second, a gradient of EtOAc/hexanes) affording (R)-3-(4-bromo-2-nitrophenoxy)dihydrofuran-2(3H)-one as a white solid (1.93 g, 46%). $^1$H-NMR (400 MHz, DMSO-d$_6$) δ 8.12 (s, 1H), 7.86 (d, 1H), 7.47 (d, 1H), 5.55 (t, 1H), 4.42 (m, 1H), 4.26 (m, 1H), 2.75 (m, 1H), 2.30 (m, 1H).

Part II—Synthesis of (S)-6-Bromo-2-(2-hydroxyethyl)-2H-benzo[b][1,4]oxazin-3(4H)-one

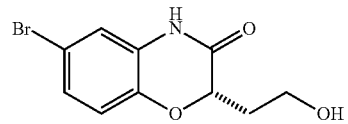

(R)-3-(4-Bromo-2-nitrophenoxy)dihydrofuran-2(3H)-one (1.93 g, 6.39 mmol) was dissolved in acetic acid and powdered iron (1.784 g, 31.95 mmol) was added. The resulting mixture was heated to 70° C. for two hours. The resulting suspension was filtered through a pad of Celite, and the pad was washed with ethyl acetate. The combined filtrates were partitioned between ethyl acetate and water, and the organic phase was washed a second time with water, washed with brine, and concentrated to provide a residue. The residue was purified via MPLC eluting with a gradient of 15-70% ethyl acetate in hexanes to afford (S)-6-bromo-2-(2-hydroxyethyl)-2H-benzo[b][1,4]oxazin-3(4H)-one as a white solid (1.32 g, 76%). $^1$H-NMR (400 MHz, DMSO-$d_6$) δ 10.73 (bs, 1H), 7.04 (d, 1H), 6.98 (s, 1H), 6.90 (d, 1H), 4.62 (m, 2H), 3.53 (m, 2H), 1.91 (m, 1H), 1.88 (m, 1H).

Part III—Synthesis of (S)-2-(6-Bromo-3,4-dihydro-2H-benzo[b][1,4]oxazin-2-yl)ethan-1-ol

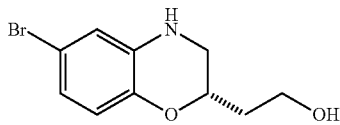 [SMILES: OCC[C@H]1CNc2cc(Br)ccc2O1]

(S)-6-Bromo-2-(2-hydroxyethyl)-2H-benzo[b][1,4]oxazin-3(4H)-one (1.32 g, 4.85 mmol) was dissolved in anhydrous THF (49 mL) under nitrogen at ambient temperature and borane-dimethylsulfide complex (1.47 g, 19.41 mmol) was added dropwise. The reaction mixture was heated to reflux for 90 minutes. Then, the reaction mixture was cooled in an ice bath and subsequently methanol was added to the reaction mixture to quench the reaction. The resulting solution was heated to reflux for 20 minutes, and then concentrated to provide a residue. The residue was partitioned between ethyl acetate and water, washed with brine, dried (Na$_2$SO$_4$), and concentrated to provide crude product. The crude product was purified by MPLC eluting with a gradient of 15-70% ethyl acetate in hexanes to afford (S)-2-(6-bromo-3,4-dihydro-2H-benzo[b][1,4]oxazin-2-yl)ethan-1-ol (1.05 g, 84%).

Part IV—Synthesis of (S)-6-Bromo-2-(2-((tert-butyldimethylsilyl)oxy)ethyl)-3,4-dihydro-2H-benzo[b][1,4]oxazine

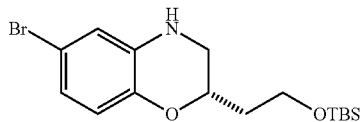

(S)-2-(6-Bromo-3,4-dihydro-2H-benzo[b][1,4]oxazin-2-yl)ethan-1-ol (0.28 g, 1.085 mmol), tert-butyldimethylchlorosilane (0.196 g, 1.302 mmol), and imidazole (0.148 g, 2.17 mmol) were dissolved in DMF (4 mL), and the reaction mixture was stirred at room temperature overnight. Next, the reaction mixture was partitioned between water and ethyl acetate, and the organic layer was washed twice more with water, washed with brine, dried (Na$_2$SO$_4$), and concentrated onto silica gel. The residue on the silica gel was purified by MPLC eluting with a gradient of 5-30% ethyl acetate in hexanes to afford (S)-6-bromo-2-(2-((tert-butyldimethylsilyl)oxy)ethyl)-3,4-dihydro-2H-benzo[b][1,4]oxazine (0.19 g, 47%). $^1$H-NMR (400 MHz, DMSO-$d_6$) δ 6.66 (s, 1H), 6.52 (s, 2H), 6.06 (bs, 1H), 4.02 (q, 1H), 3.72 (m, 2H), 3.33 (m, 1H), 2.94 (m, 1H), 1.70 (q, 2H), 0.82 (s, 9H), 0.01 (s, 6H).

Part V—Synthesis of (S)-2-(6-Bromo-4-((3-(trifluoromethyl)phenyl)sulfonyl)-3,4-dihydro-2H-benzo[b][1,4]oxazin-2-yl)ethan-1-ol

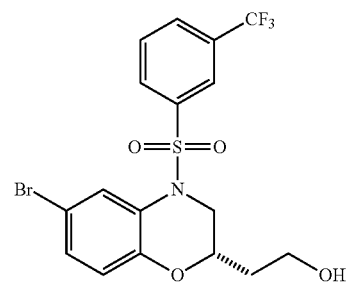

(S)-6-Bromo-2-(2-((tert-butyldimethylsilyl)oxy)ethyl)-3,4-dihydro-2H-benzo[b][1,4]oxazine (1.04 g, 2.79 mmol), 3-(trifluoromethyl)benzenesulfonyl chloride (1.025 g, 4.19 mmol), and potassium carbonate (0.772 g, 5.586 mmol) were suspended in acetone (28 mL), and the mixture was shaken at room temperature for 18 hours. The crude material was filtered, and the filtrate was concentrated onto silica gel and purified by chromatography delivering (S)-2-(6-bromo-4-((3-(trifluoromethyl)phenyl)sulfonyl)-3,4-dihydro-2H-benzo[b][1,4]oxazin-2-yl)ethan-1-ol (1.61 g, 99%). It is noted that the silyl protecting group did not hydrolyze immediately, but after several days at room temperature degradation to the alcohol was observed. $^1$H-NMR (400 MHz, DMSO-$d_6$) δ 8.11 (d, 1H), 7.95 (m, 2H), 7.84 (t, 1H), 7.78 (s, 1H), 7.25 (d, 1H), 6.80 (d, 1H), 4.56 (s, 1H), 3.39 (d, 1H), 3.41 (m, 3H), 3.28 (m, 1H), 1.63 (m, 2H).

Part VI—Synthesis of (S)-2-(6-Bromo-4-((3-(trifluoromethyl)phenyl)sulfonyl)-3,4-dihydro-2H-benzo[b][1,4]oxazin-2-yl)ethyl 4-methylbenzenesulfonate

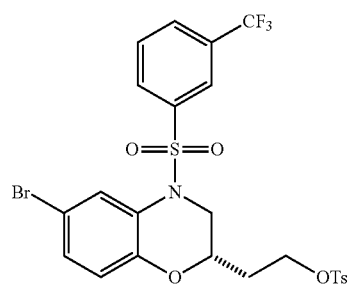 [SMILES: Cc1ccc(S(=O)(=O)OCC[C@H]2CN(S(=O)(=O)c3cccc(C(F)(F)F)c3)c3cc(Br)ccc3O2)cc1]

(S)-2-(6-Bromo-4-((3-(trifluoromethyl)phenyl)sulfonyl)-3,4-dihydro-2H-benzo[b][1,4]oxazin-2-yl)ethan-1-ol (0.13 g, 0.28 mmol) was dissolved in dichloromethane (6 mL) and triethylamine (0.058 mL, 0.42 mmol) was added followed by tosyl chloride (0.056 g, 0.293 mmol). The reaction mixture was stirred at room temperature overnight. Then, an additional 56 mg of tosyl chloride and triethylamine (60 µL) were added, and the reaction mixture was stirred for one additional day. Then, the crude solution was washed with dilute HCl, washed with brine, dried (Na$_2$SO$_4$), and concentrated onto silica gel for purification by chromatography to afford (S)-2-(6-bromo-4-((3-(trifluoromethyl)phenyl)sulfonyl)-3,4-dihydro-2H-benzo[b][1,4]oxazin-2-yl)ethyl 4-methylbenzenesulfonate as a white solid (0.14 g, 81%). ¹H-NMR (400 MHz, DMSO-d₆) δ 8.12 (d, 1H), 7.98 (m, 2H), 7.87 (t, 1H), 7.76 (s, 1H), 7.59 (d, 2H), 7.33 (d, 2H), 7.24 (dd, 1H), 6.54 (d, 1H), 4.33 (dd, 1H), 4.08 (m, 1H), 4.00 (m, 1H), 3.24 (m, 2H), 2.32 (s, 3H), 1.97 (m, 1H), 1.70 (m, 1H).

Part VII—Synthesis of (S)-3-(6-Bromo-4-((3-(trifluoromethyl)phenyl)sulfonyl)-3,4-dihydro-2H-benzo[b][1,4]oxazin-2-yl)propanenitrile

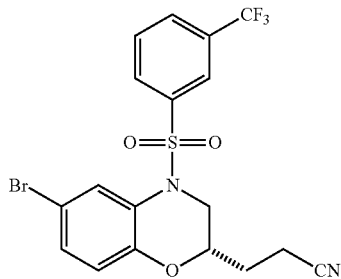 [SMILES: N#CCC[C@H]1CN(S(=O)(=O)c2cccc(C(F)(F)F)c2)c2cc(Br)ccc2O1]

(S)-2-(6-Bromo-4-((3-(trifluoromethyl)phenyl)sulfonyl)-3,4-dihydro-2H-benzo[b][1,4]oxazin-2-yl)ethyl 4-methylbenzenesulfonate (0.14 g, 0.226 mmol) was dissolved in DMSO (1 mL) and potassium cyanide (0.016 g, 0.248 mmol) was added. After one hour, additional potassium cyanide (17 mg) was added, and stirring was continued overnight. Then, the crude material was then partitioned between water and ethyl acetate. The organic phase was washed a second time, then washed with brine, dried (Na₂SO₄), and concentrated to afford (S)-3-(6-bromo-4-((3-(trifluoromethyl)phenyl)sulfonyl)-3,4-dihydro-2H-benzo[b][1,4]oxazin-2-yl)propanenitrile (0.09 g, 84%). ¹H-NMR (400 MHz, DMSO-d₆) δ 8.09 (d, 1H), 8.00 (m, 2H), 7.84 (t, 1H), 7.78 (s, 1H), 7.27 (d, 1H), 6.82 (d, 1H), 4.40 (d, 1H), 3.37 (m, 2H), 2.56 (m, 2H), 1.92 (m, 1H), 1.72 (m, 1H).

Part VIII—Synthesis of (S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanenitrile

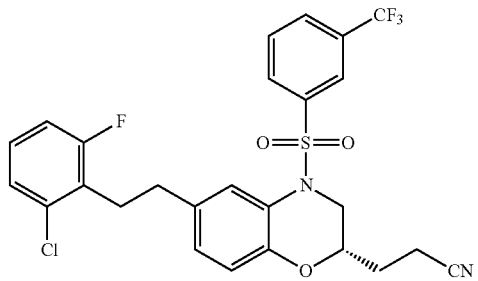 [SMILES: N#CCC[C@H]1CN(S(=O)(=O)c2cccc(C(F)(F)F)c2)c2cc(CCc3c(F)cccc3Cl)ccc2O1]

1-Chloro-3-fluoro-2-vinylbenzene (40 mg, 0.257 mmol) was dissolved in THF (2 mL) and the solution was cooled in an ice bath. A 0.5 M solution of 9-borabicyclo[3.3.1]nonane in toluene (0.52 mL, 0.26 mmol) was then added, and the reaction mixture was stirred at room temperature for five hours. (S)-3-(6-Bromo-4-((3-(trifluoromethyl)phenyl)sulfonyl)-3,4-dihydro-2H-benzo[b][1,4]oxazin-2-yl)propanenitrile (61 mg, 0.129 mmol) was mixed with triethylamine (0.027 mL, 0.193 mmol), and [1,1'-bis(diphenylphosphino)ferrocene]dichloropalladium (II) complex with dichloromethane (10 mg, 0.013 mmol) in degassed DMF (1.9 mL) and water (0.19 mL). The olefin solution was then added, and the reaction mixture was heated to 50° C. overnight. Next, the reaction mixture was cooled to room temperature, and partitioned between water and ethyl acetate. The organic phase was washed with brine, dried (Na₂SO₄), and concentrated to provide a residue. The residue was purified by MPLC eluting with a gradient of 10-40% ethyl acetate in hexanes to afford (S)-3-(6-(2-chloro-6-fluorophenethyl)-4-((3-(trifluoromethyl)phenyl)sulfonyl)-3,4-dihydro-2H-benzo[b][1,4]oxazin-2-yl)propanenitrile (20 mg, 28%). ¹H-NMR (400 MHz, DMSO-d₆) δ 8.07 (d, 1H), 7.94 (m, 2H), 7.82 (t, 1H), 7.47 (s, 1H), 7.28 (m, 2H), 7.15 (m, 1H), 6.86 (dd, 1H), 6.73 (d, 1H), 4.39 (d, 1H), 3.33 (m, 2H), 2.92 (t, 2H), 2.73 (t, 2H), 2.56 (m, 2H), 1.92 (m, 1H), 1.73 (m, 1H).

Example 6—Synthesis of (S,E)-3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propanenitrile

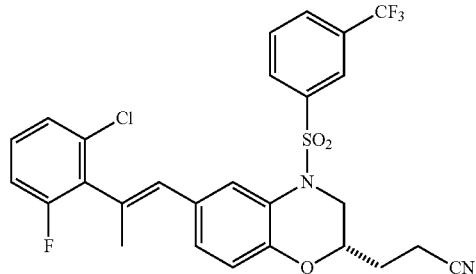 [SMILES: C/C(=C\c1ccc2c(c1)N(S(=O)(=O)c1cccc(C(F)(F)F)c1)C[C@H](CCC#N)O2)c1c(F)cccc1Cl]

Part I—Synthesis of 1-Chloro-2-ethynyl-3-fluorobenzene

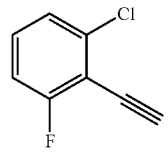

2-Chloro-6-fluorobenzaldehyde (2 g, 12.61 mmol) was dissolved in methanol (84 mL), and dimethyl (diazomethyl) phosphonate (2.39 mL, 15.77 mmol) was added followed by potassium carbonate (4.36 g, 31.53 mmol). The reaction mixture was stirred at room temperature overnight. Then, the crude mixture was diluted with methyl tert-butyl ether, washed with water, washed with brine, dried (Na₂SO₄), and concentrated to afford 1-chloro-2-ethynyl-3-fluorobenzene (1.83 g, 94%). ¹H-NMR (400 MHz, DMSO-d₆) δ 7.45 (m, 2H), 7.32 (t, 1H), 4.86 (s, 1H).

Part II—Synthesis of (E)-2-(2-(2-Chloro-6-fluorophenyl)prop-1-en-1-yl)-4,4,5,5-tetramethyl-1,3,2-dioxaborolane

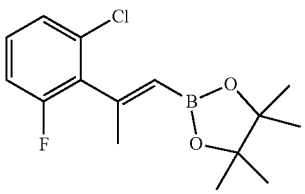

Bis(pinacolato)diborane (5.82 g, 22.92 mmol), copper (I) chloride (0.21 g, 2.08 mmol), and 4,5-bis(diphenylphosphino)-9,9-dimethylxanthene (1.21 g, 2.08 mmol) were suspended in THF (208 mL) and the mixture was degassed with nitrogen, and stirred for five minutes. A solution of sodium tert-butoxide (2.202 g, 22.92 mmol) in minimal THF was then added, and the mixture stirred for an additional five minutes. 1-Chloro-2-ethynyl-3-fluorobenzene (3.22 g, 20.83 mmol) and methyl iodide (11.83 g, 83.33 mmol) were then added to the reaction mixture, and the resulting mixture was stirred at room temperature overnight. Next, the crude product mixture was concentrated onto silica gel and purified by MPLC eluting with a gradient of 0-5% ethyl acetate in hexanes to afford (E)-2-(2-(2-chloro-6-fluorophenyl)prop-1-en-1-yl)-4,4,5,5-tetramethyl-1,3,2-dioxaborolane (2.41 g, 39%). $^1$H-NMR (400 MHz, DMSO-d$_6$) δ 7.31 (m, 2H), 7.20 (t, 1H), 5.18 (s, 1H), 2.15 (s, 3H), 1.23 (s, 12H).

Part III—Synthesis of (S,E)-3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propanenitrile

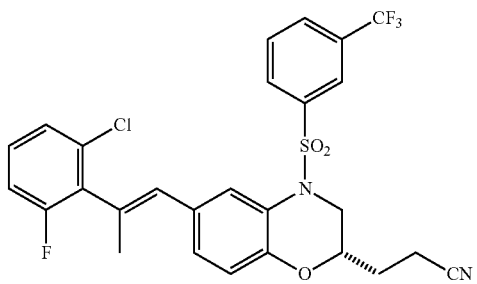 [SMILES: C/C(=C\c1ccc2c(c1)N(S(=O)(=O)c1cccc(C(F)(F)F)c1)C[C@H](CCC#N)O2)c1c(F)cccc1Cl]

(S)-3-(6-Bromo-4-((3-(trifluoromethyl)phenyl)sulfonyl)-3,4-dihydro-2H-benzo[b][1,4]oxazin-2-yl)propanenitrile (40 mg, 0.084 mmol), (E)-2-(2-(2-chloro-6-fluorophenyl)prop-1-en-1-yl)-4,4,5,5-tetramethyl-1,3,2-dioxaborolane (25 mg, 0.084 mmol), THF (3 mL), and sodium hydroxide (10 mg, 0.252 mmol) were combined in a vial, and the mixture was degassed by bubbling nitrogen. Tetrakis(triphenylphosphine)palladium (10 mg, 0.008 mmol) was added to the reaction mixture, and the resulting mixture was shaken at 70° C. overnight. Then, the crude mixture was partitioned between water and ethyl acetate. The organic phase was then washed with brine, dried (Na$_2$SO$_4$), and concentrated onto silica gel and purified by chromatography to afford (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanenitrile as a yellow oil (31 mg, 65%). $^1$H-NMR (400 MHz, DMSO-d$_6$) δ 8.03 (m, 3H), 7.82 (m, 2H), 7.67 (s, 1H), 7.35 (m, 4H), 7.11 (d, 1H), 6.89 (d, 1H), 6.38 (s, 1H), 4.42 (d, 1H), 3.40 (m, 3H), 2.60 (m, 3H), 2.07 (s, 3H), 1.96 (m, 2H), 1.78 (m, 2H), 1.20 (m, 2H), 1.02 (s, 3H).

Example 7—Synthesis of (S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanoic acid

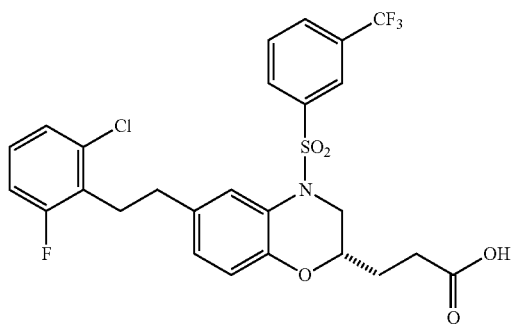 [SMILES: O=C(O)CC[C@H]1CN(S(=O)(=O)c2cccc(C(F)(F)F)c2)c2cc(CCc3c(F)cccc3Cl)ccc2O1]

Part I—Synthesis of (S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanal

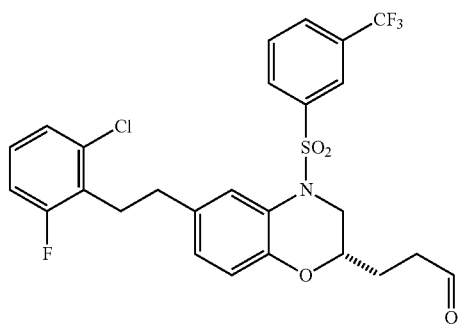 [SMILES: O=CCC[C@H]1CN(S(=O)(=O)c2cccc(C(F)(F)F)c2)c2cc(CCc3c(F)cccc3Cl)ccc2O1]

A solution of (S)-3-(6-(2-chloro-6-fluorophenethyl)-4-((3-(trifluoromethyl)phenyl)sulfonyl)-3,4-dihydro-2H-benzo[b][1,4]oxazin-2-yl)propanenitrile (80 mg, 0.145 mmol) in dichloromethane (6 mL) contained in a reaction vessel was cooled by placing the reaction vessel in an ice bath, and a 1 M solution of diisobutylaluminum hydride solution in dichloromethane (0.44 mL, 0.44 mmol) was added to the reaction vessel. The reaction mixture was stirred at 0° C. for one hour, then at room temperature for two additional hours. Then, the reaction was quenched by adding Rochelle's salt solution to the reaction mixture, and the resulting mixture was stirred at room temperature for two hours. Next, the phases of the resulting mixture were separated, and the organic phase was dried (Na$_2$SO$_4$), concentrated onto silica gel and purified by chromatography eluting with a gradient of 5-30% ethyl acetate in hexanes to afford (S)-3-(6-(2-chloro-6-fluorophenethyl)-4-((3-(trifluoromethyl)phenyl)sulfonyl)-3,4-dihydro-2H-benzo[b][1,4]oxazin-2-yl)propanal (21 mg, 26%). MS (ESI+) (M+Na)$^+$ 577.99.

Part II—Synthesis of (S)-3-(6-(2-Chloro-6-fluoro-phenethyl)-4-((3-(trifluoromethyl)phenyl)sulfonyl)-3,4-dihydro-2H-benzo[b][1,4]oxazin-2-yl)propanoic acid

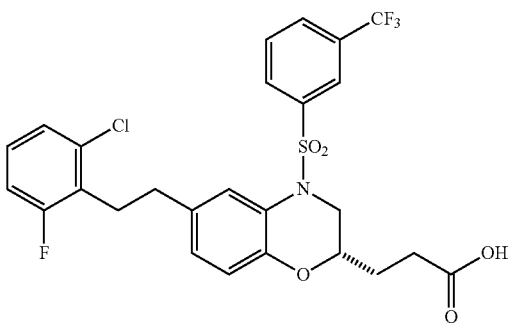 [SMILES: O=C(O)CC[C@H]1CN(S(=O)(=O)c2cccc(C(F)(F)F)c2)c2cc(CCc3c(F)cccc3Cl)ccc2O1]

(S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanal (0.038 mmol) was dissolved in tert-butanol (1 mL), and 2-methyl-2-butene (8 mg, 0.113 mmol) was added. To this mixture, a solution of sodium chlorite (3 mg, 0.038 mmol) and sodium phosphate monobasic (7 mg, 0.057 mmol) in water (1 mL) was added dropwise over several minutes, and the reaction mixture was stirred at room temperature overnight. Then, the reaction mixture was concentrated to remove the tert-butanol. The remaining aqueous mixture was diluted with water, and the solution was extracted with hexanes. The aqueous solution was acidified with 3 M HCl, and the mixture was extracted three times with ethyl acetate. The organic extracts were combined then dried (Na$_2$SO$_4$), and concentrated to provide a residue. The residue was purified by preparative HPLC providing (S)-3-(6-(2-chloro-6-fluorophenethyl)-4-((3-(trifluoromethyl)phenyl)sulfonyl)-3,4-dihydro-2H-benzo[b][1,4]oxazin-2-yl)propanoic acid. $^1$H-NMR (400 MHz, DMSO-d$_6$) δ 12.13 (bs, 1H), 8.07 (d, 1H), 7.93 (m, 2H), 7.82 (t, 1H), 7.45 (s, 1H), 7.27 (m, 2H), 7.14 (m, 1H), 6.84 (dd, 1H), 6.70 (d, 1H), 4.31 (d, 1H), 3.28 (m, 2H), 2.91 (t, 2H), 2.72 (t, 2H), 2.27 (m, 2H), 1.78 (m, 1H), 1.65 (m, 1H). MS (ESI+) (M+Na)$^+$ 593.99

Example 8—Synthesis of (7-((2-Chloro-6-fluorobenzyl)oxy)-1-((3-(trifluoromethyl) phenyl)sulfonyl)-1,2,3,4-tetrahydroquinolin-3-yl)methanol

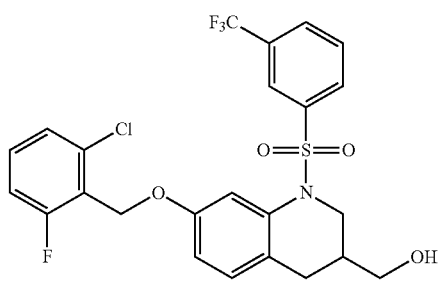 [SMILES: O=S(=O)(c1cccc(C(F)(F)F)c1)N1CC(CO)Cc2ccc(OCc3c(F)cccc3Cl)cc21]

Part I—Synthesis of Diethyl 2-(4-methoxy-2-nitrobenzylidene)malonate

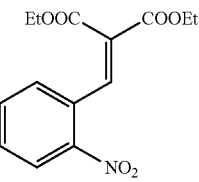

4-Methoxy-2-nitrobenzaldehyde (10 g, 55.20 mmol) was dissolved in ethanol (110 mL), and diethyl malonate (9.73 g, 60.72 mmol) was added followed by piperidine (0.94 g, 11.04 mmol) and acetic acid (0.663 g, 11.04 mmol). The reaction mixture was then heated at reflux overnight. Next, the reaction mixture was concentrated, and the resulting residue was partitioned between 1N HCl and ethyl acetate. The organic phase was washed with 10% sodium carbonate solution, washed with brine, dried (Na$_2$SO$_4$), and concentrated to provide a residue. The residue was purified by MPLC eluting with a gradient of 5-15% ethyl acetate in hexanes to afford diethyl 2-(4-methoxy-2-nitrobenzylidene)malonate as an oil (10.01 g, 56%).

Part II—Synthesis of Diethyl 2-(4-methoxy-2-nitrobenzyl)malonate

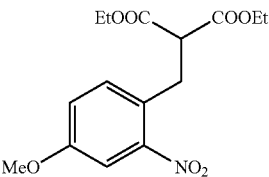 [SMILES: CCOC(=O)C(Cc1ccc(OC)cc1[N+](=O)[O-])C(=O)OCC]

Diethyl 2-(4-methoxy-2-nitrobenzylidene)malonate (10.01 g, 30.96 mmol) was dissolved in ethanol (103 mL) and the solution was cooled to 0° C. To this mixture, sodium borohydride (1.347 g, 35.606 mmol) was added, and the reaction mixture was stirred while the reaction vessel was placed in the ice bath for one hour. Next, the reaction was neutralized by adding aqueous ammonium chloride to the reaction mixture, and the resulting crude was partitioned between water and ethyl acetate. The organic phase was then washed with brine, dried (Na$_2$SO$_4$), and concentrated to afford diethyl 2-(4-methoxy-2-nitrobenzyl)malonate (9.51 g, 94%).

Part III—Synthesis of Ethyl 7-methoxy-2-oxo-1,2,3,4-tetrahydroquinoline-3-carboxylate

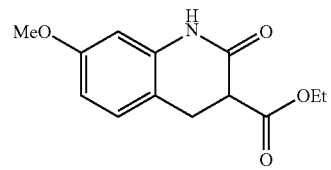 [SMILES: CCOC(=O)C1Cc2ccc(OC)cc2NC1=O]

Diethyl 2-(4-methoxy-2-nitrobenzyl)malonate (9.51 g, 29.23 mmol) was dissolved in acetic acid (147 mL) and powdered iron (6.53 g, 116.94 mmol) was added. The reaction mixture was heated to 60° C. for two hours. Then, the crude solution was filtered through a plug of Celite, and the filtrate was concentrated to provide a residue. The residue was partitioned between water and ethyl acetate. The organic phase was then washed with brine, and dried (Na$_2$SO$_4$), and concentrated to afford ethyl 7-methoxy-2-oxo-1,2,3,4-tetrahydroquinoline-3-carboxylate as a light yellow solid (5.72 g, 78%).

Part IV—Synthesis of Ethyl 7-hydroxy-2-oxo-1,2,3,4-tetrahydroquinoline-3-carboxylate

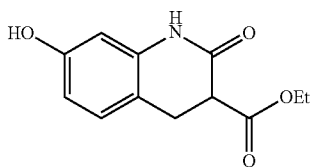 [SMILES: CCOC(=O)C1Cc2ccc(O)cc2NC1=O]

Ethyl 7-methoxy-2-oxo-1,2,3,4-tetrahydroquinoline-3-carboxylate (2 g, 8.02 mmol) was dissolved in dichloromethane (80 mL) and the solution was cooled to −78° C. to the mixture, a 1M solution of boron tribromide in THF (24.1 mL, 24.1 mmol) was added dropwise, and then the reaction mixture was stirred at −20° C. for one hour. To the resulting crude mixture ethanol was added, and solid sodium bicarbonate was added. Next, the resulting mixture was poured into a separatory funnel and diluted with dichloromethane. The organic phase was washed with brine, dried (Na$_2$SO$_4$), and concentrated to afford ethyl 7-hydroxy-2-oxo-1,2,3,4-tetrahydroquinoline-3-carboxylate (1.71 g, 91%). MS (ESI+) (M+H)$^+$236.14.

Part V—Synthesis of Ethyl 7-((2-chloro-6-fluorobenzyl)oxy)-2-oxo-1,2,3,4-tetrahydroquinoline-3-carboxylate

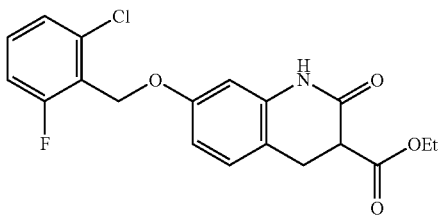 [SMILES: CCOC(=O)C1Cc2ccc(OCc3c(F)cccc3Cl)cc2NC1=O]

Ethyl 7-hydroxy-2-oxo-1,2,3,4-tetrahydroquinoline-3-carboxylate (1.5 g, 6.38 mmol), 2-chloro-6-fluorobenzyl alcohol (1.075 g, 6.70 mmol), and triphenylphosphine (2.01 g, 7.65 mmol) were suspended in dichloromethane (64 mL), and diisopropyl azodicarboxylate (1.51 mL, 7.65 mmol) was added dropwise. The reaction mixture was stirred at room temperature for one hour, and then the crude was washed with water, dried (Na$_2$SO$_4$), and concentrated to provide a residue. The residue was purified by MPLC eluting with a gradient of 10-30% ethyl acetate in hexanes to afford ethyl 7-((2-chloro-6-fluorobenzyl)oxy)-2-oxo-1,2,3,4-tetrahydroquinoline-3-carboxylate as a solid (1.4 g, 58%).

Part VI—Synthesis of (7-((2-Chloro-6-fluorobenzyl)oxy)-1,2,3,4-tetrahydroquinolin-3-yl)methanol

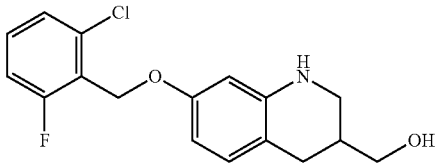 [SMILES: OCC1CNc2cc(OCc3c(F)cccc3Cl)ccc2C1]

Ethyl 7-((2-chloro-6-fluorobenzyl)oxy)-2-oxo-1,2,3,4-tetrahydroquinoline-3-carboxylate (1.4 g, 3.706 mmol) was dissolved in THF (37 mL) and borane dimethylsulfide complex (1.408 g, 18.53 mmol) was added. The reaction mixture was heated at reflux for two hours. Then, the crude solution was cooled by placing the reaction vessel in an ice bath, and the reaction carefully quenched by adding methanol to the reaction mixture. The resulting mixture was then refluxed for ten minutes, cooled and concentrated to provide a residue. The residue was partitioned between ethyl acetate and water. The organic phase was washed with brine, dried (Na$_2$SO$_4$), and concentrated to provide a residue. The residue was purified via MPLC to afford (7-((2-chloro-6-fluorobenzyl)oxy)-1,2,3,4-tetrahydroquinolin-3-yl)methanol as a light yellow oil (0.48 g, 40%).

Part VII—Synthesis of (7-((2-Chloro-6-fluorobenzyl)oxy)-1-((3-(trifluoromethyl)phenyl)sulfonyl)-1,2,3,4-tetrahydroquinolin-3-yl)methanol

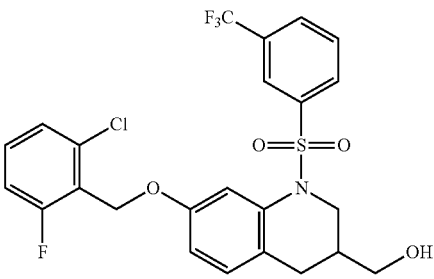 [SMILES: O=S(=O)(c1cccc(C(F)(F)F)c1)N1CC(CO)Cc2ccc(OCc3c(F)cccc3Cl)cc21]

(7-((2-Chloro-6-fluorobenzyl)oxy)-1,2,3,4-tetrahydroquinolin-3-yl)methanol (0.1 g, 0.311 mmol) was dissolved in pyridine (2 mL) and 3-(trifluoromethyl) benzenesulfonyl chloride (84 mg, 0.342 mmol) was added. The reaction mixture was heated to 50° C. overnight. Then, the reaction mixture was diluted in ethyl acetate, washed three times with 1 N HCl, washed with brine, dried (Na$_2$SO$_4$), and then concentrated to provide a residue. The residue was purified by MPLC to afford (7-((2-chloro-6-fluorobenzyl)oxy)-1-((3-(trifluoromethyl)phenyl) sulfonyl)-1,2,3,4-tetrahydroquinolin-3-yl)methanol (51 mg, 31%).

Example 9—Preparation of Additional 1,2,3,4-Tetrahydroquinolin-3-yl)methanol Compounds Compounds in Table 3 were prepared based on experimental procedures described in Example 8 and the detailed description.

TABLE 3

| No. | Structure | Name | Observed m/z |
|---|---|---|---|
| 9A | 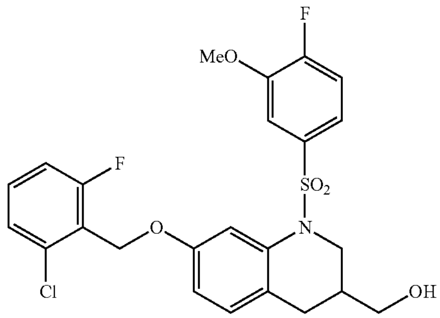 [SMILES: COc1cc(S(=O)(=O)N2CC(CO)Cc3ccc(OCc4c(F)cccc4Cl)cc32)ccc1F] | (7-((2-chloro-6-fluorobenzyl)oxy)-1-((4-fluoro-3-methoxyphenyl)sulfonyl)-1,2,3,4-tetrahydroquinolin-3-yl)methanol | 510 (M + H)+ |
| 9B | 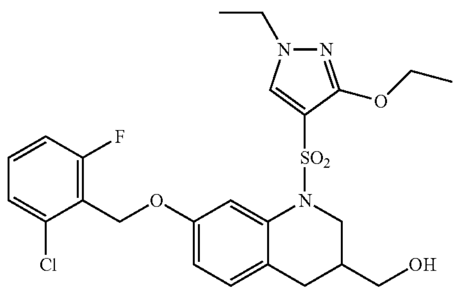 [SMILES: CCOc1nn(CC)cc1S(=O)(=O)N1CC(CO)Cc2ccc(OCc3c(F)cccc3Cl)cc21] | (7-((2-chloro-6-fluorobenzyl)oxy)-1-((3-ethoxy-1-ethyl-1H-pyrazol-4-yl)sulfonyl)-1,2,3,4-tetrahydroquinolin-3-yl)methanol | 524 (M + H)+ |
| 9C | 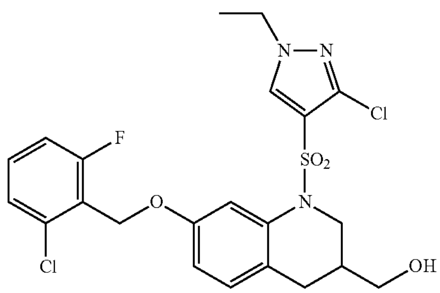 [SMILES: CCn1cc(S(=O)(=O)N2CC(CO)Cc3ccc(OCc4c(F)cccc4Cl)cc32)c(Cl)n1] | (1-((3-chloro-1-ethyl-1H-pyrazol-4-yl)sulfonyl)-7-((2-chloro-6-fluorobenzyl)oxy)-1,2,3,4-tetrahydroquinolin-3-yl)methanol | 514 (M + H)+ |
| 9D | 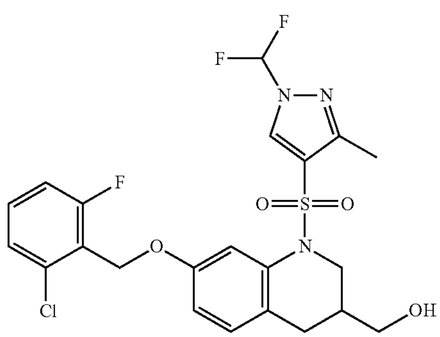 [SMILES: Cc1nn(C(F)F)cc1S(=O)(=O)N1CC(CO)Cc2ccc(OCc3c(F)cccc3Cl)cc21] | (7-((2-chloro-6-fluorobenzyl)oxy)-1-((1-(difluoromethyl)-3-methyl-1H-pyrazol-4-yl)sulfonyl)-1,2,3,4-tetrahydroquinolin-3-yl)methanol | 516 (M + H)+ |
| 9E | 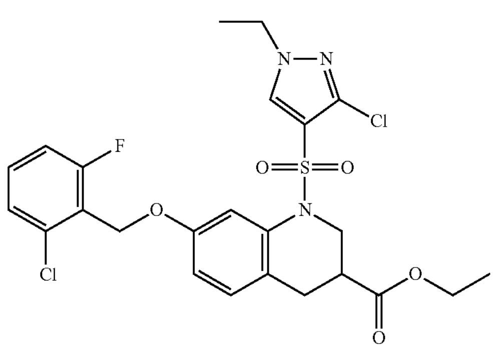 [SMILES: CCOC(=O)C1Cc2ccc(OCc3c(F)cccc3Cl)cc2N(S(=O)(=O)c2cn(CC)nc2Cl)C1] | ethyl 1-((3-chloro-1-ethyl-1H-pyrazol-4-yl)sulfonyl)-7-((2-chloro-6-fluorobenzyl)oxy)-1,2,3,4-tetrahydroquinoline-3-carboxylate | 556 (M + H)+ |

Example 10—Synthesis of 7-((2-Chloro-6-fluorobenzyl)oxy)-1-((3-(trifluoromethyl)phenyl)sulfonyl)-1,2,3,4-tetrahydroquinoline-3-carboxylic acid

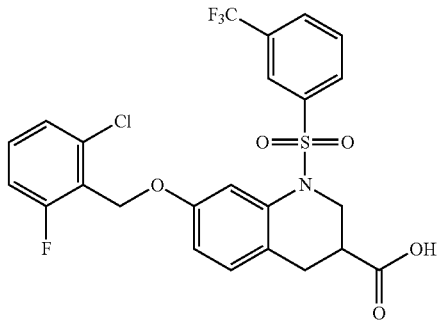 [SMILES: O=C(O)C1Cc2ccc(OCc3c(F)cccc3Cl)cc2N(S(=O)(=O)c2cccc(C(F)(F)F)c2)C1]

(7-((2-Chloro-6-fluorobenzyl)oxy)-1-((3-(trifluoromethyl)phenyl)sulfonyl)-1,2,3,4-tetrahydroquinolin-3-yl)methanol (43 mg, 0.081 mmol) was dissolved in acetone (4 mL), and Jones' reagent was added dropwise until the orange color persisted. The mixture was stirred at room temperature for two hours, then the reaction was quenched by addition of isopropyl alcohol to the reaction mixture, and the resulting mixture was concentrated to provide a residue. The residue was partitioned between 1 N HCl and ethyl acetate/THF. The organic phase was washed with brine, dried ($Na_2SO_4$), and concentrated to provide a residue. The residue was purified by MPLC eluting with a gradient of 0-10% methanol in dichloromethane to afford 7-((2-chloro-6-fluorobenzyl)oxy)-1-((3-(trifluoromethyl)phenyl)sulfonyl)-1,2,3,4-tetrahydroquinoline-3-carboxylic acid (19 mg, 43%). $^1$H-NMR (400 MHz, DMSO-$d_6$) δ 12.25 (bs, 1H), 8.08 (d, 1H), 7.95 (d, 1H), 7.80 (m, 2H), 7.48 (m, 1H), 7.40 (m, 1H), 7.28 (t, 1H), 7.18 (s, 1H), 7.07 (d, 1H), 6.83 (d, 1H), 5.08 (s, 2H), 4.19 (d, 1H), 3.67 (m, 1H), 2.53 (m, 3H). MS (ESI+) (M+Na)$^+$565.95.

Example 11—Preparation of Additional 1,2,3,4-Tetrahydroquinoline-3-carboxylic acids Compounds in Table 4 were prepared based on experimental procedures described in Example 10 and the detailed description.

TABLE 4

| No. | Structure | Name | Observed m/z |
|---|---|---|---|
| 11A | 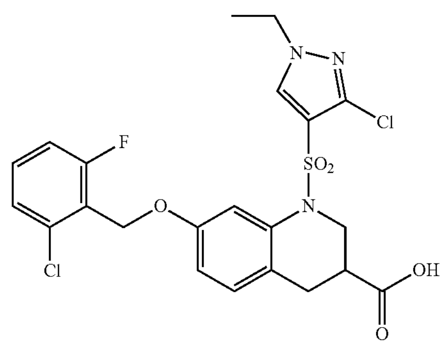 [SMILES: CCn1cc(S(=O)(=O)N2CC(C(=O)O)Cc3ccc(OCc4c(F)cccc4Cl)cc32)c(Cl)n1] | 1-((3-chloro-1-ethyl-1H-pyrazol-4-yl)sulfonyl)-7-((2-chloro-6-fluorobenzyl)oxy)-1,2,3,4-tetrahydroquinoline-3-carboxylic acid | 528 (M + H)$^+$ |
| 11B | 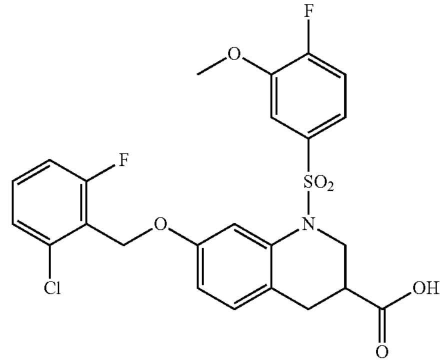 [SMILES: COc1cc(S(=O)(=O)N2CC(C(=O)O)Cc3ccc(OCc4c(F)cccc4Cl)cc32)ccc1F] | 7-((2-chloro-6-fluorobenzyl)oxy)-1-((4-fluoro-3-methoxyphenyl)sulfonyl)-1,2,3,4-tetrahydroquinoline-3-carboxylic acid | 524 (M + H)$^+$ |

TABLE 4-continued

| No. | Structure | Name | Observed m/z |
|---|---|---|---|
| 11C | 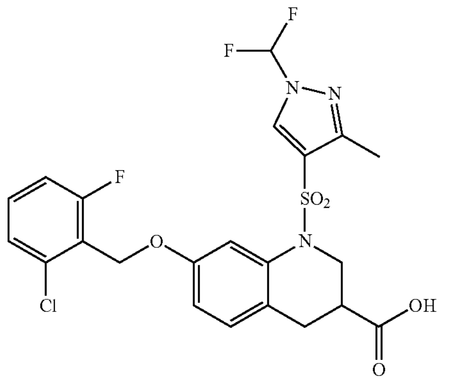 [SMILES: Cc1nn(C(F)F)cc1S(=O)(=O)N1CC(C(=O)O)Cc2ccc(OCc3c(F)cccc3Cl)cc21] | 7-((2-chloro-6-fluorobenzyl)oxy)-1-((1-(difluoromethyl)-3-methyl-1H-pyrazol-4-yl)sulfonyl)-1,2,3,4-tetrahydroquinoline-3-carboxylic acid | 530 (M + H)+ |
| 11D | 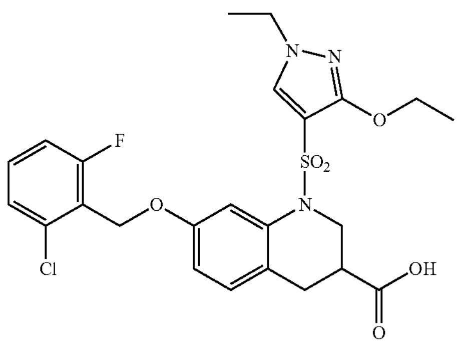 [SMILES: CCOc1nn(CC)cc1S(=O)(=O)N1CC(C(=O)O)Cc2ccc(OCc3c(F)cccc3Cl)cc21] | 7-((2-chloro-6-fluorobenzyl)oxy)-1-((3-ethoxy-1-ethyl-1H-pyrazol-4-yl)sulfonyl)-1,2,3,4-tetrahydroquinoline-3-carboxylic acid | 538 (M + H)+ |
| 11E | 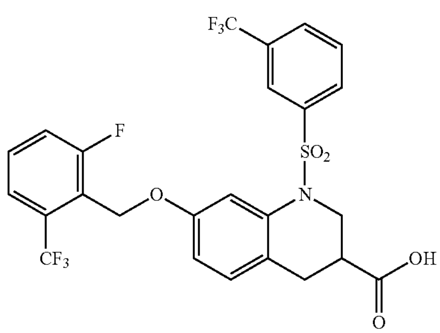 [SMILES: O=C(O)C1Cc2ccc(OCc3c(F)cccc3C(F)(F)F)cc2N(S(=O)(=O)c2cccc(C(F)(F)F)c2)C1] | 7-((2-fluoro-6-(trifluoromethyl)benzyl)oxy)-1-((3-(trifluoromethyl)phenyl) sulfonyl)-1,2,3,4-tetrahydroquinoline-3-carboxylic acid | 578 (M + H)+ |
| 11F | 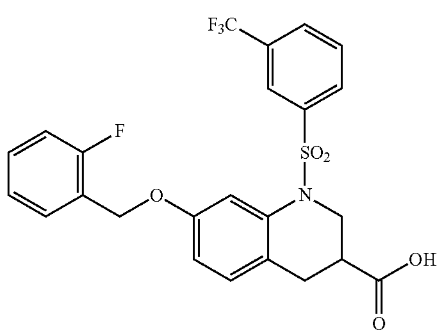 [SMILES: O=C(O)C1Cc2ccc(OCc3ccccc3F)cc2N(S(=O)(=O)c2cccc(C(F)(F)F)c2)C1] | 7-((2-fluorobenzyl)oxy)-1-((3-(trifluoromethyl)phenyl)sulfonyl)-1,2,3,4-tetrahydroquinoline-3-carboxylic acid | 510 (M + H)+ |

TABLE 4-continued

| No. | Structure | Name | Observed m/z |
|---|---|---|---|
| 11G | 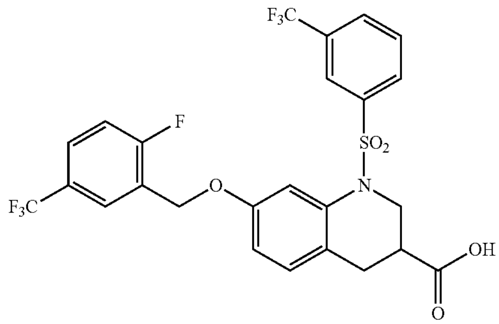 [SMILES: O=C(O)C1Cc2ccc(OCc3cc(C(F)(F)F)ccc3F)cc2N(S(=O)(=O)c2cccc(C(F)(F)F)c2)C1] | 7-((2-fluoro-5-(trifluoromethyl)benzyl)oxy)-1-((3-(trifluoromethyl)phenyl) sulfonyl)-1,2,3,4-tetrahydroquinoline-3-carboxylic acid | 578 (M + H)+ |
| 11H | 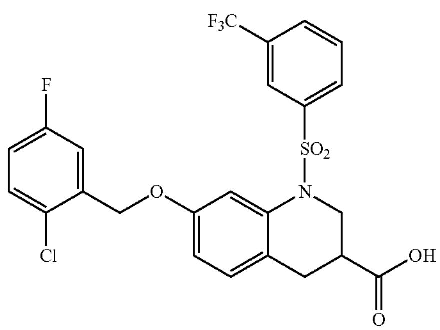 [SMILES: O=C(O)C1Cc2ccc(OCc3cc(F)ccc3Cl)cc2N(S(=O)(=O)c2cccc(C(F)(F)F)c2)C1] | 7-((2-chloro-5-fluorobenzyl)oxy)-1-((3-(trifluoromethyl)phenyl)sulfonyl)-1,2,3,4-tetrahydroquinoline-3-carboxylic acid | 544 (M + H)+ |
| 11I | 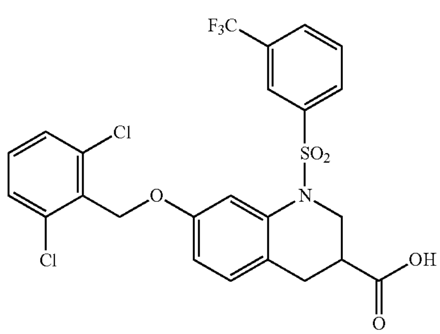 [SMILES: O=C(O)C1Cc2ccc(OCc3c(Cl)cccc3Cl)cc2N(S(=O)(=O)c2cccc(C(F)(F)F)c2)C1] | 7-((2,6-dichlorobenzyl)oxy)-1-((3-(trifluoromethyl)phenyl)sulfonyl)-1,2,3,4-tetrahydroquinoline-3-carboxylic acid | 560 (M + H)+ |
| 11J | 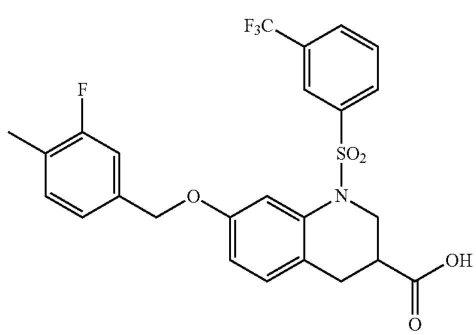 [SMILES: Cc1ccc(COc2ccc3c(c2)N(S(=O)(=O)c2cccc(C(F)(F)F)c2)CC(C(=O)O)C3)cc1F] | 7-((3-fluoro-4-methylbenzyl)oxy)-1-((3-(trifluoromethyl)phenyl)sulfonyl)-1,2,3,4-tetrahydroquinoline-3-carboxylic acid | 524 (M + H)+ |

TABLE 4-continued

| No. | Structure | Name | Observed m/z |
|---|---|---|---|
| 11K | 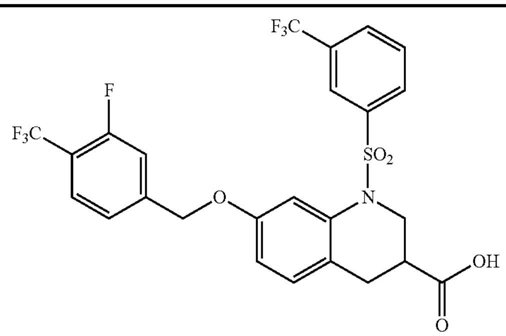 | 7-((3-fluoro-4-(trifluoromethyl)benzyl)oxy)-1-((3-(trifluoromethyl)phenyl)sulfonyl)-1,2,3,4-tetrahydroquinoline-3-carboxylic acid | 578 (M + H)⁺ |
| 11L | 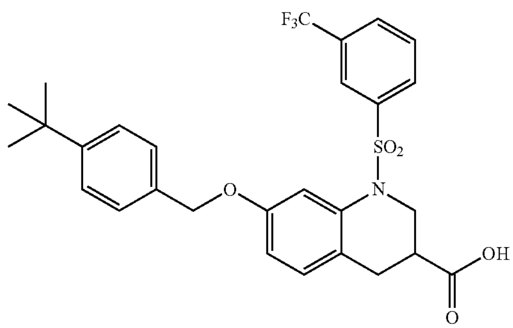 [SMILES: CC(C)(C)c1ccc(COc2ccc3c(c2)N(S(=O)(=O)c2cccc(C(F)(F)F)c2)CC(C(=O)O)C3)cc1] | 7-((4-(tert-butyl)benzyl)oxy)-1-((3-(trifluoromethyl)phenyl) sulfonyl)-1,2,3,4-tetrahydroquinoline-3-carboxylic acid | 548 (M + H)⁺ |
| 11M | 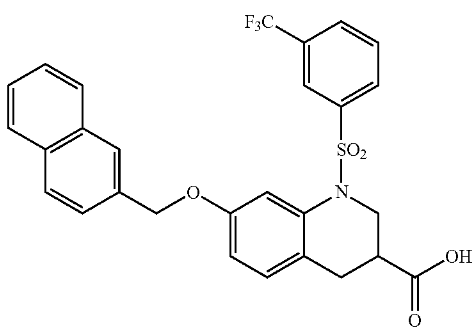 [SMILES: O=C(O)C1Cc2ccc(OCc3ccc4ccccc4c3)cc2N(S(=O)(=O)c2cccc(C(F)(F)F)c2)C1] | 7-(naphthalen-2-ylmethoxy)-1-((3-(trifluoromethyl)phenyl)sulfonyl)-1,2,3,4-tetrahydroquinoline-3-carboxylic acid | 542 (M + H)⁺ |

Example 12—Synthesis of Ethyl 7-(2-chloro-6-fluorophenethyl)-1-((3-(trifluoromethyl)phenyl)sulfonyl)-1,2,3,4-tetrahydroquinoline-3-carboxylate

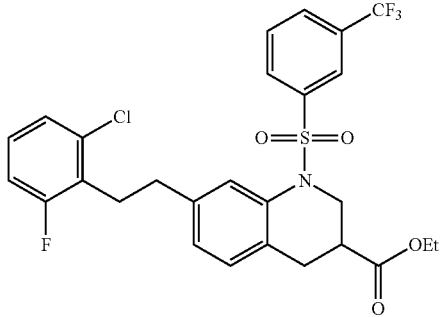 [SMILES: CCOC(=O)C1Cc2ccc(CCc3c(F)cccc3Cl)cc2N(S(=O)(=O)c2cccc(C(F)(F)F)c2)C1]

Part I—Synthesis of Ethyl 7-bromo-4-oxo-1,4-dihydroquinoline-3-carboxylate

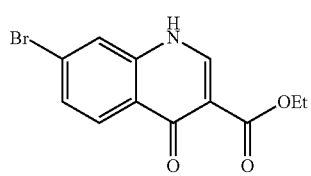 [SMILES: CCOC(=O)c1c[nH]c2cc(Br)ccc2c1=O]

3-Bromoaniline (10 g, 58.13 mmol) and diethyl 2-(ethoxymethylene)malonate (12.57 g, 58.13 mmol) were suspended in ethanol (60 mL), and the reaction mixture was heated to reflux overnight. Then, the crude mixture was concentrated, and the resulting residue was re-suspended in diphenyl ether. Next, the suspension was heated to 250° C. for 90 minutes. The mixture was then cooled to about 35-40° C. and filtered through a sintered glass funnel. The isolated solid was washed with 2:1 ethyl acetate:hexanes, and recrystallized from 70% ethanol affording ethyl 7-bromo-4-oxo-1,4-dihydroquinoline-3-carboxylate as a white solid (5.11 g, 30%).

Part II—Synthesis of Ethyl 7-bromo-4-chloroquinoline-3-carboxylate

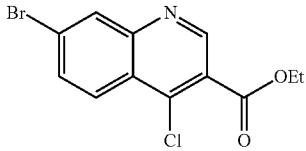 [SMILES: CCOC(=O)c1cnc2cc(Br)ccc2c1Cl]

Ethyl 7-bromo-4-oxo-1,4-dihydroquinoline-3-carboxylate (5.11 g, 17.3 mmol) was dissolved in thionyl chloride (70 mL), and DMF (0.5 mL) was added. The reaction mixture was heated to reflux overnight. The resulting solution was concentrated to provide a residue, and the residue was carefully treated with a saturated sodium carbonate solution. The resulting mixture was slurried, and then filtered. The solid isolated by filtration was washed with water, and dried in a vacuum oven to produce a yellow solid. The yellow solid was then loaded onto silica gel and purified by MPLC eluting with a gradient of 5-80% ethyl acetate in hexanes to afford ethyl 7-bromo-4-chloroquinoline-3-carboxylate as a white solid (4.12 g, 76%).

Part III—Synthesis of Ethyl 4-chloro-7-(2-chloro-6-fluorophenethyl)quinoline-3-carboxylate

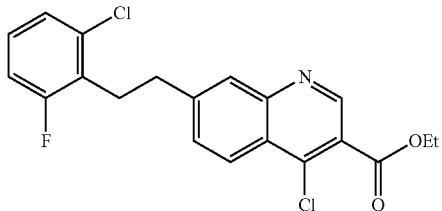 [SMILES: CCOC(=O)c1cnc2cc(CCc3c(F)cccc3Cl)ccc2c1Cl]

1-Chloro-3-fluoro-2-vinyl benzene (996 mg, 6.358 mmol) was dissolved in THF (16 mL) and the reaction vessel containing the solution was cooled in an ice bath. To this solution, a 0.5 M solution of 9-borabicyclo[3.3.1] nonane in toluene (12.7, 6.35 mmol) was added, and the resulting mixture allowed to warm to room temperature where it was held for six days. Ethyl 7-bromo-4-chloroquinoline-3-carboxylate (1 g, 3.179 mmol) was mixed with triethylamine (0.665 mL, 4.769 mmol), and [1,1'-bis(diphenylphosphino)ferrocene]dichloropalladium (II) complex with dichloromethane (243 mg, 0.318 mmol) in degassed DMF (18 mL) and water (2 mL). The olefin solution was then added to the reaction mixture, and the resulting reaction mixture was heated to 50° C. overnight. Next, the reaction mixture was cooled to room temperature, and partitioned between water and ethyl acetate. The organic phase was washed with brine, dried (Na$_2$SO$_4$), and concentrated to provide a residue. The residue was purified by MPLC eluting with a gradient of 10-30% ethyl acetate in hexanes to afford ethyl 4-chloro-7-(2-chloro-6-fluorophenethyl)quinoline-3-carboxylate (610 mg, 49%). MS (ESI+) (M+H)$^+$391.99.

Part IV—Synthesis of Ethyl 7-(2-chloro-6-fluorophenethyl)-1,2,3,4-tetrahydroquinoline-3-carboxylate

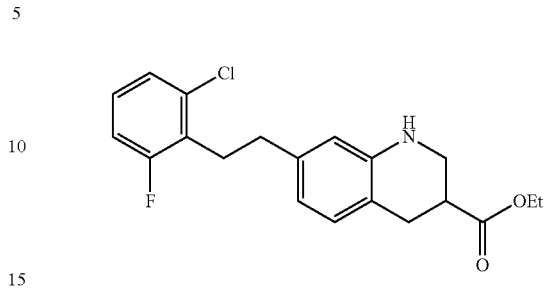

Ethyl 4-chloro-7-(2-chloro-6-fluorophenethyl)quinoline-3-carboxylate (230 mg, 0.586 mmol) was dissolved in acetic acid (4 mL) and a 8M solution of borane pyridine complex (0.147 mL, 1.173 mmol) was added. The reaction mixture was stirred at room temperature for 18 hours. Then, the reaction mixture was concentrated to provide a residue. To the residue was added 1 M sodium carbonate. The resulting mixture was extracted three times with dichloromethane. The organic extracts were combined, dried (Na$_2$SO$_4$), and concentrated to provide a residue. The residue was purified by MPLC to afford ethyl 7-(2-chloro-6-fluorophenethyl)-1,2,3,4-tetrahydroquinoline-3-carboxylate (80 mg, 38%). MS (ESI+) (M+H)$^+$362.08.

Part V—Synthesis of Ethyl 7-(2-chloro-6-fluorophenethyl)-1-((3-(trifluoromethyl)phenyl)sulfonyl)-1,2,3,4-tetrahydroquinoline-3-carboxylate

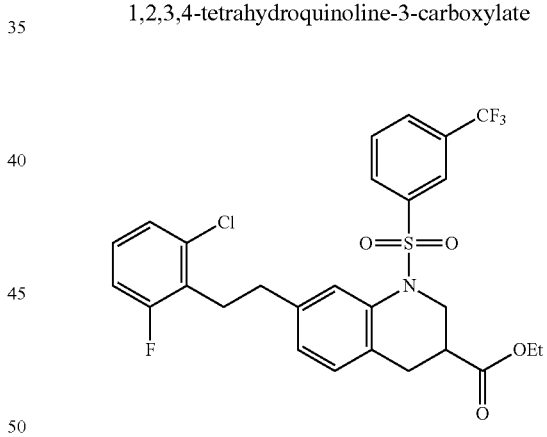

Ethyl 7-(2-chloro-6-fluorophenethyl)-1,2,3,4-tetrahydroquinoline-3-carboxylate (115 mg, 0.318 mmol) and 3-(trifluoromethyl)benzenesulfonyl chloride (311 mg, 1.271 mmol) were dissolved in acetone (2 mL), and potassium carbonate (220 mg, 1.59 mmol) was added. The mixture was shaken at room temperature overnight. Additional aliquots of 3-(trifluoromethyl)benzenesulfonyl chloride (311 mg, 1.271 mmol), and potassium carbonate (220 mg, 1.59 mmol) were then added, and the reaction mixture stirred for an additional five hours. Next, the reaction mixture was filtered, and the filtrate was concentrated onto silica gel and purified by MPLC providing ethyl 7-(2-chloro-6-fluorophenethyl)-1-((3-(trifluoromethyl)phenyl) sulfonyl)-1,2,3,4-tetrahydroquinoline-3-carboxylate (76 mg, 0.1093 mmol). MS (ESI+) (M+Na)$^+$592.04.

Example 13—Synthesis of Ethyl (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylate

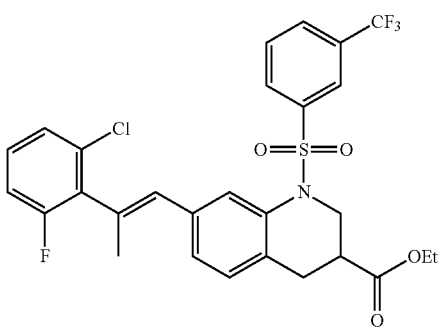 [SMILES: CCOC(=O)C1Cc2ccc(/C=C(\C)c3c(F)cccc3Cl)cc2N(S(=O)(=O)c2cccc(C(F)(F)F)c2)C1]

Part I—Synthesis of Ethyl (E)-7-(2-(2-chloro-6-fluorophenyl)prop-1-en-1-yl)-2-oxo-1,2,3,4-tetrahydroquinoline-3-carboxylate

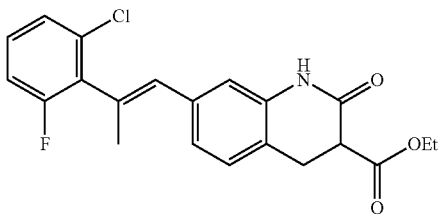 [SMILES: CCOC(=O)C1Cc2ccc(/C=C(\C)c3c(F)cccc3Cl)cc2NC1=O]

Ethyl 7-bromo-2-oxo-1,2,3,4-tetrahydroquinoline-3-carboxylate (1.7 g, 5.702 mmol), (E)-2-(2-(2-chloro-6-fluorophenyl)prop-1-en-1-yl)-4,4,5,5-tetramethyl-1,3,2-dioxaborolane (2.20 g, 7.413 mmol), dioxane (40 mL), water (10 mL), and potassium carbonate (946 mg, 6.843 mmol) were combined in a vial, and the mixture was degassed by bubbling nitrogen in. To this mixture was added [1,1'-bis(diphenylphosphino)ferrocene]dichloropalladium (II) complex with dichloromethane (435 mg, 0.57 mmol), and the resulting mixture was shaken at 70° C. for 45 minutes. Next, the crude mixture was partitioned between water and ethyl acetate. The organic phase was then washed with brine, dried (Na₂SO₄), and concentrated onto silica gel. This residue was purified by MPLC eluting with a gradient of 5-20% ethyl acetate in hexanes to afford ethyl (E)-7-(2-(2-chloro-6-fluorophenyl)prop-1-en-1-yl)-2-oxo-1,2,3,4-tetrahydroquinoline-3-carboxylate as a white solid (1.75 g, 79%). MS (ESI+) (M+K)$^+$425.95.

Part II—Synthesis of Ethyl (E)-7-(2-(2-chloro-6-fluorophenyl)prop-1-en-1-yl)-1,2,3,4-tetrahydroquinoline-3-carboxylate

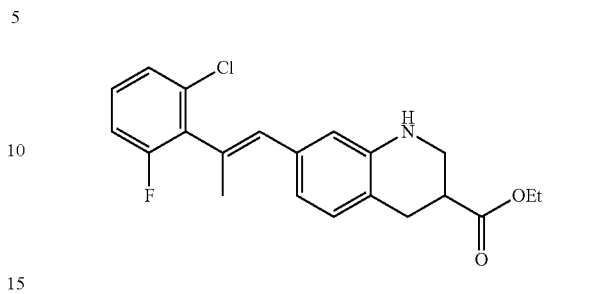

Ethyl (E)-7-(2-(2-chloro-6-fluorophenyl)prop-1-en-1-yl)-2-oxo-1,2,3,4-tetrahydroquinoline-3-carboxylate (1.06 g, 2.733 mmol) was dissolved in THF (60 mL) and the reaction vessel containing the solution was cooled in an ice bath. Borane dimethylsulfide complex (1.367 mL, 13.67 mmol) was added dropwise to the reaction mixture, and the reaction mixture was stirred at room temperature overnight. Then, the reaction was quenched by adding methanol (10 mL) to the reaction mixture, and the resulting mixture was heated to reflux for ten minutes. Then, the crude was concentrated, and next purified by chromatography providing ethyl (E)-7-(2-(2-chloro-6-fluorophenyl)prop-1-en-1-yl)-1,2,3,4-tetrahydroquinoline-3-carboxylate (0.39 g, 38%).

Part III—Synthesis of Ethyl (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylate

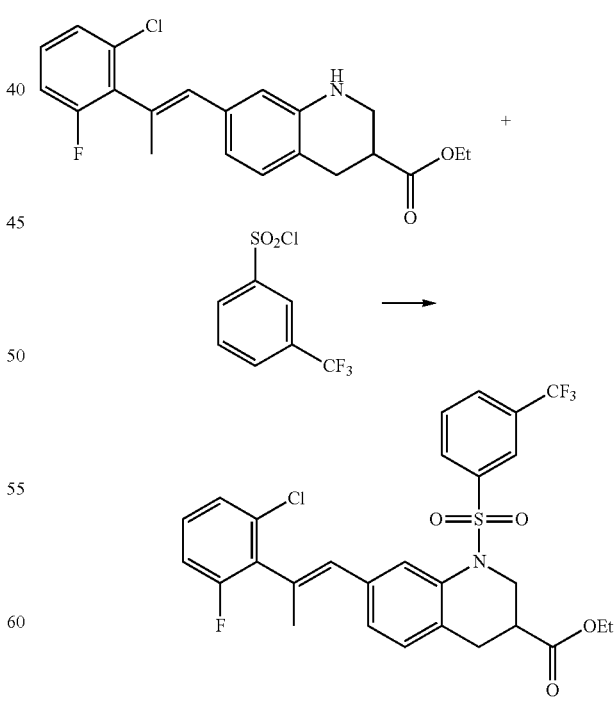

Ethyl (E)-7-(2-(2-chloro-6-fluorophenyl)prop-1-en-1-yl)-1,2,3,4-tetrahydroquinoline-3-carboxylate (460 mg, 1.23 mmol) was dissolved in pyridine (8 mL) and 3-(trifluoromethyl)benzenesulfonyl chloride (361 mg, 1.477 mmol) was added. The reaction mixture was heated to 50° C. overnight. Then, the reaction mixture was diluted with ethyl acetate. The resulting organic mixture was washed three times with 1 N HCl, washed with brine, dried ($Na_2SO_4$), and concentrated to provide a residue. The residue was purified by chromatography to afford ethyl (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylate (540 mg, 75%).

Example 14—Synthesis of (E)-7-(2-(2-Chloro-6-fluorophenyl)prop-1-en-1-yl)-1-((3-(trifluoromethyl)phenyl)sulfonyl)-1,2,3,4-tetrahydroquinoline-3-carboxylic acid and it's Sodium Salt

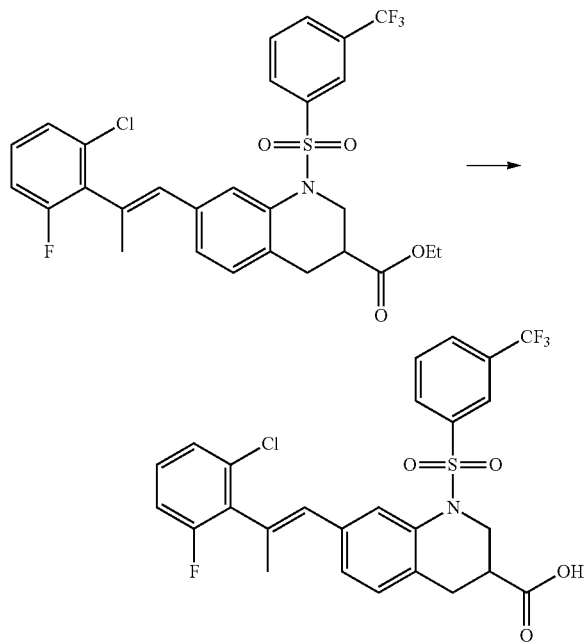

Ethyl (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylate (540 mg, 0.928 mmol) was dissolved in THF (9 mL) and water (9 mL), and lithium hydroxide (44 mg, 1.856 mmol) was added. The resulting mixture was stirred at room temperature for 3 hours. The reaction mixture was diluted with ethyl acetate, and then 1 N HCl (1 mL) was added. The organic phase was washed with brine, dried ($Na_2SO_4$), and concentrated to provide a residue. The residue was purified by MPLC eluting with a gradient of 0-10% methanol in dichloromethane to afford (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylic acid as a white solid (430 mg, 84%). $^1$H-NMR (400 MHz, DMSO-$d_6$) δ 12.73 (bs, 1H), 8.07 (d, 1H), 7.99 (d, 1H), 7.82 (m, 2H), 7.52 (s, 1H), 7.36 (m, 2H), 7.25 (m, 1H), 7.18 (d, 1H), 7.11 (d, 1H), 6.38 (s, 1H), 4.21 (d, 1H), 4.05 (m, 1H), 3.75 (m, 1H), 3.13 (s, 3H), 2.60 (m, 3H), 2.02 (s, 3H).

Preparation of sodium (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylate

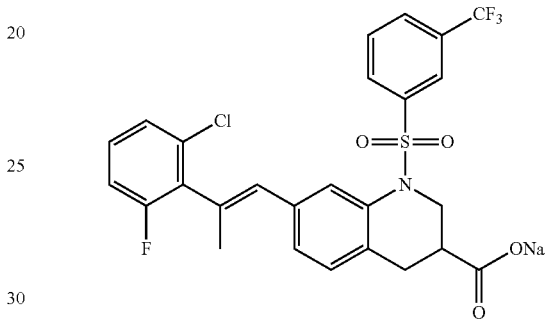

(E)-7-(2-(2-Chloro-6-fluorophenyl)prop-1-en-1-yl)-1-((3-(trifluoromethyl)phenyl)sulfonyl)-1,2,3,4-tetrahydroquinoline-3-carboxylic acid (388 mg, 0.7 mmol) was dissolved in 10 mL of 1:1 MeOH:THF, and a sodium hydroxide solution (0.219 mL of 3.2 M NaOH in water) was added. The solution was then concentrated, and held under vacuum for 18 hours to afford the title compound as a white solid (380 mg, 94%).

Example 15—Preparation of Additional Aryl-alkenylene 1,2,3,4-Tetrahydroquinolines Compounds in Table 5 were prepared based on experimental procedures described in Example 13 and 14 and the detailed description using the appropriate vinyl boronate.

TABLE 5

| No. | Structure | Name | Observed m/z |
|---|---|---|---|
| 15A | (structure shown) | (E)-1-((3-chloro-1-ethyl-1H-pyrazol-4-yl)sulfonyl)-7-(2-(2-chloro-6-fluorophenyl)prop-1-en-1-yl)-1,2,3,4-tetrahydroquinoline-3-carboxylic acid | 538 (M + H)$^+$ |

TABLE 5-continued

| No. | Structure | Name | Observed m/z |
|---|---|---|---|
| 15B | 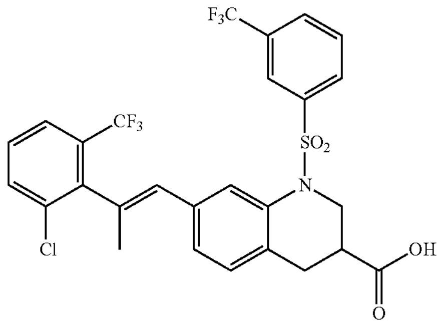 | (E)-7-(2-(2-chloro-6-(trifluoromethyl)phenyl)prop-1-en-1-yl)-1-((3-(trifluoromethyl)phenyl) sulfonyl)-1,2,3,4-tetrahydroquinoline-3-carboxylic acid | 604 (M + H)+ |
| 15C | 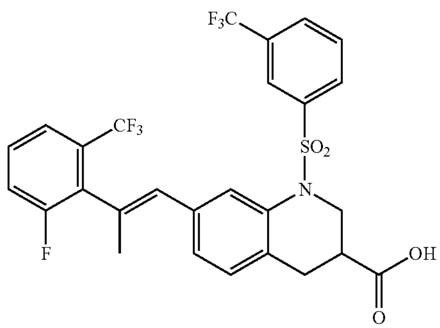 | (E)-7-(2-(2-fluoro-6-(trifluoromethyl)phenyl)prop-1-en-1-yl)-1-((3-(trifluoromethyl)phenyl) sulfonyl)-1,2,3,4-tetrahydroquinoline-3-carboxylic acid | 588 (M + H)+ |
| 15D | 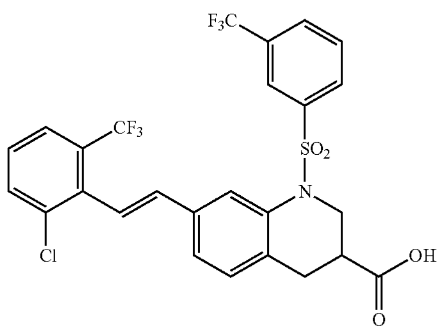 [SMILES: O=C(O)C1Cc2ccc(/C=C/c3c(Cl)cccc3C(F)(F)F)cc2N(S(=O)(=O)c2cccc(C(F)(F)F)c2)C1] | (E)-7-(2-chloro-6-(trifluoromethyl) styryl)-1-((3-(trifluoromethyl) phenyl)sulfonyl)-1,2,3,4-tetrahydroquinoline-3-carboxylic acid | 590 (M + H)+ |

Example 16—Synthesis of (S)—N-((6-((2-Chloro-6-fluorobenzyl)amino)-4-((3-(trifluoromethyl)phenyl)sulfonyl)-3,4-dihydro-2H-benzo[b][1,4]oxazin-2-yl)methyl)acetamide

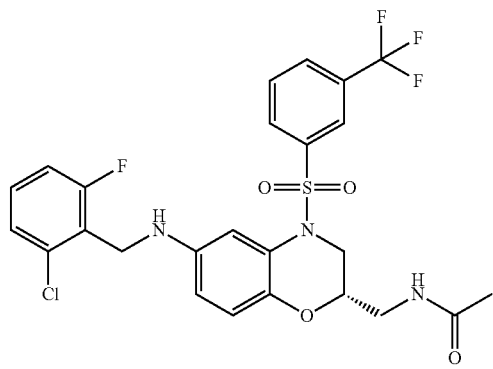 [SMILES: CC(=O)NC[C@H]1CN(S(=O)(=O)c2cccc(C(F)(F)F)c2)c2cc(NCc3c(F)cccc3Cl)ccc2O1]

Part I—Synthesis of 2-[[(2S)-3-Chloro-2-hydroxypropyl]amino]-4-nitrophenol

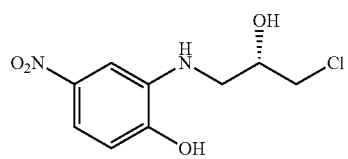 [SMILES: O=[N+]([O-])c1ccc(O)c(NC[C@H](O)CCl)c1]

A solution of 2-amino-4-nitrophenol (250 g, 1.62 mol) and (2S)-2-(chloromethyl)oxirane (330.0 g, 3.57 mol) in ethanol/water (2500/25 mL) was stirred for twelve hours at 60° C. in an oil bath. The resulting mixture was cooled and concentrated to afford 2-[[(2S)-3-chloro-2-hydroxypropyl]amino]-4-nitrophenol as a brown oil.

Part II—Synthesis of [(2R)-6-Nitro-3,4-dihydro-2H-1,4-benzoxazin-2-yl]methanol

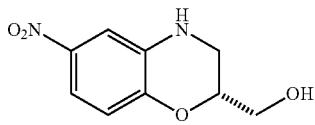 [SMILES: O=[N+]([O-])c1ccc2c(c1)NC[C@H](CO)O2]

A solution of 2-[[(2S)-3-chloro-2-hydroxypropyl]amino]-4-nitrophenol (400 g, 1.62 mol) in ethanol (2.5 L) and potassium carbonate (134.5 g, 973 mmol) was stirred for twelve hours at 90° C. in an oil bath. Then, the mixture was filtered, and the filtrate was concentrated to provide a residue. The residue was diluted with water (1.5 L) and extracted three times with ethyl acetate (1 L). The organic layers were combined and then washed with brine, dried (Na$_2$SO$_4$), and concentrated to provide a residue. The residue was purified via MPLC over silica gel eluting with ethyl acetate/petroleum ether (1:1) to afford [(2R)-6-nitro-3,4-dihydro-2H-1,4-benzoxazin-2-yl]methanol as a red solid.

Part III—Synthesis of ((R)-2-Hydroxymethyl-3,4-dihydro-2H-benzo[1,4]oxazin-6-yl)-carbamic acid tert-butyl ester

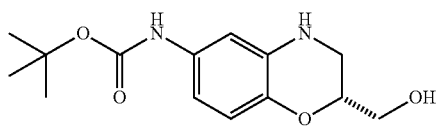 [SMILES: CC(C)(C)OC(=O)Nc1ccc2c(c1)NC[C@H](CO)O2]

The atmosphere above a solution of [(2R)-6-nitro-3,4-dihydro-2H-1,4-benzoxazin-2-yl]methanol (137 g, 652 mmol), palladium carbon (13.7 g), and di-tert-butyl dicarbonate (157 g, 717 mmol) in methanol (1400 mL) was exchanged with hydrogen. The resulting solution was stirred for twelve hours at room temperature. Next, the mixture was filtered, and the filtrate was concentrated to provide a crude product that was purified by re-crystallization from ether to afford ((R)-2-hydroxymethyl-3,4-dihydro-2H-benzo[1,4]oxazin-6-yl)-carbamic acid tert-butyl ester as an off-white solid. LRMS (ESI) calculated for C$_{14}$H$_{20}$N$_2$O$_4$ 280: Found: 225 (M-C$_4$H$_8$+H)$^+$; 281 (M+H)$^+$. $^1$H-NMR (400 MHz, CDCl$_3$): δ 6.92 (s, 1H), 6.71 (d, 1H), 6.41 (dd, 1H), 6.26 (s, 1H), 4.20-4.21 (m, 1H), 3.76-3.86 (m, 2H), 3.26-3.35 (m, 2H), 1.53 (s, 9H).

Part IV—Synthesis of (R)-tert-Butyl (2-((1,3-dioxoisoindolin-2-yl)methyl)-3,4-dihydro-2H-benzo[b][1,4]oxazin-6-yl)carbamate

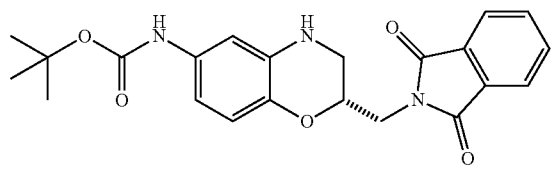 [SMILES: CC(C)(C)OC(=O)Nc1ccc2c(c1)NC[C@H](CN1C(=O)c3ccccc3C1=O)O2]

At 0° C., diisopropyl azodicarboxylate (1.38 mL, 7.12 mmol) was added slowly to a solution of (R)-tert-butyl (2-(hydroxymethyl)-3,4-dihydro-2H-benzo[b][1,4]oxazin-6-yl)carbamate (1.9 g, 6.78 mmol), triphenylphosphine (1.78 g, 6.78 mmol), and phthalimide (1.00 g, 6.78 mmol) in THF (20 mL). The reaction mixture was stirred at room temperature overnight. Then, the reaction mixture was partitioned between ethyl acetate and water. The organic layer was dried (MgSO$_4$) and concentrated to provide a residue. The residue was purified by column chromatography on silica, eluting with 50% ethyl acetate in hexane to afford (R)-tert-butyl (2-((1,3-dioxoisoindolin-2-yl)methyl)-3,4-dihydro-2H-benzo[b][1,4]oxazin-6-yl)carbamate as a yellow solid.

Part V—Synthesis of (S)-tert-Butyl (2-(aminomethyl)-3,4-dihydro-2H-benzo[b][1,4]oxazin-6-yl)carbamate

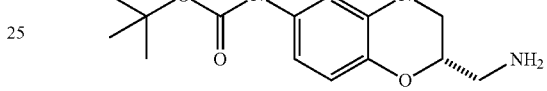

Hydrazine hydrate (2.00 g, 40.0 mmol) was added to a stirred mixture of (R)-tert-butyl (2-((1,3-dioxoisoindolin-2-yl)methyl)-3,4-dihydro-2H-benzo[b][1,4]oxazin-6-yl)carbamate (2.25 g, 5.50 mmol) in ethanol (20 mL). After sixteen hours, the reaction mixture was concentrated, and the resulting residue was triturated with dichloromethane. The resulting mixture was filtered, and the filtrate was concentrated to provide a residue. The residue was crystallized to obtain (S)-tert-butyl (2-(aminomethyl)-3,4-dihydro-2H-benzo[b][1,4]oxazin-6-yl)carbamate.

Part VI—Synthesis of (R)-tert-Butyl (2-(acetamidomethyl)-3,4-dihydro-2H-benzo[b][1,4]oxazin-6-yl)carbamate

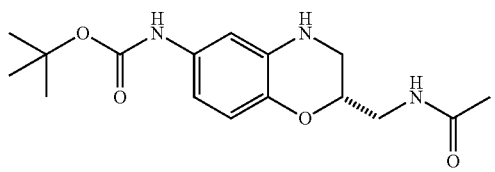 [SMILES: CC(=O)NC[C@H]1CNc2cc(NC(=O)OC(C)(C)C)ccc2O1]

To a stirred solution of (S)-tert-butyl (2-(aminomethyl)-3,4-dihydro-2H-benzo[b][1,4]oxazin-6-yl)carbamate (7.9 g, 28.3 mmol), (benzotriazol-1-yloxy)tris (dimethylamino) phosphonium hexafluorophosphate (13.8 g, 31.1 mmol), and acetic acid (1.6 mL, 28.3 mmol) in THF (141 mL) was added N,N'-diisopropylethylamine (19.8 mL, 113 mmol). After two hours, the mixture was partitioned between isopropanol/chloroform (1:3, v/v) and saturated sodium bicarbonate. The organic layer was isolated, dried (MgSO$_4$), and concentrated to afford (R)-tert-butyl (2-(acetamidomethyl)-3,4-dihydro-2H-benzo[b][1,4]oxazin-6-yl)carbamate.

Part VII—Synthesis of tert-Butyl (S)-(2-(acetamidomethyl)-4-((3-(trifluoromethyl) phenyl)sulfonyl)-3,4-dihydro-2H-benzo[b][1,4]oxazin-6-yl)carbamate

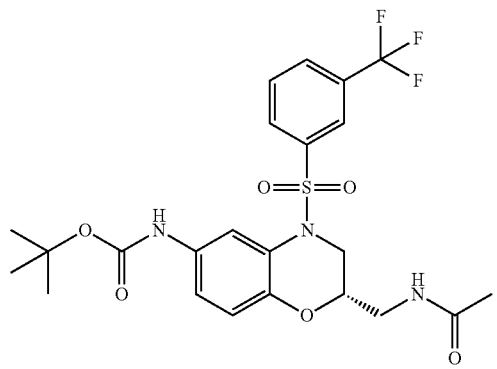 [SMILES: CC(=O)NC[C@H]1CN(S(=O)(=O)c2cccc(C(F)(F)F)c2)c2cc(NC(=O)OC(C)(C)C)ccc2O1]

To a solution of tert-butyl (R)-(2-(acetamidomethyl)-3,4-dihydro-2H-benzo[b][1,4]oxazin-6-yl)carbamate (0.3 g, 0.93 mmol) in pyridine (4 mL) was added 3-(trifluoromethyl)benzenesulfonyl chloride (0.27 g, 1.1 mmol). The solution was stirred at 60° C. for two hours. The resulting mixture was diluted with ethyl acetate, washed with 1M hydrochloric acid (3×), washed with brine, dried ($Na_2SO_4$) and concentrated. The concentrate was purified by column chromatography eluting with a gradient of ethyl acetate in hexanes. Fractions containing the title compound in pure form were combined and concentrated to provide the title compound (120 mg, 24%).

Part VIII—Synthesis of (S)—N-((6-Amino-4-((3-(trifluoromethyl)phenyl)sulfonyl)-3,4-dihydro-2H-benzo[b][1,4]oxazin-2-yl)methyl)acetamide

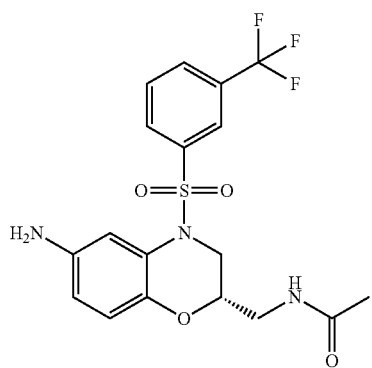 [SMILES: CC(=O)NC[C@H]1CN(S(=O)(=O)c2cccc(C(F)(F)F)c2)c2cc(N)ccc2O1]

To a solution of tert-butyl (S)-(2-(acetamidomethyl)-4-((3-(trifluoromethyl) phenyl)sulfonyl)-3,4-dihydro-2H-benzo[b][1,4]oxazin-6-yl)carbamate (0.12 g, 0.23 mmol) in dichloromethane (3 mL) was added trichloroacetic acid (3 mL), and the reaction mixture was stirred at ambient temperature for 2 hours. Then, the reaction mixture was concentrated in vacuo. The resulting concentrate was partitioned between ethyl acetate and saturated sodium bicarbonate. The organic layer was separated, washed with brine, dried ($Na_2SO_4$) and concentrated to provide the title compound (100 mg, 24%).

Part IX—Synthesis of (S)—N-((6-((2-Chloro-6-fluorobenzyl)amino)-4-((3-(trifluoromethyl)phenyl)sulfonyl)-3,4-dihydro-2H-benzo[b][1,4]oxazin-2-yl)methyl)acetamide

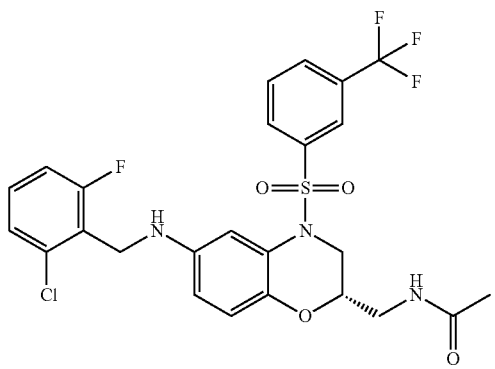 [SMILES: CC(=O)NC[C@H]1CN(S(=O)(=O)c2cccc(C(F)(F)F)c2)c2cc(NCc3c(F)cccc3Cl)ccc2O1]

To a solution of 2-chloro-6-fluorobenzaldehyde (20 mg, 0.13 mmol) and (S)—N-((6-amino-4-((3-(trifluoromethyl)phenyl)sulfonyl)-3,4-dihydro-2H-benzo[b][1,4]oxazin-2-yl)methyl)acetamide (50 mg, 0.12 mmol) in 1,2-dichloroethane (0.5 mL) was added sodium triacetoxyborohydride (32 mg, 0.15 mmol). The resulting mixture was stirred at ambient temperature overnight. Then, the reaction mixture was concentrated, and the concentrate was subjected to preparatory HPLC. Fractions containing the title compound in pure form were combined and concentrated to provide the title compound (24 mg, 36%). $^1$H-NMR (400 MHz, DMSO-$d_6$) δ 8.07-8.00 (m, 2H), 7.92 (m, 1H), 7.86 (s, 1H), 7.80 (t, 1H), 7.38 (m, 2H), 7.22 (m, 1H), 7.04 (m, 1H), 6.59 (d, 1H), 6.46 (m, 1H), 4.27 (m, 1H), 4.22 (m, 2H), 3.3-3.0 (m, 3H), 1.80 (s, 3H).

Example 17-Preparation of (S)—N-((4-((3-Chloro-1-ethyl-1H-pyrazol-4-yl)sulfonyl)-6-((2-chloro-6-fluorobenzyl)amino)-3,4-dihydro-2H-benzo[b][1,4]oxazin-2-yl)methyl)acetamide

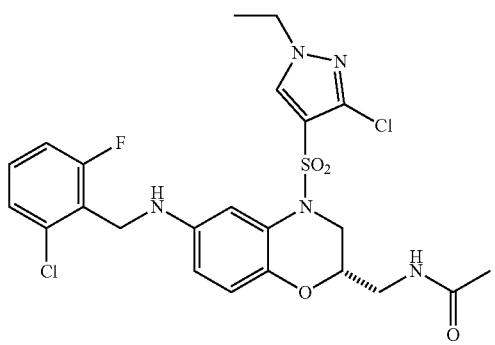 [SMILES: CCn1cc(S(=O)(=O)N2C[C@H](CNC(C)=O)Oc3ccc(NCc4c(F)cccc4Cl)cc32)c(Cl)n1]

The title compound was prepared based on experimental procedures described in Example 16 and the detailed description. (ES, m/z): (M+H)$^+$556.

Example 18—Preparation of Additional Benzylamino-3,4-dihydro-2H-benzo[b][1,4]oxazin-2-yl Compounds Compounds in Table 6 were prepared based on experimental procedures described in Examples 14 and 16 and the detailed description.

TABLE 6

| No. | Structure | Name | Observed m/z |
|---|---|---|---|
| 18A | 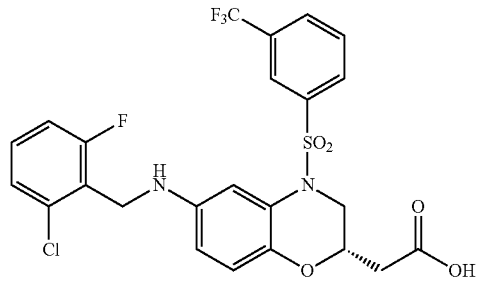 [SMILES: O=C(O)C[C@H]1CN(S(=O)(=O)c2cccc(C(F)(F)F)c2)c2cc(NCc3c(F)cccc3Cl)ccc2O1] | (S)-2-(6-((2-chloro-6-fluorobenzyl)amino)-4-((3-(trifluoromethyl)phenyl)sulfonyl)-3,4-dihydro-2H-benzo[b][1,4]oxazin-2-yl)acetic acid | 559 (M + H)+ |
| 18B | 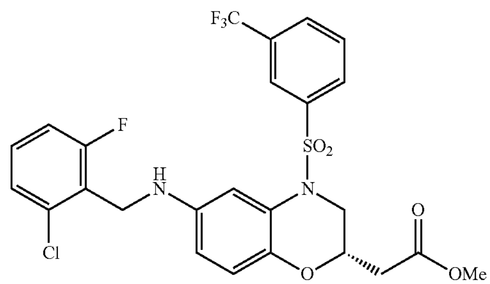 [SMILES: COC(=O)C[C@H]1CN(S(=O)(=O)c2cccc(C(F)(F)F)c2)c2cc(NCc3c(F)cccc3Cl)ccc2O1] | (S)-methyl 2-(6-((2-chloro-6-fluorobenzyl)amino)-4-((3-(trifluoromethyl)phenyl)sulfonyl)-3,4-dihydro-2H-benzo[b][1,4]oxazin-2-yl)acetate | 573 (M + H)+ |

Example 19—Synthesis of Racemic (2R,3R)-Ethyl 7-((2-chloro-6-fluorobenzyl)oxy)-1-((4-fluoro-3-methoxyphenyl)sulfonyl)-2-methyl-1,2,3,4-tetrahydroquinoline-3-carboxylate

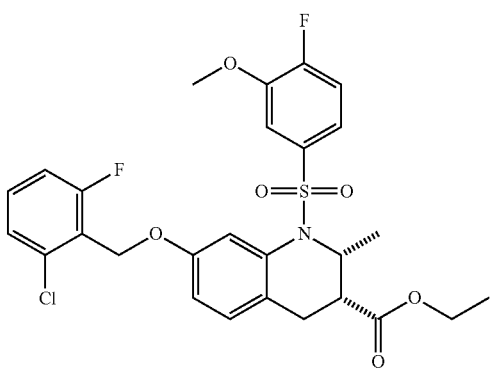 [SMILES: CCOC(=O)[C@@H]1Cc2ccc(OCc3c(F)cccc3Cl)cc2N(S(=O)(=O)c2ccc(F)c(OC)c2)[C@@H]1C]

Part I—Synthesis of Ethyl 2-(4-acetoxy-2-nitrobenzyl)-3-oxobutanoate

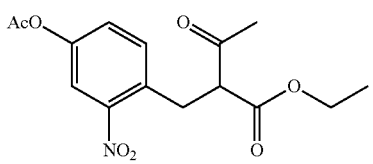

Ethyl 3-oxobutanoate (2.83 g, 21.7 mmol) was added to a mixture of THF (100 mL) and 60% sodium hydride in mineral oil (870 mg, 21.7 mmol). The resulting solution was stirred for one hour at 0° C. Then, a solution of 4-(bromomethyl)-3-nitrophenyl acetate (4.58 g, 16.71 mmol) in THF (20 mL) was added dropwise to the reaction mixture. The resulting solution was stirred for an additional three hours at room temperature. Then, the reaction was quenched by the addition of water (30 mL) to the reaction mixture. The resulting solution was extracted three times with ethyl acetate and the organic layers were combined. The organic solution was washed with water, washed with brine, dried (Na$_2$SO$_4$) and concentrated to provide a residue. The residue was purified via MPLC eluting with ethyl acetate/petroleum ether (1:10) to afford ethyl 2-[[4-(acetyloxy)-2-nitrophenyl]methyl]-3-oxobutanoate (3.75 g, 69%) as a colorless oil.

Part II—Synthesis of Racemic (2R,3R)-Ethyl 7-acetoxy-2-methyl-1,2,3,4-tetrahydroquinoline-3-carboxylate

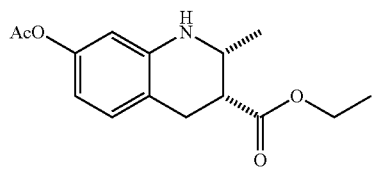 [SMILES: CCOC(=O)[C@@H]1Cc2ccc(OC(C)=O)cc2N[C@@H]1C]

In a 100-mL high-pressure reactor was placed ethyl 2-[[4-(acetyloxy)-2-nitrophenyl]methyl]-3-oxobutanoate (3.75 g, 11.60 mmol), ethyl acetate (80 mL), palladium carbon 10% containing water (380 mg, 0.10 equiv). The resulting solution was stirred for 20 hours at 40° C. under 10 atmospheres of hydrogen gas pressure. Then, the reaction mixture was cooled, the pressure in the reaction vessel was released, and the reaction mixture was filtered through Celite. The filtrate was concentrated to provide a residue that was purified via MPLC eluting with ethyl acetate/petroleum ether (1:10) to afford racemic (2R,3R)-ethyl 7-acetoxy-2-methyl-1,2,3,4-tetrahydroquinoline-3-carboxylate (1.3 g, 40%) as a colorless oil.

Part III—Synthesis of Racemic (2R,3R)-Ethyl 7-acetoxy-1-((4-fluoro-3-methoxyphenyl)sulfonyl)-2-methyl-1,2,3,4-tetrahydroquinoline-3-carboxylate

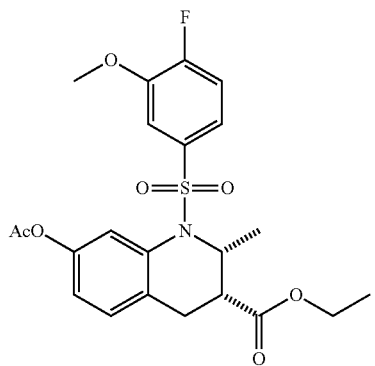 [SMILES: CCOC(=O)[C@@H]1Cc2ccc(OC(C)=O)cc2N(S(=O)(=O)c2ccc(F)c(OC)c2)[C@@H]1C]

A solution of racemic (2R,3R)-ethyl 7-(acetyloxy)-2-methyl-1,2,3,4-tetrahydroquinoline-3-carboxylate (750 mg, 2.70 mmol), dichloromethane (30 mL), triethylamine (1.37 g, 13.54 mmol), 4-fluoro-3-methoxybenzene-1-sulfonyl chloride (1.1 g, 4.90 mmol) was refluxed for 18 hours. Then, the reaction mixture was cooled and water was added to quench the reaction. The resulting mixture was extracted twice with ethyl acetate. The organic extracts were combined and washed twice with water, washed with brine, dried (Na$_2$SO$_4$) and concentrated to provide a residue. The residue was purified via MPLC eluting with ethyl acetate/petroleum ether (1:10) to afford racemic (2R,3R)-ethyl 7-acetoxy-1-((4-fluoro-3-methoxyphenyl)sulfonyl)-2-methyl-1,2,3,4-tetrahydroquinoline-3-carboxylate (730 mg, 58%) as light yellow oil.

Part IV—Synthesis of Racemic (2R,3R)-Ethyl 1-((4-fluoro-3-methoxyphenyl)sulfonyl)-7-hydroxy-2-methyl-1,2,3,4-tetrahydroquinoline-3-carboxylate

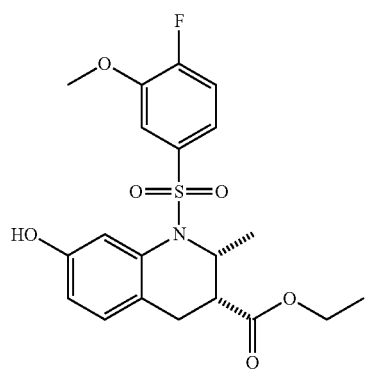 [SMILES: CCOC(=O)[C@@H]1Cc2ccc(O)cc2N(S(=O)(=O)c2ccc(F)c(OC)c2)[C@@H]1C]

To a solution of racemic (2R,3R)-ethyl 7-acetoxy-1-((4-fluoro-3-methoxyphenyl)sulfonyl)-2-methyl-1,2,3,4-tetrahydroquinoline-3-carboxylate (620 mg, 1.33 mmol) in methanol (20 mL) was added acetyl chloride (1.0 mL, 13.3 mmol). The resulting solution was stirred for one hour at room temperature, concentrated and diluted in water (30 ml). The pH value of the resulting solution was adjusted to 4-5 by adding saturated sodium bicarbonate. Next, the reaction mixture was extracted three times with ethyl acetate. The organic extracts were combined and washed with water, washed with brine, dried (Na$_2$SO$_4$) and concentrated to provide a residue. The residue was purified via MPLC eluting with ethyl acetate/petroleum ether (1:10) to afford racemic (2R,3R)-ethyl 1-((4-fluoro-3-methoxyphenyl)sulfonyl)-7-hydroxy-2-methyl-1,2,3,4-tetrahydroquinoline-3-carboxylate (560 mg, 99%) as a light yellow oil.

Part V—Synthesis of Racemic (2R,3R)-Ethyl 7-((2-chloro-6-fluorobenzyl)oxy)-1-((4-fluoro-3-methoxyphenyl)sulfonyl)-2-methyl-1,2,3,4-tetrahydroquinoline-3-carboxylate

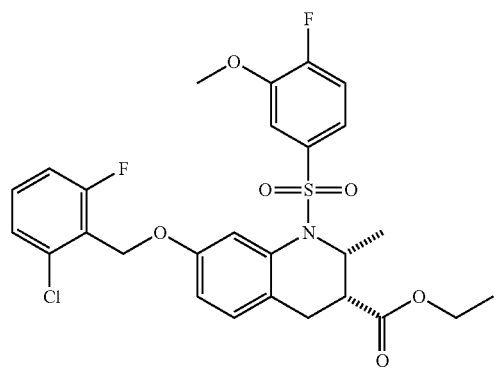 [SMILES: CCOC(=O)[C@@H]1Cc2ccc(OCc3c(F)cccc3Cl)cc2N(S(=O)(=O)c2ccc(F)c(OC)c2)[C@@H]1C]

To a solution of racemic (2R,3R)-ethyl 1-((4-fluoro-3-methoxyphenyl)sulfonyl)-7-hydroxy-2-methyl-1,2,3,4-tetrahydroquinoline-3-carboxylate (130 mg, 0.31 mmol), (2-chloro-6-fluorophenyl)methanol (59 mg, 0.37 mmol), and triphenyl phosphine (120 mg, 0.46 mmol) in THF (10 mL) was added diisopropyl azodicarboxylate (93 mg, 0.46 mmol) dropwise. The resulting solution was stirred for one hour at room temperature and then partitioned between ethyl acetate and water. The organic layer was washed twice with water, washed with brine, dried (Na$_2$SO4) and concentrated to provide a residue. The residue was applied onto a silica gel column that was eluted using ethyl acetate/petroleum ether (1:10) to afford racemic (2R,3R)-ethyl 7-((2-chloro-6-fluorobenzyl)oxy)-1-((4-fluoro-3-methoxyphenyl)sulfonyl)-2-methyl-1,2,3,4-tetrahydroquinoline-3-carboxylate (94 mg, 54%) as a white solid. $^1$H-NMR (400 MHz, CDCl$_3$): δ 7.63 (s, 1H), 7.40-7.20 (m, 3H), 7.17-7.00 (m, 4H), 6.83 (d, J=8.4 Hz, 1H), 5.20 (s, 2H), 5.00-4.90 (m, 1H), 4.25-4.20 (m, 2H), 3.74 (s, 3H), 2.90-2.80 (m, 1H), 2.60 (dd, J=18.0, 6.4 Hz, 1H), 2.30-2.20 (m, 1H), 1.12 (d, J=6.8 Hz, 3H). (ES, m/z) (M+H)$^+$566.1.

Example 20—Synthesis of Racemic (2R,3R)-Ethyl 7-((2,3-dihydro-1H-inden-1-yl)oxy)-1-((4-fluoro-3-methoxyphenyl)sulfonyl)-2-methyl-1,2,3,4-tetrahydroquinoline-3-carboxylate

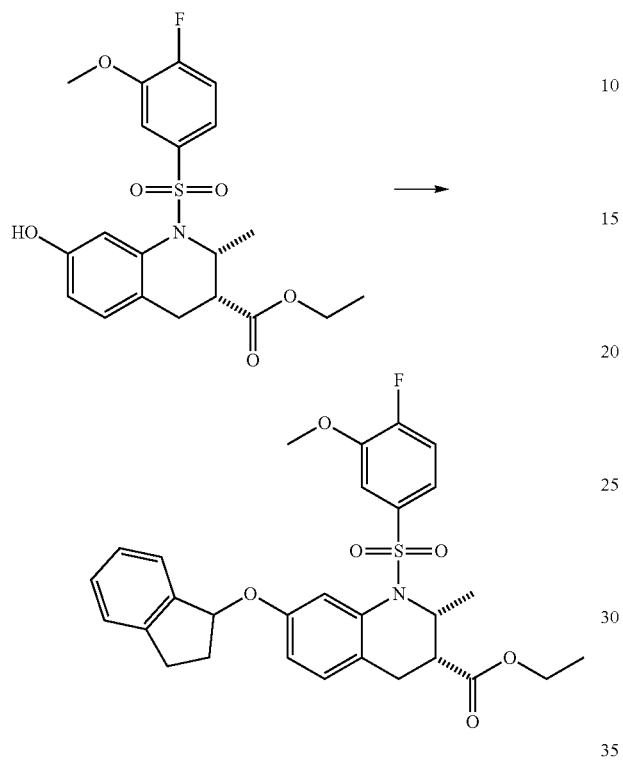

The title compound was prepared based on procedures described in Example 1, Part V. $^1$H-NMR (400 MHz, CDCl$_3$) δ 7.61 (dd, 1H), 7.50 (d, 1H), 7.40-7.45 (m, 2H), 7.09-7.31 (m, 4H), 7.01 (d, 1H), 6.82 (t, 1H), 5.79 (dd, 1H), 4.92 (m, 1H), 4.17 (m, 2H), 3.75 (s, 3H), 3.16 (m, 1H), 2.88-3.00 (m, 2H), 2.58 (m, 2H), 2.15-2.28 (m, 2H), 1.28 (t, 3H), 1.07 (d, 3H). (ES, m/z) 562 (M+Na).$^+$ Example 21—Synthesis of Racemic (2R,3R)-7-((2-Chloro-6-fluorobenzyl)oxy)-1-((4-fluoro-3-methoxyphenyl)sulfonyl)-2-methyl-1,2,3,4-tetrahydroquinoline-3-carboxylic acid

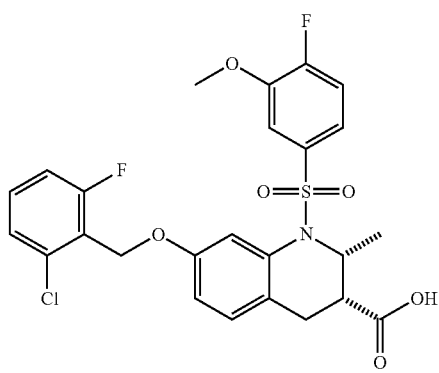 [SMILES: COc1cc(S(=O)(=O)N2c3cc(OCc4c(F)cccc4Cl)ccc3C[C@@H](C(=O)O)[C@H]2C)ccc1F]

To a solution of racemic (2R,3R)-ethyl 7-((2-chloro-6-fluorobenzyl)oxy)-1-((4-fluoro-3-methoxyphenyl)sulfo-nyl)-2-methyl-1,2,3,4-tetrahydroquinoline-3-carboxylate (70 mg, 0.12 mmol) in THF (3 mL) and water (1.5 mL) was added lithium hydroxide monohydrate (21 mg, 0.50 mmol). The resulting solution was stirred overnight at room temperature. Next, the reaction mixture was diluted with water (15 mL) and the pH of the mixture was adjusted to 4-5 by adding concentrated hydrogen chloride to the mixture. Next, the mixture was extracted three times with ethyl acetate. The organic extracts were combined, washed brine, dried (Na$_2$SO$_4$) and concentrated to provide a residue. The residue was purified by reverse phase HPLC eluting with a gradient of water (containing 0.05% trifluoroacetic acid) and acetonitrile to afford racemic (2R,3R)-7-((2-chloro-6-fluorobenzyl)oxy)-1-((4-fluoro-3-methoxyphenyl)sulfonyl)-2-methyl-1, 2,3,4-tetrahydroquinoline-3-carboxylic acid (40 mg, 60%) as a white solid. $^1$H-NMR (400 MHz, CDCl$_3$): δ 7.64 (s, 1H), 7.40-7.20 (m, 3H), 7.17-7.00 (m, 4H), 6.84 (dd, J=8.4, 2.4 Hz, 1H), 5.21 (s, 2H), 5.04-4.96 (m, 1H), 3.75 (s, 3H), 2.95-2.80 (m, 1H), 2.64 (dd, J=18.0, 6.4 Hz, 1H), 2.30-2.20 (m, 1H), 1.12 (d, J=6.8 Hz, 3H). (ES, m/z) (M+H)$^+$538.3.

Example 22—Preparation of Racemic (2R,3R)-7-((2,3-Dihydro-1H-inden-1-yl)oxy)-1-((4-fluoro-3-methoxy-phenyl)sulfonyl)-2-methyl-1,2,3,4-tetrahydroquinoline-3-carboxylic acid

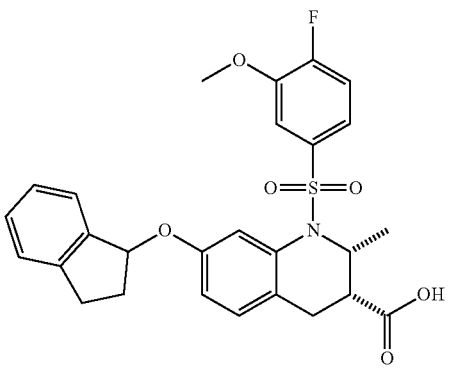 [SMILES: COc1cc(S(=O)(=O)N2c3cc(OC4CCc5ccccc54)ccc3C[C@@H](C(=O)O)[C@H]2C)ccc1F]

The title compound was prepared based on the experimental procedures described in Examples 19, 20, and 21 and the detailed description. (ES, m/z): (M+H)$^+$512.

Example 23—Synthesis of ((2R,3R)-7-((2-Chloro-6-fluorobenzyl)oxy)-1-((4-fluoro-3-methoxyphenyl)sulfonyl)-2-methyl-1,2,3,4-tetrahydroquinolin-3-yl)methanol

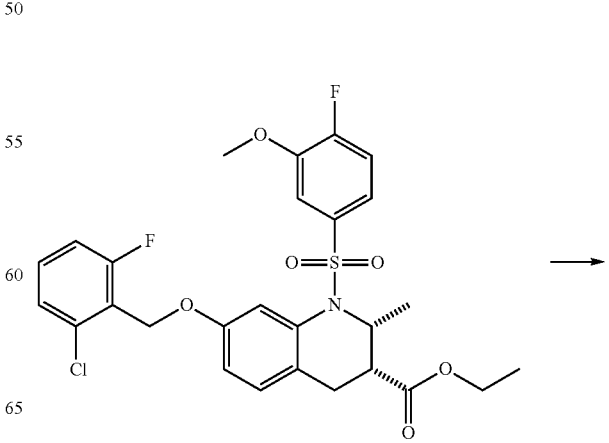

-continued

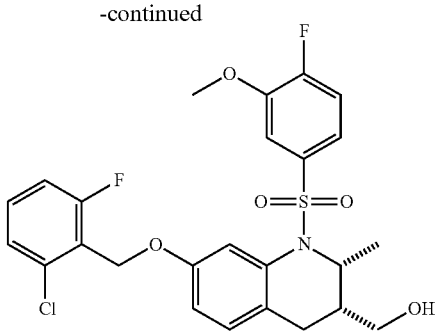

To a solution of (2R,3R)-ethyl 7-((2-chloro-6-fluorobenzyl)oxy)-1-((4-fluoro-3-methoxyphenyl)sulfonyl)-2-methyl-1,2,3,4-tetrahydroquinoline-3-carboxylate (120 mg, 0.21 mmol) in tetrahydrofuran (10 mL) was added of lithium aluminum hydride (20 mg, 0.53 mmol) in portions at room temperature. The resulting solution was stirred for two hours at room temperature. The reaction was then quenched by the addition of 15 mL of water to the reaction mixture, and the resulting mixture was stirred for 2 hours. The resulting solution was extracted three times with ethyl acetate, the organic layers were combined, and the combined organic layers were washed with water, washed with brine, and concentrated to provide a residue. The residue was purified via MPLC eluting with ethyl acetate/petroleum ether (1:4). The fraction containing the major component was purified further by preparative HPLC eluting with a gradient of aqueous 10 mM NH$_4$HCO$_3$ and acetonitrile (58.0% to 65.0%) to afford racemic ((2R,3R)-7-((2-Chloro-6-fluorobenzyl)oxy)-1-((4-fluoro-3-methoxyphenyl)sulfonyl)-2-methyl-1,2,3,4-tetrahydroquinolin-3-yl)methanol (25 mg, 23%) as a white solid. $^1$H-NMR (400 MHz, CDCl$_3$) δ 1.08 (d, J=6.8 Hz, 3H), 1.55-1.70 (m, 1H), 2.15-2.30 (m, 1H), 2.44 (dd, J=16.8, 6.0 Hz, 1H), 3.37-3.55 (m, 2H), 3.74 (s, 3H), 4.70-4.80 (m, 1H), 5.20 (s, 2H), 6.78 (dd, J=12.4, 2.8 Hz, 2H), 6.95 (d, J=8.8 Hz, 1H), 7.03-7.20 (m, 3H), 7.25-7.35 (m, 3H), 7.64 (s, 1H). (ES, m/z) 524.1 (M+H).$^+$ Example 24—Synthesis of 7-((2-Chloro-6-fluorobenzyl)oxy)-1-((4-fluoro-3-methoxyphenyl)sulfonyl)-1,2,3,4-tetrahydroquinoline

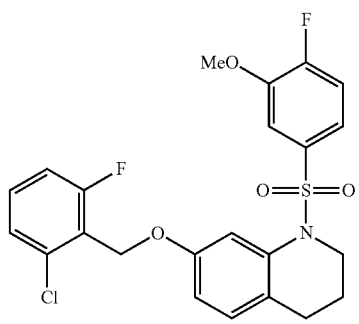 [SMILES: COc1cc(S(=O)(=O)N2CCCc3ccc(OCc4c(F)cccc4Cl)cc32)ccc1F]

Part I—Synthesis of 1-((4-Fluoro-3-methoxyphenyl)sulfonyl)-1,2,3,4-tetrahydroquinolin-7-ol

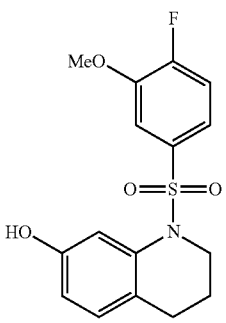

To a solution of 1,2,3,4-tetrahydroquinolin-7-ol (2.5 g, 16.76 mmol) in dichloromethane (100 mL) was added pyridine (2.6 g, 32.9 mmol) and 4-fluoro-3-methoxybenzene-1-sulfonyl chloride (5.6 g, 24.93 mmol, 1.50 equiv). The mixture was stirred for one hour at room temperature. Then, methanol (2 mL) was added to the reaction mixture, and the resulting mixture was concentrated to provide a residue. The residue was purified via MPLC eluting with dichloromethane/ethyl acetate (2:1) to afford 1-[(4-fluoro-3-methoxybenzene)sulfonyl]-1,2,3,4-tetrahydroquinolin-7-ol (7.0 g) as a red oil.

Part II—Synthesis of 7-((2-Chloro-6-fluorobenzyl)oxy)-1-((4-fluoro-3-methoxyphenyl)sulfonyl)-1,2,3,4-tetrahydroquinoline

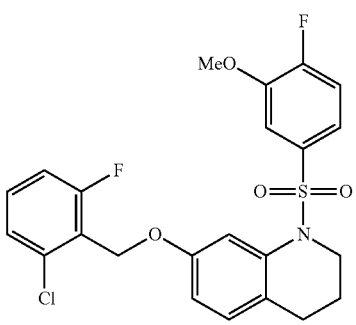 [SMILES: COc1cc(S(=O)(=O)N2CCCc3ccc(OCc4c(F)cccc4Cl)cc32)ccc1F]

To a solution of 1-[(4-fluoro-3-methoxybenzene)sulfonyl]-1,2,3,4-tetrahydroquinolin-7-ol (150 mg, 0.44 mmol), (2-chloro-6-fluorophenyl)methanol (71 mg, 0.44 mmol), triphenylphosphine (140 mg, 0.53 mmol), in anhydrous THF (5 mL) was added diisopropyl azodicarboxylate (108 mg, 0.53 mmol) dropwise at 0° C. The resulting solution was stirred overnight at 25° C., and then concentrated to provide a residue. The residue was purified by MPLC eluting with petroleum ether: ethyl acetate (3:1). The fraction containing the major component was further purified by Prep-HPLC eluting with a gradient of water (containing 0.05% trifluo roacetic acid) and acetonitrile (50.0% to 90.0% in 8 minutes) to afford the title compound (41.5 mg, 19%) as a white solid. $^1$H-NMR (400 MHz, CDCl$_3$) δ 7.61-7.60 (d, 1H), 7.36-7.28 (m, 3H), 7.15-7.02 (m, 3H), 6.96-6.94 (d, 1H), 6.81-6.78 (d, 1H), 5.21 (s, 2H), 3.84-3.81 (t, 2H), 3.71 (s, 3H), 2.44-2.40 (t, 2H), 1.67-1.58 (m, 2H). (ES, m/z): (M+H)$^+$: 480.

Example 25—Preparation of Additional 1,2,3,4-Tetrahydroquinoline Sulfonamides

Compounds in Table 7 were prepared based on experimental procedures described in Examples 19, 20, and 21 and the detailed description.

TABLE 7

| No. | Structure | Name | Observed m/z |
|-----|-----------|------|--------------|
| 25A | 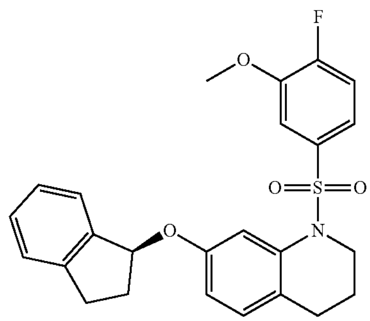 [SMILES: COc1cc(S(=O)(=O)N2CCCc3ccc(O[C@H]4CCc5ccccc54)cc32)ccc1F] | (S)-7-((2,3-dihydro-1H-inden-1-yl)oxy)-1-((4-fluoro-3-methoxyphenyl)sulfonyl)-1,2,3,4-tetrahydroquinoline | 454 (M + H)$^+$ |
| 25B | 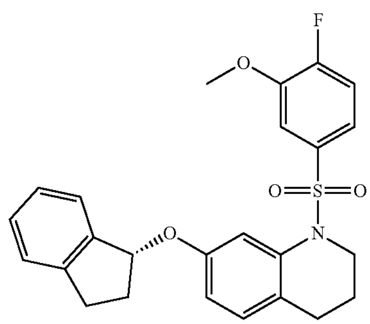 [SMILES: COc1cc(S(=O)(=O)N2CCCc3ccc(O[C@@H]4CCc5ccccc54)cc32)ccc1F] | (R)-7-((2,3-dihydro-1H-inden-1-yl)oxy)-1-((4-fluoro-3-methoxyphenyl)sulfonyl)-1,2,3,4-tetrahydroquinoline | 454 (M + H)$^+$ |
| 25C | 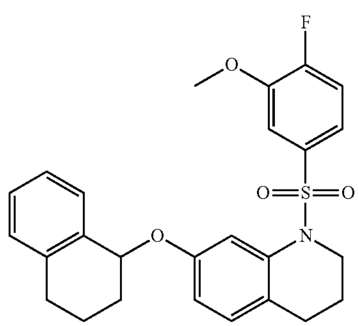 [SMILES: COc1cc(S(=O)(=O)N2CCCc3ccc(OC4CCCc5ccccc54)cc32)ccc1F] | 1-((4-fluoro-3-methoxyphenyl)sulfonyl)-7-((1,2,3,4-tetrahydronaphthalen-1-yl)oxy)-1,2,3,4-tetrahydroquinoline | 468 (M + H)$^+$ |
| 25D | 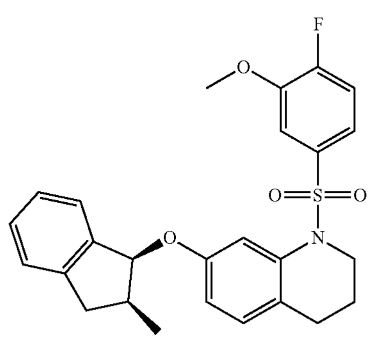 [SMILES: COc1cc(S(=O)(=O)N2CCCc3ccc(O[C@@H]4c5ccccc5C[C@@H]4C)cc32)ccc1F] | 1-((4-fluoro-3-methoxyphenyl)sulfonyl)-7-(((cis)-2-methyl-2,3-dihydro-1H-inden-1-yl)oxy)-1,2,3,4-tetrahydroquinoline | 468 (M + H)$^+$ |

TABLE 7-continued

| No. | Structure | Name | Observed m/z |
|---|---|---|---|
| 25E | 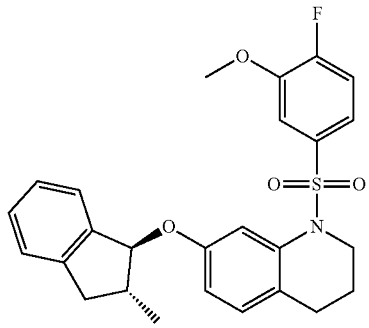 [SMILES: COc1cc(S(=O)(=O)N2CCCc3ccc(O[C@@H]4c5ccccc5C[C@H]4C)cc32)ccc1F] | 1-((4-fluoro-3-methoxyphenyl)sulfonyl)-7-(((trans)-2-methyl-2,3-dihydro-1H-inden-1-yl)oxy)-1,2,3,4-tetrahydroquinoline | 468 (M + H)+ |
| 25F | 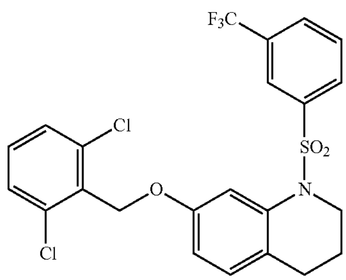 [SMILES: O=S(=O)(c1cccc(C(F)(F)F)c1)N1CCCc2ccc(OCc3c(Cl)cccc3Cl)cc21] | 7-((2,6-dichlorobenzyl)oxy)-1-((3-(trifluoromethyl)phenyl)sulfonyl)-1,2,3,4-tetrahydroquinoline | 516 (M + H)+ |
| 25G | 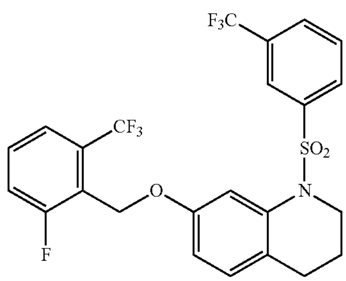 [SMILES: O=S(=O)(c1cccc(C(F)(F)F)c1)N1CCCc2ccc(OCc3c(F)cccc3C(F)(F)F)cc21] | 7-((2-fluoro-6-(trifluoromethyl)benzyl)oxy)-1-((3-(trifluoromethyl)phenyl)sulfonyl)-1,2,3,4-tetrahydroquinoline | 534 (M + H)+ |
| 25H | 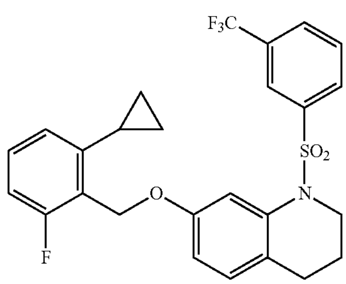 [SMILES: O=S(=O)(c1cccc(C(F)(F)F)c1)N1CCCc2ccc(OCc3c(F)cccc3C3CC3)cc21] | 7-((2-cyclopropyl-6-fluorobenzyl)oxy)-1-((3-(trifluoromethyl)phenyl)sulfonyl)-1,2,3,4-tetrahydroquinoline | 506 (M + H)+ |
| 25I | 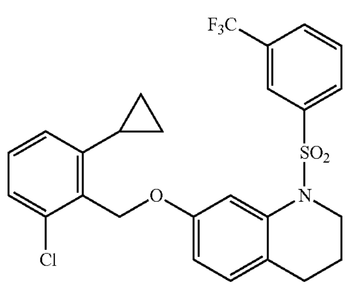 [SMILES: O=S(=O)(c1cccc(C(F)(F)F)c1)N1CCCc2ccc(OCc3c(Cl)cccc3C3CC3)cc21] | 7-((2-chloro-6-cyclopropylbenzyl)oxy)-1-((3-(trifluoromethyl)phenyl)sulfonyl)-1,2,3,4-tetrahydroquinoline | 522 (M + H)+ |

TABLE 7-continued

| No. | Structure | Name | Observed m/z |
|---|---|---|---|
| 25J | 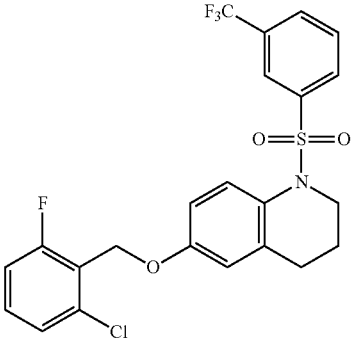 [SMILES: O=S(=O)(c1cccc(C(F)(F)F)c1)N1CCCc2cc(OCc3c(F)cccc3Cl)ccc21] | 6-((2-chloro-6-fluorobenzyl)oxy)-1-((3-(trifluoromethyl)phenyl)sulfonyl)-1,2,3,4-tetrahydroquinoline | 500 (M + H)⁺ |
| 25K | 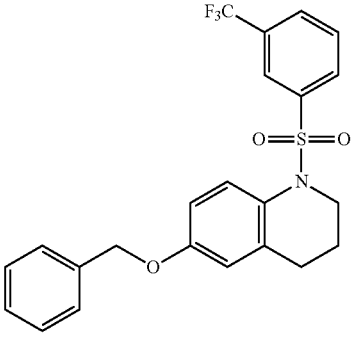 [SMILES: O=S(=O)(c1cccc(C(F)(F)F)c1)N1CCCc2cc(OCc3ccccc3)ccc21] | 6-(benzyloxy)-1-((3-(trifluoromethyl)phenyl)sulfonyl)-1,2,3,4-tetrahydroquinoline | 448 (M + H)⁺ |
| 25L | 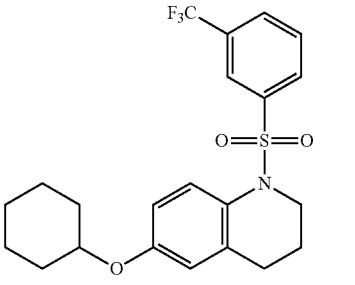 [SMILES: O=S(=O)(c1cccc(C(F)(F)F)c1)N1CCCc2cc(OC3CCCCC3)ccc21] | 6-(cyclohexyloxy)-1-((3-(trifluoromethyl)phenyl)sulfonyl)-1,2,3,4-tetrahydroquinoline | 440 (M + H)⁺ |
| 25M | 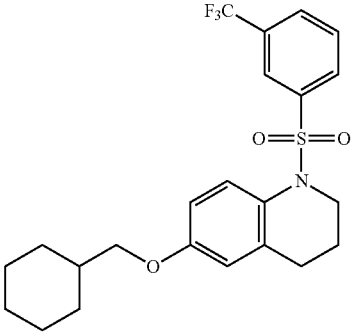 [SMILES: O=S(=O)(c1cccc(C(F)(F)F)c1)N1CCCc2cc(OCC3CCCCC3)ccc21] | 6-(cyclohexylmethoxy)-1-((3-(trifluoromethyl)phenyl)sulfonyl)-1,2,3,4-tetrahydroquinoline | 454 (M + H)⁺ |

TABLE 7-continued

| No. | Structure | Name | Observed m/z |
|---|---|---|---|
| 25N | 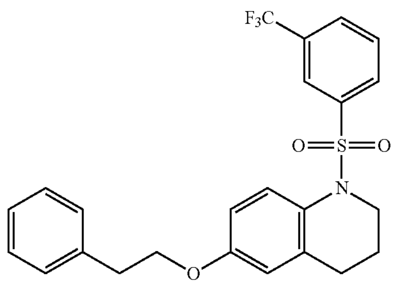 [SMILES: O=S(=O)(c1cccc(C(F)(F)F)c1)N1CCCc2cc(OCCc3ccccc3)ccc21] | 6-phenethoxy-1-((3-(trifluoromethyl)phenyl)sulfonyl)-1,2,3,4-tetrahydroquinoline | 462 (M + H)+ |
| 25O | 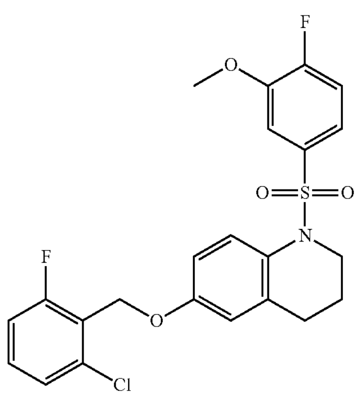 [SMILES: COc1cc(S(=O)(=O)N2CCCc3cc(OCc4c(F)cccc4Cl)ccc32)ccc1F] | 6-((2-chloro-6-fluorobenzyl)oxy)-1-((4-fluoro-3-methoxyphenyl)sulfonyl)-1,2,3,4-tetrahydroquinoline | 480 (M + H)+ |
| 25P | 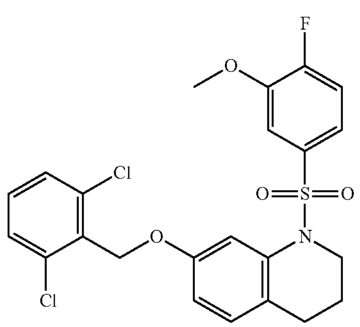 | 7-((2,6-dichlorobenzyl)oxy)-1-((4-fluoro-3-methoxyphenyl)sulfonyl)-1,2,3,4-tetrahydroquinoline | 496 (M + H)+ |
| 25Q | 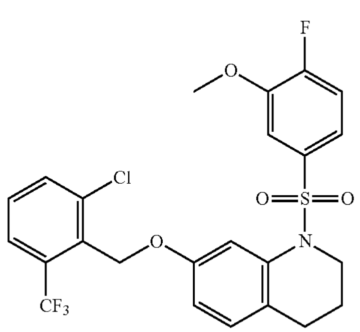 [SMILES: COc1cc(S(=O)(=O)N2CCCc3ccc(OCc4c(Cl)cccc4C(F)(F)F)cc32)ccc1F] | 7-((2-chloro-6-(trifluoromethyl)benzyl)oxy)-1-((4-fluoro-3-methoxyphenyl)sulfonyl)-1,2,3,4-tetrahydroquinoline | 530 (M + H)+ |

TABLE 7-continued

| No. | Structure | Name | Observed m/z |
|---|---|---|---|
| 25R | 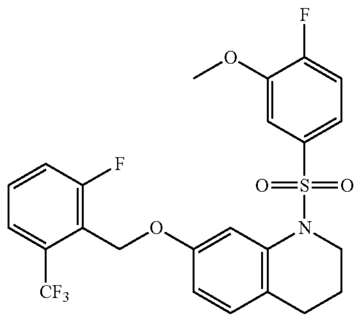 [SMILES: COc1cc(S(=O)(=O)N2CCCc3ccc(OCc4c(F)cccc4C(F)(F)F)cc32)ccc1F] | 1-((4-fluoro-3-methoxyphenyl)sulfonyl)-7-((2-fluoro-6-(trifluoromethyl)benzyl)oxy)-1,2,3,4-tetrahydroquinoline | 514 (M + H)+ |
| 25S | 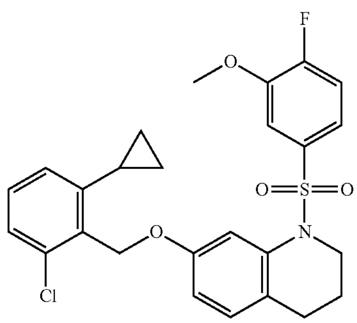 | 7-((2-chloro-6-cyclopropylbenzyl)oxy)-1-((4-fluoro-3-methoxyphenyl)sulfonyl)-1,2,3,4-tetrahydroquinoline | 502 (M + H)+ |
| 25T | 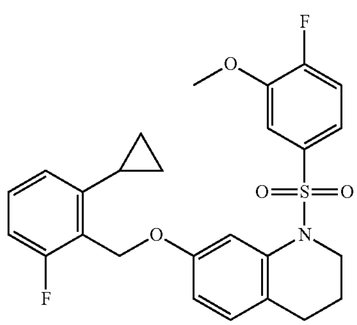 | 7-((2-cyclopropyl-6-fluorobenzyl)oxy)-1-((4-fluoro-3-methoxyphenyl)sulfonyl)-1,2,3,4-tetrahydroquinoline | 486 (M + H)+ |
| 25U | 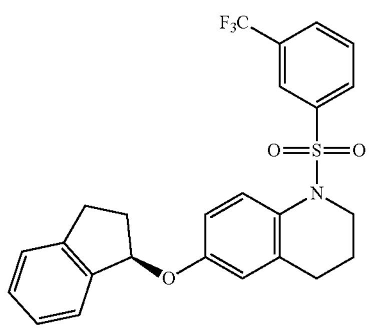 [SMILES: O=S(=O)(c1cccc(C(F)(F)F)c1)N1CCCc2cc(O[C@@H]3CCc4ccccc43)ccc21] | (R)-6-((2,3-dihydro-1H-inden-1-yl)oxy)-1-((3-(trifluoromethyl)phenyl)sulfonyl)-1,2,3,4-tetrahydroquinoline | 474 (M + H)+ |

TABLE 7-continued

| No. | Structure | Name | Observed m/z |
|---|---|---|---|
| 25V | 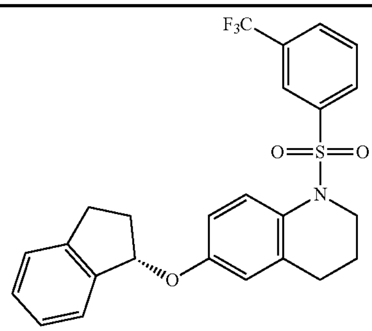 | (S)-6-((2,3-dihydro-1H-inden-1-yl)oxy)-1-((3-(trifluoromethyl)-phenyl)sulfonyl)-1,2,3,4-tetrahydroquinoline | 474 (M + H)+ |
| 25W | 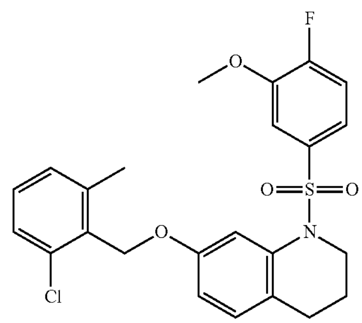 [SMILES: COc1cc(S(=O)(=O)N2CCCc3ccc(OCc4c(C)cccc4Cl)cc32)ccc1F] | 7-((2-chloro-6-methylbenzyl)oxy)-1-((4-fluoro-3-methoxyphenyl)sulfonyl)-1,2,3,4-tetrahydroquinoline | 476 (M + H)+ |

Example 26—Synthesis of (S)-Methyl 3-(7-((2-chloro-6-fluorobenzyl)oxy)-1-((4-fluoro-3-methoxyphenyl)sulfonyl)-1,2,3,4-tetrahydroquinolin-3-yl)-2,2-dimethylpropanoate

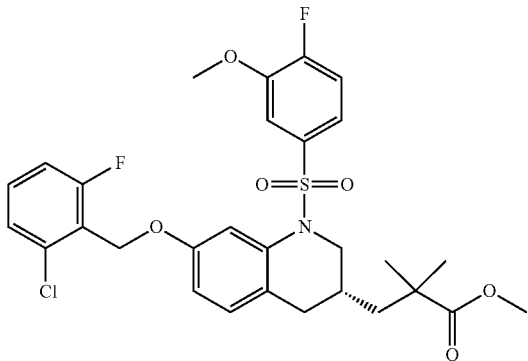 [SMILES: COC(=O)C(C)(C)C[C@@H]1Cc2ccc(OCc3c(F)cccc3Cl)cc2N(S(=O)(=O)c2ccc(F)c(OC)c2)C1]

Part I—Synthesis of 2,2-Dimethyl-5-oxo-5-[(4S)-2-oxo-4-(propan-2-yl)-1,3-oxazolidin-3-yl]pentanoic acid

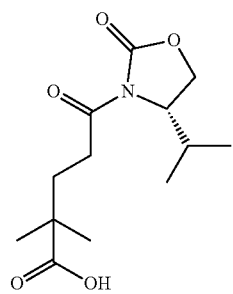 [SMILES: CC(C)[C@H]1COC(=O)N1C(=O)CCC(C)(C)C(=O)O]

To a mixture of (4S)-4-(propan-2-yl)-1,3-oxazolidin-2-one (5 g, 38.7 mmol) and lithium chloride (1.79 g, 42.6 mmol) in tetrahydrofuran (15 mL) was added triethylamine (6.97 mL, 50.1 mmol) dropwise. To this mixture was added 3,3-dimethyloxane-2,6-dione (5.78 g, 40.66 mmol) in portions. The resulting solution was stirred for two hours at room temperature, and then the reaction was quenched by the addition of brine (15 mL) to the reaction solution. The pH value of the solution was adjusted to pH 1 by adding hydrogen chloride (1 mol/L). Next, the resulting solution was extracted three times dichloromethane, organic layers were combined, and then concentrated to afford 2,2-dimethyl-5-oxo-5-[(4S)-2-oxo-4-(propan-2-yl)-1,3-oxazolidin-3-yl]pentanoic acid (11.32 g) as a colorless oil which was used without any further purification.

Part II—Synthesis of 2,2-Dimethyl-5-oxo-5-[(4S)-2-oxo-4-(propan-2-yl)-1,3-oxazolidin-3-yl]pentanoate

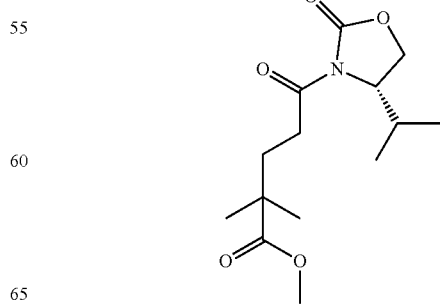

To a solution of 2,2-dimethyl-5-oxo-5-[(4S)-2-oxo-4-(propan-2-yl)-1,3-oxazolidin-3-yl]pentanoic acid (11.29 g, 41.61 mmol) in acetonitrile (78.7 mL) and methanol (7.9 mL) was added 2M solution of trimethylsilyl diazomethane in hexanes (41.6 mL) dropwise with stirring at 0° C. The resulting solution was stirred for 2 h at 0° C. in an ice bath, and then the reaction solution was concentrated to provide a residue. The residue was purified using MPLC eluting with ethyl acetate/petroleum ether (1:2) as eluent to yield methyl 2,2-dimethyl-5-oxo-5-[(4S)-2-oxo-4-(propan-2-yl)-1,3-oxazolidin-3-yl]pentanoate (2.27 g, 19%) as a light yellow oil.

Part III—Synthesis of (4S)-4-[(4-Hydroxy-2-nitrophenyl)methyl]-2,2-dimethyl-5-oxo-5-[(4S)-2-oxo-4-(propan-2-yl)-1,3-oxazolidin-3-yl]pentanoate

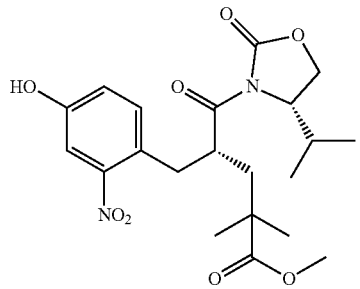 [SMILES: COC(=O)C(C)(C)C[C@H](Cc1ccc(O)cc1[N+](=O)[O-])C(=O)N1C(=O)OC[C@@H]1C(C)C]

To a solution of methyl 2,2-dimethyl-5-oxo-5-[(4S)-2-oxo-4-(propan-2-yl)-1,3-oxazolidin-3-yl]pentanoate (2.27 g, 7.96 mmol) in anhydrous tetrahydrofuran (22.8 mL) was added a 1M solution of LiHMDS in THF (8.9 mL) at −78° C., and the reaction mixture stirred for 10 minutes. To this was added a solution of 4-(bromomethyl)-3-nitrophenyl acetate (2.18 g, 7.95 mmol) in tetrahydrofuran (11.4 mL) dropwise with stirring. The resulting solution was stirred overnight at room temperature, and then the reaction was quenched by the addition of saturated ammonium chloride (100 mL) to the reaction mixture. The resulting solution was extracted three times with dichloromethane, organic layers were combined, then concentrated to provide a residue. The residue was purified using MPLC eluting with ethyl acetate/petroleum ether (1:1) to afford methyl (4S)-4-[(4-hydroxy-2-nitrophenyl)methyl]-2,2-dimethyl-5-oxo-5-[(4S)-2-oxo-4-(propan-2-yl)-1,3-oxazolidin-3-yl]pentanoate (1.84 g, 53%) as a yellow oil.

Part IV—Synthesis of (S)-Methyl 3-(7-hydroxy-2-oxo-1,2,3,4-tetrahydroquinolin-3-yl)-2,2-dimethylpropanoate

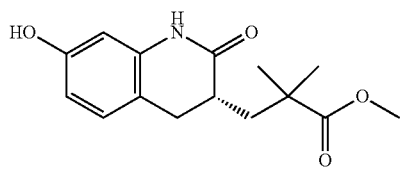 [SMILES: COC(=O)C(C)(C)C[C@@H]1Cc2ccc(O)cc2NC1=O]

A mixture of methyl (4S)-4-[(4-hydroxy-2-nitrophenyl)methyl]-2,2-dimethyl-5-oxo-5-[(4S)-2-oxo-4-(propan-2-yl)-1,3-oxazolidin-3-yl]pentanoate (1.84 g, 4.22 mmol), acetic acid (17.1 mL) and zinc (4 g, 50.6 mmol) was stirred for thirty minutes at 70° C. where the reaction vessel was placed in an oil bath. Next, the reaction was quenched by the addition of saturated sodium bicarbonate (100 mL) to the reaction mixture. The resulting mixture was extracted three times with dichloromethane, the organic layers were combined, then concentrated to provide a residue. The residue was purified via MPLC eluting with a gradient of 2:1 to 1:2 of petroleum ether to ethyl acetate to afford (S)-methyl 3-(7-hydroxy-2-oxo-1,2,3,4-tetrahydroquinolin-3-yl)-2,2-dimethylpropanoate (1.27 g) as a yellow oil.

Part V—Synthesis of (S)-Methyl 3-(7-hydroxy-1,2,3,4-tetrahydroquinolin-3-yl)-2,2-dimethylpropanoate

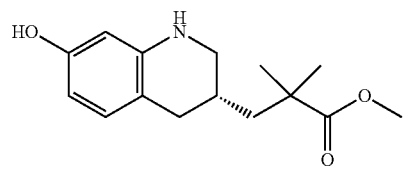 [SMILES: COC(=O)C(C)(C)C[C@H]1CNc2cc(O)ccc2C1]

To a solution of (S)-methyl 3-(7-hydroxy-2-oxo-1,2,3,4-tetrahydroquinolin-3-yl)-2,2-dimethylpropanoate (1.25 g, 4.51 mmol) in tetrahydrofuran (30 mL) was added a 1M solution of borane in THF (20.1 mL) dropwise with stirring at 0° C. The resulting solution was stirred for four hours at room temperature. Then, the reaction was quenched by adding water (100 mL) to the reaction mixture. The resulting mixture was extracted three times with dichloromethane. The organic layers were combined, then concentrated to provide a residue. The residue was purified using MPLC eluting with a gradient of petroleum ether:ethyl acetate of 4:1 to 1:1 to afford (S)-methyl 3-(7-hydroxy-1,2,3,4-tetrahydroquinolin-3-yl)-2,2-dimethylpropanoate (640 mg, 54%) as a yellow oil.

Part VI—Synthesis of (S)-Methyl 3-(1-((4-fluoro-3-methoxyphenyl)sulfonyl)-7-hydroxy-1,2,3,4-tetrahydroquinolin-3-yl)-2,2-dimethylpropanoate

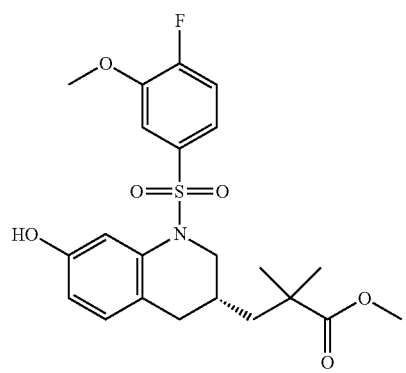 [SMILES: COC(=O)C(C)(C)C[C@@H]1Cc2ccc(O)cc2N(S(=O)(=O)c2ccc(F)c(OC)c2)C1]

A solution (S)-methyl 3-(7-hydroxy-1,2,3,4-tetrahydroquinolin-3-yl)-2,2-dimethylpropanoate (189 mg, 0.72 mmol), pyridine (0.45 mL, 5.59 mmol), 4-fluoro-3-methoxybenzene-1-sulfonyl chloride (171.4 mg, 0.76 mmol) in dichloromethane (0.11 mL) was stirred for one hour at room temperature and then concentrated to provide a residue. The residue was purified by MPLC eluting with a gradient of 4:1 to 1:1 petroleum ether:ethyl acetate to afford (S)-methyl 3-(1-((4-fluoro-3-methoxyphenyl)sulfonyl)-7-hydroxy-1,2,3,4-tetrahydroquinolin-3-yl)-2,2-dimethylpropanoate (302 mg, 93%) as a dark red solid.

Part VII—Synthesis of (S)-Methyl 3-(7-((2-chloro-6-fluorobenzyl)oxy)-1-((4-fluoro-3-methoxyphenyl)sulfonyl)-1,2,3,4-tetrahydroquinolin-3-yl)-2,2-dimethylpropanoate

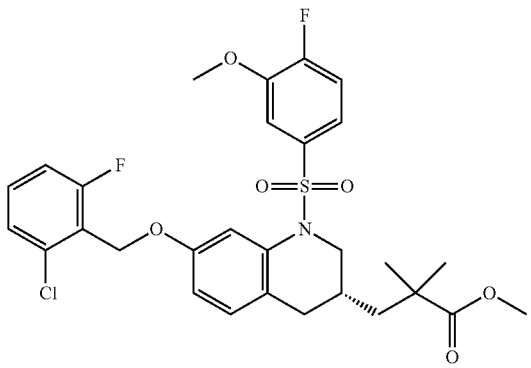 [SMILES: COC(=O)C(C)(C)C[C@@H]1Cc2ccc(OCc3c(F)cccc3Cl)cc2N(S(=O)(=O)c2ccc(F)c(OC)c2)C1]

A mixture of (S)-methyl 3-(1-((4-fluoro-3-methoxyphenyl)sulfonyl)-7-hydroxy-1,2,3,4-tetrahydroquinolin-3-yl)-2,2-dimethylpropanoate (260 mg, 0.58 mmol), potassium carbonate (79.5 mg, 0.58 mmol), and 2-(bromomethyl)-1-chloro-3-fluorobenzene (0.080 mL, 0.58 mmol) in N,N-dimethylformamide (1.0 mL) was stirred overnight at room temperature. Then, the resulting solution was diluted with water. The resulting mixture was extracted three times dichloromethane, the organic layers were combined, then concentrated to provide a residue. The residue was purified by MPLC eluting with a gradient of 10:1 to 2:1 petroleum ether:ethyl acetate. The major component was further purified by preparative HPLC with water (containing 0.05% trifluoroacetic acid) and acetonitrile (58.0% to 88.0% in 8 minutes) to afford (S)-methyl 3-(7-((2-chloro-6-fluorobenzyl)oxy)-1-((4-fluoro-3-methoxyphenyl)sulfonyl)-1,2,3,4-tetrahydroquinolin-3-yl)-2,2-dimethylpropanoate (338 mg, 99%) as a yellow oil. $^1$H-NMR (400 MHz, CDCl$_3$) δ 1.17 (s, 3H), 1.19 (s, 3H), 1.43-1.53 (m, 3H), 2.11 (dd, J=10.8 Hz, 16.8 Hz, 1H), 2.50 (dd, J=5.2 Hz, 16.4 Hz, 1H), 3.01 (dd, J=10.8 Hz, 13.6 Hz, 1H), 3.72 (s, 3H), 3.74 (s, 3H), 4.19 (dd, J=1.6 Hz, 13.2 Hz, 1H), 5.20 (d, J=1.6 Hz, 2H), 6.78 (dd, J=2.4 Hz, 8.4 Hz, 1H), 6.92 (d, J=8.4 Hz, 1H), 7.06-7.15 (m, 3H), 7.23-7.26 (m, 1H), 7.28-7.36 (m, 2H), 7.62 (d, J=2.4 Hz, 1H). (ES, m/z): (M+H)$^+$594.

Example 27-Synthesis of (S)-3-(7-((2-Chloro-6-fluorobenzyl)oxy)-1-((4-fluoro-3-methoxyphenyl)sulfonyl)-1,2,3,4-tetrahydroquinolin-3-yl)-2,2-dimethylpropanoic acid

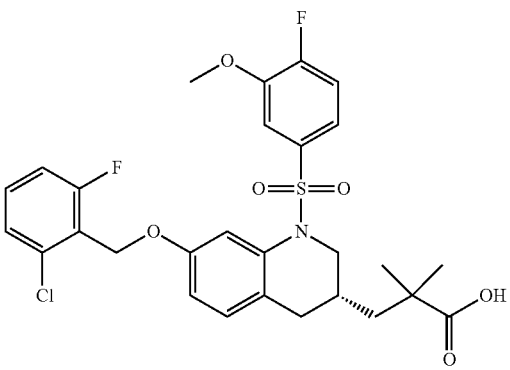 [SMILES: COc1cc(S(=O)(=O)N2C[C@H](CC(C)(C)C(=O)O)Cc3ccc(OCc4c(F)cccc4Cl)cc32)ccc1F]

A mixture of (S)-methyl 3-(7-((2-chloro-6-fluorobenzyl)oxy)-1-((4-fluoro-3-methoxyphenyl)sulfonyl)-1,2,3,4-tetrahydroquinolin-3-yl)-2,2-dimethylpropanoate (200 mg, 0.34 mmol), dioxane (1.5 mL), methanol (0.8 mL), water (0.8 mL), and lithium hydroxide monohydrate (282 mg, 6.73 mmol) was stirred for four hours at 50° C. The pH value of the solution was adjusted to pH 6 with hydrogen chloride (1 mol/L). The resulting solution was extracted three times with dichloromethane, the organic layers were combined, then concentrated to provide a crude product that was purified by Prep-HPLC eluting with a gradient of water (containing 0.05% TFA) and acetonitrile (55.0% to 80.0% in 8 minutes) to afford (S)-3-(7-((2-chloro-6-fluorobenzyl)oxy)-1-((4-fluoro-3-methoxyphenyl)sulfonyl)-1,2,3,4-tetrahydroquinolin-3-yl)-2,2-dimethylpropanoic acid (85.5 mg, 44%) as a white solid. $^1$H-NMR (400 MHz, CD$_3$OD) δ 1.15 (s, 3H), 1.18 (s, 3H), 1.41-1.57 (m, 3H), 2.22-2.10 (m, 1H), 2.59-2.51 (m, 1H), 3.03 (dd, J=10.8 Hz, 13.8 Hz), 3.69 (s, 3H), 4.31 (dd, J=2.1 Hz, 13.8 Hz, 1H), 5.22 (d, J=1.8 Hz, 2H), 6.84 (dd, J=2.7 Hz, 8.4 Hz, 1H), 6.99 (d, J=8.4 Hz, 1H), 7.04 (dd, J=1.8 Hz, 7.8 Hz, 1H), 7.15-7.45 (m, 5H), 7.53 (s, 1H). (ES, m/z): (M+H)$^+$580.

Example 28—Additional Compounds

The following additional compounds were prepared based on procedures above.

TABLE 8

| No. | Chemical Structure |
|---|---|
| 28A | 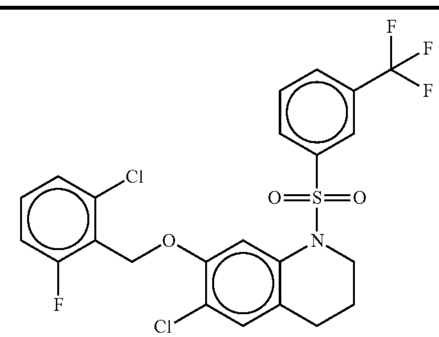 |

TABLE 8-continued
| No. | Chemical Structure |
|---|---|
| 28B | 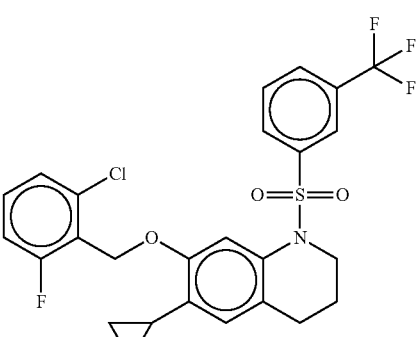 |
| 28C | 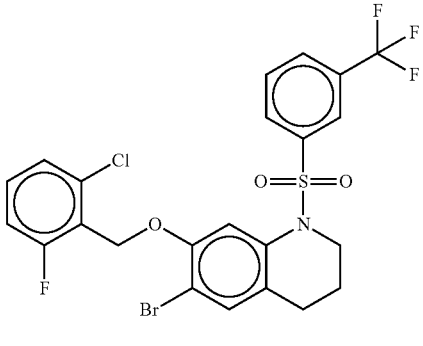 |
| 28D | 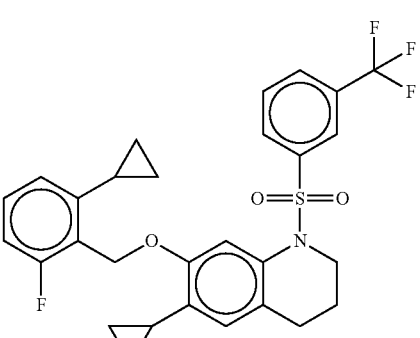 |
| 28E | 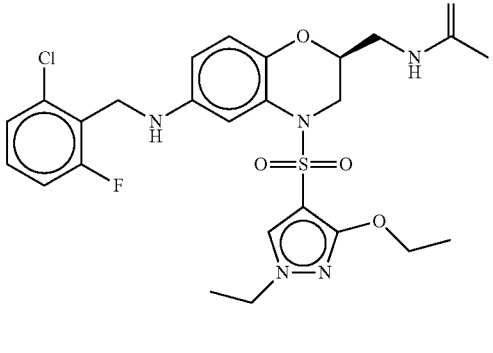 |
| 28F | 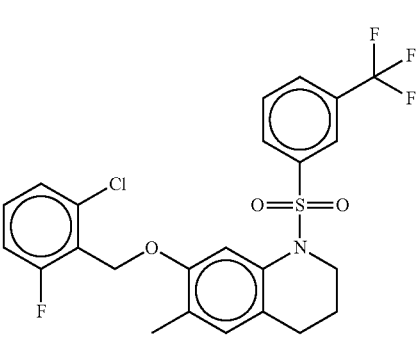 |
| 28G | 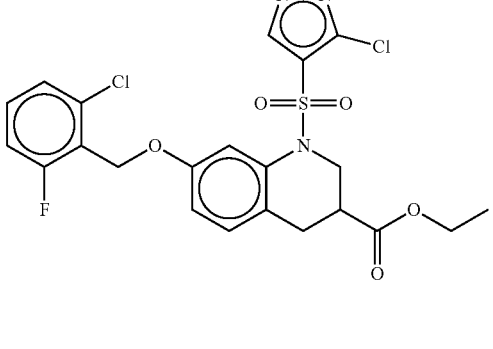 |
| 28H | 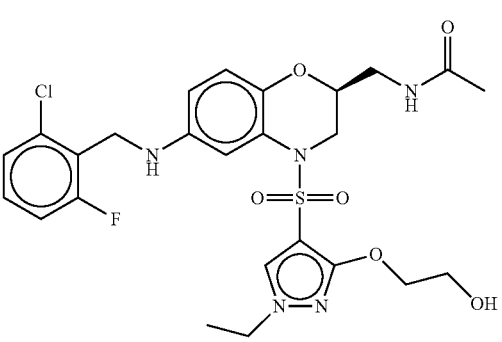 |
| 28I | 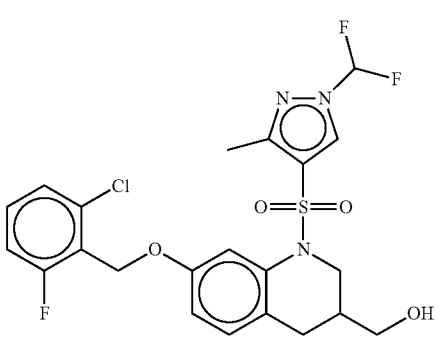 |

Example 29—Synthesis of (S,E)-3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid

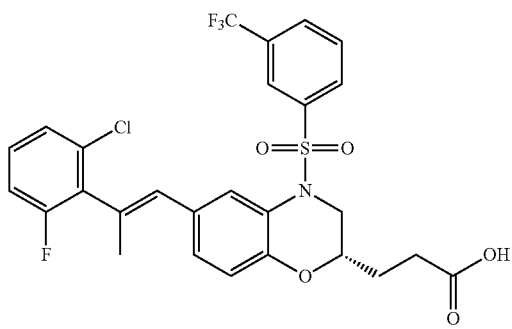

Part I—Synthesis of Dimethyl (R)-2-hydroxypentanedioate

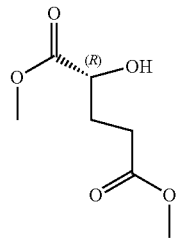

To a mixture of (2R)-5-oxotetrahydro-2-furancarboxylic acid (25 g, 192 mmol) in methanol (300 mL) was added concentrated hydrogen chloride (0.5 mL) and the mixture was refluxed overnight. Cooled to ambient temperature, added solid sodium bicarbonate and slurried for 20 minutes. The mixture was filtered and concentrated to obtain dimethyl (R)-2-hydroxypentanedioate (34.7 g, 100%).

Part II—Synthesis of Dimethyl (S)-2-(4-bromo-2-nitrophenoxy)pentanedioate

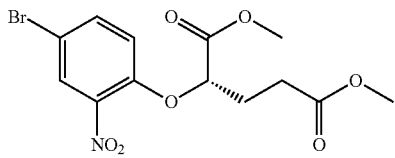 [SMILES: COC(=O)CC[C@H](Oc1ccc(Br)cc1[N+](=O)[O-])C(=O)OC]

To a solution of dimethyl (R)-2-hydroxypentanedioate (33.8 g, 192 mmol), 4-bromo-2-nitrophenol (50.2 g, 230 mmol), and triphenylphosphine (60.4 g, 230 mmol) in dichloromethane (300 mL) with activated molecular sieves at 0° C. was added a solution of diisopropyl azodicarboxylate (45.4 mL, 230 mmol) in dichloromethane (50 mL) dropwise. Stirred at 0° C. for 20 minutes, then at ambient temperature overnight. Concentrated. Removed triphenylphosphine oxide by running through a large pad of silica, eluting with dichloromethane (~6 L). The eluted material was a mixture of the drawn compound and a small amount of residual phenol. Redissolved in ethyl acetate, washed four times with 1M sodium hydroxide, washed with brine, dried (Na$_2$SO$_4$), and concentrated to yield dimethyl (S)-2-(4-bromo-2-nitrophenoxy)pentanedioate (62.84 g, 87%) as a clear oil.

Part III—Synthesis of Methyl (S)-3-(6-bromo-3-oxo-3,4-dihydro-2H-benzo[b][1,4]oxazin-2-yl)propanoate

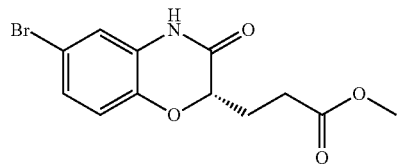 [SMILES: CNC(=O)[C@H](CCC(=O)OC)Oc1ccc(Br)cc1]

In a flask equipped with a mechanical stirrer was charged dimethyl (S)-2-(4-bromo-2-nitrophenoxy)pentanedioate (62.84 g, 167 mmol), acetic acid (500 mL), followed by powdered iron (46.7 g, 835 mmol) at ambient temperature. Heated to 60° C. for two hours. Filtered hot through a pad of Celite, washing with ethyl acetate (900 mL). The filtrates were washed three times with water, washed with brine, dried (Na$_2$SO$_4$) and concentrated to yield methyl (S)-3-(6-bromo-3-oxo-3,4-dihydro-2H-benzo[b][1,4]oxazin-2-yl)propanoate (48.06 g, 92%) as a white solid.

Part IV—Synthesis of Methyl (S)-3-(6-bromo-3,4-dihydro-2H-benzo[b][1,4]oxazin-2-yl)propanoate

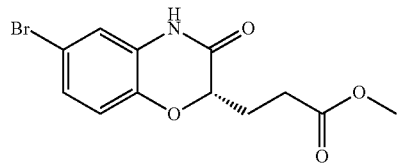 [SMILES: CNC(=O)[C@H](CCC(=O)OC)Oc1ccc(Br)cc1]

To methyl (S)-3-(6-bromo-3-oxo-3,4-dihydro-2H-benzo[b][1,4]oxazin-2-yl)propanoate (24.46 g, 77.9 mmol) in anhydrous tetrahydrofuran (200 mL) at 0° C. was added borane-methyl sulfide complex (19.5 mL, 195 mmol) dropwise. Heated to 50° C. for one hour. The reaction mixture was cooled to 0° C., then carefully quenched with methanol (150 mL). Heated to 60° C. for one hour and concentrated. The residue was partitioned between water and ethyl acetate. The organic layer was washed with brine, dried (Na$_2$SO$_4$) and concentrated. The mixture was purified by column chromatography eluting with a gradient of 5-50% ethyl acetate in hexanes to yield methyl (5)-3-(6-bromo-3,4-dihydro-2H-benzo[b][1,4]oxazin-2-yl)propanoate (17.97 g, 77%) as a white solid.

Part V—Synthesis of (S)-Methyl 3-(6-bromo-4-((3-(trifluoromethyl)phenyl)sulfonyl)-3,4-dihydro-2H-benzo[b][1,4]oxazin-2-yl)propanoate

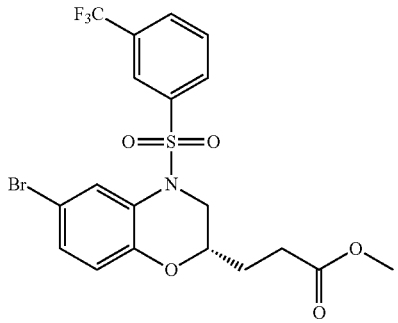 [SMILES: COC(=O)CC[C@H]1CN(S(=O)(=O)c2cccc(C(F)(F)F)c2)c2cc(Br)ccc2O1]

To a solution of (S)-3-(6-bromo-3,4-dihydro-2H-benzo[b][1,4]oxazin-2-yl)propanoate (10.0 g, 33.3 mmol) in pyridine (60 mL) was added 3-(trifluoromethyl)benzenesulfonyl chloride (8.96 g, 36.6 mmol). The mixture was heated at 50° C. for four hours, cooled, and concentrated. The residue was partitioned between ethyl acetate and 1N HCl. The organic layer was washed twice with 1 M HCl, brine, and then dried (Na$_2$SO$_4$). Activated charcoal was added, the mixture slurried, and then filtered through Celite. The filtrate was concentrated onto a small amount of silica and the residue was purified via MPLC eluting with a gradient of ethyl acetate in hexanes. The major UV-active component was concentrated to afford (S)-methyl 3-(6-bromo-4-((3-(trifluoromethyl)phenyl)sulfonyl)-3,4-dihydro-2H-benzo[b][1,4]oxazin-2-yl)propanoate (14.75 g, 87%).

Part VI—Synthesis of 1-Chloro-2-ethynyl-3-fluorobenzene

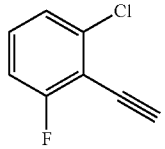

2-Chloro-6-fluorobenzaldehyde (2.00 g, 12.61 mmol) was dissolved in methanol (84 mL), and dimethyl (diazomethyl)phosphonate (2.39 mL, 15.77 mmol) was added followed by potassium carbonate (4.36 g, 31.53 mmol). The reaction mixture was stirred at room temperature overnight. The crude mixture was diluted with methyl tert-butyl ether, washed with water, washed with brine, dried (Na$_2$SO$_4$), and concentrated to afford 1-chloro-2-ethynyl-3-fluorobenzene (1.83 g, 94%). $^1$H-NMR (400 MHz, DMSO-d$_6$) δ 7.45 (m, 2H), 7.32 (t, 1H), 4.86 (s, 1H).

Part VII—Synthesis of (E)-2-(2-(2-Chloro-6-fluorophenyl)prop-1-en-1-yl)-4,4,5,5-tetramethyl-1,3,2-dioxaborolane

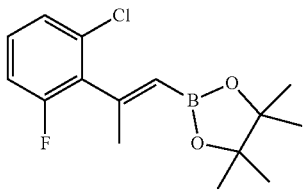 [SMILES: C/C(=C\B1OC(C)(C)C(C)(C)O1)c1c(F)cccc1Cl]

Bis(pinacolato)diborane (5.82 g, 22.92 mmol), copper (I) chloride (0.21 g, 2.08 mmol), and 4,5-bis(diphenylphosphino)-9,9-dimethylxanthene (1.21 g, 2.08 mmol) were suspended in THF (208 mL) and the mixture was degassed with nitrogen and stirred for five min. A solution of sodium tert-butoxide (2.202 g, 22.92 mmol) in minimal THF was added, and the mixture stirred for an additional five minutes. 1-Chloro-2-ethynyl-3-fluorobenzene (3.22 g, 20.83 mmol) and methyl iodide (11.83 g, 83.33 mmol) were added to the reaction mixture, and the resulting mixture was stirred at room temperature overnight. The crude product mixture was concentrated onto silica gel and purified by MPLC eluting with a gradient of 0-5% ethyl acetate in hexanes to afford (E)-2-(2-(2-chloro-6-fluorophenyl)prop-1-en-1-yl)-4,4,5,5-tetramethyl-1,3,2-dioxaborolane (2.41 g, 39%). $^1$H-NMR (400 MHz, DMSO-d$_6$) δ 7.31 (m, 2H), 7.20 (t, 1H), 5.18 (s, 1H), 2.15 (s, 3H), 1.23 (s, 12H).

Part VIII—Synthesis of (SE)-Methyl 3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoate

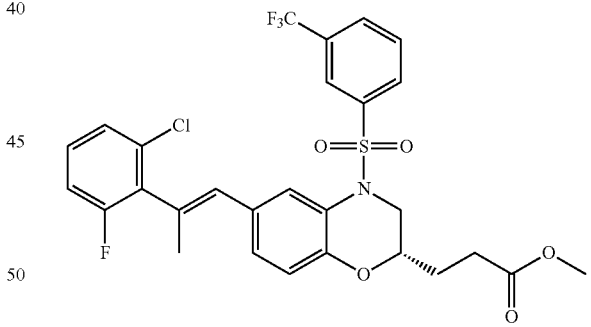

A mixture of (S)-methyl 3-(6-bromo-4-((3-(trifluoromethyl)phenyl)sulfonyl)-3,4-dihydro-2H-benzo[b][1,4]oxazin-2-yl)propanoate (7.46 g, 14.7 mmol), (E)-2-(2-(2-chloro-6-fluorophenyl)prop-1-en-1-yl)-4,4,5,5-tetramethyl-1,3,2-dioxaborolane (6.09 g, 20.5 mmol), potassium carbonate (2.84 g, 20.5 mmol) in dioxane (80 mL), and water (20 mL) was degassed and placed under an atmosphere of nitrogen. This was followed by addition of [1,1'-bis(diphenylphosphino)ferrocene]dichloropalladium(II) dichloromethane complex (1.12 g, 1.47 mmol) and heating to 70° C. for five hours. Toluene (100 mL) and a 20% solution of sodium bisulfite in water (50 mL) were added. The mixture was allowed to stir at 60° C. for an additional fifteen min., then cooled and diluted with toluene (150 mL).

The organic layer was washed with a 20% aqueous solution of sodium bisulfite, water, brine, and then dried (Na₂SO₄), and added to activated charcoal. The mixture was slurried and filtered through a pad of Celite. The filtrate was concentrated onto a small amount of silica and the residue was purified by MPLC eluting with a gradient of 0-30% ethyl acetate in hexanes to afford (S,E)-methyl 3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoate (6.8 g, 77%). ¹H-NMR (400 MHz, DMSO-d₆) δ 8.11 (d, 1H), 8.03 (d, 1H), 7.99 (s, 1H), 7.86 (t, 1H), 7.68 (d, 1H), 7.38 (m, 2H), 7.27 (m, 1H), 7.11 (dd, 1H), 6.87 (d, 1H), 6.37 (s, 1H), 4.37 (d, 1H), 3.57 (s, 3H), 3.49 (m, 1H), 3.3 (m, 1H), 2.48 (m, 2H), 2.08 (s, 3H), 1.9 (m, 1H), 1.76 (m, 1H). (ES, m/z): (M+Na)⁺=620.09, 622.10.

Part IX—Synthesis of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid

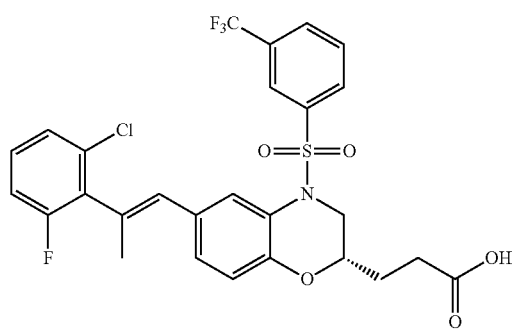

To a solution of (S,E)-methyl 3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoate (5.74 g, 9.60 mmol) in methanol (100 mL) and tetrahydrofuran (10 mL) was added 2M sodium hydroxide (14.4 mL, 28.8 mmol) in water. The reaction mixture was stirred at ambient temperature for 16 hours. The volume of the reaction mixture was reduced under vacuum, then acidified with 1M hydrogen chloride solution in water. The mixture was extracted with ethyl acetate, the combined extracts washed with brine, then dried (Na₂SO₄) and concentrated to a solid (5.54 g, 99%). The solid was converted to the sodium salt by redissolving in methanol (100 mL), then adding one equivalent of a 2.962M sodium hydroxide (3.203 mL, 9.487 mmol) solution in water and stirring for 20 min. The mixture was evaporated, then additional methanol was added and evaporated three times to remove water. The residue was dried in a vacuum oven to afford the sodium salt of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid (5.50 g, 98%) as a white solid. ¹H-NMR (400 MHz, DMSO-d₆) δ 8.1 (m, 2H), 7.89 (m, 2H), 7.69 (s, 1H), 7.37 (m, 2H), 7.26 (m, 1H), 7.08 (dd, 1H), 6.85 (d, 1H), 6.36 (s, 1H), 4.40 (d, 1H), 3.55 (m, 1H), 3.3 (m, 1H), 2.08 (s, 3H), 1.92 (m, 2H), 1.70 (m, 2H). (ES, m/z): (M+H)⁺=606.15, 608.15.

Example 30—Synthesis of (S,E)-3-(6-(2-Chloro-6-(trifluoromethyl)styryl)-4-((3-(trifluoromethyl)phenyl)sulfonyl)-3,4-dihydro-2H-benzo[b][1,4]oxazin-2-yl)propanoic acid

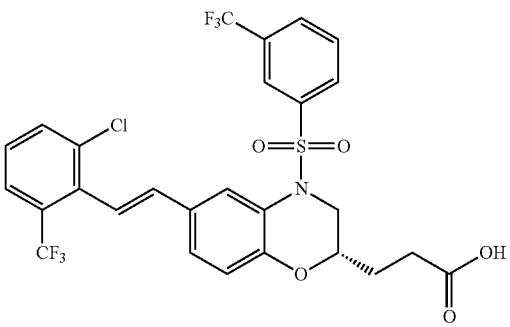 [SMILES: O=C(O)CC[C@H]1CN(S(=O)(=O)c2cccc(C(F)(F)F)c2)c2cc(/C=C/c3c(Cl)cccc3C(F)(F)F)ccc2O1]

Part I—Synthesis of 1-Chloro-2-ethynyl-3-(trifluoromethyl)benzene

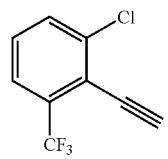

To a solution of 2-chloro-6-(trifluoromethyl)benzaldehyde (10.0 g, 47.9 mmol) in methanol (100 mL) was added dimethyl (diazomethyl)phosphonate (11.05 g, 57.5 mmol). The mixture was cooled to 0° C., and potassium carbonate (16.6 g, 119 mmol) was added. The reaction mixture was stirred at room temperature overnight. The crude mixture was diluted with ether, washed with water, washed with brine, dried (MgSO₄), and concentrated to afford 1-chloro-2-ethynyl-3-(trifluoromethyl)benzene (9.17 g, 93%).

Part II—Synthesis of (E)-2-(2-Chloro-6-(trifluoromethyl)styryl)-4,4,5,5-tetramethyl-1,3,2-dioxaborolane

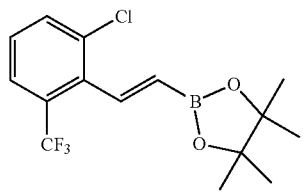 [SMILES: CC1(C)OB(/C=C/c2c(Cl)cccc2C(F)(F)F)OC1(C)C]

To [2,3-bis(1-adamantyl)imidazolidin-2-yl]-chloro-copper (0.99 g, 2.23 mmol) and sodium tert-butoxide (0.215 g, 2.23 mmol) suspended in THF (40 mL) was added bis(pinacolato)diboron (11.36 g, 44.7 mmol). The mixture was stirred for 30 minutes, and a solution of 1-chloro-2-ethynyl-3-(trifluoromethyl)benzene (9.15 g, 44.7 mmol) in THF (40 mL) and methanol (1.58 g, 49.2 mmol) was added. The mixture was stirred overnight then filtered through Celite. The filtrate was concentrated and the residue was purified via MPLC eluting with a gradient of 0-10% ethyl acetate in hexanes to afford (E)-2-(2-chloro-6-(trifluoromethyl)styryl)-4,4,5,5-tetramethyl-1,3,2-dioxaborolane (11.23 g, 76%).

Part III—Synthesis of (S,E)-Methyl 3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoate

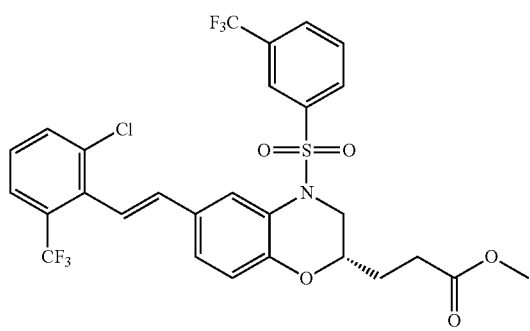

A mixture of (S)-methyl 3-(6-bromo-4-((3-(trifluoromethyl)phenyl)sulfonyl)-3,4-dihydro-2H-benzo[b][1,4]oxazin-2-yl)propanoate (2.00 g, 3.93 mmol), (E)-2-(2-chloro-6-(trifluoromethyl)styryl)-4,4,5,5-tetramethyl-1,3,2-dioxaborolane (1.83 g, 5.51 mmol), potassium carbonate (0.65 g, 4.72 mmol) in dioxane (40 mL) and water (6 mL) was degassed and was placed under an atmosphere of nitrogen. To this mixture was added [1,1'-bis(diphenylphosphino)ferrocene]-dichloropalladium(II) dichloromethane complex (0.30 g, 0.39 mmol) and the mixture heated at 70° C. overnight. The reaction mixture was cooled and partitioned between ethyl acetate and water. The organic layer was washed with brine, dried ($Na_2SO_4$) and concentrated onto a small amount of silica. The residue was purified by MPLC eluting with a gradient of 0-30% ethyl acetate in hexanes to afford (S,E)-methyl 3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoate (2.0 g, 80%). $^1$H-NMR (400 MHz, DMSO-$d_6$) δ 8.10 (d, 1H), 8.06 (d, 1H), 8.0 (s, 1H), 7.85 (m, 2H), 7.75 (m, 2H), 7.54 (t, 1H), 7.38 (dd, 1H), 6.98 (m, 1H), 6.88 (d, 1H), 6.78 (m, 1H), 4.37 (d, 1H), 3.58 (s, 3H), 3.40 (m, 1H), 3.3 (m, 1H), 2.42 (m, 2H), 1.9 (m, 1H), 1.75 (m, 1H). (ES, m/z): (M+Na)$^+$= 656.08, 658.07.

Part IV—Synthesis of (S,E)-3-(6-(2-Chloro-6-(trifluoromethyl)styryl)-4-((3-(trifluoromethyl)phenyl)sulfonyl)-3,4-dihydro-2H-benzo[b][1,4]oxazin-2-yl)propanoic acid To a solution of (S,E)-methyl 3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoate (11.8 g, 18.6 mmol) in methanol (100 mL) and tetrahydrofuran (30 mL) was added 2M sodium hydroxide (27.9 mL, 55.8 mmol) in water. The reaction mixture was stirred at ambient temperature for 16 hours. Reduced volume under vacuum. Acidified solution with 1M hydrogen chloride solution in water. Extracted with ethyl acetate, washed combined extracts with brine, dried ($Na_2SO_4$) and concentrated. Redissolved solids in dichloromethane and precipitated with hexanes. Filtered off solids and dried under vacuum. (8.73 g, 76%). The resulting solid was converted to the sodium salt by redissolving in methanol (100 mL), then adding one equivalent of a 3.109M sodium hydroxide (4.529 mL, 14.082 mmol) solution in water. Stirred ten minutes. Concentrated, and added methanol and concentrated three times. The residue was dried in a vacuum oven to afford the sodium salt of (S,E)-3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoic acid (8.70 g, 99%) as a white solid. $^1$H-NMR (400 MHz, DMSO-$d_6$) δ 8.15 (d, 1H), 8.08 (d, 1H), 7.88 (m, 3H), 7.78 (m, 2H), 7.55 (t, 1H), 7.34 (d, 1H), 6.98 (m, 1H), 6.84 (d, 1H), 6.78 (m, 1H), 4.40 (d, 1H), 3.60 (m, 1H), 3.3 (m, 1H), 1.92 (m, 2H), 1.70 (m, 2H). (ES, m/z): (M+Na)$^+$=641.93, 643.93.

Example 31—Synthesis of (S,E)-Methyl 3-(6-(1-(2-chloro-6-fluorophenyl)prop-1-en-2-yl)-4-((3-(trifluoromethyl)phenyl)sulfonyl)-3,4-dihydro-2H-benzo[b][1,4]oxazin-2-yl)propanoate

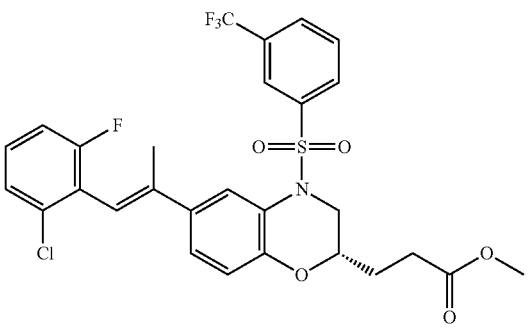 [SMILES: COC(=O)CC[C@H]1CN(S(=O)(=O)c2cccc(C(F)(F)F)c2)c2cc(/C(C)=C/c3c(F)cccc3Cl)ccc2O1]

Part I—Synthesis of 2-Chloro-6-fluorophenyl trifluoromethanesulfonate

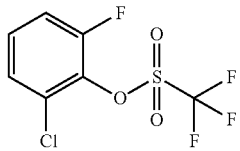 [SMILES: O=S(=O)(Oc1c(F)cccc1Cl)C(F)(F)F]

To a stirred solution of 2-chloro-6-fluorophenol (5.00 g, 34.1) in pyridine (100 mL) at 0° C. was added dropwise (trifluoromethane)sulfonyl trifluoromethanesulfonate (19.3 g, 68.4 mmol) dropwise. The mixture was allowed to warm to room temperature and was stirred overnight. The reaction mixture was concentrated and the residue was partitioned between ethyl acetate and water. The organic layer was washed with brine, dried ($Na_2SO_4$) and concentrated to afford 2-chloro-6-fluorophenyl trifluoromethanesulfonate (9.5 g, 100%) as a brown liquid.

Part II—Synthesis of 1-Chloro-3-fluoro-2-(prop-1-yn-1-yl)benzene

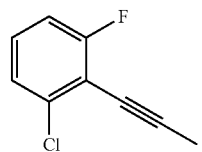

A solution of 2-chloro-6-fluorophenyl trifluoromethanesulfonate (2.78 g, 9.98 mmol) and tributyl(prop-1-yn-1-yl)stannane (3.95 g, 12.00 mmol) in toluene (50 mL) under an atmosphere of nitrogen was added tetrakis(triphenylphosphine)palladium(0) (1.15 g, 1.00 mmol). The mixture was heated at reflux for three hours, cooled, then concentrated. The residue was purified via MPLC, eluting with a gradient of (1-10%) ethyl acetate in hexanes to afford 1-chloro-3-fluoro-2-(prop-1-yn-1-yl)benzene (1.5 g, 89%) as a yellow liquid.

Part III—Synthesis of (Z)-2-(1-(2-Chloro-6-fluorophenyl)prop-1-en-2-yl)-4,4,5,5-tetramethyl-1,3,2-dioxaborolane

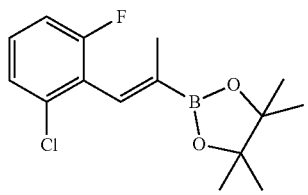 [SMILES: C/C(=C\c1c(F)cccc1Cl)B1OC(C)(C)C(C)(C)O1]

A mixture of 1-chloro-3-fluoro-2-(prop-1-yn-1-yl)benzene (1.68 g, 9.96 mmol), copper (I) chloride (60 mg, 0.61 mmol), tris(4-methoxyphenyl)phosphine (282 mg, 0.80 mmol), potassium carbonate (276 mg, 2.00 mmol), isopropanol (1.2 g, 20.00 mmol), ether (15 mL) and 4,4,5,5-tetramethyl-2-(tetramethyl-1,3,2-dioxaborolan-2-yl)-1,3,2-dioxaborolane (3 g, 11.81 mmol) was stirred overnight at room temperature under an atmosphere of nitrogen. The mixture was filtered and the filtrate was concentrated. The residue was purified via MPLC, eluting with a gradient of 1-12% ethyl acetate in petroleum ether to afford (Z)-2-(1-(2-chloro-6-fluorophenyl)prop-1-en-2-yl)-4,4,5,5-tetramethyl-1,3,2-dioxaborolane (1.5 g, 51%) as yellow oil.

Part IV—Synthesis of (S,E)-Methyl 3-(6-(1-(2-chloro-6-fluorophenyl)prop-1-en-2-yl)-4-((3-(trifluoromethyl)phenyl)sulfonyl)-3,4-dihydro-2H-benzo[b][1,4]oxazin-2-yl)propanoate

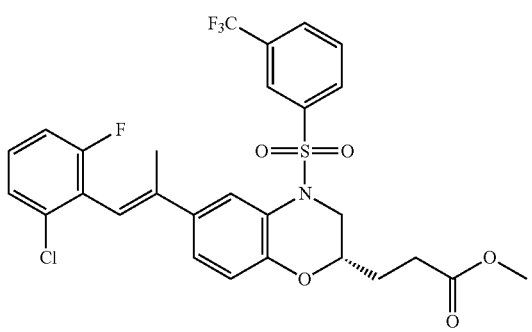 [SMILES: COC(=O)CC[C@H]1CN(S(=O)(=O)c2cccc(C(F)(F)F)c2)c2cc(/C(C)=C/c3c(F)cccc3Cl)ccc2O1]

A mixture of (S)-methyl 3-(6-bromo-4-((3-(trifluoromethyl)phenyl)sulfonyl)-3,4-dihydro-2H-benzo[b][1,4]oxazin-2-yl)propanoate (200 mg, 0.39 mmol), tetrakis(triphenylphosphine)palladium(0) (45 mg, 0.04 mmol), sodium carbonate (124 mg, 1.17 mmol), (Z)-2-(1-(2-chloro-6-fluorophenyl)prop-1-en-2-yl)-4,4,5,5-tetramethyl-1,3,2-dioxaborolane (140 mg, 0.47 mmol), toluene (10 mL), ethanol (5 mL), and water (2 mL) was stirred for three hours at 90° C. The mixture was cooled, concentrated, and the residue was purified via MPLC eluting with a gradient of 5-20% ethyl acetate in petroleum ether to afford (S,E)-methyl 3-(6-(1-(2-chloro-6-fluorophenyl)prop-1-en-2-yl)-4-((3-(trifluoromethyl)phenyl)sulfonyl)-3,4-dihydro-2H-benzo[b][1,4]oxazin-2-yl)propanoate (210 mg, 89%) as a yellow oil. $^1$H-NMR (400 MHz, $CD_3OD$) δ 7.91-7.95 (m, 4H), 7.74 (m, 1H), 7.27-7.34 (m, 3H), 7.10 (m, 1H), 6.80 (m, 1H), 6.47 (s, 1H), 4.39 (m, 1H), 3.63 (s, 3H), 3.47 (m, 1H), 3.27 (m, 1H), 2.41-2.46 (m, 2H), 1.94 (s, 3H), 1.75-1.93 (m, 2H). (ES, m/z): $(M+H)^+$598.

Example 32—Synthesis of (S,E)-3-(6-(1-(2-Chloro-6-fluorophenyl)prop-1-en-2-yl)-4-((3-(trifluoromethyl)phenyl)sulfonyl)-3,4-dihydro-2H-benzo[b][1,4]oxazin-2-yl)propanoic acid

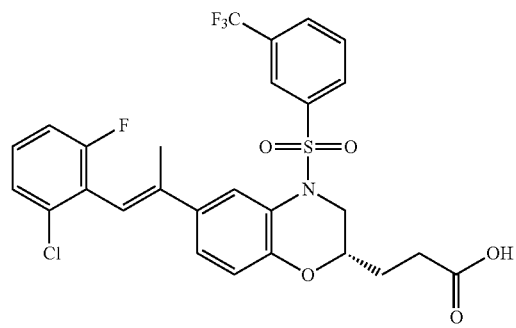 [SMILES: C/C(=C\c1c(F)cccc1Cl)c1ccc2c(c1)N(S(=O)(=O)c1cccc(C(F)(F)F)c1)C[C@H](CCC(=O)O)O2]

A mixture of (R,E)-methyl 3-(7-(1-(2-chloro-6-fluorophenyl)prop-1-en-2-yl)-1-((3-(trifluoromethyl)phenyl)sulfonyl)-1,2,3,4-tetrahydroquinolin-3-yl)propanoate (160 mg, 0.27 mmol), tetrahydrofuran (7.5 mL), water (2.5 mL) and lithium hydroxide monohydrate (34 mg, 0.81 mmol) was stirred for three hours at room temperature. The pH value of the solution was adjusted to 5 with 1M hydrogen chloride. The mixture was extracted twice with ethyl acetate. The combined organic layers were concentrated and the residue was purified by reverse phase Prep-HPLC eluting with a gradient of 62-82% acetonitrile in water with 0.05% trifluoroacetic acid to afford (S,E)-3-(6-(1-(2-chloro-6-fluorophenyl)prop-1-en-2-yl)-4-((3-(trifluoromethyl)phenyl)sulfonyl)-3,4-dihydro-2H-benzo[b][1,4]oxazin-2-yl)propanoic acid (66 mg, 42%) as a white solid. $^1$H-NMR (400 MHz, CD$_3$OD) δ 7.89-7.96 (m, 4H), 7.71-7.77 (m, 1H), 7.27-7.34 (m, 3H), 7.07-7.13 (m, 1H), 6.82 (d, J=8.4 Hz, 1H), 6.47 (s, 1H), 4.38-4.44 (m, 1H), 3.46-3.48 (m, 1H), 3.22-3.31 (m, 1H), 2.37-2.43 (m, 2H), 1.94 (s, 3H), 1.76-1.93 (m, 2H). (ES, m/z): (M+H)$^+$584.

Example 33—Synthesis of (S,E)-Methyl 3-(6-(2-(2-chloro-6-fluorophenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoate

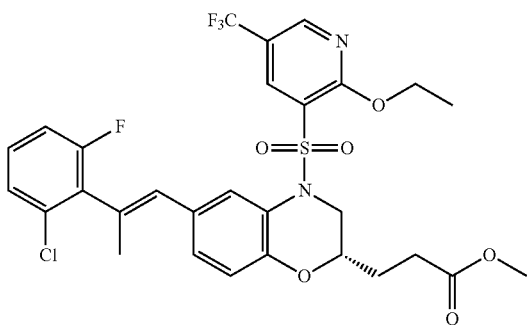 [SMILES: CCOc1ncc(C(F)(F)F)cc1S(=O)(=O)N1C[C@H](CCC(=O)OC)Oc2ccc(/C=C(\C)c3c(F)cccc3Cl)cc21]

Part I—Synthesis of 3-Bromo-2-ethoxy-5-(trifluoromethyl)pyridine

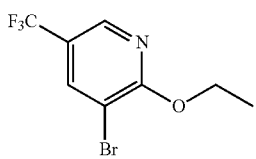

To a solution of 3-bromo-2-chloro-5-(trifluoromethyl)pyridine (4 g, 15.44 mmol) in ethanol (40 mL) was added a 0.71 M solution of sodium ethoxide in ethanol (43.5 mL, 30.8 mmol) and the mixture was stirred for two hours at room temperature. The mixture was diluted with water, and mixture was extracted three times with dichloromethane. The combined organic layers were concentrated to afford 3-bromo-2-ethoxy-5-(trifluoromethyl)pyridine (3.5 g, 84%) as a yellow oil.

Part II—Synthesis of 3-(Benzylthio)-2-ethoxy-5-(trifluoromethyl)pyridine

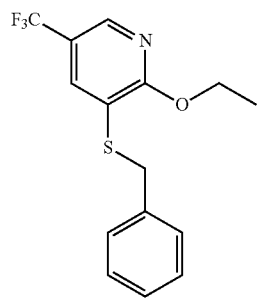 [SMILES: CCOc1ncc(C(F)(F)F)cc1SCc1ccccc1]

A mixture of 3-bromo-2-ethoxy-5-(trifluoromethyl)pyridine (5.6 g, 21.62 mmol), phenylmethanethiol (4 g, 32.26 mmol), N,N-diisopropylethylamine (5.58 g, 43.18 mmol), tris(dibenzylideneacetone)dipalladium(0) (1.98 g, 2.16 mmol), 4,5-bis(diphenylphosphino)-9,9-dimethylxanthene (1.25 g, 2.16 mmol), and toluene (60 mL) was stirred overnight at 110° C. The mixture was filtered; the filtrate was concentrated and the residue was purified via MPLC eluting with a gradient of 0% to 2.5% ethyl acetate in petroleum ether to afford 3-(benzylthio)-2-ethoxy-5-(trifluoromethyl)pyridine (4.2 g, 62%) as a white solid.

Part III—Synthesis of 2-Ethoxy-5-(trifluoromethyl)pyridine-3-sulfonyl chloride

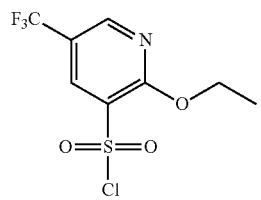 [SMILES: CCOc1ncc(C(F)(F)F)cc1S(=O)(=O)Cl]

A mixture of 3-(benzylthio)-2-ethoxy-5-(trifluoromethyl)pyridine (600 mg, 1.91 mmol), N-chlorosuccinimide (1.02 g, 7.64 mmol), acetic acid (4 mL), and water (1 mL) was stirred for one hour at room temperature and concentrated. The residue was purified via MPLC eluting with (1:6) ethyl acetate: petroleum ether to afford 2-ethoxy-5-(trifluoromethyl)pyridine-3-sulfonyl chloride (450 mg, 81%) as a yellow solid.

Part IV—Synthesis of (S,E)-Methyl 3-(6-(2-(2-chloro-6-fluorophenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoate

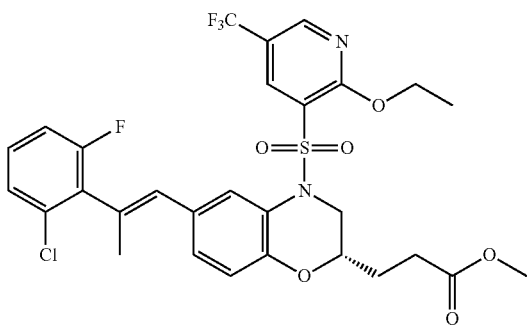

A solution of (S,E)-methyl 3-(6-(2-(2-chloro-6-fluorophenyl)prop-1-en-1-yl)-3,4-dihydro-2H-benzo[b][1,4]oxazin-2-yl)propanoate (250 mg, 0.64 mmol), pyridine (254 mg, 3.21 mmol), 4-dimethylaminopyridine (39.2 mg, 0.32 mmol), dichloromethane (5 mL), and 2-ethoxy-5-(trifluoromethyl)pyridine-3-sulfonyl chloride (371.5 mg, 1.28 mmol) was stirred overnight at room temperature. The mixture was diluted with water and was extracted three times with dichloromethane. The combined organic layers were dried (Na₂SO₄), concentrated and the residue was purified via MPLC eluting with 10% ethyl acetate in petroleum ether to afford (S,E)-methyl 3-(6-(2-(2-chloro-6-fluorophenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoate (200 mg, 49%) as a yellow oil. ¹H-NMR (400 MHz, CD₃OD) δ 8.74 (s, 1H), 8.57 (s, 1H), 7.59 (s, 1H), 7.30 (m, 2H), 7.12 (m, 1H), 7.05 (d, 1H), 6.91 (d, 1H), 6.29 (s, 1H), 4.47 (m, 2H), 4.26 (dd, 1H), 3.92 (m, 1H), 3.67 (s, 3H), 3.45 (dd, 1H), 2.56 (t, 2H), 2.10 (s, 3H), 1.96 (m, 2H), 1.32 (t, 3H). (ES, m/z): (M+H)⁺643.

Example 34—Synthesis of (S,E)-3-(6-(2-(2-Chloro-6-fluorophenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoic acid

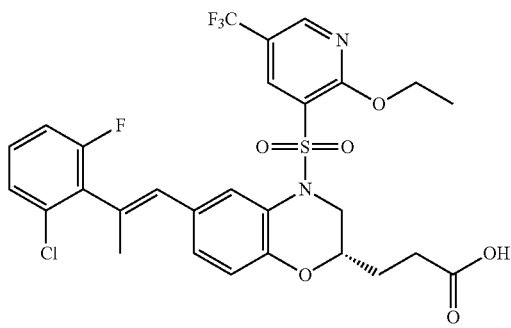 [SMILES: CCOc1ncc(C(F)(F)F)cc1S(=O)(=O)N1C[C@H](CCC(=O)O)Oc2ccc(/C=C(\C)c3c(F)cccc3Cl)cc21]

A mixture of (S,E)-methyl 3-(6-(2-(2-chloro-6-fluorophenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoate (150 mg, 0.23 mmol), tetrahydrofuran (3 mL), water (1 mL) and lithium hydroxide monohydrate (30 mg, 0.72 mmol) was stirred for two hours at room temperature. The pH value of the solution was adjusted to 5 with 1M hydrogen chloride. The mixture was extracted three times with ethyl acetate. The combined organic layers were concentrated and the residue was purified by reverse phase Prep-HPLC eluting with a gradient of 65-82% acetonitrile in water with 0.05% trifluoroacetic acid to afford (S,E)-3-(6-(2-(2-chloro-6-fluorophenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoic acid (26 mg, 18%) as a white solid. ¹H-NMR (400 MHz, CD₃OD) δ 8.74 (s, 1H), 8.57 (s, 1H), 7.57 (m, 1H), 7.30 (m, 2H), 7.12 (m, 1H), 7.05 (d, 1H), 6.94 (d, 1H), 6.30 (s, 1H), 4.48 (m, 2H), 4.28 (dd, 1H), 3.95 (m, 1H), 3.44 (dd, 1H), 2.52 (t, 2H), 2.11 (s, 3H), 1.96 (m, 2H), 1.34 (t, 3H). (ES, m/z): (M+H)⁺629.

Example 35—Synthesis of Methyl (S,E)-3-(6-(2-(2-chlorophenyl)but-1-en-1-yl)-4-((3-(trifluoromethyl)phenyl)sulfonyl)-3,4-dihydro-2H-benzo[b][1,4]oxazin-2-yl)propanoate

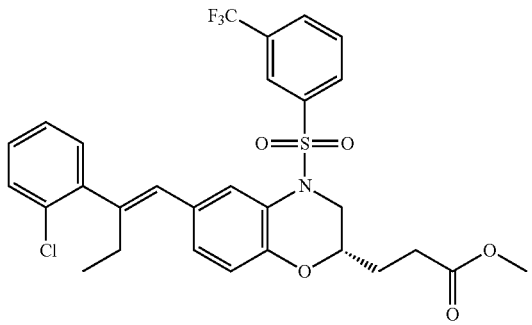

Part I—Synthesis of (Z)-2-(2-Bromo-2-(2-chlorophenyl)vinyl)-4,4,5,5-tetramethyl-1,3,2-dioxaborolane

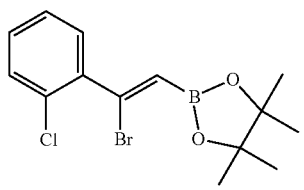 [SMILES: CC1(C)OB(/C=C(\Br)c2ccccc2Cl)OC1(C)C]

Tribromoborane (0.4 mL, 4.39 mmol) was added to a stirred solution of dichloromethane (6 mL) and 1-chloro-2- ethynylbenzene (500 mg, 3.66 mmol) at −78° C. After three hours, a solution of pinacol (519 mg, 4.39 mmol) in dichloromethane (2 mL) was added dropwise with stirring followed by N,N-diisopropylethyl amine (1.18 g, 9.15 mmol). The resulting solution was allowed to warm to room temperature and stirred for an additional two hours. The mixture was partitioned between dichloromethane and brine. The organic layer was dried (Na$_2$SO$_4$) and concentrated. The residue was purified via MPLC eluting with 1% ethyl acetate in petroleum ether to afford (Z)-2-(2-bromo-2-(2-chlorophenyl)vinyl)-4,4,5,5-tetramethyl-1,3,2-dioxaborolane (450 mg, 36%) as a yellow oil.

Part II—Synthesis of (E)-2-(2-(2-Chlorophenyl)but-1-en-1-yl)-4,4,5,5-tetramethyl-1,3,2-dioxaborolane

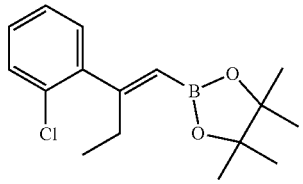 [SMILES: CC/C(=C\B1OC(C)(C)C(C)(C)O1)c1ccccc1Cl]

To a stirred solution of (Z)-2-(2-bromo-2-(2-chlorophenyl)vinyl)-4,4,5,5-tetramethyl-1,3,2-dioxaborolane (450 mg, 1.31 mmol) and bis(tri-tert-butylphosphine)-palladium (0) (47 mg, 0.06 mmol) in tetrahydrofuran (10 mL) at −78° C. was added a 1M solution of diethylzinc in THF (0.74 mL, 0.74 mmol). The mixture was stirred for 30 minutes at −78° C. and then warmed to room temperature and stirred for two additional hours and then 1M hydrogen chloride (2 mL) was added. The mixture was extracted three times with ethyl acetate. The combined organic layers were washed with brine, dried (Na$_2$SO$_4$), and concentrated. The residue was purified via MPLC, eluting with 1% ethyl acetate in petroleum ether to afford (E)-2-(2-(2-chlorophenyl)but-1-en-1-yl)-4,4,5,5-tetramethyl-1,3,2-dioxaborolane (180 mg, 47%) as a yellow oil.

Part III—Synthesis of Methyl (S,E)-3-(6-(2-(2-chlorophenyl)but-1-en-1-yl)-4-((3-(trifluoromethyl)phenyl)sulfonyl)-3,4-dihydro-2H-benzo[b][1,4]oxazin-2-yl)propanoate A stirred mixture of (E)-2-(2-(2-chlorophenyl)but-1-en-1-yl)-4,4,5,5-tetramethyl-1,3,2-dioxaborolane (180 mg, 0.62 mmol), (S)-methyl 3-(6-bromo-4-((3-(trifluoromethyl)phenyl)sulfonyl)-3,4-dihydro-2H-benzo[b][1,4]oxazin-2-yl)propanoate (200 mg, 0.39 mmol), tetrakis(triphenylphosphine)palladium(0) (23 mg, 0.02 mmol), sodium carbonate (127 mg, 1.20 mmol), toluene (10 mL), methanol (2 mL), and water (2 mL) was stirred for three hours at 80° C. The mixture was concentrated and the residue was purified by MPLC eluting with a gradient of 40-50% ethyl acetate in hexanes to afford methyl (S,E)-3-(6-(2-(2-chlorophenyl)but-1-en-1-yl)-4-((3-(trifluoromethyl)phenyl)sulfonyl)-3,4-dihydro-2H-benzo[b][1,4]oxazin-2-yl)propanoate (170 mg, 73%). $^1$H-NMR (400 MHz, CD$_3$OD) δ 7.99 (m, 2H), 7.93 (s, 1H), 7.86-7.80 (m, 2H), 7.44 (dt, J=7.2 Hz, 1.2 Hz, 1H), 7.34-7.30 (m, 3H), 7.08 (dd, J=8.4 Hz, 2.0 Hz, 1H), 6.84 (d, J=8.4 Hz, 1H), 6.32 (s, 1H), 4.43 (dd, J=14.4 Hz, 2.4 Hz, 1H), 3.67 (s, 3H), 3.34-3.33 (m, 1H), 3.27 (dd, J=14.4 Hz, 2.4 Hz, 1H), 2.76-2.72 (m, 2H), 2.49-2.45 (m, 2H), 1.81 (m, 2H), 1.0 (t, J=7.6 Hz, 3H). (ES, m/z): (M+H)$^+$616.

Example 36—Preparation of Additional Alkenes From Aryl Alkynes with Tribromoborane Compounds in Table 9 were prepared based on experimental procedures described in Examples 29, 34, and 35 and the detailed description.

TABLE 9

| No. | Structure | Name | Observed m/z |
|---|---|---|---|
| 36A | 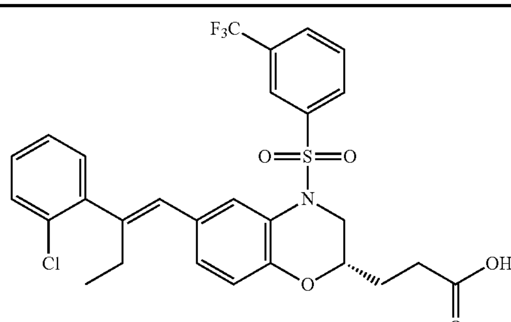 | (S,E)-3-(6-(2-(2-chlorophenyl)but-1-en-1-yl)-4-((3-(trifluoromethyl)-phenyl)sulfonyl)-3,4-dihydro-2H-benzo[b][1,4]oxazin-2-yl)propanoic acid | 580 (M + H)$^+$ |

TABLE 9-continued

| No. | Structure | Name | Observed m/z |
|---|---|---|---|
| 36B | 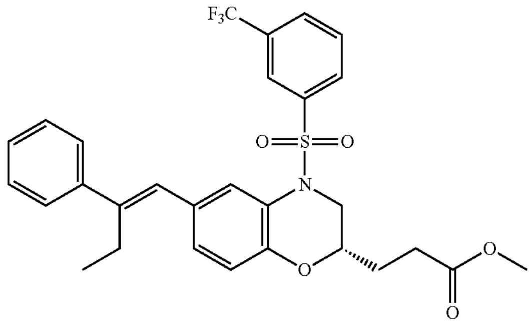 [SMILES: CC/C(=C\c1ccc2c(c1)N(S(=O)(=O)c1cccc(C(F)(F)F)c1)C[C@H](CCC(=O)OC)O2)c1ccccc1] | methyl (S,E)-3-(6-(2-phenylbut-1-en-1-yl)-4-((3-(trifluoromethyl)phenyl)sulfonyl)-3,4-dihydro-2H-benzo[b][1,4]oxazin-2-yl)propanoate | 560 (M + H)+ |
| 36C | 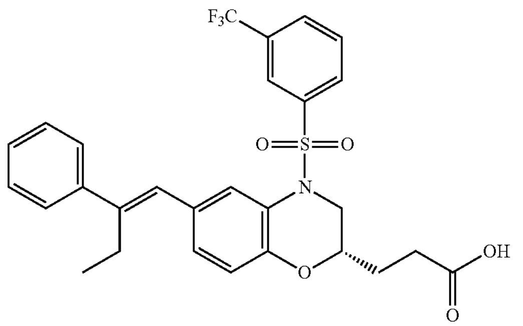 [SMILES: CC/C(=C\c1ccc2c(c1)N(S(=O)(=O)c1cccc(C(F)(F)F)c1)C[C@H](CCC(=O)O)O2)c1ccccc1] | (S,E)-3-(6-(2-phenylbut-1-en-1-yl)-4-((3-(trifluoromethyl)phenyl)sulfonyl)-3,4-dihydro-2H-benzo[b][1,4]oxazin-2-yl)propanoic acid | 546 (M + H)+ |

Example 37—Synthesis of (S,E)-3-(6-((3,4-Dihydronaphthalen-1(2H)-ylidene)methyl)-4-((3-(trifluoromethyl)phenyl)sulfonyl)-3,4-dihydro-2H-benzo[b][1,4]oxazin-2-yl)propanoic acid

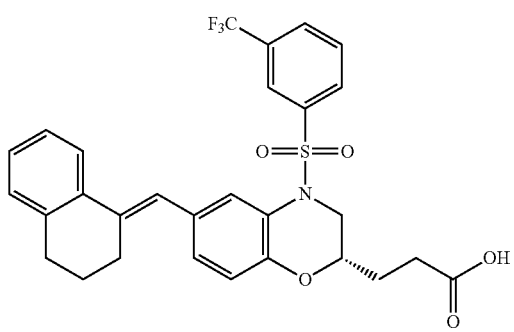

Part I—Synthesis of (E)-1-(Bromomethylene)-1,2,3,4-tetrahydronaphthalene

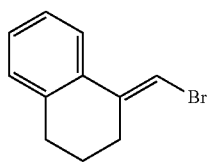 [SMILES: Br/C=C1\CCCc2ccccc21]

A solution of 1,2,3,4-tetrahydronaphthalen-1-one (2 g, 13.68 mmol) in dichloromethane (15 mL) was added to a solution of titanium tetrachloride (0.9 g, 10.9 mmol) and magnesium turnings (3.2 g, 137 mmol) in dichloromethane (50 mL) at −78° C. A solution of bromoform (3.9 mL, 44.8 mmol) in ethylene glycol dimethyl ether (20 mL) at −78° C. was then added and the reaction mixture was slowly warmed to 0° C. during a period of two hours. Saturated potassium carbonate was added and the mixture was filtered. The filtrate was extracted twice with dichloromethane and the combined organic layers were dried (Na$_2$SO$_4$) and concentrated. The residue was purified via MPLC eluting with petroleum ether to afford (E)-1-(bromomethylene)-1,2,3,4-tetrahydronaphthalene (600 mg, 20%) as a colorless oil.

Part II—Synthesis of (E)-2-((3,4-Dihydronaphthalen-1(2H)-ylidene)methyl)-4,4,5,5-tetramethyl-1,3,2-dioxaborolane

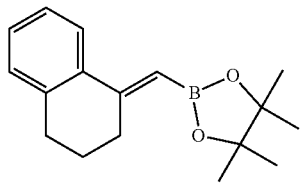 [SMILES: CC1(C)OB(/C=C2\CCCc3ccccc32)OC1(C)C]

A mixture of (E)-1-(bromomethylene)-1,2,3,4-tetrahydronaphthalene (500 mg, 2.24 mmol), 4,4,5,5-tetramethyl-2-(tetramethyl-1,3,2-dioxaborolan-2-yl)-1,3,2-dioxaborolane (858 mg, 3.38 mmol), potassium acetate (662 mg, 6.75 mmol), tetrakis(triphenylphosphine)-palladium(0) (260 mg, 0.22 mmol), toluene (20 mL), ethanol (10 mL) and water (5 mL) was stirred for two hours at 90° C. The resulting mixture was cooled and concentrated. The residue was purified via MPLC eluting with 1% ethyl acetate in petroleum ether to afford (E)-2-((3,4-dihydronaphthalen-1 (2H)-ylidene)methyl)-4,4,5,5-tetramethyl-1,3,2-dioxaborolane (200 mg, 33%) as a colorless oil.

Part III—Synthesis of Methyl (S,E)-3-(6-((3,4-dihydronaphthalen-1(2H)-ylidene)methyl)-4-((3-(trifluoromethyl)phenyl)sulfonyl)-3,4-dihydro-2H-benzo[b][1,4]oxazin-2-yl)propanoate

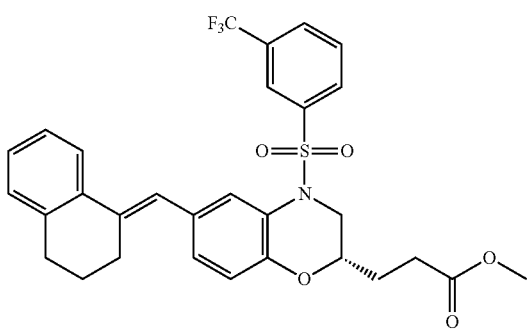 [SMILES: COC(=O)CC[C@H]1CN(S(=O)(=O)c2cccc(C(F)(F)F)c2)c2cc(/C=C3\CCOc4ccccc43)ccc2O1]

A mixture of (S)-methyl 3-(6-bromo-4-((3-(trifluoromethyl)phenyl)sulfonyl)-3,4-dihydro-2H-benzo[b][1,4]oxazin-2-yl)propanoate (200 mg, 0.39 mmol), (E)-2-((3,4-dihydronaphthalen-1 (2H)-ylidene)methyl)-4,4,5,5-tetramethyl-1,3,2-dioxaborolane (117 mg, 0.43 mmol), potassium acetate (116 mg, 1.18 mmol), tetrakis(triphenylphosphine)palladium(0) (46 mg, 0.04 mmol), toluene (4 mL), ethanol (2 mL), and water (1 mL) was stirred for two hours at 90° C. The mixture was concentrated and the residue was purified via MPLC eluting with 20% ethyl acetate in petroleum ether to afford methyl (S,E)-3-(6-((3,4-dihydronaphthalen-1 (2H)-ylidene)methyl)-4-((3-(trifluoromethyl)phenyl)sulfonyl)-3,4-dihydro-2H-benzo[b][1,4]oxazin-2-yl)propanoate (100 mg, 44%) as a colorless oil.

Part IV—Synthesis of (S,E)-3-(6-((3,4-Dihydronaphthalen-1(2H)-ylidene)methyl)-4-((3-(trifluoromethyl)phenyl)sulfonyl)-3,4-dihydro-2H-benzo[b][1,4]oxazin-2-yl)propanoic acid

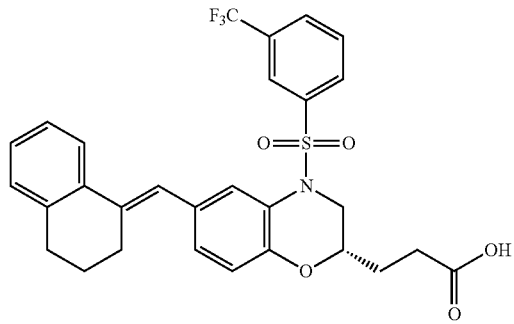

A mixture of methyl (S,E)-3-(6-((3,4-dihydronaphthalen-1 (2H)-ylidene)methyl)-4-((3-(trifluoromethyl)phenyl)sulfonyl)-3,4-dihydro-2H-benzo[b][1,4]oxazin-2-yl)propanoate (120 mg, 0.21 mmol), methanol (3 mL), water (1 mL), and lithium hydroxide (101 mg, 4.22 mmol) was stirred for two hours at room temperature. The pH value of the solution was adjusted to 5 with 1M HCl. The mixture was extracted twice with ethyl acetate. The combined organic layers were dried ($Na_2SO_4$) and concentrated. The residue was purified by Prep-HPLC eluting with a gradient of 65-78% acetonitrile in water with 0.05% trifluoroacetic acid to afford (S,E)-3-(6-((3,4-dihydronaphthalen-1(2H)-ylidene)methyl)-4-((3-(trifluoromethyl)phenyl)sulfonyl)-3,4-dihydro-2H-benzo[b][1,4]oxazin-2-yl)propanoic acid (10.4 mg, 9%) as a colorless solid. $^1$H-NMR (300 MHz, $CD_3OD$) δ 7.96 (s, 1H), 7.87-7.79 (m, 3H), 7.70-7.64 (m, 1H), 7.62-7.60 (m, 1H), 7.26-7.19 (m, 1H), 7.17-7.08 (m, 2H), 6.96 (s, 1H), 6.82-6.79 (d, J=8.4 Hz, 1H), 4.36-4.31 (m, 1H), 3.56-3.53 (m, 1H), 3.29-3.20 (m, 1H), 2.86-2.71 (m, 4H), 2.57-2.46 (m, 2H), 1.98-1.77 (m, 4H). (ES, m/z): $(M+H)^+$558.

Example 38—Preparation of Additional Alkenes

Compounds in Table 10 were prepared based on experimental procedures described in Examples 29 and 37 and the detailed description.

TABLE 10

| No. | Structure | Name | Observed m/z |
|---|---|---|---|
| 38A | 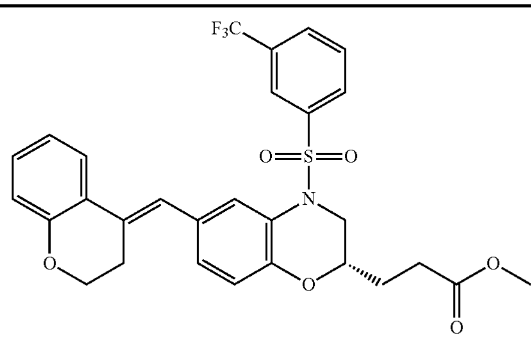 | methyl (S,E)-3-(6-(chroman-4-ylidenemethyl)-4-((3-(trifluoromethyl)phenyl)sulfonyl)-3,4-dihydro-2H-benzo[b][1,4]oxazin-2-yl)propanoate | 574 (M + H)$^+$ |

TABLE 10-continued

| No. | Structure | Name | Observed m/z |
|---|---|---|---|
| 38B | 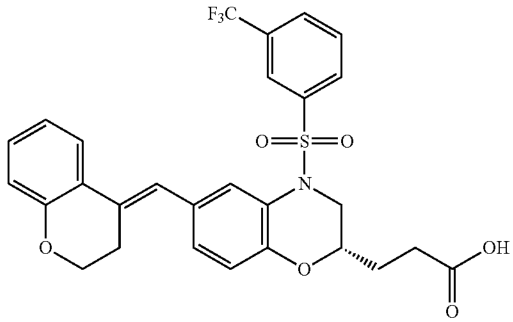 [SMILES: O=C(O)CC[C@H]1CN(S(=O)(=O)c2cccc(C(F)(F)F)c2)c2cc(/C=C3\CCOc4ccccc43)ccc2O1] | (S,E)-3-(6-(chroman-4-ylidene-methyl)-4-((3-(trifluoromethyl)phenyl)sulfonyl)-3,4-dihydro-2H-benzo[b][1,4]oxazin-2-yl)propanoic acid | 560 (M + H)+ |
| 38C | 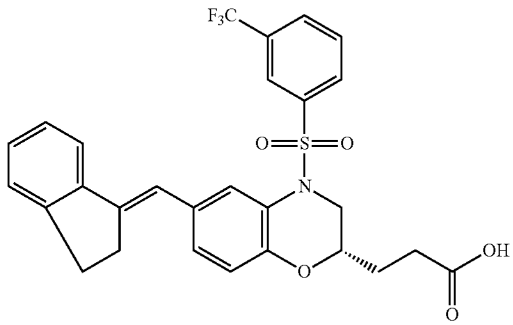 [SMILES: O=C(O)CC[C@H]1CN(S(=O)(=O)c2cccc(C(F)(F)F)c2)c2cc(/C=C3\CCc4ccccc43)ccc2O1] | (S,E)-3-(6-((2,3-dihydro-1H-inden-1-ylidene)methyl)-4-((3-(trifluoromethyl)phenyl)sulfonyl)-3,4-dihydro-2H-benzo[b][1,4]-oxazin-2-yl)propanoic acid | 544 (M + H)+ |

Example 39—Synthesis of Methyl (S,E)-3-(6-(2-chloro-6-fluorostyryl)-4-((3-(difluoromethoxy)phenyl)sulfonyl)-3,4-dihydro-2H-benzo[b][1,4]oxazin-2-yl)propanoate

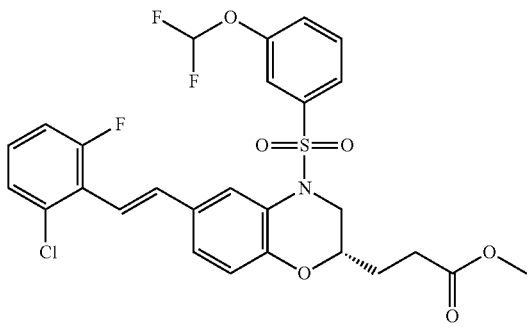 [SMILES: COC(=O)CC[C@H]1CN(S(=O)(=O)c2cccc(OC(F)F)c2)c2cc(/C=C/c3c(F)cccc3Cl)ccc2O1]

Part I—Synthesis of Methyl (S,E)-3-(6-(2-chloro-6-fluorostyryl)-3,4-dihydro-2H-benzo[b][1,4]oxazin-2-yl)propanoate

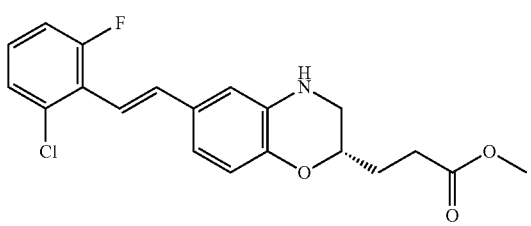 [SMILES: COC(=O)CC[C@H]1CNc2cc(/C=C/c3c(F)cccc3Cl)ccc2O1]

A mixture of methyl (S)-3-(6-bromo-3,4-dihydro-2H-benzo[b][1,4]oxazin-2-yl)propanoate (620 mg, 2.07 mmol), (E)-2-(2-chloro-6-fluorostyryl)-4,4,5,5-tetramethyl-1,3,2-dioxaborolane (877.3 mg, 3.27 mmol), ethanol (2.4 mL), water (8.5 mL), toluene (16.9 mL), sodium carbonate (1.80 g, 16.9 mmol), and tetrakis(triphenylphosphine)palladium (0) (288 mg, 0.25 mmol) was stirred overnight at 95° C. The mixture was diluted with water and extracted three times with dichloromethane. The combined organic layers were dried (Na₂SO₄), concentrated, and the residue was purified by MPLC eluting with a gradient of 10-33% ethyl acetate in petroleum ether to afford methyl (S,E)-3-(6-(2-chloro-6-fluorostyryl)-3,4-dihydro-2H-benzo[b][1,4]oxazin-2-yl)propanoate (720 mg, 93%) as a yellow oil.

Part II—Synthesis of Methyl (S,E)-3-(6-(2-chloro-6-fluorostyryl)-4-((3-(difluoromethoxy)phenyl)sulfonyl)-3,4-dihydro-2H-benzo[b][1,4]oxazin-2-yl)propanoate

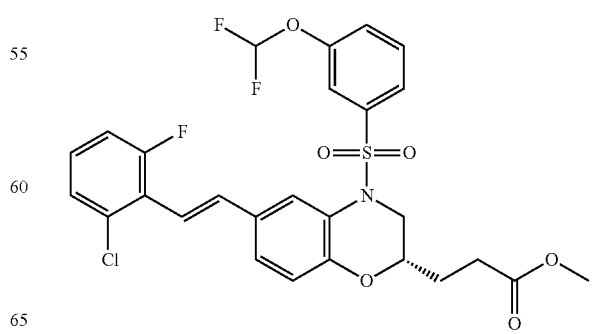

A solution of (S,E)-3-(6-(2-chloro-6-fluorostyryl)-3,4-dihydro-2H-benzo[b][1,4]oxazin-2-yl)propanoate (165 mg, 0.44 mmol), pyridine (0.18 mL, 2.2 mmol), 4-dimethylaminopyridine (26.8 mg, 0.22 mmol), 3-(difluoromethoxy)benzene-1-sulfonyl chloride (128 mg, 0.53 mmol) in dichloromethane (2.2 mL) was stirred overnight at room temperature. Brine was added, and the mixture was extracted three times with dichloromethane. The combined organic layers were dried (Na$_2$SO$_4$) and concentrated. The residue was purified by MPLC eluting with a gradient of 20-50% ethyl acetate in petroleum ether. The major UV component was concentrated and the residue was further purified by reverse phase HPLC eluting with a gradient of 63-83% acetonitrile in water with 0.05% trifluoroacetic acid to afford methyl (S,E)-3-(6-(2-chloro-6-fluorostyryl)-4-((3-(difluoromethoxy)phenyl)sulfonyl)-3,4-dihydro-2H-benzo[b][1,4]oxazin-2-yl)propanoate (28.3 mg, 11%) as a colorless oil. $^1$H-NMR (400 MHz, CDCl$_3$) δ 1.76-1.92 (m, 2H), 2.47 (dt, J=1.8 Hz, 7.2 Hz, 2H), 3.19 (dd, J=9.9 Hz, 14.4 Hz, 1H), 3.44-3.51 (m, 1H), 3.69 (s, 3H), 4.31 (dd, J=2.1 Hz, 14.4 Hz, 1H), 6.56 (t, J=72.9 Hz, 1H), 6.83 (d, J=8.7 Hz, 1H), 7.02-7.27 (m, 4H), 7.32-7.37 (m, 3H), 7.45-7.51 (m, 3H), 7.98 (d, J=1.8 Hz, 1H). (ES, m/z): (M+H)$^+$582.

Example 40—Synthesis of (S,E)-3-(6-(2-Chloro-6-fluorostyryl)-4-((3-(difluoromethoxy)phenyl)sulfonyl)-3,4-dihydro-2H-benzo[b][1,4]oxazin-2-yl)propanoic acid

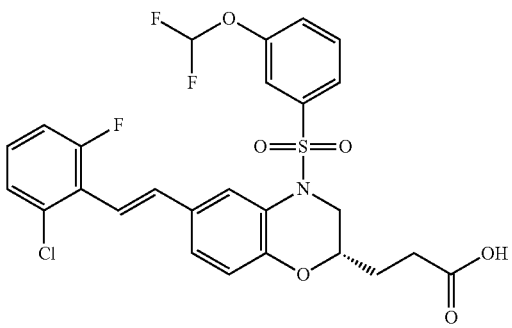 [SMILES: O=C(O)CC[C@H]1CN(S(=O)(=O)c2cccc(OC(F)F)c2)c2cc(/C=C/c3c(F)cccc3Cl)ccc2O1]

Based on the procedure in Example 34, (S,E)-3-(6-(2-chloro-6-fluorostyryl)-4-((3-(difluoromethoxy)phenyl)sulfonyl)-3,4-dihydro-2H-benzo[b][1,4]oxazin-2-yl)propanoic acid was prepared. $^1$H-NMR (300 MHz, CDCl$_3$) δ 1.78-1.95 (m, 2H), 2.49-2.58 (m, 2H), 3.21 (d, J=9.9 Hz, 14.4 Hz, 1H), 3.47-3.53 (m, 1H), 4.32 (dd, J=2.4 Hz, 14.4 Hz, 1H), 6.50 (t, J=72.6 Hz, 1H), 6.84 (d, J=8.4 Hz, 1H), 7.02-7.25 (m, 4H), 7.27-7.38 (m, 3H), 7.45-7.53 (m, 3H), 7.98 (d, J=1.8 Hz, 1H). (ES, m/z): (M+H)$^+$568.

Example 41—Synthesis of (S,E)-Methyl 3-(6-(2-(2-chloro-6-fluorophenyl)prop-1-en-1-yl)-7-fluoro-4-((3-(trifluoromethyl)phenyl)sulfonyl)-3,4-dihydro-2H-benzo[b][1,4]oxazin-2-yl)propanoate

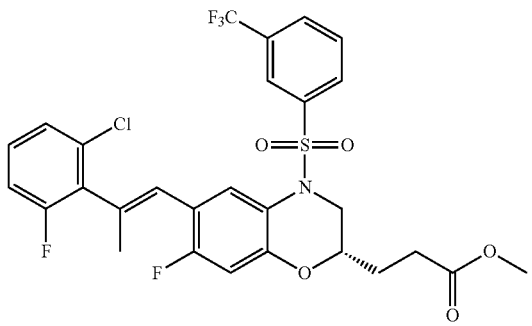 [SMILES: COC(=O)CC[C@H]1CN(S(=O)(=O)c2cccc(C(F)(F)F)c2)c2cc(/C=C(\C)c3c(F)cccc3Cl)c(F)cc2O1]

Part I—Synthesis of 4-Bromo-5-fluoro-2-nitrophenol

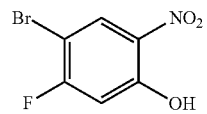

To a stirred mixture of 4-bromo-3-fluorophenol (10.23 g, 53.56 mmol), dichloromethane (108 mL), and sulfuric acid (6 mL, 107 mmol) at 0° C. was added 65% nitric acid (3.8 mL, 53.6 mmol). After one hour at 0° C., the mixture was diluted with water. The resulting mixture was extracted three times with dichloromethane. The combined organic layers were concentrated, and the resulting residue was purified by MPLC eluting with a gradient of 10:1 to 2:1 hexane:ethyl acetate to afford 4-bromo-5-fluoro-2-nitrophenol (9.47 g, 75%) as a yellow solid.

Part II—Synthesis of (S)-Dimethyl 2-(4-bromo-5-fluoro-2-nitrophenoxy)pentanedioate

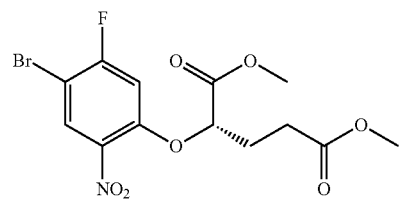

To a stirred solution of 1,5-dimethyl (2R)-2-hydroxypentanedioate (5.52 g, 31.33 mmol), 4-bromo-5-fluoro-2-nitrophenol (8.88 g, 37.63 mmol), dichloromethane (160 mL), and triphenyl phosphine (12.63 g, 48.15 mmol) at 0° C. was added dropwise diisopropyl azodicarboxylate (7.3 mL, 37.6 mmol). The resulting mixture was stirred overnight at room temperature and then diluted with saturated sodium bicarbonate (500 mL). The resulting mixture was extracted three times with dichloromethane. The organic layers were combined and concentrated. The resulting residue was purified by MPLC eluting with a gradient of 10-66% ethyl acetate in petroleum ether to afford (S)-dimethyl 2-(4-bromo-5-fluoro-2-nitrophenoxy)pentanedioate (18.86 g) as an oil.

Part III—Synthesis of (S)-Methyl 3-(6-bromo-7-fluoro-3-oxo-3,4-dihydro-2H-benzo[b][1,4]oxazin-2-yl)propanoate

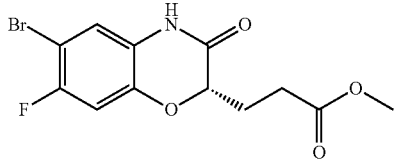 [SMILES: COC(=O)CC[C@@H]1Oc2cc(F)c(Br)cc2NC1=O]

A mixture of (S)-dimethyl 2-(4-bromo-5-fluoro-2-nitrophenoxy)pentanedioate (12 g, 30.45 mmol), acetic acid (100 mL), and iron powder (25.07 g, 0.448 mol) was stirred for one hour at 100° C. The mixture was filtered, and the filtrate was concentrated. The resulting residue was diluted with saturated sodium bicarbonate, and extracted three times with dichloromethane. The combined organic layers were concentrated and the resulting residue was purified by MPLC eluting with a gradient of 20-50% ethyl acetate in petroleum ether to afford (S)-methyl 3-(6-bromo-7-fluoro-3-oxo-3,4-dihydro-2H-benzo[b][1,4]oxazin-2-yl)propanoate (14.74 g) as a yellow solid.

Part IV—Synthesis of (S)-Methyl 3-(6-bromo-7-fluoro-3,4-dihydro-2H-benzo[b][1,4]-oxazin-2-yl)propanoate

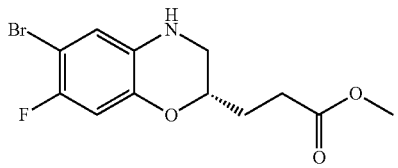 [SMILES: COC(=O)CC[C@H]1CNc2cc(Br)c(F)cc2O1]

A 10M solution of borane dimethyl sulfide in THF (12.5 mL, 125 mmol) was added dropwise to a solution of (S)-methyl 3-(6-bromo-7-fluoro-3-oxo-3,4-dihydro-2H-benzo[b][1,4]oxazin-2-yl)propanoate (10.1 g, 30.4 mmol) in tetrahydrofuran (100 mL). The solution was stirred overnight at room temperature, and then quenched by the slow addition of methanol (100 mL). The resulting mixture was concentrated, diluted with saturated sodium bicarbonate, and extracted three times with ethyl acetate. The combined organic layers were concentrated, and the resulting residue was purified MPLC eluting with a gradient of 20-80% ethyl acetate in petroleum ether to afford (S)-methyl 3-(6-bromo-7-fluoro-3,4-dihydro-2H-benzo[b][1,4]-oxazin-2-yl)propanoate (9.09 g, 94%) as a pink solid.

Part V—Synthesis of (S,E)-Methyl 3-(6-(2-(2-chloro-6-fluorophenyl)prop-1-en-1-yl)-7-fluoro-3,4-dihydro-2H-benzo[b][1,4]oxazin-2-yl)propanoate

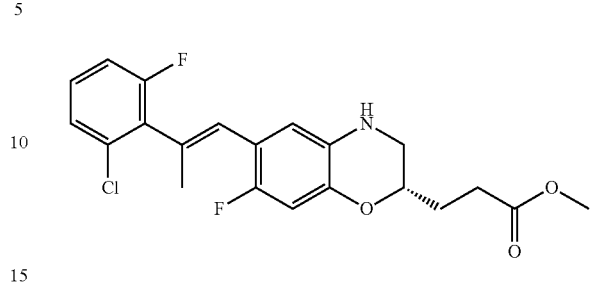

A mixture of (S)-methyl 3-(6-bromo-7-fluoro-3,4-dihydro-2H-benzo[b][1,4]-oxazin-2-yl)propanoate (528 mg, 1.66 mmol), (E)-2-(2-(2-chloro-6-fluorophenyl)prop-1-en-1-yl)-4,4,5,5-tetramethyl-1,3,2-dioxaborolane (740 mg, 2.50 mmol), ethanol (1.9 mL), water (6.8 mL) and toluene (13.6 mL) was purged with nitrogen and maintained under an atmosphere of nitrogen. Sodium carbonate (1.44 g, 13.59 mmol) and tetrakis(triphenylphosphine)palladium(0) (231.4 mg, 0.20 mmol) were added and the stirred mixture was heated overnight at 95° C., then cooled, and diluted with water. The resulting mixture was extracted three times with dichloromethane and the combined organic layers were concentrated. The resulting residue was purified by MPLC eluting with a gradient of 20-50% ethyl acetate in petroleum ether to afford (S,E)-methyl 3-(6-(2-(2-chloro-6-fluorophenyl)prop-1-en-1-yl)-7-fluoro-3,4-dihydro-2H-benzo[b][1,4]oxazin-2-yl)propanoate (1.16 g) as an oil.

Part VI—Synthesis of (S,E)-Methyl 3-(6-(2-(2-chloro-6-fluorophenyl)prop-1-en-1-yl)-7-fluoro-4-((3-(trifluoromethyl)phenyl)sulfonyl)-3,4-dihydro-2H-benzo[b][1,4]oxazin-2-yl)propanoate

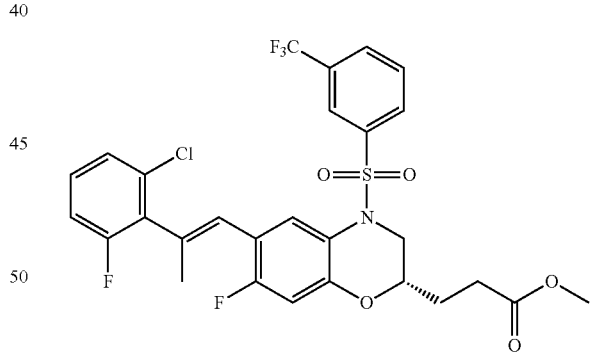

A mixture of (S,E)-methyl 3-(6-(2-(2-chloro-6-fluorophenyl)prop-1-en-1-yl)-7-fluoro-3,4-dihydro-2H-benzo[b][1,4]oxazin-2-yl)propanoate (163 mg, 0.40 mmol), dichloromethane (2 mL), pyridine (0.16 mL, 2 mmol), 4-dimethylaminopyridine (24.4 mg, 0.20 mmol), and 3-(trifluoromethyl)benzene-1-sulfonyl chloride (0.077 mL, 0.48 mmol) was stirred overnight at room temperature, and then diluted with brine. The resulting mixture was extracted three times with dichloromethane and the combined organic layers were concentrated. The resulting residue was purified by MPLC eluting with a gradient of 20-50% ethyl acetate in petroleum ether to afford (S,E)-methyl 3-(6-(2-(2-chloro-6-fluorophenyl)prop-1-en-1-yl)-7-fluoro-4-((3-(trifluoromethyl)-phenyl)sulfonyl)-3,4-dihydro-2H-benzo[b][1,4]oxazin-2-yl)propanoate (23.7 mg, 10%) as a colorless oil. ¹H-NMR (300 MHz, CD₃OD) δ 1.72-1.97 (m, 2H), 2.15 (s, 3H), 2.37-2.56 (m, 2H), 3.23-3.27 (m, 1H), 3.32-3.43 (m, 1H), 4.42 (dd, J=2.1 Hz, 14.7 Hz, 1H), 6.35 (s, 1H), 6.65 (d, J=10.8 Hz, 1H), 7.11-7.17 (m, 1H), 7.31-7.36 (m, 2H), 7.78-7.88 (m, 2H), 7.95-8.02 (m, 3H). (ES, m/z): (M+H)⁺ 616.

Example 42—Synthesis of (S,E)-3-(6-(2-(2-Chloro-6-fluorophenyl)prop-1-en-1-yl)-7-fluoro-4-((3-(trifluoromethyl)phenyl)sulfonyl)-3,4-dihydro-2H-benzo[b][1,4]oxazin-2-yl)propanoic acid

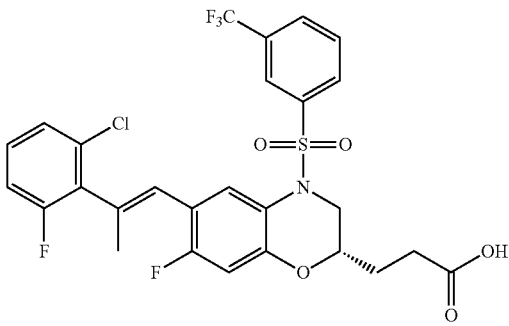 [SMILES: C/C(=C\c1cc2c(cc1F)O[C@@H](CCC(=O)O)CN2S(=O)(=O)c1cccc(C(F)(F)F)c1)c1c(F)cccc1Cl]

A mixture of (S,E)-methyl 3-(6-(2-(2-chloro-6-fluorophenyl)prop-1-en-1-yl)-7-fluoro-4-((3-(trifluoromethyl)-phenyl)sulfonyl)-3,4-dihydro-2H-benzo[b][1,4]oxazin-2-yl)propanoate (86 mg, 0.14 mmol), tetrahydrofuran (1.2 mL), water (0.3 mL), and lithium hydroxide monohydrate (17.6 mg, 0.42 mmol) was stirred overnight at room temperature. The pH value of the mixture was adjusted to 1 with 1M hydrogen chloride. The resulting mixture was extracted three times with dichloromethane and the combined organic layers were concentrated. The resulting residue was purified by Prep-HPLC eluting with a gradient of 65-85% acetonitrile with 0.05% trifluoroacetic acid to afford (S,E)-3-(6-(2-(2-chloro-6-fluorophenyl)prop-1-en-1-yl)-7-fluoro-4-((3-(trifluoromethyl)phenyl)sulfonyl)-3,4-dihydro-2H-benzo[b][1,4]oxazin-2-yl)propanoic acid (34.3 mg, 41%) as a white solid. ¹H-NMR (300 MHz, CDCl₃) δ 1.77-1.96 (m, 2H), 2.17 (s, 3H), 2.49-2.55 (m, 2H), 3.21 (dd, J=9.9 Hz, 14.4 Hz, 1H), 3.47-3.53 (m, 1H), 4.33 (dd, J=2.4 Hz, 14.4 Hz, 1H), 6.40 (s, 1H), 6.58 (d, J=10.5 Hz, 1H), 7.04 (dt, J=2.4 Hz, 6.9 Hz, 1H), 7.16-7.23 (m, 2H), 7.65 (t, J=7.8 Hz, 1H), 7.80-7.89 (m, 3H), 8.00 (s, 1H). (ES, m/z): (M+H)⁺602.

Example 43—Synthesis of (S,E)-Methyl 3-(6-(2-(2-chloro-6-fluorophenyl)prop-1-en-1-yl)-4-((3-(difluoromethoxy)phenyl)sulfonyl)-7-fluoro-3,4-dihydro-2H-benzo[b][1,4]oxazin-2-yl)propanoate

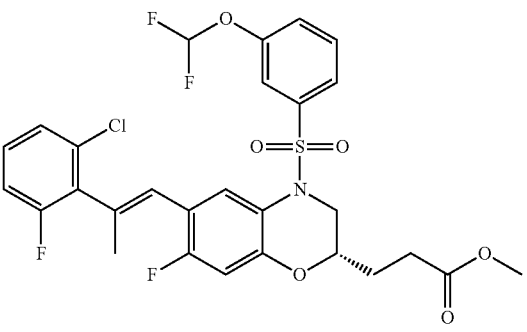 [SMILES: COC(=O)CC[C@H]1CN(S(=O)(=O)c2cccc(OC(F)F)c2)c2cc(/C=C(\C)c3c(F)cccc3Cl)c(F)cc2O1]

Based on the procedure in Example 41, (S,E)-methyl 3-(6-(2-(2-chloro-6-fluorophenyl)prop-1-en-1-yl)-4-((3-(difluoromethoxy)phenyl)sulfonyl)-7-fluoro-3,4-dihydro-2H-benzo[b][1,4]oxazin-2-yl)propanoate was prepared. ¹H-NMR (300 MHz, CDCl₃) δ 1.72-1.88 (m, 2H), 2.19 (s, 3H), 2.44 (dt, J=2.1 Hz, 7.2 Hz, 2H), 3.15 (dd, J=10.2 Hz, 14.7 Hz, 1H), 3.39-3.40 (m, 1H), 3.67 (s, 3H), 4.28 (dd, J=2.4 Hz, 14.4 Hz, 1H), 6.41 (s, 1H), 6.56 (d, J=10.5 Hz, 1H), 6.59 (t, J=72.6 Hz, 1H), 7.00-7.06 (m, 1H), 7.19-7.25 (m, 2H), 7.35 (d, J=7.5 Hz, 1H), 7.42-7.52 (m, 3H), 7.92 (d, J=7.8 Hz, 1H). (ES, m/z): (M+H)⁺614.

Example 44—Synthesis of (S,E)-3-(6-(2-(2-Chloro-6-fluorophenyl)prop-1-en-1-yl)-4-((3-(difluoromethoxy)phenyl)sulfonyl)-7-fluoro-3,4-dihydro-2H-benzo[b][1,4]oxazin-2-yl)propanoic acid

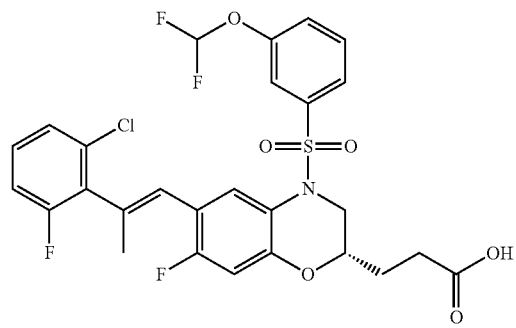 [SMILES: C/C(=C\c1cc2c(cc1F)O[C@@H](CCC(=O)O)CN2S(=O)(=O)c1cccc(OC(F)F)c1)c1c(F)cccc1Cl]

Based on the procedure in Example 42, (S,E)-3-(6-(2-(2-chloro-6-fluorophenyl)prop-1-en-1-yl)-4-((3-(difluoromethoxy)phenyl)sulfonyl)-7-fluoro-3,4-dihydro-2H-benzo[b][1,4]oxazin-2-yl)propanoic acid was prepared. ¹H-NMR (300 MHz, CDCl₃) δ 1.77-1.90 (m, 2H), 2.19 (s, 3H), 2.52 (dt, J=1.8 Hz, 7.2 Hz, 2H), 3.17 (dd, J=10.2 Hz, 14.4 Hz, 1H), 3.37-3.44 (m, 1H), 4.29 (dd, J=2.1 Hz, 14.4 Hz, 1H), 6.41 (s, 1H), 6.54 (t, J=72.6 Hz, 1H), 6.57 (d, J=10.5 Hz, 1H), 7.03 (dt, J=2.1 Hz, 6.9 Hz, 1H), 7.16-7.23 (m, 2H), 7.34-7.37 (m, 1H), 7.44-7.53 (m, 3H), 7.92 (d, J=7.8 Hz, 1H). (ES, m/z): (M+H)⁺600.

Example 45—Synthesis of (S,E)-Methyl 3-(7-chloro-6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoate

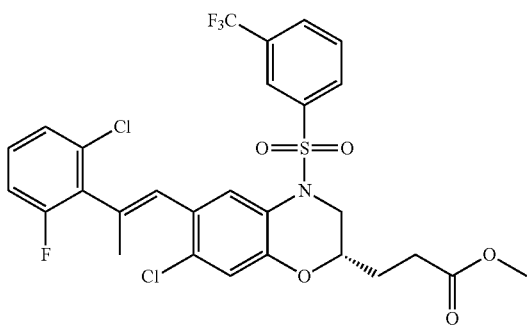 [SMILES: COC(=O)CC[C@H]1CN(S(=O)(=O)c2cccc(C(F)(F)F)c2)c2cc(/C=C(\C)c3c(F)cccc3Cl)c(Cl)cc2O1]

Part I—Synthesis of 4-Bromo-5-chloro-2-nitrophenol

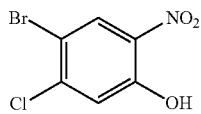

A solution of 65% nitric acid (3.6 mL, 52 mmol) in acetic acid (9.8 mL) was added dropwise to a stirred solution of 4-bromo-3-chlorophenol (10.13 g, 48.83 mmol) in acetic acid (16.3 mL) and the mixture was stirred for one hour at room temperature. Ice water was added and the mixture was extracted three times with dichloromethane. The combined organic layers were concentrated, and the resulting residue was purified by MPLC eluting with a gradient of 10-33% ethyl acetate in petroleum ether to afford 4-bromo-5-chloro-2-nitrophenol (10.58 g, 86%) as a red solid.

Part II—Synthesis of (S)-Dimethyl 2-(4-bromo-5-chloro-2-nitrophenoxy)pentanedioate

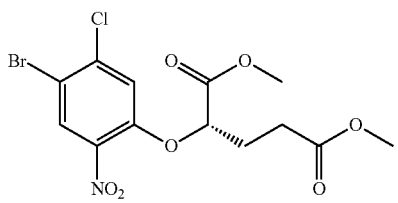 [SMILES: COC(=O)CC[C@H](Oc1cc(Cl)c(Br)cc1[N+](=O)[O-])C(=O)OC]

To a stirred solution of 1,5-dimethyl (2R)-2-hydroxypentanedioate (5.80 g, 32.9 mmol), 4-bromo-5-chloro-2-nitrophenol (9.97 g, 39.5 mmol), dichloromethane (160 mL), and triphenyl phosphine (12.9 g, 49.2 mmol) at 0° C. was added dropwise diisopropyl azodicarboxylate (7.4 mL, 39 mmol). The mixture was stirred overnight at room temperature and then diluted with saturated sodium bicarbonate (500 mL).

The mixture was extracted three times with dichloromethane. The organic layers were combined and concentrated. The resulting residue was purified by MPLC eluting with a gradient of 10-66% ethyl acetate in petroleum ether to afford (S)-dimethyl 2-(4-bromo-5-chloro-2-nitrophenoxy)pentanedioate (20.06 g) as a yellow solid.

Part III—Synthesis of (S)-Methyl 3-(6-bromo-7-chloro-3-oxo-3,4-dihydro-2H-benzo[b][1,4]oxazin-2-yl)propanoate

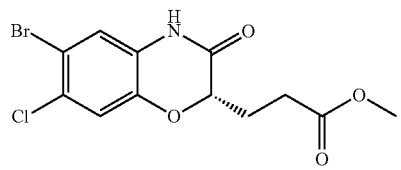 [SMILES: COC(=O)CC[C@@H]1Oc2cc(Cl)c(Br)cc2NC1=O]

A mixture of (S)-dimethyl 2-(4-bromo-5-chloro-2-nitrophenoxy)pentanedioate (13.5 g, 32.9 mmol), acetic acid (100 mL), and iron powder (15.0 g, 0.27 mol) was stirred for one hour at 100° C. The mixture was filtered, and the filtrate was concentrated. The resulting residue was diluted with saturated sodium bicarbonate, and extracted three times with dichloromethane. The combined organic layers were concentrated and the resulting residue was purified by MPLC eluting with a gradient of 20-50% ethyl acetate in petroleum ether to afford (S)-methyl 3-(6-bromo-7-chloro-3-oxo-3,4-dihydro-2H-benzo[b][1,4]oxazin-2-yl)propanoate (11.5 g) as a light brown solid.

Part IV—Synthesis of (S)-Methyl 3-(6-bromo-7-chloro-3,4-dihydro-2H-benzo[b][1,4]-oxazin-2-yl)propanoate

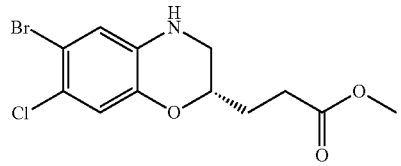 [SMILES: COC(=O)CC[C@H]1CNc2cc(Br)c(Cl)cc2O1]

A 10 M solution of borane dimethyl sulfide in THF (4.3 mL, 43 mmol) was added dropwise to a solution of (S)-methyl 3-(6-bromo-7-chloro-3-oxo-3,4-dihydro-2H-benzo[b][1,4]oxazin-2-yl)propanoate (11.5 g, 33 mmol) in tetrahydrofuran (100 mL). The solution was stirred overnight at room temperature, and then quenched by the slow addition of methanol (100 mL). The mixture was concentrated, diluted with saturated sodium bicarbonate, and extracted three times with ethyl acetate. The combined organic layers were concentrated, and the resulting residue was purified MPLC eluting with a gradient of 20-50% ethyl acetate in petroleum ether to afford (S)-methyl 3-(6-bromo-7-chloro-3,4-dihydro-2H-benzo[b][1,4]-oxazin-2-yl)propanoate (15.0 g) as a pink solid.

Part V—Synthesis of (S,E)-Methyl 3-(6-(2-(2-chloro-6-fluorophenyl)prop-1-en-1-yl)-7-chloro-3,4-dihydro-2H-benzo[b][1,4]oxazin-2-yl)propanoate

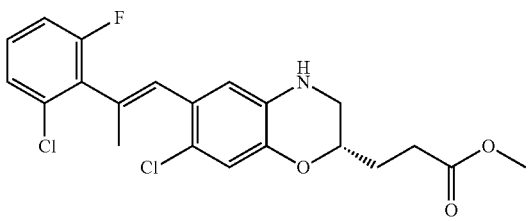 [SMILES: COC(=O)CC[C@H]1CNc2cc(/C=C(\C)c3c(F)cccc3Cl)c(Cl)cc2O1]

A mixture of (S)-methyl 3-(6-bromo-7-chloro-3,4-dihydro-2H-benzo[b][1,4]-oxazin-2-yl)propanoate (540 mg, 1.61 mmol), (E)-2-(2-(2-chloro-6-fluorophenyl)prop-1-en-1-yl)-4,4,5,5-tetramethyl-1,3,2-dioxaborolane (756 mg, 2.55 mmol), ethanol (1.9 mL), water (7.0 mL) and toluene (13.6 mL) was purged with nitrogen and maintained under an atmosphere of nitrogen. Sodium carbonate (1.48 g, 14 mmol) and tetrakis(triphenylphosphine)palladium(0) (237 mg, 0.20 mmol) were added and the stirred mixture was heated overnight at 95° C., then cooled, and diluted with water. The mixture was extracted three times with dichloromethane and the combined organic layers were concentrated. The resulting residue was purified by MPLC eluting with a gradient of 20-50% ethyl acetate in petroleum ether to afford (S,E)-methyl 3-(6-(2-(2-chloro-6-fluorophenyl)prop-1-en-1-yl)-7-chloro-3,4-dihydro-2H-benzo[b][1,4]oxazin-2-yl)propanoate (1.13 g) as a yellow solid.

Part VI—Synthesis of (S,E)-Methyl 3-(6-(2-(2-chloro-6-fluorophenyl)prop-1-en-1-yl)-7-chloro-4-((3-(trifluoromethyl)phenyl)sulfonyl)-3,4-dihydro-2H-benzo[b][1,4]oxazin-2-yl)propanoate

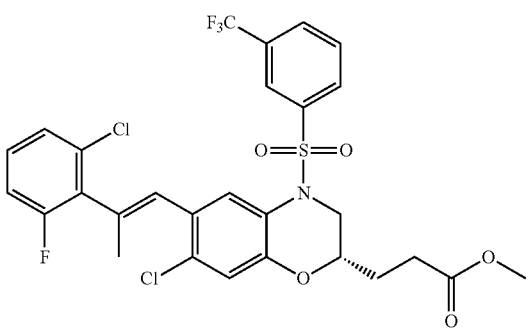

A mixture of (S,E)-methyl 3-(6-(2-(2-chloro-6-fluorophenyl)prop-1-en-1-yl)-7-chloro-3,4-dihydro-2H-benzo[b][1,4]oxazin-2-yl)propanoate (184 mg, 0.43 mmol), dichloromethane (2.2 mL), pyridine (0.17 mL, 2.1 mmol), 4-dimethylaminopyridine (26.5 mg, 0.22 mmol), and 3-(trifluoromethyl)benzene-1-sulfonyl chloride (0.084 mL, 0.52 mmol) was stirred overnight at room temperature, and then diluted with brine. The mixture was extracted three times with dichloromethane and the combined organic layers were concentrated. The resulting residue was purified by MPLC eluting with a gradient of 20-50% ethyl acetate in petroleum ether to afford (S,E)-methyl 3-(6-(2-(2-chloro-6-fluorophenyl)prop-1-en-1-yl)-7-chloro-4-((3-(trifluoromethyl)-phenyl)sulfonyl)-3,4-dihydro-2H-benzo[b][1,4]oxazin-2-yl)propanoate (17.8 mg, 6%) as a colorless oil. $^1$H-NMR (300 MHz, CDCl$_3$) δ 1.81-1.85 (m, 1H), 1.88-1.93 (m, 1H), 2.12 (s, 3H), 2.43-2.48 (m, 2H), 3.23 (dd, J=9.6 Hz, 14.0 Hz, 1H), 3.53-3.54 (m, 1H), 3.68 (s, 3H), 4.32 (dd, J=2.8 Hz, 14.4 Hz, 1H), 6.46 (d, J=1.2 Hz, 1H), 6.92 (s, 1H), 7.04 (dt, J=1.6 Hz, 7.6 Hz, 1H), 7.20-7.25 (m, 2H), 7.66 (t, J=8.0 Hz, 1H), 7.83-7.88 (m, 3H), 8.02 (s, 1H). (ES, m/z): (M+H)$^+$632.

Example 46—Synthesis of (S,E)-3-(7-Chloro-6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid

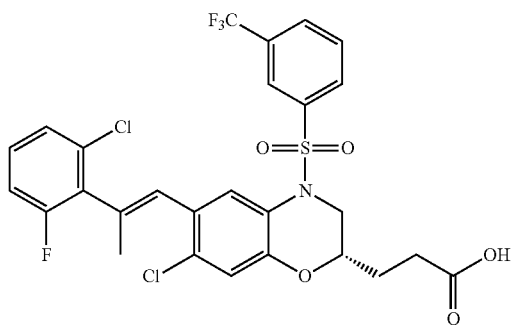 [SMILES: C/C(=C\c1cc2c(cc1Cl)O[C@@H](CCC(=O)O)CN2S(=O)(=O)c1cccc(C(F)(F)F)c1)c1c(F)cccc1Cl]

Based on the procedure in Example 42, (S,E)-3-(7-chloro-6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid was prepared. $^1$H-NMR (300 MHz, CDCl$_3$) δ 1.80-1.98 (m, 2H), 2.14 (s, 3H), 2.51-2.55 (m, 2H), 3.26 (dd, J=10.0 Hz, 14.4 Hz, 1H), 3.55-3.57 (m, 1H), 4.34 (dd, J=2.4 Hz, 14.0 Hz, 1H), 6.48 (s, 1H), 6.95 (s, 1H), 7.06 (t, J=8.0 Hz, 1H), 7.20-7.25 (m, 2H), 7.68 (t, J=8.0 Hz, 1H), 7.85-7.90 (m, 3H), 8.04 (s, 1H). (ES, m/z): (M+Na)$^+$640.

Example 47-Synthesis of (S,E)-Methyl 3-(6-(2-(2-chloro-6-fluorophenyl)prop-1-en-1-yl)-4-((3-(difluoromethoxy)phenyl)sulfonyl)-7-chloro-3,4-dihydro-2H-benzo[b][1,4]oxazin-2-yl)propanoate

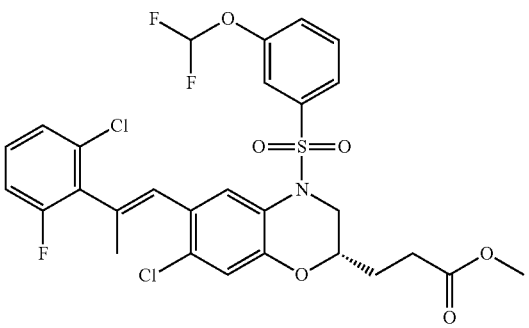

Based on the procedure in Example 41, (S,E)-methyl 3-(6-(2-(2-chloro-6-fluorophenyl)prop-1-en-1-yl)-4-((3-(difluoromethoxy)phenyl)sulfonyl)-7-chloro-3,4-dihydro-2H-benzo[b][1,4]oxazin-2-yl)propanoate was prepared. $^1$H-NMR (300 MHz, CDCl$_3$) δ 1.77-1.82 (m, 1H), 1.84-1.95 (m, 1H), 2.17 (s, 3H), 2.47 (dt, J=2.8 Hz, 7.2 Hz, 2H), 3.20

(dd, J=10.0 Hz, 14.4 Hz, 1H), 3.42-3.47 (m, 1H), 3.69 (s, 3H), 4.30 (dd, J=2.0 Hz, 14.4 Hz, 1H), 6.49 (s, 1H), 6.61 (t, J=72.4 Hz, 1H), 6.93 (s, 1H), 7.05 (t, J=8.0 Hz, 1H), 7.20-7.25 (m, 2H), 7.38 (d, J=8.0 Hz, 1H), 7.47-7.54 (m, 3H), 7.92 (s, 1H). (ES, m/z): (M+H)⁺630.

Example 48—Synthesis of (S,E)-3-(6-(2-(2-Chloro-6-fluorophenyl)prop-1-en-1-yl)-4-((3-(difluoromethoxy)phenyl)sulfonyl)-7-chloro-3,4-dihydro-2H-benzo[b][1,4]oxazin-2-yl)propanoate

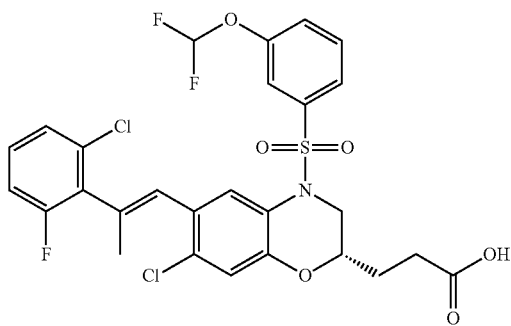

Based on the procedure in Example 42, (S,E)-3-(6-(2-(2-chloro-6-fluorophenyl)prop-1-en-1-yl)-4-((3-(difluoromethoxy)phenyl)sulfonyl)-7-chloro-3,4-dihydro-2H-benzo[b][1,4]oxazin-2-yl)propanoate was prepared. ¹H-NMR (300 MHz, CDCl₃) δ 1.77-1.96 (m, 2H), 2.17 (s, 3H), 2.50-2.54 (m, 2H), 3.22 (dd, J=10.0 Hz, 14.4 Hz, 1H), 3.45-3.49 (m, 1H), 4.30 (dd, J=2.0 Hz, 14.8 Hz, 1H), 6.49 (s, 1H), 6.56 (t, J=72.4 Hz, 1H), 6.94 (s, 1H), 7.06 (t, J=8.0 Hz, 1H), 7.20-7.25 (m, 2H), 7.38 (d, J=6.8 Hz, 1H), 7.49-7.55 (m, 3H), 7.92 (s, 1H). (ES, m/z): (M+H)⁺616.

Example 49—Synthesis of (S,E)-Methyl 3-(6-(2-(2-chloro-6-fluorophenyl)prop-1-en-1-yl)-8-fluoro-4-((3-(trifluoromethyl)phenyl)sulfonyl)-3,4-dihydro-2H-benzo[b][1,4]oxazin-2-yl)propanoate

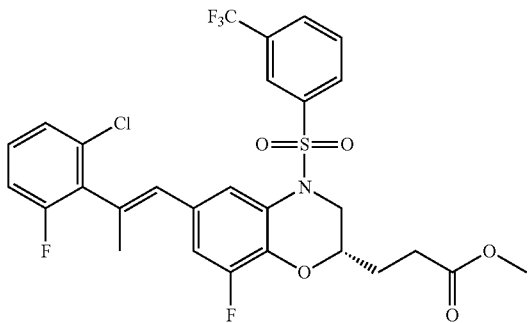

Based on the procedure in Example 41, (S,E)-methyl 3-(6-(2-(2-chloro-6-fluorophenyl)prop-1-en-1-yl)-8-fluoro-4-((3-(trifluoromethyl)phenyl)sulfonyl)-3,4-dihydro-2H-benzo[b][1,4]oxazin-2-yl)propanoate was prepared. ¹H-NMR (300 MHz, CD₃OD) δ 7.90 (m, 3H), 7.71 (t, J=8 Hz, 1H), 7.55 (s, 1H), 7.22-7.19 (m, 2H), 7.05-7.00 (m, 1H), 6.87 (dd, J=7.6 Hz, 2 Hz, 1H), 6.23 (s, 1H), 4.37 (dd, J=14.4 Hz, 2.4 Hz, 1H), 3.57 (s, 3H), 3.46-3.43 (m, 1H), 3.29-3.21 (m, 1H), 2.38 (t, J=7.2 Hz, 2H), 2.06 (s, 3H), 1.90-1.73 (m, 2H). (ES, m/z): (M+H)⁺616.

Example 50—Synthesis of (S,E)-3-(6-(2-(2-Chloro-6-fluorophenyl)prop-1-en-1-yl)-8-fluoro-4-((3-(trifluoromethyl)phenyl)sulfonyl)-3,4-dihydro-2H-benzo[b][1,4]oxazin-2-yl)propanoic acid

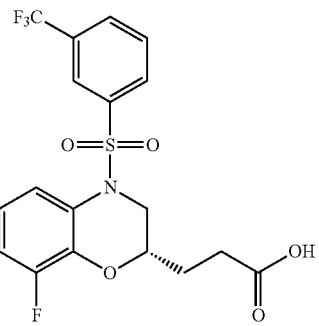

Based on the procedure in Example 42, (S,E)-3-(6-(2-(2-chloro-6-fluorophenyl)prop-1-en-1-yl)-8-fluoro-4-((3-(trifluoromethyl)phenyl)sulfonyl)-3,4-dihydro-2H-benzo[b][1,4]oxazin-2-yl)propanoic acid was prepared. ¹H-NMR (300 MHz, CD₃OD) δ 8.04-7.99 (m, 3H), 7.83 (t, J=8 Hz, 1H), 7.67 (s, 1H), 7.34-7.31 (m, 2H), 7.16-7.12 (m, 1H), 7.0 (d, J=8.8 Hz, 1H), 6.35 (s, 1H), 4.50 (dd, J=14.8 Hz, 2.4 Hz, 1H), 3.58-3.55 (m, 1H), 3.40-3.33 (m, 1H), 2.50-2.45 (m, 2H), 2.18 (d, J=1.2 Hz, 3H), 1.99-1.83 (m, 2H). (ES, m/z): (M+H)⁺602.

Example 51—Synthesis of Methyl (S,E)-3-(6-(2-(2-chloro-6-fluorophenyl)prop-1-en-1-yl)-4-((3-(difluoromethoxy)phenyl)sulfonyl)-8-fluoro-3,4-dihydro-2H-benzo[b][1,4]oxazin-2-yl)propanoate

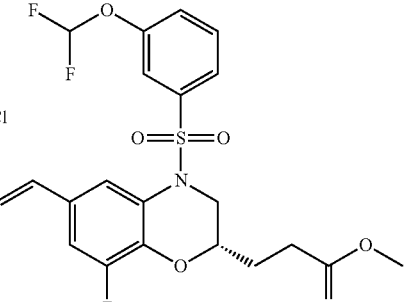

Based on the procedure in Example 41, methyl (S,E)-3-(6-(2-(2-chloro-6-fluorophenyl)prop-1-en-1-yl)-4-((3-(difluoromethoxy)phenyl)sulfonyl)-8-fluoro-3,4-dihydro-2H-benzo[b][1,4]oxazin-2-yl)propanoate was prepared. ¹H-NMR (300 MHz, CD₃OD) δ 7.57 (s, 1H), 7.51 (t, 1H), 7.34-7.45 (m, 3H), 7.20 (m, 2H), 7.03 (m, 1H), 6.86 (d, 1H), 6.82 (t, J=72 Hz, 1H), 6.23 (s, 1H), 4.32 (d, 1H), 3.57 (s, 3H), 3.36 (m, 1H), 3.20 (m, 1H), 2.38 (t, 2H), 2.07 (s, 3H), 1.84 (m, 1H), 1.75 (m, 1H). (ES, m/z): (M+H)⁺614.

Example 52—Synthesis of (S,E)-3-(6-(2-(2-Chloro-6-fluorophenyl)prop-1-en-1-yl)-4-((3-(difluoromethoxy)phenyl)sulfonyl)-8-fluoro-3,4-dihydro-2H-benzo[b][1,4]oxazin-2-yl)propanoic acid

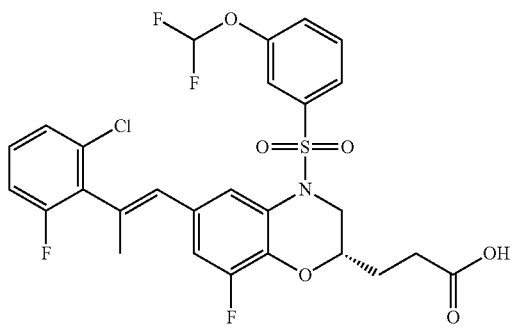 [SMILES: C/C(=C\c1cc(F)c2c(c1)N(S(=O)(=O)c1cccc(OC(F)F)c1)C[C@H](CCC(=O)O)O2)c1c(F)cccc1Cl]

Based on the procedure in Example 42, (S,E)-3-(6-(2-(2-chloro-6-fluorophenyl)prop-1-en-1-yl)-4-((3-(difluoromethoxy)phenyl)sulfonyl)-8-fluoro-3,4-dihydro-2H-benzo[b][1,4]oxazin-2-yl)propanoic acid was prepared. $^1$H-NMR (300 MHz, CD$_3$OD) δ 7.67 (s, 1H), 7.50-7.67 (m, 4H), 7.32 (m, 2H), 7.14 (m, 1H), 7.01 (d, 1H), 6.91 (t, J=72 Hz, 1H), 6.35 (s, 1H), 4.44 (d, 1H), 3.48 (m, 1H), 3.31 (m, 1H), 2.47 (t, 2H), 2.19 (s, 3H), 1.96 (m, 1H), 1.85 (m, 1H). (ES, m/z): (M+H)$^+$600.

Example 53—Synthesis of (S,E)-Methyl 3-(6-(2-(2-chloro-6-fluorophenyl)prop-1-en-1-yl)-4-((3-(difluoromethoxy)phenyl)sulfonyl)-7-methyl-3,4-dihydro-2H-benzo[b][1,4]oxazin-2-yl)propanoate

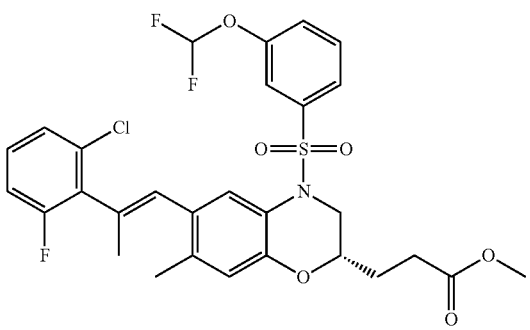

Based on the procedure in Example 41, (S,E)-methyl 3-(6-(2-(2-chloro-6-fluorophenyl)prop-1-en-1-yl)-4-((3-(difluoromethoxy)phenyl)sulfonyl)-7-methyl-3,4-dihydro-benzo[b][1,4]oxazin-2-yl)propanoate was prepared. $^1$H-NMR (300 MHz, CD$_3$OD) δ 1.74 (m, 1H), 1.86 (m, 1H), 2.01 (s, 3H), 2.39 (s, 3H), 2.42 (t, 2H), 3.20 (dd, 1H), 3.31 (m, 1H), 3.63 (s, 3H), 4.30 (dd, 1H), 6.36 (s, 1H), 6.67 (s, 1H), 6.85 (t, J=72 Hz, 1H), 6.93 (s, 1H), 7.07 (m, 1H), 7.22 (m, 2H), 7.42-7.60 (m, 4H), 7.69 (s, 1H).

Example 54—Synthesis of (S,E)-3-(6-(2-(2-Chloro-6-fluorophenyl)prop-1-en-1-yl)-4-((3-(difluoromethoxy)phenyl)sulfonyl)-7-methyl-3,4-dihydro-2H-benzo[b][1,4]oxazin-2-yl)propanoic acid

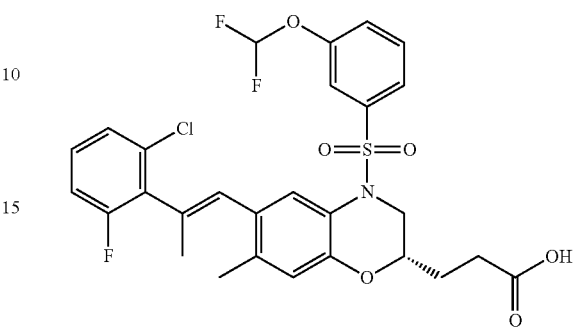

Based on the procedure in Example 42, (S,E)-3-(6-(2-(2-chloro-6-fluorophenyl)prop-1-en-1-yl)-4-((3-(difluoromethoxy)phenyl)sulfonyl)-7-methyl-3,4-dihydro-2H-benzo[b][1,4]oxazin-2-yl)propanoic acid was prepared. $^1$H-NMR (300 MHz, CD$_3$OD) δ 7.72 (s, 1H), 7.60 (m, 1H), 7.54 (m, 1H), 7.44 (m, 2H), 7.32 (m, 2H), 7.15 (m, 1H), 6.87 (t, 1H), 6.72 (s, 1H), 6.41 (s, 1H), 4.37 (m, 1H), 3.42 (m, 1H), 3.24 (m, 1H), 2.43 (m, 2H), 2.24 (s, 3H), 2.06 (s, 3H), 1.87 (m, 1H), 1.75 (m, 1H). (ES, m/z): (M+H)$^+$596.

Example 55—Synthesis of Methyl (S,E)-3-(6-(2-(2-chloro-6-fluorophenyl)prop-1-en-1-yl)-7-methyl-4-((3-(trifluoromethyl)phenyl)sulfonyl)-3,4-dihydro-2H-benzo[b][1,4]oxazin-2-yl)propanoate

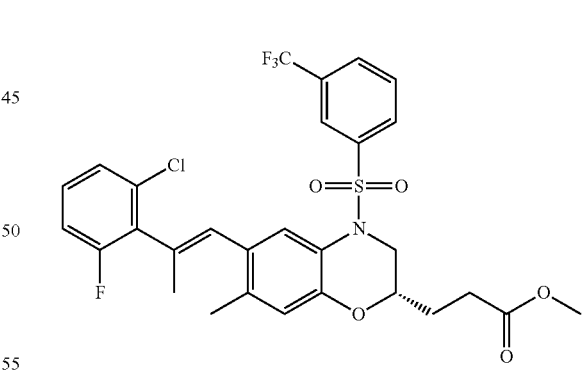

Based on the procedure in Example 41, methyl (S,E)-3-(6-(2-(2-chloro-6-fluorophenyl)prop-1-en-1-yl)-7-methyl-4-((3-(trifluoromethyl)phenyl)sulfonyl)-3,4-dihydro-2H-benzo[b][1,4]oxazin-2-yl)propanoate was prepared. $^1$H-NMR (300 MHz, CD$_3$OD) δ 7.89-7.96 (m, 3H), 7.72-7.77 (m, 1H), 7.64 (s, 1H), 7.25-7.29 (m, 2H), 7.07-7.11 (m, 1H), 6.67 (s, 1H), 6.35 (s, 1H), 4.32-4.38 (m, 1H), 3.62 (s, 3H), 3.46-3.48 (m, 1H), 3.22-3.31 (m, 1H), 2.38-2.44 (m, 2H), 2.19 (s, 3H), 1.99 (s, 3H), 1.73-1.93 (m, 2H). (ES, m/z): (M+Na)$^+$634.

Example 56—Synthesis of (S,E)-3-(6-(2-(2-Chloro-6-fluorophenyl)prop-1-en-1-yl)-7-methyl-4-((3-(trifluoromethyl)phenyl)sulfonyl)-3,4-dihydro-2H-benzo[b][1,4]oxazin-2-yl)propanoic acid

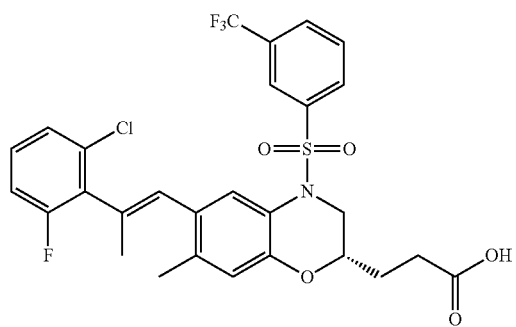 [SMILES: C/C(=C\c1cc2c(cc1C)O[C@@H](CCC(=O)O)CN2S(=O)(=O)c1cccc(C(F)(F)F)c1)c1c(F)cccc1Cl]

Based on the procedure in Example 42, (S,E)-3-(6-(2-(2-chloro-6-fluorophenyl)prop-1-en-1-yl)-7-methyl-4-((3-(trifluoromethyl)phenyl)sulfonyl)-3,4-dihydro-2H-benzo[b][1,4]oxazin-2-yl)propanoic acid was prepared. $^1$H-NMR (300 MHz, CD$_3$OD) δ 7.89-7.96 (m, 3H), 7.72-7.77 (m, 1H), 7.64 (s, 1H), 7.25-7.29 (m, 2H), 7.07-7.11 (m, 1H), 6.68 (s, 1H), 6.36 (s, 1H), 4.32-4.39 (m, 1H), 3.46-3.48 (m, 1H), 3.22-3.31 (m, 1H), 2.35-2.41 (m, 2H), 2.19 (s, 3H), 1.99 (s, 3H), 1.73-1.93 (m, 2H). (ES, m/z): (M+H)$^+$598.

Example 57-Synthesis of Methyl (S,E)-3-(6-(2-(2-chloro-6-fluorophenyl)prop-1-en-1-yl)-5-methyl-4-((3-(trifluoromethyl)phenyl)sulfonyl)-3,4-dihydro-2H-benzo[b][1,4]oxazin-2-yl)propanoate

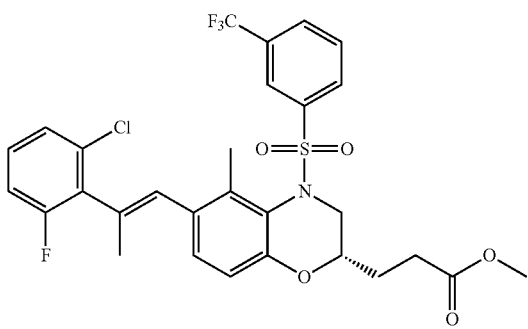

A solution of bromine (10.2 g, 63.83 mmol) in acetic acid (10 mL) was added to a solution of 3-methyl-2-nitrophenol (10 g, 65.30 mmol) in acetic acid (50 mL) dropwise and the mixture was stirred for two hours at room temperature. Ice water was added, and the mixture was extracted twice with ethyl acetate. The combined organic layers were washed three times with water, dried (Na$_2$SO$_4$) and concentrated. The resulting residue was purified via MPLC eluting with 10% ethyl acetate in petroleum ether to afford 4-bromo-3-methyl-2-nitrophenol (12 g, 79%) as a yellow solid.

From 4-bromo-3-methyl-2-nitrophenol, based on the procedure in Example 41, methyl (S,E)-3-(6-(2-(2-chloro-6-fluorophenyl)prop-1-en-1-yl)-5-methyl-4-((3-(trifluoromethyl)phenyl)sulfonyl)-3,4-dihydro-2H-benzo[b][1,4]oxazin-2-yl)propanoate was prepared. $^1$H-NMR (300 MHz, CD$_3$OD) δ 8.01-7.94 (m, 2H), 7.79-7.75 (m, 2H), 7.36-7.34 (m, 2H), 7.33-7.13 (m, 2H), 6.68-6.66 (d, J=8.4 Hz, 1H), 6.45 (s, 1H), 4.87-4.37 (m, 1H), 3.95-3.90 (m, 1H), 3.66 (s, 3H), 3.34-3.12 (m, 1H), 2.50-2.32 (m, 5H), 1.98 (s, 3H), 1.86-1.78 (m, 1H), 1.69-1.60 (m, 1H). (ES, m/z): (M+Na)$^+$ 612.

Example 58—Synthesis of (S,E)-3-(6-(2-(2-Chloro-6-fluorophenyl)prop-1-en-1-yl)-5-methyl-4-((3-(trifluoromethyl)phenyl)sulfonyl)-3,4-dihydro-2H-benzo[b][1,4]oxazin-2-yl)propanoic acid

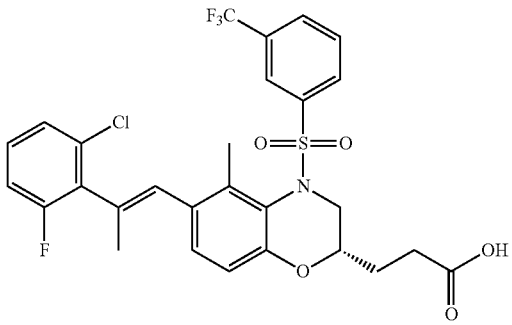 [SMILES: C/C(=C\c1ccc2c(c1C)N(S(=O)(=O)c1cccc(C(F)(F)F)c1)C[C@H](CCC(=O)O)O2)c1c(F)cccc1Cl]

Based on the procedure in Example 42, (S,E)-3-(6-(2-(2-chloro-6-fluorophenyl)prop-1-en-1-yl)-5-methyl-4-((3-(trifluoromethyl)phenyl)sulfonyl)-3,4-dihydro-2H-benzo[b][1,4]oxazin-2-yl)propanoic acid was prepared. $^1$H-NMR (300 MHz, CD$_3$OD) δ 8.00-7.98 (m, 2H), 7.79-7.75 (m, 2H), 7.36-7.34 (m, 2H), 7.33-7.13 (m, 2H), 6.70-6.68 (d, J=8.4 Hz 1H), 6.45 (s, 1H), 4.87-4.37 (m, 1H), 3.95-3.90 (m, 1H), 3.15-3.09 (m, 1H), 2.43 (s, 3H), 2.38-2.30 (m, 2H), 1.98 (s, 3H), 1.82-1.76 (m, 1H), 1.69-1.60 (m, 1H). (ES, m/z): (M+H)$^+$598.

Example 59—Synthesis of Methyl (S,E)-3-(6-(2-(2-chloro-6-fluorophenyl)prop-1-en-1-yl)-4-((3-(difluoromethoxy)phenyl)sulfonyl)-5-methyl-3,4-dihydro-2H-benzo[b][1,4]oxazin-2-yl)propanoate

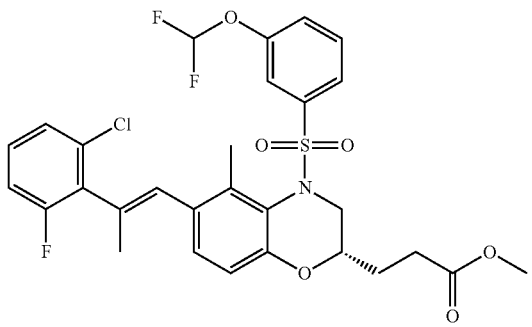 [SMILES: COC(=O)CC[C@H]1CN(S(=O)(=O)c2cccc(OC(F)F)c2)c2c(ccc(/C=C(\C)c3c(F)cccc3Cl)c2C)O1]

From 4-bromo-3-methyl-2-nitrophenol, based on the procedure in Example 41, methyl (S,E)-3-(6-(2-(2-chloro-6-fluorophenyl)prop-1-en-1-yl)-4-((3-(difluoromethoxy)phenyl)sulfonyl)-5-methyl-3,4-dihydro-2H-benzo[b][1,4]oxazin-2-yl)propanoate was prepared. $^1$H-NMR (300 MHz, CD$_3$OD) δ 7.59 (t, 1H), 7.49 (m, 2H), 7.31-7.39 (m, 3H), 7.13-7.19 (m, 2H), 6.88 (t, J=72 Hz, 1H), 6.70 (d, 1H), 6.44 (s, 1H), 4.33 (m, 1H), 3.88 (m, 1H), 3.67 (s, 3H), 3.10 (m, 1H), 2.42 (s, 3H), 2.41 (t, 2H), 1.98 (s, 3H), 1.84 (m, 1H), 1.75 (m, 1H). (ES, m/z): (M+Na)⁺610.

Example 60—Synthesis of (S,E)-3-(6-(2-(2-Chloro-6-fluorophenyl)prop-1-en-1-yl)-4-((3-(difluoromethoxy)phenyl)sulfonyl)-5-methyl-3,4-dihydro-2H-benzo[b][1,4]oxazin-2-yl)propanoic acid

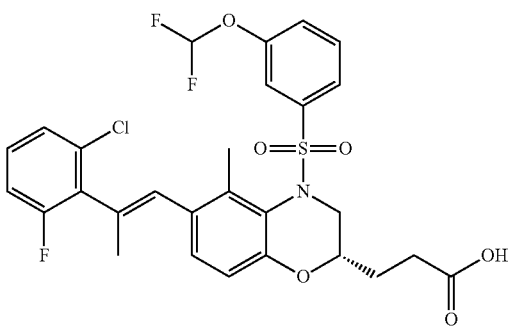 [SMILES: C/C(=C\c1ccc2c(c1C)N(S(=O)(=O)c1cccc(OC(F)F)c1)C[C@H](CCC(=O)O)O2)c1c(F)cccc1Cl]

Based on the procedure in Example 42, (S,E)-3-(6-(2-(2-chloro-6-fluorophenyl)prop-1-en-1-yl)-4-((3-(difluoromethoxy)phenyl)sulfonyl)-5-methyl-3,4-dihydro-2H-benzo[b][1,4]oxazin-2-yl)propanoic acid was prepared. ¹H-NMR (300 MHz, CD₃OD) δ 7.59 (t, 1H), 7.53 (m, 1H), 7.48 (m, 1H), 7.31-7.39 (m, 3H), 7.13-7.19 (m, 2H), 6.88 (t, J=72 Hz, 1H), 6.72 (d, 1H), 6.44 (s, 1H), 4.30 (m, 1H), 3.88 (m, 1H), 3.10 (m, 1H), 2.42 (s, 3H), 2.40 (t, 2H), 1.99 (s, 3H), 1.89 (m, 1H), 1.68 (m, 1H). (ES, m/z): (M+H)⁺596.

Example 61—Synthesis of Methyl (S,E)-3-(6-(2-(2-chloro-6-fluorophenyl)prop-1-en-1-yl)-5-fluoro-4-((3-(trifluoromethyl)phenyl)sulfonyl)-3,4-dihydro-2H-benzo[b][1,4]oxazin-2-yl)propanoate

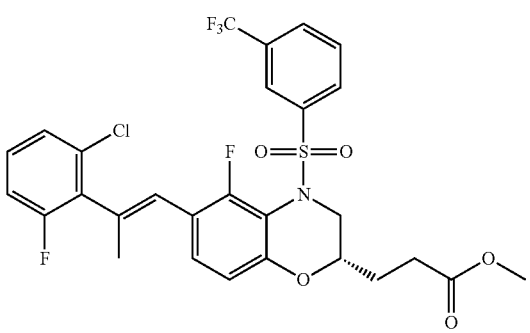

A solution of 3-fluoro-2-nitrophenol (14.4 g, 91.7 mmol), N-bromosuccinimide (19.6 g, 110 mmol), and sulfuric acid (100 mL) was stirred overnight at 65° C. Then, the reaction mixture was poured onto ice. Next, the resulting mixture was extracted three times with dichloromethane and the organic layers were combined and concentrated. The resulting residue was purified by MPLC eluting with 20% ethyl acetate in petroleum ether to afford 4-bromo-3-fluoro-2-nitrophenol (3.6 g, 17%) as a yellow solid.

From 4-bromo-3-fluoro-2-nitrophenol, by the procedure of Example 41, methyl (S,E)-3-(6-(2-(2-chloro-6-fluorophenyl)prop-1-en-1-yl)-5-fluoro-4-((3-(trifluoromethyl)phenyl)sulfonyl)-3,4-dihydro-2H-benzo[b][1,4]oxazin-2-yl)propanoate was prepared. ¹H-NMR (300 MHz, CDCl₃) δ 1.94-1.98 (m, 1H), 2.01-2.14 (m, 4H), 2.55-2.72 (m, 2H), 3.05 (dd, J=9.9 Hz, 14.1 Hz, 1H), 3.73 (s, 3H), 4.10 (dd, J=2.7 Hz, 14.1 Hz, 1H), 4.39-4.45 (m, 1H), 6.33 (s, 1H), 6.75 (d, J=7.5 Hz, 1H), 6.98-7.04 (m, 1H), 7.15-7.23 (m, 3H), 7.71 (t, J=8.1 Hz, 1H), 7.88 (d, J=7.8 Hz, 1H), 8.19 (d, J=7.8 Hz, 1H), 8.25 (s, 1H). (ES, m/z): (M+H)⁺616.

Example 62—Synthesis of (S,E)-3-(6-(2-(2-Chloro-6-fluorophenyl)prop-1-en-1-yl)-5-fluoro-4-((3-(trifluoromethyl)phenyl)sulfonyl)-3,4-dihydro-2H-benzo[b][1,4]oxazin-2-yl)propanoic acid

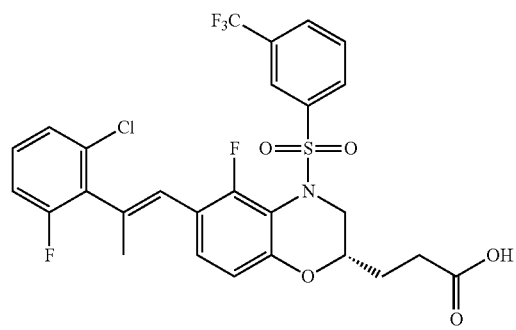

Based on the procedure in Example 42, (S,E)-3-(6-(2-(2-chloro-6-fluorophenyl)prop-1-en-1-yl)-5-fluoro-4-((3-(trifluoromethyl)phenyl)sulfonyl)-3,4-dihydro-2H-benzo[b][1,4]oxazin-2-yl)propanoic acid was prepared. ¹H-NMR (300 MHz, CD₃OD) δ 1.89-2.00 (m, 2H), 2.03 (s, 3H), 2.46-2.51 (m, 2H), 3.14 (dd, J=10.5 Hz, 15.0 Hz, 1H), 4.27 (dd, J=2.7 Hz, 14.7 Hz, 1H), 6.26 (s, 1H), 6.80 (d, J=8.7 Hz, 1H), 7.07-7.19 (m, 2H), 7.22-7.33 (m, 2H), 7.84 (t, J=7.8 Hz, 1H), 8.01 (d, J=7.8 Hz, 1H), 8.21 (s, 1H), 8.27 (d, J=7.8 Hz, 1H). (ES, m/z): (M+NH₄)⁺619.

Example 63—Synthesis of Methyl (S,E)-3-(6-(2-(2-chloro-6-fluorophenyl)prop-1-en-1-yl)-4-((3-(difluoromethoxy)phenyl)sulfonyl)-5-fluoro-3,4-dihydro-2H-benzo[b][1,4]oxazin-2-yl)propanoate

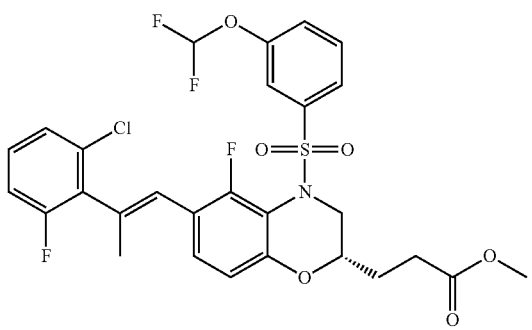 [SMILES: COC(=O)CC[C@H]1CN(S(=O)(=O)c2cccc(OC(F)F)c2)c2c(ccc(/C=C(\C)c3c(F)cccc3Cl)c2F)O1]

Based on the procedure in Example 41, methyl (S,E)-3-(6-(2-(2-chloro-6-fluorophenyl)prop-1-en-1-yl)-4-((3-(difluoromethoxy)phenyl)sulfonyl)-5-fluoro-3,4-dihydro-2H-benzo[b][1,4]oxazin-2-yl)propanoate was prepared. ¹H-NMR (300 MHz, CDCl₃) δ 1.90-1.97 (m, 1H), 2.00-2.09 (m, 4H), 2.57-2.66 (m, 2H), 3.01 (d, J=9.9 Hz, 14.1 Hz, 1H), 3.72 (s, 3H), 4.06 (d, J=2.4 Hz, 14.1 Hz, 1H), 4.31-4.38 (m, 1H), 6.35-6.83 (m, 3H), 7.02 (dt, J=2.7 Hz, 6.9 Hz, 1H), 7.15-7.23 (m, 3H), 7.39 (d, J=8.1 Hz, 1H), 7.56 (t, J=8.1 Hz, 1H), 7.75 (s, 1H), 7.82 (d, J=7.8 Hz, 1H). (ES, m/z): (M+H)⁺614.

Example 64—Synthesis of (S,E)-3-(6-(2-(2-Chloro-6-fluorophenyl)prop-1-en-1-yl)-4-((3-(difluoromethoxy)phenyl)sulfonyl)-5-fluoro-3,4-dihydro-2H-benzo[b][1,4]oxazin-2-yl)propanoic acid

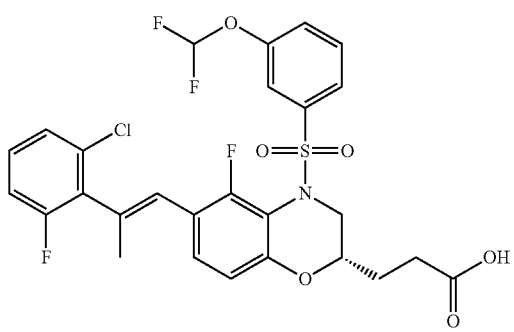

Based on the procedure in Example 42, (S,E)-3-(6-(2-(2-chloro-6-fluorophenyl)prop-1-en-1-yl)-4-((3-(difluoromethoxy)phenyl)sulfonyl)-5-fluoro-3,4-dihydro-2H-benzo[b][1,4]oxazin-2-yl)propanoic acid was prepared. ¹H-NMR (300 MHz, CDCl₃) δ 1.88-1.98 (m, 1H), 2.01-2.09 (m, 4H), 2.58-2.77 (m, 2H), 3.03 (dd, J=9.9 Hz, 14.1 Hz, 1H), 4.07 (dd, J=2.4 Hz, 14.1 Hz, 1H), 4.33-4.40 (m, 1H), 6.34-6.82 (m, 3H), 6.98-7.06 (m, 1H), 7.15-7.24 (m, 3H), 7.39 (d, J=8.1 Hz, 1H), 7.56 (t, J=8.1 Hz, 1H), 7.75 (s, 1H), 7.83 (d, J=7.8 Hz, 1H). (ES, m/z): (M+H)⁺600.

Example 65—Synthesis of Methyl (S,E)-3-(6-(2-(2-chloro-6-fluorophenyl)prop-1-en-1-yl)-4-((2-ethoxy-4,5,6,7-tetrahydropyrazolo[1,5-a]pyridin-3-yl)sulfonyl)-3,4-dihydro-2H-benzo[b][1,4]oxazin-2-yl)propanoate

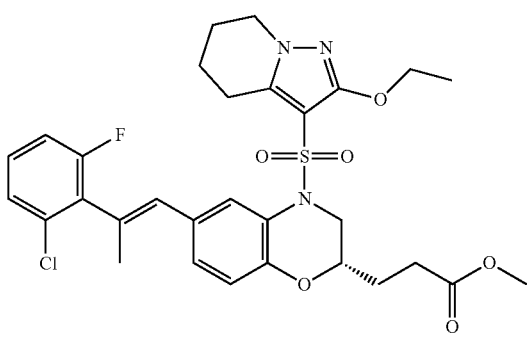 [SMILES: CCOc1nn2c(c1S(=O)(=O)N1C[C@H](CCC(=O)OC)Oc3ccc(/C=C(\C)c4c(F)cccc4Cl)cc31)CCCC2]

Part I—Synthesis of Ethyl 7-chloro-3-oxoheptanoate

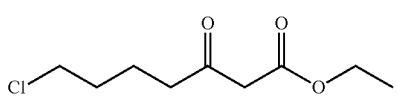

A solution of ethyl 3-oxobutanoate (1.95 g, 14.98 mmol) in tetrahydrofuran (20 mL) was added dropwise to a stirred 1 M solution of lithium diisopropylamine (30 mL, 30 mmol) at −78° C. The solution was stirred for an additional hour at −78° C., and then a solution of 1-chloro-3-iodopropane (3.07 g, 15.02 mmol) in tetrahydrofuran (50 mL) was added. The resulting solution was allowed to warm to room temperature and stirred for an additional two hours. Water was added, and the mixture was extracted twice with ethyl acetate. The combined organic layers were dried (Na₂SO₄) and concentrated. The resulting residue was purified via MPLC eluting with a gradient of 20-50% ethyl acetate in petroleum ether to afford ethyl 7-chloro-3-oxoheptanoate (2.8 g, 90%) as an oil.

Part II—Synthesis of 4,5,6,7-Tetrahydropyrazolo[1,5-a]pyridin-2-ol

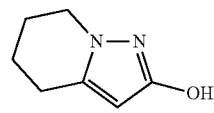

A mixture of ethyl 7-chloro-3-oxoheptanoate (2.8 g, 13.55 mmol), hydrazine (2.5 mL, 0.04 mol) and ethanol (20 mL) was stirred for four hours at 100° C. Cooled, concentrated, and purified the resulting residue by MPLC eluting with a gradient of 20-50% ethyl acetate in petroleum ether to afford 4,5,6,7-tetrahydropyrazolo[1,5-a]pyridin-2-ol (1.14 g, 61%) as a white solid.

Part III—Synthesis of 2-Ethoxy-4,5,6,7-tetrahydropyrazolo[1,5-a]pyridine

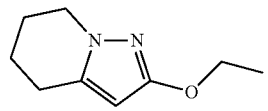

A mixture of 4,5,6,7-tetrahydropyrazolo[1,5-a]pyridin-2-ol (1.14 g, 8.02 mmol), bromoethane (4.5 g, 41.30 mmol), potassium carbonate (5.66 g, 40.95 mmol), and N,N-dimethylformamide (20 mL) was stirred overnight at room temperature. Water was added, and the mixture was extracted three times with ethyl acetate. The combined organic layers were dried (Na₂SO₄) and concentrated. The resulting residue was purified via MPLC eluting with a gradient of 20-50% ethyl acetate in petroleum ether to afford 2-ethoxy-4,5,6,7-tetrahydropyrazolo[1,5-a]pyridine (1.18 g, 86%) as a yellow oil.

Part IV—Synthesis of 2-Ethoxy-4,5,6,7-tetrahydropyrazolo[1,5-a]pyridine-3-sulfonyl chloride

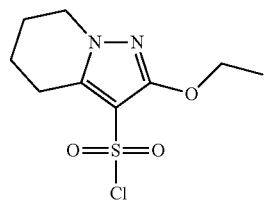 [SMILES: CCOc1nn2c(c1S(=O)(=O)Cl)CCCC2]

A mixture of 2-ethoxy-4,5,6,7-tetrahydropyrazolo[1,5-a]pyridine (1.18 g, 7.10 mmol), chlorosulfonic acid (10 mL) and dichloromethane (20 mL) was stirred for three hours at reflux. The mixture was cooled, and washed with water. The aqueous layer was reextracted three times with dichloromethane. The combined organic layers were dried (Na$_2$SO$_4$) and concentrated. The resulting residue was purified via MPLC eluting with a gradient of 20-50% ethyl acetate in petroleum ether to afford 2-ethoxy-4,5,6,7-tetrahydropyrazolo[1,5-a]pyridine-3-sulfonyl chloride (1.13 g, 60%) as a colorless solid.

Part V—Synthesis of Methyl (S,E)-3-(6-(2-(2-chloro-6-fluorophenyl)prop-1-en-1-yl)-4-((2-ethoxy-4,5,6,7-tetrahydropyrazolo[1,5-a]pyridin-3-yl)sulfonyl)-3,4-dihydro-2H-benzo[b][1,4]oxazin-2-yl)propanoate

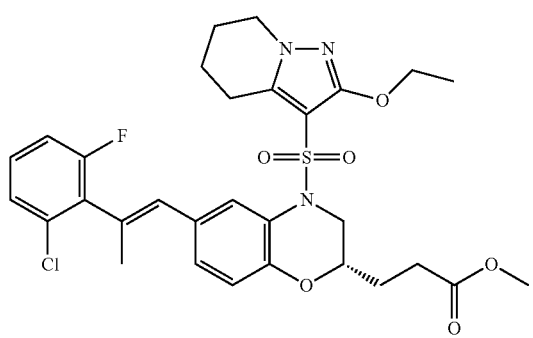 [SMILES: CCOc1nn2c(c1S(=O)(=O)N1C[C@H](CCC(=O)OC)Oc3ccc(/C=C(\C)c4c(F)cccc4Cl)cc31)CCCC2]

Based on the procedure in Example 29, methyl (S,E)-3-(6-(2-(2-chloro-6-fluorophenyl)prop-1-en-1-yl)-4-((2-ethoxy-4,5,6,7-tetrahydropyrazolo[1,5-a]pyridin-3-yl)sulfonyl)-3,4-dihydro-2H-benzo[b][1,4]oxazin-2-yl)propanoate was prepared. $^1$H-NMR (300 MHz, CD$_3$OD) δ 7.77 (s, 1H), 7.32-7.29 (m, 2H), 7.13-7.05 (m, 2H), 6.89 (d, J=8.4 Hz, 1H), 6.33 (s, 1H), 4.30 (dd, J=14.4 Hz, 2.4 Hz, 1H), 4.16-4.10 (m, 2H), 3.97-3.91 (m, 3H), 3.71 (s, 3H), 3.25 (dd, J=14.4 Hz, 2.4 Hz, 1H), 2.94 (m, 1H), 2.79 (m, 1H), 2.61-2.57 (m, 2H), 2.15 (s, 3H), 2.02-1.86 (m, 6H), 1.23 (t, J=7.2 Hz, 3H). (ES, m/z): (M+H)$^+$618.

Example 66—Synthesis of (S,E)-3-(6-(2-(2-Chloro-6-fluorophenyl)prop-1-en-1-yl)-4-((2-ethoxy-4,5,6,7-tetrahydropyrazolo[1,5-a]pyridin-3-yl)sulfonyl)-3,4-dihydro-2H-benzo[b][1,4]oxazin-2-yl)propanoic acid

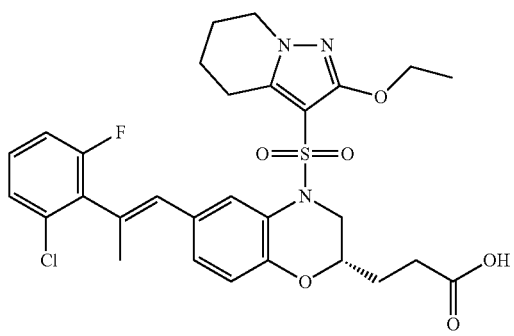 [SMILES: CCOc1nn2c(c1S(=O)(=O)N1C[C@H](CCC(=O)O)Oc3ccc(/C=C(\C)c4c(F)cccc4Cl)cc31)CCCC2]

Based on the procedure in Example 42, (S,E)-3-(6-(2-(2-chloro-6-fluorophenyl)prop-1-en-1-yl)-4-((2-ethoxy-4,5,6,7-tetrahydropyrazolo[1,5-a]pyridin-3-yl)sulfonyl)-3,4-dihydro-2H-benzo[b][1,4]oxazin-2-yl)propanoic acid was prepared. $^1$H-NMR (300 MHz, CD$_3$OD) δ 7.78 (s, 1H), 7.32-7.29 (m, 2H), 7.15-7.05 (m, 2H), 6.90 (d, J=8.4 Hz, 1H), 6.34 (s, 1H), 4.32 (dd, J=14.4 Hz, 2.4 Hz, 1H), 4.17-4.10 (m, 2H), 3.96-3.92 (m, 3H), 3.24 (dd, J=14.4 Hz, 2.4 Hz, 1H), 2.93 (m, 1H), 2.79 (m, 1H), 2.56-2.53 (m, 2H), 2.15 (s, 3H), 2.01-1.87 (m, 6H), 1.23 (t, J=7.2 Hz, 3H). (ES, m/z): (M+H)$^+$604.

Example 67-Synthesis of Methyl (S,E)-3-(4-((5-chloro-2-ethoxypyridin-3-yl)sulfonyl)-6-(2-(2-chloro-6-fluorophenyl)prop-1-en-1-yl)-3,4-dihydro-2H-benzo[b][1,4]oxazin-2-yl)propanoate

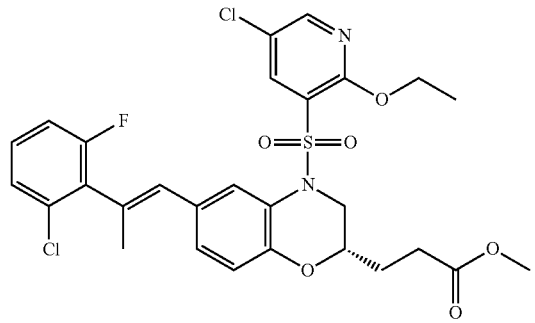 [SMILES: CCOc1ncc(Cl)cc1S(=O)(=O)N1C[C@H](CCC(=O)OC)Oc2ccc(/C=C(\C)c3c(F)cccc3Cl)cc21]

Part I—Synthesis of 3-Bromo-5-chloro-2-ethoxypyridine

To a solution of 3-bromo-2-chloro-5-(trifluoromethyl)pyridine (5.0 g, 22.0 mmol) in ethanol (50 mL) was added sodium ethoxide (4.5 g, 66 mmol) and the mixture was microwaved for ten minutes at 150° C. The mixture was diluted with water, extracted twice with ethyl acetate, the combined organic layers were dried (Na$_2$SO$_4$) and concentrated to afford 3-bromo-5-chloro-2-ethoxypyridine (5.0 g, 96%) as a colorless oil.

Part II—Synthesis of 3-(Benzylthio)-5-chloro-2-ethoxypyridine

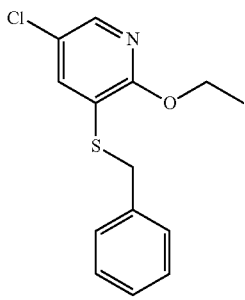 [SMILES: CCOc1ncc(Cl)cc1SCc1ccccc1]

A mixture of 3-bromo-5-chloro-2-ethoxypyridine (4.8 g, 20.3 mmol), phenylmethanethiol (2.53 g, 20.4 mmol), N,N-diisopropylethylamine (5.2 g, 40.2 mmol), tris(dibenzylideneacetone)dipalladium(0) (0.90 g, 0.98 mmol), 4,5-bis(diphenylphosphino)-9,9-dimethylxanthene (1.2 g, 2.07 mmol), and toluene (50 mL) was stirred for two hours at 110° C. The mixture was filtered; the filtrate was concentrated and the resulting residue was purified via MPLC eluting with a gradient of 0-2.5% ethyl acetate in petroleum ether to afford 3-(benzylthio)-5-chloro-2-ethoxypyridine (4.8 g, 85%) as a white solid.

Part III—Synthesis of 5-Chloro-2-ethoxypyridine-3-sulfonyl chloride

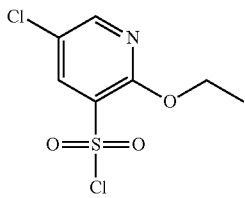

A mixture of 3-(benzylthio)-5-chloro-2-ethoxypyridine (2.00 g, 7.15 mmol), N-chlorosuccinimide (3.70 g, 27.7 mmol), acetic acid (20 mL), and water (6 mL) was stirred for one hour at room temperature and concentrated. The resulting residue was purified via MPLC eluting with (1:10) ethyl acetate: petroleum ether to afford 5-chloro-2-ethoxypyridine-3-sulfonyl chloride (1.80 g, 98%) as a white solid.

Part IV—Synthesis of Methyl (S,E)-3-(4-((5-chloro-2-ethoxypyridin-3-yl)sulfonyl)-6-(2-(2-chloro-6-fluorophenyl)prop-1-en-1-yl)-3,4-dihydro-2H-benzo[b][1,4]oxazin-2-yl)propanoate

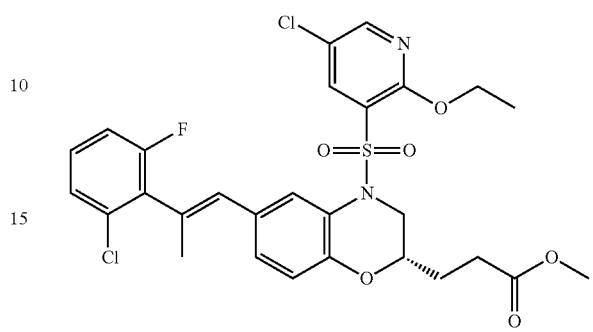

Using the method of 29, methyl (S,E)-3-(4-((5-chloro-2-ethoxypyridin-3-yl)sulfonyl)-6-(2-(2-chloro-6-fluorophenyl)prop-1-en-1-yl)-3,4-dihydro-2H-benzo[b][1,4]oxazin-2-yl)propanoate was prepared. $^{1}$H-NMR (400 MHz, CD$_{3}$OD) δ 8.40-8.36 (d, J=15.6 Hz 2H), 7.58 (s, 1H), 7.33-7.27 (m, 2H), 7.14-7.10 (m, 1H), 7.04-7.02 (d, J=8.4 Hz, 1H), 6.93-6.91 (d, J=8.4 Hz, 1H), 6.31 (s, 1H), 4.43-4.32 (m, 2H), 4.28-4.24 (d, J=14 Hz, 1H), 3.95 (s, 1H), 3.69 (s, 3H), 3.49-3.43 (m, 1H), 2.59-2.55 (t, J=6.8 Hz, 2H), 2.11 (s, 3H), 2.04-1.89 (m, 2H), 1.23-1.20 (t, J=7.2 Hz, 3H). (ES, m/z): (M+H)$^{+}$609.

Example 68—Synthesis of (S,E)-3-(4-((5-Chloro-2-ethoxypyridin-3-yl)sulfonyl)-6-(2-(2-chloro-6-fluorophenyl)prop-1-en-1-yl)-3,4-dihydro-2H-benzo[b][1,4]oxazin-2-yl)propanoic acid

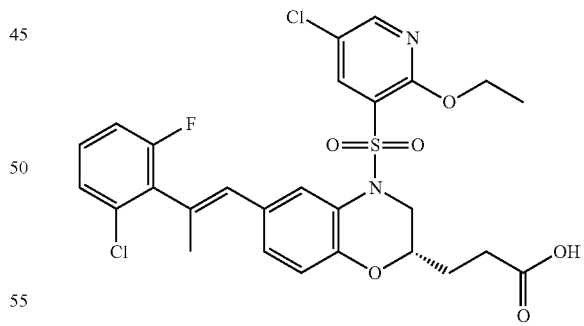

Based on the procedure in Example 42, (S,E)-3-(4-((5-chloro-2-ethoxypyridin-3-yl)sulfonyl)-6-(2-(2-chloro-6-fluorophenyl)prop-1-en-1-yl)-3,4-dihydro-2H-benzo[b][1,4]oxazin-2-yl)propanoic acid was prepared. $^{1}$H-NMR (300 MHz, CD$_{3}$OD) δ 8.39-8.36 (d, J=12.4 Hz, 2H), 7.58 (s, 1H), 7.33-7.27 (m, 2H), 7.14-7.10 (m, 1H), 7.04-7.02 (d, J=8.0 Hz, 1H), 6.95-6.93 (d, J=8.4 Hz, 1H), 6.31 (s, 1H), 4.45-4.34 (m, 2H), 4.30-4.26 (d, J=14 Hz, 1H), 3.98 (s, 1H), 3.49-3.43 (m, 1H), 2.55-2.52 (t, J=7.2 Hz, 2H), 2.11 (s, 3H), 2.03-1.88 (m, 2H), 1.39-1.28 (t, J=3.6 Hz, 3H). (ES, m/z): (M+H)$^{+}$595.

Example 69—Synthesis of Methyl (S,E)-3-(4-((5-chloro-2-(2-hydroxyethoxy)pyridin-3-yl)sulfonyl)-6-(2-(2-chloro-6-fluorophenyl)prop-1-en-1-yl)-3,4-dihydro-2H-benzo[b][1,4]oxazin-2-yl)propanoate

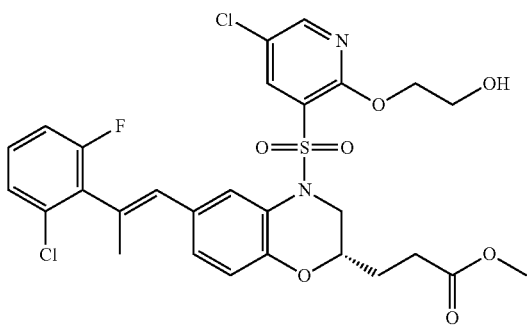

Part I—Synthesis of 2-((3-Bromo-5-chloropyridin-2-yl)oxy)ethan-1-ol

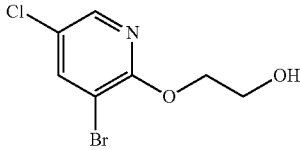 [SMILES: OCCOc1ncc(Cl)cc1Br]

A mixture of ethane-1,2-diol (3.72 g, 59.93 mmol), 3-bromo-2,5-dichloropyridine (2.47 g, 10.9 mmol), potassium hydroxide (1.22 g, 21.7 mmol), 1,4,7,10,13,16-hexaoxacyclooctadecane (1.15 g, 4.35 mmol), and toluene (50 mL) was stirred for four hours at 120° C. The mixture was cooled, and diluted with water. The mixture was extracted three times with dichloromethane. The combined organic layers were concentrated, and the resulting residue was purified by MPLC eluting with a gradient of 20-50% ethyl acetate in petroleum ether to afford 2-((3-bromo-5-chloropyridin-2-yl)oxy)ethan-1-ol (1.69 g, 61%) as a colorless oil.

Part II—Synthesis of 2-((3-(Benzylthio)-5-chloropyridin-2-yl)oxy)ethan-1-ol

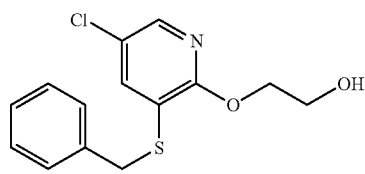 [SMILES: OCCOc1ncc(Cl)cc1SCc1ccccc1]

A mixture of 2-((3-bromo-5-chloropyridin-2-yl)oxy)ethan-1-ol (1.47 g, 5.82 mmol), phenylmethanethiol (0.69 mL, 11.64 mmol), N,N-diisopropylethyl amine (2 mL), 4,5-bis(diphenylphosphino)-9,9-dimethylxanthene (340 mg, 0.59 mmol), toluene (20 mL), and tris(dibenzylideneacetone)dipalladium(0) (270 mg, 0.29 mmol) was stirred for one hour at 110° C. The mixture was cooled, diluted with saturated sodium bicarbonate, and extracted three times with dichloromethane. The combined organic layers were concentrated, and the resulting residue was purified via MPLC eluting with a gradient of 20-50% ethyl acetate in petroleum ether to afford 2-((3-(benzylthio)-5-chloropyridin-2-yl)oxy)ethan-1-ol (1.57 g, 91%) as an oil.

Part III—Synthesis of 2-((3-(Benzylthio)-5-chloropyridin-2-yl)oxy)ethyl acetate

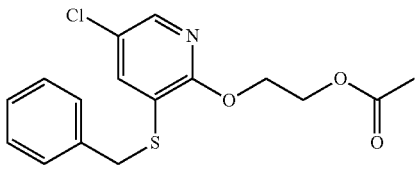

A mixture of 2-((3-(benzylthio)-5-chloropyridin-2-yl)oxy)ethan-1-ol (1.47 g, 4.97 mmol), dichloromethane (15 mL), pyridine (1 mL), acetic anhydride (1 mL), and 4-dimethylaminopyridine (60.6 mg, 0.50 mmol) was stirred overnight at room temperature. Saturated ammonium chloride was added and the mixture was extracted three times with dichloromethane. The combined organic layers were concentrated and the resulting residue was purified MPLC eluting with a gradient of 10-33% ethyl acetate in petroleum ether to afford 2-((3-(benzylthio)-5-chloropyridin-2-yl)oxy) ethyl acetate (1.75 g) as a yellow oil.

Part IV—Synthesis of 2-((5-Chloro-3-(chlorosulfonyl)pyridin-2-yl)oxy)ethyl acetate

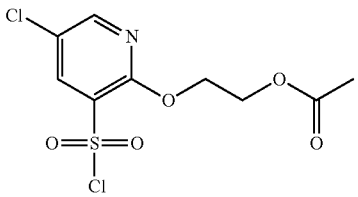 [SMILES: CC(=O)OCCOc1ncc(Cl)cc1S(=O)(=O)Cl]

A mixture of 2-((3-(benzylthio)-5-chloropyridin-2-yl)oxy)ethyl acetate (1.59 g, 4.71 mmol), acetic acid (10.4 mL), water (3.5 mL), and N-chlorosuccinimide (2.51 g, 18.80 mmol) was stirred for two hours at room temperature and then concentrated. The resulting residue was diluted with saturated sodium bicarbonate and extracted three times with dichloromethane. The combined organic layers were concentrated, and the resulting residue was purified by MPLC eluting with a gradient of 10-33% ethyl acetate in petroleum ether to afford 2-((5-chloro-3-(chlorosulfonyl)pyridin-2-yl) oxy)ethyl acetate (1.32 g, 89%) as a colorless oil.

269

Part V—Synthesis of Methyl (S,E)-3-(4-((2-(2-acetoxyethoxy)-5-chloropyridin-3-yl)sulfonyl)-6-(2-(2-chloro-6-fluorophenyl)prop-1-en-1-yl)-3,4-dihydro-2H-benzo[b][1,4]oxazin-2-yl)propanoate

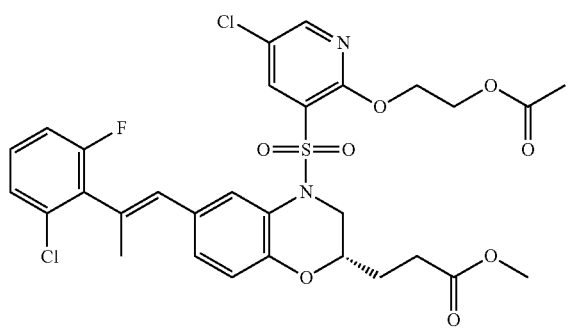 [SMILES: COC(=O)CC[C@H]1CN(S(=O)(=O)c2cc(Cl)cnc2OCCOC(C)=O)c2cc(/C=C(\C)c3c(F)cccc3Cl)ccc2O1]

A mixture of (S,E)-methyl 3-(6-(2-(2-chloro-6-fluorophenyl)prop-1-en-1-yl)-3,4-dihydro-2H-benzo[b][1,4]oxazin-2-yl)propanoate (730 mg, 1.87 mmol), dichloromethane (9.4 mL), pyridine (0.75 mL, 9.35 mmol), 4-dimethylaminopyridine (114.2 mg, 0.93 mmol), and 2-((5-chloro-3-(chlorosulfonyl)pyridin-2-yl)oxy)ethyl acetate (705.3 mg, 2.25 mmol) was stirred overnight at room temperature. The reaction mixture was diluted with brine and extracted three times with dichloromethane. The combined organic layers were concentrated and the resulting residue was purified by MPLC eluting with a gradient of 20-50% ethyl acetate in petroleum ether to afford methyl (S,E)-3-(4-((2-(2-acetoxyethoxy)-5-chloropyridin-3-yl)sulfonyl)-6-(2-(2-chloro-6-fluorophenyl)prop-1-en-1-yl)-3,4-dihydro-2H-benzo[b][1,4]oxazin-2-yl)propanoate (1.05 g, 84%) as a yellow oil.

Part VI—Synthesis of Methyl (S,E)-3-(4-((5-chloro-2-(2-hydroxyethoxy)pyridin-3-yl)sulfonyl)-6-(2-(2-chloro-6-fluorophenyl)prop-1-en-1-yl)-3,4-dihydro-2H-benzo[b][1,4]oxazin-2-yl)propanoate

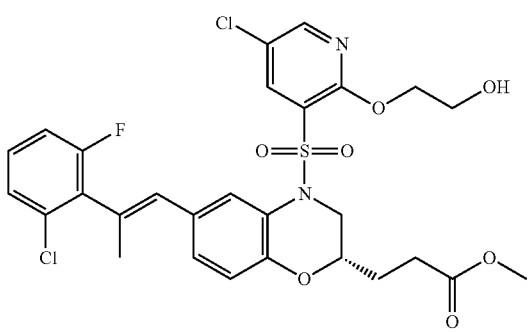

A mixture of methyl (S,E)-3-(4-((2-(2-acetoxyethoxy)-5-chloropyridin-3-yl)sulfonyl)-6-(2-(2-chloro-6-fluorophenyl)prop-1-en-1-yl)-3,4-dihydro-2H-benzo[b][1,4]oxazin-2-yl)propanoate (319 mg, 0.48 mmol), methanol (0.5 mL), dichloromethane (0.5 mL), and sodium methoxide (52 mg, 0.96 mmol) was stirred for thirty minutes at room temperature. The pH value of the solution was adjusted to 1 with 1M hydrogen chloride and concentrated. The resulting residue was purified via MPLC eluting with a gradient of 33-66% ethyl acetate in petroleum ether to afford methyl (S,E)-3-

270

(4-((5-chloro-2-(2-hydroxyethoxy)pyridin-3-yl)sulfonyl)-6-(2-(2-chloro-6-fluorophenyl)prop-1-en-1-yl)-3,4-dihydro-2H-benzo[b][1,4]oxazin-2-yl)propanoate as a white solid. $^1$H-NMR (300 MHz, CD$_3$OD) δ 1.92-2.06 (m, 2H), 2.13 (s, 3H), 2.59 (t, J=6.9 Hz, 2H), 3.44 (dd, J=9.0 Hz, 13.8 Hz, 1H), 3.70 (s, 3H), 3.74-3.83 (m, 2H), 4.00-4.03 (m, 1H), 4.34 (dd, J=2.4 Hz, 13.8 Hz, 1H), 4.51-4.52 (m, 2H), 6.33 (s, 1H), 6.88 (d, J=8.4 Hz, 1H), 6.98-7.05 (m, 2H), 7.14-7.24 (m, 2H), 7.57 (d, J=1.8 Hz, 1H), 8.29 (dd, J=2.4 Hz, 9.0 Hz, 2H). (ES, m/z): (M+H)$^+$625.

Example 70—Synthesis of (S,E)-3-(4-((5-Chloro-2-(2-hydroxyethoxy)pyridin-3-yl)sulfonyl)-6-(2-(2-chloro-6-fluorophenyl)prop-1-en-1-yl)-3,4-dihydro-2H-benzo[b][1,4]oxazin-2-yl)propanoic acid

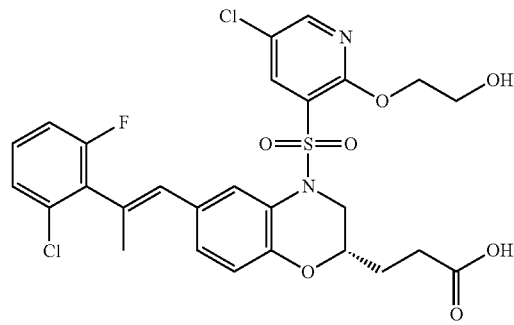

Based on the procedure in Example 42, (S,E)-3-(4-((5-chloro-2-(2-hydroxyethoxy)pyridin-3-yl)sulfonyl)-6-(2-(2-chloro-6-fluorophenyl)prop-1-en-1-yl)-3,4-dihydro-2H-benzo[b][1,4]oxazin-2-yl)propanoic acid was prepared. $^1$H-NMR (300 MHz, CDCl$_3$) δ 1.92-2.01 (m, 2H), 2.13 (s, 3H), 2.54-2.74 (m, 2H), 3.44 (dd, J=9.6 Hz, 12.0 Hz, 1H), 3.81 (brs, 2H), 4.01-4.06 (m, 1H), 4.33-4.38 (m, 1H), 4.51 (brs, 1H), 6.33 (s, 1H), 6.89 (d, J=8.7 Hz, 1H), 6.94-7.05 (m, 2H), 7.14-7.23 (m, 2H), 7.55 (s, 1H), 8.25-8.28 (m, 2H). (ES, m/z): (M+H)$^+$611.

Example 71—Synthesis of (S,E)-3-(6-(2-(2-Chloro-6-fluorophenyl)prop-1-en-1-yl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid

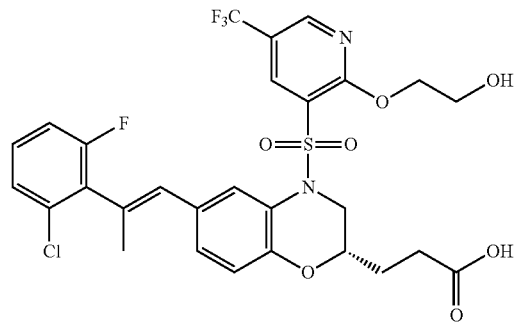

Part I—Synthesis of 2-((3-Bromo-5-(trifluoromethyl)pyridin-2-yl)oxy)ethan-1-ol

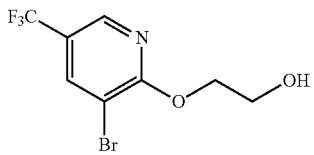 [SMILES: OCCOc1ncc(C(F)(F)F)cc1Br]

A mixture of ethane-1,2-diol (40 mL), 3-bromo-2-chloro-5-(trifluoromethyl)-pyridine (4.0 g, 15.44 mmol), potassium carbonate (6.4 g, 46.31 mmol), and DMF (80 mL) was stirred for three hours at 50° C. The mixture was allowed to cool and diluted with water. The mixture was concentrated and the resulting residue was purified by MPLC eluting 20% ethyl acetate in petroleum ether to afford 2-((3-bromo-5-(trifluoromethyl)pyridin-2-yl)oxy)ethan-1-ol (4.0 g, 91%) as a colorless oil.

Part II—Synthesis of 2-((3-(Benzylthio)-5-(trifluoromethyl)pyridin-2-yl)oxy)ethan-1-ol

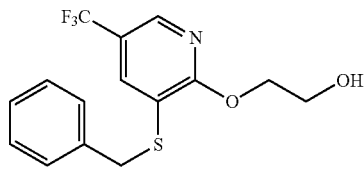 [SMILES: OCCOc1ncc(C(F)(F)F)cc1SCc1ccccc1]

A mixture of 2-((3-bromo-5-(trifluoromethyl)pyridin-2-yl)oxy)ethan-1-ol (4.0 g, 14.0 mmol), phenylmethanethiol (1.83 g, 14.8 mmol), N,N-diisopropylethyl amine (3.6 g, 27.9 mmol), 4,5-bis(diphenylphosphino)-9,9-dimethylxanthene (810 mg, 1.40 mmol), toluene (50 mL), and tris(dibenzylideneacetone)dipalladium(0) (1.28 g, 1.40 mmol) was stirred overnight at 110° C. The mixture was cooled, concentrated, and the resulting residue was purified via MPLC eluting with 20% ethyl acetate in petroleum ether to afford 2-((3-(benzylthio)-5-(trifluoromethyl)pyridin-2-yl)oxy)ethan-1-ol (4.16 g, 90%) as an oil.

Part III—Synthesis of 2-((3-(Benzylthio)-5-(trifluoromethyl)pyridin-2-yl)oxy)ethyl acetate

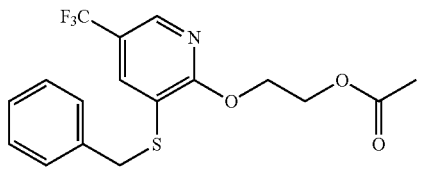 [SMILES: CC(=O)OCCOc1ncc(C(F)(F)F)cc1SCc1ccccc1]

A mixture of 2-((3-(benzylthio)-5-(trifluoromethyl)pyridin-2-yl)oxy)ethan-1-ol (4.0 g, 12.1 mmol), pyridine (40 mL), acetic anhydride (1.86 g, 18.2 mmol), and 4-dimethylaminopyridine (740 mg, 6.06 mmol) was stirred for two hours at room temperature. The mixture was concentrated and the resulting residue was purified MPLC eluting with 20% ethyl acetate in petroleum ether to afford 2-((3-(benzylthio)-5-(trifluoromethyl)pyridin-2-yl)oxy)ethyl acetate (4.0 g, 89%) as a yellow oil.

Part IV—Synthesis of 2-((3-(Chlorosulfonyl)-5-(trifluoromethyl)pyridin-2-yl)oxy)ethyl acetate

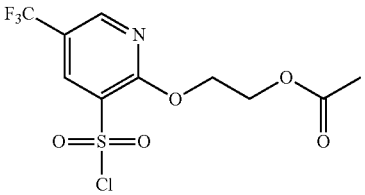 [SMILES: CC(=O)OCCOc1ncc(C(F)(F)F)cc1S(=O)(=O)Cl]

A mixture of 2-((3-(benzylthio)-5-(trifluoromethyl)pyridin-2-yl)oxy)ethyl acetate (4.0 g, 10.7 mmol), acetic acid (40 mL), water (10 mL), and N-chlorosuccinimide (5.70 g, 42.7 mmol) was stirred for two hours at room temperature and then concentrated. The resulting residue was diluted with saturated sodium bicarbonate and extracted three times with dichloromethane. The combined organic layers were concentrated, and the resulting residue was purified by MPLC eluting with 20% ethyl acetate in petroleum ether to afford 2-((3-(chlorosulfonyl)-5-(trifluoromethyl)pyridin-2-yl)oxy)ethyl acetate (2.0 g, 53%) as a colorless oil.

Part V—Synthesis of Methyl (S,E)-3-(4-((2-(2-acetoxyethoxy)-5-(trifluoromethyl)pyridin-3-yl)sulfonyl)-6-(2-(2-chloro-6-fluorophenyl)prop-1-en-1-yl)-3,4-dihydro-2H-benzo[b][1,4]oxazin-2-yl)propanoate

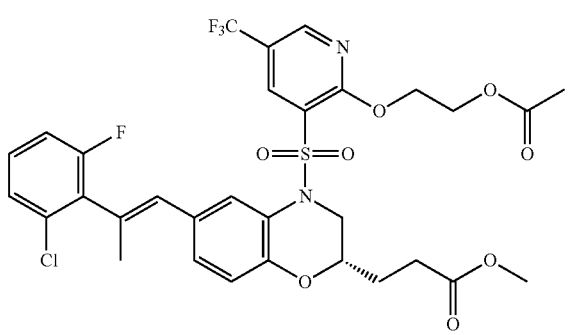 [SMILES: COC(=O)CC[C@H]1CN(S(=O)(=O)c2cc(C(F)(F)F)cnc2OCCOC(C)=O)c2cc(/C=C(\C)c3c(F)cccc3Cl)ccc2O1]

A mixture of (S,E)-methyl 3-(6-(2-(2-chloro-6-fluorophenyl)prop-1-en-1-yl)-3,4-dihydro-2H-benzo[b][1,4]oxazin-2-yl)propanoate (500 mg, 1.28 mmol), pyridine (5.0 mL), 4-dimethylaminopyridine (78 mg, 0.64 mmol), 2-((3-(chlorosulfonyl)-5-(trifluoromethyl)pyridin-2-yl)oxy)ethyl acetate (669 mg, 1.92 mmol) was stirred for two hours at room temperature. The mixture was concentrated and the resulting residue was purified by MPLC eluting with 20% ethyl acetate in petroleum ether to afford methyl (S,E)-3-(4-((2-(2-acetoxyethoxy)-5-(trifluoromethyl)pyridin-3-yl)sulfonyl)-6-(2-(2-chloro-6-fluorophenyl)prop-1-en-1-yl)-3,4-dihydro-2H-benzo[b][1,4]oxazin-2-yl)propanoate (260 mg, 29%) as a yellow oil.

Part VI—Synthesis of (S,E)-3-(6-(2-(2-Chloro-6-fluorophenyl)prop-1-en-1-yl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid

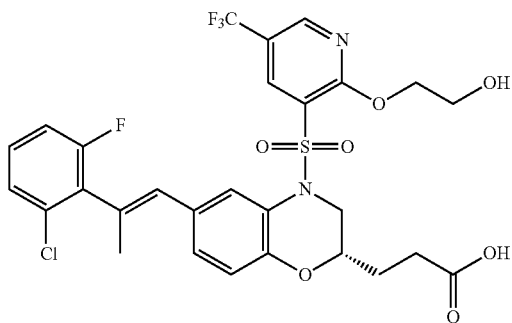

A mixture of methyl (S,E)-3-(4-((2-(2-acetoxyethoxy)-5-(trifluoromethyl)pyridin-3-yl)sulfonyl)-6-(2-(2-chloro-6-fluorophenyl)prop-1-en-1-yl)-3,4-dihydro-2H-benzo[b][1,4]oxazin-2-yl)propanoate (200 mg, 0.29 mmol), lithium hydroxide (36 mg, 0.86 mmol), tetrahydrofuran (3 mL), and water (1 mL) was stirred for two hours at room temperature. The mixture was filtered. The solids were purified by Prep-HPLC eluting with a gradient of 61-71% acetonitrile in water with 0.05% trifluoroacetic acid to afford (S,E)-3-(6-(2-(2-chloro-6-fluorophenyl)prop-1-en-1-yl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid (36 mg, 20%) as a white solid. $^1$H-NMR (300 MHz, CD$_3$OD) δ 8.89 (s, 1H), 8.75 (s, 1H), 7.44 (s, 1H), 7.30-7.33 (m, 2H), 7.10-7.13 (m, 1H), 7.01-7.03 (m, 1H), 6.93-6.95 (m, 1H), 4.56-4.79 (m, 2H), 4.42-4.54 (m, 1H), 4.11 (s, 1H), 3.78-3.82 (m, 2H), 3.60-3.66 (m, 1H), 2.55-2.78 (m, 2H), 1.93-2.07 (m, 5H). (ES, m/z): (M+H)$^+$645.

Example 72—Synthesis of Methyl (S,E)-3-(6-(2-(2-chloro-6-fluorophenyl)prop-1-en-1-yl)-4-((5-ethoxy-2-ethylthiazol-4-yl)sulfonyl)-3,4-dihydro-2H-benzo[b][1,4]oxazin-2-yl)propanoate

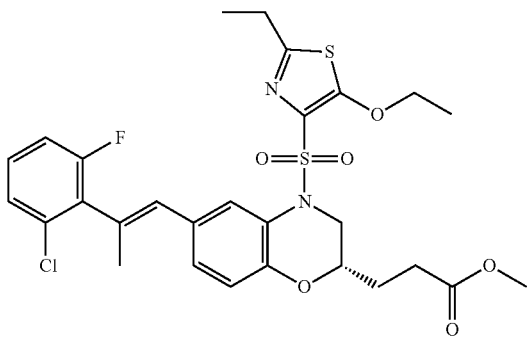 [SMILES: CCOc1sc(CC)nc1S(=O)(=O)N1C[C@H](CCC(=O)OC)Oc2ccc(/C=C(\C)c3c(F)cccc3Cl)cc21]

Part I—Synthesis of 5-Ethoxy-2-ethylthiazole

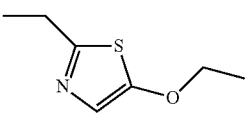

A solution of ethyl 2-propanamidoacetate (6 g, 37.69 mmol) in dioxane (150 mL) and phosphorous pentasulfide (17 g, 76.48 mmol) was stirred overnight at 60° C. The reaction was then quenched by the addition of 2 M sodium hydroxide (50 mL). The mixture was extracted three times with dichloromethane. The combined organic layers were dried (Na$_2$SO$_4$) and concentrated. The resulting residue was purified by MPLC eluting with a 40% ether in petroleum ether to afford 5-ethoxy-2-ethylthiazole (800 mg, 13%) as a yellow oil.

Part II—Synthesis of 5-Ethoxy-2-ethylthiazole-4-sulfonic acid

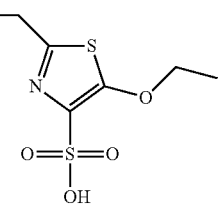

Sulfonoperoxoyl chloride (1.1 g, 9.44 mmol) was added dropwise to a stirred solution of 5-ethoxy-2-ethyl-1,3-thiazole (300 mg, 1.91 mmol) in chloroform (5 mL) at room temperature. The resulting solution was stirred for two hours at 60° C. The resulting mixture was concentrated to afford 5-ethoxy-2-ethylthiazole-4-sulfonic acid (310 mg, 68%) of 5-ethoxy-2-ethyl-1,3-thiazole-4-sulfonic acid as yellow oil.

Part III—Synthesis of 5-Ethoxy-2-ethylthiazole-4-sulfonyl chloride

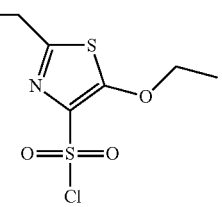

A mixture of 5-ethoxy-2-ethyl-1,3-thiazole-4-sulfonic acid (2.7 g, 11 mmol) and thionyl chloride (20 mL, 56 mmol) was stirred for two hours at 78° C. The reaction was then quenched by the addition of ice water (100 mL). The mixture was extracted twice with dichloromethane. The combined organic layers were dried (Na$_2$SO$_4$) and concentrated. The resulting residue was purified by MPLC eluting with 3:1 ether:petroleum ether to afford 5-ethoxy-2-ethylthiazole-4-sulfonyl chloride (260 mg, 9%) as a brown solid.

Part IV—Synthesis of Methyl (S,E)-3-(6-(2-(2-chloro-6-fluorophenyl)prop-1-en-1-yl)-4-((5-ethoxy-2-ethylthiazol-4-yl)sulfonyl)-3,4-dihydro-2H-benzo[b][1,4]oxazin-2-yl)propanoate

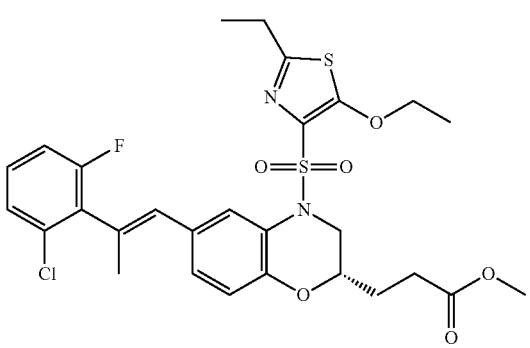 [SMILES: CCOc1sc(CC)nc1S(=O)(=O)N1C[C@H](CCC(=O)OC)Oc2ccc(/C=C(\C)c3c(F)cccc3Cl)cc21]

Using the method of Example 29, methyl (S,E)-3-(6-(2-(2-chloro-6-fluorophenyl)prop-1-en-1-yl)-4-((5-ethoxy-2-ethylthiazol-4-yl)sulfonyl)-3,4-dihydro-2H-benzo[b][1,4]oxazin-2-yl)propanoate was prepared. $^1$H-NMR (300 MHz, CD$_3$OD) δ 7.80 (s, 1H), 7.29-7.31 (m, 2H), 7.10-7.15 (m, 1H), 7.05 (d, J=7.8 Hz, 1H), 6.87 (d, J=8.4 Hz, 1H), 6.30 (s, 1H), 4.37-4.41 (m, 1H), 4.18-4.22 (m, 1H), 4.05-4.18 (m, 2H), 3.72 (s, 3H), 3.33-3.34 (m, 2H), 2.85-2.91 (m, 2H), 2.57-2.61 (m, 2H), 2.17 (s, 3H), 1.92-2.02 (m, 2H), 1.27-1.36 (m, 6H). (ES, m/z): (M+H)$^+$609.

Example 73—Synthesis of (S,E)-3-(6-(2-(2-Chloro-6-fluorophenyl)prop-1-en-1-yl)-4-((5-ethoxy-2-ethylthiazol-4-yl)sulfonyl)-3,4-dihydro-2H-benzo[b][1,4]oxazin-2-yl)propanoic acid

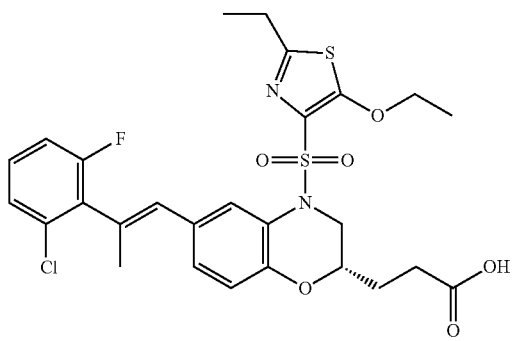 [SMILES: CCOc1sc(CC)nc1S(=O)(=O)N1C[C@H](CCC(=O)O)Oc2ccc(/C=C(\C)c3c(F)cccc3Cl)cc21]

Based on the procedure in Example 42, (S,E)-3-(6-(2-(2-chloro-6-fluorophenyl)prop-1-en-1-yl)-4-((5-ethoxy-2-ethylthiazol-4-yl)sulfonyl)-3,4-dihydro-2H-benzo[b][1,4]oxazin-2-yl)propanoic acid was prepared. $^1$H-NMR (400 MHz, CD$_3$OD) δ 7.78 (s, 1H), 7.24-7.29 (m, 2H), 7.03-7.13 (m, 2H), 7.05 (d, J=8 Hz, 1H), 6.87 (d, J=8.4 Hz, 1H), 6.30 (s, 1H), 4.37-4.41 (m, 1H), 4.04-4.22 (m, 3H), 3.33-3.34 (m, 1H), 2.82-2.91 (m, 2H), 2.57-2.61 (m, 2H), 2.16 (s, 3H), 1.92-2.02 (m, 2H), 1.27-1.36 (m, 6H). (ES, m/z): (M+H)$^+$ 595.

Example 74—Synthesis of Methyl (S,E)-3-(6-(2-(2-chloro-6-fluorophenyl)prop-1-en-1-yl)-4-((5-(trifluoromethyl)pyridin-3-yl)sulfonyl)-3,4-dihydro-2H-benzo[b][1,4]oxazin-2-yl)propanoate

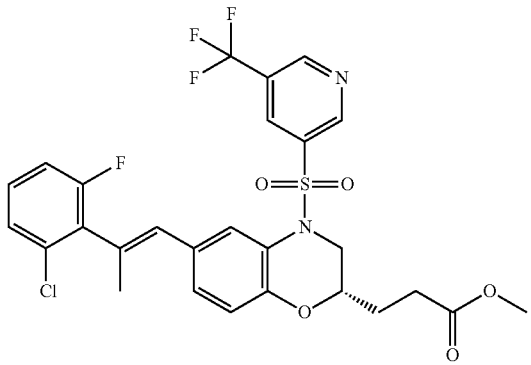 [SMILES: COC(=O)CC[C@H]1CN(S(=O)(=O)c2cncc(C(F)(F)F)c2)c2cc(/C=C(\C)c3c(F)cccc3Cl)ccc2O1]

Part I—Synthesis of 3-(Benzylthio)-5-(trifluoromethyl)pyridine

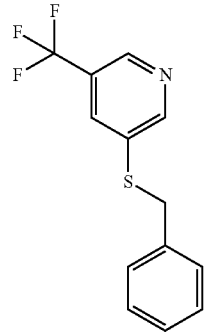 [SMILES: FC(F)(F)c1cncc(SCc2ccccc2)c1]

A mixture of 3-bromo-5-(trifluoromethyl)pyridine (586 mg, 2.59 mmol), phenylmethanethiol (0.31 mL, 2.59 mmol), toluene (8.9 mL), N,N-diisopropylethyl amine (0.89 mL, 5.12 mmol), tris(dibenzylideneacetone)dipalladium(0) (118.3 mg, 0.13 mmol), 4,5-bis(diphenylphosphino)-9,9-dimethylxanthene (148.9 mg, 0.26 mmol) was stirred for two hours at 110° C. The mixture was diluted aqueous sodium bicarbonate and extracted three times with dichloromethane. The combined organic layers were dried (Na$_2$SO$_4$) and concentrated. The resulting residue was purified by MPLC eluting with a gradient of 5-20% ethyl acetate in petroleum ether to afford 3-(benzylthio)-5-(trifluoromethyl)pyridine (960 mg) as a yellow oil.

Part II—Synthesis of 5-(Trifluoromethyl)pyridine-3-sulfonyl chloride

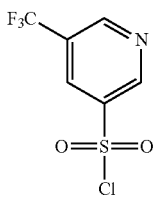 [SMILES: O=S(=O)(Cl)c1cncc(C(F)(F)F)c1]

A solution of 3-(benzylthio)-5-(trifluoromethyl)pyridine (610 mg, 2.27 mmol), acetic acid (5 mL), water (1.7 mL), and N-chlorosuccinimide (1.21 g, 9.06 mmol) was stirred for one hour at room temperature. The mixture was concentrated and the resulting residue was purified by MPLC eluting with a gradient of 5-20% ethyl acetate in petroleum ether to afford 5-(trifluoromethyl)pyridine-3-sulfonyl chloride (202 mg, 36%) as a colorless oil.

Part III—Synthesis of Methyl (S,E)-3-(6-(2-(2-chloro-6-fluorophenyl)prop-1-en-1-yl)-4-((5-(trifluoromethyl)pyridin-3-yl)sulfonyl)-3,4-dihydro-2H-benzo[b][1,4]oxazin-2-yl)propanoate

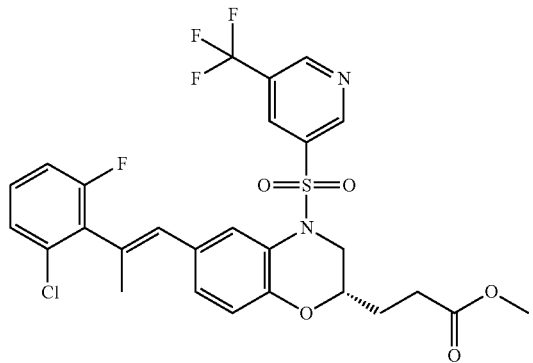 [SMILES: COC(=O)CC[C@H]1CN(S(=O)(=O)c2cncc(C(F)(F)F)c2)c2cc(/C=C(\C)c3c(F)cccc3Cl)ccc2O1]

Using the method of Example 29, methyl (S,E)-3-(6-(2-(2-chloro-6-fluorophenyl)prop-1-en-1-yl)-4-((5-(trifluoromethyl)pyridin-3-yl)sulfonyl)-3,4-dihydro-2H-benzo[b][1,4]oxazin-2-yl)propanoate was prepared. $^1$H-NMR (400 MHz, CDCl$_3$) δ 1.78-1.90 (m, 1H), 1.91-1.98 (m, 1H), 2.20 (s, 3H), 2.52 (t, J=7.2 Hz, 2H), 3.29 (dd, J=10.0 Hz, 14.4 Hz, 1H), 3.65-3.68 (m, 1H), 3.71 (s, 3H), 4.40 (dd, J=2.4 Hz, 14.0 Hz, 1H), 6.41 (s, 1H), 6.85 (d, J=8.4 Hz, 1H), 7.05 (t, J=9.2 Hz, 1H), 7.15-7.25 (m, 3H), 7.85 (s, 1H), 8.24 (s, 1H), 9.07 (s, 1H). (ES, m/z): (M+H)$^+$599.

Example 75—Synthesis of (S,E)-3-(6-(2-(2-Chloro-6-fluorophenyl)prop-1-en-1-yl)-4-((5-(trifluoromethyl)pyridin-3-yl)sulfonyl)-3,4-dihydro-2H-benzo[b][1,4]oxazin-2-yl)propanoic acid

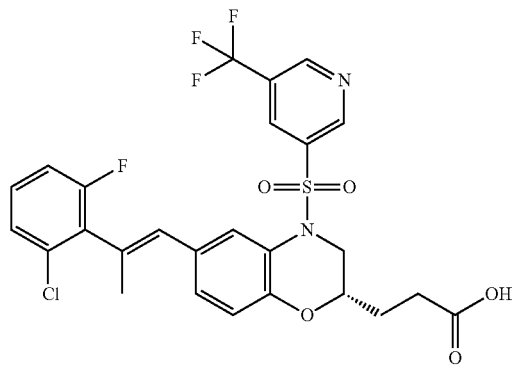 [SMILES: C/C(=C\c1ccc2c(c1)N(S(=O)(=O)c1cncc(C(F)(F)F)c1)C[C@H](CCC(=O)O)O2)c1c(F)cccc1Cl]

Based on the procedure in Example 42, (S,E)-3-(6-(2-(2-chloro-6-fluorophenyl)prop-1-en-1-yl)-4-((5-(trifluoromethyl)pyridin-3-yl)sulfonyl)-3,4-dihydro-2H-benzo[b][1,4]oxazin-2-yl)propanoic acid was prepared. $^1$H-NMR (300 MHz, CD$_3$OD) δ 1.80-1.85 (m, 1H), 1.93-1.98 (m, 1H), 2.18 (s, 3H), 2.45-2.50 (m, 2H), 3.32-3.41 (m, 1H), 3.62-3.64 (m, 1H), 4.52 (dd, J=2.4 Hz, 14.4 Hz, 1H), 6.40 (s, 1H), 6.91 (d, J=8.4 Hz, 1H), 7.12-7.18 (m, 2H), 7.31-7.33 (m, 2H), 7.86 (d, J=1.6 Hz, 1H), 8.37 (s, 1H), 9.12 (d, J=2.0 Hz, 1H), 9.17 (s, 1H). (ES, m/z): (M+H)$^+$585.

Example 76—Synthesis of Methyl (S,E)-3-(6-(2-(2-chloro-6-(trifluoromethyl)phenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoate

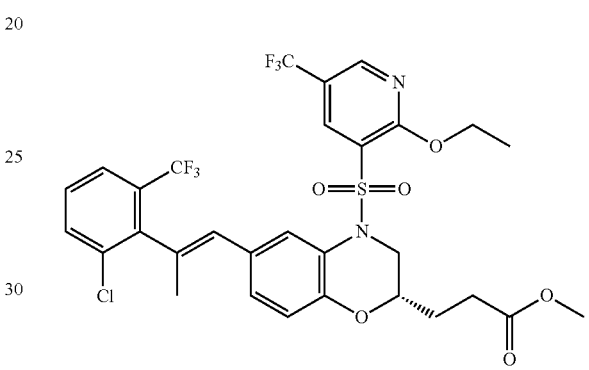

Part I—Synthesis of Methyl (S,Z)-3-(6-(2-(4,4,5,5-tetramethyl-1,3,2-dioxaborolan-2-yl)prop-1-en-1-yl)-3,4-dihydro-2H-benzo[b][1,4]oxazin-2-yl)propanoate

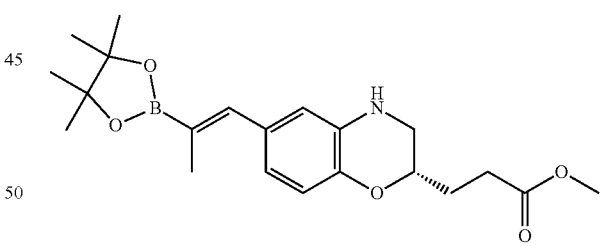

A mixture of methyl (S)-3-(6-bromo-3,4-dihydro-2H-benzo[b][1,4]oxazin-2-yl)propanoate (1 g, 3.33 mmol), 4,4,5,5-tetramethyl-2-(prop-1-en-2-yl)-1,3,2-dioxaborolane (672 mg, 4.00 mmol), tri-tert-butylphosphonium tetrafluoroborate (0.23 g, 0.83 mmol), tris(dibenzylideneacetone)dipalladium(0) (150 mg, 0.16 mmol), triethylamine (1.7 g, 16.8 mmol), and toluene (20 mL) was stirred overnight at 80° C. The mixture was concentrated and the resulting residue was purified by MPLC eluting with 20% ethyl acetate in petroleum ether to afford methyl (S,Z)-3-(6-(2-(4,4,5,5-tetramethyl-1,3,2-dioxaborolan-2-yl)prop-1-en-1-yl)-3,4-dihydro-2H-benzo[b][1,4]oxazin-2-yl)propanoate (0.8 g, 62%) as a yellow oil.

Part II—Synthesis of Methyl (S,E)-3-(6-(2-(2-chloro-6-(trifluoromethyl)phenyl)prop-1-en-1-yl)-3,4-dihydro-2H-benzo[b][1,4]oxazin-2-yl)propanoate

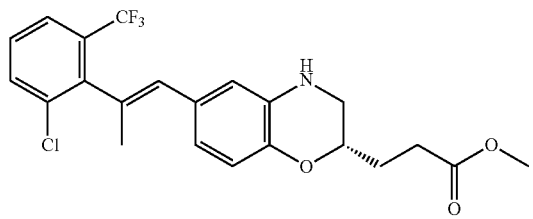 [SMILES: COC(=O)CC[C@H]1CNc2cc(/C=C(\C)c3c(Cl)cccc3C(F)(F)F)ccc2O1]

A mixture of methyl (S,Z)-3-(6-(2-(4,4,5,5-tetramethyl-1,3,2-dioxaborolan-2-yl)prop-1-en-1-yl)-3,4-dihydro-2H-benzo[b][1,4]oxazin-2-yl)propanoate (1 g, 2.58 mmol), 2-bromo-1-chloro-3-(trifluoromethyl)benzene (1 g, 3.85 mmol), sodium carbonate (800 mg, 7.48 mmol), tetrakis(triphenylphosphine)palladium(0) (300 mg, 0.26 mmol), toluene (20 mL), methanol (10 mL) and water (5 mL) was stirred overnight at 90° C. The mixture was diluted with water, and extracted twice with dichloromethane. The combined organic layers were dried (Na₂SO₄) and concentrated. The resulting residue was purified via MPLC eluting with 20% ethyl acetate in petroleum ether to afford methyl (S,E)-3-(6-(2-(2-chloro-6-(trifluoromethyl)phenyl)prop-1-en-1-yl)-3,4-dihydro-2H-benzo[b][1,4]oxazin-2-yl)propanoate (250 mg, 22%) as a colorless oil.

Part III—Synthesis of Methyl (S,E)-3-(6-(2-(2-chloro-6-(trifluoromethyl)phenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoate

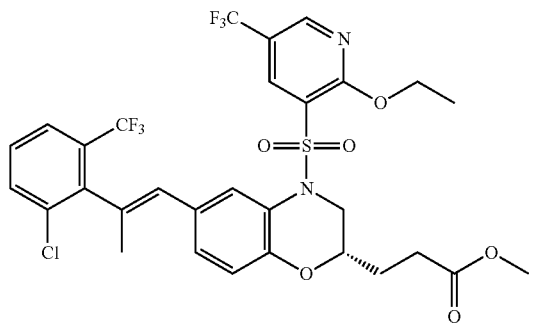 [SMILES: CCOc1ncc(C(F)(F)F)cc1S(=O)(=O)N1C[C@H](CCC(=O)OC)Oc2ccc(/C=C(\C)c3c(Cl)cccc3C(F)(F)F)cc21]

Based on the procedure in Example 29, methyl (S,E)-3-(6-(2-(2-chloro-6-(trifluoromethyl)phenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoate was prepared. ¹H-NMR (300 MHz, CD₃OD) δ 8.75 (s, 1H), 8.56 (d, J=2.0 Hz, 1H), 7.72 (m, 2H), 7.57 (m, 1H), 7.48 (m, 1H), 7.02 (m, 1H), 6.93 (m, 1H), 6.21 (s, 1H), 4.48 (m, 2H), 4.29 (m, 1H), 3.94 (m, 2H), 3.68 (s, 3H), 3.48 (m, 1H), 2.56 (m, 2H), 2.10 (s, 3H), 1.20-1.92 (m, 2H), 1.25-1.21 (m, 3H). (ES, m/z): (M+H)⁺693.

Example 77-Synthesis of (S,E)-3-(6-(2-(2-Chloro-6-(trifluoromethyl)phenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoic acid

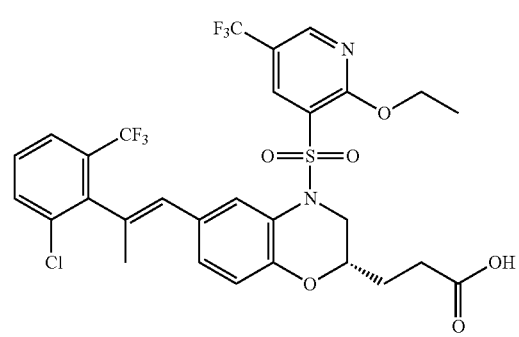 [SMILES: CCOc1ncc(C(F)(F)F)cc1S(=O)(=O)N1C[C@H](CCC(=O)O)Oc2ccc(/C=C(\C)c3c(Cl)cccc3C(F)(F)F)cc21]

Based on the procedure in Example 42, (S,E)-3-(6-(2-(2-chloro-6-(trifluoromethyl)phenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)propanoic acid was prepared. ¹H-NMR (300 MHz, CD₃OD) δ 8.74 (s, 1H), 8.56 (d, J=2.0 Hz, 1H), 7.72 (m, 2H), 7.57 (m, 1H), 7.48 (m, 1H), 7.02 (m, 1H), 6.93 (m, 1H), 6.21 (s, 1H), 4.54-4.45 (m, 2H), 4.31 (m, 1H), 3.96 (m, 2H), 3.48 (m, 1H), 2.53 (t, J=7.2 Hz, 2H), 2.10 (s, 3H), 1.99-1.89 (m, 2H), 1.24 (m, 3H). (ES, m/z): (M+H)⁺679.

Example 78—Synthesis of Methyl 3-((S)-6-((E)-2-chloro-6-fluorostyryl)-4-((2-((R)-2-hydroxypropoxy)-5-(trifluoromethyl)pyridin-3-yl)sulfonyl)-3,4-dihydro-2H-benzo[b][1,4]oxazin-2-yl)propanoate

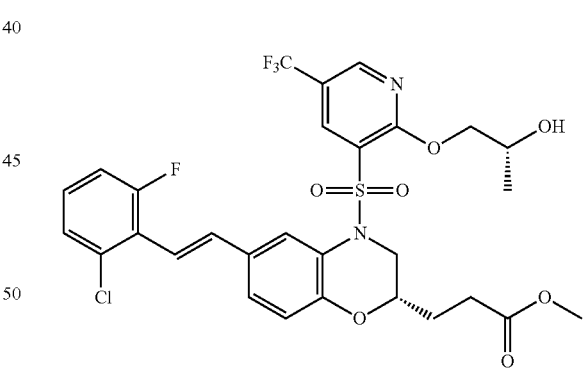

Part I—Synthesis of Methyl (R)-2-((tert-butyldimethylsilyl)oxy)propanoate

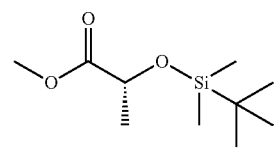

A mixture of methyl (R)-2-hydroxypropanoate (5.1 g, 48.99 mmol), dichloromethane (50 mL), imidazole (5 g, 75 mmol) and tert-butyldimethylsilyl chloride (8.85 g) was stirred for two hours at room temperature. The mixture was diluted with water and extracted three times with dichloromethane. The combined organic layers were dried (Na$_2$SO$_4$) and concentrated. The resulting residue was purified by MPLC eluting with 5% ethyl acetate in petroleum ether to afford methyl (R)-2-((tert-butyldimethylsilyl)oxy)propanoate (10.67 g, 100%) as a colorless oil.

Part II—Synthesis of (R)-2-((tert-Butyldimethylsilyl)oxy)propan-1-ol

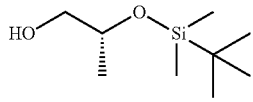

Lithium borohydride (4.04 g, 185 mmol) was added to a solution of methyl (R)-2-((tert-butyldimethylsilyl)oxy)propanoate (10.12 g, 46.34 mmol) in tetrahydrofuran (60 mL). The resulting solution was stirred for four hours at room temperature. Saturated ammonium chloride was added and the pH of the mixture was adjusted to 1 with 1 M hydrogen chloride. The mixture was extracted three times with dichloromethane and the organic layers were combined, dried (Na$_2$SO$_4$), and concentrated. The resulting residue was purified via MPLC eluting with 10% ethyl acetate in petroleum ether to afford (R)-2-((tert-butyldimethylsilyl)oxy)propan-1-ol (8.45 g, 96%) as a colorless oil.

Part III—Synthesis of (R)-3-Bromo-2-(2-((tert-butyldimethylsilyl)oxy)propoxy)-5-(trifluoromethyl)pyridine

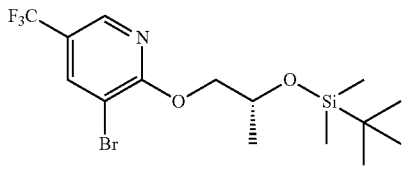 [SMILES: C[C@H](COc1ncc(C(F)(F)F)cc1Br)O[Si](C)(C)C(C)(C)C]

Sodium hydride (2.49 g, 62.25 mmol, 60% in mineral oil) was added to a solution of (R)-2-((tert-butyldimethylsilyl)oxy)propan-1-ol (8.45 g, 44.39 mmol) in tetrahydrofuran (44.5 mL) at 0° C. The mixture was stirred for twenty min., and 3-bromo-2-chloro-5-(trifluoromethyl)pyridine (3.7 g, 14.21 mmol) was then added to the reaction mixture. The resulting solution was stirred overnight at room temperature, diluted with brine, and extracted three times with dichloromethane. The combined organic layers were dried (Na$_2$SO$_4$), concentrated, and the resulting residue was purified by MPLC eluting with a gradient of 1-5% ethyl acetate in petroleum ether to afford (R)-3-bromo-2-(2-((tert-butyldimethylsilyl)oxy)propoxy)-5-(trifluoromethyl)pyridine (7.79 g) as a colorless oil.

Part IV—Synthesis of (R)-3-(Benzylthio)-2-(2-((tert-butyldimethylsilyl)oxy)propoxy)-5-(trifluoromethyl)pyridine

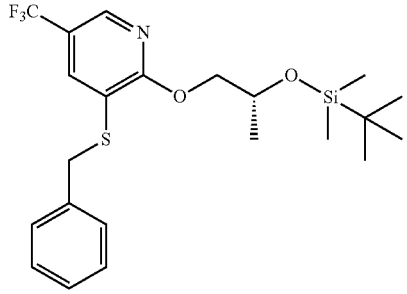 [SMILES: C[C@H](COc1ncc(C(F)(F)F)cc1SCc1ccccc1)O[Si](C)(C)C(C)(C)C]

A mixture of (R)-3-bromo-2-(2-((tert-butyldimethylsilyl)oxy)propoxy)-5-(trifluoromethyl)pyridine (7.52 g, 18.15 mmol), benzylthiol (2.1 mL, 17.9 mmol), N,N-diisopropylethyl amine (6 mL, 34.5 mmol), toluene (50 mL), tris(dibenzylideneacetone)dipalladium(0) (829 mg, 0.91 mmol), 4,5-bis(diphenylphosphino)-9,9-dimethylxanthene (1.043 g, 1.80 mmol) was stirred for one hour at 110° C. The mixture was diluted with water and extracted three times with dichloromethane. The combined organic layers were dried (Na$_2$SO$_4$), concentrated, and the resulting residue was purified by MPLC eluting with a gradient of 1-5% ethyl acetate in petroleum ether to afford (R)-3-(benzylthio)-2-(2-((tert-butyldimethylsilyl)oxy)propoxy)-5-(trifluoromethyl)pyridine (8.37 g) as a yellow oil.

Part V—Synthesis of (R)-1-((3-(Benzylthio)-5-(trifluoromethyl)pyridin-2-yl)oxy)propan-2-ol

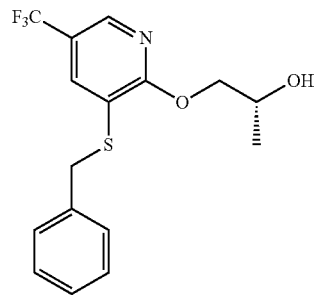 [SMILES: C[C@@H](O)COc1ncc(C(F)(F)F)cc1SCc1ccccc1]

A solution of (R)-3-(benzylthio)-2-(2-((tert-butyldimethylsilyl)oxy)propoxy)-5-(trifluoromethyl)pyridine (7.25 g, 15.84 mmol), THF (32 mL) and a 1 M solution of tetrabutylammonium fluoride (19 mL, 19 mmol) in THF was stirred for one hour at room temperature. The mixture was concentrated, diluted with water, and extracted three times with dichloromethane. The combined organic layers were dried (Na$_2$SO$_4$), concentrated and the resulting residue was purified by MPLC eluting with a gradient of 5-20% ethyl acetate in petroleum ether to afford (R)-1-((3-(benzylthio)-5-(trifluoromethyl)pyridin-2-yl)oxy)propan-2-ol (5.01 g, 92%) as a yellow oil.

Part VI—Synthesis of (R)-1-((3-(Benzylthio)-5-(trifluoromethyl)pyridin-2-yl)oxy)propan-2-yl acetate

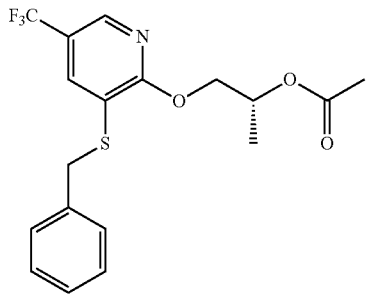 [SMILES: CC(=O)O[C@H](C)COc1ncc(C(F)(F)F)cc1SCc1ccccc1]

A mixture of (R)-1-((3-(benzylthio)-5-(trifluoromethyl)pyridin-2-yl)oxy)propan-2-ol (4.7 g, 13.69 mmol), dichloromethane (40.3 mL), pyridine (2.8 mL), acetic anhydride (2.8 mL), and 4-dimethylaminopyridine (167.2 mg, 1.37 mmol) was stirred for one hour at room temperature. The reaction mixture was diluted with saturated ammonium chloride and extracted three times with dichloromethane. The combined organic layers were dried ($Na_2SO_4$) and concentrated. The resulting residue was purified by MPLC eluting with a gradient of 2-10% ethyl acetate in petroleum ether to afford (R)-1-((3-(benzylthio)-5-(trifluoromethyl)pyridin-2-yl)oxy)propan-2-yl acetate (4.88 g, 93%) as a yellow solid.

Part VII—Synthesis of (R)-1-((3-(Chlorosulfonyl)-5-(trifluoromethyl)pyridin-2-yl)oxy)propan-2-yl acetate

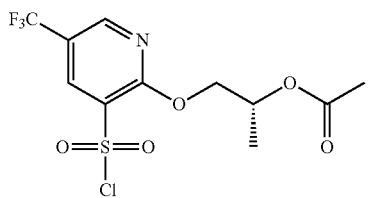 [SMILES: CC(=O)O[C@H](C)COc1ncc(C(F)(F)F)cc1S(=O)(=O)Cl]

A solution of (R)-1-((3-(benzylthio)-5-(trifluoromethyl)pyridin-2-yl)oxy)propan-2-yl acetate (4.69 g, 12.17 mmol), acetic acid (26.9 mL), water (9 mL), and N-chlorosuccinimide (6.5 g, 48.68 mmol) was stirred for one hour at room temperature. The mixture was concentrated, diluted with aqueous sodium bicarbonate, and extracted three times with dichloromethane. The combined organic layers were dried ($Na_2SO_4$) and concentrated. The resulting residue was purified by MPLC eluting with a gradient of 5-20% ethyl acetate in petroleum ether to afford (R)-1-((3-(chlorosulfonyl)-5-(trifluoromethyl)pyridin-2-yl)oxy)propan-2-yl acetate (4.2 g, 95%) as a colorless oil.

Part VIII—Synthesis of Methyl 3-((S)-4-((2-((R)-2-acetoxypropoxy)-5-(trifluoromethyl)pyridin-3-yl)sulfonyl)-6-((E)-2-chloro-6-fluorostyryl)-3,4-dihydro-2H-benzo[b][1,4]oxazin-2-yl)propanoate

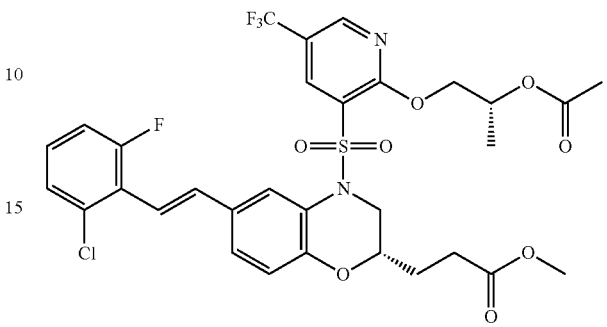

A mixture of (S,E)-3-(6-(2-chloro-6-fluorostyryl)-3,4-dihydro-2H-benzo[b][1,4]oxazin-2-yl)propanoate (205 mg, 0.55 mmol), dichloromethane (2.7 mL), pyridine (0.2 mL), 4-dimethylaminopyridine (33.3 mg, 0.27 mmol), and ((R)-1-((3-(chlorosulfonyl)-5-(trifluoromethyl)pyridin-2-yl)oxy)propan-2-yl acetate (473.7 mg, 1.31 mmol) was stirred overnight at room temperature. The mixture was diluted with brine and was extracted three times with dichloromethane. The combined organic layers were dried ($Na_2SO_4$), concentrated, and the resulting residue was purified by MPLC eluting with 33% ethyl acetate in petroleum ether to afford methyl 3-((S)-4-((2-((R)-2-acetoxypropoxy)-5-(trifluoromethyl)pyridin-3-yl)sulfonyl)-6-((E)-2-chloro-6-fluorostyryl)-3,4-dihydro-2H-benzo[b][1,4]oxazin-2-yl)propanoate (276 mg, 72%) as a light yellow oil.

Part IX—Synthesis of Methyl 3-((S)-6-((E)-2-chloro-6-fluorostyryl)-4-((2-((R)-2-hydroxypropoxy)-5-(trifluoromethyl)pyridin-3-yl)sulfonyl)-3,4-dihydro-2H-benzo[b][1,4]oxazin-2-yl)propanoate

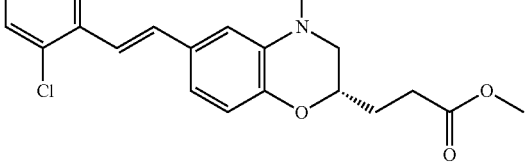

Based on the procedure in Example 69, methyl 3-((S)-6-((E)-2-chloro-6-fluorostyryl)-4-((2-((R)-2-hydroxypropoxy)-5-(trifluoromethyl)pyridin-3-yl)sulfonyl)-3,4-dihydro-2H-benzo[b][1,4]oxazin-2-yl)propanoate was prepared. $^1$H-NMR (300 MHz, $CD_3OD$) δ 1.17 (d, J=6.4 Hz, 3H), 1.90-2.04 (m, 2H), 2.57 (t, J=6.8 Hz, 2H), 3.52 (dd, J=9.2 Hz, 14.0 Hz, 1H), 3.69 (s, 3H), 3.91-3.96 (m, 2H), 4.14 (dd, J=4.8 Hz, 11.2 Hz, 1H), 4.39 (dd, J=2.4 Hz, 14.4 Hz, 1H), 4.51 (dd, J=6.8 Hz, 10.8 Hz, 1H), 6.93 (d, J=8.4 Hz, 1H), 7.07-7.17 (m, 2H), 7.22-7.32 (m, 4H), 7.68 (d, J=1.6 Hz, 1H), 8.62 (d, J=2.4 Hz, 1H), 8.74 (s, 1H). (ES, m/z): (M+H)+659.

Example 79—Synthesis of 3-((S)-6-((E)-2-Chloro-6-fluorostyryl)-4-((2-((R)-2-hydroxypropoxy)-5-(trifluoromethyl)pyridin-3-yl)sulfonyl)-3,4-dihydro-2H-benzo[b][1,4]oxazin-2-yl)propanoic acid

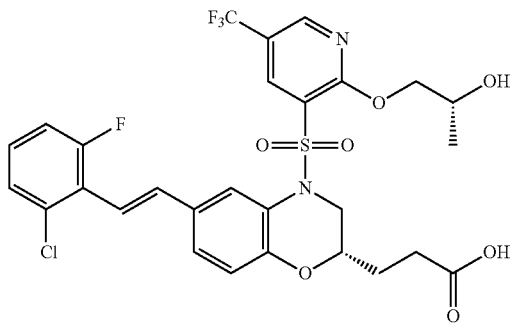 [SMILES: C[C@@H](O)COc1ncc(C(F)(F)F)cc1S(=O)(=O)N1C[C@H](CCC(=O)O)Oc2ccc(/C=C/c3c(F)cccc3Cl)cc21]

Based on the procedure in Example 42, 3-((S)-6-((E)-2-chloro-6-fluorostyryl)-4-((2-((R)-2-hydroxypropoxy)-5-(trifluoromethyl)pyridin-3-yl)sulfonyl)-3,4-dihydro-2H-benzo[b][1,4]oxazin-2-yl)propanoic acid was prepared. $^1$H-NMR (300 MHz, CD$_3$OD) δ 1.15 (d, J=6.4 Hz, 3H), 1.90-1.97 (m, 2H), 2.52 (t, J=7.2 Hz, 2H), 3.50 (dd, J=9.2 Hz, 14.0 Hz, 1H), 3.92-3.94 (m, 2H), 4.15 (dd, J=4.4 Hz, 10.8 Hz, 1H), 4.38 (dd, J=2.4 Hz, 14.4 Hz, 1H), 4.49 (dd, J=6.8 Hz, 11.2 Hz, 1H), 6.92 (d, J=8.8 Hz, 1H), 7.05-7.15 (m, 2H), 7.21-7.30 (m, 4H), 7.66 (d, J=2.0 Hz, 1H), 8.59 (d, J=2.4 Hz, 1H), 8.71 (s, 1H). (ES, m/z): (M+H)+645.

Example 80—Synthesis of (S,E)-3-(6-(2-(2-Chloro-6-fluorophenyl)prop-1-en-1-yl)-4-((1-ethyl-3-(2-hydroxyethoxy)-1H-pyrazol-4-yl)sulfonyl)-3,4-dihydro-2H-benzo[b][1,4]oxazin-2-yl)propanoic acid

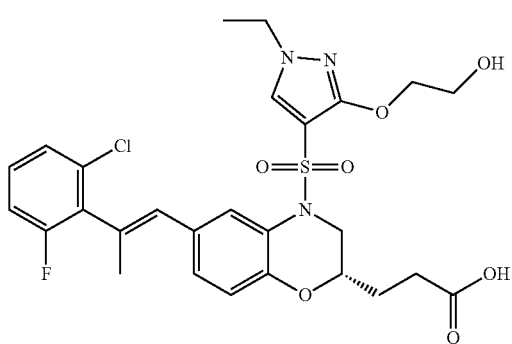 [SMILES: CCn1cc(S(=O)(=O)N2C[C@H](CCC(=O)O)Oc3ccc(/C=C(\C)c4c(F)cccc4Cl)cc32)c(OCCO)n1]

Part I—Synthesis of Methyl 2-((1-acetyl-1H-pyrazol-3-yl)oxy)acetate

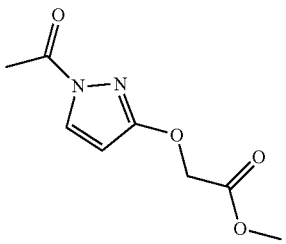

Methyl bromoacetate (72.78 g, 475.8 mmol) was added to a mixture of 1-acetyl-1,2-dihydro-3H-pyrazol-3-one (50.0 g, 396.5 mmol) and potassium carbonate (82.2 g, 594.7 mmol) in DMF (396 mL) and stirred at room temperature overnight. The mixture was partitioned between ethyl acetate (500 mL) and water (1 L). The organic layer was washed with water and brine, dried (Na$_2$SO$_4$), and concentrated. The resulting residue was triturated with methanol (375 mL) and filtered to obtain methyl 2-((1-acetyl-1H-pyrazol-3-yl)oxy)acetate as a white solid (42.0 g, 53%).

Part II—Synthesis of Methyl 2-((1H-pyrazol-3-yl)oxy)acetate

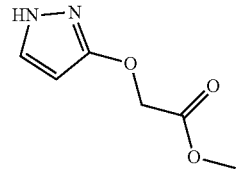

Sodium methoxide (13.74 g, 254.3 mmol) was added to a stirred suspension of methyl 2-((1-acetyl-1H-pyrazol-3-yl)oxy)acetate (42.0 g, 211.9 mmol) in methanol (212 mL) at 0° C. The mixture was stirred overnight at room temperature. The reaction was quenched with 2 M HCl (125 mL) and concentrated to remove the methanol. The mixture was partitioned between ethyl acetate and brine. The organic layer was dried (Na$_2$SO$_4$) and concentrated to afford methyl 2-((1H-pyrazol-3-yl)oxy)acetate (26.38 g, 80%) as an off-white solid.

Part III—Synthesis of Methyl 2-((1-ethyl-1H-pyrazol-3-yl)oxy)acetate

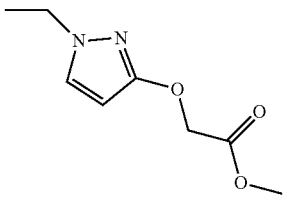

A 60% suspension of sodium hydride in mineral oil (9.71 g, 253.4 mmol) was added to a stirred solution of methyl 2-((1H-pyrazol-3-yl)oxy)acetate (26.38 g, 169.0 mmol) in DMF (225 mL) at 0° C. Iodoethane (27.7 g, 177 mmol) was added and the mixture was stirred at 0° C. for an additional thirty min. and then at room temperature overnight. The mixture was diluted with water and extracted twice with ethyl acetate. The combined organic layers were washed with brine, dried (Na₂SO₄), and concentrated to afford methyl 2-((1-ethyl-1H-pyrazol-3-yl)oxy)acetate (17.65 g, 57%).

Part IV—Synthesis of methyl 2-((4-(chlorosulfonyl)-1-ethyl-1H-pyrazol-3-yl)oxy)acetate

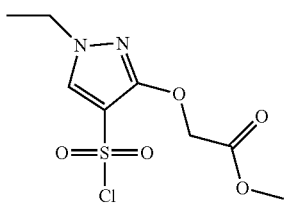 [SMILES: CCn1cc(S(=O)(=O)Cl)c(OCC(=O)OC)n1]

Chlorosulfonic acid (21.29 g, 182.7 mmol) was added dropwise to a stirred solution of methyl 2-((1-ethyl-1H-pyrazol-3-yl)oxy)acetate (30.6 g, 166.1 mmol) in dichloromethane (415 mL) at −10° C. The mixture was allowed to warm to room temperature and was stirred overnight. The mixture was cooled to −10° C., and pyridine was added (14.455 g, 182.8 mmol). Stirred for thirty minutes, and then phosphorous pentachloride (38.06 g, 182.8 mmol) was added in portions and stirred an additional thirty minutes at −10° C. The mixture was allowed to warm to room temperature and was stirred overnight. The mixture was poured onto ice, and the mixture was extracted three times with dichloromethane. The combined organic layers were washed with brine, dried (Na₂SO₄) and concentrated. The resulting residue was first purified via MPLC eluting with a gradient of 10-30% ethyl acetate in hexanes. The major UV fraction was concentrated and treated with a mixture of ethyl acetate (12 mL) and hexanes (52 mL). Crystallization began, and additional hexanes (75 mL) and ethyl acetate (13 mL) was added. The mixture was triturated, filtered, and dried to afford methyl 2-((4-(chlorosulfonyl)-1-ethyl-1H-pyrazol-3-yl)oxy)acetate (11.1 g, 24%) as a white solid.

Part V—Synthesis of Methyl (S)-3-(6-bromo-4-((1-ethyl-3-(2-methoxy-2-oxoethoxy)-1H-pyrazol-4-yl)sulfonyl)-3,4-dihydro-2H-benzo[b][1,4]oxazin-2-yl)propanoate

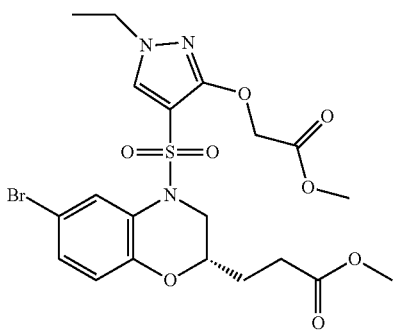 [SMILES: CCn1cc(S(=O)(=O)N2C[C@H](CCC(=O)OC)Oc3ccc(Br)cc32)c(OCC(=O)OC)n1]

A mixture of methyl (S)-3-(6-bromo-3,4-dihydro-2H-benzo[b][1,4]oxazin-2-yl)propanoate (500 mg, 1.67 mmol), methyl 2-((4-(chlorosulfonyl)-1-ethyl-1H-pyrazol-3-yl)oxy)acetate (706 mg, 2.50 mmol) and pyridine (5 mL) was stirred at 50° C. overnight. The mixture was partitioned between ethyl acetate and 1 M HCl. The organic layer was washed twice with 1 M HCl, washed with brine, dried (Na₂SO₄), and concentrated. The resulting residue was purified by MPLC eluting with a gradient of 10-100% ethyl acetate in hexanes to afford methyl (S)-3-(6-bromo-4-((1-ethyl-3-(2-methoxy-2-oxoethoxy)-1H-pyrazol-4-yl)sulfonyl)-3,4-dihydro-2H-benzo[b][1,4]oxazin-2-yl)propanoate (600 mg, 66%) as an oil.

Part VI—Synthesis of Methyl (S)-3-(6-bromo-4-((1-ethyl-3-(2-hydroxyethoxy)-1H-pyrazol-4-yl)sulfonyl)-3,4-dihydro-2H-benzo[b][1,4]oxazin-2-yl)propanoate

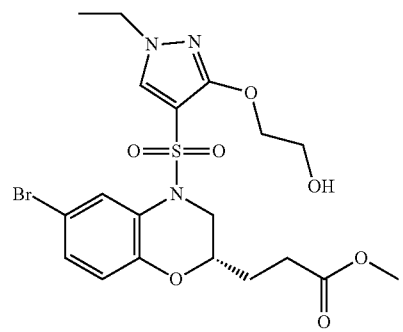 [SMILES: CCn1cc(S(=O)(=O)N2C[C@H](CCC(=O)OC)Oc3ccc(Br)cc32)c(OCCO)n1]

Sodium borohydride (756 mg, 20.0 mmol) was added portionwise to a stirred solution of methyl (S)-3-(6-bromo-4-((1-ethyl-3-(2-methoxy-2-oxoethoxy)-1H-pyrazol-4-yl)sulfonyl)-3,4-dihydro-2H-benzo[b][1,4]oxazin-2-yl)propanoate (3.64 g, 6.66 mmol) in methanol at 0° C. After twenty minutes, additional sodium borohydride (756 mg, 20 mmol) was added. After stirring for 1 hour the reaction was quenched with 1 M HCl. The mixture was diluted with water and extracted three times with ethyl acetate. The combined organic layers were washed with brine, dried (Na₂SO₄), and concentrated. The resulting residue was purified by MPLC eluting with a gradient of 20-100% ethyl acetate in hexanes to afford methyl (S)-3-(6-bromo-4-((1-ethyl-3-(2-hydroxyethoxy)-1H-pyrazol-4-yl)sulfonyl)-3,4-dihydro-2H-benzo[b][1,4]oxazin-2-yl)propanoate (2.06 g, 60%).

Part VII—Synthesis of Methyl (S,E)-3-(6-(2-(2-chloro-6-fluorophenyl)prop-1-en-1-yl)-4-((1-ethyl-3-(2-hydroxyethoxy)-1H-pyrazol-4-yl)sulfonyl)-3,4-dihydro-2H-benzo[b][1,4]oxazin-2-yl)propanoate

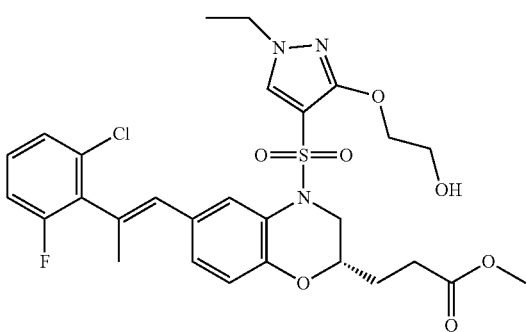 [SMILES: CCn1cc(S(=O)(=O)N2C[C@H](CCC(=O)OC)Oc3ccc(/C=C(\C)c4c(F)cccc4Cl)cc32)c(OCCO)n1]

A mixture of methyl (S)-3-(6-bromo-4-((1-ethyl-3-(2-hydroxyethoxy)-1H-pyrazol-4-yl)sulfonyl)-3,4-dihydro-2H-benzo[b][1,4]oxazin-2-yl)propanoate (2.22 g, 4.28 mmol), (E)-2-(2-(2-chloro-6-fluorophenyl)prop-1-en-1-yl)-4,4,5,5-tetramethyl-1,3,2-dioxaborolane (1.78 g, 6.00 mmol), potassium carbonate (0.83 g, 6.00 mmol), [1,1'-bis(diphenylphosphino)ferrocene]dichloropalladium(II) dichloromethane complex (330 mg, 0.42 mmol), dioxane (30 mL), and water (5 mL) was heated to 80° C. overnight. The mixture was partitioned between ethyl acetate and water. The organic layer was washed with brine, dried ($Na_2SO_4$) and concentrated. The resulting residue was purified via MPLC eluting with a gradient of 0-100% ethyl acetate in hexanes to afford methyl (S,E)-3-(6-(2-(2-chloro-6-fluorophenyl)prop-1-en-1-yl)-4-((1-ethyl-3-(2-hydroxyethoxy)-1H-pyrazol-4-yl)sulfonyl)-3,4-dihydro-2H-benzo[b][1,4]oxazin-2-yl)propanoate (1.94 g, 74%).

Part VIII—Synthesis of (S,E)-3-(6-(2-(2-Chloro-6-fluorophenyl)prop-1-en-1-yl)-4-((1-ethyl-3-(2-hydroxyethoxy)-1H-pyrazol-4-yl)sulfonyl)-3,4-dihydro-2H-benzo[b][1,4]oxazin-2-yl)propanoic acid

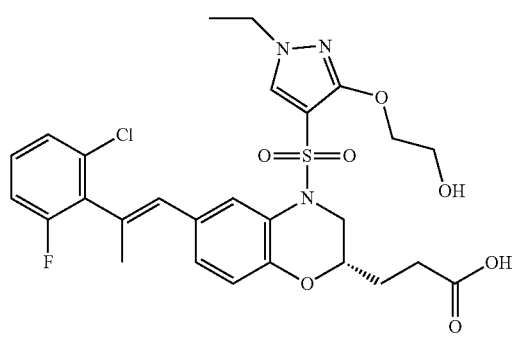 [SMILES: CCn1cc(S(=O)(=O)N2C[C@H](CCC(=O)O)Oc3ccc(/C=C(\C)c4c(F)cccc4Cl)cc32)c(OCCO)n1]

Aqueous sodium hydroxide (2 M, 4.79 mL, 9.58 mmol) was added to a solution of methyl (S,E)-3-(6-(2-(2-chloro-6-fluorophenyl)prop-1-en-1-yl)-4-((1-ethyl-3-(2-hydroxyethoxy)-1H-pyrazol-4-yl)sulfonyl)-3,4-dihydro-2H-benzo[b][1,4]oxazin-2-yl)propanoate (1.94 g, 3.19 mmol) in THF (10 mL) and methanol (20 mL). The mixture was stirred at room temperature for four hours, then concentrated and diluted with 1 M HCl. The mixture was extracted three times with ethyl acetate. The combined extracts were washed with water, brine, dried ($Na_2SO_4$), and concentrated to afford (S,E)-3-(6-(2-(2-chloro-6-fluorophenyl)prop-1-en-1-yl)-4-((1-ethyl-3-(2-hydroxyethoxy)-1H-pyrazol-4-yl)sulfonyl)-3,4-dihydro-2H-benzo[b][1,4]oxazin-2-yl)propanoic acid (1.85 g, 98%). A solution of sodium hydroxide (120 mg, 3.12 mmol) in water (1.05 mL) was added to a solution of (S,E)-3-(6-(2-(2-chloro-6-fluorophenyl)prop-1-en-1-yl)-4-((1-ethyl-3-(2-hydroxyethoxy)-1H-pyrazol-4-yl)sulfonyl)-3,4-dihydro-2H-benzo[b][1,4]oxazin-2-yl)propanoic acid (1.85 g, 3.12 mmol) in ethanol (30 mL). The mixture was stirred for thirty minutes and concentrated. The residue was co-evaportaed three times with ethanol and dried in a vacuum oven to afford the sodium salt of (S,E)-3-(6-(2-(2-chloro-6-fluorophenyl)prop-1-en-1-yl)-4-((1-ethyl-3-(2-hydroxyethoxy)-1H-pyrazol-4-yl)sulfonyl)-3,4-dihydro-2H-benzo[b][1,4]oxazin-2-yl)propanoic acid (1.65 g, 89%). $^1$H-NMR (400 MHz, $CDCl_3$) DMSO-$d_6$) δ 8.18 (s, 1H), 7.62 (d, 1H), 7.36 (m, 2H), 7.26 (m, 1H), 7.01 (d, 1H), 6.86 (d, 1H), 6.34 (s, 1H), 4.35 (m, 1H), 4.15 (m, 1H), 4.05 (m, 1H), 3.94 (m, 2H), 3.60 (m, 2H), 3.22 (m, 1H), 2.08 (s, 3H), 1.99 (m, 2H), 1.8 (m, 2H), 1.24 (t, 3H). MS (ESI+) $(M+Na)^+$ 616.21.

Example 81—Synthesis of Methyl (S,E)-3-(6-(2-chloro-6-(trifluoromethyl)styryl)-4-((3-(difluoromethyl)phenyl)sulfonyl)-3,4-dihydro-2H-benzo[b][1,4]oxazin-2-yl)propanoate

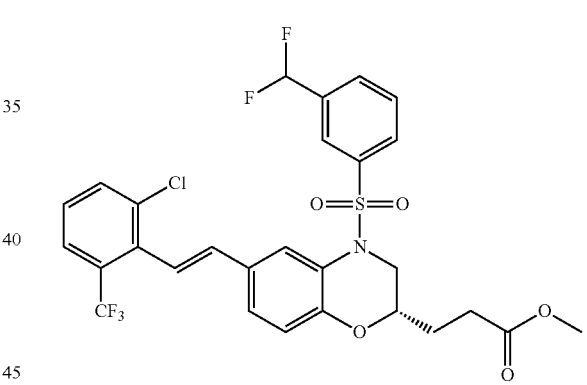

Part I—Synthesis of 1-Bromo-3-(difluoromethyl)benzene

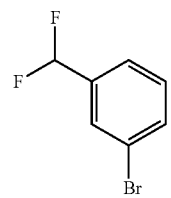

Diethylaminosulfur trifluoride (2.5 g, 67.39 mmol) was added dropwise to a stirred solution of 3-bromobenzaldehyde (1 g, 5.40 mmol) in dichloromethane (10 mL). The mixture was stirred for four hours at room temperature, diluted with saturated sodium bicarbonate and extracted twice with dichloromethane. The combined organic layers were dried (Na$_2$SO$_4$) and concentrated to afford 1-bromo-3-(difluoromethyl)benzene (600 mg, 54%) as a colorless liquid.

Part II—Synthesis of Benzyl(3-(difluoromethyl)phenyl)sulfane

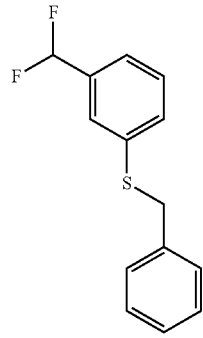 [SMILES: FC(F)c1cccc(SCc2ccccc2)c1]

A mixture of 1-bromo-3-(difluoromethyl)benzene (600 mg, 2.90 mmol), phenylmethanethiol (397 mg, 3.20 mmol), N,N-diisopropylethylamine (751 mg, 5.81 mmol), [1,1'-bis(diphenylphosphino)ferrocene]dichloropalladium(II) dichloromethane complex (133 mg, 0.15 mmol), 4,5-bis(diphenylphosphino)-9,9-dimethylxanthene (174 mg, 0.30 mmol), and toluene (20 mL) was stirred for three hours at 110° C. The mixture was concentrated and the resulting residue was purified via MPLC eluting with 5% ethyl acetate in petroleum ether to afford benzyl(3-(difluoromethyl)phenyl)sulfane (200 mg, 28%) as a colorless oil.

Part III—Synthesis of 3-(Difluoromethyl)benzenesulfonyl chloride

A mixture of benzyl(3-(difluoromethyl)phenyl)sulfane (700 mg, 2.80 mmol) acetic acid (18 mL), water (6 mL), and N-chlorosuccinimide (1.5 g, 11.23 mmol) was stirred for one hour at room temperature. The mixture was concentrated and the resulting residue was dissolved in dichloromethane. The solution was washed twice with saturated sodium bicarbonate, dried (Na$_2$SO$_4$), and concentrated. The resulting residue was purified via MPLC eluting with 5% ethyl acetate in petroleum ether to afford 3-(difluoromethyl)benzenesulfonyl chloride (500 mg, 79%) as a colorless liquid.

Part IV—Synthesis of Methyl (S,E)-3-(6-(2-chloro-6-(trifluoromethyl)styryl)-4-((3-(difluoromethyl)phenyl)sulfonyl)-3,4-dihydro-2H-benzo[b][1,4]oxazin-2-yl)propanoate

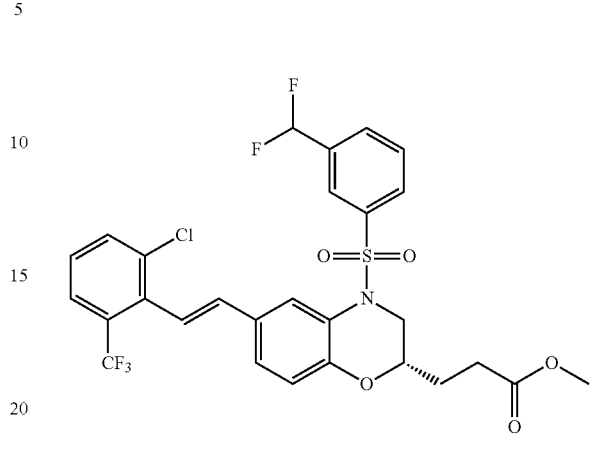

A solution of methyl (S,E)-3-(6-(2-chloro-6-(trifluoromethyl)styryl)-3,4-dihydro-2H-benzo[b][1,4]oxazin-2-yl)propanoate (50 mg, 0.12 mmol), 3-(difluoromethyl)benzene-1-sulfonyl chloride (40 mg, 0.18 mmol), dichloromethane (10 mL) and pyridine (2 mL) was stirred overnight at room temperature. The mixture was diluted with dichloromethane and washed twice with 1 M HCl. The organic layer was dried (Na$_2$SO$_4$) and concentrated. The resulting residue was purified by Prep-HPLC eluting with a gradient of 68-90% acetonitrile in water with 0.05% trifluoroacetic acid to afford methyl (S,E)-3-(6-(2-chloro-6-(trifluoromethyl)styryl)-4-((3-(difluoromethyl)phenyl)sulfonyl)-3,4-dihydro-2H-benzo[b][1,4]oxazin-2-yl)propanoate (17.3 mg, 24%) as an off-white solid. $^1$H-NMR (400 MHz, CD$_3$OD δ 7.95 (m, 2H), 7.87-7.67 (m, 5H), 7.46 (t, J=8.0 Hz, 1H), 7.31 (m, 1H), 7.04 (m, 1H), 6.88-6.74 (m, 3H), 4.42 (dd, J=2.4 Hz, 14.4 Hz, 1H), 3.68 (s, 3H), 3.43 (m, 1H), 3.29 (m, 1H), 2.49-2.46 (m, 2H), 1.93 (m, 1H), 1.85-1.75 (m, 1H). (ES, m/z): (M+H)$^+$616.

Example 82—Synthesis of (S,E)-3-(6-(2-Chloro-6-(trifluoromethyl)styryl)-4-((3-(difluoromethyl)phenyl)sulfonyl)-3,4-dihydro-2H-benzo[b][1,4]oxazin-2-yl)propanoic acid

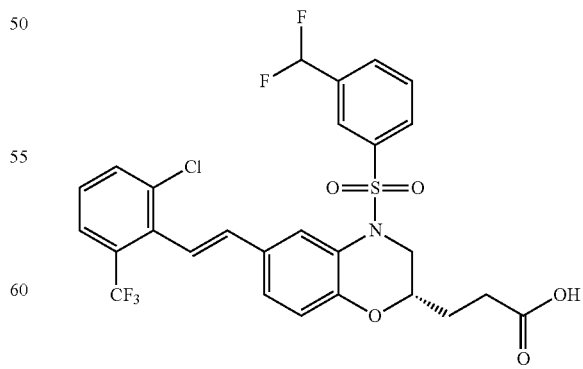

Based on the procedure in Example 42, (S,E)-3-(6-(2-chloro-6-(trifluoromethyl)styryl)-4-((3-(difluoromethyl)phenyl)sulfonyl)-3,4-dihydro-2H-benzo[b][1,4]oxazin-2-yl)

propanoic acid was prepared. ¹H-NMR (300 MHz, CD₃OD) δ 7.94 (d, J=22 Hz, 1H), 7.84 (d, J=7.2 Hz, 1H), 7.81-7.76 (m, 2H), 7.75-7.66 (m, 3H), 7.58-7.44 (m, 1H), 7.31 (d, J=8.8 Hz 1H), 7.03 (t, J=16.4 Hz, 1H), 6.88-6.73 (m, 3H), 4.43 (dd, J=2.0 Hz, 14.4 Hz, 1H), 3.50-3.43 (m, 1H), 3.33-3.24 (m, 1H), 2.51-2.37 (m, 2H), 1.94-1.86 (m, 1H), 1.84-1.75 (m, 1H). (ES, m/z): (M+H)⁺602.

Example 83—Synthesis of Methyl (S,E)-3-(6-(2-chloro-6-(trifluoromethyl)styryl)-4-((3-(1,1-difluoroethyl)phenyl)sulfonyl)-3,4-dihydro-2H-benzo[b][1,4]oxazin-2-yl)propanoate

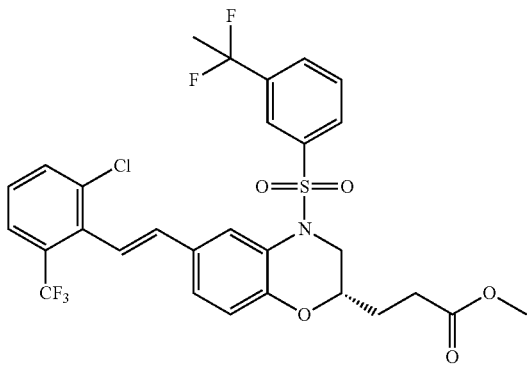 [SMILES: COC(=O)CC[C@H]1CN(S(=O)(=O)c2cccc(C(C)(F)F)c2)c2cc(/C=C/c3c(Cl)cccc3C(F)(F)F)ccc2O1]

Based on the procedure in Example 81, methyl (S,E)-3-(6-(2-chloro-6-(trifluoromethyl)styryl)-4-((3-(1,1-difluoroethyl)phenyl)sulfonyl)-3,4-dihydro-2H-benzo[b][1,4]oxazin-2-yl)propanoate was prepared from 3-bromoacetophenone. ¹H-NMR (300 MHz, CD₃OD) δ 8.00 (d, J=2.0 Hz, 1H), 7.85-7.66 (m, 6H), 7.47 (t, J=8.4 Hz, 1H), 7.32 (m, 1H), 7.06 (m, 1H), 6.87-6.78 (m, 2H), 4.42 (dd, J=2.4 Hz, 14.4 Hz, 1H), 3.68 (s, 3H), 3.42 (m, 1H), 3.33-3.24 (m, 1H), 2.49-2.45 (m, 2H), 1.95-1.77 (m, 5H). (ES, m/z): (M+H)⁺630.

Example 84—Synthesis of (S,E)-3-(6-(2-Chloro-6-(trifluoromethyl)styryl)-4-((3-(1,1-difluoroethyl)phenyl)sulfonyl)-3,4-dihydro-2H-benzo[b][1,4]oxazin-2-yl)propanoic acid

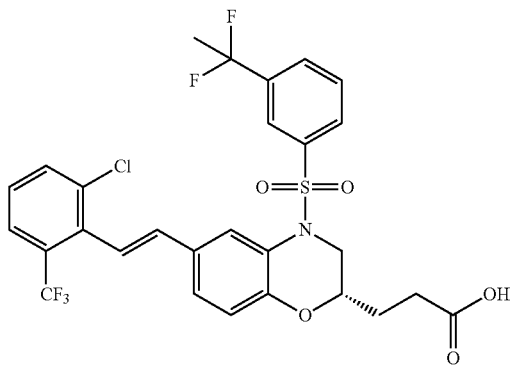 [SMILES: CC(F)(F)c1cccc(S(=O)(=O)N2C[C@H](CCC(=O)O)Oc3ccc(/C=C/c4c(Cl)cccc4C(F)(F)F)cc32)c1]

Based on the procedure in Example 42, (S,E)-3-(6-(2-chloro-6-(trifluoromethyl)styryl)-4-((3-(1,1-difluoroethyl)phenyl)sulfonyl)-3,4-dihydro-2H-benzo[b][1,4]oxazin-2-yl)propanoic acid was prepared. ¹H-NMR (300 MHz, CD₃OD) δ 8.00 (s, 1H), 7.85-7.82 (m, 2H), 7.78-7.66 (m, 4H), 7.47 (t, J=8.0 Hz, 1H), 7.32 (m, 1H), 7.06 (m, 1H), 6.88-6.78 (m, 2H), 4.44 (dd, J=2.4 Hz, 14.4 Hz, 1H), 3.38 (m, 1H), 3.25 (m, 1H), 2.50-2.36 (m, 2H), 1.99-1.77 (m, 5H). (ES, m/z): (M+H)⁺616.

Example 85—Synthesis of (S,E)-3-(6-(2-(2-Chloro-6-fluorophenyl)prop-1-en-1-yl)-4-((1-cyclopropyl-3-(2-hydroxyethoxy)-1H-pyrazol-4-yl)sulfonyl)-3,4-dihydro-2H-benzo[b][1,4]oxazin-2-yl)propanoic acid

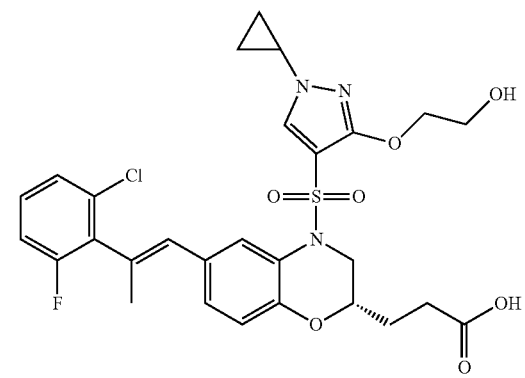 [SMILES: C/C(=C\c1ccc2c(c1)N(S(=O)(=O)c1cn(C3CC3)nc1OCCO)C[C@H](CCC(=O)O)O2)c1c(F)cccc1Cl]

Part I—Synthesis of Methyl 2-((1-cyclopropyl-1H-pyrazol-3-yl)oxy)acetate

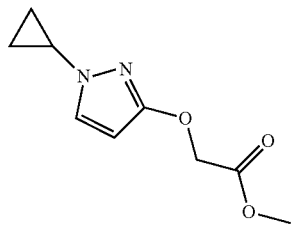

To a suspension of methyl 2-((1H-pyrazol-3-yl)oxy)acetate (0.5 g, 3.2 mmol), sodium carbonate (0.75 g, 7.0 mmol), and potassium cyclopropyl(trifluoro)boranuide (0.95 g, 6.4 mmol) in anhydrous 1,2-dichloroethane (10 mL) under a nitrogen atmosphere was added copper (II) acetate (0.64 g, 3.5 mmol) and 2,2'-bipyridyl (0.55 g, 3.5 mmol). The reaction mixture was heated to 70° C. overnight. The cooled reaction was partitioned between dichloromethane and saturated ammonium chloride. The aqueous layer was extracted once more with dichloromethane, then the combined extracts were washed with saturated ammonium chloride, then dried (Na₂SO₄) and concentrated. The mixture was purified by column chromatography eluting with a gradient of 0-50% ethyl acetate in hexanes. Pure fractions were combined and concentrated to afford methyl 2-((1-cyclopropyl-1H-pyrazol-3-yl)oxy)acetate (0.27 g, 43%).

Part II—Synthesis of (S,E)-3-(6-(2-(2-Chloro-6-fluorophenyl)prop-1-en-1-yl)-4-((1-cyclopropyl-3-(2-hydroxyethoxy)-1H-pyrazol-4-yl)sulfonyl)-3,4-dihydro-2H-benzo[b][1,4]oxazin-2-yl)propanoic acid Based on the procedure in Example 80, methyl 2-((1-cyclopropyl-1H-pyrazol-3-yl)oxy)acetate was converted to (S,E)-3-(6-(2-(2-chloro-6-fluorophenyl)prop-1-en-1-yl)-4-((1-cyclopropyl-3-(2-hydroxyethoxy)-1H-pyrazol-4-yl)sulfonyl)-3,4-dihydro-2H-benzo[b][1,4]oxazin-2-yl)propanoic acid. $^1$H-NMR (400 MHz, DMSO-d$_6$) δ 8.22 (s, 1H), 7.60 (d, 1H), 7.37 (m, 2H), 7.26 (m, 1H), 7.01 (dd, 1H), 6.86 (d, 1H), 6.32 (d, 1H), 4.31 (m, 1H), 4.10 (m, 1H), 4.06 (m, 1H), 3.95 (m, 1H), 3.60 (m, 3H), 3.26 (m, 1H), 2.07 (s, 3H), 1.99 (m, 2H), 1.79 (m, 2H), 1.00 (m, 1H), 0.95 (m, 1H), 0.86 (m, 2H). MS (ESI+) 628.11 (M+Na)$^+$.

Example 86—Preparation of Additional Substituted (S,E)-3-(Aryl or heteroaryl)prop-1-en-1-yl)-4-(aryl or heteroaryl)-sulfonyl)-3,4-dihydro-2H-benzo[b][1,4]oxazin-2-yl) Compounds Compounds in the table below were prepared based on experimental procedures described in Example 29 and the detailed description.

| No. | Structure | Name | Observed m/z |
|---|---|---|---|
| 86A | 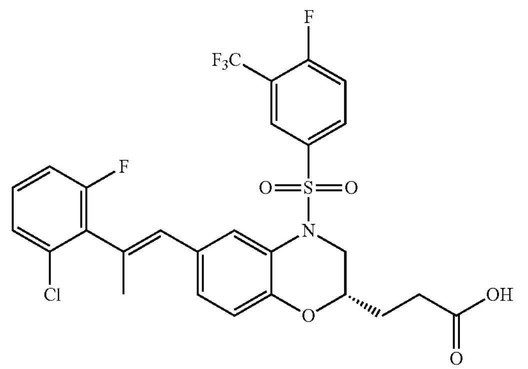 [SMILES: C/C(=C\c1ccc2c(c1)N(S(=O)(=O)c1ccc(F)c(C(F)(F)F)c1)C[C@H](CCC(=O)O)O2)c1c(F)cccc1Cl] | (S,E)-3-(6-(2-(2-chloro-6-fluorophenyl)prop-1-en-1-yl)-4-((4-fluoro-3-(trifluoromethyl)-phenyl)sulfonyl)-3,4-dihydro-2H-benzo[b][1,4]oxazin-2-yl)-propanoic acid | 602 (M + H)$^+$ |
| 86B | 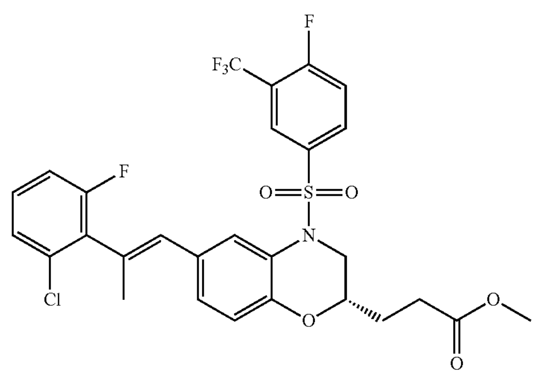 [SMILES: COC(=O)CC[C@H]1CN(S(=O)(=O)c2ccc(F)c(C(F)(F)F)c2)c2cc(/C=C(\C)c3c(F)cccc3Cl)ccc2O1] | (S,E)-methyl 3-(6-(2-(2-chloro-6-fluorophenyl)prop-1-en-1-yl)-4-((4-fluoro-3-(trifluoromethyl)-phenyl)sulfonyl)-3,4-dihydro-2H-benzo[b][1,4]oxazin-2-yl)propanoate | 616 (M + H)$^+$ |
| 86C | 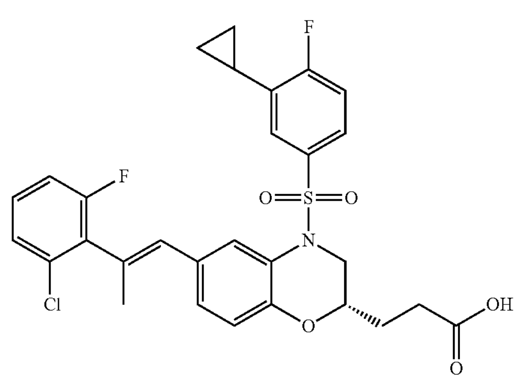 [SMILES: C/C(=C\c1ccc2c(c1)N(S(=O)(=O)c1ccc(F)c(C3CC3)c1)C[C@H](CCC(=O)O)O2)c1c(F)cccc1Cl] | (S,E)-3-(6-(2-(2-chloro-6-fluorophenyl)prop-1-en-1-yl)-4-((3-cyclopropyl-4-fluorophenyl)-sulfonyl)-3,4-dihydro-2H-benzo[b][1,4]oxazin-2-yl)-propanoic acid | 574 (M + H)$^+$ |

-continued

| No. | Structure | Name | Observed m/z |
|---|---|---|---|
| 86D | 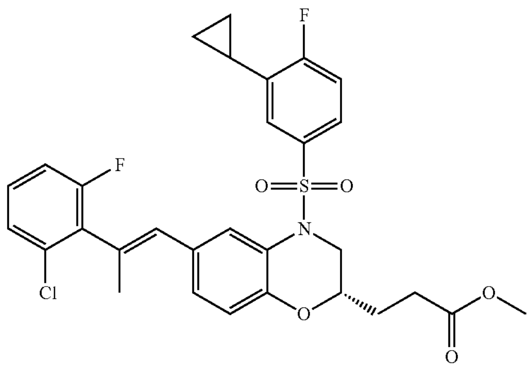 [SMILES: COC(=O)CC[C@H]1CN(S(=O)(=O)c2ccc(F)c(C3CC3)c2)c2cc(/C=C(\C)c3c(F)cccc3Cl)ccc2O1] | (S,E)-methyl 3-(6-(2-(2-chloro-6-fluorophenyl)prop-1-en-1-yl)-4-((3-cyclopropyl-4-fluorophenyl)-sulfonyl)-3,4-dihydro-2H-benzo[b][1,4]oxazin-2-yl)propanoate | 588 (M + H)+ |
| 86E | 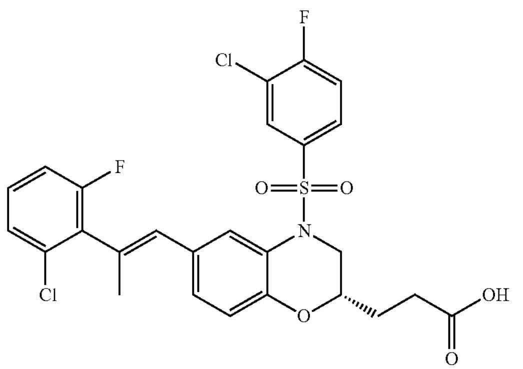 [SMILES: C/C(=C\c1ccc2c(c1)N(S(=O)(=O)c1ccc(F)c(Cl)c1)C[C@H](CCC(=O)O)O2)c1c(F)cccc1Cl] | (S,E)-3-(4-((3-chloro-4-fluorophenyl)sulfonyl)-6-(2-(2-chloro-6-fluorophenyl)prop-1-en-1-yl)-3,4-dihydro-2H-benzo[b][1,4]oxazin-2-yl)propanoic acid | 568 (M + H)+ |
| 86F | 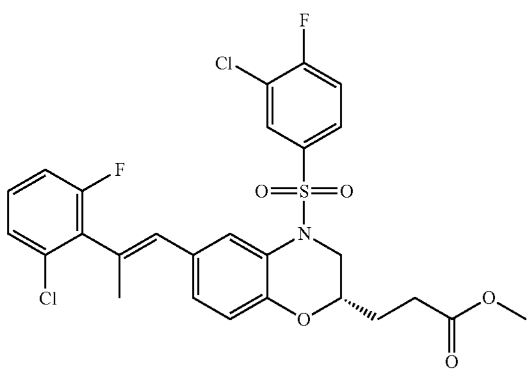 | (S,E)-methyl 3-(4-((3-chloro-4-fluorophenyl)sulfonyl)-6-(2-(2-chloro-6-fluorophenyl)prop-1-en-1-yl)-3,4-dihydro-2H-benzo-[b][1,4]oxazin-2-yl)propanoate | 582 (M + H)+ |
| 86G | 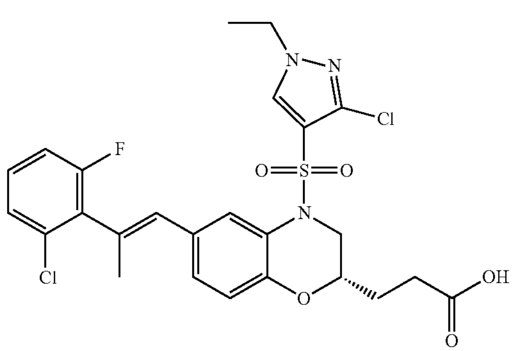 [SMILES: CCn1cc(S(=O)(=O)N2C[C@H](CCC(=O)O)Oc3ccc(/C=C(\C)c4c(F)cccc4Cl)cc32)c(Cl)n1] | (S,E)-3-(4-((3-chloro-1-ethyl-1H-pyrazol-4-yl)sulfonyl)-6-(2-(2-chloro-6-fluorophenyl)prop-1-en-1-yl)-3,4-dihydro-2H-benzo[b][1,4]oxazin-2-yl)propanoic acid | 568 (M + H)+ |

-continued

| No. | Structure | Name | Observed m/z |
|---|---|---|---|
| 86H | 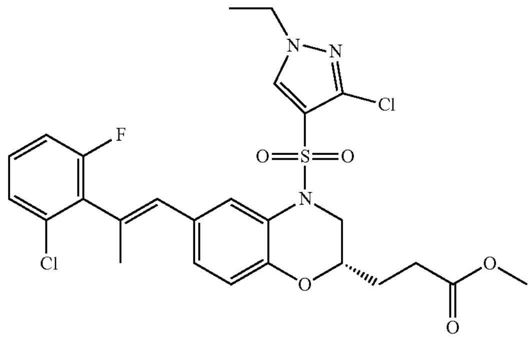 [SMILES: CCn1cc(S(=O)(=O)N2C[C@H](CCC(=O)OC)Oc3ccc(/C=C(\C)c4c(F)cccc4Cl)cc32)c(Cl)n1] | (S,E)-methyl 3-(4-((3-chloro-1-ethyl-1H-pyrazol-4-yl)sulfonyl)-6-(2-(2-chloro-6-fluorophenyl)prop-1-en-1-yl)-3,4-dihydro-2H-benzo[b][1,4]oxazin-2-yl)propanoate | 582 (M + H)+ |
| 86I | 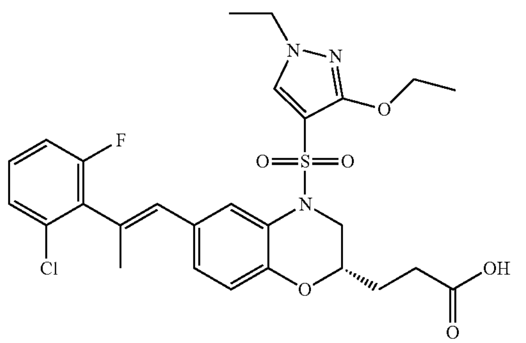 [SMILES: CCOc1nn(CC)cc1S(=O)(=O)N1C[C@H](CCC(=O)O)Oc2ccc(/C=C(\C)c3c(F)cccc3Cl)cc21] | (S,E)-3-(6-(2-(2-chloro-6-fluorophenyl)prop-1-en-1-yl)-4-((3-ethoxy-1-ethyl-1H-pyrazol-4-yl)sulfonyl)-3,4-dihydro-2H-benzo[b][1,4]oxazin-2-yl)propanoic acid | 578 (M + H)+ |
| 86J | 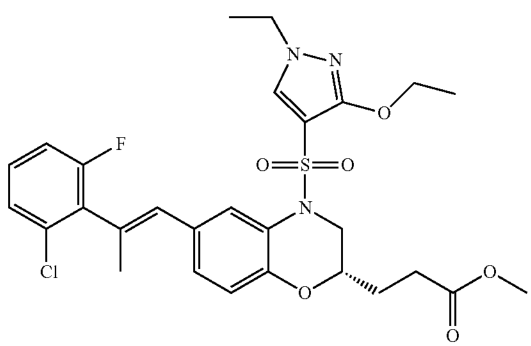 [SMILES: CCOc1nn(CC)cc1S(=O)(=O)N1C[C@H](CCC(=O)OC)Oc2ccc(/C=C(\C)c3c(F)cccc3Cl)cc21] | (S,E)-methyl 3-(6-(2-(2-chloro-6-fluorophenyl)prop-1-en-1-yl)-4-((3-ethoxy-1-ethyl-1H-pyrazol-4-yl)sulfonyl)-3,4-dihydro-2H-benzo[b][1,4]oxazin-2-yl)propanoate | 592 (M + H)+ |
| 86K | 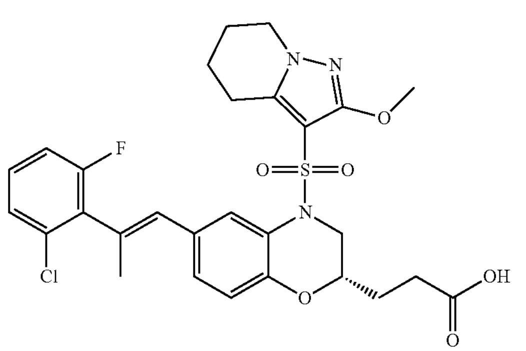 [SMILES: COc1nn2c(c1S(=O)(=O)N1C[C@H](CCC(=O)O)Oc3ccc(/C=C(\C)c4c(F)cccc4Cl)cc31)CCCC2] | (S,E)-3-(6-(2-(2-chloro-6-fluorophenyl)prop-1-en-1-yl)-4-((2-methoxy-4,5,6,7-tetrahydropyrazolo[1,5-a]pyridin-3-yl)sulfonyl)-3,4-dihydro-2H-benzo[b][1,4]oxazin-2-yl)propanoic acid | 590 (M + H)+ |

| No. | Structure | Name | Observed m/z |
|---|---|---|---|
| 86L | 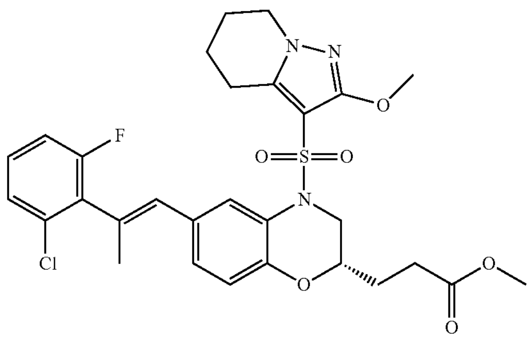 [SMILES: COC(=O)CC[C@H]1CN(S(=O)(=O)c2c(OC)nn3c2CCCC3)c2cc(/C=C(\C)c3c(F)cccc3Cl)ccc2O1] | (S,E)-methyl 3-(6-(2-(2-chloro-6-fluorophenyl)prop-1-en-1-yl)-4-((2-methoxy-4,5,6,7-tetrahydro-pyrazolo[1,5-a]pyridin-3-yl)-sulfonyl)-3,4-dihydro-2H-benzo[b][1,4]oxazin-2-yl)-propanoate | 604 (M + H)+ |
| 86M | 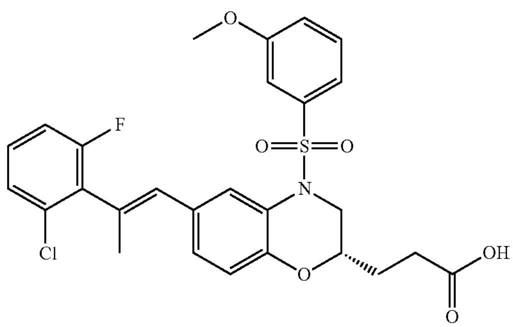 [SMILES: COc1cccc(S(=O)(=O)N2C[C@H](CCC(=O)O)Oc3ccc(/C=C(\C)c4c(F)cccc4Cl)cc32)c1] | (S,E)-3-(6-(2-(2-chloro-6-fluorophenyl)prop-1-en-1-yl)-4-((3-methoxyphenyl)sulfonyl)-3,4-dihydro-2H-benzo[b][1,4]oxazin-2-yl)propanoic acid | 546 (M + H)+ |
| 86N | 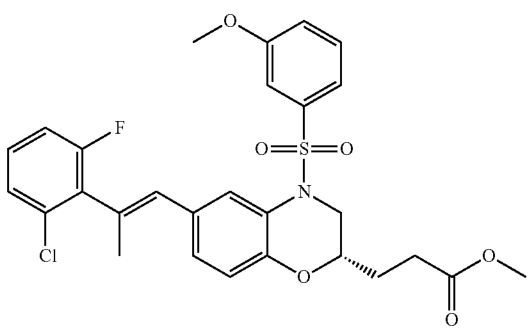 [SMILES: COC(=O)CC[C@H]1CN(S(=O)(=O)c2cccc(OC)c2)c2cc(/C=C(\C)c3c(F)cccc3Cl)ccc2O1] | (S,E)-methyl 3-(6-(2-(2-chloro-6-fluorophenyl)prop-1-en-1-yl)-4-((3-methoxyphenyl)sulfonyl)-3,4-dihydro-2H-benzo[b][1,4]oxazin-2-yl)propanoate | 560 (M + H)+ |
| 86O | 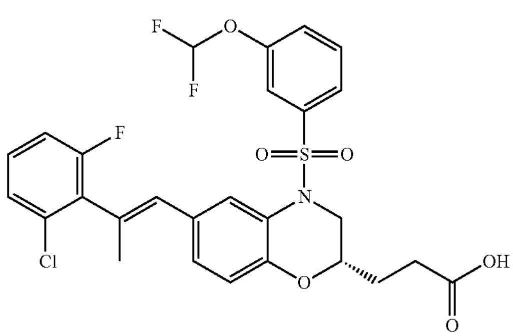 [SMILES: C/C(=C\c1ccc2c(c1)N(S(=O)(=O)c1cccc(OC(F)F)c1)C[C@H](CCC(=O)O)O2)c1c(F)cccc1Cl] | (S,E)-3-(6-(2-(2-chloro-6-fluorophenyl)prop-1-en-1-yl)-4-((3-(difluoromethoxy)phenyl)-sulfonyl)-3,4-dihydro-2H-benzo[b][1,4]oxazin-2-yl)propanoic acid | 582 (M + H)+ |

| No. | Structure | Name | Observed m/z |
|---|---|---|---|
| 86P | 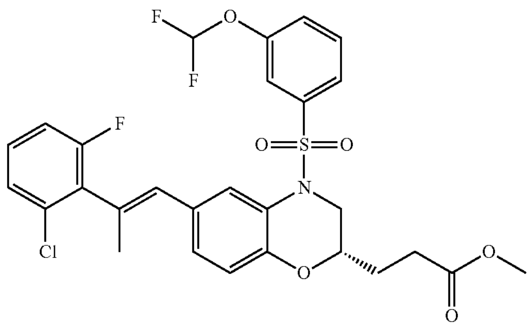 [SMILES: COC(=O)CC[C@H]1CN(S(=O)(=O)c2cccc(OC(F)F)c2)c2cc(/C=C(\C)c3c(F)cccc3Cl)ccc2O1] | (S,E)-methyl 3-(6-(2-(2-chloro-6-fluorophenyl)prop-1-en-1-yl)-4-((3-(difluoromethoxy)phenyl)sulfonyl)-3,4-dihydro-2H-benzo[b][1,4]oxazin-2-yl)propanoate | 596 (M + H)+ |
| 86Q | 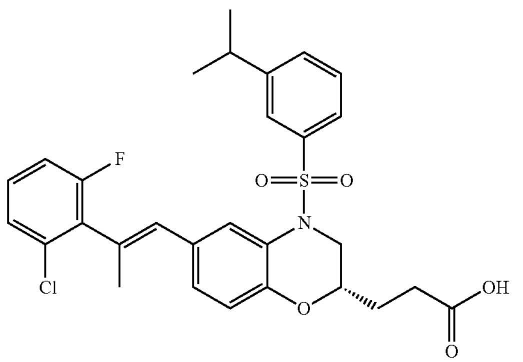 [SMILES: C/C(=C\c1ccc2c(c1)N(S(=O)(=O)c1cccc(C(C)C)c1)C[C@H](CCC(=O)O)O2)c1c(F)cccc1Cl] | (S,E)-3-(6-(2-(2-chloro-6-fluorophenyl)prop-1-en-1-yl)-4-((3-isopropylphenyl)sulfonyl)-3,4-dihydro-2H-benzo[b][1,4]oxazin-2-yl)propanoic acid | 558 (M + H)+ |
| 86R | 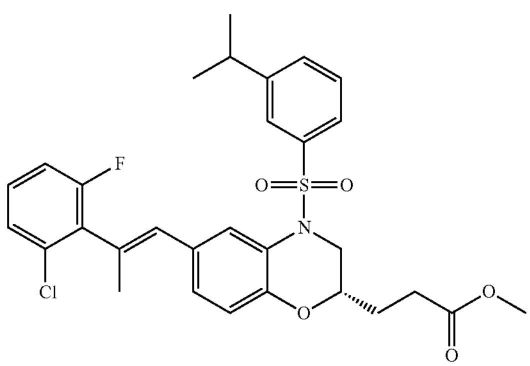 [SMILES: COC(=O)CC[C@H]1CN(S(=O)(=O)c2cccc(C(C)C)c2)c2cc(/C=C(\C)c3c(F)cccc3Cl)ccc2O1] | (S,E)-methyl 3-(6-(2-(2-chloro-6-fluorophenyl)prop-1-en-1-yl)-4-((3-isopropylphenyl)sulfonyl)-3,4-dihydro-2H-benzo[b][1,4]oxazin-2-yl)propanoate | 572 (M + H)+ |
| 86S | 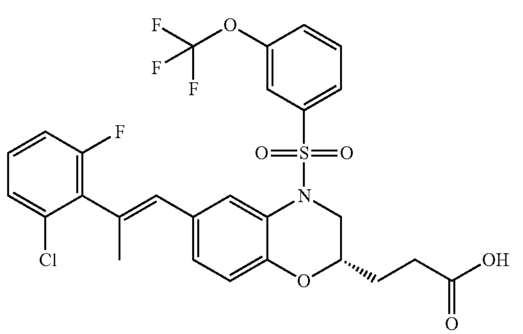 [SMILES: C/C(=C\c1ccc2c(c1)N(S(=O)(=O)c1cccc(OC(F)(F)F)c1)C[C@H](CCC(=O)O)O2)c1c(F)cccc1Cl] | (S,E)-3-(6-(2-(2-chloro-6-fluorophenyl)prop-1-en-1-yl)-4-((3-(trifluoromethoxy)phenyl)sulfonyl)-3,4-dihydro-2H-benzo[b][1,4]oxazin-2-yl)propanoic acid | 600 (M + H)+ |

-continued

| No. | Structure | Name | Observed m/z |
|---|---|---|---|
| 86T | 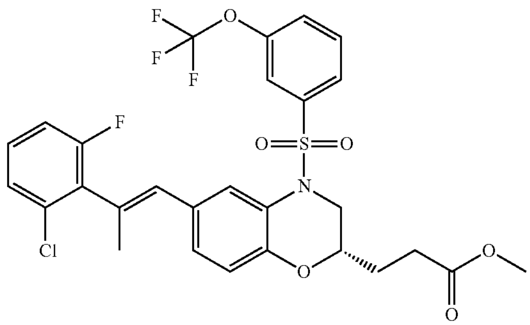 [SMILES: COC(=O)CC[C@H]1CN(S(=O)(=O)c2cccc(OC(F)(F)F)c2)c2cc(/C=C(\C)c3c(F)cccc3Cl)ccc2O1] | (S,E)-methyl 3-(6-(2-(2-chloro-6-fluorophenyl)prop-1-en-1-yl)-4-((3-(trifluoromethoxy)phenyl)sulfonyl)-3,4-dihydro-2H-benzo[b][1,4]oxazin-2-yl)propanoate | 614 (M + H)+ |
| 86U | 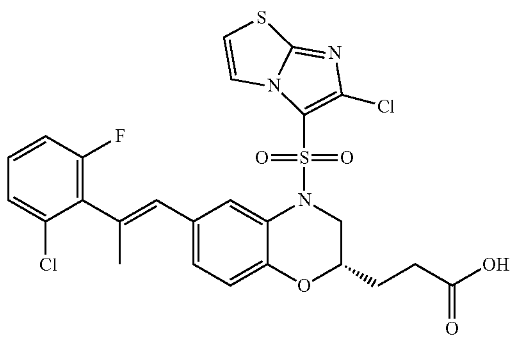 [SMILES: C/C(=C\c1ccc2c(c1)N(S(=O)(=O)c1c(Cl)nc3sccn13)C[C@H](CCC(=O)O)O2)c1c(F)cccc1Cl] | (S,E)-3-(6-(2-(2-chloro-6-fluorophenyl)prop-1-en-1-yl)-4-((6-chloroimidazo[2,1-b]thiazol-5-yl)sulfonyl)-3,4-dihydro-2H-benzo[b][1,4]oxazin-2-yl)propanoic acid | 596 (M + H)+ |
| 86V | 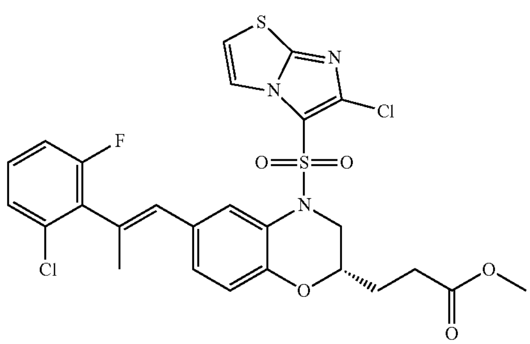 [SMILES: COC(=O)CC[C@H]1CN(S(=O)(=O)c2c(Cl)nc3sccn23)c2cc(/C=C(\C)c3c(F)cccc3Cl)ccc2O1] | (S,E)-methyl 3-(6-(2-(2-chloro-6-fluorophenyl)prop-1-en-1-yl)-4-((6-chloroimidazo[2,1-b]thiazol-5-yl)sulfonyl)-3,4-dihydro-2H-benzo[b][1,4]oxazin-2-yl)propanoate | 610 (M + H)+ |
| 86W | 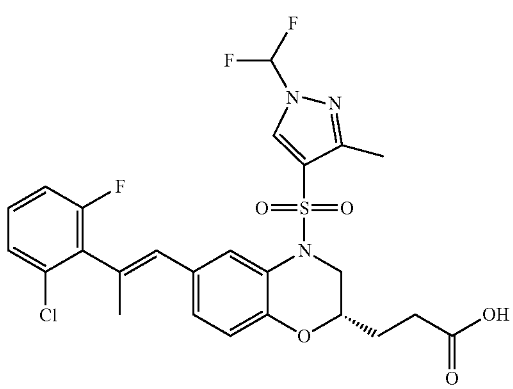 [SMILES: C/C(=C\c1ccc2c(c1)N(S(=O)(=O)c1cn(C(F)F)nc1C)C[C@H](CCC(=O)O)O2)c1c(F)cccc1Cl] | (S,E)-3-(6-(2-(2-chloro-6-fluorophenyl)prop-1-en-1-yl)-4-((1-(difluoromethyl)-3-methyl-1H-pyrazol-4-yl)sulfonyl)-3,4-dihydro-2H-benzo[b][1,4]oxazin-2-yl)propanoic acid | 570 (M + H)+ |

| No. | Structure | Name | Observed m/z |
|---|---|---|---|
| 86X | 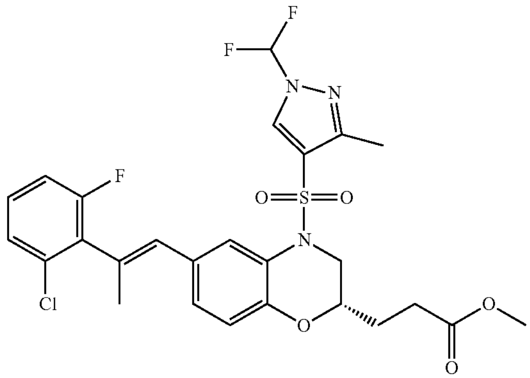 [SMILES: COC(=O)CC[C@H]1CN(S(=O)(=O)c2cn(C(F)F)nc2C)c2cc(/C=C(\C)c3c(F)cccc3Cl)ccc2O1] | (S,E)-methyl 3-(6-(2-(2-chloro-6-fluorophenyl)prop-1-en-1-yl)-4-((1-(difluoromethyl)-3-methyl-1H-pyrazol-4-yl)sulfonyl)-3,4-dihydro-2H-benzo[b][1,4]oxazin-2-yl)propanoate | 584 (M + H)+ |
| 86Y | 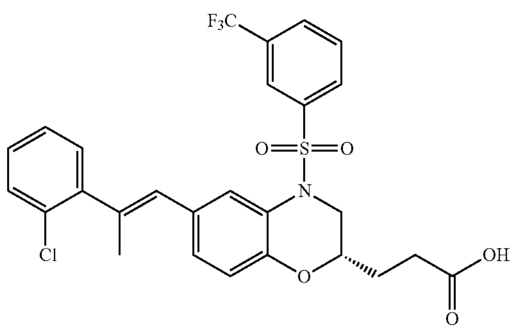 [SMILES: C/C(=C\c1ccc2c(c1)N(S(=O)(=O)c1cccc(C(F)(F)F)c1)C[C@H](CCC(=O)O)O2)c1ccccc1Cl] | (S,E)-3-(6-(2-(2-chlorophenyl)-prop-1-en-1-yl)-4-((3-(trifluoromethyl)phenyl)sulfonyl)-3,4-dihydro-2H-benzo[b][1,4]oxazin-2-yl)propanoic acid | 566 (M + H)+ |
| 86Z | 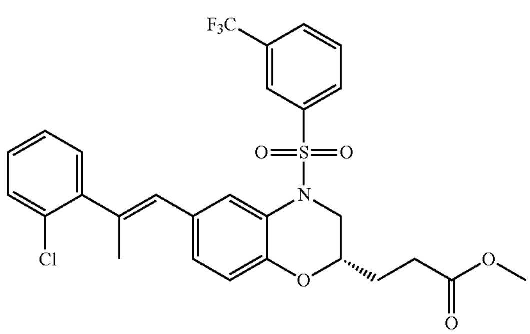 [SMILES: COC(=O)CC[C@H]1CN(S(=O)(=O)c2cccc(C(F)(F)F)c2)c2cc(/C=C(\C)c3ccccc3Cl)ccc2O1] | (S,E)-methyl 3-(6-(2-(2-chlorophenyl)prop-1-en-1-yl)-4-((3-(trifluoromethyl)phenyl)-sulfonyl)-3,4-dihydro-2H-benzo[b][1,4]oxazin-2-yl)propanoate | 580 (M + H)+ |
| 86AA | 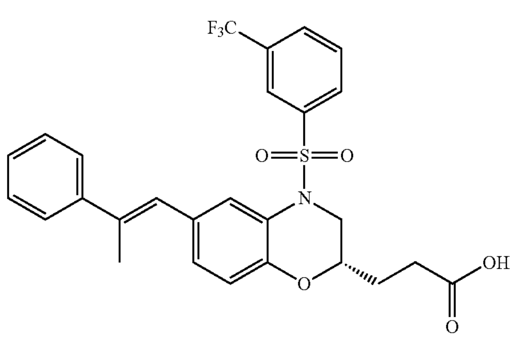 [SMILES: C/C(=C\c1ccc2c(c1)N(S(=O)(=O)c1cccc(C(F)(F)F)c1)C[C@H](CCC(=O)O)O2)c1ccccc1] | (S,E)-3-(6-(2-phenylprop-1-en-1-yl)-4-((3-(trifluoromethyl)phenyl)-sulfonyl)-3,4-dihydro-2H-benzo[b][1,4]oxazin-2-yl)propanoic acid | 532 (M + H)+ |

-continued

| No. | Structure | Name | Observed m/z |
|---|---|---|---|
| 86AB | 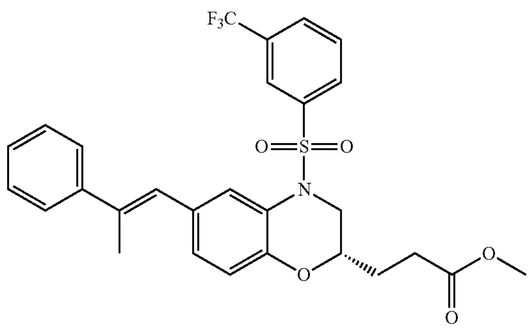 [SMILES: COC(=O)CC[C@H]1CN(S(=O)(=O)c2cccc(C(F)(F)F)c2)c2cc(/C=C(\C)c3ccccc3)ccc2O1] | (S,E)-methyl 3-(6-(2-phenylprop-1-en-1-yl)-4-((3-(trifluoromethyl)phenyl)sulfonyl)-3,4-diydro-2H-benzo[b][1,4]oxazin-2-yl)propanoate | 546 (M + H)+ |
| 86AC | 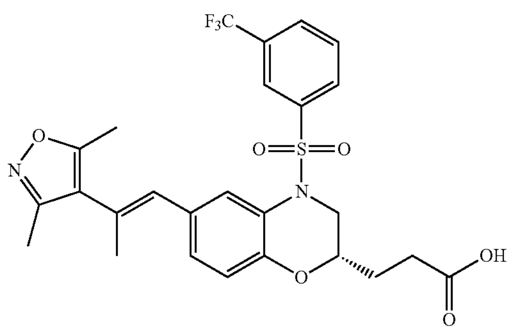 [SMILES: C/C(=C\c1ccc2c(c1)N(S(=O)(=O)c1cccc(C(F)(F)F)c1)C[C@H](CCC(=O)O)O2)c1c(C)noc1C] | (S,E)-3-(6-(2-(3,5-dimethylisoxazol-4-yl)prop-1-en-1-yl)-4-((3-(trifluoromethyl)phenyl)sulfonyl)-3,4-dihydro-2H-benzo[b][1,4]oxazin-2-yl)propanoic acid | 551 (M + H)+ |
| 86AD | 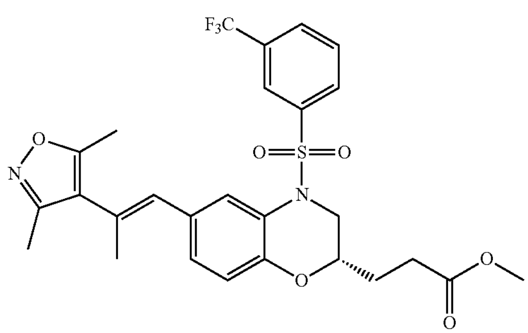 [SMILES: COC(=O)CC[C@H]1CN(S(=O)(=O)c2cccc(C(F)(F)F)c2)c2cc(/C=C(\C)c3c(C)noc3C)ccc2O1] | (S,E)-methyl 3-(6-(2-(3,5-dimethylisoxazol-4-yl)prop-1-en-1-yl)-4-((3-(trifluoromethyl)phenyl)sulfonyl)-3,4-dihydro-2H-benzo[b][1,4]oxazin-2-yl)-propanoate | 565 (M + H)+ |
| 86AE | 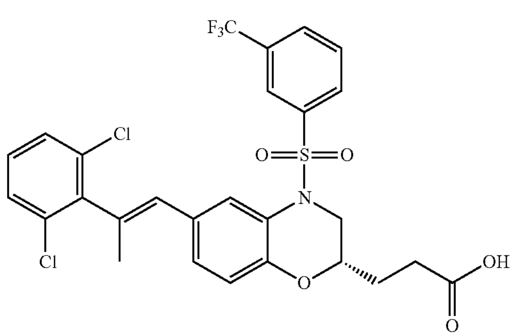 [SMILES: C/C(=C\c1ccc2c(c1)N(S(=O)(=O)c1cccc(C(F)(F)F)c1)C[C@H](CCC(=O)O)O2)c1c(Cl)cccc1Cl] | (S,E)-3-(6-(2-(2,6-dichlorophenyl)prop-1-en-1-yl)-4-((3-(trifluoromethyl)phenyl)sulfonyl)-3,4-dihydro-2H-benzo[b][1,4]oxazin-2-yl)propanoic acid | 600 (M + H)+ |

| No. | Structure | Name | Observed m/z |
|---|---|---|---|
| 86AF | 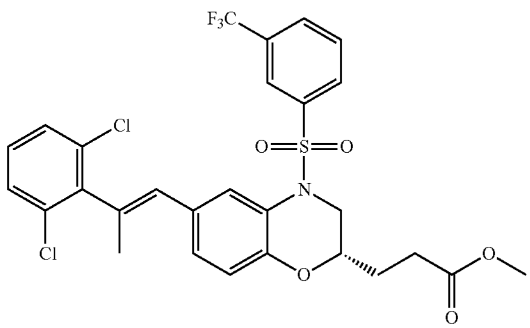 [SMILES: COC(=O)CC[C@H]1CN(S(=O)(=O)c2cccc(C(F)(F)F)c2)c2cc(/C=C(\C)c3c(Cl)cccc3Cl)ccc2O1] | (S,E)-methyl 3-(6-(2-(2,6-dichlorophenyl)prop-1-en-1-yl)-4-((3-(trifluoromethyl)phenyl)-sulfonyl)-3,4-dihydro-2H-benzo[b][1,4]oxazin-2-yl)propanoate | 614 (M + H)+ |
| 86AG | 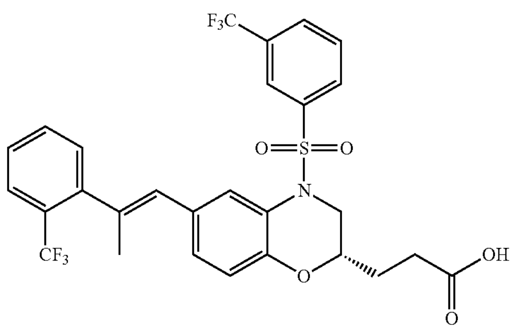 | (S,E)-3-(6-(2-(2-(trifluoromethyl)-phenyl)prop-1-en-1-yl)-4-((3-(trifluoromethyl)phenyl)sulfonyl)-3,4-dihydro-2H-benzo[b][1,4]-oxazin-2-yl)propanoic acid | 600 (M + H)+ |
| 86AH | 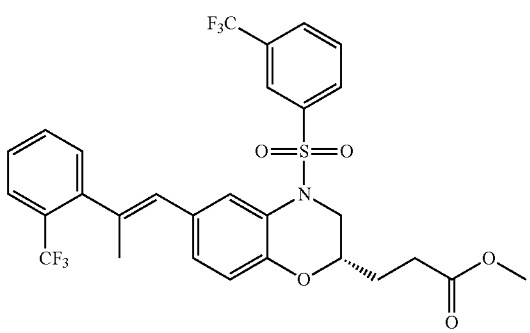 [SMILES: COC(=O)CC[C@H]1CN(S(=O)(=O)c2cccc(C(F)(F)F)c2)c2cc(/C=C(\C)c3ccccc3C(F)(F)F)ccc2O1] | (S,E)-methyl 3-(6-(2-(2-(trifluoro-methyl)phenyl)prop-1-en-1-yl)-4-((3-(trifluoromethyl)phenyl)-sulfonyl)-3,4-dihydro-2H-benzo[b][1,4]oxazin-2-yl)propanoate | 614 (M + H)+ |
| 86AI | 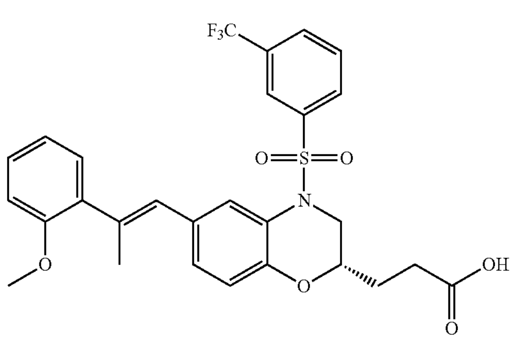 [SMILES: COc1ccccc1/C(C)=C/c1ccc2c(c1)N(S(=O)(=O)c1cccc(C(F)(F)F)c1)C[C@H](CCC(=O)O)O2] | (S,E)-3-(6-(2-(2-methoxy-phenyl)prop-1-en-1-yl)-4-((3-(trifluoromethyl)phenyl)sulfonyl)-3,4-dihydro-2H-benzo[b][1,4]-oxazin-2-yl)propanoic acid | 562 (M + H)+ |

-continued

| No. | Structure | Name | Observed m/z |
|---|---|---|---|
| 86AJ | 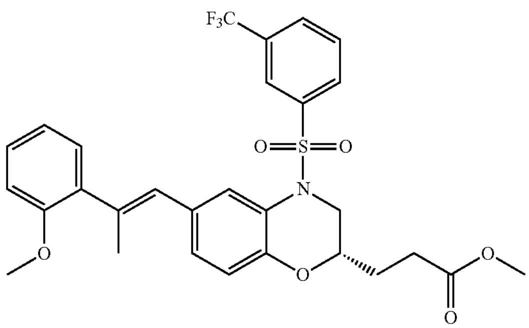 [SMILES: COC(=O)CC[C@H]1CN(S(=O)(=O)c2cccc(C(F)(F)F)c2)c2cc(/C=C(\C)c3ccccc3OC)ccc2O1] | (S,E)-methyl 3-(6-(2-(2-methoxy-phenyl)prop-1-en-1-yl)-4-((3-(trifluoromethyl)phenyl)sulfonyl)-3,4-dihydro-2H-benzo[b][1,4]-oxazin-2-yl)propanoate | 576 (M + H)+ |
| 86AK | 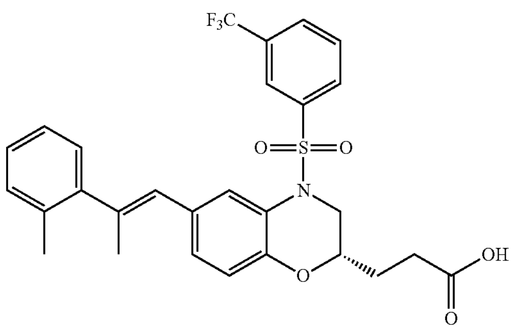 [SMILES: C/C(=C\c1ccc2c(c1)N(S(=O)(=O)c1cccc(C(F)(F)F)c1)C[C@H](CCC(=O)O)O2)c1ccccc1C] | (S,E)-3-(6-(2-(o-tolyl)prop-1-en-1-yl)-4-((3-(trifluoromethyl)-phenyl)sulfonyl)-3,4-dihydro-2H-benzo[b][1,4]oxazin-2-yl)propanoic acid | 546 (M + H)+ |
| 86AL | 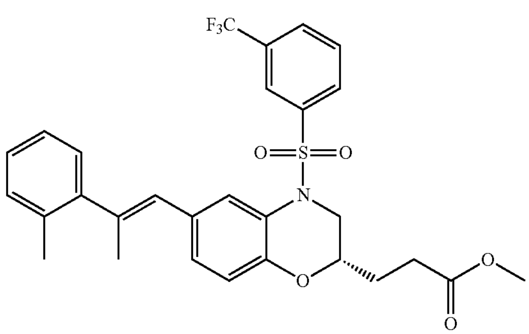 | (S,E)-methyl 3-(6-(2-(o-tolyl)prop-1-en-1-yl)-4-((3-(trifluoromethyl)-phenyl)sulfonyl)-3,4-dihydro-2H-benzo[b][1,4]oxazin-2-yl)propanoate | 560 (M + H)+ |
| 86AM | 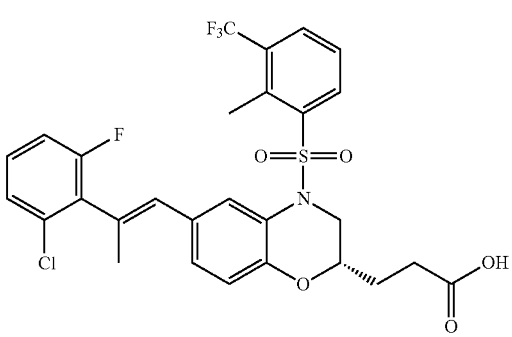 [SMILES: C/C(=C\c1ccc2c(c1)N(S(=O)(=O)c1cccc(C(F)(F)F)c1C)C[C@H](CCC(=O)O)O2)c1c(F)cccc1Cl] | (S,E)-3-(6-(2-(2-chloro-6-fluorophenyl)prop-1-en-1-yl)-4-((2-methyl-3-(trifluoromethyl)-phenyl)sulfonyl)-3,4-dihydro-2H-benzo[b][1,4]oxazin-2-yl)propanoic acid | 598 (M + H)+ |

| No. | Structure | Name | Observed m/z |
|---|---|---|---|
| 86AN | 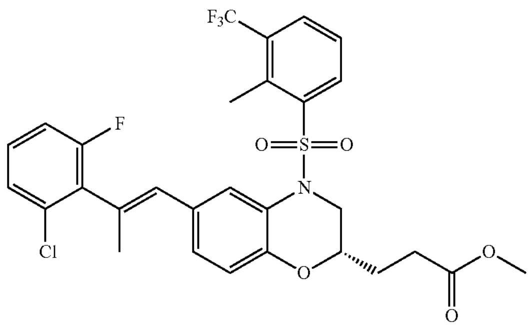 [SMILES: COC(=O)CC[C@H]1CN(S(=O)(=O)c2cccc(C(F)(F)F)c2C)c2cc(/C=C(\C)c3c(F)cccc3Cl)ccc2O1] | (S,E)-methyl 3-(6-(2-(2-chloro-6-fluorophenyl)prop-1-en-1-yl)-4-((2-methyl-3-(trifluoromethyl)-phenyl)sulfonyl)-3,4-dihydro-2H-benzo[b][1,4]oxazin-2-yl)propanoate | 612 (M + H)+ |
| 86AO | 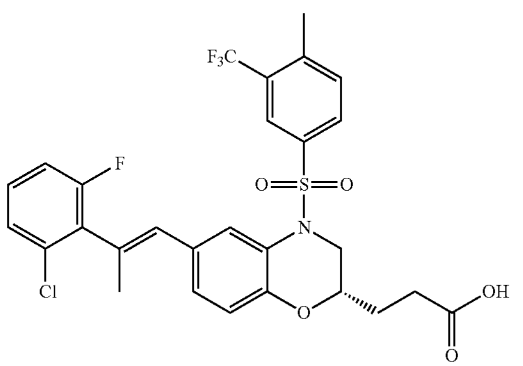 [SMILES: C/C(=C\c1ccc2c(c1)N(S(=O)(=O)c1ccc(C)c(C(F)(F)F)c1)C[C@H](CCC(=O)O)O2)c1c(F)cccc1Cl] | (S,E)-3-(6-(2-(2-chloro-6-fluorophenyl)prop-1-en-1-yl)-4-((4-methyl-3-(trifluoromethyl)-phenyl)sulfonyl)-3,4-dihydro-2H-benzo[b][1,4]oxazin-2-yl)propanoic acid | 598 (M + H)+ |
| 86AP | 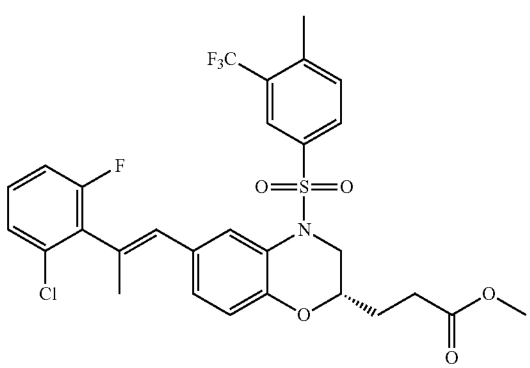 [SMILES: COC(=O)CC[C@H]1CN(S(=O)(=O)c2ccc(C)c(C(F)(F)F)c2)c2cc(/C=C(\C)c3c(F)cccc3Cl)ccc2O1] | (S,E)-methyl 3-(6-(2-(2-chloro-6-fluorophenyl)prop-1-en-1-yl)-4-((2-methyl-3-(trifluoromethyl)-phenyl)sulfonyl)-3,4-dihydro-2H-benzo[b][1,4]oxazin-2-yl)propanoate | 612 (M + H)+ |
| 86AQ | 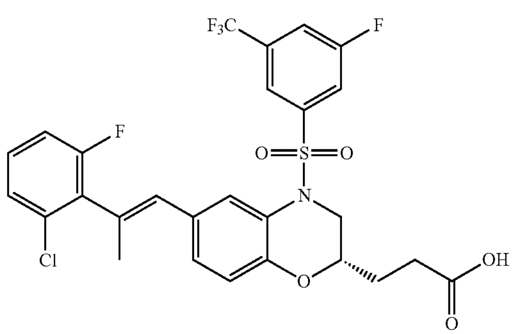 [SMILES: C/C(=C\c1ccc2c(c1)N(S(=O)(=O)c1cc(F)cc(C(F)(F)F)c1)C[C@H](CCC(=O)O)O2)c1c(F)cccc1Cl] | (S,E)-3-(6-(2-(2-chloro-6-fluorophenyl)-prop-1-en-1-yl)-4-((3-fluoro-5-(trifluoromethyl)-phenyl)sulfonyl)-3,4-dihydro-2H-benzo[b][1,4]oxazin-2-yl)propanoic acid | 602 (M + H)+ |

| No. | Structure | Name | Observed m/z |
|---|---|---|---|
| 86AR | 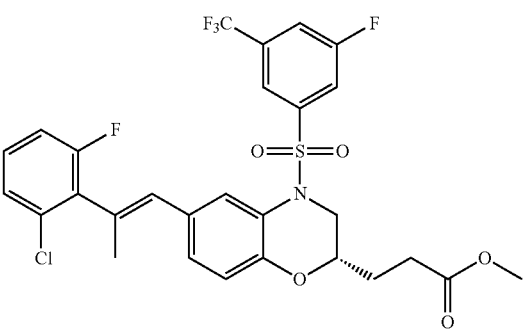 [SMILES: COC(=O)CC[C@H]1CN(S(=O)(=O)c2cc(F)cc(C(F)(F)F)c2)c2cc(/C=C(\C)c3c(F)cccc3Cl)ccc2O1] | (S,E)-methyl 3-(6-(2-(2-chloro-6-fluorophenyl)prop-1-en-1-yl)-4-((3-fluoro-5-(trifluoromethyl)-phenyl)sulfonyl)-3,4-dihydro-2H-benzo[b][1,4]oxazin-2-yl)propanoate | 616 (M + H)+ |
| 86AS | 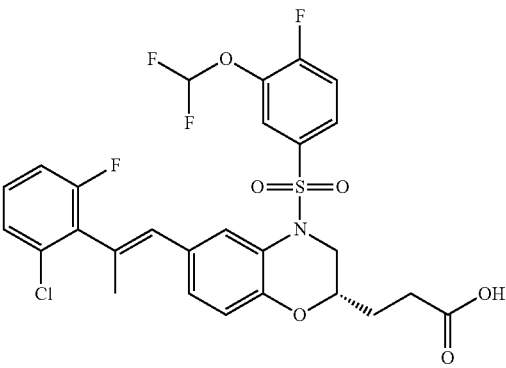 [SMILES: C/C(=C\c1ccc2c(c1)N(S(=O)(=O)c1ccc(F)c(OC(F)F)c1)C[C@H](CCC(=O)O)O2)c1c(F)cccc1Cl] | (S,E)-3-(6-(2-(2-chloro-6-fluorophenyl)prop-1-en-1-yl)-4-((3-(difluoromethoxy)-4-fluorophenyl)sulfonyl)-3,4-dihydro-2H-benzo[b][1,4]oxazin-2-yl)propanoic acid | 600 (M + H)+ |
| 86AT | 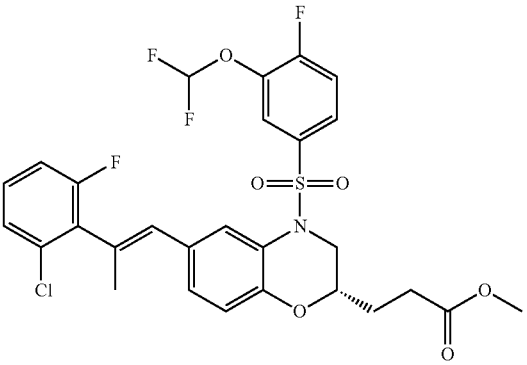 [SMILES: COC(=O)CC[C@H]1CN(S(=O)(=O)c2ccc(F)c(OC(F)F)c2)c2cc(/C=C(\C)c3c(F)cccc3Cl)ccc2O1] | (S,E)-methyl 3-(6-(2-(2-chloro-6-fluorophenyl)prop-1-en-1-yl)-4-((3-(difluoromethoxy)-4-fluorophenyl)sulfonyl)-3,4-dihydro-2H-benzo[b][1,4]oxazin-2-yl)propanoate | 614 (M + H)+ |
| 86AU | 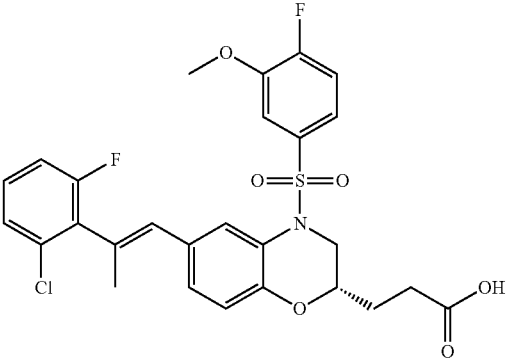 [SMILES: COc1cc(S(=O)(=O)N2C[C@H](CCC(=O)O)Oc3ccc(/C=C(\C)c4c(F)cccc4Cl)cc32)ccc1F] | (S,E)-3-(6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)propanoic acid | 564 (M + H)+ |

| No. | Structure | Name | Observed m/z |
|---|---|---|---|
| 86AV | 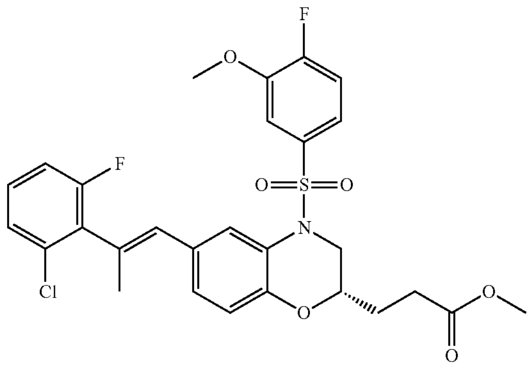 [SMILES: COC(=O)CC[C@H]1CN(S(=O)(=O)c2ccc(F)c(OC)c2)c2cc(/C=C(\C)c3c(F)cccc3Cl)ccc2O1] | methyl (S,E)-3-(6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)propanoate | 578 (M + H)+ |
| 86AW | 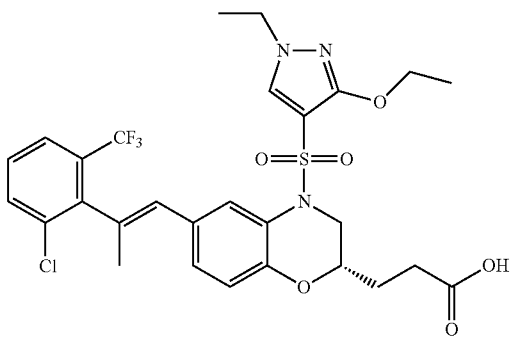 [SMILES: CCOc1nn(CC)cc1S(=O)(=O)N1C[C@H](CCC(=O)O)Oc2ccc(/C=C(\C)c3c(Cl)cccc3C(F)(F)F)cc21] | (S,E)-3-(6-(2-(2-chloro-6-(trifluoromethyl)phenyl)prop-1-en-1-yl)-4-((3-ethoxy-1-ethyl-1H-pyrazol-4-yl)sulfonyl)-3,4-dihydro-2H-benzo[b][1,4]oxazin-2-yl)propanoic acid | 628 (M + H)+ |
| 86AX | 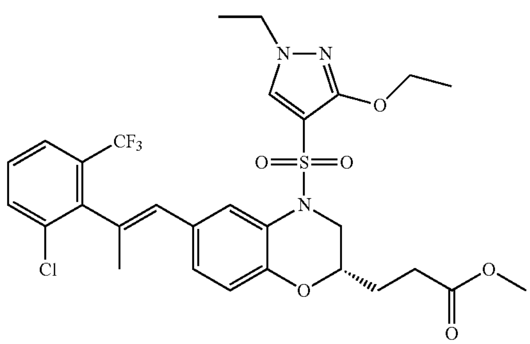 [SMILES: CCOc1nn(CC)cc1S(=O)(=O)N1C[C@H](CCC(=O)OC)Oc2ccc(/C=C(\C)c3c(Cl)cccc3C(F)(F)F)cc21] | methyl (S,E)-3-(6-(2-(2-chloro-6-(trifluoromethyl)phenyl)prop-1-en-1-yl)-4-((3-ethoxy-1-ethyl-1H-pyrazol-4-yl)sulfonyl)-3,4-dihydro-2H-benzo[b][1,4]oxazin-2-yl)propanoate | 642 (M + H)+ |
| 86AY | 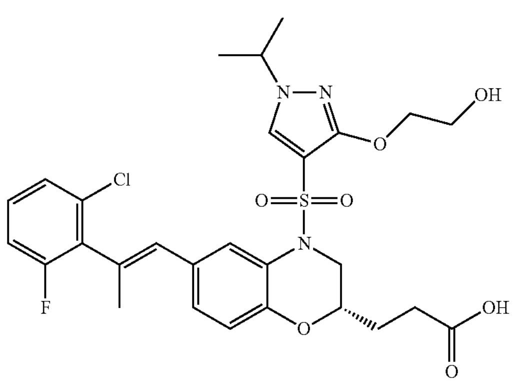 [SMILES: C/C(=C\c1ccc2c(c1)N(S(=O)(=O)c1cn(C(C)C)nc1OCCO)C[C@H](CCC(=O)O)O2)c1c(F)cccc1Cl] | (S,E)-3-(6-(2-(2-chloro-6-fluorophenyl)prop-1-en-1-yl)-4-((3-(2-hydroxyethoxy)-1-isopropyl-1H-pyrazol-4-yl)sulfonyl)-3,4-dihydro-2H-benzo[b][1,4]oxazin-2-yl)propanoic acid | 608 (M + H)+ |

| No. | Structure | Name | Observed m/z |
|---|---|---|---|
| 86AZ | 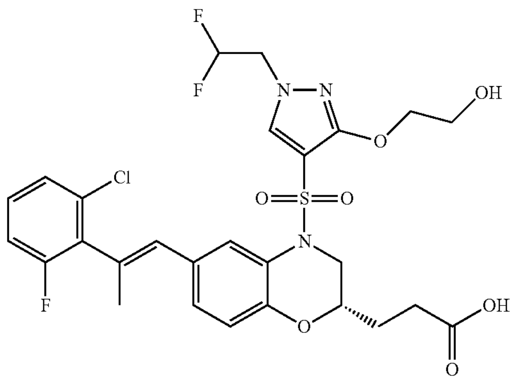 [SMILES: C/C(=C\c1ccc2c(c1)N(S(=O)(=O)c1cn(CC(F)F)nc1OCCO)C[C@H](CCC(=O)O)O2)c1c(F)cccc1Cl] | (S,E)-3-(6-(2-(2-chloro-6-fluorophenyl)prop-1-en-1-yl)-4-((1-(2,2-difluoroethyl)-3-(2-hydroxyethoxy)-1H-pyrazol-4-yl)sulfonyl)-3,4-dihydro-2H-benzo[b][1,4]oxazin-2-yl)propanoic acid | 630 (M + H)+ |
| 86BA | 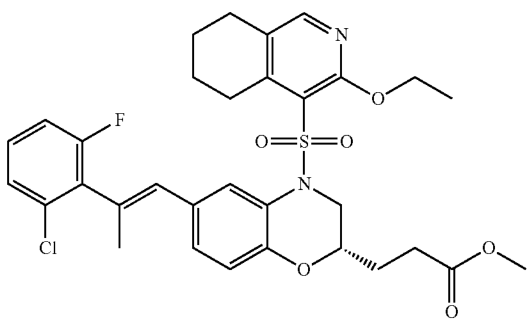 [SMILES: CCOc1ncc2c(c1S(=O)(=O)N1C[C@H](CCC(=O)OC)Oc3ccc(/C=C(\C)c4c(F)cccc4Cl)cc31)CCCC2] | methyl (S,E)-3-(6-(2-(2-chloro-6-fluorophenyl)prop-1-en-1-yl)-4-((3-ethoxy-5,6,7,8-tetrahydroisoquinolin-4-yl)sulfonyl)-3,4-dihydro-2H-benzo[b][1,4]oxazin-2-yl)propanoate | 629 (M + H)+ |
| 86BB | 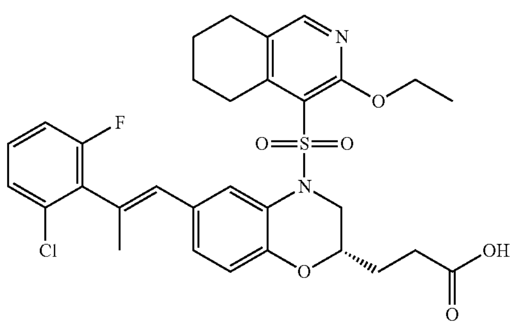 [SMILES: CCOc1ncc2c(c1S(=O)(=O)N1C[C@H](CCC(=O)O)Oc3ccc(/C=C(\C)c4c(F)cccc4Cl)cc31)CCCC2] | (S,E)-3-(6-(2-(2-chloro-6-fluorophenyl)prop-1-en-1-yl)-4-((3-ethoxy-5,6,7,8-tetrahydroisoquinolin-4-yl)sulfonyl)-3,4-dihydro-2H-benzo[b][1,4]oxazin-2-yl)propanoic acid | 615 (M + H)+ |
| 86BC | 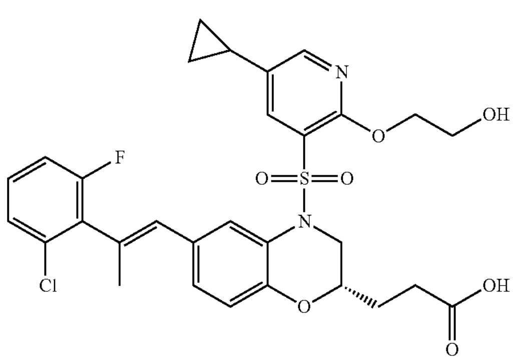 [SMILES: C/C(=C\c1ccc2c(c1)N(S(=O)(=O)c1cc(C3CC3)cnc1OCCO)C[C@H](CCC(=O)O)O2)c1c(F)cccc1Cl] | (S,E)-3-(6-(2-(2-chloro-6-fluorophenyl)prop-1-en-1-yl)-4-((5-cyclopropyl-2-(2-hydroxyethoxy)pyridin-3-yl)sulfonyl)-3,4-dihydro-2H-benzo[b][1,4]oxazin-2-yl)propanoic acid | 617 (M + H)+ |

| No. | Structure | Name | Observed m/z |
|---|---|---|---|
| 86BD | 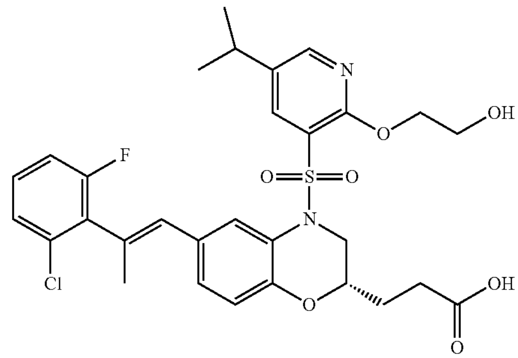 [SMILES: C/C(=C\c1ccc2c(c1)N(S(=O)(=O)c1cc(C(C)C)cnc1OCCO)C[C@H](CCC(=O)O)O2)c1c(F)cccc1Cl] | (S,E)-3-(6-(2-(2-chloro-6-fluorophenyl)prop-1-en-1-yl)-4-((2-(2-hydroxyethoxy)-5-isopropylpyridin-3-yl)sulfonyl)-3,4-dihydro-2H-benzo[b][1,4]oxazin-2-yl)propanoic acid | 619 (M + H)+ |

Example 87-Synthesis of Methyl (S,E)-3-(4-((3-ethoxy-1-ethyl-1H-pyrazol-4-yl)sulfonyl)-6-(2-fluoro-6-(trifluoromethyl)styryl)-3,4-dihydro-2H-benzo[b][1,4]oxazin-2-yl)propanoate

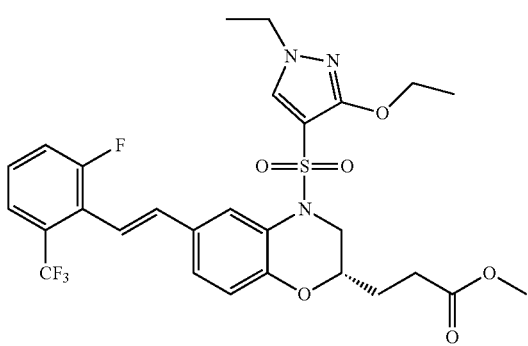

Part I—Synthesis of Methyl (S)-3-(6-bromo-4-((3-ethoxy-1-ethyl-1H-pyrazol-4-yl)sulfonyl)-3,4-dihydro-2H-benzo[b][1,4]oxazin-2-yl)propanoate

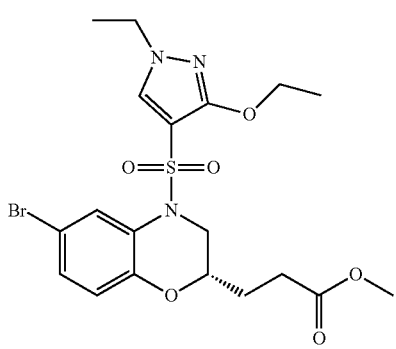 [SMILES: CCOc1nn(CC)cc1S(=O)(=O)N1C[C@H](CCC(=O)OC)Oc2ccc(Br)cc21]

A solution of methyl (S)-3-(6-bromo-3,4-dihydro-2H-benzo[b][1,4]oxazin-2-yl)propanoate (3.35 g, 11.09 mmol), 3-ethoxy-1-ethyl-1H-pyrazole-4-sulfonyl chloride (4.0 g, 16.76 mmol), and pyridine (45 mL) was stirred overnight at room temperature. The pH value of the solution was adjusted to 3-4 with 2 M HCl. The mixture was extracted three times with ethyl acetate. The combined organic layers were dried (Na₂SO₄) and concentrated. The resulting residue was purified by MPLC eluting with a gradient of 10-20% ethyl acetate in petroleum ether to afford methyl (S)-3-(6-bromo-4-((3-ethoxy-1-ethyl-1H-pyrazol-4-yl)sulfonyl)-3,4-dihydro-2H-benzo[b][1,4]oxazin-2-yl)propanoate (5.11 g, 91%) as a yellow oil.

Part II—Synthesis of Methyl 3-((2S)-4-((3-ethoxy-1-ethyl-1H-pyrazol-4-yl)sulfonyl)-6-((E)-2-(4,4,6-trimethyl-1,3,2-dioxaborinan-2-yl)vinyl)-3,4-dihydro-2H-benzo[b][1,4]oxazin-2-yl)propanoate

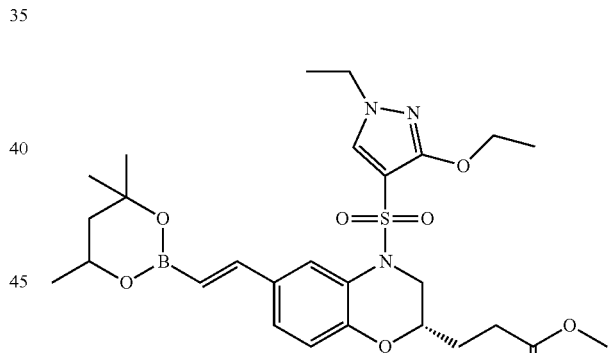

A mixture of methyl (S)-3-(6-bromo-4-((3-ethoxy-1-ethyl-1H-pyrazol-4-yl)sulfonyl)-3,4-dihydro-2H-benzo[b][1,4]oxazin-2-yl)propanoate (500 mg, 1.00 mmol), 4,4,6-trimethyl-2-vinyl-1,3,2-dioxaborinane (184.8 mg, 1.20 mmol), bis(tri-tert-butylphosphine)palladium(0) (51.1 mg, 0.10 mmol), triethylamine (8 mL), and toluene (15 mL) was stirred for 24 hours at 80° C. The pH value of the solution was adjusted to 3-4 with 2 M HCl. The resulting solution was extracted three times with ethyl acetate. The combined organic layers were washed with brine, dried (Na₂SO₄) and concentrated. The resulting residue was purified via MPLC eluting with a gradient of 10-20% ethyl acetate in petroleum ether to afford methyl 3-((2S)-4-((3-ethoxy-1-ethyl-1H-pyrazol-4-yl)sulfonyl)-6-((E)-2-(4,4,6-trimethyl-1,3,2-dioxaborinan-2-yl)vinyl)-3,4-dihydro-2H-benzo[b][1,4]oxazin-2-yl)propanoate (480 mg, 84%) as a yellow oil.

Part III—Synthesis of Methyl (S,E)-3-(4-((3-ethoxy-1-ethyl-1H-pyrazol-4-yl)sulfonyl)-6-(2-fluoro-6-(trifluoromethyl)styryl)-3,4-dihydro-2H-benzo[b][1,4]oxazin-2-yl)propanoate

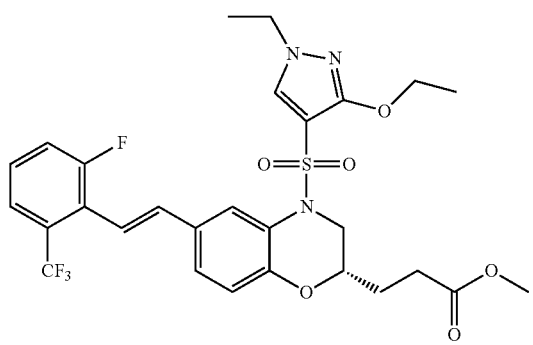

A mixture of methyl 3-((2S)-4-((3-ethoxy-1-ethyl-1H-pyrazol-4-yl)sulfonyl)-6-((E)-2-(4,4,6-trimethyl-1,3,2-dioxaborinan-2-yl)vinyl)-3,4-dihydro-2H-benzo[b][1,4]oxazin-2-yl)propanoate (303 mg, 0.53 mmol), 2-bromo-1-fluoro-3-(trifluoromethyl)benzene (192.1 mg, 0.79 mmol), ethanol (0.6 mL), water (2.2 mL), toluene (4.3 mL), sodium carbonate (458 mg, 4.32 mmol), and tetrakis(triphenylphosphine)palladium(0) (73.4 mg, 0.06 mmol) was stirred overnight at 95° C. The mixture was diluted with water and was extracted three times with dichloromethane. The combined organic layers were dried (Na$_2$SO$_4$) and concentrated. The resulting residue was purified by MPLC eluting with a gradient of 33-66% ethyl acetate in petroleum ether to afford methyl (S,E)-3-(4-((3-ethoxy-1-ethyl-1H-pyrazol-4-yl)sulfonyl)-6-(2-fluoro-6-(trifluoromethyl)styryl)-3,4-dihydro-2H-benzo[b][1,4]oxazin-2-yl)propanoate as a white solid. $^1$H-NMR (400 MHz, CDCl$_3$) δ 1.30 (t, J=7.2 Hz, 3H), 1.39 (t, J=7.2 Hz, 3H), 1.95-2.01 (m, 2H), 2.54-2.59 (m, 2H), 3.32 (dd, J=9.2 Hz, 14.0 Hz, 1H), 3.71 (s, 3H), 3.94 (q, J=7.2 Hz, 2H), 4.02-4.08 (m, 1H), 4.18-4.23 (m, 2H), 4.38 (dd, J=2.4 Hz, 14.0 Hz, 1H), 6.85 (d, J=8.4 Hz, 1H), 6.92-7.00 (m, 1H), 7.16-7.21 (m, 2H), 7.28-7.31 (m, 2H), 7.48-7.50 (m, 1H), 7.64 (s, 1H), 7.87 (s, 1H). (ES, m/z): (M+H)$^+$612.

Example 88—Synthesis of (S,E)-3-(4-((3-Ethoxy-1-ethyl-1H-pyrazol-4-yl)sulfonyl)-6-(2-fluoro-6-(trifluoromethyl)styryl)-3,4-dihydro-2H-benzo[b][1,4]oxazin-2-yl)propanoic acid

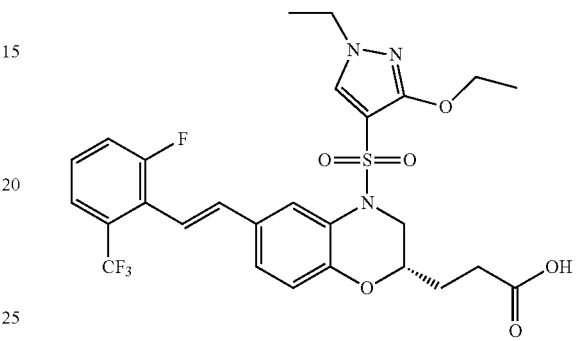

Based on the procedure in Example 42, (S,E)-3-(4-((3-ethoxy-1-ethyl-1H-pyrazol-4-yl)sulfonyl)-6-(2-fluoro-6-(trifluoromethyl)styryl)-3,4-dihydro-2H-benzo[b][1,4]oxazin-2-yl)propanoic acid was prepared. $^1$H-NMR (300 MHz, CD$_3$OD) δ 1.31 (t, J=7.2 Hz, 3H), 1.38 (t, J=7.2 Hz, 3H), 1.93-2.06 (m, 2H), 2.61-2.67 (m, 2H), 3.34 (dd, J=9.0 Hz, 13.8 Hz, 1H), 3.34 (q, J=7.2 Hz, 2H), 4.07-4.12 (m, 1H), 4.21 (q, J=6.9 Hz, 2H), 4.39 (dd, J=2.1 Hz, 13.8 Hz, 1H), 6.86 (d, J=8.4 Hz, 1H), 6.97 (dd, J=2.1 Hz, 16.8 Hz, 1H), 7.16-7.22 (m, 2H), 7.27-7.34 (m, 2H), 7.48-7.51 (m, 1H), 7.64 (s, 1H), 7.87 (d, J=1.8 Hz, 1H). (ES, m/z): (M+H)$^+$598.

Example 89—Preparation of Additional Substituted (S,E)-3-(6-(Aryl or heteroaryl)-4-(aryl or heteroaryl)sulfonyl)-3,4-dihydro-2H-benzo[b][1,4]oxazin-2-yl)propanoates and Propionic Acids Compounds in Table 11 were prepared based on experimental procedures described in Examples 30 and 87 and the detailed description.

TABLE 11

| No. | Structure | Name | Observed m/z |
|---|---|---|---|
| 89A | ![structure] | (S,E)-3-(6-(2-chloro-6-fluorostyryl)-4-((3-(difluoromethoxy)phenyl)sulfonyl)-3,4-dihydro-2H-benzo[b][1,4]oxazin-2-yl)propanoic acid | 568 (M + H)$^+$ |

TABLE 11-continued

| No. | Structure | Name | Observed m/z |
|---|---|---|---|
| 89B | 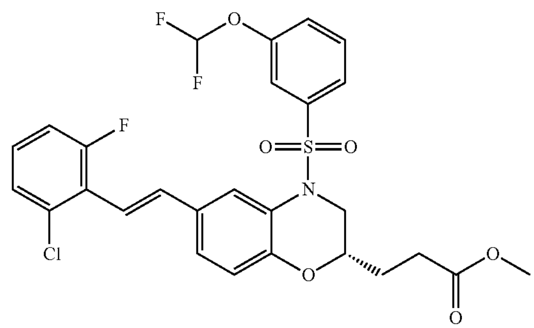 [SMILES: COC(=O)CC[C@H]1CN(S(=O)(=O)c2cccc(OC(F)F)c2)c2cc(/C=C/c3c(F)cccc3Cl)ccc2O1] | (S,E)-methyl 3-(6-(2-chloro-6-fluorostyryl)-4-((3-(difluoromethoxy)phenyl)sulfonyl)-3,4-dihydro-2H-benzo[b][1,4]oxazin-2-yl)propanoate | 582 (M + H)+ |
| 89C | 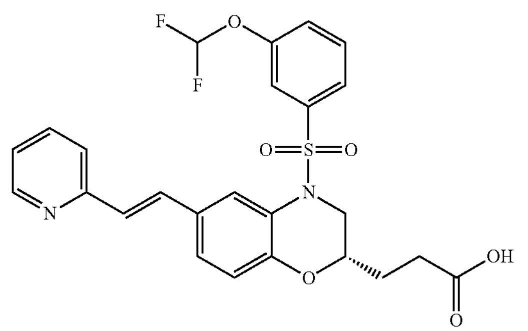 | (S,E)-3-(4-((3-(difluoromethoxy)phenyl)sulfonyl)-6-(2-(pyridin-2-yl)vinyl)-3,4-dihydro-2H-benzo[b][1,4]oxazin-2-yl)propanoic acid | 517 (M + H)+ |
| 89D | 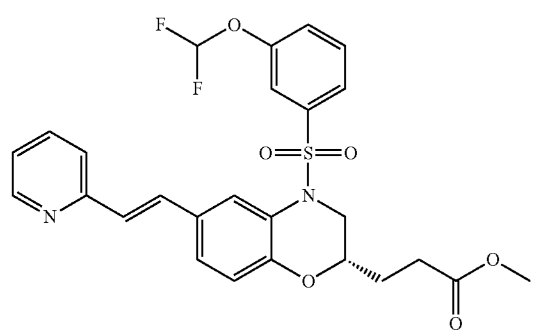 | (S,E)-methyl 3-(4-((3-(difluoromethoxy)phenyl)sulfonyl)-6-(2-(pyridin-2-yl)vinyl)-3,4-dihydro-2H-benzo[b][1,4]oxazin-2-yl)propanoate | 531 (M + H)+ |
| 89E | 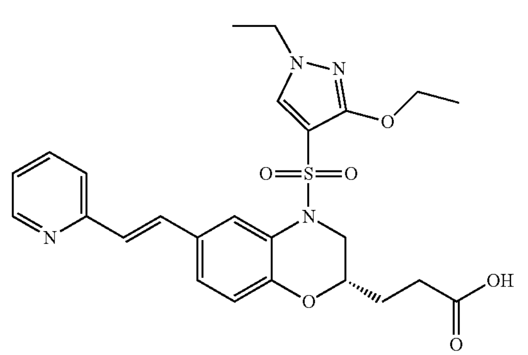 [SMILES: CCOc1nn(CC)cc1S(=O)(=O)N1C[C@H](CCC(=O)O)Oc2ccc(/C=C/c3ccccn3)cc21] | (S,E)-3-(4-((3-ethoxy-1-ethyl-1H-pyrazol-4-yl)sulfonyl)-6-(2-(pyridin-2-yl)vinyl)-3,4-dihydro-2H-benzo[b][1,4]oxazin-2-yl)propanoic acid | 513 (M + H)+ |

TABLE 11-continued

| No. | Structure | Name | Observed m/z |
|---|---|---|---|
| 89F | 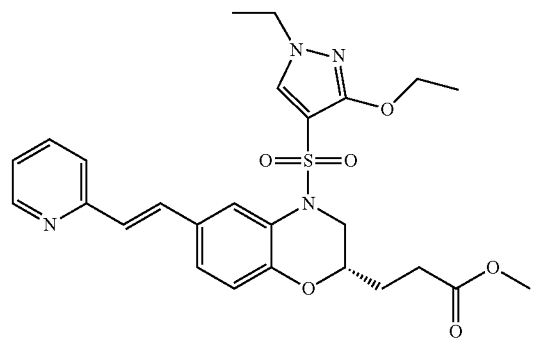 [SMILES: CCOc1nn(CC)cc1S(=O)(=O)N1C[C@H](CCC(=O)OC)Oc2ccc(/C=C/c3ccccn3)cc21] | (S,E)-methyl 3-(4-((3-ethoxy-1-ethyl-1H-pyrazol-4-yl)sulfonyl)-6-(2-(pyridin-2-yl)vinyl)-3,4-dihydro-2H-benzo[b][1,4]oxazin-2-yl)propanoate | 527 (M + H)+ |
| 89G | 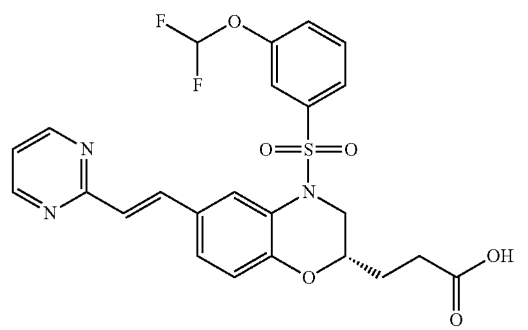 [SMILES: O=C(O)CC[C@H]1CN(S(=O)(=O)c2cccc(OC(F)F)c2)c2cc(/C=C/c3ncccn3)ccc2O1] | (S,E)-3-(4-((3-(difluoromethoxy)-phenyl)sulfonyl)-6-(2-(pyrimidin-2-yl)vinyl)-3,4-dihydro-2H-benzo[b][1,4]oxazin-2-yl)propanoic acid | 518 (M + H)+ |
| 89H | 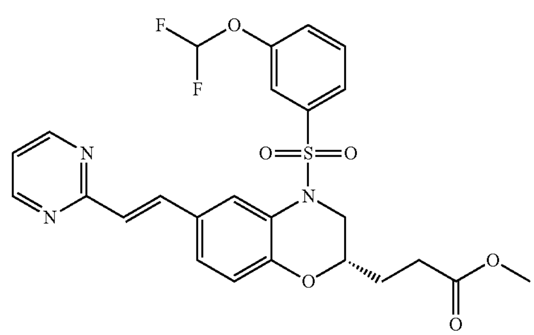 [SMILES: COC(=O)CC[C@H]1CN(S(=O)(=O)c2cccc(OC(F)F)c2)c2cc(/C=C/c3ncccn3)ccc2O1] | (S,E)-methyl 3-(4-((3-(difluoromethoxy)-phenyl)sulfonyl)-6-(2-(pyrimidin-2-yl)vinyl)-3,4-dihydro-2H-benzo[b][1,4]oxazin-2-yl)propanoate | 532 (M + H)+ |
| 89I | 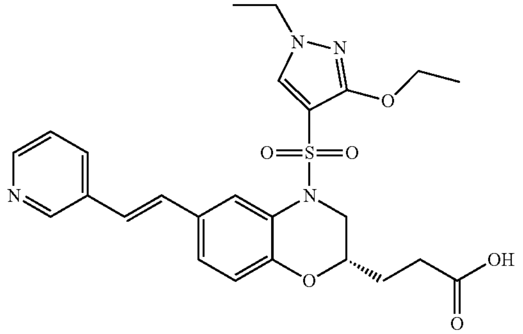 [SMILES: CCOc1nn(CC)cc1S(=O)(=O)N1C[C@H](CCC(=O)O)Oc2ccc(/C=C/c3cccnc3)cc21] | (S,E)-3-(4-((3-ethoxy-1-ethyl-1H-pyrazol-4-yl)sulfonyl)-6-(2-(pyridin-3-yl)vinyl)-3,4-dihydro-2H-benzo[b][1,4]oxazin-2-yl)propanoic acid | 513 (M + H)+ |

TABLE 11-continued

| No. | Structure | Name | Observed m/z |
|---|---|---|---|
| 89J | 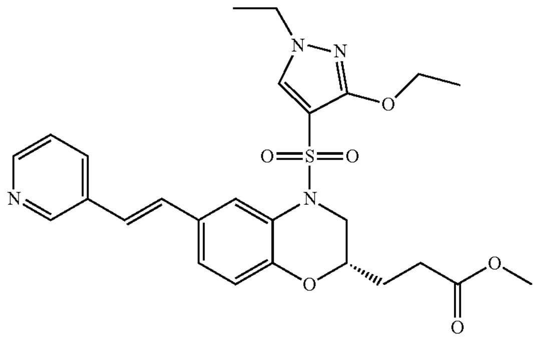 [SMILES: CCOc1nn(CC)cc1S(=O)(=O)N1C[C@H](CCC(=O)OC)Oc2ccc(/C=C/c3cccnc3)cc21] | (S,E)-methyl 3-(4-((3-ethoxy-1-ethyl-1H-pyrazol-4-yl)sulfonyl)-6-(2-(pyridin-3-yl)vinyl)-3,4-dihydro-2H-benzo[b][1,4]oxazin-2-yl)propanoate | 527 (M + H)+ |
| 89K | 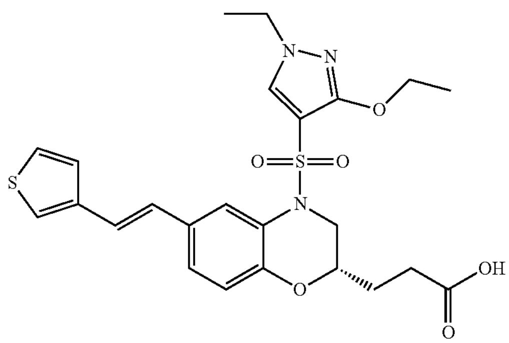 [SMILES: CCOc1nn(CC)cc1S(=O)(=O)N1C[C@H](CCC(=O)O)Oc2ccc(/C=C/c3ccsc3)cc21] | (S,E)-3-(4-((3-ethoxy-1-ethyl-1H-pyrazol-4-yl)sulfonyl)-6-(2-(thiophen-3-yl)vinyl)-3,4-dihydro-2H-benzo[b][1,4]oxazin-2-yl)propanoic acid | 518 (M + H)+ |
| 89L | 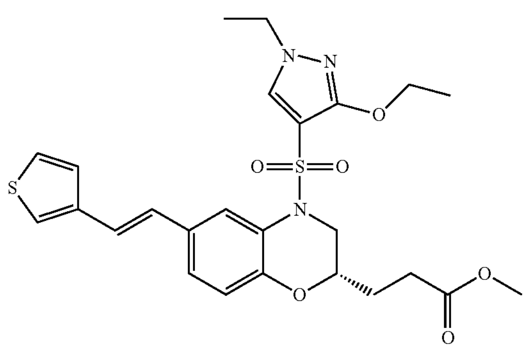 [SMILES: CCOc1nn(CC)cc1S(=O)(=O)N1C[C@H](CCC(=O)OC)Oc2ccc(/C=C/c3ccsc3)cc21] | (S,E)-methyl 3-(4-((3-ethoxy-1-ethyl-1H-pyrazol-4-yl)sulfonyl)-6-(2-(thiophen-3-yl)vinyl)-3,4-dihydro-2H-benzo[b][1,4]oxazin-2-yl)propanoate | 532 (M + H)+ |
| 89M | 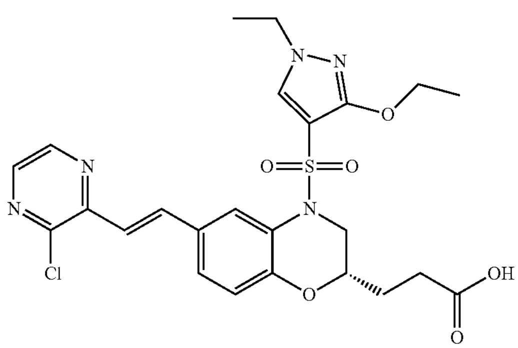 [SMILES: CCOc1nn(CC)cc1S(=O)(=O)N1C[C@H](CCC(=O)O)Oc2ccc(/C=C/c3nccnc3Cl)cc21] | (S,E)-3-(6-(2-(3-chloropyrazin-2-yl)vinyl)-4-((3-ethoxy-1-ethyl-1H-pyrazol-4-yl)sulfonyl)-3,4-dihydro-2H-benzo[b][1,4]oxazin-2-yl)propanoic acid | 548 (M + H)+ |

TABLE 11-continued

| No. | Structure | Name | Observed m/z |
|---|---|---|---|
| 89N | 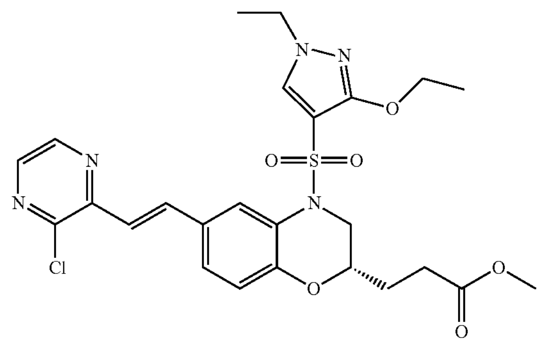 [SMILES: CCOc1nn(CC)cc1S(=O)(=O)N1C[C@H](CCC(=O)OC)Oc2ccc(/C=C/c3nccnc3Cl)cc21] | (S,E)-methyl 3-(6-(2-(3-chloropyrazin-2-yl)vinyl)-4-((3-ethoxy-1-ethyl-1H-pyrazol-4-yl)sulfonyl)-3,4-dihydro-2H-benzo[b][1,4]oxazin-2-yl)propanoate | 562 (M + H)+ |
| 89O | 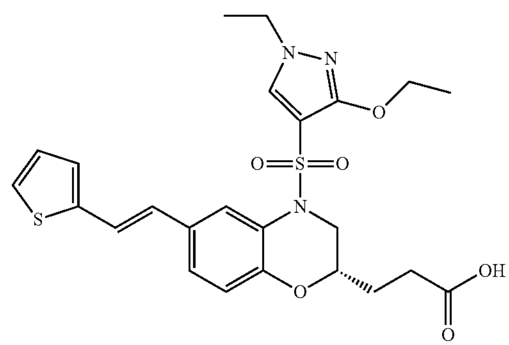 [SMILES: CCOc1nn(CC)cc1S(=O)(=O)N1C[C@H](CCC(=O)O)Oc2ccc(/C=C/c3cccs3)cc21] | (S,E)-3-(4-((3-ethoxy-1-ethyl-1H-pyrazol-4-yl)sulfonyl)-6-(2-(thiophen-2-yl)vinyl)-3,4-dihydro-2H-benzo[b][1,4]oxazin-2-yl)propanoic acid | 518 (M + H)+ |
| 89P | 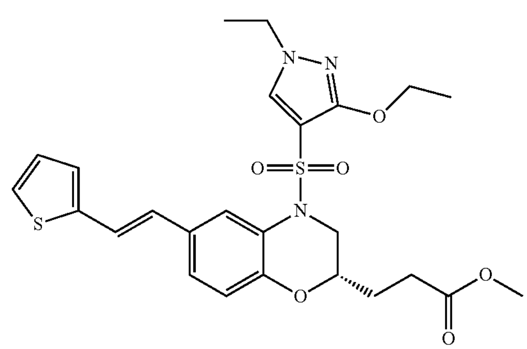 [SMILES: CCOc1nn(CC)cc1S(=O)(=O)N1C[C@H](CCC(=O)OC)Oc2ccc(/C=C/c3cccs3)cc21] | (S,E)-methyl 3-(4-((3-ethoxy-1-ethyl-1H-pyrazol-4-yl)sulfonyl)-6-(2-(thiophen-2-yl)vinyl)-3,4-dihydro-2H-benzo[b][1,4]oxazin-2-yl)propanoate | 532 (M + H)+ |
| 89Q | 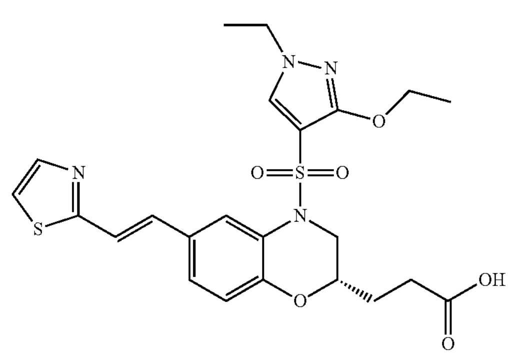 | (S,E)-3-(4-((3-ethoxy-1-ethyl-1H-pyrazol-4-yl)sulfonyl)-6-(2-(thiazol-2-yl)vinyl)-3,4-dihydro-2H-benzo[b][1,4]oxazin-2-yl)propanoic acid | 519 (M + H)+ |

TABLE 11-continued

| No. | Structure | Name | Observed m/z |
|---|---|---|---|
| 89R | 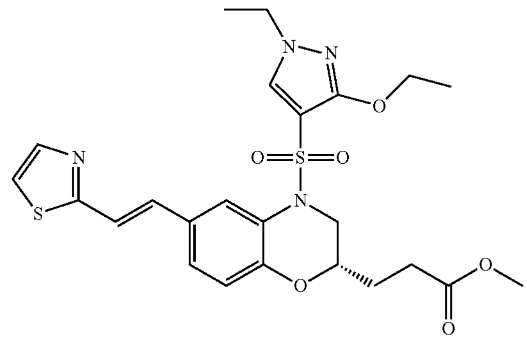 [SMILES: CCOc1nn(CC)cc1S(=O)(=O)N1C[C@H](CCC(=O)OC)Oc2ccc(/C=C/c3nccs3)cc21] | (S,E)-methyl 3-(4-((3-ethoxy-1-ethyl-1H-pyrazol-4-yl)sulfonyl)-6-(2-(thiazol-2-yl)vinyl)-3,4-dihydro-2H-benzo[b][1,4]oxazin-2-yl)propanoate | 533 (M + H)+ |
| 89S | 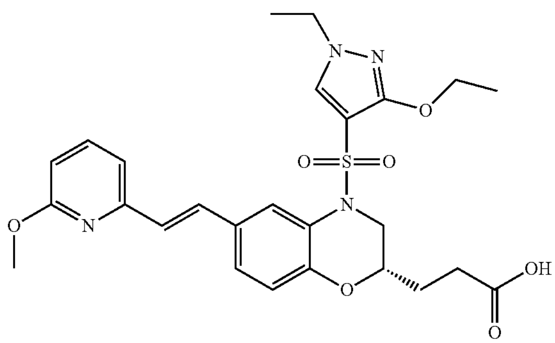 [SMILES: CCOc1nn(CC)cc1S(=O)(=O)N1C[C@H](CCC(=O)O)Oc2ccc(/C=C/c3cccc(OC)n3)cc21] | (S,E)-3-(4-((3-ethoxy-1-ethyl-1H-pyrazol-4-yl)sulfonyl)-6-(2-(6-methoxypyridin-2-yl)vinyl)-3,4-dihydro-2H-benzo[b][1,4]-oxazin-2-yl)propanoic acid | 543 (M + H)+ |
| 89T | 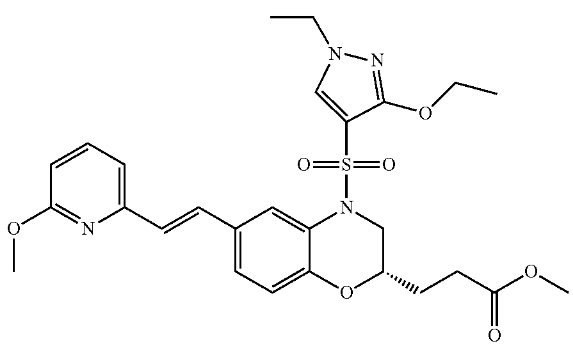 [SMILES: CCOc1nn(CC)cc1S(=O)(=O)N1C[C@H](CCC(=O)OC)Oc2ccc(/C=C/c3cccc(OC)n3)cc21] | (S,E)-methyl 3-(4-((3-ethoxy-1-ethyl-1H-pyrazol-4-yl)-sulfonyl)-6-(2-(6-methoxy-pyridin-2-yl)vinyl)-3,4-dihydro-2H-benzo[b][1,4]-oxazin-2-yl)propanoate | 557 (M + H)+ |
| 89U | 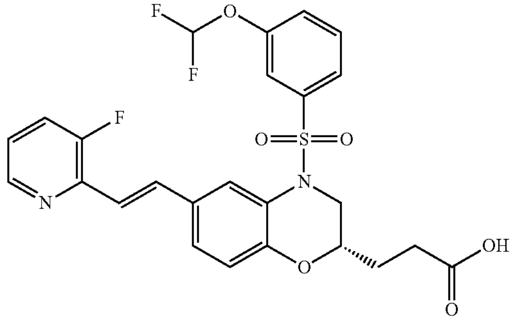 [SMILES: O=C(O)CC[C@H]1CN(S(=O)(=O)c2cccc(OC(F)F)c2)c2cc(/C=C/c3ncccc3F)ccc2O1] | (S,E)-3-(4-((3-(difluoro-methoxy)phenyl)sulfonyl)-6-(2-(3-fluoropyridin-2-yl)vinyl)-3,4-dihydro-2H-benzo[b][1,4]-oxazin-2-yl)propanoic acid | 535 (M + H)+ |

TABLE 11-continued

| No. | Structure | Name | Observed m/z |
|---|---|---|---|
| 89V | 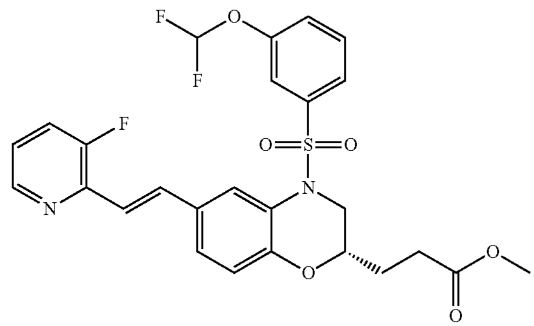 | (S,E)-methyl 3-(4-((3-(difluoro-methoxy)phenyl)sulfonyl)-6-(2-(3-fluoropyridin-2-yl)vinyl)-3,4-dihydro-2H-benzo[b][1,4]-oxazin-2-yl)propanoate | 535 (M + H)+ |
| 89W | 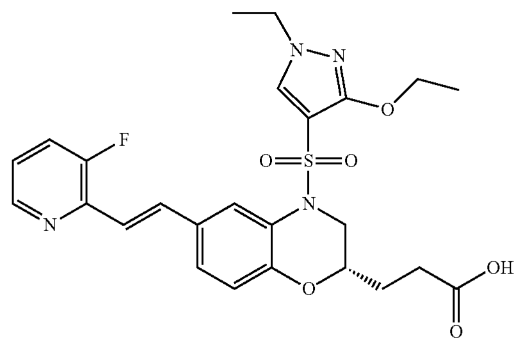 [SMILES: CCOc1nn(CC)cc1S(=O)(=O)N1C[C@H](CCC(=O)O)Oc2ccc(/C=C/c3ncccc3F)cc21] | (S,E)-3-(4-((3-ethoxy-1-ethyl-1H-pyrazol-4-yl)sulfonyl)-6-(2-(3-fluoropyridin-2-yl)vinyl)-3,4-dihydro-2H-benzo[b][1,4]-oxazin-2-yl)propanoic acid | 531 (M + H)+ |
| 89X | 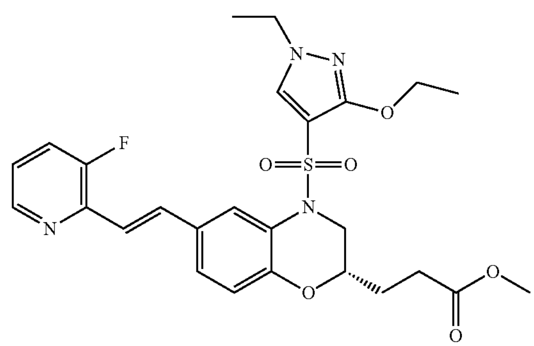 [SMILES: CCOc1nn(CC)cc1S(=O)(=O)N1C[C@H](CCC(=O)OC)Oc2ccc(/C=C/c3ncccc3F)cc21] | (S,E)-methyl 3-(4-((3-ethoxy-1-ethyl-1H-pyrazol-4-yl)-sulfonyl)-6-(2-(3-fluoropyridin-2-yl)vinyl)-3,4-dihydro-2H-benzo[b][1,4]oxazin-2-yl)propanoate | 545 (M + H)+ |
| 89Y | 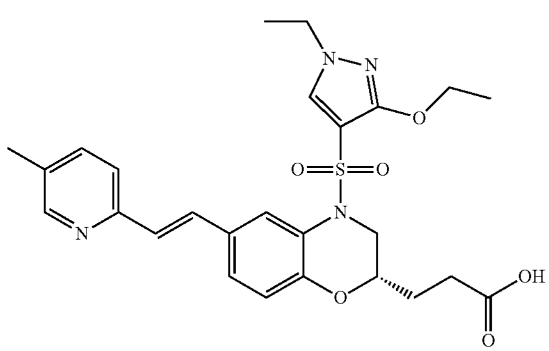 [SMILES: CCOc1nn(CC)cc1S(=O)(=O)N1C[C@H](CCC(=O)O)Oc2ccc(/C=C/c3ccc(C)cn3)cc21] | (S,E)-3-(4-((3-ethoxy-1-ethyl-1H-pyrazol-4-yl)sulfonyl)-6-(2-(5-methylpyridin-2-yl)vinyl)-3,4-dihydro-2H-benzo[b][1,4]oxazin-2-yl)propanoic acid | 527 (M + H)+ |

TABLE 11-continued

| No. | Structure | Name | Observed m/z |
|---|---|---|---|
| 89Z | 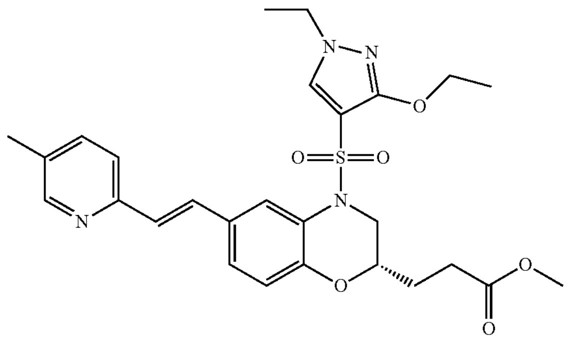 | (S,E)-methyl 3-(4-((3-ethoxy-1-ethyl-1H-pyrazol-4-yl)sulfonyl)-6-(2-(5-methylpyridin-2-yl)vinyl)-3,4-dihydro-2H-benzo[b][1,4]oxazin-2-yl)propanoate | 541 (M + H)+ |
| 89AA | 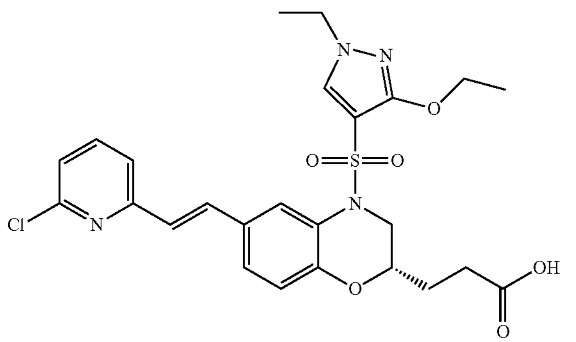 [SMILES: CCOc1nn(CC)cc1S(=O)(=O)N1C[C@H](CCC(=O)O)Oc2ccc(/C=C/c3cccc(Cl)n3)cc21] | (S,E)-3-(6-(2-(6-chloropyridin-2-yl)vinyl)-4-((3-ethoxy-1-ethyl-1H-pyrazol-4-yl)sulfonyl)-3,4-dihydro-2H-benzo[b][1,4]oxazin-2-yl)propanoic acid | 547 (M + H)+ |
| 89AB | 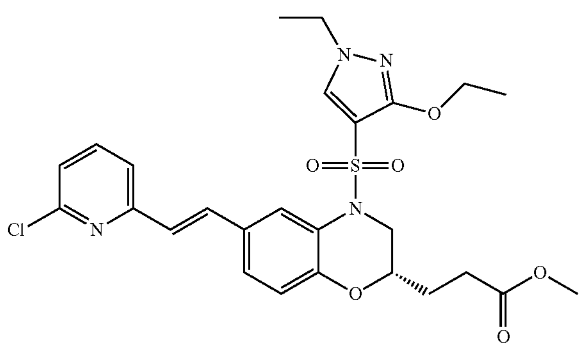 [SMILES: CCOc1nn(CC)cc1S(=O)(=O)N1C[C@H](CCC(=O)OC)Oc2ccc(/C=C/c3cccc(Cl)n3)cc21] | (S,E)-methyl 3-(6-(2-(6-chloropyridin-2-yl)vinyl)-4-((3-ethoxy-1-ethyl-1H-pyrazol-4-yl)sulfonyl)-3,4-dihydro-2H-benzo[b][1,4]oxazin-2-yl)propanoate | 561 (M + H)+ |
| 89AC | 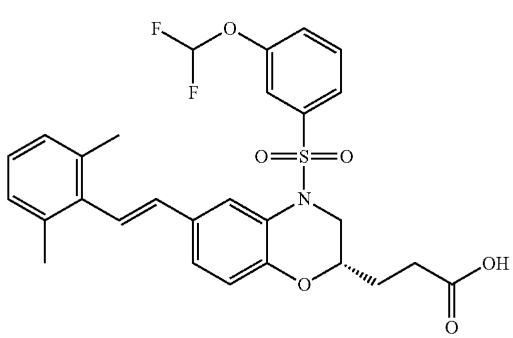 [SMILES: Cc1cccc(C)c1/C=C/c1ccc2c(c1)N(S(=O)(=O)c1cccc(OC(F)F)c1)C[C@H](CCC(=O)O)O2] | (S,E)-3-(4-((3-(difluoromethoxy)phenyl)sulfonyl)-6-(2,6-dimethylstyryl)-3,4-dihydro-2H-benzo[b][1,4]-oxazin-2-yl)propanoic acid | 544 (M + H)+ |

TABLE 11-continued

| No. | Structure | Name | Observed m/z |
|---|---|---|---|
| 89AD | 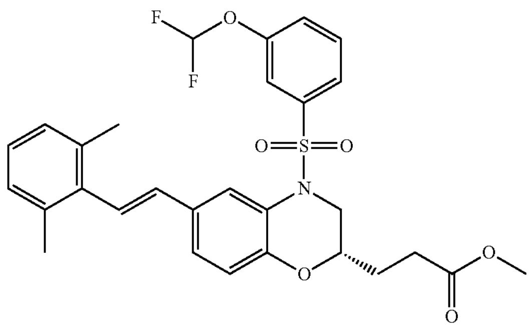 [SMILES: COC(=O)CC[C@H]1CN(S(=O)(=O)c2cccc(OC(F)F)c2)c2cc(/C=C/c3c(C)cccc3C)ccc2O1] | (S,E)-methyl 3-(4-((3-(difluoromethoxy)phenyl)-sulfonyl)-6-(2,6-dimethyl-styryl)-3,4-dihydro-2H-benzo[b][1,4]-oxazin-2-yl)propanoate | 558 (M + H)+ |
| 89AE | 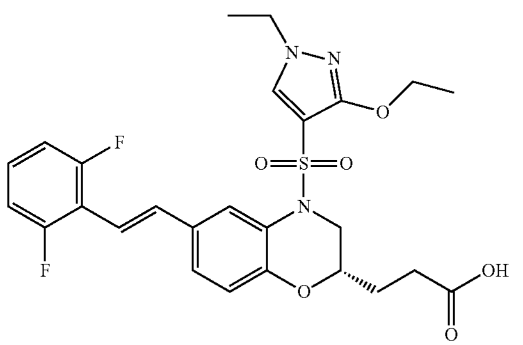 | (S,E)-3-(6-(2,6-difluorostyryl)-4-((3-ethoxy-1-ethyl-1H-pyrazol-4-yl)sulfonyl)-3,4-dihydro-2H-benzo[b][1,4]-oxazin-2-yl)propanoic acid | 548 (M + H)+ |
| 89AF | 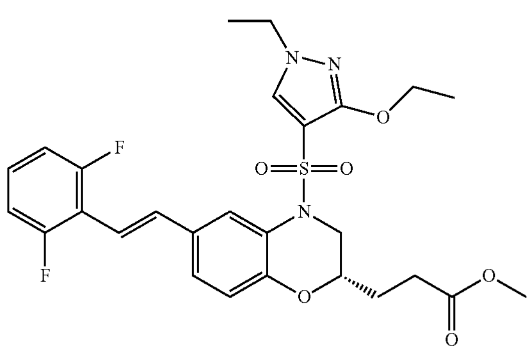 [SMILES: CCOc1nn(CC)cc1S(=O)(=O)N1C[C@H](CCC(=O)OC)Oc2ccc(/C=C/c3c(F)cccc3F)cc21] | (S,E)-methyl 3-(6-(2,6-difluorostyryl)-4-((3-ethoxy-1-ethyl-1H-pyrazol-4-yl)sulfonyl)-3,4-dihydro-2H-benzo[b][1,4]oxazin-2-yl)propanoate | 562 (M + H)+ |
| 89AG | 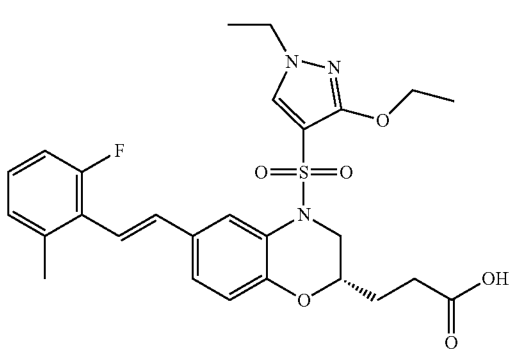 [SMILES: CCOc1nn(CC)cc1S(=O)(=O)N1C[C@H](CCC(=O)O)Oc2ccc(/C=C/c3c(C)cccc3F)cc21] | (S,E)-3-(4-((3-ethoxy-1-ethyl-1H-pyrazol-4-yl)sulfonyl)-6-(2-fluoro-6-methylstyryl)-3,4-dihydro-2H-benzo[b][1,4]-oxazin-2-yl)propanoic acid | 544 (M + H)+ |

TABLE 11-continued

| No. | Structure | Name | Observed m/z |
|---|---|---|---|
| 89AH | 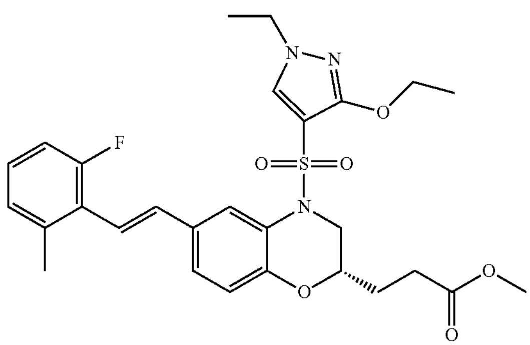 [SMILES: CCOc1nn(CC)cc1S(=O)(=O)N1C[C@H](CCC(=O)OC)Oc2ccc(/C=C/c3c(C)cccc3F)cc21] | (S,E)-methyl 3-(4-((3-ethoxy-1-ethyl-1H-pyrazol-4-yl)sulfonyl)-6-(2-fluoro-6-methylstyryl)-3,4-dihydro-2H-benzo[b][1,4]-oxazin-2-yl)propanoate | 558 (M + H)+ |
| 89AI | 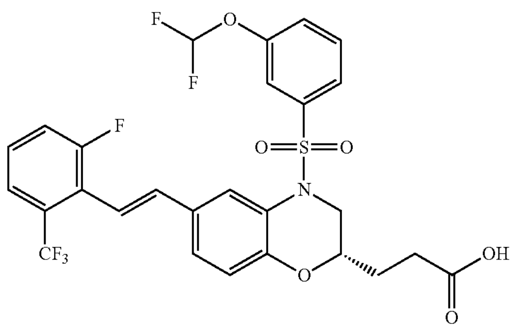 | (S,E)-3-(4-((3-(difluoromethoxy)phenyl)sulfonyl)-6-(2-fluoro-6-(trifluoromethyl)-styryl)-3,4-dihyro-2H-benzo[b][1,4]oxazin-2-yl)propanoic acid | 602 (M + H)+ |
| 89AJ | 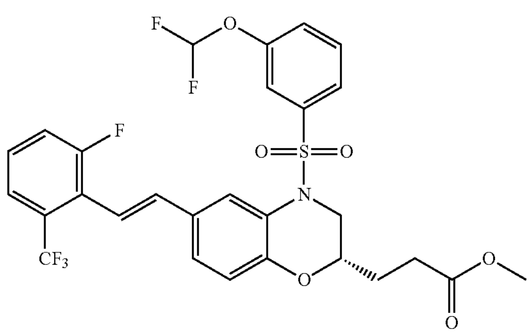 | (S,E)-methyl 3-(4-((3-(difluoromethoxy)phenyl)sulfonyl)-6-(2-fluoro-6-(trifluoromethyl)-styryl)-3,4-dihydro-2H-benzo[b][1,4]oxazin-2-yl)propanoate | 616 (M + H)+ |
| 89AK | 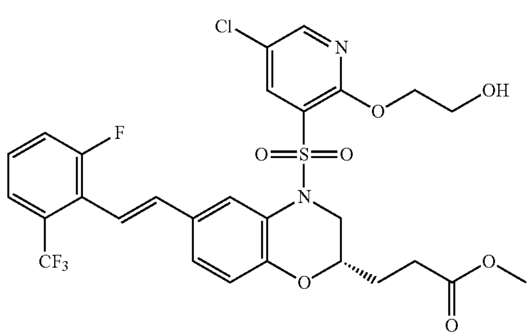 | methyl (S,E)-3-(4-((5-chloro-2-(2-hydroxyethoxy)pyridin-3-yl)sulfonyl)-6-(2-chloro-6-fluorostyryl)-3,4-dihydro-2H-benzo[b][1,4]oxazin-2-yl)propanoate | 625 (M + H)+ |

TABLE 11-continued

| No. | Structure | Name | Observed m/z |
|---|---|---|---|
| 89AL | 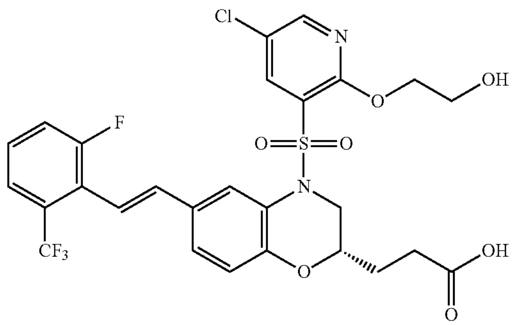 [SMILES: O=C(O)CC[C@H]1CN(S(=O)(=O)c2cc(Cl)cnc2OCCO)c2cc(/C=C/c3c(F)cccc3C(F)(F)F)ccc2O1] | (S,E)-3-(4-((5-chloro-2-(2-hydroxyethoxy)pyridin-3-yl)sulfonyl)-6-(2-chloro-6-fluorostyryl)-3,4-dihydro-2H-benzo[b][1,4]oxazin-2-yl)propanoic acid | 611 (M + H)+ |
| 89AM | 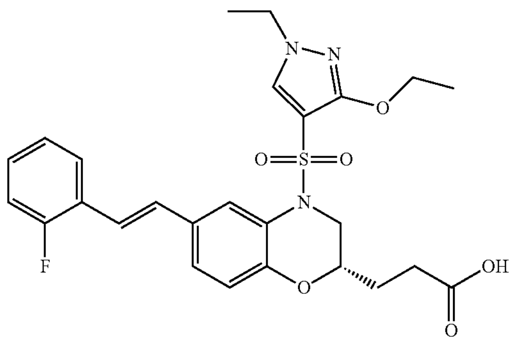 [SMILES: CCOc1nn(CC)cc1S(=O)(=O)N1C[C@H](CCC(=O)O)Oc2ccc(/C=C/c3ccccc3F)cc21] | (S,E)-3-(4-((3-ethoxy-1-ethyl-1H-pyrazol-4-yl)sulfonyl)-6-(2-fluorostyryl)-3,4-dihydro-2H-benzo[b][1,4]oxazin-2-yl)propanoic acid | 530 (M + H)+ |
| 89AN | 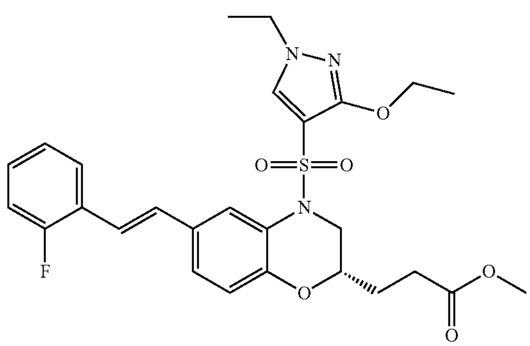 | (S,E)-methyl 3-(4-((3-ethoxy-1-ethyl-1H-pyrazol-4-yl)sulfonyl)-6-(2-fluorostyryl)-3,4-dihydro-2H-benzo[b][1,4]oxazin-2-yl)propanoate | 544 (M + H)+ |
| 89AO | 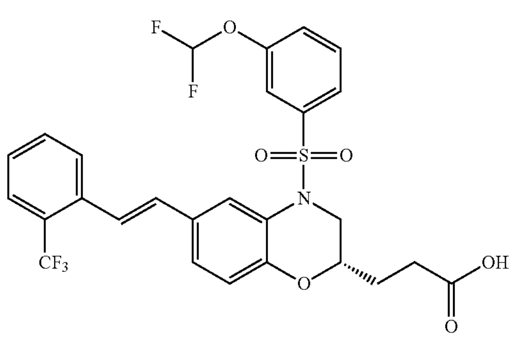 [SMILES: O=C(O)CC[C@H]1CN(S(=O)(=O)c2cccc(OC(F)F)c2)c2cc(/C=C/c3ccccc3C(F)(F)F)ccc2O1] | (S,E)-3-(4-((3-(difluoromethoxy)phenyl)sulfonyl)-6-(2-(trifluoromethyl)styryl)-3,4-dihydro-2H-benzo[b][1,4]oxazin-2-yl)propanoic acid | 584 (M + H)+ |

TABLE 11-continued

| No. | Structure | Name | Observed m/z |
|---|---|---|---|
| 89AP | 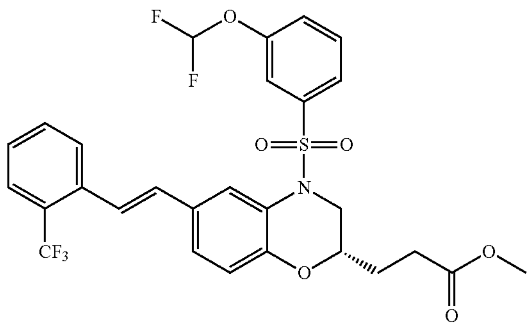 [SMILES: COC(=O)CC[C@H]1CN(S(=O)(=O)c2cccc(OC(F)F)c2)c2cc(/C=C/c3ccccc3C(F)(F)F)ccc2O1] | (S,E)-methyl 3-(4-((3-(difluoromethoxy)phenyl)sulfonyl)-6-(2-(trifluoromethyl)styryl)-3,4-dihydro-2H-benzo[b][1,4]-oxazin-2-yl)propanoate | 598 (M + H)+ |
| 89AQ | 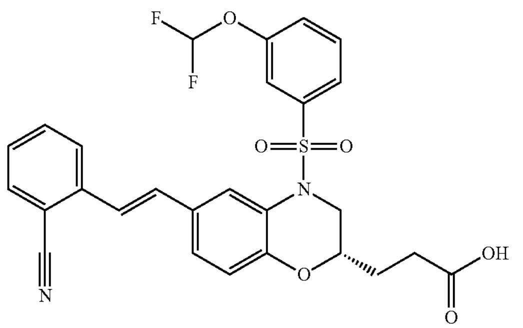 [SMILES: N#Cc1ccccc1/C=C/c1ccc2c(c1)N(S(=O)(=O)c1cccc(OC(F)F)c1)C[C@H](CCC(=O)O)O2] | (S,E)-3-(6-(2-cyanostyryl)-4-((3-(difluoromethoxy)phenyl)sulfonyl)-3,4-dihydro-2H-benzo[b][1,4]oxazin-2-yl)propanoic acid | 541 (M + H)+ |
| 89AR | 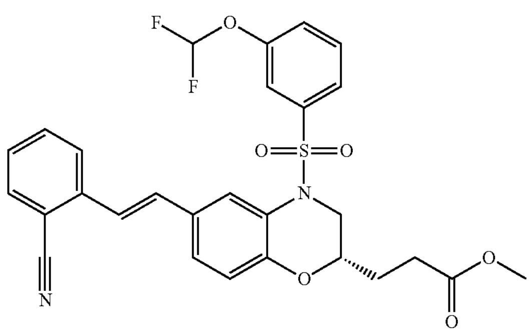 [SMILES: COC(=O)CC[C@H]1CN(S(=O)(=O)c2cccc(OC(F)F)c2)c2cc(/C=C/c3ccccc3C#N)ccc2O1] | (S,E)-methyl 3-(6-(2-cyanostyryl)-4-((3-(difluoromethoxy)phenyl)sulfonyl)-3,4-dihydro-2H-benzo[b][1,4]-oxazin-2-yl)propanoate | 555 (M + H)+ |
| 89AS | 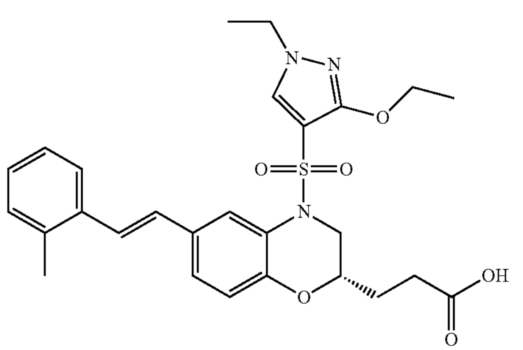 [SMILES: CCOc1nn(CC)cc1S(=O)(=O)N1C[C@H](CCC(=O)O)Oc2ccc(/C=C/c3ccccc3C)cc21] | (S,E)-3-(4-((3-ethoxy-1-ethyl-1H-pyrazol-4-yl)sulfonyl)-6-(2-methylstyryl)-3,4-dihydro-2H-benzo[b][1,4]oxazin-2-yl)propanoic acid | 526 (M + H)+ |

TABLE 11-continued

| No. | Structure | Name | Observed m/z |
|---|---|---|---|
| 89AT | 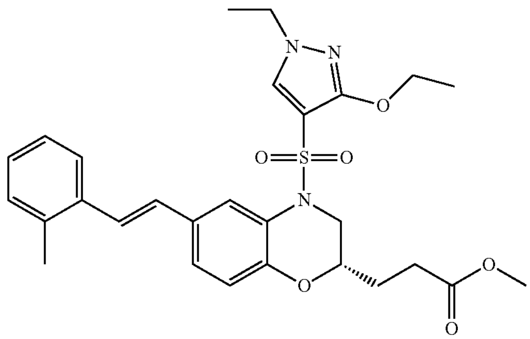 [SMILES: CCOc1nn(CC)cc1S(=O)(=O)N1C[C@H](CCC(=O)OC)Oc2ccc(/C=C/c3ccccc3C)cc21] | (S,E)-methyl 3-(4-((3-ethoxy-1-ethyl-1H-pyrazol-4-yl)sulfonyl)-6-(2-methylstyryl)-3,4-dihydro-2H-benzo[b][1,4]oxazin-2-yl)propanoate | 540 (M + H)+ |
| 89AU | 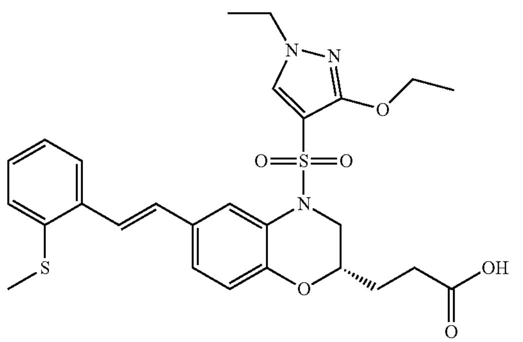 [SMILES: CCOc1nn(CC)cc1S(=O)(=O)N1C[C@H](CCC(=O)O)Oc2ccc(/C=C/c3ccccc3SC)cc21] | (S,E)-3-(4-((3-ethoxy-1-ethyl-1H-pyrazol-4-yl)sulfonyl)-6-(2-(methylthio)styryl)-3,4-dihydro-2H-benzo[b][1,4]oxazin-2-yl)propanoic acid | 558 (M + H)+ |
| 89AV | 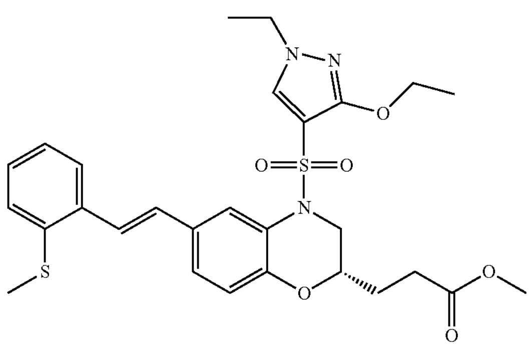 [SMILES: CCOc1nn(CC)cc1S(=O)(=O)N1C[C@H](CCC(=O)OC)Oc2ccc(/C=C/c3ccccc3SC)cc21] | (S,E)-methyl 3-(4-((3-ethoxy-1-ethyl-1H-pyrazol-4-yl)sulfonyl)-6-(2-(methylthio)styryl)-3,4-dihydro-2H-benzo[b][1,4]oxazin-2-yl)propanoate | 572 (M + H)+ |
| 89AW | 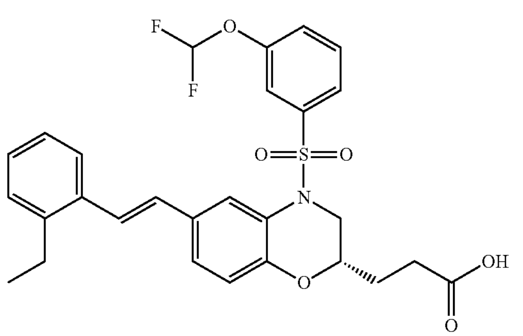 | (S,E)-3-(4-((3-(difluoromethoxy)phenyl)sulfonyl)-6-(2-ethylstyryl)-3,4-dihydro-2H-benzo[b][1,4]oxazin-2-yl)propanoic acid | 544 (M + H)+ |

TABLE 11-continued

| No. | Structure | Name | Observed m/z |
|---|---|---|---|
| 89AX | 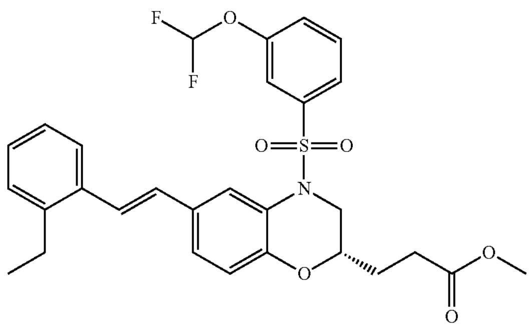 | (S,E)-methyl 3-(4-((3-(difluoromethoxy)phenyl)sulfonyl)-6-(2-ethylstyryl)-3,4-dihydro-2H-benzo[b][1,4]oxazin-2-yl)propanoate | 558 (M + H)+ |
| 89AY | 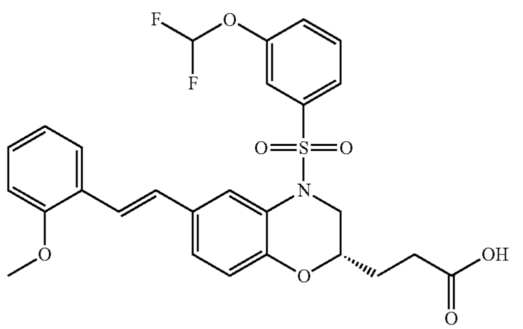 [SMILES: CCc1ccccc1/C=C/c1ccc2c(c1)N(S(=O)(=O)c1cccc(OC(F)F)c1)C[C@H](CCC(=O)O)O2] | (S,E)-3-(4-((3-(difluoromethoxy)phenyl)sulfonyl)-6-(2-methoxystyryl)-3,4-dihydro-2H-benzo[b][1,4]oxazin-2-yl)propanoic acid | 546 (M + H)+ |
| 89AZ | 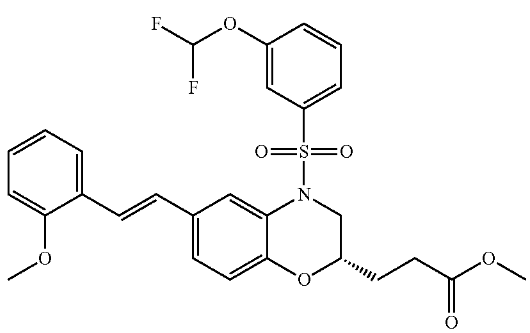 [SMILES: CCc1ccccc1/C=C/c1ccc2c(c1)N(S(=O)(=O)c1cccc(OC(F)F)c1)C[C@H](CCC(=O)OC)O2] | (S,E)-methyl 3-(4-((3-(difluoromethoxy)phenyl)sulfonyl)-6-(2-methoxystyryl)-3,4-dihydro-2H-benzo[b][1,4]oxazin-2-yl)propanoate | 560 (M + H)+ |
| 89BA | 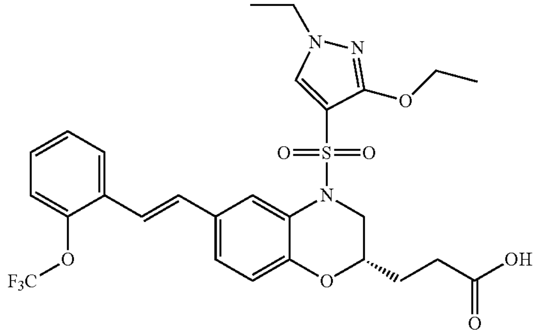 [SMILES: CCOc1nn(CC)cc1S(=O)(=O)N1C[C@H](CCC(=O)O)Oc2ccc(/C=C/c3ccccc3OC(F)(F)F)cc21] | (S,E)-3-(4-((3-ethoxy-1-ethyl-1H-pyrazol-4-yl)sulfonyl)-6-(2-(trifluoromethoxy)styryl)-3,4-dihydro-2H-benzo[b][1,4]oxazin-2-yl)propanoic acid | 596 (M + H)+ |

TABLE 11-continued

| No. | Structure | Name | Observed m/z |
|---|---|---|---|
| 89BB | 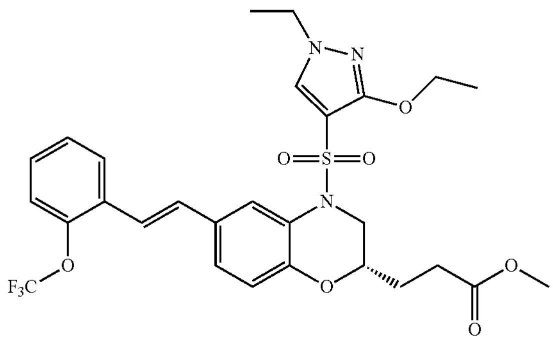 [SMILES: CCOc1nn(CC)cc1S(=O)(=O)N1C[C@H](CCC(=O)OC)Oc2ccc(/C=C/c3ccccc3OC(F)(F)F)cc21] | (S,E)-methyl 3-(4-((3-ethoxy-1-ethyl-1H-pyrazol-4-yl)sulfonyl)-6-(2-(trifluoromethoxy)styryl)-3,4-dihydro-2H-benzo[b][1,4]-oxazin-2-yl)propanoate | 610 (M + H)+ |
| 89BC | 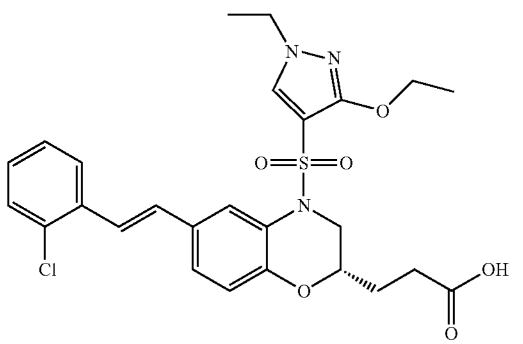 | (S,E)-3-(6-(2-chlorostyryl)-4-((3-ethoxy-1-ethyl-1H-pyrazol-4-yl)sulfonyl)-3,4-dihydro-2H-benzo[b][1,4]oxazin-2-yl)propanoic acid | 546 (M + H)+ |
| 89BD | 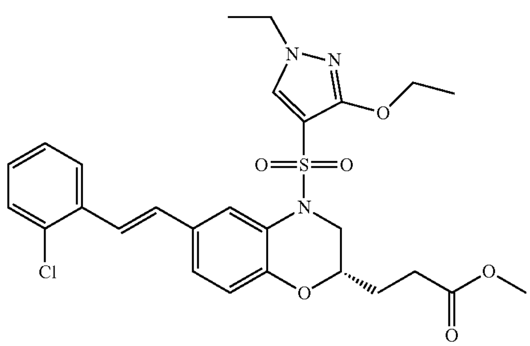 | (S,E)-methyl 3-(6-(2-chlorostyryl)-4-((3-ethoxy-1-ethyl-1H-pyrazol-4-yl)sulfonyl)-3,4-dihydro-2H-benzo[b][1,4]-oxazin-2-yl)propanoate | 560 (M + H)+ |
| 89BE | 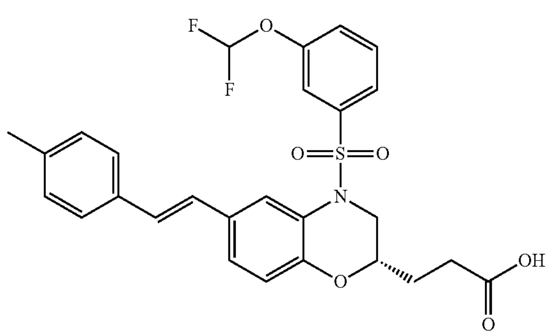 [SMILES: Cc1ccc(/C=C/c2ccc3c(c2)N(S(=O)(=O)c2cccc(OC(F)F)c2)C[C@H](CCC(=O)O)O3)cc1] | (S,E)-3-(4-((3-(difluoro-methoxy)phenyl)sulfonyl)-6-(4-methylstyryl)-3,4-dihydro-2H-benzo[b][1,4]oxazin-2-yl)propanoic acid | 530 (M + H)+ |

TABLE 11-continued

| No. | Structure | Name | Observed m/z |
|---|---|---|---|
| 89BF | 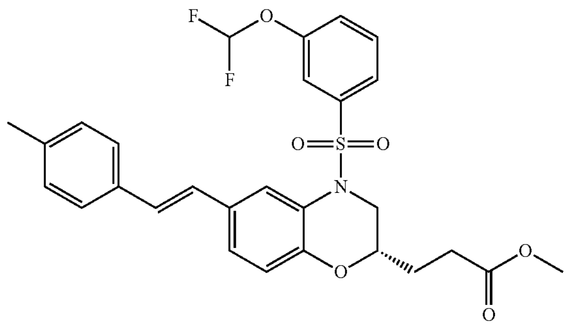 | (S,E)-methyl 3-(4-((3-(difluoro-methoxy)phenyl)sulfonyl)-6-(4-methylstyryl)-3,4-dihydro-2H-benzo[b][1,4]oxazin-2-yl)propanoate | 544 (M + H)+ |
| 89BG | 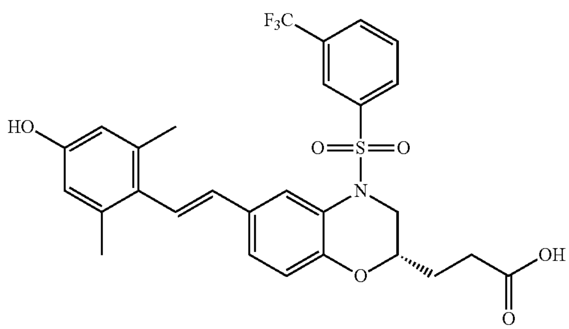 [SMILES: Cc1cc(O)cc(C)c1/C=C/c1ccc2c(c1)N(S(=O)(=O)c1cccc(C(F)(F)F)c1)C[C@H](CCC(=O)O)O2] | (S,E)-3-(6-(4-hydroxy-2,6-dimethylstyryl)-4-((3-(trifluoromethyl)phenyl)sulfonyl)-3,4-dihydro-2H-benzo[b][1,4]oxazin-2-yl)propanoic acid | 562 (M + H)+ |
| 89BH | 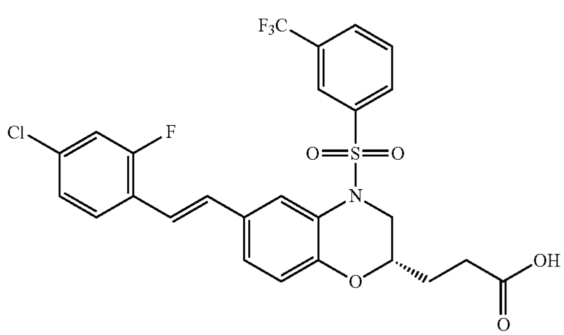 [SMILES: O=C(O)CC[C@H]1CN(S(=O)(=O)c2cccc(C(F)(F)F)c2)c2cc(/C=C/c3ccc(Cl)cc3F)ccc2O1] | (S,E)-3-(6-(4-chloro-2-fluorostyryl)-4-((3-(trifluoromethyl)phenyl)sulfonyl)-3,4-dihydro-2H-benzo[b][1,4]oxazin-2-yl)propanoic acid | 570 (M + H)+ |
| 89BI | 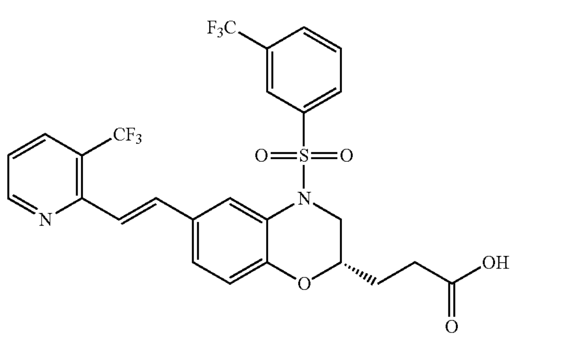 | (S,E)-3-(4-((3-(trifluoromethyl)phenyl)sulfonyl)-6-(2-(3-(trifluoromethyl)pyridin-2-yl)vinyl)-3,4-dihydro-2H-benzo[b][1,4]oxazin-2-yl)propanoic acid | 587 (M + H)+ |

TABLE 11-continued

| No. | Structure | Name | Observed m/z |
|---|---|---|---|
| 89BJ | 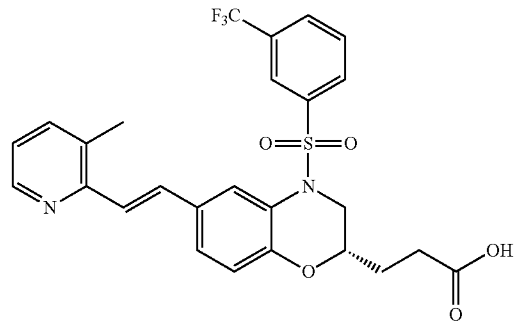 [SMILES: Cc1cccnc1/C=C/c1ccc2c(c1)N(S(=O)(=O)c1cccc(C(F)(F)F)c1)C[C@H](CCC(=O)O)O2] | (S,E)-3-(6-(2-(3-methylpyridin-2-yl)vinyl)-4-((3-(trifluoromethyl)phenyl)sulfonyl)-3,4-dihydro-2H-benzo[b][1,4]oxazin-2-yl)propanoic acid | 533 (M + H)+ |
| 89BK | 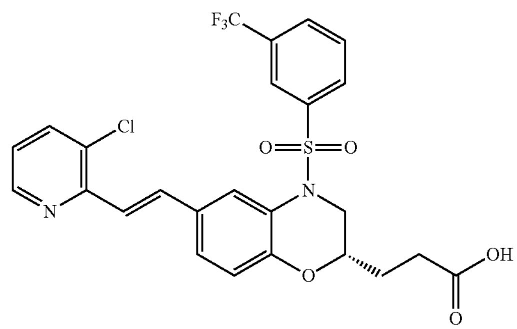 [SMILES: O=C(O)CC[C@H]1CN(S(=O)(=O)c2cccc(C(F)(F)F)c2)c2cc(/C=C/c3ncccc3Cl)ccc2O1] | (S,E)-3-(6-(2-(3-chloropyridin-2-yl)vinyl)-4-((3-(trifluoromethyl)phenyl)sulfonyl)-3,4-dihydro-2H-benzo[b][1,4]oxazin-2-yl)propanoic acid | 553 (M + H)+ |
| 89BL | 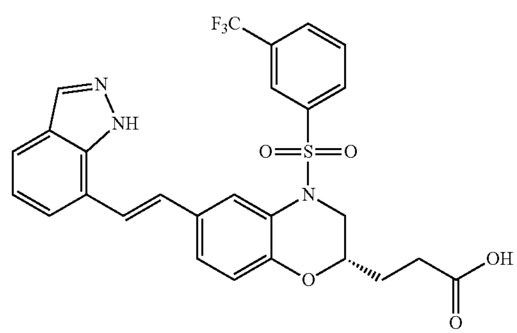 [SMILES: O=C(O)CC[C@H]1CN(S(=O)(=O)c2cccc(C(F)(F)F)c2)c2cc(/C=C/c3cccc4cn[nH]c34)ccc2O1] | (S,E)-3-(6-(2-(1H-indazol-7-yl)vinyl)-4-((3-(trifluoromethyl)phenyl)sulfonyl)-3,4-dihydro-2H-benzo[b][1,4]oxazin-2-yl)propanoic acid | 558 (M + H)+ |
| 89BM | 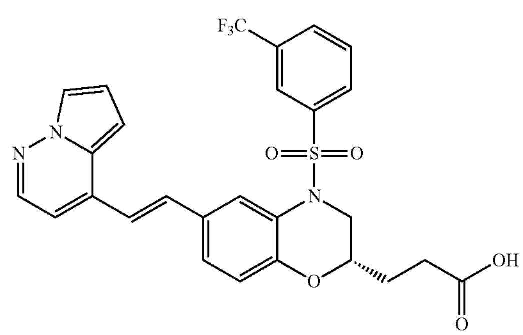 [SMILES: O=C(O)CC[C@H]1CN(S(=O)(=O)c2cccc(C(F)(F)F)c2)c2cc(/C=C/c3ccnn4cccc34)ccc2O1] | (S,E)-3-(6-(2-(pyrrolo[1,2-b]pyridazin-4-yl)vinyl)-4-((3-(trifluoromethyl)phenyl)sulfonyl)-3,4-dihydro-2H-benzo[b][1,4]oxazin-2-yl)propanoic acid | 558 (M + H)+ |

TABLE 11-continued

| No. | Structure | Name | Observed m/z |
|---|---|---|---|
| 89BN | 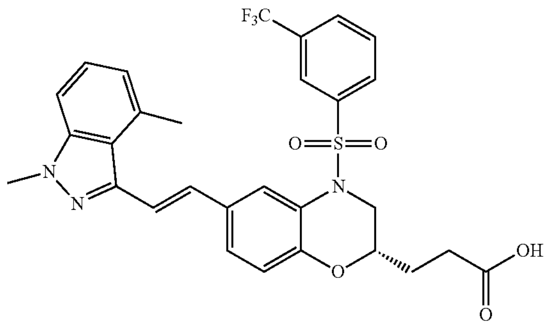 [SMILES: Cc1cccc2c1c(/C=C/c1ccc3c(c1)N(S(=O)(=O)c1cccc(C(F)(F)F)c1)C[C@H](CCC(=O)O)O3)nn2C] | (S,E)-3-(6-(2-(1,4-dimethyl-1H-indazol-3-yl)vinyl)-4-((3-(trifluoromethyl)phenyl)sulfonyl)-3,4-dihydro-2H-benzo[b][1,4]oxazin-2-yl)propanoic acid | 586 (M + H)+ |
| 89BO | 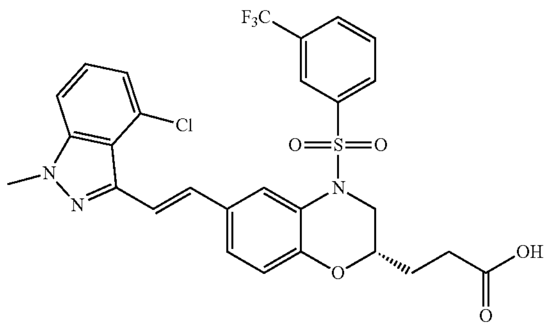 | (S,E)-3-(6-(2-(4-chloro-1-methyl-1H-indazol-3-yl)vinyl)-4-((3-(trifluoromethyl)phenyl)sulfonyl)-3,4-dihydro-2H-benzo[b][1,4]-oxazin-2-yl)propanoic acid | 606 (M + H)+ |
| 89BP | 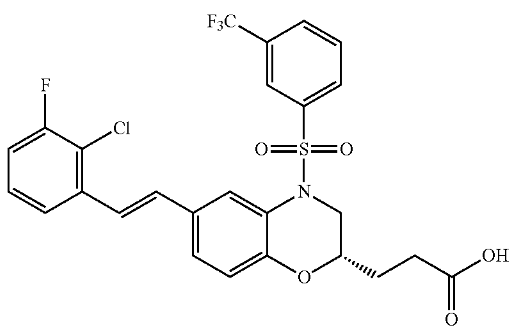 [SMILES: O=C(O)CC[C@H]1CN(S(=O)(=O)c2cccc(C(F)(F)F)c2)c2cc(/C=C/c3cccc(F)c3Cl)ccc2O1] | (S,E)-3-(6-(2-chloro-3-fluorostyryl)-4-((3-(trifluoromethyl)phenyl)sulfonyl)-3,4-dihydro-2H-benzo[b][1,4]oxazin-2-yl)propanoic acid | 570 (M + H)+ |
| 89BQ | 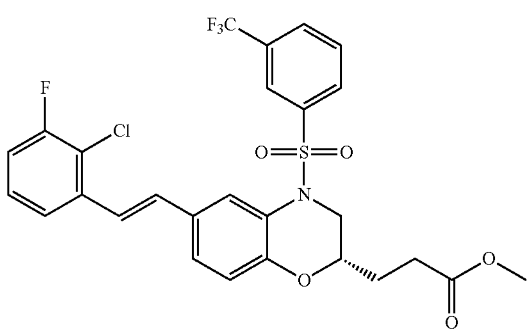 [SMILES: COC(=O)CC[C@H]1CN(S(=O)(=O)c2cccc(C(F)(F)F)c2)c2cc(/C=C/c3cccc(F)c3Cl)ccc2O1] | (S,E)-methyl 3-(6-(2-chloro-3-fluorostyryl)-4-((3-(trifluoromethyl)phenyl)sulfonyl)-3,4-dihydro-2H-benzo[b][1,4]oxazin-2-yl)propanoate | 584 (M + H)+ |

TABLE 11-continued

| No. | Structure | Name | Observed m/z |
|---|---|---|---|
| 89BR | 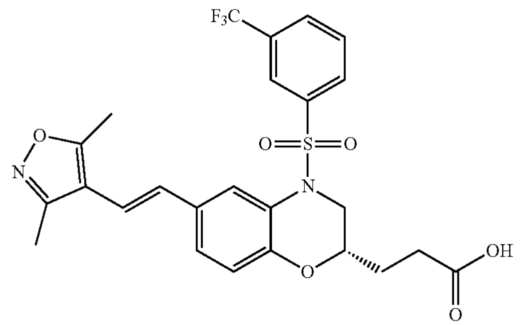 [SMILES: Cc1noc(C)c1/C=C/c1ccc2c(c1)N(S(=O)(=O)c1cccc(C(F)(F)F)c1)C[C@H](CCC(=O)O)O2] | (S,E)-3-(6-(2-(3,5-dimethyl-isoxazol-4-yl)vinyl)-4-((3-(trifluoromethyl)phenyl)sulfonyl)-3,4-dihydro-2H-benzo[b][1,4]-oxazin-2-yl)propanoic acid | 537 (M + H)+ |
| 89BS | 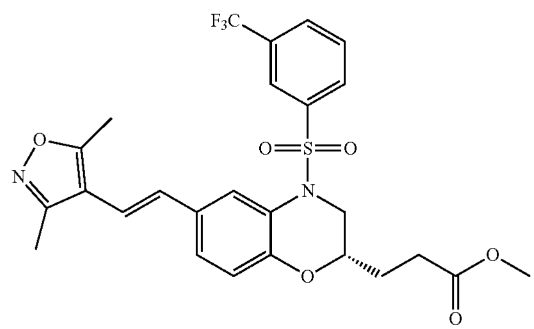 [SMILES: COC(=O)CC[C@H]1CN(S(=O)(=O)c2cccc(C(F)(F)F)c2)c2cc(/C=C/c3c(C)noc3C)ccc2O1] | (S,E)-methyl 3-(6-(2-(3,5-dimethyl-isoxazol-4-yl)vinyl)-4-((3-(trifluoromethyl)phenyl)-sulfonyl)-3,4-dihydro-2H-benzo[b][1,4]-oxazin-2-yl)propanoate | 551 (M + H)+ |
| 89BT | 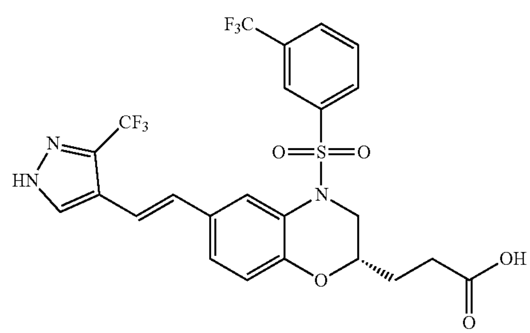 [SMILES: O=C(O)CC[C@H]1CN(S(=O)(=O)c2cccc(C(F)(F)F)c2)c2cc(/C=C/c3c[nH]nc3C(F)(F)F)ccc2O1] | (S,E)-3-(6-(2-(3-(trifluoro-methyl)-1H-pyrazol-4-yl)vinyl)-4-((3-(trifluoromethyl)phenyl)-sulfonyl)-3,4-dihydro-2H-benzo[b][1,4]oxazin-2-yl)propanoic acid | 576 (M + H)+ |
| 89BU | 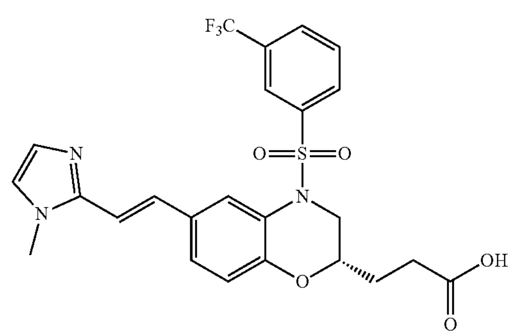 [SMILES: Cn1ccnc1/C=C/c1ccc2c(c1)N(S(=O)(=O)c1cccc(C(F)(F)F)c1)C[C@H](CCC(=O)O)O2] | (S,E)-3-(6-(2-(1-methyl-1H-imidazol-2-yl)vinyl)-4-((3-(trifluoromethyl)phenyl)sulfonyl)-3,4-dihydro-2H-benzo[b][1,4]-oxazin-2-yl)propanoic acid | 522 (M + H)+ |

TABLE 11-continued

| No. | Structure | Name | Observed m/z |
|---|---|---|---|
| 89BV | 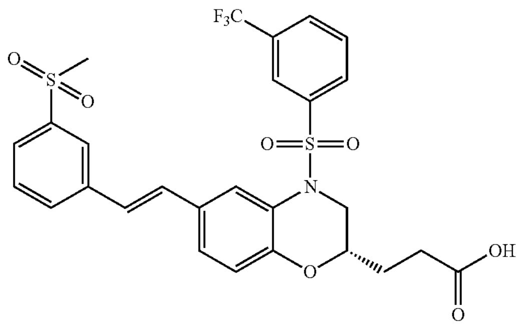 [SMILES: CS(=O)(=O)c1cccc(/C=C/c2ccc3c(c2)N(S(=O)(=O)c2cccc(C(F)(F)F)c2)C[C@H](CCC(=O)O)O3)c1] | (S,E)-3-(6-(3-(methylsulfonyl)-styryl)-4-((3-(trifluoromethyl)-phenyl)sulfonyl)-3,4-dihydro-2H-benzo[b][1,4]oxazin-2-yl)propanoic acid | 596 (M + H)+ |
| 89BW | 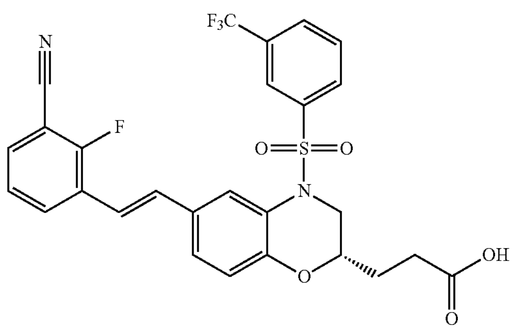 [SMILES: N#Cc1cccc(/C=C/c2ccc3c(c2)N(S(=O)(=O)c2cccc(C(F)(F)F)c2)C[C@H](CCC(=O)O)O3)c1F] | (S,E)-3-(6-(3-cyano-2-fluorostyryl)-4-((3-(trifluoromethyl)phenyl)sulfonyl)-3,4-dihydro-2H-benzo[b][1,4]oxazin-2-yl)propanoic acid | 561 (M + H)+ |
| 89BX | 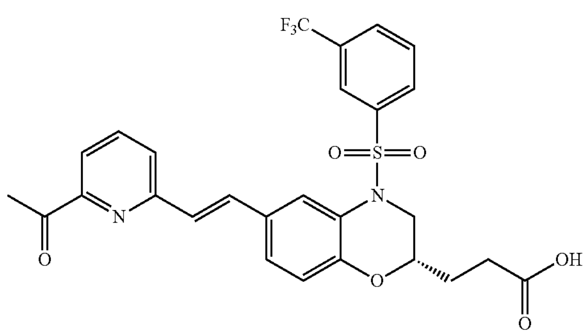 [SMILES: CC(=O)c1cccc(/C=C/c2ccc3c(c2)N(S(=O)(=O)c2cccc(C(F)(F)F)c2)C[C@H](CCC(=O)O)O3)n1] | (S,E)-3-(6-(2-(6-acetylpyridin-2-yl)vinyl)-4-((3-(trifluoromethyl)-phenyl)sulfonyl)-3,4-dihydro-2H-benzo[b][1,4]oxazin-2-yl)propanoic acid | 561 (M + H)+ |
| 89BY | 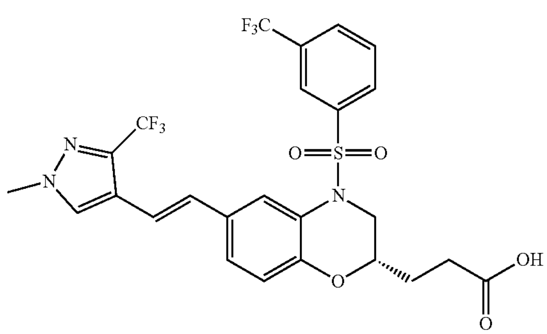 [SMILES: Cn1cc(/C=C/c2ccc3c(c2)N(S(=O)(=O)c2cccc(C(F)(F)F)c2)C[C@H](CCC(=O)O)O3)c(C(F)(F)F)n1] | (S,E)-3-(6-(2-(1-methyl-3-(trifluoromethyl)-1H-pyrazol-4-yl)vinyl)-4-((3-(trifluoromethyl)-phenyl)sulfonyl)-3,4-dihydro-2H-benzo[b][1,4]oxazin-2-yl)propanoic acid | 590 (M + H)+ |

TABLE 11-continued

| No. | Structure | Name | Observed m/z |
|---|---|---|---|
| 89BZ | 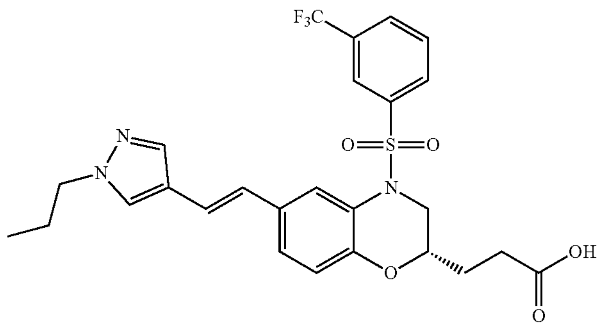 [SMILES: CCCn1cc(/C=C/c2ccc3c(c2)N(S(=O)(=O)c2cccc(C(F)(F)F)c2)C[C@H](CCC(=O)O)O3)cn1] | (S,E)-3-(6-(2-(1-propyl-1H-pyrazol-3-yl)vinyl)-4-((3-(trifluoromethyl)phenyl)sulfonyl)-3,4-dihydro-2H-benzo[b][1,4]oxazin-2-yl)propanoic acid | 550 (M + H)+ |
| 89CA | 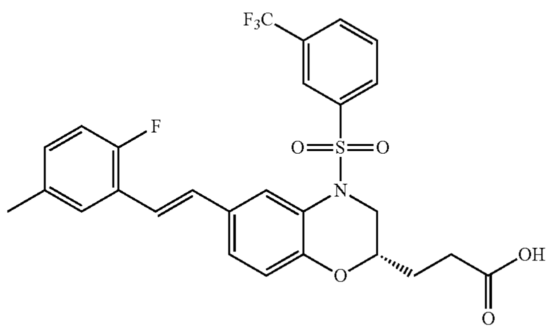 [SMILES: Cc1ccc(F)c(/C=C/c2ccc3c(c2)N(S(=O)(=O)c2cccc(C(F)(F)F)c2)C[C@H](CCC(=O)O)O3)c1] | (S,E)-3-(6-(2-fluoro-5-methylstyryl)-4-((3-trifluoromethyl)phenyl)sulfonyl)-3,4-dihydro-2H-benzo[b][1,4]oxazin-2-yl)propanoic acid | 550 (M + H)+ |
| 89CB | 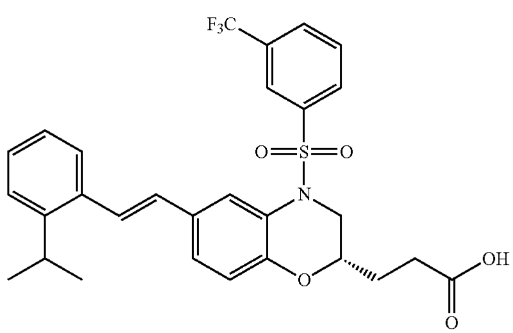 [SMILES: CC(C)c1ccccc1/C=C/c1ccc2c(c1)N(S(=O)(=O)c1cccc(C(F)(F)F)c1)C[C@H](CCC(=O)O)O2] | (S,E)-3-(6-(2-isopropylstyryl)-4-((3-(trifluoromethyl)-phenyl)-sulfonyl)-3,4-dihydro-2H-benzo[b][1,4]oxazin-2-yl)propanoic acid | 560 (M + H)+ |
| 89CC | 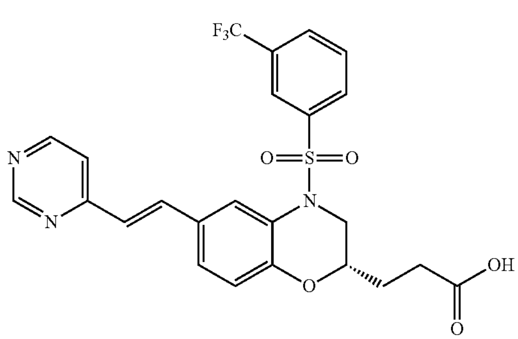 [SMILES: O=C(O)CC[C@H]1CN(S(=O)(=O)c2cccc(C(F)(F)F)c2)c2cc(/C=C/c3ccncn3)ccc2O1] | (S,E)-3-(6-(2-(pyrimidin-4-yl)vinyl)-4-((3-(trifluoromethyl)-phenyl)sulfonyl)-3,4-dihydro-2H-benzo[b][1,4]oxazin-2-yl)propanoic acid | 520 (M + H)+ |

TABLE 11-continued

| No. | Structure | Name | Observed m/z |
|---|---|---|---|
| 89CD | 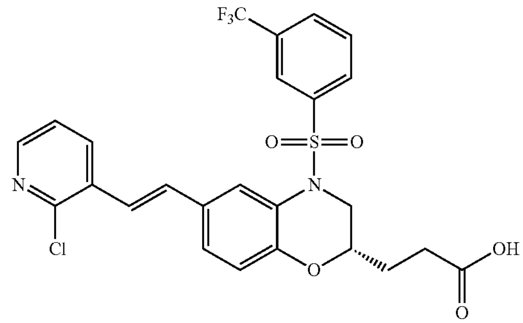 [SMILES: O=C(O)CC[C@H]1CN(S(=O)(=O)c2cccc(C(F)(F)F)c2)c2cc(/C=C/c3cccnc3Cl)ccc2O1] | (S,E)-3-(6-(2-(2-chloropyridin-3-yl)vinyl)-4-((3-(trifluoromethyl)-phenyl)sulfonyl)-3,4-dihydro-2H-benzo[b][1,4]oxazin-2-yl)-propanoic acid | 553 (M + H)+ |
| 89CE | 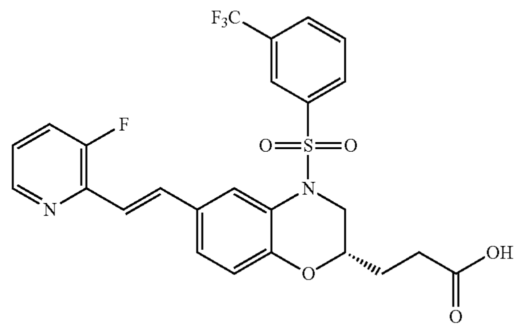 [SMILES: O=C(O)CC[C@H]1CN(S(=O)(=O)c2cccc(C(F)(F)F)c2)c2cc(/C=C/c3ncccc3F)ccc2O1] | (S,E)-3-(6-(2-(3-fluoropyridin-2-yl)vinyl)-4-((3-(trifluoromethyl)phenyl)sulfonyl)-3,4-dihydro-2H-benzo[b][1,4]oxazin-2-yl)propanoic acid | 537 (M + H)+ |
| 89CF | 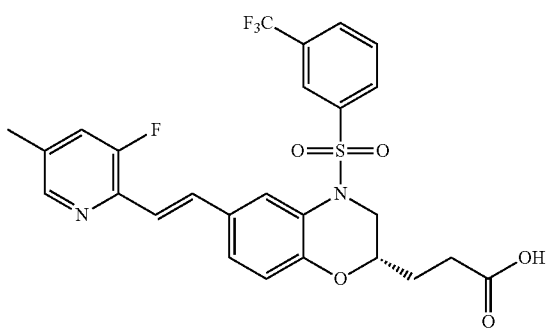 [SMILES: Cc1cnc(/C=C/c2ccc3c(c2)N(S(=O)(=O)c2cccc(C(F)(F)F)c2)C[C@H](CCC(=O)O)O3)c(F)c1] | (S,E)-3-(6-(2-(3-fluoro-5-methylpyridin-2-yl)vinyl)-4-((3-(trifluoromethyl)phenyl)sulfonyl)-3,4-dihydro-2H-benzo[b][1,4]-oxazin-2-yl)propanoic acid | 551 (M + H)+ |
| 89CG | 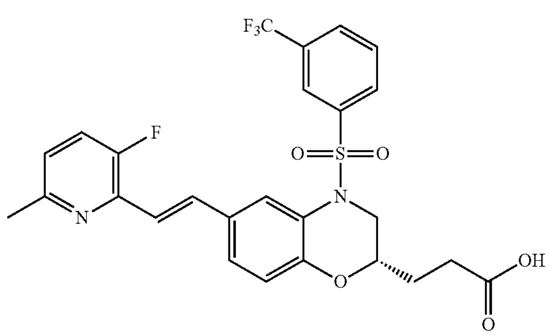 [SMILES: Cc1ccc(F)c(/C=C/c2ccc3c(c2)N(S(=O)(=O)c2cccc(C(F)(F)F)c2)C[C@H](CCC(=O)O)O3)n1] | (S,E)-3-(6-(2-(3-fluoro-6-methylpyridin-2-yl)vinyl)-4-((3-(trifluoromethyl)phenyl)sulfonyl)-3,4-dihydro-2H-benzo[b][1,4]-oxazin-2-yl)propanoic acid | 551 (M + H)+ |

TABLE 11-continued

| No. | Structure | Name | Observed m/z |
|---|---|---|---|
| 89CH | 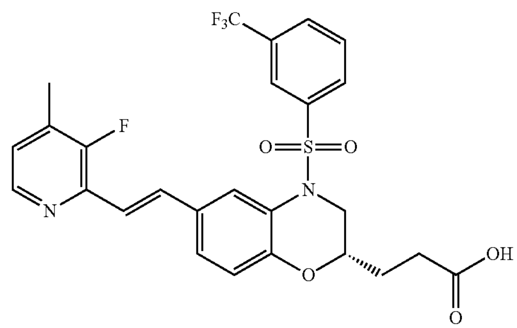 [SMILES: Cc1ccnc(/C=C/c2ccc3c(c2)N(S(=O)(=O)c2cccc(C(F)(F)F)c2)C[C@H](CCC(=O)O)O3)c1F] | (S,E)-3-(6-(2-(3-fluoro-4-methylpyridin-2-yl)vinyl)-4-((3-(trifluoromethyl)phenyl)sulfonyl)-3,4-dihydro-2H-benzo[b][1,4]-oxazin-2-yl)propanoic acid | 551 (M + H)+ |
| 89CI | 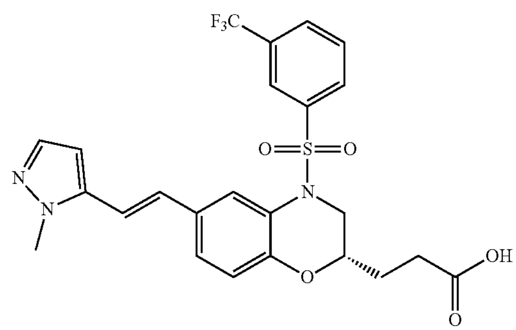 [SMILES: Cn1ncnc1/C=C/c1ccc2c(c1)N(S(=O)(=O)c1cccc(C(F)(F)F)c1)C[C@H](CCC(=O)O)O2] | (S,E)-3-(6-(2-(1-methyl-1H-pyrazol-5-yl)vinyl)-4-((3-(trifluoromethyl)phenyl)sulfonyl)-3,4-dihydro-2H-benzo[b][1,4]-oxazin-2-yl)propanoic acid | 522 (M + H)+ |
| 89CJ | 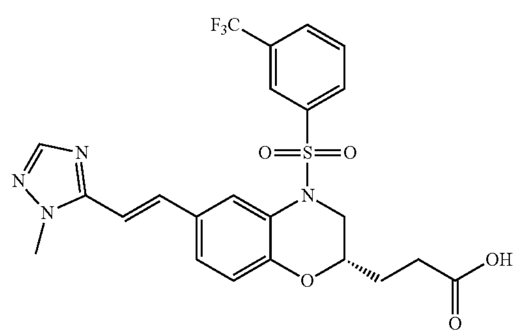 | (S,E)-3-(6-(2-(1-methyl-1H-1,2,4-triazol-5-yl)vinyl)-4-((3-(trifluoromethyl)phenyl)sulfonyl)-3,4-dihydro-2H-benzo[b][1,4]-oxazin-2-yl)propanoic acid | 523 (M + H)+ |
| 89CK | 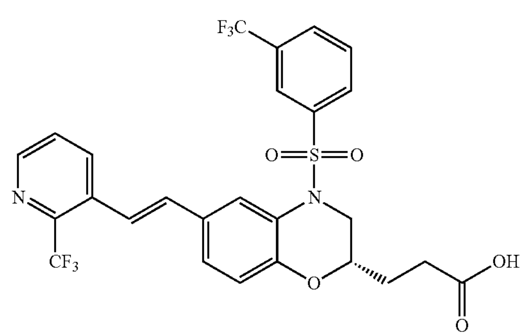 | (S,E)-3-(4-((3-(trifluoromethyl)-phenyl)sulfonyl)-6-(2-(2-(trifluoromethyl)pyridin-3-yl)vinyl)-3,4-dihydro-2H-benzo[b][1,4]oxazin-2-yl)propanoic acid | 587 (M + H)+ |

TABLE 11-continued

| No. | Structure | Name | Observed m/z |
|---|---|---|---|
| 89CL | 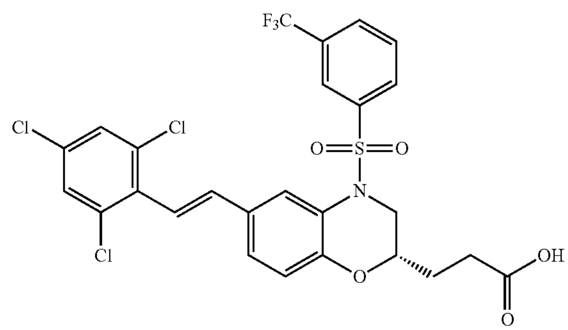 [SMILES: O=C(O)CC[C@H]1CN(S(=O)(=O)c2cccc(C(F)(F)F)c2)c2cc(/C=C/c3c(Cl)cc(Cl)cc3Cl)ccc2O1] | (S,E)-3-(6-(2,4,6-trichlorostyryl)-4-((3-(trifluoromethyl)-phenyl)sulfonyl)-3,4-dihydro-2H-benzo[b][1,4]oxazin-2-yl)propanoic acid | 620 (M + H)+ |
| 89CM | 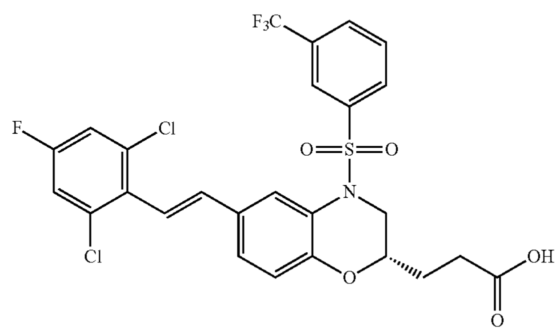 [SMILES: O=C(O)CC[C@H]1CN(S(=O)(=O)c2cccc(C(F)(F)F)c2)c2cc(/C=C/c3c(Cl)cc(F)cc3Cl)ccc2O1] | (S,E)-3-(6-(2,6-dichloro-4-fluorostyryl)-4-((3-(trifluoromethyl)phenyl)sulfonyl)-3,4-dihydro-2H-benzo[b][1,4]-oxazin-2-yl)propanoic acid | 604 (M + H)+ |
| 89CN | 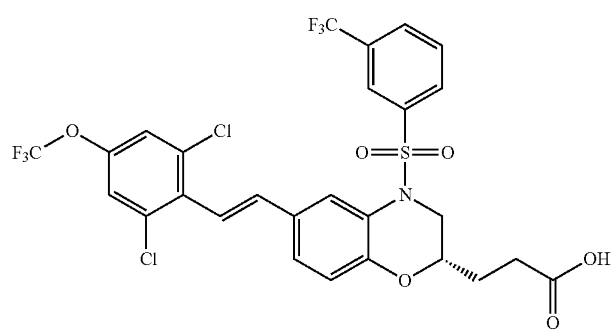 [SMILES: O=C(O)CC[C@H]1CN(S(=O)(=O)c2cccc(C(F)(F)F)c2)c2cc(/C=C/c3c(Cl)cc(OC(F)(F)F)cc3Cl)ccc2O1] | (S,E)-3-(6-(2,6-dichloro-4-(trifluoromethoxy)styryl)-4-((3-(trifluoromethyl)phenyl)sulfonyl)-3,4-dihydro-2H-benzo[b][1,4]-oxazin-2-yl)propanoic acid | 670 (M + H)+ |
| 89CO | 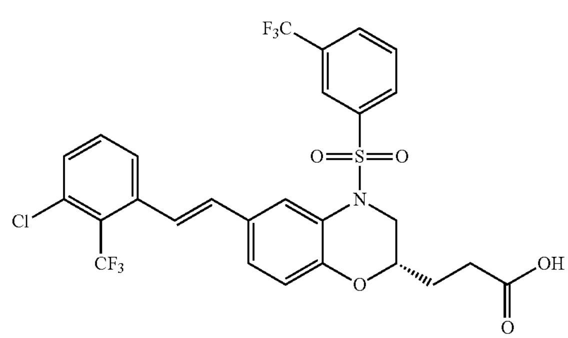 [SMILES: O=C(O)CC[C@H]1CN(S(=O)(=O)c2cccc(C(F)(F)F)c2)c2cc(/C=C/c3cccc(Cl)c3C(F)(F)F)ccc2O1] | (S,E)-3-(6-(3-chloro-2-(trifluoromethyl)styryl)-4-((3-(trifluoromethyl)phenyl)sulfonyl)-3,4-dihydro-2H-benzo[b][1,4]oxazin-2-yl)propanoic acid | 620 (M + H)+ |

TABLE 11-continued

| No. | Structure | Name | Observed m/z |
|---|---|---|---|
| 89CP | 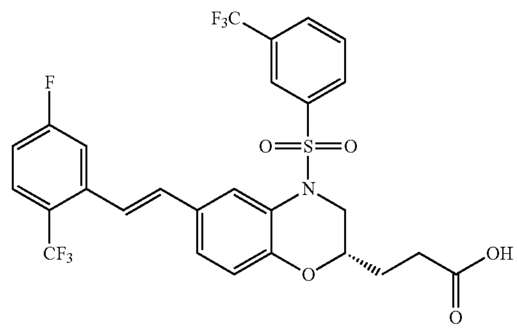 [SMILES: O=C(O)CC[C@H]1CN(S(=O)(=O)c2cccc(C(F)(F)F)c2)c2cc(/C=C/c3cc(F)ccc3C(F)(F)F)ccc2O1] | (S,E)-3-(6-(5-fluoro-2-(trifluoromethyl)styryl)-4-((3-(trifluoromethyl)phenyl)sulfonyl)-3,4-dihydro-2H-benzo[b][1,4]-oxazin-2-yl)propanoic acid | 604 (M + H)+ |
| 89CQ | 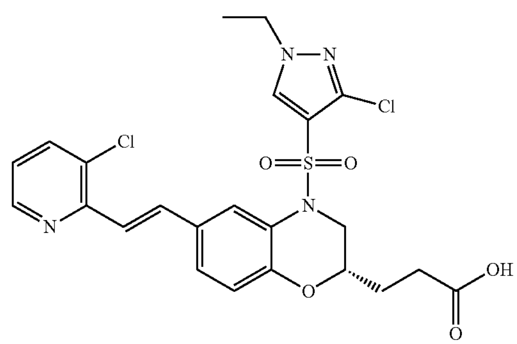 | (S,E)-3-(4-((3-chloro-1-ethyl-1H-pyrazol-4-yl)sulfonyl)-6-(2-(3-chloropyridin-2-yl)vinyl)-3,4-dihydro-2H-benzo[b][1,4]oxazin-2-yl)propanoic acid | 604 (M + H)+ |
| 89CR | 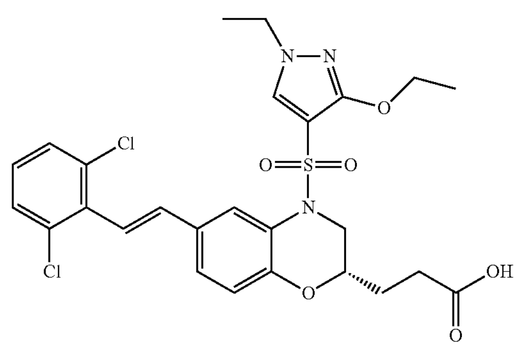 | (S,E)-3-(6-(2,6-dichlorostyryl)-4-((3-ethoxy-1-ethyl-1H-pyrazol-4-yl)sulfonyl)-3,4-dihydro-2H-benzo[b][1,4]oxazin-2-yl)-propanoic acid | 580 (M + H)+ |
| 89CS | 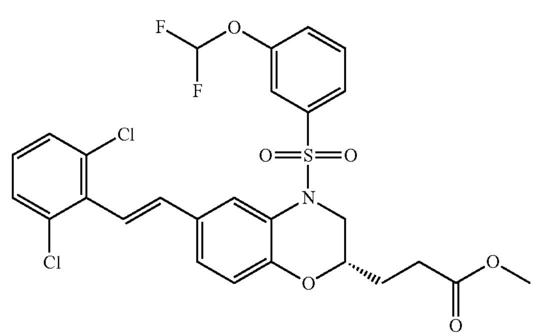 [SMILES: COC(=O)CC[C@H]1CN(S(=O)(=O)c2cccc(OC(F)F)c2)c2cc(/C=C/c3c(Cl)cccc3Cl)ccc2O1] | methyl (S,E)-3-(6-(2,6-dichlorostyryl)-4-((3-(difluoro-methoxy)phenyl)sulfonyl)-3,4-dihydro-2H-benzo[b][1,4]-oxazin-2-yl)propanoate | 598 (M + H)+ |

TABLE 11-continued

| No. | Structure | Name | Observed m/z |
|---|---|---|---|
| 89CT | 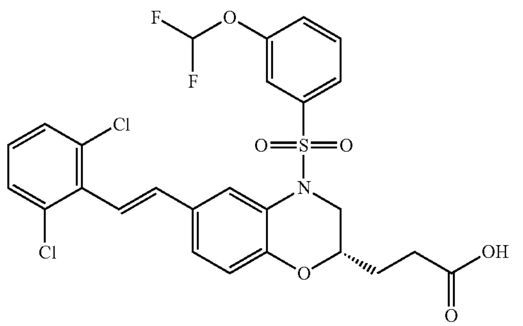 [SMILES: O=C(O)CC[C@H]1CN(S(=O)(=O)c2cccc(OC(F)F)c2)c2cc(/C=C/c3c(Cl)cccc3Cl)ccc2O1] | (S,E)-3-(6-(2,6-dichlorostyryl)-4-((3-(difluoromethoxy)phenyl)-sulfonyl)-3,4-dihydro-2H-benzo[b][1,4]oxazin-2-yl)propanoic acid | 584 (M + H)+ |
| 89CU | 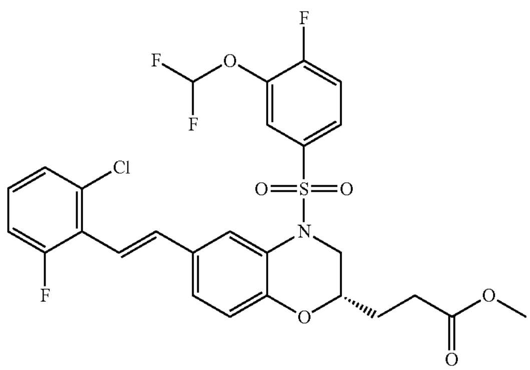 [SMILES: COC(=O)CC[C@H]1CN(S(=O)(=O)c2ccc(F)c(OC(F)F)c2)c2cc(/C=C/c3c(F)cccc3Cl)ccc2O1] | methyl (S,E)-3-(6-(2-chloro-6-fluorostyryl)-4-((3-(difluoro-methoxy)-4-fluorophenyl)-sulfonyl)-3,4-dihydro-2H-benzo[b][1,4]oxazin-2-yl)propanoate | 600 (M + H)+ |
| 89CV | 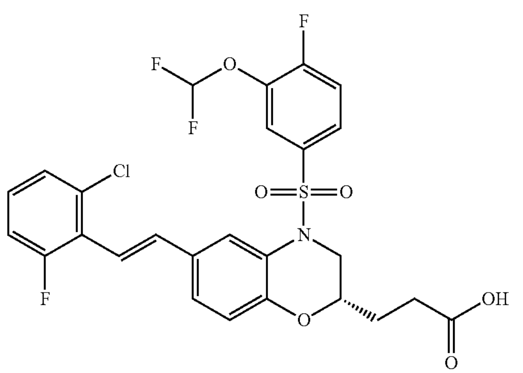 [SMILES: O=C(O)CC[C@H]1CN(S(=O)(=O)c2ccc(F)c(OC(F)F)c2)c2cc(/C=C/c3c(F)cccc3Cl)ccc2O1] | (S,E)-3-(6-(2-chloro-6-fluorostyryl)-4-((3-(difluoro-methoxy)-4-fluorophenyl)-sulfonyl)-3,4-dihydro-2H-benzo[b][1,4]oxazin-2-yl)propanoic acid | 586 (M + H)+ |
| 89CW | 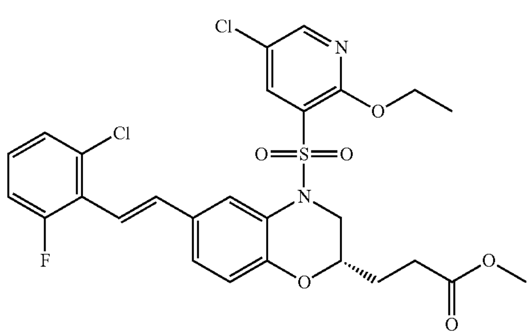 [SMILES: CCOc1ncc(Cl)cc1S(=O)(=O)N1C[C@H](CCC(=O)OC)Oc2ccc(/C=C/c3c(F)cccc3Cl)cc21] | methyl (S,E)-3-(4-((5-chloro-2-ethoxypyridin-3-yl)sulfonyl)-6-(2-chloro-6-fluorostyryl)-3,4-dihydro-2H-benzo[b][1,4]oxazin-2-yl)propanoate | 595 (M + H)+ |

TABLE 11-continued

| No. | Structure | Name | Observed m/z |
|---|---|---|---|
| 89CX | 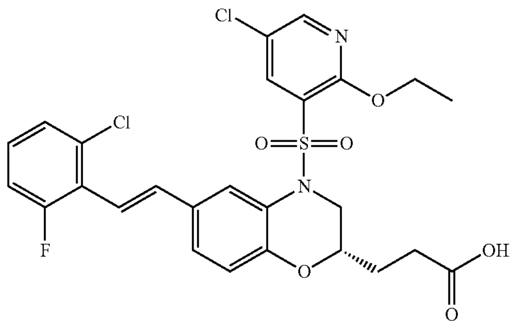 [SMILES: CCOc1ncc(Cl)cc1S(=O)(=O)N1C[C@H](CCC(=O)O)Oc2ccc(/C=C/c3c(F)cccc3Cl)cc21] | (S,E)-3-(4-((5-chloro-2-ethoxypyridin-3-yl)sulfonyl)-6-(2-chloro-6-fluorostyryl)-3,4-dihydro-2H-benzo[b][1,4]oxazin-2-yl)propanoic acid | 581 (M + H)+ |
| 89CY | 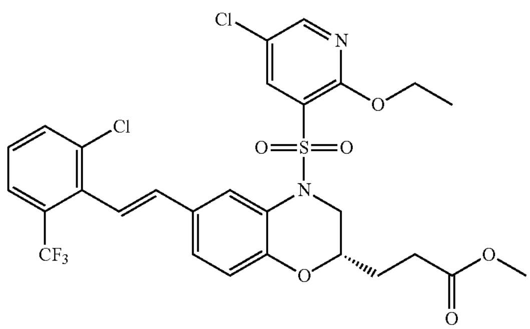 [SMILES: CCOc1ncc(Cl)cc1S(=O)(=O)N1C[C@H](CCC(=O)OC)Oc2ccc(/C=C/c3c(Cl)cccc3C(F)(F)F)cc21] | methyl (S,E)-3-(4-((5-chloro-2-ethoxypyridin-3-yl)sulfonyl)-6-(2-chloro-6-(trifluoromethyl)-styryl)-3,4-dihydro-2H-benzo-[b][1,4]oxazin-2-yl)propanoate | 645 (M + H)+ |
| 89CZ | 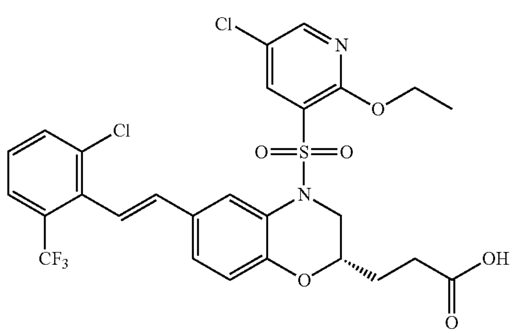 | (S,E)-3-(4-((5-chloro-2-ethoxypyridin-3-yl)sulfonyl)-6-(2-chloro-6-(trifluoromethyl)-styryl)-3,4-dihydro-2H-benzo-[b][1,4]oxazin-2-yl)propanoic acid | 631 (M + H)+ |
| 89DA | 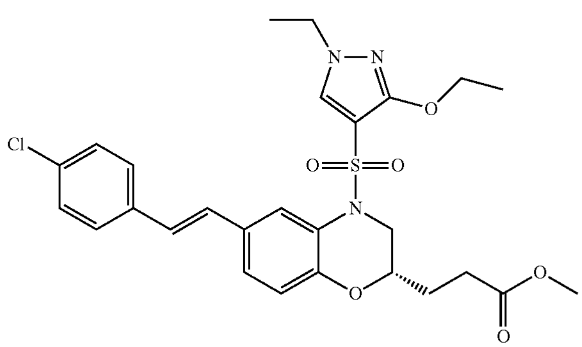 [SMILES: CCOc1nn(CC)cc1S(=O)(=O)N1C[C@H](CCC(=O)OC)Oc2ccc(/C=C/c3ccc(Cl)cc3)cc21] | methyl (S,E)-3-(6-(4-chlorostyryl)-4-((3-ethoxy-1-ethyl-1H-pyrazol-4-yl)sulfonyl)-3,4-dihydro-2H-benzo[b][1,4]oxazin-2-yl)propanoate | 560 (M + H)+ |

TABLE 11-continued

| No. | Structure | Name | Observed m/z |
|---|---|---|---|
| 89DB | 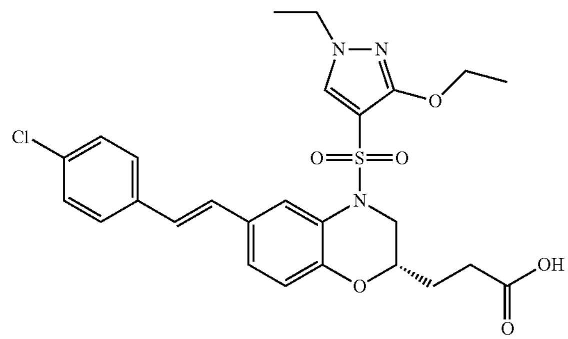 [SMILES: CCOc1nn(CC)cc1S(=O)(=O)N1C[C@H](CCC(=O)O)Oc2ccc(/C=C/c3ccc(Cl)cc3)cc21] | (S,E)-3-(6-(4-chlorostyryl)-4-((3-ethoxy-1-ethyl-1H-pyrazol-4-yl)sulfonyl)-3,4-dihydro-2H-benzo[b][1,4]oxazin-2-yl)propanoic acid | 546 (M + H)+ |
| 89DC | 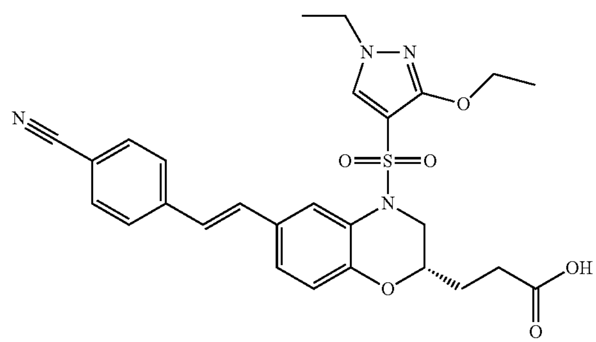 [SMILES: CCOc1nn(CC)cc1S(=O)(=O)N1C[C@H](CCC(=O)O)Oc2ccc(/C=C/c3ccc(C#N)cc3)cc21] | (S,E)-3-(6-(4-cyanostyryl)-4-((3-ethoxy-1-ethyl-1H-pyrazol-4-yl)sulfonyl)-3,4-dihydro-2H-benzo[b][1,4]oxazin-2-yl)propanoic acid | 537 (M + H)+ |
| 89DD | 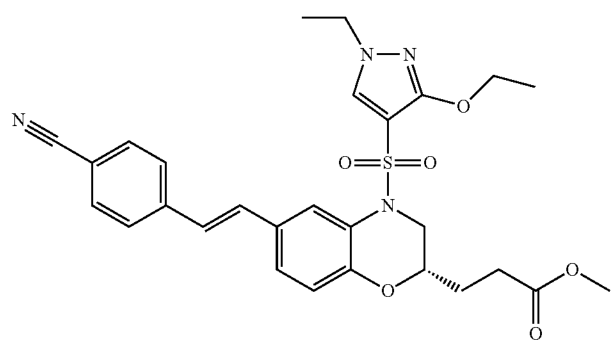 [SMILES: CCOc1nn(CC)cc1S(=O)(=O)N1C[C@H](CCC(=O)OC)Oc2ccc(/C=C/c3ccc(C#N)cc3)cc21] | methyl (S,E)-3-(6-(4-cyanostyryl)-4-((3-ethoxy-1-ethyl-1H-pyrazol-4-yl)sulfonyl)-3,4-dihydro-2H-benzo[b][1,4]oxazin-2-yl)propanoate | 551 (M + H)+ |
| 89DE | 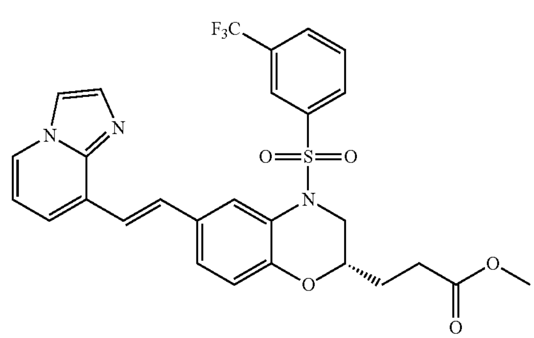 [SMILES: COC(=O)CC[C@H]1CN(S(=O)(=O)c2cccc(C(F)(F)F)c2)c2cc(/C=C/c3cccn4ccnc34)ccc2O1] | methyl (S,E)-3-(6-(2-(imidazo[1,2-a]pyridin-8-yl)vinyl)-4-((3-(trifluoromethyl)phenyl)sulfonyl)-3,4-dihydro-2H-benzo[b][1,4]oxazin-2-yl)propanoate | 572 (M + H)+ |

TABLE 11-continued

| No. | Structure | Name | Observed m/z |
|---|---|---|---|
| 89DF | 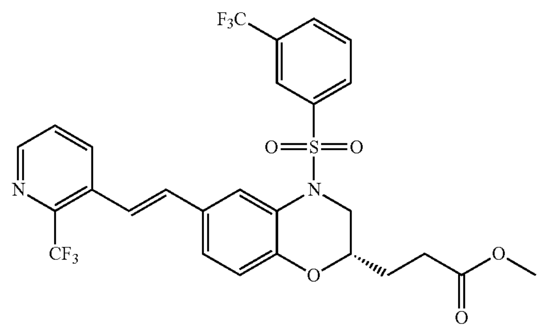 [SMILES: COC(=O)CC[C@H]1CN(S(=O)(=O)c2cccc(C(F)(F)F)c2)c2cc(/C=C/c3cccnc3C(F)(F)F)ccc2O1] | methyl (S,E)-3-(4-((3-(trifluoromethyl)phenyl)-sulfonyl)-6-(2-(2-(trifluoromethyl)pyridin-3-yl)vinyl)-3,4-dihydro-2H-benzo[b][1,4]oxazin-2-yl)propanoate | 601 (M + H)+ |
| 89DG | 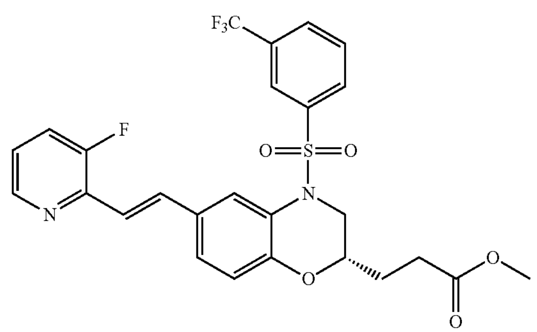 [SMILES: COC(=O)CC[C@H]1CN(S(=O)(=O)c2cccc(C(F)(F)F)c2)c2cc(/C=C/c3ncccc3F)ccc2O1] | methyl (S,E)-3-(6-(2-(3-fluoropyridin-2-yl)vinyl)-4-((3-(trifluoromethyl)phenyl)-sulfonyl)-3,4-dihydro-2H-benzo[b][1,4]oxazin-2-yl)propanoate | 551 (M + H)+ |
| 89DH | 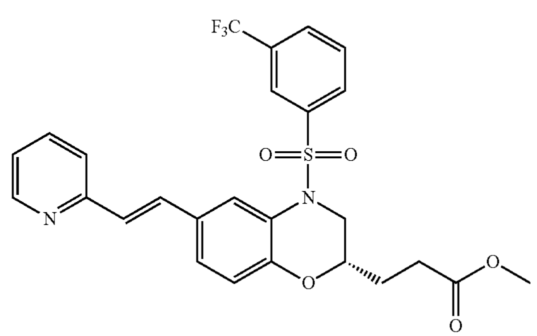 [SMILES: COC(=O)CC[C@H]1CN(S(=O)(=O)c2cccc(C(F)(F)F)c2)c2cc(/C=C/c3ccccn3)ccc2O1] | methyl (S,E)-3-(6-(2-(pyridin-2-yl)vinyl)-4-((3-(trifluoromethyl)phenyl)sulfonyl)-3,4-dihydro-2H-benzo[b][1,4]oxazin-2-yl)propanoate | 533 (M + H)+ |
| 89DI | 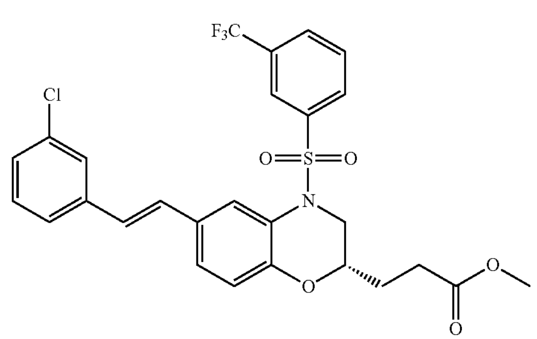 [SMILES: COC(=O)CC[C@H]1CN(S(=O)(=O)c2cccc(C(F)(F)F)c2)c2cc(/C=C/c3cccc(Cl)c3)ccc2O1] | methyl (S,E)-3-(6-(3-chlorostyryl)-4-((3-(trifluoromethyl)phenyl)-sulfonyl)-3,4-dihydro-2H-benzo[b][1,4]oxazin-2-yl)propanoate | 566 (M + H)+ |

TABLE 11-continued

| No. | Structure | Name | Observed m/z |
|---|---|---|---|
| 89DJ | 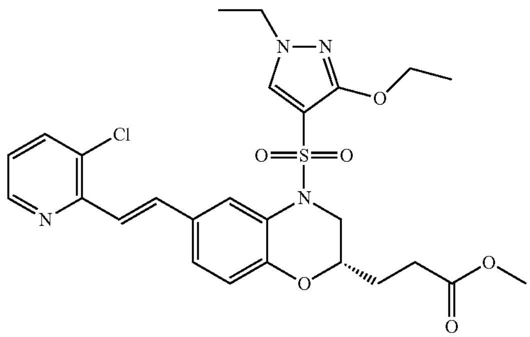 [SMILES: CCOc1nn(CC)cc1S(=O)(=O)N1C[C@H](CCC(=O)OC)Oc2ccc(/C=C/c3ncccc3Cl)cc21] | methyl (S,E)-3-(6-(2-(3-chloropyridin-2-yl)vinyl)-4-((3-ethoxy-1-ethyl-1H-pyrazol-4-yl)sulfonyl)-3,4-dihydro-2H-benzo[b][1,4]oxazin-2-yl)propanoate | 561 (M + H)+ |
| 89DK | 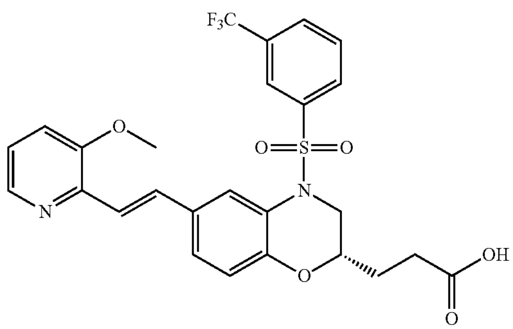 [SMILES: COc1cccnc1/C=C/c1ccc2c(c1)N(S(=O)(=O)c1cccc(C(F)(F)F)c1)C[C@H](CCC(=O)O)O2] | (S,E)-3-(6-(2-(3-methoxypyridin-2-yl)vinyl)-4-((3-(trifluoromethyl)phenyl)-sulfonyl)-3,4-dihydro-2H-benzo[b][1,4]oxazin-2-yl)propanoic acid | 549 (M + H)+ |
| 89DL | 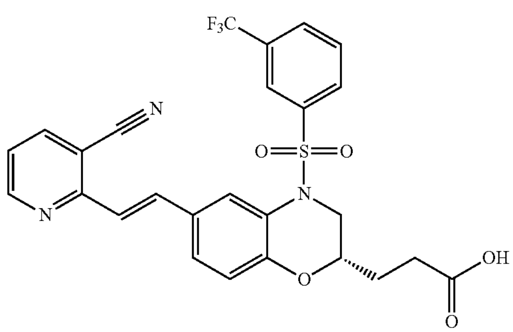 [SMILES: N#Cc1cccnc1/C=C/c1ccc2c(c1)N(S(=O)(=O)c1cccc(C(F)(F)F)c1)C[C@H](CCC(=O)O)O2] | (S,E)-3-(6-(2-(3-cyanopyridin-2-yl)vinyl)-4-((3-(trifluoromethyl)-phenyl)sulfonyl)-3,4-dihydro-2H-benzo[b][1,4]oxazin-2-yl)propanoic acid | 544 (M + H)+ |
| 89DM | 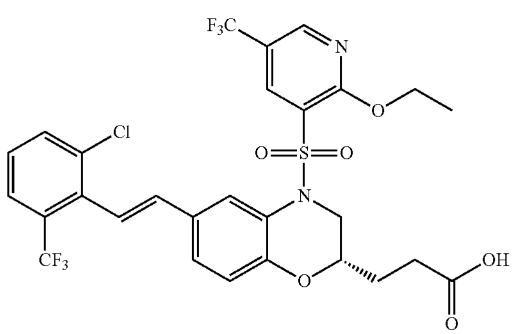 [SMILES: CCOc1ncc(C(F)(F)F)cc1S(=O)(=O)N1C[C@H](CCC(=O)O)Oc2ccc(/C=C/c3c(Cl)cccc3C(F)(F)F)cc21] | (S,E)-3-(6-(2-chloro-6-(trifluoromethyl)styryl)-4-((2-ethoxy-5-(trifluoromethyl)-pyridin-3-yl)sulfonyl)-3,4-dihydro-2H-benzo[b][1,4]-oxazin-2-yl)propanoic acid | 665 (M + H)+ |

TABLE 11-continued

| No. | Structure | Name | Observed m/z |
|---|---|---|---|
| 89DN | 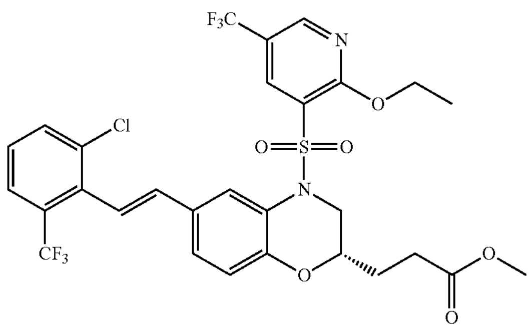 [SMILES: CCOc1ncc(C(F)(F)F)cc1S(=O)(=O)N1C[C@H](CCC(=O)OC)Oc2ccc(/C=C/c3c(Cl)cccc3C(F)(F)F)cc21] | methyl (S,E)-3-(6-(2-chloro-6-(trifluoromethyl)styryl)-4-((2-ethoxy-5-(trifluoromethyl)-pyridin-3-yl)sulfonyl)-3,4-dihydro-2H-benzo[b][1,4]-oxazin-2-yl)propanoate | 679 (M + H)+ |
| 89DO | 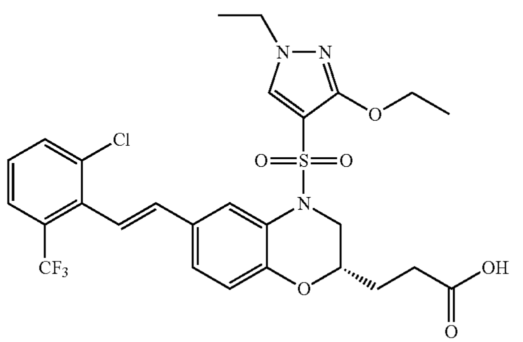 [SMILES: CCOc1nn(CC)cc1S(=O)(=O)N1C[C@H](CCC(=O)O)Oc2ccc(/C=C/c3c(Cl)cccc3C(F)(F)F)cc21] | (S,E)-3-(6-(2-chloro-6-(trifluoromethyl)styryl)-4-((3-ethoxy-1-ethyl-1H-pyrazol-4-yl)sulfonyl)-3,4-dihydro-2H-benzo[b][1,4]oxazin-2-yl)propanoic acid | 614 (M + H)+ |
| 89DP | 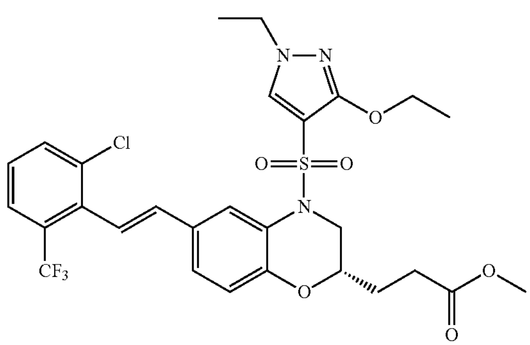 [SMILES: CCOc1nn(CC)cc1S(=O)(=O)N1C[C@H](CCC(=O)OC)Oc2ccc(/C=C/c3c(Cl)cccc3C(F)(F)F)cc21] | methyl (S,E)-3-(6-(2-chloro-6-(trifluoromethyl)styryl)-4-((3-ethoxy-1-ethyl-1H-pyrazol-4-yl)sulfonyl)-3,4-dihydro-2H-benzo[b][1,4]oxazin-2-yl)propanoate | 628 (M + H)+ |
| 89DQ | 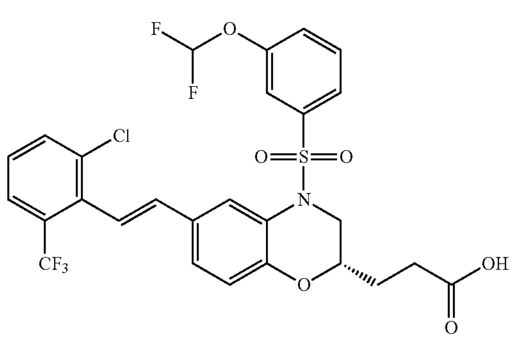 | (S,E)-3-(6-(2-chloro-6-(trifluoromethyl)styryl)-4-((3-(difluoromethoxy)phenyl)sulfonyl)-3,4-dihydro-2H-benzo[b][1,4]oxazin-2-yl)propanoic acid | 618 (M + H)+ |

TABLE 11-continued

| No. | Structure | Name | Observed m/z |
|---|---|---|---|
| 89DR | 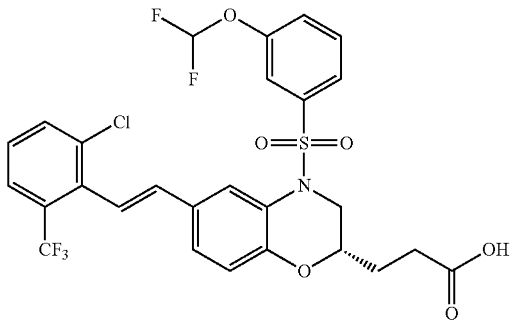 | (S,E)-3-(6-(2-chloro-6-(trifluoromethyl)styryl)-4-((3-(difluoromethoxy)phenyl)sulfonyl)-3,4-dihydro-2H-benzo[b][1,4]oxazin-2-yl)propanoic acid | 632 (M + H)+ |
| 89DS | 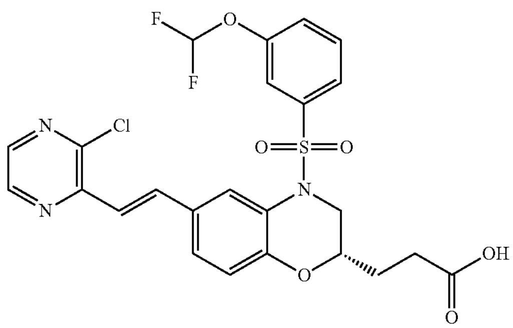 | (S,E)-3-(6-(2-(3-chloropyrazin-2-yl)vinyl)-4-((3-(difluoromethoxy)phenyl)sulfonyl)-3,4-dihydro-2H-benzo[b][1,4]-oxazin-2-yl)propanoic acid | 552 (M + H)+ |
| 89DT | 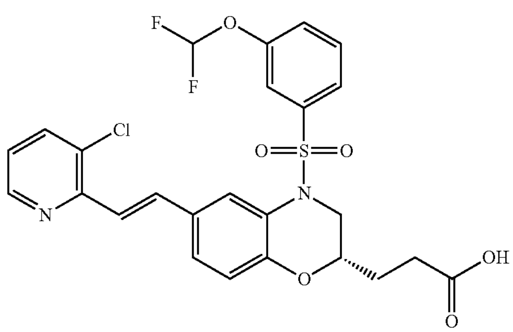 | (S,E)-3-(6-(2-(3-chloropyridin-2-yl)vinyl)-4-((3-(difluoromethoxy)phenyl)sulfonyl)-3,4-dihydro-2H-benzo[b][1,4]-oxazin-2-yl)propanoic acid | 551 (M + H)+ |
| 89DU | 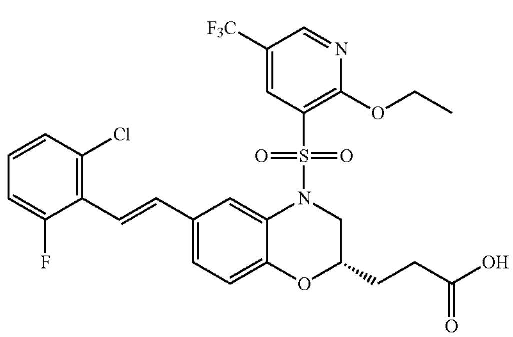 [SMILES: CCOc1ncc(C(F)(F)F)cc1S(=O)(=O)N1C[C@H](CCC(=O)O)Oc2ccc(/C=C/c3c(F)cccc3Cl)cc21] | (S,E)-3-(6-(2-chloro-6-fluorostyryl)-4-((2-ethoxy-5-(trifluoromethyl)pyridin-3-yl)sulfonyl)-3,4-dihydro-2H-benzo[b][1,4]oxazin-2-yl)propanoic acid | 615 (M + H)+ |

TABLE 11-continued

| No. | Structure | Name | Observed m/z |
|---|---|---|---|
| 89DV | 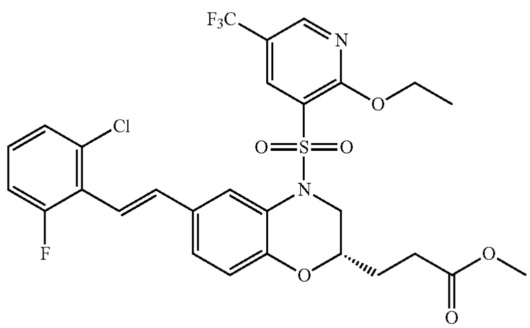 [SMILES: CCOc1ncc(C(F)(F)F)cc1S(=O)(=O)N1C[C@H](CCC(=O)OC)Oc2ccc(/C=C/c3c(F)cccc3Cl)cc21] | methyl (S,E)-3-(6-(2-chloro-6-fluorostyryl)-4-((2-ethoxy-5-(trifluoromethyl)pyridin-3-yl)sulfonyl)-3,4-dihydro-2H-benzo[b][1,4]oxazin-2-yl)propanoate | 629 (M + H)+ |
| 89DW | 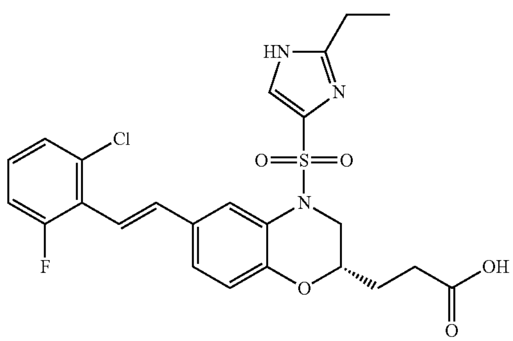 [SMILES: CCc1nc(S(=O)(=O)N2C[C@H](CCC(=O)O)Oc3ccc(/C=C/c4c(F)cccc4Cl)cc32)c[nH]1] | (S,E)-3-(6-(2-chloro-6-fluorostyryl)-4-((2-ethyl-1H-imidazol-4-yl)sulfonyl)-3,4-dihydro-2H-benzo[b][1,4]-oxazin-2-yl)propanoic acid | 520 (M + H)+ |
| 89DX | 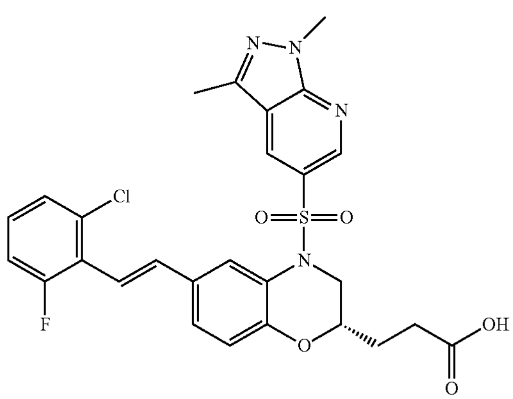 [SMILES: Cc1nn(C)c2ncc(S(=O)(=O)N3C[C@H](CCC(=O)O)Oc4ccc(/C=C/c5c(F)cccc5Cl)cc43)cc12] | (S,E)-3-(6-(2-chloro-6-fluorostyryl)-4-((1,3-dimethyl-1H-pyrazolo[3,4-b]pyridin-5-yl)sulfonyl)-3,4-dihydro-2H-benzo[b][1,4]oxazin-2-yl)propanoic acid | 571 (M + H)+ |
| 89DY | 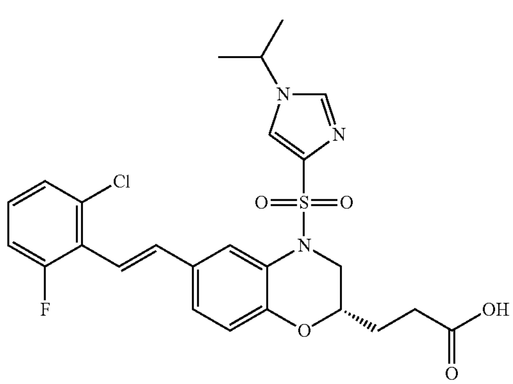 [SMILES: CC(C)n1cnc(S(=O)(=O)N2C[C@H](CCC(=O)O)Oc3ccc(/C=C/c4c(F)cccc4Cl)cc32)c1] | (S,E)-3-(6-(2-chloro-6-fluorostyryl)-4-((1-isopropyl-1H-imidazol-4-yl)sulfonyl)-3,4-dihydro-2H-benzo[b][1,4]-oxazin-2-yl)propanoic acid | 534 (M + H)+ |

TABLE 11-continued

| No. | Structure | Name | Observed m/z |
|---|---|---|---|
| 89DZ | 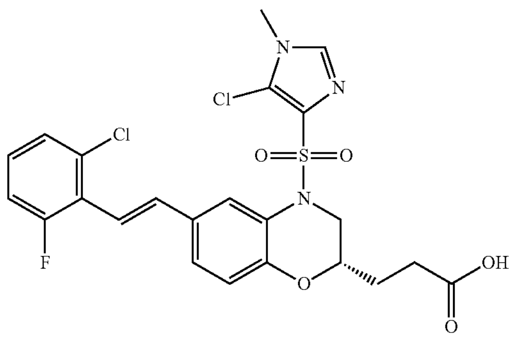 [SMILES: Cn1cnc(S(=O)(=O)N2C[C@H](CCC(=O)O)Oc3ccc(/C=C/c4c(F)cccc4Cl)cc32)c1Cl] | (S,E)-3-(4-((5-chloro-1-methyl-1H-imidazol-4-yl)sulfonyl)-6-(2-chloro-6-fluorostyryl)-3,4-dihydro-2H-benzo[b][1,4]-oxazin-2-yl)propanoic acid | 540 (M + H)+ |
| 89EA | 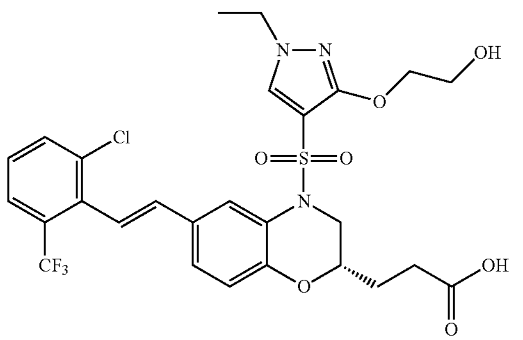 | (S,E)-3-(6-(2-chloro-6-(trifluoromethyl)styryl)-4-((1-ethyl-3-(2-hydroxyethoxy)-1H-pyrazol-4-yl)sulfonyl)-3,4-dihydro-2H-benzo[b][1,4]oxazin-2-yl)propanoic acid | 540 (M + H)+ |
| 89EB | 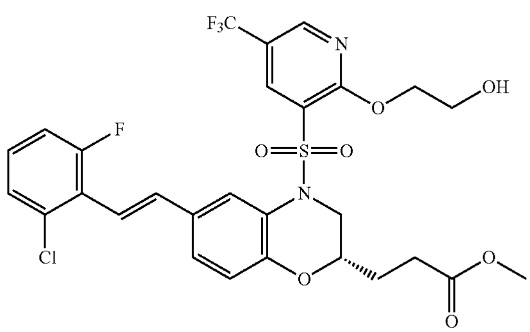 | methyl (S,E)-3-(6-(2-chloro-6-fluorostyryl)-4-((2-(2-hydroxyethoxy)-5-(trifluoromethyl)pyridin-3-yl)sulfonyl)-3,4-dihydro-2H-benzo[b][1,4]oxazin-2-yl)propanoate | 631 (M + H)+ |
| 89EC | 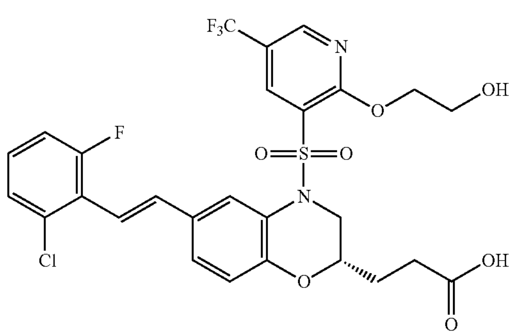 [SMILES: O=C(O)CC[C@H]1CN(S(=O)(=O)c2cc(C(F)(F)F)cnc2OCCO)c2cc(/C=C/c3c(F)cccc3Cl)ccc2O1] | (S,E)-3-(6-(2-chloro-6-fluorostyryl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 645 (M + H)+ |

TABLE 11-continued

| No. | Name | Observed m/z |
|---|---|---|
| 89ED | (S,E)-3-(6-(2-chloro-6-(trifluoromethyl)styryl)-4-((3-(2-hydroxyethoxy)-1-isopropyl-1H-pyrazol-4-yl)sulfonyl)-3,4-dihydro-2H-benzo[b][1,4]oxazin-2-yl)propanoic acid | 644 (M + H)+ |
| 89EE | (S,E)-3-(6-(2-(3-chloropyridin-2-yl)vinyl)-4-((3-ethoxy-1-ethyl-1H-pyrazol-4-yl)sulfonyl)-3,4-dihydro-2H-benzo[b][1,4]oxazin-2-yl)propanoic acid | 547 (M + H)+ |
| 89EF | (S,E)-3-(6-(2-chloro-6-(trifluoromethyl)styryl)-4-((1-(2,2-difluoroethyl)-3-(2-hydroxyethoxy)-1H-pyrazol-4-yl)sulfonyl)-3,4-dihydro-2H-benzo[b][1,4]oxazin-2-yl)propanoic acid | 666 (M + H)+ |
| 89EG | (S,E)-3-(6-(2-chloro-6-(trifluoromethyl)styryl)-4-((1-cyclopropyl-3-(2-hydroxyethoxy)-1H-pyrazol-4-yl)sulfonyl)-3,4-dihydro-2H-benzo[b][1,4]oxazin-2-yl)propanoic acid | 642 (M + H)+ |

TABLE 11-continued

| No. | Structure | Name | Observed m/z |
|---|---|---|---|
| 89EH | 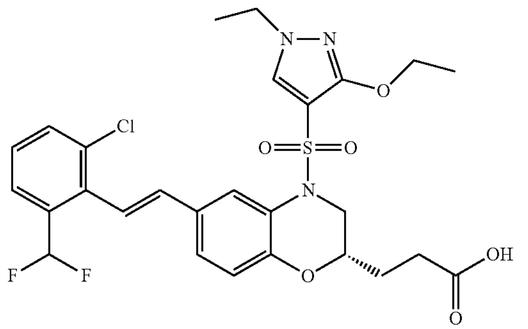 [SMILES: CCOc1nn(CC)cc1S(=O)(=O)N1C[C@H](CCC(=O)O)Oc2ccc(/C=C/c3c(Cl)cccc3C(F)F)cc21] | (S,E)-3-(6-(2-chloro-6-(difluoromethyl)styryl)-4-((3-ethoxy-1-ethyl-1H-pyrazol-4-yl)sulfonyl)-3,4-dihydro-2H-benzo[b][1,4]oxazin-2-yl)propanoic acid | 596 (M + H)+ |
| 89EI | 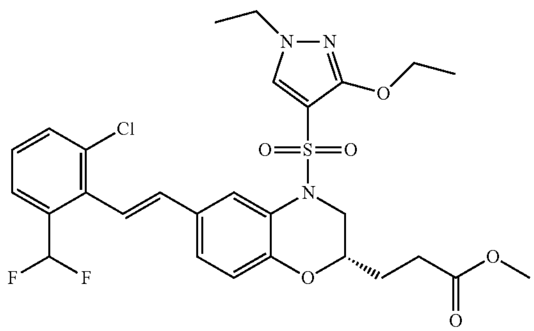 [SMILES: CCOc1nn(CC)cc1S(=O)(=O)N1C[C@H](CCC(=O)OC)Oc2ccc(/C=C/c3c(Cl)cccc3C(F)F)cc21] | methyl (S,E)-3-(6-(2-chloro-6-(difluoromethyl)styryl)-4-((3-ethoxy-1-ethyl-1H-pyrazol-4-yl)sulfonyl)-3,4-dihydro-2H-benzo[b][1,4]oxazin-2-yl)propanoate | 610 (M + H)+ |
| 89EJ | 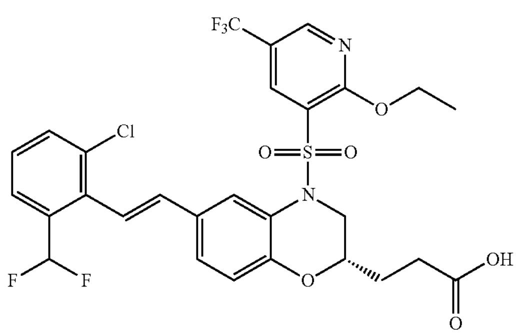 [SMILES: CCOc1ncc(C(F)(F)F)cc1S(=O)(=O)N1C[C@H](CCC(=O)O)Oc2ccc(/C=C/c3c(Cl)cccc3C(F)F)cc21] | (S,E)-3-(6-(2-chloro-6-(difluoromethyl)styryl)-4-((2-ethoxy-5-(trifluoromethyl)-pyridin-3-yl)sulfonyl)-3,4-dihydro-2H-benzo[b][1,4]-oxazin-2-yl)propanoic acid | 647 (M + H)+ |
| 89EK | 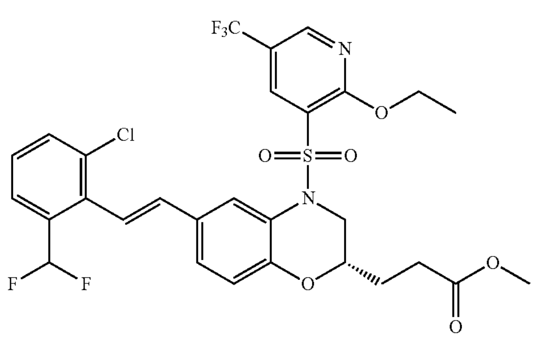 [SMILES: CCOc1ncc(C(F)(F)F)cc1S(=O)(=O)N1C[C@H](CCC(=O)OC)Oc2ccc(/C=C/c3c(Cl)cccc3C(F)F)cc21] | methyl (S,E)-3-(6-(2-chloro-6-(difluoromethyl)styryl)-4-((2-ethoxy-5-(trifluoromethyl)-pyridin-3-yl)sulfonyl)-3,4-dihydro-2H-benzo[b][1,4]-oxazin-2-yl)propanoate | 661 (M + H)+ |

TABLE 11-continued

| No. | Structure | Name | Observed m/z |
|---|---|---|---|
| 89EL | 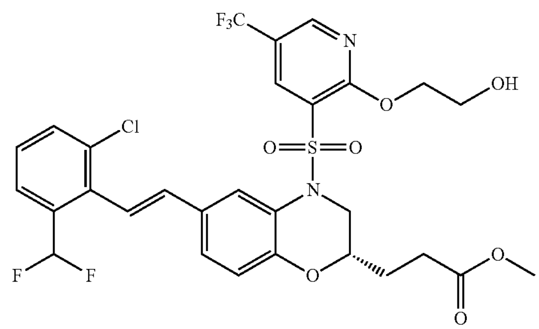 [SMILES: COC(=O)CC[C@H]1CN(S(=O)(=O)c2cc(C(F)(F)F)cnc2OCCO)c2cc(/C=C/c3c(Cl)cccc3C(F)F)ccc2O1] | methyl (S,E)-3-(6-(2-chloro-6-(difluoromethyl)styryl)-4-((2-(2-hydroxyethoxy)-5-(trifluoromethyl)pyridin-3-yl)sulfonyl)-3,4-dihydro-2H-benzo[b][1,4]oxazin-2-yl)propanoate | 677 (M + H)+ |
| 89EM | 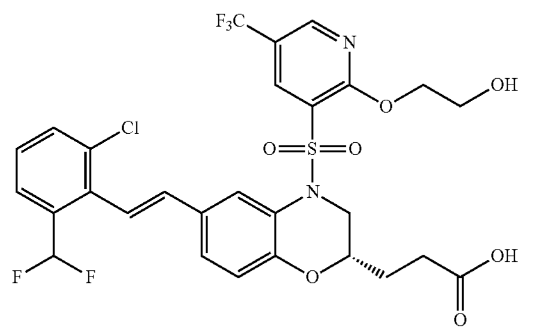 [SMILES: O=C(O)CC[C@H]1CN(S(=O)(=O)c2cc(C(F)(F)F)cnc2OCCO)c2cc(/C=C/c3c(Cl)cccc3C(F)F)ccc2O1] | (S,E)-3-(6-(2-chloro-6-(difluoromethyl)styryl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 663 (M + H)+ |
| 89EN | 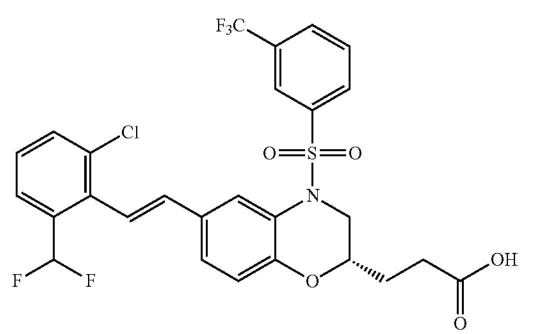 [SMILES: O=C(O)CC[C@H]1CN(S(=O)(=O)c2cccc(C(F)(F)F)c2)c2cc(/C=C/c3c(Cl)cccc3C(F)F)ccc2O1] | (S,E)-3-(6-(2-chloro-6-(difluoromethyl)styryl)-4-((3-(trifluoromethyl)phenyl)sulfonyl)-3,4-dihydro-2H-benzo[b][1,4]oxazin-2-yl)propanoic acid | 602 (M + H)+ |
| 89EO | 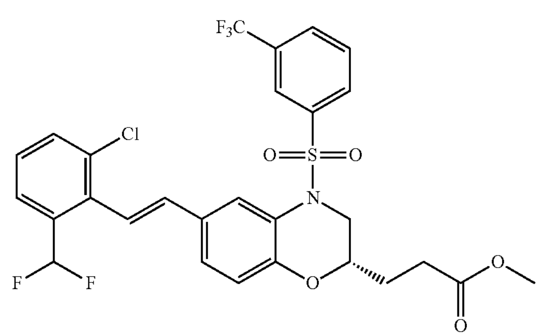 [SMILES: COC(=O)CC[C@H]1CN(S(=O)(=O)c2cccc(C(F)(F)F)c2)c2cc(/C=C/c3c(Cl)cccc3C(F)F)ccc2O1] | methyl (S,E)-3-(6-(2-chloro-6-(difluoromethyl)styryl)-4-((3-(trifluoromethyl)phenyl)sulfonyl)-3,4-dihydro-2H-benzo[b][1,4]oxazin-2-yl)propanoate | 616 (M + H)+ |

TABLE 11-continued

| No. | Structure | Name | Observed m/z |
|---|---|---|---|
| 89EP | 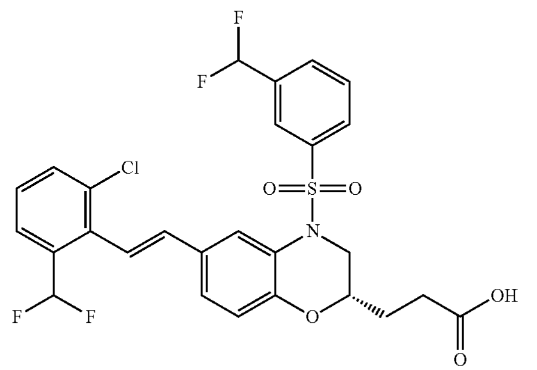 [SMILES: O=C(O)CC[C@H]1CN(S(=O)(=O)c2cccc(C(F)F)c2)c2cc(/C=C/c3c(Cl)cccc3C(F)F)ccc2O1] | (S-3-(6-(2-chloro-6-(difluoromethyl)styryl)-4-((3-(difluoromethyl)phenyl)-sulfonyl)-3,4-dihydro-2H-benzo[b][1,4]oxazin-2-yl)propanoic acid | 584 (M + H)+ |
| 89EQ | 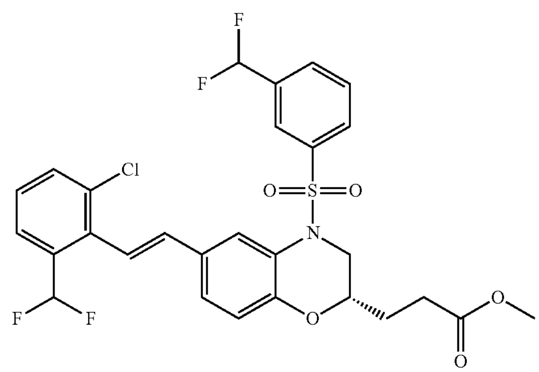 [SMILES: COC(=O)CC[C@H]1CN(S(=O)(=O)c2cccc(C(F)F)c2)c2cc(/C=C/c3c(Cl)cccc3C(F)F)ccc2O1] | methyl (S,E)-3-(6-(2-chloro-6-(difluoromethyl)styryl)-4-((3-(difluoromethyl)phenyl)-sulfonyl)-3,4-dihydro-2H-benzo[b][1,4]oxazin-2-yl)propanoate | 598 (M + H)+ |
| 89ER | 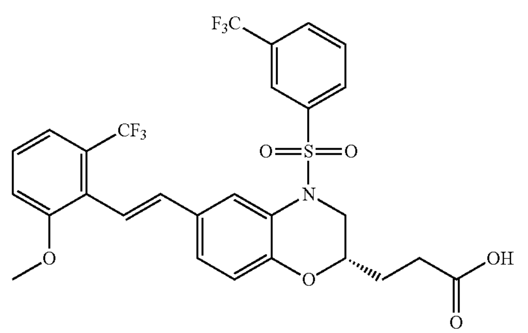 [SMILES: COc1cccc(C(F)(F)F)c1/C=C/c1ccc2c(c1)N(S(=O)(=O)c1cccc(C(F)(F)F)c1)C[C@H](CCC(=O)O)O2] | (S,E)-3-(6-(2-methoxy-6-(trifluoromethyl)styryl)-4-((3-(trifluoromethyl)phenyl)-sulfonyl)-3,4-dihydro-2H-benzo[b][1,4]oxazin-2-yl)propanoic acid | 616 (M + H)+ |
| 89ES | 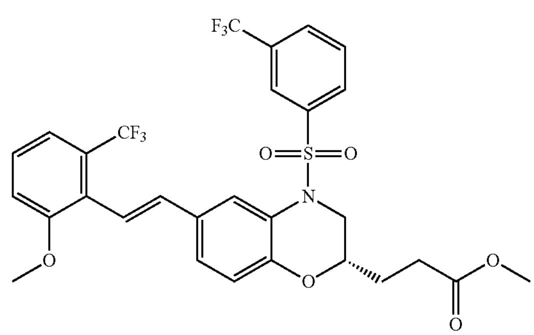 [SMILES: COC(=O)CC[C@H]1CN(S(=O)(=O)c2cccc(C(F)(F)F)c2)c2cc(/C=C/c3c(OC)cccc3C(F)(F)F)ccc2O1] | methyl (S,E)-3-(6-(2-methoxy-6-(trifluoromethyl)styryl)-4-((3-(trifluoromethyl)phenyl)-sulfonyl)-3,4-dihydro-2H-benzo[b][1,4]oxazin-2-yl)propanoate | 630 (M + H)+ |

TABLE 11-continued

| No. | Structure | Name | Observed m/z |
|---|---|---|---|
| 89ET | 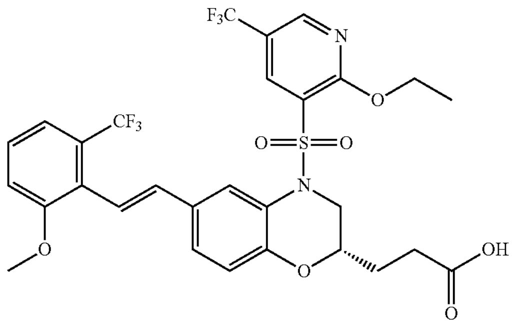 | (S,E)-3-(4-((2-ethoxy-5-(trifluoromethyl)pyridin-3-yl)sulfonyl)-6-(2-methoxy-6-(trifluoromethyl)styryl)-3,4-dihydro-2H-benzo[b][1,4]-oxazin-2-yl)propanoic acid | 661 (M + H)+ |
| 89EU | 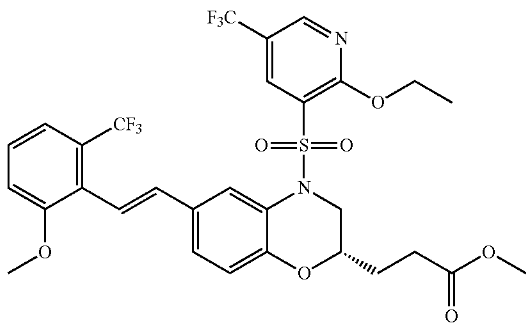 [SMILES: CCOc1ncc(C(F)(F)F)cc1S(=O)(=O)N1C[C@H](CCC(=O)OC)Oc2ccc(/C=C/c3c(OC)cccc3C(F)(F)F)cc21] | methyl (S,E)-3-(4-((2-ethoxy-5-(trifluoromethyl)pyridin-3-yl)sulfonyl)-6-(2-methoxy-6-(trifluoromethyl)styryl)-3,4-dihydro-2H-benzo[b][1,4]-oxazin-2-yl)propanoate | 675 (M + H)+ |
| 89EV | 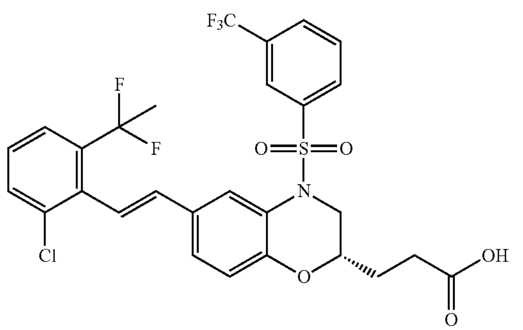 [SMILES: CC(F)(F)c1cccc(Cl)c1/C=C/c1ccc2c(c1)N(S(=O)(=O)c1cccc(C(F)(F)F)c1)C[C@H](CCC(=O)O)O2] | (S,E)-3-(6-(2-chloro-6-(1,1-difluoroethyl)styryl)-4-((3-(trifluoromethyl)phenyl)-sulfonyl)-3,4-dihydro-2H-benzo[b][1,4]oxazin-2-yl)propanoic acid | 616 (M + H)+ |
| 89EW | 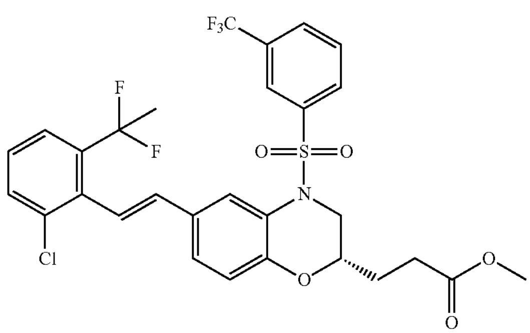 [SMILES: COC(=O)CC[C@H]1CN(S(=O)(=O)c2cccc(C(F)(F)F)c2)c2cc(/C=C/c3c(Cl)cccc3C(C)(F)F)ccc2O1] | methyl (S,E)-3-(6-(2-chloro-6-(1,1-difluoroethyl)styryl)-4-((3-(trifluoromethyl)phenyl)-sulfonyl)-3,4-dihydro-2H-benzo[b][1,4]oxazin-2-yl)propanoate | 630 (M + H)+ |
| 89EX | 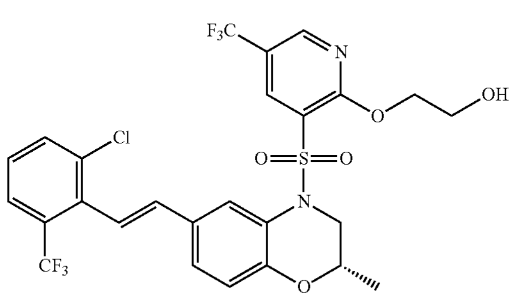 [SMILES: C[C@H]1CN(S(=O)(=O)c2cc(C(F)(F)F)cnc2OCCO)c2cc(/C=C/c3c(Cl)cccc3C(F)(F)F)ccc2O1] | (S,E)-2-((3-((6-(2-chloro-6-(trifluoromethyl)styryl)-2-methyl-2,3-dihydro-4H-benzo[b][1,4]oxazin-4-yl)sulfonyl)-5-(trifluoromethyl)-pyridin-2-yl)oxy)ethan-1-ol | 623 (M + H)+ |

TABLE 11-continued

| No. | Structure | Name | Observed m/z |
|---|---|---|---|
| 89EY | 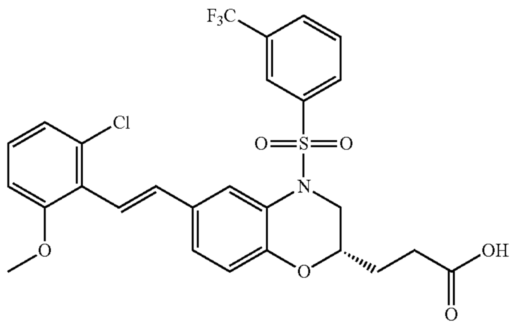 | (S,E)-3-(6-(2-chloro-6-methoxystyryl)-4-((3-(trifluoromethyl)phenyl)-sulfonyl)-3,4-dihydro-2H-benzo[b][1,4]oxazin-2-yl)propanoic acid | 582 (M + H)+ |
| 89EZ | 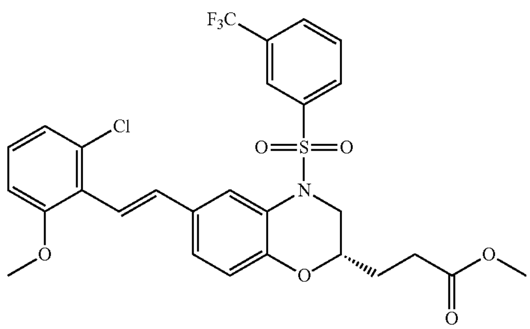 [SMILES: COC(=O)CC[C@H]1CN(S(=O)(=O)c2cccc(C(F)(F)F)c2)c2cc(/C=C/c3c(Cl)cccc3OC)ccc2O1] | methyl (S,E)-3-(6-(2-chloro-6-methoxystyryl)-4-((3-(trifluoromethyl)phenyl)-sulfonyl)-3,4-dihydro-2H-benzo[b][1,4]oxazin-2-yl)propanoate | 596 (M + H)+ |
| 89FA | 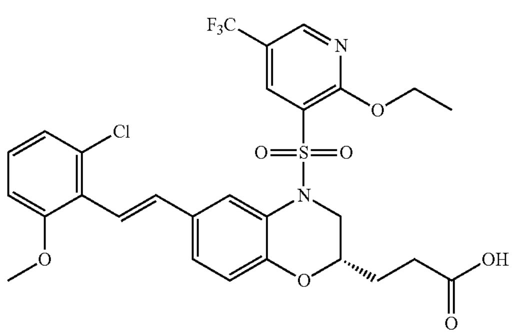 [SMILES: CCOc1ncc(C(F)(F)F)cc1S(=O)(=O)N1C[C@H](CCC(=O)O)Oc2ccc(/C=C/c3c(Cl)cccc3OC)cc21] | (S,E)-3-(6-(2-chloro-6-methoxystyryl)-4-((2-ethoxy-5-(trifluoromethyl)pyridin-3-yl)sulfonyl)-3,4-dihydro-2H-benzo[b][1,4]oxazin-2-yl)propanoic acid | 627 (M + H)+ |
| 89FB | 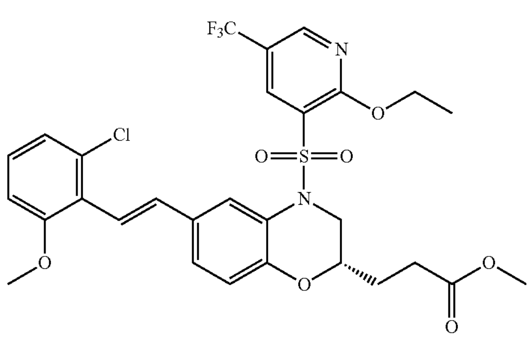 [SMILES: CCOc1ncc(C(F)(F)F)cc1S(=O)(=O)N1C[C@H](CCC(=O)OC)Oc2ccc(/C=C/c3c(Cl)cccc3OC)cc21] | methyl (S,E)-3-(6-(2-chloro-6-methoxystyryl)-4-((2-ethoxy-5-(trifluoromethyl)pyridin-3-yl)sulfonyl)-3,4-dihydro-2H-benzo[b][1,4]oxazin-2-yl)propanoate | 641 (M + H)+ |

TABLE 11-continued

| No. | Structure | Name | Observed m/z |
|---|---|---|---|
| 89FC | 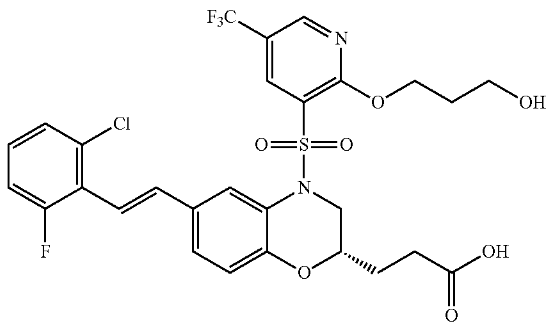 [SMILES: O=C(O)CC[C@H]1CN(S(=O)(=O)c2cc(C(F)(F)F)cnc2OCCCO)c2cc(/C=C/c3c(F)cccc3Cl)ccc2O1] | (S,E)-3-(6-(2-chloro-6-fluorostyryl)-4-((2-(3-hydroxypropoxy)-5-(trifluoromethyl)pyridin-3-yl)sulfonyl)-3,4-dihydro-2H-benzo[b][1,4]-oxazin-2-yl)propanoic acid | 645 (M + H)+ |
| 89FD | 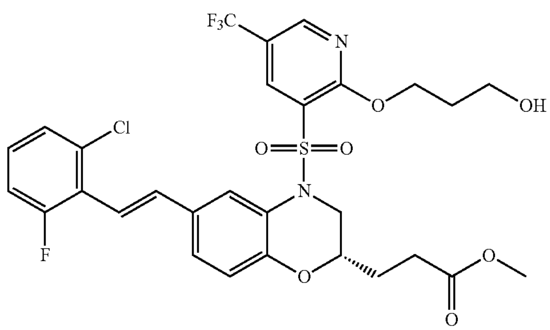 [SMILES: COC(=O)CC[C@H]1CN(S(=O)(=O)c2cc(C(F)(F)F)cnc2OCCCO)c2cc(/C=C/c3c(F)cccc3Cl)ccc2O1] | methyl (S,E)-3-(6-(2-chloro-6-fluorostyryl)-4-((2-(3-hydroxypropoxy)-5-(trifluoromethyl)pyridin-3-yl)sulfonyl)-3,4-dihydro-2H-benzo[b][1,4]-oxazin-2-yl)propanoate | 659 (M + H)+ |
| 89FE | 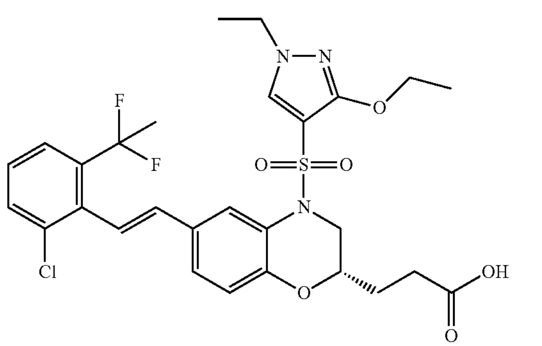 [SMILES: CCOc1nn(CC)cc1S(=O)(=O)N1C[C@H](CCC(=O)O)Oc2ccc(/C=C/c3c(Cl)cccc3C(C)(F)F)cc21] | (S,E)-3-(6-(2-chloro-6-(1,1-difluoroethyl)styryl)-4-((3-ethoxy-1-ethyl-1H-pyrazol-4-yl)sulfonyl)-3,4-dihydro-2H-benzo[b][1,4]oxazin-2-yl)propanoic acid | 610 (M + H)+ |
| 89FF | 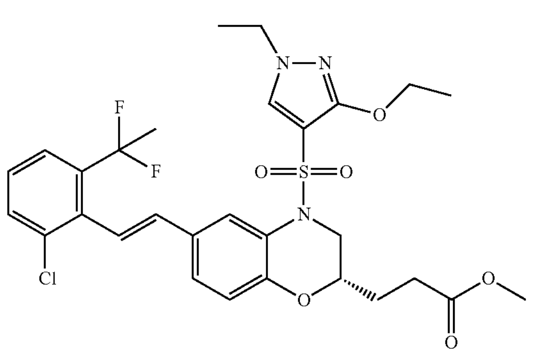 [SMILES: CCOc1nn(CC)cc1S(=O)(=O)N1C[C@H](CCC(=O)OC)Oc2ccc(/C=C/c3c(Cl)cccc3C(C)(F)F)cc21] | methyl (S,E)-3-(6-(2-chloro-6-(1,1-difluoroethyl)styryl)-4-((3-ethoxy-1-ethyl-1H-pyrazol-4-yl)sulfonyl)-3,4-dihydro-2H-benzo[b][1,4]oxazin-2-yl)propanoate | 624 (M + H)+ |

TABLE 11-continued

| No. | Structure | Name | Observed m/z |
|---|---|---|---|
| 89FG | 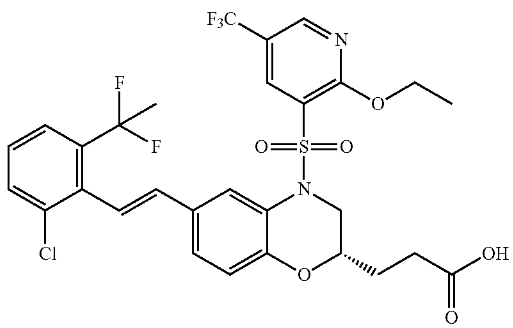 [SMILES: CCOc1ncc(C(F)(F)F)cc1S(=O)(=O)N1C[C@H](CCC(=O)O)Oc2ccc(/C=C/c3c(Cl)cccc3C(C)(F)F)cc21] | (S,E)-3-(6-(2-chloro-6-(1,1-difluoroethyl)styryl)-4-((2-ethoxy-5-(trifluoromethyl)-pyridin-3-yl)sulfonyl)-3,4-dihydro-2H-benzo[b][1,4]-oxazin-2-yl)propanoic acid | 661 (M + H)+ |
| 89FH | 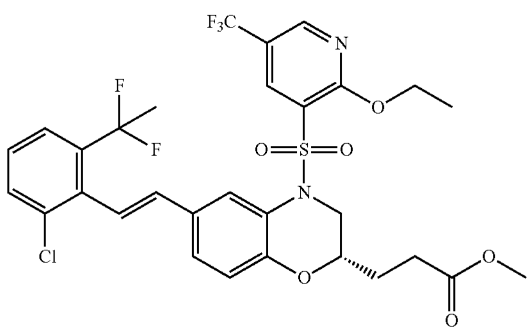 [SMILES: CCOc1ncc(C(F)(F)F)cc1S(=O)(=O)N1C[C@H](CCC(=O)OC)Oc2ccc(/C=C/c3c(Cl)cccc3C(C)(F)F)cc21] | methyl (S,E)-3-(6-(2-chloro-6-(1,1-difluoroethyl)styryl)-4-((2-ethoxy-5-(trifluoromethyl)-pyridin-3-yl)sulfonyl)-3,4-dihydro-2H-benzo[b][1,4]-oxazin-2-yl)propanoate | 675 (M + H)+ |
| 89FI | 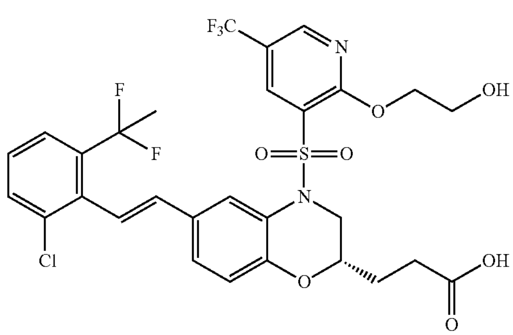 [SMILES: CC(F)(F)c1cccc(Cl)c1/C=C/c1ccc2c(c1)N(S(=O)(=O)c1cc(C(F)(F)F)cnc1OCCO)C[C@H](CCC(=O)O)O2] | (S,E)-3-(6-(2-chloro-6-(1,1-difluoroethyl)styryl)-4-((2-(2-hydroxyethoxy)-5-(trifluoromethyl)pyridin-3-yl)sulfonyl)-3,4-dihydro-2H-benzo[b][1,4]-oxazin-2-yl)propanoic acid | 677 (M + H)+ |
| 89FJ | 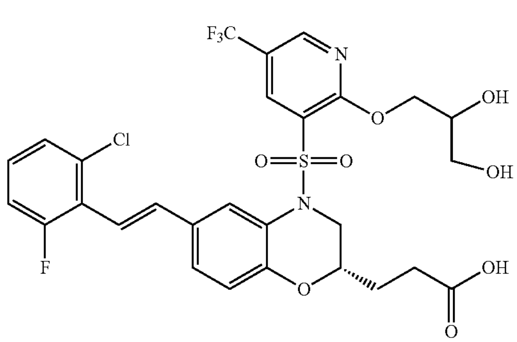 [SMILES: O=C(O)CC[C@H]1CN(S(=O)(=O)c2cc(C(F)(F)F)cnc2OCC(O)CO)c2cc(/C=C/c3c(F)cccc3Cl)ccc2O1] | 3-((2S)-6-((E)-2-chloro-6-fluorostyryl)-4-((2-(2,3-dihydroxypropoxy)-5-(trifluoromethyl)pyridin-3-yl)sulfonyl)-3,4-dihydro-2H-benzo[b][1,4]oxazin-2-yl)propanoic acid | 661 (M + H)+ |

TABLE 11-continued

| No. | Structure | Name | Observed m/z |
|---|---|---|---|
| 89FK | 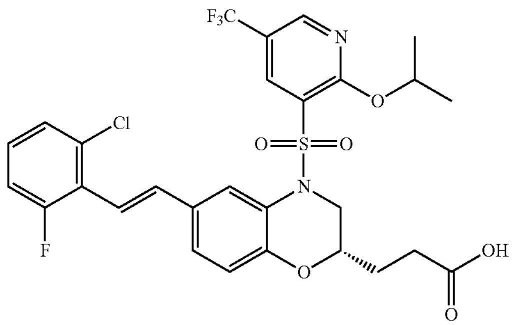 [SMILES: CC(C)Oc1ncc(C(F)(F)F)cc1S(=O)(=O)N1C[C@H](CCC(=O)O)Oc2ccc(/C=C/c3c(F)cccc3Cl)cc21] | (S,E)-3-(6-(2-chloro-6-fluorostyryl)-4-((2-isopropoxy-5-(trifluoromethyl)pyridin-3-yl)sulfonyl)-3,4-dihydro-2H-benzo[b][1,4]oxazin-2-yl)propanoic acid | 629 (M + H)+ |
| 89FL | 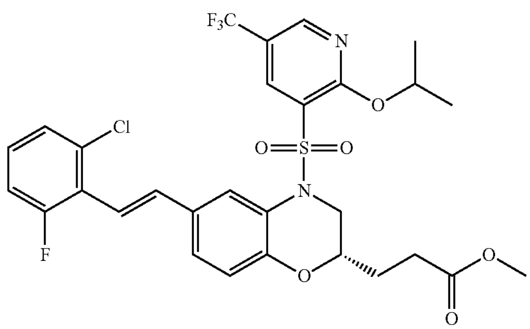 [SMILES: COC(=O)CC[C@H]1CN(S(=O)(=O)c2cc(C(F)(F)F)cnc2OC(C)C)c2cc(/C=C/c3c(F)cccc3Cl)ccc2O1] | methyl (S,E)-3-(6-(2-chloro-6-fluorostyryl)-4-((2-isopropoxy-5-(trifluoromethyl)pyridin-3-yl)sulfonyl)-3,4-dihydro-2H-benzo[b][1,4]oxazin-2-yl)propanoate | 643 (M + H)+ |
| 89FM | 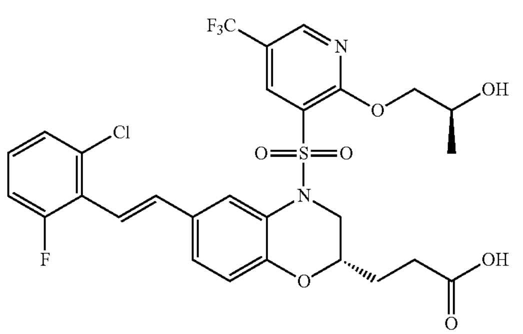 [SMILES: C[C@H](O)COc1ncc(C(F)(F)F)cc1S(=O)(=O)N1C[C@H](CCC(=O)O)Oc2ccc(/C=C/c3c(F)cccc3Cl)cc21] | 3-((S)-6-((E)-2-chloro-6-fluorostyryl)-4-((2-((S)-2-hydroxypropoxy)-5-(trifluoromethyl)pyridin-3-yl)sulfonyl)-3,4-dihydro-2H-benzo[b][1,4]oxazin-2-yl)propanoic acid | 645 (M + H)+ |
| 89FN | 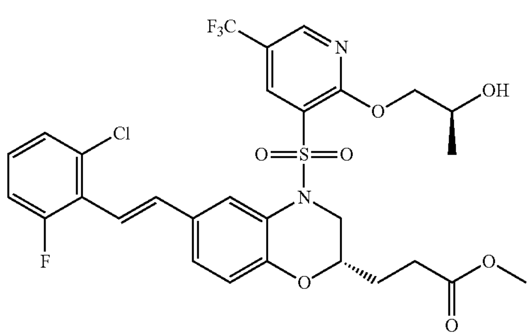 [SMILES: COC(=O)CC[C@H]1CN(S(=O)(=O)c2cc(C(F)(F)F)cnc2OC[C@H](C)O)c2cc(/C=C/c3c(F)cccc3Cl)ccc2O1] | methyl 3-((S)-6-((E)-2-chloro-6-fluorostyryl)-4-((2-((S)-2-hydroxypropoxy)-5-(trifluoromethyl)pyridin-3-yl)sulfonyl)-3,4-dihydro-2H-benzo[b][1,4]oxazin-2-yl)propanoate | 659 (M + H)+ |

TABLE 11-continued

| No. | Structure | Name | Observed m/z |
|---|---|---|---|
| 89FO | 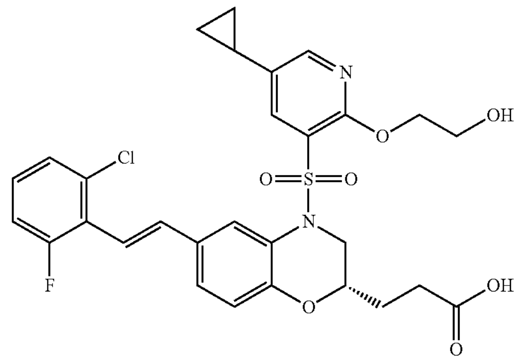 [SMILES: O=C(O)CC[C@H]1CN(S(=O)(=O)c2cc(C3CC3)cnc2OCCO)c2cc(/C=C/c3c(F)cccc3Cl)ccc2O1] | (S,E)-3-(6-(2-chloro-6-fluorostyryl)-4-((5-cyclopropyl-2-(2-hydroxyethoxy)pyridin-3-yl)sulfonyl)-3,4-dihydro-2H-benzo[b][1,4]oxazin-2-yl)propanoic acid | 603 (M + H)+ |
| 89FP | 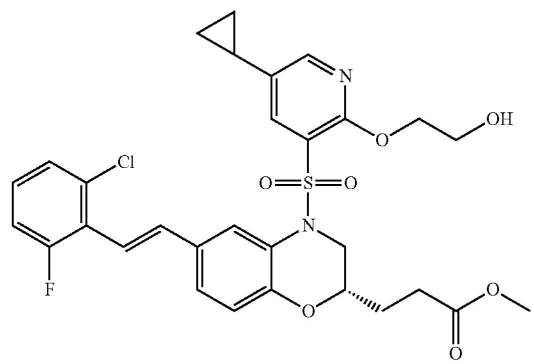 [SMILES: COC(=O)CC[C@H]1CN(S(=O)(=O)c2cc(C3CC3)cnc2OCCO)c2cc(/C=C/c3c(F)cccc3Cl)ccc2O1] | methyl (S,E)-3-(6-(2-chloro-6-fluorostyryl)-4-((5-cyclopropyl-2-(2-hydroxyethoxy)pyridin-3-yl)sulfonyl)-3,4-dihydro-2H-benzo[b][1,4]oxazin-2-yl)propanoate | 617 (M + H)+ |

Example 90—Synthesis of Methyl (S)-3-(6-(cyclohexylidenemethyl)-4-((3-(trifluoromethyl)phenyl)sulfonyl)-3,4-dihydro-2H-benzo[b][1,4]oxazin-2-yl)propanoate

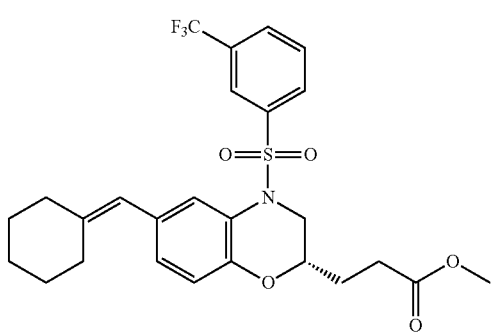 [SMILES: COC(=O)CC[C@H]1CN(S(=O)(=O)c2cccc(C(F)(F)F)c2)c2cc(C=C3CCCCC3)ccc2O1]

Part I—Synthesis of Cyclohexylidenemethyl trifluoromethanesulfonate

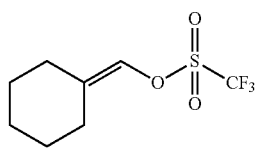 [SMILES: O=S(=O)(OC=C1CCCCC1)C(F)(F)F]

A solution of cyclohexanecarbaldehyde (500 mg, 4.46 mmol), triflic anhydride (1.51 g, 5.35 mmol), dichloromethane (20 mL), and 2,6-di-tert-butyl-4-methylpyridine (1.1 g, 5.36 mmol) was stirred for two hours at 60° C. The mixture was partitioned between petroleum ether and water. The organic layer was washed twice with 1 M HCl, three times with brine, dried (Na₂SO₄) and concentrated to afford cyclohexylidenemethyl trifluoromethanesulfonate (330 mg, 30%) as a yellow oil.

Part II—Synthesis of Methyl (S)-3-(6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)propanoate

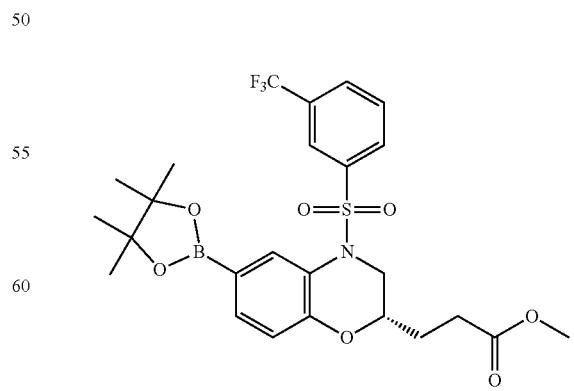

A mixture of (S)-methyl 3-(6-bromo-4-((3-(trifluoromethyl)phenyl)sulfonyl)-3,4-dihydro-2H-benzo[b][1,4]oxazin-2-yl)propanoate (1.00 g, 1.96 mmol), [1,1'-bis(diphenyl-phosphino)ferrocene]dichloropalladium(II) (143 mg, 0.20 mmol), potassium acetate (770.4 mg, 7.85 mmol), 4,4,5,5-tetramethyl-2-(tetramethyl-1,3,2-dioxaborolan-2-yl)-1,3,2-dioxaborolane (998 mg, 3.93 mmol), and ethylene glycol dimethyl ether (50 mL) was stirred for three hours at 80° C. The mixture was concentrated and the resulting residue was purified via MPLC eluting with a gradient of 15-50% ethyl acetate in hexane to afford methyl (S)-3-(6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)propanoate (1.07 g, 98%) as a light yellow oil.

Part III—Synthesis of Methyl (S)-3-(6-(cyclohexylidenemethyl)-4-((3-(trifluoromethyl)phenyl)sulfonyl)-3,4-dihydro-2H-benzo[b][1,4]oxazin-2-yl)propanoate

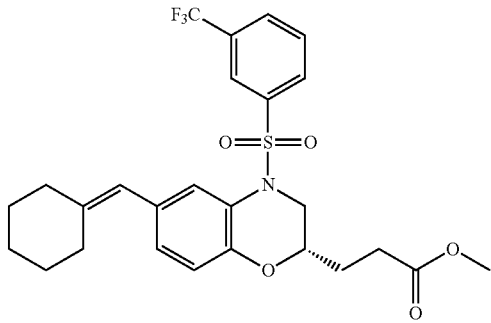 [SMILES: COC(=O)CC[C@H]1CN(S(=O)(=O)c2cccc(C(F)(F)F)c2)c2cc(C=C3CCCCC3)ccc2O1]

A mixture of cyclohexylidenemethyl trifluoromethanesulfonate (330 mg, 1.35 mmol), tetrakis(triphenylphosphine)-palladium(0) (52 mg, 0.04 mmol), potassium phosphate (573 mg, 2.70 mmol), methyl (S)-3-(6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)propanoate (500 mg, 0.90 mmol), toluene (4 mL), ethanol (1 mL), and water (1 mL) was stirred for two hours at 90° C. The mixture was cooled, concentrated, and the resulting residue was purified via MPLC eluting with 16% ethyl acetate in petroleum to afford methyl (S)-3-(6-(cyclohexylidenemethyl)-4-((3-(trifluoromethyl)phenyl)sulfonyl)-3,4-dihydro-2H-benzo[b][1,4]oxazin-2-yl)propanoate (200 mg, 28%) as a yellow oil. $^1$H-NMR (300 MHz, CD$_3$OD) δ 7.95-7.98 (m, 2H), 7.87 (s, 1H), 7.78 (t, 1H), 7.61 (s, 1H), 6.91 (d, 1H), 6.74 (d, 1H), 6.18 (s, 1H), 4.39 (dd, 1H), 3.67 (s, 3H), 3.41 (s, 1H), 3.24 (dd, 1H), 2.36-2.48 (m, 4H), 2.27-2.30 (m, 2H), 1.90 (m, 1H), 1.77 (m, 1H), 1.55-1.69 (m, 6H). (ES, m/z): (M+H)$^+$524.

Example 91—Synthesis of (S)-3-(6-(Cyclohexylidenemethyl)-4-((3-(trifluoromethyl)phenyl)sulfonyl)-3,4-dihydro-2H-benzo[b][1,4]oxazin-2-yl)propanoic acid

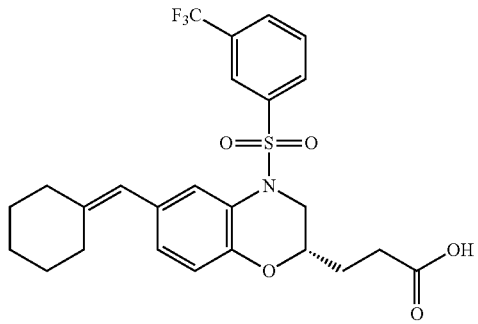 [SMILES: O=C(O)CC[C@H]1CN(S(=O)(=O)c2cccc(C(F)(F)F)c2)c2cc(C=C3CCCCC3)ccc2O1]

A mixture of methyl (S)-3-(6-(cyclohexylidenemethyl)-4-((3-(trifluoromethyl)phenyl)sulfonyl)-3,4-dihydro-2H-benzo[b][1,4]oxazin-2-yl)propanoate (180 mg, 0.34 mmol), tetrahydrofuran (3 mL), water (1 mL), lithium hydroxide (41 mg, 0.98 mmol) was stirred for two hours at room temperature. The pH value of the mixture was adjusted to 5 with 1M hydrogen chloride and then partitioned between ethyl acetate and water. The organic layer was dried (Na$_2$SO$_4$) and concentrated. The resulting residue was purified by Prep-HPLC eluting with a gradient of 70-95% acetonitrile in water with 0.05% trifluoroacetic acid to afford (S)-3-(6-(cyclohexylidenemethyl)-4-((3-(trifluoromethyl)phenyl)sulfonyl)-3,4-dihydro-2H-benzo[b][1,4]oxazin-2-yl)propanoic acid (75.8 mg, 43%) as a white solid. $^1$H-NMR (300 MHz, CD$_3$OD) δ 8.00-7.96 (t, J=8 Hz, 2H), 7.83 (s, 1H), 7.80-7.76 (t, J=8 Hz, 1H), 7.62 (s, 1H), 6.93-6.91 (dd, J=4 Hz, 8 Hz, 1H), 6.78-6.76 (d, J=8 Hz, 1H), 6.19 (s, 1H), 4.44-4.39 (dd, J=4 Hz, 12 Hz, 1H), 3.40-3.34 (m, 1H), 3.27-3.21 (m, 1H), 2.46-2.36 (m, 4H), 2.32-2.29 (m, 2H), 1.91-1.73 (m, 2H), 1.72-1.60 (m, 6H). (ES, m/z): (M+H)$^+$510.

Example 92—Synthesis of (S)-3-(6-(Cyclopentylidenemethyl)-4-((3-(trifluoromethyl)phenyl)sulfonyl)-3,4-dihydro-2H-benzo[b][1,4]oxazin-2-yl)propanoic acid

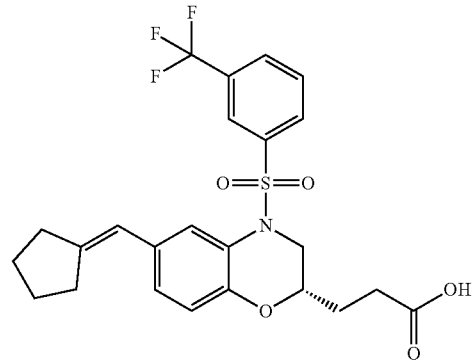 [SMILES: O=C(O)CC[C@H]1CN(S(=O)(=O)c2cccc(C(F)(F)F)c2)c2cc(C=C3CCCC3)ccc2O1]

Based on the procedure in Example 90 and 91, (S)-3-(6-(cyclopentylidenemethyl)-4-((3-(trifluoromethyl)phenyl)sulfonyl)-3,4-dihydro-2H-benzo[b][1,4]oxazin-2-yl)propanoic acid was prepared. $^1$H-NMR (300 MHz, CD$_3$OD) δ 7.98-7.94 (m, 2H), 7.86 (s, 1H), 7.78-7.74 (m, 2H), 7.00 (m, 1H), 6.75 (m, 1H), 6.29 (m, 1H), 4.39 (dd, J=14.4 Hz, 2.0 Hz, 1H), 3.38 (m, 1H), 3.29 (dd, J=14.4 Hz, 2.0 Hz, 1H), 2.51 (m, 4H), 2.40 (m, 2H), 1.87-1.66 (m, 6H). (ES, m/z): (M+H)$^+$496.

Example 93—Synthesis of (S)-3-(6-(Cyclohexylmethyl)-4-((3-(trifluoromethyl)phenyl)sulfonyl)-3,4-dihydro-2H-benzo[b][1,4]oxazin-2-yl)propanoic acid

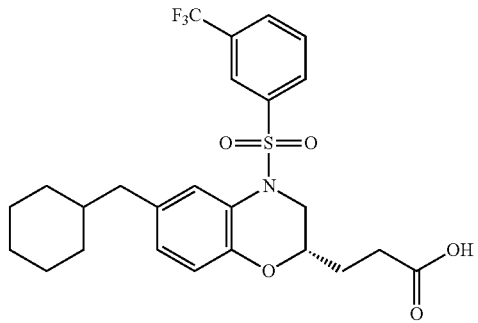 [SMILES: O=C(O)CC[C@H]1CN(S(=O)(=O)c2cccc(C(F)(F)F)c2)c2cc(CC3CCCCC3)ccc2O1]

Part I—Synthesis of Methyl (S)-3-(6-(cyclohexylmethyl)-3,4-dihydro-2H-benzo[b][1,4]-oxazin-2-yl)propanoate

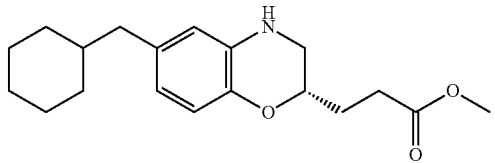 [SMILES: COC(=O)CC[C@H]1CNc2cc(CC3CCCCC3)ccc2O1]

A mixture of methyl (S)-3-(6-(cyclohexylidenemethyl)-3,4-dihydro-2H-benzo[b][1,4]oxazin-2-yl)propanoate (500 mg, 1.59 mmol), 10% palladium on carbon (500 mg), and ethyl acetate (15 mL) was stirred overnight at room temperature under an atmosphere of hydrogen. The mixture was filtered through Celite and the filtrate was concentrated. The resulting residue was purified via MPLC eluting with 16% ethyl acetate in petroleum ether to afford methyl (S)-3-(6-(cyclohexylmethyl)-3,4-dihydro-2H-benzo[b][1,4]-oxazin-2-yl)propanoate (300 mg, 60%) as a clear oil.

Part II—Synthesis of Methyl (S)-3-(6-(cyclohexylmethyl)-4-((3-(trifluoromethyl)phenyl)sulfonyl)-3,4-dihydro-2H-benzo[b][1,4]oxazin-2-yl)propanoate

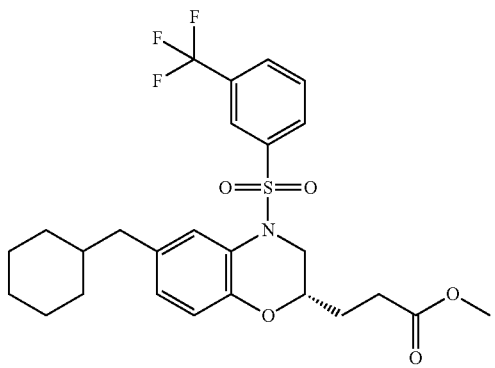 [SMILES: COC(=O)CC[C@H]1CN(S(=O)(=O)c2cccc(C(F)(F)F)c2)c2cc(CC3CCCCC3)ccc2O1]

A mixture of methyl (S)-3-(6-(cyclohexylmethyl)-3,4-dihydro-2H-benzo[b][1,4]-oxazin-2-yl)propanoate (270 mg, 0.85 mmol), dichloromethane (10 mL), 3-(trifluoromethyl)benzene-1-sulfonyl chloride (415.6 mg, 1.70 mmol), 4-dimethylaminopyridine (52 mg, 0.43 mmol) and pyridine (0.3 mL) was stirred overnight at room temperature. The mixture was concentrated and the resulting residue was purified via MPLC eluting with 16% ethyl acetate in petroleum ether to afford methyl (S)-3-(6-(cyclohexylmethyl)-4-((3-(trifluoromethyl)phenyl)sulfonyl)-3,4-dihydro-2H-benzo[b][1,4]oxazin-2-yl)propanoate (420 mg, 94%) as an oil.

Part III—Synthesis of (S)-3-(6-(Cyclohexylmethyl)-4-((3-(trifluoromethyl)phenyl)sulfonyl)-3,4-dihydro-2H-benzo[b][1,4]oxazin-2-yl)propanoic acid

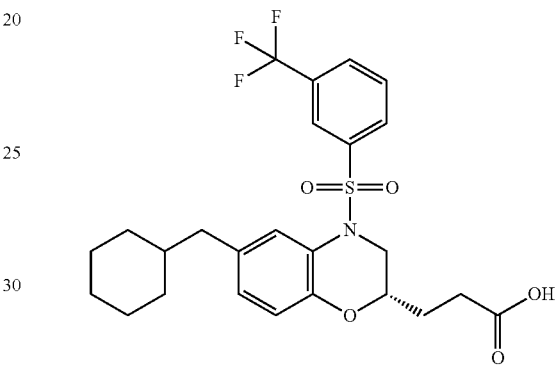

Based on the procedure in Example 42, (S)-3-(6-(cyclohexylmethyl)-4-((3-(trifluoromethyl)phenyl)sulfonyl)-3,4-dihydro-2H-benzo[b][1,4]oxazin-2-yl)propanoic acid was prepared. $^1$H-NMR (300 MHz, CDCl$_3$) δ 0.95-1.07 (m, 2H), 1.12-1.32 (m, 3H), 1.52 (m, 1H), 1.62-1.82 (m, 6H), 1.89 (m, 1H), 2.31-2.51 (m, 4H), 3.21 (m, 1H), 3.39 (m, 1H), 4.41 (d, J=14.4 Hz, 1H), 6.73 (m, 1H), 6.90 (m, 1H), 7.58 (s, 1H), 7.78 (m, 2H), 7.97 (m, 2H). (ES, m/z): (M+H)$^+$512.

Example 94—Synthesis of (S)-3-(6-(Cyclohexylidenemethyl)-4-((3-(trifluoromethyl)phenyl)sulfonyl)-3,4-dihydro-2H-benzo[b][1,4]oxazin-2-yl)propanoic acid

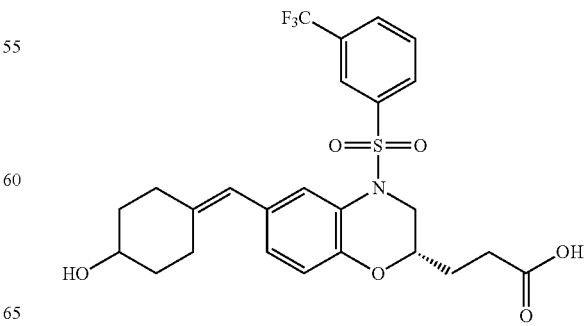

Part I—Synthesis of 8-(bromomethylene)-1,4-dioxaspiro[4.5]decane

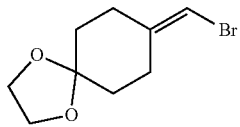 [SMILES: BrC=C1CCC2(CC1)OCCO2]

A 1 M solution of lithium hexamethyldisilazide (17 mL, 0.017 mol) in THF was added dropwise to a stirred solution of (bromomethyl)triphenyl-2⁵-phosphane (5.9 g, 0.017 mol) in THF (20 mL) at −78° C. The reaction mixture was warmed to room temperature and stirred for one hour. 1,4-Dioxaspiro[4.5]decan-8-one (2 g, 0.013 mol) was added dropwise and the reaction stirred overnight at room temperature. The mixture was partitioned between saturated ammonium chloride and dichloromethane. The organic layer was dried ($Na_2SO_4$) and concentrated. The resulting residue was purified by MPLC eluting with 3% ethyl acetate in petroleum ether to afford 8-(bromomethylene)-1,4-dioxaspiro[4.5]decane (2.0 g, 67%) as a colorless liquid.

Part II—Synthesis of Methyl (S)-3-(6-((1,4-dioxaspiro[4.5]decan-8-ylidene)methyl)-3,4-dihydro-2H-benzo[b][1,4]oxazin-2-yl)propanoate

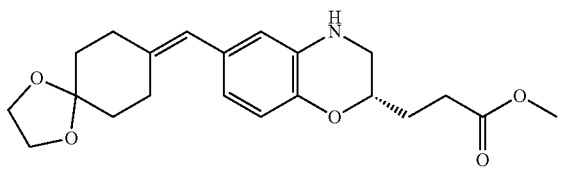 [SMILES: COC(=O)CC[C@H]1CNc2cc(C=C3CCC4(CC3)OCCO4)ccc2O1]

A mixture of 8-(bromomethylene)-1,4-dioxaspiro[4.5]decane (1 g, 2.88 mmol), 8-(bromomethylidene)-1,4-dioxaspiro[4.5]decane (700 mg, 3.74 mmol), cesium carbonate (2.6 g, 11.52 mmol), [1,1′-bis(diphenyl-phosphino)ferrocene]dichloropalladium(II) (0.15 g, 0.288 mmol), THF (10 mL), and water (10 mL) was stirred overnight at 90° C. The mixture was diluted with water and extracted twice with ethyl acetate. The combined organic layers were dried ($Na_2SO_4$) and concentrated. The resulting residue was purified via MPLC eluting with 66% ethyl acetate in petroleum ether to afford methyl (S)-3-(6-((1,4-dioxaspiro[4.5]decan-8-ylidene)methyl)-3,4-dihydro-2H-benzo[b][1,4]oxazin-2-yl)propanoate (500 mg, 46%) as a colorless oil.

Part III—Synthesis of Methyl (S)-3-(6-((4-oxocyclohexylidene)methyl)-3,4-dihydro-2H-benzo[b][1,4]oxazin-2-yl)propanoate

A solution of (S)-3-(6-((1,4-dioxaspiro[4.5]decan-8-ylidene)methyl)-3,4-dihydro-2H-benzo[b][1,4]oxazin-2-yl)propanoate (500 mg, 1.34 mmol) in acetone (20 mL) and 10% HCl in water was stirred for four hours at room temperature. The reaction mixture was diluted with water and extracted twice with ethyl acetate. The combined organic layers were dried ($Na_2SO_4$) and concentrated to afford methyl (S)-3-(6-((4-oxocyclohexylidene)methyl)-3,4-dihydro-2H-benzo[b][1,4]oxazin-2-yl)propanoate (350 mg, 79%) as a colorless oil.

Part IV—Synthesis of Methyl 3-((2S)-6-((4-hydroxycyclohexylidene)methyl)-3,4-dihydro-2H-benzo[b][1,4]oxazin-2-yl)propanoate

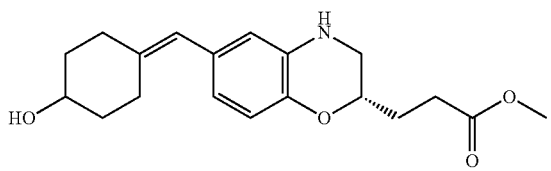 [SMILES: COC(=O)CC[C@H]1CNc2cc(C=C3CCC(O)CC3)ccc2O1]

Sodium borohydride (173 mg, 4.70 mmol) was added to a solution of methyl (S)-3-(6-((4-oxocyclohexylidene)methyl)-3,4-dihydro-2H-benzo[b][1,4]oxazin-2-yl)propanoate (300 mg, 0.91 mmol) in methanol (10 mL). The mixture was stirred for two hours at room temperature. The mixture was diluted with water and extracted twice with ethyl acetate. The combined organic layers were dried ($Na_2SO_4$) and concentrated. The resulting residue was purified by MPLC eluting with ethyl acetate to afford methyl 3-((2S)-6-((4-hydroxycyclohexylidene)methyl)-3,4-dihydro-2H-benzo[b][1,4]oxazin-2-yl)propanoate (220 mg, 73%) as a colorless oil.

Part V—Synthesis of Methyl (S)-3-(6-(cyclohexylidenemethyl)-4-((3-(trifluoromethyl)phenyl)sulfonyl)-3,4-dihydro-2H-benzo[b][1,4]oxazin-2-yl)propanoate

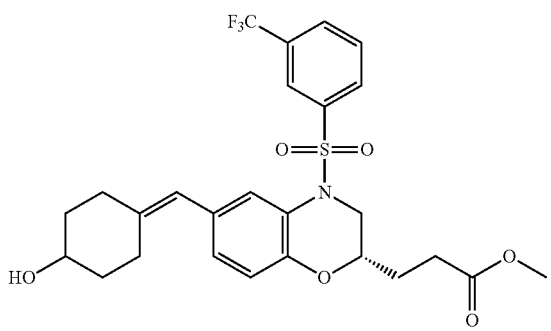 [SMILES: COC(=O)CC[C@H]1CN(S(=O)(=O)c2cccc(C(F)(F)F)c2)c2cc(C=C3CCC(O)CC3)ccc2O1]

A solution of methyl 3-((2S)-6-((4-hydroxycyclohexylidene)methyl)-3,4-dihydro-2H-benzo[b][1,4]oxazin-2-yl)propanoate (100 mg, 0.30 mmol), dichloromethane (5 mL), pyridine (119 mg, 1.50 mmol), 3-(trifluoromethyl)benzene-1-sulfonyl chloride (110 mg, 0.45 mmol), and 4-dimethylaminopyridine (18 mg, 0.15 mmol) was stirred overnight at room temperature. The solution was diluted dichloromethane and washed twice with 1 M HCl, washed with water, dried ($Na_2SO_4$), and concentrated. The resulting residue was purified by MPLC eluting with 33% ethyl acetate in petroleum ether to afford methyl (S)-3-(6-(cyclohexylidenemethyl)-4-((3-(trifluoromethyl)phenyl)sulfonyl)-3,4-dihydro-2H-benzo[b][1,4]oxazin-2-yl)propanoate (100 mg, 61%) as a colorless oil.

Part VI—Synthesis of (S)-3-(6-(Cyclohexylidenemethyl)-4-((3-(trifluoromethyl)phenyl)sulfonyl)-3,4-dihydro-2H-benzo[b][1,4]oxazin-2-yl)propanoic acid

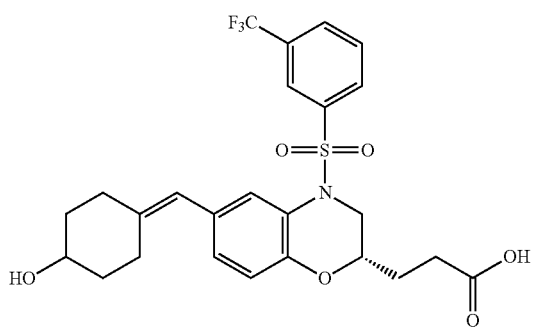 [SMILES: O=C(O)CC[C@H]1CN(S(=O)(=O)c2cccc(C(F)(F)F)c2)c2cc(C=C3CCC(O)CC3)ccc2O1]

Based on the procedure in Example 42, (S)-3-(6-(cyclohexylidenemethyl)-4-((3-(trifluoromethyl)phenyl)sulfonyl)-3,4-dihydro-2H-benzo[b][1,4]oxazin-2-yl)propanoic acid was prepared. $^1$H-NMR (300 MHz, CD$_3$OD) δ 7.97 (m, 2H), 7.81-7.75 (m, 2H), 7.64-7.62 (m, 1H), 6.93 (d, J=11.6 Hz, 1H), 6.76 (d, J=11.2 Hz, 1H), 4.40 (dd, J=2.8 Hz, 19.2 Hz, 1H), 3.83 (m, 1H), 3.35 (m, 1H), 3.23 (m, 1H), 2.74 (m, 1H), 2.48-2.37 (m, 3H), 2.37-2.11 (m, 2H), 1.98-1.75 (m, 4H), 1.54-1.43 (m, 2H). (ES, m/z): (M+H)$^+$526.

Example 95—Preparation of Additional Substituted 6-Alkenyl-Benzoxazines

Compounds in Table 12 were prepared based on experimental procedures described in Examples 42, 90, 93, and 94 and the detailed description.

TABLE 12

| No. | Structure | Name | Observed m/z |
|---|---|---|---|
| 95A | 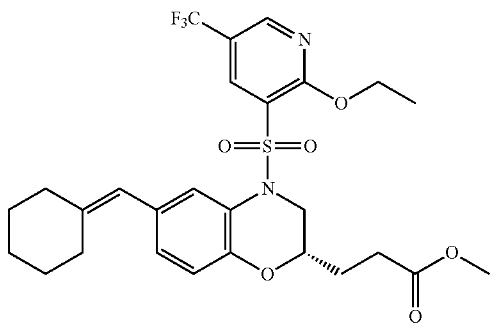 [SMILES: CCOc1ncc(C(F)(F)F)cc1S(=O)(=O)N1C[C@H](CCC(=O)OC)Oc2ccc(C=C3CCCCC3)cc21] | methyl (S)-3-(6-(cyclohexylidenemethyl)-4-((2-ethoxy-5-(trifluoromethyl)pyridin-3-yl)sulfonyl)-3,4-dihydro-2H-benzo[b][1,4]oxazin-2-yl)propanoate | 569 (M + H)$^+$ |
| 95B | 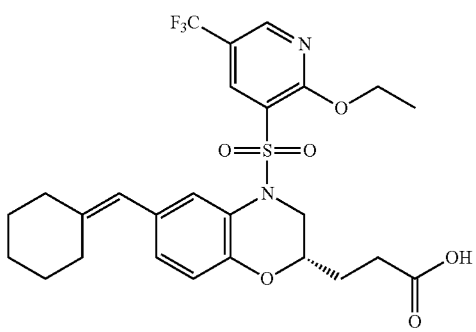 [SMILES: CCOc1ncc(C(F)(F)F)cc1S(=O)(=O)N1C[C@H](CCC(=O)O)Oc2ccc(C=C3CCCCC3)cc21] | (S)-3-(6-(cyclohexylidenemethyl)-4-((2-ethoxy-5-(trifluoromethyl)pyridin-3-yl)sulfonyl)-3,4-dihydro-2H-benzo[b][1,4]oxazin-2-yl)propanoic acid | 555 (M + H)$^+$ |
| 95C | 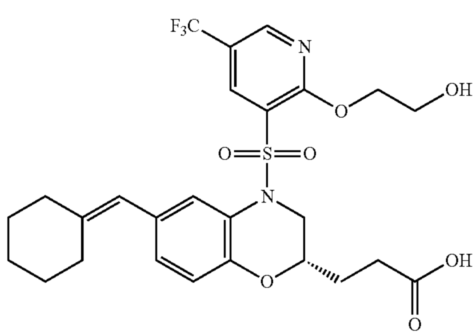 [SMILES: O=C(O)CC[C@H]1CN(S(=O)(=O)c2cc(C(F)(F)F)cnc2OCCO)c2cc(C=C3CCCCC3)ccc2O1] | (S)-3-(6-(cyclohexylidenemethyl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 571 (M + H)$^+$ |

TABLE 12-continued

| No. | Structure | Name | Observed m/z |
|---|---|---|---|
| 95D | 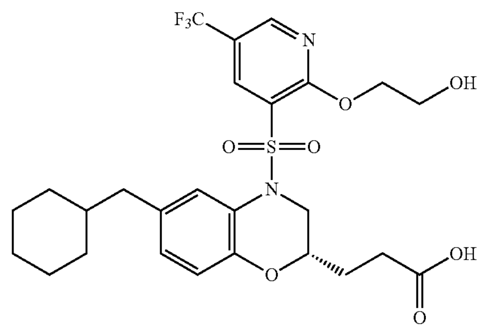 [SMILES: O=C(O)CC[C@H]1CN(S(=O)(=O)c2cc(C(F)(F)F)cnc2OCCO)c2cc(CC3CCCCC3)ccc2O1] | (S)-3-(6-(cyclohexylmethyl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 573 (M + H)+ |
| 95E | 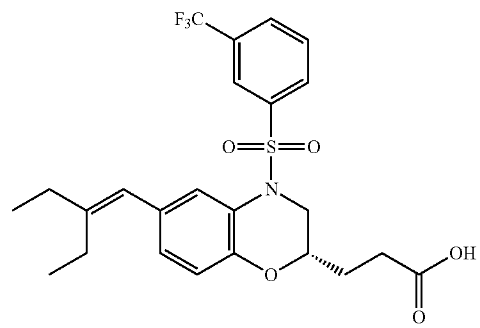 [SMILES: CCC(=Cc1ccc2c(c1)N(S(=O)(=O)c1cccc(C(F)(F)F)c1)C[C@H](CCC(=O)O)O2)CC] | (S)-3-(6-(2-ethylbut-1-en-1-yl)-4-((3-(trifluoromethyl)phenyl)-sulfonyl)-3,4-dihydro-2H-benzo[b][1,4]oxazin-2-yl)propanoic acid | 498 (M + H)+ |
| 95F | 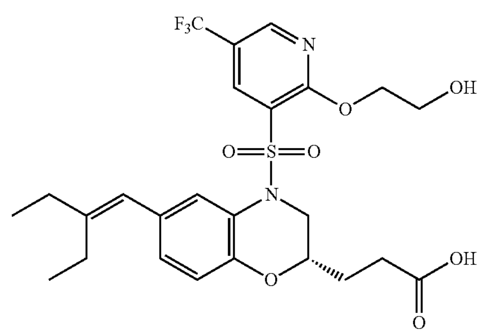 [SMILES: CCC(=Cc1ccc2c(c1)N(S(=O)(=O)c1cc(C(F)(F)F)cnc1OCCO)C[C@H](CCC(=O)O)O2)CC] | (S)-3-(6-(2-ethylbut-1-en-1-yl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 559 (M + H)+ |
| 95G | 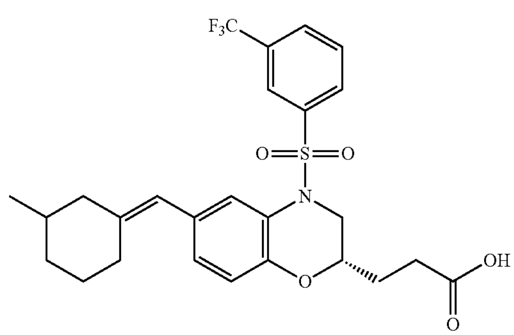 [SMILES: CC1CCC/C(=C\c2ccc3c(c2)N(S(=O)(=O)c2cccc(C(F)(F)F)c2)C[C@H](CCC(=O)O)O3)C1] | 3-((2S)-6-((E)-(3-methylcyclohexylidene)methyl)-4-((3-(trifluoromethyl)phenyl)sulfonyl)-3,4-dihydro-2H-benzo[b][1,4]-oxazin-2-yl)propanoic acid | 524 (M + H)+ |

TABLE 12-continued

| No. | Structure | Name | Observed m/z |
|---|---|---|---|
| 95H | 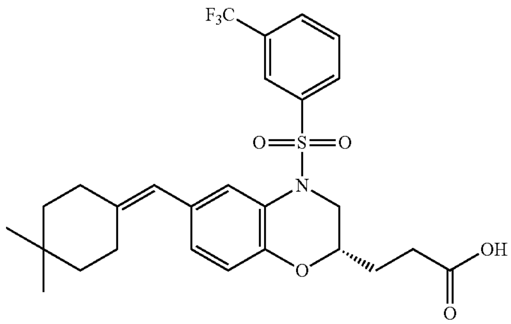 [SMILES: CC1(C)CCC(=Cc2ccc3c(c2)N(S(=O)(=O)c2cccc(C(F)(F)F)c2)C[C@H](CCC(=O)O)O3)CC1] | (S)-3-(6-((4,4-dimethylcyclohexylidene)methyl)-4-((3-(trifluoromethyl)phenyl)sulfonyl)-3,4-dihydro-2H-benzo[b][1,4]oxazin-2-yl)propanoic acid | 538 (M + H)+ |
| 95I | 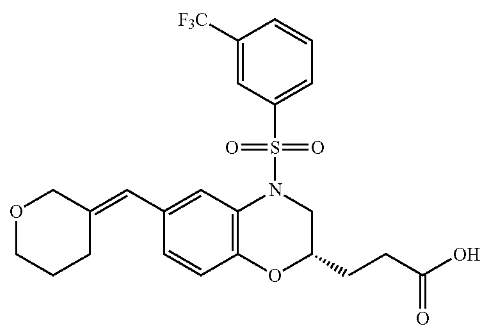 [SMILES: O=C(O)CC[C@H]1CN(S(=O)(=O)c2cccc(C(F)(F)F)c2)c2cc(/C=C3\CCCOC3)ccc2O1] | (S,E)-3-(6-((dihydro-2H-pyran-3(4H)-ylidene)methyl)-4-((3-(trifluoromethyl)phenyl)sulfonyl)-3,4-dihydro-2H-benzo[b][1,4]oxazin-2-yl)propanoic acid | 512 (M + H)+ |
| 95J | 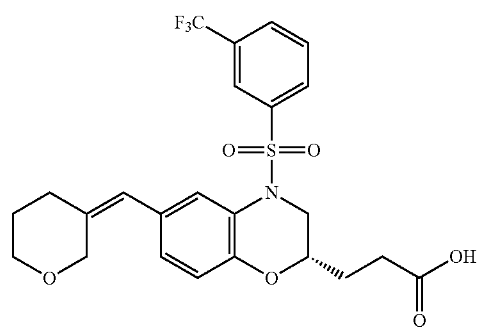 | (S,Z)-3-(6-((dihydro-2H-pyran-3(4H)-ylidene)methyl)-4-((3-(trifluoromethyl)phenyl)sulfonyl)-3,4-dihydro-2H-benzo[b][1,4]oxazin-2-yl)propanoic acid | 512 (M + H)+ |
| 95K | 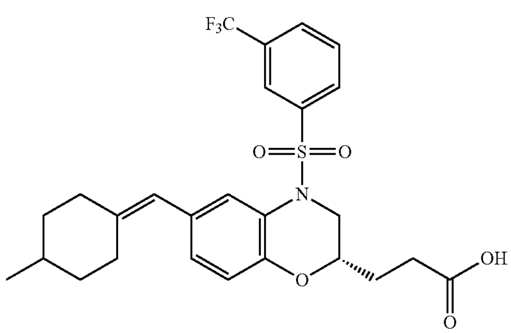 [SMILES: CC1CCC(=Cc2ccc3c(c2)N(S(=O)(=O)c2cccc(C(F)(F)F)c2)C[C@H](CCC(=O)O)O3)CC1] | 3-((2S)-6-((4-methylcyclohexylidene)methyl)-4-((3-(trifluoromethyl)phenyl)sulfonyl)-3,4-dihydro-2H-benzo[b][1,4]oxazin-2-yl)propanoic acid | 524 (M + H)+ |

TABLE 12-continued

| No. | Structure | Name | Observed m/z |
|---|---|---|---|
| 95L | 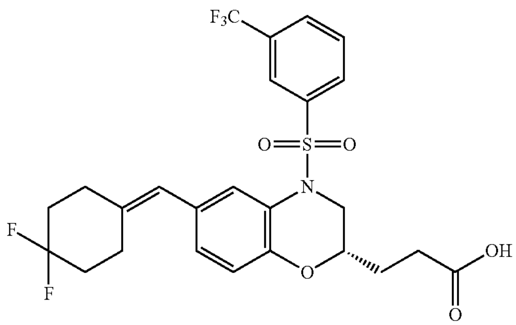 [SMILES: O=C(O)CC[C@H]1CN(S(=O)(=O)c2cccc(C(F)(F)F)c2)c2cc(C=C3CCC(F)(F)CC3)ccc2O1] | (S)-3-(6-((4,4-difluorocyclo-hexylidene)methyl)-4-((3-(trifluoromethyl)phenyl)sulfonyl)-3,4-dihydro-2H-benzo[b][1,4]oxazin-2-yl)propanoic acid | 546 (M + H)+ |
| 95M | 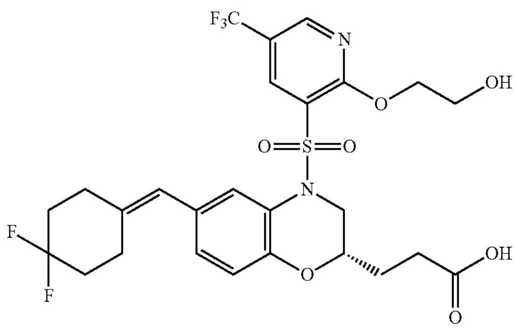 [SMILES: O=C(O)CC[C@H]1CN(S(=O)(=O)c2cc(C(F)(F)F)cnc2OCCO)c2cc(C=C3CCC(F)(F)CC3)ccc2O1] | (S)-3-(6-((4,4-difluorocyclohexylidene)methyl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 607 (M + H)+ |
| 95N | 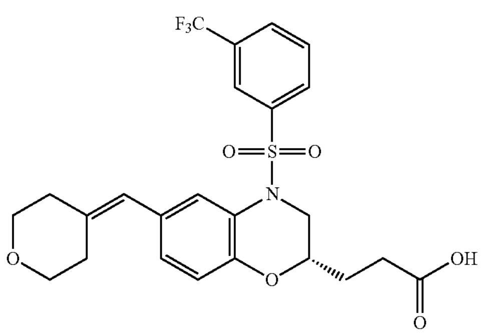 [SMILES: O=C(O)CC[C@H]1CN(S(=O)(=O)c2cccc(C(F)(F)F)c2)c2cc(C=C3CCOCC3)ccc2O1] | (S)-3-(6-((tetrahydro-4H-pyran-4-ylidene)methyl)-4-((3-(trifluoromethyl)phenyl)sulfonyl)-3,4-dihydro-2H-benzo[b][1,4]oxazin-2-yl)propanoic acid | 512 (M + H)+ |
| 95O | 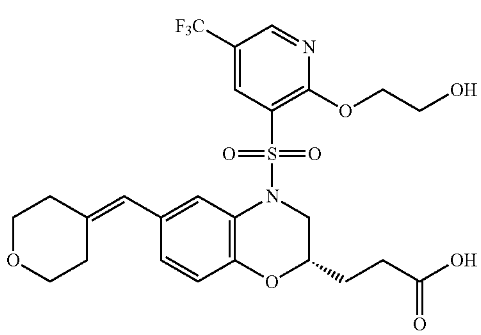 [SMILES: O=C(O)CC[C@H]1CN(S(=O)(=O)c2cc(C(F)(F)F)cnc2OCCO)c2cc(C=C3CCOCC3)ccc2O1] | (S)-3-(4-((2-(2-hydroxyethoxy)-5-(trifluoromethyl)pyridin-3-yl)sulfonyl)-6-((tetrahydro-4H-pyran-4-ylidene)methyl)-3,4-dihydro-2H-benzo[b][1,4]oxazin-2-yl)propanoic acid | 573 (M + H)+ |

TABLE 12-continued

| No. | Structure | Name | Observed m/z |
|---|---|---|---|
| 95P | 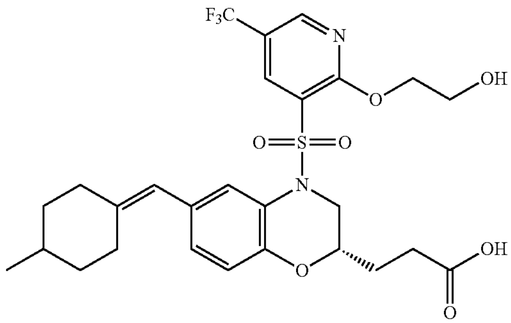 [SMILES: CC1CCC(=Cc2ccc3c(c2)N(S(=O)(=O)c2cc(C(F)(F)F)cnc2OCCO)C[C@H](CCC(=O)O)O3)CC1] | 3-((2S)-4-((2-(2-hydroxyethoxy)-5-(trifluoromethyl)pyridin-3-yl)sulfonyl)-6-((4-methylcyclohexylidene)methyl)-3,4-dihydro-2H-benzo[b][1,4]oxazin-2-yl)propanoic acid | 585 (M + H)+ |
| 95Q | 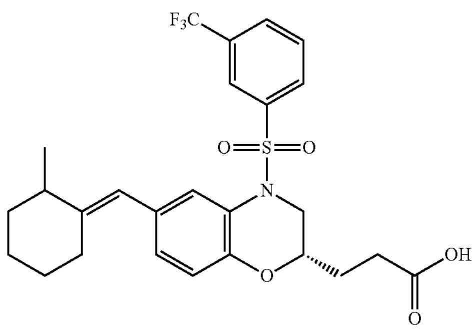 | 3-((2S)-6-((E)-(2-methylcyclohexylidene)methyl)-4-((3-(trifluoromethyl)phenyl)-sulfonyl)-3,4-dihydro-2H-benzo[b][1,4]oxazin-2-yl)propanoic acid | 524 (M + H)+ |
| 95R | 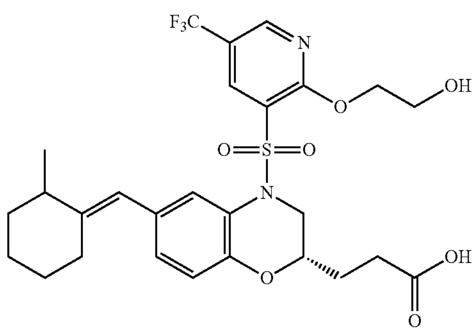 [SMILES: CC1CCCC/C1=C\c1ccc2c(c1)N(S(=O)(=O)c1cc(C(F)(F)F)cnc1OCCO)C[C@H](CCC(=O)O)O2] | 3-((2S)-4-((2-(2-hydroxyethoxy)-5-(trifluoromethyl)pyridin-3-yl)sulfonyl)-6-((E)-(2-methylcyclohexylidene)methyl)-3,4-dihydro-2H-benzo[b][1,4]oxazin-2-yl)propanoic acid | 585 (M + H)+ |
| 95S | 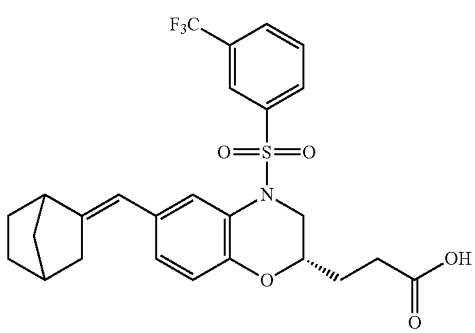 [SMILES: O=C(O)CC[C@H]1CN(S(=O)(=O)c2cccc(C(F)(F)F)c2)c2cc(/C=C3\CC4CCC3C4)ccc2O1] | 3-((2S)-6-((E)-bicyclo[2.2.1]heptan-2-ylidenemethyl)-4-((3-(trifluoromethyl)phenyl)sulfonyl)-3,4-dihydro-2H-benzo[b][1,4]oxazin-2-yl)propanoic acid | 522 (M + H)+ |

TABLE 12-continued

| No. | Structure | Name | Observed m/z |
|---|---|---|---|
| 95T | 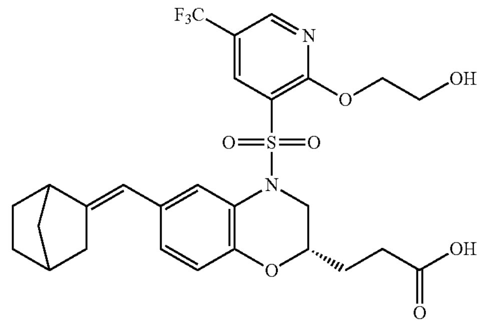 [SMILES: O=C(O)CC[C@H]1CN(S(=O)(=O)c2cc(C(F)(F)F)cnc2OCCO)c2cc(/C=C3\CC4CCC3C4)ccc2O1] | 3-((2S)-6-((E)-bicyclo[2.2.1]heptan-2-ylidenemethyl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 583 (M + H)+ |
| 95U | 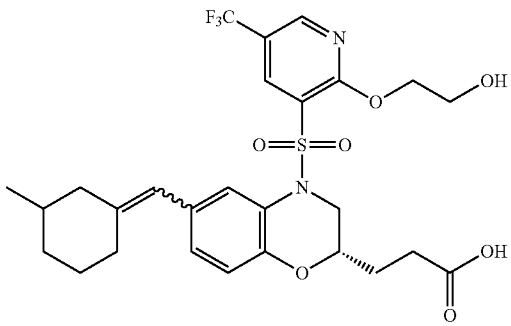 [SMILES: CC1CCCC(=Cc2ccc3c(c2)N(S(=O)(=O)c2cc(C(F)(F)F)cnc2OCCO)C[C@H](CCC(=O)O)O3)C1] | 3-((2S)-4-((2-(2-hydroxyethoxy)-5-(trifluoromethyl)pyridin-3-yl)sulfonyl)-6-((3-methylcyclohexylidene)methyl)-3,4-dihydro-2H-benzo[b][1,4]oxazin-2-yl)propanoic acid | 585 (M + H)+ |
| 95V | 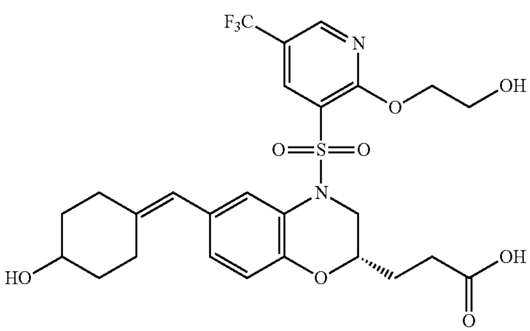 [SMILES: O=C(O)CC[C@H]1CN(S(=O)(=O)c2cc(C(F)(F)F)cnc2OCCO)c2cc(C=C3CCC(O)CC3)ccc2O1] | 3-((2S)-6-((4-hydroxycyclohexylidene)-methyl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 587 (M + H)+ |
| 95W | 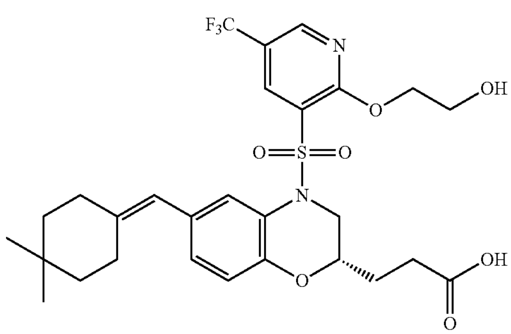 [SMILES: CC1(C)CCC(=Cc2ccc3c(c2)N(S(=O)(=O)c2cc(C(F)(F)F)cnc2OCCO)C[C@H](CCC(=O)O)O3)CC1] | (S)-3-(6-((4,4-dimethyl-cyclohexylidene)methyl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 599 (M + H)+ |

TABLE 12-continued

| No. | Structure | Name | Observed m/z |
|---|---|---|---|
| 95X | 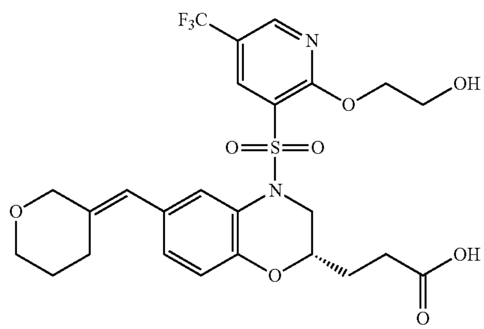 [SMILES: O=C(O)CC[C@H]1CN(S(=O)(=O)c2cc(C(F)(F)F)cnc2OCCO)c2cc(/C=C3\CCCOC3)ccc2O1] | (S,E)-3-(6-((dihydro-2H-pyran-3(4H)-ylidene)methyl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 573 (M + H)+ |
| 95Y | 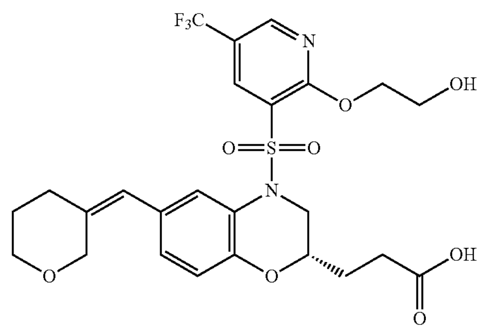 [SMILES: O=C(O)CC[C@H]1CN(S(=O)(=O)c2cc(C(F)(F)F)cnc2OCCO)c2cc(/C=C3/CCCOC3)ccc2O1] | (S,Z)-3-(6-((dihydro-2H-pyran-3(4H)-ylidene)methyl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 573 (M + H)+ |
| 95Z | 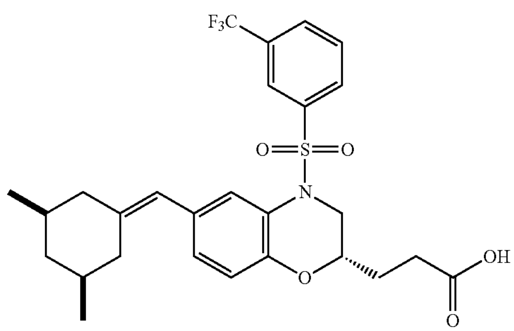 [SMILES: C[C@@H]1C/C(=C\c2ccc3c(c2)N(S(=O)(=O)c2cccc(C(F)(F)F)c2)C[C@H](CCC(=O)O)O3)C[C@H](C)C1] | 3-((S)-6-((E)-((3R,5S)-3,5-dimethylcyclohexylidene)-methyl)-4-((3-(trifluoromethyl)-phenyl)sulfonyl)-3,4-dihydro-2H-benzo[b][1,4]oxazin-2-yl)propanoic acid | 538 (M + H)+ |
| 95AA | 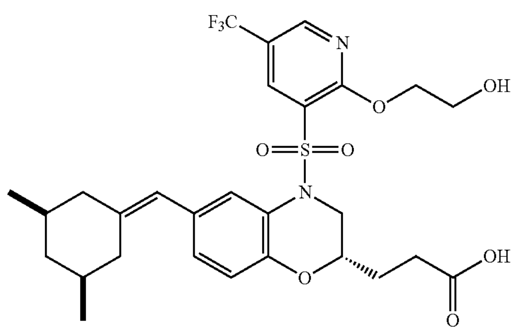 [SMILES: C[C@@H]1C/C(=C\c2ccc3c(c2)N(S(=O)(=O)c2cc(C(F)(F)F)cnc2OCCO)C[C@H](CCC(=O)O)O3)C[C@H](C)C1] | 3-((S)-6-((E)-((3R,5S)-3,5-dimethylcyclohexylidene)-methyl)-4-((2-(2-hydroxy-ethoxy)-5-(trifluoromethyl)-pyridin-3-yl)sulfonyl)-3,4-dihydro-2H-benzo[b][1,4]-oxazin-2-yl)propanoic acid | 599 (M + H)+ |

TABLE 12-continued

| No. | Structure | Name | Observed m/z |
|---|---|---|---|
| 95AB | 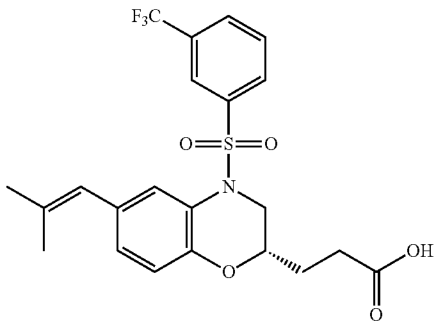 [SMILES: CC(C)=Cc1ccc2c(c1)N(S(=O)(=O)c1cccc(C(F)(F)F)c1)C[C@H](CCC(=O)O)O2] | (S)-3-(6-(2-methylprop-1-en-1-yl)-4-((3-(trifluoromethyl)-phenyl)sulfonyl)-3,4-dihydro-2H-benzo[b][1,4]oxazin-2-yl)propanoic acid | 470 (M + H)+ |
| 95AC | 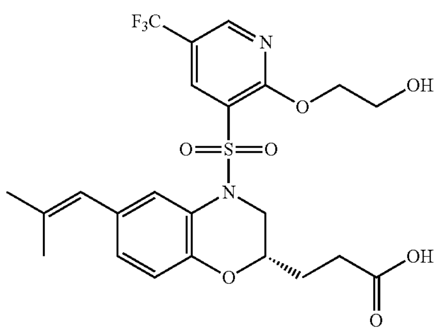 [SMILES: CC(C)=Cc1ccc2c(c1)N(S(=O)(=O)c1cc(C(F)(F)F)cnc1OCCO)C[C@H](CCC(=O)O)O2] | (S)-3-(4-((2-(2-hydroxyethoxy)-5-(trifluoromethyl)pyridin-3-yl)sulfonyl)-6-(2-methylprop-1-en-1-yl)-3,4-dihydro-2H-benzo[b][1,4]oxazin-2-yl)propanoic acid | 531 (M + H)+ |
| 95AD | 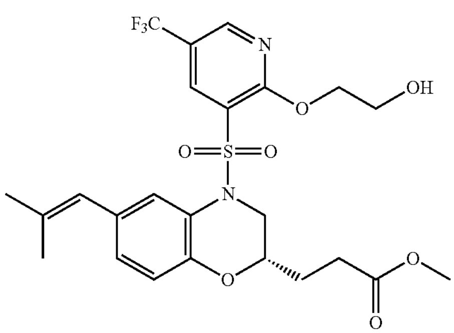 [SMILES: COC(=O)CC[C@H]1CN(S(=O)(=O)c2cc(C(F)(F)F)cnc2OCCO)c2cc(C=C(C)C)ccc2O1] | methyl (S)-3-(4-((2-(2-hydroxyethoxy)-5-(trifluoromethyl)pyridin-3-yl)sulfonyl)-6-(2-methylprop-1-en-1-yl)-3,4-dihydro-2H-benzo[b][1,4]oxazin-2-yl)propanoate | 545 (M + H)+ |
| 95AE | 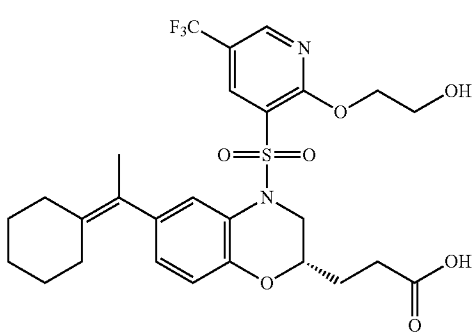 [SMILES: CC(=C1CCCCC1)c1ccc2c(c1)N(S(=O)(=O)c1cc(C(F)(F)F)cnc1OCCO)C[C@H](CCC(=O)O)O2] | (S)-3-(6-(1-cyclohexylideneethyl)-4-((2-(2-hydroxyethoxy)-5-(trifluoromethyl)pyridin-3-yl)sulfonyl)-3,4-dihydro-2H-benzo[b][1,4]oxazin-2-yl)propanoic acid | 585 (M + H)+ |

Example 96—Synthesis of (S)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-ol

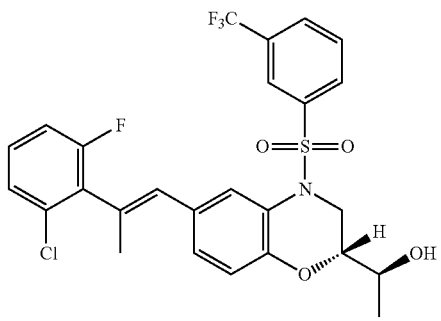

Part I—Synthesis of (Ethyl (2R,3S)-2-hydroxy-3-((tetrahydro-2H-pyran-2-yl)oxy)butanoate

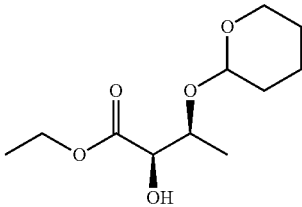 [SMILES: CCOC(=O)[C@H](O)[C@H](C)OC1CCCCO1]

A mixture of ethyl (2R,3S)-2,3-dihydroxybutanoate (5.5 g, 3.12 mmol), dichloromethane (80 mL), 3,4-dihydro-2H-pyran (3.1 g, 36.85 mmol), and pyridin-1-ium 4-methylbenzene-1-sulfonate (186 mg, 0.74 mmol) was stirred overnight at room temperature. The mixture was diluted with saturated sodium bicarbonate and extracted three times with dichloromethane. The combined organic layers were dried ($Na_2SO_4$) and concentrated. The resulting residue was purified via MPLC eluting with 15% ethyl acetate in petroleum ether to yield ethyl (2R,3S)-2-hydroxy-3-((tetrahydro-2H-pyran-2-yl)oxy)butanoate (4.8 g, 56%) as a colorless oil.

Part II—Synthesis of Ethyl (2S,3S)-2-(4-bromo-2-nitrophenoxy)-3-((tetrahydro-2H-pyran-2-yl)oxy)butanoate

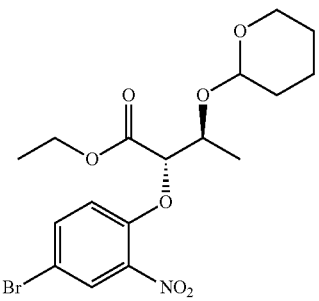 [SMILES: CCOC(=O)[C@@H](Oc1ccc(Br)cc1[N+](=O)[O-])[C@H](C)OC1CCCCO1]

A solution of diisopropyl azodicarboxylate (4.57 g, 22.60 mmol) in tetrahydrofuran (10 mL) was added dropwise to a stirred solution of ethyl (2R,3S)-2-hydroxy-3-((tetrahydro-2H-pyran-2-yl)oxy)butanoate (2.62 g, 11.28 mmol), triphenylphosphine (5.92 g, 22.57 mmol), and 4-bromo-2-nitrophenol (4.93 g, 22.61 mmol) in tetrahydrofuran (50 mL) at 0° C. The mixture was stirred overnight at room temperature and for an additional three hours at 60° C. The mixture was cooled, diluted with saturated sodium bicarbonate and extracted three times with ethyl acetate. The combined organic layers were washed with brine, dried ($Na_2SO_4$), and concentrated. The resulting residue was purified via MPLC eluting with 25% ethyl acetate in petroleum ether to afford ethyl (2S,3S)-2-(4-bromo-2-nitrophenoxy)-3-((tetrahydro-2H-pyran-2-yl)oxy)butanoate (3.11 g, 64%) as a yellow oil.

Part III—Synthesis of Ethyl (2S,3S)-2-(4-bromo-2-nitrophenoxy)-3-hydroxybutanoate

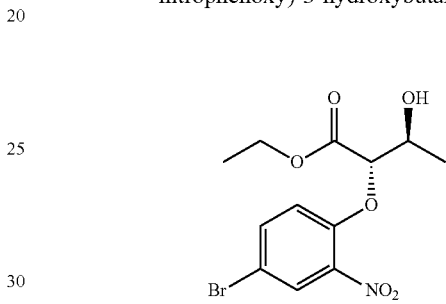

A mixture of ethyl (2S,3S)-2-(4-bromo-2-nitrophenoxy)-3-((tetrahydro-2H-pyran-2-yl)oxy)butanoate (3.11 g, 7.19 mmol), 5 M HCl (20 mL) and ethyl acetate (20 mL) was stirred for five hours at room temperature. The mixture was extracted four times with ether. The combined organic layers were washed with saturated sodium bicarbonate, dried ($Na_2SO_4$), and concentrated to afford ethyl (2S,3S)-2-(4-bromo-2-nitrophenoxy)-3-hydroxybutanoate (1.32 g, 53%) as a light yellow oil.

Part IV—Synthesis of (S)-6-Bromo-2-((S)-1-hydroxyethyl)-2H-benzo[b][1,4]oxazin-3(4H)-one

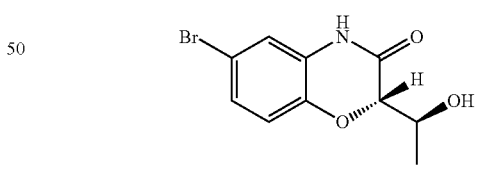

A mixture of ethyl (2S,3S)-2-(4-bromo-2-nitrophenoxy)-3-hydroxybutanoate (1.32 g, 3.79 mmol), iron (640 mg, 11.4 mmol), and acetic acid (8 mL) was stirred for one hour at 100° C. The mixture was cooled and diluted with ethanol. The mixture was filtered, and the filtrate was concentrated. The resulting residue was diluted with saturated sodium bicarbonate and extracted three times with ethyl acetate. The combined organic layers were washed with brine, dried ($Na_2SO_4$) and concentrated to afford (S)-6-bromo-2-((S)-1-hydroxyethyl)-2H-benzo[b][1,4]oxazin-3(4H)-one (1.13 g) as a colorless oil.

Part V—Synthesis of (S)-1-((R)-6-Bromo-3,4-di-hydro-2H-benzo[b][1,4]oxazin-2-yl)ethan-1-ol

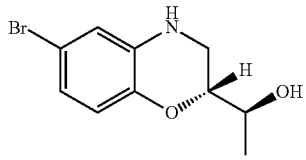

A 1 M solution of borane in THF (11 mL, 11 mmol) was added to a solution of (S)-6-bromo-2-((S)-1-hydroxyethyl)-2H-benzo[b][1,4]oxazin-3(4H)-one (1.0 g, 3.68 mmol) in tetrahydrofuran (10 mL). The mixture was stirred for three hours at room temperature and poured onto water. The mixture was extracted three times with ethyl acetate. The combined organic layers were washed with brine, dried (Na$_2$SO$_4$), and concentrated to afford (S)-1-((R)-6-bromo-3,4-dihydro-2H-benzo[b][1,4]oxazin-2-yl)ethan-1-ol (800 mg, 84%) as a colorless oil.

Part VI—Synthesis of (S)-1-((R)-6-((E)-2-(2-Chloro-6-fluorophenyl)prop-1-en-1-yl)-3,4-dihydro-2H-benzo[b][1,4]oxazin-2-yl)ethan-1-ol

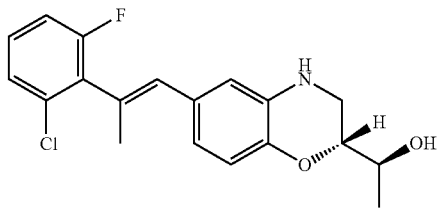

A mixture of (S)-1-((R)-6-((E)-2-(2-chloro-6-fluorophenyl)prop-1-en-1-yl)-3,4-dihydro-2H-benzo[b][1,4]oxazin-2-yl)ethan-1-ol (1.11 g, 4.30 mmol), (E)-2-(2-(2-chloro-6-fluorophenyl)prop-1-en-1-yl)-4,4,5,5-tetramethyl-1,3,2-dioxaborolane (1.91 g, 6.44 mmol), sodium carbonate (1.37 g, 12.93 mmol), tetrakis(triphenylphosphine)palladium(0) (250 mg, 0.22 mmol), toluene (27 mL), ethanol (27 mL) and water (27 mL) was stirred overnight at 80° C. The mixture was cooled, diluted with water, and extracted twice with ethyl acetate. The combined organic layers were dried (Na$_2$SO$_4$) and concentrated. The resulting residue was purified via MPLC eluting with 50% ethyl acetate in petroleum ether to afford (S)-1-((R)-6-((E)-2-(2-chloro-6-fluorophenyl)prop-1-en-1-yl)-3,4-dihydro-2H-benzo[b][1,4]oxazin-2-yl)ethan-1-ol (1.3 g, 87%) as a yellow oil.

Part VII—Synthesis of (S)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-ol

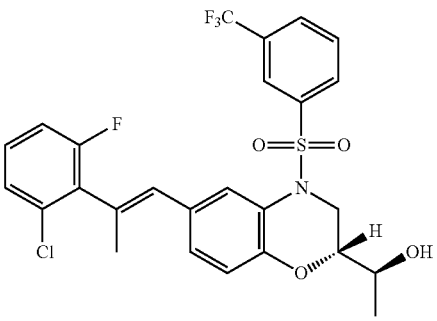

A solution of (S)-1-((R)-6-((E)-2-(2-chloro-6-fluorophenyl)prop-1-en-1-yl)-3,4-dihydro-2H-benzo[b][1,4]oxazin-2-yl)ethan-1-ol (100 mg, 0.29 mmol), pyridine (5 mL) and 3-(trifluoromethyl)benzene-1-sulfonyl chloride (99 mg, 0.40 mmol) was stirred overnight at room temperature. The mixture was diluted with ethyl acetate, washed three times with 1 M HCl, dried (Na$_2$SO$_4$) and concentrated. The resulting residue was purified by Prep-HPLC eluting with a gradient of 70-90% acetonitrile in water with 0.05% trifluoroacetic acid to afford (S)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-ol (50 mg, 31%) as an off-white solid. $^1$H-NMR (300 MHz, CD$_3$OD) δ 8.01-7.95 (m, 3H), 7.89 (s, 3H), 7.82-7.78 (t, J=8.0 Hz, 1H), 7.35-7.28 (m, 2H), 7.15-7.11 (m, 2H), 6.90-6.88 (d, J=8.4 Hz, 1H), 6.39 (s, 1H), 4.62-4.58 (dd, J=2 Hz, 14.8 Hz, 1H), 3.76-3.69 (m, 1H), 3.37-3.32 (m, 1H), 3.15-3.08 (m, 1H), 2.19 (s, 3H), 1.21-1.92 (d, J=6.4 Hz, 3H). (ES, m/z): (M+H)$^+$556.

Example 97-Synthesis of (S)-1-((R)-4-((3-Chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethan-1-ol

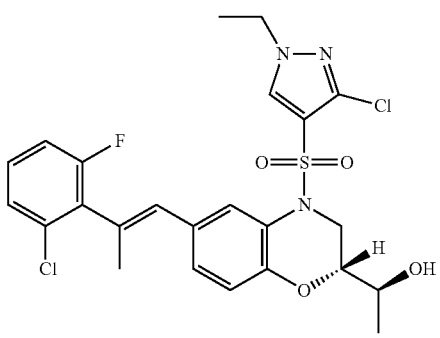

3-Chloro-1-ethyl-1H-pyrazole-4-sulfonyl chloride (99 mg, 0.43 mmol) was added to a solution of (S)-1-((R)-6-((E)-2-(2-chloro-6-fluorophenyl)prop-1-en-1-yl)-3,4-dihydro-2H-benzo[b][1,4]oxazin-2-yl)ethan-1-ol (100 mg, 0.29 mmol) in pyridine (5 mL). Stirred overnight at room temperature and then diluted with ethyl acetate. The mixture was washed three times with 1 M HCl, dried (Na$_2$SO$_4$) and concentrated. The resulting residue was purified by Prep-HPLC eluting with a gradient of 55-73% acetonitrile in water with 0.05% trifluoroacetic acid to afford (S)-1-((R)-4-((3-chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethan-1-ol (73.5 mg, 47%). $^1$H-NMR (300 MHz, CD$_3$OD) δ 8.21 (s, 1H), 7.80-7.79 (d, J=2.0 Hz, 1H), 7.34-7.27 (m, 2H), 7.17-7.01 (m, 2H), 6.95-6.93 (d, J=8.8 Hz, 1H), 6.36 (s, 1H), 4.57-4.52 (dd, J=2.4 Hz, 14.4 Hz, 1H), 4.19-4.14 (m, 2H), 3.87-3.80 (m, 1H), 3.57-3.50 (m, 1H), 3.35-3.30 (m, 1H), 2.17 (s, 3H), 1.46-1.42 (t, J=7.2 Hz, 3H), 1.31-1.29 (d, J=8.0 Hz, 3H). (ES, m/z): (M+H)$^+$520.

Example 98—Synthesis of (R)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-ol

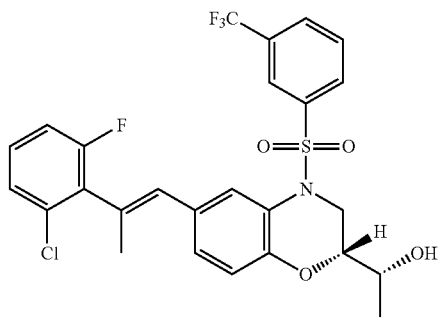

Part I—Synthesis of (R)-1-((R)-6-((E)-2-(2-Chloro-6-fluorophenyl)prop-1-en-1-yl)-3,4-dihydro-2H-benzo[b][1,4]oxazin-2-yl)ethyl 4-nitrobenzoate

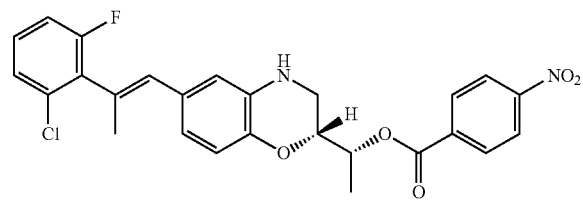

Diisopropyl azodicarboxylate (291 mg, 2.22 mmol) was added dropwise to a stirred solution of (S)-1-((R)-6-((E)-2-(2-chloro-6-fluorophenyl)prop-1-en-1-yl)-3,4-dihydro-2H-benzo[b][1,4]oxazin-2-yl)ethan-1-ol (500 mg, 1.44 mmol), 4-nitrobenzoic acid (241 mg, 1.44 mmol), and triphenylphosphine (378 mg, 1.44 mmol) in THF (20 mL) at 0° C. The mixture was stirred for three additional hours at room temperature and diluted with water. The mixture was extracted three times with ethyl acetate and the combined organic layers washed with water, dried (Na$_2$SO$_4$), and concentrated. The resulting residue was purified via MPLC eluting with 33% ethyl acetate in petroleum ether to afford (R)-1-((R)-6-((E)-2-(2-chloro-6-fluorophenyl)prop-1-en-1-yl)-3,4-dihydro-2H-benzo[b][1,4]oxazin-2-yl)ethyl 4-nitrobenzoate (600 mg, 84%) as an oil.

Part II—Synthesis of (R)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl 4-nitrobenzoate

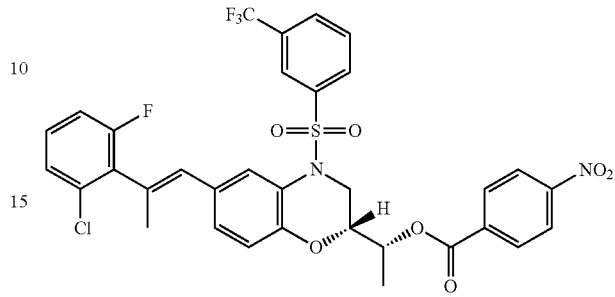

A solution of (R)-1-((R)-6-((E)-2-(2-chloro-6-fluorophenyl)prop-1-en-1-yl)-3,4-dihydro-2H-benzo[b][1,4]oxazin-2-yl)ethyl 4-nitrobenzoate (150 mg, 0.30 mmol), pyridine (5 mL) and 3-(trifluoromethyl)benzene-1-sulfonyl chloride (111 mg, 0.45 mmol) was stirred overnight at room temperature. The mixture was diluted with ethyl acetate and washed three times with 1M hydrogen chloride, dried (Na$_2$SO$_4$), and concentrated to afford (R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl 4-nitrobenzoate (150 mg, 70%) as an oil.

Part III—Synthesis of (R)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-ol

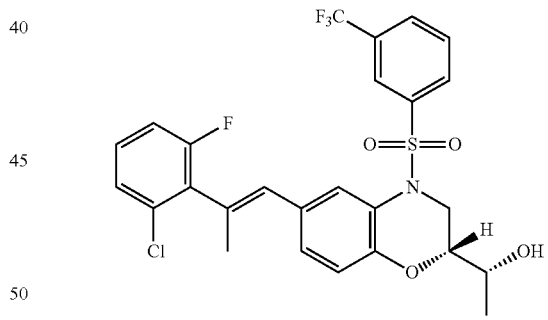

A mixture of (R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl 4-nitrobenzoate (100 mg, 0.14 mmol), tetrahydrofuran (8 mL), water (2 mL), and sodium hydroxide (28 mg, 0.70 mmol) was stirred for two hours at room temperature. The mixture was diluted with water, and extracted twice with ethyl acetate. The combined organic layers were washed with brine, dried (Na$_2$SO$_4$), and concentrated. The resulting residue was purified by Prep-HPLC eluting with a gradient of 66-88% acetonitrile in water with 0.05% trifluoroacetic acid to afford (R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-ol (48.3 mg, 61%) as a white solid. $^1$H-NMR (300 MHz, CD$_3$OD) δ

8.01-7.95 (m, 3H), 7.87-7.76 (m, 2H), 7.32-7.30 (m, 2H), 7.19-7.10 (m, 2H), 6.93-6.90 (d, J=11.2 Hz, 1H), 6.38 (s, 1H), 4.46-4.40 (dd, J=3.2, 19.2 Hz, 1H), 3.83-3.80 (m, 1H), 3.45-3.37 (m, 1H), 3.23-3.20 (m, 1H), 2.19 (s, 3H), 1.21-1.82 (d, J=8.4 Hz, 3H). (ES, m/z): (M+H)$^+$556.

Example 99—Synthesis of (R)-1-((R)-4-((3-Chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethan-1-ol

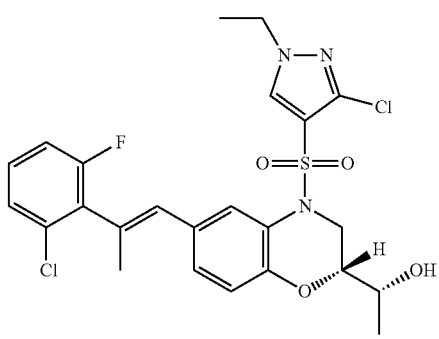

Part I—Synthesis of (R)-1-((R)-4-((3-Chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethyl 4-nitrobenzoate

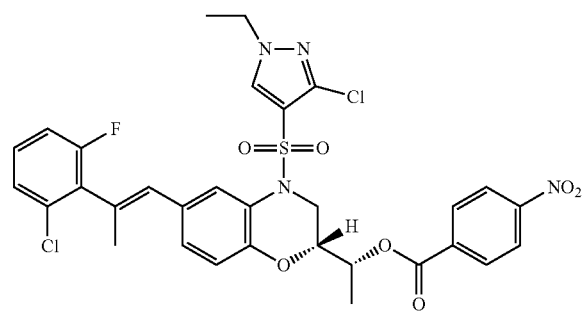

3-Chloro-1-ethyl-4,5-dihydro-1H-pyrazole-4-sulfonyl chloride (104 mg, 0.45 mmol) was added to a solution of (R)-1-((R)-6-((E)-2-(2-chloro-6-fluorophenyl)prop-1-en-1-yl)-3,4-dihydro-2H-benzo[b][1,4]oxazin-2-yl)ethyl 4-nitrobenzoate (150 mg, 0.30 mmol) in pyridine (5 mL). The mixture was stirred overnight at room temperature, diluted with ethyl acetate, and was washed three times with 1 M HCl, dried (Na$_2$SO$_4$), and concentrated to afford (R)-1-((R)-4-((3-chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethyl 4-nitrobenzoate (150 mg, 72%) as an oil.

Part II—Synthesis of (R)-1-((R)-4-((3-Chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethan-1-ol

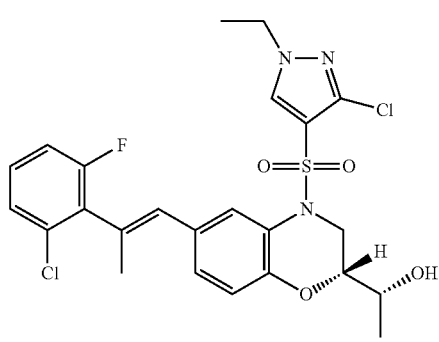

A mixture of (R)-1-((R)-4-((3-chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethyl 4-nitrobenzoate (100 mg, 0.14 mmol) in tetrahydrofuran (8 mL), water (2 mL), and sodium hydroxide (29 mg, 0.73 mmol) was stirred for two hours at room temperature. The mixture was diluted with water and extracted twice with ethyl acetate. The combined organic layers were washed with brine, dried (Na$_2$SO$_4$) and concentrated. The resulting residue was purified by Prep-HPLC eluting with a gradient of 62-82% acetonitrile in water with 0.05% trifluorofluoroacetic acid to afford (R)-1-((R)-4-((3-chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethan-1-ol (46.5 mg, 59%) as a white solid. $^1$H-NMR (300 MHz, CD$_3$OD) δ 8.19 (s, 1H), 7.78-7.77 (d, J=1.8 Hz, 1H), 7.34-7.28 (m, 2H), 7.25-7.09 (m, 2H), 7.00-6.95 (d, J=8.7 Hz, 1H), 6.35 (s, 1H), 4.85-4.74 (m, 1H), 4.40-4.11 (m, 2H), 3.95-3.87 (m, 1H), 3.67-3.61 (m, 1H), 3.55-3.37 (m, 1H), 2.17 (s, 3H), 1.44-1.39 (t, J=7.2 Hz, 3H), 1.30-1.28 (d, J=6.6 Hz, 3H). (ES, m/z): (M+H)$^+$540.

Example 100—Synthesis of (R)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine

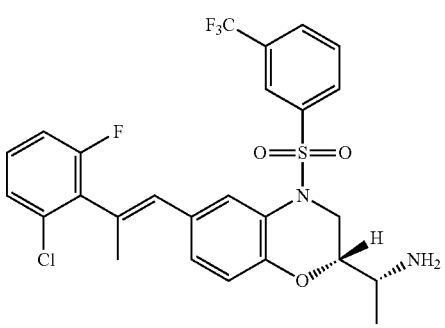

Part I—Synthesis of 2-((R)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)isoindoline-1,3-dione

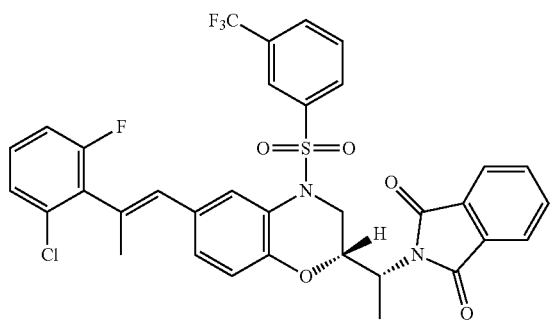

Diisopropyl azodicarboxylate (364 mg, 2.78 mmol) was added dropwise to a stirred solution of (S)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-ol (500 mg, 0.90 mmol), 2,3-dihydro-1H-isoindole-1,3-dione (265 mg, 1.80 mmol), triphenylphosphine (472 mg, 1.80 mmol) and THF (20 mL) at 0° C. The mixture was stirred overnight at room temperature and then concentrated. The resulting residue was purified via MPLC eluting with a gradient of 5-50% ethyl acetate in petroleum ether to afford 2-((R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)isoindoline-1,3-dione (430 mg, 70%) as a yellow oil.

Part II—Synthesis of (R)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine

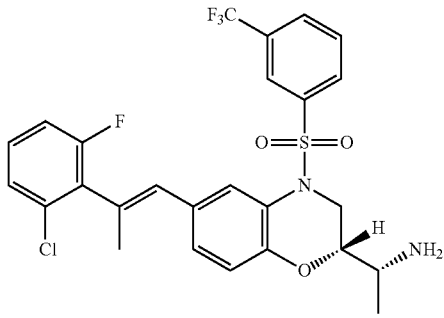

A solution of 2-((R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl) isoindoline-1,3-dione (40 mg, 0.06 mmol), methanol (4 mL), and hydrazine hydrate (16 mg, 0.33 mmol) was stirred for one hour at 65° C. The mixture was diluted with water (10 mL) and extracted twice with ethyl acetate. The combined organic layers were dried (Na$_2$SO$_4$) and concentrated. The resulting residue was purified by Prep-HPLC eluting with a gradient of 35-68% acetonitrile in water with 0.05% trifluoroacetic acid to afford (R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl) ethan-1-amine (10.7 mg, 33%) as a white solid. $^1$H-NMR (300 MHz, CD$_3$OD) δ 8.09-8.02 (m, 3H), 7.87-7.83 (m, 2H), 7.36-7.29 (m, 2H), 7.19-7.12 (m, 2H), 7.02 (d, J=8.4 Hz, 1H), 6.39 (s, 1H), 4.53 (dd, J=8 Hz, 20.4 Hz, 1H), 3.49 (m, 1H), 2.16 (s, 3H), 1.36 (d, J=6.4 Hz, 3H). (ES, m/z): (M+H)$^+$555.

Example 101—Synthesis of (R)-1-((R)-4-((3-Chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethan-1-amine

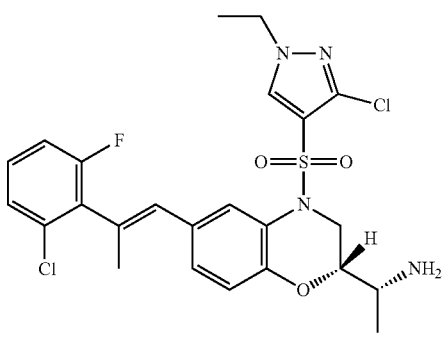 [SMILES: CCn1cc(S(=O)(=O)N2C[C@@H]([C@@H](C)N)Oc3ccc(/C=C(\C)c4c(F)cccc4Cl)cc32)c(Cl)n1]

Part I—Synthesis of 2-((R)-1-((R)-4-((3-chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethyl)isoindoline-1,3-dione

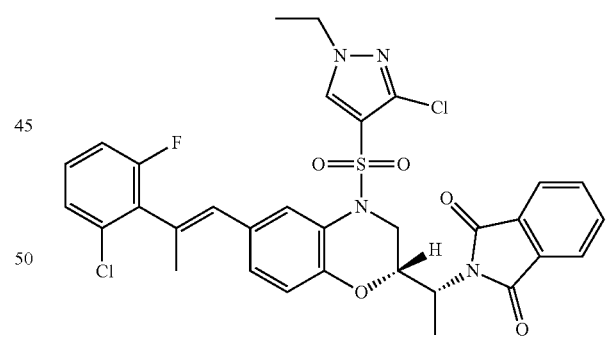

A solution of 2-((R)-1-((R)-6-((E)-2-(2-chloro-6-fluorophenyl)prop-1-en-1-yl)-3,4-dihydro-2H-benzo[b][1,4]oxazin-2-yl)ethyl)isoindoline-1,3-dione (700 mg, 1.47 mmol), pyridine (20 mL), and 3-chloro-1-ethyl-1H-pyrazole-4-sulfonyl chloride (503 mg, 2.20 mmol) was stirred overnight at room temperature. The mixture was diluted in ethyl acetate and washed three times with 1 M HCl, once with saturated sodium bicarbonate, dried (Na$_2$SO$_4$), and concentrated to afford 2-((R)-1-((R)-4-((3-chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethyl)isoindoline-1,3-dione (700 mg, 71%) as a red oil.

Part II—Synthesis of (R)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine

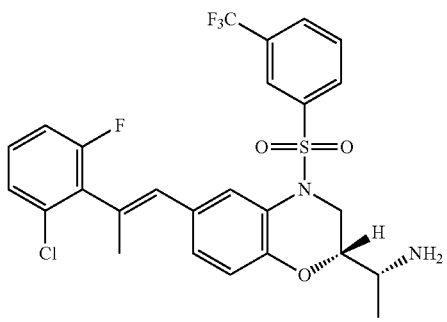

A solution of 2-((R)-1-((R)-4-((3-chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethyl)isoindoline-1,3-dione (700 mg, 1.04 mmol), methanol (15 mL), and hydrazine hydrate (288 mg, 5.72 mmol) was stirred for five hours at 65° C. The mixture was diluted with water and extracted three times with ethyl acetate. The combined organic layers were dried (Na$_2$SO$_4$) and concentrated. The resulting residue was purified by MPLC eluting with 10% methanol in dichloromethane to afford (R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine (300 mg, 53%) as a colorless oil. $^1$H-NMR (300 MHz, CD$_3$OD) δ 8.31 (s, 1H), 7.75-7.74 (d, J=1.6 Hz, 1H), 7.35-7.30 (m, 2H), 7.28-7.06 (m, 3H), 6.37 (s, 1H), 4.50-4.46 (dd, J=2.4 Hz, 14.4 Hz, 1H), 4.20-4.15 (m, 2H), 4.01-3.97 (m, 1H), 3.58-3.52 (m, 2H), 2.15 (s, 3H), 1.47-1.43 (m, 6H). (ES, m/z): (M+H)$^+$539.

Example 102—Synthesis of N—((R)-1-((R)-4-((3-Chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethyl)acetamide

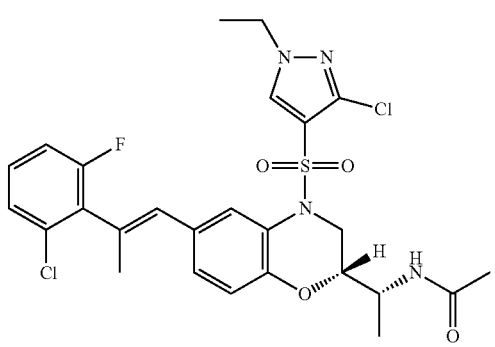

A solution of (R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine (70 mg, 0.13 mmol), dichloromethane (4 mL), triethylamine (36 mg, 0.36 mmol), and acetyl chloride (15 mg, 0.19 mmol) was stirred for twenty minutes at room temperature. The mixture was diluted with water and extracted twice with dichloromethane. The combined organic layers were dried (Na$_2$SO$_4$) and concentrated. The resulting residue was purified by Prep-HPLC eluting with a gradient of 60-80% acetonitrile in water with 0.05% trifluoroacetic acid to afford N—((R)-1-((R)-4-((3-chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethyl)acetamide (63.6 mg, 84%) as a white solid. $^1$H-NMR (300 MHz, CD$_3$OD) δ 8.19 (s, 1H), 7.79-7.78 (d, J=2.0 Hz, 1H), 7.30-7.25 (m, 2H), 7.13-7.09 (m, 2H), 6.96-6.94 (d, J=8.4 Hz, 1H), 6.34 (s, 1H), 4.39-4.35 (dd, J=2.4 Hz, 14.8 Hz, 1H), 4.28-4.16 (m, 1H), 4.14-4.11 (m, 2H), 3.78-3.74 (m, 1H), 3.31-3.19 (m, 1H), 2.16 (s, 3H), 1.98 (s, 3H), 1.43-1.39 (t, J=14.4 Hz, 3H), 1.27-1.25 (d, J=6.8 Hz, 3H). (ES, m/z): (M+H)$^+$581.

Example 103—Synthesis of N—((R)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)acetamide

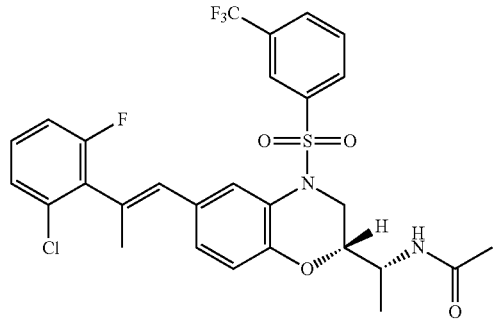

Based on the procedure in Example 102, N—((R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)acetamide was prepared. $^1$H-NMR (300 MHz, CD$_3$OD) δ 8.7.86-8.04 (m, 3H), 7.88 (s, 1H), 7.82 (t, 1H), 7.32 (t, 2H), 7.11-7.17 (m, 2H), 6.92 (d, 1H), 6.39 (s, 1H), 4.45 (dd, 1H), 4.17 (m, 1H), 3.36 (m, 1H), 3.24 (dd, 1H), 2.19 (s, 3H), 1.96 (s, 3H), 1.18 (d, 3H). (ES, m/z): (M+H)$^+$597.

Example 104—Synthesis of N—((R)-1-((R)-4-((3-Chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethyl)methanesulfonamide

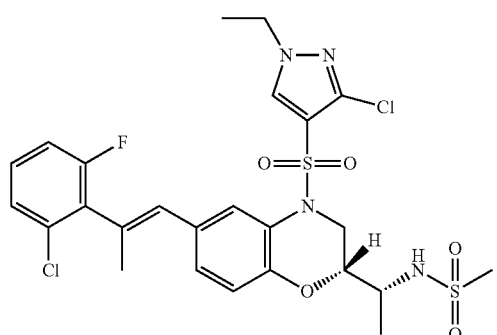

A solution of (R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine (70 mg, 0.13 mmol), dichloromethane (4 mL), triethylamine (36 mg, 0.36 mmol) and methanesulfonyl chloride (22 mg, 0.19 mmol) was stirred for twenty minutes at room temperature. The mixture was diluted with water and extracted twice with dichloromethane. The combined organic layers were dried (Na$_2$SO$_4$) and concentrated. The resulting residue was purified by Prep-HPLC eluting with a gradient of 62-82% acetonitrile with 0.05% trifluoroacetic acid to afford N—((R)-1-((R)-4-((3-chloro-1-ethyl-1H-pyrazol-4-yl)sulfonyl)-6-((E)-2-(2-chloro-6-fluorophenyl)prop-1-en-1-yl)-3,4-dihydro-2H-benzo[b][1,4]oxazin-2-yl)ethyl)methanesulfonamide (57.8 mg, 72%) as a white solid. $^1$H-NMR (300 MHz, CD$_3$OD) δ 8.19 (s, 1H), 7.82-7.81 (d, J=2.0 Hz, 1H), 7.32-7.25 (m, 2H), 7.14-7.09 (m, 2H), 6.96-6.93 (d, J=8.8 Hz, 1H), 6.35 (s, 1H), 4.42-4.38 (dd, J=2.0 Hz, 16.4 Hz, 1H), 4.17-4.11 (m, 2H), 3.76-3.69 (m, 2H), 3.40-3.33 (m, 1H), 3.31-3.19 (m, 1H), 3.00 (s, 3H), 2.17 (s, 3H), 1.43-1.39 (t, J=14.4 Hz, 3H), 1.27-1.25 (d, J=6.8 Hz, 3H). (ES, m/z): (M+H)$^+$617.

Example 105—Synthesis of N—((R)-1-((R)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)methanesulfonamide

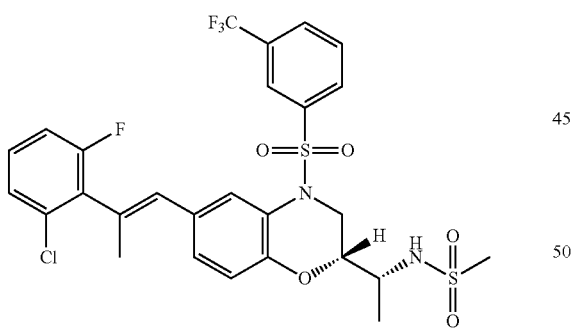

Based on the procedure in Example 104, N—((R)-1-((R)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)methanesulfonamide was prepared. $^1$H-NMR (300 MHz, CD$_3$OD) δ 7.98-8.03 (m, 2H), 7.93 (s, 1H), 7.88 (s, 1H), 7.81 (t, 1H), 7.32 (m, 2H), 7.12-7.17 (m, 2H), 6.92 (d, 1H), 6.40 (s, 1H), 4.48 (m, 1H), 3.67 (m, 1H), 3.38-3.44 (m, 2H), 2.99 (s, 3H), 2.19 (s, 3H), 1.26 (d, 3H). (ES, m/z): (M+H)$^+$633.

Example 106—Synthesis of (S,E)-2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-ol

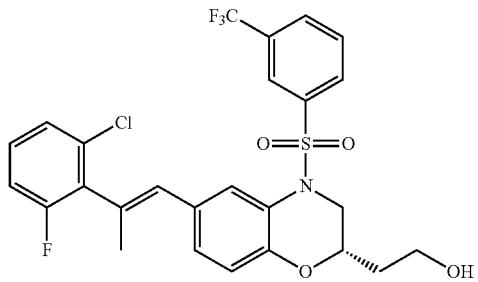 [SMILES: C/C(=C\c1ccc2c(c1)N(S(=O)(=O)c1cccc(C(F)(F)F)c1)C[C@H](CCO)O2)c1c(F)cccc1Cl]

Part I—Synthesis of (R)-3-(4-Bromo-2-nitrophenoxy)dihydrofuran-2(3H)-one

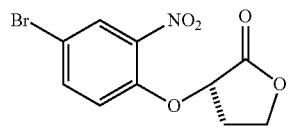 [SMILES: O=C1OCC[C@@H]1Oc1ccc(Br)cc1[N+](=O)[O-]]

4-Bromo-2-nitrophenol (3 g, 13.76 mmol), (3R)-3-hydroxytetrahydrofuran-2-one (1.405 g, 13.76 mmol), and triphenylphosphine (4.33 g, 16.51 mmol) were suspended in dichloromethane (36 mL), and diisopropylazodicarboxylate (3.25 mL, 16.5 mmol) was added dropwise. The reaction mixture was stirred at room temperature for one hour, washed with water, dried (Na$_2$SO$_4$), and concentrated onto silica gel. The resulting residue on the silica gel was purified by MPLC (2 columns: first, dichloromethane; second, a gradient of EtOAc/hexanes) affording (R)-3-(4-bromo-2-nitrophenoxy)dihydrofuran-2(3H)-one as a white solid (1.93 g, 46%). $^1$H-NMR (400 MHz, DMSO-d$_6$) δ 8.12 (s, 1H), 7.86 (d, 1H), 7.47 (d, 1H), 5.55 (t, 1H), 4.42 (m, 1H), 4.26 (m, 1H), 2.75 (m, 1H), 2.30 (m, 1H).

Part II—Synthesis of (S)-6-Bromo-2-(2-hydroxyethyl)-2H-benzo[b][1,4]oxazin-3(4H)-one

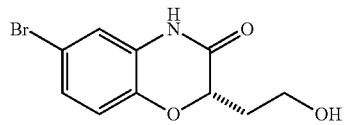 [SMILES: O=C1Nc2cc(Br)ccc2O[C@H]1CCO]

(R)-3-(4-Bromo-2-nitrophenoxy)dihydrofuran-2(3H)-one (1.93 g, 6.39 mmol) was dissolved in acetic acid and powdered iron (1.784 g, 31.95 mmol) was added. The resulting mixture was heated to 70° C. for two hours. The resulting suspension was filtered through a pad of Celite, and the pad was washed with ethyl acetate. The combined filtrates were partitioned between ethyl acetate and water, and the organic phase was washed a second time with water, washed with brine, and concentrated to provide a residue. The residue was purified via MPLC eluting with a gradient of 15-70% ethyl acetate in hexanes to afford (S)-6-bromo-2-(2-hydroxyethyl)-2H-benzo[b][1,4]oxazin-3(4H)-one as a white solid (1.32 g, 76%). ¹H-NMR (400 MHz, DMSO-d₆) δ 10.73 (bs, 1H), 7.04 (d, 1H), 6.98 (s, 1H), 6.90 (d, 1H), 4.62 (m, 2H), 3.53 (m, 2H), 1.91 (m, 1H), 1.88 (m, 1H).

Part III—Synthesis of (S)-2-(6-Bromo-3,4-dihydro-2H-benzo[b][1,4]oxazin-2-yl)ethan-1-ol

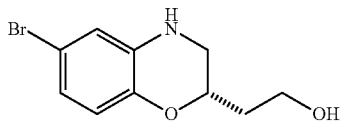 [SMILES: OCC[C@H]1CNc2cc(Br)ccc2O1]

(S)-6-Bromo-2-(2-hydroxyethyl)-2H-benzo[b][1,4]oxazin-3(4H)-one (1.32 g, 4.85 mmol) was dissolved in anhydrous THF (49 mL) under nitrogen at ambient temperature and borane-dimethylsulfide complex (1.47 g, 19.41 mmol) was added dropwise. The reaction mixture was heated to reflux for 90 minutes. Then, the reaction mixture was cooled in an ice bath and subsequently methanol was added to the reaction mixture to quench the reaction. The resulting solution was heated to reflux for 20 minutes, and then concentrated to provide a residue. The residue was partitioned between ethyl acetate and water, washed with brine, dried (Na₂SO₄), and concentrated to provide crude product. The crude product was purified by MPLC eluting with a gradient of 15-70% ethyl acetate in hexanes to afford (S)-2-(6-bromo-3,4-dihydro-2H-benzo[b][1,4]oxazin-2-yl)ethan-1-ol (1.05 g, 84%).

Part IV—Synthesis of (S)-6-Bromo-2-(2-((tert-butyldimethylsilyl)oxy)ethyl)-3,4-dihydro-2H-benzo[b][1,4]oxazine

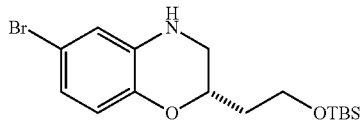 [SMILES: CC(C)(C)[Si](C)(C)OCC[C@H]1CNc2cc(Br)ccc2O1]

(S)-2-(6-Bromo-3,4-dihydro-2H-benzo[b][1,4]oxazin-2-yl)ethan-1-ol (0.28 g, 1.085 mmol), tert-butyldimethylchlorosilane (0.196 g, 1.302 mmol), and imidazole (0.148 g, 2.17 mmol) were dissolved in DMF (4 mL), and the reaction mixture was stirred at room temperature overnight. Next, the reaction mixture was partitioned between water and ethyl acetate, and the organic layer was washed twice more with water, washed with brine, dried (Na₂SO₄), and concentrated onto silica gel. The residue on the silica gel was purified by MPLC eluting with a gradient of 5-30% ethyl acetate in hexanes to afford (S)-6-bromo-2-(2-((tert-butyldimethylsilyl)oxy)ethyl)-3,4-dihydro-2H-benzo[b][1,4]oxazine (0.19 g, 47%). ¹H-NMR (400 MHz, DMSO-d₆) δ 6.66 (s, 1H), 6.52 (s, 2H), 6.06 (bs, 1H), 4.02 (q, 1H), 3.72 (m, 2H), 3.33 (m, 1H), 2.94 (m, 1H), 1.70 (q, 2H), 0.82 (s, 9H), 0.01 (s, 6H).

Part V—Synthesis of (S)-6-Bromo-2-(2-((tert-butyldimethylsilyl)oxy)ethyl)-4-((3-(trifluoromethyl)phenyl)sulfonyl)-3,4-dihydro-2H-benzo[b][1,4]oxazine

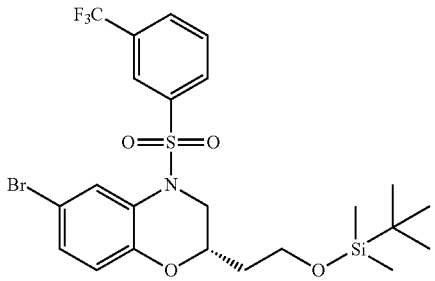 [SMILES: CC(C)(C)[Si](C)(C)OCC[C@H]1CN(S(=O)(=O)c2cccc(C(F)(F)F)c2)c2cc(Br)ccc2O1]

To a solution of (S)-2-(6-bromo-4-((3-(trifluoromethyl)phenyl)sulfonyl)-3,4-dihydro-2H-benzo[b][1,4]oxazin-2-yl)ethan-1-ol (1.60 g, 4.30 mmol) in pyridine (15 mL) was added 3-(trifluoromethyl)benzenesulfonyl chloride (1.26 g, 5.15 mmol). The mixture was stirred at 50° C. for two hours, cooled, and partitioned between ethyl acetate and 1 M HCl. The organic layer was washed three times with 1 M HCl, brine, and dried (Na₂SO₄). Charcoal was added to the mixture, slurried, and filtered through Celite. The filtrate was concentrated and the resulting residue was purified by MPLC eluting with a gradient of ethyl acetate in hexanes to afford (S)-6-bromo-2-(2-((tert-butyldimethylsilyl)oxy)ethyl)-4-((3-(trifluoromethyl)phenyl)sulfonyl)-3,4-dihydro-2H-benzo[b][1,4]oxazine (2.40 g, 100%).

Part VI—Synthesis of (S,E)-2-(2-((tert-Butyldimethylsilyl)oxy)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

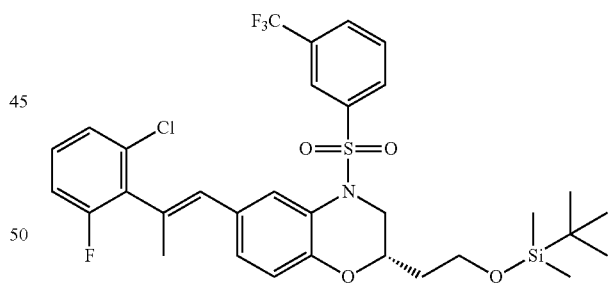

To degassed mixture of (S)-6-bromo-2-(2-((tert-butyldimethylsilyl)oxy)ethyl)-4-((3-(trifluoromethyl)phenyl)sulfonyl)-3,4-dihydro-2H-benzo[b][1,4]oxazine (1.78 g, 6.03 mmol) potassium carbonate (833 mg, 6.03 mmol), (E)-2-(2-(2-chloro-6-fluorophenyl)prop-1-en-1-yl)-4,4,5,5-tetramethyl-1,3,2-dioxaborolane (1.788 g, 6.03 mmol), dioxane (25 mL) and water (5 mL) was added [1,1'-bis(diphenylphosphino)ferrocene]dichloropalladium(II) dichloromethane complex (0.328 g, 0.431 mmol). The mixture was heated to 70° C. for five hours. The mixture was cooled and partitioned between ethyl acetate and saturated ammonium chloride. The organic layer was washed with brine, dried (Na₂SO₄), and concentrated. The resulting residue was purified by MPLC eluting with a gradient of 0-50% ethyl acetate in hexanes to afford (S,E)-2-(2-((tert-butyldimethylsilyl)oxy)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (2.40 g, 83%)

Part VII—Synthesis of (S,E)-2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethanol

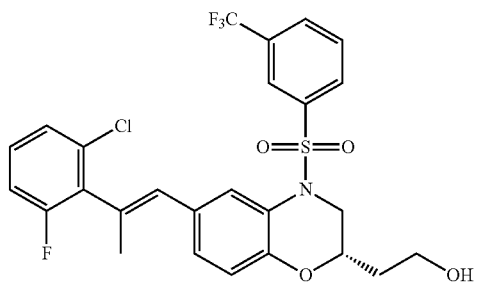 [SMILES: C/C(=C\c1ccc2c(c1)N(S(=O)(=O)c1cccc(C(F)(F)F)c1)C[C@H](CCO)O2)c1c(F)cccc1Cl]

To a solution of (S,E)-2-(2-((tert-butyldimethylsilyl)oxy)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (2.40 g, 3.58 mmol) in THF (24 mL) was added a 1 M solution of tetrabutylammonium fluoride (1.40 g, 5.37 mmol) in THF (5.37 mL). The mixture was stirred for one hour, and concentrated onto a small amount of silica. The residue was purified by MPLC eluting with a gradient of 0-100% ethyl acetate in hexanes to afford (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethanol (1.55 g, 78%). $^1$H-NMR (400 MHz, DMSO-d$_6$) δ 8.17 (d, 1H), 8.05 (m, 2H), 7.92 (t, 1H), 7.77 (s, 1H), 7.43 (m, 2H), 7.33 (m, 1H), 7.17 (d, 1H), 6.93 (d, 1H), 6.44 (s, 1H), 4.66 (t, 1H), 4.51 (m, 1H), 3.6-3.3 (m, 4H), 2.15 (s, 3H), 1.75 (m, 2H). MS (ESI+) (M+Na)$^+$578.17.

Example 107-Synthesis of (S,E)-2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)acetic acid

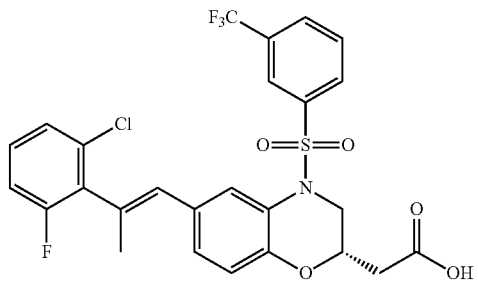

To a solution of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethanol (0.22 g, 0.40 mmol) in acetone (4 mL) was added Jones' reagent dropwise until a red color persisted. The reaction mixture was stirred at room temperature an additional thirty minutes, then isopropanol (1 mL) was added. After stirring for ten more minutes the reaction mixture was concentrated. The resulting residue was purified first by MPLC eluting with a gradient of 0-10% methanol in dichloromethane. The fractions containing the major UV-active component were concentrated and the residue further purified by Prep-HPLC eluting with a gradient of 5-95% acetonitrile in water with 0.1% trifluoroacetic acid to afford (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)acetic acid (26 mg, 11%) as a white solid. $^1$H-NMR (400 MHz, DMSO-d$_6$) δ 12.6 (br s, 1H), 8.12 (m, 1H), 7.98 (m, 2H), 7.85 (t, 1H), 7.76 (s, 1H), 7.39 (m, 2H), 7.28 (m, 1H), 7.14 (d, 1H), 6.85 (d, 1H), 6.40 (s, 1H), 4.52 (m, 1H), 3.75 (m, 1H), 3.4 (m, 1H), 2.65 (m, 1H), 2.55 (m, 1H), 2.12 (s, 3H). MS (ESI+) (M+Na)$^+$592.23.

Example 108—Synthesis of (S,E)-N-((6-(2-(2-Chloro-6-fluorophenyl)prop-1-en-1-yl)-8-fluoro-4-((4-fluoro-3-methoxyphenyl)sulfonyl)-3,4-dihydro-2H-benzo[b][1,4]oxazin-2-yl)methyl)acetamide

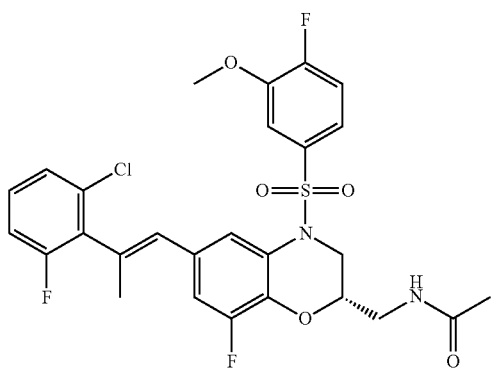

Part I—Synthesis of (R)-(6-Bromo-8-fluoro-3,4-dihydro-2H-benzo[b][1,4]-oxazin-2-yl)methanol

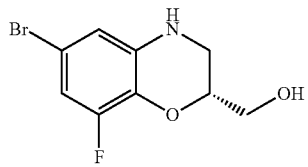 [SMILES: OC[C@H]1CNc2cc(Br)cc(F)c2O1]

A mixture of 2-amino-4-bromo-6-fluorophenol (5.0 g, 24.3 mmol) and 2-(S)-2-(chloromethyl)oxirane (4.49 g, 48.5 mmol) in ethanol (50 mL) and water (0.5 mL) was stirred at 60° C. overnight. The reaction mixture was concentrated, then ethanol (50 mL) and potassium carbonate (10.1 g, 72.8 mmol) were added. The reaction mixture was refluxed for three hours, cooled, and filtered through Celite. The filtrate was concentrated and the resulting residue was partitioned between ethyl acetate and water. The organic layer was washed with brine, dried (Na$_2$SO$_4$), and concentrated. The resulting residue was purified by MPLC eluting with a gradient of 0-5% methanol in dichloromethane to afford (R)-(6-bromo-8-fluoro-3,4-dihydro-2H-benzo[b][1,4]-oxazin-2-yl)methanol (2.23 g, 35%).

Part II—Synthesis (R)-2-((6-Bromo-8-fluoro-3,4-dihydro-2H-benzo[b][1,4]oxazin-2-yl)methyl)isoindoline-1,3-dione

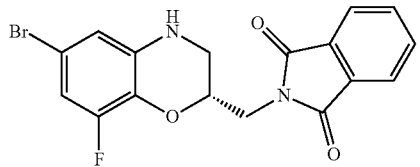 [SMILES: O=C1c2ccccc2C(=O)N1C[C@H]1CNc2cc(Br)cc(F)c2O1]

Diisopropyl azodicarboxylate (2.06 g, 10.2 mmol) was added dropwise to a solution of triphenyl phosphine (2.45 g, 9.36 mmol), phthalamide (1.38 g, 9.36 mmol), and (R)-(6-bromo-8-fluoro-3,4-dihydro-2H-benzo[b][1,4]-oxazin-2-yl)methanol (2.23 g, 8.51 mmol) in THF (30 mL) at 0° C., then warmed to room temperature and stirred overnight. The reaction mixture was concentrated and purified by MPLC eluting with a gradient of 20-100% ethyl acetate in hexanes. The fractions containing the major UV-active component were concentrated and re-purified by MPLC eluting with a gradient of 0-10% methanol in dichloromethane to afford (R)-2-((6-bromo-8-fluoro-3,4-dihydro-2H-benzo[b][1,4]oxazin-2-yl)methyl)isoindoline-1,3-dione (2.95 g) as a yellow solid.

Part III—Synthesis (S)-2-((6-Bromo-8-fluoro-4-((4-fluoro-3-methoxyphenyl)sulfonyl)-3,4-dihydro-2H-benzo[b][1,4]oxazin-2-yl)methyl)isoindoline-1,3-dione

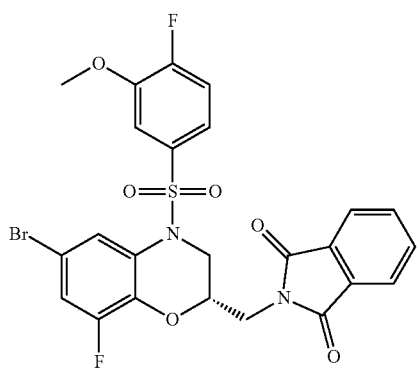 [SMILES: COc1cc(S(=O)(=O)N2C[C@H](CN3C(=O)c4ccccc4C3=O)Oc3c(F)cc(Br)cc32)ccc1F]

4-Fluoro-3-methoxybenzenesulfonyl chloride (287 mg, 1.28 mmol) was added to a solution of (R)-2-((6-bromo-8-fluoro-3,4-dihydro-2H-benzo[b][1,4]oxazin-2-yl)methyl)isoindoline-1,3-dione (500 mg, 1.28 mmol) in pyridine (8 mL), then heated at 50° C. overnight. The reaction mixture was cooled and partitioned between ethyl acetate and 1 M HCl. The organic layer was washed with 1 M HCl, brine, dried ($Na_2SO_4$), and concentrated. The resulting residue was purified by MPLC eluting with a gradient of 10-100% ethyl acetate in hexanes to afford (S)-2-((6-bromo-8-fluoro-4-((4-fluoro-3-methoxyphenyl)sulfonyl)-3,4-dihydro-2H-benzo[b][1,4]oxazin-2-yl)methyl)isoindoline-1,3-dione (290 mg, 39%) as a white solid.

Part IV—Synthesis (S)-(6-Bromo-8-fluoro-4-((4-fluoro-3-methoxyphenyl)sulfonyl)-3,4-dihydro-2H-benzo[b][1,4]oxazin-2-yl)methanamine

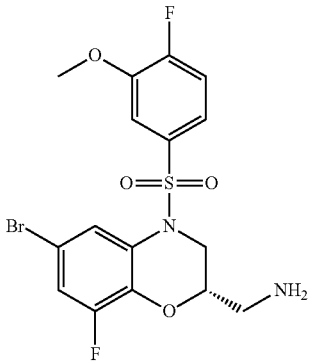 [SMILES: COc1cc(S(=O)(=O)N2C[C@H](CN)Oc3c(F)cc(Br)cc32)ccc1F]

A mixture of (S)-2-((6-bromo-8-fluoro-4-((4-fluoro-3-methoxyphenyl)sulfonyl)-3,4-dihydro-2H-benzo[b][1,4]oxazin-2-yl)methyl)isoindoline-1,3-dione (290 mg, 0.50 mmol) and hydrazine hydrate (125 mg, 2.50 mmol) in ethanol (5 mL) was heated to 60° C. overnight. The reaction mixture was cooled, filtered, and the filtrate concentrated. The residue was partitioned between ethyl acetate and brine. The organic layer was dried ($Na_2SO_4$) and concentrated to afford (S)-(6-bromo-8-fluoro-4-((4-fluoro-3-methoxyphenyl)sulfonyl)-3,4-dihydro-2H-benzo[b][1,4]oxazin-2-yl)methanamine (180 mg, 80%).

Part V—Synthesis (S)—N-((6-Bromo-8-fluoro-4-((4-fluoro-3-methoxyphenyl)sulfonyl)-3,4-dihydro-2H-benzo[b][1,4]oxazin-2-yl)methyl)acetamide

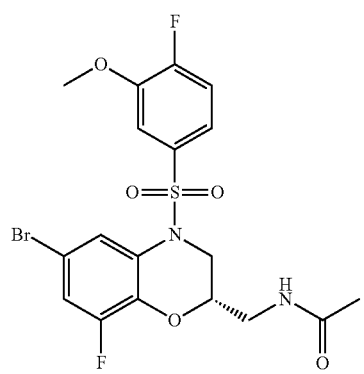 [SMILES: COc1cc(S(=O)(=O)N2C[C@H](CNC(C)=O)Oc3c(F)cc(Br)cc32)ccc1F]

Acetic anhydride (40 mg, 0.4 mmol) was added to a solution of (S)-(6-bromo-8-fluoro-4-((4-fluoro-3-methoxyphenyl)sulfonyl)-3,4-dihydro-2H-benzo[b][1,4]oxazin-2-yl)methanamine (180 mg, 0.40 mmol) in THF (3 mL). The mixture was stirred one hour at room temperature and concentrated. The resulting residue was purified by MPLC eluting with a gradient of 10-100% ethyl acetate in hexanes to afford (S)—N-((6-bromo-8-fluoro-4-((4-fluoro-3-methoxyphenyl)sulfonyl)-3,4-dihydro-2H-benzo[b][1,4]oxazin-2-yl)methyl)acetamide (95 mg, 48%).

Part VI—Synthesis (S,E)-N-((6-(2-(2-Chloro-6-fluorophenyl)prop-1-en-1-yl)-8-fluoro-4-((4-fluoro-3-methoxyphenyl)sulfonyl)-3,4-dihydro-2H-benzo[b][1,4]oxazin-2-yl)methyl)acetamide

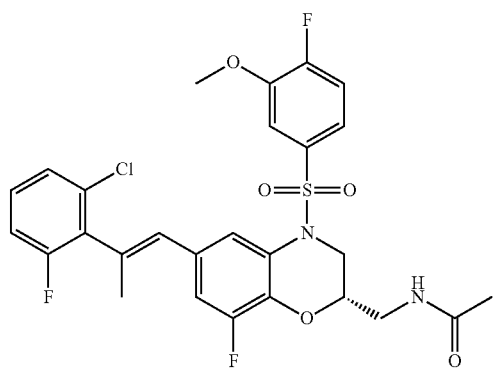

A mixture of (S)—N-((6-bromo-8-fluoro-4-((4-fluoro-3-methoxyphenyl)sulfonyl)-3,4-dihydro-2H-benzo[b][1,4]oxazin-2-yl)methyl)acetamide (90 mg, 0.18 mmol), potassium carbonate (40 mg, 0.27 mmol), [1,1'-bis(diphenylphosphino)ferrocene]dichloropalladium(II) dichloromethane complex (10 mg, 0.02 mmol), (E)-2-(2-(2-chloro-6-fluorophenyl)prop-1-en-1-yl)-4,4,5,5-tetramethyl-1,3,2-dioxaborolane (70 mg, 0.22 mmol) in dioxane (2 mL), and water (0.5 mL) was heated to 80° C. for four hours. The reaction mixture was cooled and partitioned between water and ethyl acetate. The organic layer was washed with brine, dried (Na$_2$SO$_4$), and concentrated. The resulting residue was purified by MPLC eluting with a gradient of ethyl acetate in hexanes to afford (S,E)-N-((6-(2-(2-chloro-6-fluorophenyl)prop-1-en-1-yl)-8-fluoro-4-((4-fluoro-3-methoxyphenyl)sulfonyl)-3,4-dihydro-2H-benzo[b][1,4]oxazin-2-yl)methyl)acetamide (25 mg, 23%) as a white solid. $^1$H-NMR (400 MHz, DMSO-d$_6$) δ 8.10 (t, 1H), 7.60 (s, 1H), 7.44 (m, 1H), 7.37 (m, 3H), 7.24 (m, 2H), 7.14 (dd, 1H), 6.37 (s, 1H), 4.37 (m, 1H), 3.82 (s, 3H), 3.45-3.3 (m, 3H), 3.18 (m, 1H), 2.12 (s, 3H), 1.82 (s, 3H). MS (ESI+) (M+Na)$^+$603.15.

Example 109—Preparation of Additional Substituted Dihydro-2H-benzo[b][1,4]oxazin-2-yl)methyl)acetamides Compounds in Table 13 were prepared based on experimental procedures described in Examples 87, 108, and 132, and the detailed description.

TABLE 13

| No. | Structure | Name | Observed m/z |
|---|---|---|---|
| 109A | 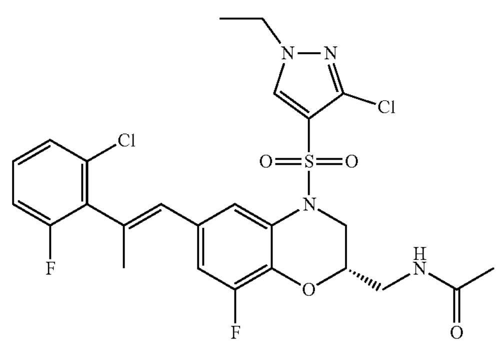 | (S,E)-N-((4-((3-chloro-1-ethyl-1H-pyrazol-4-yl)sulfonyl)-6-(2-(2-chloro-6-fluorophenyl)prop-1-en-1-yl)-8-fluoro-3,4-dihydro-2H-benzo[b][1,4]oxazin-2-yl)methyl)acetamide | 585 (M + H)$^+$ |
| 109B | 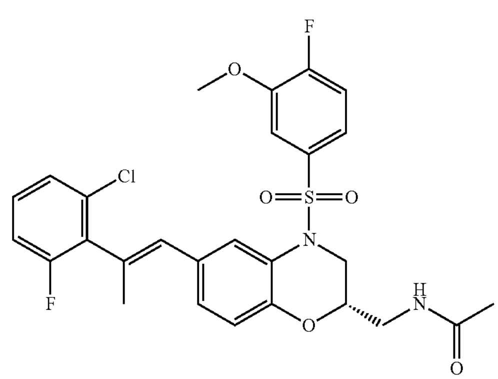 [SMILES: COc1cc(S(=O)(=O)N2C[C@H](CNC(C)=O)Oc3ccc(/C=C(\C)c4c(F)cccc4Cl)cc32)ccc1F] | (S,E)-N-((6-(2-(2-chloro-6-fluorophenyl)prop-1-en-1-yl)-4-((4-fluoro-3-methoxyphenyl)-sulfonyl)-3,4-dihydro-2H-benzo[b][1,4]oxazin-2-yl)methyl)acetamide | 563 (M + H)$^+$ |

TABLE 13-continued

| No. | Structure | Name | Observed m/z |
|---|---|---|---|
| 109C | 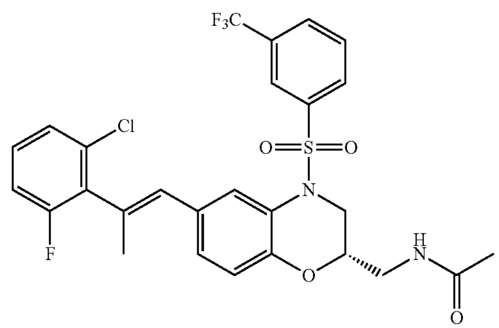 [SMILES: CC(=O)NC[C@H]1CN(S(=O)(=O)c2cccc(C(F)(F)F)c2)c2cc(/C=C(\C)c3c(F)cccc3Cl)ccc2O1] | (S,E)-N-((6-(2-(2-chloro-6-fluorophenyl)prop-1-en-1-yl)-4-((3-(trifluoromethyl)phenyl)-sulfonyl)-3,4-dihydro-2H-benzo[b][1,4]oxazin-2-yl)methyl)acetamide | 583 (M + H)+ |
| 109D | 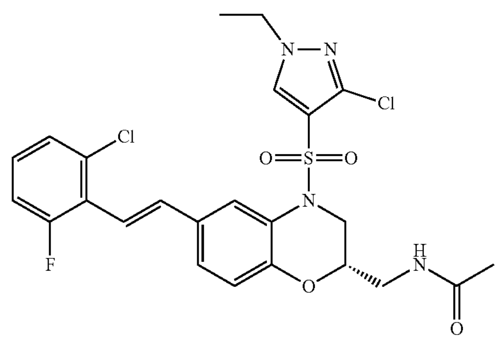 [SMILES: CCn1cc(S(=O)(=O)N2C[C@H](CNC(C)=O)Oc3ccc(/C=C/c4c(F)cccc4Cl)cc32)c(Cl)n1] | (S,E)-N-((4-((3-chloro-1-ethyl-1H-pyrazol-4-yl)sulfonyl)-6-(2-chloro-6-fluorostyryl)-3,4-dihydro-2H-benzo[b][1,4]oxazin-2-yl)methyl)acetamide | 553 (M + H)+ |
| 109E | 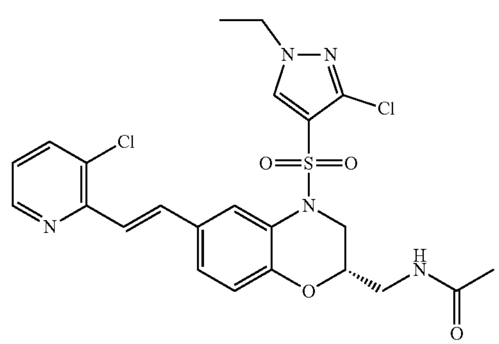 [SMILES: CCn1cc(S(=O)(=O)N2C[C@H](CNC(C)=O)Oc3ccc(/C=C/c4ncccc4Cl)cc32)c(Cl)n1] | (S,E)-N-((4-((3-chloro-1-ethyl-1H-pyrazol-4-yl)sulfonyl)-6-(2-(3-chloropyridin-2-yl)vinyl)-3,4-dihydro-2H-benzo[b][1,4]-oxazin-2-yl)methyl)acetamide | 536 (M + H)+ |
| 109F | 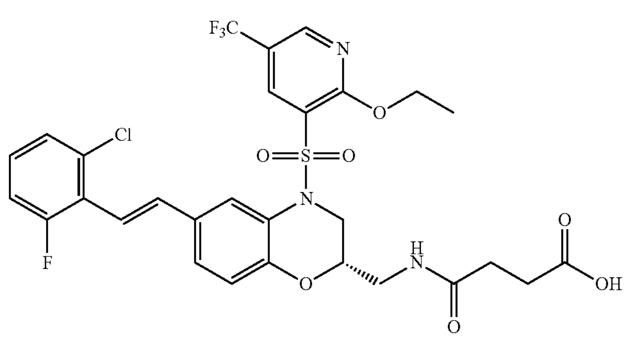 [SMILES: CCOc1ncc(C(F)(F)F)cc1S(=O)(=O)N1C[C@H](CNC(=O)CCC(=O)O)Oc2ccc(/C=C/c3c(F)cccc3Cl)cc21] | (S,E)-4-(((6-(2-chloro-6-fluorostyryl)-4-((2-ethoxy-5-(trifluoro-methyl)pyridin-3-yl)sulfonyl)-3,4-dihydro-2H-benzo[b][1,4]oxazin-2-yl)methyl)amino)-4-oxobutanoic acid | 672 (M + H)+ |

Example 110—Synthesis of tert-Butyl (S,E)-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)carbamate

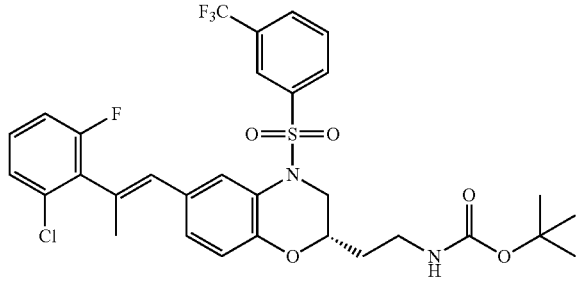 [SMILES: C/C(=C\c1ccc2c(c1)N(S(=O)(=O)c1cccc(C(F)(F)F)c1)C[C@H](CCNC(=O)OC(C)(C)C)O2)c1c(F)cccc1Cl]

Part I—Synthesis of tert-Butyl (S)-(2-(6-bromo-4-((3-(trifluoromethyl)phenyl)sulfonyl)-3,4-dihydro-2H-benzo[b][1,4]oxazin-2-yl)ethyl)carbamate

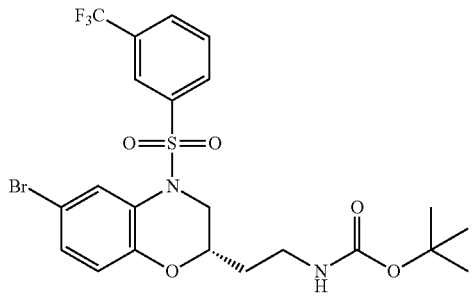 [SMILES: CC(C)(C)OC(=O)NCC[C@H]1CN(S(=O)(=O)c2cccc(C(F)(F)F)c2)c2cc(Br)ccc2O1]

Diphenylphosphoryl azide (1.23 g, 4.47 mmol) was added to a mixture of (S)-3-(6-bromo-4-((3-(trifluoromethyl)phenyl)sulfonyl)-3,4-dihydro-2H-benzo[b][1,4]oxazin-2-yl)propanoic acid (1.84 g, 3.72 mmol), dioxane (24 mL), tert-butyl alcohol (1.38 g, 18.6 mmol) and triethylamine (0.83 g, 8.19 mmol) at room temperature. The mixture was heated to 100° C. for three hours, then cooled, filtered, and partitioned between ethyl acetate and 1 M HCl. The organic layer was dried (Na$_2$SO$_4$) and concentrated. The resulting residue was purified by MPLC eluting with a gradient of 0-50% ethyl acetate in hexanes to afford tert-butyl (S)-(2-(6-bromo-4-((3-(trifluoromethyl)phenyl)sulfonyl)-3,4-dihydro-2H-benzo[b][1,4]oxazin-2-yl)ethyl)carbamate (0.40 g, 19%) as a white solid.

Part II—Synthesis of tert-Butyl (S,E)-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)carbamate

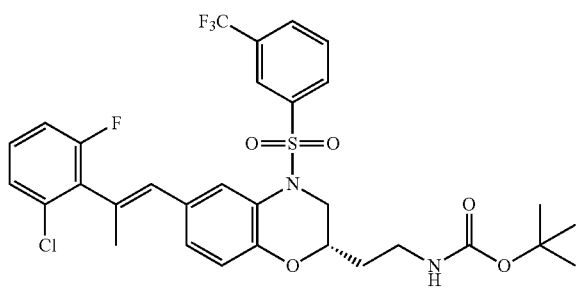 [SMILES: C/C(=C\c1ccc2c(c1)N(S(=O)(=O)c1cccc(C(F)(F)F)c1)C[C@H](CCNC(=O)OC(C)(C)C)O2)c1c(F)cccc1Cl]

A mixture of tert-butyl (S)-(2-(6-bromo-4-((3-(trifluoromethyl)phenyl)sulfonyl)-3,4-dihydro-2H-benzo[b][1,4]oxazin-2-yl)ethyl)carbamate (400 mg, 0.71 mmol), potassium carbonate (160 mg, 1.13 mmol), [1,1'-bis(diphenylphosphino)ferrocene]dichloropalladium(II) dichloromethane complex (50 mg, 0.07 mmol), (E)-2-(2-(2-chloro-6-fluorophenyl)prop-1-en-1-yl)-4,4,5,5-tetramethyl-1,3,2-dioxaborolane (340 mg, 1.13 mmol) in dioxane (15 mL) and water (3 mL) was heated to 70° C. overnight. The reaction mixture was cooled and partitioned between saturated ammonium chloride and ethyl acetate. The organic layer was washed with brine, dried (Na$_2$SO$_4$), and concentrated. The resulting residue was purified by MPLC eluting with a gradient of 0-60% ethyl acetate in hexanes to afford tert-butyl (S,E)-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)carbamate (290 mg, 61%) as a white solid. $^1$H-NMR (400 MHz, DMSO-d$_6$) δ 8.10 (m, 2H), 8.02 (s, 1H), 7.86 (t, 1H), 7.65 (s, 1H), 7.37 (m, 2H), 7.26 (m, 1H), 7.10 (d, 1H), 6.85 (m, 2H), 6.36 (s, 1H), 4.35 (d, 1H), 3.61 (m, 1H), 3.42 (m, 1H), 3.0 (m, 2H), 2.06 (s, 3H), 1.72 (m, 2H), 1.34 (s, 9H). MS (ESI+) (M+Na)$^+$677.32.

Example 111—Synthesis of (S,E)-2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine

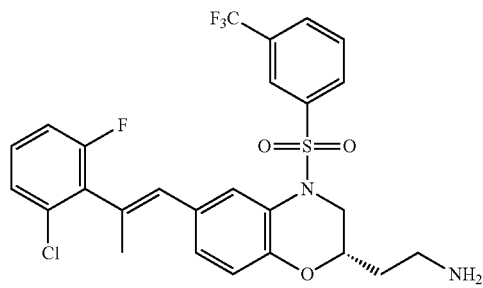 [SMILES: C/C(=C\c1ccc2c(c1)N(S(=O)(=O)c1cccc(C(F)(F)F)c1)C[C@H](CCN)O2)c1c(F)cccc1Cl]

A mixture of tert-butyl (S,E)-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)carbamate (270 mg, 0.41 mmol) in 4 M HCl in dioxane (4 mL) was stirred at room temperature for one hour, then concentrated to afford (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine as the hydrochloride salt (240 mg) as white solid. $^1$H-NMR (400 MHz, DMSO-d$_6$) δ 8.12 (m, 3H), 7.88 (t, 1H), 7.79 (br s, 2H), 7.59 (s, 1H), 7.37 (m, 2H), 7.27 (m, 1H), 7.10 (d, 1H), 6.88 (m, 1H), 6.36 (s, 1H), 4.40 (dd, 1H), 3.88 (m, 1H), 3.55 (m, 1H), 2.94 (m, 2H), 2.04 (s, 3H), 1.98 (m, 1H), 1.84 (m, 1H). MS (ESI+) (M+H)$^+$555.18.

Example 112—Synthesis of (S,E)-N-(2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)acetamide

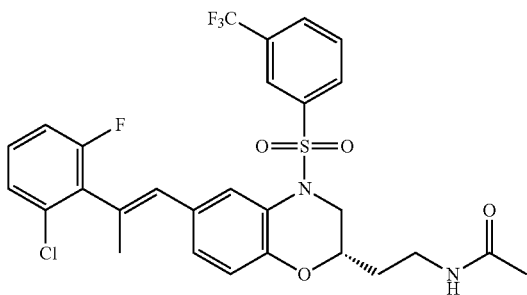 [SMILES: CC(=O)NCC[C@H]1CN(S(=O)(=O)c2cccc(C(F)(F)F)c2)c2cc(/C=C(\C)c3c(F)cccc3Cl)ccc2O1]

Acetic anhydride (10 mg, 0.09 mmol) was added to a solution of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine hydrochloride salt (40 mg, 0.078 mmol), N,N-diisopropylethylamine (30 mg, 0.23 mmol), and THF (0.5 mL). The mixture was stirred for one hour and concentrated. The resulting residue was purified by MPLC eluting with a gradient of 0-60% ethyl acetate in hexanes to afford (S,E)-N-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)acetamide (32 mg, 68%) as a white solid. $^1$H-NMR (400 MHz, DMSO-$d_6$) δ 8.10 (m, 2H), 8.01 (s, 1H), 7.87 (m, 2H), 7.66 (s, 1H), 7.37 (m, 2H), 7.27 (m, 1H), 7.09 (dd, 1H), 6.88 (d, 1H), 6.37 (s, 1H), 4.36 (m, 1H), 3.60 (m, 1H), 3.42 (m, 1H), 3.20 (m, 1H), 3.18 (m, 1H), 2.07 (s, 3H), 1.78 (s, 3H), 1.73 (m, 1H), 1.65 (m, 1H). MS (ESI+) (M+Na)$^+$619.13.

Example 113—Synthesis of (S,E)-N-(2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)cyclopropanecarboxamide

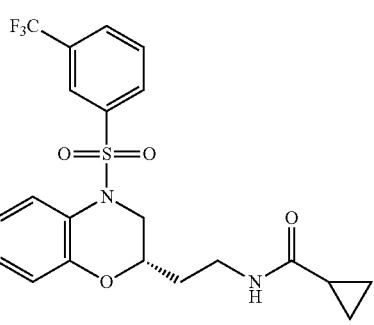

Cyclopropanecarbonyl chloride (10 mg, 0.09 mmol) was added to a solution of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine hydrochloride salt (40 mg, 0.078 mmol), N,N-diisopropylethylamine (30 mg, 0.23 mmol), and THF (0.5 mL). The mixture was stirred for one hour and concentrated. The resulting residue was purified by MPLC eluting with a gradient of 0-60% ethyl acetate in hexanes to afford (S,E)-N-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)cyclopropanecarboxamide (16 mg, 34%) as a white solid. $^1$H-NMR (400 MHz, DMSO-$d_6$) δ 8.10 (m, 3H), 7.99 (s, 1H), 7.86 (t, 1H), 7.66 (s, 1H), 7.37 (m, 2H), 7.27 (m, 1H), 7.10 (dd, 1H), 6.88 (d, 1H), 6.37 (s, 1H), 4.36 (m, 1H), 3.60 (m, 1H), 3.42 (m, 1H), 3.22 (m, 1H), 3.13 (m, 1H), 2.07 (s, 3H), 1.8-1.6 (m, 2H), 1.51 (m, 1H), 0.63 (m, 4H). MS (ESI+) (M+Na)$^+$645.17.

Example 114—Synthesis of (S,E)-N-(2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)methanesulfonamide

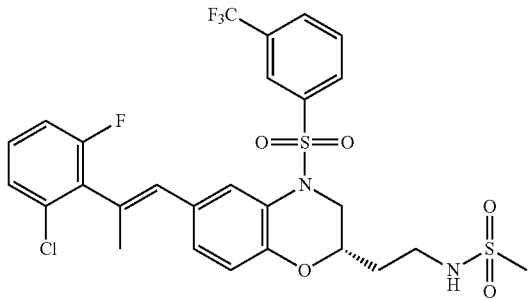 [SMILES: C/C(=C\c1ccc2c(c1)N(S(=O)(=O)c1cccc(C(F)(F)F)c1)C[C@H](CCNS(C)(=O)=O)O2)c1c(F)cccc1Cl]

Methanesulfonic acid anhydride (10 mg, 0.08 mmol) was added to a solution of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine hydrochloride salt (40 mg, 0.078 mmol), N,N-diisopropylethylamine (30 mg, 0.23 mmol), and THF (0.5 mL). The mixture was stirred for one hour and concentrated. The resulting residue was purified by MPLC eluting with a gradient of 0-60% ethyl acetate in hexanes to afford (S,E)-N-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)methanesulfonamide (20 mg, 46%) as a white solid. $^1$H-NMR (400 MHz, DMSO-$d_6$) δ 8.11 (m, 2H), 7.98 (s, 1H), 7.87 (t, 1H), 7.66 (s, 1H), 7.38 (m, 2H), 7.28 (m, 1H), 7.10 (dd, 1H), 7.04 (m, 1H), 6.89 (d, 1H), 6.37 (s, 1H), 4.39 (m, 1H), 3.67 (m, 1H), 3.45 (m, 1H), 3.05 (m, 2H), 2.97 (m, 3H), 2.07 (s, 3H), 1.83-1.70 (m, 2H). MS (ESI+) (M+Na)$^+$655.13.

Example 115—Synthesis of (S,E)-N-(2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-2-hydroxy-2-methylpropanamide

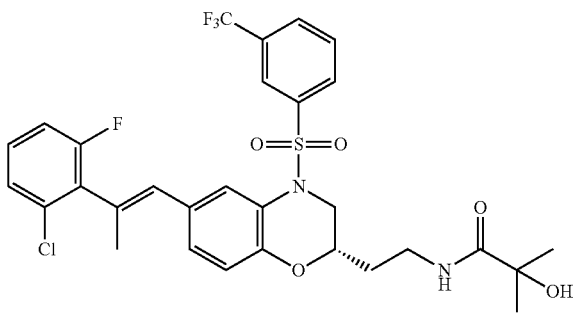 [SMILES: C/C(=C\c1ccc2c(c1)N(S(=O)(=O)c1cccc(C(F)(F)F)c1)C[C@H](CCNC(=O)C(C)(C)O)O2)c1c(F)cccc1Cl]

Benzotriazol-1-yl-oxytripyrrolidinophosphonium hexafluorophosphate (120 mg, 0.23 mmol) was added to a solution of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethan-1-amine hydrochloride salt (90 mg, 0.15 mmol), N,N-diisopropylethylamine (40 mg, 0.31 mmol), 2-hydroxy-2-methylpropanoic acid (20 mg, 0.23 mmol) and DMF (2 mL). The mixture was stirred for three hours. The mixture was partitioned between ethyl acetate and 1 M HCl. The organic layer was washed with water, brine, dried (Na$_2$SO$_4$) and concentrated. The resulting residue was purified by MPLC eluting with a gradient of 0-60% ethyl acetate in hexanes to afford (S,E)-N-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-2-hydroxy-2-methylpropanamide (60 mg, 59%) as a white solid. $^1$H-NMR (400 MHz, DMSO-d$_6$) δ 8.12 (m, 2H), 8.01 (s, 1H), 7.87 (t, 1H), 7.77 (t, 1H), 7.65 (s, 1H), 7.38 (m, 2H), 7.27 (m, 1H), 7.10 (dd, 1H), 6.88 (d, 1H), 6.36 (s, 1H), 5.31 (s, 1H), 4.36 (m, 1H), 3.64 (m, 1H), 3.45 (m, 1H), 3.18 (m, 2H), 2.06 (s, 3H), 1.83-1.70 (m, 2H), 1.21 (m, 6H). MS (ESI+) (M+Na)$^+$663.36.

Example 116—Preparation of Additional Benzoxazines and Tetrahydroquinolines Substituted with an N-Linked Amide, Urea, Carbamate or Sulfonamide Compounds in Table 14 were prepared based on experimental procedures described in Examples 42, 110-115, and 147, and the detailed description.

TABLE 14

| No. | Structure | Name | Observed m/z |
|---|---|---|---|
| 116A | 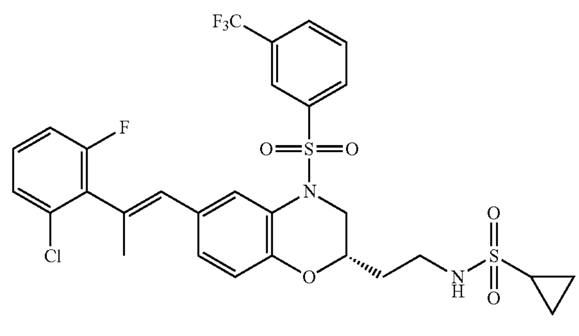 [SMILES: C/C(=C\c1ccc2c(c1)N(S(=O)(=O)c1cccc(C(F)(F)F)c1)C[C@H](CCNS(=O)(=O)C1CC1)O2)c1c(F)cccc1Cl] | (S,E)-N-(2-(6-(2-(2-chloro-6-fluorophenyl)prop-1-en-1-yl)-4-((3-(trifluoromethyl)phenyl)-sulfonyl)-3,4-dihydro-2H-benzo[b][1,4]oxazin-2-yl)ethyl)cyclopropane-sulfonamide | 659 (M + H)$^+$ |
| 116B | 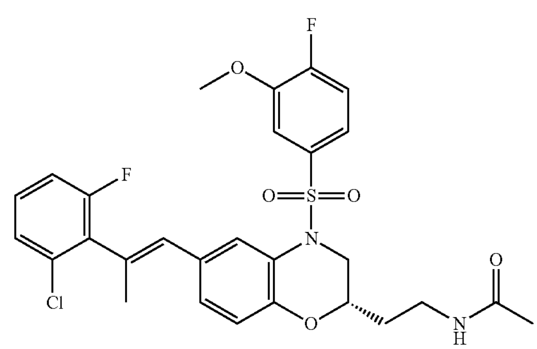 [SMILES: COc1cc(S(=O)(=O)N2C[C@H](CCNC(C)=O)Oc3ccc(/C=C(\C)c4c(F)cccc4Cl)cc32)ccc1F] | (S,E)-N-(2-(6-(2-(2-chloro-6-fluorophenyl)prop-1-en-1-yl)-4-((4-fluoro-3-methoxyphenyl)-sulfonyl)-3,4-dihydro-2H-benzo[b][1,4]oxazin-2-yl)ethyl)acetamide | 577 (M + H)$^+$ |

TABLE 14-continued

| No. | Structure | Name | Observed m/z |
|---|---|---|---|
| 116C | 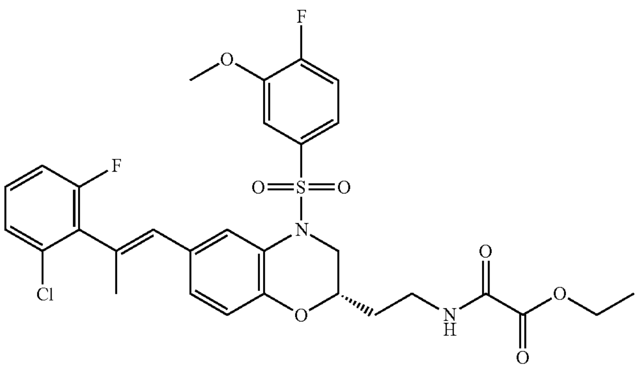 [SMILES: CCOC(=O)C(=O)NCC[C@H]1CN(S(=O)(=O)c2ccc(F)c(OC)c2)c2cc(/C=C(\C)c3c(F)cccc3Cl)ccc2O1] | ethyl (S,E)-2-((2-(6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)ethyl)amino)-2-oxoacetate | 635 (M + H)+ |
| 116D | 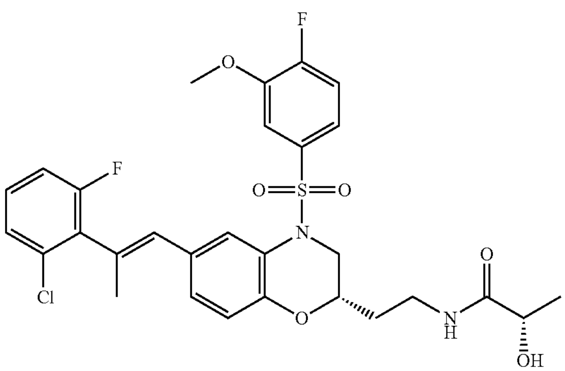 [SMILES: COc1cc(S(=O)(=O)N2C[C@H](CCNC(=O)[C@H](C)O)Oc3ccc(/C=C(\C)c4c(F)cccc4Cl)cc32)ccc1F] | (S)-N-(2-((S)-6-((E)-2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)ethyl)-2-hydroxypropanamide | 607 (M + H)+ |
| 116E | 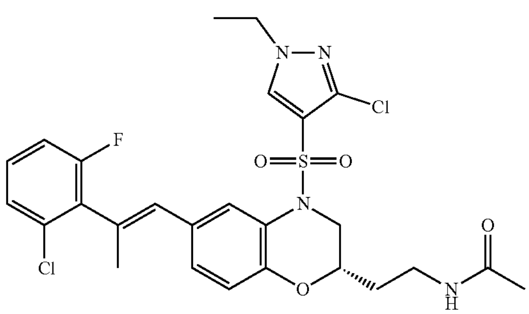 [SMILES: CCn1cc(S(=O)(=O)N2C[C@H](CCNC(C)=O)Oc3ccc(/C=C(\C)c4c(F)cccc4Cl)cc32)c(Cl)n1] | (S,E)-N-(2-(4-((3-chloro-1-ethyl-1H-pyrazol-4-yl)sulfonyl)-6-(2-(2-chloro-6-fluorophenyl)-prop-1-en-1-yl)-3,4-dihydro-2H-benzo[b][1,4]oxazin-2-yl)ethyl)acetamide | 581 (M + H)+ |
| 116F | 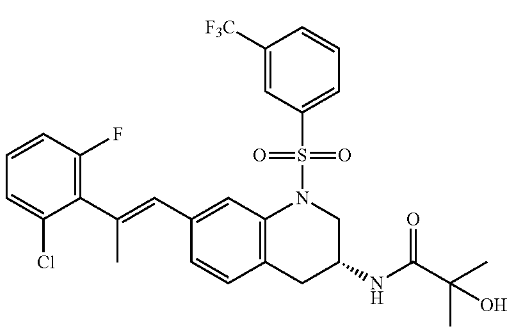 [SMILES: C/C(=C\c1ccc2c(c1)N(S(=O)(=O)c1cccc(C(F)(F)F)c1)C[C@H](NC(=O)C(C)(C)O)C2)c1c(F)cccc1Cl] | (R,E)-N-(7-(2-(2-chloro-6-fluorophenyl)prop-1-en-1-yl)-1-((3-(trifluoromethyl)-phenyl)sulfonyl)-1,2,3,4-tetrahydroquinolin-3-yl)-2-hydroxy-2-methylpropanamide | 611 (M + H)+ |

TABLE 14-continued

| No. | Structure | Name | Observed m/z |
|---|---|---|---|
| 116G | 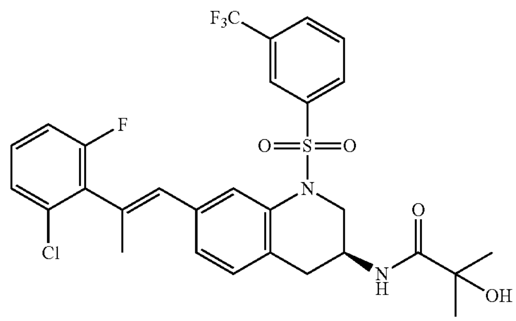 [SMILES: C/C(=C\c1ccc2c(c1)N(S(=O)(=O)c1cccc(C(F)(F)F)c1)C[C@@H](NC(=O)C(C)(C)O)C2)c1c(F)cccc1Cl] | (S,E)-N-(7-(2-(2-chloro-6-fluorophenyl)prop-1-en-1-yl)-1-((3-(trifluoromethyl)-phenyl)sulfonyl)-1,2,3,4-tetrahydroquinolin-3-yl)-2-hydroxy-2-methylpropanamide | 611 (M + H)+ |
| 116H | 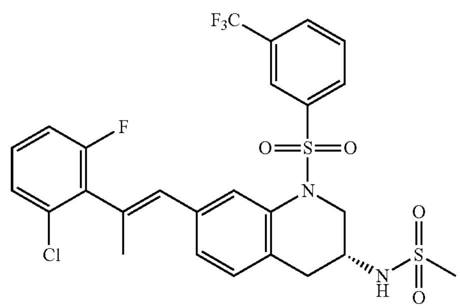 [SMILES: C/C(=C\c1ccc2c(c1)N(S(=O)(=O)c1cccc(C(F)(F)F)c1)C[C@H](NS(C)(=O)=O)C2)c1c(F)cccc1Cl] | (R,E)-N-(7-(2-(2-chloro-6-fluorophenyl)prop-1-en-1-yl)-1-((3-(trifluoromethyl)phenyl)-sulfonyl)-1,2,3,4-tetrahydroquinolin-3-yl)methanesulfonamide | 603 (M + H)+ |
| 116I | 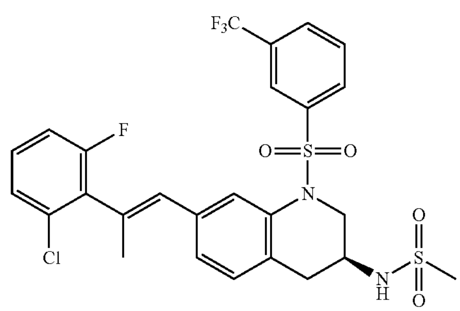 [SMILES: C/C(=C\c1ccc2c(c1)N(S(=O)(=O)c1cccc(C(F)(F)F)c1)C[C@@H](NS(C)(=O)=O)C2)c1c(F)cccc1Cl] | (S,E)-N-(7-(2-(2-chloro-6-fluorophenyl)prop-1-en-1-yl)-1-((3-(trifluoromethyl)phenyl)-sulfonyl)-1,2,3,4-tetrahydroquinolin-3-yl)methanesulfonamide | 603 (M + H)+ |
| 116J | 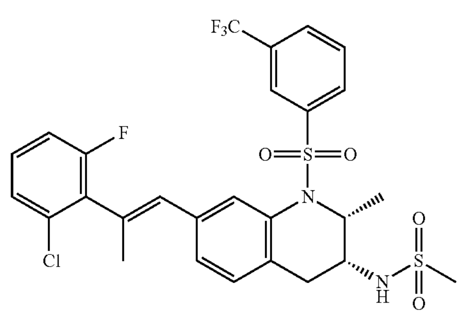 [SMILES: C/C(=C\c1ccc2c(c1)N(S(=O)(=O)c1cccc(C(F)(F)F)c1)[C@H](C)[C@H](NS(C)(=O)=O)C2)c1c(F)cccc1Cl] | N-((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)methanesulfonamide | 617 (M + H)+ |

TABLE 14-continued

| No. | Structure | Name | Observed m/z |
|---|---|---|---|
| 116K | 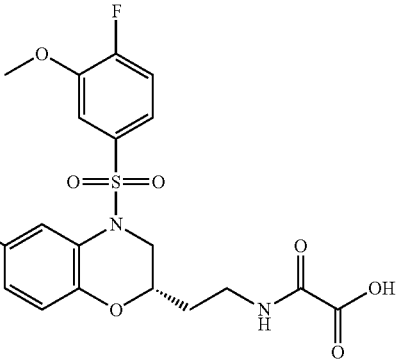 | (S,E)-2-((2-(6-(2-(2-chloro-6-fluorophenyl)prop-1-en-1-yl)-4-((4-fluoro-3-methoxyphenyl)sulfonyl)-3,4-dihydro-2H-benzo[b][1,4]-oxazin-2-yl)ethyl)amino)-2-oxoacetic acid | 607 (M + H)+ |
| 116L | 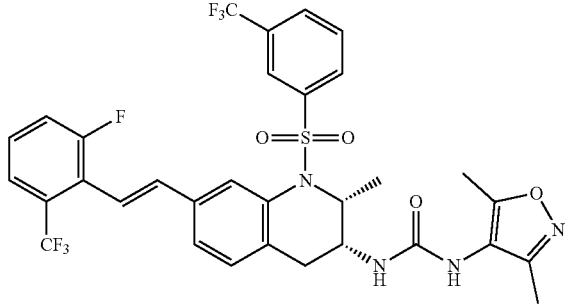 [SMILES: Cc1noc(C)c1NC(=O)N[C@@H]1Cc2ccc(/C=C/c3c(F)cccc3C(F)(F)F)cc2N(S(=O)(=O)c2cccc(C(F)(F)F)c2)[C@@H]1C] | 1-(3,5-dimethylisoxazol-4-yl)-3-((2R,3R)-7-((E)-2-fluoro-6-(trifluoromethyl)styryl)-2-methyl-1-((3-(trifluoromethyl)phenyl)sulfonyl)-1,2,3,4-tetrahydroquinolin-3-yl)urea | 697 (M + H)+ |
| 116M | 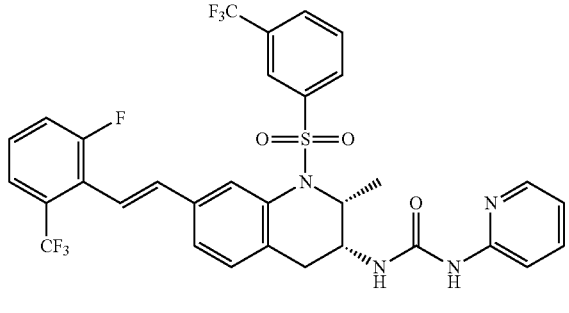 [SMILES: C[C@@H]1[C@H](NC(=O)Nc2ccccn2)Cc2ccc(/C=C/c3c(F)cccc3C(F)(F)F)cc2N1S(=O)(=O)c1cccc(C(F)(F)F)c1] | 1-((2R,3R)-7-((E)-2-fluoro-6-(trifluoromethyl)styryl)-2-methyl-1-((3-(trifluoromethyl)phenyl)sulfonyl)-1,2,3,4-tetrahydroquinolin-3-yl)-3-(pyridin-2-yl)urea | 679 (M + H)+ |
| 116N | 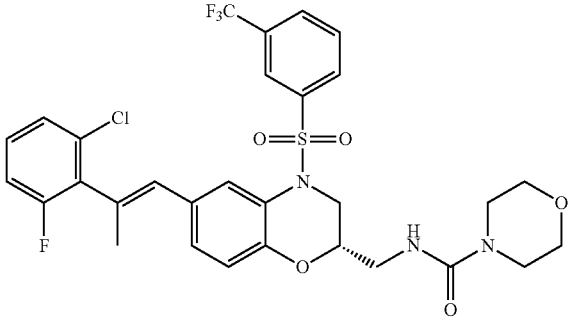 [SMILES: C/C(=C\c1ccc2c(c1)N(S(=O)(=O)c1cccc(C(F)(F)F)c1)C[C@H](CNC(=O)N1CCOCC1)O2)c1c(F)cccc1Cl] | (S,E)-N-((6-(2-(2-chloro-6-fluorophenyl)prop-1-en-1-yl)-4-((3-(trifluoromethyl)phenyl)sulfonyl)-3,4-dihydro-2H-benzo[b][1,4]-oxazin-2-yl)methyl)morpholine-4-carboxamide | 654 (M + H)+ |

TABLE 14-continued

| No. | Structure | Name | Observed m/z |
|---|---|---|---|
| 116O | 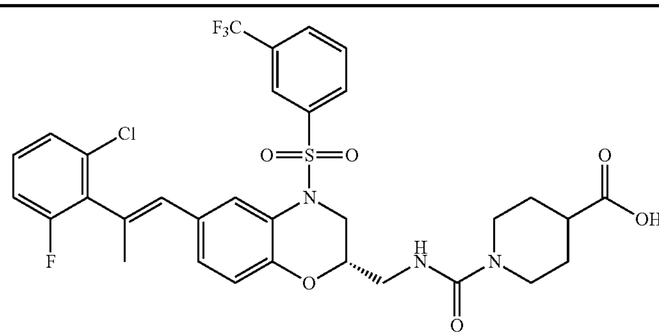 | (S,E)-1-(((6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)methyl)carbamoyl)piperidine-4-carboxylic acid | 696 (M + H)+ |
| 116P | 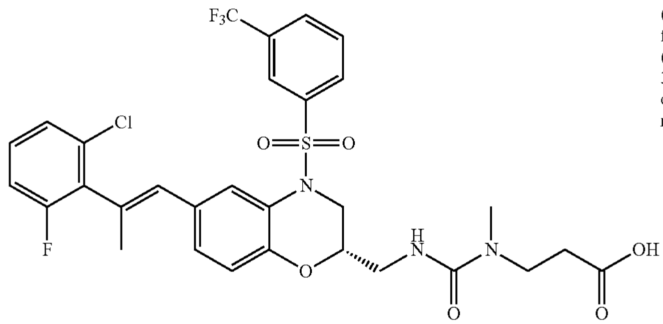 [SMILES: C/C(=C\c1ccc2c(c1)N(S(=O)(=O)c1cccc(C(F)(F)F)c1)C[C@H](CNC(=O)N(C)CCC(=O)O)O2)c1c(F)cccc1Cl] | (S,E)-3-(3-((6-(2-(2-chloro-6-fluorophenyl)prop-1-en-1-yl)-4-((3-(trifluoromethyl)phenyl)sulfonyl)-3,4-dihydro-2H-benzo[b][1,4]-oxazin-2-yl)methyl)-1-methlyureido)propanoic acid | 670 (M + H)+ |

Example 117-Synthesis of (S,E)-6-(2-(2-Chloro-6-fluorophenyl)prop-1-en-1-yl)-2-(3-(pyrrolidin-1-yl)propyl)-4-((3-(trifluoromethyl)phenyl)sulfonyl)-3,4-dihydro-2H-benzo[b][1,4]oxazine

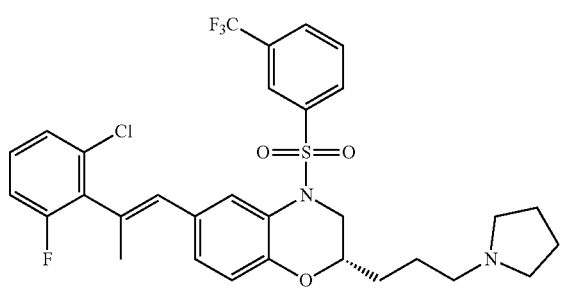 [SMILES: C/C(=C\c1ccc2c(c1)N(S(=O)(=O)c1cccc(C(F)(F)F)c1)C[C@H](CCCN1CCCC1)O2)c1c(F)cccc1Cl]

Part I—Synthesis of (S)-3-(6-Bromo-3,4-dihydro-2H-benzo[b][1,4]oxazin-2-yl)propan-1-ol

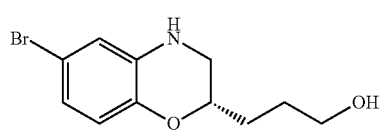 [SMILES: OCCC[C@H]1CNc2cc(Br)ccc2O1]

To (S)-3-(6-bromo-3-oxo-3,4-dihydro-2H-benzo[b][1,4]oxazin-2-yl)propanoate (6.4 g, 20.4 mmol) in anhydrous tetrahydrofuran (60 mL) was added borane-methyl sulfide complex (8.2 mL, 82 mmol) and the mixture was heated to 50° C. for 2 hours. The reaction mixture was cooled to ambient temperature, then carefully quenched with methanol (25 mL) and heated to 60° C. for 20 minutes. The mixture was concentrated, then redissolved in ethyl acetate, washed with water, then brine, dried (Na$_2$SO$_4$) and concentrated to an oil. The mixture was purified by column chromatography eluting with a gradient of 5-100% ethyl acetate in hexanes. Fractions containing (S)-3-(6-bromo-3,4-dihydro-2H-benzo[b][1,4]oxazin-2-yl)propan-1-ol were combined and concentrated to give a solid. (2.77 g, 50%).

Part II—Synthesis of (S)-6-Bromo-2-(3-((tert-butyldimethylsilyl)oxy)propyl)-3,4-dihydro-2H-benzo[b][1,4]oxazine

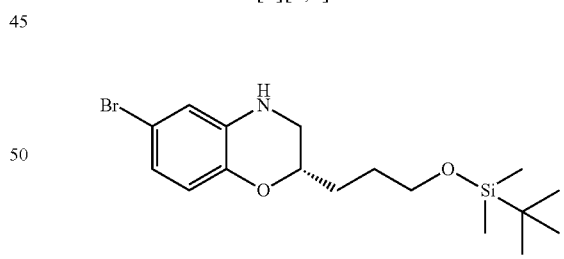

To a solution of (S)-3-(6-bromo-3,4-dihydro-2H-benzo[b][1,4]oxazin-2-yl)propan-1-ol (3.50 g, 12.9 mmol) in dichloromethane (40 mL) was added diisopropylethylamine (2.49 g, 19.3 mmol), tert-butyldimethylchlorosilane (2.33 g, 15.4 mmol), and 4-dimethylaminopyridine (0.157 g, 1.29 mmol). The mixture was stirred at room temperature overnight. The mixture was washed with aqueous 10% citric acid. The organic layer was dried (Na$_2$SO$_4$), and concentrated. The resulting residue was purified via MPLC eluting with a gradient of ethyl acetate in hexanes to afford (S)-6-bromo-2-(3-((tert-butyldimethylsilyl)oxy)propyl)-3,4-dihydro-2H-benzo[b][1,4]oxazine (3.80 g, 76%).

Part III—Synthesis of (S)-6-Bromo-2-(3-((tert-butyldimethylsilyl)oxy)propyl)-4-((3-(trifluoromethyl)phenyl)sulfonyl)-3,4-dihydro-2H-benzo[b][1,4]oxazine

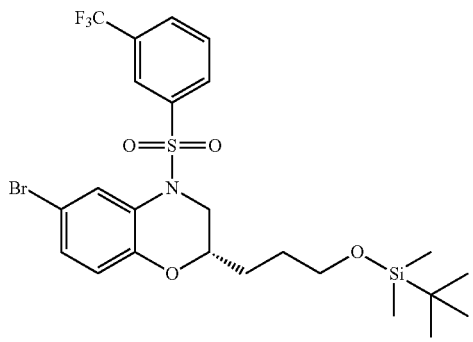 [SMILES: CC(C)(C)[Si](C)(C)OCCC[C@H]1CN(S(=O)(=O)c2cccc(C(F)(F)F)c2)c2cc(Br)ccc2O1]

To a solution of (S)-6-bromo-2-(3-((tert-butyldimethylsilyl)oxy)propyl)-3,4-dihydro-2H-benzo[b][1,4]oxazine (1.80 g, 4.67 mmol) in pyridine (15 mL) was added 3-(trifluoromethyl)benzenesulfonyl chloride (1.37 g, 5.59 mmol). The mixture was stirred at 50° C. for two hours, cooled, and partitioned between ethyl acetate and 1 M HCl. The organic layer was washed three times with 1 M HCl, then brine, and dried (Na$_2$SO$_4$). Charcoal was added to the mixture, slurried, and filtered through Celite. The filtrate was concentrated and the resulting residue was purified by MPLC eluting with a gradient of ethyl acetate in hexanes to afford (S)-6-bromo-2-(2-((tert-butyldimethylsilyl)oxy)ethyl)-4-((3-(trifluoromethyl)phenyl)sulfonyl)-3,4-dihydro-2H-benzo[b][1,4]oxazine (2.45 g, 88%).

Part IV—Synthesis of (S,E)-2-(3-((tert-Butyldimethylsilyl)oxy)propyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

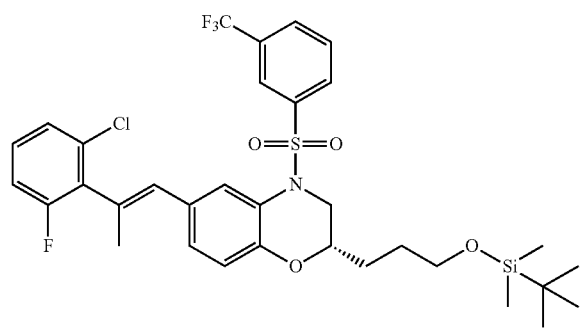 [SMILES: C/C(=C\c1ccc2c(c1)N(S(=O)(=O)c1cccc(C(F)(F)F)c1)C[C@H](CCCO[Si](C)(C)C(C)(C)C)O2)c1c(F)cccc1Cl]

To a degassed mixture of (S)-6-bromo-2-(2-((tert-butyldimethylsilyl)oxy)ethyl)-4-((3-(trifluoromethyl)phenyl)sulfonyl)-3,4-dihydro-2H-benzo[b][1,4]oxazine (2.45 g, 4.12 mmol), potassium carbonate (800 mg, 5.77 mmol), (E)-2-(2-(2-chloro-6-fluorophenyl)prop-1-en-1-yl)-4,4,5,5-tetramethyl-1,3,2-dioxaborolane (1.71 g, 5.77 mmol), dioxane (30 mL) and water (5 mL) was added [1,1'-bis(diphenylphosphino)ferrocene]dichloropalladium(II) dichloromethane complex (0.31 g, 0.41 mmol). The mixture was heated to 70° C. for five hours. The mixture was cooled, then partitioned between ethyl acetate and saturated aqueous ammonium chloride. The organic layer was washed with brine, dried (Na$_2$SO$_4$), and then concentrated. The resulting residue was purified by MPLC eluting with a gradient of 0-50% ethyl acetate in hexanes to afford (S,E)-2-(3-((tert-butyldimethylsilyl)oxy)propyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (2.47 g, 88%).

Part V—Synthesis of (S,E)-3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propan-1-ol

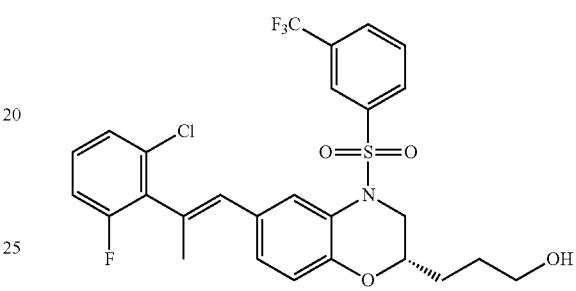

To a solution of (S,E)-2-(3-((tert-Butyldimethylsilyl)oxy)propyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (2.47 g, 3.61 mmol) in THF (24 mL) was added a 1 M solution of tetrabutylammonium fluoride (1.42 g, 5.41 mmol) in THF (5.41 mL). The mixture was stirred for one hour, then concentrated onto a small amount of silica gel. The residue was purified by MPLC eluting with a gradient of 0-100% ethyl acetate in hexanes to afford (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propan-1-ol (1.75 g, 85%).

Part VI—Synthesis of (S,E)-3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propyl methanesulfonate

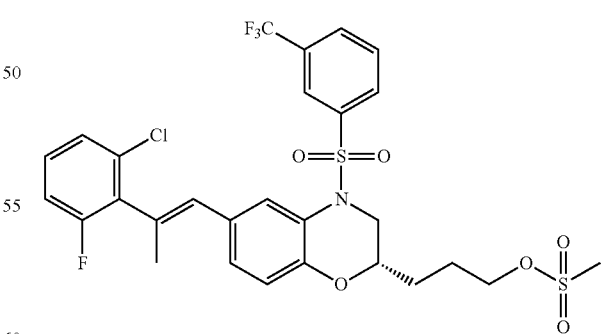

Methanesulfonic anhydride (240 mg, 1.39 mmol) was added to a solution of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propan-1-ol (0.53 g, 0.93 mmol) and diisopropylethylamine (0.24 g, 1.86 mmol) in dichloromethane (10 mL) at 0° C. The mixture was stirred at room temperature for two hours, then partitioned between dichloromethane and 1 M HCl. The organic layer was dried (Na$_2$SO$_4$) and concentrated to afford (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propyl methanesulfonate (0.58 g, 96%).

Part VII—Synthesis of (S,E)-6-(2-(2-Chloro-6-fluorophenyl)prop-1-en-1-yl)-2-(3-(pyrrolidin-1-yl)propyl)-4-((3-(trifluoromethyl)phenyl)sulfonyl)-3,4-dihydro-2H-benzo[b][1,4]oxazine

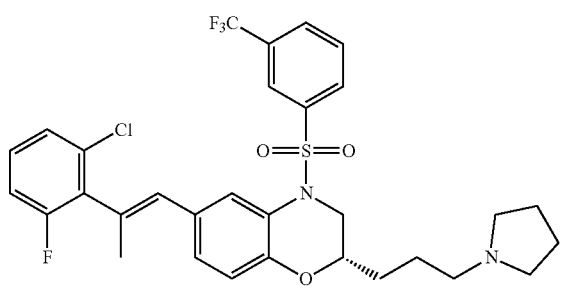 [SMILES: C/C(=C\c1ccc2c(c1)N(S(=O)(=O)c1cccc(C(F)(F)F)c1)C[C@H](CCCN1CCCC1)O2)c1c(F)cccc1Cl]

Pyrrolidine (22 mg, 0.31 mmol) was added to a solution of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propyl methanesulfonate (50 mg, 0.077 mmol) in DMF (0.5 mL). The mixture was stirred at 70° C. overnight, cooled, and concentrated. The resulting residue was purified by MPLC eluting with a gradient of 0-5% methanol in dichloromethane to afford (S,E)-6-(2-(2-chloro-6-fluorophenyl)prop-1-en-1-yl)-2-(3-(pyrrolidin-1-yl)propyl)-4-((3-(trifluoromethyl)phenyl)sulfonyl)-3,4-dihydro-2H-benzo[b][1,4]oxazine (29 mg, 57%). $^1$H-NMR (400 MHz, CDCl$_3$) δ 8.05 (m, 1H), 7.84 (br m, 2H), 7.62 (t, 1H), 7.28-7.16 (m, 3H), 7.12 (dd, 1H), 7.02 (t, 1H), 6.82 (d, 1H), 6.38 (s, 1H), 4.34 (m, 1H), 3.45 (m, 1H), 3.22 (m, 1H), 2.70-2.50 (br m, 6H), 2.18 (s, 3H), 1.84 (br m, 4H), 1.7-1.5 (br m, 4H). MS (ESI+) (M+H)$^+$623.37.

Example 118—Synthesis of (S,E)-6-(2-(2-Chloro-6-fluorophenyl)prop-1-en-1-yl)-2-(2-(pyrrolidin-1-yl)ethyl)-4-((3-(trifluoromethyl)phenyl)sulfonyl)-3,4-dihydro-2H-benzo[b][1,4]oxazine

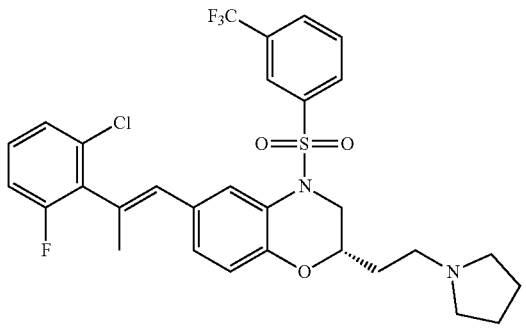 [SMILES: C/C(=C\c1ccc2c(c1)N(S(=O)(=O)c1cccc(C(F)(F)F)c1)C[C@H](CCN1CCCC1)O2)c1c(F)cccc1Cl]

Part I—Synthesis of (S)-6-Bromo-2-(2-((tert-butyldimethylsilyl)oxy)ethyl)-4-((3-(trifluoromethyl)phenyl)sulfonyl)-3,4-dihydro-2H-benzo[b][1,4]oxazine

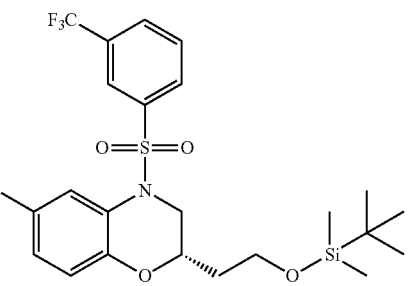

To a solution of (S)-2-(6-bromo-4-((3-(trifluoromethyl)phenyl)sulfonyl)-3,4-dihydro-2H-benzo[b][1,4]oxazin-2-yl)ethan-1-ol (1.60 g, 4.30 mmol) in pyridine (15 mL) was added 3-(trifluoromethyl)benzenesulfonyl chloride (1.26 g, 5.15 mmol). The mixture was stirred at 50° C. for two hours, cooled, and partitioned between ethyl acetate and 1 M HCl. The organic layer was washed three times with 1 M HCl, brine, and dried (Na$_2$SO$_4$). Charcoal was added to the mixture, slurried, and filtered through Celite. The filtrate was concentrated and the resulting residue was purified by MPLC eluting with a gradient of ethyl acetate in hexanes to afford (S)-6-bromo-2-(2-((tert-butyldimethylsilyl)oxy)ethyl)-4-((3-(trifluoromethyl)phenyl)sulfonyl)-3,4-dihydro-2H-benzo[b][1,4]oxazine (2.40 g, 100%).

Part II—Synthesis of (S,E)-2-(2-((tert-Butyldimethylsilyl)oxy)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

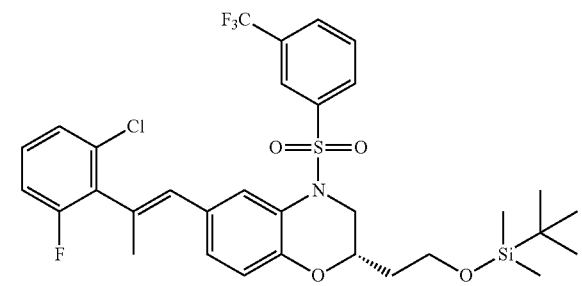 [SMILES: C/C(=C\c1ccc2c(c1)N(S(=O)(=O)c1cccc(C(F)(F)F)c1)C[C@H](CCO[Si](C)(C)C(C)(C)C)O2)c1c(F)cccc1Cl]

To a degassed mixture of (S)-6-bromo-2-(2-((tert-butyldimethylsilyl)oxy)ethyl)-4-((3-(trifluoromethyl)phenyl)sulfonyl)-3,4-dihydro-2H-benzo[b][1,4]oxazine (1.78 g, 6.03 mmol), potassium carbonate (833 mg, 6.03 mmol), (E)-2-(2-(2-chloro-6-fluorophenyl)prop-1-en-1-yl)-4,4,5,5-tetramethyl-1,3,2-dioxaborolane (1.788 g, 6.03 mmol), dioxane (25 mL) and water (5 mL) was added [1,1'-bis(diphenylphosphino)ferrocene]dichloropalladium(II) dichloromethane complex (0.328 g, 0.431 mmol). The mixture was heated to 70° C. for five hours. The mixture was cooled, and partitioned between ethyl acetate and saturated aqueous ammonium chloride. The organic layer was washed with brine, dried (Na$_2$SO$_4$), and concentrated. The resulting residue was purified by MPLC eluting with a gradient of 0-50% ethyl acetate in hexanes to afford (S,E)-2-(2-((tert-butyldimethylsilyl)oxy)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (2.40 g, 83%).

Part III—Synthesis of (S,E)-2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethanol

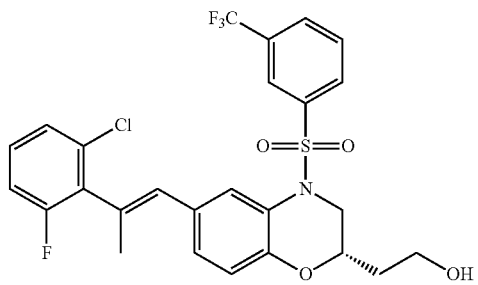 [SMILES: C/C(=C\c1ccc2c(c1)N(S(=O)(=O)c1cccc(C(F)(F)F)c1)C[C@H](CCO)O2)c1c(F)cccc1Cl]

To a solution of (S,E)-2-(2-((tert-butyldimethylsilyl)oxy)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (2.40 g, 3.58 mmol) in THF (24 mL) was added a 1 M solution of tetrabutylammonium fluoride (1.40 g, 5.37 mmol) in THF (5.37 mL). The mixture was stirred for one hour, then concentrated onto a small amount of silica gel. The residue was purified by MPLC eluting with a gradient of 0-100% ethyl acetate in hexanes to afford (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethanol (1.55 g, 78%).

Part IV—Synthesis of (S,E)-2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl methanesulfonate

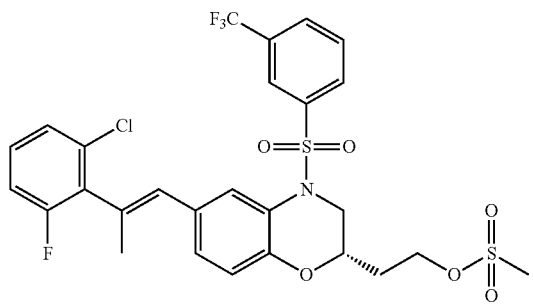 [SMILES: C/C(=C\c1ccc2c(c1)N(S(=O)(=O)c1cccc(C(F)(F)F)c1)C[C@H](CCOS(C)(=O)=O)O2)c1c(F)cccc1Cl]

Methanesulfonic anhydride (211 mg, 1.21 mmol) was added to a solution of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethanol (0.45 g, 0.81 mmol) and diisopropylethylamine (0.21 g, 1.62 mmol) in dichloromethane (10 mL) at 0° C. The mixture was stirred at room temperature for two hours, then partitioned between dichloromethane and 1 M HCl. The organic layer was dried ($Na_2SO_4$) and concentrated to afford (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl methanesulfonate (0.48 g, 94%).

Part V—Synthesis of (S,E)-6-(2-(2-Chloro-6-fluorophenyl)prop-1-en-1-yl)-2-(2-(pyrrolidin-1-yl)ethyl)-4-((3-(trifluoromethyl)phenyl)sulfonyl)-3,4-dihydro-2H-benzo[b][1,4]oxazine

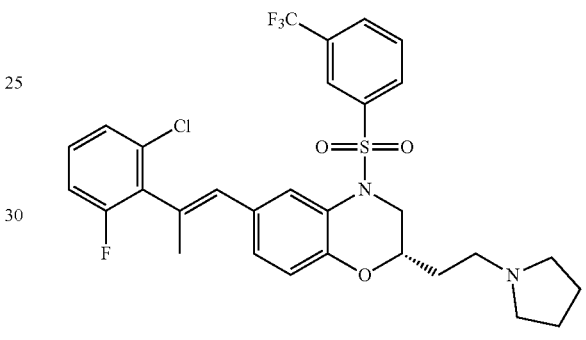

Pyrrolidine (22 mg, 0.315 mmol) was added to a solution of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl methanesulfonate (50 mg, 0.079 mmol) in DMF (0.5 mL). The mixture was stirred at 70° C. overnight, cooled then concentrated. The resulting residue was purified by MPLC eluting with a gradient of 0-5% methanol in dichloromethane to afford (S,E)-6-(2-(2-chloro-6-fluorophenyl)prop-1-en-1-yl)-2-(2-(pyrrolidin-1-yl)ethyl)-4-((3-(trifluoromethyl)phenyl)sulfonyl)-3,4-dihydro-2H-benzo[b][1,4]oxazine (23 mg, 47%). $^1$H-NMR (400 MHz, $CDCl_3$) δ 7.88 (s, 1H), 7.82 (m, 2H), 7.74 (m, 1H), 7.58 (t, 1H), 7.4 (m, 1H), 7.22 (m, 2H), 7.16 (m, 1H), 7.04 (m, 2H), 6.88 (d, 1H), 6.82 (m, 1H), 6.38 (s, 1H), 4.16 (m, 3H), 3.24 (m, 2H), 2.18 (s, 3H), 1.94 (m, 2H). MS (ESI+) (M+H)$^+$ 606.13.

Example 119—Preparation of Additional N-Linked Cycloalkyl or Cyclic Heteroalkyl Benzoxazines Compounds in Table 15 were prepared based on experimental procedures described in Examples 117 and 118 and the detailed description.

TABLE 15

| No. | Structure | Name | Observed m/z |
|---|---|---|---|
| 119A | 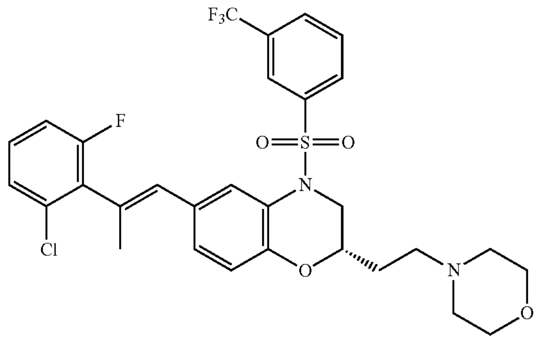 [SMILES: C/C(=C\c1ccc2c(c1)N(S(=O)(=O)c1cccc(C(F)(F)F)c1)C[C@H](CCN1CCOCC1)O2)c1c(F)cccc1Cl] | (S,E)-6-(2-(2-chloro-6-fluorophenyl)prop-1-en-1-yl)-2-(2-morpholinoethyl)-4-((3-(trifluoromethyl)phenyl)sulfonyl)-3,4-dihydro-2H-benzo[b][1,4]oxazine | 625 (M + H)+ |
| 119B | 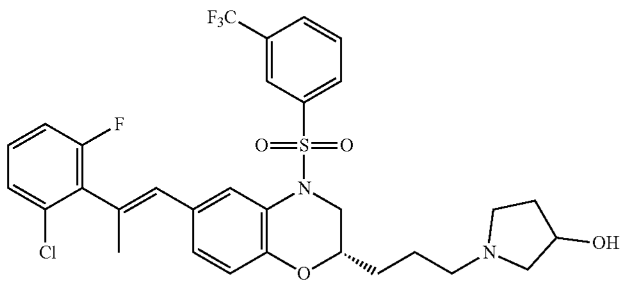 [SMILES: C/C(=C\c1ccc2c(c1)N(S(=O)(=O)c1cccc(C(F)(F)F)c1)C[C@H](CCCN1CCC(O)C1)O2)c1c(F)cccc1Cl] | 1-(3-((S)-6-((E)-2-(2-chloro-6-fluorophenyl)prop-1-en-1-yl)-4-((3-(trifluoromethyl)-phenyl)-sulfonyl)-3,4-dihydro-2H-benzo[b][1,4]-oxazin-2-yl)propyl)-pyrrolidin-3-ol | 639 (M + H)+ |
| 119C | 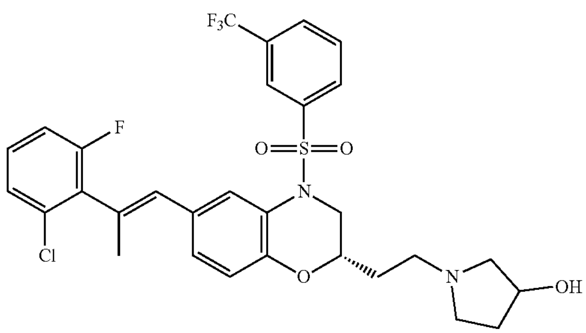 [SMILES: C/C(=C\c1ccc2c(c1)N(S(=O)(=O)c1cccc(C(F)(F)F)c1)C[C@H](CCN1CCC(O)C1)O2)c1c(F)cccc1Cl] | 1-(2-((S)-6-((E)-2-(2-chloro-6-fluorophenyl)prop-1-en-1-yl)-4-((3-(trifluoromethyl)-phenyl)sulfonyl)-3,4-dihydro-2H-benzo[b][1,4]oxazin-2-yl)ethyl)pyrrolidin-3-ol | 625 (M + H)+ |
| 119D | 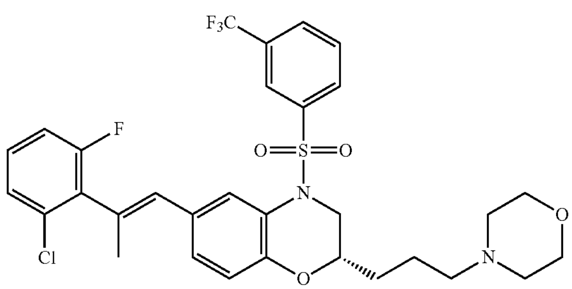 [SMILES: C/C(=C\c1ccc2c(c1)N(S(=O)(=O)c1cccc(C(F)(F)F)c1)C[C@H](CCCN1CCOCC1)O2)c1c(F)cccc1Cl] | (S,E)-6-(2-(2-chloro-6-fluorophenyl)prop-1-en-1-yl)-2-(3-morpholinopropyl)-4-((3-(trifluoromethyl)-phenyl)sulfonyl)-3,4-dihydro-2H-benzo[b][1,4]oxazine | 639 (M + H)+ |
| 119E | 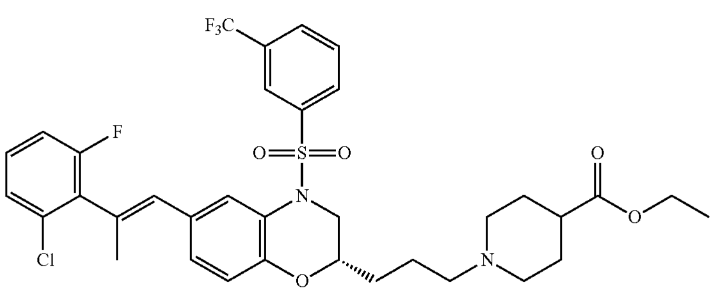 [SMILES: CCOC(=O)C1CCN(CCC[C@H]2CN(S(=O)(=O)c3cccc(C(F)(F)F)c3)c3cc(/C=C(\C)c4c(F)cccc4Cl)ccc3O2)CC1] | ethyl (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propyl)piperidine-4-carboxylate | 709 (M + H)+ |

TABLE 15-continued

| No. | Structure | Name | Observed m/z |
|---|---|---|---|
| 119F | 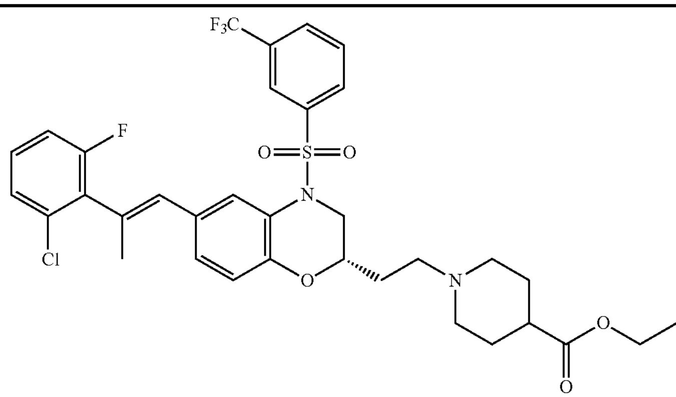 | ethyl (S,E)-1-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)piperidine-4-carboxylate | 695 (M + H)+ |
| 119G | 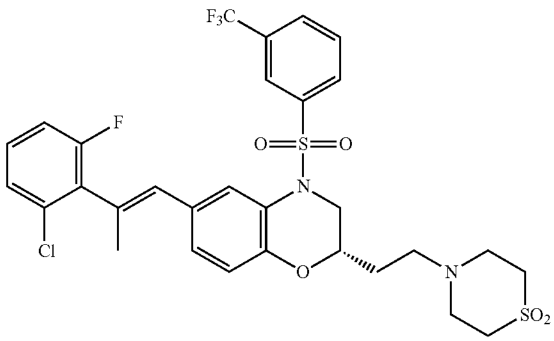 [SMILES: C/C(=C\c1ccc2c(c1)N(S(=O)(=O)c1cccc(C(F)(F)F)c1)C[C@H](CCN1CCS(=O)(=O)CC1)O2)c1c(F)cccc1Cl] | (S,E)-4-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)thiomorpholine 1,1-dioxide | 673 (M + H)+ |
| 119H | 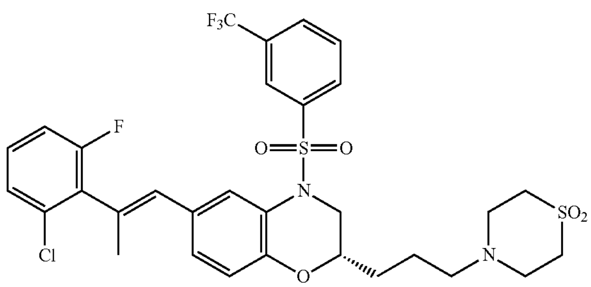 [SMILES: C/C(=C\c1ccc2c(c1)N(S(=O)(=O)c1cccc(C(F)(F)F)c1)C[C@H](CCCN1CCS(=O)(=O)CC1)O2)c1c(F)cccc1Cl] | (S,E)-4-(3-(6-(2-(2-chloro-6-fluorophenyl)prop-1-en-1-yl)-4-((3-(trifluoromethyl)-phenyl)sulfonyl)-3,4-dihydro-2H-benzo[b][1,4]oxazin-2-yl)propyl)thiomorpholine 1,1-dioxide | 687 (M + H)+ |

Example 120—Synthesis of (S,E)-4-(6-(2-(2-Chloro-6-fluorophenyl)prop-1-en-1-yl)-4-((4-fluoro-3-methoxyphenyl)sulfonyl)-3,4-dihydro-2H-benzo[b][1,4]oxazin-2-yl)-2-methylbutan-2-ol

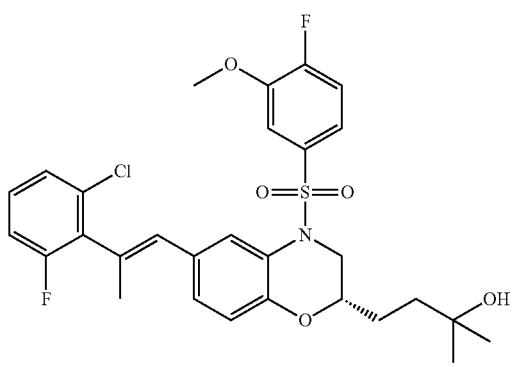 [SMILES: COc1cc(S(=O)(=O)N2C[C@H](CCC(C)(C)O)Oc3ccc(/C=C(\C)c4c(F)cccc4Cl)cc32)ccc1F]

To a stirred solution of methyl (S,E)-3-(6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl) propanoate (50 mg, 0.087 mmol) in THF (1 mL) at room temperature was added 1 M methyl magnesium bromide (0.69 mL, 0.69 mmol). The mixture was stirred for one hour, then quenched with saturated ammonium chloride. The mixture was partitioned between ethyl acetate and water. The organic layer was washed with brine, dried (Na$_2$SO$_4$), and concentrated. The resulting residue was purified by Prep HPLC eluting with a gradient of 5-95% acetonitrile in water with 0.1% trifluoroacetic acid to afford (S,E)-4-(6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)-2-methylbutan-2-ol (26 mg, 52%) as a white solid. $^1$H-NMR (400 MHz, DMSO-d$_6$) δ 7.75 (d, 1H), 7.45 (t, 1H), 7.38 (m, 3H), 7.28 (m, 2H), 7.12 (dd, 1H), 6.88 (d, 1H), 6.38 (s, 1H), 4.30 (m, 1H), 3.80 (s, 3H), 3.3 (m, 2H), 2.12 (s, 3H), 1.58 (m, 2H), 1.42 (m, 1H), 1.34 (m, 1H), 1.05 (s, 6H). MS (ESI+) (M+Na)+600.35.

Example 121—Preparation of Additional Substituted 3,4-Dihydro-2H-benzo[b][1,4]oxazin-2-yl)-2-methylbutan-2-ols Compounds in Table 16 were prepared based on experimental procedures described in Examples 120 and the detailed description.

TABLE 16

| No. | Structure | Name | Observed m/z |
|---|---|---|---|
| 121A | 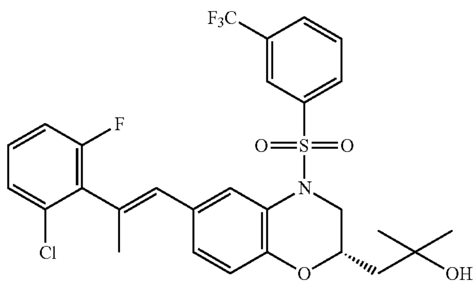 [SMILES: C/C(=C\c1ccc2c(c1)N(S(=O)(=O)c1cccc(C(F)(F)F)c1)C[C@H](CC(C)(C)O)O2)c1c(F)cccc1Cl] | (S,E)-1-(6-(2-(2-chloro-6-fluorophenyl)prop-1-en-1-yl)-4-((3-(trifluoromethyl)-phenyl)sulfonyl)-3,4-dihydro-2H-benzo[b][1,4]oxazin-2-yl)-2-methylpropan-2-ol | 584 (M + H)+ |
| 121B | 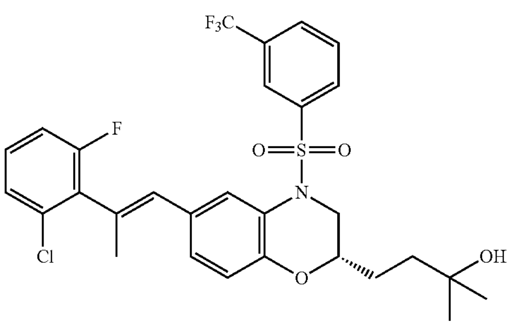 [SMILES: C/C(=C\c1ccc2c(c1)N(S(=O)(=O)c1cccc(C(F)(F)F)c1)C[C@H](CCC(C)(C)O)O2)c1c(F)cccc1Cl] | (S,E)-4-(6-(2-(2-chloro-6-fluorophenyl)prop-1-en-1-yl)-4-((3-(trifluoromethyl)-phenyl)sulfonyl)-3,4-dihydro-2H-benzo[b][1,4]oxazin-2-yl)-2-methylbutan-2-ol | 598 (M + H)+ |
| 121C | 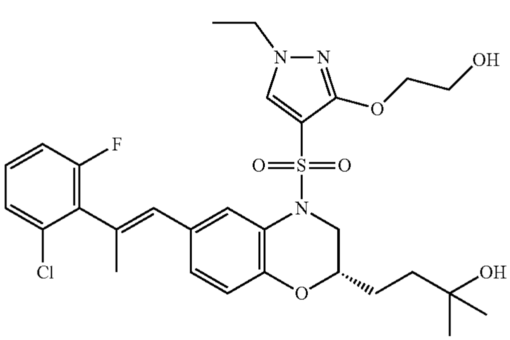 [SMILES: CCn1cc(S(=O)(=O)N2C[C@H](CCC(C)(C)O)Oc3ccc(/C=C(\C)c4c(F)cccc4Cl)cc32)c(OCCO)n1] | (S,E)-4-(6-(2-(2-chloro-6-fluorophenyl)prop-1-en-1-yl)-4-((1-ethyl-3-(2-hydroxyethoxy)-1H-pyrazol-4-yl)sulfonyl)-3,4-dihydro-2H-benzo[b][1,4]oxazin-2-yl)-2-methylbutan-2-ol | 608 (M + H)+ |

Example 122—Synthesis of (S,E)-1-(2-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)piperidine-4-carboxylic acid

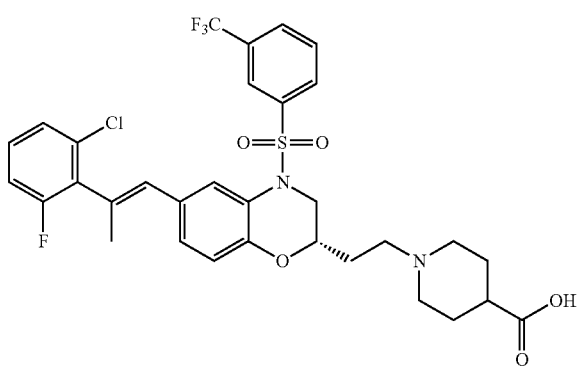 [SMILES: C/C(=C\c1ccc2c(c1)N(S(=O)(=O)c1cccc(C(F)(F)F)c1)C[C@H](CCN1CCC(C(=O)O)CC1)O2)c1c(F)cccc1Cl]

Based on the procedure in Example 42, (S,E)-1-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)piperidine-4-carboxylic acid was prepared. $^1$H-NMR (400 MHz, DMSO-$d_6$) δ 12.55 (br s, 1H), 9.11 (br s, 1H), 8.12 (m, 3H), 7.87 (t, 1H), 7.65 (s, 1H), 7.38 (m, 2H), 7.27 (m, 1H), 7.13 (d, 1H), 6.89 (d, 1H), 6.38 (s, 1H), 4.45 (m, 1H), 3.8-3.55 (m, 4H), 3.19 (m, 2H), 2.94 (m, 2H), 2.06 (m, 6H), 1.92 (m, 2H), 1.67 (m, 2H). MS (ESI+) (M+H)$^+$ 667.24.

Example 123—Synthesis of (S,E)-1-(3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propyl)piperidine-4-carboxylic acid

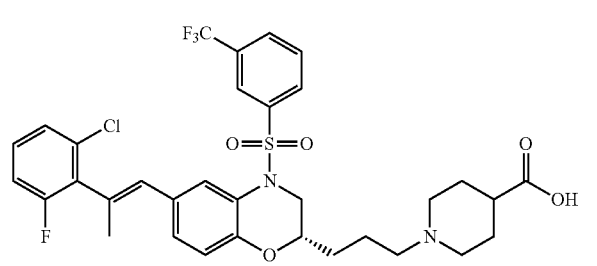 [SMILES: C/C(=C\c1ccc2c(c1)N(S(=O)(=O)c1cccc(C(F)(F)F)c1)C[C@H](CCCN1CCC(C(=O)O)CC1)O2)c1c(F)cccc1Cl]

Based on the procedure in Example 42, (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propyl)piperidine-4-carboxylic acid was prepared. $^1$H-NMR (400 MHz, DMSO-$d_6$) δ 12.55 (br s, 1H), 9.0 (br s, 1H), 8.09 (m, 3H), 7.88 (t, 1H), 7.65 (s, 1H), 7.38 (m, 2H), 7.27 (m, 1H), 7.12 (d, 1H), 6.88 (d, 1H), 6.37 (s, 1H), 4.38 (m, 1H), 3.62-3.35 (m, 5H), 3.1-2.9 (m, 4H), 2.06 (m, 5H), 1.7 (m, 6H). MS (ESI+) (M+H)$^+$ 681.27.

Example 124—Synthesis of (2-((S)-6-((E)-2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-L-proline

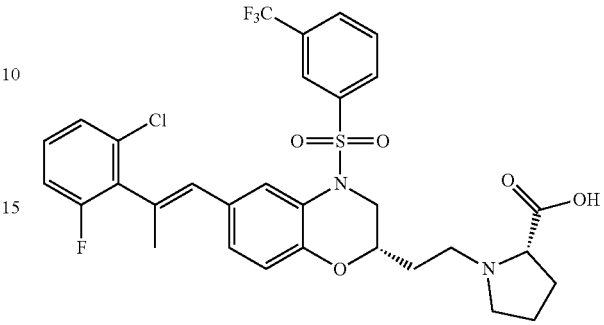

Based on the procedure in Example 42, (2-((S)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-L-proline was prepared. $^1$H-NMR (400 MHz, DMSO-$d_6$) δ 9.4 (br s, 1H), 8.82 (br s, 1H), 8.12 (m, 3H), 7.88 (t, 1H), 7.63 (s, 1H), 7.38 (m, 2H), 7.28 (m, 1H), 7.11 (d, 1H), 6.90 (d, 1H), 6.37 (s, 1H), 4.45-4.25 (m, 4H), 3.80 (m, 1H), 3.5-3.2 (m, 5H), 2.06 (s, 3H), 1.92 (m, 4H). MS (ESI+) (M+H)$^+$ 653.43.

Example 125—Synthesis of (R,E)-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)methanol

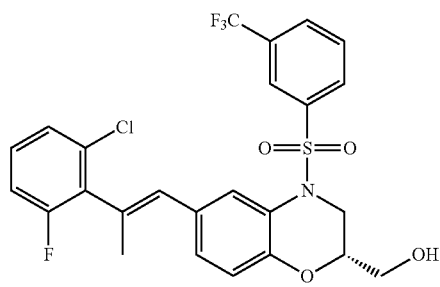 [SMILES: C/C(=C\c1ccc2c(c1)N(S(=O)(=O)c1cccc(C(F)(F)F)c1)C[C@H](CO)O2)c1c(F)cccc1Cl]

Part I—Synthesis of Methyl (2S)-2-(4-bromo-2-nitro-phenoxy)-3-[tert-butyl(diphenyl)silyl]oxy-propanoate

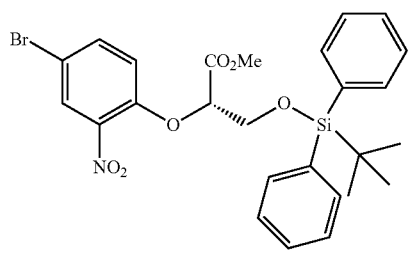 [SMILES: COC(=O)[C@H](CO[Si](c1ccccc1)(c1ccccc1)C(C)(C)C)Oc1ccc(Br)cc1[N+](=O)[O-]]

To a solution of (2R)-3-[tert-butyl(diphenyl)silyl]oxy-2-hydroxy-propanoate (28.6 g, 79.8 mmol) [see Goubert, Marlene et al. *Tetrahedron*, 63 (34), 8255-8266; 2007], 4-bromo-2-nitrophenol (22.5 g, 103 mmol), and triphenylphosphine (27.1 g, 103 mmol) in THF (400 mL) at 0° C. was added diisopropyl azodicarboxylate (20.5 mL, 104 mmol). The reaction mixture was allowed to warm to room temperature, and stirred overnight. The reaction mixture was then concentrated, and residue was dissolved in methyl tert-butyl ether (400 mL). Hexanes (500 mL) was added slowly and the solution became cloudy. The solution was allowed to crystallize overnight and the mixture was filtered. The filtrate was concentrated and the resulting residue was purified by filtering through a pad of silica gel eluting with 25% ethyl acetate in hexanes to afford methyl (2S)-2-(4-bromo-2-nitro-phenoxy)-3-[tert-butyl(diphenyl)silyl]oxy-propanoate (47.5 g, 91%).

Part II—Synthesis of (2S)-6-Bromo-2-[[tert-butyl(diphenyl)silyl]oxymethyl]-4H-1,4-benzoxazin-3-one

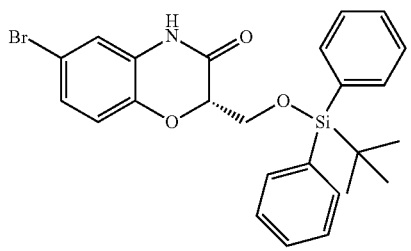 [SMILES: CC(C)(C)[Si](OC[C@@H]1Oc2ccc(Br)cc2NC1=O)(c1ccccc1)c1ccccc1]

Methyl (2S)-2-(4-bromo-2-nitro-phenoxy)-3-[tert-butyl(diphenyl)silyl]oxy-propanoate (44.6 g, 79.8 mmol) was dissolved in acetic acid (300 mL) and powdered iron (22.55 g, 404 mmol) was added. The mixture was heated to 70° C. overnight. The mixture was filtered through a pad of Celite, and the material was rinsed with ethyl acetate. The combined filtrates were then partitioned between ethyl acetate and water, and the organic phase was washed a second time with water, washed with brine, and concentrated to provide (2S)-6-bromo-2-[[tert-butyl(diphenyl)silyl]oxymethyl]-4H-1,4-benzoxazin-3-one.

Part III—Synthesis of [(2R)-6-Bromo-3,4-dihydro-2H-1,4-benzoxazin-2-yl]methoxy-tert-butyl-diphenyl-silane

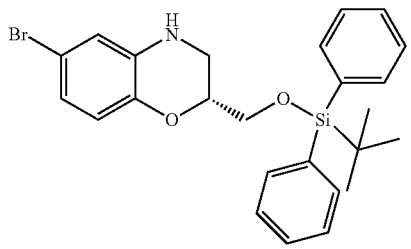 [SMILES: CC(C)(C)[Si](OC[C@H]1CNc2cc(Br)ccc2O1)(c1ccccc1)c1ccccc1]

A 10 M solution of borane-methyl sulfide complex in THF (32 mL, 320 mmol) was added dropwise to a solution of (2S)-6-bromo-2-[[tert-butyl(diphenyl)silyl]oxymethyl]-4H-1,4-benzoxazin-3-one (39.62 g, 79.8 mmol) in THF (350 mL) at 0° C. The mixture was then stirred at 60° C. for 2.5 hours, quenched with methanol (1 mL) and refluxed for ten minutes. The mixture was concentrated, and the resulting residue was purified by filtering through a plug of silica gel with 50% methyl tert-butyl ether and hexanes to afford [(2R)-6-bromo-3,4-dihydro-2H-1,4-benzoxazin-2-yl]methoxy-tert-butyl-diphenyl-silane (33.0 g, 73%) as an orange oil.

Part IV—Synthesis of [(2R)-6-Bromo-4-[3-(trifluoromethyl)phenyl]sulfonyl-2,3-dihydro-1,4-benzoxazin-2-yl]methoxy-tert-butyl-diphenyl-silane

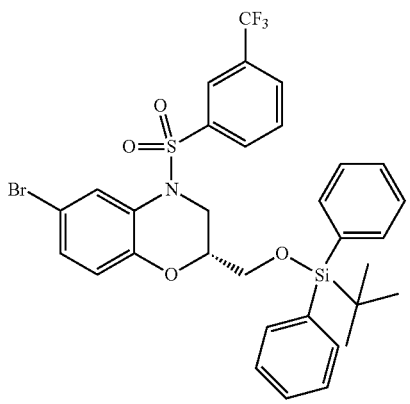 [SMILES: CC(C)(C)[Si](OC[C@H]1CN(S(=O)(=O)c2cccc(C(F)(F)F)c2)c2cc(Br)ccc2O1)(c1ccccc1)c1ccccc1]

[(2R)-6-Bromo-3,4-dihydro-2H-1,4-benzoxazin-2-yl]methoxy-tert-butyl-diphenyl-silane (3.21 g, 5.66 mmol) was dissolved in pyridine (10 mL) and 3-(trifluoromethyl) benzenesulfonyl chloride (1.5 mL, 9.36 mmol) was added. The reaction mixture was heated to 50° C. overnight. Then, the reaction mixture was diluted in methyl tert-butyl ether, washed twice times with 1 M HCl, washed with brine, dried (Na₂SO₄), and concentrated. The resulting residue was purified by MPLC with 0% to 10% ethyl acetate and hexanes to afford [(2R)-6-bromo-4-[3-(trifluoromethyl)phenyl]sulfonyl-2,3-dihydro-1,4-benzoxazin-2-yl]methoxy-tert-butyl-diphenyl-silane (3.02 g, 77%) as a light yellow oil.

Part V—Synthesis of tert-butyl-[[(2R)-6-[(E)-2-(2-chloro-6-fluoro-phenyl)prop-1-enyl]-4-[3-(trifluoromethyl)phenyl]sulfonyl-2,3-dihydro-1,4-benzoxazin-2-yl]methoxy]-diphenyl-silane

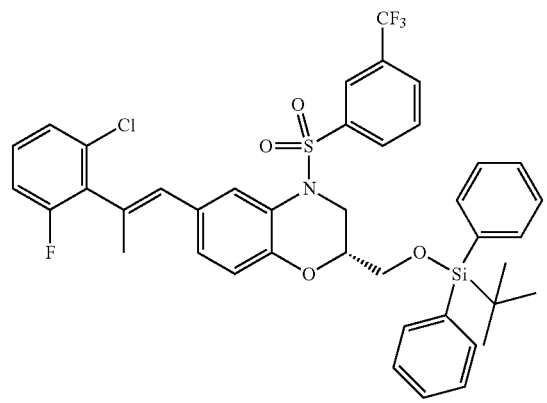 [SMILES: C/C(=C\c1ccc2c(c1)N(S(=O)(=O)c1cccc(C(F)(F)F)c1)C[C@H](CO[Si](c1ccccc1)(c1ccccc1)C(C)(C)C)O2)c1c(F)cccc1Cl]

[(2R)-6-bromo-4-[3-(trifluoromethyl)phenyl]sulfonyl-2,3-dihydro-1,4-benzoxazin-2-yl]methoxy-tert-butyl-diphenyl-silane (2.85 g, 4.13 mmol), (E)-2-(2-(2-chloro-6-fluorophenyl)prop-1-en-1-yl)-4,4,5,5-tetramethyl-1,3,2-dioxaborolane (1.72 g, 5.79 mmol), dioxane (18 mL), water (3 mL), and potassium carbonate (0.849 g, 6.14 mmol) were combined, and the mixture was degassed. To this mixture was added [1,1'-bis(diphenylphosphino)-ferrocene] dichloropalladium (II) complex with dichloromethane (0.399 g, 0.523 mmol), and the resulting mixture was stirred overnight at 70° C. The mixture was partitioned between water and ethyl acetate. The organic phase was washed with brine, dried (Na$_2$SO$_4$), and concentrated. The resulting residue was purified by MPLC eluting with a gradient of 5-10% ethyl acetate in hexanes to afford tert-butyl-[[(2R)-6-[(E)-2-(2-chloro-6-fluoro-phenyl)prop-1-enyl]-4-[3-(trifluoromethyl)phenyl]sulfonyl-2,3-dihydro-1,4-benzoxazin-2-yl]methoxy]-diphenyl-silane (2.95 g, 92%) as an oil.

Part VI—Synthesis of (R,E)-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)methanol

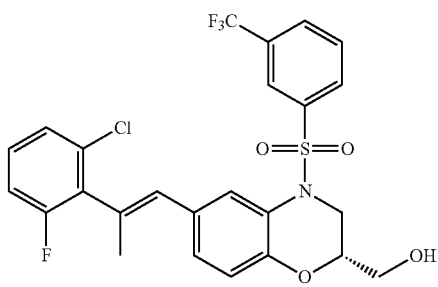 [SMILES: C/C(=C\c1ccc2c(c1)N(S(=O)(=O)c1cccc(C(F)(F)F)c1)C[C@H](CO)O2)c1c(F)cccc1Cl]

To a solution of tert-butyl-[[(2R)-6-[(E)-2-(2-chloro-6-fluoro-phenyl)prop-1-enyl]-4-[3-(trifluoromethyl)phenyl]sulfonyl-2,3-dihydro-1,4-benzoxazin-2-yl]methoxy]-diphenyl-silane (0.714 g, 0.915 mmol) in THF (10 mL) at 0° C. was added 1 M tetrabutylammonium fluoride in THF (1.8 mL, 1.80 mmol). After four hours, the reaction was quenched with saturated aqueous ammonium chloride solution. The mixture was extracted with ethyl acetate. The organic layer was dried (Na$_2$SO$_4$) and concentrated. The resulting residue was purified by MPLC eluting with a gradient of 0% to 50% ethyl acetate and hexanes to afford (R,E)-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)methanol (0.462 g, 92%) as an oil. $^1$H-NMR (400 MHz, CDCl$_3$) δ 8.01 (s, 1H), 7.88-7.80 (m, 2H), 7.64 (t, 1H), 7.24-7.00 (m, 4H), 6.86 (d, 1H), 6.38 (s, 1H), 4.36-4.31 (m, 1H), 3.82-3.45 (m, 4H), 2.18 (s, 3H), 1.82-1.79 (m, 1H). (ES, m/z): (M+H)$^+$542.

Example 126—Synthesis of (S,E)-3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)-1-(pyrrolidin-1-yl)propan-1-one

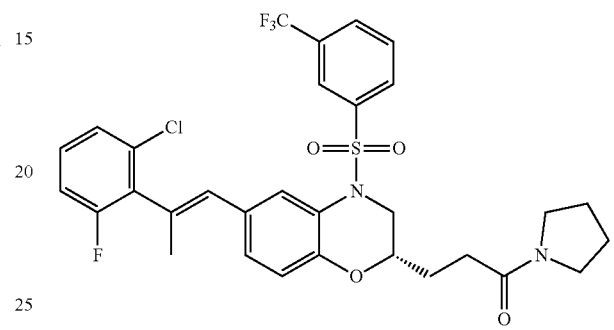

To (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid (0.19 g, 0.33 mmol), N,N-diisopropylethylamine (0.17 mL, 0.98 mmol), and pyrrolidine (0.04 mL, 0.49 mmol) in N,N-dimethylformamide (3 mL) was added (1-[Bis(dimethylamino)methylene]-1H-1,2,3-triazolo[4,5-b]pyridinium 3-oxid hexafluorophosphate) (HATU; 0.19 g, 0.49 mmol) and the reaction mixture was stirred at room temperature for two hours. The solution was diluted with ethyl acetate, washed with water, brine, dried (Na$_2$SO$_4$) and concentrated. The mixture was purified by MPLC eluting with a gradient of ethyl acetate in hexanes. Pure fractions were combined and concentrated to afford (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)-1-(pyrrolidin-1-yl)propan-1-one (0.16 g, 77%). $^1$H-NMR (400 MHz, DMSO-d$_6$) δ 8.09 (d, 1H), 8.01 (d, 1H), 7.97 (s, 1H), 7.83 (t, 1H), 7.67 (s, 1H), 7.36 (m, 2H), 7.26 (m, 1H), 7.10 (dd, 1H), 6.86 (d, 1H), 6.36 (s, 1H), 4.39 (m, 1H), 3.50 (m, 1H), 3.38-3.22 (m, 3H), 2.31 (m, 2H), 2.07 (s, 3H), 1.83 (m, 4H), 1.74 (m, 4H). MS (ESI+) (M+Na)$^+$659.27.

Example 127-Preparation of Additional Substituted Benzoxazines with 3-(CH$_2$)$_n$CONRR' Substituents Compounds in Table 17 were prepared based on experimental procedures described in Example 126 and the detailed description.

TABLE 17

| No. | Structure | Name | Observed m/z |
|---|---|---|---|
| 127A | 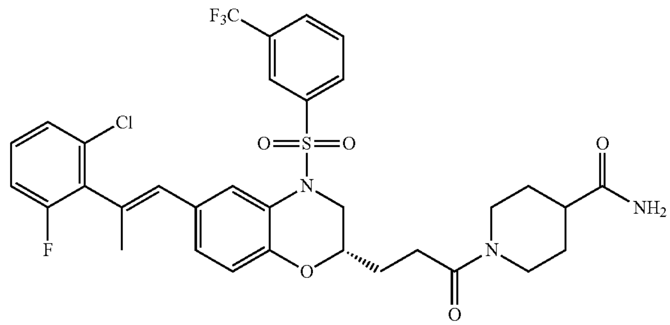 [SMILES: C/C(=C\c1ccc2c(c1)N(S(=O)(=O)c1cccc(C(F)(F)F)c1)C[C@H](CCC(=O)N1CCC(C(N)=O)CC1)O2)c1c(F)cccc1Cl] | (S,E)-1-(3-(6-(2-(2-chloro-6-fluorophenyl)-prop-1-en-1-yl)-4-((3-(trifluoromethyl)phenyl)sulfonyl)-3,4-dihydro-2H-benzo[b][1,4]oxazin-2-yl)propanoyl)piperidine-4-carboxamide | 694 (M + H)+ |
| 127B | 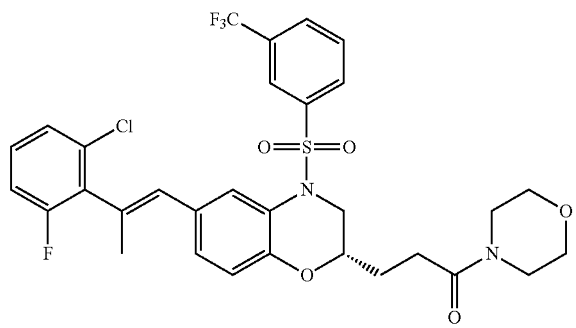 [SMILES: C/C(=C\c1ccc2c(c1)N(S(=O)(=O)c1cccc(C(F)(F)F)c1)C[C@H](CCC(=O)N1CCOCC1)O2)c1c(F)cccc1Cl] | (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)-1-morpholinopropan-1-one | 653 (M + H)+ |
| 127C | 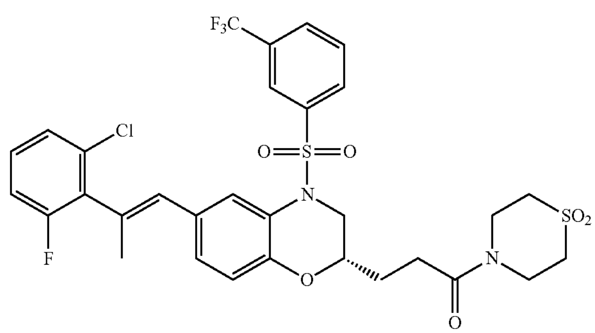 [SMILES: C/C(=C\c1ccc2c(c1)N(S(=O)(=O)c1cccc(C(F)(F)F)c1)C[C@H](CCC(=O)N1CCS(=O)(=O)CC1)O2)c1c(F)cccc1Cl] | (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)-1-(1,1-dioxidothiomorpholino)propan-1-one | 701 (M + H)+ |
| 127D | 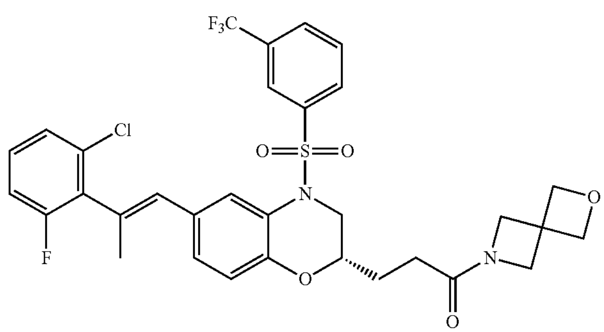 | (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)-1-(2-oxa-6-azaspiro[3.3]heptan-6-yl)propan-1-one | 665 (M + H)+ |

TABLE 17-continued

| No. | Structure | Name | Observed m/z |
|---|---|---|---|
| 127E | 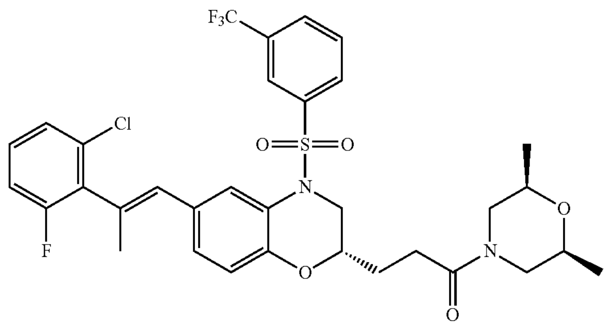 [SMILES: C/C(=C\c1ccc2c(c1)N(S(=O)(=O)c1cccc(C(F)(F)F)c1)C[C@H](CCC(=O)N1C[C@@H](C)O[C@@H](C)C1)O2)c1c(F)cccc1Cl] | 3-((S)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)-1-((2S,6R)-2,6-dimethylmorpholino)propan-1-one | 681 (M + H)+ |
| 127F | 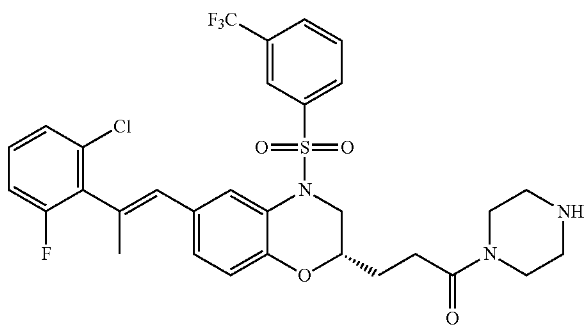 [SMILES: C/C(=C\c1ccc2c(c1)N(S(=O)(=O)c1cccc(C(F)(F)F)c1)C[C@H](CCC(=O)N1CCNCC1)O2)c1c(F)cccc1Cl] | (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)-1-(piperazin-1-yl)propan-1-one | 652 (M + H)+ |
| 127G | 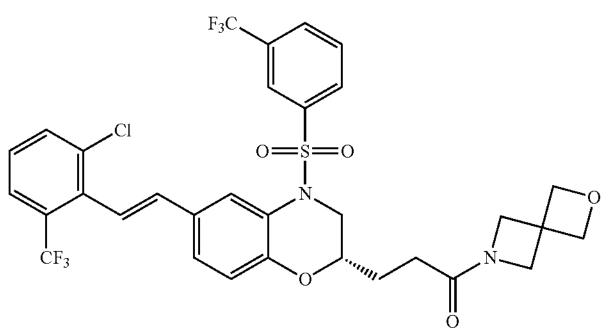 [SMILES: O=C(CC[C@H]1CN(S(=O)(=O)c2cccc(C(F)(F)F)c2)c2cc(/C=C/c3c(Cl)cccc3C(F)(F)F)ccc2O1)N1CC2(COC2)C1] | (S,E)-3-(6-(2-chloro-6-(trifluoromethyl)styryl)-4-((3-(trifluoromethyl)phenyl)sulfonyl)-3,4-dihydro-2H-benzo[b][1,4]oxazin-2-yl)-1-(2-oxa-6-azaspiro[3.3]heptan-6-yl)propan-1-one | 701 (M + H)+ |
| 127H | 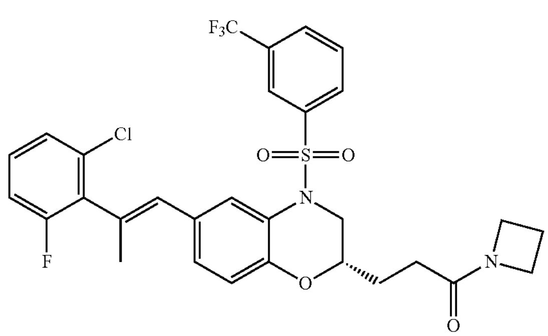 [SMILES: C/C(=C\c1ccc2c(c1)N(S(=O)(=O)c1cccc(C(F)(F)F)c1)C[C@H](CCC(=O)N1CCC1)O2)c1c(F)cccc1Cl] | (S,E)-1-(azetidin-1-yl)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propan-1-one | 623 (M + H)+ |

TABLE 17-continued

| No. | Structure | Name | Observed m/z |
|---|---|---|---|
| 127I | 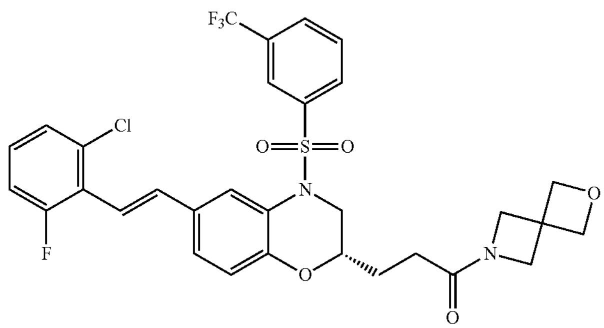 [SMILES: O=C(CC[C@H]1CN(S(=O)(=O)c2cccc(C(F)(F)F)c2)c2cc(/C=C/c3c(F)cccc3Cl)ccc2O1)N1CC2(COC2)C1] | (S,E)-3-(6-(2-chloro-6-fluorostyryl)-4-((3-(trifluoromethyl)phenyl)sulfonyl)-3,4-dihydro-2H-benzo[b][1,4]oxazin-2-yl)-1-(2-oxa-6-azaspiro[3.3]heptan-6-yl)propan-1-one | 651 (M + H)+ |
| 127J | 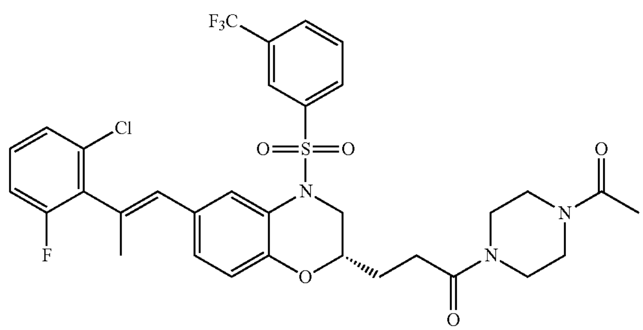 [SMILES: CC(=O)N1CCN(C(=O)CC[C@H]2CN(S(=O)(=O)c3cccc(C(F)(F)F)c3)c3cc(/C=C(\C)c4c(F)cccc4Cl)ccc3O2)CC1] | (S,E)-1-(4-acetyl-piperazin-1-yl)-3-(6-(2-(2-chloro-6-fluorophenyl)prop-1-en-1-yl)-4-((3-(trifluoro-methyl)-phenyl)sulfonyl)-3,4-dihydro-2H-benzo[b][1,4]oxazin-2-yl)propan-1-one | 694 (M + H)+ |
| 127K | 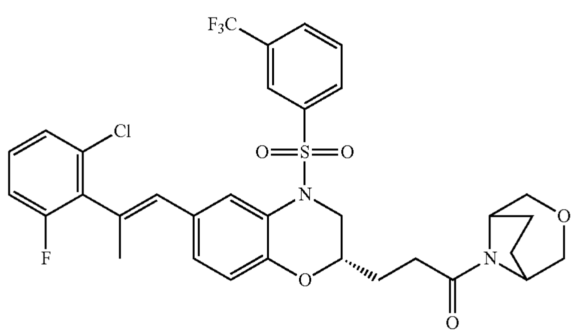 [SMILES: C/C(=C\c1ccc2c(c1)N(S(=O)(=O)c1cccc(C(F)(F)F)c1)C[C@H](CCC(=O)N1C3CCC1COC3)O2)c1c(F)cccc1Cl] | 1-(3-oxa-8-azabicyclo-[3.2.1]octan-8-yl)-3-((S)-6-((E)-2-(2-chloro-6-fluorophenyl)prop-1-en-1-yl)-4-((3-(trifluoro-methyl)phenyl)sulfonyl)-3,4-dihydro-2H-benzo[b][1,4]oxazin-2-yl)propan-1-one | 679 (M + H)+ |
| 127L | 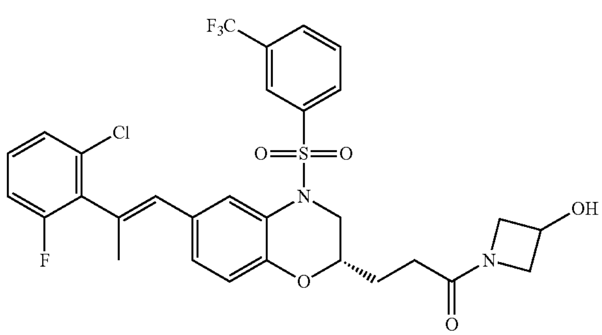 [SMILES: C/C(=C\c1ccc2c(c1)N(S(=O)(=O)c1cccc(C(F)(F)F)c1)C[C@H](CCC(=O)N1CC(O)C1)O2)c1c(F)cccc1Cl] | (S,E)-3-(6-(2-(2-chloro-6-fluorophenyl)prop-1-en-1-yl)-4-((3-(trifluoro-methyl)phenyl)sulfonyl)-3,4-dihydro-2H-benzo[b][1,4]oxazin-2-yl)-1-(3-hydroxyazetidin-1-yl)propan-1-one | 639 (M + H)+ |

TABLE 17-continued

| No. | Structure | Name | Observed m/z |
|---|---|---|---|
| 127M | 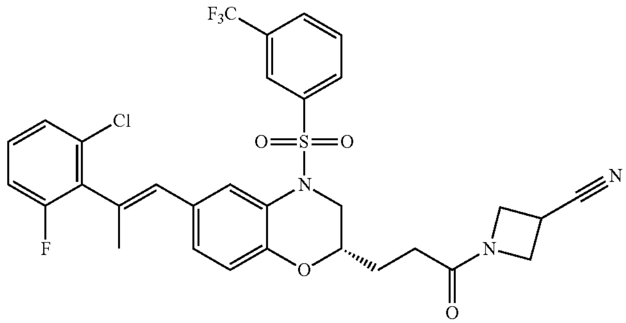 [SMILES: C/C(=C\c1ccc2c(c1)N(S(=O)(=O)c1cccc(C(F)(F)F)c1)C[C@H](CCC(=O)N1CC(C#N)C1)O2)c1c(F)cccc1Cl] | (S,E)-1-(3-(6-(2-(2-chloro-6-fluorophenyl)-prop-1-en-1-yl)-4-((3-(trifluoromethyl)phenyl)-sulfonyl)-3,4-dihydro-2H-benzo[b][1,4]oxazin-2-yl)propanoyl)azetidine-3-carbonitrile | 648 (M + H)+ |
| 127N | 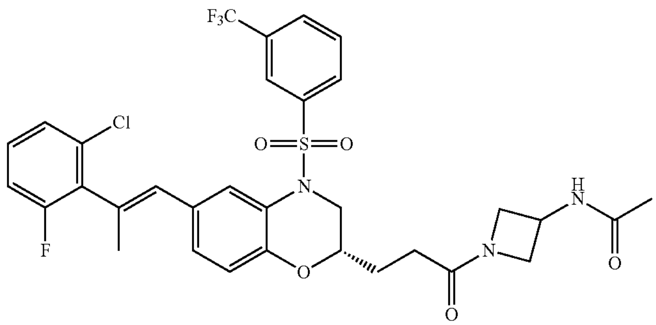 [SMILES: CC(=O)NC1CN(C(=O)CC[C@H]2CN(S(=O)(=O)c3cccc(C(F)(F)F)c3)c3cc(/C=C(\C)c4c(F)cccc4Cl)ccc3O2)C1] | (S,E)-N-(1-(3-(6-(2-(2-chloro-6-fluorophenyl)-prop-1-en-1-yl)-4-((3-(trifluoromethyl)phenyl)-sulfonyl)-3,4-dihydro-2H-benzo[b][1,4]oxazin-2-yl)propanoyl)azetidin-3-yl)acetamide | 680 (M + H)+ |

Example 128—Synthesis of the Sodium Salt of (S,E)-1-(3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl) piperidine-4-carboxylic acid

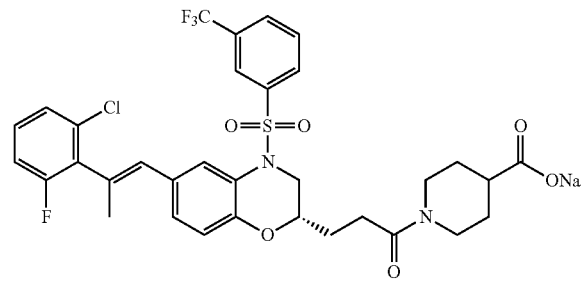

Part I—Synthesis of Ethyl (S,E)-1-(3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylate

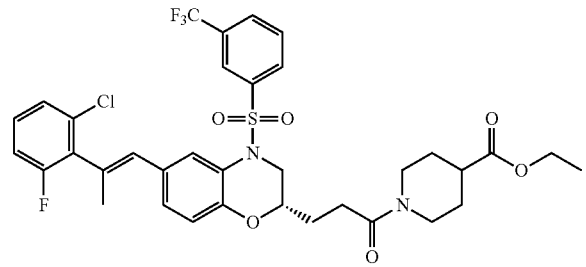 [SMILES: CCOC(=O)C1CCN(C(=O)CC[C@H]2CN(S(=O)(=O)c3cccc(C(F)(F)F)c3)c3cc(/C=C(\C)c4c(F)cccc4Cl)ccc3O2)CC1]

In a round bottomed flask was combined (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid (0.20 g, 0.34 mmol), N,N-diisopropylethylamine (0.12 mL, 0.69 mmol), and ethyl isonipecotate (81 mg, 0.51 mmol) in N,N-dimethylformamide (3 mL). Added benzotriazol-1-yl-oxytripyrrolidino-phosphonium hexafluorophosphate (0.19 g, 0.49 mmol) and stirred the reaction at ambient temperature for 3 hours. The solution was diluted with ethyl acetate, washed with 1 M aqueous hydrogen chloride, water, brine, dried (Na2SO4) and concentrated. The mixture was purified by column chromatography eluting with a gradient of 20-100% ethyl acetate in hexanes. Pure fractions were combined and concentrated to afford ethyl (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylate (0.25 g, 93%).

Part II—Synthesis of the Sodium Salt of (S,E)-1-(3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylic acid

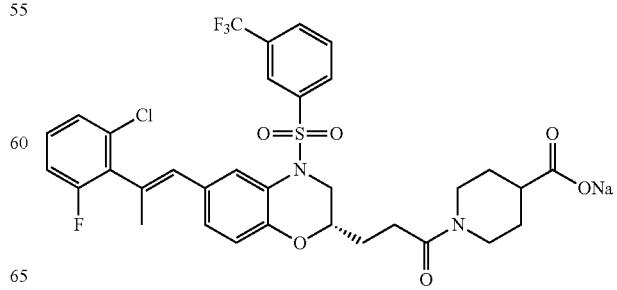

To a solution of ethyl (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylate (0.25 g, 0.35 mmol) in ethanol (5 mL) and tetrahydrofuran (2 mL) was added 2 M sodium hydroxide (0.52 mL, 1.04 mmol) in water. The reaction mixture was stirred at ambient temperature for 16 hours. Acidified solution with 1 M hydrogen chloride solution in water. Extracted with ethyl acetate, washed combined extracts with brine, dried ($Na_2SO_4$) and concentrated to a solid (113 mg, 72%), which was (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylic acid having the following chemical formula:

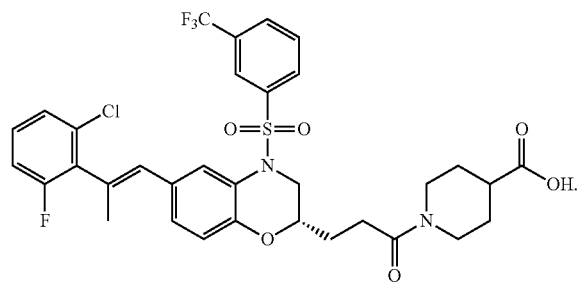 [SMILES: C/C(=C\c1ccc2c(c1)N(S(=O)(=O)c1cccc(C(F)(F)F)c1)C[C@H](CCC(=O)N1CCC(C(=O)O)CC1)O2)c1c(F)cccc1Cl]

The resulting solid carboxylic acid compound from above was converted to the sodium salt by redissolving the compound in methanol (2 mL), then adding one equivalent of a 2.962 M sodium hydroxide (55 μL) solution in water. The mixture was stirred twenty minutes, then the mixture was concentrated, then methanol was added and subsequently concentrated three times. The resulting residue was dried in a vacuum oven to afford the sodium salt of (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylic acid (110 mg, 94%) as a white solid. $^1$H-NMR (400 MHz, DMSO-$d_6$) δ 8.10 (d, 1H), 8.0 (m, 2H), 7.86 (t, 1H), 7.70 (s, 1H), 7.38 (m, 2H), 7.28 (m, 1H), 7.10 (dd, 1H), 6.88 (d, 1H), 6.37 (s, 1H), 4.41 (m, 1H), 4.03 (m, 1H), 3.68 (m, 1H), 3.48 m, 1H), 3.4 (m, 2H), 3.0 (m, 1H), 2.75 (m, 1H), 2.37 (m, 2H), 2.09 (s, 3H), 2.02 (m, 1H), 1.84 (m, 1H), 1.7 (m, 2H), 1.45 (m, 1H), 1.35 (m, 1H). MS (ESI+)×717.26 (M+Na)$^+$.

Example 129—Preparation of Additional Amino Acids N-linked to Substituted Benzoxazine Carboxylic Acids Compounds in Table 18 were prepared based on experimental procedures described in Example 128 and the detailed description.

TABLE 18

| No. | Structure | Name | Observed m/z |
|---|---|---|---|
| 129A | (structure) | (S,E)-1-(3-(6-(2-chloro-6-(trifluoromethyl)styryl)-4-((3-(trifluoromethyl)phenyl)sulfonyl)-3,4-dihydro-2H-benzo[b]-[1,4]oxazin-2-yl)propanoyl)piperidine-4-carboxylic acid | 731 (M + H)$^+$ |
| 129B | (structure) | (R)-1-(3-((S)-6-((E)-2-(2-chloro-6-fluorophenyl)-prop-1-en-1-yl)-4-((3-(trifluoromethyl)phenyl)sulfonyl)-3,4-dihydro-2H-benzo[b][1,4]oxazin-2-yl)propanoyl)pyrrolidine-3-carboxylic acid | 681 (M + H)$^+$ |

TABLE 18-continued

| No. | Structure | Name | Observed m/z |
|---|---|---|---|
| 129C | 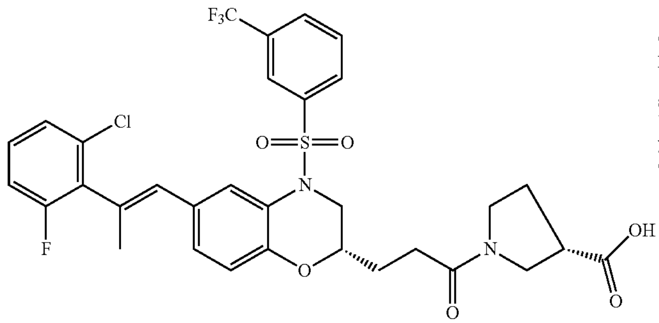 [SMILES: C/C(=C\c1ccc2c(c1)N(S(=O)(=O)c1cccc(C(F)(F)F)c1)C[C@H](CCC(=O)N1CC[C@H](C(=O)O)C1)O2)c1c(F)cccc1Cl] | (S)-1-(3-((S)-6-((E)-2-(2-chloro-6-fluorophenyl)-prop-1-en-1-yl)-4-((3-(trifluoromethyl)phenyl)sulfonyl)-3,4-dihydro-2H-benzo[b][1,4]oxazin-2-yl)propanoyl)pyrrolidine-3-carboxylic acid | 681 (M + H)+ |
| 129D | 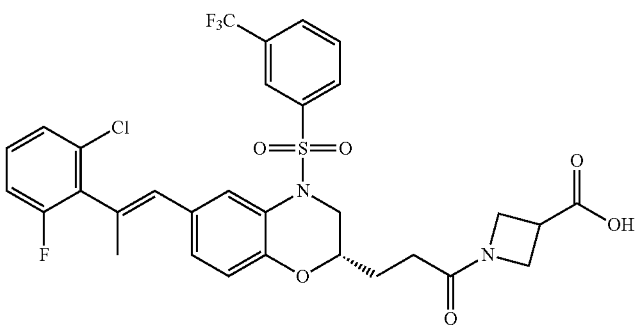 [SMILES: C/C(=C\c1ccc2c(c1)N(S(=O)(=O)c1cccc(C(F)(F)F)c1)C[C@H](CCC(=O)N1CC(C(=O)O)C1)O2)c1c(F)cccc1Cl] | (S,E)-1-(3-(6-(2-(2-chloro-6-fluorophenyl)-prop-1-en-1-yl)-4-((3-(trifluoromethyl)phenyl)sulfonyl)-3,4-dihydro-2H-benzo[b][1,4]oxazin-2-yl)propanoyl)azetidine-3-carboxylic acid | 667 (M + H)+ |
| 129E | 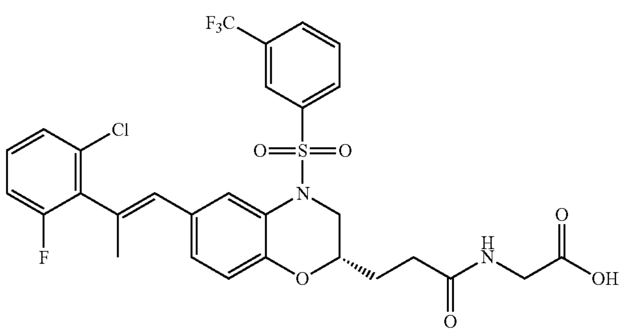 [SMILES: C/C(=C\c1ccc2c(c1)N(S(=O)(=O)c1cccc(C(F)(F)F)c1)C[C@H](CCC(=O)NCC(=O)O)O2)c1c(F)cccc1Cl] | (S,E)-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)glycine | 641 (M + H)+ |
| 129F | 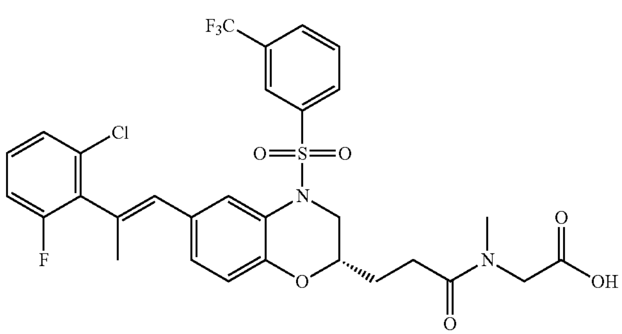 [SMILES: C/C(=C\c1ccc2c(c1)N(S(=O)(=O)c1cccc(C(F)(F)F)c1)C[C@H](CCC(=O)N(C)CC(=O)O)O2)c1c(F)cccc1Cl] | (S,E)-N-(3-(6-(2-(2-chloro-6-fluorophenyl)-prop-1-en-1-yl)-4-((3-(trifluoromethyl)phenyl)sulfonyl)-3,4-dihydro-2H-benzo[b][1,4]oxazin-2-yl)propanoyl)-N-methylglycine | 655 (M + H)+ |

TABLE 18-continued

| No. | Structure | Name | Observed m/z |
|---|---|---|---|
| 129G | 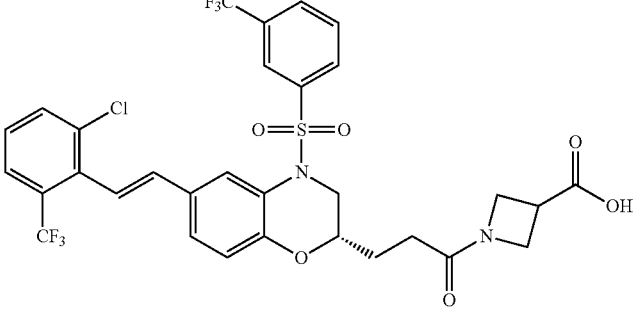 | (S,E)-1-(3-(6-(2-chloro-6-(trifluoromethyl)styryl)-4-((3-(trifluoromethyl)-phenyl)sulfonyl)-3,4-dihydro-2H-benzo[b][1,4]oxazin-2-yl)propanoyl)azetidine-3-carboxylic acid | 703 (M + H)$^+$ |
| 129H | 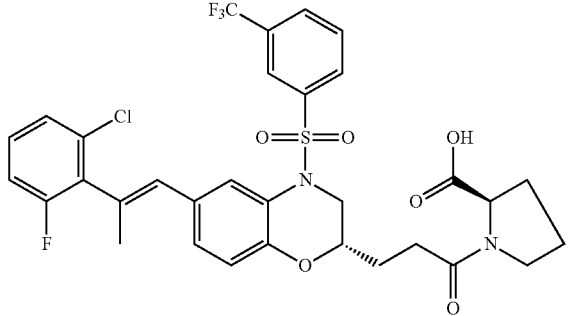 [SMILES: C/C(=C\c1ccc2c(c1)N(S(=O)(=O)c1cccc(C(F)(F)F)c1)C[C@H](CCC(=O)N1CCC[C@@H]1C(=O)O)O2)c1c(F)cccc1Cl] | (3-((S)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)-D-proline | 681 (M + H)$^+$ |
| 129I | 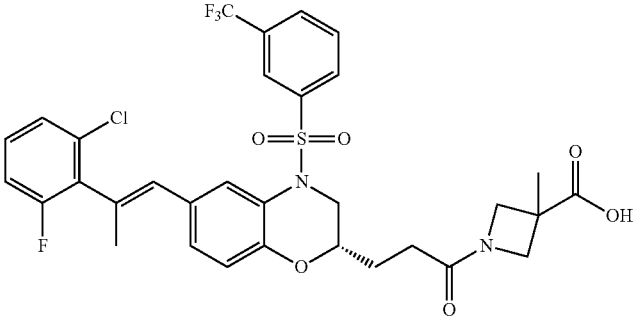 [SMILES: C/C(=C\c1ccc2c(c1)N(S(=O)(=O)c1cccc(C(F)(F)F)c1)C[C@H](CCC(=O)N1CC(C)(C(=O)O)C1)O2)c1c(F)cccc1Cl] | (S,E)-1-(3-(6-(2-(2-chloro-6-fluorophenyl)-prop-1-en-1-yl)-4-((3-(trifluoromethyl)phenyl)sulfonyl)-3,4-dihydro-2H-benzo[b][1,4]oxazin-2-yl)propanoyl)-3-methylazetidine-3-carboxylic acid | 681 (M + H)$^+$ |
| 129J | 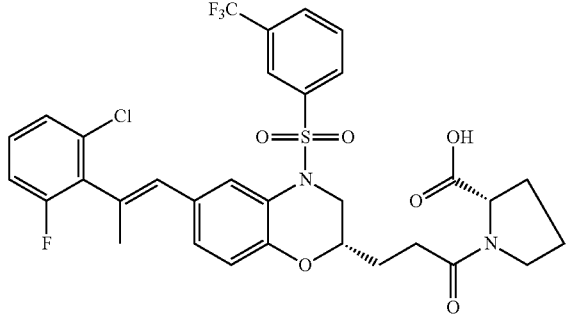 [SMILES: C/C(=C\c1ccc2c(c1)N(S(=O)(=O)c1cccc(C(F)(F)F)c1)C[C@H](CCC(=O)N1CCC[C@H]1C(=O)O)O2)c1c(F)cccc1Cl] | (3-((S)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)-L-proline | 681 (M + H)$^+$ |

TABLE 18-continued

| No. | Structure | Name | Observed m/z |
|---|---|---|---|
| 129K | 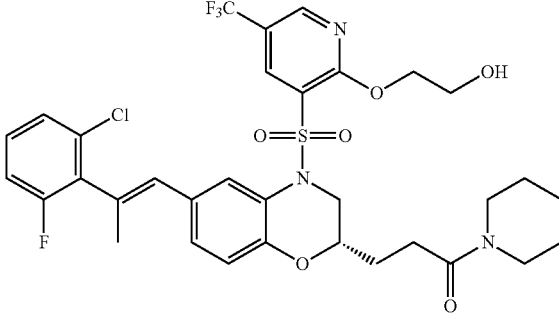 | (S,E)-1-(3-(6-(2-(2-chloro-6-fluorophenyl)-prop-1-en-1-yl)-4-((2-(2-hydroxyethoxy)-5-(trifluoromethyl)pyridin-3-yl)sulfonyl)-3,4-dihydro-2H-benzo[b][1,4]oxazin-2-yl)propanoyl)piperidine-4-carboxylic acid | 756 (M + H)+ |
| 129L | 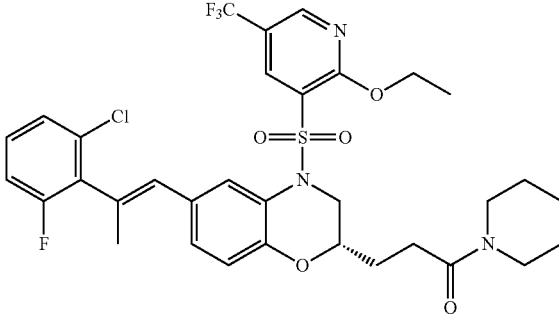 | (S,E)-1-(3-(6-(2-(2-chloro-6-fluorophenyl)-prop-1-en-1-yl)-4-((2-ethoxy-5-(trifluoro-methyl)pyridin-3-yl)sulfonyl)-3,4-dihydro-2H-benzo[b][1,4]oxazin-2-yl)propanoyl)-piperidine-4-carboxylic acid | 740 (M + H)+ |
| 129M | 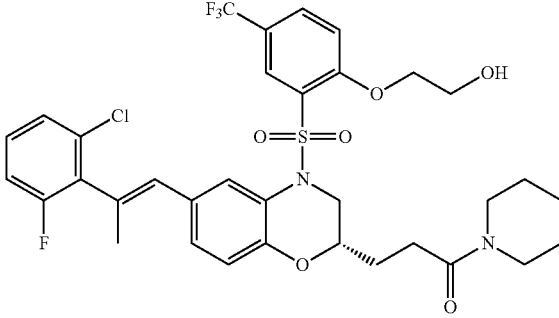 | (S,E)-1-(3-(6-(2-(2-chloro-6-fluorophenyl)-prop-1-en-1-yl)-4-((2-(2-hydroxyethoxy)-5-(trifluoromethyl)phenyl)sulfonyl)-3,4-dihydro-2H-benzo[b][1,4]oxazin-2-yl)propanoyl)piperidine-4-carboxylic acid | 755 (M + H)+ |
| 129N | 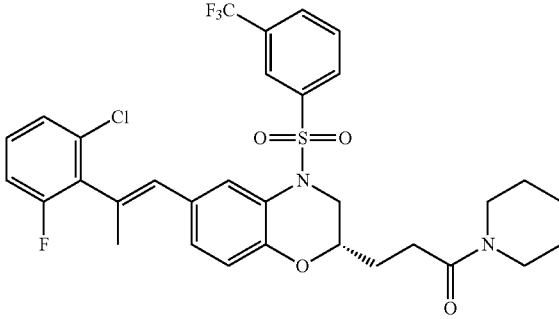 | (S,E)-1-(3-(6-(2-(2-chloro-6-fluorophenyl)-prop-1-en-1-yl)-4-((3-(trifluoromethyl)phenyl)sulfonyl)-3,4-dihydro-2H-benzo[b][1,4]oxazin-2-yl)propanoyl)-4-methylpiperidine-4-carboxylic acid | 709 (M + H)+ |

TABLE 18-continued

| No. | Structure | Name | Observed m/z |
|---|---|---|---|
| 129O | 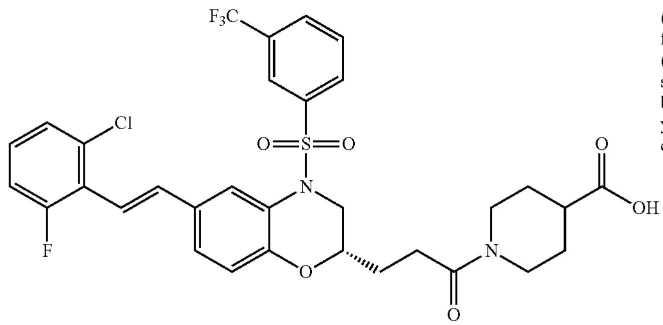 | (S,E)-1-(3-(6-(2-chloro-6-fluorostyryl)-4-((3-(trifluoromethyl)phenyl)sulfonyl)-3,4-dihydro-2H-benzo[b][1,4]oxazin-2-yl)propanoyl)piperidine-4-carboxylic acid | 681 (M + H)+ |
| 129P | 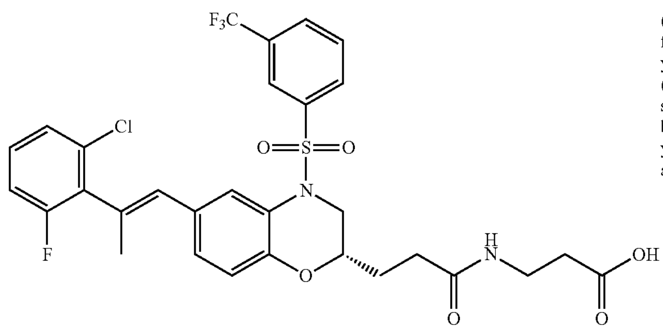 [SMILES: C/C(=C\c1ccc2c(c1)N(S(=O)(=O)c1cccc(C(F)(F)F)c1)C[C@H](CCC(=O)NCCC(=O)O)O2)c1c(F)cccc1Cl] | (S,E)-3-(3-(6-(2-(2-chloro-6-fluorophenyl)-prop-1-en-1-yl)-4-((3-(trifluoromethyl)phenyl)-sulfonyl)-3,4-dihydro-2H-benzo[b][1,4]oxazin-2-yl)propanamido)-propanoic acid | 655 (M + H)+ |
| 129Q | 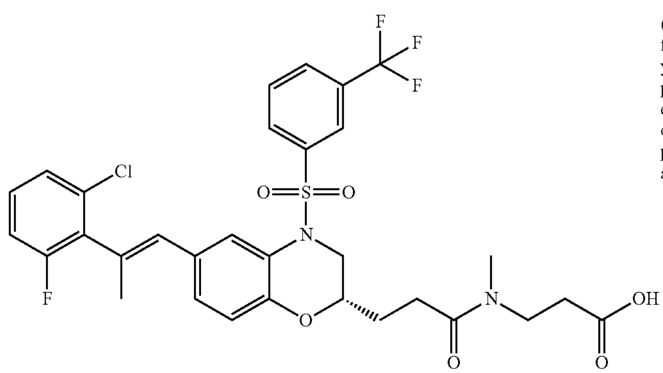 [SMILES: C/C(=C\c1ccc2c(c1)N(S(=O)(=O)c1cccc(C(F)(F)F)c1)C[C@H](CCC(=O)N(C)CCC(=O)O)O2)c1c(F)cccc1Cl] | (S,E)-3-(3-(6-(2-(2-chloro-6-fluorophenyl)prop-1-en-1-yl)-4-((3-(trifluoromethyl)-phenyl)sulfonyl)-3,4-dihydro-2H-benzo[b][1,4]-oxazin-2-yl)-N-methyl-propanamido)-propanoic acid | 669 (M + H)+ |
| 129R | 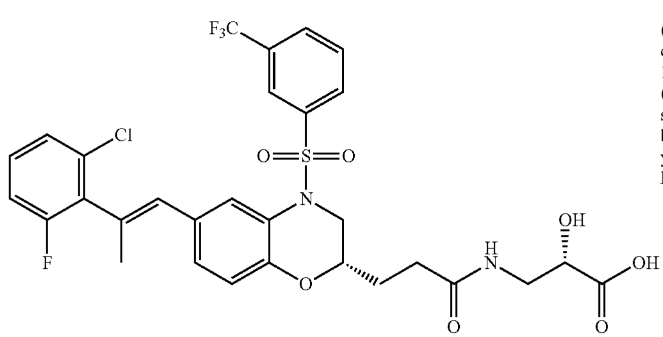 [SMILES: C/C(=C\c1ccc2c(c1)N(S(=O)(=O)c1cccc(C(F)(F)F)c1)C[C@H](CCC(=O)NC[C@H](O)C(=O)O)O2)c1c(F)cccc1Cl] | (S)-3-(3-((S)-6-((E)-2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanamido)-2-hydroxypropanoic acid | 671 (M + H)+ |

| No. | Structure | Name | Observed m/z |
|---|---|---|---|
| 129S | 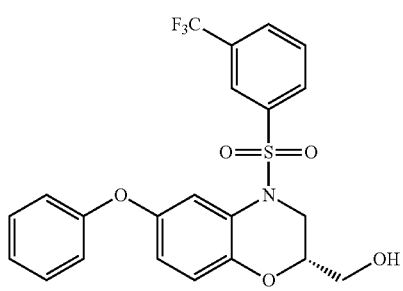 [SMILES: O=S(=O)(c1cccc(C(F)(F)F)c1)N1C[C@H](CO)Oc2ccc(Oc3ccccc3)cc21] | (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]-oxazin-2-yl)propanoyl)-4-hydroxypiperidine-4-carboxylic acid | 711 (M + H)+ |

Example 130—Synthesis of (R)-(6-Phenoxy-4-((3-(trifluoromethyl)phenyl)sulfonyl)-3,4-dihydro-2H-benzo[b][1,4]oxazin-2-yl)methanol

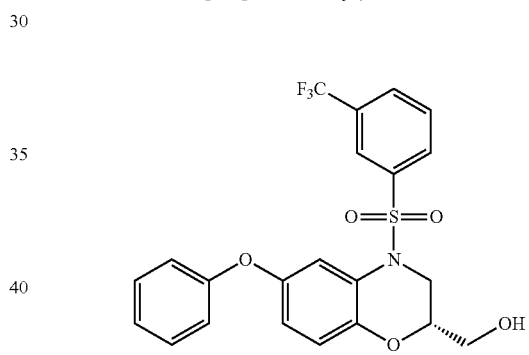

Part I—Synthesis of tert-Butyl-[[(2R)-6-phenoxy-4-[3-(trifluoromethyl)phenyl]sulfonyl-2,3-dihydro-1,4-benzoxazin-2-yl]methoxy]-diphenyl-silane

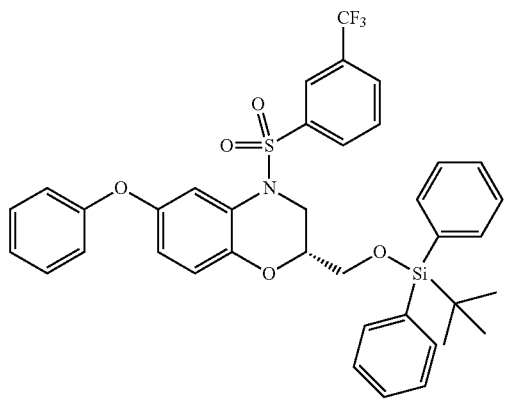 [SMILES: CC(C)(C)[Si](OC[C@H]1CN(S(=O)(=O)c2cccc(C(F)(F)F)c2)c2cc(Oc3ccccc3)ccc2O1)(c1ccccc1)c1ccccc1]

A solution of [(2R)-6-bromo-4-[3-(trifluoromethyl)phenyl]sulfonyl-2,3-dihydro-1,4-benzoxazin-2-yl]methoxy-tert-butyl-diphenyl-silane (0.304 g, 0.440 mmol), phenol (0.092 g, 0.98 mmol), potassium carbonate (0.154 g, 1.12 mmol) and copper(II) oxide (0.113 g, 1.42 mmol) in pyridine (5 mL) was heated overnight at 170° C. The cooled mixture was filtered through a pad of Celite and rinsed with ethyl acetate. The filtrate was concentrated and the resulting residue was purified by MPLC eluting with a gradient of 0-10% ethyl acetate in hexanes to afford tert-butyl-[[(2R)-6-phenoxy-4-[3-(trifluoromethyl)phenyl]sulfonyl-2,3-dihydro-1,4-benzoxazin-2-yl]methoxy]-diphenyl-silane (0.162 g, 52%).

Part II—Synthesis of (R)-(6-Phenoxy-4-((3-(trifluoromethyl)phenyl)sulfonyl)-3,4-dihydro-2H-benzo[b][1,4]oxazin-2-yl)methanol To a solution of tert-butyl-[[(2R)-6-phenoxy-4-[3-(trifluoromethyl)phenyl]sulfonyl-2,3-dihydro-1,4-benzoxazin-2-yl]methoxy]-diphenylsilane (0.160 g, 0.227 mmol) in THF (5 mL) at 0° C. was added 1M tetrabutylammonium fluoride in THF (0.25 mL, 0.25 mmol). After two hours, the reaction was quenched with saturated aqueous ammonium chloride solution. The mixture was extracted with ethyl acetate. The organic layer was dried (Na$_2$SO$_4$) and concentrated. The resulting residue was purified by MPLC eluting with a gradient of 0% to 75% ethyl acetate and hexanes to afford [(2R)-6-phenoxy-4-[3-(trifluoromethyl)phenyl]sulfonyl-2,3-dihydro-1,4-benzoxazin-2-yl]methanol (0.071 g, 66%) as a yellow oil. 1H-NMR (400 MHz, CDCl$_3$) δ 7.93 (s, 1H), 7.86-7.83 (m, 1H), 7.62 (t, 1H), 7.49-7.48 (m, 1H), 7.36-7.31 (m, 2H), 7.12-7.07 (m, 1H), 6.98-6.77 (m, 4H), 4.35-4.30 (m, 1H), 3.83-3.43 (m, 4H), 1.81-1.78 (m, 1H). (ES, m/z): (M+Na)+488.

Example 131—Synthesis of (R)-(6-(2-Chlorophenoxy)-4-((3-(trifluoromethyl)phenyl)sulfonyl)-3,4-dihydro-2H-benzo[b][1,4]oxazin-2-yl)methanol

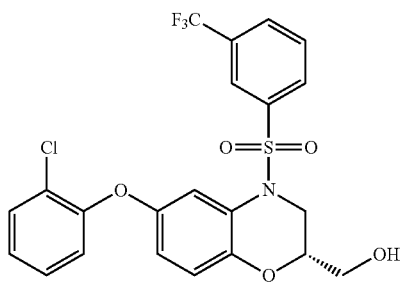 [SMILES: O=S(=O)(c1cccc(C(F)(F)F)c1)N1C[C@H](CO)Oc2ccc(Oc3ccccc3Cl)cc21]

Based on the procedure in Example 130, (R)-(6-(2-chlorophenoxy)-4-((3-(trifluoromethyl)phenyl)sulfonyl)-3,4-dihydro-2H-benzo[b][1,4]oxazin-2-yl)methanol was prepared. $^1$H-NMR (400 MHz, CDCl$_3$) δ 7.93-6.72 (m, 11H), 4.37-4.27 (m, 1H), 3.82-3.40 (m, 4H), 1.82-1.76 (m, 1H). (ES, m/z): (M+Na)$^+$522/524.

Example 132—Synthesis of (S,E)-4-((((6-(2-(2-Chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)amino)-4-oxobutanoic acid

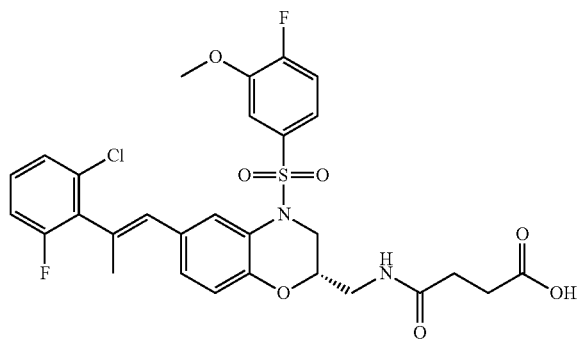 [SMILES: COc1cc(S(=O)(=O)N2C[C@H](CNC(=O)CCC(=O)O)Oc3ccc(/C=C(\C)c4c(F)cccc4Cl)cc32)ccc1F]

Part I—Synthesis of [(2R)-6-Bromo-3,4-dihydro-2H-1,4-benzoxazin-2-yl]methanol

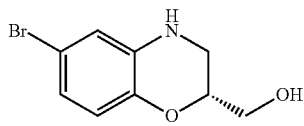

A 1 M solution of tetrabutylammonium fluoride in THF (30 mL, 30 mmol) was added to a solution of [(2R)-6-bromo-3,4-dihydro-2H-1,4-benzoxazin-2-yl]methoxy-tert-butyldiphenylsilane (12.9 g, 26.7 mmol) in THF (250 mL) at 0° C. The mixture was stirred overnight at room temperature. The mixture was quenched with saturated ammonium chloride, and concentrated to remove the THF. The mixture was extracted five times with ethyl acetate. The combined organic layers were dried (Na$_2$SO$_4$) and concentrated. The resulting residue was purified by MPLC eluting with a gradient of 0 to 100% ethyl acetate and hexanes to afford [(2R)-6-bromo-3,4-dihydro-2H-1,4-benzoxazin-2-yl]methanol (3.99 g, 56%) as a brown solid.

Part II—Synthesis of (R)-2-((6-Bromo-3,4-dihydro-2H-benzo[b][1,4]oxazin-2-yl)methyl)isoindoline-1,3-dione

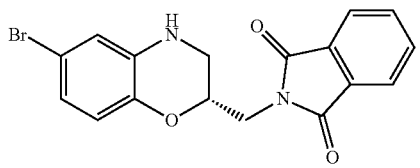 [SMILES: O=C1c2ccccc2C(=O)N1C[C@H]1CNc2cc(Br)ccc2O1]

To a solution of [(2R)-6-bromo-3,4-dihydro-2H-1,4-benzoxazin-2-yl]methanol (3.99 g, 16.3 mmol), phthalimide (3.00 g, 20.4 mmol) and triphenylphosphine (5.33 g, 20.3 mmol) in THF (50 mL) at 0° C., was added diisopropyl azodicarboxylate (4 mL, 20.3 mmol). The reaction mixture was stirred one hour at room temperature, and concentrated. The resulting residue was purified by MPLC eluting with a gradient of methyl tert-butyl ether and 1:1 hexanes to dichloromethane to afford (R)-2-((6-bromo-3,4-dihydro-2H-benzo[b][1,4]oxazin-2-yl)methyl)isoindoline-1,3-dione (5.08 g, 83%) as a yellow solid.

Part III—Synthesis of (S)-2-((6-Bromo-4-((3-fluoro-4-methoxyphenyl)sulfonyl)-3,4-dihydro-2H-benzo[b][1,4]oxazin-2-yl)methyl)isoindoline-1,3-dione

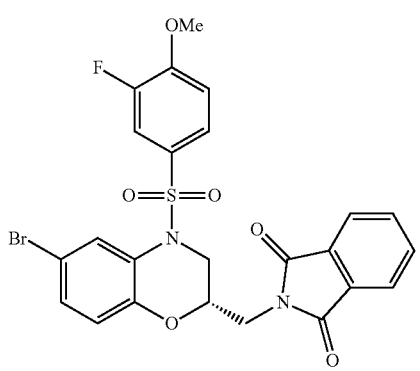 [SMILES: COc1ccc(S(=O)(=O)N2C[C@H](CN3C(=O)c4ccccc4C3=O)Oc3ccc(Br)cc32)cc1F]

To a solution of 2-[[(2R)-6-bromo-3,4-dihydro-2H-1,4-benzoxazin-2-yl]methyl]isoindoline-1,3-dione (1.01 g, 2.70 mmol) in pyridine (10 mL) was added 4-fluoro-3-methoxy-benzenesulfonyl chloride (0.907 g, 4.04 mmol). The reaction mixture was heated to 50° C. overnight. It was then concentrated and the resulting residue was purified by MPLC eluting with a gradient of 0-10% ethyl acetate in hexanes to afford (S)-2-((6-bromo-4-((3-fluoro-4-methoxyphenyl)sulfonyl)-3,4-dihydro-2H-benzo[b][1,4]oxazin-2-yl)methyl)isoindoline-1,3-dione (1.5 g, 99%) as a brown oil.

Part IV—Synthesis of (S,E)-2-((6-(2-(2-Chloro-6-fluorophenyl)prop-1-en-1-yl)-4-((3-fluoro-4-methoxyphenyl)sulfonyl)-3,4-dihydro-2H-benzo[b][1,4]oxazin-2-yl)methyl)isoindoline-1,3-dione

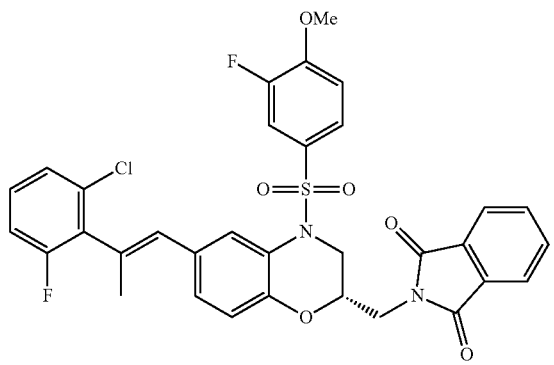 [SMILES: COc1ccc(S(=O)(=O)N2C[C@H](CN3C(=O)c4ccccc4C3=O)Oc3ccc(/C=C(\C)c4c(F)cccc4Cl)cc32)cc1F]

(S)-2-((6-Bromo-4-((3-fluoro-4-methoxyphenyl)sulfonyl)-3,4-dihydro-2H-benzo[b][1,4]oxazin-2-yl)methyl)isoindoline-1,3-dione (1.50 g, 2.67 mmol), (E)-2-(2-(2-chloro-6-fluorophenyl)prop-1-en-1-yl)-4,4,5,5-tetramethyl-1,3,2-dioxaborolane (1.16 g, 3.91 mmol), dioxane (18 mL), water (3 mL), and potassium carbonate (0.553 g, 4.00 mmol) were combined, and the mixture was degassed. To this mixture was added [1,1'-bis(diphenylphosphino)-ferrocene]dichloropalladium (II) complex with dichloromethane (0.277 g, 0.363 mmol), and the resulting mixture was stirred overnight at 70° C. The mixture was partitioned between water and ethyl acetate. The organic phase was washed with brine, dried (Na$_2$SO$_4$), and concentrated. The resulting residue was purified by MPLC eluting with a gradient of 5-10% ethyl acetate in hexanes to afford (S,E)-2-((6-(2-(2-chloro-6-fluorophenyl)prop-1-en-1-yl)-4-((3-fluoro-4-methoxyphenyl)sulfonyl)-3,4-dihydro-2H-benzo[b][1,4]oxazin-2-yl)methyl)isoindoline-1,3-dione (1.26 g, 72%) as a brown/red semi-solid.

Part V—Synthesis of (S,E)-(6-(2-(2-Chloro-6-fluorophenyl)prop-1-en-1-yl)-4-((3-fluoro-4-methoxyphenyl)sulfonyl)-3,4-dihydro-2H-benzo[b][1,4]oxazin-2-yl)methanamine

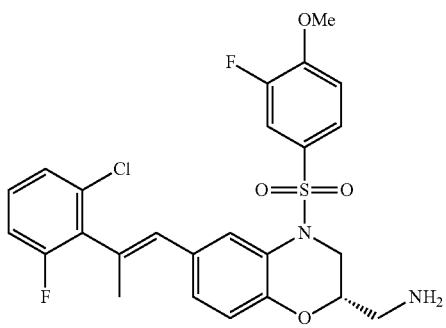 [SMILES: COc1ccc(S(=O)(=O)N2C[C@H](CN)Oc3ccc(/C=C(\C)c4c(F)cccc4Cl)cc32)cc1F]

To a solution (S,E)-2-((6-(2-(2-chloro-6-fluorophenyl)prop-1-en-1-yl)-4-((3-fluoro-4-methoxyphenyl)sulfonyl)-3,4-dihydro-2H-benzo[b][1,4]oxazin-2-yl)methyl)isoindoline-1,3-dione (1.2 g, 1.84 mmol) in methanol (20 mL) and methyl tert-butyl ether (20 mL) was added hydrazine monohydrate (1.0 mL, 20.6 mmol). The mixture was stirred at room temperature overnight, and then diluted with methyl tert-butyl ether (50 mL). The mixture was filtered, and the filtrate was concentrated. The resulting residue was dissolved in chloroform, dried (Na$_2$SO$_4$) and concentrated to afford (S,E)-(6-(2-(2-chloro-6-fluorophenyl)prop-1-en-1-yl)-4-((3-fluoro-4-methoxyphenyl)sulfonyl)-3,4-dihydro-2H-benzo[b][1,4]oxazin-2-yl)methanamine (0.791 g, 82%) as an oil.

Part VI—Synthesis of (S,E)-4-(((6-(2-(2-Chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)amino)-4-oxobutanoic acid

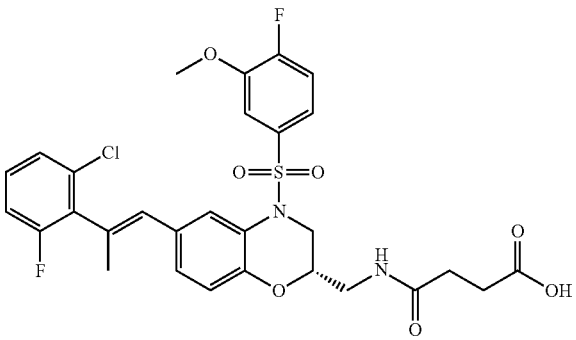 [SMILES: COc1cc(S(=O)(=O)N2C[C@H](CNC(=O)CCC(=O)O)Oc3ccc(/C=C(\C)c4c(F)cccc4Cl)cc32)ccc1F]

To a solution of (S,E)-(6-(2-(2-chloro-6-fluorophenyl)prop-1-en-1-yl)-4-((3-fluoro-4-methoxyphenyl)sulfonyl)-3,4-dihydro-2H-benzo[b][1,4]oxazin-2-yl)methanamine (0.073 g, 0.141 mmol) in 1,4-dioxane (2 mL) was added succinic anhydride (0.0173 g, 0.173 mmol). The reaction mixture was warmed to 50° C., and stirred overnight. The reaction mixture was concentrated and the resulting residue was suspended in water (5 mL). The mixture was filtered and the solid was dried under vacuum to afford (S,E)-4-(((6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)amino)-4-oxobutanoic acid (0.042 g, 44%) as an off white solid. $^1$H-NMR (400 MHz, CDCl$_3$) δ 7.88 (d, 1H), 7.37-7.00 (m, 6H), 6.83 (d, 1H), 6.38 (s, 1H0, 6.07 (t, 1H), 4.33-4.28 (m, 1H), 4.31 (dd, 1H), 3.76 (s, 3H), 3.58-3.42 (m, 3H), 3.24-3.18 (m, 1H), 2.75-2.48 (m, 4H), 2.19 (s, 3H).

Example 133—Synthesis of Methyl (S,E)-4-(((6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)carbamoyl)benzoate

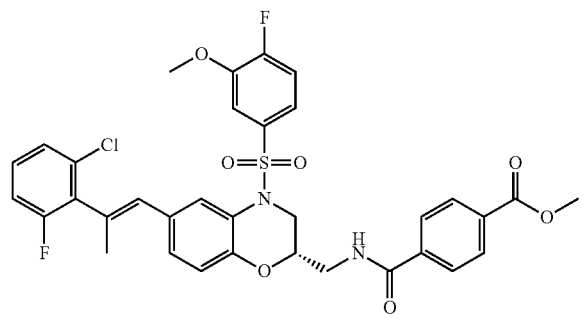 [SMILES: COC(=O)c1ccc(C(=O)NC[C@H]2CN(S(=O)(=O)c3ccc(F)c(OC)c3)c3cc(/C=C(\C)c4c(F)cccc4Cl)ccc3O2)cc1]

To a solution of (S,E)-(6-(2-(2-chloro-6-fluorophenyl)prop-1-en-1-yl)-4-((3-fluoro-4-methoxyphenyl)sulfonyl)-3,4-dihydro-2H-benzo[b][1,4]oxazin-2-yl)methanamine (0.068 g, 0.13 mmol) and triethylamine (0.037 mL, 0.27 mmol) dissolved in dichloromethane (2 mL) at 0° C. was added methyl 4-(chlorocarbonyl)benzoate (0.0323 g, 0.163 mmol). The reaction mixture was stirred overnight, with warming to room temperature. The solvent was removed and the resulting residue was purified by MPLC eluting with a gradient of ethyl acetate and hexanes to afford methyl (S,E)-4-(((6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)carbamoyl)benzoate (0.048 g, 53%) as a light yellow oil. $^1$H-NMR (400 MHz, CDCl$_3$) δ 8.13-8.10 (m, 2H), 7.88-7.81 (m, 3H), 7.33-7.00 (m, 7H), 6.87 (d, 1H), 6.53 (t, 1H), 6.38 (s, 1H), 4.35 (dd, 1H), 3.95 (s, 3H), 3.77 (s, 3H), 3.76-3.62 (m, 3H), 3.34 (dd, 1H), 2.19 (s, 1H).

Example 134—Synthesis of (S,E)-4-(((6-(2-(2-Chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)carbamoyl)benzoic acid

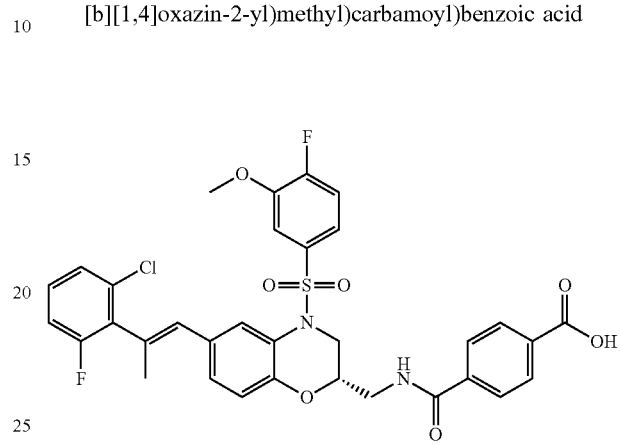

Based on the procedure in Example 42, (S,E)-4-(((6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)carbamoyl)benzoic acid was prepared. $^1$H-NMR (400 MHz, CDCl$_3$) δ 8.18 (d, 2H), 7.88-7.85 (m, 3H), 7.34-7.00 (m, 7H), 6.87 (d, 1H), 6.56 (t, 1H), 6.38 (s, 1H), 4.38-4.34 (m, 1H), 3.78 (s, 3H), 3.75-3.63 (m, 3H), 3.38-3.32 (m, 1H), 2.20 (s, 3H). (ES, m/z): (M–H)$^{-667/669}$.

Example 135—Preparation of Additional Benzoxazines N-Linked to a Dicarboxylic Acid Compounds in Table 19 were prepared based on experimental procedures described in Example 128 and the detailed description.

TABLE 19

| No. | Structure | Name | Observed m/z |
|---|---|---|---|
| 135A | 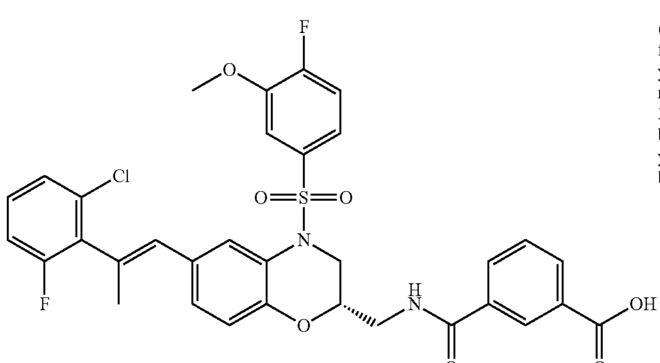 | (S,E)-3-(((6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)carbamoyl)benzoic acid | 669 (M + H)$^+$ |

TABLE 19-continued

| No. | Structure | Name | Observed m/z |
|---|---|---|---|
| 135B | 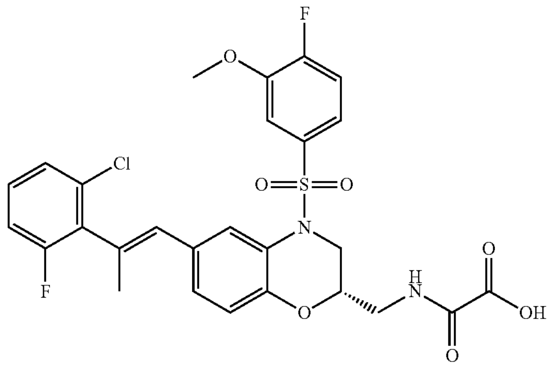 | (S,E)-2-(((6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)amino)-2-oxoacetic acid | 593 (M + H)+ |
| 135C | 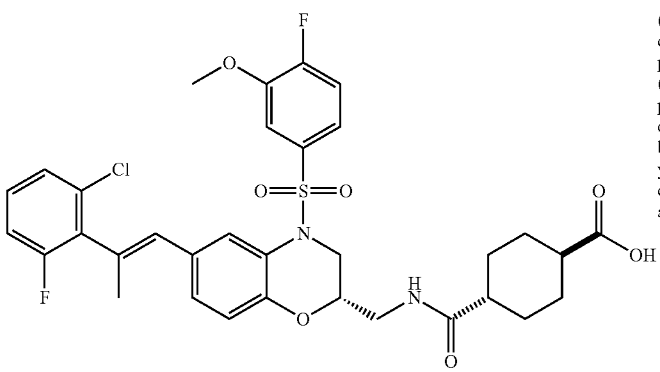 [SMILES: COc1cc(S(=O)(=O)N2C[C@H](CNC(=O)c3ccc(C(=O)O)cc3)Oc3ccc(/C=C(\C)c4c(F)cccc4Cl)cc32)ccc1F] | (1S,4r)-4-(((((S)-6-((E)-2-(2-chloro-6-fluoro-phenyl)prop-1-en-1-yl)-4-((4-fluoro-3-methoxy-phenyl)sulfonyl)-3,4-dihydro-2H-benzo[b][1,4]oxazin-2-yl)methyl)carbamoyl)-cyclohexane-1-carboxylic acid | 675 (M + H)+ |

Example 136—Synthesis of ((2R,3R)-6-((E)-2-Chloro-6-fluorostyryl)-4-((4-fluoro-3-methoxyphenyl)sulfonyl)-3-methyl-3,4-dihydro-2H-benzo[b][1,4]oxazin-2-yl)methanol

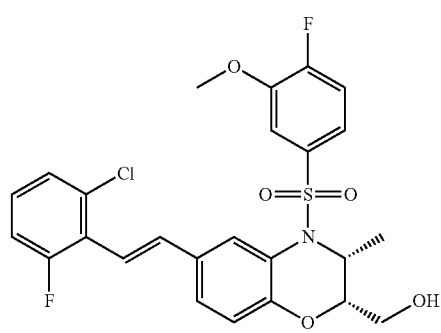 [SMILES: COc1cc(S(=O)(=O)N2c3cc(/C=C/c4c(F)cccc4Cl)ccc3O[C@@H](CO)[C@H]2C)ccc1F]

Part I—Synthesis of (2R,3R)-3-((4-Bromo-2-fluorophenyl)amino)butane-1,2-diol

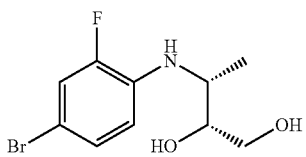

5-Bromo-2-fluoroaniline (6.5 g, 34.21 mmol) and hexaethoxytungsten (772 mg, 1.70 mmol) were added to a solution of [(2S,3S)-3-methyloxiran-2-yl]methanol (1.5 g, 17.03 mmol) in acetonitrile (100 mL) and was stirred overnight at 55° C. The mixture was concentrated and the resulting residue was purified by MPLC eluting with a gradient of 5-66% ethyl acetate in petroleum ether to afford (2R,3R)-3-((4-bromo-2-fluorophenyl)amino)butane-1,2-diol (2.8 g, 59%) as a yellow oil.

519

Part II—Synthesis of (2R,3R)-3-((4-((E)-2-Chloro-6-fluorostyryl)-2-fluorophenyl)-amino)butane-1,2-diol

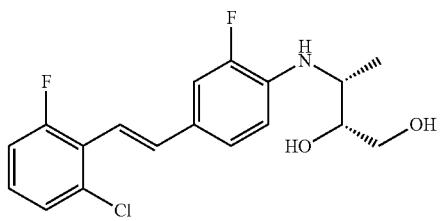 [SMILES: C[C@@H](Nc1ccc(/C=C/c2c(F)cccc2Cl)cc1F)[C@@H](O)CO]

A mixture of (2R,3R)-3-((4-bromo-2-fluorophenyl)amino)butane-1,2-diol (1.8 g, 6.47 mmol), toluene (48 mL), ethanol (16 mL), water (8 mL), tetrakis(triphenyl-phosphine)palladium(0) (750 mg, 0.65 mmol), sodium carbonate (2.8 g, 26.42 mmol), and (E)-2-(2-chloro-6-fluorostyryl)-4,4,5,5-tetramethyl-1,3,2-dioxaborolane (2.2 g, 7.79 mmol) was stirred for four hours at 80° C. The mixture was concentrated. The resulting residue was purified via MPLC eluting with a gradient of 5-66% ethyl acetate in petroleum ether to afford (2R,3R)-3-((4-((E)-2-chloro-6-fluorostyryl)-2-fluorophenyl)-amino)butane-1,2-diol (1.6 g, 70%) as a yellow oil.

Part III—Synthesis of (2R,3R)-1-((tert-Butyldimethylsilyl)oxy)-3-((4-((E)-2-chloro-6-fluorostyryl)-2-fluorophenyl)amino)butan-2-ol

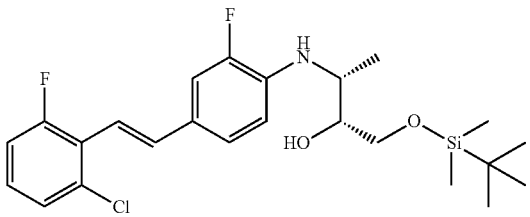 [SMILES: C[C@@H](Nc1ccc(/C=C/c2c(F)cccc2Cl)cc1F)[C@@H](O)CO[Si](C)(C)C(C)(C)C]

tert-Butyldimethylsilyl chloride (746 mg, 4.97 mmol) and imidazole (1.22 g, 17.92 mmol) were added to a solution of (2R,3R)-3-((4-((E)-2-chloro-6-fluorostyryl)-2-fluorophenyl)-amino)butane-1,2-diol (1.6 g, 4.52 mmol) in dichloromethane (60 mL). The mixture was stirred overnight at room temperature. The solution was washed twice with water, brine, dried ($Na_2SO_4$) and concentrated to afford (2R,3R)-1-((tert-butyldimethylsilyl)oxy)-3-((4-((E)-2-chloro-6-fluorostyryl)-2-fluorophenyl)amino)butan-2-ol (1.8 g, 85%) as a yellow oil.

520

Part IV—Synthesis of N-((2R,3R)-4-((tert-Butyldimethylsilyl)oxy)-3-hydroxybutan-2-yl)-N-(4-((E)-2-chloro-6-fluorostyryl)-2-fluorophenyl)-4-fluoro-3-methoxybenzenesulfonamide

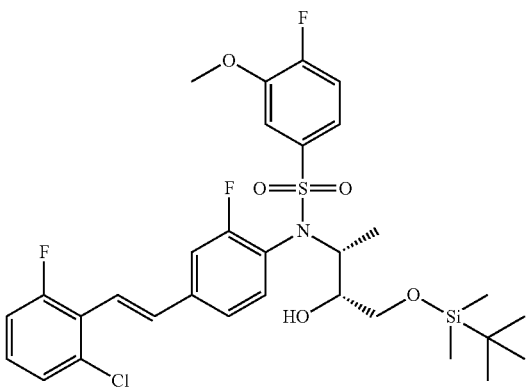 [SMILES: COc1cc(S(=O)(=O)N(c2ccc(/C=C/c3c(F)cccc3Cl)cc2F)[C@H](C)[C@@H](O)CO[Si](C)(C)C(C)(C)C)ccc1F]

A mixture of (2R,3R)-1-((tert-butyldimethylsilyl)oxy)-3-((4-((E)-2-chloro-6-fluorostyryl)-2-fluorophenyl)amino)butan-2-ol (1.8 g, 3.85 mmol), pyridine (50 mL), and 4-fluoro-3-methoxybenzene-1-sulfonyl chloride (1.7 g, 7.57 mmol) was stirred overnight at room temperature. The mixture was concentrated, and the resulting residue was purified via MPLC eluting with a gradient of 5-50% ethyl acetate in petroleum ether to afford N-((2R,3R)-4-((tert-butyldimethylsilyl)oxy)-3-hydroxybutan-2-yl)-N-(4-((E)-2-chloro-6-fluorostyryl)-2-fluorophenyl)-4-fluoro-3-methoxybenzenesulfonamide (243 mg, 10%) as a yellow oil.

Part V—Synthesis of (2R,3R)-2-(((tert-Butyldimethylsilyl)oxy)methyl)-6-((E)-2-chloro-6-fluorostyryl)-4-((4-fluoro-3-methoxyphenyl)sulfonyl)-3-methyl-3,4-dihydro-2H-benzo[b][1,4]oxazine

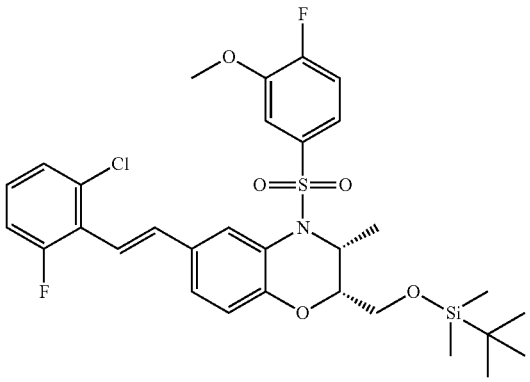 [SMILES: COc1cc(S(=O)(=O)N2c3cc(/C=C/c4c(F)cccc4Cl)ccc3O[C@@H](CO[Si](C)(C)C(C)(C)C)[C@H]2C)ccc1F]

A mixture of N-((2R,3R)-4-((tert-butyldimethylsilyl)oxy)-3-hydroxybutan-2-yl)-N-(4-((E)-2-chloro-6-fluorostyryl)-2-fluorophenyl)-4-fluoro-3-methoxybenzenesulfonamide (243 mg, 0.37 mmol), tetrahydrofuran (10 mL) and potassium tert-butoxide (124 mg, 1.11 mmol) was heated at reflux for two hours. The reaction mixture was cooled, concentrated, and the resulting residue was purified by MPLC eluting with a gradient of 2-20% ethyl acetate to petroleum ether to afford (2R,3R)-2-(((tert-butyldimethylsilyl)oxy)methyl)-6-((E)-2-chloro-6-fluorostyryl)-4-((4-fluoro-3-methoxyphenyl)sulfonyl)-3-methyl-3,4-dihydro-2H-benzo[b][1,4]oxazine (150 mg, 64%) as a white solid.

Part VI—Synthesis of ((2R,3R)-6-((E)-2-Chloro-6-fluorostyryl)-4-((4-fluoro-3-methoxyphenyl)sulfonyl)-3-methyl-3,4-dihydro-2H-benzo[b][1,4]oxazin-2-yl)methanol

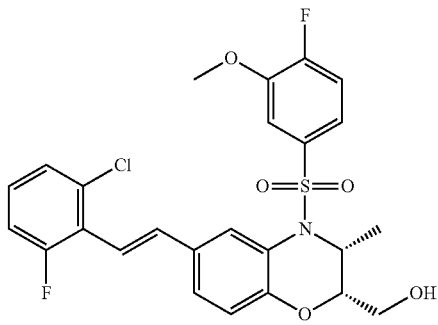 [SMILES: COc1cc(S(=O)(=O)N2c3cc(/C=C/c4c(F)cccc4Cl)ccc3O[C@@H](CO)[C@H]2C)ccc1F]

6M Hydrogen chloride (3 mL) was added to a solution of (2R,3R)-2-(((tert-butyldimethylsilyl)oxy)methyl)-6-((E)-2-chloro-6-fluorostyryl)-4-((4-fluoro-3-methoxyphenyl)sulfonyl)-3-methyl-3,4-dihydro-2H-benzo[b][1,4]oxazine (150 mg, 0.24 mmol) in tetrahydrofuran (10 mL). The solution was stirred for two hours at room temperature. The pH value of the solution was adjusted to 8-9 with solid sodium carbonate. The resulting solution was extracted twice with ethyl acetate. The combined organic layers were washed with water, brine, dried (Na$_2$SO$_4$) and concentrated. The resulting residue was re-crystallized from n-heptane to afford ((2R,3R)-6-((E)-2-chloro-6-fluorostyryl)-4-((4-fluoro-3-methoxyphenyl)sulfonyl)-3-methyl-3,4-dihydro-2H-benzo[b][1,4]oxazin-2-yl)methanol (105 mg, 85%) as an off-white solid. $^1$H-NMR (400 MHz, CD$_3$OD) δ 8.10 (s, 1H), 7.14-7.40 (m, 9H), 6.91 (d, J=8.4 Hz, 1H), 4.62-4.67 (m, 1H), 3.81 (s, 3H), 3.65 (m, 1H), 3.48-3.58 (m, 1H), 3.26 (m, 1H), 1.18 (d, J=6.8 Hz, 3H). (ES, m/z): (M+H)$^+$522.

Example 137-Synthesis of (S,E)-N-((6-(2-(2-Chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)acetamide

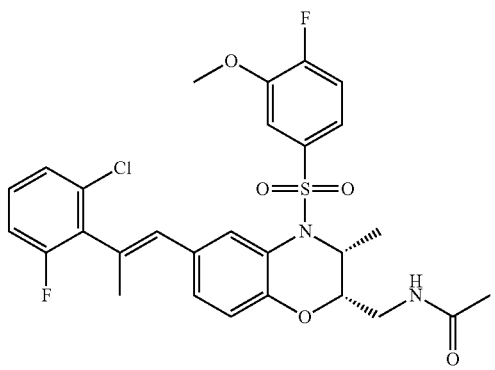 [SMILES: COc1cc(S(=O)(=O)N2c3cc(/C=C(\C)c4c(F)cccc4Cl)ccc3O[C@@H](CNC(C)=O)[C@H]2C)ccc1F]

Part I—Synthesis of (2R,3R)-3-((4-((E)-2-(2-Chloro-6-fluorophenyl)prop-1-en-1-yl)-2-fluorophenyl)amino)butane-1,2-diol

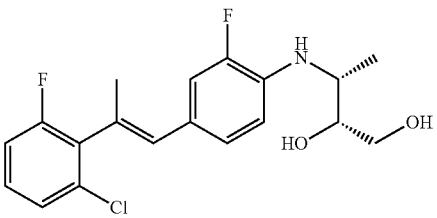 [SMILES: C/C(=C\c1ccc(N[C@H](C)[C@@H](O)CO)c(F)c1)c1c(F)cccc1Cl]

A mixture of (2R,3R)-3-((4-bromo-2-fluorophenyl)amino)butane-1,2-diol (1.8 g, 6.47 mmol), toluene (33 mL), ethanol (11 mL), water (5.5 mL), tetrakis(triphenyl-phosphine)palladium(0) (416 mg, 0.36 mmol), sodium carbonate (1.53 g, 14.44 mmol), and (E)-2-(2-(2-chloro-6-fluorophenyl)prop-1-en-1-yl)-4,4,5,5-tetramethyl-1,3,2-dioxaborolane (1.3 g, 4.38 mmol) was stirred for four hours at 80° C. The resulting mixture was concentrated. The resulting residue was purified via MPLC eluting with a gradient of 5-50% ethyl acetate in petroleum ether to afford (2R,3R)-3-((4-((E)-2-(2-chloro-6-fluorophenyl)prop-1-en-1-yl)-2-fluorophenyl)amino)butane-1,2-diol (1.3 g, 98%) as a yellow oil.

Part II—Synthesis of (2R,3R)-1-((tert-Butyldimethylsilyl)oxy)-3-((4-((E)-2-(2-chloro-6-fluorophenyl)prop-1-en-1-yl)-2-fluorophenyl)amino)butan-2-ol

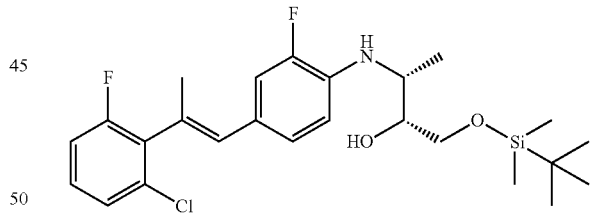

tert-Butyldimethylsilyl chloride (583 mg, 3.89 mmol) and imidazole (0.952 g, 14.0 mmol) were added to a solution of (2R,3R)-3-((4-((E)-2-(2-chloro-6-fluorophenyl)prop-1-en-1-yl)-2-fluorophenyl)amino)butane-1,2-diol (1.3 g, 3.53 mmol) in dichloromethane (50 mL). The mixture was stirred for four hours at room temperature. The solution was washed twice with water, brine, dried (Na$_2$SO$_4$) and concentrated to afford (2R,3R)-1-((tert-butyldimethylsilyl)oxy)-3-((4-((E)-2-(2-chloro-6-fluorophenyl)prop-1-en-1-yl)-2-fluorophenyl)amino)butan-2-ol (1.40 g, 82%) as a yellow oil.

Part III—Synthesis of N-((2R,3R)-4-((tert-Butyldimethylsilyl)oxy)-3-hydroxybutan-2-yl)-N-(4-((E)-2-(2-chloro-6-fluorophenyl)prop-1-en-1-yl)-2-fluorophenyl)-4-fluoro-3-methoxybenzenesulfonamide

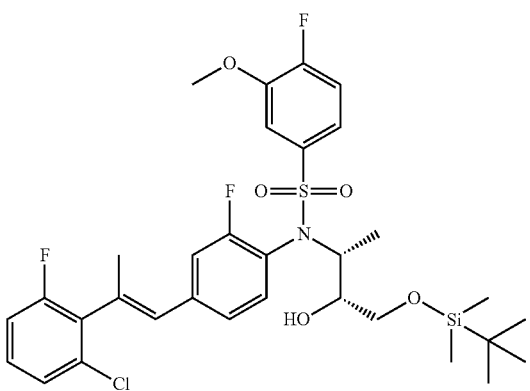 [SMILES: COc1cc(S(=O)(=O)N(c2ccc(/C=C(\C)c3c(F)cccc3Cl)cc2F)[C@H](C)[C@@H](O)CO[Si](C)(C)C(C)(C)C)ccc1F]

A mixture of (2R,3R)-1-((tert-butyldimethylsilyl)oxy)-3-((4-((E)-2-(2-chloro-6-fluorophenyl)prop-1-en-1-yl)-2-fluorophenyl)amino)butan-2-ol (1.4 g, 2.90 mmol), pyridine (50 mL), and 4-fluoro-3-methoxybenzene-1-sulfonyl chloride (1.3 g, 5.8 mmol) was stirred overnight at room temperature. The mixture was concentrated, and the resulting residue was purified via MPLC eluting with a gradient of 5-50% ethyl acetate in petroleum ether to afford N-((2R,3R)-4-((tert-butyldimethylsilyl)oxy)-3-hydroxybutan-2-yl)-N-(4-((E)-2-(2-chloro-6-fluorophenyl)prop-1-en-1-yl)-2-fluorophenyl)-4-fluoro-3-methoxybenzenesulfonamide (230 mg, 12%) as a yellow oil.

Part IV—Synthesis (2R,3R)-2-(((tert-Butyldimethylsilyl)oxy)methyl)-6-((E)-2-(2-chloro-6-fluorophenyl)prop-1-en-1-yl)-4-((4-fluoro-3-methoxyphenyl)sulfonyl)-3-methyl-3,4-dihydro-2H-benzo[b][1,4]oxazine

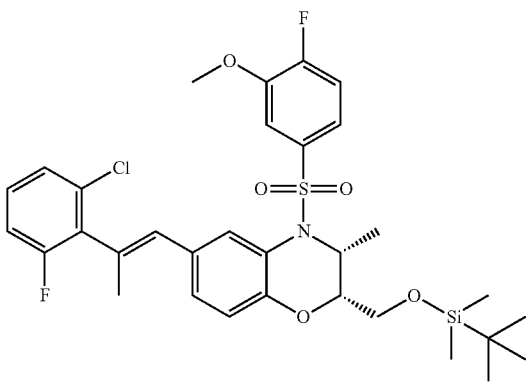 [SMILES: COc1cc(S(=O)(=O)N2c3cc(/C=C(\C)c4c(F)cccc4Cl)ccc3O[C@@H](CO[Si](C)(C)C(C)(C)C)[C@H]2C)ccc1F]

A mixture of N-((2R,3R)-4-((tert-butyldimethylsilyl)oxy)-3-hydroxybutan-2-yl)-N-(4-((E)-2-(2-chloro-6-fluorophenyl)prop-1-en-1-yl)-2-fluorophenyl)-4-fluoro-3-methoxybenzenesulfonamide (230 mg, 0.34 mmol), tetrahydrofuran (10 mL) and potassium tert-butoxide (115 mg, 1.02 mmol) was was heated at reflux for two hours. The reaction mixture was cooled, concentrated, and the resulting residue was purified by MPLC eluting with a gradient of 5-20% ethyl acetate to petroleum ether to afford (2R,3R)-2-(((tert-butyldimethylsilyl)oxy)methyl)-6-((E)-2-(2-chloro-6-fluorophenyl)prop-1-en-1-yl)-4-((4-fluoro-3-methoxyphenyl)sulfonyl)-3-methyl-3,4-dihydro-2H-benzo[b][1,4]oxazine (165 mg, 74%) as a yellow oil.

Part V—Synthesis of ((2R,3R)-6-((E)-2-(2-Chloro-6-fluorophenyl)prop-1-en-1-yl)-4-((4-fluoro-3-methoxyphenyl)sulfonyl)-3-methyl-3,4-dihydro-2H-benzo[b][1,4]oxazin-2-yl)methanol

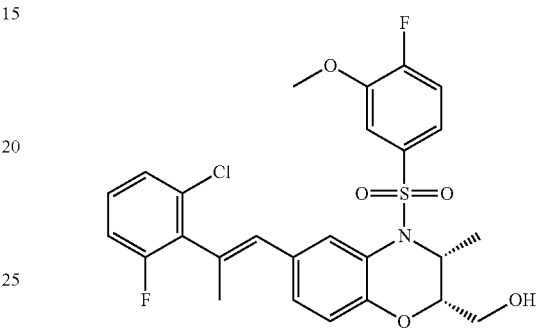

6 M Hydrogen chloride (3 mL) was added to a solution of (2R,3R)-2-(((tert-butyldimethylsilyl)oxy)methyl)-6-((E)-2-(2-chloro-6-fluorophenyl)prop-1-en-1-yl)-4-((4-fluoro-3-methoxyphenyl)sulfonyl)-3-methyl-3,4-dihydro-2H-benzo[b][1,4]oxazine (165 mg, 0.25 mmol) in tetrahydrofuran (10 mL). The solution was stirred for two hours at room temperature. The pH value of the solution was adjusted to 8-9 with solid sodium carbonate. The resulting solution was extracted twice with ethyl acetate. The combined organic layers were washed with water, brine, dried ($Na_2SO_4$) and concentrated. The resulting residue was re-crystallized from n-heptane to afford ((2R,3R)-6-((E)-2-(2-chloro-6-fluorophenyl)prop-1-en-1-yl)-4-((4-fluoro-3-methoxyphenyl)sulfonyl)-3-methyl-3,4-dihydro-2H-benzo[b][1,4]oxazin-2-yl)methanol (125 mg, 92%) as a white solid.

Part VI—Synthesis of 2-(((2S,3R)-6-((E)-2-(2-Chloro-6-fluorophenyl)prop-1-en-1-yl)-4-((4-fluoro-3-methoxyphenyl)sulfonyl)-3-methyl-3,4-dihydro-2H-benzo[b][1,4]oxazin-2-yl)methyl)isoindoline-1,3-dione

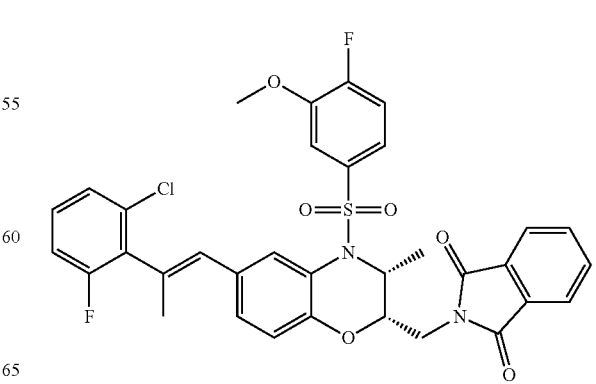

Diisopropyl diazodicarboxylate (94 mg, 0.46 mmol) was added to a solution of ((2R,3R)-6-((E)-2-(2-chloro-6-fluorophenyl)prop-1-en-1-yl)-4-((4-fluoro-3-methoxyphenyl)sulfonyl)-3-methyl-3,4-dihydro-2H-benzo[b][1,4]oxazin-2-yl)methanol (125 mg, 0.23 mmol), triphenylphosphine (122 mg, 0.47 mmol), tetrahydrofuran (15 mL), and 2,3-dihydro-1H-isoindole-1,3-dione (68 mg, 0.46 mmol). The resulting solution was stirred overnight at room temperature and concentrated. The resulting residue was purified via MPLC eluting with a gradient of 5-50% ethyl acetate in petroleum ether to afford 2-(((2S,3R)-6-((E)-2-(2-chloro-6-fluorophenyl)prop-1-en-1-yl)-4-((4-fluoro-3-methoxyphenyl)sulfonyl)-3-methyl-3,4-dihydro-2H-benzo[b][1,4]oxazin-2-yl)methyl)isoindoline-1,3-dione (152 mg, 98%) as a yellow oil.

Part VII—Synthesis of ((2S,3R)-6-((E)-2-(2-Chloro-6-fluorophenyl)prop-1-en-1-yl)-4-((4-fluoro-3-methoxyphenyl)sulfonyl)-3-methyl-3,4-dihydro-2H-benzo[b][1,4]oxazin-2-yl)methanamine

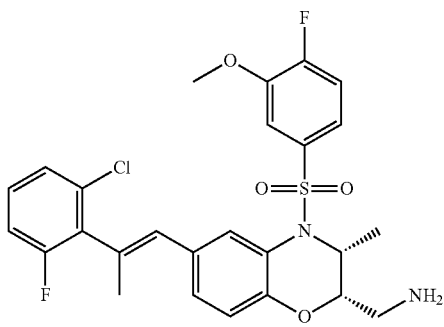 [SMILES: COc1cc(S(=O)(=O)N2c3cc(/C=C(\C)c4c(F)cccc4Cl)ccc3O[C@@H](CN)[C@H]2C)ccc1F]

A mixture of 2-(((2S,3R)-6-((E)-2-(2-chloro-6-fluorophenyl)prop-1-en-1-yl)-4-((4-fluoro-3-methoxyphenyl)sulfonyl)-3-methyl-3,4-dihydro-2H-benzo[b][1,4]oxazin-2-yl)methyl)isoindoline-1,3-dione (152 mg, 0.23 mmol), tetrahydrofuran (10 mL), and hydrazine hydrate (3 mL) was stirred overnight at 50° C. The resulting mixture was concentrated and was diluted with water. The mixture was extracted three times with ethyl acetate. The combined organic layers were washed with water, brine, dried (Na$_2$SO$_4$), and concentrated to afford ((2S,3R)-6-((E)-2-(2-chloro-6-fluorophenyl)prop-1-en-1-yl)-4-((4-fluoro-3-methoxyphenyl)sulfonyl)-3-methyl-3,4-dihydro-2H-benzo[b][1,4]oxazin-2-yl)methanamine (101 mg, 83%) as a yellow oil.

Part VIII—Synthesis of (S,E)-N-((6-(2-(2-Chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)acetamide

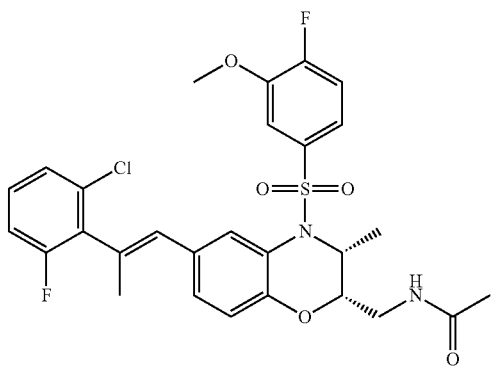 [SMILES: COc1cc(S(=O)(=O)N2c3cc(/C=C(\C)c4c(F)cccc4Cl)ccc3O[C@@H](CNC(C)=O)[C@H]2C)ccc1F]

A mixture of ((2S,3R)-6-((E)-2-(2-chloro-6-fluorophenyl)prop-1-en-1-yl)-4-((4-fluoro-3-methoxyphenyl)sulfonyl)-3-methyl-3,4-dihydro-2H-benzo[b][1,4]oxazin-2-yl)methanamine (100 mg, 0.19 mmol) in dichloromethane (10 mL), TEA (76 mg, 0.75 mmol, 4.00 equiv). This was followed by the addition of acetic anhydride (23 mg, 0.23 mmol, 1.20 equiv) dropwise with stirring. The resulting solution was stirred for 3 h at room temperature. The reaction was then quenched by the addition of water (20 mL). The resulting solution was extracted twice with dichloromethane and the organic layers were combined, dried (Na$_2$SO$_4$), and concentrated. The resulting residue was purified by Prep-HPLC eluting with 0.05% trifluoroacetic acid to afford 35 mg (32%) of (S,E)-N-((6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)methyl)acetamide as a white solid. $^1$H-NMR (400 MHz, CD$_3$OD) δ 8.01 (s, 1H), 7.27-7.35 (m, 4H), 7.12-7.19 (m, 4H), 6.91 (d, J=8.4 Hz, 1H), 6.40 (s, 1H), 4.53-4.59 (m, 1H), 3.74 (s, 3H), 3.33-3.41 (m, 1H), 3.15-3.32 (m, 2H), 2.24 (s, 3H), 1.97 (s, 3H), 1.18 (d, J=6.8 Hz, 3H). (ES, m/z): (M+H)$^+$577.

Example 138—Synthesis of (R)-(7-((2-Chloro-6-fluorobenzyl)oxy)-1-((4-fluoro-3-methoxyphenyl)sulfonyl)-2-methyl-1,2-dihydroquinolin-3-yl)methanol

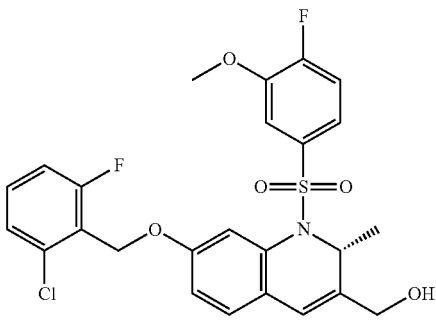 [SMILES: COc1cc(S(=O)(=O)N2c3cc(OCc4c(F)cccc4Cl)ccc3C=C(CO)[C@H]2C)ccc1F]

Part I—Synthesis of 4-Hydroxy-2-nitrobenzaldehyde

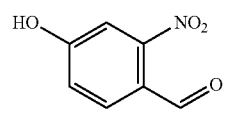

To a stirred solution of 4-methoxy-2-nitrobenzaldehyde (4.5 g, 24.84 mmol) in dichloromethane (100 mL) at 0° C. was added boron tribromide (8 mL, 84.5 mmol) dropwise. The mixture was stirred for thirty minutes at 0° C. and an additional four hours at room temperature. The reaction mixture was poured into ice water (200 mL) and stirred for two days. The mixture was extracted twice with ethyl acetate. The combined organic layers were washed with water, brine, dried (Na$_2$SO$_4$) and concentrated. The resulting residue was purified via MPLC eluting with a gradient of ethyl acetate/petroleum ether (1:15-1:5) to afford 4-hydroxy-2-nitrobenzaldehyde (2.55 g, 61%) as an orange solid.

Part II—Synthesis of 4-((2-Chloro-6-fluorobenzyl)oxy)-2-nitrobenzaldehyde

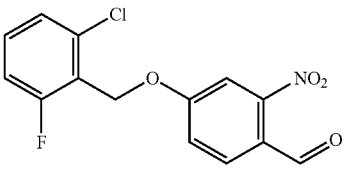 [SMILES: O=Cc1ccc(OCc2c(F)cccc2Cl)cc1[N+](=O)[O-]]

To a stirred mixture of 4-hydroxy-2-nitrobenzaldehyde (2.55 g, 15.26 mmol) and potassium carbonate (6.33 g, 45.80 mmol) in acetonitrile (50 mL) was added 2-(bromomethyl)-1-chloro-3-fluorobenzene (4.47 g, 20.00 mmol) dropwise. The mixture was stirred overnight and concentrated. The resulting residue was diluted with water, and extracted three times with ethyl acetate. The combined organic layers were washed with water, brine, dried ($Na_2SO_4$) and concentrated. The resulting residue was purified via MPLC eluting with a gradient of ethyl acetate/petroleum ether (1:40-1:20) to afford 4-((2-chloro-6-fluorobenzyl)oxy)-2-nitrobenzaldehyde (2.83 g, 60%) as a yellow solid.

Part III—Synthesis of 2-amino-4-((2-chloro-6-fluorobenzyl)oxy)benzaldehyde

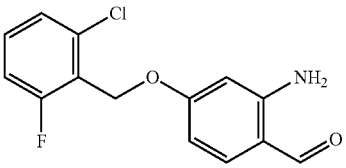

A mixture of powdered iron (3.2 g, 55 mmol), ethanol (100 mL), water (15 mL), and acetic acid (660 mg, 10.99 mmol) was heated to reflux for thirty minutes. This was followed by the addition of 4-[(2-chloro-6-fluorophenyl)methoxy]-2-nitrobenzaldehyde (3.5 g, 11.30 mmol) in ethanol (30 mL) dropwise with stirring. The mixture was refluxed for an additional three hours, cooled, and filtered. The filtrate was concentrated, diluted with water, and extracted three times ethyl acetate. The combined organic layers were washed with water, brine, dried ($Na_2SO_4$) and concentrated. The resulting residue was purified via MPLC eluting with a gradient of ethyl acetate/petroleum ether (1:20-1:15) to afford 2-amino-4-((2-chloro-6-fluorobenzyl)oxy)benzaldehyde (2.42 g, 77%) as a yellow solid.

Part IV—Synthesis of N-(5-((2-chloro-6-fluorobenzyl)oxy)-2-formylphenyl)-4-fluoro-3-methoxybenzenesulfonamide

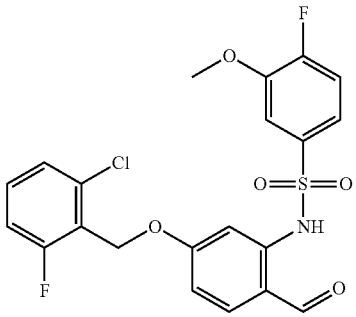 [SMILES: COc1cc(S(=O)(=O)Nc2cc(OCc3c(F)cccc3Cl)ccc2C=O)ccc1F]

To a mixture of 2-amino-4-((2-chloro-6-fluorobenzyl)oxy)benzaldehyde (1.0 g, 3.58 mmol), dichloromethane (40 mL), and 4-fluoro-3-methoxybenzene-1-sulfonyl chloride (1.6 g, 7.12 mmol) was added pyridine (1.4 g, 17.70 mmol) dropwise. The mixture was refluxed for overnight, cooled, and diluted with water. The mixture was extracted with ethyl acetate. The organic layer was washed with 1 M HCl, water, brine, dried ($Na_2SO_4$), and concentrated. The resulting residue was purified via MPLC eluting with ethyl acetate/petroleum ether (1:10) to afford N-(5-((2-chloro-6-fluorobenzyl)oxy)-2-formylphenyl)-4-fluoro-3-methoxybenzenesulfonamide (1.0 g, 60%) as a yellow solid.

Part V—Synthesis of (R)-7-((2-Chloro-6-fluorobenzyl)oxy)-1-((4-fluoro-3-methoxyphenyl)sulfonyl)-2-methyl-1,2-dihydroquinoline-3-carbaldehyde

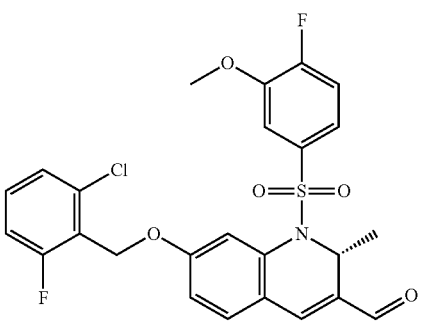 [SMILES: COc1cc(S(=O)(=O)N2c3cc(OCc4c(F)cccc4Cl)ccc3C=C(C=O)[C@H]2C)ccc1F]

A mixture of N-(5-((2-chloro-6-fluorobenzyl)oxy)-2-formylphenyl)-4-fluoro-3-methoxybenzenesulfonamide (1.1 g, 2.35 mmol), dichloromethane (30 mL), 4 Å MS (1.0 g), sodium acetate (580 mg, 7.05 mmol), and (2E)-but-2-enal (830 mg, 11.84 mmol) was stirred for ten minutes. To the mixture was added (2S)-2-diphenyl[(triethylsilyl)oxy]methylpyrrolidine (110 mg, 0.30 mmol). The reaction mixture was stirred for a day at room temperature. Added water and extracted twice with ethyl acetate. The organic layers were combined, washed with water, brine, dried ($Na_2SO_4$) and concentrated. The resulting residue was purified via MPLC eluting with a gradient of ethyl acetate/petroleum ether (1:10-1:8) to afford (R)-7-((2-chloro-6-fluorobenzyl)oxy)-1-((4-fluoro-3-methoxyphenyl)sulfonyl)-2-methyl-1,2-dihydroquinoline-3-carbaldehyde (960 mg, 79%) as a light yellow solid.

Part VI—Synthesis of (R)-(7-((2-Chloro-6-fluorobenzyl)oxy)-1-((4-fluoro-3-methoxyphenyl)sulfonyl)-2-methyl-1,2-dihydroquinolin-3-yl)methanol

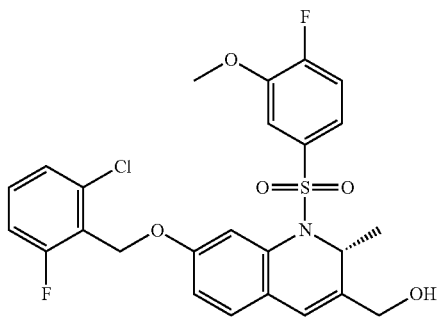 [SMILES: COc1cc(S(=O)(=O)N2c3cc(OCc4c(F)cccc4Cl)ccc3C=C(CO)[C@H]2C)ccc1F]

To a solution of (R)-7-((2-chloro-6-fluorobenzyl)oxy)-1-((4-fluoro-3-methoxyphenyl)sulfonyl)-2-methyl-1,2-dihydroquinoline-3-carbaldehyde (120 mg, 0.23 mmol) in methanol (10 mL) at 0° C. was added cerium (III) chloride heptahydrate (130 mg, 0.35 mmol). After thirty minutes, sodium borohydride (10 mg, 0.26 mmol) was added in small portions at 0° C. The resulting solution was stirred an additional thirty minutes at 0° C., and then water was added. The mixture was extracted three times with ethyl acetate. The combined organic layers were washed with water, brine, dried ($Na_2SO_4$) and concentrated. The resulting residue was purified via MPLC eluting with a gradient of ethyl acetate/petroleum ether (1:4-1:2). The major UV active fraction was concentrated and further purified by reverse phase Prep-HPLC eluting with a gradient of acetonitrile in water (50.0% to 72.0%) to afford (R)-(7-((2-chloro-6-fluorobenzyl)oxy)-1-((4-fluoro-3-methoxyphenyl)sulfonyl)-2-methyl-1,2-dihydroquinolin-3-yl)methanol (39.9 mg, 33%) as a white solid. $^1$H-NMR (400 MHz, $CDCl_3$) δ 1.20 (d, J=6.8 Hz, 3H), 3.66 (s, 3H), 4.02 (s, 2H), 4.92 (q, J=6.8 Hz, 1H), 5.25 (s, 2H), 5.93 (s, 1H), 6.82-6.88 (m, 2H), 6.90-7.03 (m, 2H), 7.05-7.14 (m, 2H), 7.25-7.38 (m, 2H), 7.49 (s, 1H). (ES, m/z): $(M+H-H_2O)^+$ 504.1.

Example 139—Synthesis of (R)-(7-((2-Chloro-6-fluorobenzyl)oxy)-1-((4-fluoro-3-methoxyphenyl)sulfonyl)-2-methyl-1,2-dihydroquinolin-3-yl)methanamine

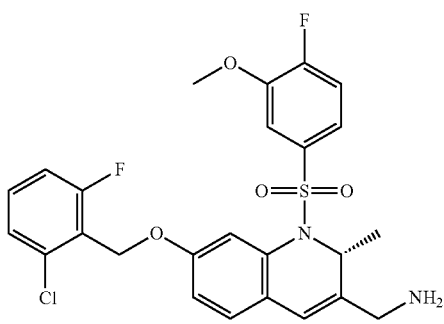 [SMILES: COc1cc(S(=O)(=O)N2c3cc(OCc4c(F)cccc4Cl)ccc3C=C(CN)[C@H]2C)ccc1F]

Part I—Synthesis of (R)-2-((7-((2-chloro-6-fluorobenzyl)oxy)-1-((4-fluoro-3-methoxyphenyl)sulfonyl)-2-methyl-1,2-dihydroquinolin-3-yl)methyl)isoindoline-1,3-dione

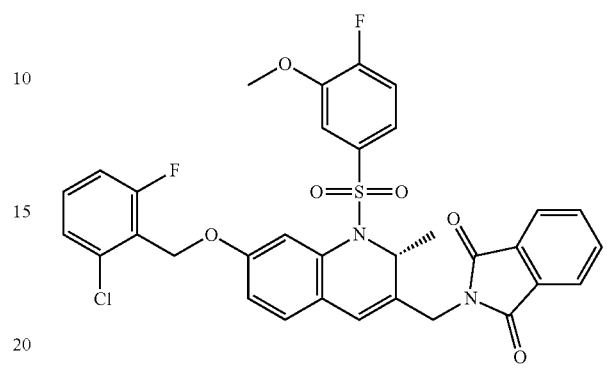

To a stirred solution of (R)-(7-((2-chloro-6-fluorobenzyl)oxy)-1-((4-fluoro-3-methoxyphenyl)sulfonyl)-2-methyl-1,2-dihydroquinolin-3-yl)methanol (525 mg, 1.00 mmol), triphenylphosphine (520 mg, 1.98 mmol), and 2,3-dihydro-1H-isoindole-1,3-dione (220 mg, 1.50 mmol) in anhydrous tetrahydrofuran (30 mL) at room temperature was added diisopropyldiazodicarboxylate (404 mg, 2.00 mmol) dropwise. The mixture was stirred for one hour and then diluted with water. The mixture was extracted three times with ethyl acetate. The combined organic layers were washed with water, brine, dried ($Na_2SO_4$) and concentrated. The resulting residue was purified via MPLC eluting with ethyl acetate/petroleum ether (1:8) as eluent to afford (R)-2-((7-((2-chloro-6-fluorobenzyl)oxy)-1-((4-fluoro-3-methoxyphenyl)sulfonyl)-2-methyl-1,2-dihydroquinolin-3-yl)methyl)isoindoline-1,3-dione (620 mg, 95%) as a light yellow solid.

Part II—Synthesis of (R)-(7-((2-Chloro-6-fluorobenzyl)oxy)-1-((4-fluoro-3-methoxyphenyl)sulfonyl)-2-methyl-1,2-dihydroquinolin-3-yl)methanamine

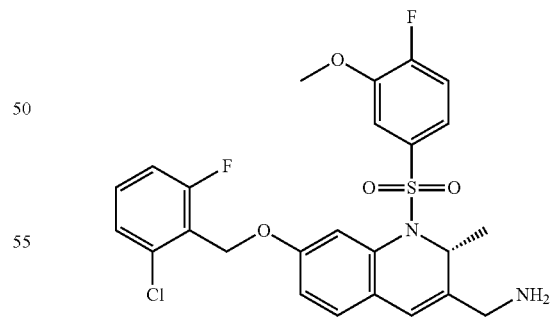

To a solution of (R)-2-((7-((2-chloro-6-fluorobenzyl)oxy)-1-((4-fluoro-3-methoxyphenyl)sulfonyl)-2-methyl-1,2-dihydroquinolin-3-yl)methyl)isoindoline-1,3-dione (150 mg, 0.23 mmol) in ethanol (10 mL) was added 80% hydrazine in water (80%, 1 mL). The reaction mixture was heated to reflux for two hours and then concentrated. The resulting residue was diluted with water and the pH value of the solution was adjusted to 10 with saturated sodium carbonate.

Extracted three times with ethyl acetate. The combined organic layers were washed three times with water, once with brine, dried (Na$_2$SO$_4$) and concentrated. The resulting residue was purified by reverse phase Prep-HPLC eluting with a gradient of 50-66% acetonitrile in water with 10 mM ammonium carbonate to afford (R)-(7-((2-chloro-6-fluorobenzyl)oxy)-1-((4-fluoro-3-methoxyphenyl)sulfonyl)-2-methyl-1,2-dihydroquinolin-3-yl)methanamine (24 mg, 20%) as an off-white solid. $^1$H-NMR (400 MHz, CDCl$_3$) δ 1.17 (d, J=6.8 Hz, 3H), 3.28 (AB q, J=16.0 Hz, 2H), 3.63 (s, 3H), 4.80 (q, J=6.8 Hz, 1H), 5.24 (s, 2H), 5.92 (s, 1H), 6.75-6.95 (m, 3H), 6.98-7.16 (m, 3H), 7.22-7.36 (m, 2H), 7.46 (s, 1H). (ES, m/z): (M+H-NH$_3$)$^+$504.1.

Example 140—Synthesis of (R)—N-((7-((2-Chloro-6-fluorobenzyl)oxy)-1-((4-fluoro-3-methoxyphenyl)sulfonyl)-2-methyl-1,2-dihydroquinolin-3-yl)methyl)acetamide

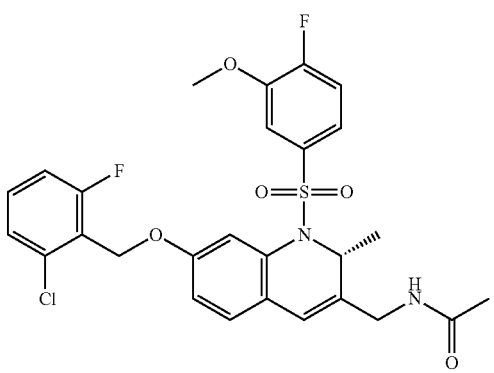 [SMILES: COc1cc(S(=O)(=O)N2c3cc(OCc4c(F)cccc4Cl)ccc3C=C(CNC(C)=O)[C@H]2C)ccc1F]

To a stirred room temperature solution of (R)-(7-((2-chloro-6-fluorobenzyl)oxy)-1-((4-fluoro-3-methoxyphenyl)sulfonyl)-2-methyl-1,2-dihydroquinolin-3-yl)methanamine (100 mg, 0.19 mmol) and triethylamine (190 mg, 1.88 mmol) in dichloromethane (15 mL) was added acetyl chloride (60 mg, 0.76 mmol) dropwise. The mixture was stirred overnight, diluted with water and extracted two times with ethyl acetate. The combined organic layers were washed twice with water, once with brine, dried (Na$_2$SO$_4$) and concentrated. The resulting residue was purified via MPLC eluting with a gradient of ethyl acetate/petroleum ether (1:2-2:1). The residue from the concentration of the major UV fraction was further purified by reverse phase Prep-HPLC eluting with a gradient of acetonitrile in water (50-66%) with 10 mM ammonium bicarbonate to afford (R)—N-((7-((2-chloro-6-fluorobenzyl)oxy)-1-((4-fluoro-3-methoxyphenyl)sulfonyl)-2-methyl-1,2-dihydroquinolin-3-yl)methyl)acetamide (43 mg, 40%) as a white solid. $^1$H-NMR (CDCl$_3$, 400 MHz) δ 1.18 (d, J=6.8 Hz, 3H), 2.03 (s, 3H), 3.66 (s, 3H), 3.79 (d, J=5.6 Hz, 2H), 4.72 (q, J=6.8 Hz, 1H), 5.15-5.30 (br s, 1H), 5.25 (s, 2H), 5.84 (s, 1H), 6.75-6.95 (m, 3H), 7.02-7.18 (m, 3H), 7.25-7.35 (m, 2H), 7.45 (s, 1H). (ES, m/z): (M+H-CH$_3$CONH$_2$) 504.2.

Example 141—Synthesis of Methyl (2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylate

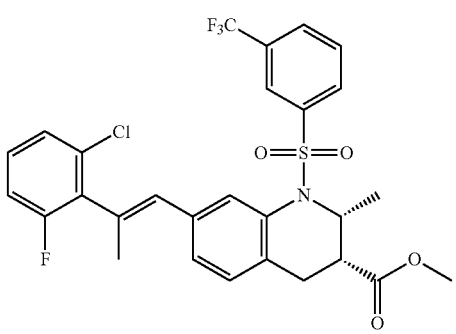 [SMILES: COC(=O)[C@@H]1Cc2ccc(/C=C(\C)c3c(F)cccc3Cl)cc2N(S(=O)(=O)c2cccc(C(F)(F)F)c2)[C@@H]1C]

Part I—Synthesis of Methyl (R)-3-(3-(trifluoromethyl)phenylsulfonamido)butanoate

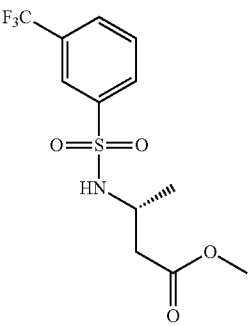 [SMILES: COC(=O)C[C@@H](C)NS(=O)(=O)c1cccc(C(F)(F)F)c1]

To a mixture of methyl (3R)-3-aminobutanoate hydrochloride (6.10 g, 39.7 mmol) and 3-(trifluoromethyl)benzenesulfonyl chloride (10.69 g, 43.7 mmol) in methylene chloride was added diisopropylethylamine (14.4 g, 111 mmol). The mixture was stirred overnight, and partitioned between dichloromethane and saturated ammonium chloride. The organic layer was washed with saturated sodium bicarbonate, brine, dried (Na$_2$SO$_4$) and concentrated. The resulting residue was purified by MPLC eluting with a gradient of 9:1 to 3:2 hexane: ethyl acetate to afford methyl (R)-3-(3-(trifluoromethyl)phenylsulfonamido)butanoate (9.23 g, 71%) as a clear oil.

Part II—Synthesis of Methyl (2R,3R)-2-(2,4-dibromobenzyl)-3-(3-(trifluoromethyl)phenyl-sulfonamido)butanoate

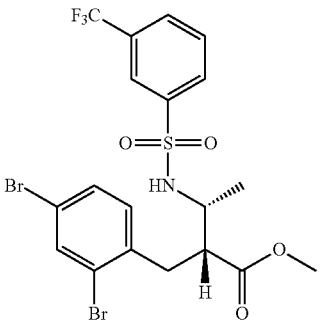 [SMILES: COC(=O)[C@H](Cc1ccc(Br)cc1Br)[C@@H](C)NS(=O)(=O)c1cccc(C(F)(F)F)c1]

To a 1 M solution of lithium hexamethylsilazide in THF (75.2 mL, 75.2 mmol) at −78° C. was added a solution of methyl (R)-3-(3-(trifluoromethyl)phenylsulfonamido)butanoate (11.65 g, 35.8 mmol) in THF dropwise. After completion of the addition, the mixture was stirred an additional thirty minutes allowing the mixture's temperature to rise to −40° C. The mixture was cooled again at −78° C., and then a solution of 2,4-dibromo-1-(bromomethyl)benzene in THF was added dropwise. The cooling bath was removed and the mixture was allowed to warm to room temperature. The mixture was quenched with saturated ammonium chloride, and partitioned between ethyl acetate and water. The organic layer was washed with brine, dried ($Na_2SO_4$), and concentrated. The resulting residue was purified by MPLC eluting with a gradient of ethyl acetate and hexanes to afford methyl (2R,3R)-2-(2,4-dibromobenzyl)-3-(3-(trifluoromethyl)phenyl-sulfonamido)butanoate (12.14 g, 59%) as a white solid.

Part III—Synthesis of Methyl (2R,3R)-7-bromo-2-methyl-1-((3-(trifluoromethyl)-phenyl)sulfonyl)-1,2,3,4-tetrahydroquinoline-3-carboxylate

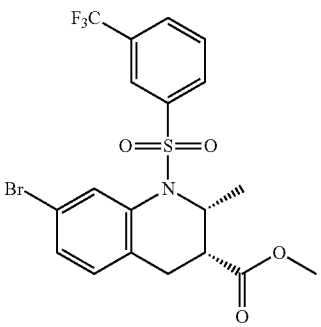 [SMILES: COC(=O)[C@@H]1Cc2ccc(Br)cc2N(S(=O)(=O)c2cccc(C(F)(F)F)c2)[C@@H]1C]

A mixture of (2R,3R)-methyl 2-(2,4-dibromobenzyl)-3-(3-(trifluoromethyl)phenyl-sulfonamido)butanoate (4.63 g, 8.08 mmol), copper (I) iodide (0.62 g, 3.23 mmol), N,N'-dimethylethylenediamine (0.71 g, 8.08 mmol) and potassium phosphate (5.14 g, 24.2 mmol) in toluene was heated at reflux overnight. The mixture was cooled, and partitioned between ethyl acetate and saturated ammonium chloride. The organic layer was washed with brine, dried ($Na_2SO_4$) and concentrated. The resulting residue was purified by MPLC eluting with a gradient of hexanes and ethyl acetate to afford (2R,3R)-methyl 7-bromo-2-methyl-1-((3-(trifluoromethyl)-phenyl)sulfonyl)-1,2,3,4-tetrahydroquinoline-3-carboxylate (3.23 g, 81%). Note: This material contained some (2R,3R)-methyl 7-iodo-2-methyl-1-((3-(trifluoromethyl)-phenyl)sulfonyl)-1,2,3,4-tetrahydroquinoline-3-carboxylate and was used without further purification.

Part IV—Synthesis of (2R,3R)-Methyl 7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylate

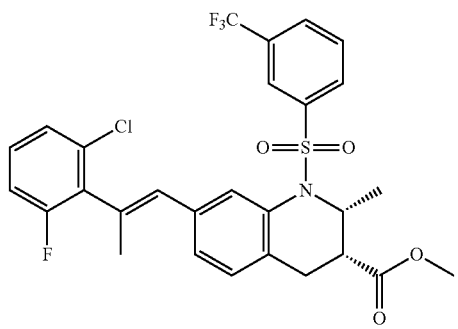 [SMILES: COC(=O)[C@@H]1Cc2ccc(/C=C(\C)c3c(F)cccc3Cl)cc2N(S(=O)(=O)c2cccc(C(F)(F)F)c2)[C@@H]1C]

To a degassed mixture of ((2R,3R)-methyl 7-bromo-2-methyl-1-((3-(trifluoromethyl)-phenyl)sulfonyl)-1,2,3,4-tetrahydroquinoline-3-carboxylate (3.23 g, 6.56 mmol), potassium carbonate (1.36 g, 9.84 mmol), (E)-2-(2-(2-chloro-6-fluorophenyl)prop-1-en-1-yl)-4,4,5,5-tetramethyl-1,3,2-dioxaborolane (2.14 g, 7.22 mmol), dioxane and water was added [1,1'-bis(diphenylphosphino)ferrocene]dichloropalladium(II) dichloromethane complex (0.54 g, 0.66 mmol). The mixture was heated to 70° C. for five hours. The mixture was cooled, and partitioned between ethyl acetate and water. The organic layer was washed with brine, dried ($Na_2SO_4$), and concentrated. The resulting residue was purified by MPLC eluting with a gradient of 0-50% ethyl acetate in hexanes to afford (2R,3R)-methyl 7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylate (2.69 g, 70%).

Example 142—Synthesis of (2R,3R)-7-((E)-2-(2-Chloro-6-fluorophenyl)prop-1-en-1-yl)-2-methyl-1-((3-(trifluoromethyl)phenyl)sulfonyl)-1,2,3,4-tetrahydroquinoline-3-carboxylate

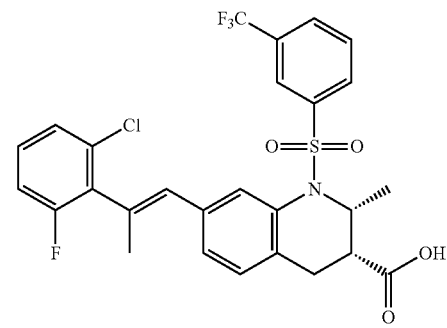 [SMILES: C/C(=C\c1ccc2c(c1)N(S(=O)(=O)c1cccc(C(F)(F)F)c1)[C@H](C)[C@H](C(=O)O)C2)c1c(F)cccc1Cl]

Based on the procedure in Example 42, (2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylate was prepared. $^{1}$H-NMR (400 MHz, DMSO-$d_6$) 12.83 (bs, 1H), 8.10 (d, 1H), 7.94 (d, 1H), 7.86 (m, 2H), 7.66 (s, 1H), 7.38 (m, 2H), 7.26 (m, 2H), 7.18 (dd, 1H), 6.42 (s, 1H), 4.83 (sext, 1H), 3.14 (s, 2H), 2.85 (dd, 1H), 2.70 (dd, 1H), 2.27 (m, 1H), 2.10 (s, 3H), 0.98 (d, 3H). (ES, m/z): (M+H)$^{+}$568.

Example 143—Synthesis of Methyl ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)carbamate

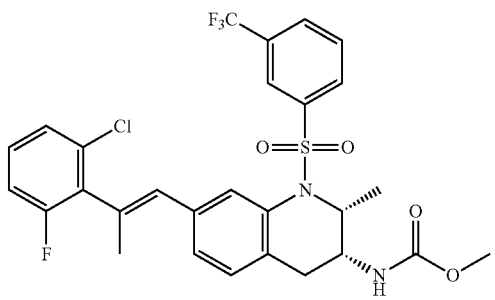 [SMILES: COC(=O)N[C@@H]1Cc2ccc(/C=C(\C)c3c(F)cccc3Cl)cc2N(S(=O)(=O)c2cccc(C(F)(F)F)c2)[C@@H]1C]

A mixture of (2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylate (120 mg, 0.211 mmol), diphenylphosphoryl azide (60 mg, 0.232 mmol), toluene (4 mL), and triethylamine (30 mg, 0.25 mmol) was heated to 95° C. for two hours. Cooled and added methanol (2 mL) and heated at 70° C. overnight. Cooled, and partitioned between ethyl acetate and 1N HCl. The organic layer was dried (Na$_2$SO$_4$) and concentrated. The resulting residue was purified by MPLC eluting with a gradient of 0-10% methanol in methylene chloride to afford methyl ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)carbamate (76 mg, 54%) as a white solid. $^{1}$H-NMR (400 MHz, DMSO-$d_6$) δ 8.08 (d, 1H), 7.83 (m, 4H), 7.36 (m, 4H), 7.15 (m, 2H), 6.43 (s, 1H), 4.65 (m, 1H), 3.57 (s, 3H), 2.60 (m, 2H), 2.15 (s, 3H), 1.20 (m, 1H), 0.95 (m, 3H). (ES, m/z): (M+Na)$^{+}$619.27.

Example 144—Synthesis of tert-Butyl ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)carbamate

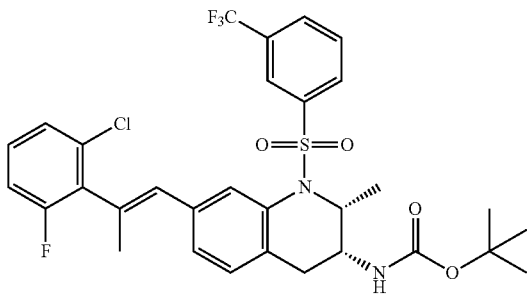 [SMILES: C/C(=C\c1ccc2c(c1)N(S(=O)(=O)c1cccc(C(F)(F)F)c1)[C@H](C)[C@H](NC(=O)OC(C)(C)C)C2)c1c(F)cccc1Cl]

Based on the procedure in Example 144, tert-butyl ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)carbamate was prepared.

Example 145—Synthesis of 1-((2R,3R)-7-((E)-2-(2-Chloro-6-fluorophenyl)prop-1-en-1-yl)-2-methyl-1-((3-(trifluoromethyl)phenyl)sulfonyl)-1,2,3,4-tetrahydroquinolin-3-yl)-3-methylurea

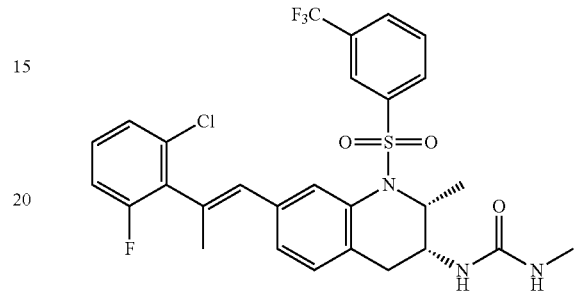

A mixture of (2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylate (120 mg, 0.211 mmol), diphenylphosphoryl azide (60 mg, 0.232 mmol), toluene (4 mL), and triethylamine (30 mg, 0.25 mmol) was heated to 95° C. for two hours. Cooled and added 2M methylamine (2 mL, 4 mmol) and heated at 70° C. overnight. Cooled, and partitioned between ethyl acetate and 1N HCl. The organic layer was dried (Na$_2$SO$_4$) and concentrated. The resulting residue was purified by MPLC eluting with a gradient of 0-10% methanol in methylene chloride to afford 1-((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)-3-methylurea (59 mg, 44%) as a white solid. $^{1}$H-NMR (400 MHz, DMSO-$d_6$) δ 7.90 (m, 5H), 7.33 (m, 3H), 7.14 (m, 2H), 6.42 (s, 1H), 5.95 (d, 1H), 5.72 (s, 1H), 5.63 (m, 1H), 4.72 (m, 1H), 4.07 (m, 1H), 3.55 (m, 1H), 3.15 (d, 3H), 2.53 (m, 3H), 2.15 (s, 3H), 0.98 (m, 5H). (ES, m/z): (M+Na)$^{+}$618.26.

Example 146—Synthesis of 3-((2R,3R)-7-((E)-2-(2-Chloro-6-fluorophenyl)prop-1-en-1-yl)-2-methyl-1-((3-(trifluoromethyl)phenyl)sulfonyl)-1,2,3,4-tetrahydroquinolin-3-yl)-1,1-dimethylurea

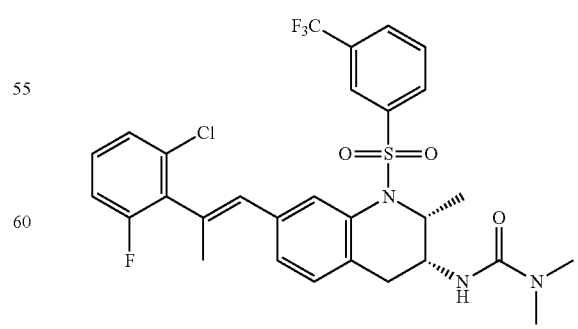

A mixture of (2R,3R)-7-((E)-2-(2-chloro-6-fluorophenyl)prop-1-en-1-yl)-2-methyl-1-((3-(trifluoromethyl)phenyl)

sulfonyl)-1,2,3,4-tetrahydroquinoline-3-carboxylate (120 mg, 0.211 mmol), diphenylphosphoryl azide (60 mg, 0.232 mmol), toluene (4 mL), and triethylamine (30 mg, 0.25 mmol) was heated to 95° C. for two hours. Cooled and added 2M methylamine (2 mL, 4 mmol) and heated at 70° C. overnight. Cooled, and partitioned between ethyl acetate and 1N HCl. The organic layer was dried (Na$_2$SO$_4$) and concentrated. The resulting residue was purified by MPLC eluting with a gradient of 0-10% methanol in methylene chloride to afford 3-((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)-1,1-dimethylurea (61 mg, 45%) as a white solid. $^1$H-NMR (400 MHz, DMSO-d$_6$) δ 7.96 (m, 4H), 7.77 (t, 1H), 7.35 (m, 3H), 7.13 (m, 2H), 6.43 (s, 1H), 6.05 (d, 1H), 5.73 (s, 1H), 4.80 (m, 1H), 3.47 (m, 1H), 3.14 (s, 3H), 2.78 (s, 6H), 2.60 (m, 2H), 2.15 (s, 3H), 0.97 (d, 3H). (ES, m/z): (M+Na)$^+$632.31.

Example 147-Synthesis of (2R,3R)-7-((E)-2-(2-Chloro-6-fluorophenyl)prop-1-en-1-yl)-2-methyl-1-((3-(trifluoromethyl)phenyl)sulfonyl)-1,2,3,4-tetrahydroquinolin-3-amine

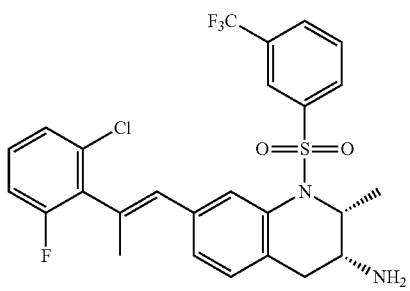 [SMILES: C/C(=C\c1ccc2c(c1)N(S(=O)(=O)c1cccc(C(F)(F)F)c1)[C@H](C)[C@H](N)C2)c1c(F)cccc1Cl]

Trifluoroacetic acid (1.43 g, 12.5 mmol) was added to a solution of tert-butyl ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)carbamate (100 mg, 0.156 mmol) in dichloromethane (5 mL). The mixture was stirred for three hours, concentrated, partitioned between dichloromethane and saturated sodium bicarbonate. The organic layer was dried (Na$_2$SO$_4$) and concentrated to afford (2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-amine (80 mg, 88%) as an oil. $^1$H-NMR (400 MHz, DMSO-d$_6$) δ 8.10 (m, 4H), 7.89 (m, 2H), 7.63 (s, 1H), 7.37 (s, 2H), 7.25 (m, 3H), 6.43 (s, 1H), 4.82 (m, 1H), 3.21 (m, 1H), 2.80 (m, 2H), 2.10 (s, 3H), 1.10 (d, 3H). (ES, m/z): (M+H)$^+$539.23.

Example 148—Synthesis of N-((2R,3R)-7-((E)-2-(2-Chloro-6-fluorophenyl)prop-1-en-1-yl)-2-methyl-1-((3-(trifluoromethyl)phenyl)sulfonyl)-1,2,3,4-tetrahydroquinolin-3-yl)acetamide

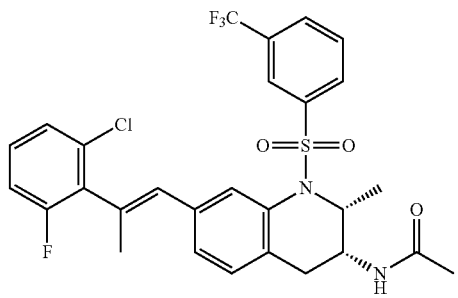 [SMILES: CC(=O)N[C@@H]1Cc2ccc(/C=C(\C)c3c(F)cccc3Cl)cc2N(S(=O)(=O)c2cccc(C(F)(F)F)c2)[C@@H]1C]

A solution of (2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-amine (40 mg, 0.074 mmol), triethylamine (10 mg, 0.078 mmol), dichloromethane (2 mL) and acetyl chloride (10 mg, 0.078 mmol) was stirred at room temperature overnight. The mixture was washed with water, brine, dried (Na$_2$SO$_4$), and concentrated. The resulting residue was purified via MPLC eluting with a gradient of 0-10% methanol in dichloromethane to afford N-((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)acetamide (29 mg, 60%) as an oil. $^1$H-NMR (400 MHz, DMSO-d$_6$) δ 8.05 (d, 1H), 7.91 (m, 4H), 7.79 (m, 2H), 7.34 (m, 3H), 7.16 (s, 2H), 6.44 (s, 1H), 5.73 (s, 3H), 4.70 (m, 1H), 3.58 (m, 2H), 3.15 (d, 1H), 2.57 (m, 3H), 1.97 (s, 3H), 1.80 (s, 3H), 0.98 (d, 3H). (ES, m/z): (M+Na)$^+$603.30.

Example 149—Synthesis of (2R,3R)-6-((E)-2-(2-Chloro-6-fluorophenyl)prop-1-en-1-yl)-2-methyl-1-((3-(trifluoromethyl)phenyl)sulfonyl)-1,2,3,4-tetrahydroquinoline-3-carboxylic acid

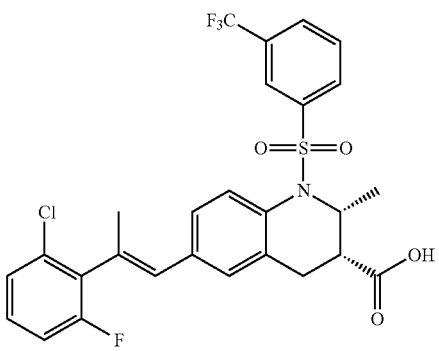 [SMILES: C/C(=C\c1ccc2c(c1)C[C@@H](C(=O)O)[C@@H](C)N2S(=O)(=O)c1cccc(C(F)(F)F)c1)c1c(F)cccc1Cl]

Part I—Synthesis of Ethyl 2-(2-nitrobenzyl)-3-oxobutanoate

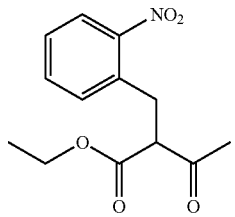 [SMILES: CCOC(=O)C(Cc1ccccc1[N+](=O)[O-])C(C)=O]

Ethyl acetoacetate (6.02 g, 46.3 mmol) was added dropwise to a mixture of 60% sodium hydride in mineral oil (1.85 g, 46.3 mmol) in THF (140 mL) at 0° C. The mixture was stirred for forty-five minutes, and then 1-(bromomethy)-2-nitrobenzene (10.0 g, 46.3 mmol) in THF (15 mL) was added dropwise. The mixture was warmed to room temperature and stirred overnight. The mixture was quenched with saturated ammonium chloride, and partitioned between ethyl acetate and water. The organic layer was washed with brine, dried ($Na_2SO_4$) and concentrated. The resulting residue was purified by MPLC eluting with a gradient of 0-100% ethyl acetate in hexanes to afford ethyl 2-(2-nitrobenzyl)-3-oxobutanoate (11.2 g, 91%) as a yellow oil.

Part II—Synthesis of Ethyl (2R,3R)-2-methyl-1,2,3,4-tetrahydroquinoline-3-carboxylate

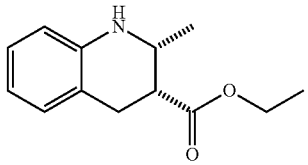 [SMILES: CCOC(=O)[C@@H]1Cc2ccccc2N[C@@H]1C]

A mixture of ethyl 2-(2-nitrobenzyl)-3-oxobutanoate (1.0 g, 3.77 mmol) and 10% platinum on carbon (0.29 g) under 50 psi hydrogen was shaken for three hours. The mixture was filtered through Celite, and the filtrate was concentrated. The resulting residue was purified by MPLC eluting with a mixture of 10-100% ethyl acetate in hexanes to afford ethyl (2R,3R)-2-methyl-1,2,3,4-tetrahydroquinoline-3-carboxylate (570 mg, 69%).

Part III—Synthesis of Ethyl (2R,3R)-2-methyl-1-((3-(trifluoromethyl)phenyl)sulfonyl)-1,2,3,4-tetrahydroquinoline-3-carboxylate

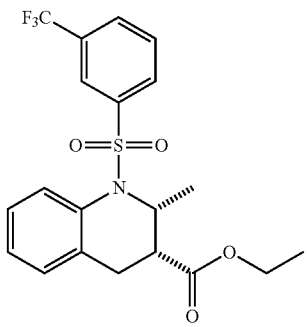 [SMILES: CCOC(=O)[C@@H]1Cc2ccccc2N(S(=O)(=O)c2cccc(C(F)(F)F)c2)[C@@H]1C]

A solution of ethyl (2R,3R)-2-methyl-1,2,3,4-tetrahydroquinoline-3-carboxylate (500 mg, 2.28 mmol), 3-(trifluoromethyl)benzenesulfonyl choride (610 mg, 2.50 mmol) and pyridine (12 mL) was heated at 50° C. overnight. The mixture was diluted in ethyl acetate and washed three times with 1N HCl. The organic layer was washed with brine, dried ($Na_2SO_4$) and concentrated. The resulting residue was purified via MPLC eluting with a gradient of 0-60% ethyl acetate in hexanes to afford ethyl (2R,3R)-2-methyl-1-((3-(trifluoromethyl)phenyl)sulfonyl)-1,2,3,4-tetrahydroquinoline-3-carboxylate (860 mg, 88%).

Part IV—Synthesis of Ethyl (2R,3R)-6-bromo-2-methyl-1-((3-(trifluoromethyl)phenyl)sulfonyl)-1,2,3,4-tetrahydroquinoline-3-carboxylate

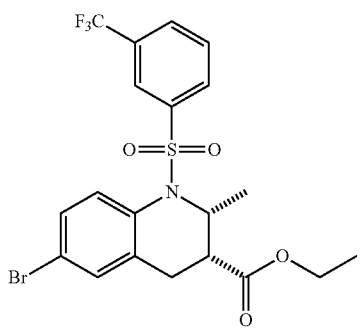 [SMILES: CCOC(=O)[C@@H]1Cc2cc(Br)ccc2N(S(=O)(=O)c2cccc(C(F)(F)F)c2)[C@@H]1C]

Bromine (300 mg, 1.87 mmol) was added to a solution of ethyl (2R,3R)-2-methyl-1-((3-(trifluoromethyl)phenyl)sulfonyl)-1,2,3,4-tetrahydroquinoline-3-carboxylate (760 mg, 1.78 mmol) in DMF (9 mL). The mixture was stirred overnight at room temperature. The mixture was partitioned between ethyl acetate and water. The organic phase was washed twice with water, brine, dried ($Na_2SO_4$) and concentrated. The resulting residue was purified by MPLC eluting with a gradient of 0-50% ethyl acetate in hexanes to afford ethyl (2R,3R)-6-bromo-2-methyl-1-((3-(trifluoromethyl)phenyl)sulfonyl)-1,2,3,4-tetrahydroquinoline-3-carboxylate (820 mg, 91%).

Part V—Synthesis of Ethyl (2R,3R)-6-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylic acid

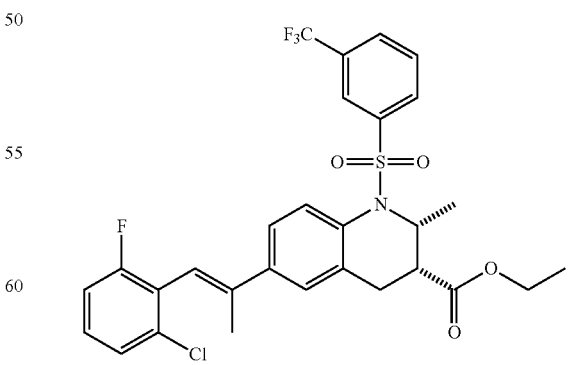

A mixture of ethyl (2R,3R)-6-bromo-2-methyl-1-((3-(trifluoromethyl)phenyl)sulfonyl)-1,2,3,4-tetrahydroquinoline-3-carboxylate (80 mg, 0.16 mmol), potassium carbonate (30 mg, 0.19 mmol), (E)-2-(2-(2-chloro-6-fluorophenyl)prop-1-en-1-yl)-4,4,5,5-tetramethyl-1,3,2-dioxaborolane (60 mg, 0.21 mmol), [1,1'-bis(diphenylphosphino)ferrocene]dichloropalladium(II) dichloromethane complex (10 mg, 0.016 mmol) in dioxane (2 mL) and water (0.5 mL) was heated at 70° C. overnight. The mixture was partitioned between ethyl acetate and water. The organic phase was washed with brine, dried (Na$_2$SO$_4$) and concentrated to afford ethyl (2R,3R)-6-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylic acid (58 mg, 61%) as a clear oil.

Part VI—Synthesis of (2R,3R)-6-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylic acid

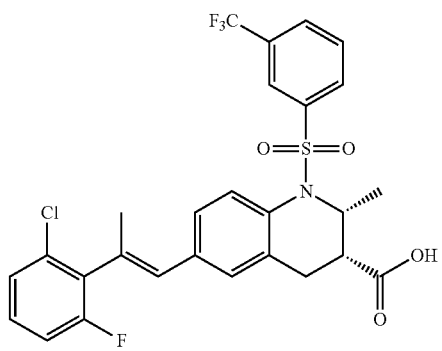 [SMILES: C/C(=C\c1ccc2c(c1)C[C@@H](C(=O)O)[C@@H](C)N2S(=O)(=O)c1cccc(C(F)(F)F)c1)c1c(F)cccc1Cl]

Based on the procedure in Example 42, (2R,3R)-6-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylic acid was prepared. $^1$H-NMR (400 MHz, DMSO-d$_6$) δ 12.82 (bs, 1H), 8.08 (d, 1H), 7.88 (d, 1H), 7.80 (m, 2H), 7.69 (d, 1H), 7.27 (m, 5H), 6.36 (s, 1H), 4.79 (m, 1H), 4.05 (m, 1H), 3.57 (m, 1H), 2.82 (m, 1H), 2.65 (m, 1H), 2.12 (s, 3H), 0.97 (d, 3H). (ES, m/z): (M+Na)$^+$ 590.15.

Example 150—Synthesis of (E)-2-(6-(2-(2-Chloro-6-fluorophenyl)prop-1-en-1-yl)-1-((3-(trifluoromethyl)phenyl)sulfonyl)-1,2,3,4-tetrahydroquinolin-3-yl)acetic acid

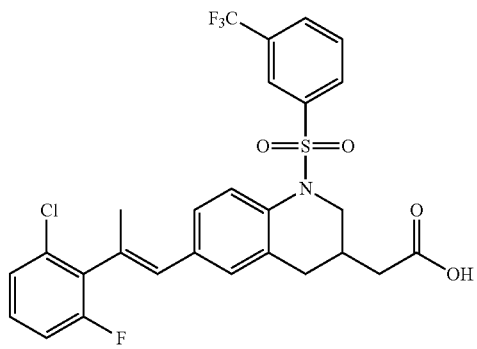 [SMILES: C/C(=C\c1ccc2c(c1)CC(CC(=O)O)CN2S(=O)(=O)c1cccc(C(F)(F)F)c1)c1c(F)cccc1Cl]

Part I—Synthesis of Ethyl 2-(2-oxo-1,2,3,4-tetrahydroquinolin-3-yl)acetate

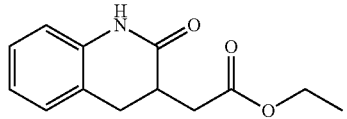 [SMILES: CCOC(=O)CC1Cc2ccccc2NC1=O]

A mixture of diethyl (2E)-2-[(2-nitrophenyl)methylene]butanedioate (7.94 g, 25.8 mmol), 10% palladium on carbon (1.37 g, 1.29 mmol), methanol (150 mL) and acetic acid (10 mL) was shaken on a Parr shaker at 50 psi overnight. The mixture was filtered through a pad of Celite, the filtrate was concentrated and the resulting residue was purified via MPLC eluting with a gradient of 10-40% ethyl acetate in hexanes to afford ethyl 2-(2-oxo-1,2,3,4-tetrahydroquinolin-3-yl)acetate (5.06 g, 84%).

Part II—Synthesis of Ethyl 2-(6-bromo-2-oxo-1,2,3,4-tetrahydroquinolin-3-yl)acetate

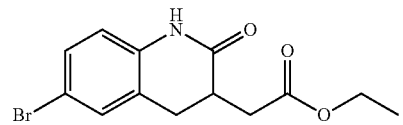 [SMILES: CCOC(=O)CC1Cc2cc(Br)ccc2NC1=O]

A mixture of ethyl 2-(2-oxo-1,2,3,4-tetrahydroquinolin-3-yl)acetate (1.0 g, 4.29 mmol), N-bromosuccinimide (800 mg, 4.50 mmol) and DMF (9 mL) was stirred at 0° C. for two hours. The mixture was partitioned between water and ethyl acetate. The organic layer was washed twice with water, brine, dried (Na$_2$SO$_4$) and concentrated. The resulting residue was purified via MPLC eluting with a gradient of 10-50% ethyl acetate in hexanes to afford ethyl 2-(6-bromo-2-oxo-1,2,3,4-tetrahydroquinolin-3-yl)acetate (860 mg, 64%).

Part III—Synthesis of Ethyl (E)-2-(6-(1-(2-chloro-6-fluorophenyl)prop-1-en-2-yl)-2-oxo-1,2,3,4-tetrahydroquinolin-3-yl)acetate

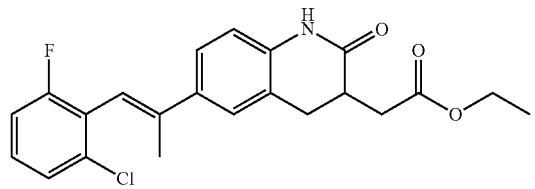 [SMILES: CCOC(=O)CC1Cc2cc(/C(C)=C/c3c(F)cccc3Cl)ccc2NC1=O]

A mixture of ethyl 2-(6-bromo-2-oxo-1,2,3,4-tetrahydroquinolin-3-yl)acetate (200 mg, 0.64 mmol), (E)-2-(2-(2-chloro-6-fluorophenyl)prop-1-en-1-yl)-4,4,5,5-tetramethyl-1,3,2-dioxaborolane (250 mg, 0.83 mmol), potassium carbonate (110 mg, 0.77 mmol), [1,1'-bis(diphenylphosphino)ferrocene]dichloropalladium(II) dichloromethane complex (50 mg, 0.064 mmol), dioxane (6 mL) and water (1.5 mL) was heated at 70° C. overnight. The mixture was partitioned between ethyl acetate and water. The organic layer was washed with brine, dried (Na$_2$SO$_4$), and concen- Part IV—Synthesis of Ethyl (E)-2-(6-(1-(2-chloro-6-fluorophenyl)prop-1-en-2-yl)-1,2,3,4-tetrahydroquinolin-3-yl)acetate

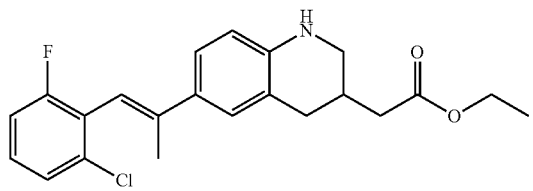 [SMILES: CCOC(=O)CC1CNc2ccc(/C(C)=C/c3c(F)cccc3Cl)cc2C1]

A 10 M solution of borane-methyl sulfide complex in THF (0.24 mL, 2.4 mmol) was added dropwise to a solution of ethyl (E)-2-(6-(1-(2-chloro-6-fluorophenyl)prop-1-en-2-yl)-2-oxo-1,2,3,4-tetrahydroquinolin-3-yl)acetate (190 mg, 0.47 mmol) in THF (9 mL) at 0° C. The mixture was stirred for 3 hours, quenched with methanol (1 mL) and refluxed for ten minutes. The mixture was concentrated, and the resulting residue was purified by MPLC eluting with a gradient of 10-75% ethyl acetate in hexanes to afford ethyl (E)-2-(6-(1-(2-chloro-6-fluorophenyl)prop-1-en-2-yl)-1,2,3,4-tetrahydroquinolin-3-yl)acetate (73 mg, 40%).

Part V—Synthesis of Ethyl (E)-2-(6-(2-(2-chloro-6-fluorophenyl)prop-1-en-1-yl)-1-((3-(trifluoromethyl)phenyl)sulfonyl)-1,2,3,4-tetrahydroquinolin-3-yl)acetate

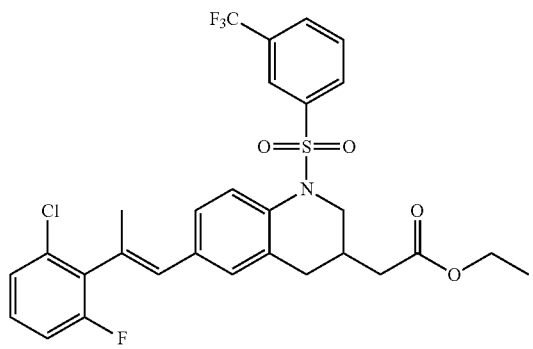 [SMILES: CCOC(=O)CC1Cc2cc(/C=C(\C)c3c(F)cccc3Cl)ccc2N(S(=O)(=O)c2cccc(C(F)(F)F)c2)C1]

A mixture of ethyl (E)-2-(6-(1-(2-chloro-6-fluorophenyl)prop-1-en-2-yl)-1,2,3,4-tetrahydroquinolin-3-yl)acetate (70 mg, 0.19 mmol), 3-(trifluoromethyl)benzenesulfonyl chloride (50 mg, 0.21 mmol), and pyridine (2 mL) was heated to 50° C. overnight. The mixture was concentrated, and the resulting residue was partitioned between ethyl acetate and 1 M HCl. The organic layer was washed twice with 1 M HCl, brine, dried (Na$_2$SO$_4$) and concentrated. The resulting residue was purified by MPLC eluting with a gradient of 5-25% ethyl acetate in hexanes to afford ethyl (E)-2-(6-(2-(2-chloro-6-fluorophenyl)prop-1-en-1-yl)-1-((3-(trifluoromethyl)phenyl)sulfonyl)-1,2,3,4-tetrahydroquinolin-3-yl)acetate (71 mg, 63%) as a white solid.

Part VI—Synthesis of (E)-2-(6-(2-(2-Chloro-6-fluorophenyl)prop-1-en-1-yl)-1-((3-(trifluoromethyl)phenyl)sulfonyl)-1,2,3,4-tetrahydroquinolin-3-yl)acetic acid

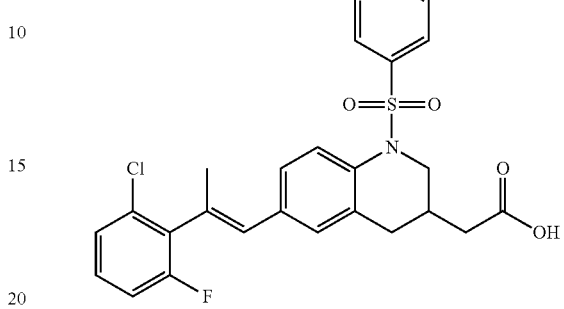

Based on the procedure in Example 42, (E)-2-(6-(2-(2-chloro-6-fluorophenyl)prop-1-en-1-yl)-1-((3-(trifluoromethyl)phenyl)sulfonyl)-1,2,3,4-tetrahydroquinolin-3-yl)acetic acid was prepared. $^1$H-NMR (400 MHz, DMSO-d$_6$) δ 12.25 (bs, 1H), 8.04 (d, 1H), 7.88 (m, 2H), 7.78 (t, 1H), 7.71 (d, 1H), 7.35 (dd, 2H), 7.25 (m, 2H), 7.09 (s, 1H), 6.33 (s, 1H), 4.27 (d, 1H), 3.25 (m, 2H), 2.60 (dd, 1H), 2.21 (m, 3H), 2.07 (s, 3H), 1.78 (m, 1H). (ES, m/z): (M+Na)$^+$590.15.

Example 151—Synthesis of ((2R,3R)-7-((2-Chloro-6-fluorobenzyl)oxy)-1-((4-fluoro-3-methoxyphenyl)sulfonyl)-2-methyl-1,2,3,4-tetrahydroquinolin-3-yl)methanol

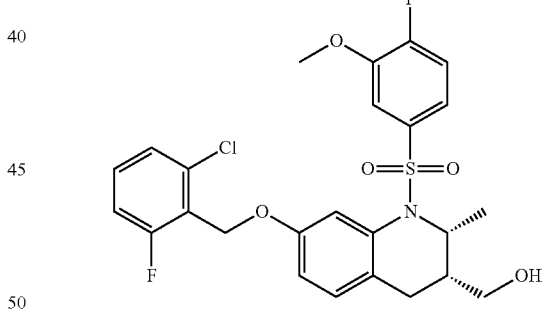

To a solution of racemic (2R,3R)-ethyl 7-((2-chloro-6-fluorobenzyl)oxy)-1-((4-fluoro-3-methoxyphenyl)sulfonyl)-2-methyl-1,2,3,4-tetrahydroquinoline-3-carboxylate (120 mg, 0.21 mmol) in anhydrous tetrahydrofuran (10 mL) was added lithium aluminum hydride (20 mg) in portions at room temperature. The resulting solution was stirred for two hours at room temperature. The reaction was then quenched by the addition of water (15 mL) and stirred for two hours. The resulting solution was extracted three times with ethyl acetate and the organic layers were combined, washed with water, brine, dried (MgSO$_4$), and concentrated. The resulting residue was first purified via MPLC eluting with ethyl acetate/petroleum ether (1:4) as eluent and further purified via reverse phase Prep-HPLC eluting with a gradient of 58-65% acetonitrile in water with 10 mM ammonium carbonate to afford ((2R,3R)-7-((2-chloro-6-fluorobenzyl)oxy)-

1-((4-fluoro-3-methoxyphenyl)sulfonyl)-2-methyl-1,2,3,4-tetrahydroquinolin-3-yl)methanol (25 mg, 23%) as a white solid. $^1$H-NMR (400 MHz, CDCl$_3$) δ 1.08 (d, J=6.8 Hz, 3H), 1.62 (m, 1H), 2.22 (m, 1H), 2.44 (dd, J=16.8, 6.0 Hz, 1H), 3.37-3.55 (m, 2H), 3.74 (s, 3H), 4.75 (m, 1H), 5.20 (s, 2H), 6.78 (dd, J=12.4, 2.8 Hz, 2H), 6.95 (d, J=8.8 Hz, 1H), 7.03-7.20 (m, 3H), 7.25-7.35 (m, 3H), 7.64 (s, 1H). (ES, m/z): (M+H)$^+$524.1.

Example 152—Synthesis of N-(((2R,3S)-7-((2-Chloro-6-fluorobenzyl)oxy)-1-((4-fluoro-3-methoxyphenyl)sulfonyl)-2-methyl-1,2,3,4-tetrahydroquinolin-3-yl)methyl)acetamide

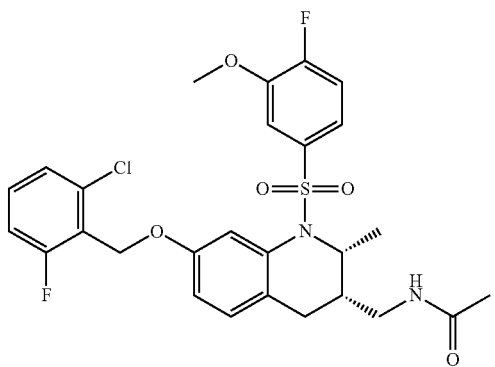 [SMILES: COc1cc(S(=O)(=O)N2c3cc(OCc4c(F)cccc4Cl)ccc3C[C@@H](CNC(C)=O)[C@H]2C)ccc1F]

Part I—Synthesis of 2-(((2R,3S)-7-((2-Chloro-6-fluorobenzyl)oxy)-1-((4-fluoro-3-methoxyphenyl)sulfonyl)-2-methyl-1,2,3,4-tetrahydroquinolin-3-yl)methyl)isoindoline-1,3-dione

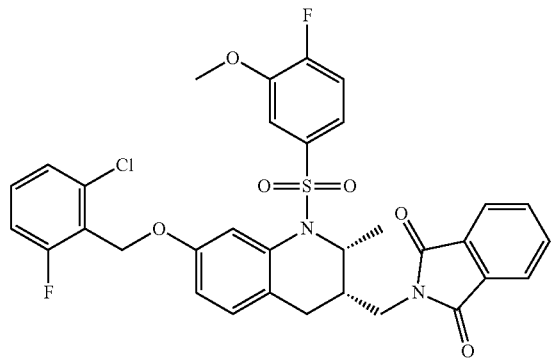 [SMILES: COc1cc(S(=O)(=O)N2c3cc(OCc4c(F)cccc4Cl)ccc3C[C@@H](CN3C(=O)c4ccccc4C3=O)[C@H]2C)ccc1F]

To a stirred room temperature solution of ((2R,3R)-7-((2-chloro-6-fluorobenzyl)oxy)-1-((4-fluoro-3-methoxyphenyl)sulfonyl)-2-methyl-1,2,3,4-tetrahydroquinolin-3-yl)methanol (130 mg, 0.25 mmol), 2,3-dihydro-1H-isoindole-1,3-dione (55 mg, 0.37 mmol) and triphenylphosphine (131 mg, 0.50 mmol) in anhydrous tetrahydrofuran (10 mL) was added diisopropyldiazodicarboxylate (100 mg, 0.49 mmol) dropwise. The mixture was stirred for one hour at room temperature, and quenched by the addition of water (15 mL). The resulting solution was extracted three times with ethyl acetate. The combined organic layers were washed twice with water, washed with brine, dried (Na$_2$SO$_4$) and concentrated. The resulting residue was purified via MPLC eluting with ethyl acetate/petroleum ether (1:5) as eluent to yield 2-(((2R,3S)-7-((2-chloro-6-fluorobenzyl)oxy)-1-((4-fluoro-3-methoxyphenyl)sulfonyl)-2-methyl-1,2,3,4-tetrahydroquinolin-3-yl)methyl)isoindoline-1,3-dione (130 mg, 80%) as a yellow oil.

Part II—Synthesis of ((2R,3S)-7-((2-Chloro-6-fluorobenzyl)oxy)-1-((4-fluoro-3-methoxyphenyl)sulfonyl)-2-methyl-1,2,3,4-tetrahydroquinolin-3-yl)methanamine

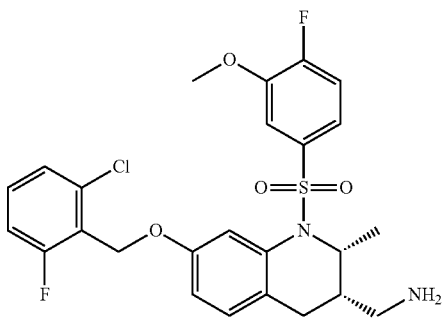 [SMILES: COc1cc(S(=O)(=O)N2c3cc(OCc4c(F)cccc4Cl)ccc3C[C@@H](CN)[C@H]2C)ccc1F]

To a solution of 2-(((2R,3S)-7-((2-chloro-6-fluorobenzyl)oxy)-1-((4-fluoro-3-methoxyphenyl)sulfonyl)-2-methyl-1,2,3,4-tetrahydroquinolin-3-yl)methyl)isoindoline-1,3-dione (130 mg, 0.20 mmol) in ethanol (20 mL) was added a solution of hydrazine (80% in water, 1 mL). The resulting solution was heated to reflux for two hours. The mixture was concentrated to remove the ethanol. The resulting mixture was diluted with water (20 mL) and extracted three times with ethyl acetate. The combined organic layers were washed twice with water, washed with brine, dried (Na$_2$SO$_4$) and concentrated under vacuum to afford ((2R,3S)-7-((2-chloro-6-fluorobenzyl)oxy)-1-((4-fluoro-3-methoxyphenyl)sulfonyl)-2-methyl-1,2,3,4-tetrahydroquinolin-3-yl)methanamine (90 mg, 86%) as a yellow oil.

Part III—Synthesis of N-(((2R,3S)-7-((2-Chloro-6-fluorobenzyl)oxy)-1-((4-fluoro-3-methoxyphenyl)sulfonyl)-2-methyl-1,2,3,4-tetrahydroquinolin-3-yl)methyl)acetamide

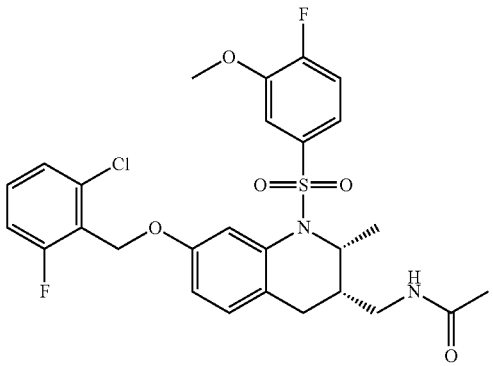 [SMILES: COc1cc(S(=O)(=O)N2c3cc(OCc4c(F)cccc4Cl)ccc3C[C@@H](CNC(C)=O)[C@H]2C)ccc1F]

To a stirred room temperature solution of ((2R,3S)-7-((2-chloro-6-fluorobenzyl)oxy)-1-((4-fluoro-3-methoxyphenyl)sulfonyl)-2-methyl-1,2,3,4-tetrahydroquinolin-3-yl)methanamine (90 mg, 0.17 mmol) in dichloromethane (5 mL) and triethylamine (0.15 mL, 0.85 mmol) was added acetyl chloride (0.05 mL, 0.68 mmol) dropwise. The mixture was stirred for four hours and quenched by the addition of water (2 mL). The mixture was concentrated and the resulting residue was purified via MPLC eluting with ethyl acetate/petroleum ether (2:1) as eluent to provide N-(((2R,3S)-7-((2-chloro-6-fluorobenzyl)oxy)-1-((4-fluoro-3-methoxyphenyl)sulfonyl)-2-methyl-1,2,3,4-tetrahydroquinolin-3-yl)methyl)acetamide (56 mg, 58%) as a white solid. $^1$H-NMR (400 MHz, CDCl$_3$) δ 1.13 (d, J=6.4 Hz, 3H), 1.80 (br s, 1H), 2.09 (s, 3H), 2.35 (m, 1H), 2.57 (dd, J=17.2, 6.4 Hz, 1H), 2.16 (br s, 2H), 3.74 (s, 3H), 4.55 (m, 1H), 5.19 (s, 2H), 5.60 (br s, 1H), 6.81 (dd, J=8.4, 2.4 Hz, 1H), 6.98 (d, J=8.4 Hz, 1H), 7.05-7.20 (m, 3H), 7.27-7.38 (m, 3H), 7.56 (s, 1H). (ES, m/z): (M+H)$^+$565.1.

Example 153—Synthesis of Methyl (S,E)-3-(7-(2-chloro-6-fluorostyryl)-1-((4-fluoro-3-methoxyphenyl)sulfonyl)-1,2,3,4-tetrahydroquinolin-3-yl)-2,2-dimethylpropanoate

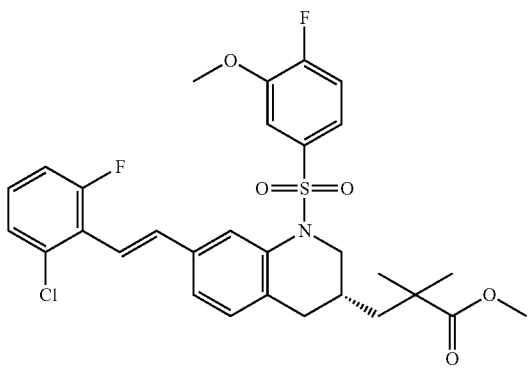

A mixture of methyl (S,E)-3-(7-(2-chloro-6-fluorostyryl)-1-((4-fluoro-3-methoxyphenyl)sulfonyl)-1,2,3,4-tetrahydroquinolin-3-yl)-2,2-dimethylpropanoate (50 mg, 0.09 mmol), toluene (2 mL), ethanol (1 mL), water (0.5 mL), 2-[(E)-2-(2-chloro-6-fluorophenyl)ethenyl]-4,4,5,5-tetramethyl-1,3,2-dioxaborolane (36.2 mg, 0.13 mmol), potassium acetate (25.2 mg, 0.26 mmol), and tetrakis(triphenylphosphine)palladium(0) (9.9 mg, 0.01 mmol) was stirred overnight at 90° C. The resulting mixture was concentrated and the resulting residue was purified by Prep-HPLC eluting with a gradient of 65-95% acetonitrile in water with 0.05% trifluoroacetic acid to afford methyl (S,E)-3-(7-(2-chloro-6-fluorostyryl)-1-((4-fluoro-3-methoxyphenyl)sulfonyl)-1,2,3,4-tetrahydroquinolin-3-yl)-2,2-dimethylpropanoate (7.6 mg, 15%) as a white solid. $^1$H-NMR (400 MHz, CD$_3$OD) δ 8.02 (s, 1H), 7.39-7.23 (m, 4H), 7.28-7.01 (m, 5H), 4.31-4.27 (dd, J=4 Hz, 12 Hz, 1H), 3.72 (s, 3H), 3.12-3.09 (t, J=6 Hz, 1H), 2.68-2.62 (dd, J=8 Hz, 20 Hz, 1H), 2.27-2.20 (m, 1H), 1.67-1.49 (m, 3H), 1.26-1.24 (d, J=8 Hz, 6H). (ES, m/z): (M+H)$^+$590.

Example 154-Preparation of Additional Substituted 1,2,3,4-Tetrahydroquinolin-3-yl)-2,2-dimethylpropanoates and Propanoic Acids Compounds in Table 20 were prepared based on experimental procedures described in Example 153 and the detailed description using the appropriate vinyl boronate.

TABLE 20

| No. | Structure | Name | Observed m/z |
|---|---|---|---|
| 154A | 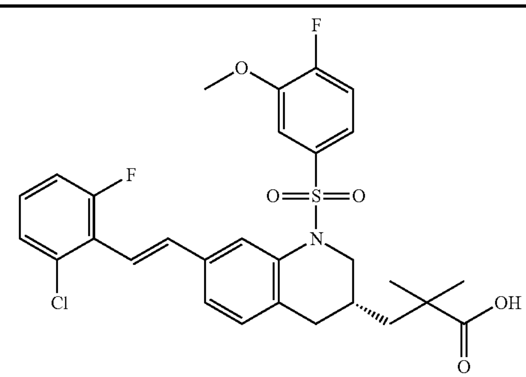 | (S,E)-3-(7-(2-chloro-6-fluorostyryl)-1-((4-fluoro-3-methoxyphenyl)sulfonyl)-1,2,3,4-tetrahydroquinolin-3-yl)-2,2-dimethylpropanoic acid | 576 (M + H)$^+$ |
| 154B | 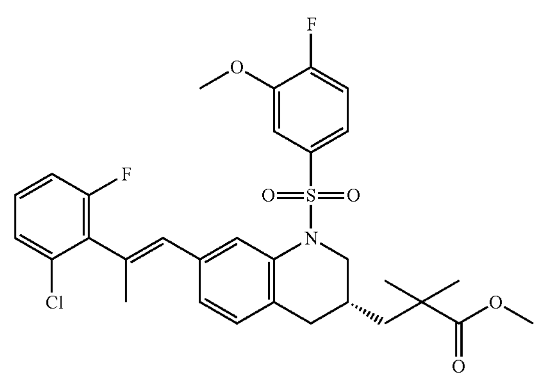 [SMILES: COC(=O)C(C)(C)C[C@@H]1Cc2ccc(/C=C(\C)c3c(F)cccc3Cl)cc2N(S(=O)(=O)c2ccc(F)c(OC)c2)C1] | methyl (S,E)-3-(7-(2-(2-chloro-6-fluorophenyl)prop-1-en-1-yl)-1-((4-fluoro-3-methoxyphenyl)sulfonyl)-1,2,3,4-tetrahydroquinolin-3-yl)-2,2-dimethylpropanoate | 604 (M + H)$^+$ |

TABLE 20-continued

| No. | Structure | Name | Observed m/z |
|---|---|---|---|
| 154C | 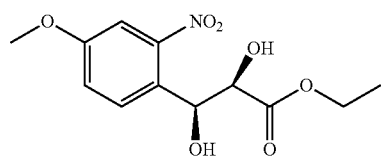 | (S,E)-3-(7-(2-(2-chloro-6-fluorophenyl)prop-1-en-1-yl)-1-((4-fluoro-3-methoxyphenyl)sulfonyl)-1,2,3,4-tetrahydroquinolin-3-yl)-2,2-dimethylpropanoic acid | 590 (M + H)+ |

Example 155—Synthesis of (R)-7-((2-Chloro-6-fluorobenzyl)oxy)-1-((3-(trifluoromethyl)phenyl)sulfonyl)-1,2,3,4-tetrahydroquinolin-3-ol

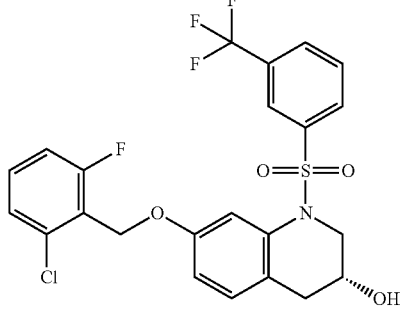

Part I—Synthesis of (E)-Ethyl 3-(4-methoxy-2-nitrophenyl)acrylate

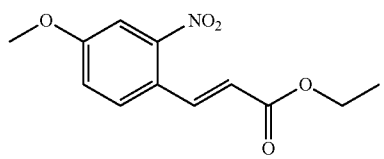 [SMILES: CCOC(=O)/C=C/c1ccc(OC)cc1[N+](=O)[O-]]

A mixture of 1-iodo-4-methoxy-2-nitrobenzene (279 mg, 1.00 mmol), palladium acetate (11.2 mg, 0.05 mmol), triethylamine (202 mg, 2.00 mmol), and ethyl acrylate (110 mg, 1.10 mmol) was heated to reflux for five hours. The mixture was cooled, concentrated and diluted with ethyl acetate. The mixture was washed with water, brine, dried (Na$_2$SO$_4$) and concentrated. The resulting residue was purified via MPLC eluting with 3:1 hexane: ethyl acetate to afford (E)-ethyl 3-(4-methoxy-2-nitrophenyl)acrylate (201 mg, 80%) as a yellow solid.

Part II—Synthesis of (2R,3S)-Ethyl 2,3-dihydroxy-3-(4-methoxy-2-nitrophenyl)propanoate To a solution of (E)-ethyl 3-(4-methoxy-2-nitrophenyl)acrylate (5 g, 19.90 mmol) in tert-butanol/water (1:1) (150 mL) was added methanesulfonamide (2 g, 21.03 mmol) followed by the addition of AD-mix-α (16.4 g, 21.05 mmol) in several portions at 0° C. The reaction mixture was stirred overnight at room temperature and quenched by the addition of saturated aqueous sodium bisulfite (200 mL). The mixture was extracted three times with ethyl acetate, and the combined organic layers were concentrated. The resulting residue was purified via MPLC eluting with ethyl acetate/petroleum ether (4:1). Concentration of the major UV component afforded (2R,3S)-ethyl 2,3-dihydroxy-3-(4-methoxy-2-nitrophenyl)propanoate (4.95 g, 87%) as a yellow solid.

Part III—Synthesis of (4R,5S)-Ethyl 5-(4-methoxy-2-nitrophenyl)-1,3,2-dioxathiolane-4-carboxylate 2-oxide

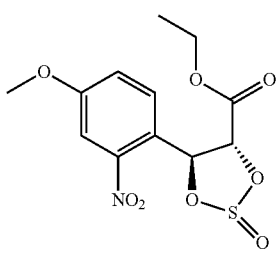

To a stirred solution of ethyl (2R,3S)-2,3-dihydroxy-3-(4-methoxy-2-nitrophenyl)propanoate (5 g, 17.53 mmol)

and triethylamine (5.3 g, 52.38 mmol) in dichloromethane (150 mL) at 0° C. was added thionyl chloride (2.7 g, 22.69 mmol) dropwise. The mixture was stirred for one hour, and quenched by the addition of water. The mixture was extracted three times with dichloromethane. The combined organic layers were dried (Na₂SO₄) and concentrated. The resulting residue was purified via MPLC eluting with a gradient of ethyl acetate/petroleum ether (1:10-1:2). Concentration of the major UV-active component afforded (4R, 5S)-ethyl 5-(4-methoxy-2-nitrophenyl)-1,3,2-dioxathiolane-4-carboxylate 2-oxide (5.2 g, 90%) as a yellow oil.

Part IV—Synthesis of (R)-7-Methoxy-1,2,3,4-tetrahydroquinolin-3-ol

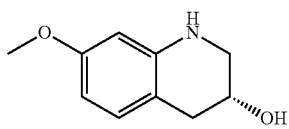

To a solution of (4R,5S)-ethyl 5-(4-methoxy-2-nitrophenyl)-1,3,2-dioxathiolane-4-carboxylate 2-oxide (1.5 g, 4.53 mmol) in 190 proof ethanol (60 mL) at 0° C. was added cobalt (II) chloride hexahydrate (213 mg, 0.90 mmol) followed by the addition of sodium borohydride (1.33 g, 36.1 mmol). The mixture was stirred overnight at room temperature. The mixture was poured into ice water (100 mL), and extracted four times with ethyl acetate. The combined organic layers were concentrated and the resulting residue was purified via MPLC eluting with acetate/petroleum ether (1:1) to afford (R)-7-methoxy-1,2,3,4-tetrahydroquinolin-3-ol (550 mg, 68%) as a yellow solid.

Part V—Synthesis of (R)-7-Methoxy-1-((3-(trifluoromethyl)phenyl)sulfonyl)-1,2,3,4-tetrahydroquinolin-3-ol

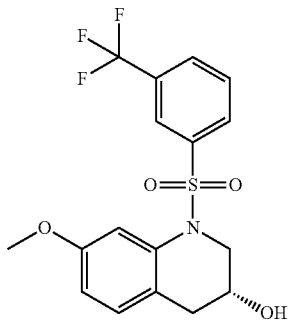 [SMILES: COc1ccc2c(c1)N(S(=O)(=O)c1cccc(C(F)(F)F)c1)C[C@H](O)C2]

To a room temperature solution of (R)-7-methoxy-1,2,3,4-tetrahydroquinolin-3-ol (400 mg, 2.23 mmol) in dichloromethane (12 mL) and pyridine (12 mL) was added 3-(trifluoromethyl)benzene-1-sulfonyl chloride (600 mg, 2.45 mmol). The mixture was stirred for two hours, diluted with dichloromethane and washed twice with 1M hydrogen chloride. The organic layer was dried (Na₂SO₄) and concentrated to afford (R)-7-methoxy-1-((3-(trifluoromethyl)phenyl)sulfonyl)-1,2,3,4-tetrahydroquinolin-3-ol (650 mg, 75%) as a colorless oil.

Part VI—Synthesis of (R)-1-((3-(Trifluoromethyl)phenyl)sulfonyl)-1,2,3,4-tetrahydroquinoline-3,7-diol

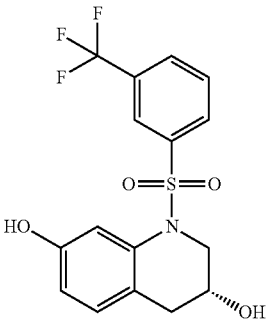 [SMILES: O=S(=O)(c1cccc(C(F)(F)F)c1)N1C[C@H](O)Cc2ccc(O)cc21]

To a solution of (R)-7-methoxy-1-((3-(trifluoromethyl)phenyl)sulfonyl)-1,2,3,4-tetrahydroquinolin-3-ol (1.1 g, 2.84 mmol) in dichloromethane (20 mL) at −78° C. was added boron tribromide (11.2 g, 44.7 mmol) dropwise. The reaction mixture was allowed to warm to room temperature and was stirred for two hours. The mixture was quenched with water, and extracted twice with dichloromethane. The combined organic layers were dried (Na₂SO₄) and concentrated. The resulting residue was purified via MPLC eluting with petroleum ether: ethyl acetate (1:1). Concentration of the major UV component afforded (R)-1-((3-(trifluoromethyl)phenyl)sulfonyl)-1,2,3,4-tetrahydroquinoline-3,7-diol (900 mg, 85%) as a colorless oil.

Part VII—Synthesis of (R)-7-((2-Chloro-6-fluorobenzyl)oxy)-1-((3-(trifluoromethyl)phenyl)sulfonyl)-1,2,3,4-tetrahydroquinolin-3-ol

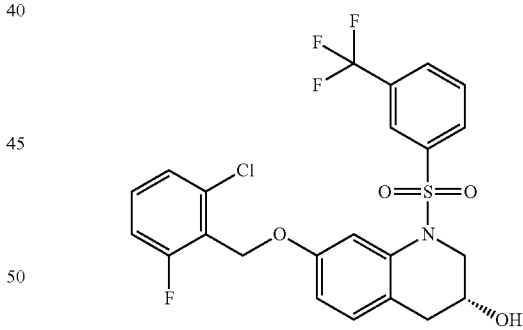

A mixture of (R)-1-((3-(trifluoromethyl)phenyl)sulfonyl)-1,2,3,4-tetrahydroquinoline-3,7-diol (100 mg, 0.27 mmol), 2-(bromomethyl)-1-chloro-3-fluorobenzene (65 mg, 0.29 mmol), potassium carbonate (111 mg, 0.80 mmol) and acetonitrile (5 mL) was stirred overnight at 70° C. The reaction mixture was cooled, diluted with water, and extracted twice with ethyl acetate. The combined organic layers were dried (Na₂SO₄) and concentrated. The resulting residue was purified by reverse phase Prep-HPLC to afford (R)-7-((2-chloro-6-fluorobenzyl)oxy)-1-((3-(trifluoromethyl)phenyl)sulfonyl)-1,2,3,4-tetrahydroquinolin-3-ol (23.7 mg, 17%) as a white solid. ¹H-NMR (300 MHz, CDCl₃) δ 8.03 (1H, s), 7.93 (1H, t, J=5.4 Hz), 7.79 (1H, d, J=7.5 Hz), 7.58 (1H, t, J=8.1 Hz), 7.43 (1H, d, J=2.4 Hz), 7.25 (2H, s), 7.05 (1H, t, J=8.1 Hz), 6.94 (1H, d, J=8.4 Hz), 6.78 (1H, d, J=8.4 Hz), 5.15 (2H, s), 4.10 (1H, m), 3.96 (1H, m), 3.80 (1H, m), 2.75 (1H, m), 2.47 (1H, m). (ES, m/z): (M+H)$^+$516.

Example 156—Synthesis of (R)-Methyl 2-((7-((2-chloro-6-fluorobenzyl)oxy)-1-((3-(trifluoromethyl)phenyl)sulfonyl)-1,2,3,4-tetrahydroquinolin-3-yl)oxy)acetate

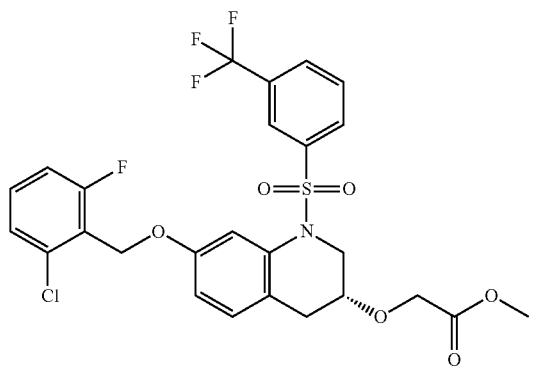 [SMILES: COC(=O)CO[C@@H]1Cc2ccc(OCc3c(F)cccc3Cl)cc2N(S(=O)(=O)c2cccc(C(F)(F)F)c2)C1]

To a stirred solution of (R)-7-((2-chloro-6-fluorobenzyl)oxy)-1-((3-(trifluoromethyl)phenyl)sulfonyl)-1,2,3,4-tetrahydroquinolin-3-ol (200 mg, 0.39 mmol) in N,N-dimethylformamide (10 mL) at 0° C. was added 60% sodium hydride (31 mg, 1.29 mmol) followed by methyl 2-bromoacetate (71 mg, 0.46 mmol). The reaction mixture was stirred at room temperature for two hours, and quenched by the addition of water. The mixture was extracted twice with ethyl acetate. The combined organic layers were dried (Na$_2$SO$_4$) and concentrated. The resulting residue was purified via MPLC, eluting with petroleum ether: ethyl acetate (1:1) to afford (R)-methyl 2-((7-((2-chloro-6-fluorobenzyl)oxy)-1-((3-(trifluoromethyl)phenyl)sulfonyl)-1,2,3,4-tetrahydroquinolin-3-yl)oxy)acetate (21.7 mg, 10%) as a white solid.

Example 157-Synthesis of (R)-2-((7-((2-Chloro-6-fluorobenzyl)oxy)-1-((3-(trifluoromethyl)phenyl)sulfonyl)-1,2,3,4-tetrahydroquinolin-3-yl)oxy)acetic acid

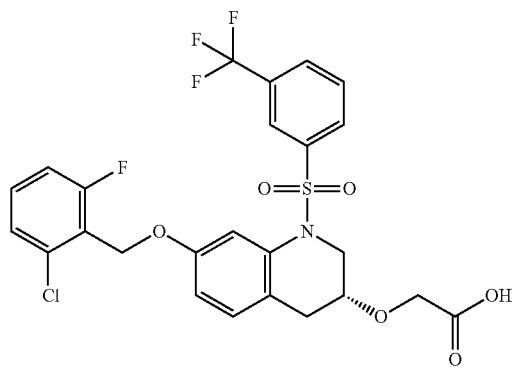 [SMILES: O=C(O)CO[C@@H]1Cc2ccc(OCc3c(F)cccc3Cl)cc2N(S(=O)(=O)c2cccc(C(F)(F)F)c2)C1]

To a solution of (R)-methyl 2-((7-((2-chloro-6-fluorobenzyl)oxy)-1-((3-(trifluoromethyl)phenyl)sulfonyl)-1,2,3,4-tetrahydroquinolin-3-yl)oxy)acetate (100 mg, 0.17 mmol) in tetrahydrofuran (9 mL) and water (3 mL) was added lithium hydroxide (20 mg, 0.84 mmol). The mixture was stirred for two hours at room temperature. The pH value of the solution was adjusted to 5 with 1 M HCl. The mixture was extracted twice with ethyl acetate, dried (Na$_2$SO$_4$), and concentrated. The resulting residue was purified by reverse phase Prep-HPLC to provide (R)-2-((7-((2-chloro-6-fluorobenzyl)oxy)-1-((3-(trifluoromethyl)phenyl)sulfonyl)-1,2,3,4-tetrahydroquinolin-3-yl)oxy)acetic acid (18.3 mg, 19%) as a white solid. $^1$H-NMR-(400 MHz, CDCl$_3$) δ 8.06 (1H, s), 7.92 (1H, d), 7.82 (1H, d), 7.58 (1H, t), 7.37 (1H, s), 7.30 (1H, m), 7.07 (t, 1H), 6.99 (1H, d), 6.81 (1H, d), 5.19 (2H, s), 4.16 (2H, m), 4.00 (2H, m), 3.82 (1H, t), 2.80 (1H, m), 2.55 (1H, m). (ES, m/z): (M+H)$^+$574.

Example 158—Synthesis of (S)-7-((2-chloro-6-fluorobenzyl)oxy)-1-((3-(trifluoromethyl)phenyl)sulfonyl)-1,2,3,4-tetrahydroquinolin-3-ol

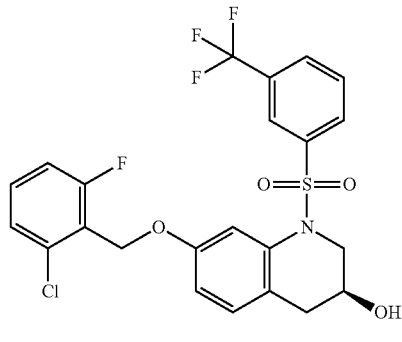 [SMILES: O=S(=O)(c1cccc(C(F)(F)F)c1)N1C[C@@H](O)Cc2ccc(OCc3c(F)cccc3Cl)cc21]

Part I—Synthesis of (2S,3R)-Ethyl 2,3-dihydroxy-3-(4-methoxy-2-nitrophenyl)propanoate

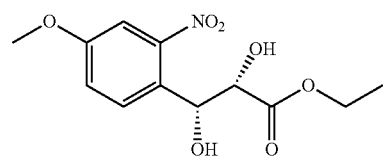 [SMILES: CCOC(=O)[C@@H](O)[C@H](O)c1ccc(OC)cc1[N+](=O)[O-]]

To a solution of (E)-ethyl 3-(4-methoxy-2-nitrophenyl)acrylate (4.72 g, 18.8 mmol) in tert-butanol/water (1:1) (150 mL) was added methanesulfonamide (2.7 g) followed by the addition of AD-mix-β (27.7 g, 19.8 mmol) in several portions at 0° C. The resulting solution was stirred overnight at room temperature. The reaction was then quenched by the addition of saturated aqueous sodium bisulfite (200 mL). The mixture was extracted three times with ethyl acetate, and the combined organic layers were concentrated. The resulting residue was purified via MPLC eluting with ethyl acetate/petroleum ether (4:1). Concentration of the major UV component afforded (2S,3R)-ethyl 2,3-dihydroxy-3-(4-methoxy-2-nitrophenyl)propanoate (4.65 g) as a yellow solid.

Part II-VI—Synthesis of (S)-7-((2-Chloro-6-fluorobenzyl)oxy)-1-((3-(trifluoromethyl)phenyl)sulfonyl)-1,2,3,4-tetrahydroquinolin-3-ol

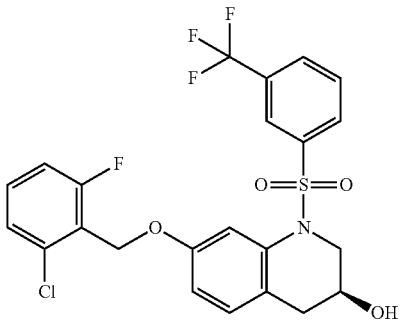 [SMILES: O=S(=O)(c1cccc(C(F)(F)F)c1)N1C[C@@H](O)Cc2ccc(OCc3c(F)cccc3Cl)cc21]

Parts II-IV were performed as done on the enantiomer in Example 155. The NMR and MS were identical to the material of Example 155. Each was greater than 98% ee as determined by a chiral HPLC.

Example 159—Synthesis of (R)-7-((2-Chloro-6-fluorobenzyl)oxy)-1-((3-(trifluoromethyl)phenyl)sulfonyl)-1,2,3,4-tetrahydroquinolin-3-amine

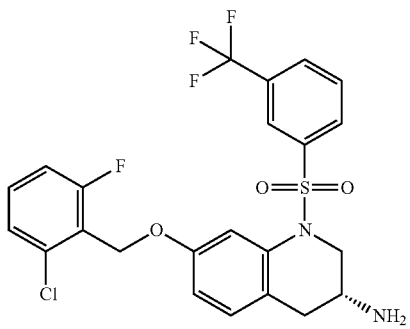 [SMILES: N[C@@H]1Cc2ccc(OCc3c(F)cccc3Cl)cc2N(S(=O)(=O)c2cccc(C(F)(F)F)c2)C1]

Part I—Synthesis of (S)-7-((2-Chloro-6-fluorobenzyl)oxy)-1-((3-(trifluoromethyl)phenyl)sulfonyl)-1,2,3,4-tetrahydroquinolin-3-yl methanesulfonate

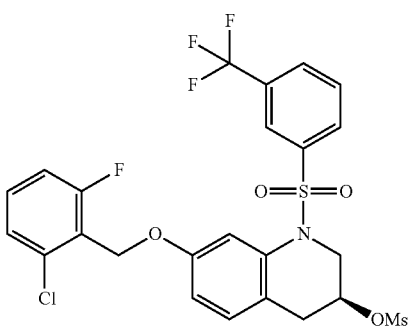 [SMILES: CS(=O)(=O)O[C@H]1Cc2ccc(OCc3c(F)cccc3Cl)cc2N(S(=O)(=O)c2cccc(C(F)(F)F)c2)C1]

To a stirred solution of (S)-7-((2-chloro-6-fluorobenzyl)oxy)-1-((3-(trifluoromethyl)phenyl)sulfonyl)-1,2,3,4-tetrahydroquinolin-3-ol (550 mg, 1.06 mmol) and diisopropylethylamine (0.37 mL, 2.12 mmol) in dichloromethane (7.9 mL) at −10° C. was added methanesulfonyl chloride (0.099 mL, 1.27 mmol) dropwise. The mixture was warmed to room temperature and stirred for 2 hours. The resulting solution was diluted with saturated sodium bicarbonate and extracted three times with dichloromethane. The organic layers were combined and concentrated to afford (S)-7-((2-chloro-6-fluorobenzyl)oxy)-1-((3-(trifluoromethyl)phenyl)sulfonyl)-1,2,3,4-tetrahydroquinolin-3-yl methanesulfonate (600 mg) as a yellow oil.

Part II—Synthesis of (R)-3-azido-7-((2-chloro-6-fluorobenzyl)oxy)-1-((3-(trifluoromethyl)phenyl)sulfonyl)-1,2,3,4-tetrahydroquinoline

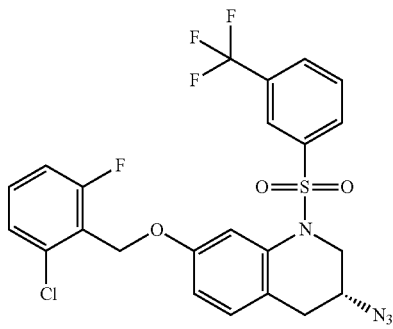

A mixture of (S)-7-((2-chloro-6-fluorobenzyl)oxy)-1-((3-(trifluoromethyl)phenyl)sulfonyl)-1,2,3,4-tetrahydroquinolin-3-yl methanesulfonate (633 mg, 1.06 mmol), N,N-dimethylformamide (1.2 mL), and sodium azide (138.5 mg, 2.13 mmol) was stirred for two hours at 80° C. The mixture was diluted in water, extracted three times with dichloromethane and the organic layers were combined and concentrated. The crude product was purified by MPLC eluting with a gradient of petroleum ether: ethyl acetate=20:1 increasing to petroleum ether: ethyl acetate=4:1 to afford (R)-3-azido-7-((2-chloro-6-fluorobenzyl)oxy)-1-((3-(trifluoromethyl)phenyl)sulfonyl)-1,2,3,4-tetrahydroquinoline (450 mg, 78%) as a yellow oil.

Part III—Synthesis of (R)-7-((2-Chloro-6-fluorobenzyl)oxy)-1-((3-(trifluoromethyl)phenyl)sulfonyl)-1,2,3,4-tetrahydroquinolin-3-amine

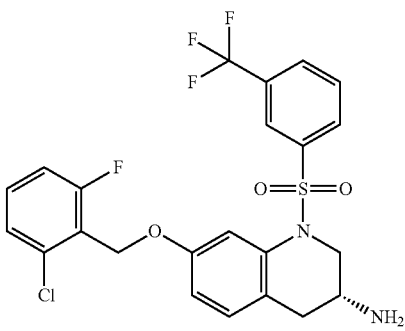 [SMILES: N[C@@H]1Cc2ccc(OCc3c(F)cccc3Cl)cc2N(S(=O)(=O)c2cccc(C(F)(F)F)c2)C1]

To a solution of (R)-3-azido-7-((2-chloro-6-fluorobenzyl)oxy)-1-((3-(trifluoromethyl)phenyl)sulfonyl)-1,2,3,4-tetrahydroquinoline (410 mg, 0.76 mmol) in water (0.0824 mL, 4.58 mmol) and tetrahydrofuran (2.2 mL) at 0° C. was added triphenylphosphine (397.6 mg, 1.52 mmol) in portions. The mixture was stirred overnight at 50° C., cooled, and concentrated. The resulting residue was diluted with water, and extracted three times with dichloromethane. The combined organic layers were concentrated and the resulting residue was purified via MPLC eluting with a gradient of 1-20% methanol in dichloromethane. The major UV active component was further purified via reverse phase Prep HPLC to provide (R)-7-((2-chloro-6-fluorobenzyl)oxy)-1-((3-(trifluoromethyl)phenyl)sulfonyl)-1,2,3,4-tetrahydroquinolin-3-amine (30.2 mg, 8%) as a white solid. $^1$H-NMR (400 MHz, CD$_3$OD) δ 2.65 (m, 1H), 2.90 (dd, J=5.6 Hz, 16.4 Hz, 1H), 3.53 (m, 1H), 3.69 (dd, J=8.4 Hz, 13.2 Hz, 1H), 4.40 (dd, J=3.6 Hz, 13.2 Hz, 1H), 5.21 (s, 2H), 6.92 (dd, J=2.4 Hz, 8.8 Hz, 1H), 7.12 (d, J=8.4 Hz, 1H), 7.18 (t, J=8.8 Hz, 1H), 7.36 (d, J=8.0 Hz, 1H), 7.41-7.47 (m, 2H), 7.82 (t, J=7.6 Hz, 1H), 7.98-8.07 (m, 3H). (ES, m/z): (M+H+MeCN)$^+$556.

Example 160—Synthesis of (R)—N-(7-((2-chloro-6-fluorobenzyl)oxy)-1-((3-(trifluoromethyl)phenyl)sulfonyl)-1,2,3,4-tetrahydroquinolin-3-yl)acetamide

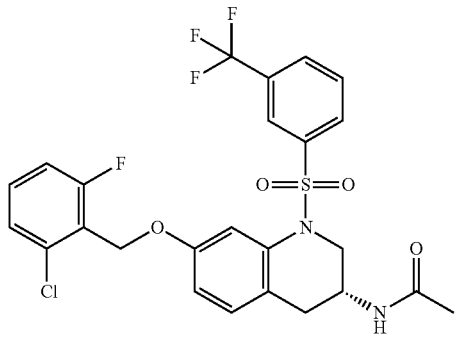 [SMILES: CC(=O)N[C@@H]1Cc2ccc(OCc3c(F)cccc3Cl)cc2N(S(=O)(=O)c2cccc(C(F)(F)F)c2)C1]

To a solution of (R)-7-((2-chloro-6-fluorobenzyl)oxy)-1-((3-(trifluoromethyl)phenyl)sulfonyl)-1,2,3,4-tetrahydroquinolin-3-amine (350 mg, 0.68 mmol) in dichloromethane (6.5 mL) and triethylamine (0.28 mL, 2.04 mmol) was added acetyl chloride (0.12 mL, 1.7 mmol). The reaction mixture was stirred overnight at room temperature and then diluted with saturated aqueous sodium bicarbonate. The mixture was extracted three times with dichloromethane. The combined organic layers were concentrated and the resulting residue was purified via reverse phase Prep-HPLC eluting with a gradient of 40-80% acetonitrile in water with 0.05% TFA to afford (R)—N-(7-((2-chloro-6-fluorobenzyl)oxy)-1-((3-(trifluoromethyl)phenyl)sulfonyl)-1,2,3,4-tetrahydroquinolin-3-yl)acetamide (83.3 mg, 22%) as a white solid. $^1$H-NMR (400 MHz, CDCl$_3$) δ 2.00 (s, 3H), 2.51 (dd, J=11.1 Hz, 15.6 Hz, 1H), 2.78 (dd, J=4.2 Hz, 15.6 Hz, 1H), 3.76 (dd, J=6.0 Hz, 12.9 Hz, 1H), 3.98 (d, J=12.3 Hz, 1H), 4.23 (brs, 1H), 5.12 (s, 2H), 5.56-5.58 (m, 1H), 6.80 (dd, J=2.4 Hz, 8.4 Hz, 1H), 6.94 (d, J=17.1 Hz, 1H), 7.06 (dt, J=1.2 Hz, 9.0 Hz, 1H), 7.27-7.35 (m, 2H), 7.40 (d, J=2.4 Hz, 1H), 7.67 (t, J=8.1 Hz, 1H), 7.84 (d, J=8.1 Hz, 1H), 8.00 (brs, 2H). (ES, m/z): (M+Na)$^+$598.

Example 161—Synthesis of (S,E)-7-(2-(2-Chloro-6-fluorophenyl)prop-1-en-1-yl)-1-((3-(trifluoromethyl)phenyl)sulfonyl)-1,2,3,4-tetrahydroquinolin-3-ol

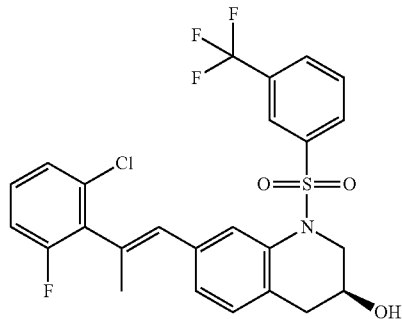 [SMILES: C/C(=C\c1ccc2c(c1)N(S(=O)(=O)c1cccc(C(F)(F)F)c1)C[C@@H](O)C2)c1c(F)cccc1Cl]

Part I—Synthesis of (S)-3-Hydroxy-1-((3-(trifluoromethyl)phenyl)sulfonyl)-1,2,3,4-tetrahydroquinolin-7-yl trifluoromethanesulfonate

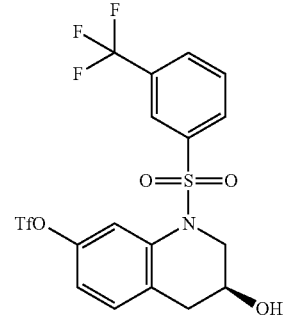 [SMILES: O=S(=O)(c1cccc(C(F)(F)F)c1)N1C[C@@H](O)Cc2ccc(OS(=O)(=O)C(F)(F)F)cc21]

To a stirred solution of (S)-1-((3-(trifluoromethyl)phenyl)sulfonyl)-1,2,3,4-tetrahydroquinoline-3,7-diol (800 mg, 2.14 mmol) and pyridine (676 mg, 8.55 mmol) in dichloromethane (70 mL) was added a solution of trifluoromethanesulfonic anhydride (847 mg, 3.00 mmol) in dichloromethane (5 mL) dropwise. The reaction mixture was stirred for two hours at room temperature. The reaction mixture was diluted with water. The resulting mixture was extracted with dichloromethane. The organic layer was washed with water, brine, and concentrated. The resulting residue was purified via MPLC eluting with ethyl acetate/petroleum ether (1:10-1:3) to afford (S)-3-hydroxy-1-((3-(trifluoromethyl)phenyl)sulfonyl)-1,2,3,4-tetrahydroquinolin-7-yl trifluoromethanesulfonate (950 mg, 88%) as a yellow oil.

Part II—Synthesis of (S,E)-7-(2-(2-Chloro-6-fluorophenyl)prop-1-en-1-yl)-1-((3-(trifluoromethyl)phenyl)sulfonyl)-1,2,3,4-tetrahydroquinolin-3-ol

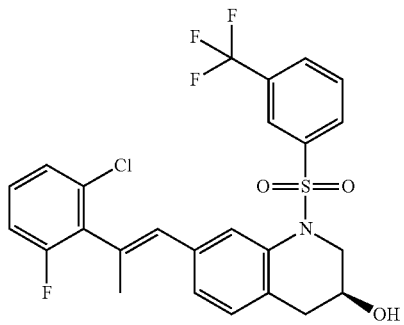 [SMILES: C/C(=C\c1ccc2c(c1)N(S(=O)(=O)c1cccc(C(F)(F)F)c1)C[C@@H](O)C2)c1c(F)cccc1Cl]

To a flask, which was purged and maintained with an inert atmosphere of nitrogen, was placed a solution of (S)-3-hydroxy-1-((3-(trifluoromethyl)phenyl)sulfonyl)-1,2,3,4-tetrahydroquinolin-7-yl trifluoromethanesulfonate (400 mg, 0.79 mmol) in toluene (12 mL), ethanol (4 mL), water (2 mL), 2-[(1E)-2-(2-chloro-6-fluorophenyl)prop-1-en-1-yl]-4,4,5,5-tetramethyl-1,3,2-dioxaborolane (258 mg, 0.87 mmol), and potassium acetate (232 mg, 2.36 mmol). Tetrakis(triphenylphosphane) palladium (91 mg, 0.08 mmol) was added to the reaction and it was stirred for three hours at 90° C. The mixture was cooled and was extracted three times with ethyl acetate. The organic layers were combined and concentrated. The resulting residue was purified via MPLC eluting with ethyl acetate/petroleum ether (1:10-2:1) to afford (S,E)-7-(2-(2-chloro-6-fluorophenyl)prop-1-en-1-yl)-1-((3-(trifluoromethyl)phenyl)sulfonyl)-1,2,3,4-tetrahydroquinolin-3-ol (215 mg, 52%) as a yellow oil. $^1$H-NMR (300 MHz, CD$_3$OD) δ 7.93-8.05 (m, 3H), 7.70-7.76 (m, 2H), 7.26-7.35 (m, 2H), 7.09-7.17 (m, 3H), 6.39 (s, 1H), 4.11 (m, 1H), 3.92 (m, 1H), 3.61-3.38 (m, 1H), 2.76 (m, 1H), 2.46 (m, 1H), 2.12 (s, 3H). (ES, m/z): (M+H)$^+$526.

Example 162—Synthesis of (R,E)-7-(2-(2-Chloro-6-fluorophenyl)prop-1-en-1-yl)-1-((3-(trifluoromethyl)phenyl)sulfonyl)-1,2,3,4-tetrahydroquinolin-3-ol

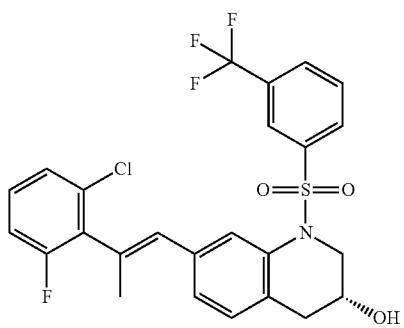 [SMILES: C/C(=C\c1ccc2c(c1)N(S(=O)(=O)c1cccc(C(F)(F)F)c1)C[C@H](O)C2)c1c(F)cccc1Cl]

The title compound was prepared based on procedures described in Example 161, using the enantiomer.

Example 163—Synthesis of (R,E)-7-(2-Chloro-6-fluorostyryl)-1-((3-(trifluoromethyl)phenyl)sulfonyl)-1,2,3,4-tetrahydroquinolin-3-ol

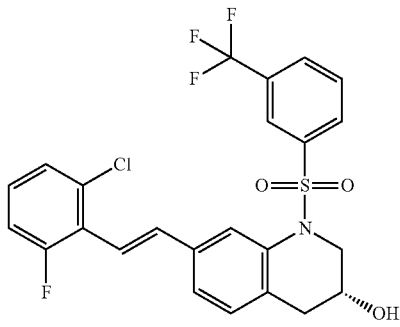 [SMILES: O=S(=O)(c1cccc(C(F)(F)F)c1)N1C[C@H](O)Cc2ccc(/C=C/c3c(F)cccc3Cl)cc21]

Part I—Synthesis of (E)-2-(2-Chloro-6-fluorostyryl)-4,4,5,5-tetramethyl-1,3,2-dioxaborolane

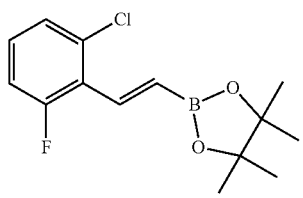 [SMILES: CC1(C)OB(/C=C/c2c(F)cccc2Cl)OC1(C)C]

To a flask, which was purged and maintained with an inert atmosphere of nitrogen, was placed copper (I) chloride (3.8 mg, 0.04 mmol), sodium tert-butoxide (7.5 mg, 0.078 mmol), 4,5-bis(diphenylphosphino)-9,9-dimethylxanthene (22.4 mg, 0.04 mmol), and tetrahydrofuran (3 mL). The mixture was stirred for thirty minutes at room temperature. 4,4,5,5-Tetramethyl-2-(tetramethyl-1,3,2-dioxaborolan-2-yl)-1,3,2-dioxaborolane (328.6 mg, 1.29 mmol) was added. After ten minutes, a solution of 1-chloro-2-ethynyl-3-fluorobenzene (200 mg, 1.29 mmol, 1.00 equiv) and methanol (0.105 mL) was added. The reaction mixture was stirred overnight at room temperature. The reaction mixture was diluted with water, and extracted three times with dichloromethane. The combined organic layers were dried (Na$_2$SO$_4$) and concentrated. The resulting residue was purified via MPLC eluting with a gradient of ethyl acetate/petroleum ether (0-5%) to provide (E)-2-(2-chloro-6-fluorostyryl)-4,4,5,5-tetramethyl-1,3,2-dioxaborolane (100 mg, 27%) as a colorless liquid.

Part II—Synthesis of (R,E)-7-(2-Chloro-6-fluorostyryl)-1-((3-(trifluoromethyl)phenyl)-sulfonyl)-1,2,3,4-tetrahydroquinolin-3-ol

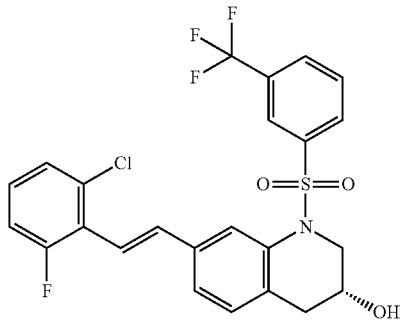 [SMILES: O=S(=O)(c1cccc(C(F)(F)F)c1)N1C[C@H](O)Cc2ccc(/C=C/c3c(F)cccc3Cl)cc21]

To a flask purged and maintained with an inert atmosphere of nitrogen, was placed (R)-3-hydroxy-1-((3-(trifluoromethyl)phenyl)sulfonyl)-1,2,3,4-tetrahydroquinolin-7-yl trifluoromethanesulfonate (100 mg, 0.20 mmol), (E)-2-(2-chloro-6-fluorostyryl)-4,4,5,5-tetramethyl-1,3,2-dioxaborolane (84 mg, 0.37 mmol), potassium acetate (50 mg, 0.51 mmol), toluene (4 mL), ethanol (2 mL), and water (1 mL). Tetrakis(triphenylphosphine)palladium(0) (22.9 mg, 0.02 mmol) was added and the mixture was stirred overnight at 90° C. The reaction mixture was cooled, extracted with ethyl acetate and was concentrated. The resulting residue was purified by reverse phase Prep-HPLC eluting with a gradient of 55-88% acetonitrile in water with 0.05% TFA to afford (R,E)-7-(2-chloro-6-fluorostyryl)-1-((3-(trifluoromethyl)phenyl)-sulfonyl)-1,2,3,4-tetrahydroquinolin-3-ol (39 mg, 39%) as a white solid. $^1$H-NMR (400 MHz, CDCl$_3$) δ 8.07 (s, 1H), 7.97 (d, J=8 Hz, 1H), 7.86 (m, 2H), 7.64 (t, J=8 Hz, 1H), 7.35 (m, 2H), 7.29-7.24 (m, 3H), 7.20-7.15 (m, 3H), 7.14-7.04 (m, 2H), 4.18 (m, 1H), 4.01 (m, 1H), 3.85 (m, 1H), 2.84 (m, 1H), 2.57 (m, 1H). (ES, m/z): (M+NH$_4$)$^+$529.

Example 164—Synthesis of (R,E)-7-(2-(2-Chloro-6-fluorophenyl)prop-1-en-1-yl)-1-((3-(trifluoromethyl)phenyl)sulfonyl)-1,2,3,4-tetrahydroquinolin-3-amine

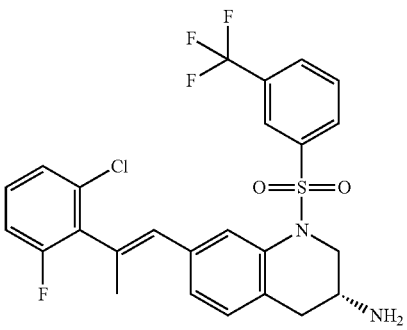 [SMILES: C/C(=C\c1ccc2c(c1)N(S(=O)(=O)c1cccc(C(F)(F)F)c1)C[C@H](N)C2)c1c(F)cccc1Cl]

Part I—Synthesis of (S,E)-7-(2-(2-Chloro-6-fluorophenyl)prop-1-en-1-yl)-1-((3-(trifluoromethyl)phenyl)sulfonyl)-1,2,3,4-tetrahydroquinolin-3-yl methanesulfonate

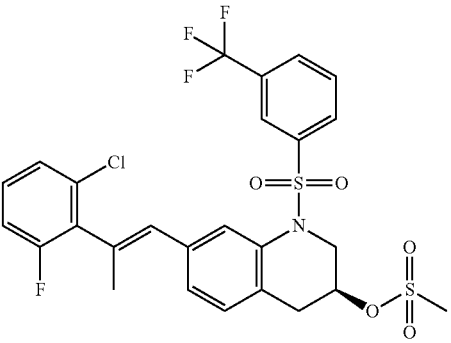 [SMILES: C/C(=C\c1ccc2c(c1)N(S(=O)(=O)c1cccc(C(F)(F)F)c1)C[C@@H](OS(C)(=O)=O)C2)c1c(F)cccc1Cl]

To a stirred solution of (S,E)-7-(2-(2-chloro-6-fluorophenyl)prop-1-en-1-yl)-1-((3-(trifluoromethyl)phenyl)sulfonyl)-1,2,3,4-tetrahydroquinolin-3-ol (360 mg, 0.68 mmol) and triethyl amine (274 mg, 2.71 mmol) in dichloromethane (15 mL) was added methanesulfonyl chloride (117 mg, 1.02 mmol) dropwise at room temperature. The reaction mixture was stirred for two hours, and diluted with water. The mixture was extracted with dichloromethane. The organic layer was washed twice with water, once with brine, dried (Na$_2$SO$_4$) and concentrated to afford (S,E)-7-(2-(2-chloro-6-fluorophenyl)prop-1-en-1-yl)-1-((3-(trifluoromethyl)phenyl)sulfonyl)-1,2,3,4-tetrahydroquinolin-3-yl methanesulfonate (360 mg, 87%) as a yellow oil.

Part II—Synthesis of (R,E)-3-Azido-7-(2-(2-chloro-6-fluorophenyl)prop-1-en-1-yl)-1-((3-(trifluoromethyl)phenyl)sulfonyl)-1,2,3,4-tetrahydroquinoline

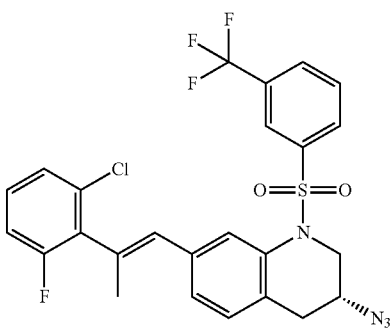 [SMILES: C/C(=C\c1ccc2c(c1)N(S(=O)(=O)c1cccc(C(F)(F)F)c1)C[C@H](N=[N+]=[N-])C2)c1c(F)cccc1Cl]

A solution of (S,E)-7-(2-(2-chloro-6-fluorophenyl)prop-1-en-1-yl)-1-((3-(trifluoromethyl)phenyl)sulfonyl)-1,2,3,4-tetrahydroquinolin-3-yl methanesulfonate (340 mg, 0.56 mmol), sodium azide (110 mg, 1.69 mmol) in N,N-dimethylformamide (10 mL) was stirred for four hours at 80° C. The reaction mixture was cooled, diluted with water, and extracted three times with ethyl acetate. The combined organic layers were washed with water, brine, and concentrated to yield (R,E)-3-azido-7-(2-(2-chloro-6-fluorophenyl)prop-1-en-1-yl)-1-((3-(trifluoromethyl)phenyl)sulfonyl)-1,2,3,4-tetrahydroquinoline (310 mg, 100%) as a yellow oil.

Part III—Synthesis of (R,E)-7-(2-(2-Chloro-6-fluorophenyl)prop-1-en-1-yl)-1-((3-(trifluoromethyl)phenyl)sulfonyl)-1,2,3,4-tetrahydroquinolin-3-amine

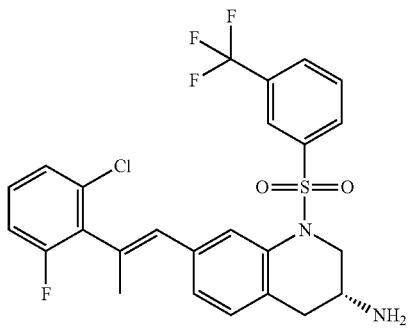 [SMILES: C/C(=C\c1ccc2c(c1)N(S(=O)(=O)c1cccc(C(F)(F)F)c1)C[C@H](N)C2)c1c(F)cccc1Cl]

To a solution of (R,E)-3-azido-7-(2-(2-chloro-6-fluorophenyl)prop-1-en-1-yl)-1-((3-(trifluoromethyl)phenyl)sulfonyl)-1,2,3,4-tetrahydroquinoline (320 mg, 0.58 mmol) in tetrahydrofuran (20 mL) and water (2 mL) was added triphenylphosphine (304 mg, 1.16 mmol). The reaction mixture was stirred overnight at room temperature and concentrated. The resulting residue was purified via MPLC eluting with a gradient of dichloromethane/methanol (100:1-10:1). The major UV active component was further purified by reverse phase Prep-HPLC eluting with 65% acetonitrile in water with 0.05% TFA to afford (R,E)-7-(2-(2-chloro-6-fluorophenyl)prop-1-en-1-yl)-1-((3-(trifluoromethyl)phenyl)sulfonyl)-1,2,3,4-tetrahydroquinolin-3-amine (300 mg, 98%) as a yellow oil. $^1$H-NMR (300 MHz, CD$_3$OD) δ 8.05 (m, 3H), 7.85 (m, 1H), 7.72 (s, 1H), 7.31-7.36 (m, 2H), 7.20-7.26 (m, 2H), 7.15 (m, 1H), 6.42 (s, 1H), 4.44 (m, 1H), 3.77 (m, 1H), 3.61 (m, 1H), 3.04 (m, 1H), 2.77 (m, 1H), 2.13 (s, 3H). (ES, m/z): (M+H)$^+$524.

Example 165—Synthesis of (R,E)-N-(7-(2-(2-Chloro-6-fluorophenyl)prop-1-en-1-yl)-1-((3-(trifluoromethyl)phenyl)sulfonyl)-1,2,3,4-tetrahydroquinolin-3-yl)acetamide

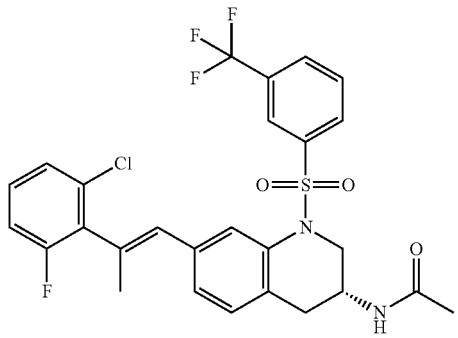 [SMILES: CC(=O)N[C@@H]1Cc2ccc(/C=C(\C)c3c(F)cccc3Cl)cc2N(S(=O)(=O)c2cccc(C(F)(F)F)c2)C1]

To a solution of (R,E)-7-(2-(2-chloro-6-fluorophenyl)prop-1-en-1-yl)-1-((3-(trifluoromethyl)phenyl)sulfonyl)-1,2,3,4-tetrahydroquinolin-3-amine (150 mg, 0.29 mmol) and triethylamine (115 mg, 1.14 mmol) in dichloromethane (15 mL) was added acetyl chloride (33.5 mg, 0.427 mmol) at room temperature. The reaction mixture was stirred overnight at room temperature, diluted with water, and extracted twice with dichloromethane. The combined organic layers were dried (Na$_2$SO$_4$) and concentrated. The resulting residue was purified via MPLC eluting with a gradient of ethyl acetate/petroleum ether (1:5-5:1). The major UV component was further purified by reverse phase Prep-HPLC eluting with a gradient of 60-67% acetonitrile in water with 0.05% TFA to provide (R,E)-N-(7-(2-(2-chloro-6-fluorophenyl)prop-1-en-1-yl)-1-((3-(trifluoromethyl)phenyl)sulfonyl)-1,2,3,4-tetrahydroquinolin-3-yl)acetamide (41.6 mg, 26%) as a white solid. $^1$H-NMR (400 MHz, CD$_3$OD) δ 8.05 (m, 1H), 7.94 (m, 1H), 7.90 (s, 1H), 7.76-7.82 (m, 2H), 7.29-7.36 (m, 2H), 7.12-7.18 (m, 3H), 6.42 (s, 1H), 4.38 (m, 1H), 3.88 (m, 1H), 3.46 (m, 1H), 2.80 (m, 1H), 2.55 (m, 1H), 2.17 (s, 3H), 1.95 (s, 3H). (ES, m/z): (M+H)$^+$567.

Example 166—Synthesis of (S,E)-7-(2-(2-Chloro-6-fluorophenyl)prop-1-en-1-yl)-1-((3-(trifluoromethyl)phenyl)sulfonyl)-1,2,3,4-tetrahydroquinolin-3-amine

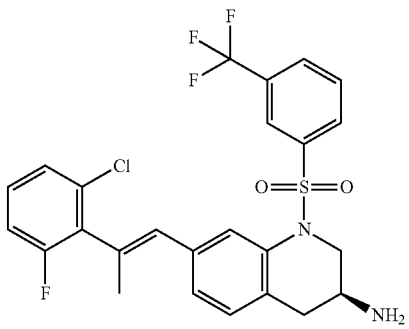

This compound was prepared as by Example 164, using the enantiomer as the starting material.

Example 167-Synthesis of (S,E)-N-(7-(2-(2-chloro-6-fluorophenyl)prop-1-en-1-yl)-1-((3-(trifluoromethyl)phenyl)sulfonyl)-1,2,3,4-tetrahydroquinolin-3-yl)acetamide

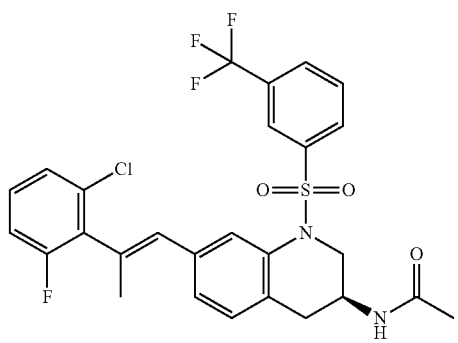 [SMILES: CC(=O)N[C@H]1Cc2ccc(/C=C(\C)c3c(F)cccc3Cl)cc2N(S(=O)(=O)c2cccc(C(F)(F)F)c2)C1]

This compound was prepared as by Example 165, using the enantiomer as the starting material.

Example 168—Synthesis of Racemic (2R,3R)-7-((E)-2-Chloro-6-fluorostyryl)-1-((4-fluoro-3-methoxyphenyl)sulfonyl)-2-methyl-1,2,3,4-tetrahydroquinolin-3-ol

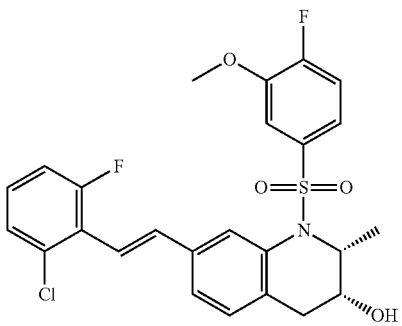 [SMILES: COc1cc(S(=O)(=O)N2c3cc(/C=C/c4c(F)cccc4Cl)ccc3C[C@@H](O)[C@H]2C)ccc1F]

Part I—Synthesis of Racemic (2R,3R,4R)-7-Bromo-3-hydroxy-2-methyl-1,2,3,4-tetrahydroquinolin-4-yl acetate

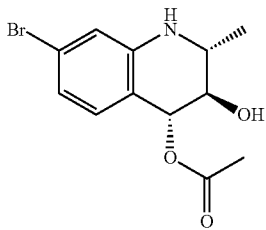

Ceric ammonium nitrate (663 mg, 1.21 mmol) was added a stirred solution of racemic (1aR,2R,7bS)-5-bromo-3-((4-fluoro-3-methoxyphenyl)sulfonyl)-2-methyl-1a,2,3,7b-tetrahydrooxireno[2,3-c]quinoline (6.84 g, 19.81 mmol) in acetic acid (60 mL) at room temperature. The reaction mixture was stirred overnight at room temperature, and then it was diluted with water (500 mL). The mixture was extracted three times with dichloromethane. The combined organic layers were washed three times with saturated sodium bicarbonate and concentrated. The resulting residue was purified by MPLC eluting with a gradient of 10% to 90% ethyl acetate in petroleum ether to afford racemic (2R,3R,4R)-7-bromo-3-hydroxy-2-methyl-1,2,3,4-tetrahydroquinolin-4-yl acetate (2.23, 28%) as a light yellow foam.

Part II—Synthesis of Racemic (2R,3R,4R)-7-Bromo-2-methyl-3-((methylsulfonyl)oxy)-1,2,3,4-tetrahydroquinolin-4-yl acetate

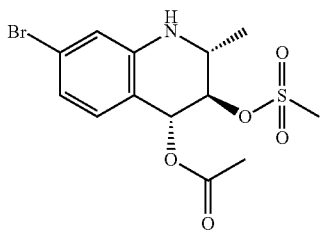 [SMILES: CC(=O)O[C@@H]1c2ccc(Br)cc2N[C@H](C)[C@H]1OS(C)(=O)=O]

To a stirred solution of racemic (2R,3R,4R)-7-bromo-3-hydroxy-2-methyl-1,2,3,4-tetrahydroquinolin-4-yl acetate (1.99 g, 4.91 mmol) in dichloromethane (41 mL) at 0° C. was added dropwise triethyl amine (1.2 mL, 8.84 mmol). Methane sulfonyl chloride (0.62 mL, 7.86 mmol) was then added dropwise. The resulting solution was stirred for one hour at 0° C., and then quenched by the addition of saturated ammonium chloride (100 mL). The mixture was extracted three times with dichloromethane. The combined organic layers were concentrated, and the resulting residue was purified by MPLC eluting with a gradient of 33-66% ethyl acetate in petroleum ether to afford racemic (2R,3R,4R)-7-bromo-2-methyl-3-((methylsulfonyl)oxy)-1,2,3,4-tetrahydroquinolin-4-yl acetate (2.45 g) as a light yellow foam.

Part III—Synthesis of Racemic (2R,3R)-7-Bromo-2-methyl-1,2,3,4-tetrahydroquinolin-3-ol

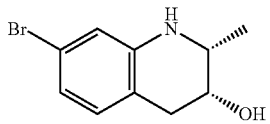

A 1M solution of lithium triethylborohydride in THF (49.2 mL, 49.2 mmol) was added dropwise to a stirred solution of racemic (2R,3R,4R)-7-bromo-2-methyl-3-((methylsulfonyl)oxy)-1,2,3,4-tetrahydroquinolin-4-yl acetate (2.37 g, 4.90 mmol) in tetrahydrofuran (15 mL) at 0° C. The resulting solution was stirred for an addition hour at room temperature, and then quenched by the addition of saturated ammonium chloride (100 mL). The mixture was extracted three times with dichloromethane. The combined organic layers were concentrated, and the resulting residue was purified by MPLC eluting with a gradient of 20-50% ethyl acetate in petroleum ether to afford racemic (2R,3R)-7-bromo-2-methyl-1,2,3,4-tetrahydroquinolin-3-ol (1.3 g) as a brown oil Part IV—Synthesis of Racemic ((2R,3R)-7-((E)-2-Chloro-6-fluorostyryl)-2-methyl-1,2,3,4-tetrahydroquinolin-3-ol

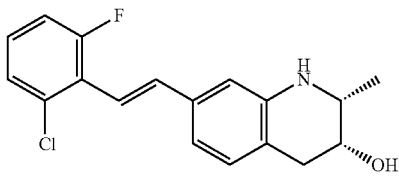 [SMILES: C[C@H]1Nc2cc(/C=C/c3c(F)cccc3Cl)ccc2C[C@H]1O]

To a mixture of racemic (2R,3R)-7-bromo-2-methyl-1,2,3,4-tetrahydroquinolin-3-ol (592 mg, 2.45 mmol), (E)-2-(2-(2-chloro-6-fluorophenyl)prop-1-en-1-yl)-4,4,5,5-tetramethyl-1,3,2-dioxaborolane (1.04 g, 3.68 mmol), ethanol (2.8 mL), water (10 mL), and toluene (20.1 mL) was added sodium carbonate (2.13 g, 20.10 mmol) and tetrakis(triphenylphosphine)-palladium(0) (340.9 mg, 0.30 mmol) under nitrogen. The mixture was stirred for one hour at 95° C., cooled, and diluted with water (100 mL). The mixture was extracted three times with dichloromethane, and the combined organic layers were concentrated. The resulting residue was purified by MPLC eluting with a gradient of 20-50% ethyl acetate in petroleum ether to afford racemic ((2R,3R)-7-((E)-2-chloro-6-fluorostyryl)-2-methyl-1,2,3,4-tetrahydroquinolin-3-ol (340 mg, 44%) as an oil.

Part V—Synthesis of Racemic (2R,3R)-7-((E)-2-Chloro-6-fluorostyryl)-1-((4-fluoro-3-methoxyphenyl)sulfonyl)-2-methyl-1,2,3,4-tetrahydroquinolin-3-ol

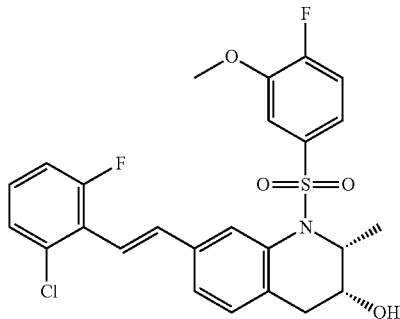 [SMILES: COc1cc(S(=O)(=O)N2c3cc(/C=C/c4c(F)cccc4Cl)ccc3C[C@@H](O)[C@H]2C)ccc1F]

To a solution of racemic ((2R,3R)-7-((E)-2-chloro-6-fluorostyryl)-2-methyl-1,2,3,4-tetrahydroquinolin-3-ol (95 mg, 0.30 mmol) in dichloromethane (1.5 mL) was added pyridine (0.12 mL, 1.5 mmol), 4-dimethylaminopyridine (18.2 mg, 0.15 mmol), and 4-fluoro-3-methoxybenzene-1-sulfonyl chloride (80.7 mg, 0.36 mmol). The mixture was stirred overnight at room temperature and then diluted with brine. The mixture was extracted three times with dichloromethane. The organic layers were combined and concentrated. The resulting residue was purified by Prep-HPLC eluting with a gradient of 62-68% acetonitrile in water with 0.05% trifluoroacetic acid to afford racemic (2R,3R)-7-((E)-2-chloro-6-fluorostyryl)-1-((4-fluoro-3-methoxyphenyl)sulfonyl)-2-methyl-1,2,3,4-tetrahydroquinolin-3-ol (34.3 mg, 23%) as a light yellow solid. $^1$H-NMR (300 MHz, CDCl$_3$) δ 7.95 (s, 1H), 7.27-7.37 (m, 4H), 7.22 (s, 1H), 7.02-7.19 (m, 5H), 4.47 (m, 1H), 3.84 (m, 1H), 3.70 (s, 3H), 2.55 (m, 2H), 1.24 (d, J=6.9 Hz, 3H). (ES, m/z): (M+H)$^+$506.

Example 169—Synthesis of Racemic (2R,3R)-7-((E)-2-(2-Chloro-6-fluorophenyl)prop-1-en-1-yl)-1-((4-fluoro-3-methoxyphenyl)sulfonyl)-2-methyl-1,2,3,4-tetrahydroquinolin-3-ol

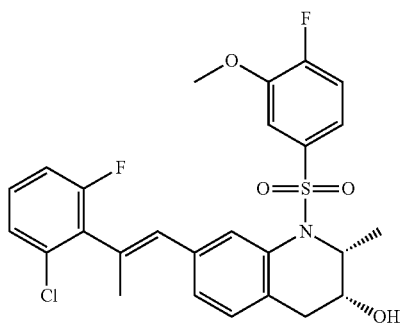 [SMILES: COc1cc(S(=O)(=O)N2c3cc(/C=C(\C)c4c(F)cccc4Cl)ccc3C[C@@H](O)[C@H]2C)ccc1F]

Part I—Synthesis of Racemic (2R,3R)-7-((E)-2-(2-Chloro-6-fluorophenyl)prop-1-en-1-yl)-2-methyl-1,2,3,4-tetrahydroquinolin-3-ol

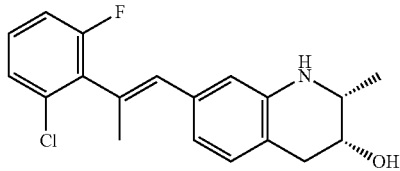 [SMILES: C/C(=C\c1ccc2c(c1)N[C@H](C)[C@H](O)C2)c1c(F)cccc1Cl]

A mixture of racemic (2R,3R)-7-bromo-2-methyl-1,2,3,4-tetrahydroquinolin-3-ol (520 mg, 2.15 mmol), (E)-2-(2-(2-chloro-6-fluorophenyl)prop-1-en-1-yl)-4,4,5,5-tetramethyl-1,3,2-dioxaborolane (957 mg, 3.23 mmol), ethanol (2.5 mL), water (8.8 mL), and toluene (17.6 mL) was purged and maintained with an inert atmosphere of nitrogen. Sodium carbonate (1.87 g, 17.64 mmol) and tetrakis(triphenylphosphine)palladium(0) (299.4 mg, 0.26 mmol) were added and the resulting mixture was stirred for three hours at 95° C. The mixture was diluted with water (100 mL), and extracted three times with dichloromethane. The combined organic layers were combined and concentrated. The resulting residue was purified by MPLC eluting with a gradient of 10%-90% ethyl acetate in petroleum ether to afford racemic (2R,3R)-7-((E)-2-(2-chloro-6-fluorophenyl)prop-1-en-1-yl)-2-methyl-1,2,3,4-tetrahydroquinolin-3-ol (220 mg, 31%) as a yellow oil.

Part II—Synthesis of Racemic (2R,3R)-7-((E)-2-(2-Chloro-6-fluorophenyl)prop-1-en-1-yl)-1-((4-fluoro-3-methoxyphenyl)sulfonyl)-2-methyl-1,2,3,4-tetrahydroquinolin-3-ol

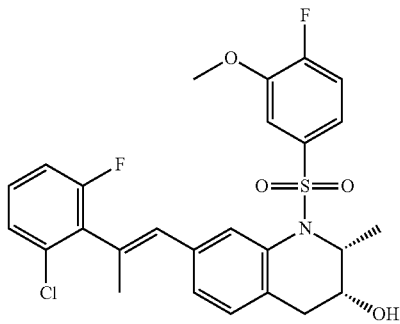 [SMILES: COc1cc(S(=O)(=O)N2c3cc(/C=C(\C)c4c(F)cccc4Cl)ccc3C[C@@H](O)[C@H]2C)ccc1F]

To a solution of racemic (2R,3R)-7-((E)-2-(2-chloro-6-fluorophenyl)prop-1-en-1-yl)-2-methyl-1,2,3,4-tetrahydroquinolin-3-ol (111 mg, 0.33 mmol) in dichloromethane (1.7 mL) was added pyridine (0.13 mL, 1.65 mmol), 4-dimethylaminopyridine (20.4 mg, 0.17 mmol), and 4-fluoro-3-methoxybenzene-1-sulfonyl chloride (90.3 mg, 0.40 mmol). The mixture was stirred overnight at room temperature and then diluted with brine. The mixture was extracted three times with dichloromethane. The organic layers were combined and concentrated. The resulting residue was purified by Prep-HPLC eluting with a gradient of 55-75% acetonitrile in water with 0.05% trifluoroacetic acid to afford racemic (2R,3R)-7-((E)-2-(2-chloro-6-fluorophenyl)prop-1-en-1-yl)-1-((4-fluoro-3-methoxyphenyl)sulfonyl)-2-methyl- 1,2,3,4-tetrahydroquinolin-3-ol (34.3 mg, 23%) as a light yellow solid. $^1$H-NMR (300 MHz, CDCl$_3$) δ 7.61 (s, 1H), 7.37 (m, 1H), 7.00-7.25 (m, 7H), 6.40 (s, 1H), 4.36 (m, 1H), 3.76 (s, 3H), 3.75 (m, 1H), 2.79 (dd, J=4.2 Hz, 15.6 Hz, 1H), 2.17 (d, J=1.5 Hz, 3H), 2.07 (dd, J=7.2 Hz, 16.2 Hz, 1H), 1.37 (d, J=6.6 Hz, 3H). (ES, m/z): (M+H)$^+$520.

Example 170—Synthesis of Racemic (2R,3R)-7-((E)-2-Chloro-6-fluorostyryl)-2-methyl-1-((3-(trifluoromethyl)phenyl)sulfonyl)-1,2,3,4-tetrahydroquinolin-3-ol

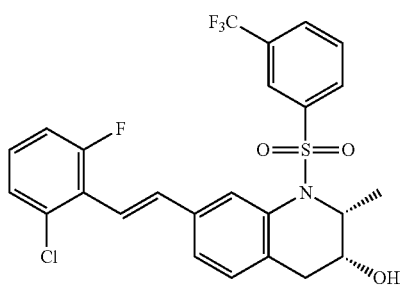 [SMILES: C[C@@H]1[C@H](O)Cc2ccc(/C=C/c3c(F)cccc3Cl)cc2N1S(=O)(=O)c1cccc(C(F)(F)F)c1]

By the procedure utilized in Example 168, (2R,3R)-7-((E)-2-chloro-6-fluorostyryl)-2-methyl-1-((3-(trifluoromethyl)phenyl)sulfonyl)-1,2,3,4-tetrahydroquinolin-3-ol was prepared. $^1$H-NMR (300 MHz, CDCl$_3$) δ 7.92 (m, 2H), 7.82 (m, 2H), 7.60 (t, J=8.0 Hz, 1H), 7.25 (m, 2H), 7.17 (m, 1H), 7.02-7.10 (m, 2H), 4.49 (m, 1H), 3.89 (m, 1H), 2.61 (dd, J=8.8 Hz, 16.8 Hz, 1H), 2.51 (dd, J=5.6 Hz, 16.8 Hz, 1H), 1.26 (d, J=6.8 Hz, 3H). (ES, m/z): (M+H)$^+$526.

Example 171—Synthesis of Racemic (2R,3R)-7-((E)-2-(2-Chloro-6-fluorophenyl)prop-1-en-1-yl)-2-methyl-1-((3-(trifluoromethyl)phenyl)sulfonyl)-1,2,3,4-tetrahydroquinolin-3-ol

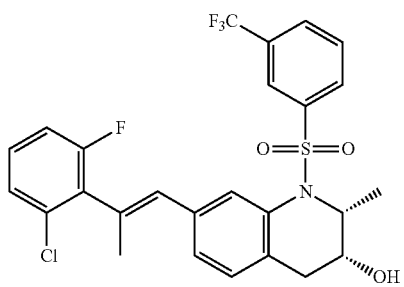 [SMILES: C/C(=C\c1ccc2c(c1)N(S(=O)(=O)c1cccc(C(F)(F)F)c1)[C@H](C)[C@H](O)C2)c1c(F)cccc1Cl]

By the procedure utilized in Example 169, (2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-ol was prepared. $^1$H-NMR (300 MHz, CDCl$_3$) δ 1.26 (d, J=6.8 Hz, 3H), 2.23 (s, 3H), 2.53 (dd, J=6.0 Hz, 10.0 Hz, 1H), 2.61 (dd, J=8.4 Hz, 16.0 Hz, 1H), 3.88-3.93 (m, 1H), 4.45-4.51 (m, 1H), 6.45 (s, 1H), 7.02-7.10 (m, 2H), 7.19-7.25 (m, 3H), 7.61 (t, J=8.0 Hz, 1H), 7.81-7.83 (m, 3H), 7.93 (s, 1H). (ES, m/z): (M+H)$^+$540.

Example 172—Synthesis of (R)-2-((7-((2-Chloro-6-fluorobenzyl)oxy)-1-((3-(trifluoromethyl)phenyl)sulfonyl)-1,2,3,4-tetrahydroquinolin-3-yl)oxy)-2-methylpropanoic acid

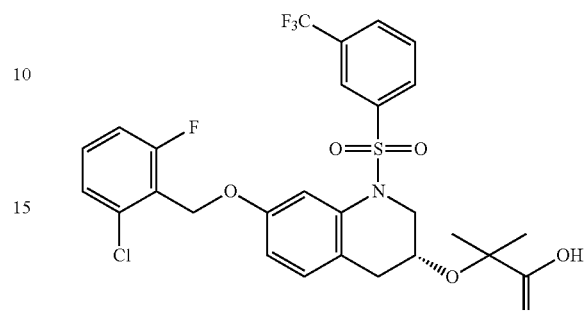

Part I—Synthesis of Methyl (R)-2-((7-((2-chloro-6-fluorobenzyl)oxy)-1-((3-(trifluoromethyl)phenyl)sulfonyl)-1,2,3,4-tetrahydroquinolin-3-yl)oxy)-2-methylpropanoate

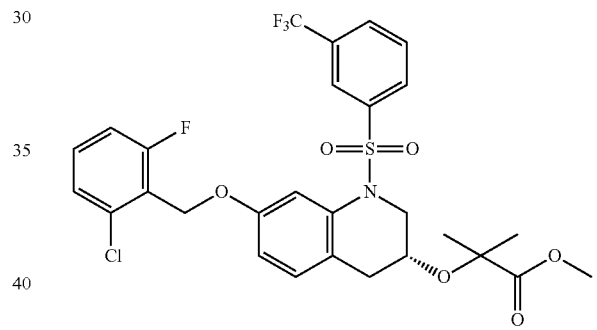

Sodium hydride (15.2 mg, 0.38 mmol) was added in portions to a stirred solution of (R)-7-((2-chloro-6-fluorobenzyl)oxy)-1-((3-(trifluoromethyl)phenyl)sulfonyl)-1,2,3,4-tetrahydroquinolin-3-ol (100 mg, 0.19 mmol) in N,N-dimethylformamide (10 mL) at 0° C. Methyl 2-bromo-2-methylpropanoate (69 mg, 0.38 mmol) was added dropwise and the resulting solution was stirred for thirty minutes at 0° C. The mixture was warmed to room temperature and stirred an additional two hours. Water was added, and the mixture was extracted three times with ethyl acetate. The combined organic layers were washed three times with water, brine, dried (Na$_2$SO$_4$), and concentrated. The resulting residue was purified via MPLC eluting with a gradient of 5-50% ethyl acetate in petroleum ether to afford methyl (R)-2-((7-((2-chloro-6-fluorobenzyl)oxy)-1-((3-(trifluoromethyl)phenyl)sulfonyl)-1,2,3,4-tetrahydroquinolin-3-yl)oxy)-2-methylpropanoate (35 mg, 29%) as a yellow oil.

Part II—Synthesis of (R)-2-((7-((2-Chloro-6-fluorobenzyl)oxy)-1-((3-(trifluoromethyl)phenyl)sulfonyl)-1,2,3,4-tetrahydroquinolin-3-yl)oxy)-2-methylpropanoic acid

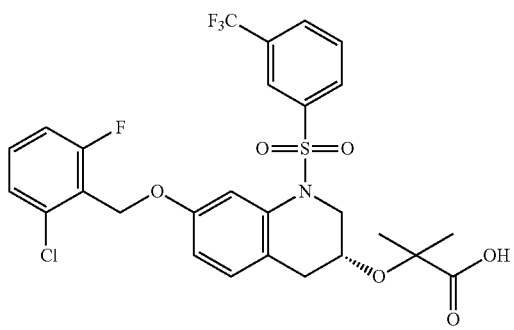 [SMILES: CC(C)(O[C@@H]1Cc2ccc(OCc3c(F)cccc3Cl)cc2N(S(=O)(=O)c2cccc(C(F)(F)F)c2)C1)C(=O)O]

Based on the procedure in Example 42, (R)-2-((7-((2-chloro-6-fluorobenzyl)oxy)-1-((3-(trifluoromethyl)phenyl)sulfonyl)-1,2,3,4-tetrahydroquinolin-3-yl)oxy)-2-methylpropanoic acid was prepared. $^1$H-NMR (300 MHz, CD$_3$OD) δ 7.94 (m, 1H), 7.82 (s, 1H), 7.71 (m, 1H), 7.43 (m, 2H), 7.34 (m, 1H), 7.19 (m, 1H), 7.02 (m, 1H), 6.84 (m, 1H), 5.21 (s, 2H), 4.35-4.40 (m, 1H), 3.57 (m, 1H), 3.41 (m, 1H), 2.73 (m, 1H), 2.37 (m, 1H), 1.29 (s, 3H), 1.39 (s, 3H). (ES, m/z): (M−H)$^-$600.

Example 173—Preparation of Additional Substituted 1,2,3,4-Tetrahydroquinolin-3-yl)oxy)-acetates Compounds in Table 21 were prepared based on experimental procedures described in Example 172 and the detailed description.

TABLE 21

| No. | Structure | Name | Observed m/z |
|---|---|---|---|
| 173A | 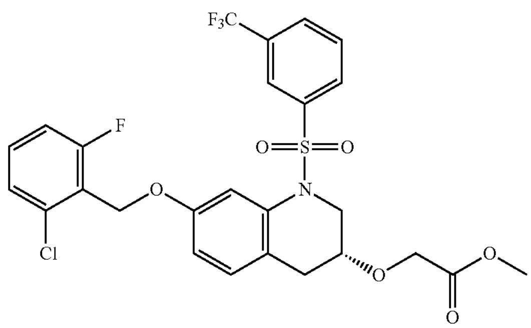 [SMILES: COC(=O)CO[C@@H]1Cc2ccc(OCc3c(F)cccc3Cl)cc2N(S(=O)(=O)c2cccc(C(F)(F)F)c2)C1] | methyl (R)-2-((7-((2-chloro-6-fluorobenzyl)oxy)-1-((3-(trifluoromethyl)phenyl)sulfonyl)-1,2,3,4-tetrahydroquinolin-3-yl)oxy)acetate | 588 (M + H)$^+$ |
| 173B | 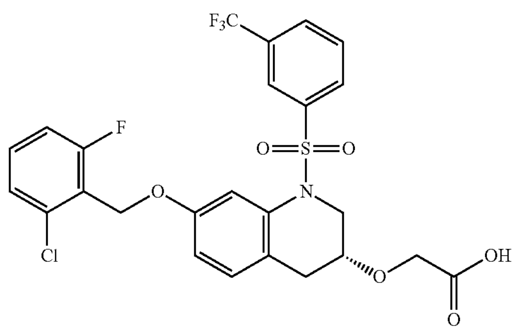 [SMILES: O=C(O)CO[C@@H]1Cc2ccc(OCc3c(F)cccc3Cl)cc2N(S(=O)(=O)c2cccc(C(F)(F)F)c2)C1] | (R)-2-((7-((2-chloro-6-fluorobenzyl)oxy)-1-((3-(trifluoromethyl)phenyl)sulfonyl)-1,2,3,4-tetrahydroquinolin-3-yl)oxy)acetic acid | 574 (M + H)$^+$ |
| 173C | 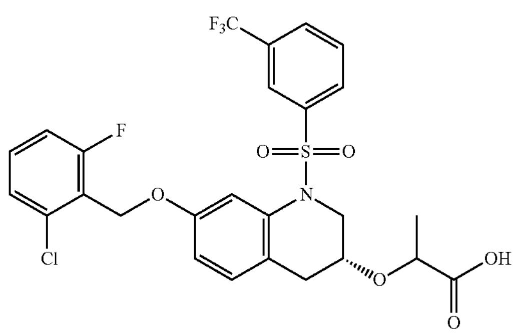 [SMILES: CC(O[C@@H]1Cc2ccc(OCc3c(F)cccc3Cl)cc2N(S(=O)(=O)c2cccc(C(F)(F)F)c2)C1)C(=O)O] | 2-(((R)-7-((2-chloro-6-fluorobenzyl)oxy)-1-((3-(trifluoromethyl)phenyl)sulfonyl)-1,2,3,4-tetrahydroquinolin-3-yl)oxy)propanoic acid | 588 (M + H)$^+$ |

TABLE 21-continued

| No. | Structure | Name | Observed m/z |
|---|---|---|---|
| 173D | 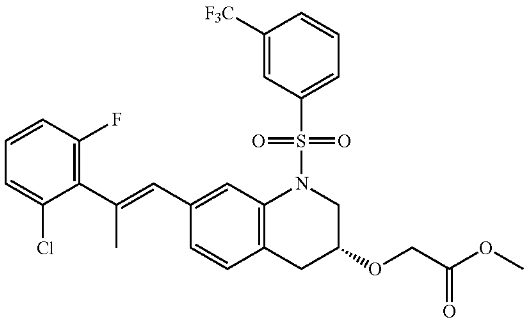 [SMILES: COC(=O)CO[C@@H]1Cc2ccc(/C=C(\C)c3c(F)cccc3Cl)cc2N(S(=O)(=O)c2cccc(C(F)(F)F)c2)C1] | methyl (R,E)-2-((7-(2-(2-chloro-6-fluorophenyl)prop-1-en-1-yl)-1-((3-trifluoromethyl)-phenyl)sulfonyl)-1,2,3,4-tetrahydroquinolin-3-yl)oxy)acetate | 598 (M + H)+ |
| 173E | 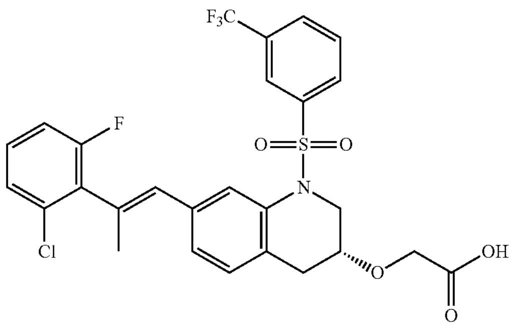 [SMILES: C/C(=C\c1ccc2c(c1)N(S(=O)(=O)c1cccc(C(F)(F)F)c1)C[C@H](OCC(=O)O)C2)c1c(F)cccc1Cl] | (R,E)-2-((7-(2-(2-chloro-6-fluorophenyl)prop-1-en-1-yl)-1-((3-(trifluoromethyl)-phenyl)sulfonyl)-1,2,3,4-tetrahydroquinolin-3-yl)oxy)acetic acid | 584 (M + H)+ |
| 173F | 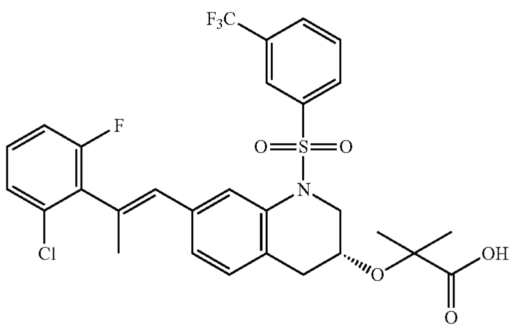 [SMILES: C/C(=C\c1ccc2c(c1)N(S(=O)(=O)c1cccc(C(F)(F)F)c1)C[C@H](OC(C)(C)C(=O)O)C2)c1c(F)cccc1Cl] | (R,E)-2-((7-(2-(2-chloro-6-fluorophenyl)prop-1-en-1-yl)-1-((3-(trifluoromethyl)phenyl)-sulfonyl)-1,2,3,4-tetrahydroquinolin-3-yl)oxy)-2-methylpropanoic acid | 612 (M + H)+ |

Example 174—Synthesis of rac-(2R,3S)-7-((E)-2-Chloro-6-fluorostyryl)-1-((4-fluoro-3-methoxyphenyl)sulfonyl)-2-methyl-1,2,3,4-tetrahydroquinolin-3-ol

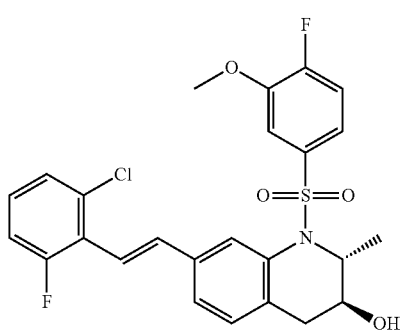 [SMILES: COc1cc(S(=O)(=O)N2c3cc(/C=C/c4c(F)cccc4Cl)ccc3C[C@H](O)[C@H]2C)ccc1F]

Part I—Synthesis of rac-7-Bromo-2-methyl-1,2-dihydroquinoline

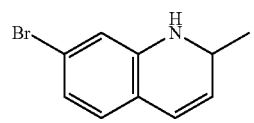

To a stirred solution of 7-bromoquinoline (2.06 g, 9.90 mmol) in ether (47 mL) at −78° C. was added a 1.6 M solution of methyl lithium in ether (6.2 mL, 9.9 mmol) dropwise. The reaction mixture was warmed to 0° C. was stirred for ten minutes. The reaction was quenched by the addition of saturated aqueous ammonium chloride. The mixture was extracted three times with dichloromethane and the combined organic layers were concentrated to afford rac-7-bromo-2-methyl-1,2-dihydroquinoline (2.22 g, 100%) as a brown solid.

Part II—Synthesis of rac-(7-Bromo-2-methylquino-lin-1(2H)-yl)(phenyl)methanone

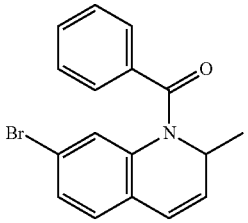 [SMILES: CC1C=Cc2ccc(Br)cc2N1C(=O)c1ccccc1]

To a stirred solution of rac-7-bromo-2-methyl-1,2-dihydroquinoline (11.35 g, 50.7 mmol) in dichloromethane (70 mL) at 0° C. was added a solution of sodium hydroxide (2.48 g, 62.0 mmol) in water (70 mL) followed by the addition of benzoyl chloride (7.2 mL, 62.0 mmol) dropwise. The reaction mixture was warmed to room temperature and was stirred for two hours. The resulting solution was diluted with water, and extracted three times with dichloromethane. The combined organic layers were dried (Na$_2$SO$_4$) and concentrated to afford (7-bromo-2-methylquinolin-1(2H)-yl)(phenyl)methanone (19.28 g) as a brown oil.

Part III—Synthesis of rac-((1aR,2R,7bS)-5-Bromo-2-methyl-1a,2-dihydrooxireno[2,3-c]quinolin-3(7bH)-yl)(phenyl)methanone

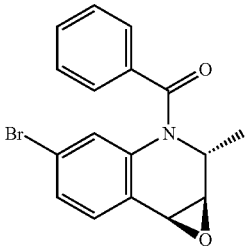 [SMILES: C[C@@H]1[C@H]2O[C@H]2c2ccc(Br)cc2N1C(=O)c1ccccc1]

To a stirred solution of rac-(7-bromo-2-methylquinolin-1(2H)-yl)(phenyl)methanone (16.6 g, 50.4 mmol) in dichloromethane (160 mL) at 0° C. was added meta-chloroperbenzoic acid (21.4 g, 121 mmol) in several portions. The reaction mixture was stirred for two hours at 0° C., and then it was quenched with 20% sodium carbonate. The mixture was extracted three times with dichloromethane. The combined organic layers were concentrated. The resulting residue was purified via MPLC eluting with ethyl acetate/petroleum ether (1:2) to afford rac-((1aR,2R,7bS)-5-bromo-2-methyl-1a,2-dihydrooxireno[2,3-c]quinolin-3(7bH)-yl)(phenyl)methanone (10.04 g, 58%) as a yellow foam.

Part IV—Synthesis of rac-(2R,3S)-7-Bromo-2-methyl-1,2,3,4-tetrahydroquinolin-3-ol

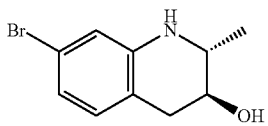

To a stirred solution of rac-((1aR,2R,7bS)-5-bromo-2-methyl-1a,2-dihydrooxireno[2,3-c]quinolin-3(7bH)-yl)(phenyl)methanone (2.99 g, 8.66 mmol) in tetrahydrofuran (10 mL) was added a 1 M solution of lithium triethylborohydride in THF (86 mL, 86 mmol) dropwise. The reaction mixture was stirred for two hours at room temperature. The reaction was then quenched by the addition saturated aqueous ammonium chloride. The mixture was extracted three times with dichloromethane and the combined organic layers were concentrated. The resulting residue was purified by MPLC eluting with a gradient of petroleum ether: ethyl acetate=10:1 increasing to petroleum ether: ethyl acetate=2:1 to provide rac-(2R,3S)-7-bromo-2-methyl-1,2,3,4-tetrahydroquinolin-3-ol (1.15 g, 55%) as a brown oil.

Part V—Synthesis of rac-(2R,3S)-7-((E)-2-Chloro-6-fluorostyryl)-2-methyl-1,2,3,4-tetrahydroquinolin-3-ol

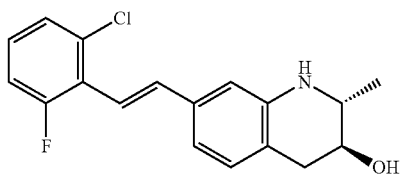 [SMILES: C[C@H]1Nc2cc(/C=C/c3c(F)cccc3Cl)ccc2C[C@@H]1O]

A stirred mixture of rac-(2R,3S)-7-bromo-2-methyl-1,2,3,4-tetrahydroquinolin-3-ol (500 mg, 2.07 mmol), (E)-2-(2-chloro-6-fluorostyryl)-4,4,5,5-tetramethyl-1,3,2-dioxaborolane (877.1 mg, 3.10 mmol), ethanol (2.4 mL), water (8.5 mL), toluene (16.9 mL), and sodium carbonate (1.8 g, 16.98 mmol) was purged with nitrogen. To the mixture was added tetrakis(triphenylphosphine)palladium(0) (287.9 mg, 0.25 mmol). The mixture was stirred for four hours at 95° C. The mixture was cooled and diluted with water; and extracted three times with dichloromethane. The combined organic layers were concentrated. The resulting residue was purified by MPLC eluting with a gradient of 10:1 petroleum ether: ethyl acetate increasing to 1:2 petroleum ether:ethyl acetate to afford rac-(2R,3S)-7-((E)-2-chloro-6-fluorostyryl)-2-methyl-1,2,3,4-tetrahydroquinolin-3-ol (330 mg, 50%) as a yellow oil.

Part VI—Synthesis of rac-(2R,3S)-7-((E)-2-Chloro-6-fluorostyryl)-1-((4-fluoro-3-methoxyphenyl)sulfonyl)-2-methyl-1,2,3,4-tetrahydroquinolin-3-ol

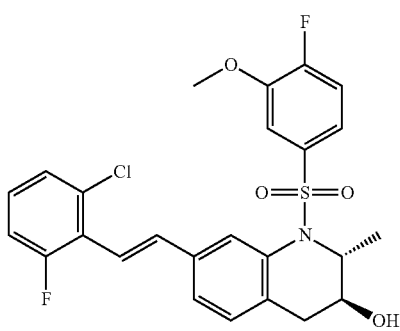 [SMILES: COc1cc(S(=O)(=O)N2c3cc(/C=C/c4c(F)cccc4Cl)ccc3C[C@H](O)[C@H]2C)ccc1F]

To a solution of rac-(2R,3S)-7-((E)-2-chloro-6-fluorostyryl)-2-methyl-1,2,3,4-tetrahydroquinolin-3-ol (70 mg, 0.22 mmol) and 4-dimethylaminopyridine (13.4 mg, 0.11 mmol) in dichloromethane (1.1 mL) and pyridine (0.089 mL, 1.1 mmol) was added 4-fluoro-3-methoxybenzene-1-sulfonyl chloride (59.4 mg, 0.26 mmol). The reaction mixture was stirred for four hours at room temperature and diluted with brine. The mixture was extracted three times with dichloromethane. The combined organic layers were concentrated, and the resulting residue was purified by reverse phase Prep-HPLC eluting with 57-76% acetonitrile in water with 0.05% TFA to provide rac-(2R,3S)-7-((E)-2-chloro-6-fluorostyryl)-1-((4-fluoro-3-methoxyphenyl)sulfonyl)-2-methyl-1,2,3,4-tetrahydroquinolin-3-ol (24.9 mg, 22%) as a light yellow solid. $^1$H-NMR (400 MHz, CDCl$_3$) δ 1.37 (d, J=6.6 Hz, 3H), 2.06 (m, 1H), 2.79 (dd, J=4.5 Hz, 16.2 Hz, 1H), 3.73 (s, 3H), 3.77 (m, 1H), 4.38 (m, 1H), 7.01-7.24 (m, 7H), 7.28-7.36 (m, 2H), 7.38-7.43 (m, 1H), 7.86 (s, 1H). (ES, m/z): (M+H)$^+$506.

Example 175—Synthesis of rac-(2R,3S)-7-((E)-2-(2-Chloro-6-fluorophenyl)prop-1-en-1-yl)-1-((4-fluoro-3-methoxyphenyl)sulfonyl)-2-methyl-1,2,3,4-tetrahydroquinolin-3-ol

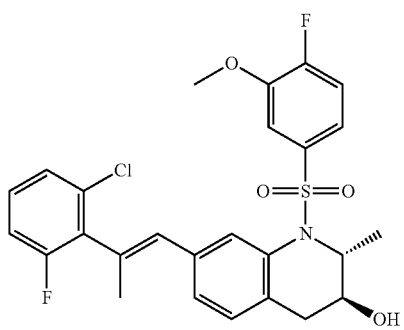

Part I—Synthesis of rac-(2R,3S)-7-((E)-2-(2-Chloro-6-fluorophenyl)prop-1-en-1-yl)-2-methyl-1,2,3,4-tetrahydroquinolin-3-ol

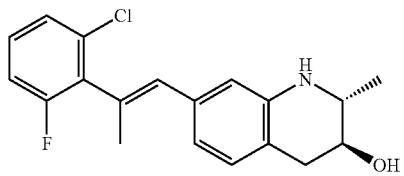 [SMILES: C/C(=C\c1ccc2c(c1)N[C@H](C)[C@@H](O)C2)c1c(F)cccc1Cl]

To a flask purged and maintained with an inert atmosphere of nitrogen, was placed rac-(2R,3S)-7-bromo-2-methyl-1,2,3,4-tetrahydroquinolin-3-ol (520 mg, 2.15 mmol), 2-[(1E)-2-(2-chloro-6-fluorophenyl)prop-1-en-1-yl]-4,4,5,5-tetramethyl-1,3,2-dioxaborolane (957.3 mg, 3.23 mmol), ethanol (2.5 mL), water (8.8 mL), toluene (17.6 mL), and sodium carbonate (1.87 g, 17.64 mmol) followed by tetrakis(triphenylphosphine)palladium(0) (299.4 mg, 0.26 mmol). The reaction mixture was stirred for three hours at 95° C. The mixture was diluted with water and extracted three times with dichloromethane. The combined organic layers were concentrated, and the resulting residue was purified by MPLC eluting with a gradient of 10:1 petroleum ether:ethyl acetate increasing to 1:2 petroleum ether:ethyl acetate to afford rac-(2R,3S)-7-((E)-2-(2-chloro-6-fluorophenyl)prop-1-en-1-yl)-2-methyl-1,2,3,4-tetrahydroquinolin-3-ol (220 mg, 31%) as a yellow oil.

Part II—Synthesis of rac-(2R,3S)-7-((E)-2-(2-Chloro-6-fluorophenyl)prop-1-en-1-yl)-1-((4-fluoro-3-methoxyphenyl)sulfonyl)-2-methyl-1,2,3,4-tetrahydroquinolin-3-ol

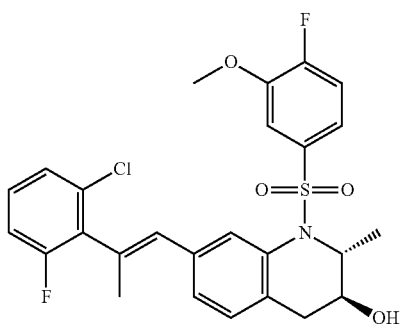 [SMILES: COc1cc(S(=O)(=O)N2c3cc(/C=C(\C)c4c(F)cccc4Cl)ccc3C[C@H](O)[C@H]2C)ccc1F]

To a solution of rac-(2R,3S)-7-((E)-2-(2-chloro-6-fluorophenyl)prop-1-en-1-yl)-2-methyl-1,2,3,4-tetrahydroquinolin-3-ol (111 mg, 0.33 mmol) and 4-dimethylaminopyridine (20.4 mg, 0.17 mmol) in dichloromethane (1.7 mL) and pyridine (0.13 mL, 1.65 mmol) was added 4-fluoro-3-methoxybenzene-1-sulfonyl chloride (90.3 mg, 0.40 mmol). The reaction mixture was stirred overnight at room temperature and then diluted with water. The mixture was extracted three times with dichloromethane. The combined organic layers were concentrated and the resulting residue was purified via reverse phase Prep-HPLC eluting with a gradient of 55-75% acetonitrile in water with 0.05% TFA to afford rac-(2R,3S)-7-((E)-2-(2-chloro-6-fluorophenyl)prop-1-en-1-yl)-1-((4-fluoro-3-methoxyphenyl)sulfonyl)-2-methyl-1,2,3,4-tetrahydroquinolin-3-ol (30.5 mg, 18%) as a light pink solid. $^1$H-NMR (400 MHz, CDCl$_3$) δ 1.37 (d, J=6.6 Hz, 3H), 2.07 (dd, J=7.2 Hz, 16.2 Hz, 1H), 2.17 (d, J=1.5 Hz, 3H), 2.79 (dd, J=4.2 Hz, 15.6 Hz, 1H), 3.75 (m, 1H), 3.76 (s, 3H), 4.36 (m, 1H), 6.40 (s, 1H), 7.00-7.25 (m, 7H), 7.35-7.40 (m, 1H), 7.61 (s, 1H). (ES, m/z): (M+H)$^+$520.

Example 176—Synthesis of rac-(2R,3S)-7-((E)-2-Chloro-6-fluorostyryl)-2-methyl-1-((3-(trifluoromethyl)phenyl)sulfonyl)-1,2,3,4-tetrahydroquinolin-3-ol

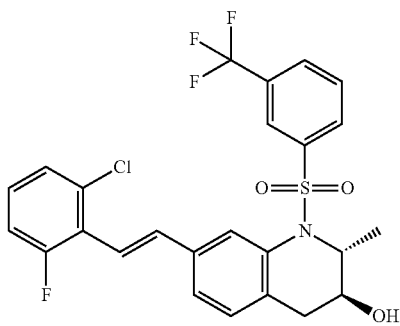 [SMILES: C[C@@H]1[C@@H](O)Cc2ccc(/C=C/c3c(F)cccc3Cl)cc2N1S(=O)(=O)c1cccc(C(F)(F)F)c1]

Based on the procedure in Example 174, rac-(2R,3S)-7-((E)-2-chloro-6-fluorostyryl)-2-methyl-1-((3-(trifluoromethyl)phenyl)sulfonyl)-1,2,3,4-tetrahydroquinolin-3-ol was prepared. $^1$H-NMR (400 MHz, CDCl$_3$) δ 1.35 (d, J=6.9 Hz, 3H), 2.10 (dd, J=6.3 Hz, 16.2 Hz), 2.81 (dd, J=4.8 Hz, 16.5 Hz), 3.80 (q, J=6.4 Hz, 1H), 4.42-4.46 (m, 1H), 7.01-7.25 (m, 5H), 7.29-7.36 (m, 2H), 7.56 (t, J=7.8 Hz, 1H), 7.77 (d, J=7.8 Hz, 1H), 7.85 (d, J=1.2 Hz, 1H), 7.96 (d, J=8.1 Hz, 1H), 8.03 (s, 1H). (ES, m/z): (M+H)$^+$526.

Example 177-Synthesis of rac-(2R,3S)-7-((E)-2-(2-Chloro-6-fluorophenyl)prop-1-en-1-yl)-2-methyl-1-((3-(trifluoromethyl)phenyl)sulfonyl)-1,2,3,4-tetrahydroquinolin-3-ol

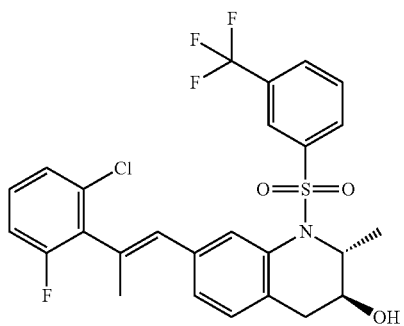

Based on the procedure in Example 175, rac-(2R,3S)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-ol was prepared. $^1$H-NMR (400 MHz, CDCl$_3$) δ 1.36 (d, J=6.6 Hz, 3H), 2.07-2.14 (m, 1H), 2.15 (s, 3H), 2.82 (dd, J=4.5 Hz, 16.2 Hz, 1H), 3.80 (q, J=4.8 Hz, 1H), 4.39-4.47 (m, 1H), 6.40 (s, 1H), 6.99-7.25 (m, 5H), 7.57 (t, J=7.8 Hz, 1H), 7.72 (s, 1H), 7.78 (d, J=8.1 Hz, 1H), 7.95 (d, J=8.1 Hz, 1H), 8.02 (s, 1H). (ES, m/z): (M+H)$^+$540.

Example 178—Synthesis of Methyl 3-(6-((2-chloro-6-fluorobenzyl)oxy)-4-((4-fluoro-3-methoxyphenyl)sulfonyl)chroman-2-yl)propanoate

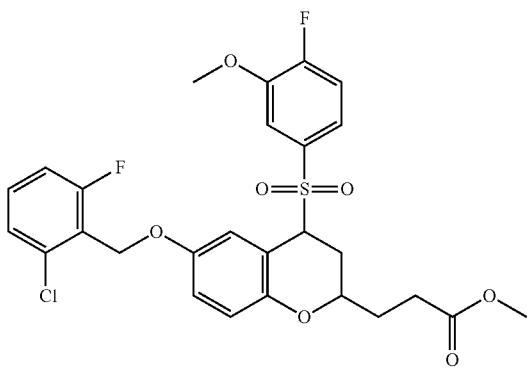

Part I—Synthesis of 1-(5-((2-Chloro-6-fluorobenzyl)oxy)-2-hydroxyphenyl)ethanone

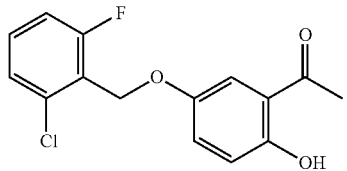 [SMILES: CC(=O)c1cc(OCc2c(F)cccc2Cl)ccc1O]

A mixture of 1-(2,5-dihydroxyphenyl)ethan-1-one (1.52 g, 9.99 mmol), 1-chloro-2-(chloromethyl)-3-fluorobenzene (1.96 g, 10.95 mmol), and potassium carbonate (2.76 g, 19.97 mmol) in acetone (30 mL) was refluxed overnight and concentrated. The resulting residue was purified via MPLC eluting with a gradient of ethyl acetate/hexane (1:20-1:5) to yield 1-(5-((2-chloro-6-fluorobenzyl)oxy)-2-hydroxyphenyl)ethanone (2.1 g, 71%) as a yellow solid.

Part II—Synthesis of Methyl 3-(6-((2-chloro-6-fluorobenzyl)oxy)-4-oxochroman-2-yl)propanoate

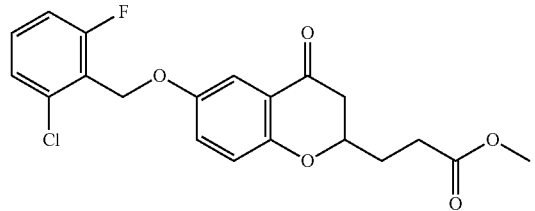 [SMILES: COC(=O)CCC1CC(=O)c2cc(OCc3c(F)cccc3Cl)ccc2O1]

To a solution of 1-(5-((2-chloro-6-fluorobenzyl)oxy)-2-hydroxyphenyl)ethanone (2.0 g, 6.79 mmol) in methanol (50 mL) were added pyrrolidine (965 mg, 13.57 mmol) and methyl 4-oxobutanoate (790 mg, 6.80 mmol). The mixture was refluxed for two hours and concentrated. The resulting residue was diluted with saturated aqueous sodium bicarbonate and extracted twice with ethyl acetate. The combined organic layers were concentrated. The resulting residue was purified via MPLC eluting with a gradient of ethyl acetate/petroleum ether (1:20-1:3) to yield methyl 3-(6-((2-chloro-6-fluorobenzyl)oxy)-4-oxochroman-2-yl)propanoate (2.3 g, 72%) as a yellow solid.

Part III—Synthesis of Methyl 3-(6-((2-chloro-6-fluorobenzyl)oxy)-4-hydroxychroman-2-yl)propanoate

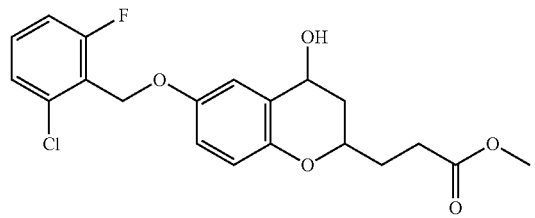 [SMILES: COC(=O)CCC1CC(O)c2cc(OCc3c(F)cccc3Cl)ccc2O1]

To a stirred solution of methyl 3-(6-((2-chloro-6-fluorobenzyl)oxy)-4-oxochroman-2-yl)propanoate (500 mg, 1.27 mmol) in methanol (15 mL) at 0° C. was added sodium borohydride (121 mg, 3.20 mmol). After one hour, water was added and the mixture was extracted twice with ethyl acetate. The combined organic layers were dried (Na₂SO₄) and concentrated to afford methyl 3-(6-((2-chloro-6-fluorobenzyl)oxy)-4-hydroxychroman-2-yl)propanoate (500 mg, 99%) as a light yellow solid.

Part IV—Synthesis of Methyl 3-(6-((2-chloro-6-fluorobenzyl)oxy)-4-((4-fluoro-3-methoxyphenyl)thio)chroman-2-yl)propanoate

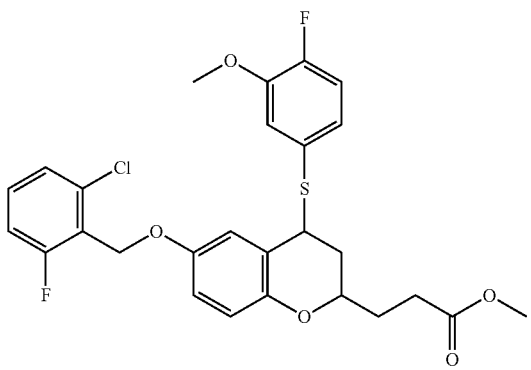 [SMILES: COC(=O)CCC1CC(Sc2ccc(F)c(OC)c2)c2cc(OCc3c(F)cccc3Cl)ccc2O1]

Under an atmosphere of nitrogen, a mixture of methyl 3-(6-((2-chloro-6-fluorobenzyl)oxy)-4-hydroxychroman-2-yl)propanoate (500 mg, 1.27 mmol), 4-fluoro-3-methoxybenzene-1-thiol (401 mg, 2.53 mmol), zinc iodide (525 mg, 1.64 mmol) and dichloromethane (10 mL) was stirred for two hours at room temperature. The mixture was diluted with water and extracted twice with dichloromethane. The combined organic layers were concentrated and the resulting residue was purified via MPLC eluting with petroleum ether: ethyl acetate (5:1) to yield methyl 3-(6-((2-chloro-6-fluorobenzyl)oxy)-4-((4-fluoro-3-methoxyphenyl)thio)chroman-2-yl)propanoate (550 mg, 81%) as a colorless oil.

Part V—Synthesis of Methyl 3-(6-((2-chloro-6-fluorobenzyl)oxy)-4-((4-fluoro-3-methoxyphenyl)sulfonyl)chroman-2-yl)propanoate

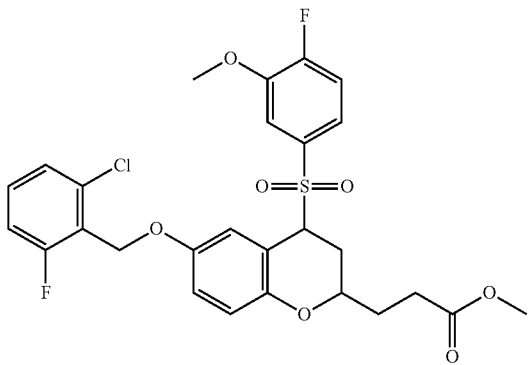 [SMILES: COC(=O)CCC1CC(S(=O)(=O)c2ccc(F)c(OC)c2)c2cc(OCc3c(F)cccc3Cl)ccc2O1]

To a solution of methyl 3-(6-((2-chloro-6-fluorobenzyl)oxy)-4-((4-fluoro-3-methoxyphenyl)thio)chroman-2-yl)propanoate (100 mg, 0.19 mmol) in dichloromethane (5 mL) was added meta-chloroperbenzoic acid (65 mg, 0.38 mmol). Stirred for two hours at room temperature and diluted with dichloromethane. Washed with saturated aqueous sodium bicarbonate, dried (Na₂SO₄) and concentrated. The resulting residue was purified by reverse phase Prep-HPLC eluting with a gradient of 50-78% acetonitrile in water with 0.05% TFA to afford methyl 3-(6-((2-chloro-6-fluorobenzyl)oxy)-4-((4-fluoro-3-methoxyphenyl)sulfonyl)chroman-2-yl)propanoate (44.3 mg, 42%) an off-white solid. ¹H-NMR (400 MHz, CDCl₃) δ 7.38 (m, 1H), 7.37 (m, 2H), 7.31-7.29 (m, 2H), 7.04 (m, 1H), 6.93 (m, 1H), 6.77 (d, J=8.8 Hz 1H), 6.74 (d, J=18.8 Hz 1H), 5.16-4.98 (m, 2H), 4.28 (d, J=6.0 Hz 1H), 4.12 (m, 1H), 3.80 (s, 3H), 3.70 (s, 3H), 2.63-2.49 (m, 3H), 1.99-1.87 (m, 3H). (ES, m/z): (M+Na)⁺589.

Example 179—Synthesis of 3-(6-((2-Chloro-6-fluorobenzyl)oxy)-4-((4-fluoro-3-methoxyphenyl)sulfonyl)chroman-2-yl)propanoic acid

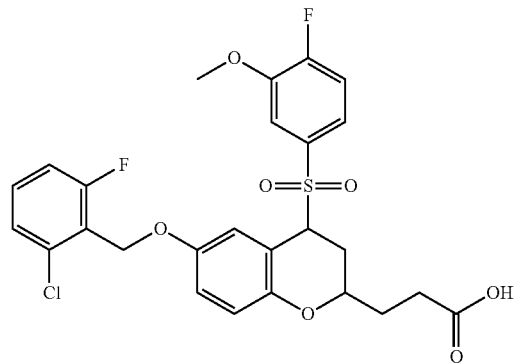 [SMILES: COc1cc(S(=O)(=O)C2CC(CCC(=O)O)Oc3ccc(OCc4c(F)cccc4Cl)cc32)ccc1F]

To a solution of methyl 3-(6-((2-chloro-6-fluorobenzyl)oxy)-4-((4-fluoro-3-methoxyphenyl)sulfonyl)chroman-2-yl)propanoate (100 mg, 0.18 mmol) in tetrahydrofuran (9 mL) and water (3 mL) was added lithium hydroxide (21 mg, 0.88 mmol). The mixture was stirred for three hours at room temperature and then the pH value of the solution was adjusted to 5 with 1 M hydrogen chloride. The mixture was extracted twice with ethyl acetate and the combined organic layers were concentrated. The crude product was purified by reverse phase Prep-HPLC eluting with a gradient of 47-64% acetonitrile in water with 0.05% TFA to afford 3-(6-((2-chloro-6-fluorobenzyl)oxy)-4-((4-fluoro-3-methoxyphenyl)sulfonyl)chroman-2-yl)propanoic acid (60 mg, 62%) as a white solid. ¹H-NMR (400 MHz, CDCl₃) δ 7.42 (m, 1H), 7.40-7.32 (m, 2H), 7.31-7.21 (m, 2H), 7.06 (m, 1H), 6.97 (m, 1H), 6.81 (d, J=8.8 Hz 1H), 6.73 (d, J=18.8 Hz 1H), 5.01 (m, 2H), 4.31 (d, J=6.0 Hz 1H), 4.15 (m, 1H), 3.82 (s, 3H), 2.67-2.59 (m, 3H), 2.01-1.90 (m, 3H). (ES, m/z): (M+NH₄)⁺ 570.

Example 180—Synthesis of (E)-(6-(2-(2-Chloro-6-fluorophenyl)prop-1-en-1-yl)-4-((3-(trifluoromethyl)phenyl)sulfonyl)chroman-2-yl)methanamine

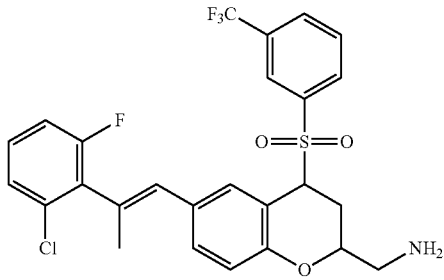 [SMILES: C/C(=C\c1ccc2c(c1)C(S(=O)(=O)c1cccc(C(F)(F)F)c1)CC(CN)O2)c1c(F)cccc1Cl]

Part I—Synthesis of tert-Butyl ((6-bromo-4-oxochroman-2-yl)methyl)carbamate

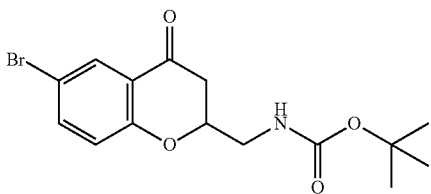 [SMILES: CC(C)(C)OC(=O)NCC1CC(=O)c2cc(Br)ccc2O1]

A mixture of 1-(5-bromo-2-hydroxyphenyl)ethan-1-one (3.31 g, 15.39 mmol), tert-butyl N-(2-oxoethyl)carbamate (4.89 g, 30.72 mmol), and pyrrolidine (2.56 mL, 30.7 mmol) in methanol (31 mL) was stirred for two hours at 70° C. The mixture was concentrated and the resulting residue was purified via MPLC eluting with ethyl acetate/petroleum ether (1:2) to afford tert-butyl ((6-bromo-4-oxochroman-2-yl)methyl)carbamate (4.76 g, 87%) as a brown solid.

Part II—Synthesis of tert-Butyl ((6-bromo-4-hydroxychroman-2-yl)methyl)carbamate

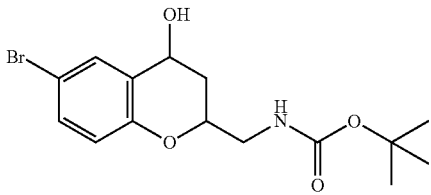 [SMILES: CC(C)(C)OC(=O)NCC1CC(O)c2cc(Br)ccc2O1]

To a solution of tert-butyl ((6-bromo-4-oxochroman-2-yl)methyl)carbamate (4.62 g, 12.97 mmol) in methanol (48 mL) was added sodium borohydride (990 mg, 26.17 mmol) in portions. The resulting solution was stirred for additional thirty minutes at room temperature, and then it was diluted with water. The mixture was extracted three times with dichloromethane. The combined organic layers were concentrated and the resulting residue was purified by MPLC eluting with a gradient of petroleum ether: ethyl acetate=20:1 increasing to petroleum ether: ethyl acetate=0:1 to afford tert-butyl ((6-bromo-4-hydroxychroman-2-yl)methyl)carbamate (1.41 g, 30%) as a yellow solid.

Part III—Synthesis of tert-Butyl ((6-bromo-4-((3-(trifluoromethyl)phenyl)thio)chroman-2-yl)methyl)carbamate

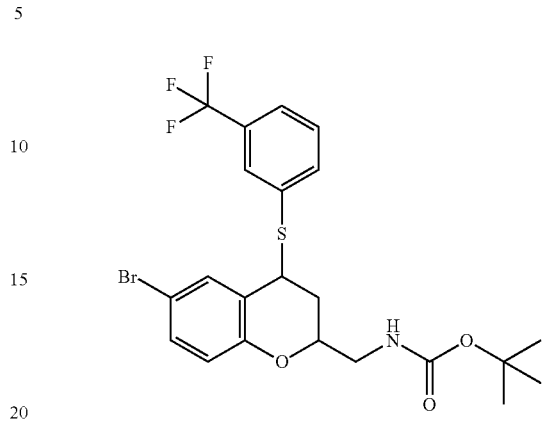

To a solution of tert-butyl ((6-bromo-4-hydroxychroman-2-yl)methyl)carbamate (720 mg, 2.01 mmol) in dichloromethane (8 mL) at 0° C. was added 3-(trifluoromethyl)benzene-1-thiol (0.54 mL, 4.0 mmol) in portions. To this was added triphenylphosphine (1.07 g, 4.08 mmol) and then diisopropyldiazodicarboxylate (0.79 mL, 4.08 mmol). The mixture was warmed to room temperature and stirred for two hours. To the reaction mixture was added to 1 M sodium hydroxide, and the resultant mixture extracted three times with dichloromethane. The combined organic layers were concentrated, and the resulting residue was purified via MPLC eluting with a gradient of 5-20% petroleum ether in ethyl acetate to afford tert-butyl ((6-bromo-4-((3-(trifluoromethyl)phenyl)thio)chroman-2-yl)methyl)carbamate (500 mg, 48%) as a light yellow oil.

Part IV—Synthesis of tert-Butyl ((6-bromo-4-((3-(trifluoromethyl)phenyl)thio)chroman-2-yl)methyl)carbamate

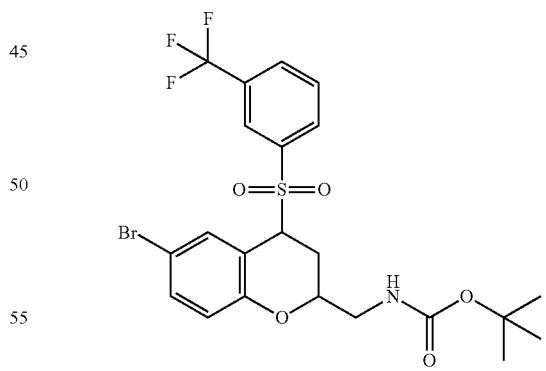

To a solution of tert-butyl ((6-bromo-4-((3-(trifluoromethyl)phenyl)thio)chroman-2-yl)methyl)carbamate (14 mg, 0.03 mmol) in dichloromethane (0.5 mL) was added meta-chloroperbenzoic acid (9.4 mg, 0.06 mmol) was added to the reaction mixture. The resulting solution was stirred for one hour at room temperature. The reaction was quenched by the addition of saturated aqueous sodium thiosulfate (1 mL). The mixture was diluted with water, extracted three times with dichloromethane. The combined organic layers were washed with saturated sodium bicarbonate, dried (Na₂SO₄) and concentrated to afford tert-butyl ((6-bromo-4-((3-(trifluoromethyl)phenyl)thio)chroman-2-yl)methyl)carbamate (16 mg, 100%).

Part V—Synthesis of (E)-tert-Butyl ((6-(2-(2-chloro-6-fluorophenyl)prop-1-en-1-yl)-4-((3-(trifluoromethyl)phenyl)sulfonyl)chroman-2-yl)methyl) carbamate

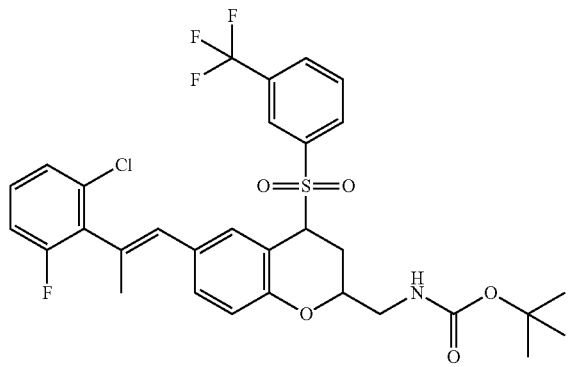 [SMILES: C/C(=C\c1ccc2c(c1)C(S(=O)(=O)c1cccc(C(F)(F)F)c1)CC(CNC(=O)OC(C)(C)C)O2)c1c(F)cccc1Cl]

Under an inert atmosphere of nitrogen, to a solution of tert-butyl ((6-bromo-4-((3-(trifluoromethyl)phenyl)thio)chroman-2-yl)methyl)carbamate (470 mg, 0.85 mmol), 2-[(1E)-2-(2-chloro-6-fluorophenyl)prop-1-en-1-yl]-4,4,5,5-tetramethyl-1,3,2-dioxaborolane (380.7 mg, 1.28 mmol), ethanol (1 mL), toluene (7 mL), and water (3.5 mL) was added sodium carbonate (742.8 mg, 7.01 mmol) and tetrakis(triphenylphosphine)palladium(0) (119.1 mg, 0.10 mmol). The resulting solution was stirred overnight at 95° C., diluted with water and extracted three times with dichloromethane. The combined organic layers were concentrated. The resulting residue was purified by MPLC eluting with a gradient of petroleum ether: ethyl acetate=10:1 increasing to petroleum ether: ethyl acetate=1:2 to afford (E)-tert-butyl ((6-(2-(2-chloro-6-fluorophenyl)prop-1-en-1-yl)-4-((3-(trifluoromethyl)phenyl)sulfonyl)chroman-2-yl)methyl)carbamate (310 mg, 57%) as a light yellow foam.

Part VI—Synthesis of (E)-(6-(2-(2-Chloro-6-fluorophenyl)prop-1-en-1-yl)-4-((3-(trifluoromethyl)phenyl)sulfonyl)chroman-2-yl)methanamine

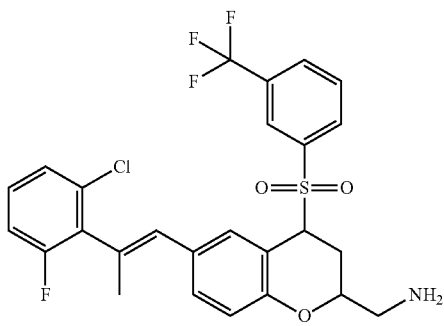 [SMILES: C/C(=C\c1ccc2c(c1)C(S(=O)(=O)c1cccc(C(F)(F)F)c1)CC(CN)O2)c1c(F)cccc1Cl]

A solution of (E)-tert-butyl ((6-(2-(2-chloro-6-fluorophenyl)prop-1-en-1-yl)-4-((3-(trifluoromethyl)phenyl)sulfonyl)chroman-2-yl)methyl)carbamate (300 mg, 0.47 mmol) in trifluoroacetic acid (10 mL) and dichloromethane (10 mL) was stirred for a half hour at room temperature. The mixture was concentrated and the resulting residue was purified by reverse phase Prep-HPLC eluting with a gradient of 34-53% acetonitrile in water with 0.05% TFA to provide (E)-(6-(2-(2-chloro-6-fluorophenyl)prop-1-en-1-yl)-4-((3-(trifluoromethyl)phenyl)sulfonyl)-chroman-2-yl)methanamine (253 mg, 83%) as a red solid. ¹H-NMR (400 MHz, CD₃OD) δ 2.00 (s, 3H), 2.03-2.18 (m, 1H), 2.54 (d, J=15.0 Hz, 1H), 2.90 (dd, J=7.5 Hz, 13.2 Hz, 1H), 3.03 (dd, J=3.6 Hz, 13.5 Hz, 1H), 4.66-4.72 (m, 1H), 4.84-4.87 (m, 1H), 6.18 (s, 1H), 6.87 (s, 1H), 6.98 (d, J=8.4 Hz, 1H), 7.07-7.14 (m, 1H), 7.28-7.30 (m, 3H), 7.89 (t, J=7.8 Hz, 1H), 8.04-8.11 (m, 2H), 8.18 (d, J=8.1 Hz, 1H). (ES, m/z): (M+H)⁺540.

Example 181—Synthesis of (E)-N-((6-(2-(2-Chloro-6-fluorophenyl)prop-1-en-1-yl)-4-((3-(trifluoromethyl)phenyl)sulfonyl)chroman-2-yl)methyl)acetamide

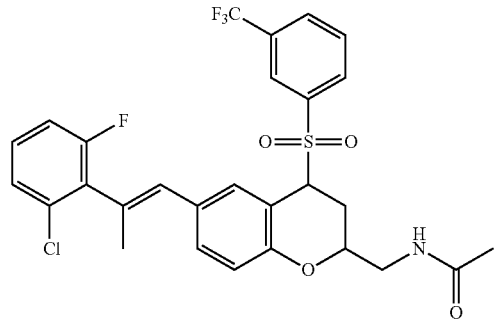 [SMILES: CC(=O)NCC1CC(S(=O)(=O)c2cccc(C(F)(F)F)c2)c2cc(/C=C(\C)c3c(F)cccc3Cl)ccc2O1]

To a solution (E)-(6-(2-(2-chloro-6-fluorophenyl)prop-1-en-1-yl)-4-((3-(trifluoromethyl)phenyl)sulfonyl)-chroman-2-yl)methanamine (100 mg, 0.19 mmol) in dichloromethane (1.5 mL) and pyridine (0.15 mL, 1.90 mmol) was added acetic anhydride (0.0873 mL, 0.95 mmol). The resulting solution was stirred overnight at room temperature, and then concentrated. The resulting residue was purified by reverse phase Prep-HPLC eluting with a gradient of 52-72% acetonitrile in water with 0.05% TFA to afford (E)-N-((6-(2-(2-chloro-6-fluorophenyl)prop-1-en-1-yl)-4-((3-(trifluoromethyl)phenyl)sulfonyl)chroman-2-yl)methyl)acetamide (63.1 mg, 59%) as a white solid. ¹H-NMR (400 MHz, CDCl₃) δ 1.98 (s, 3H), 2.01 (s, 3H), 2.06 (m, 1H), 2.56 (d, J=14.0 Hz, 1H), 3.55 (d, J=13.6 Hz, 1H), 3.73 (d, J=14.4 Hz, 1H), 4.37 (d, J=5.6 Hz, 1H), 4.75 (d, J=10.8 Hz, 1H), 5.95 (brs, 1H), 6.22 (s, 1H), 6.83 (s, 1H), 6.95 (d, J=8.4 Hz, 1H), 7.04 (m, 1H), 7.18-7.25 (m, 2H), 7.32 (d, J=3.6 Hz, 1H), 7.76 (t, J=8.0 Hz, 1H), 7.97 (d, J=7.6 Hz, 1H), 8.03 (d, J=8.4 Hz, 1H), 8.10 (s, 1H). (ES, m/z): (M−H)⁺580.

Example 182—Synthesis of (E)-N-((6-(2-(2-Chloro-6-fluorophenyl)prop-1-en-1-yl)-4-((3-(trifluoromethyl)phenyl)sulfonyl)chroman-2-yl)methyl)-2-hydroxy-2-methylpropanamide

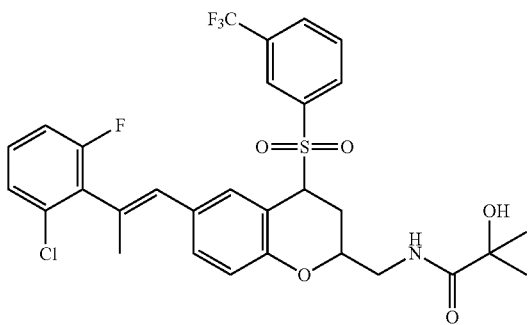 [SMILES: C/C(=C\c1ccc2c(c1)C(S(=O)(=O)c1cccc(C(F)(F)F)c1)CC(CNC(=O)C(C)(C)O)O2)c1c(F)cccc1Cl]

To a solution of 2-hydroxy-2-methylpropanoic acid (9.4 mg, 0.09 mmol), (E)-(6-(2-(2-chloro-6-fluorophenyl)prop-1-en-1-yl)-4-((3-(trifluoromethyl)phenyl)sulfonyl)-chroman-2-yl)methanamine (50 mg, 0.09 mmol) in N,N-dimethylformamide (1.1 mL) was added HATU (50.6 mg, 0.13 mmol) and diisopropylethylamine (0.0722 mL, 0.40 mmol). The mixture was stirred for two hours at room temperature and concentrated. The resulting residue was purified by reverse phase eluting with a gradient of 52-69% acetonitrile in water with 0.05% TFA to afford (E)-N-((6-(2-(2-chloro-6-fluorophenyl)prop-1-en-1-yl)-4-((3-(trifluoromethyl)phenyl)sulfonyl)-chroman-2-yl)methyl)-2-hydroxy-2-methylpropanamide (29.9 mg, 53%) as a white solid. $^1$H-NMR (400 MHz, CDCl$_3$) δ 1.51 (s, 3H), 1.51 (s, 3H), 2.05 (s, 3H), 2.11 (m, 1H), 2.60 (d, J=15.2 Hz, 1H), 3.56 (m, 1H), 3.71 (m, 1H), 4.38 (d, J=5.6 Hz, 1H), 4.74 (d, J=9.6 Hz, 1H), 6.22 (s, 1H), 6.82 (s, 1H), 6.96 (d, J=8.8 Hz, 1H), 7.04 (t, J=6.8 Hz, 1H), 7.18-7.25 (m, 3H), 7.34 (dd, J=1.6 Hz, 8.4 Hz, 1H), 7.76 (m, 1H), 7.97 (d, J=7.6 Hz, 1H), 8.02 (d, J=7.6 Hz, 1H), 8.09 (s, 1H). (ES, m/z): (M+H)$^+$626.

Example 183—Synthesis of (E)-N-((6-(2-(2-Chloro-6-fluorophenyl)prop-1-en-1-yl)-4-((3-(trifluoromethyl)phenyl)sulfonyl)chroman-2-yl)methyl)cyclopropanecarboxamide

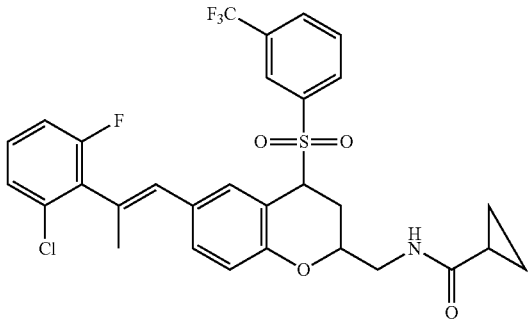 [SMILES: C/C(=C\c1ccc2c(c1)C(S(=O)(=O)c1cccc(C(F)(F)F)c1)CC(CNC(=O)C1CC1)O2)c1c(F)cccc1Cl]

Based on the procedure in Example 182, (E)-N-((6-(2-(2-chloro-6-fluorophenyl)prop-1-en-1-yl)-4-((3-(trifluoromethyl)phenyl)sulfonyl)chroman-2-yl)methyl)cyclopropanecarboxamide was prepared. $^1$H-NMR (400 MHz, CDCl$_3$) δ 0.80 (m, 2H), 0.99 (m, 2H), 1.41 (m, 1H), 2.07 (s, 3H), 2.08 (m, 1H), 2.54 (d, J=15.2 Hz, 1H), 3.61 (m, 1H), 3.72 (m, 1H), 4.38 (d, J=5.6 Hz, 1H), 4.72-4.76 (m, 1H), 6.06-6.07 (m, 1H), 6.24 (s, 1H), 6.88 (d, J=1.6 Hz, 1H), 6.96 (d, J=8.4 Hz, 1H), 7.04 (dt, J=2.0 Hz, 7.6 Hz, 1H), 7.20-7.25 (m, 2H), 7.34 (d, J=1.6 Hz, 1H), 7.76 (t, J=8.0 Hz, 1H), 7.97 (d, J=8.0 Hz, 1H), 8.03 (d, J=7.6 Hz, 1H), 8.10 (s, 1H). (ES, m/z): (M+H)$^+$608.

Example 184—Synthesis of (E)-N-((6-(2-(2-Chloro-6-fluorophenyl)prop-1-en-1-yl)-4-((3-(trifluoromethyl)phenyl)sulfonyl)chroman-2-yl)methyl)methanesulfonamide

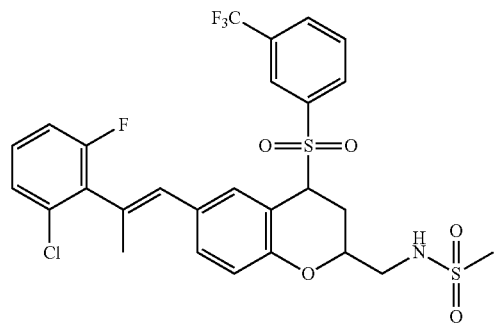 [SMILES: C/C(=C\c1ccc2c(c1)C(S(=O)(=O)c1cccc(C(F)(F)F)c1)CC(CNS(C)(=O)=O)O2)c1c(F)cccc1Cl]

To a solution of (E)-(6-(2-(2-chloro-6-fluorophenyl)prop-1-en-1-yl)-4-((3-(trifluoromethyl)phenyl)sulfonyl)-chroman-2-yl)methanamine (20 mg, 0.04 mmol) and triethylamine (0.017 mL, 0.13 mmol) in dichloromethane (1.6 mL) was added methanesulfonyl chloride (0.0042 mL, 0.06 mmol). The resulting solution was stirred for 15 minutes at room temperature, and then it was diluted with water. The mixture was extracted three times with dichloromethane. The combined organic layers were concentrated. The resulting residue was purified by reverse phase Prep-HPLC eluting with a gradient of 52-72% acetonitrile in water with 0.05% TFA to provide (E)-N-((6-(2-(2-chloro-6-fluorophenyl)prop-1-en-1-yl)-4-((3-(trifluoromethyl)phenyl)sulfonyl)chroman-2-yl)methyl)methanesulfonamide (22 mg, 100%) as a white solid. $^1$H-NMR (400 MHz, CDCl$_3$) δ 2.02 (s, 3H), 2.23 (m, 1H), 2.66 (d, J=14.8 Hz, 1H), 3.07 (s, 3H), 3.41 (m, 1H), 3.60 (m, 1H), 4.40 (d, J=5.6 Hz, 1H), 4.73 (m, 1H), 4.86 (m, 1H), 6.19 (s, 1H), 6.68 (d, J=2.0 Hz, 1H), 6.92 (d, J=8.4 Hz, 1H), 7.04 (dt, J=2.4 Hz, 7.2 Hz, 1H), 7.20-7.25 (m, 2H), 7.33 (dd, J=2.0 Hz, 8.4 Hz, 1H), 7.76 (t, J=8.0 Hz, 1H), 7.97-8.02 (m, 2H), 8.10 (s, 1H). (ES, m/z): (M+H)$^+$618.

Example 185—Synthesis of Ethyl 3-(6-((2-chloro-6-fluorobenzyl)oxy)-4-((4-fluoro-3-methoxyphenyl)sulfonyl)chroman-2-yl)-2,2-dimethylpropanoate

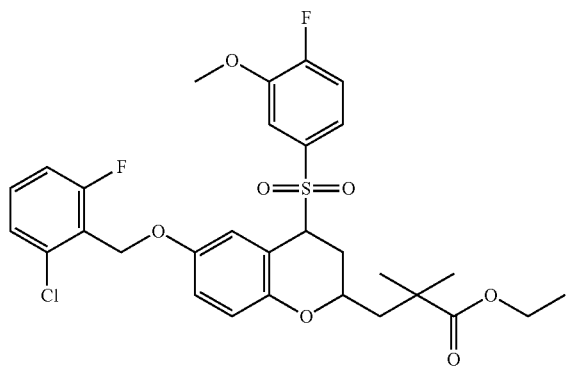 [SMILES: CCOC(=O)C(C)(C)CC1CC(S(=O)(=O)c2ccc(F)c(OC)c2)c2cc(OCc3c(F)cccc3Cl)ccc2O1]

Part I—Synthesis of Ethyl 4,5-dihydroxy-2,2-dimethylpentanoate

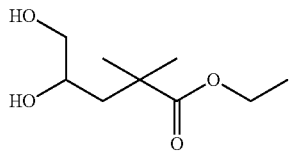

A mixture of 2-ethoxy-3,3-dimethylhexa-1,5-diene (3.5 g, 22.69 mmol), dichloromethane (50 mL), N-methyl morpholine oxide (3.2 g, 27.32 mmol) and osmium oxide (0.006 g) was stirred for one hour at 0° C., allowed to warm to room temperature and stirred overnight. The mixture was concentrated, diluted with ethyl acetate, washed twice with water, and the organic layer was dried ($Na_2SO_4$) and concentrated to afford ethyl 4,5-dihydroxy-2,2-dimethylpentanoate (4 g, 94%) as a tan solid.

Part II—Synthesis of Ethyl 2,2-dimethyl-4-oxobutanoate

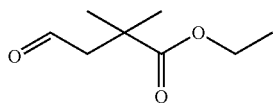

A solution of sodium metaperiodate (11.7 g, 54.6 mmol) in water (50 mL) was added dropwise to a stirred solution of ethyl 4,5-dihydroxy-2,2-dimethylpentanoate (4 g, 21.03 mmol) in acetone (50 mL) at 0° C. The mixture was warmed to room temperature and stirred for ninety minutes. The mixture was extracted twice with dichloromethane. The combined organic layers were washed with brine, dried ($Na_2SO_4$), and concentrated to afford ethyl 2,2-dimethyl-4-oxobutanoate (3 g, 90%) as a tan oil.

Part III—Synthesis of Ethyl 3-(6-((2-chloro-6-fluorobenzyl)oxy)-4-oxochroman-2-yl)-2,2-dimethylpropanoate

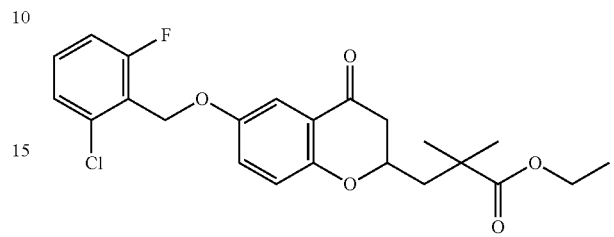

A mixture of 1-(5-((2-chloro-6-fluorobenzyl)oxy)-2-hydroxyphenyl)ethanone (1.2 g, 4.07 mmol), ethyl 2,2-dimethyl-4-oxobutanoate (650 mg, 4.11 mmol), pyrrolidine (600 mg, 8.44 mmol) and methanol (20 mL) was stirred for two hours at 65° C. The mixture was diluted with saturated sodium bicarbonate and was extracted twice with ethyl acetate. The combined organic layers were dried ($Na_2SO_4$) and concentrated. The resulting residue was purified via MPLC eluting with 10% ethyl acetate in petroleum ether to afford ethyl 3-(6-((2-chloro-6-fluorobenzyl)oxy)-4-oxochroman-2-yl)-2,2-dimethylpropanoate (1.5 g, 85%) as a yellow oil.

Part IV—Synthesis of Ethyl 3-(6-((2-chloro-6-fluorobenzyl)oxy)-4-hydroxychroman-2-yl)-2,2-dimethylpropanoate

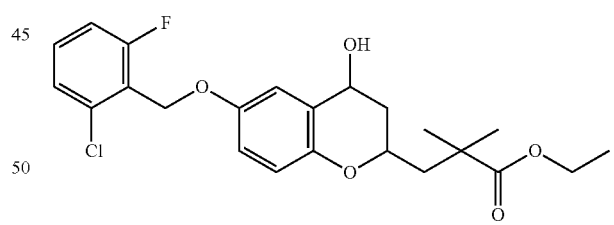

Sodium borohydride (200 mg, 5.29 mmol) was added to the solution of ethyl 3-(6-((2-chloro-6-fluorobenzyl)oxy)-4-oxochroman-2-yl)-2,2-dimethylpropanoate (1.5 g, 3.45 mmol) in methanol (20 mL) at 0° C. and the mixture was stirred for one hour. The mixture was concentrated, diluted with water, and extracted twice with ethyl acetate. The combined organic layers were dried ($Na_2SO_4$) and concentrated to afford ethyl 3-(6-((2-chloro-6-fluorobenzyl)oxy)-4-hydroxychroman-2-yl)-2,2-dimethylpropanoate (1.3 g, 86%) as a yellow oil.

Part V—Synthesis of Ethyl 3-(6-((2-chloro-6-fluorobenzyl)oxy)-4-((4-fluoro-3-methoxyphenyl)thio)chroman-2-yl)-2,2-dimethylpropanoate

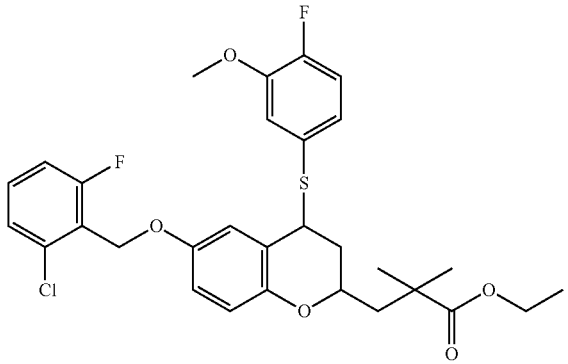 [SMILES: CCOC(=O)C(C)(C)CC1CC(Sc2ccc(F)c(OC)c2)c2cc(OCc3c(F)cccc3Cl)ccc2O1]

A mixture of ethyl 3-(6-((2-chloro-6-fluorobenzyl)oxy)-4-hydroxychroman-2-yl)-2,2-dimethylpropanoate (400 mg, 0.92 mmol), 4-fluoro-3-methoxybenzene-1-thiol (290 mg, 1.83 mmol), zinc iodide (379 mg, 1.19 mmol) and dichloromethane (10 mL) was stirred for two hours at room temperature. The mixture was diluted with water, and was extracted twice with dichloromethane. The combined organic layers were dried ($Na_2SO_4$) and concentrated. The resulting residue was purified via MPLC eluting with 16% ethyl acetate in petroleum ether to afford ethyl 3-(6-((2-chloro-6-fluorobenzyl)oxy)-4-((4-fluoro-3-methoxyphenyl)thio)chroman-2-yl)-2,2-dimethylpropanoate (370 mg, 70%) as a colorless oil.

Part VI—Synthesis of Ethyl 3-(6-((2-chloro-6-fluorobenzyl)oxy)-4-((4-fluoro-3-methoxyphenyl)sulfonyl)chroman-2-yl)-2,2-dimethylpropanoate

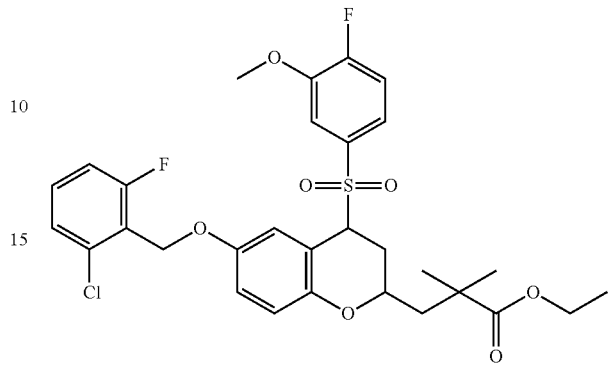

meta-Chloroperbenzoic acid (222 mg, 1.28 mmol) was added to a stirred solution of ethyl 3-(6-((2-chloro-6-fluorobenzyl)oxy)-4-((4-fluoro-3-methoxyphenyl)thio)chroman-2-yl)-2,2-dimethylpropanoate (370 mg, 0.64 mmol) in dichloromethane (10 mL). The solution was stirred for two hours at room temperature. The mixture was diluted dichloromethane and washed twice with saturated sodium bicarbonate, dried ($Na_2SO_4$) and concentrated. The resulting residue was purified by Prep-HPLC eluting with a 70% acetonitrile in water with 0.05% trifluoroacetic acid to afford ethyl 3-(6-((2-chloro-6-fluorobenzyl)oxy)-4-((4-fluoro-3-methoxyphenyl)sulfonyl)chroman-2-yl)-2,2-dimethylpropanoate (360 mg, 92%) as a light yellow oil. $^1$H-NMR (400 MHz, $CDCl_3$) δ 7.40 (m, 1H), 7.31 (m, 1H), 7.28-7.18 (m, 3H), 7.06 (m, 1H), 6.92 (m, 1H), 6.80 (d, J=3.1 Hz, 1H), 6.71 (d, J=8.8 Hz, 1H), 5.02 (m, 2H), 4.28 (d, J=6.0 Hz, 1H), 4.18-4.13 (m, 3H), 3.81 (s, 3H), 2.57 (d, J=14.8 Hz, 1H), 2.05-1.97 (m, 2H), 1.75 (m, 1H), 1.28-1.21 (m, 9H). (ES, m/z): $(M+NH_4)^+$626.

Example 186—Preparation of Additional Substituted 4-(Arylsulfonyl)chromanes

Compounds in Table 22 were prepared based on experimental procedures described in Examples 178-185 and the detailed description.

TABLE 22

| No. | Structure | Name | Observed m/z |
|---|---|---|---|
| 186A | (structure shown) | 3-(6-((2-chloro-6-fluorobenzyl)oxy)-4-((3-(trifluoromethyl)phenyl)sulfonyl)chroman-2-yl)propanoic acid | 363 (M-$C_7H_4F_3O_2S$)$^+$ |

TABLE 22-continued

| No. | Structure | Name | Observed m/z |
|---|---|---|---|
| 186B | 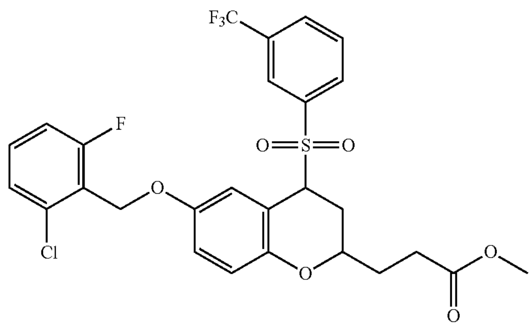 | methyl 3-(6-((2-chloro-6-fluorobenzyl)oxy)-4-((3-(trifluoromethyl)phenyl)sulfonyl)chroman-2-yl)propanoate | 609 (M + Na)+ |
| 186C | 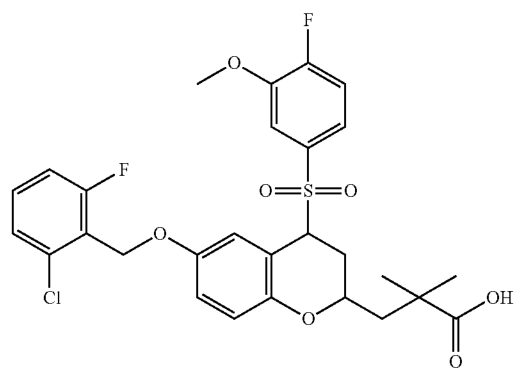 | 3-(6-((2-chloro-6-fluorobenzyl)oxy)-4-((4-fluoro-3-methoxyphenyl)sulfonyl)chroman-2-yl)-2,2-dimethylpropanoic acid | 598 (M + NH$_4$)+ |
| 186D | 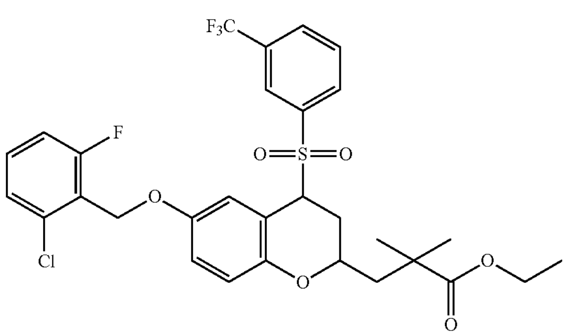 [SMILES: CCOC(=O)C(C)(C)CC1CC(S(=O)(=O)c2cccc(C(F)(F)F)c2)c2cc(OCc3c(F)cccc3Cl)ccc2O1] | ethyl 3-(6-((2-chloro-6-fluorobenzyl)oxy)-4-((3-(trifluoromethyl)phenyl)-sulfonyl)chroman-2-yl)-2,2-dimethylpropanoate | 651 (M + Na)+ |
| 186E | 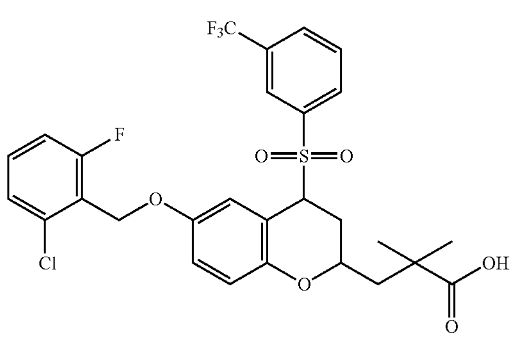 | 3-(6-((2-chloro-6-fluorobenzyl)oxy)-4-((3-(trifluoromethyl)phenyl)-sulfonyl)chroman-2-yl)-2,2-dimethylpropanoic acid | 618 (M + NH$_4$)+ |

TABLE 22-continued

| No. | Structure | Name | Observed m/z |
|---|---|---|---|
| 186F | 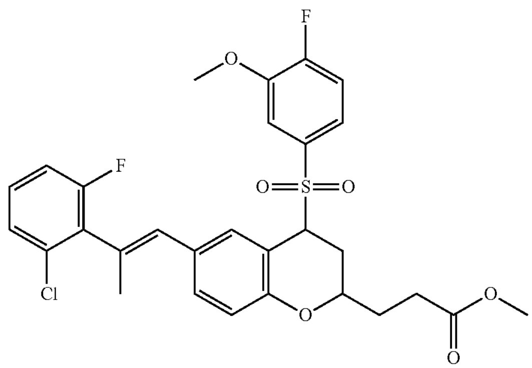 [SMILES: COC(=O)CCC1CC(S(=O)(=O)c2ccc(F)c(OC)c2)c2cc(/C=C(\C)c3c(F)cccc3Cl)ccc2O1] | methyl (E)-3-(6-(2-(2-chloro-6-fluorophenyl)prop-1-en-1-yl)-4-((4-fluoro-3-methoxyphenyl)sulfonyl)chroman-2-yl)propanoate | 594 (M + NH$_4$)$^+$ |
| 186G | 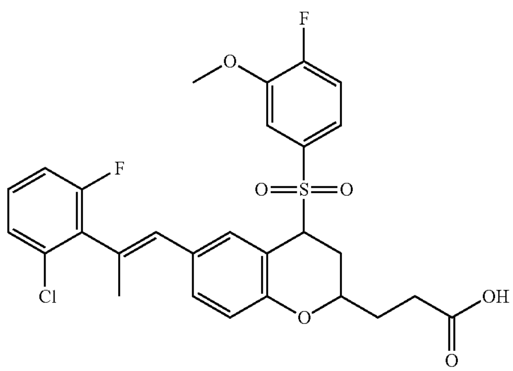 [SMILES: COc1cc(S(=O)(=O)C2CC(CCC(=O)O)Oc3ccc(/C=C(\C)c4c(F)cccc4Cl)cc32)ccc1F] | (E)-3-(6-(2-(2-chloro-6-fluorophenyl)prop-1-en-1-yl)-4-((4-fluoro-3-methoxyphenyl)-sulfonyl)chroman-2-yl)propanoic acid | 580 (M + NH$_4$)$^+$ |
| 186H | 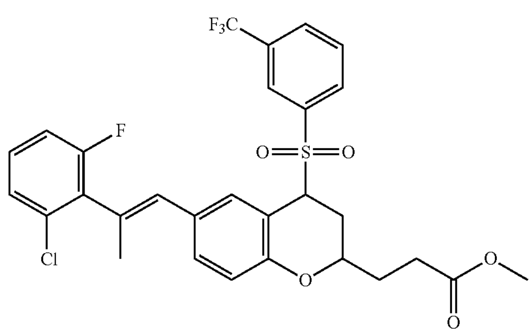 [SMILES: COC(=O)CCC1CC(S(=O)(=O)c2cccc(C(F)(F)F)c2)c2cc(/C=C(\C)c3c(F)cccc3Cl)ccc2O1] | methyl (E)-3-(6-(2-(2-chloro-6-fluorophenyl)prop-1-en-1-yl)-4-((3-(trifluoromethyl)phenyl)-sulfonyl)chroman-2-yl)propanoate | 614 (M + NH$_4$)$^+$ |
| 186I | 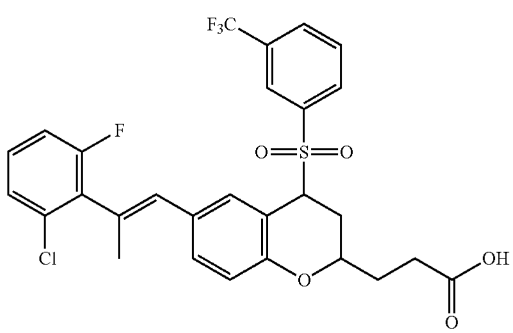 | (E)-3-(6-(2-(2-chloro-6-fluorophenyl)prop-1-en-1-yl)-4-((3-(trifluoromethyl)phenyl)-sulfonyl)chroman-2-yl)propanoic acid | 600 (M + NH$_4$)$^+$ |

TABLE 22-continued

| No. | Structure | Name | Observed m/z |
|---|---|---|---|
| 186J | 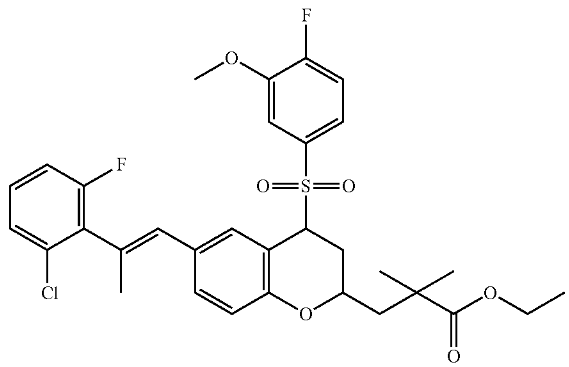 [SMILES: CCOC(=O)C(C)(C)CC1CC(S(=O)(=O)c2ccc(F)c(OC)c2)c2cc(/C=C(\C)c3c(F)cccc3Cl)ccc2O1] | ethyl (E)-3-(6-(2-(2-chloro-6-fluorophenyl)prop-1-en-1-yl)-4-((4-fluoro-3-methoxyphenyl)-sulfonyl)chroman-2-yl)-2,2-dimethylpropanoate | 619 (M + H)+ |
| 186K | 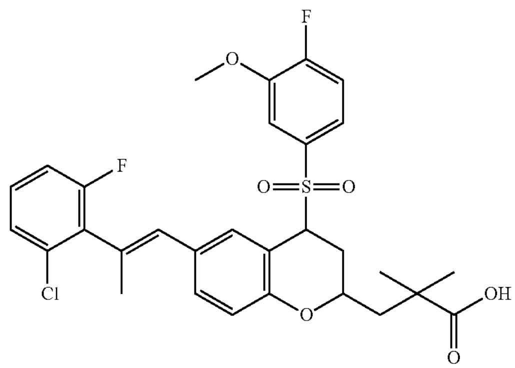 | (E)-3-(6-(2-(2-chloro-6-fluorophenyl0prop-1-en-1-yl)-4-((4-fluoro-3-methoxyphenyl)-sulfonyl)chroman-2-yl)-2,2-dimethylpropanoic acid | 613 (M + Na)+ |
| 186L | 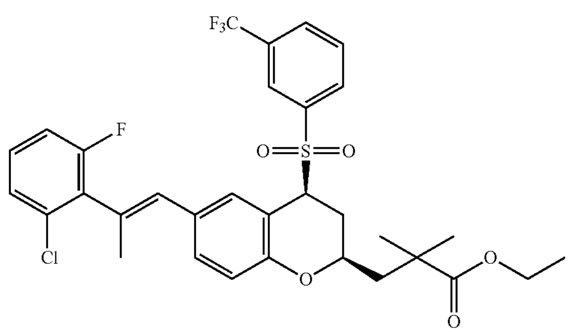 [SMILES: CCOC(=O)C(C)(C)C[C@@H]1C[C@H](S(=O)(=O)c2cccc(C(F)(F)F)c2)c2cc(/C=C(\C)c3c(F)cccc3Cl)ccc2O1] | ethyl 3-((2R,4S)-6-((E)-2-(2-chloro-6-fluorophenyl)prop-1-en-1-yl)-4-((3-(trifluoromethyl)phenyl)-sulfonyl)chroman-2-yl)-2,2-dimethylpropanoate | 637 (M − H)− |
| 186M | 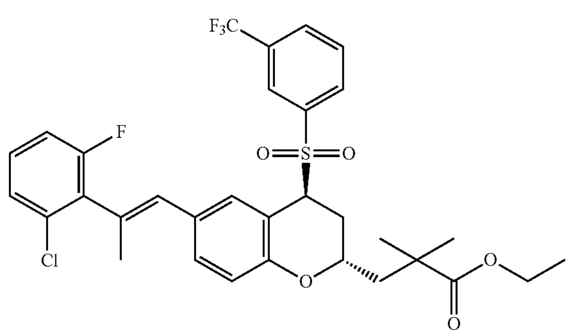 [SMILES: CCOC(=O)C(C)(C)C[C@H]1C[C@H](S(=O)(=O)c2cccc(C(F)(F)F)c2)c2cc(/C=C(\C)c3c(F)cccc3Cl)ccc2O1] | ethyl 3-((2S,4S)-6-((E)-2-(2-chloro-6-fluorophenyl)prop-1-en-1-yl)-4-((3-(trifluoromethyl)-phenyl)sulfonyl)chroman-2-yl)-2,2-dimethylpropanoate | 661 (M + Na)+ |

TABLE 22-continued

| No. | Structure | Name | Observed m/z |
|---|---|---|---|
| 186N | 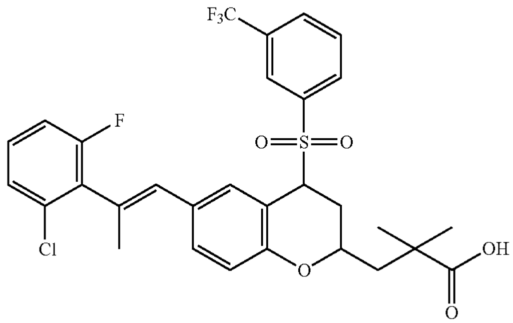 | (E)-3-(6-(2-(2-chloro-6-fluorophenyl)prop-1-en-1-yl)-4-((3-(trifluoromethyl)phenyl)-sulfonyl)chroman-2-yl)-2,2-dimethylpropanoic acid | 609 (M − H)⁻ |

Example 187-Synthesis of (E)-6-(2-(2-Chloro-6-fluorophenyl)prop-1-en-1-yl)-4-((3-(trifluoromethyl)phenyl)sulfonyl)-3,4-dihydro-2H-benzo[b][1,4]thiazine

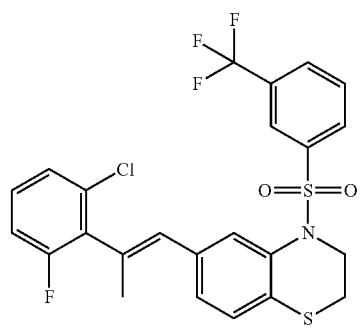 [SMILES: C/C(=C\c1ccc2c(c1)N(S(=O)(=O)c1cccc(C(F)(F)F)c1)CCS2)c1c(F)cccc1Cl]

Part I—Synthesis of 6-Bromo-4-((3-(trifluoromethyl)phenyl)sulfonyl)-3,4-dihydro-2H-benzo[b][1,4]thiazine

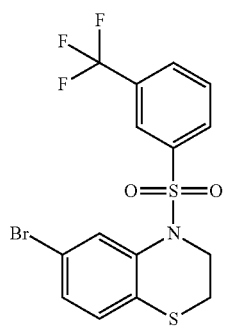 [SMILES: O=S(=O)(c1cccc(C(F)(F)F)c1)N1CCSc2ccc(Br)cc21]

To 6-bromo-3,4-dihydro-2H-benzo[b][1,4]thiazine (0.1 g, 0.44 mmol) in pyridine (3 mL) was added 3-(trifluoromethyl)benzenesulfonyl chloride (0.08 mL, 0.48 mmol) and heated to 70° C. for two hours. The reaction mixture was cooled, diluted with ethyl acetate, washed three times with 1 M aqueous hydrogen chloride three times, and washed with brine. The organic layer was dried (Na₂SO₄) and concentrated. The resulting residue was purified by MPLC eluting with a gradient of 0-50% ethyl acetate in hexanes. Pure fractions were combined and concentrated to afford 6-bromo-4-((3-(trifluoromethyl)phenyl)sulfonyl)-3,4-dihydro-2H-benzo[b][1,4]thiazine (135 mg, 71%).

Part II—Synthesis of (E)-6-(2-(2-Chloro-6-fluorophenyl)prop-1-en-1-yl)-4-((3-(trifluoromethyl)phenyl)sulfonyl)-3,4-dihydro-2H-benzo[b][1,4]thiazine

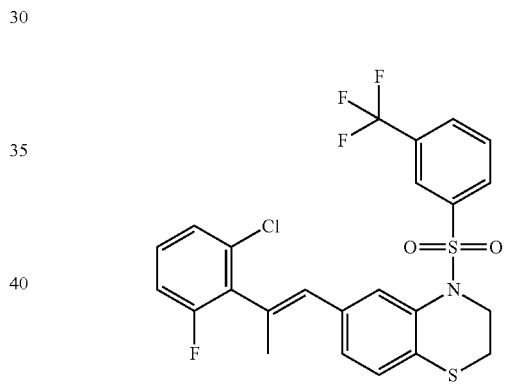

To 6-bromo-4-((3-(trifluoromethyl)phenyl)sulfonyl)-3,4-dihydro-2H-benzo[b][1,4]thiazine (0.13 g, 0.30 mmol) in 1,4-dioxane (4 mL) was added potassium carbonate (0.061 g, 0.44 mmol), 2-[(E)-2-(2-chloro-6-fluoro-phenyl)prop-1-enyl]-4,4,5,5-tetramethyl-1,3,2-dioxaborolane (0.13 g, 0.44 mmol), and water (1 mL). This was followed by the addition of [1,1'-bis(diphenylphosphino)ferrocene]dichloropalladium (II) complex with dichloromethane (23 mg, 0.03 mmol). The reaction mixture was heated to 80° C. for 2.5 hours. The reaction mixture was diluted with ethyl acetate, washed with 50% brine, dried (Na₂SO₄) and concentrated. The resulting residue was purified by MPLC eluting with a gradient of 0-50% ethyl acetate in hexanes. Pure fractions were combined and concentrated to afford (E)-6-(2-(2-chloro-6-fluorophenyl)prop-1-en-1-yl)-4-((3-(trifluoromethyl)phenyl)sulfonyl)-3,4-dihydro-2H-benzo[b][1,4]thiazine (145 mg, 93%). $^1$H-NMR (400 MHz, DMSO-d$_6$) δ 8.08 (d, 1H), 8.00 (d, 1H), 7.82 (t, 1H), 7.75 (s, 1H), 7.52 (m, 1H), 7.38 (m, 2H), 7.26 (m, 1H), 7.18 (m, 2H), 6.38 (s, 1H), 4.00 (m, 2H), 2.98 (m, 2H), 2.10 (s, 3H). MS (ESI+) (M+Na)⁺ 550.04.

Example 188—Synthesis of (E)-7-(2-(2-chloro-6-fluorophenyl)prop-1-en-1-yl)-1-((3-(trifluoromethyl)phenyl)sulfonyl)-2,3-dihydroquinolin-4(1H)-one

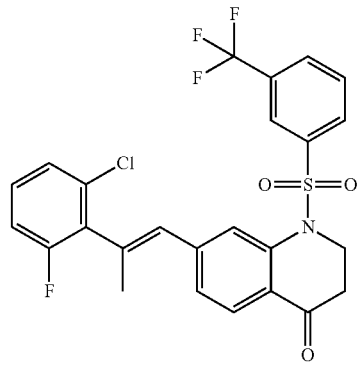 [SMILES: C/C(=C\c1ccc2c(c1)N(S(=O)(=O)c1cccc(C(F)(F)F)c1)CCC2=O)c1c(F)cccc1Cl]

Part I—Synthesis of 7-Bromo-1-((3-(trifluoromethyl)phenyl)sulfonyl)-2,3-dihydroquinolin-4(1H)-one

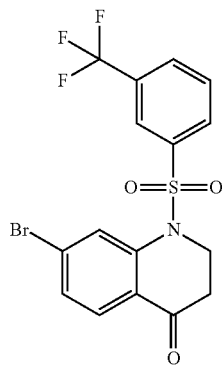 [SMILES: O=C1CCN(S(=O)(=O)c2cccc(C(F)(F)F)c2)c2cc(Br)ccc21]

To 7-bromo-2,3-dihydroquinolin-4(1H)-one (0.25 g, 1.1 mmol) in pyridine (5 mL) was added 3-(trifluoromethyl)benzenesulfonyl chloride (0.18 mL, 1.1 mmol) and heated overnight at 70° C. The reaction mixture was cooled, diluted with ethyl acetate, washed with 1 M aqueous hydrogen chloride three times, and followed by washing with brine. The organic layer was dried (Na₂SO₄) and concentrated. The resulting residue was purified by MPLC eluting with a gradient of 0-50% ethyl acetate in hexanes. Pure fractions were combined and concentrated to afford 7-bromo-1-((3-(trifluoromethyl)phenyl)sulfonyl)-2,3-dihydroquinolin-4(1H)-one (230 mg, 48%).

Part II—Synthesis of (E)-7-(2-(2-chloro-6-fluorophenyl)prop-1-en-1-yl)-1-((3-(trifluoromethyl)phenyl)sulfonyl)-2,3-dihydroquinolin-4(1H)-one

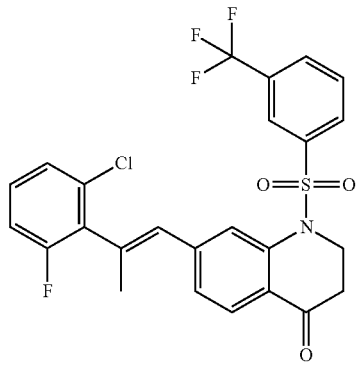 [SMILES: C/C(=C\c1ccc2c(c1)N(S(=O)(=O)c1cccc(C(F)(F)F)c1)CCC2=O)c1c(F)cccc1Cl]

To 7-bromo-1-((3-(trifluoromethyl)phenyl)sulfonyl)-2,3-dihydroquinolin-4(1H)-one (0.10 g, 0.23 mmol), 2-[(E)-2-(2-chloro-6-fluoro-phenyl)prop-1-enyl]-4,4,5,5-tetramethyl-1,3,2-dioxaborolane (0.10 g, 0.35 mmol), and potassium carbonate (48 mg, 0.35 mmol) in 1,4-dioxane (3 mL) and water (1 mL) was added [1,1'-bis(diphenylphosphino)ferrocene]dichloropalladium (II) complex with dichloromethane (18 mg, 0.02 mmol) and heated overnight at 80° C. The cooled solution was partitioned between ethyl acetate and water, washed with brine, dried (Na₂SO₄) and concentrated. The resulting residue was purified by MPLC eluting with a gradient of 0-60% ethyl acetate in hexanes. The major UV fractions were combined and concentrated to afford (E)-7-(2-(2-chloro-6-fluorophenyl)prop-1-en-1-yl)-1-((3-(trifluoromethyl)phenyl)sulfonyl)-2,3-dihydroquinolin-4(1H)-one (0.1 g, 81%). ¹H-NMR (400 MHz, CDCl₃) 8.04 (s, 1H), 7.98 (m, 1H), 7.88 (m, 3H), 7.64 (m, 1H), 7.3-7.2 (m, 3H), 7.06 (m, 1H), 6.49 (s, 1H), 4.25 (m, 2H), 2.44 (m, 2H), 2.24 (s, 3H). MS (ESI+) (M+H)⁺524.09.

Example 189—Synthesis of (E)-7-(2-(2-Chloro-6-fluorophenyl)prop-1-en-1-yl)-4,4-difluoro-1-((3-(trifluoromethyl)phenyl)sulfonyl)-1,2,3,4-tetrahydroquinoline

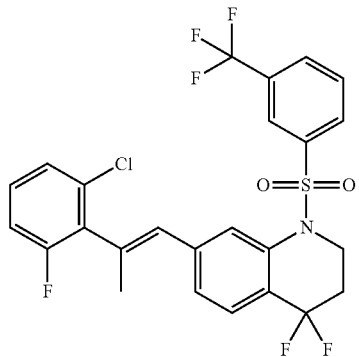 [SMILES: C/C(=C\c1ccc2c(c1)N(S(=O)(=O)c1cccc(C(F)(F)F)c1)CCC2(F)F)c1c(F)cccc1Cl]

To (E)-7-(2-(2-chloro-6-fluorophenyl)prop-1-en-1-yl)-1-((3-(trifluoromethyl)phenyl)sulfonyl)-2,3-dihydroquinolin-4(1H)-one (50 mg, 0.095 mmol) in anhydrous 1,2-dimethoxyethane (0.5 mL) was added bis(2-methoxyethyl)

aminosulfur trifluoride (0.6 g, 2.7 mmol). Stirred at 65° C. overnight. The reaction mixture was cooled to ambient temperature then poured into ice cold 2M aqueous sodium hydroxide. Added dichloromethane and slurried mixture. Extracted with dichloromethane three times. The combined organics were dried (Na$_2$SO$_4$) and concentrated. The resulting residue was purified by MPLC eluting with a gradient of 0-40% ethyl acetate in hexanes. Pure fractions were combined and concentrated to afford (E)-7-(2-(2-chloro-6-fluorophenyl)prop-1-en-1-yl)-4,4-difluoro-1-((3-(trifluoromethyl)phenyl)sulfonyl)-1,2,3,4-tetrahydroquinoline (15 mg, 28%). $^1$H-NMR (400 MHz, DMSO-d$_6$) 8.14 (m, 2H), 7.97 (s, 1H), 7.88 (m, 1H), 7.64 (m, 2H), 7.4-7.25 (m, 4H), 6.52 (s, 1H), 4.14 (m, 2H), 2.22 (m, 2H), 2.06 (s, 3H). MS (ESI+) (M+Na)$^+$568.16.

Example 190—Synthesis of (S,E)-3-(6-(2-cyclohexylprop-1-en-1-yl)-4-((4-fluoro-3-methoxyphenyl)sulfonyl)-3,4-dihydro-2H-benzo[b][1,4]oxazin-2-yl)propanoic acid

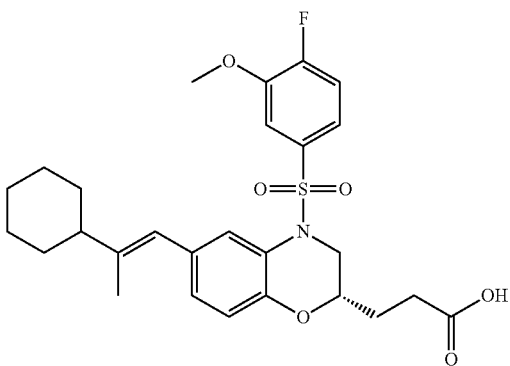 [SMILES: COc1cc(S(=O)(=O)N2C[C@H](CCC(=O)O)Oc3ccc(/C=C(\C)C4CCCCC4)cc32)ccc1F]

Part I—Synthesis of (Z)-2-(2-Bromo-2-cyclohexylvinyl)-4,4,5,5-tetramethyl-1,3,2-dioxaborolane

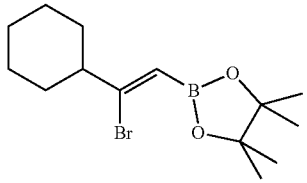 [SMILES: CC1(C)OB(/C=C(\Br)C2CCCCC2)OC1(C)C]

To a solution of ethynylcyclohexane (0.5 g, 4.6 mmol) in dichloromethane (10 mL) at −78° C. was added a 1 M solution of boron tribromide in dichloromethane (5.1 mL, 5.1 mmol). The reaction mixture was stirred at −78° C. for one hour, then at ambient temperature for another hour. Recooled solution to −78° C., and then added a solution of pinacol (0.66 g, 5.5 mmol) in dichloromethane (5 mL). Stirred at −78° C. for another hour followed by one hour at ambient temperature. The solution was washed with brine, dried (Na$_2$SO$_4$) and concentrated. The resulting residue was purified by MPLC eluting with a gradient of ethyl acetate in hexanes. Pure fractions were combined and concentrated to afford (Z)-2-(2-bromo-2-cyclohexylvinyl)-4,4,5,5-tetramethyl-1,3,2-dioxaborolane (510 mg, 35%).

Part II—Synthesis of (E)-2-(2-Cyclohexylprop-1-en-1-yl)-4,4,5,5-tetramethyl-1,3,2-dioxaborolane

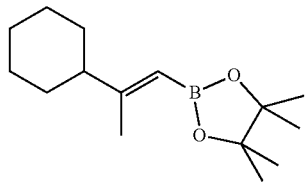 [SMILES: C/C(=C\B1OC(C)(C)C(C)(C)O1)C1CCCCC1]

To a suspension of zinc bromide (0.43 g, 1.9 mmol) in anhydrous tetrahydrofuran (5 mL) at 0° C. was added 1 M methyl magnesium bromide solution in tetrahydrofuran (1.9 mL, 1.9 mmol). The solution was stirred for 30 minutes. The resulting mixture was added to a stirred solution of (Z)-2-(2-bromo-2-cyclohexylvinyl)-4,4,5,5-tetramethyl-1,3,2-dioxaborolane (0.5 g, 1.6 mmol), dichlorobis(triphenylphosphine)palladium (11 mg, 0.016 mmol) in anhydrous tetrahydrofuran (5 mL) at 0° C. The cooling bath was removed and the reaction stirred at ambient temperature for ninety minutes. Quenched with 1 M aqueous hydrogen chloride, then extracted twice with ethyl acetate. The combined extracts were washed with saturated sodium bicarbonate, brine, dried (Na$_2$SO$_4$) and concentrated. The resulting residue was purified by MPLC eluting with a gradient of ethyl acetate in hexanes to afford (E)-2-(2-cyclohexylprop-1-en-1-yl)-4,4,5,5-tetramethyl-1,3,2-dioxaborolane (0.12 g, 23%).

Part III—Synthesis of Methyl (S,E)-3-(6-(2-cyclohexylprop-1-en-1-yl)-4-((4-fluoro-3-methoxyphenyl)sulfonyl)-3,4-dihydro-2H-benzo[b][1,4]oxazin-2-yl)propanoate

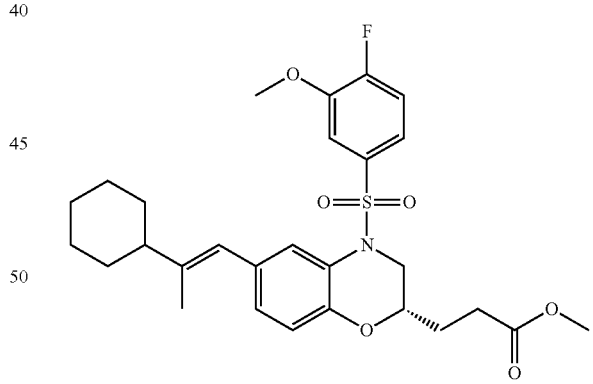

A mixture of (S)-3-(6-bromo-4-((4-fluoro-3-methoxyphenyl)sulfonyl)-3,4-dihydro-2H-benzo[b][1,4]oxazin-2-yl)propanoic acid (0.15 g, 0.31 mmol), (E)-2-(2-cyclohexylprop-1-en-1-yl)-4,4,5,5-tetramethyl-1,3,2-dioxaborolane (0.12 g, 0.46 mmol), and potassium carbonate (64 mg, 0.46 mmol) in 1,4-dioxane (4 mL) and water (1 mL) was degassed. Added [1,1'-bis(diphenylphosphino)ferrocene]dichloropalladium (II) dichloromethane complex (23 mg, 0.031 mmol) and heated to 70° C. for two hours. The cooled solution was partitioned between ethyl acetate and brine, dried (Na$_2$SO$_4$) and concentrated. The material was purified by MPLC eluting with a gradient of 0-40% ethyl acetate in hexanes. Pure fractions were combined and concentrated to afford methyl (S,E)-3-(6-(2-cyclohexylprop-1-en-1-yl)-4-((4-fluoro-3-methoxyphenyl)sulfonyl)-3,4-dihydro-2H-benzo[b][1,4]oxazin-2-yl)propanoate (95 mg, 58%).

Part IV—Synthesis of (S,E)-3-(6-(2-Cyclohexyl-prop-1-en-1-yl)-4-((4-fluoro-3-methoxyphenyl)sulfonyl)-3,4-dihydro-2H-benzo[b][1,4]oxazin-2-yl) propanoic acid

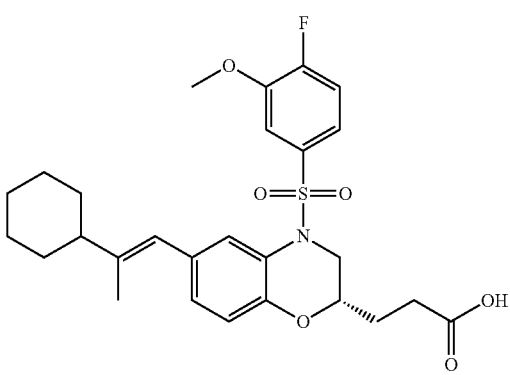 [SMILES: COc1cc(S(=O)(=O)N2C[C@H](CCC(=O)O)Oc3ccc(/C=C(\C)C4CCCCC4)cc32)ccc1F]

To methyl (S,E)-3-(6-(2-cyclohexylprop-1-en-1-yl)-4-((4-fluoro-3-methoxyphenyl)sulfonyl)-3,4-dihydro-2H-benzo[b][1,4]oxazin-2-yl)propanoate (90 mg, 0.17 mmol) in tetrahydrofuran (1 mL) and methanol (1 mL) was added 2M aqueous sodium hydroxide (0.25 mL, 0.50 mmol). The reaction mixture was stirred at ambient temperature for four hours. The solution was acidified with 1M aqueous hydrogen chloride, extracted with ethyl acetate, washed with brine, dried ($Na_2SO_4$) and concentrated. The mixture was purified by MPLC eluting with a gradient of 30-100% ethyl acetate in hexanes. Pure fractions were combined and concentrated to afford (S,E)-3-(6-(2-cyclohexylprop-1-en-1-yl)-4-((4-fluoro-3-methoxyphenyl)sulfonyl)-3,4-dihydro-2H-benzo[b][1,4]oxazin-2-yl)propanoic acid (45 mg, 50%). $^1$H-NMR (400 MHz, DMSO-$d_6$) 12.2 (br s, 1H), 7.56 (s, 1H), 7.42 (m, 1H), 7.27 (m, 1H), 7.20 (m, 1H), 6.94 (d, 1H), 6.78 (d, 1H), 6.17 (s, 1H), 4.30 (m, 1H), 3.76 (s, 3H), 3.3 (m, 2H), 2.30 (m, 2H), 1.98 (m, 1H), 1.8-1.62 (m, 9H), 1.3-1.1 (m, 6H). MS (ESI+) (M+Na)$^+$540.33.

Example 191—Preparation of Additional Alkenes From Alkynes with Tribromoborane

Compounds in Table 22 were prepared based on experimental procedures described in Example 190 and the detailed description.

TABLE 22

| No. | Structure | Name | Observed m/z |
|---|---|---|---|
| 191A | 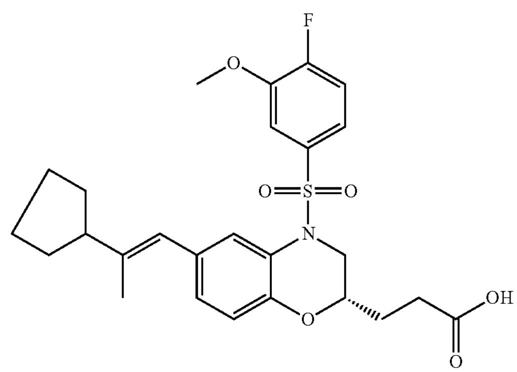 [SMILES: COc1cc(S(=O)(=O)N2C[C@H](CCC(=O)O)Oc3ccc(/C=C(\C)C4CCCC4)cc32)ccc1F] | (S,E)-3-(6-(2-cyclopentylprop-1-en-1-yl)-4-((4-fluoro-3-methoxyphenyl)sulfonyl)-3,4-dihydro-2H-benzo[b][1,4]-oxazin-2-yl)propanoic acid | 504 (M + H)$^+$ |
| 191B | 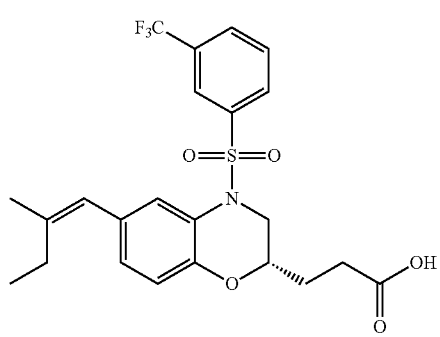 [SMILES: CC/C(C)=C\c1ccc2c(c1)N(S(=O)(=O)c1cccc(C(F)(F)F)c1)C[C@H](CCC(=O)O)O2] | (S,Z)-3-(6-(2-methylbut-1-en-1-yl)-4-((3-(trifluoromethyl)-phenyl)sulfonyl)-3,4-dihydro-2H-benzo[b][1,4]oxazin-2-yl)propanoic acid | 484 (M + H)$^+$ |

TABLE 22-continued

| No. | Structure | Name | Observed m/z |
|---|---|---|---|
| 191C | 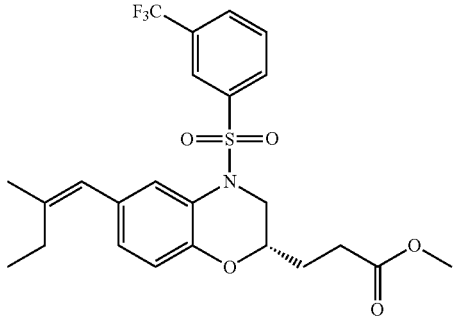 [SMILES: CC/C(C)=C\c1ccc2c(c1)N(S(=O)(=O)c1cccc(C(F)(F)F)c1)C[C@H](CCC(=O)OC)O2] | methyl (S,Z)-3-(6-(2-methylbut-1-en-1-yl)-4-((3-(trifluoromethyl)phenyl)-sulfonyl)-3,4-dihydro-2H-benzo[b][1,4]oxazin-2-yl)propanoate | 498 (M + H)+ |
| 191D | 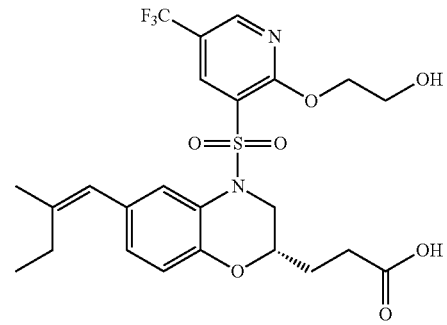 [SMILES: CC/C(C)=C\c1ccc2c(c1)N(S(=O)(=O)c1cc(C(F)(F)F)cnc1OCCO)C[C@H](CCC(=O)O)O2] | (S,Z)-3-(4-((2-(2-hydroxyethoxy)-5-(trifluoromethyl)pyridin-3-yl)sulfonyl)-6-(2-methylbut-1-en-1-yl)-3,4-dihydro-2H-benzo[b][1,4]oxazin-2-yl)propanoic acid | 545 (M + H)+ |
| 191E | 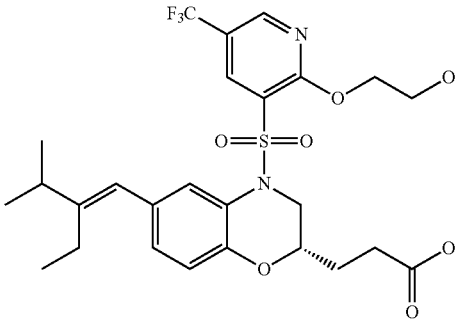 | (S,E)-3-(6-(2-ethyl-3-methylbut-1-en-1-yl)-4-((2-(2-hydroxy-ethoxy)-5-(trifluoromethyl)-pyridin-3-yl)sulfonyl)-3,4-dihydro-2H-benzo[b][1,4]oxazin-2-yl)propanoic acid | 573 (M + H)+ |
| 191F | 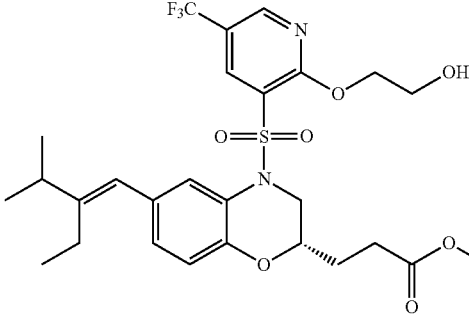 | methyl (S,E)-3-(6-(2-ethyl-3-methylbut-1-en-1-yl)-4-((2-(2-hydroxyethoxy)-5-(trifluoromethyl)pyridin-3-yl)sulfonyl)-3,4-dihydro-2H-benzo[b][1,4]oxazin-2-yl)propanoate | 587 (M + H)+ |

TABLE 22-continued

| No. | Structure | Name | Observed m/z |
|---|---|---|---|
| 191G | 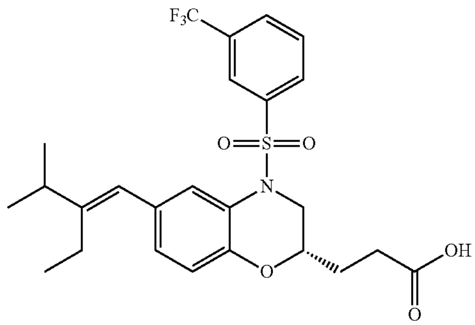 [SMILES: CC/C(=C\c1ccc2c(c1)N(S(=O)(=O)c1cccc(C(F)(F)F)c1)C[C@H](CCC(=O)O)O2)C(C)C] | (S,E)-3-(6-(2-ethyl-3-methylbut-1-en-1-yl)-4-((3-(trifluoromethyl)phenyl)sulfonyl)-3,4-dihydro-2H-benzo[b][1,4]oxazin-2-yl)propanoic acid | 512 (M + H)+ |
| 191H | 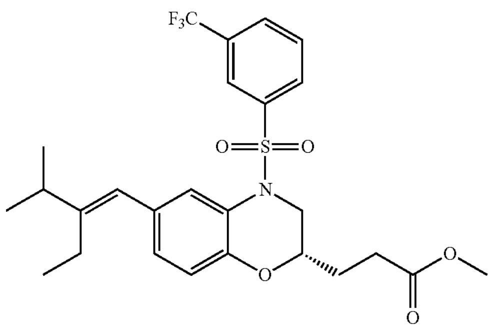 [SMILES: CC/C(=C\c1ccc2c(c1)N(S(=O)(=O)c1cccc(C(F)(F)F)c1)C[C@H](CCC(=O)OC)O2)C(C)C] | methyl (S,E)-3-(6-(2-ethyl-3-methylbut-1-en-1-yl)-4-((3-(trifluoromethyl)phenyl)sulfonyl)-3,4-dihydro-2H-benzo[b][1,4]-oxazin-2-yl)propanoate | 526 (M + H)+ |

Example 192—Synthesis of (S)-3-(6-(cyclopent-1-en-1-yl)-4-((3-(trifluoromethyl)phenyl)sulfonyl)-3,4-dihydro-2H-benzo[b][1,4]oxazin-2-yl)propanoic acid

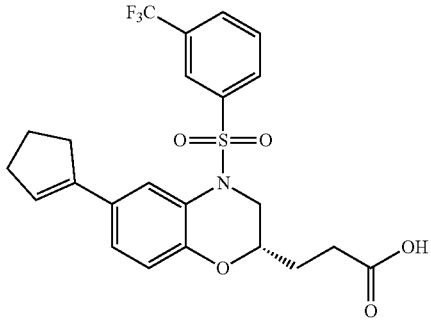 [SMILES: O=C(O)CC[C@H]1CN(S(=O)(=O)c2cccc(C(F)(F)F)c2)c2cc(C3=CCCC3)ccc2O1]

Part I—Synthesis of methyl (S)-3-(6-(cyclopent-1-en-1-yl)-4-((3-(trifluoromethyl)phenyl)sulfonyl)-3,4-dihydro-2H-benzo[b][1,4]oxazin-2-yl)propanoate

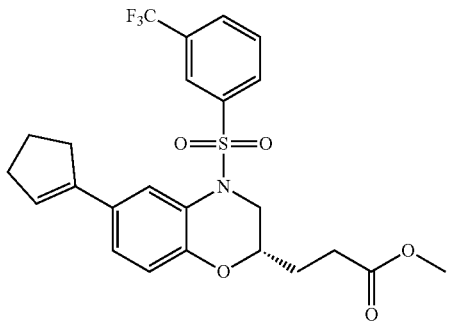 [SMILES: COC(=O)CC[C@H]1CN(S(=O)(=O)c2cccc(C(F)(F)F)c2)c2cc(C3=CCCC3)ccc2O1]

A mixture of (S)-methyl 3-(6-bromo-4-((3-(trifluoromethyl)phenyl)sulfonyl)-3,4-dihydro-2H-benzo[b][1,4]oxazin-2-yl)propanoate (150 mg, 0.29 mmol), tetrahydrofuran (5 mL), sodium carbonate (94 mg, 0.89 mmol), ethanol (1 mL), water (1 mL), 2-(cyclopent-1-en-1-yl)-4,4,5,5-tetramethyl-1,3,2-dioxaborolane (115 mg, 0.59 mmol), and tetrakis(triphenyl-phosphine)palladium(0) (34 mg, 0.03 mmol) was stirred for three hours at 90° C. The resulting mixture was concentrated, and the residue was purified by MPLC eluting with 25% ethyl acetate in petroleum ether to afford methyl (S)-3-(6-(cyclopent-1-en-1-yl)-4-((3-(trifluoromethyl)phenyl)sulfonyl)-3,4-dihydro-2H-benzo[b][1,4]oxazin-2-yl)propanoate (108 mg, 74%) as an oil.

Part II—Synthesis of (S)-3-(6-(cyclopent-1-en-1-yl)-4-((3-(trifluoromethyl)phenyl)sulfonyl)-3,4-dihydro-2H-benzo[b][1,4]oxazin-2-yl)propanoic acid

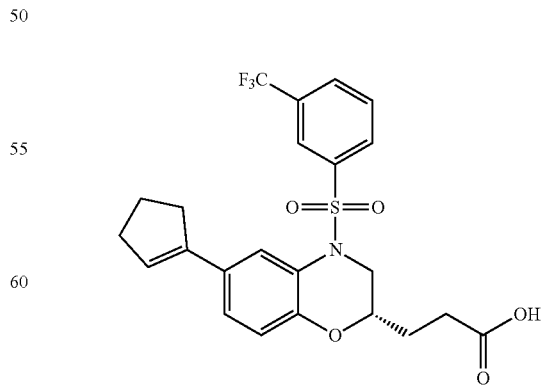

Based on the procedure in Example 42, (S)-3-(6-(cyclopent-1-en-1-yl)-4-((3-(trifluoromethyl)phenyl)sulfonyl)-3, 4-dihydro-2H-benzo[b][1,4]oxazin-2-yl)propanoic acid was prepared. $^1$H-NMR (400 MHz, CDCl$_3$) δ 7.98 (s, 1H), 7.79-7.82 (m, 3H), 7.57 (m, 1H), 6.76 (d, J=8.4 Hz, 1H), 6.10 (s, 1H), 4.31 (dd, J=14.4, 2.4 Hz, 1H), 3.51 (m, 1H), 3.22 (m, 1H), 2.63-2.68 (m, 2H), 2.48-2.59 (m, 4H), 1.99-2.12 (m, 2H), 1.76-1.95 (m, 2H). (ES, m/z): (M+H)$^+$482.

Example 193—Synthesis of (S)-3-(6-(cyclohex-1-en-1-yl)-4-((3-(trifluoromethyl)phenyl)sulfonyl)-3,4-dihydro-2H-benzo[b][1,4]oxazin-2-yl)propanoic acid

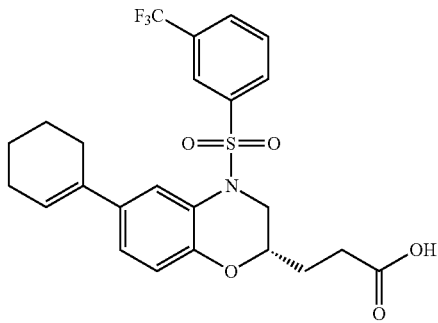 [SMILES: O=C(O)CC[C@H]1CN(S(=O)(=O)c2cccc(C(F)(F)F)c2)c2cc(C3=CCCCC3)ccc2O1]

Based on the procedure in Example 192, (S)-3-(6-(cyclohex-1-en-1-yl)-4-((3-(trifluoromethyl)phenyl)sulfonyl)-3,4-dihydro-2H-benzo[b][1,4]oxazin-2-yl)propanoic acid was prepared. $^1$H-NMR (400 MHz, CDCl$_3$) δ 7.98 (s, 1H), 7.77-7.81 (m, 3H), 7.52 (m, 1H), 7.11 (d, 1H), 6.72 (d, 1H), 6.06 (m, 1H), 4.31 (dd, 1H), 3.51 (m, 1H), 3.22 (dd, 1H), 2.43 (m, 2H), 2.37 (m, 2H), 2.21 (m, 2H), 1.88 (m, 1H), 1.75-1.83 (m, 3H), 1.65 (m, 2H). (ES, m/z): (M+H)$^+$496.

Example 194—Synthesis of (S)-3-(6-cyclohexyl-4-((3-(trifluoromethyl)phenyl)sulfonyl)-3,4-dihydro-2H-benzo[b][1,4]oxazin-2-yl)propanoic acid

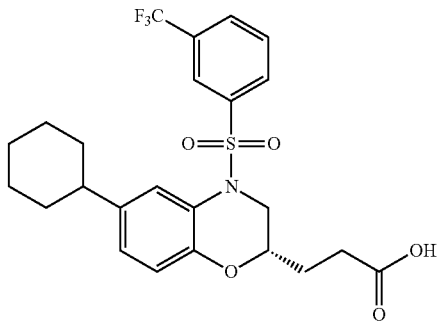 [SMILES: O=C(O)CC[C@H]1CN(S(=O)(=O)c2cccc(C(F)(F)F)c2)c2cc(C3CCCCC3)ccc2O1]

Part I—Synthesis of methyl (S)-3-(6-cyclohexyl-4-((3-(trifluoromethyl)phenyl)sulfonyl)-3,4-dihydro-2H-benzo[b][1,4]oxazin-2-yl)propanoate

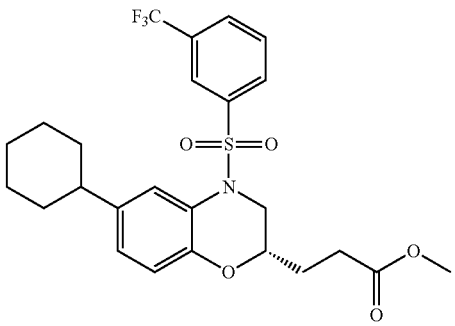 [SMILES: COC(=O)CC[C@H]1CN(S(=O)(=O)c2cccc(C(F)(F)F)c2)c2cc(C3CCCCC3)ccc2O1]

A mixture of methyl (S)-3-(6-(cyclohex-1-en-1-yl)-4-((3-(trifluoromethyl)phenyl)-sulfonyl)-3,4-dihydro-2H-benzo[b][1,4]oxazin-2-yl)propanoate (154 mg, 0.30 mmol), ethyl acetate (10 mL), and 10% palladium on carbon (200 mg) was stirred under an atmosphere of hydrogen for three hours at room temperature. Then, the mixture was filtered through Celite, and concentrated to afford methyl (S)-3-(6-cyclohexyl-4-((3-(trifluoromethyl)phenyl)sulfonyl)-3,4-dihydro-2H-benzo[b][1,4]oxazin-2-yl)propanoate (150 mg, 97%) as an oil.

Part II—Synthesis of (S)-3-(6-cyclohexyl-4-((3-(trifluoromethyl)phenyl)sulfonyl)-3,4-dihydro-2H-benzo[b][1,4]oxazin-2-yl)propanoic acid

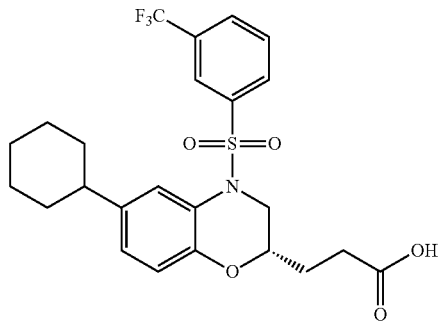 [SMILES: O=C(O)CC[C@H]1CN(S(=O)(=O)c2cccc(C(F)(F)F)c2)c2cc(C3CCCCC3)ccc2O1]

Based on the procedure in Example 42, (S)-3-(6-cyclohexyl-4-((3-(trifluoromethyl)phenyl)sulfonyl)-3,4-dihydro-2H-benzo[b][1,4]oxazin-2-yl)propanoic acid was prepared. $^1$H-NMR (400 MHz, CDCl$_3$) δ 7.93 (s, 1H), 7.81-7.85 (m, 2H), 7.67 (s, 1H), 7.61 (m, 1H), 6.94 (m, 1H), 6.73 (d, J=8.0 Hz, 1H), 4.31 (dd, J=14.4, 2.4 Hz, 1H), 3.55 (m, 1H), 3.23 (m, 1H), 2.47-2.57 (m, 3H), 1.76-1.96 (m, 7H), 1.36-1.44 (m, 4H), 1.30 (m, 1H). (ES, m/z): (M+H)$^+$498.

Example 195—Preparation of Additional Substituted 4-(aryl or heteroaryl)-sulfonyl)-3,4-dihydro-2H-benzo[b][1,4]oxazin-2-yl) Compounds Compounds in the Table 23 below were prepared based on experimental procedures described in Examples 29 and 70 and the detailed descripting utilizing (R)-6-oxotetrahydro-2H-pyran-2-carboxylic acid as the starting lactone.

TABLE 23

| No. | Structure | Name | Observed m/z |
|---|---|---|---|
| 195A | 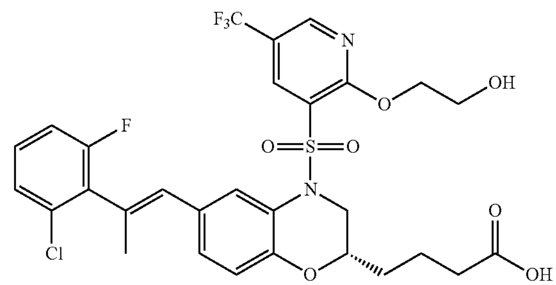 [SMILES: C/C(=C\c1ccc2c(c1)N(S(=O)(=O)c1cc(C(F)(F)F)cnc1OCCO)C[C@H](CCCC(=O)O)O2)c1c(F)cccc1Cl] | (S,E)-4-(6-(2-(2-chloro-6-fluorophenyl)prop-1-en-1-yl)-4-((2-(2-hydroxyethoxy)-5-(trifluoromethyl)pyridin-3-yl)sulfonyl)-3,4-dihydro-2H-benzo[b][1,4]oxazin-2-yl)butanoic acid | 659 (M + H)+ |
| 195B | 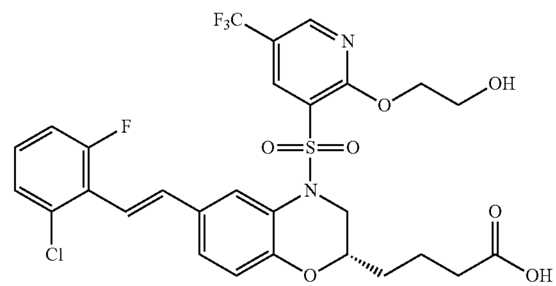 [SMILES: O=C(O)CCC[C@H]1CN(S(=O)(=O)c2cc(C(F)(F)F)cnc2OCCO)c2cc(/C=C/c3c(F)cccc3Cl)ccc2O1] | (S,E)-4-(6-(2-chloro-6-fluorostyryl)-4-((2-(2-hydroxyethoxy)-5-(trifluoromethyl)pyridin-3-yl)sulfonyl)-3,4-dihydro-2H-benzo[b][1,4]-oxazin-2-yl)butanoic acid | 645 (M + H)+ |
| 195C | 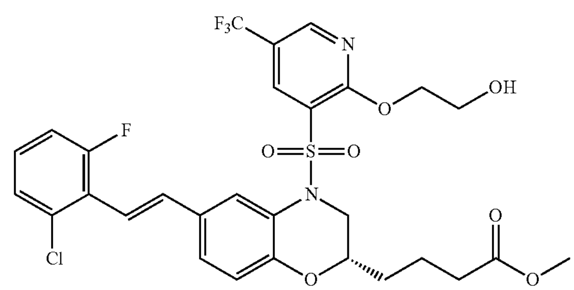 [SMILES: COC(=O)CCC[C@H]1CN(S(=O)(=O)c2cc(C(F)(F)F)cnc2OCCO)c2cc(/C=C/c3c(F)cccc3Cl)ccc2O1] | methyl (S,E)-4-(6-(2-chloro-6-fluorostyryl)-4-((2-(2-hydroxyethoxy)-5-(trifluoromethyl)pyridin-3-yl)sulfonyl)-3,4-dihydro-2H-benzo[b][1,4]-oxazin-2-yl)butanoate | 659 (M + H)+ |
| 195D | 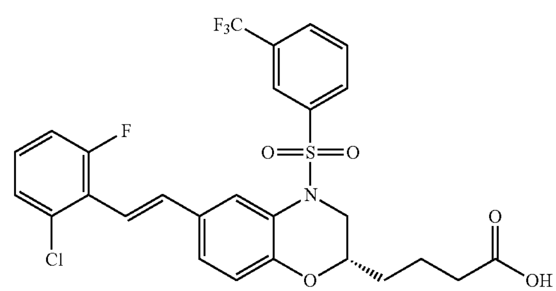 [SMILES: O=C(O)CCC[C@H]1CN(S(=O)(=O)c2cccc(C(F)(F)F)c2)c2cc(/C=C/c3c(F)cccc3Cl)ccc2O1] | (S,E)-4-(6-(2-chloro-6-fluorostyryl)-4-((3-(trifluoromethyl)phenyl)sulfonyl)-3,4-dihydro-2H-benzo[b][1,4]oxazin-2-yl)butanoic acid | 584 (M + H)+ |
| 195E | 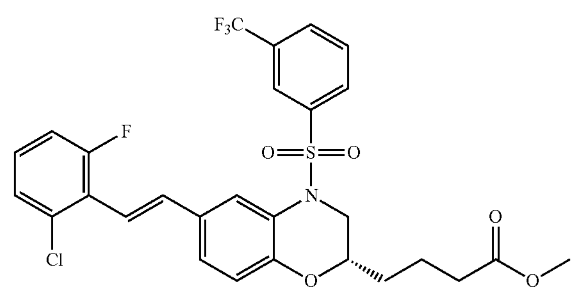 [SMILES: COC(=O)CCC[C@H]1CN(S(=O)(=O)c2cccc(C(F)(F)F)c2)c2cc(/C=C/c3c(F)cccc3Cl)ccc2O1] | methyl (S,E)-4-(6-(2-chloro-6-fluorostyryl)-4-((3-(trifluoromethyl)phenyl)sulfonyl)-3,4-dihydro-2H-benzo[b][1,4]oxazin-2-yl)butanoate | 598 (M + H)+ |

TABLE 23-continued

| No. | Structure | Name | Observed m/z |
|---|---|---|---|
| 195F | 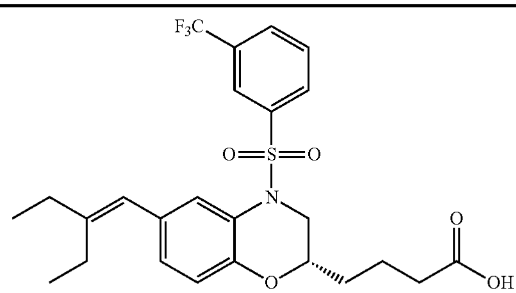 | (S)-4-(6-(2-ethylbut-1-en-1-yl)-4-((3-(trifluoromethyl)phenyl)-sulfonyl)-3,4-dihydro-2H-benzo[b][1,4]oxazin-2-yl)butanoic acid | 512 (M + H)+ |
| 195G | 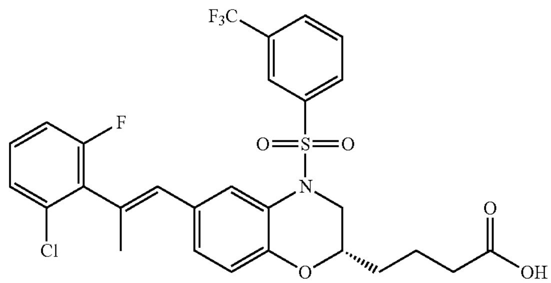 [SMILES: C/C(=C\c1ccc2c(c1)N(S(=O)(=O)c1cccc(C(F)(F)F)c1)C[C@H](CCCC(=O)O)O2)c1c(F)cccc1Cl] | (S,E)-4-(6-(2-(2-chloro-6-fluorophenyl)prop-1-en-1-yl)-4-((3-(trifluoromethyl)phenyl)-sulfonyl)-3,4-dihydro-2H-benzo[b][1,4]oxazin-2-yl)butanoic acid | 598 (M + H)+ |
| 195H | 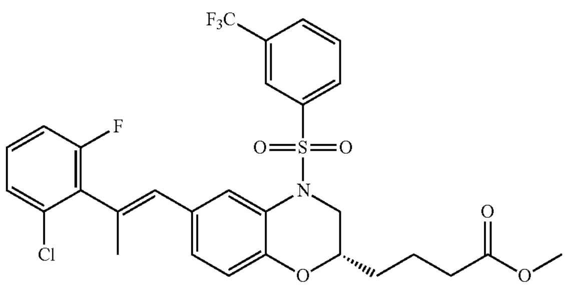 [SMILES: COC(=O)CCC[C@H]1CN(S(=O)(=O)c2cccc(C(F)(F)F)c2)c2cc(/C=C(\C)c3c(F)cccc3Cl)ccc2O1] | methyl (S,E)-4-(6-(2-(2-chloro-6-fluorophenyl)prop-1-en-1-yl)-4-((3-(trifluoromethyl)phenyl)-sulfonyl)-3,4-dihydro-2H-benzo[b][1,4]oxazin-2-yl)butanoate | 612 (M + H)+ |

Example 196-Biological Assays for Agonist Activity Towards RORγ

Exemplary compounds from the above Examples were tested for ability to increase RORγ activity using (i) a RORγ-Ligand Binding Domain (LBD) TR-FRET Assay, and (ii) a Gal4-RORγ Luciferase Reporter Assay in HEK-293T Cells. Assay procedures and results are described below.

Part I—Procedures for RORγ-Ligand Binding Domain TR-FRET Assay

HIS-tagged RORγ-LBD protein was expressed in SF9 cells using a baculovirus expression system. The lysate was diluted in assay buffer (50 mM Tris pH 7.0, 50 mM KCl, 1 mM EDTA, 0.1 mM DTT, 0.01% BSA) to obtain RORγ-LBD final concentration of ~3 nM in a 384-well assay plate (need to titrate for each batch of protein).

A stock of biotinylated-LXXLL peptide from coactivator SRC1 (Biotin-CPSSHSSLTERHKILHRLLQEGSPS) was prepared in assay buffer and added to each well (200 nM final concentration). A solution of Europium tagged anti-HIS antibody (0.6 nM final concentration) and APC-conjugated streptavidin (30 nM final concentration) were also added to each well. RORγ antagonist ursolic acid was also included at a final concentration of 2 μM. Compounds were diluted in DMSO and further diluted in assay buffer with a final DMSO concentration at 1%. The highest concentration of test compound analyzed was 10 μM.

The final assay mixture was incubated overnight at 4° C. or 2 hours at room temperature, and the fluorescence signal was measured on an Envision plate reader: (Excitation filter=340 nm; APC emission=665 nm; Europium emission=615 nm; dichroic mirror=D400/D630; delay time=100 μs, integration time=200 μs). 50% Effective concentration ($EC_{50}$) values for test compounds were calculated from the quotient of the fluorescence signal at 665 nm divided by the fluorescence signal at 615 nm. The quotient of the fluorescence signals in the absence of ursolic acid or test compound is set as 100. Max Response is defined as the upper plateau in the signal as determined by line-fit using a 4-parameter logistic model in PRISM (GraphPad).

Part II—Procedures for Gal4-RORγ Luciferase Reporter Assay in HEK-293T Cells

Transfection of HEK-293 Cells

In the following protocol, HEK-293 cells were transfected with a construct comprising the Gal4 DNA binding domain fused to the ligand binding domain of RORγ (Gal4-RORγ-LBD) in a pcDNA3.1neo plasmid, and also with a reporter construct comprising pGL4.31 Gal4-luciferase (Promega). Control cells were prepared similarly using empty pcDNA3.1neo and pGL4.31 vectors.

Trans-IT reagent (Mirus, 60 µL) at room temperature was added drop wise to OptiMEM (Invitrogen, 1.5 ml). This reagent mixture was mixed by inversion then incubated for 5 to 30 minutes at room temperature. It then was added to a solution of both expression vectors (5 µg each), mixed, and incubated at room temperature for about 20 minutes. HEK-293 cells were harvested from incubation flasks by removing the media, treating with TrypLE Express (Invitrogen), and incubating until the cells detached from the bottom of the flask (approximately 2-5 minutes). 10 Million cells were collected by centrifugation and re-suspended in 10 mL of Dulbecco's Modified Eagle Medium, High Glucose (DMEM, Invitrogen) containing 10% Fetal Bovine Serum and 100 IU each of penicillin and streptomycin. The re-suspended cells and the transfection mixture were added to a T75 flask, mixed and incubated overnight at 37° C. and 5% $CO_2$.

Assay for RORγ Activity

The cells were harvested as described above, counted, and centrifuged to obtain the desired number of cells, then re-suspended in complete growth media at $0.75 \times 10^6$ cells/mL. The RORγ antagonist, ursolic acid, was added to the cells at a final concentration of 2 µM. Cells were plated at 20 µL of cell suspension/well (10,000-15,000 cells/well) in white tissue culture treated 384 well plates. Test compounds were dissolved at 10 mM in DMSO then diluted into complete growth medium to 5× the final intended test concentration. These drug stock solutions, 5 µL/well were added to the tissue culture plate. The final DMSO concentration was 0.2%. The plates were briefly centrifuged then incubated overnight at 37° C. and 5% $CO_2$. To conduct the assay, the tissue culture plates were allowed to equilibrate to room temperature and One-Glo luciferase reagent (Promega, 25 µL/well) was added. The plates were briefly centrifuged then incubated at room temperature for 10 minutes. The luciferase intensity was read on an Envision plate reader (Perkin Elmer). RORγ activity was determined relative to controls and plotted as a function of test compound concentration using PRISM (GraphPad) to determine a 50% effective concentration ($EC_{50}$). The luciferase signal in the absence of ursolic acid or test compound is defined at 100. The Max Response is the upper plateau in the signal as determined by line-fit using a 4-parameter logistic model in PRISM (GraphPad).

Part III—Results

Experimental results are provided in Tables 24-26 below. The symbol "++++" indicates an $EC_{50}$ less than 0.5 µM. The symbol "+++" indicates an $EC_{50}$ in the range of 0.5 µM to 5 µM. The symbol "++" indicates an $EC_{50}$ in the range of greater than 5 µM to 10 µM. The symbol "+" indicates an $EC_{50}$ greater than 10 µM. The symbol "N/A" indicates that no data was available. The symbol "**" indicates a value greater than 200. The symbol "*" indicates a value in the range of greater than 150 to 200. The symbol "**" indicates a value in the range of greater than 90 to 150. The symbol "*" indicates a value in the range of 30 to 90.

TABLE 24

Assay Results for Sulfonamido Compounds.

| Compound Structure | TR-FRET Assay | | Gal4-RORγ Assay | |
|---|---|---|---|---|
| | $EC_{50}$ | Max Response | $EC_{50}$ | Max Response |
| [structure] | ++++ | *** | +++ | ** |
| [structure] | + | ** | N/A | N/A |

TABLE 24-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (4-tert-butylbenzyl ether / 3-CF3 phenylsulfonyl tetrahydroquinoline-3-carboxylic acid) | + | ** | N/A | N/A |
| (3-fluoro-4-trifluoromethylbenzyl ether / 3-CF3 phenylsulfonyl tetrahydroquinoline-3-carboxylic acid) | ++ | ** | N/A | N/A |
| (3-fluoro-4-methylbenzyl ether / 3-CF3 phenylsulfonyl tetrahydroquinoline-3-carboxylic acid) | + | ** | N/A | N/A |
| (2,6-dichlorobenzyl ether / 3-CF3 phenylsulfonyl tetrahydroquinoline-3-carboxylic acid) | ++++ | ** | N/A | N/A |

TABLE 24-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (structure) | ++++ | ** | N/A | N/A |
| (structure) | ++++ | ** | N/A | N/A |
| (structure) | ++++ | ** | N/A | N/A |
| (structure) | ++++ | ** | N/A | N/A |

TABLE 24-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (structure) | ++++ | *** | N/A | N/A |
| (structure) | ++++ | ** | N/A | N/A |
| (structure) | ++++ | ** | N/A | N/A |
| (structure) | ++++ | *** | N/A | N/A |

TABLE 24-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (structure: 1-ethyl-5-chloro-pyrazole-4-sulfonyl on tetrahydroquinoline-3-carboxylic acid with 2-chloro-6-fluorophenyl propenyl substituent) | ++++ | *** | N/A | N/A |
| (structure: 1-ethyl-5-ethoxy-pyrazole-4-sulfonyl on tetrahydroquinoline-3-carboxylic acid with 2-chloro-6-fluorobenzyloxy substituent) | ++++ | **** | + | **** |
| (structure: 1-difluoromethyl-5-methyl-pyrazole-4-sulfonyl on tetrahydroquinoline-3-carboxylic acid with 2-chloro-6-fluorobenzyloxy substituent) | +++ | **** | N/A | N/A |
| (structure: 4-fluoro-3-methoxyphenyl-sulfonyl on tetrahydroquinoline-3-carboxylic acid with 2-chloro-6-fluorobenzyloxy substituent) | ++++ | **** | N/A | N/A |

TABLE 24-continued

Assay Results for Sulfonamido Compounds.

| Compound Structure | TR-FRET Assay | | Gal4-RORγ Assay | |
| --- | --- | --- | --- | --- |
| | EC$_{50}$ | Max Response | EC$_{50}$ | Max Response |
| (structure) | ++++ | **** | N/A | N/A |
| (structure) | ++++ | *** | +++ | *** |
| (structure) | ++++ | **** | N/A | N/A |
| (structure) | ++++ | **** | N/A | N/A |

TABLE 24-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (structure) | ++++ | **** | N/A | N/A |
| (structure) | ++++ | **** | N/A | N/A |
| (structure) | ++++ | **** | N/A | N/A |
| (structure) | ++++ | *** | +++ | *** |

TABLE 24-continued
Assay Results for Sulfonamido Compounds.
| | TR-FRET Assay | | Gal4-RORγ Assay | |
|---|---|---|---|---|
| Compound Structure | EC$_{50}$ | Max Response | EC$_{50}$ | Max Response |
| 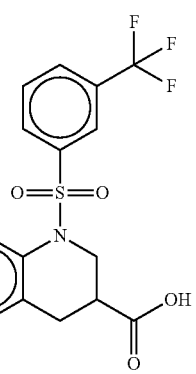 | ++++ | * | +++ | * |
| 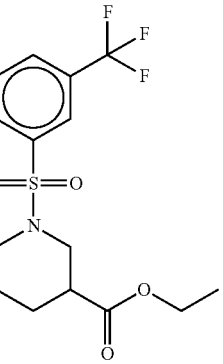 | ++++ | ** | +++ |  |
| 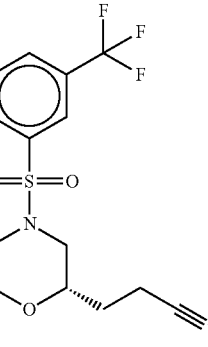 | ++++ | ** | ++++ | * |
| 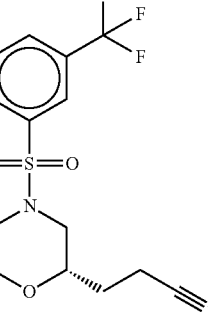 | ++++ | ** | ++++ | * |

TABLE 24-continued
Assay Results for Sulfonamido Compounds.
| Compound Structure | TR-FRET Assay | | Gal4-RORγ Assay | |
|---|---|---|---|---|
| | EC$_{50}$ | Max Response | EC$_{50}$ | Max Response |
| 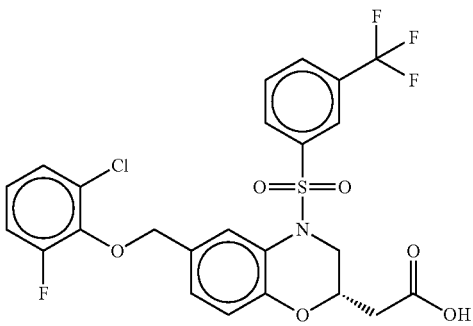 | ++++ | ** | ++++ |  |
| 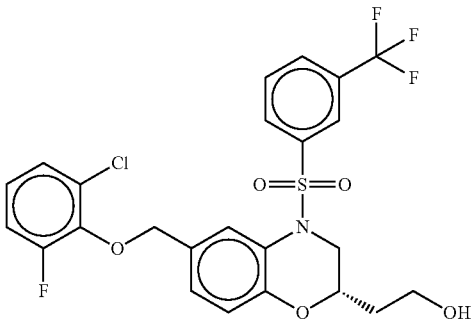 | ++++ | ** | +++ | * |
| 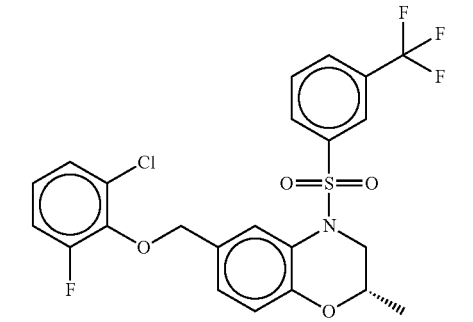 | ++++ | ** | +++ |  |
| 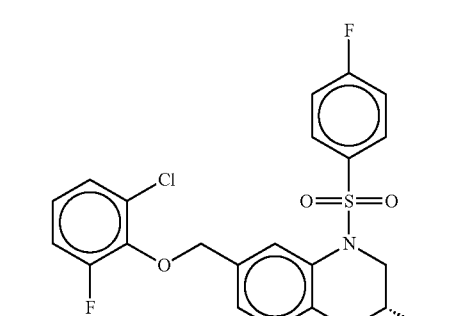 | ++++ | ** | ++ |  |

TABLE 25

Assay Results for Additional Compounds.

| Title Compound from Example No. | TR-FRET Assay EC$_{50}$ | TR-FRET Assay Max Response | Gal4-ROR$\gamma$ Assay EC$_{50}$ | Gal4-ROR$\gamma$ Assay Max Response |
|---|---|---|---|---|
| 9D | ++++ | **** | N/A | N/A |
| 9E | ++++ | **** | N/A | N/A |
| 15B | ++++ | **** | N/A | N/A |
| 15C | ++++ | **** | +++ | ** |
| 15D | ++++ | **** | +++ | ** |
| 15E | +++ | ** | N/A | N/A |
| 15F | ++++ | *** | +++ | ** |
| 15G | ++++ | *** | +++ | ** |
| 15H | ++++ | *** | +++ | ** |
| 15I | ++++ | ** | N/A | N/A |
| 15J | ++++ | ** | ++++ | ** |
| 15K | ++++ | ** | N/A | N/A |
| 15L | ++++ | ** | +++ | ** |
| 15M | ++++ | ** | +++ | ** |
| 15N | ++++ | ** | +++ | * |
| 15O | ++++ | *** | +++ | ** |
| 15P | ++++ | ** | N/A | N/A |
| 15Q | ++++ | ** | +++ | ** |
| 15R | ++++ | * | N/A | N/A |
| 15S | ++++ | ** | ++ | * |
| 15T | +++ | ** | N/A | N/A |
| 20 | ++++ | *** | ++++ | ** |
| 21 | ++++ | **** | N/A | N/A |
| 22 | ++++ | *** | +++ | ** |
| 24 | ++++ | **** | N/A | N/A |
| 25A | ++++ | *** | N/A | N/A |
| 25B | ++++ | ** | N/A | N/A |
| 25C | ++++ | ** | ++++ | *** |
| 25D | ++++ | ** | N/A | N/A |
| 25E | ++++ | ** | +++ | ** |
| 25J | ++++ | *** | +++ | ** |
| 25K | ++++ | ** | N/A | N/A |
| 25L | ++++ | * | N/A | N/A |
| 25M | ++++ | ** | N/A | N/A |
| 25N | ++++ | ** | N/A | N/A |
| 25O | ++++ | *** | N/A | N/A |
| 25P | ++++ | **** | ++++ | ** |
| 25Q | ++++ | ** | ++++ | ** |
| 25R | ++++ | ** | ++++ | ** |
| 25S | ++++ | ** | N/A | N/A |
| 25T | ++++ | ** | N/A | N/A |
| 25U | + | N/A | N/A | N/A |
| 25V | +++ | ** | N/A | N/A |
| 25W | ++++ | *** | ++++ | ** |
| 26 | ++++ | *** | ++++ | ** |
| 27 | ++++ | *** | ++++ | ** |
| 28A | ++++ | *** | N/A | N/A |
| 28B | ++++ | * | N/A | N/A |
| 28C | ++++ | ** | N/A | N/A |
| 28D | ++++ | *** | N/A | N/A |
| 28E | ++++ | * | N/A | N/A |
| 28F | ++++ | **** | N/A | N/A |
| 28G | ++++ | ** | N/A | N/A |
| 29 | ++++ | *** | ++++ | ** |
| 30 | ++++ | **** | +++ | *** |
| 31 | ++++ | *** | +++ | ** |
| 32 | ++++ | ** | ++ | *** |
| 33 | ++++ | *** | +++ | ** |
| 34 | ++++ | ** | +++ | ** |
| 35 | ++++ | *** | +++ | ** |
| 36A | N/A | N/A | ++++ | ** |
| 36B | N/A | N/A | + | N/A |
| 36C | ++++ | ** | +++ | * |
| 37 | ++++ | ** | ++++ | ** |
| 38A | ++++ | ** | +++ | * |
| 38B | ++++ | ** | +++ | * |
| 38C | N/A | N/A | +++ | ** |
| 41 | ++++ | *** | ++++ | ** |
| 42 | ++++ | *** | +++ | ** |
| 43 | ++++ | *** | ++++ | ** |
| 44 | ++++ | *** | +++ | *** |
| 45 | ++++ | ** | +++ | * |
| 46 | ++++ | ** | ++++ | ** |
| 47 | ++++ | ** | ++ | ** |
| 48 | +++ | ** | ++++ | * |
| 49 | ++++ | *** | +++ | ** |
| 50 | ++++ | *** | ++++ | ** |
| 51 | ++++ | *** | ++++ | ** |
| 52 | ++++ | *** | +++ | **** |
| 53 | ++++ | ** | +++ | ** |
| 54 | ++++ | ** | +++ | ** |
| 55 | ++++ | ** | ++++ | ** |
| 56 | ++++ | ** | + | N/A |
| 57 | ++++ | ** | + | N/A |
| 58 | ++++ | ** | +++ | ** |
| 59 | ++++ | *** | +++ | ** |
| 60 | ++++ | *** | +++ | *** |
| 61 | ++++ | *** | +++ | ** |
| 62 | ++++ | *** | +++ | ** |
| 63 | ++++ | *** | +++ | ** |
| 64 | ++++ | ** | +++ | ** |
| 65 | N/A | N/A | +++ | ** |
| 66 | N/A | N/A | ++++ | ** |
| 67 | ++++ | **** | +++ | ** |
| 68 | ++++ | **** | +++ | ** |
| 69 | ++++ | *** | + | N/A |
| 70 | ++++ | **** | ++++ | ** |
| 71 | ++++ | **** | ++++ | ** |
| 72 | ++++ | ** | ++++ | * |
| 73 | ++++ | ** | ++++ | ** |
| 74 | ++++ | *** | +++ | ** |
| 75 | ++++ | *** | +++ | *** |
| 76 | ++++ | **** | +++ | ** |
| 77 | ++++ | **** | +++ | ** |
| 78 | +++ | **** | +++ | ** |
| 79 | ++++ | *** | +++ | ** |
| 80 | ++++ | *** | +++ | ** |
| 81 | ++++ | **** | ++++ | *** |
| 82 | ++++ | **** | ++++ | *** |
| 83 | ++++ | **** | +++ | *** |
| 84 | ++++ | **** | ++++ | *** |
| 85 | ++++ | **** | ++++ | ** |
| 86A | ++++ | *** | +++ | ** |
| 86AA | ++++ | ** | + | *** |
| 86AB | ++++ | *** | +++ | ** |
| 86AC | ++++ | * | + | * |
| 86AD | ++++ | * | +++ | * |
| 86AE | N/A | N/A | ++++ | *** |
| 86AF | ++++ | *** | +++ | *** |
| 86AG | ++++ | ** | ++++ | ** |
| 86AH | ++++ | *** | +++ | ** |
| 86AI | N/A | N/A | ++++ | ** |
| 86AJ | N/A | N/A | ++++ | * |
| 86AK | ++++ | *** | ++++ | ** |
| 86AL | ++++ | *** | +++ | ** |
| 86AM | ++++ | ** | +++ | ** |
| 86AN | ++++ | ** | +++ | ** |
| 86AO | ++++ | *** | ++++ | ** |
| 86AP | ++++ | *** | ++++ | ** |
| 86AQ | N/A | N/A | ++++ | ** |
| 86AR | ++++ | *** | +++ | ** |
| 86AS | ++++ | **** | ++++ | ** |
| 86AT | ++++ | **** | ++++ | ** |
| 86AU | ++++ | ** | +++ | ** |
| 86AW | ++++ | **** | ++++ | ** |
| 86AX | ++++ | **** | +++ | ** |
| 86AY | ++++ | **** | ++++ | ** |
| 86AZ | ++++ | **** | +++ | ** |
| 86B | ++++ | *** | ++++ | *** |
| 86C | ++++ | *** | ++++ | *** |
| 86D | ++++ | *** | ++++ | ** |
| 86E | ++++ | *** | +++ | ** |
| 86F | ++++ | *** | ++++ | ** |
| 86G | ++++ | *** | +++ | ** |
| 86H | ++++ | *** | +++ | **** |
| 86I | ++++ | **** | +++ | ** |

TABLE 25-continued

Assay Results for Additional Compounds.

| Title Compound from Example No. | TR-FRET Assay | | Gal4-RORγ Assay | |
|---|---|---|---|---|
| | EC$_{50}$ | Max Response | EC$_{50}$ | Max Response |
| 86J | ++++ | *** | ++++ | ** |
| 86K | ++++ | *** | ++++ | ** |
| 86L | ++++ | *** | ++++ | ** |
| 86M | ++++ | *** | +++ | **** |
| 86N | ++++ | *** | ++++ | ** |
| 86O | ++++ | *** | +++ | ** |
| 86P | ++++ | *** | +++ | *** |
| 86Q | ++++ | *** | ++++ | ** |
| 86R | ++++ | *** | ++++ | ** |
| 86S | ++++ | *** | +++ | ** |
| 86T | ++++ | *** | +++ | ** |
| 86U | ++++ | *** | +++ | * |
| 86V | ++++ | ** | +++ | ** |
| 86W | ++++ | *** | + | N/A |
| 86X | ++++ | ** | +++ | * |
| 86Y | ++++ | *** | +++ | ** |
| 86Z | ++++ | *** | ++++ | ** |
| 87 | ++++ | **** | +++ | ** |
| 88 | ++++ | **** | +++ | ** |
| 89A | ++++ | *** | +++ | *** |
| 89AA | +++ | * | + | N/A |
| 89AB | +++ | * | + | N/A |
| 89AC | ++++ | **** | +++ | ** |
| 89AE | ++++ | **** | +++ | ** |
| 89AF | ++++ | **** | + | N/A |
| 89AG | ++++ | **** | ++++ | ** |
| 89AH | ++++ | **** | ++++ | ** |
| 89AI | ++++ | **** | +++ | ** |
| 89AJ | ++++ | **** | +++ | ** |
| 89AK | ++++ | **** | +++ | * |
| 89AL | ++++ | *** | +++ | *** |
| 89AM | ++++ | ** | + | N/A |
| 89AN | +++ | **** | + | N/A |
| 89AO | ++++ | **** | +++ | ** |
| 89AP | ++++ | **** | +++ | ** |
| 89AQ | ++++ | **** | +++ | ** |
| 89AR | ++++ | **** | +++ | *** |
| 89AS | ++++ | **** | + | N/A |
| 89AT | ++++ | **** | +++ | ** |
| 89AU | ++++ | **** | ++++ | ** |
| 89AV | ++++ | **** | ++++ | ** |
| 89AW | ++++ | **** | +++ | ** |
| 89AX | ++++ | **** | +++ | ** |
| 89AY | ++++ | **** | +++ | ** |
| 89AZ | ++++ | **** | ++++ | *** |
| 89B | ++++ | *** | +++ | *** |
| 89BA | ++++ | *** | +++ | * |
| 89BB | ++++ | **** | +++ | * |
| 89BC | ++++ | *** | +++ | * |
| 89BD | ++++ | **** | + | N/A |
| 89BE | +++ | ** | + | N/A |
| 89BF | +++ | **** | + | N/A |
| 89BG | ++++ | *** | +++ | ** |
| 89BH | ++++ | ** | + | N/A |
| 89BI | ++++ | *** | ++++ | ** |
| 89BJ | ++++ | *** | +++ | ** |
| 89BK | ++++ | *** | ++++ | ** |
| 89BL | + | N/A | N/A | N/A |
| 89BM | +++ | ** | N/A | N/A |
| 89BN | ++++ | ** | +++ | ** |
| 89BO | ++++ | ** | +++ | ** |
| 89BP | ++++ | ** | + | N/A |
| 89BQ | ++++ | ** | +++ | * |
| 89BR | + | N/A | N/A | N/A |
| 89BS | ++++ | * | N/A | N/A |
| 89BT | + | N/A | N/A | N/A |
| 89BU | ++ | ** | N/A | N/A |
| 89BV | + | N/A | N/A | N/A |
| 89BW | ++++ | ** | + | N/A |
| 89BX | + | N/A | N/A | N/A |
| 89BY | + | N/A | N/A | N/A |
| 89BZ | + | N/A | N/A | N/A |
| 89C | +++ | * | ++ | * |
| 89CA | ++++ | ** | + | N/A |
| 89CB | N/A | N/A | +++ | * |
| 89CC | + | **** | + | N/A |
| 89CD | ++++ | ** | +++ | N/A |
| 89CE | ++++ | *** | +++ | N/A |
| 89CF | +++ | ** | + | N/A |
| 89CG | ++++ | *** | ++ | N/A |
| 89CH | ++++ | ** | + | N/A |
| 89CI | + | N/A | + | N/A |
| 89CJ | + | N/A | + | N/A |
| 89CK | ++++ | ** | +++ | ** |
| 89CL | +++ | *** | N/A | N/A |
| 89CM | ++++ | *** | +++ | ** |
| 89CN | +++ | **** | N/A | N/A |
| 89CO | ++++ | *** | +++ | ** |
| 89CP | ++++ | *** | ++++ | ** |
| 89CQ | ++++ | *** | +++ | * |
| 89CR | ++++ | **** | ++++ | ** |
| 89CS | ++++ | **** | ++++ | *** |
| 89CT | ++++ | **** | ++++ | *** |
| 89CU | ++++ | **** | +++ | ** |
| 89CV | ++++ | **** | ++++ | ** |
| 89CW | ++++ | **** | +++ | * |
| 89CX | ++++ | *** | +++ | ** |
| 89CY | ++++ | **** | +++ | ** |
| 89CZ | ++++ | **** | +++ | ** |
| 89D | ++++ | **** | +++ | *** |
| 89DA | + | N/A | + | N/A |
| 89DB | + | N/A | + | N/A |
| 89DC | + | N/A | + | N/A |
| 89DE | ++++ | ** | + | N/A |
| 89DF | N/A | N/A | + | N/A |
| 89DG | N/A | N/A | + | N/A |
| 89DH | ++++ | ** | +++ | * |
| 89DI | ++++ | ** | + | N/A |
| 89DJ | ++++ | **** | +++ | ** |
| 89DK | ++++ | **** | +++ | *** |
| 89DL | ++++ | **** | +++ | *** |
| 89DM | ++++ | **** | ++++ | ** |
| 89DN | ++++ | **** | +++ | ** |
| 89DO | ++++ | **** | ++++ | ** |
| 89DP | ++++ | **** | ++++ | ** |
| 89DQ | ++++ | **** | ++++ | ** |
| 89DS | + | N/A | N/A | N/A |
| 89DT | ++++ | **** | +++ | * |
| 89DU | ++++ | **** | +++ | ** |
| 89DV | ++++ | **** | +++ | *** |
| 89DW | + | N/A | + | N/A |
| 89DX | +++ | *** | + | N/A |
| 89DY | ++++ | *** | +++ | ** |
| 89DZ | +++ | *** | + | ** |
| 89E | + | N/A | + | N/A |
| 89EA | ++++ | **** | ++++ | ** |
| 89EB | ++++ | **** | ++++ | ** |
| 89EC | ++++ | **** | +++ | ** |
| 89ED | ++++ | **** | ++++ | ** |
| 89EE | ++++ | **** | +++ | ** |
| 89EF | ++++ | **** | ++++ | *** |
| 89EG | ++++ | **** | +++ | *** |
| 89EH | ++++ | **** | ++++ | ** |
| 89EI | ++++ | **** | ++++ | ** |
| 89EJ | ++++ | **** | ++++ | ** |
| 89EK | ++++ | **** | +++ | *** |
| 89EL | ++++ | **** | ++++ | ** |
| 89EM | ++++ | **** | ++++ | *** |
| 89EN | ++++ | **** | ++++ | *** |
| 89EP | ++++ | **** | ++++ | *** |
| 89EQ | ++++ | **** | ++++ | ** |
| 89ER | ++++ | **** | ++++ | *** |
| 89ES | ++++ | **** | +++ | *** |
| 89ET | ++++ | **** | ++++ | ** |
| 89EU | ++++ | **** | +++ | *** |
| 89EV | ++++ | **** | ++ | ** |

TABLE 25-continued

Assay Results for Additional Compounds.

| Title Compound from Example No. | TR-FRET Assay | | Gal4-RORγ Assay | |
|---|---|---|---|---|
| | EC$_{50}$ | Max Response | EC$_{50}$ | Max Response |
| 89EW | ++++ | **** | ++++ | ** |
| 89EX | ++++ | **** | +++ | * |
| 89EY | ++++ | *** | +++ | *** |
| 89EZ | ++++ | **** | ++++ | ** |
| 89FA | ++++ | *** | ++++ | *** |
| 89FB | ++++ | *** | +++ | ** |
| 89FC | ++++ | *** | +++ | ** |
| 89FD | ++++ | *** | +++ | **** |
| 89FE | ++++ | *** | ++++ | ** |
| 89FF | ++++ | **** | +++ | *** |
| 89FG | ++++ | *** | ++++ | ** |
| 89FH | ++++ | *** | ++++ | ** |
| 89FI | ++++ | **** | ++++ | *** |
| 89FJ | ++++ | **** | +++ | ** |
| 89FK | ++++ | *** | + | N/A |
| 89FL | +++ | *** | N/A | N/A |
| 89FM | ++++ | *** | +++ | ** |
| 89FN | ++++ | **** | +++ | ** |
| 89G | +++ | *** | + | N/A |
| 89H | ++++ | *** | + | N/A |
| 89I | + | N/A | + | N/A |
| 89J | +++ | ** | + | N/A |
| 89K | ++++ | *** | +++ | ** |
| 89L | ++++ | **** | +++ | ** |
| 89M | + | N/A | + | N/A |
| 89N | ++ | ** | + | N/A |
| 89O | ++++ | *** | + | N/A |
| 89P | +++ | *** | + | N/A |
| 89Q | + | N/A | + | N/A |
| 89R | ++ | ** | + | N/A |
| 89S | +++ | * | + | N/A |
| 89T | + | N/A | + | N/A |
| 89W | ++ | ** | + | N/A |
| 89X | +++ | **** | + | N/A |
| 90 | ++++ | *** | +++ | *** |
| 91 | ++++ | *** | +++ | *** |
| 92 | ++++ | ** | +++ | ** |
| 93 | ++++ | **** | +++ | ** |
| 94 | ++++ | **** | +++ | *** |
| 95A | +++ | **** | N/A | N/A |
| 95AA | ++++ | **** | +++ | **** |
| 95AB | ++++ | ** | +++ | ** |
| 95AC | + | N/A | + | N/A |
| 95AD | ++++ | ** | +++ | * |
| 95B | ++++ | **** | +++ | * |
| 95C | ++++ | *** | +++ | *** |
| 95D | ++++ | *** | +++ | ** |
| 95E | ++++ | **** | ++++ | *** |
| 95F | ++++ | *** | +++ | ** |
| 95G | ++++ | **** | +++ | *** |
| 95H | ++++ | ** | +++ | ** |
| 95I | N/A | N/A | +++ | ** |
| 95J | ++++ | **** | +++ | **** |
| 95K | ++++ | *** | +++ | *** |
| 95L | ++++ | **** | ++++ | **** |
| 95M | ++++ | **** | +++ | *** |
| 95N | ++++ | **** | +++ | **** |
| 95O | ++++ | *** | +++ | ** |
| 95P | ++++ | *** | +++ | ** |
| 95Q | ++++ | *** | ++++ | **** |
| 95R | ++++ | *** | ++++ | *** |
| 95S | ++++ | *** | ++++ | ** |
| 95T | ++++ | *** | +++ | ** |
| 95U | ++++ | *** | +++ | ** |
| 95V | +++ | **** | N/A | N/A |
| 95W | ++++ | ** | +++ | * |
| 95X | +++ | ** | N/A | N/A |
| 95Y | ++++ | **** | +++ | *** |
| 95Z | ++++ | **** | +++ | *** |
| 96 | ++++ | *** | ++++ | N/A |
| 97 | ++++ | *** | ++++ | ** |
| 98 | ++++ | *** | ++++ | ** |
| 99 | ++++ | *** | +++ | ** |
| 100 | ++++ | *** | +++ | ** |
| 101 | ++++ | *** | + | N/A |
| 102 | ++++ | ** | ++++ | * |
| 103 | ++++ | *** | ++++ | ** |
| 104 | ++++ | *** | + | N/A |
| 105 | ++++ | ** | ++++ | ** |
| 106 | ++++ | *** | ++++ | ** |
| 107 | ++++ | ** | +++ | ** |
| 108 | ++++ | ** | ++++ | * |
| 109A | ++++ | *** | ++++ | * |
| 109B | ++++ | ** | ++++ | * |
| 109C | ++++ | ** | ++++ | ** |
| 109D | ++++ | *** | +++ | ** |
| 109E | ++++ | **** | +++ | ** |
| 109F | ++++ | *** | +++ | ** |
| 110 | ++++ | *** | +++ | ** |
| 111 | ++++ | *** | +++ | ** |
| 112 | ++++ | *** | ++++ | ** |
| 113 | ++++ | *** | ++++ | ** |
| 114 | ++++ | *** | ++++ | ** |
| 115 | ++++ | *** | ++++ | * |
| 116A | ++++ | *** | ++++ | ** |
| 116B | ++++ | *** | ++++ | * |
| 116C | ++++ | *** | +++ | ** |
| 116D | ++++ | *** | ++++ | ** |
| 116E | ++++ | *** | ++++ | ** |
| 116F | ++++ | *** | +++ | * |
| 116G | ++++ | *** | ++++ | * |
| 116H | ++++ | *** | ++++ | ** |
| 116I | ++++ | *** | +++ | ** |
| 116J | ++++ | *** | +++ | *** |
| 116K | ++++ | *** | +++ | ** |
| 116L | ++++ | *** | N/A | N/A |
| 116M | +++ | *** | N/A | N/A |
| 117 | ++++ | *** | +++ | ** |
| 118 | ++++ | *** | +++ | ** |
| 119A | ++++ | **** | ++++ | ** |
| 119B | ++++ | *** | +++ | ** |
| 119C | ++++ | *** | +++ | ** |
| 119D | ++++ | *** | ++++ | ** |
| 119E | ++++ | *** | +++ | ** |
| 119F | ++++ | *** | + | N/A |
| 119G | ++++ | *** | ++++ | * |
| 119H | ++++ | *** | ++++ | ** |
| 120 | ++++ | *** | ++++ | ** |
| 121A | ++++ | *** | ++++ | ** |
| 121B | ++++ | ** | ++++ | ** |
| 121C | ++++ | **** | ++++ | ** |
| 122 | ++++ | *** | ++++ | ** |
| 123 | ++++ | ** | +++ | ** |
| 124 | ++++ | *** | +++ | ** |
| 125 | ++++ | *** | ++++ | ** |
| 126 | ++++ | ** | ++++ | ** |
| 127 | ++++ | *** | ++++ | ** |
| 127A | ++++ | **** | ++++ | ** |
| 127B | ++++ | **** | ++++ | ** |
| 127C | ++++ | **** | ++++ | ** |
| 127D | ++++ | **** | ++++ | ** |
| 127E | ++++ | *** | ++++ | * |
| 127F | ++++ | **** | +++ | ** |
| 127G | ++++ | **** | +++ | * |
| 127H | ++++ | *** | ++++ | ** |
| 127I | ++++ | *** | +++ | ** |
| 127J | ++++ | *** | ++++ | ** |
| 127K | N/A | N/A | N/A | ** |
| 127L | N/A | N/A | N/A | * |
| 127M | N/A | N/A | ++++ | ** |
| 127N | N/A | N/A | ++++ | ** |
| 128 | ++++ | **** | ++++ | ** |
| 129A | ++++ | **** | ++++ | ** |
| 129B | ++++ | **** | ++++ | ** |
| 129C | ++++ | **** | ++++ | ** |
| 129D | ++++ | **** | ++++ | ** |

TABLE 25-continued

Assay Results for Additional Compounds.

| Title Compound from Example No. | TR-FRET Assay EC$_{50}$ | TR-FRET Assay Max Response | Gal4-RORγ Assay EC$_{50}$ | Gal4-RORγ Assay Max Response |
|---|---|---|---|---|
| 129E | ++++ | **** | +++ | ** |
| 129F | ++++ | *** | ++++ | *** |
| 129G | ++++ | **** | ++++ | ** |
| 129H | ++++ | *** | ++++ | *** |
| 129I | ++++ | *** | ++++ | ** |
| 129J | ++++ | **** | +++ | *** |
| 129K | ++++ | *** | +++ | ** |
| 129L | ++++ | *** | ++++ | * |
| 129M | ++++ | *** | +++ | ** |
| 129N | ++++ | *** | ++++ | ** |
| 129O | ++++ | *** | ++++ | ** |
| 129P | N/A | N/A | ++++ | *** |
| 130 | ++++ | *** | +++ | ** |
| 131 | ++++ | *** | ++++ | ** |
| 132 | ++++ | **** | +++ | *** |
| 133 | ++++ | **** | ++++ | * |
| 134 | ++++ | **** | ++++ | *** |
| 135A | ++++ | *** | +++ | * |
| 135B | ++++ | **** | + | N/A |
| 135C | ++++ | *** | +++ | * |
| 136 | ++++ | **** | ++++ | ** |
| 137 | ++++ | **** | ++++ | ** |
| 138 | ++++ | ** | ++++ | *** |
| 139 | ++++ | ** | +++ | ** |
| 140 | ++++ | ** | ++++ | ** |
| 142 | ++++ | ** | ++++ | ** |
| 143 | ++++ | ** | N/A | N/A |
| 145 | ++++ | ** | N/A | N/A |
| 146 | ++++ | ** | + | N/A |
| 147 | ++++ | *** | +++ | ** |
| 148 | ++++ | ** | N/A | N/A |
| 149 | + | N/A | N/A | N/A |
| 150 | + | N/A | N/A | N/A |
| 151 | ++++ | ** | N/A | N/A |
| 152 | ++++ | *** | ++++ | ** |
| 153 | ++++ | *** | + | * |
| 154A | ++++ | ** | ++++ | * |
| 154B | ++++ | ** | N/A | N/A |
| 154C | ++++ | ** | +++ | ** |
| 155 | ++++ | ** | ++++ | ** |
| 157 | ++++ | ** | +++ | ** |
| 158 | ++++ | ** | ++++ | ** |
| 159 | ++++ | *** | +++ | ** |
| 160 | ++++ | ** | ++++ | * |
| 161 | ++++ | ** | ++++ | ** |
| 162 | ++++ | *** | ++++ | ** |
| 163 | ++++ | ** | ++++ | ** |
| 164 | ++++ | *** | +++ | * |
| 165 | ++++ | *** | ++++ | * |
| 166 | ++++ | *** | +++ | ** |
| 167 | ++++ | *** | +++ | ** |
| 168 | ++++ | *** | ++++ | * |
| 169 | ++++ | *** | ++++ | * |
| 170 | ++++ | *** | +++ | *** |
| 171 | ++++ | *** | +++ | ** |
| 172 | ++++ | ** | +++ | ** |
| 173A | ++++ | ** | ++++ | * |
| 173B | ++++ | ** | +++ | ** |
| 173C | ++++ | ** | ++++ | ** |
| 173D | ++++ | ** | ++++ | ** |
| 173E | ++++ | ** | +++ | ** |
| 173F | ++++ | *** | ++++ | ** |
| 174 | ++++ | ** | +++ | * |
| 175 | ++++ | ** | +++ | * |
| 176 | ++++ | *** | +++ | ** |
| 177 | ++++ | ** | +++ | ** |
| 178 | ++++ | ** | +++ | ** |
| 179 | ++++ | ** | +++ | *** |
| 180 | ++++ | *** | +++ | * |
| 181 | ++++ | ** | ++++ | ** |
| 182 | ++++ | *** | ++++ | ** |
| 183 | ++++ | *** | +++ | ** |
| 184 | ++++ | *** | ++++ | ** |
| 185 | ++++ | ** | N/A | N/A |
| 186A | ++++ | ** | +++ | ** |
| 186B | ++++ | ** | ++++ | ** |
| 186C | ++++ | *** | + | ** |
| 186D | ++++ | *** | N/A | N/A |
| 186E | ++++ | ** | +++ | ** |
| 186F | ++++ | *** | ++++ | * |
| 186G | ++++ | ** | +++ | ** |
| 186H | ++++ | *** | ++++ | ** |
| 186I | ++++ | ** | ++++ | ** |
| 186J | ++++ | ** | +++ | ** |
| 186K | ++++ | *** | N/A | N/A |
| 186L | ++++ | *** | N/A | N/A |
| 186M | ++++ | *** | ++++ | * |
| 186N | ++++ | *** | ++++ | ** |
| 187 | ++++ | **** | ++++ | ** |
| 188 | ++++ | **** | +++ | ** |
| 189 | ++++ | *** | +++ | ** |
| 190 | N/A | N/A | + | N/A |
| 191A | ++++ | ** | +++ | ** |
| 191B | ++++ | *** | +++ | *** |
| 191C | ++++ | **** | +++ | ** |
| 191D | ++++ | ** | + | N/A |

TABLE 26

Assay Results for Additional Compounds.

| Title Compound from Example No. | TR-FRET Assay EC$_{50}$ | TR-FRET Assay Max Response | Gal4-RORγ Assay EC$_{50}$ | Gal4-RORγ Assay Max Response |
|---|---|---|---|---|
| 86BC | ++++ | *** | N/A | N/A |
| 89FO | ++++ | **** | ++++ | ** |
| 89FP | ++++ | **** | ++++ | ** |
| 116N | ++++ | **** | ++++ | * |
| 116O | ++++ | **** | ++++ | ** |
| 116P | ++++ | **** | ++++ | ** |
| 129Q | ++++ | **** | ++++ | ** |
| 191E | ++++ | *** | +++ | *** |
| 191F | ++++ | **** | +++ | ** |
| 191G | ++++ | **** | ++++ | **** |
| 191H | ++++ | **** | ++++ | ** |
| 192 | ++++ | **** | +++ | ** |
| 193 | ++++ | **** | ++++ | *** |
| 194 | ++++ | **** | ++++ | *** |
| 195B | ++++ | **** | ++++ | ** |
| 195C | ++++ | **** | +++ | * |
| 195D | ++++ | **** | ++++ | *** |
| 195E | ++++ | **** | +++ | ** |
| 195F | ++++ | **** | ++++ | *** |
| 195G | ++++ | **** | N/A | N/A |
| 195H | ++++ | **** | N/A | N/A |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:
1. A compound represented by Formula I:

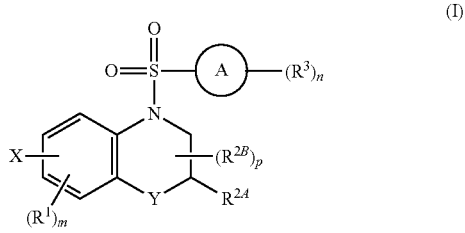

or a pharmaceutically acceptable salt thereof; wherein:
A is phenylene, 5-6 membered heteroarylene, or $C_{3-6}$ heterocycloalkylene;
$R^1$ represents independently for each occurrence halogen, $C_{1-6}$ alkyl, $C_{1-6}$ haloalkyl, or $C_{3-6}$ cycloalkyl;
$R^{2A}$ is one of the following:
(i) $C_{1-6}$ alkyl, $C_{1-3}$ haloalkyl, $C_{3-6}$ cycloalkyl, —($C_{1-6}$ alkylene)-($C_{3-6}$ cycloalkyl), —O—($C_{1-6}$ alkylene)-$CO_2R^4$, —O—($C_{1-6}$ alkylene)-C(O)—($C_{1-6}$ alkyl), —N($R^4$)—($C_{1-6}$ alkylene)-$CO_2R^4$, or —N($R^4$)—($C_{1-6}$ alkylene)-C(O)—($C_{1-6}$ alkyl), wherein the $C_{1-6}$ alkyl, $C_{3-6}$ cycloalkyl, and $C_{1-6}$ alkylene are optionally substituted with 1 or 2 substituents independently selected from the group consisting of —$CO_2R^4$, —C(O)N($R^4$)($R^5$), —C(O)—N($R^4$)—($C_{1-4}$ alkylene)-$CO_2R^4$, —N($R^4$)C(O)$R^8$, —CN, halogen, hydroxyl, $C_{1-6}$ alkoxy, $C_{1-6}$ haloalkoxy, $C_{1-6}$ haloalkyl, —N($R^4$)($R^5$), —N($R^4$)C(O)N($R^4$)($R^5$), —N($R^4$)$CO_2R^9$, —N($R^4$)S(O)$_2R^9$, and —N($R^4$) S(O)$_2$N($R^4$)($R^5$); or
(ii) —$CO_2R^4$, —N($R^4$)C(O)$R^9$, —N($R^4$)$CO_2R^9$, —N($R^4$)C(O)N($R^4$)($R^5$), —N($R^4$)C(O)N($R^4$)(heteroaryl), —N($R^4$)S(O)$_2R^9$, —N($R^4$)($R^5$), or —OH;
$R^{2B}$ is $C_{1-6}$ alkyl, $C_{1-3}$ haloalkyl, or fluoro;
$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —N($R^4$)($R^8$), —O—($C_{1-6}$ hydroxyalkyl), or —O—($C_{1-6}$ alkylene)-$CO_2R^4$; or two vicinal occurrences of $R^3$ are taken together with intervening atoms to form a 4-6 membered ring;
$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring;
$R^6$ and $R^7$ each represent independently for each occurrence hydrogen, fluoro, or $C_{1-6}$ alkyl, or $R^6$ and $R^7$ are taken together with the carbon atom to which they are attached to form a 3-6 membered carbocyclic ring; or $R^6$ and a vicinal occurrence of $R^{2B}$ are taken together to form a bond;
$R^8$ represents independently for each occurrence $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, and —$CO_2R^4$; or $R^8$ is —$CO_2R^4$;
$R^9$ represents independently for each occurrence $C_{1-6}$ alkyl, $C_{3-6}$ cycloalkyl, —($C_{1-6}$ alkylene)-($C_{3-6}$ cycloalkyl), $C_{1-6}$ haloalkyl, or $C_{1-6}$ hydroxyalkyl;
X is one of the following:
(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$;
(ii) —S-aralkyl, —S-heteroaralkyl, —S-phenyl, —S-heteroaryl, —S-(partially unsaturated bicyclic carbocyclyl), —S—($C_{1-6}$ alkylene)-($C_{3-6}$ cycloalkyl), or —S—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$;
(iii) —($C_{2-6}$ alkenylene)-phenyl, —($C_{2-6}$ alkenylene)-heteroaryl, —($C_{2-6}$ alkenylene)-(partially unsaturated 8-10 membered bicyclic ring containing 0-3 heteroatoms), —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), —($C_{1-6}$ alkylene)-($C_3$-$C_6$ cycloalkyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$;
(iv) —($C_{2-6}$ alkenylene)-($C_{1-6}$ alkyl), —($C_{2-6}$ alkenylene)-($C_{3-6}$ cycloalkyl), or

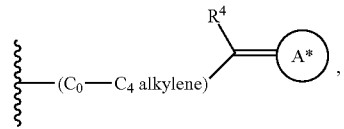

each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$, wherein A* is a 5-8 membered, partially saturated carbocyclic or heterocyclic ring; or
(v) —($C_{1-6}$ alkylene)-$Z^1$ or —($C_{2-6}$ alkenylene)-$Z^1$, wherein $Z^1$ is —O-aralkyl, —O— heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$ alkylene)-($C_{3-6}$ cycloalkyl), or —N($R^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$;

Y is —C($R^6$)($R^7$)—, —C(O)—, or —S(O)$_p$—;

m and p each represent independently for each occurrence 0, 1, or 2; and n is 1, 2, or 3.

2. The compound of claim 1, wherein the compound is represented by Formula I-A:

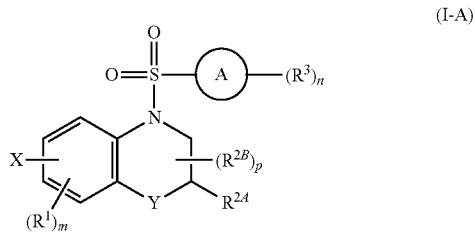

(I-A)

or a pharmaceutically acceptable salt thereof; wherein:

A is phenylene or a 5-6 membered heteroarylene;

$R^1$ represents independently for each occurrence halogen, $C_{1-6}$ alkyl, or $C_{3-6}$ cycloalkyl;

$R^{2A}$ is $C_{1-6}$ alkyl or $C_{3-6}$ cycloalkyl, wherein the $C_{1-6}$ alkyl or $C_{3-6}$ cycloalkyl are optionally substituted with 1 or 2 substituents independently selected from the group consisting of —CO$_2R^4$, —N($R^4$)C(O)($C_{1-6}$ alkyl), —CN, halogen, hydroxyl, $C_{1-6}$ alkoxy, $C_{1-6}$ haloalkoxy, $C_{1-6}$ haloalkyl, and —N($R^4$)($R^5$); or $R^{2A}$ is —CO$_2R^4$ or —N($R^4$)C(O)($C_{1-6}$ alkyl);

$R^{2B}$ is $C_{1-6}$ alkyl or $C_{1-3}$ haloalkyl;

$R^3$ represents independently for each occurrence hydrogen, $C_{1-6}$ haloalkyl, halogen, hydroxyl, $C_{1-6}$ alkyl, $C_{1-6}$ alkoxy, $C_{1-6}$ haloalkoxy, or —O—($C_{1-6}$ alkylene)-OH; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring;

X is one of the following:

(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

(ii) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy; or (iii) —($C_{1-6}$ alkylene)-$Z^1$ or —($C_{2-6}$ alkenylene)-$Z^1$, wherein $Z^1$ is —O-aralkyl, —O— heteroaralkyl, —O-phenyl, —O-heteroaryl, —O-(partially unsaturated bicyclic carbocyclyl), —O—($C_{1-6}$alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

Y is —C($R^6$)($R^7$)—;

m and p are independently 0, 1, or 2; and n is 1, 2, or 3.

3. The compound of claim 2, wherein $R^{2A}$ is $C_{1-6}$ alkyl optionally substituted with 1 or 2 substituents independently selected from the group consisting of —CO$_2R^4$, —N($R^4$)C(O)($C_{1-6}$ alkyl), —CN, halogen, hydroxyl, $C_{1-6}$ alkoxy, $C_{1-6}$ haloalkoxy, and —N($R^4$)($R^5$).

4. The compound of claim 2, wherein $R^{2A}$ is $C_{1-6}$ alkyl substituted with 1 or 2 substituents independently selected from the group consisting of —CO$_2R^4$, —N($R^4$)C(O)($C_{1-6}$ alkyl), —CN, hydroxyl, and $C_{1-6}$ alkoxy.

5. The compound of claim 2, wherein $R^{2A}$ is —CO$_2R^4$.

6. The compound of claim 2, wherein $R^{2B}$ is methyl.

7. The compound of claim 2, wherein A is phenylene.

8. The compound of claim 7, wherein n is 1.

9. The compound of claim 7, wherein $R^3$ represents independently for each occurrence $C_{1-6}$ haloalkyl, halogen, $C_{1-6}$ alkyl, $C_{1-6}$ alkoxy, or —O—($C_{1-6}$ alkylene)-OH.

10. The compound of claim 8, wherein $R^3$ is trifluoromethyl.

11. The compound of claim 7, wherein X is —O-aralkyl or —N($R^4$)-aralkyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

12. The compound of claim 9, wherein X is —O-benzyl or —N($R^4$)-benzyl, each of which is substituted with 1 or 2 substituents independently selected from the group consisting of chloro, bromo, and fluoro.

13. The compound of claim 7, wherein X is —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

14. The compound of claim 9, wherein X is —($C_{2-6}$ alkenylene)-phenyl, —($C_{1-6}$ alkylene)-phenyl, or —($C_{1-6}$ alkylene)-heteroaryl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

15. The compound of claim 1, wherein Y is —C($R^6$)($R^7$)—.

16. The compound of claim 2, wherein $R^6$ and $R^7$ are independently hydrogen or methyl.

17. The compound of claim 7, wherein Y is —C(R⁶)(R⁷)—, R⁶ and R⁷ are independently hydrogen or methyl, and X is attached at the 7-position of the 1,2,3,4-tetrahydroquinolinyl ring.
18. The compound of claim 10, wherein m is 0.
19. The compound of claim 10, wherein p is 0.
20. The compound of claim 6, wherein p is 1.
21. A compound in Table 1-1, 1-A-1, 24-1, or 25-1 below, or a pharmaceutically acceptable salt thereof:
TABLE 1-1
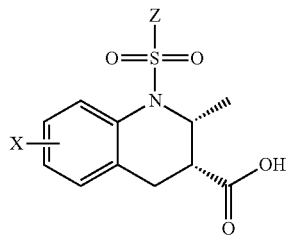
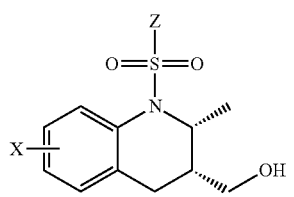
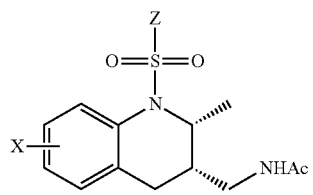
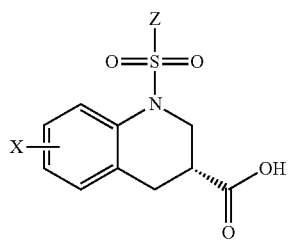
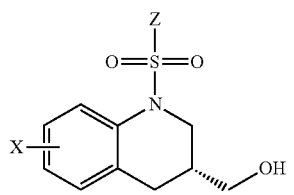
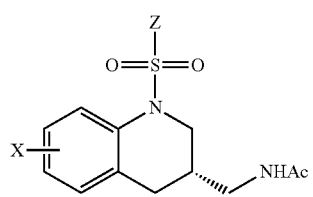
TABLE 1-1-continued
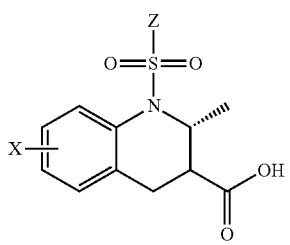
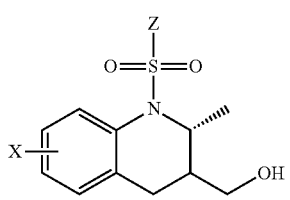
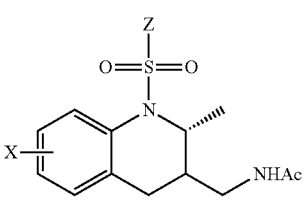
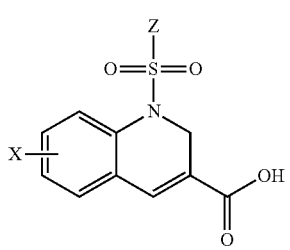
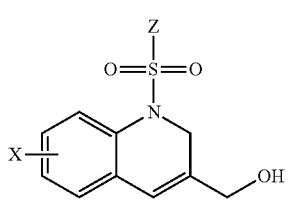
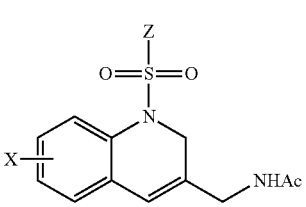
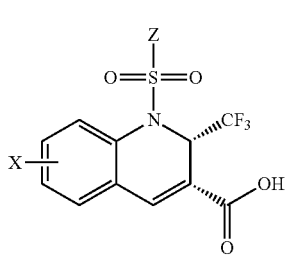

TABLE 1-1-continued

651
TABLE 1-1-continued
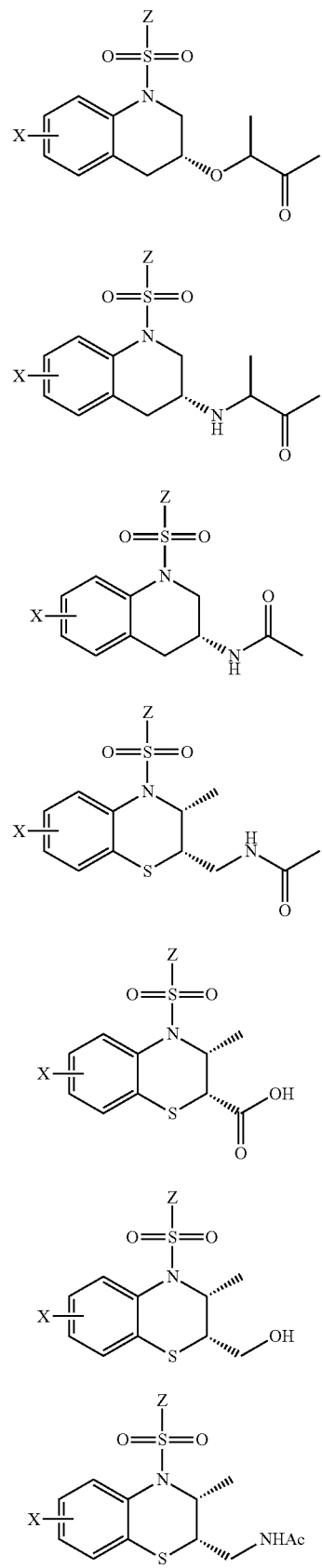
652
TABLE 1-1-continued
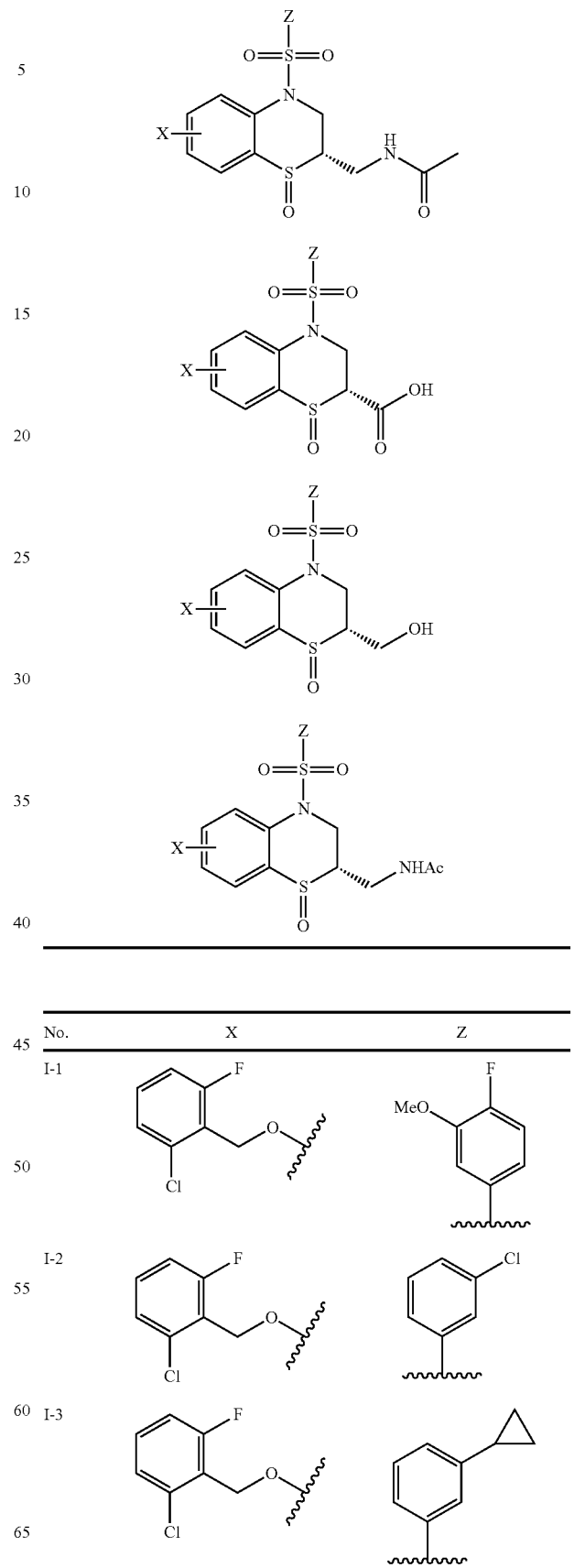

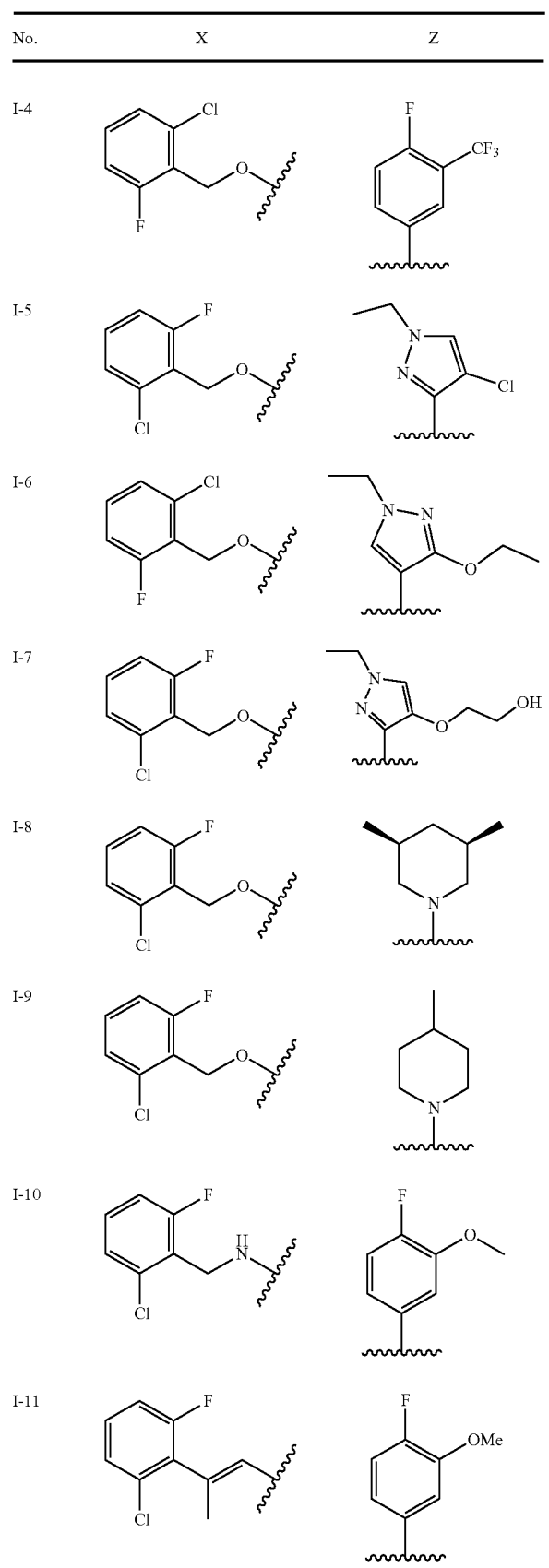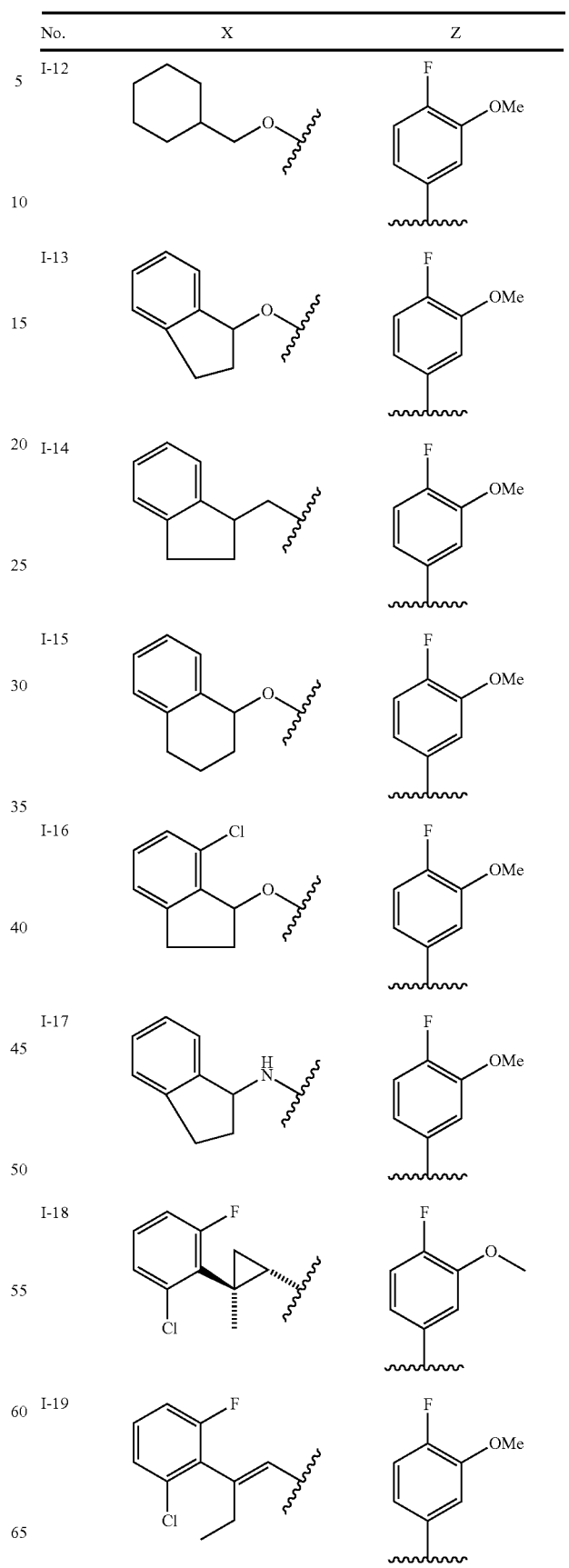

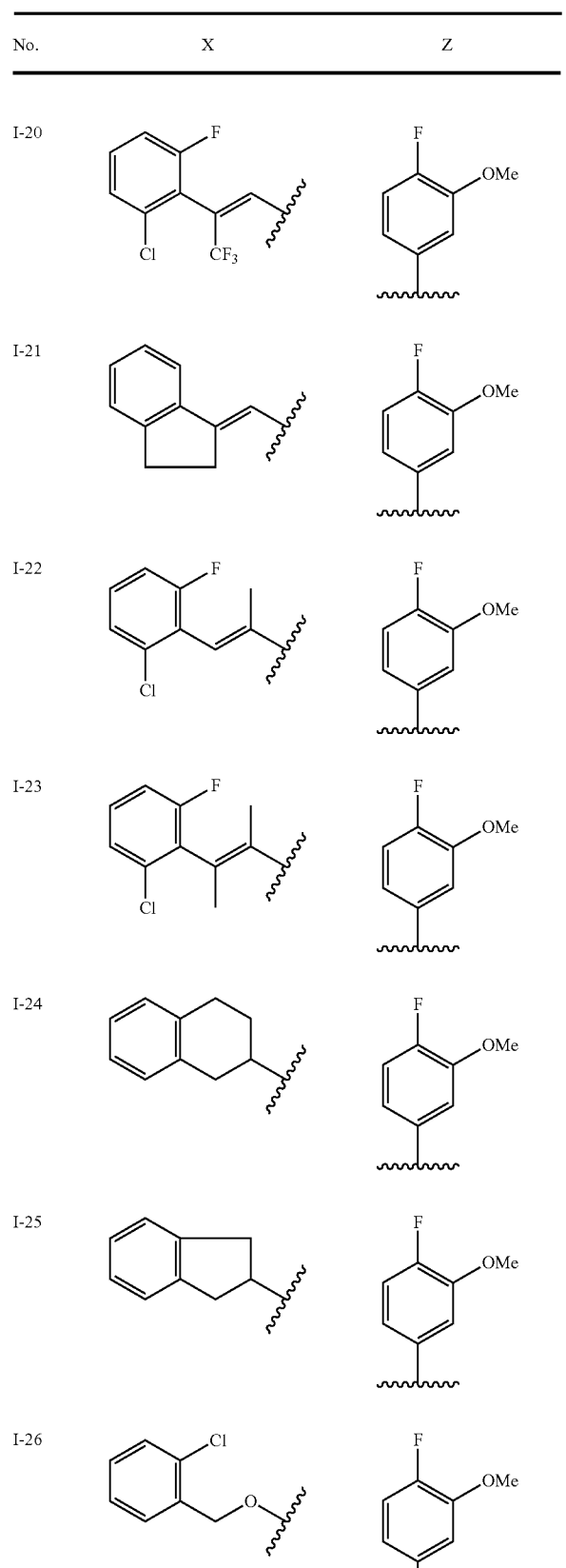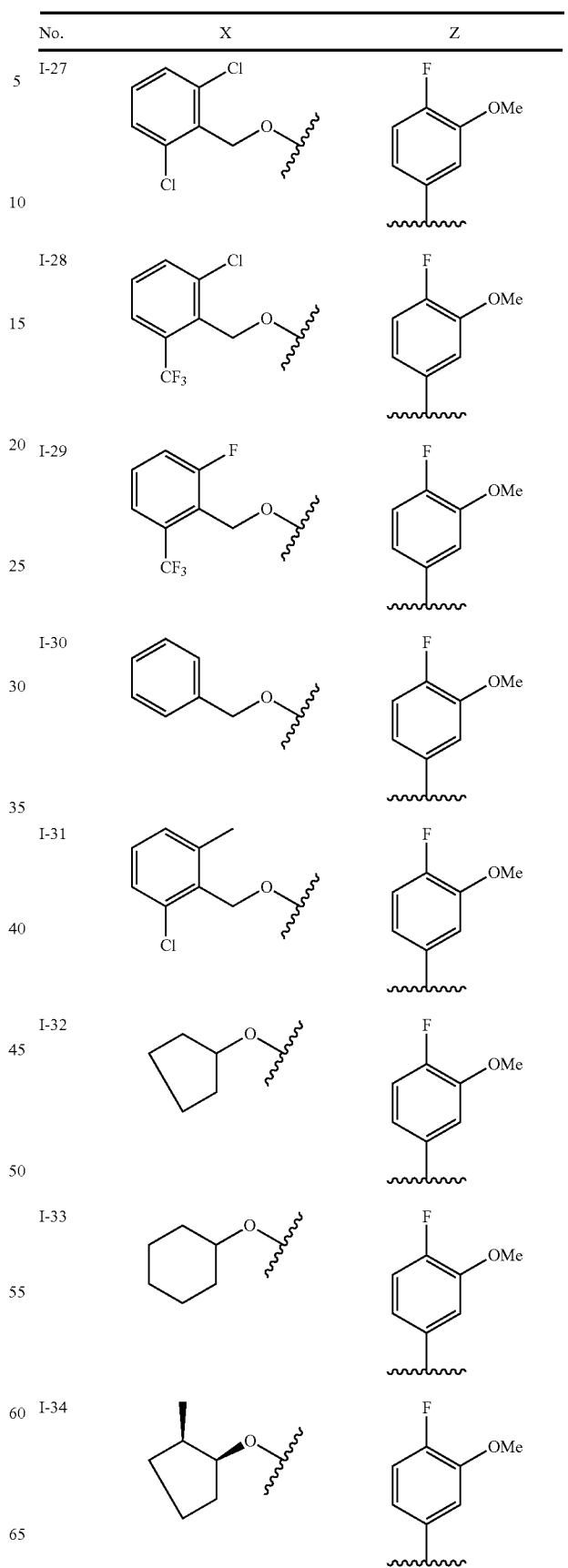

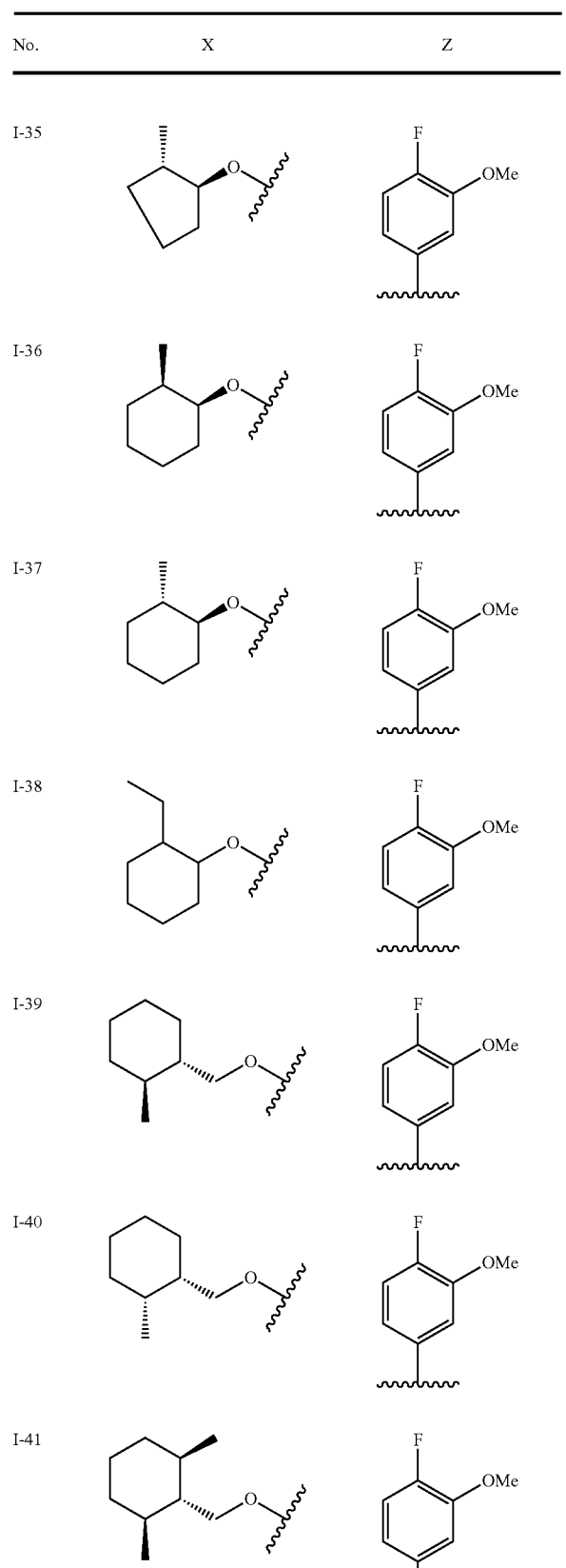
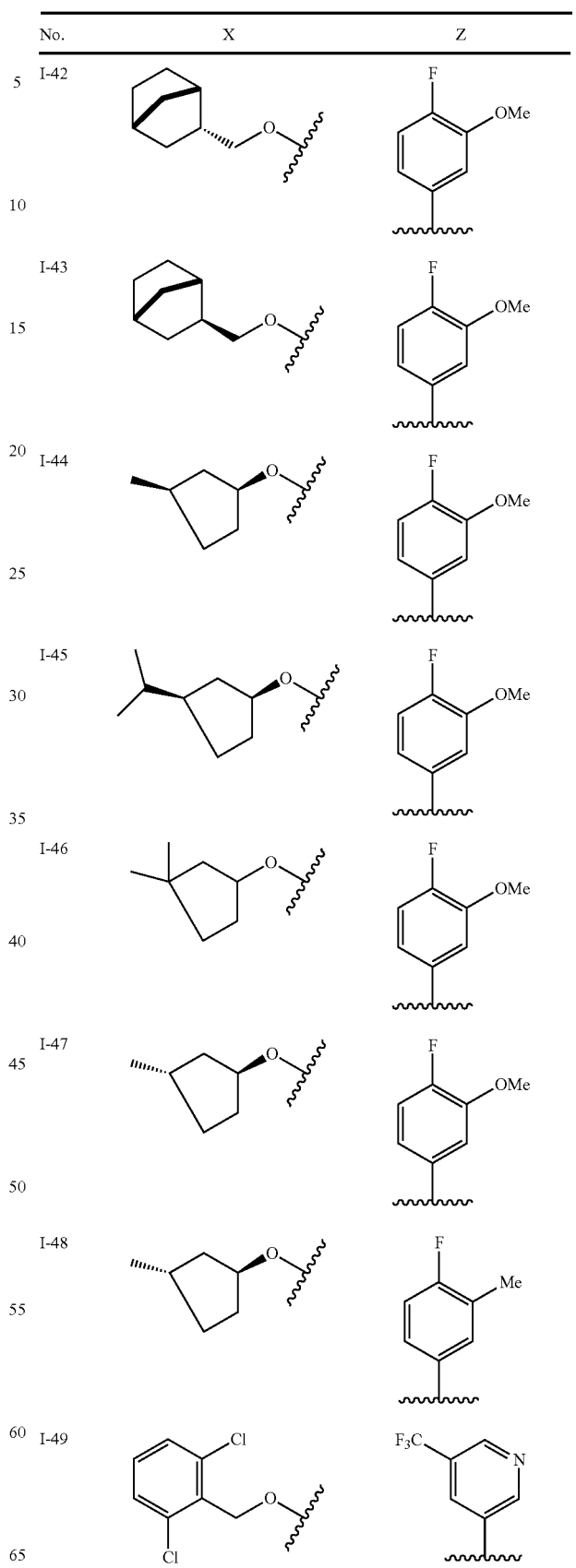

-continued
| No. | X | Z |
|---|---|---|
| I-50 | 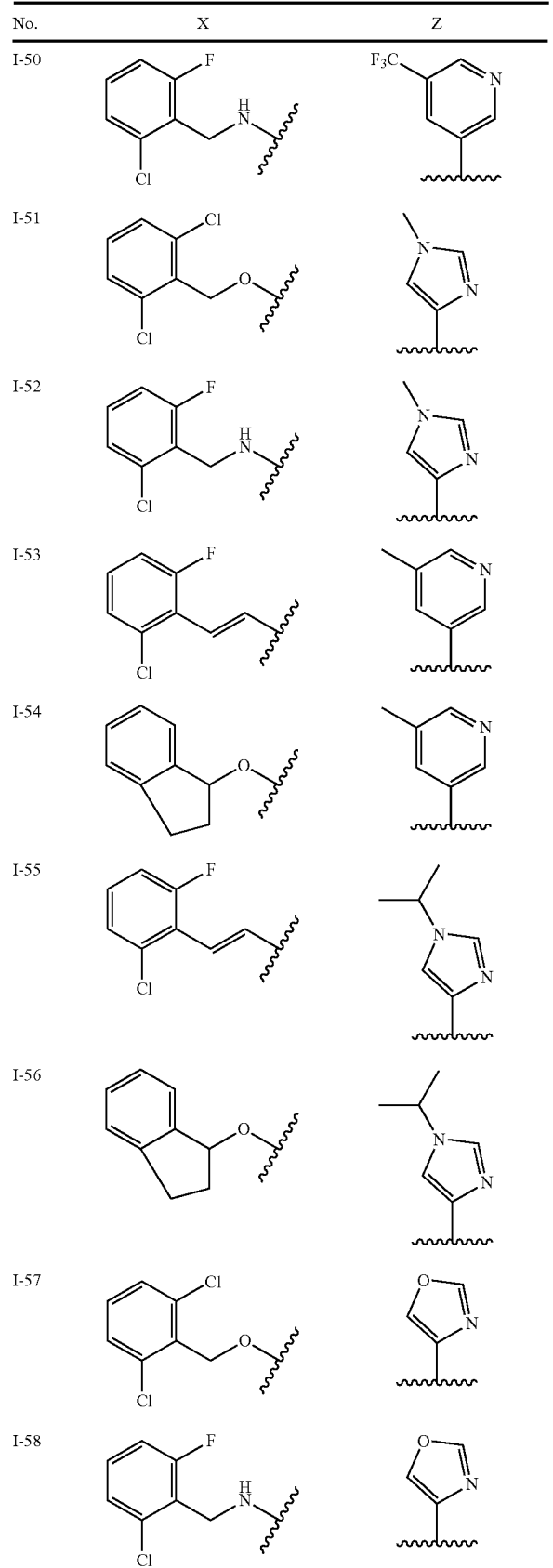 | |
| I-51 | | |
| I-52 | | |
| I-53 | | |
| I-54 | | |
| I-55 | | |
| I-56 | | |
| I-57 | | |
| I-58 | | |
-continued
| No. | X | Z |
|---|---|---|
| I-59 | 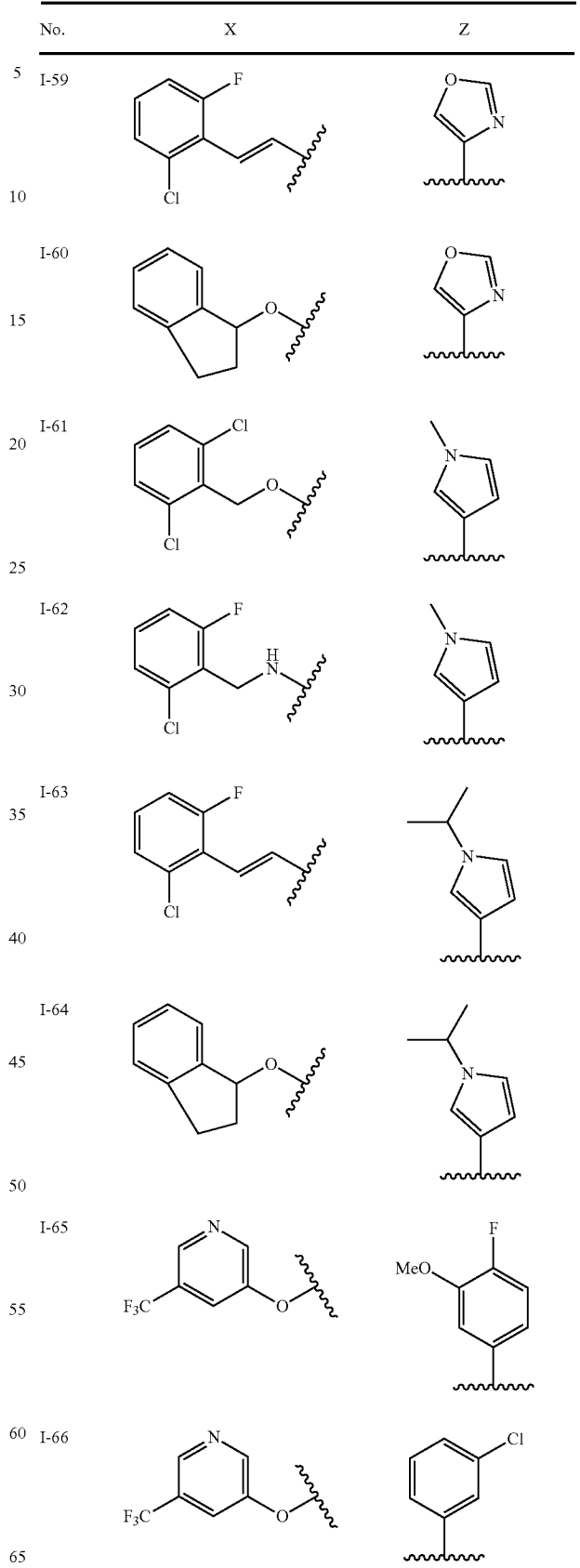 | |
| I-60 | | |
| I-61 | | |
| I-62 | | |
| I-63 | | |
| I-64 | | |
| I-65 | | |
| I-66 | | |

| No. | X | Z |
|---|---|---|
| I-67 | 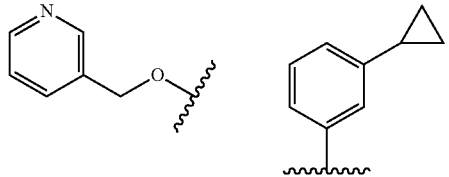 | |
| I-68 | 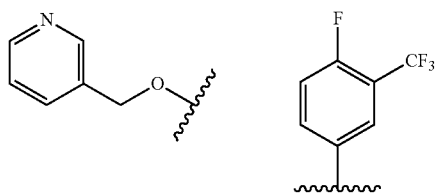 | |
| I-69 | 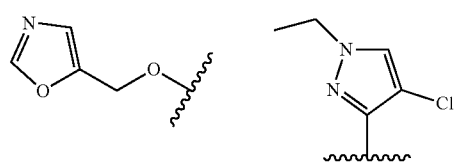 | |
| I-70 | 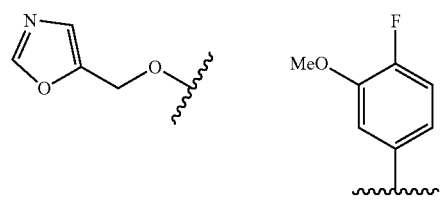 | |
| I-71 | 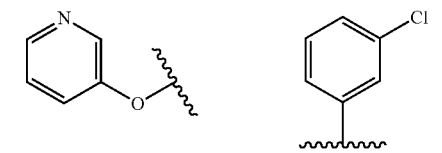 | |
| I-72 | 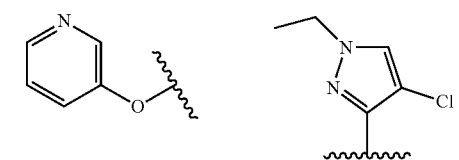 | |
| I-73 | 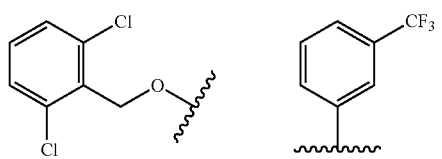 | |
| I-74 | 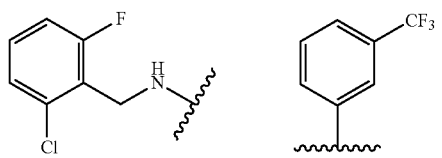 | |
| I-75 | 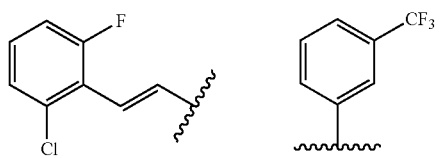 | |
| No. | X | Z |
|---|---|---|
| I-76 | 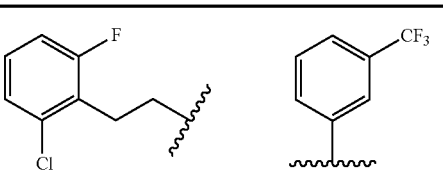 | |
| I-77 | 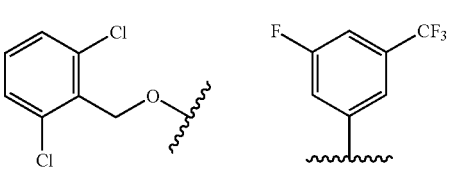 | |
| I-78 | 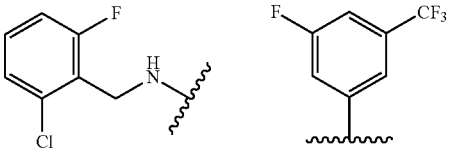 | |
| I-79 | 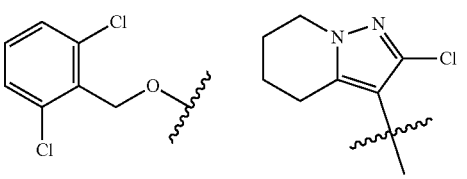 | |
| I-80 | 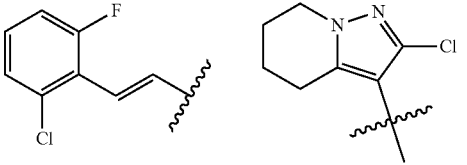 | |
| I-81 | 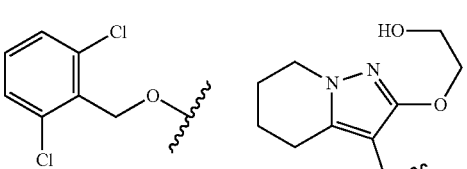 | |
| I-82 | 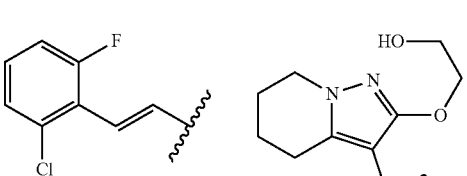 | |
| I-83 | 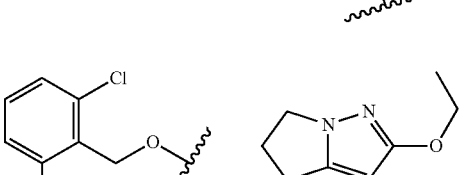 | |

663
-continued
| No. | X | Z |
|---|---|---|
| I-84 | 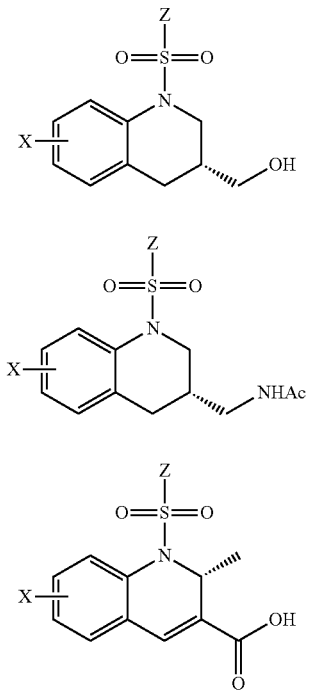 | |
| I-85 | | |
| I-86 | | |
TABLE 1-A-1
664
TABLE 1-A-1-continued
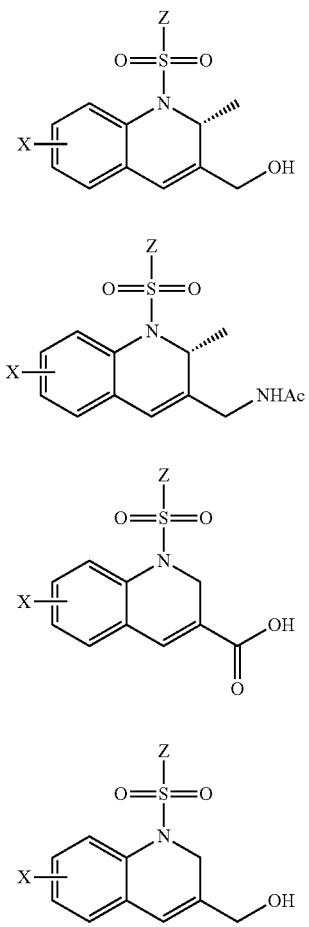

TABLE 1-A-1-continued
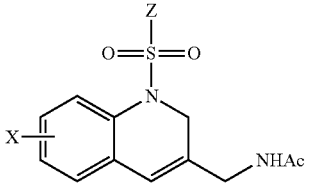
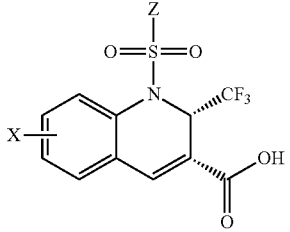
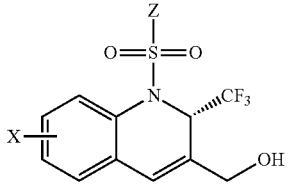
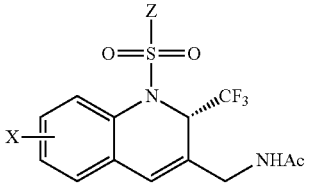
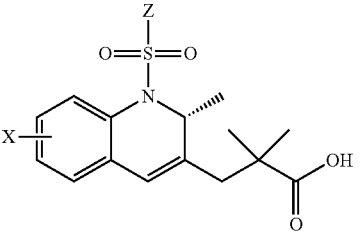
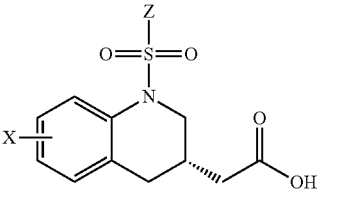
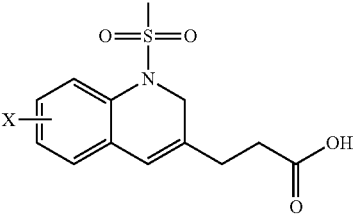
TABLE 1-A-1-continued
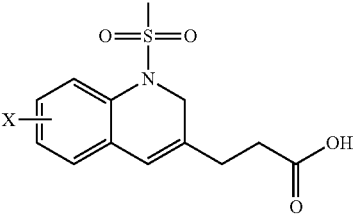
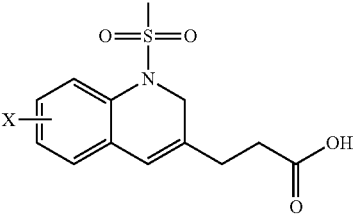
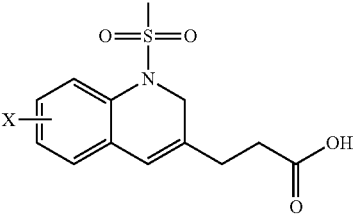
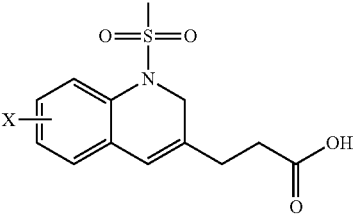
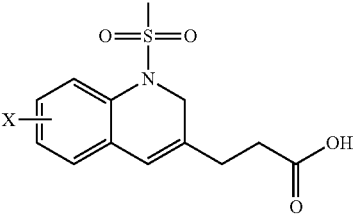
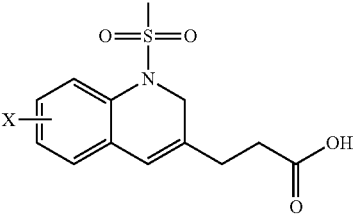

TABLE 1-A-1-continued
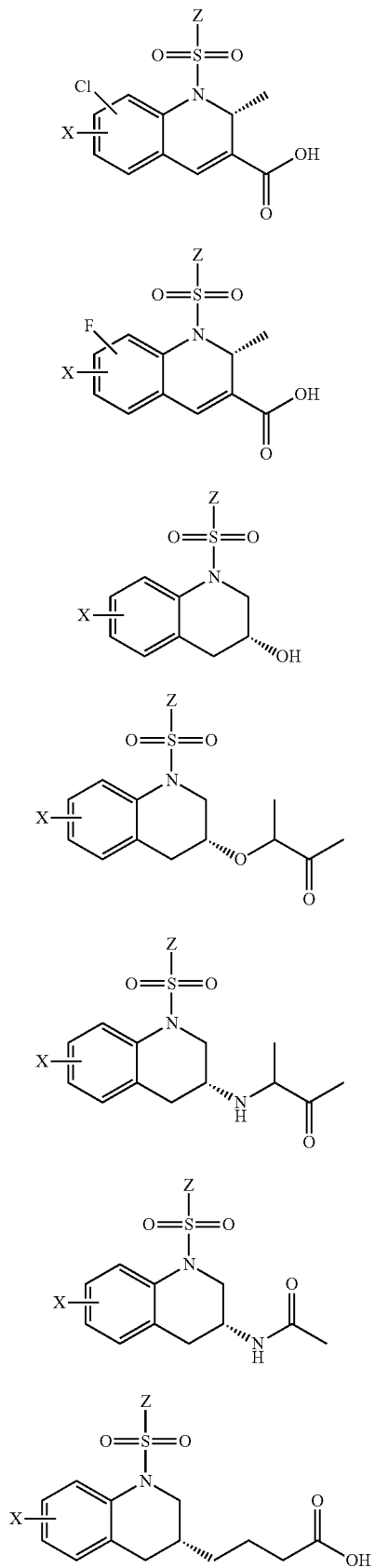
TABLE 1-A-1-continued
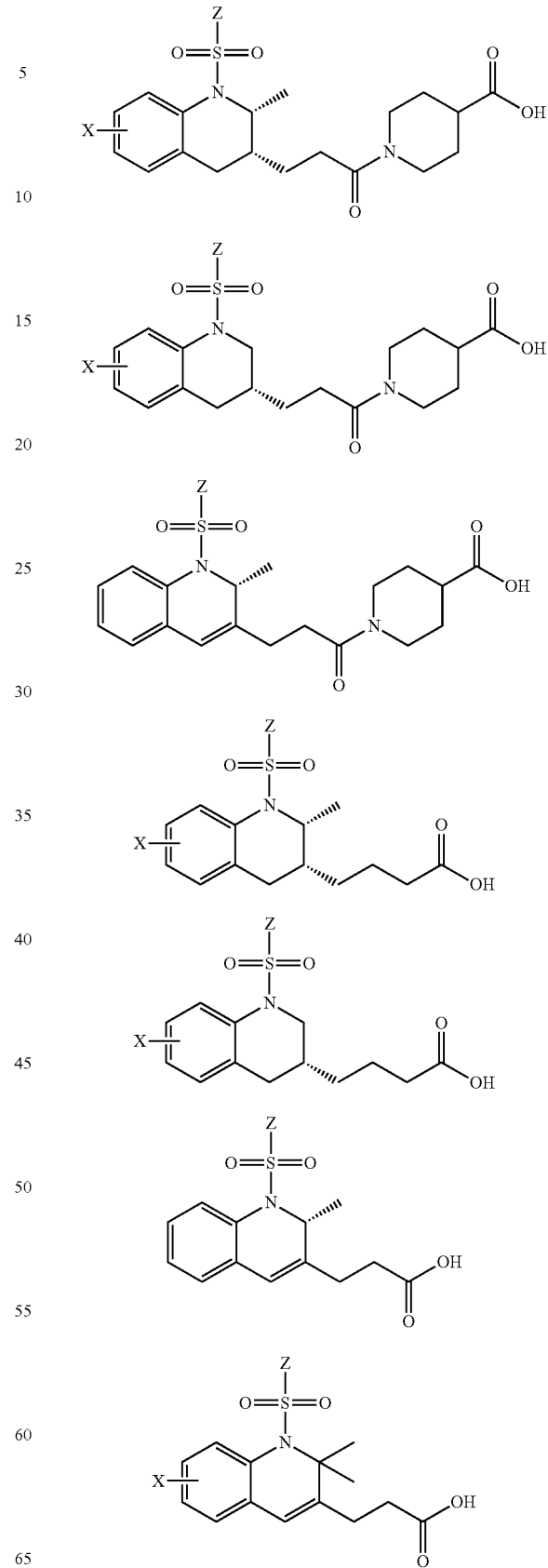

TABLE 1-A-1-continued
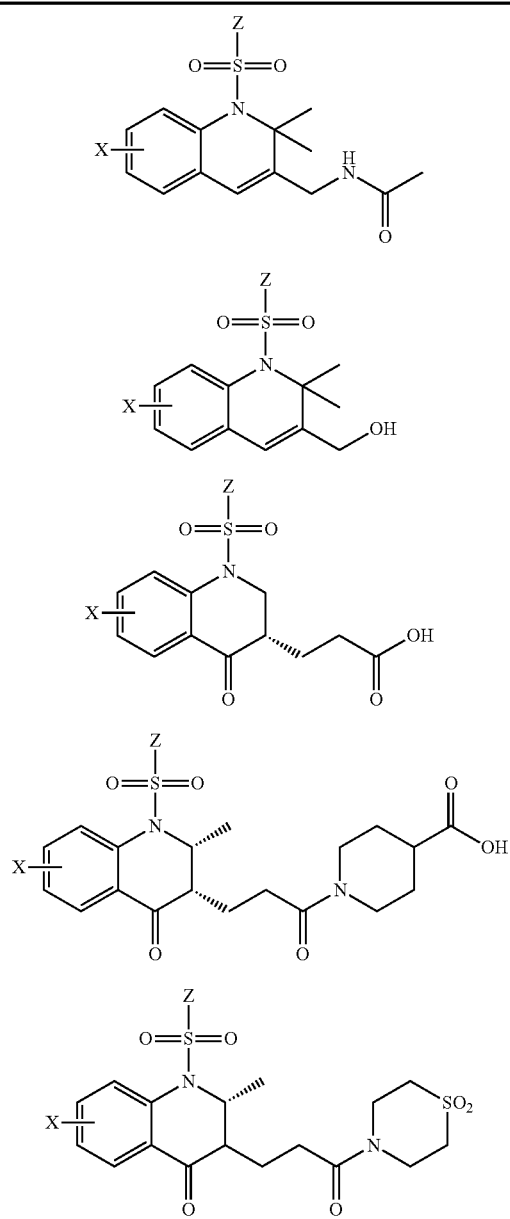
TABLE 1-A-1-continued
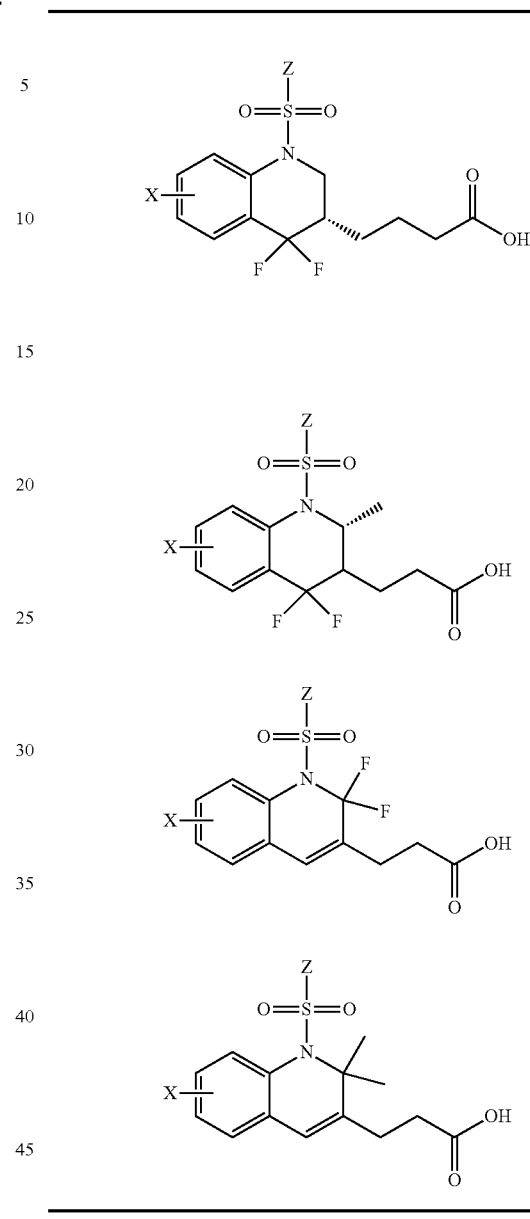

-continued
| No. | X | Z |
|---|---|---|
| I-A3 | 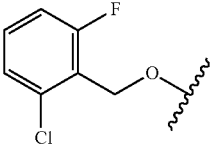 [SMILES: *OCc1c(F)cccc1Cl] | 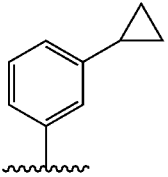 [SMILES: *c1cccc(C2CC2)c1] |
| I-A4 | 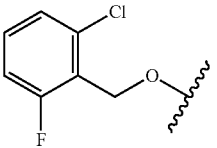 [SMILES: *OCc1c(F)cccc1Cl] | 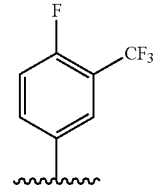 |
| I-A5 | 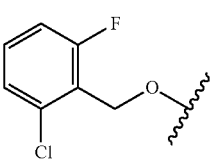 [SMILES: *OCc1c(F)cccc1Cl] | 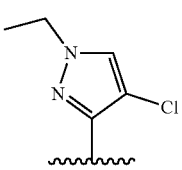 [SMILES: *c1nn(CC)cc1Cl] |
| I-A6 | 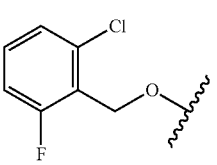 [SMILES: *OCc1c(F)cccc1Cl] | 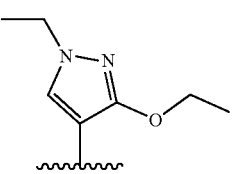 [SMILES: *c1cn(CC)nc1OCC] |
| I-A7 | 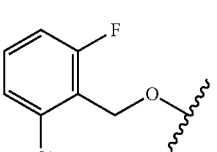 | 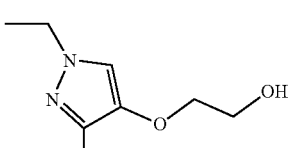 |
| I-A8 | 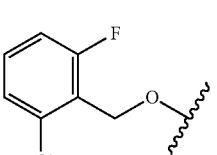 | 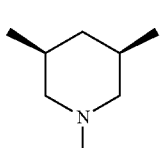 |
| I-A9 | 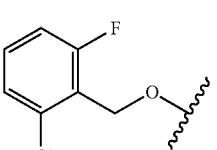 | 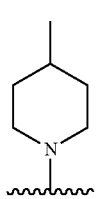 |
| I-A10 | 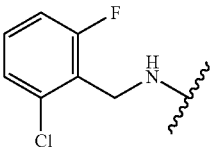 [SMILES: *NCc1c(F)cccc1Cl] | 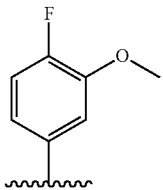 [SMILES: *c1ccc(F)c(OC)c1] |

-continued

| No. | X | Z |
|---|---|---|
| I-A11 | 2-F, 6-Cl phenyl with propenyl linker | 4-F, 3-OMe phenyl |
| I-A12 | cyclohexylmethyl-O- | 4-F, 3-OMe phenyl |
| I-A13 | indan-1-yl-O- | 4-F, 3-OMe phenyl |
| I-A14 | indan-1-yl-CH2- | 4-F, 3-OMe phenyl |
| I-A15 | 1,2,3,4-tetrahydronaphthalen-1-yl-O- | 4-F, 3-OMe phenyl |
| I-A16 | 7-Cl-indan-1-yl-O- | 4-F, 3-OMe phenyl |
| I-A17 | indan-1-yl-NH- | 4-F, 3-OMe phenyl |
| I-A18 | 2-F, 6-Cl phenyl with methylcyclopropyl linker | 4-F, 3-OMe phenyl |

-continued
| No. | X | Z |
|---|---|---|
| I-A19 | 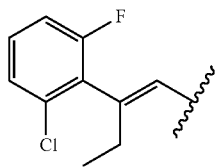 [SMILES: */C=C(\CC)c1c(F)cccc1Cl] | 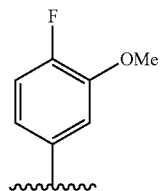 [SMILES: *c1ccc(F)c(OC)c1] |
| I-A20 | 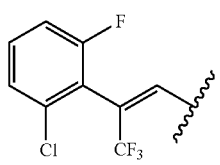 [SMILES: */C=C(/c1c(F)cccc1Cl)C(F)(F)F] | 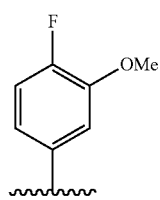 [SMILES: *c1ccc(F)c(OC)c1] |
| I-A21 | 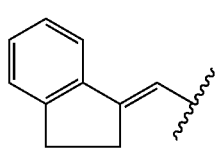 [SMILES: */C=C1\CCc2ccccc21] | 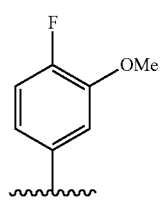 [SMILES: *c1ccc(F)c(OC)c1] |
| I-A22 | 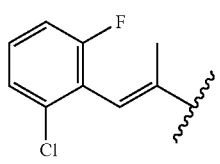 [SMILES: */C(C)=C/c1c(F)cccc1Cl] | 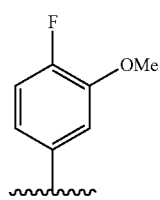 [SMILES: *c1ccc(F)c(OC)c1] |
| I-A23 | 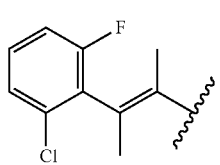 [SMILES: */C(C)=C(\C)c1c(F)cccc1Cl] | 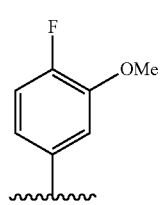 [SMILES: *c1ccc(F)c(OC)c1] |
| I-A24 | 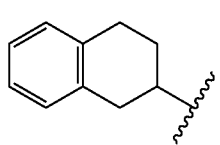 [SMILES: *C1CCc2ccccc2C1] | 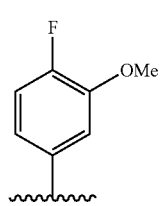 [SMILES: *c1ccc(F)c(OC)c1] |
| I-A25 | 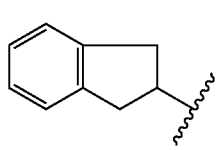 [SMILES: *C1Cc2ccccc2C1] | 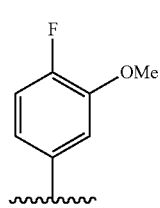 [SMILES: *c1ccc(F)c(OC)c1] |

-continued

| No. | X | Z |
|---|---|---|
| I-A26 | 2-Cl-benzyl-O- | 4-F-3-OMe-phenyl |
| I-A27 | 2,6-diCl-benzyl-O- | 4-F-3-OMe-phenyl |
| I-A28 | 2-Cl-6-CF₃-benzyl-O- | 4-F-3-OMe-phenyl |
| I-A29 | 2-F-6-CF₃-benzyl-O- | 4-F-3-OMe-phenyl |
| I-A30 | benzyl-O- | 4-F-3-OMe-phenyl |
| I-A31 | 2-Cl-6-Me-benzyl-O- | 4-F-3-OMe-phenyl |
| I-A32 | cyclopentyl-O- | 4-F-3-OMe-phenyl |
| I-A33 | cyclohexyl-O- | 4-F-3-OMe-phenyl |

-continued
| No. | X | Z |
|---|---|---|
| I-A34 | 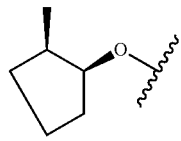 [SMILES: *O[C@H]1CCC[C@H]1C] | 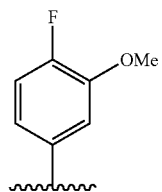 [SMILES: *c1ccc(F)c(OC)c1] |
| I-A35 | 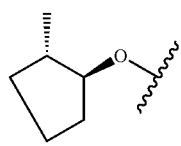 [SMILES: *O[C@H]1CCC[C@@H]1C] | 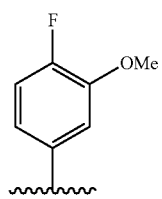 [SMILES: *c1ccc(F)c(OC)c1] |
| I-A36 | 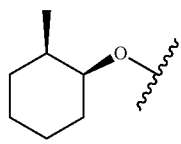 [SMILES: *O[C@H]1CCCC[C@H]1C] | 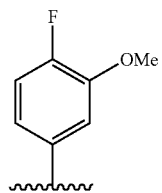 [SMILES: *c1ccc(F)c(OC)c1] |
| I-A37 | 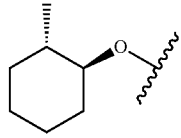 [SMILES: *O[C@H]1CCCC[C@@H]1C] | 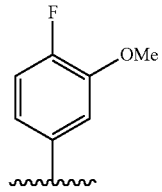 [SMILES: *c1ccc(F)c(OC)c1] |
| I-A38 | 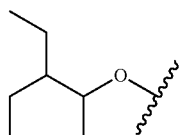 | 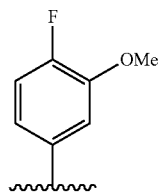 [SMILES: *c1ccc(F)c(OC)c1] |
| I-A39 | 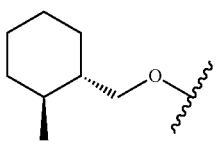 [SMILES: *OC[C@H]1CCCC[C@@H]1C] | 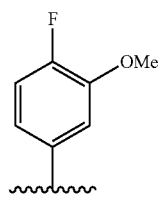 [SMILES: *c1ccc(F)c(OC)c1] |
| I-A40 | 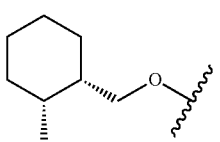 | 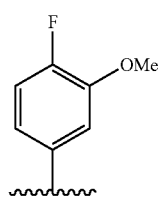 [SMILES: *c1ccc(F)c(OC)c1] |

-continued
| No. | X | Z |
|---|---|---|
| I-A41 | 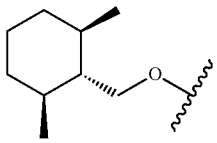 [SMILES: *OC[C@H]1[C@H](C)CCC[C@@H]1C] | 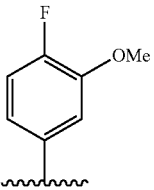 [SMILES: *c1ccc(F)c(OC)c1] |
| I-A42 | 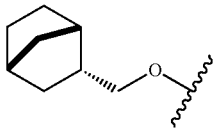 | 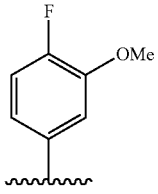 [SMILES: *c1ccc(F)c(OC)c1] |
| I-A43 | 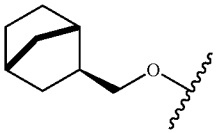 | 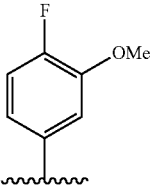 [SMILES: *c1ccc(F)c(OC)c1] |
| I-A44 | 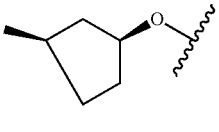 [SMILES: *O[C@H]1CC[C@@H](C)C1] | 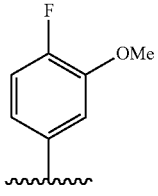 [SMILES: *c1ccc(F)c(OC)c1] |
| I-A45 | 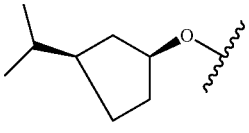 [SMILES: *O[C@H]1CC[C@@H](C(C)C)C1] | 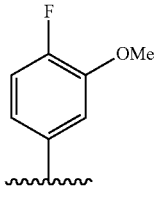 [SMILES: *c1ccc(F)c(OC)c1] |
| I-A46 | 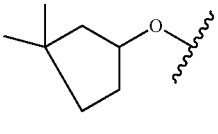 [SMILES: *OC1CCC(C)(C)C1] | 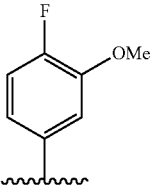 [SMILES: *c1ccc(F)c(OC)c1] |
| I-A47 | 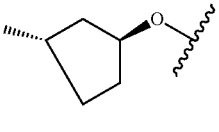 [SMILES: *O[C@H]1CC[C@H](C)C1] | 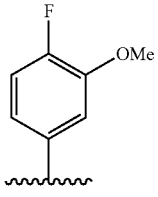 [SMILES: *c1ccc(F)c(OC)c1] |
| I-A48 | 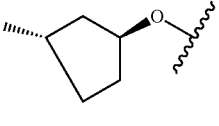 [SMILES: *O[C@H]1CC[C@H](C)C1] | 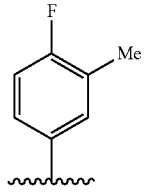 [SMILES: *c1ccc(F)c(C)c1] |

-continued
| No. | X | Z |
|---|---|---|
| I-A49 | 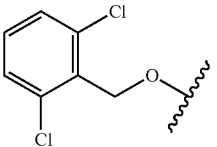 [SMILES: *OCc1c(Cl)cccc1Cl] | 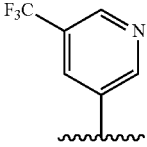 [SMILES: *c1cncc(C(F)(F)F)c1] |
| I-A50 | 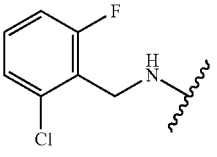 [SMILES: *NCc1c(F)cccc1Cl] | 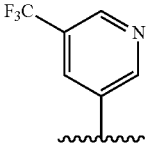 |
| I-A51 | 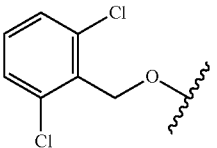 [SMILES: *OCc1c(Cl)cccc1Cl] | 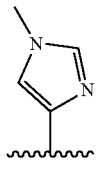 [SMILES: *c1cn(C)cn1] |
| I-A52 | 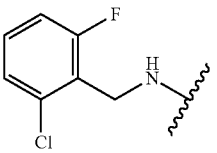 [SMILES: *NCc1c(F)cccc1Cl] | 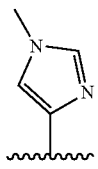 |
| I-A53 | 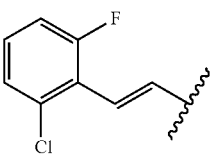 [SMILES: */C=C/c1c(F)cccc1Cl] | 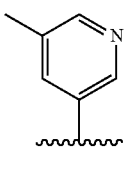 |
| I-A54 | 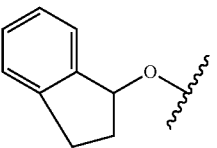 [SMILES: *OC1CCc2ccccc21] | 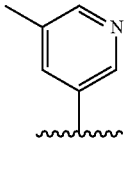 |
| I-A55 | 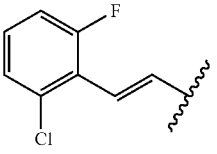 [SMILES: */C=C/c1c(F)cccc1Cl] | 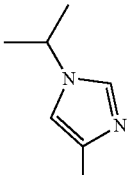 |
| I-A56 | 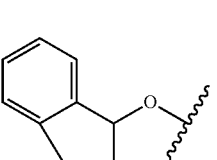 | 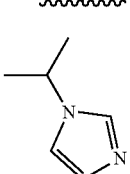 |
| I-A57 | 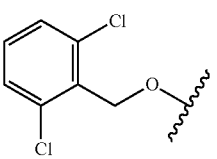 [SMILES: *OCc1c(Cl)cccc1Cl] | 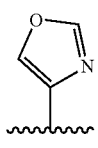 |

-continued
| No. | X | Z |
|---|---|---|
| I-A58 | 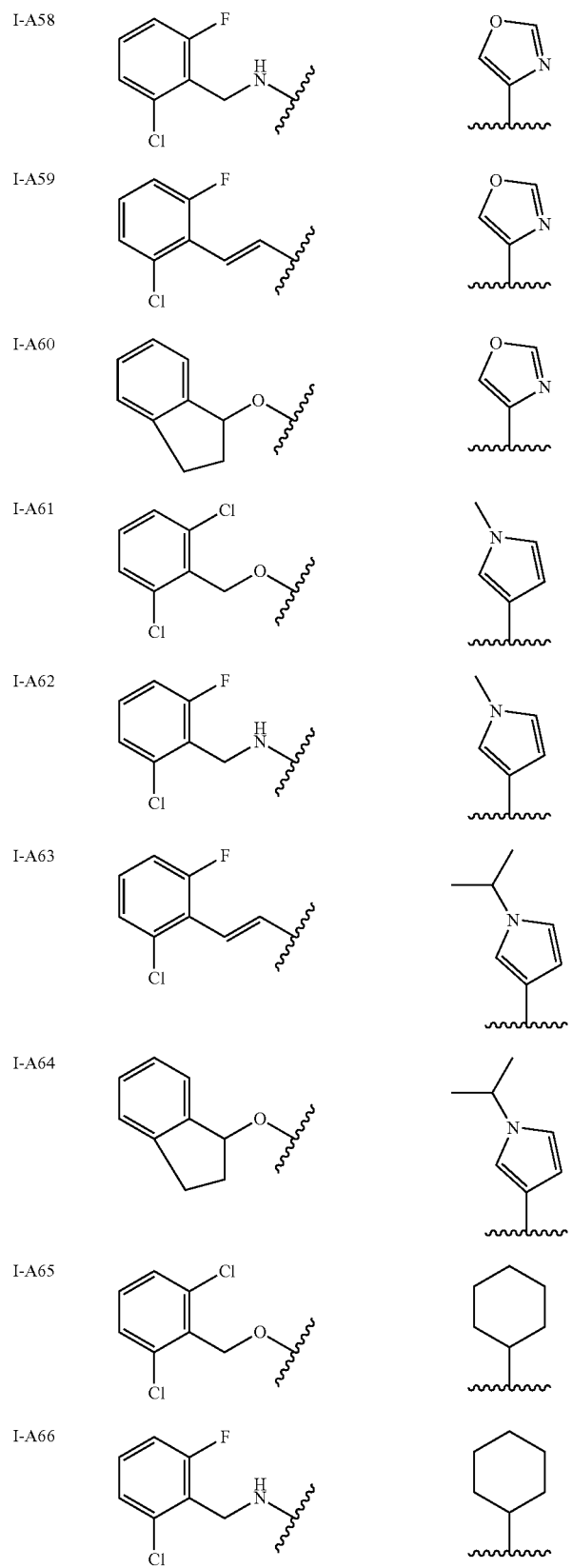 | |
| I-A59 | | |
| I-A60 | | |
| I-A61 | | |
| I-A62 | | |
| I-A63 | | |
| I-A64 | | |
| I-A65 | | |
| I-A66 | | |

-continued
| No. | X | Z |
|---|---|---|
| I-A67 | 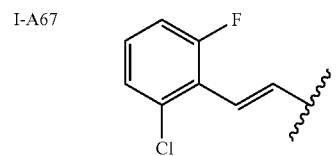 | 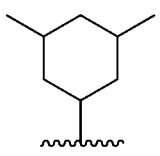 |
| I-A68 | 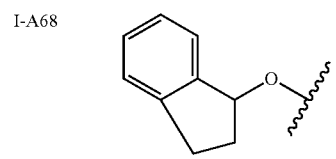 | 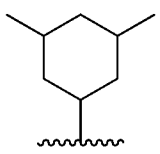 |
| I-A69 | 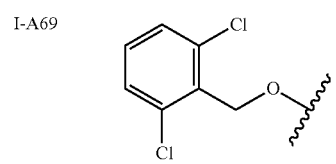 | 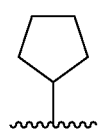 |
| I-A70 | 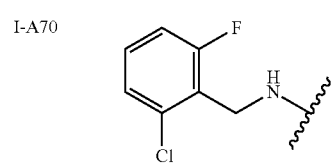 | 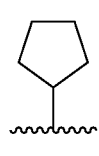 |
| I-A71 | 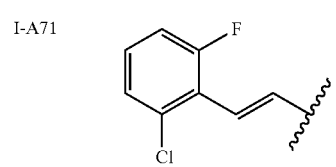 | 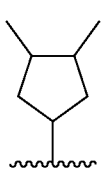 |
| I-A72 | 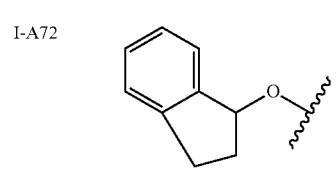 | 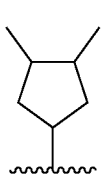 |
| I-A73 | 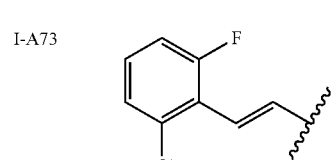 | 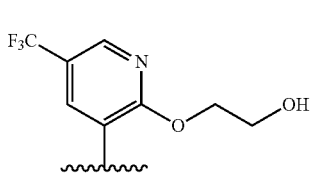 [SMILES: *c1cc(C(F)(F)F)cnc1OCCO] |
| I-A74 | 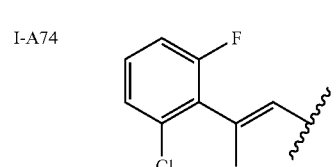 | 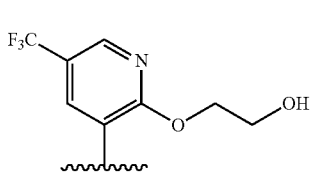 [SMILES: *c1cc(C(F)(F)F)cnc1OCCO] |
| I-A75 | 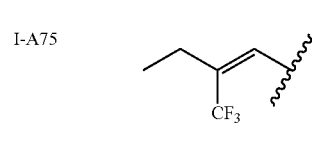 | 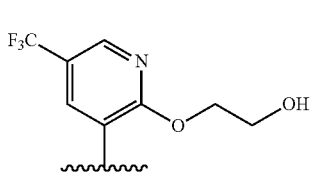 [SMILES: *c1cc(C(F)(F)F)cnc1OCCO] |

-continued

| No. | X | Z |
|---|---|---|
| I-A76 | 2,6-dichlorobenzyl-O- | 3-(trifluoromethyl)phenyl |
| I-A77 | 2-chloro-6-fluorobenzyl-NH- | 3-(trifluoromethyl)phenyl |
| I-A78 | (E)-2-(2-chloro-6-fluorophenyl)vinyl- | 3-(trifluoromethyl)phenyl |
| I-A79 | 2-(2-chloro-6-fluorophenyl)ethyl- | 3-(trifluoromethyl)phenyl |
| I-A80 | 2,6-dichlorobenzyl-O- | 3-fluoro-5-(trifluoromethyl)phenyl |
| I-A81 | 2-chloro-6-fluorobenzyl-NH- | 3-fluoro-5-(trifluoromethyl)phenyl |
| I-A82 | 3,3,3-trifluoro-2-(2,2,2-trifluoroethyl)propenyl- | 2-(2-hydroxyethoxy)-5-(trifluoromethyl)pyridin-3-yl |
| I-A83 | (E)-2-(2-chloro-6-fluorophenyl)-1-methylvinyl- | 2-(2-hydroxyethoxy)-4-methyl-5-(trifluoromethyl)pyridin-3-yl |
| I-A84 | (E)-2-(2-chloro-6-fluorophenyl)-1-methylvinyl- | 2-(2-hydroxyethoxy)-6-methyl-5-(trifluoromethyl)pyridin-3-yl |

-continued

| No. | X | Z |
|---|---|---|
| I-A85 | F₃C-C(=CH-)-CH₂CH₃ | 5-(CF₃)-pyridin-2-yl with OCH₂CH₂OH |
| I-A86 | 2-Cl-6-F-phenyl-C(CH₃)=CH- | 5-cyclopropyl-pyridin-2-yl with OCH₂CH₂OH |
| I-A87 | 2-Cl-6-F-phenyl-C(CH₃)=CH- | 5-(CF₃)-pyridin-2-yl with NHCH₂CH₂OH |
| I-A88 | 2-Cl-6-F-phenyl-C(CH₃)=CH- | 5-(CF₃)-pyridin-2-yl with OCHF₂ |
| I-A89 | cyclohexylidene-CH- | 5-(CF₃)-pyridin-2-yl with OCH₂CH₂OH |
| I-A90 | cyclohexylidene-CH- | 3-(CF₃)-phenyl |
| I-A91 | 2,2-difluorocyclohexylidene-CH- | 3-(CF₃)-phenyl |
| I-A92 | CH₃CH₂-C(CF₃)=CH- | 5-(CF₃)-pyridin-2-yl with NHCH₂CH₂OH |
| I-A93 | cyclohexyl-CH₂- | 5-(CF₃)-pyridin-2-yl with OCH₂CH₂OH |

| No. | X | Z |
|---|---|---|
| I-A94 | 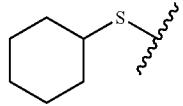 | 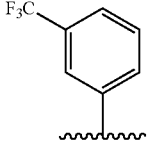 [SMILES: *c1cccc(C(F)(F)F)c1] |
| I-A95 | 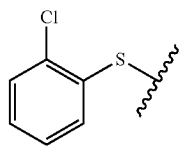 [SMILES: *Sc1ccccc1Cl] | 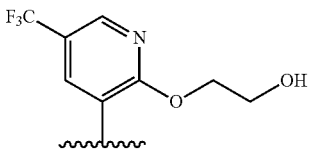 [SMILES: *c1cc(C(F)(F)F)cnc1OCCO] |
| I-A96 | 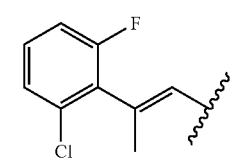 [SMILES: */C=C(\C)c1c(F)cccc1Cl] | 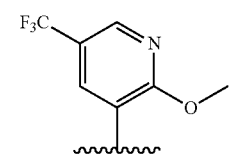 [SMILES: *c1cc(C(F)(F)F)cnc1OC] |
| I-A97 | 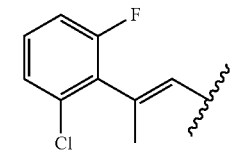 [SMILES: */C=C(\C)c1c(F)cccc1Cl] | 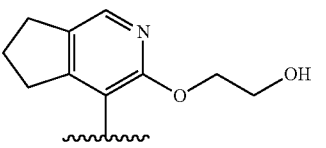 [SMILES: *c1c(OCCO)ncc2c1CCC2] |
| I-A98 | 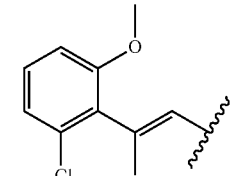 | 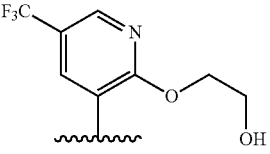 [SMILES: *c1cc(C(F)(F)F)cnc1OCCO] |
| I-A99 | 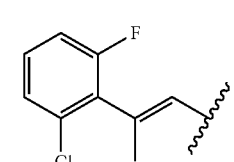 | 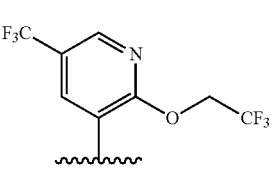 [SMILES: *c1cc(C(F)(F)F)cnc1OCC(F)(F)F] |
| I-A100 | 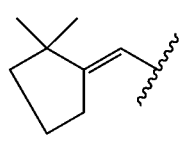 [SMILES: */C=C1\CCCC1(C)C] | 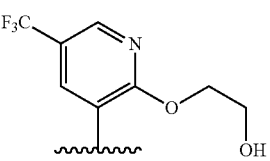 |
| I-A101 | 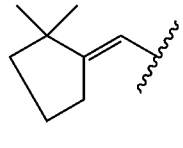 [SMILES: */C=C1\CCCC1(C)C] | 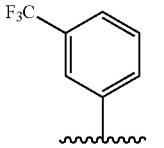 [SMILES: *c1cccc(C(F)(F)F)c1] |
| I-A102 | 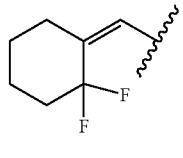 [SMILES: */C=C1/CCCCC1(F)F] | 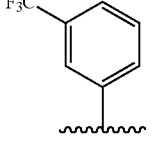 |

US 10,442,798 B2
-continued
| No. | X | Z |
|---|---|---|
| I-A103 | 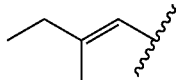 | 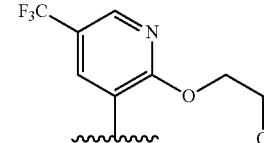 |
| I-A104 | 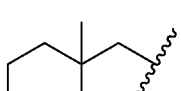 | 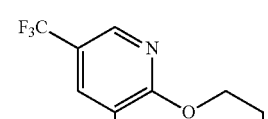 |
| I-A105 | 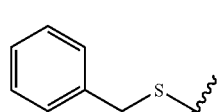 | 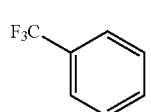 |
| I-A106 | 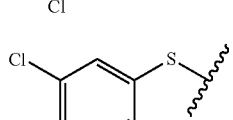 | 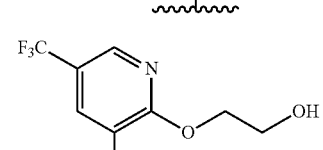 |
TABLE 24-1
Compound Structure TABLE 24-1-continued Compound Structure TABLE 24-1-continued
Compound Structure
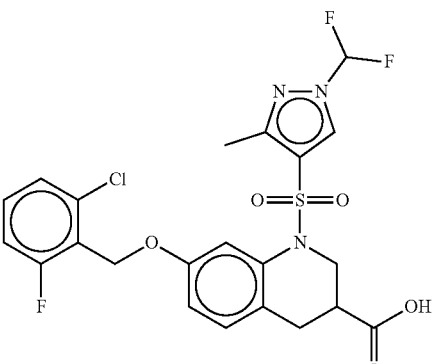
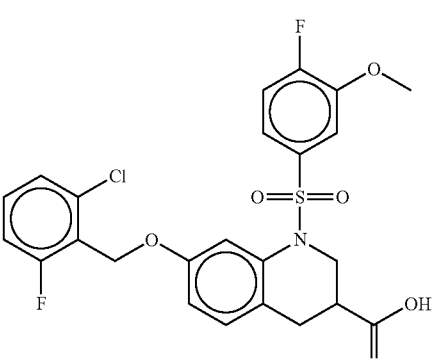
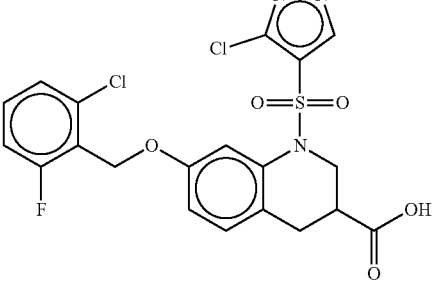
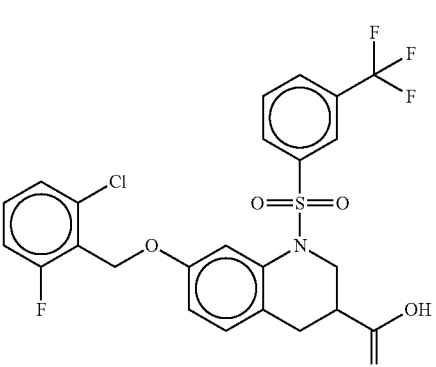
TABLE 24-1-continued
Compound Structure
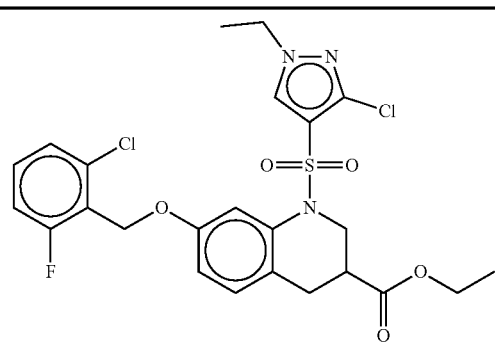

TABLE 24-1-continued
Compound Structure
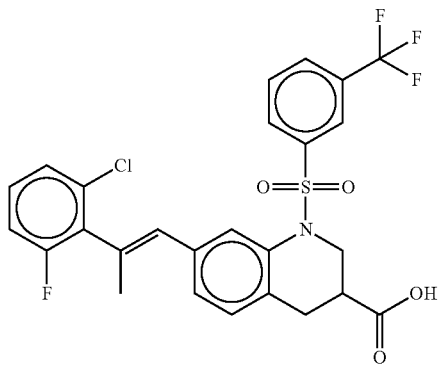
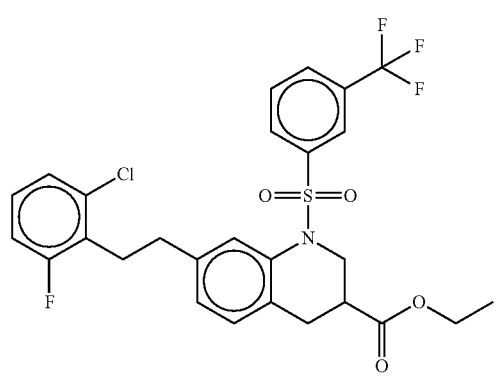
TABLE 25-1
| Title Compound from Example No. | Compound Structure |
| --- | --- |
| 9D | 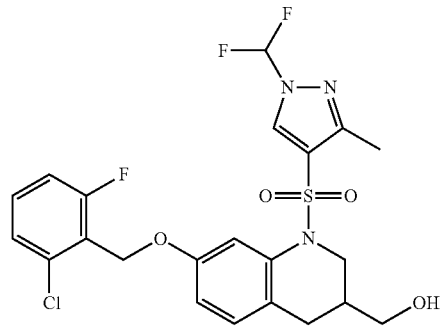 [SMILES: Cc1nn(C(F)F)cc1S(=O)(=O)N1CC(CO)Cc2ccc(OCc3c(F)cccc3Cl)cc21] |
TABLE 25-1-continued
| Title Compound from Example No. | Compound Structure |
| --- | --- |
| 9E | 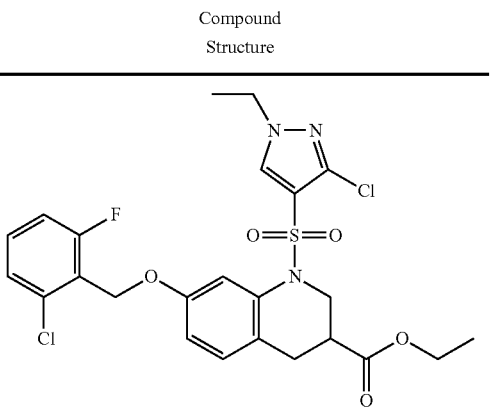 |
| 15B | 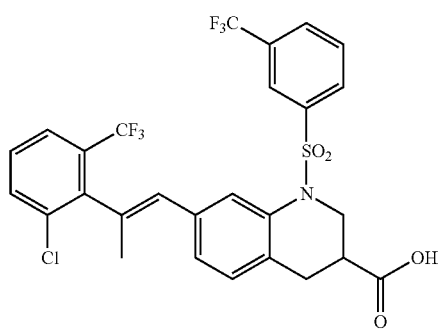 [SMILES: C/C(=C\c1ccc2c(c1)N(S(=O)(=O)c1cccc(C(F)(F)F)c1)CC(C(=O)O)C2)c1c(Cl)cccc1C(F)(F)F] |
| 15C | 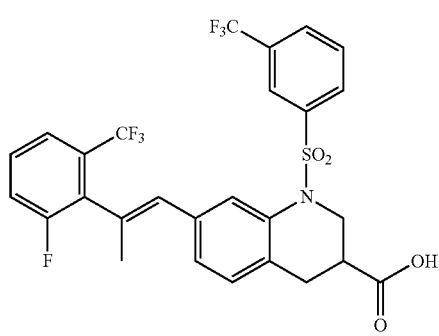 |
| 15D | 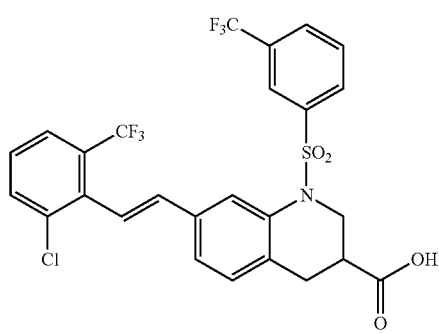 [SMILES: O=C(O)C1Cc2ccc(/C=C/c3c(Cl)cccc3C(F)(F)F)cc2N(S(=O)(=O)c2cccc(C(F)(F)F)c2)C1] |

TABLE 25-1-continued
| Title Compound from Example No. | Compound Structure |
|---|---|
| 20 | 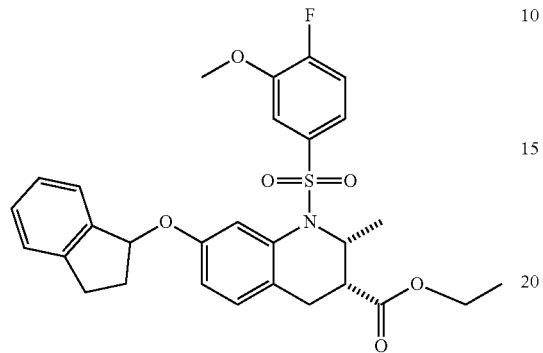 |
| 21 | 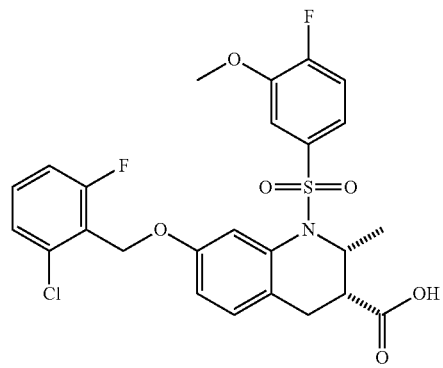 [SMILES: COc1cc(S(=O)(=O)N2c3cc(OCc4c(F)cccc4Cl)ccc3C[C@@H](C(=O)O)[C@H]2C)ccc1F] |
| 22 | 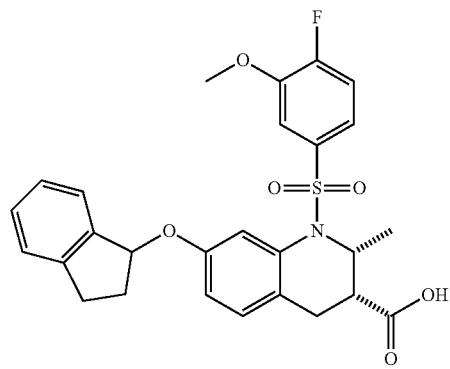 [SMILES: COc1cc(S(=O)(=O)N2c3cc(OC4CCc5ccccc54)ccc3C[C@@H](C(=O)O)[C@H]2C)ccc1F] |
| 24 | 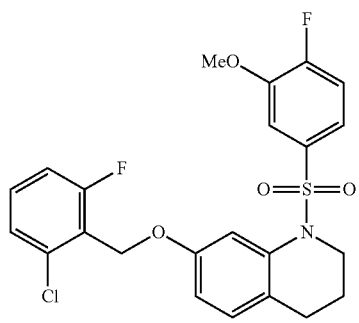 [SMILES: COc1cc(S(=O)(=O)N2CCCc3ccc(OCc4c(F)cccc4Cl)cc32)ccc1F] |
| 25A | 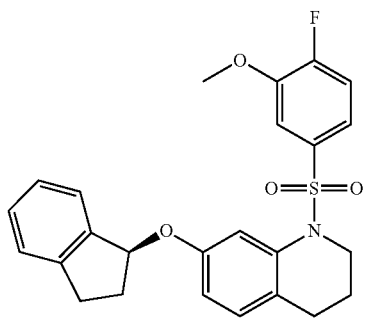 [SMILES: COc1cc(S(=O)(=O)N2CCCc3ccc(O[C@H]4CCc5ccccc54)cc32)ccc1F] |
| 25B | 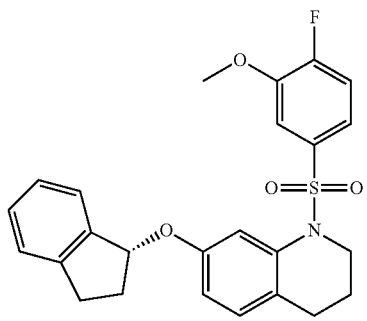 [SMILES: COc1cc(S(=O)(=O)N2CCCc3ccc(O[C@@H]4CCc5ccccc54)cc32)ccc1F] |
| 25C | 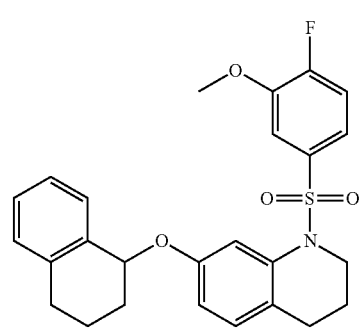 [SMILES: COc1cc(S(=O)(=O)N2CCCc3ccc(OC4CCCc5ccccc54)cc32)ccc1F] |
| 25D | 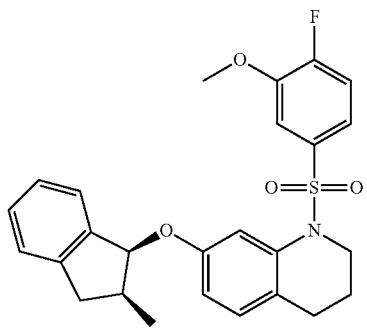 [SMILES: COc1cc(S(=O)(=O)N2CCCc3ccc(O[C@@H]4c5ccccc5C[C@@H]4C)cc32)ccc1F] |

TABLE 25-1-continued

| Title Compound from Example No. | Compound Structure |
|---|---|
| 25E | 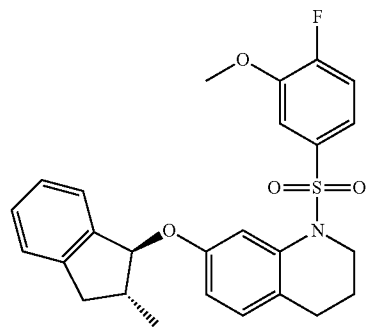 [SMILES: COc1cc(S(=O)(=O)N2CCCc3ccc(O[C@@H]4c5ccccc5C[C@H]4C)cc32)ccc1F] |
| 25J | 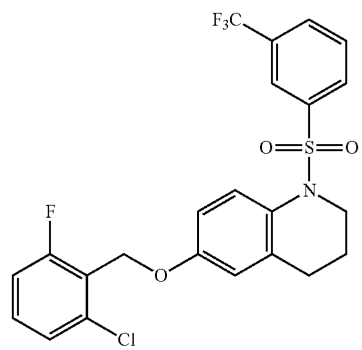 [SMILES: O=S(=O)(c1cccc(C(F)(F)F)c1)N1CCCc2cc(OCc3c(F)cccc3Cl)ccc21] |
| 25K | 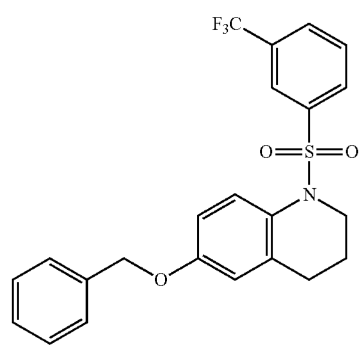 [SMILES: O=S(=O)(c1cccc(C(F)(F)F)c1)N1CCCc2cc(OCc3ccccc3)ccc21] |
| 25L | 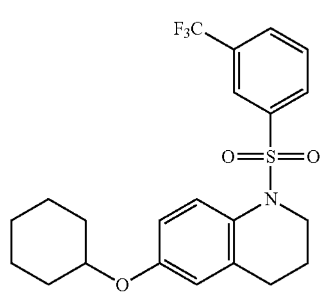 [SMILES: O=S(=O)(c1cccc(C(F)(F)F)c1)N1CCCc2cc(OC3CCCCC3)ccc21] |
| 25M | |
| 25N | |
| 25O | |
| 25P | |

TABLE 25-1-continued
| Title Compound from Example No. | Compound Structure |
|---|---|
| 25Q | 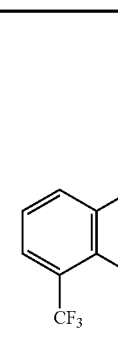 |
| 25R | 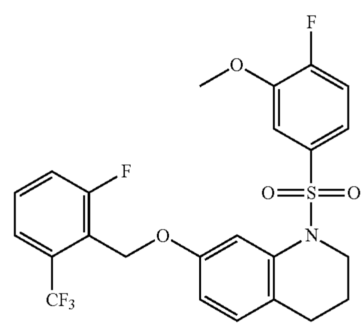 |
| 25S | 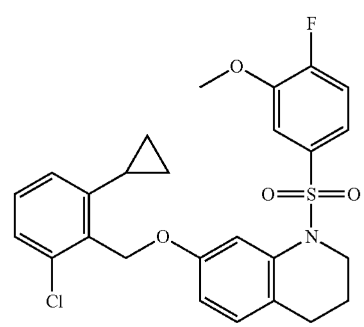 [SMILES: COc1cc(S(=O)(=O)N2CCCc3ccc(OCc4c(Cl)cccc4C4CC4)cc32)ccc1F] |
| 25T | 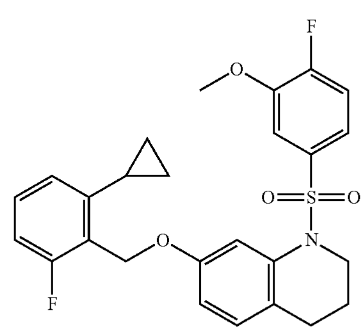 [SMILES: COc1cc(S(=O)(=O)N2CCCc3ccc(OCc4c(F)cccc4C4CC4)cc32)ccc1F] |
TABLE 25-1-continued
| Title Compound from Example No. | Compound Structure |
|---|---|
| 25U | 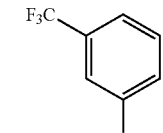 |
| 25V | 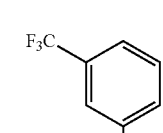 |
| 25W | 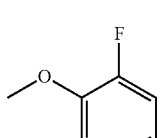 |
| 26 | 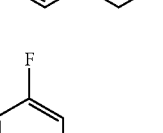 |

TABLE 25-1-continued
| Title Compound from Example No. | Compound Structure |
|---|---|
| 27 | 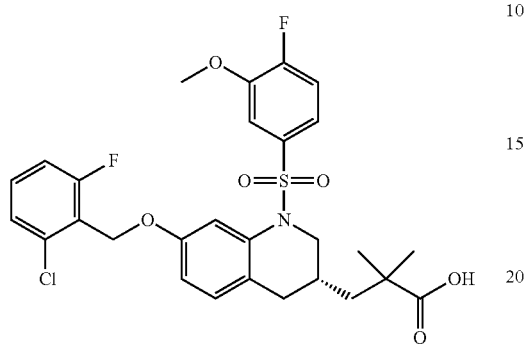 |
| 28A | 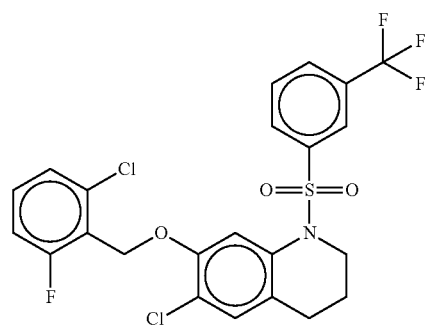 |
| 28B | 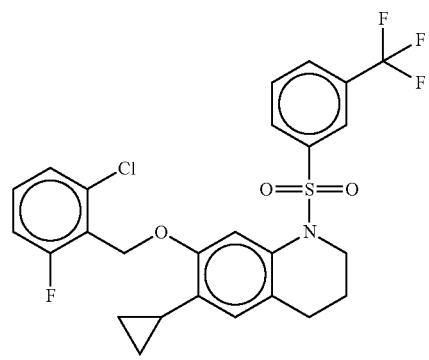 |
| 28C | 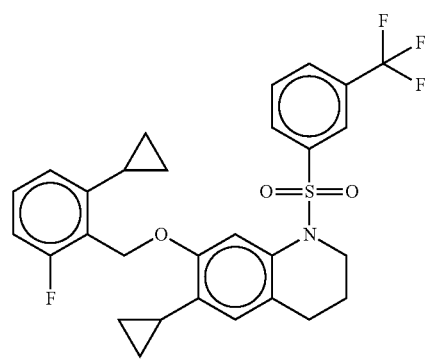 |
| 28D | 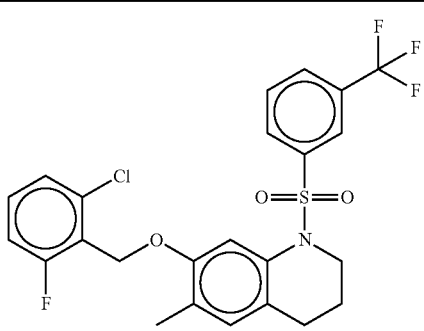 |
| 28F | 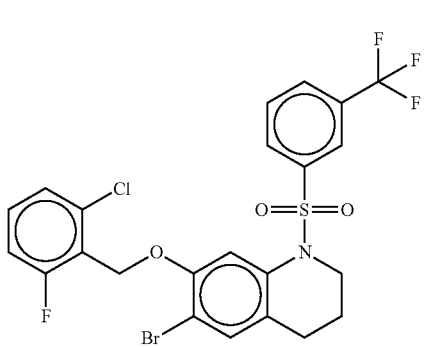 |
| 116F | 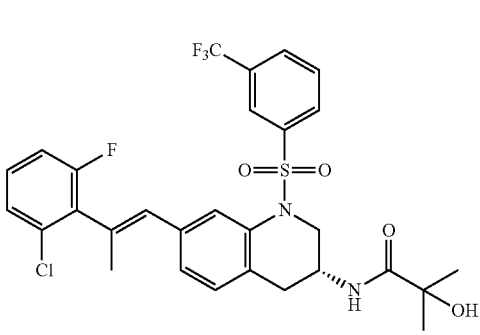 [SMILES: C/C(=C\c1ccc2c(c1)N(S(=O)(=O)c1cccc(C(F)(F)F)c1)C[C@H](NC(=O)C(C)(C)O)C2)c1c(F)cccc1Cl] |
| 116G | 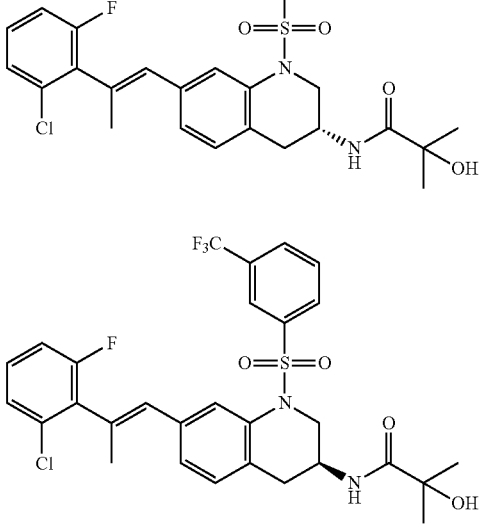 |

TABLE 25-1-continued
| Title Compound from Example No. | Compound Structure |
|---|---|
| 116H | 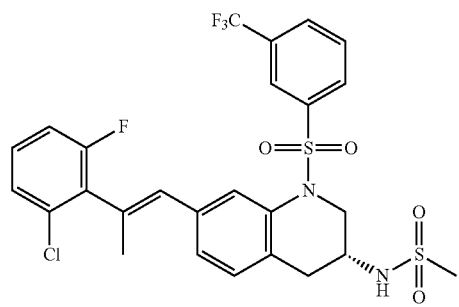 |
| 116I | 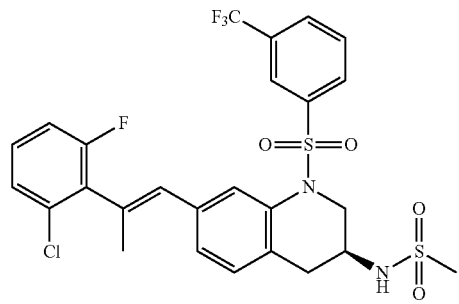 [SMILES: C/C(=C\c1ccc2c(c1)N(S(=O)(=O)c1cccc(C(F)(F)F)c1)C[C@@H](NS(C)(=O)=O)C2)c1c(F)cccc1Cl] |
| 116J | 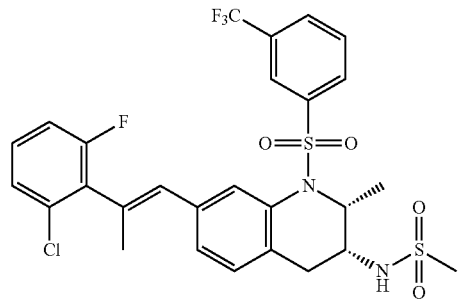 [SMILES: C/C(=C\c1ccc2c(c1)N(S(=O)(=O)c1cccc(C(F)(F)F)c1)[C@H](C)[C@H](NS(C)(=O)=O)C2)c1c(F)cccc1Cl] |
| 116L | 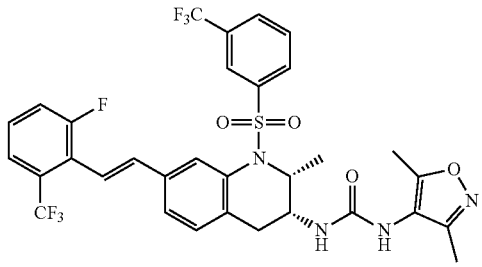 [SMILES: Cc1noc(C)c1NC(=O)N[C@@H]1Cc2ccc(/C=C/c3c(F)cccc3C(F)(F)F)cc2N(S(=O)(=O)c2cccc(C(F)(F)F)c2)[C@@H]1C] |
| 116M | 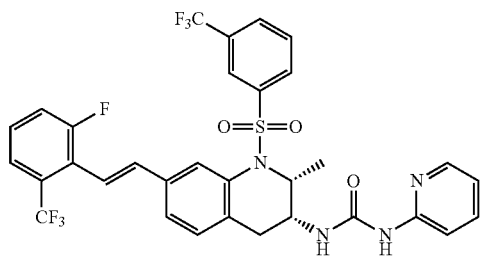 [SMILES: C[C@@H]1[C@H](NC(=O)Nc2ccccn2)Cc2ccc(/C=C/c3c(F)cccc3C(F)(F)F)cc2N1S(=O)(=O)c1cccc(C(F)(F)F)c1] |
TABLE 25-1-continued
| Title Compound from Example No. | Compound Structure |
|---|---|
| 138 | 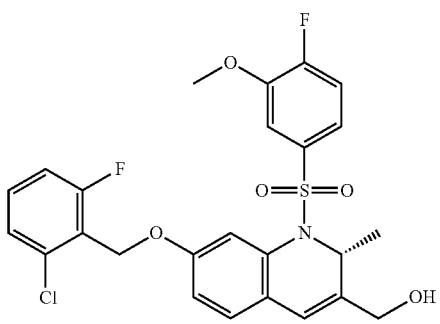 [SMILES: COc1cc(S(=O)(=O)N2c3cc(OCc4c(F)cccc4Cl)ccc3C=C(CO)[C@H]2C)ccc1F] |
| 139 | 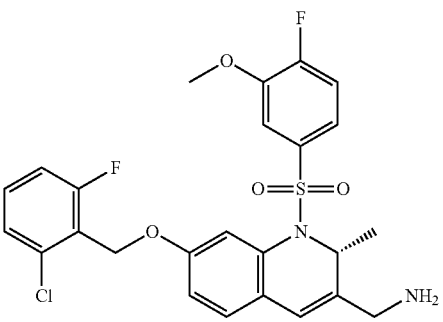 [SMILES: COc1cc(S(=O)(=O)N2c3cc(OCc4c(F)cccc4Cl)ccc3C=C(CN)[C@H]2C)ccc1F] |
| 140 | 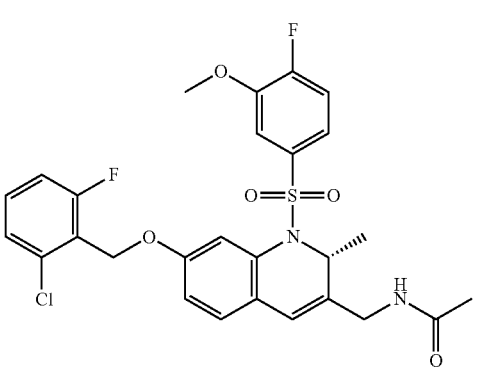 [SMILES: COc1cc(S(=O)(=O)N2c3cc(OCc4c(F)cccc4Cl)ccc3C=C(CNC(C)=O)[C@H]2C)ccc1F] |
| 142 | 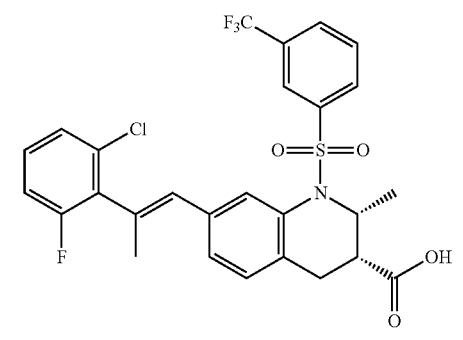 [SMILES: C/C(=C\c1ccc2c(c1)N(S(=O)(=O)c1cccc(C(F)(F)F)c1)[C@H](C)[C@H](C(=O)O)C2)c1c(F)cccc1Cl] |

TABLE 25-1-continued
| Title Compound from Example No. | Compound Structure |
|---|---|
| 143 | 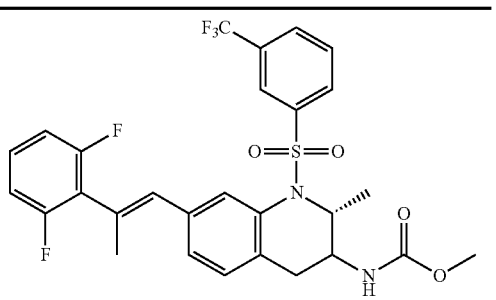 |
| 145 | 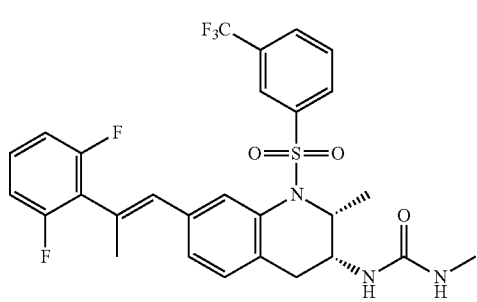 [SMILES: CNC(=O)N[C@@H]1Cc2ccc(/C=C(\C)c3c(F)cccc3F)cc2N(S(=O)(=O)c2cccc(C(F)(F)F)c2)[C@@H]1C] |
| 146 | 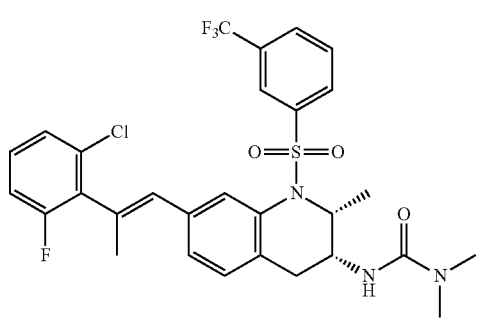 [SMILES: C/C(=C\c1ccc2c(c1)N(S(=O)(=O)c1cccc(C(F)(F)F)c1)[C@H](C)[C@H](NC(=O)N(C)C)C2)c1c(F)cccc1Cl] |
| 147 | 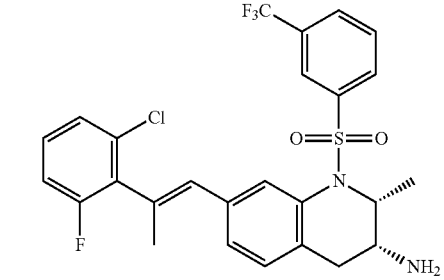 [SMILES: C/C(=C\c1ccc2c(c1)N(S(=O)(=O)c1cccc(C(F)(F)F)c1)[C@H](C)[C@H](N)C2)c1c(F)cccc1Cl] |
| 148 | 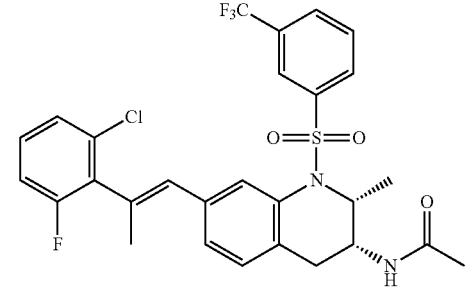 [SMILES: CC(=O)N[C@@H]1Cc2ccc(/C=C(\C)c3c(F)cccc3Cl)cc2N(S(=O)(=O)c2cccc(C(F)(F)F)c2)[C@@H]1C] |
TABLE 25-1-continued
| Title Compound from Example No. | Compound Structure |
|---|---|
| 149 | 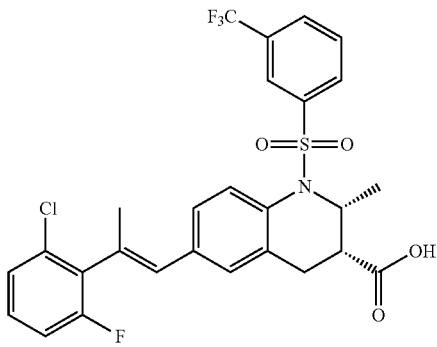 [SMILES: C/C(=C\c1ccc2c(c1)C[C@@H](C(=O)O)[C@@H](C)N2S(=O)(=O)c1cccc(C(F)(F)F)c1)c1c(F)cccc1Cl] |
| 150 | 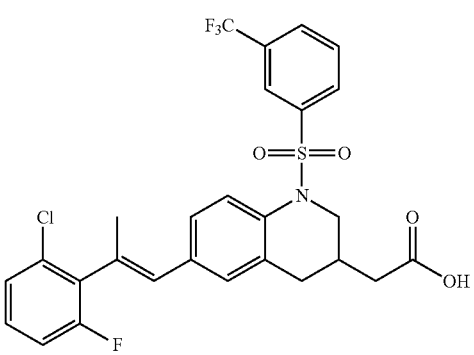 [SMILES: C/C(=C\c1ccc2c(c1)CC(CC(=O)O)CN2S(=O)(=O)c1cccc(C(F)(F)F)c1)c1c(F)cccc1Cl] |
| 151 | 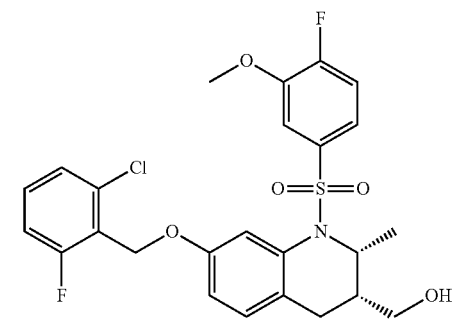 [SMILES: COc1cc(S(=O)(=O)N2c3cc(OCc4c(F)cccc4Cl)ccc3C[C@@H](CO)[C@H]2C)ccc1F] |
| 152 | 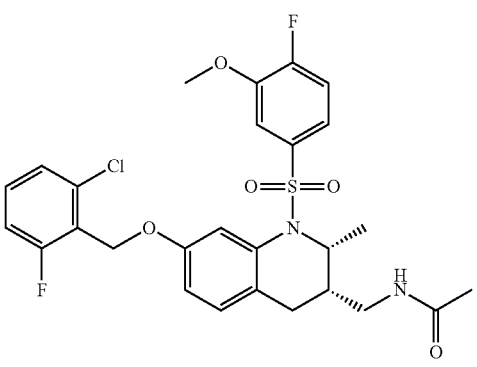 [SMILES: COc1cc(S(=O)(=O)N2c3cc(OCc4c(F)cccc4Cl)ccc3C[C@@H](CNC(C)=O)[C@H]2C)ccc1F] |

TABLE 25-1-continued
| Title Compound from Example No. | Compound Structure |
|---|---|
| 153 | 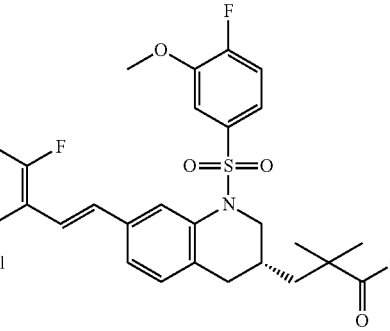 |
| 154A | 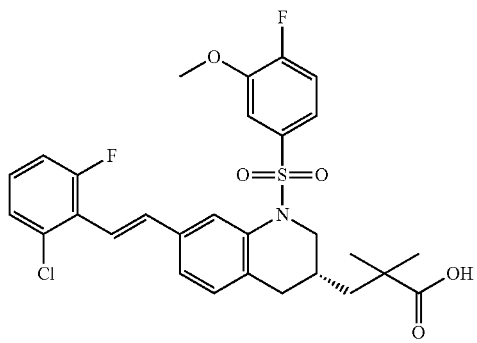 [SMILES: COc1cc(S(=O)(=O)N2C[C@H](CC(C)(C)C(=O)O)Cc3ccc(/C=C/c4c(F)cccc4Cl)cc32)ccc1F] |
| 154B | 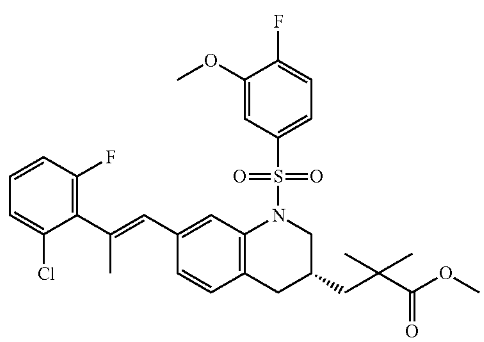 [SMILES: COC(=O)C(C)(C)C[C@@H]1Cc2ccc(/C=C(\C)c3c(F)cccc3Cl)cc2N(S(=O)(=O)c2ccc(F)c(OC)c2)C1] |
| 154C | 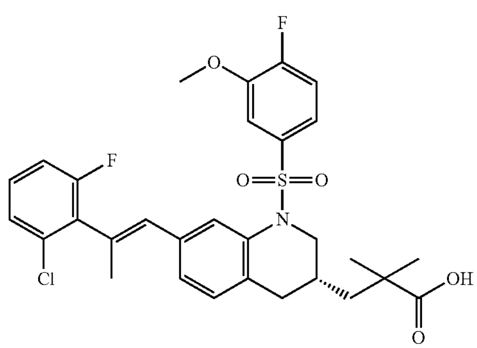 [SMILES: COc1cc(S(=O)(=O)N2C[C@H](CC(C)(C)C(=O)O)Cc3ccc(/C=C(\C)c4c(F)cccc4Cl)cc32)ccc1F] |
TABLE 25-1-continued
| Title Compound from Example No. | Compound Structure |
|---|---|
| 155 | 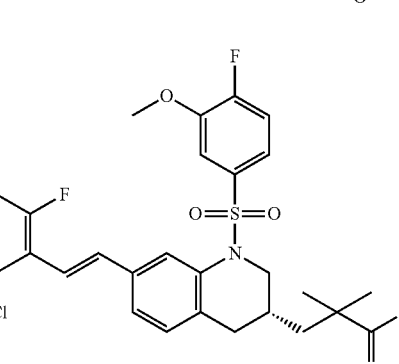 |
| 157 | 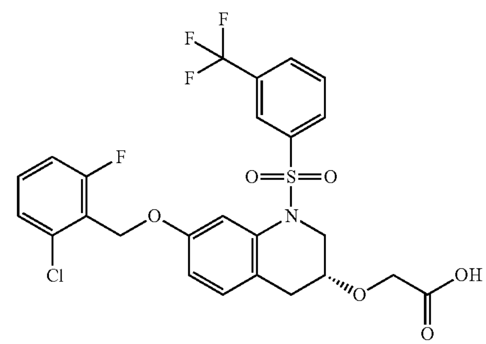 [SMILES: O=C(O)CO[C@@H]1Cc2ccc(OCc3c(F)cccc3Cl)cc2N(S(=O)(=O)c2cccc(C(F)(F)F)c2)C1] |
| 158 | 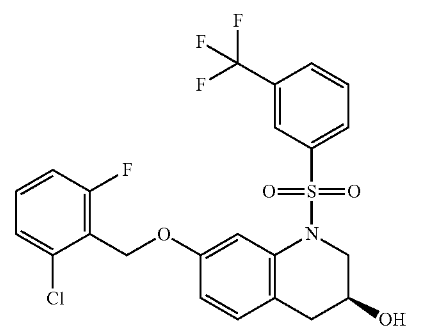 [SMILES: O=S(=O)(c1cccc(C(F)(F)F)c1)N1C[C@@H](O)Cc2ccc(OCc3c(F)cccc3Cl)cc21] |
| 159 | 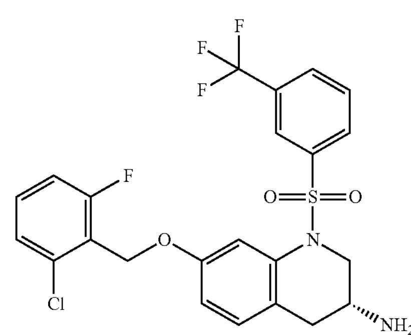 |

TABLE 25-1-continued
| Title Compound from Example No. | Compound Structure |
|---|---|
| 160 | 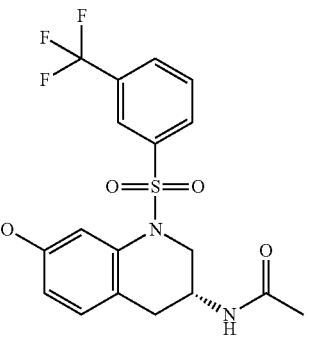 |
| 161 | 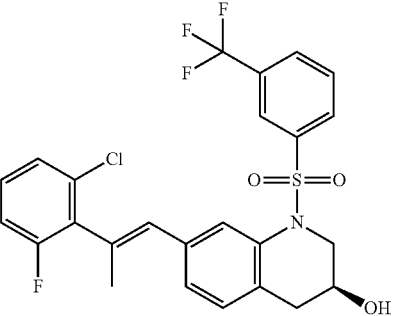 |
| 162 | 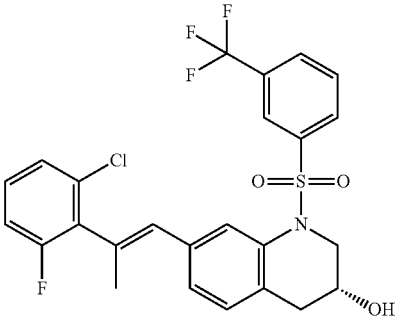 [SMILES: C/C(=C\c1ccc2c(c1)N(S(=O)(=O)c1cccc(C(F)(F)F)c1)C[C@H](O)C2)c1c(F)cccc1Cl] |
| 163 | 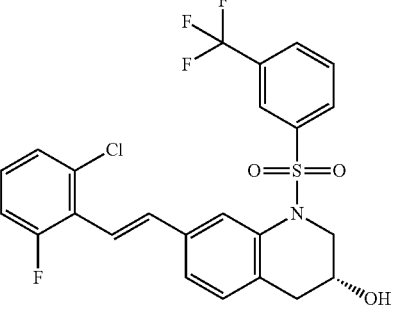 |//
TABLE 25-1-continued
| Title Compound from Example No. | Compound Structure |
|---|---|
| 164 | 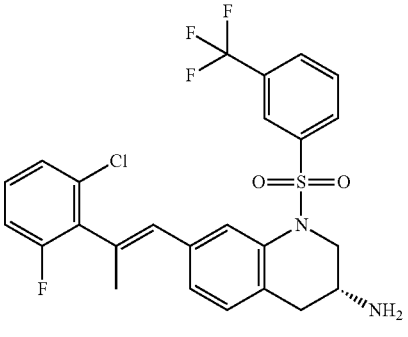 |
| 165 | 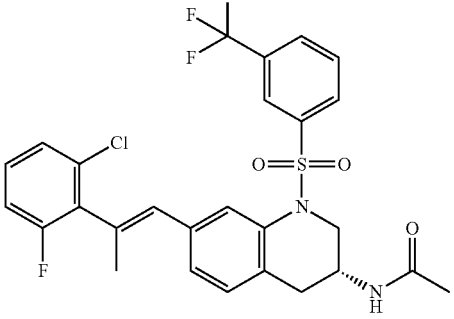 |
| 166 | 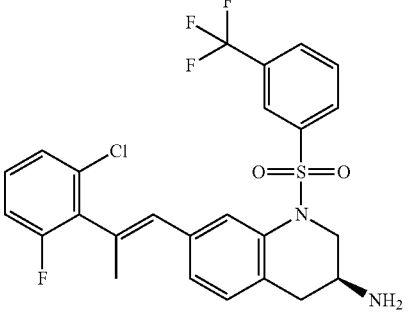 |
| 167 | 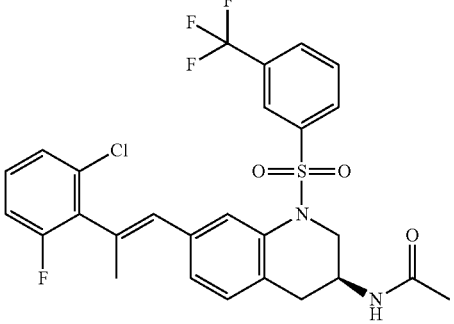 |

TABLE 25-1-continued

| Title Compound from Example No. | Compound Structure |
|---|---|
| 168 | (structure) |
| 169 | (structure) |
| 170 | (structure) |
| 171 | (structure) |
| 172 | (structure) |
| 173A | (structure) |
| 173B | (structure) |
| 173C | (structure) |

TABLE 25-1-continued
| Title Compound from Example No. | Compound Structure |
|---|---|
| 173D | 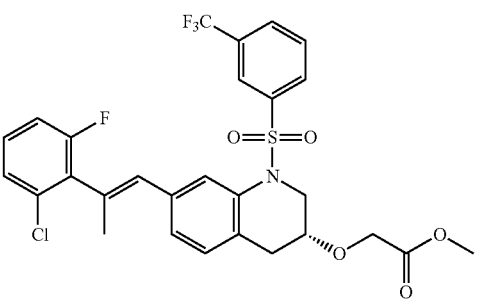 [SMILES: COC(=O)CO[C@@H]1Cc2ccc(/C=C(\C)c3c(F)cccc3Cl)cc2N(S(=O)(=O)c2cccc(C(F)(F)F)c2)C1] |
| 173E | 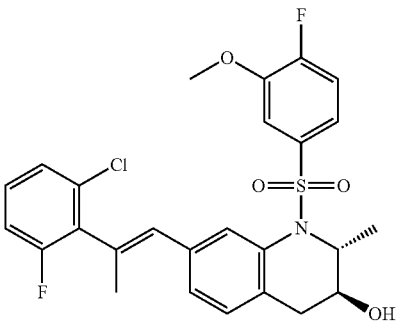 |
| 173F | 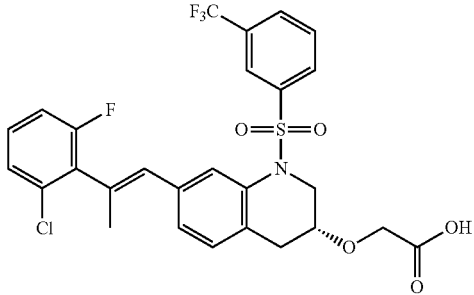 [SMILES: C/C(=C\c1ccc2c(c1)N(S(=O)(=O)c1cccc(C(F)(F)F)c1)C[C@H](OCC(=O)O)C2)c1c(F)cccc1Cl] |
| 174 | 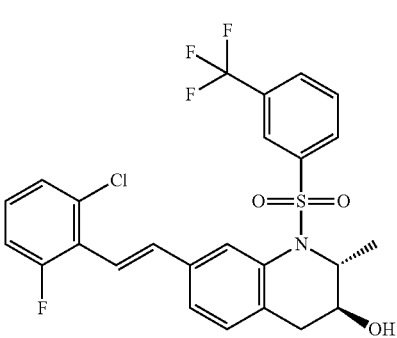 |
TABLE 25-1-continued
| Title Compound from Example No. | Compound Structure |
|---|---|
| 175 | 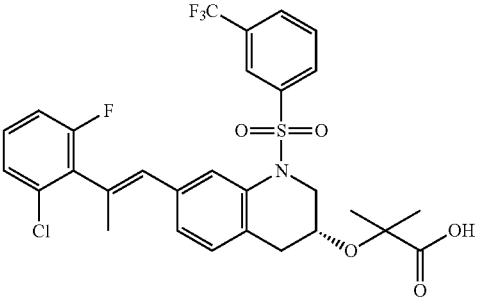 [SMILES: C/C(=C\c1ccc2c(c1)N(S(=O)(=O)c1cccc(C(F)(F)F)c1)C[C@H](OC(C)(C)C(=O)O)C2)c1c(F)cccc1Cl] |
| 176 | 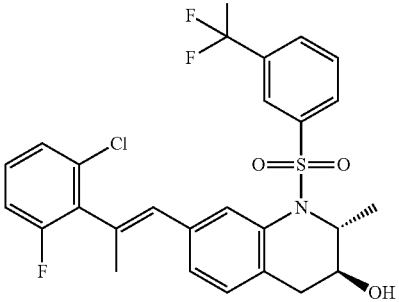 |
| 177 | 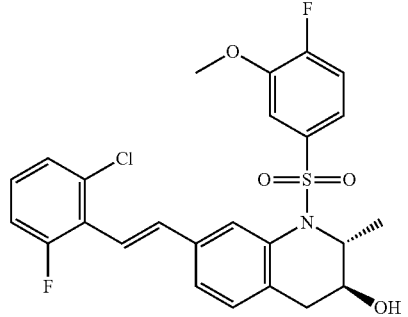 [SMILES: COc1cc(S(=O)(=O)N2c3cc(/C=C/c4c(F)cccc4Cl)ccc3C[C@H](O)[C@H]2C)ccc1F] |
| 187 | 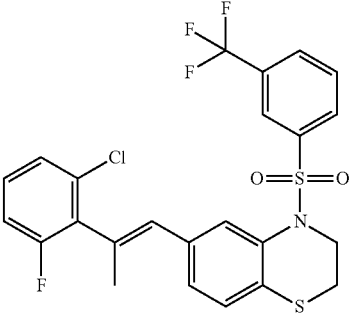 [SMILES: C/C(=C\c1ccc2c(c1)N(S(=O)(=O)c1cccc(C(F)(F)F)c1)CCS2)c1c(F)cccc1Cl] |

TABLE 25-1-continued

Title Compound from Example No. | Compound Structure
---|---
188 | 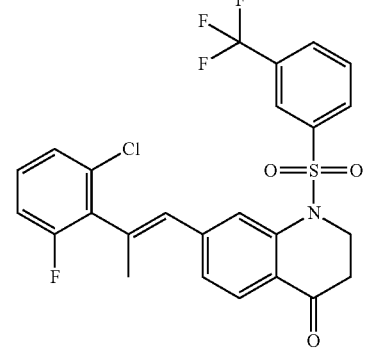
189 | 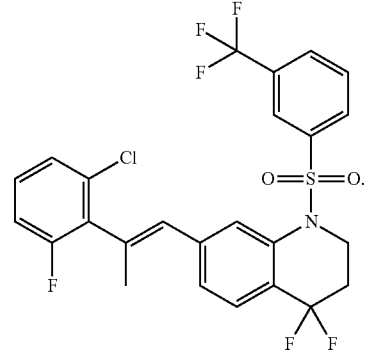 [SMILES: C/C(=C\c1ccc2c(c1)N(S(=O)(=O)c1cccc(C(F)(F)F)c1)CCC2(F)F)c1c(F)cccc1Cl]

22. A pharmaceutical composition comprising a compound of claim 1 and a pharmaceutically acceptable carrier.

23. A method of treating a disorder selected from the group consisting of cancer, bacterial infection, and fungal infection, comprising administering a therapeutically effective amount of a compound of claim 1 to a subject in need thereof to ameliorate a symptom of the disorder, wherein the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, or retinoblastoma.

24. The method of claim 23, wherein the disorder is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, or retinoblastoma.

25. A method of increasing the amount of IL-17 in a subject, comprising administering to a subject an effective amount of a compound of claim 1 to increase the amount of IL-17 in the subject.

26. The method of claim 23, wherein the subject is a human.

27. A method of promoting the activity of RORγ, comprising exposing a RORγ to an effective amount of a compound of claim 1 to promote the activity of said RORγ.

28. A compound represented by Formulae III or IV:

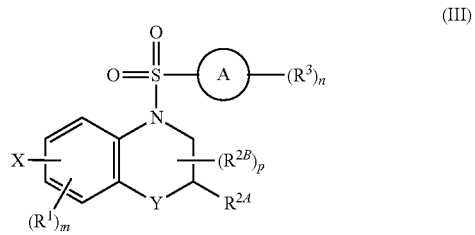

or a pharmaceutically acceptable salt thereof; wherein:

A is phenylene, 5-6 membered heteroarylene, or $C_{3-6}$ heterocycloalkylene;

$R^1$ represents independently for each occurrence halogen, $C_{1-6}$ alkyl, $C_{1-6}$ haloalkyl, or $C_{3-6}$ cycloalkyl;

$R^{2A}$ is —($C_{1-2}$ alkylene)-(2-8 membered heteroalkylene)-$CO_2R^4$, —($C_{1-6}$ alkylene)-$C(O)N(R^4)(C_{1-6}$ hydroxyalkylene)-$CO_2R^4$, or —($C_{1-6}$ alkylene)-$N(R^4)C(O)N(R^4)$—($C_{1-6}$ alkylene)-$CO_2R^4$; wherein the $C_{1-6}$ alkylene is optionally substituted with 1 or 2 substituents independently selected from the group consisting of —$CO_2R^4$, —$C(O)N(R^4)(R^5)$, —CN, halogen, hydroxyl, $C_{1-6}$ alkoxy, $C_{1-6}$ haloalkoxy, $C_{1-6}$ haloalkyl, and —$N(R^4)(R^5)$;

$R^{2B}$ is $C_{1-6}$ alkyl, $C_{1-3}$ haloalkyl, or fluoro;

$R^3$ represents independently for each occurrence hydrogen, $C_{1-6}$ haloalkyl, halogen, hydroxyl, $C_{1-6}$ alkyl, $C_3$-6 cycloalkyl, $C_{1-6}$ alkoxy, $C_{1-6}$ haloalkoxy, —$N(R^4)(R^8)$, —O—($C_{1-6}$ hydroxyalkyl), or —O—($C_{1-6}$ alkylene)-$CO_2R^4$; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-8 membered heterocyclic ring;

$R^6$ and $R^7$ each represent independently for each occurrence hydrogen, fluoro, or $C_{1-6}$ alkyl, or $R^6$ and $R^7$ are taken together with the carbon atom to which they are attached to form a 3-6 membered carbocyclic ring; or $R^6$ and a vicinal occurrence of $R^{2B}$ are taken together to form a bond;

$R^8$ represents independently for each occurrence $C_{1-6}$ alkyl, $C_{3-6}$ cycloalkyl, —($C_{1-6}$ alkylene)-($C_{3-6}$ cycloalkyl), or aryl, each of which is optionally substituted with 1, 2, or 3 substituents independently selected from the group consisting of halogen, hydroxyl, and —$CO_2R^4$; or $R^8$ is —$CO_2R^4$;

$R^9$ represents independently for each occurrence $C_{1-6}$ alkyl, $C_{3-6}$ cycloalkyl, —($C_{1-6}$ alkylene)-($C_{3-6}$ cycloalkyl), $C_{1-6}$ haloalkyl, or $C_{1-6}$ hydroxyalkyl;

X is one of the following:

(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —$N(R^4)$-aralkyl, —$N(R^4)$- phenyl, —N(R⁴)-(partially unsaturated bicyclic carbocyclyl), or —N(R⁴)—(C₁₋₆ alkylene)-(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

(ii) —S-aralkyl, —S-heteroaralkyl, —S-phenyl, —S-heteroaryl, —S-(partially unsaturated bicyclic carbocyclyl), —S—(C₁₋₆ alkylene)-(C₃₋₆ cycloalkyl), or —S—(C₃-6 cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

(iii) —(C₂₋₆ alkenylene)-phenyl, —(C₂₋₆ alkenylene)-heteroaryl, —(C₂₋₆ alkenylene)-(partially unsaturated 8-10 membered bicyclic ring containing 0-3 heteroatoms), —(C₁₋₆ alkylene)-phenyl, —(C₁₋₆ alkylene)-heteroaryl, —(C₁₋₆ alkylene)-(partially unsaturated bicyclic heterocyclyl), —(C₁₋₆ alkylene)-(partially unsaturated bicyclic oxo-heterocyclyl), —(C₁₋₆ alkylene)-(C₃-C₆ cycloalkyl), -(5-6 membered heterocycloalkylene)-phenyl, or —(C₃₋₆ cycloalkyl ene)-phenyl, each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

(iv) —(C₂₋₆ alkenylene)-(C₁₋₆ alkyl), —(C₂₋₆ alkenylene)-(C₃₋₆ cycloalkyl), or

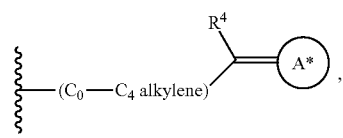

each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹, wherein A* is a 5-8 membered, partially saturated carbocyclic or heterocyclic ring; or (v) —(C₁₋₆ alkylene)-Z¹ or —(C₂₋₆ alkenylene)-Z¹, wherein Z¹ is —O-aralkyl, —O— heteroaralkyl, —O-phenyl, —O-heteroaryl, —O-(partially unsaturated bicyclic carbocyclyl), —O—(C₁₋₆ alkylene)-(C₃₋₆ cycloalkyl), —O—(C₃₋₆ cycloalkyl), —N(R⁴)-aralkyl, —N(R⁴)-phenyl, —N(R⁴)-(partially unsaturated bicyclic carbocyclyl), —N(R⁴)—(C₁₋₆ alkylene)-(C₃₋₆ cycloalkyl), or —N(R⁴)—(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

Y is —C(R⁶)(R⁷)—, —C(O)—, or —S(O)$_p$—;

m and p each represent independently for each occurrence 0, 1, or 2; and n is 1, 2, or 3; and Formula IV is represented by:

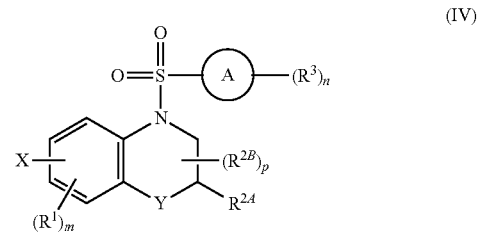

or a pharmaceutically acceptable salt thereof; wherein:

A is phenylene, 5-6 membered heteroarylene, or C₃₋₆ heterocycloalkylene;

R¹ represents independently for each occurrence halogen, C₁₋₆ alkyl, C₁₋₆ haloalkyl, or C₃₋₆ cycloalkyl;

R²ᴬ is one of the following:
(i) hydrogen, C₁₋₆ alkyl, C₁₋₃ haloalkyl, C₃₋₆ cycloalkyl, —(C₁₋₆ alkylene)-(C₃₋₆ cycloalkyl), —O—(C₁₋₆ alkylene)-CO₂R⁴, —O—(C₁₋₆ alkylene)-C(O)—(C₁₋₆ alkyl), —N(R⁴)—(C₁₋₆ alkylene)-CO₂R⁴, or —N(R⁴)—(C₁₋₆ alkylene)-C(O)—(C₁₋₆ alkyl), wherein the C₁₋₆ alkyl, C₃₋₆ cycloalkyl, and C₁₋₆ alkylene are optionally substituted with 1 or 2 substituents independently selected from the group consisting of —CO₂R⁴, —C(O)N(R⁴)(R⁵), —C(O)—N(R⁴)—(C₁₋₄ alkylene)-CO₂R⁴, —N(R⁴)C(O)R⁸, —CN, halogen, hydroxyl, C₁₋₆ alkoxy, C₁₋₆ haloalkoxy, C₁₋₆ haloalkyl, —N(R⁴)(R⁵), —N(R⁴)C(O)N(R⁴)(R⁵), —N(R⁴)CO₂R⁹, —N(R⁴)S(O)₂R⁹, and —N(R⁴) S(O)₂N(R⁴)(R⁵); or
(ii) —CO₂R⁴, —N(R⁴)C(O)R⁹, —N(R⁴)CO₂R⁹, —N(R⁴)C(O)N(R⁴)(R⁵), —N(R⁴)C(O)N(R⁴)(heteroaryl), —N(R⁴)S(O)₂R⁹, —N(R⁴)(R⁵), —OH, or —(C₁₋₂ alkylene)-(2-8 membered heteroalkylene)-CO₂R⁴;

R²ᴮ is C₁₋₆ alkyl, C₁₋₃ haloalkyl, or fluoro;

R³ represents independently for each occurrence hydrogen, C₁₋₆ haloalkyl, halogen, hydroxyl, C₁₋₆ alkyl, C₃-6 cycloalkyl, C₁₋₆ alkoxy, C₁₋₆ haloalkoxy, —N(R⁴)(R⁸), —O—(C₁₋₆ hydroxyalkyl), or —O—(C₁₋₆ alkylene)-CO₂R⁴; or two vicinal occurrences of R³ are taken together with intervening atoms to form a 4-6 membered ring;

R⁴ and R⁵ each represent independently for each occurrence hydrogen, C₁₋₆ alkyl, or C₃-6 cycloalkyl; or an occurrence of R⁴ and R⁵ attached to the same nitrogen atom are taken together with the nitrogen atom to which they are attached to form a 3-8 membered heterocyclic ring;

R⁶ and R⁷ each represent independently for each occurrence hydrogen, fluoro, or C₁₋₆ alkyl, or R⁶ and R⁷ are taken together with the carbon atom to which they are attached to form a 3-6 membered carbocyclic ring; or R⁶ and a vicinal occurrence of R²ᴮ are taken together to form a bond;

R⁸ represents independently for each occurrence C₁₋₆ alkyl, C₃₋₆ cycloalkyl, —(C₁₋₆ alkylene)-(C₃₋₆ cycloalkyl), or aryl, each of which is optionally substituted with 1, 2, or 3 substituents independently selected from the group consisting of halogen, hydroxyl, and —CO₂R⁴; or R⁸ is —CO₂R⁴;

R⁹ represents independently for each occurrence C₁₋₆ alkyl, C₃₋₆ cycloalkyl, —(C₁₋₆ alkylene)-(C₃₋₆ cycloalkyl), C₁₋₆ haloalkyl, or C₁₋₆ hydroxyalkyl;

X is C₄₋₇ cycloalkenyl, C₃₋₇ cycloalkyl, or an 8-10 membered, bicyclic partially saturated carbocyclyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$;

Y is —C($R^6$)($R^7$)—, —C(O)—, or —S(O)$_p$—;

m and p each represent independently for each occurrence 0, 1, or 2; and n is 1, 2, or 3.

29. A pharmaceutical composition comprising a compound of claim 28, and a pharmaceutically acceptable carrier.

30. A method of treating a disorder selected from the group consisting of cancer, bacterial infection, and fungal infection, comprising administering a therapeutically effective amount of a compound of claim 28 to a subject in need thereof to ameliorate a symptom of the disorder, wherein the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, or retinoblastoma.

* * * * *